(12) United States Patent
Romero et al.

(10) Patent No.: US 12,187,758 B2
(45) Date of Patent: Jan. 7, 2025

(54) COMPOUNDS AND METHODS FOR TREATING DISEASE

(71) Applicant: ROME Therapeutics, Inc., Boston, MA (US)

(72) Inventors: Donna L. Romero, Boston, MA (US); Oliver Saunders, Fresno, CA (US); Gregory Stuart Bisacchi, Plymouth, MA (US); Dennis Zaller, Lexington, MA (US); Rosana Kapeller-Libermann, Chestnut Hill, MA (US)

(73) Assignee: ROME Therapeutics, Inc., Boston, MA (US)

( * ) Notice: Subject to any disclaimer, the term of this patent is extended or adjusted under 35 U.S.C. 154(b) by 0 days.

(21) Appl. No.: 18/359,297

(22) Filed: Jul. 26, 2023

(65) Prior Publication Data

US 2023/0374058 A1 Nov. 23, 2023

Related U.S. Application Data

(63) Continuation of application No. PCT/US2023/064373, filed on Mar. 15, 2023.

(60) Provisional application No. 63/424,723, filed on Nov. 11, 2022, provisional application No. 63/354,620, filed on Jun. 22, 2022, provisional application No. 63/269,375, filed on Mar. 15, 2022.

(51) Int. Cl.
| | |
|---|---|
| C07H 19/06 | (2006.01) |
| A61P 37/06 | (2006.01) |
| C07H 19/067 | (2006.01) |
| C07H 19/073 | (2006.01) |
| C07H 19/10 | (2006.01) |
| C07H 19/12 | (2006.01) |
| C07H 19/16 | (2006.01) |

(52) U.S. Cl.
CPC ............ *C07H 19/06* (2013.01); *A61P 37/06* (2018.01); *C07H 19/10* (2013.01); *C07H 19/12* (2013.01); *C07H 19/16* (2013.01)

(58) Field of Classification Search
None
See application file for complete search history.

(56) References Cited

U.S. PATENT DOCUMENTS

| | | | |
|---|---|---|---|
| 6,060,592 A | 5/2000 | Acevedo et al. | |
| 6,225,460 B1 | 5/2001 | Bischofberger et al. | |
| 7,601,489 B2 | 10/2009 | Boeke et al. | |
| 8,835,615 B2 * | 9/2014 | Chang | C07H 19/14 536/22.1 |
| 8,877,733 B2 | 11/2014 | Cho et al. | |
| 9,073,960 B2 | 7/2015 | Beigelman et al. | |
| 9,890,188 B2 | 2/2018 | Wang et al. | |
| 10,100,307 B2 | 10/2018 | Prochiantz et al. | |
| 10,464,965 B2 | 11/2019 | Beigelman et al. | |
| 10,485,815 B2 | 11/2019 | Wang et al. | |
| 11,021,509 B2 | 6/2021 | Beigelman et al. | |
| 2003/0003468 A1 | 1/2003 | Crow | |
| 2004/0110717 A1 | 6/2004 | Carroll et al. | |
| 2007/0004669 A1 | 1/2007 | Carroll et al. | |
| 2007/0196824 A1 | 8/2007 | Stuyver et al. | |
| 2008/0070861 A1 | 3/2008 | Clark | |
| 2008/0261216 A1 | 10/2008 | Markovitz et al. | |
| 2009/0318380 A1 | 12/2009 | Sofia et al. | |
| 2010/0003213 A1 | 1/2010 | Devos et al. | |
| 2010/0016251 A1 | 1/2010 | Sofia et al. | |
| 2010/0081628 A1 | 4/2010 | Du et al. | |
| 2010/0151001 A1 | 6/2010 | Schott et al. | |
| 2012/0321637 A1 | 12/2012 | Dong et al. | |
| 2013/0165400 A1 | 6/2013 | Beigelman et al. | |
| 2014/0235566 A1 | 8/2014 | Amblard et al. | |
| 2014/0377758 A1 | 12/2014 | Dubnau et al. | |
| 2015/0011497 A1 | 1/2015 | Beigelman et al. | |
| 2015/0051167 A1 | 2/2015 | Wang et al. | |
| 2015/0105341 A1 | 4/2015 | Beigelman et al. | |
| 2015/0225441 A1 | 8/2015 | Smith et al. | |
| 2015/0246067 A1 | 9/2015 | Kaplan et al. | |
| 2015/0306227 A1 | 10/2015 | Cruise et al. | |
| 2015/0315228 A1 | 11/2015 | Beigelman et al. | |
| 2015/0366887 A1 | 12/2015 | Blatt et al. | |
| 2015/0366888 A1 | 12/2015 | Blatt et al. | |
| 2016/0022724 A1 | 1/2016 | Chanda et al. | |
| 2016/0045528 A1 | 2/2016 | Blatt et al. | |
| 2016/0052953 A1 | 2/2016 | Clarke et al. | |

(Continued)

FOREIGN PATENT DOCUMENTS

| | | |
|---|---|---|
| CA | 2502109 A1 | 9/2005 |
| CN | 114288313 A | 4/2022 |

(Continued)

OTHER PUBLICATIONS

Strittmatter et al., ARKIVOC (Gainsville, Fl, USA) 2016, vol. 2, pp. 46-59. (Year: 2016).*
U.S. Appl. No. 18/297,548, Compounds and Methods for Treating Disease, filed Apr. 7, 2023.
Beck-Engeser, G.B. et al., "An autoimmune disease prevented by anti-retroviral drugs," *Retrovirology*, 8:91 (2011).
Berdis, A.J., "Inhibiting DNA Polymerases as a Therapeutic Intervention against Cancer," *Frontiers in Molecular Biosciences*, vol. 4, Article 78, pp. 1-12 (2017).

(Continued)

*Primary Examiner* — Traviss C McIntosh, III
(74) *Attorney, Agent, or Firm* — Dechert LLP; Andrea L. C. Reid; Chad E. Davis

(57) ABSTRACT

The invention provides compounds, compositions and methods for treating medical disorders, such as cancer, an autoimmune disorder, and/or a neurological disorder, and inhibiting LINE1 reverse transcriptase and/or HERV-K reverse transcriptase using a compound according to Formula I or a pharmaceutically acceptable salt thereof, or a related compound provided herein.

26 Claims, 13 Drawing Sheets
Specification includes a Sequence Listing.

(56) References Cited

U.S. PATENT DOCUMENTS

| | | |
|---|---|---|
| 2016/0115190 A1 | 4/2016 | Serebryany et al. |
| 2016/0176910 A1 | 6/2016 | Wang et al. |
| 2016/0220595 A1 | 8/2016 | Liotta et al. |
| 2017/0100385 A1 | 4/2017 | Washburn |
| 2017/0143751 A1 | 5/2017 | Blatt et al. |
| 2017/0232031 A1 | 8/2017 | Smith et al. |
| 2017/0296664 A1 | 10/2017 | Smith et al. |
| 2017/0327526 A1 | 11/2017 | Clarke et al. |
| 2017/0335320 A1 | 11/2017 | Prochiantz et al. |
| 2018/0044369 A1 | 2/2018 | Beigelman et al. |
| 2018/0117042 A1 | 5/2018 | Chanda et al. |
| 2018/0185404 A1 | 7/2018 | Iyer et al. |
| 2019/0022116 A1 | 1/2019 | Painter et al. |
| 2019/0083520 A1 | 3/2019 | Painter et al. |

FOREIGN PATENT DOCUMENTS

| | | |
|---|---|---|
| EP | 2177527 A1 | 4/2010 |
| JP | 1997328497 A | 12/1997 |
| JP | 2017057200 A | 3/2017 |
| WO | WO-2000069876 A1 | 11/2000 |
| WO | WO-2005069880 A2 | 8/2005 |
| WO | WO-2005072748 A1 | 8/2005 |
| WO | WO-2009067409 A1 | 5/2009 |
| WO | WO-2010030858 A1 | 3/2010 |
| WO | WO-2010132513 A1 | 11/2010 |
| WO | WO-2010135690 A1 | 11/2010 |
| WO | WO-2012041965 A1 | 4/2012 |
| WO | WO-2012048113 A2 | 4/2012 |
| WO | WO-2012092153 A1 | 7/2012 |
| WO | WO-2013096679 A1 | 6/2013 |
| WO | WO-2013142525 A1 | 9/2013 |
| WO | WO-2014047117 A1 | 3/2014 |
| WO | WO-2014209979 A1 | 12/2014 |
| WO | WO-2015054465 A1 | 4/2015 |
| WO | WO-2015120237 A2 | 8/2015 |
| WO | WO-2015148746 A1 | 10/2015 |
| WO | WO-2015200697 A1 | 12/2015 |
| WO | WO-2016014398 A1 | 1/2016 |
| WO | WO-2016049415 A1 | 3/2016 |
| WO | WO-2016100569 A1 | 6/2016 |
| WO | WO-2016138425 A1 | 9/2016 |
| WO | WO-2016145142 A1 | 9/2016 |
| WO | WO-2016149366 A1 | 9/2016 |
| WO | WO-2017059122 A1 | 4/2017 |
| WO | WO-2017222911 A1 | 12/2017 |
| WO | WO-2018081449 A1 | 5/2018 |
| WO | WO-2018093777 A1 | 5/2018 |
| WO | WO-2018136920 A1 | 7/2018 |
| WO | WO-2018208727 A1 | 11/2018 |
| WO | WO-2018222774 A1 | 12/2018 |
| WO | WO-2019133712 A1 | 7/2019 |
| WO | WO-2019157087 A1 | 8/2019 |
| WO | WO-2019246376 A1 | 12/2019 |
| WO | WO-2020142629 A1 | 7/2020 |
| WO | WO-2020154656 A1 | 7/2020 |
| WO | WO-2021154687 A1 | 8/2021 |
| WO | WO-2021169861 A1 | 9/2021 |
| WO | WO-2021188910 A1 | 9/2021 |
| WO | WO-2022066880 A1 | 3/2022 |
| WO | WO-2022066882 A1 | 3/2022 |
| WO | WO-2022197689 A1 | 9/2022 |
| WO | WO-2022217153 A2 | 10/2022 |
| WO | WO-2022217154 A2 | 10/2022 |
| WO | WO-2022245814 A1 | 11/2022 |

OTHER PUBLICATIONS

Chang, J., "4'-Modified Nucleosides for Antiviral Drug Discovery: Achievements and Perspectives," *Acc. Chem. Res.* (2022) vol. 55(4), pp. 565-578.

CIRM Grant Award: Reverse transcriptase inhibitors as a novel therapeutic approach for neurological autoimmune disorders (obtained from Internet on May 28, 2021).

Clarke, M.O. et al., "Discovery of B-D-2'-deoxy-2'-a-fluoro-4'-a-cyano-5-aza-7,9-dideaza adenosine as a potent nucleoside inhibitor of respiratory syncytial virus with excellent selectivity over mitochondrial RNA and DNA polymerases," *Bioorg. Med. Chem. Lett.* (2015), vol. 25, pp. 2484-2487.

De Clercq, E., "The design of drugs for HIV and HCV," Drug Discovery, vol. 6, pp. 1001-1018 (2007).

Fowler, B.J. et al., "Nuceoside reverse transcriptase inhibitors Possess intrinsic anti-inflammatory activity," Science, 346(6212): 1000-1003.

Henry, N.L. and Hayes, D.F., "Cancer biomarkers," *Mol. Oncology*, vol. 6, pp. 140-146 (2012).

Liu, P. et al., "Fluorinated Nucleosides: Synthesis and Biological Implication," *J. Fluor. Chem.*, pp. 1-67 (2008).

Mustelin, T. et al., "Sources of Pathogenic Nucleic Acids in Systemic Lupus Erythematosus," *Frontiers in Immunology*, vol. 10, Article 1028, pp. 1-13 (2019).

Otto, M.J., "New nucleoside reverse transcriptase inhibitors for the treatment of HIV infections," *Current Opinion in Pharmacology*, vol. 4, pp. 431-436 (2004).

Quaglia, M. et al., "Viral Infections and Systemic Lupus Erythematosus: New Players in an Old Story," *Viruses*, vol. 13, 277, pp. 1-29(2021).

Saleh, A. et al., "Transposable Elements, Inflammation, and Neurological Disease," Frontiers in Neurology, vol. 10, Article 894, pp. 1-16 (2019).

Sciamanna, I. et al., "The Reverse Transcriptase Encoded by LINE-1 Retrotransposons in the Genesis, Progression, and Therapy of Cancer," Frontiers in Chemistry, vol. 4, Article 6, pp. 1-10 (2016).

SciFinder Database Entry for CAS Registry No. 1654751-88-8 (retrieved Jan. 2023).

SciFinder Database Entry for CAS Registry No. 1803129-38-5 (retrieved Jan. 2023).

SciFinder Database Entry for CAS Registry No. 1803129-53-4 (retrieved Jan. 2023).

SciFinder Database Entry for CAS Registry No. 1948281-51-3 (retrieved Jan. 2023).

SciFinder Database Entry for CAS Registry No. 1948281-56-8 (retrieved Jan. 2023).

SciFinder Database Entry for CAS Registry No. 1948282-22-1 (retrieved Jan. 2023).

Simon, M. et al., "Inhibition of retrotransposition improves health and extends lifespan of SIRT6 knockout mice," bioRxiv preprint (posted on Internet on Nov. 4, 2018).

Simon, M. et al., "LINE1 Derepression in Aged Wild-Type and SIRT6-Deficient Mice Drives Inflammation," Cell Metabolism, vol. 30, pp. 871-885 (2019).

Talotta, R., et al., "Retroviruses in the pathogenesis of systemic lupus erythematosus: Are they potential therapeutic targets?," *Autoimmunity*, vol. 53, No. 4, pp. 177-191 (2020).

Ting, D.T. et al., "Aberrant Overexpression of Satellite Repeats in Pancreatic and Other Epithelial Cancers," *Science*, 331(6017): 593-596. doi:10.1126/science.1200801 (2011).

Tugnet, N. et al., "Human Endogenous Retroviruses (HERVs) and Autoimmune Rheumatic Disease: Is There a Link?," *The Open Rheumatology Journal*,vol. 7, pp. 13-21 (2013).

Ukadike, U. and Mustelin, T., "Implications of Endogenous Retroelements in the Etiopathogenesis of Systemic Lupus Erythematosus," *J. Clin. Med.*,, vol. 10, pp. 1-18 (2021).

Wang, G. et al., "Discovery of 4'-Chloromethyl-2'-deoxy-3',5'-di-O-isobutyryl-2'-fluorocytidine (ALS-8176), A First-in-Class RSV Polymerase Inhibitor for Treatment of Human Respiratory Syncytial Virus Infection," *J. Med. Chem.*, vol. 58, pp. 1862-1878 (2015).

Zhang, X. et al., "New Understanding of the Relevant Role of Line-1 Retrotransportation in Human Disease and Immune Modulation," *Frontiers in Cell and Developmental Biology*, vol. 8, Article 657, pp. 1-10 (2020).

SciFinder Database Entry for CAS Registry No. 1053245-79-6; (entry date: Sep. 2008).

Zhang, Y. et al., "FNC efficiently inhibits mantle cell lymphoma growth," *PLoS ONE*, 12(3): e0174112 (2017); DOI: 10.1371/journal.pone.0174112.

(56) References Cited

OTHER PUBLICATIONS

International Search Report for International Application No. PCT/US2023/064373, mailed Jun. 19, 2023 (10 pages).

\* cited by examiner

SEQUENCE LISTING

```
Sequence total quantity: 12
SEQ ID NO: 1           moltype = RNA   length = 36
FEATURE                Location/Qualifiers
source                 1..36
                       mol_type = other RNA
                       organism = synthetic construct
SEQUENCE: 1
gtaactagag atccctcaga ccctttagt cagaat                                36

SEQ ID NO: 2           moltype = DNA   length = 25
FEATURE                Location/Qualifiers
source                 1..25
                       mol_type = other DNA
                       organism = synthetic construct
SEQUENCE: 2
```

```
ttctgactaa aagggtctga gggat                                          25

SEQ ID NO: 3            moltype = DNA   length = 27
FEATURE                 Location/Qualifiers
source                  1..27
                        mol_type = other DNA
                        organism = synthetic construct
SEQUENCE: 3
tcccagactc cctagagatc aatcaac                                        27

SEQ ID NO: 4            moltype = DNA   length = 14
FEATURE                 Location/Qualifiers
source                  1..14
                        mol_type = other DNA
                        organism = synthetic construct
SEQUENCE: 4
agggtctgag ggat                                                      14

SEQ ID NO: 5            moltype = DNA   length = 20
FEATURE                 Location/Qualifiers
source                  1..20
                        mol_type = other DNA
                        organism = synthetic construct
SEQUENCE: 5
gtggctttgg agttgcagtt                                                20

SEQ ID NO: 6            moltype = DNA   length = 21
FEATURE                 Location/Qualifiers
source                  1..21
                        mol_type = other DNA
                        organism = synthetic construct
SEQUENCE: 6
cagccaccat gaatattgta c                                              21

SEQ ID NO: 7            moltype = DNA   length = 20
FEATURE                 Location/Qualifiers
source                  1..20
                        mol_type = other DNA
                        organism = synthetic construct
SEQUENCE: 7
gtggctttgg agttgcagtt                                                20

SEQ ID NO: 8            moltype = DNA   length = 20
FEATURE                 Location/Qualifiers
source                  1..20
                        mol_type = other DNA
                        organism = synthetic construct
SEQUENCE: 8
gaagcagatt tgggtaccac                                                20

SEQ ID NO: 9            moltype = DNA   length = 18
FEATURE                 Location/Qualifiers
source                  1..18
                        mol_type = other DNA
                        organism = synthetic construct
SEQUENCE: 9
cgggtgacgg ggaatcag                                                  18

SEQ ID NO: 10           moltype = DNA   length = 17
FEATURE                 Location/Qualifiers
source                  1..17
                        mol_type = other DNA
                        organism = synthetic construct
SEQUENCE: 10
cactacctcc ccgggtc                                                   17

SEQ ID NO: 11           moltype = DNA   length = 22
FEATURE                 Location/Qualifiers
source                  1..22
                        mol_type = other DNA
                        organism = synthetic construct
SEQUENCE: 11
agatccctcc aaaatcaagt gg                                             22

SEQ ID NO: 12           moltype = DNA   length = 21
FEATURE                 Location/Qualifiers
source                  1..21
                        mol_type = other DNA
                        organism = synthetic construct
```

```
SEQUENCE: 12
ggcagagatg atgacccttt t                              21
```

COMPOUNDS AND METHODS FOR TREATING DISEASE

CROSS REFERENCE TO RELATED APPLICATIONS

This application is a continuation of international patent application no. PCT/US2023/064373, filed Mar. 15, 2023, which claims the benefit of and priority to U.S. Provisional Patent Application Ser. No. 63/424,723, filed Nov. 11, 2022; U.S. Provisional Patent Application Ser. No. 63/354,620, filed Jun. 22, 2022; and U.S. Provisional Patent Application Ser. No. 63/269,375, filed Mar. 15, 2022; the contents of each of which are hereby incorporated by reference in their entirety.

REFERENCE TO AN ELECTRONIC SEQUENCE LISTING

This application contains a Sequence Listing which has been submitted electronically via Patent Center in XML format and is hereby incorporated by reference in its entirety. Said XML copy, created on Jul. 25, 2023, is named 201843_seqlist.xml and is 11,405 bytes in size.

FIELD OF THE INVENTION

The invention provides compounds, compositions and methods for treating medical disorders, such as cancer, autoimmune disorders, and/or neurological disorders, and modulating LINE1 reverse transcriptase and/or HERV-K reverse transcriptase using a compound according to Formula I or a pharmaceutically acceptable salt thereof, or a related compound provided herein.

BACKGROUND

Transposable elements (or transposons) are genomic DNA sequences that have the ability to move within the genome which leads to altering its organization, increase its size and creates duplications and redundancy. (Ukadike and Mustelin, *J. Clin. Med.*, 10:856 (2021)). These genomic sequences are believed to have been introduced into the human genome by either an infection by exogenous retroviruses that infected human ancestors millions of years ago or ancient descendants of retroviruses which retained the ability to embed and replicate in human germline genome. (Ukadike and Mustelin, 2021).

Long Interspersed Nuclear Element 1 (LINE-1) are class I transposable elements in the DNA of some organisms and comprise about 17% of the human genome. LINE-1 harbors two open reading frames, ORF1 and ORF2, which in turn respectively encode ORF1p, which has nucleic acid chaperone activity, and ORF2p, with reverse transcriptase (RT) and endonuclease activities. (Reviewed in Babushok and Kazazian, *Hum. Mut.* 28:527-539, (2007)). LINE-1 retrotransposition activity is mediated by ORF2p. The majority of LINE-1 elements in the human genome contain inactivating mutations but a small percentage of LINE-1 elements are intact and have retained the ability to retrotranspose. This ability varies both among individuals and among cell types within an individual. Active LINE-1 elements are thought to disrupt the genome through insertions, deletions, rearrangements and recombinations. (Garcia-Perez et al, *Development*, 143:4101-4114 (2016)). LINE-1 activity is normally tightly regulated in the germline by DNA methylation, histone modifications, and piRNA.

Retrotransposons are transposable elements which are associated with the pathogenesis of many diseases such as cancer, autoimmune disease, neurological disorders and aging, among others. (Zhang, et al, *Frontiers in Cell and Dev. Bio.*, 8:657 (August 2020); Kuriyama et al, *Nature: Scientific Reports*, 11:23146 (2021)). LINE-1 RNA and protein overexpression can promote apoptosis, DNA damage and repair, and cellular plasticity, which can promote tumor progression. Furthermore, genomic hypomethylation can induce expression of repetitive sequences which can drive a pro-inflammatory response characterized by overproduction of type 1 interferon. (Zhang, 2020).

Pathogenic interferon production is a characteristic feature of type I interferonopathies. These include rare genetic diseases with occurrence rates from 1:10,000 to 1:1,000,000. Pathological induction of type I interferon causes immune system hyperactivation that leads to systemic inflammation which can affect the nervous system, lung and blood vessels, among other organ systems. (Nesterova et al. "Congenital and Acquired Interferonopathies: Differentiated Approaches to Interferon Therapy". *Innate Immunity in Health and Disease*, Ed. Saxena and Prakash, IntechOpen, 2020). Aicardi-Goutieres Syndrome (AGS) is a monogenic inflammatory encephalomyopathy driven by mutations in genes that are critical in maintaining homeostatic cytosolic nucleic acid oligomers. As a result, increased level of cytoplasmic nucleic acid accumulation leads heightened interferon response. The double stranded DNA products of LINE-1 reverse transcription are potential triggers of DNA sensing receptors such as cGAS, which is a DNA sensor that activates the STING pathway leading to type I interferon production. (Zhao, *J. Autoimmunity*, 90:105-115 (2018)). LINE-1 reverse transcriptase products have been implicated as a primary source of pro-inflammatory nucleic acids in AGS patients. Administering a combination of three nucleoside reverse transcriptase inhibitors to AGS patients for 12 months effectively reduced their systemic interferon response. The pathogenic interferon response responsible for AGS has also been implicated in the pathogenesis of SLE, with several case studies identifying monogenic forms of SLE driven by hypomorphic alleles of nucleic acid metabolizing enzymes such as TREX1.

Hypomethylated and highly expressed LINE-1 has been found in many patients with autoimmune diseases such as systemic lupus erythematosus (SLE), cutaneous lupus, Sjögren's syndrome (SS) and psoriasis. (Zhang et al). LINE-1 has also been found to be significantly upregulated in patients with dermatomyositis (DM), with significantly elevated levels of interferon α and interferon β. (Kuriyama et al, *J. Am. Acad, Dermatol.*, 84(4):1103-1105 (2020)).

LINE-1 has also been implicated in neurological disorders such as ataxia telangiectasia (AT), Rett syndrome, Friederichs's ataxia, parasupranuclear palsy, amyotrophic lateral sclerosis, frontotemporal dementia and schizophrenia. Increased retrotransposition as well as elevated levels of type 1 interferon have been identified in each of these diseases. LINE-1 is also implicated in the aging process and frontotemporal lobe degeneration. (Zhang, 2020).

Cancer continues to be a significant health problem despite the substantial research efforts and scientific advances reported in the literature for treating this disease. Solid tumors, including prostate cancer, breast cancer, and lung cancer remain highly prevalent among the world population. Leukemias and lymphomas also account for a significant proportion of new cancer diagnoses. Current treatment options for these cancers are not effective for all patients and/or can have substantial adverse side effects. New therapies are needed to address this unmet need in cancer therapy.

High LINE-1 activity has been found in many tumor tissues. LINE-1 RT uses a procedure termed target-site-primed reverse transcription (TPRT) which involves nicking of the genomic DNA followed by reverse transcription and insertion of LINE-1 into the genome. LINE-1 mediated gene rearrangement can trigger oncogene amplification. Additionally, LINE-1 can mediate the deletion of tumor suppressor genes (Zhang, 2020). Inhibition of LINE-1 RT in cancer cells, either via RNA interference-dependent silencing of active LINE-1 elements or using RT inhibitory compounds can reduce cancer cell proliferation, promote cancer cell differentiation and can retard tumor progression in certain animal models. (Sciamann et al, *Frontiers in Chemistry*, 4:6 (February 2016)). LINE1 has also been shown to promote tumor metastasis. Furthermore, chronic production of type 1 interferon in the tumor microenviorment has been linked to resistance to immunosurveillance with therapeutic blockade of interferon signaling increased anti-cancer immune responses.

Human endogenous retroviruses (HERVs) comprise nearly 8% of the human genome and are believed to be derived from ancient integrations of retroviruses into the germline. The biology of HERVs is poorly defined, but there is accumulating evidence supporting pathological roles in diverse diseases such as cancer, autoimmune, neurodegenerative diseases, and aging. Functional proteins are produced by HERV-encoded genes including reverse transcriptases (RTs), which could be a contributor to the pathology attributed to aberrant HERV-K expression.

HERVs play a role in early development by rewiring the gene regulatory network of the preimplantation embryo (Fu et al, *Biomolecules*, 11(6):829 (2021)). HERV expression appears to be a hallmark of the undifferentiated state, the acquisition of phenotypic plasticity and stem cell character (Balestrieri et al, *Frontiers in Microbiology*, 9:1448 (2018)); traits associated with aggressive cancer and poor patient outcomes. HERV expression is normally tightly controlled in normal adult tissues but is reported to be aberrantly expressed in cancer (Downey et al, *Int. J. Cancer*, 137(6): 1249-1257 (2015)), inflammatory diseases (Greenig, PeerJ 7:e6711 (2019)), neurological diseases (Kury et al, *Trends Mol. Med.*, 24(4):379-394 (2018)), aging (Gorbunova et al, *Nature*, 596(7870):43-53 (2021)), and viral disease (Romer, *Frontiers in Neuroscience*, 15:648629-648629 (2021)). There are numerous reports of upregulation of HERV-K [HML-2 (human endogenous MMTV-like) subtype derived mRNA and protein in a variety of solid and liquid tumor types (Dervan et al, *Front. Onc.*, 11:658489 (2021); Hohn et al, *Front. Onc.*, 3:246 (2013)). The disease association with endogenous retroviruses and the expression of HERV encoded proteins during disease states suggests that anti-retroviral therapy could be explored in the management of these conditions.

Accordingly, the need exists for new therapeutic methods that provide improved efficacy and/or reduced side effects for treating medical disorders, such as cancer, autoimmune disease, neurological disorders, aging, and diseases associated with aging. The present invention addresses the foregoing needs and provides other related advantages.

SUMMARY

Provided herein are compounds and compositions which are useful for, among other uses, the treatment of cancer, an autoimmune disorder, and/or a neurological disorder. The compounds inhibit LINE1 reverse transcriptase activity and/or HERV-K reverse transcriptase activity. The compounds may be formulated in a pharmaceutical composition. Therapeutic methods and methods of inhibiting LINE1 reverse transcriptase activity are provided.

One aspect of the disclosure provides compounds having a superior combination of properties including potent inhibitory activity towards LINE1 reverse transcriptase, selectivity for inhibiting LINE1 reverse transcriptase, and superior physical properties that render the compounds well-suited for use as an orally administered medicine. Selectivity for inhibiting LINE1 reverse transcriptase can be characterized according to ability of the compounds to inhibit LINE1 reverse transcriptase while having substantially less inhibitory activity towards DNA polymerases (e.g., $\alpha$, $\beta$ and $\gamma$). In part because inhibition of DNA polymerases, such as DNA polymerase gamma, can result in toxicity in the form of mitotoxicity, compounds demonstrating potent inhibitory activity towards LINE1 reverse transcriptase while having substantially less inhibitory activity towards DNA polymerases are an important discovery and significant scientific advance. The potent inhibitory activity towards LINE1 reverse transcriptase in combination with low inhibitory activity towards DNA polymerases contributes to a high therapeutic index for subject compounds, thereby providing a superior performance profile for the compound in medical therapy. Experimental results herein demonstrate these benefits.

Another aspect of the disclosure provides compounds having a superior combination of properties including potent inhibitory activity towards LINE1 reverse transcriptase, selectivity for inhibiting LINE1 reverse transcriptase, potent inhibition of pathogenic interferon response in inflammatory tissues, and superior physical properties that render the compounds well-suited for use as an orally administered medicine. As described above, selectivity for inhibiting LINE1 reverse transcriptase can be characterized according to ability of the compounds to inhibit LINE1 reverse transcriptase while having substantially less inhibitory activity towards DNA polymerases (e.g., $\alpha$, $\beta$ and $\gamma$). In part because inhibition of DNA polymerases, such as DNA polymerase gamma, can result in toxicity in the form of mitotoxicity, compounds demonstrating potent inhibitory activity towards LINE1 reverse transcriptase while having substantially less inhibitory activity towards DNA polymerases are an important discovery and significant scientific advance. Compounds having potent inhibition of pathogenic interferon response in inflammatory tissues are useful for treating cancer, autoimmune disease (e.g., SLE and CLE), neurological disorders, aging, and diseases associated with aging. The potent inhibitory activity towards LINE1 reverse transcriptase in combination with low inhibitory activity towards DNA polymerases (e.g., $\alpha$, $\beta$ and $\gamma$) contributes to a high therapeutic index for subject compounds, thereby providing a superior performance profile for the compound in medical therapy.

Another aspect of the disclosure provides compounds having a superior combination of properties including potent inhibitory activity towards HERV-K reverse transcriptase, selectivity for inhibiting HERV-K reverse transcriptase, and superior physical properties that render the compounds well-suited for use as an orally administered medicine. Selectivity for inhibiting HERV-K reverse transcriptase can be characterized according to ability of the compounds to inhibit HERV-K reverse transcriptase while having substantially less inhibitory activity towards DNA polymerases (e.g., α, β and γ). In part because inhibition of DNA polymerases, such as DNA polymerase gamma, can result in toxicity in the form of mitotoxicity, compounds demonstrating potent inhibitory activity towards HERV-K reverse transcriptase while having substantially less inhibitory activity towards DNA polymerases are an important significant scientific advance. Compounds that are potent inhibitors of HERV-K reverse transcriptase are useful for treating HERV-K reverse transcriptase associated disorders. The potent inhibitory activity towards HERV-K reverse transcriptase in combination with low inhibitory activity towards DNA polymerases contributes to a high therapeutic index for subject compounds, thereby providing a superior performance profile for the compound in medical therapy.

Accordingly, one aspect of the disclosure provides compounds represented by Formula I:

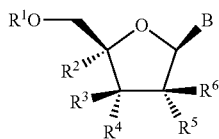

(I)

or a pharmaceutically acceptable salt thereof, wherein B, $R^1$, $R^2$, $R^3$, $R^4$, $R^5$ and $R^6$ are as described herein. Also provided herein are pharmaceutical compositions comprising the compounds of Formula I.

Another aspect of the disclosure provides a collection of compounds, such as a compound represented by Formula II:

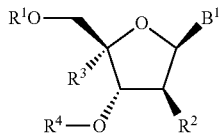

(II)

or a pharmaceutically acceptable salt thereof, wherein the variables are as described herein. Also provided herein are pharmaceutical compositions comprising the compounds of Formula II.

Another aspect of the disclosure provides a collection of compounds, such as a compound represented by Formula III:

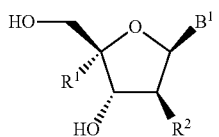

(III)

or a pharmaceutically acceptable salt thereof, wherein the variables are as described herein. Also provided herein are pharmaceutical compositions comprising the compounds of Formula III.

Another aspect of the disclosure provides a collection of compounds, such as a compound represented by Formula IV:

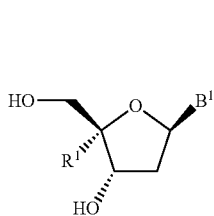

(IV)

or a pharmaceutically acceptable salt thereof, wherein the variables are as described herein. Also provided herein are pharmaceutical compositions comprising the compounds of Formula IV.

Another aspect of the disclosure provides a collection of compounds, such as a compound represented by Formula V:

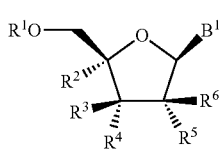

(V)

or a pharmaceutically acceptable salt thereof, wherein the variables are as described herein. Also provided herein are pharmaceutical compositions comprising the compounds of Formula V.

Another aspect of the disclosure provides a collection of compounds, such as a compound represented by Formula VI:

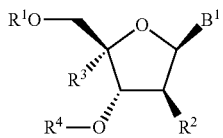

(VI)

or a pharmaceutically acceptable salt thereof, wherein the variables are as described herein. Also provided herein are pharmaceutical compositions comprising the compounds of Formula VI.

The disclosed compounds and compositions are designed for treating medical disorders by inhibiting LINE1 reverse transcriptase and/or HERV-K reverse transcriptase using the disclosed compounds. In particular, one aspect of the disclosure provides the compounds according to Formula I, or a pharmaceutically acceptable salt thereof, in a method of treating a disorder selected from the group consisting of cancer, an autoimmune disorder, and a neurological disorder. Further description of additional collections of compounds useful in the method are described in the detailed description, including compounds of Formula II, III, IV, V, and VI. Additional features of the method are described in the detailed description.

Another aspect of the disclosure provides the compounds according to Formula I, or a pharmaceutically acceptable salt thereof, in a method of inhibiting LINE1 reverse transcriptase activity in a subject suffering from a disorder selected from the group consisting of cancer, an autoimmune disorder, and a neurological disorder. The method comprises contacting a LINE1 reverse transcriptase with an effective amount of a compound of Formula I, or a pharmaceutically acceptable salt thereof, in order to inhibit the activity of said LINE1 reverse transcriptase. Further description of additional compounds useful in the method are described in the detailed description, including compounds of Formula II, III, IV, V, and VI. Additional features of the method are described in the detailed description.

Another aspect of the disclosure provides the compounds according to Formula I, or a pharmaceutically acceptable salt thereof, in a method of inhibiting HERV-K reverse transcriptase activity in a subject suffering from a disorder selected from the group consisting of cancer, an autoimmune disorder, and a neurological disorder. The method comprises contacting a HERV-K reverse transcriptase with an effective amount of a compound of Formula I, or a pharmaceutically acceptable salt thereof, in order to inhibit the activity of said HERV-K reverse transcriptase. Further description of additional collections of compounds useful in the method are described in the detailed description, including compounds of Formula II, III, IV, V, and VI. Additional features of the method are described in the detailed description.

BRIEF DESCRIPTION OF FIGURES

FIG. 3A depicts a representative high responder, and FIG. 3B depicts a representative moderate responder.

DETAILED DESCRIPTION

Figure 1A:
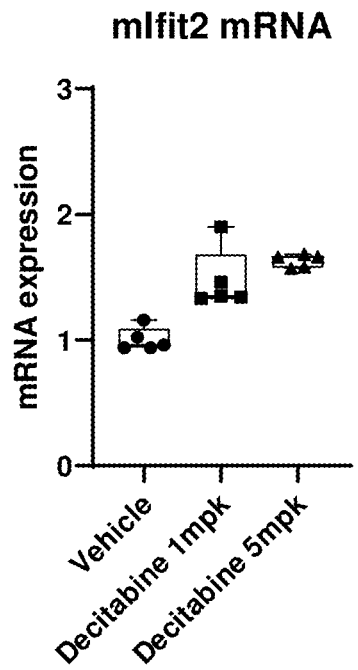
FIGS. 1A and 1B show, in the in vivo decitabine challenge model, that repeated dosing of decitabine induces interferon-stimulated gene (ISG) response in the spleen in the vehicle control animals, as described in Example 108.

In certain embodiments, the present disclosure provides a compound of Formula I:

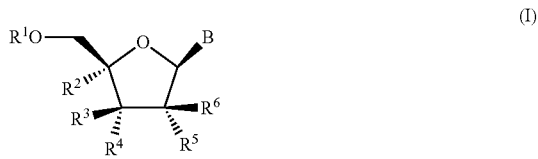

or a pharmaceutically acceptable salt thereof, wherein B is

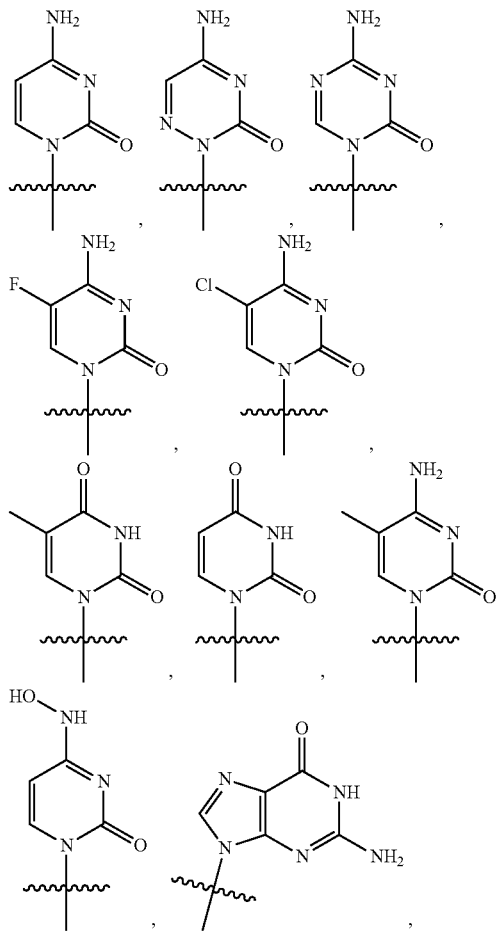

-continued

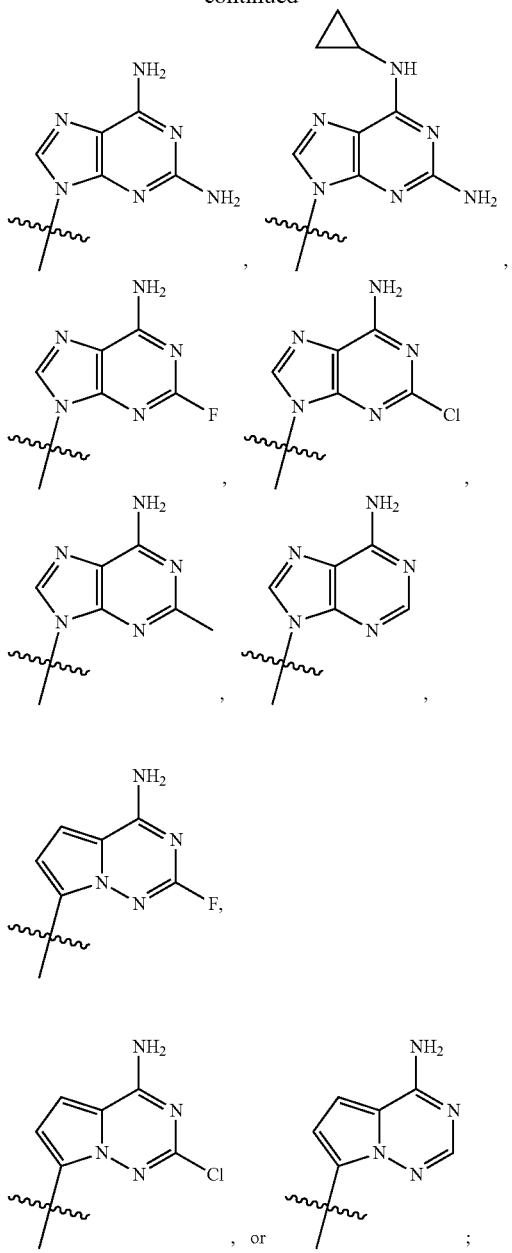

R¹ is —H or

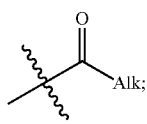

Alk is independently for each occurrence a $C_2$-$C_6$ aliphatic group;

R² is —H, $C_1$-$C_6$ aliphatic, $C_1$-$C_3$ haloaliphatic, $C_1$-$C_3$ hydroxyaliphatic, cyclopropyl, —CN, —$N_3$, —O—($C_1$-$C_3$ aliphatic), —F or —Cl;

R³ is —H;

R⁴ is —OH, —Cl, —OCH₃, —F, —$N_3$, or

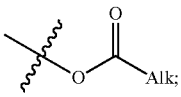

R⁵ is —H or —F; and

R⁶ is —H, —F, —Cl, $C_1$-$C_6$ aliphatic, $C_1$-$C_4$ haloaliphatic, —O—($C_1$-$C_4$ aliphatic), cyclopropyl, or —OH.

The invention further provides compounds of Formula II, III, IV, V, or VI, as described herein. The invention further provides compositions of the compounds of Formula I and methods for treating medical disorders, such as cancer, autoimmune disorders, and/or neurological disorders, and inhibiting LINE1 reverse transcriptase and/or HERV-K reverse transcriptase using a compound according to Formula I, or a pharmaceutically acceptable salt thereof, or a related compound provided herein (such as a compound of Formula II, III, IV, V, or VI).

The invention further provides compounds of Formula I-A, II-A, III-A, III-B, IV-A, and IV-B, as described herein. The invention further provides compositions of the compounds of Formula I and methods for treating medical disorders, such as cancer, autoimmune disorders, and/or neurological disorders, and inhibiting LINE1 reverse transcriptase and/or HERV-K reverse transcriptase using a compound according to Formula I, or a pharmaceutically acceptable salt thereof, or a related compound provided herein (such as a compound of Formula I-A, II-A, III-A, III-B, IV-A, and IV-B).

Various aspects of the invention are set forth below in sections; however, aspects of the invention described in one particular section are not to be limited to any particular section. Further, when a variable is not accompanied by a definition, the previous definition of the variable controls.

Definitions

Compounds of the present invention include those described generally herein, and are further illustrated by the classes, subclasses, and species disclosed herein. As used herein, the following definitions shall apply unless otherwise indicated. These definitions apply regardless of whether a term is used by itself or in combination with other terms, unless otherwise indicated. Hence, the definition of "aliphatic" applies to "aliphatic" as well as the "aliphatic" portions of "—O-aliphatic" etc. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5' Ed., Ed.: Smith, M. B. and March, J., John Wiley & Sons, New York: 2001, the entire contents of which are hereby incorporated by reference.

When used in the description of a chemical group that may have multiple points of attachment, a hyphen (-) designates the point of attachment of that group to the variable to which it is attached. Likewise, use of the symbol "↯" denotes a point of attachment of a group to the structure.

The term "aliphatic" used alone or as part of a larger moiety, such as "haloaliphatic", and the like, means a saturated or unsaturated, straight-chain or branched monovalent hydrocarbon radical. Unless otherwise specified, an aliphatic group typically has 1-6 carbon atoms. Examples of aliphatic groups include methyl, ethyl, ethynyl, ethenyl, propyl, propenyl, isopropyl, butyl, isobutyl, tert-butyl, and the like.

The term "haloaliphatic" includes mono-, poly-, and per-haloaliphatic groups where the halogens are independently selected from F, Cl, Br and I, and the aliphatic group is as described above. Examples of a "haloaliphatic" group include —$CF_3$, —$CH_2F$, —CFClH, —$CH_2CH_2F$, —$CH_2CH_2Cl$, —CH=CHF, —$CF_2CF_3$, —$CH_2Cl$, and the like.

The term "alkyl" used alone or as part of a larger moiety, such as "haloalkyl" and the like, means a saturated, straight-chain or branched monovalent hydrocarbon radical. Unless otherwise specified, an alkyl group typically has 1-6 carbon atoms. Examples of alkyl groups include methyl, ethyl, propyl, isopropyl, butyl, isobutyl, tert-butyl, and the like.

The term "haloalkyl" includes mono-, poly-, and per-haloalkykl groups where the halogens are independently selected from F, Cl, Br and I, and the alkyl group is as described above. Examples of a "haloalkyl" group include —$CF_3$, —$CH_2F$, —CFClH, —$CH_2CH_2F$, —$CH_2CH_2Cl$, —$CF_2CF_3$, —$CH_2Cl$, and the like. The term "halomethyl" refers to a haloalkyl group containing a single carbon atom. The term "deuterohalomethyl" refers to a halomethyl group containing one or two deuterium atoms.

The term "alkoxy" means an aliphatic radical attached through an oxygen linking atom, also represented by —O-aliphatic, wherein the aliphatic group is as described above. Examples of "alkoxy" groups include —$OCH_3$, —$OCH_2CH_3$, —OCH=$CH_2$, and the like.

The term "hydroxyaliphatic" means an aliphatic group, as described above, substituted with one or more —OH. Examples of a "hydroxyaliphatic" group include —$CH_2OH$, —C(H)(OH)$CH_3$, —$CH_2$C(H)(OH)$CH_2OH$, and the like.

The term "halogen" means F, Cl, Br, or I.

The term "unsaturated," as used herein, means that a moiety has one or more units of unsaturation. For example, "unsaturated" aliphatic groups include both alkenyl and alkynyl moieties, such as ethynyl, ethenyl, 2-propenyl, 3-propenyl, 2-propynyl, and the like.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid; or with organic acids such as acetic acid, oxalic acid, maleic acid, tartaric acid, citric acid, succinic acid, or malonic acid; or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium, and $N^+(C_{1-4}$aliphatic$)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower aliphatic sulfonate, and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^3$C- or $^{14}$C-enriched carbon are within the scope of this invention. Such compounds are useful, for example, as analytical tools, as probes in biological assays, or as therapeutic agents in accordance with the present invention.

Unless indicated otherwise, when a D is specifically recited at a position or is shown in a chemical formula, this D represents a mixture of hydrogen and deuterium where the amount of deuterium is about 100% (i.e., the abundance of deuterium ranges from at least 90% up to 100%). In certain embodiments, the abundance of deuterium in D is from 95% to 100%, or from 97% to 100%. Deuterium ($^2$H) is a stable, non-radioactive isotope of $^1$H hydrogen and has an atomic weight of 2.014. Hydrogen naturally occurs as a mixture of the isotopes $^1$H hydrogen (i.e., protium), deuterium ($^2$H), and tritium (3H). The natural abundance of deuterium is 0.015%. One of ordinary skill in the art recognizes that in all chemical compounds with an H atom, the H atom actually represents a mixture of $^1$H hydrogen, deuterium ($^2$H), and tritium ($^3$H), where about 0.015% is deuterium.

When the stereochemistry of a disclosed compound is named or depicted by structure, the named or depicted stereoisomer is at least 60%, 70%, 80%, 90%, 95%, 99%, 99.5% or 99.9% by weight pure relative to all of the other stereoisomers. Percent by weight pure relative to other stereoisomers is the ratio of the weight of one stereoisomer over the weight of all stereoisomers. When a single enantiomer is named or depicted by structure, the depicted or named enantiomer is at least 60%, 70%, 80%, 90%, 95%, 99%, 99.5% or 99.9% optically pure. Percent optical purity is determined by chiral liquid chromatography using area percent.

The terms "a" and "an" as used herein mean "one or more" and include the plural, unless the context is inappropriate.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

As used herein, the terms "subject" and "patient" are used interchangeably and refer to organisms to be treated by the methods of the present invention. Such organisms preferably include, but are not limited to, mammals (e.g., murines, simians, equines, bovines, porcines, canines, felines, and the like), and most preferably includes humans.

The term "inhibit", "inhibition", or "inhibiting" includes a decrease in the baseline activity of a biological activity or process.

As used herein, the term "effective amount" refers to the amount of a compound that will elicit a biological or medical response in a subject, for example, the reduction or inhibition of enzyme or protein activity relative to the baseline levels before treatment. Typically, an "effective amount" of a compound is one which is sufficient to effect some beneficial change or desired results (e.g., a therapeutic, ameliorative, inhibitory, or preventative result). An effective amount can be administered in one or more administrations, applications or dosages and is not intended to be limited to a particular formulation or administration route. As used herein, the term "treating" includes any effect, e.g., lessening, reducing, modulating, ameliorating, or eliminating, that results in the improvement of the condition, disease, disorder, and the like, or ameliorating a symptom thereof. For example, treatment of cancer may mean prolonging the period of time where tumor burden does not increase (progression-free survival), reduction of the tumor burden, extension of the overall survival time of a patient, amelioration of symptoms associated with the cancer, prevention of metastasis, slowing of metastasis, and the like. Treatment of an autoimmune disease includes reduction of the symptoms of the disease, extension of time between disease flare-ups, remission of disease, prevention of worsening of the disease, and the like. Treatment of neurological disease may include improvement of cognitive function, reduction of the rate of cognitive loss, reduction of symptoms, and the like.

In some embodiments, treatment is administered after one or more symptoms have developed. In some embodiments, treatment is administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein, the term "pharmaceutical composition" refers to the combination of an active agent with a carrier, adjuvant, or vehicle, inert or active, making the composition especially suitable for diagnostic or therapeutic use in vivo or ex vivo.

As used herein, the term "pharmaceutically acceptable carrier, adjuvant, and/or vehicle" refers to any non-toxic carrier, adjuvant, and/or vehicle that does not destroy the pharmacological activity of the compound with which it is formulated. Pharmaceutically acceptable carriers, adjuvants, and/or vehicles that are used in the compositions of this invention include, but are not limited to, ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as potassium sorbate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, emulsions (e.g., such as an oil/water or water/oil emulsions), and various types of wetting agents. The compositions also can include stabilizers and/or preservatives. For examples of carriers, vehicles and adjuvants, see e.g., Martin, Remington's Pharmaceutical Sciences, 15th Ed., Mack Publ. Co., Easton, PA [1975].

The term "combination" refers to simultaneous, separate, or sequential administration. In one aspect of the disclosure, "combination" refers to simultaneous administration. In another aspect of the disclosure, "combination" refers to separate administration. In another aspect of the disclosure, "combination" refers to sequential administration. Where the administration is separate or sequential, the delay in administering the one or more additional therapeutic agents is done at an interval designed such as not to lose the beneficial effect of the combination.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As used herein, the term "comprising" or "comprises" is used in reference to compounds, uses, compositions, methods, and respective component(s) thereof that are essential to the method or composition, yet open to the inclusion of unspecified elements, whether essential or not. The term "consisting of" refers to compounds, uses, compositions, methods, and respective component(s) thereof as described herein which are exclusive of any element not recited in that description of the embodiment. The term "consisting essentially of" refers to those elements required for a given embodiment. The term permits the presence of elements that do not materially affect the basic and novel functional characteristic(s) of that embodiment.

As a general matter, compositions specifying a percentage are by weight unless otherwise specified.

I. DESCRIPTION OF EXEMPLARY COMPOUNDS

In a first embodiment, the present disclosure provides a compound of Formula I:

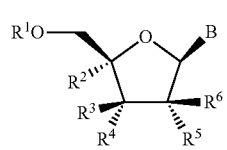

(I)

or a pharmaceutically acceptable salt thereof, wherein

B is

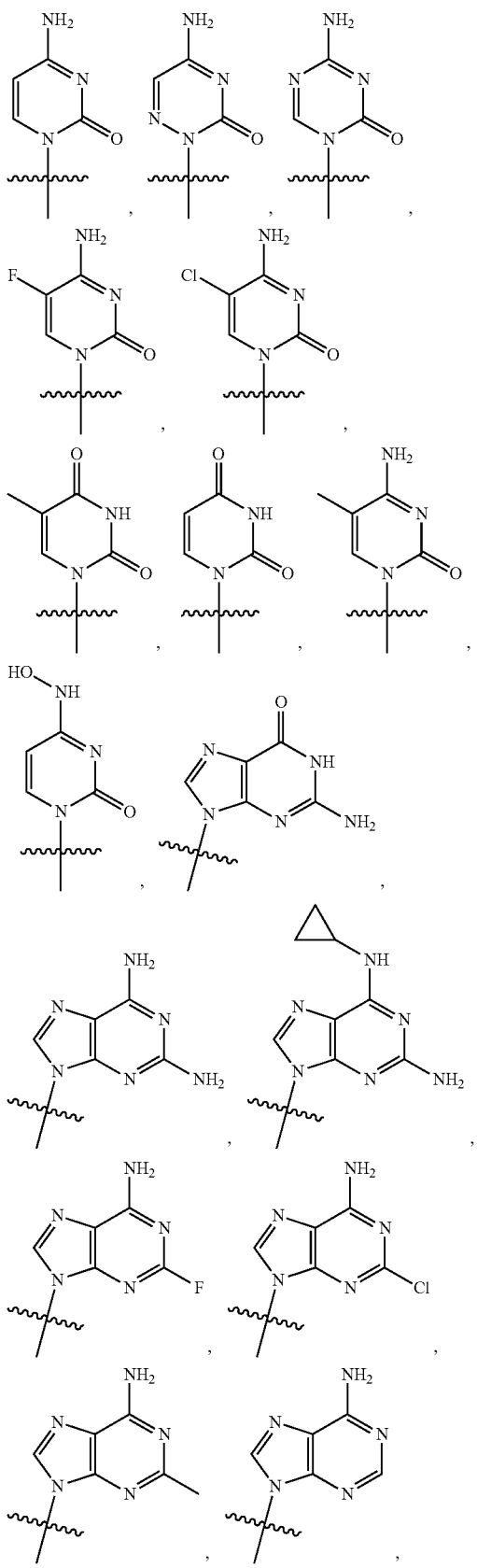

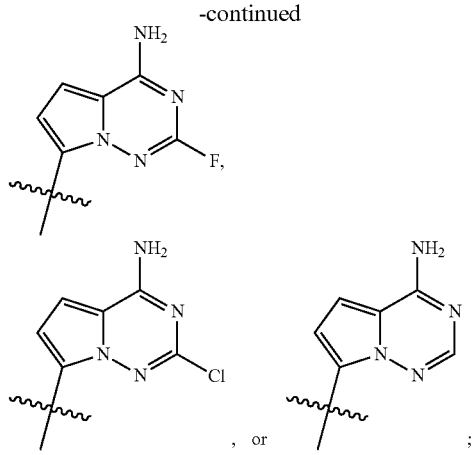

, or

;

$R^1$ is —H or

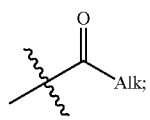

Alk is independently for each occurrence a $C_2$-$C_6$ aliphatic group;
$R^2$ is —H, $C_1$-$C_6$ aliphatic, $C_1$-$C_3$ haloaliphatic, $C_1$-$C_3$ hydroxyalkyl, cyclopropyl, —CN, —$N_3$, —O—($C_1$-$C_3$ aliphatic), —F, or —Cl;
$R^3$ is —H;
$R^4$ is —OH, —Cl, —$OCH_3$, —F, —$N_3$, or

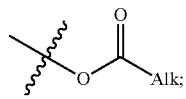

$R^5$ is —H or —F; and
$R^6$ is —H, —F, —Cl, $C_1$-$C_6$ aliphatic, $C_1$-$C_4$ haloaliphatic, —O—($C_1$-$C_4$ aliphatic), cyclopropyl, or —OH.

In a second embodiment, Alk incorporated into the options for $R^1$ and $R^4$ of Formula I is independently for each occurrence ethyl, propyl, isopropyl, sec-butyl, tert-butyl or iso-butyl, and the remaining variables are as described above for Formula I.

In a third embodiment, $R^1$ in Formula I is —H or

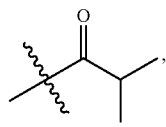 [SMILES: *C(=O)C(C)C]

and the remaining variables are as described above for Formula I.

In a fourth embodiment, $R^1$ in Formula I is —H, and the remaining variables are as described above for Formula I or for any of the previous embodiments.

In a fifth embodiment, $R^5$ in Formula I is —H, and the remaining variables are as described above for Formula I or for any of the previous embodiments.

In a sixth embodiment, $R^2$ in Formula I is not —H, and the remaining variables are as described above for Formula I or for any of the previous embodiments.

In a seventh embodiment, $R^4$ in Formula I is —OH

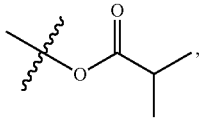 [SMILES: *OC(=O)C(C)C]

and the remaining variables are as described above for Formula I or for any of the previous embodiments.

In an eighth embodiment, $R^6$ in Formula I is —H, —F, —CH$_3$, —CH$_2$CH$_3$, —OCH$_3$, —OCH$_2$CH$_3$, —CH=CH$_2$, —CH$_2$F, or —CH$_2$Cl, and the remaining variables are as described above for Formula I or for any of the previous embodiments.

In a ninth embodiment, $R^6$ in Formula I is —H or —F, and the remaining variables are as described for Formula I or for any of embodiments one through seven above.

In a tenth embodiment, $R^6$ in Formula I is —H, and the remaining variables are as described for Formula I or for any of embodiments one through seven above.

In a tenth embodiment, $R^6$ in Formula I is —F, and the remaining variables are as described for Formula I or for any of embodiments one through seven above.

In an twelfth embodiment, B in Formula I is

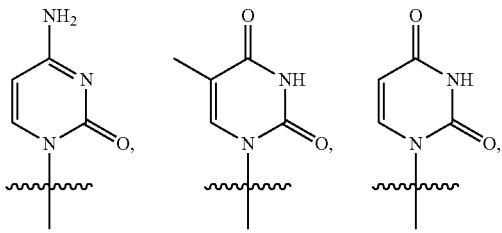

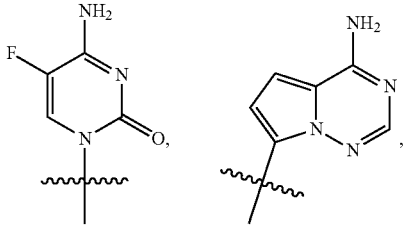

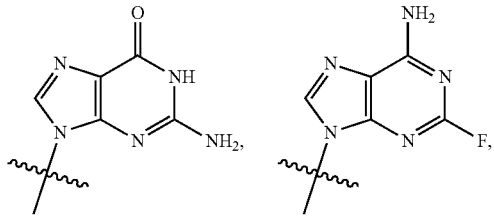

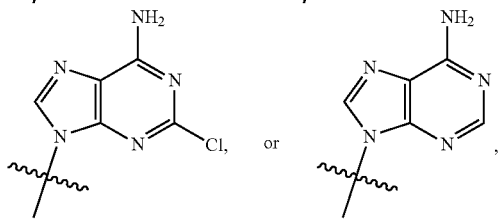

and the remaining variables are as described above for Formula I or for any of the previous embodiments.

In a further embodiments, B is

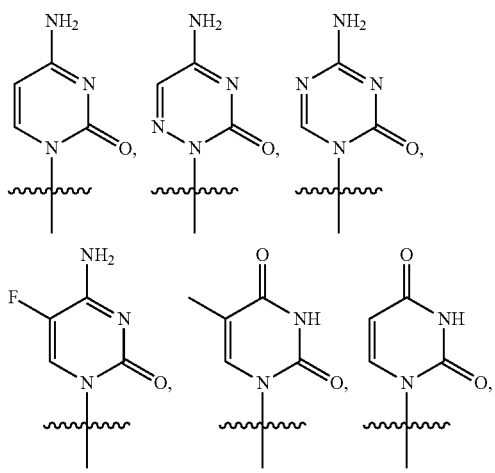

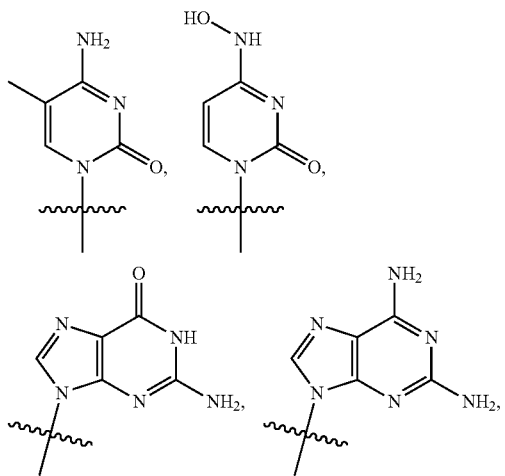

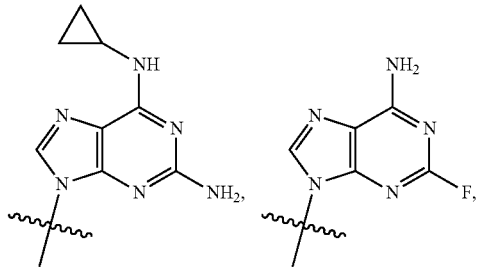

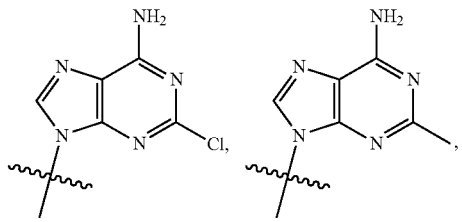

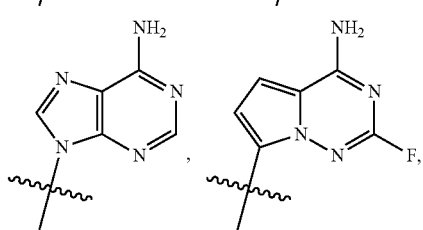

-continued

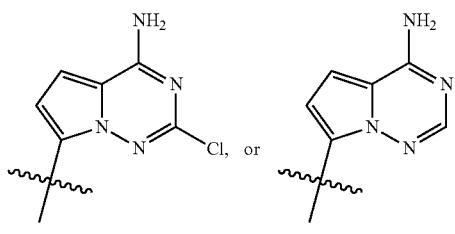 [SMILES: *c1ccc2c(N)nc(Cl)nn12 ; *c1ccc2c(N)ncnn12]
Cl, or

In one aspect of this embodiment, B is

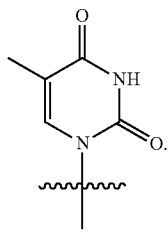 [SMILES: *n1cc(C)c(=O)[nH]c1=O]

In another aspect of this embodiment, B is

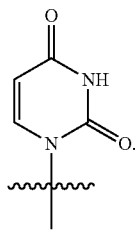

In another aspect of this embodiment, B is

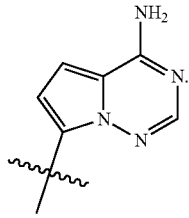 [SMILES: *c1ccc2c(N)ncnn12]

In a further aspect of this embodiment, B is

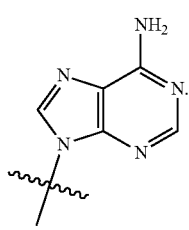 [SMILES: *n1cnc2c(N)ncnc21]

In another aspect of this embodiment, B is

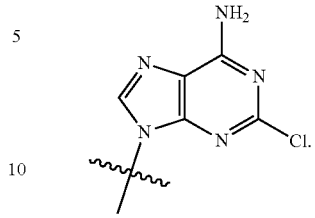

In one aspect of this embodiment, B is

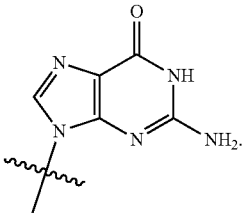 [SMILES: *n1cnc2c(=O)[nH]c(N)nc21]

In any of these aspects of the twelfth embodiment, the remaining variables of Formula I are as described above for any of the disclosed embodiments.

In a thirteenth embodiment, B in Formula I is

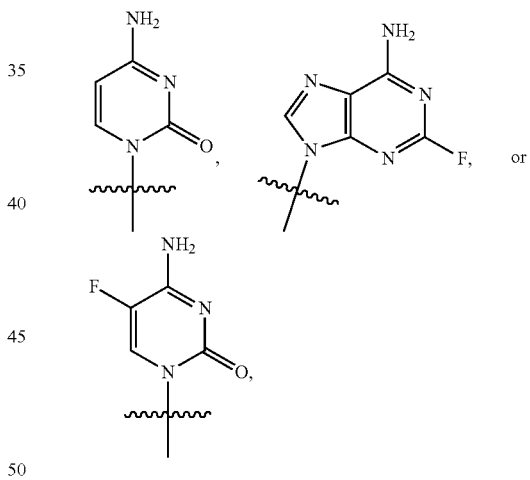

and the remaining variables are as described above for Formula I or for any of the previous embodiments. In one aspect of this embodiment, B is

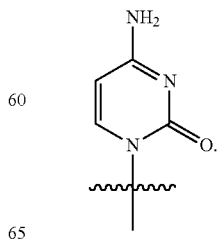

In another aspect of this embodiment, B is

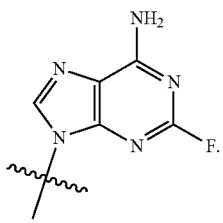 [SMILES: *n1cnc2c(N)nc(F)nc21]

In a further aspect of this embodiment, B is

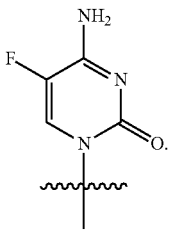 [SMILES: *n1cc(F)c(N)nc1=O]

In any of these aspects of the thirteenth embodiment, the remaining variables of Formula I are as described above for any of the disclosed embodiments.

In a fourteenth embodiment, $R^2$ of Formula I is —CH$_3$, —CF$_3$, —N$_3$, —OCH$_3$, —CH$_2$Cl, —CH$_2$F, —CHF$_2$, —CHCl$_2$, —CHClF, —CH$_2$CH$_3$, —CH=CH$_2$, cyclopropyl, or —C≡CH, and the remaining variables are as described above for Formula I or for any of the previous embodiments.

In a fifteenth embodiment, $R^2$ of Formula I is —N$_3$, —CH$_3$, —CH$_2$Cl, —CH$_2$F, —CH=CH$_2$, or —C≡CH, and the remaining variables are as described above for Formula I or for any of embodiments one through thirteen. In one aspect of this embodiment, $R^2$ is —N$_3$. In another aspect of this embodiment, $R^2$ is —CH=CH$_2$. In a further aspect, $R^2$ is —CH$_2$F. In any aspects of this embodiment, the remaining variables are as described above for Formula I or for any of embodiments one through thirteen.

In a sixteenth embodiment, $R^2$ of Formula I is —CH$_2$Cl, —CH$_2$F or —C≡CH, and the remaining variables are as described above for Formula I or for any of embodiments one through thirteen.

In a seventeenth embodiment, $R^2$ of Formula I is —CH$_2$Cl or —C≡CH, and the remaining variables are as described above for Formula I or for any of embodiments one through thirteen. In one aspect of this embodiment, $R^2$ is —CH$_2$Cl. In another aspect of this embodiment, $R^2$ is —C≡CH. In any aspects of this embodiment, the remaining variables are as described above for Formula I or for any of embodiments one through thirteen.

In an eighteenth embodiment, in the compound of Formula I, $R^4$ is —OH, $R^5$ is —H, and $R^6$ is —H, and the remaining variables are as described above in any of embodiments one, two, three, four, twelve, thirteen, fourteen, fifteen, sixteen and seventeen above. In one aspect of this embodiment, $R^2$ of Formula I is —CH$_2$Cl, and the remaining variables are as described in the first through fourth embodiments above.

In a nineteenth embodiment, the compound of Formula I is selected from Table 1:

TABLE 1

| Compound No. | Structure | Name |
|---|---|---|
| 1 | 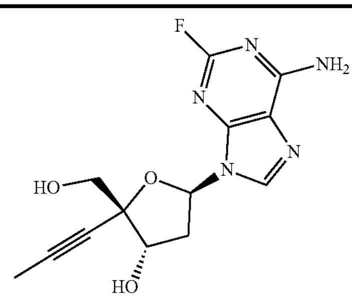 | (2R,3S,5R)-5-(6-amino-2-fluoro-9H-purin-9-yl)-2-(hydroxymethyl)-2-(prop-1-yn-1-yl)tetrahydrofuran-3-ol |
| 2 | 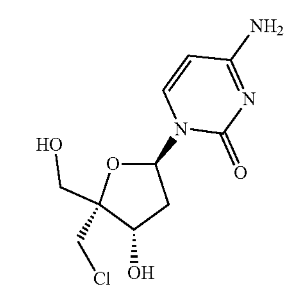 [SMILES: Nc1ccn([C@H]2C[C@H](O)[C@](CO)(CCl)O2)c(=O)n1] | 4-amino-1-((2R,4S,5R)-5-(chloromethyl)-4-hydroxy-5-(hydroxymethyl)tetrahydrofuran-2-yl)pyrimidin-2(1H)-one |
| 3 | 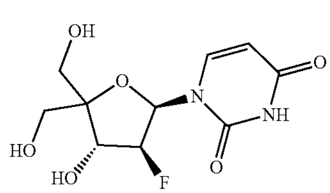 [SMILES: O=c1ccn([C@@H]2OC(CO)(CO)[C@@H](O)[C@@H]2F)c(=O)[nH]1] | 1-((2R,3S,4R)-3-fluoro-4-hydroxy-5,5-bis(hydroxymethyl)tetrahydrofuran-2-yl)pyrimidine-2,4(1H,3H)-dione |

TABLE 1-continued

| Compound No. | Structure | Name |
|---|---|---|
| 4 | 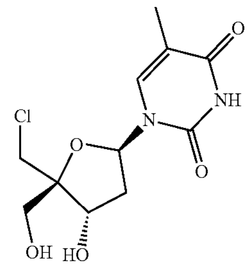 [SMILES: Cc1cn([C@H]2C[C@H](O)[C@](CO)(CCl)O2)c(=O)[nH]c1=O] | 1-((2R,4S,5R)-5-(chloromethyl)-4-hydroxy-5-(hydroxymethyl)tetrahydrofuran-2-yl)-5-methylpyrimidine-2,4(1H,3H)-dione |
| 5 | 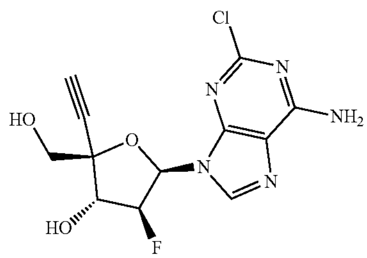 [SMILES: C#C[C@]1(CO)O[C@@H](n2cnc3c(N)nc(Cl)nc32)[C@@H](F)[C@@H]1O] | (2R,3R,4S,5R)-5-(6-amino-2-chloro-9H-purin-9-yl)-2-ethynyl-4-fluoro-2-(hydroxymethyl)tetrahydrofuran-3-ol |
| 6 | 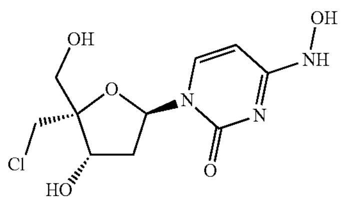 [SMILES: O=c1nc(NO)ccn1[C@H]1C[C@H](O)[C@](CO)(CCl)O1] | 1-((2R,4S,5R)-5-(chloromethyl)-4-hydroxy-5-(hydroxymethyl)tetrahydrofuran-2-yl)-4-(hydroxyamino)pyrimidin-2(1H)-one |
| 7 | 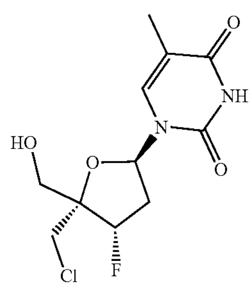 [SMILES: Cc1cn([C@H]2C[C@H](F)[C@](CO)(CCl)O2)c(=O)[nH]c1=O] | 1-((2R,4S,5R)-5-(chloromethyl)-4-fluoro-5-(hydroxymethyl)tetrahydrofuran-2-yl)-5-methylpyrimidine-2,4(1H,3H)-dione |
| 8 | 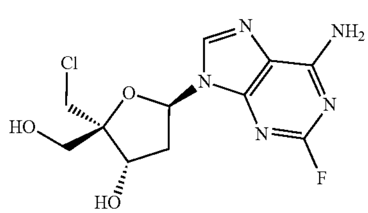 [SMILES: Nc1nc(F)nc2c1ncn2[C@H]1C[C@H](O)[C@](CO)(CCl)O1] | (2R,3S,5R)-5-(6-amino-2-fluoro-9H-purin-9-yl)-2-(chloromethyl)-2-(hydroxymethyl)tetrahydrofuran-3-ol |
| 9 | 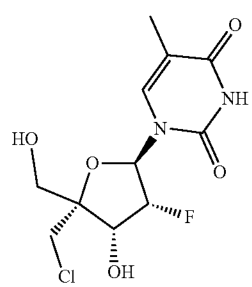 [SMILES: Cc1cn([C@@H]2O[C@@](CO)(CCl)[C@@H](O)[C@H]2F)c(=O)[nH]c1=O] | 1-((2R,3R,4R,5R)-5-(chloromethyl)-3-fluoro-4-hydroxy-5-(hydroxymethyl)tetrahydrofuran-2-yl)-5-methylpyrimidine-2,4(1H,3H)-dione |

TABLE 1-continued

| Compound No. | Structure | Name |
|---|---|---|
| 10 | 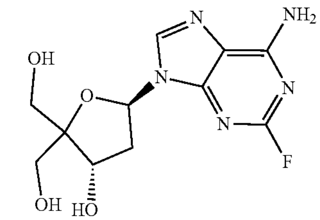 [SMILES: Nc1nc(F)nc2c1ncn2[C@H]1C[C@H](O)C(CO)(CO)O1] | ((3S,5R)-5-(6-amino-2-fluoro-9H-purin-9-yl)-3-hydroxy tetrahydrofuran-2,2-diyl)dimethanol |
| 11 | 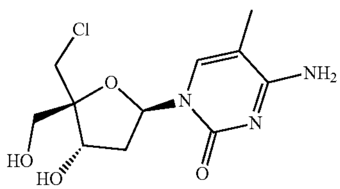 [SMILES: Cc1cn([C@H]2C[C@H](O)[C@](CO)(CCl)O2)c(=O)nc1N] | 4-amino-1-((2R,4S,5R)-5-(chloromethyl)-4-hydroxy-5-(hydroxymethyl)tetrahydrofuran-2-yl)-5-methylpyrimidin-2(1H)-one |
| 12 | 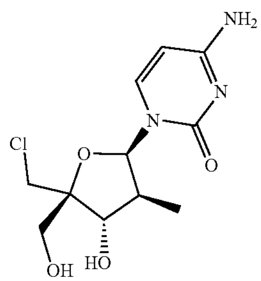 [SMILES: C[C@@H]1[C@H](n2ccc(N)nc2=O)O[C@@](CO)(CCl)[C@H]1O] | 4-amino-1-((2R,3S,4S,5R)-5-(chloromethyl)-4-hydroxy-5-(hydroxymethyl)-3-methyl tetrahydrofuran-2-yl)pyrimidin-2(1H)-one |
| 13 | 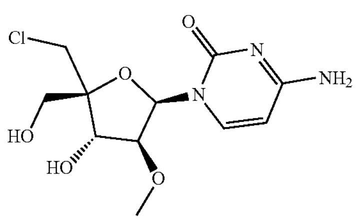 [SMILES: CO[C@@H]1[C@H](n2ccc(N)nc2=O)O[C@@](CO)(CCl)[C@H]1O] | 4-amino-1-((2R,3S,4S,5R)-5-(chloromethyl)-4-hydroxy-5-(hydroxymethyl)-3-methoxy tetrahydrofuran-2-yl)pyrimidin-2(1H)-one |
| 14 | 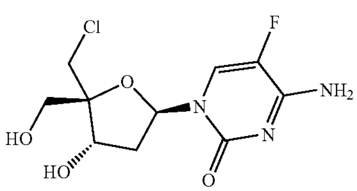 [SMILES: Nc1nc(=O)n([C@H]2C[C@H](O)[C@](CO)(CCl)O2)cc1F] | 4-amino-1-((2R,4S,5R)-5-(chloromethyl)-4-hydroxy-5-(hydroxymethyl)tetrahydrofuran-2-yl)-5-fluoropyrimidin-2(1H)-one |
| 15 | 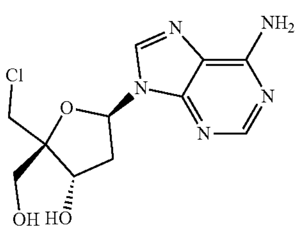 [SMILES: Nc1ncnc2c1ncn2[C@H]1C[C@H](O)[C@](CO)(CCl)O1] | (2R,3S,5R)-5-(6-amino-9H-purin-9-yl)-2-(chloromethyl)-2-(hydroxymethyl)tetrahydrofuran-3-ol |
| 16 | 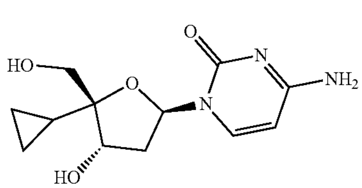 [SMILES: Nc1ccn([C@H]2C[C@H](O)[C@](CO)(C3CC3)O2)c(=O)n1] | 4-amino-1-((2R,4S,5R)-5-cyclopropyl-4-hydroxy-5-(hydroxymethyl)tetrahydrofuran-2-yl)pyrimidin-2(1H)-one |

TABLE 1-continued

| Compound No. | Structure | Name |
|---|---|---|
| 17 | 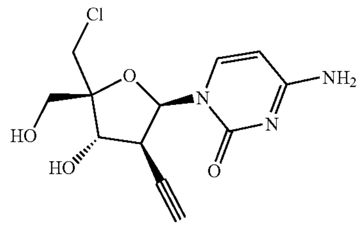 [SMILES: C#C[C@@H]1[C@H](n2ccc(N)nc2=O)O[C@@](CO)(CCl)[C@H]1O] | 4-amino-1-((2R,3S,4S,5R)-5-(chloromethyl)-3-ethynyl-4-hydroxy-5-(hydroxymethyl)tetrahydrofuran-2-yl)pyrimidin-2(1H)-one |
| 18 | 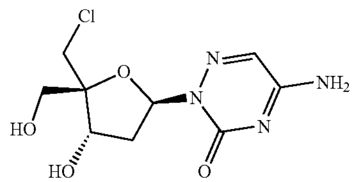 [SMILES: Nc1cnn([C@H]2C[C@H](O)[C@](CO)(CCl)O2)c(=O)n1] | 5-amino-2-((2R,4S,5R)-5-(chloromethyl)-4-hydroxy-5-(hydroxymethyl)tetrahydrofuran-2-yl)-1,2,4-triazin-3(2H)-one |
| 19 | 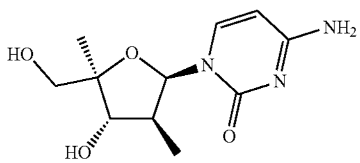 [SMILES: C[C@@H]1[C@H](n2ccc(N)nc2=O)O[C@](C)(CO)[C@H]1O] | 4-amino-1-((2R,3S,4S,5R)-4-hydroxy-5-(hydroxymethyl)-3,5-dimethyltetrahydrofuran-2-yl)pyrimidin-2(1H)-one |
| 20 | 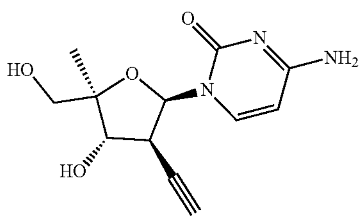 [SMILES: C#C[C@@H]1[C@H](n2ccc(N)nc2=O)O[C@](C)(CO)[C@H]1O] | 4-amino-1-((2R,3S,4S,5R)-3-ethynyl-4-hydroxy-5-(hydroxymethyl)-5-methyltetrahydrofuran-2-yl)pyrimidin-2(1H)-one |
| 21 | 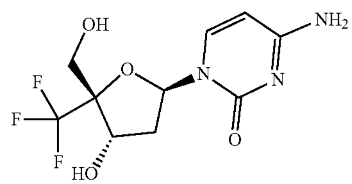 [SMILES: Nc1ccn([C@H]2C[C@H](O)[C@](CO)(C(F)(F)F)O2)c(=O)n1] | 4-amino-1-((2R,4S,5R)-4-hydroxy-5-(hydroxymethyl)-5-(trifluoromethyl)tetrahydrofuran-2-yl)pyrimidin-2(1H)-one |
| 22 | | 4-amino-5-fluoro-1-((2R,4S,5R)-5-(fluoromethyl)-4-hydroxy-5-(hydroxymethyl)tetrahydrofuran-2-yl)pyrimidin-2(1H)-one | or a pharmaceutically acceptable salt thereof. In one aspect, the compound of Formula I is selected from the compounds in Table 1.

In a twentieth embodiment, the present disclosure provides a compound in Table 1, 1-A, or 1-B, herein, or a pharmaceutically acceptable salt thereof. In certain embodiments, the compound is a compound in Table 1, 1-A, or 1-B, herein. In certain embodiments, the compound is a compound in Table 1 or 1-A, herein, or a pharmaceutically acceptable salt thereof. In certain embodiments, the compound is a compound in Table 1 or 1-A, herein. In certain embodiments, the compound is a compound in Table 1-A, below, or a pharmaceutically acceptable salt thereof. In certain embodiments, the compound is a compound in Table 1-A, below. In certain embodiments, the compound is a compound in Table 1-B, below, or a pharmaceutically acceptable salt thereof. In certain embodiments, the compound is a compound in Table 1-B, below.

In certain embodiments, the present disclosure provides a compound in Table 1, 1-A, 1-B, or 1-C, herein, or a pharmaceutically acceptable salt thereof. In certain embodiments, the present disclosure provides a compound in Table 1, 1-A, 1-B, or 1-C, herein. In certain embodiments, the compound is a compound in Table 1-C, below, or a pharmaceutically acceptable salt thereof. In certain embodiments, the compound is a compound in Table 1-C, below.

In certain embodiments, the present disclosure provides a compound in Table 1, 1-A, 1-B, or 1-C, herein, or a pharmaceutically acceptable salt thereof, wherein the compound is a compound of Formula II, Formula III, or Formula IV, or a pharmaceutically acceptable salt thereof. In certain embodiments, the present disclosure provides a compound in Table 1, 1-A, 1-B, or 1-C, herein, wherein the compound is a compound of Formula II, Formula III, or Formula IV. In certain embodiments, the present disclosure provides a compound in Table 1, 1-A, 1-B, or 1-C, herein, or a pharmaceutically acceptable salt thereof, wherein the compound is a compound of Formula II, or a pharmaceutically acceptable salt thereof. In certain embodiments, the present disclosure provides a compound in Table 1, 1-A, 1-B, or 1-C, herein, wherein the compound is a compound of Formula II. In certain embodiments, the present disclosure provides a compound in Table 1, 1-A, 1-B, or 1-C, herein, or a pharmaceutically acceptable salt thereof, wherein the compound is a compound of Formula III, or a pharmaceutically acceptable salt thereof. In certain embodiments, the present disclosure provides a compound in Table 1, 1-A, 1-B, or 1-C, herein, wherein the compound is a compound of Formula III. In certain embodiments, the present disclosure provides a compound in Table 1, 1-A, 1-B, or 1-C, herein, or a pharmaceutically acceptable salt thereof, wherein the compound is a compound of Formula IV, or a pharmaceutically acceptable salt thereof. In certain embodiments, the present disclosure provides a compound in Table 1, 1-A, 1-B, or 1-C, herein, wherein the compound is a compound of Formula IV.

In certain embodiments, the present disclosure provides a compound in Table 1, 1-A, 1-B, or 1-C, herein, or a pharmaceutically acceptable salt thereof. In certain embodiments, the present disclosure provides a compound in Table 1, 1-A, 1-B, or 1-C, herein. In certain embodiments, the compound is a compound in Table 1-C, below, or a pharmaceutically acceptable salt thereof. In certain embodiments, the compound is a compound in Table 1-C, below.

In certain embodiments, the present disclosure provides a compound in Table 1, 1-A, 1-B, 1-C, or 1-D herein, or a pharmaceutically acceptable salt thereof, wherein the compound is a compound of Formula II, Formula III, or Formula IV, or a pharmaceutically acceptable salt thereof. In certain embodiments, the present disclosure provides a compound in Table 1, 1-A, 1-B, 1-C, or 1-D, herein, wherein the compound is a compound of Formula II, Formula III, or Formula IV. In certain embodiments, the present disclosure provides a compound in Table 1, 1-A, 1-B, 1-C, or 1-D, herein, or a pharmaceutically acceptable salt thereof, wherein the compound is a compound of Formula II, or a pharmaceutically acceptable salt thereof. In certain embodiments, the present disclosure provides a compound in Table 1, 1-A, 1-1B, 1-C, or 1-1D, herein, wherein the compound is a compound of Formula II. In certain embodiments, the present disclosure provides a compound in Table 1, 1-A, 1-1B, 1-C, or 1-1D, herein, or a pharmaceutically acceptable salt thereof, wherein the compound is a compound of Formula III, or a pharmaceutically acceptable salt thereof. In certain embodiments, the present disclosure provides a compound in Table 1, 1-A, 1-B, 1-C, or 1-D, herein, wherein the compound is a compound of Formula III. In certain embodiments, the present disclosure provides a compound in Table 1, 1-A, 1-1B, 1-C, or 1-1D, herein, or a pharmaceutically acceptable salt thereof, wherein the compound is a compound of Formula IV, or a pharmaceutically acceptable salt thereof. In certain embodiments, the present disclosure provides a compound in Table 1, 1-A, 1-1B, 1-C, or 1-1D, herein, wherein the compound is a compound of Formula IV.

TABLE 1-A

| Compound No. | Structure | Name |
| --- | --- | --- |
| 52 | 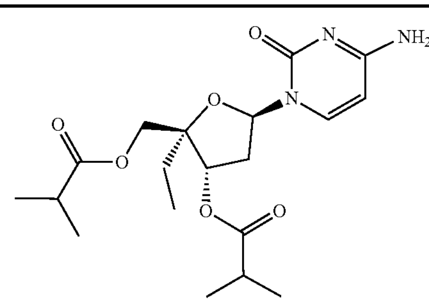 | (2R,3S,5R)-5-(4-amino-2-oxopyrimidin-1(2H)-yl)-2-ethyl-2-((isobutyryloxy)methyl)tetrahydro-furan-3-yl isobutyrate |
| 53 | 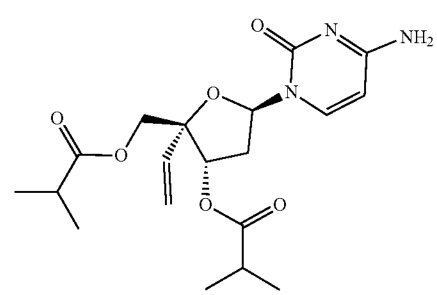 [SMILES: C=C[C@]1(COC(=O)C(C)C)O[C@@H](n2ccc(N)nc2=O)C[C@@H]1OC(=O)C(C)C] | (2R,3S,5R)-5-(4-amino-2-oxopyrimidin-1(2H)-yl)-2-((isobutyryloxy)methyl)-2-vinyltetrahydrofuran-3-yl isobutyrate |

TABLE 1-A-continued

| Compound No. | Structure | Name |
|---|---|---|
| 54 | 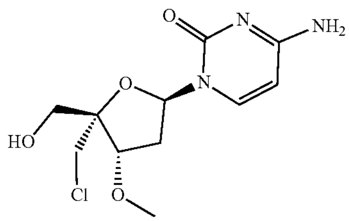 [SMILES: CO[C@H]1C[C@H](n2ccc(N)nc2=O)O[C@@]1(CO)CCl] | 4-amino-1-((2R,4S,5R)-5-(chloromethyl)-5-(hydroxymethyl)-4-methoxytetrahydrofuran-2-yl)pyrimidin-2(1H)-one |
| 55 | 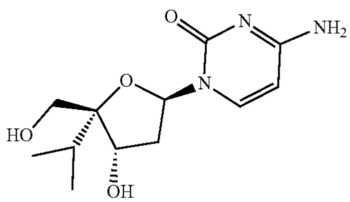 [SMILES: CC(C)[C@]1(CO)O[C@@H](n2ccc(N)nc2=O)C[C@@H]1O] | 4-amino-1-((2R,4S,5R)-4-hydroxy-5-(hydroxymethyl)-5-isopropyltetrahydrofuran-2-yl)pyrimidin-2(1H)-one |
| 56 | 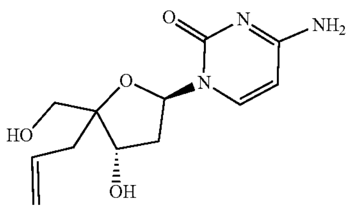 [SMILES: C=CCC1(CO)O[C@@H](n2ccc(N)nc2=O)C[C@@H]1O] | 1-((2R,4S)-5-allyl-4-hydroxy-5-(hydroxymethyl)tetrahydrofuran-2-yl)-4-aminopyrimidin-2(1H)-one |
| 57 | 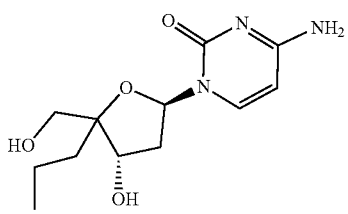 [SMILES: CCCC1(CO)O[C@@H](n2ccc(N)nc2=O)C[C@@H]1O] | 4-amino-1-((2R,4S,5R)-4-hydroxy-5-(hydroxymethyl)-5-propyltetrahydrofuran-2-yl)pyrimidin-2(1H)-one 4-amino-1-((2R,4S)-4-hydroxy-5-(hydroxymethyl)-5-propyltetrahydrofuran-2-yl)pyrimidin-2(1H)-one |
| 58 | 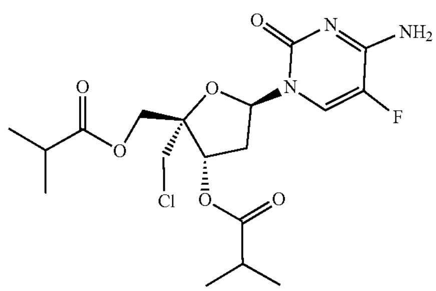 [SMILES: CC(C)C(=O)OC[C@@]1(CCl)O[C@@H](n2cc(F)c(N)nc2=O)C[C@@H]1OC(=O)C(C)C] | (2R,3S,5R)-5-(4-amino-5-fluoro-2-oxopyrimidin-1(2H)-yl)-2-(chloromethyl)-2-((isobutyryloxy)-methyl)tetrahydrofuran-3-yl isobutyrate |
| 59 | 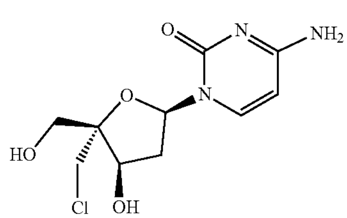 [SMILES: Nc1ccn([C@H]2C[C@@H](O)[C@](CO)(CCl)O2)c(=O)n1] | 4-amino-1-((2R,4R,5R)-5-(chloromethyl)-4-hydroxy-5-(hydroxymethyl)tetrahydrofuran-2-yl)pyrimidin-2(1H)-one |
| 60 | 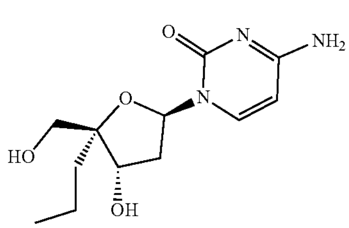 [SMILES: CCC[C@]1(CO)O[C@@H](n2ccc(N)nc2=O)C[C@@H]1O] | 4-amino-1-((2R,4S,5R)-4-hydroxy-5-(hydroxymethyl)-5-propyltetrahydrofuran-2-yl)pyrimidin-2(1H)-one |

TABLE 1-A-continued

| Compound No. | Structure | Name |
|---|---|---|
| 61 | 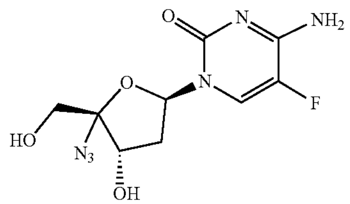 [SMILES: [N-]=[N+]=N[C@]1(CO)O[C@@H](n2cc(F)c(N)nc2=O)C[C@@H]1O] | 4-amino-1-((2R,4S,5R)-5-azido-4-hydroxy-5-(hydroxymethyl)tetrahydrofuran-2-yl)-5-fluoropyrimidin-2(1H)-one |
| 62 | 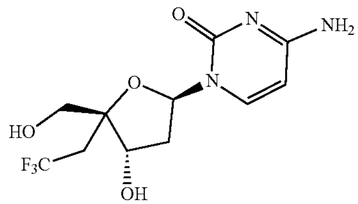 [SMILES: Nc1ccn([C@H]2C[C@H](O)[C@](CO)(CC(F)(F)F)O2)c(=O)n1] | 4-amino-1-((2R,4S,5R)-4-hydroxy-5-(hydroxymethyl)-5-(2,2,2-trifluoroethyl)tetrahydrofuran-2-yl)pyrimidin-2(1H)-one |
| 63 | 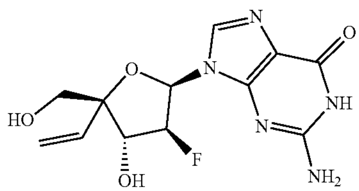 [SMILES: C=C[C@]1(CO)O[C@@H](n2cnc3c(=O)[nH]c(N)nc32)[C@@H](F)[C@@H]1O] | 2-amino-9-((2R,3S,4R,5R)-3-fluoro-4-hydroxy-5-(hydroxymethyl)-5-vinyltetrahydrofuran-2-yl)-1,9-dihydro-6H-purin-6-one |
| 64 | 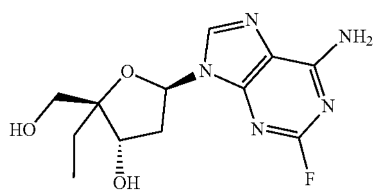 [SMILES: CC[C@]1(CO)O[C@@H](n2cnc3c(N)nc(F)nc32)C[C@@H]1O] | (2R,3S,5R)-5-(6-amino-2-fluoro-9H-purin-9-yl)-2-ethyl-2-(hydroxymethyl)tetrahydrofuran-3-ol |
| 65 | 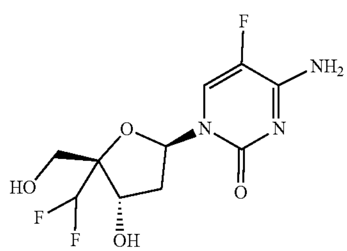 [SMILES: Nc1nc(=O)n([C@H]2C[C@H](O)[C@](CO)(C(F)F)O2)cc1F] | 4-amino-1-((2R,4S,5R)-5-(difluoromethyl)-4-hydroxy-5-(hydroxymethyl)tetrahydrofuran-2-yl)-5-fluoropyrimidin-2(1H)-one |
| 66 | 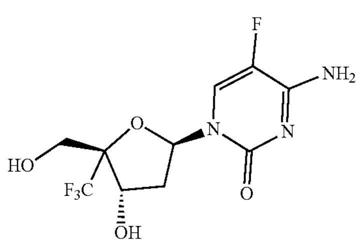 [SMILES: Nc1nc(=O)n([C@H]2C[C@H](O)[C@](CO)(C(F)(F)F)O2)cc1F] | 4-amino-5-fluoro-1-((2R,4S,5R)-4-hydroxy-5-(hydroxymethyl)-5-(2,2,2-trifluoroethyl)-tetrahydrofuran-2-yl)pyrimidin-2(1H)-one |
| 67 | 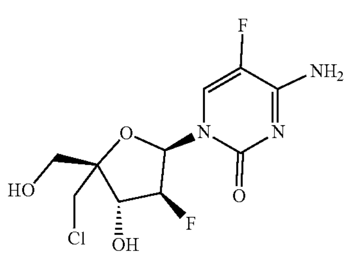 [SMILES: Nc1nc(=O)n([C@@H]2O[C@@](CO)(CCl)[C@@H](O)[C@@H]2F)cc1F] | 4-amino-1-((2R,3S,4R,5R)-5-(chloromethyl)-3-fluoro-4-hydroxy-5-(hydroxymethyl)-tetrahydrofuran-2-yl)-5-fluoropyrimidin-2(1H)-one |

TABLE 1-A-continued

| Compound No. | Structure | Name |
|---|---|---|
| 68 | 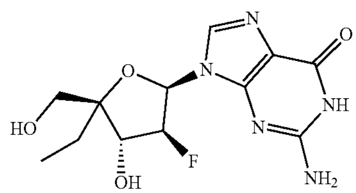 [SMILES: CC[C@]1(CO)O[C@@H](n2cnc3c(=O)[nH]c(N)nc32)[C@@H](F)[C@@H]1O] | 2-amino-9-((2R,3S,4R,5R)-5-ethyl-3-fluoro-4-hydroxy-5-(hydroxymethyl)tetrahydrofuran-2-yl)-1,9-dihydro-6H-purin-6-one |
| 69 | 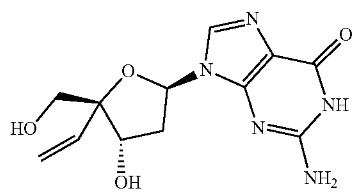 [SMILES: C=C[C@]1(CO)O[C@@H](n2cnc3c(=O)[nH]c(N)nc32)C[C@@H]1O] | 2-amino-9-((2R,4S,5R)-4-hydroxy-5-(hydroxymethyl)-5-vinyltetrahydrofuran-2-yl)-1,9-dihydro-6H-purin-6-one |
| 70 | 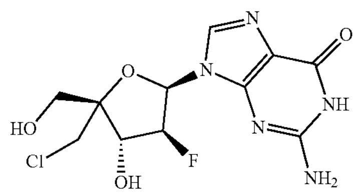 [SMILES: Nc1nc2c(ncn2[C@@H]2O[C@@](CO)(CCl)[C@@H](O)[C@@H]2F)c(=O)[nH]1] | 2-amino-9-((2R,3S,4R,5R)-5-(chloromethyl)-3-fluoro-4-hydroxy-5-(hydroxymethyl)-tetrahydrofuran-2-yl)-1,9-dihydro-6H-purin-6-one |
| 71 | 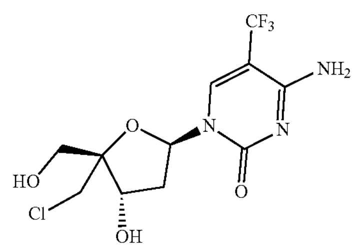 [SMILES: Nc1nc(=O)n([C@H]2C[C@H](O)[C@](CO)(CCl)O2)cc1C(F)(F)F] | 4-amino-1-((2R,4S,5R)-5-(chloromethyl)-4-hydroxy-5-(hydroxymethyl)tetrahydrofuran-2-yl)-5-(trifluoromethyl)-pyrimidin-2(1H)-one |
| 72 | 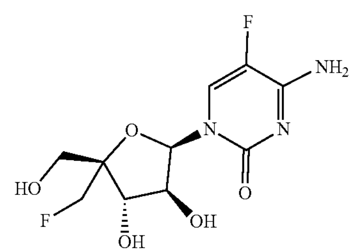 [SMILES: Nc1nc(=O)n([C@@H]2O[C@@](CO)(CF)[C@@H](O)[C@@H]2O)cc1F] | 4-amino-5-fluoro-1-((2R,3S,4S,5R)-5-(fluoromethyl)-3,4-dihydroxy-5-(hydroxymethyl)tetrahydrofuran-2-yl)pyrimidin-2(1H)-one |
| 73 | 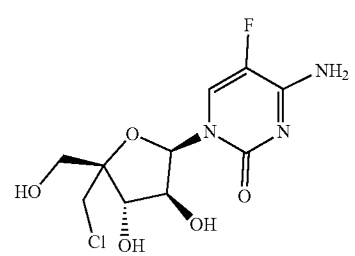 [SMILES: Nc1nc(=O)n([C@@H]2O[C@@](CO)(CCl)[C@@H](O)[C@@H]2O)cc1F] | 4-amino-1-((2R,3S,4S,5R)-5-(chloromethyl)-3,4-dihydroxy-5-(hydroxymethyl)tetrahydrofuran-2-yl)-5-fluoropyrimidin-2(1H)-one |
| 74 | 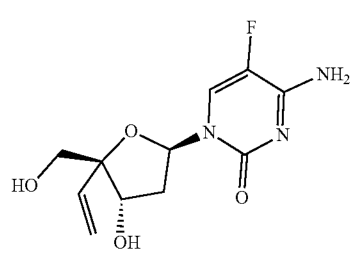 [SMILES: C=C[C@]1(CO)O[C@@H](n2cc(F)c(N)nc2=O)C[C@@H]1O] | 4-amino-5-fluoro-1-((2R,4S,5R)-4-hydroxy-5-(hydroxymethyl)-5-vinyltetrahydrofuran-2-yl)pyrimidin-2(1H)-one |

TABLE 1-A-continued

| Compound No. | Structure | Name |
|---|---|---|
| 75 | 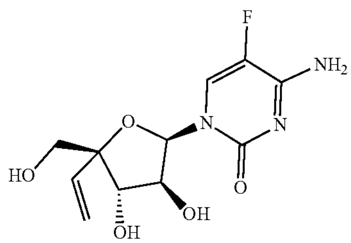 [SMILES: C=C[C@]1(CO)O[C@@H](n2cc(F)c(N)nc2=O)[C@@H](O)[C@@H]1O] | 4-amino-1-((2R,3S,4S,5R)-3,4-dihydroxy-5-(hydroxymethyl)-5-vinyltetrahydrofuran-2-yl)-5-fluoropyrimidin-2(1H)-one |
| 76 | 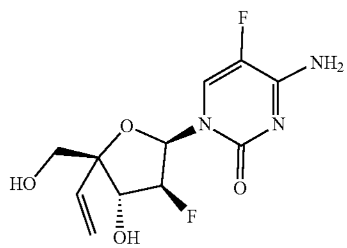 [SMILES: C=C[C@]1(CO)O[C@@H](n2cc(F)c(N)nc2=O)[C@@H](F)[C@@H]1O] | 4-amino-5-fluoro-1-((2R,3S,4R,5R)-3-fluoro-4-hydroxy-5-(hydroxymethyl)-5-vinyltetrahydrofuran-2-yl)pyrimidin-2(1H)-one |
| 77 | 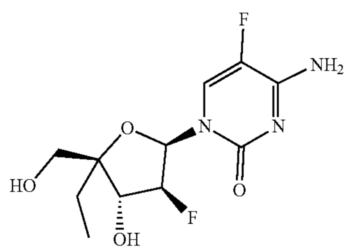 [SMILES: CC[C@]1(CO)O[C@@H](n2cc(F)c(N)nc2=O)[C@@H](F)[C@@H]1O] | 4-amino-1-((2R,3S,4R,5R)-5-ethyl-3-fluoro-4-hydroxy-5-(hydroxymethyl)tetrahydrofuran-2-yl)-5-fluoropyrimidin-2(1H)-one |
| 78 | 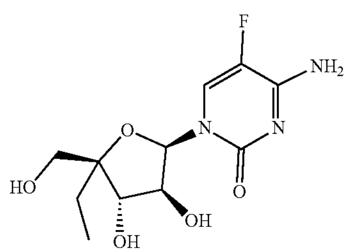 [SMILES: CC[C@]1(CO)O[C@@H](n2cc(F)c(N)nc2=O)[C@@H](O)[C@@H]1O] | 4-amino-1-((2R,3S,4S,5R)-5-ethyl-3,4-dihydroxy-5-(hydroxymethyl)tetrahydrofuran-2-yl)-5-fluoropyrimidin-2(1H)-one |
| 79 | 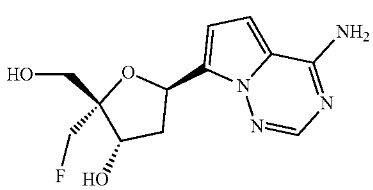 [SMILES: Nc1ncnn2c([C@H]3C[C@H](O)[C@](CO)(CF)O3)ccc12] | (2R,3S,5R)-5-(4-aminopyrrolo[2,1-f][1,2,4]triazin-7-yl)-2-(fluoromethyl)-2-(hydroxymethyl)-tetrahydrofuran-3-ol |
| 80 | 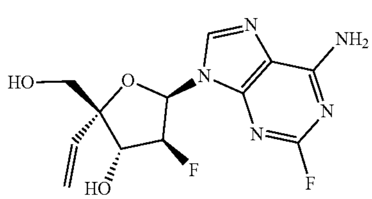 [SMILES: C=C[C@]1(CO)O[C@@H](n2cnc3c(N)nc(F)nc32)[C@@H](F)[C@@H]1O] | (2R,3R,4S,5R)-5-(6-amino-2-fluoro-9H-purin-9-yl)-4-fluoro-2-(hydroxymethyl)-2-vinyltetrahydrofuran-3-ol |
| 81 | 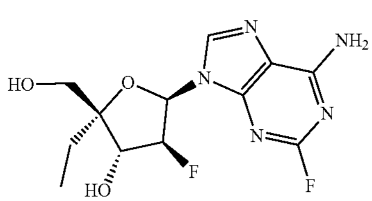 [SMILES: CC[C@]1(CO)O[C@@H](n2cnc3c(N)nc(F)nc32)[C@@H](F)[C@@H]1O] | (2R,3R,4S,5R)-5-(6-amino-2-fluoro-9H-purin-9-yl)-2-ethyl-4-fluoro-2-(hydroxymethyl)-tetrahydrofuran-3-ol |

TABLE 1-A-continued

| Compound No. | Structure | Name |
|---|---|---|
| 82 | 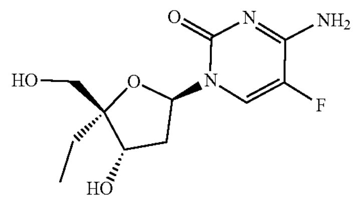 [SMILES: CC[C@]1(CO)O[C@@H](n2cc(F)c(N)nc2=O)C[C@@H]1O] | 4-amino-1-((2R,4S,5R)-5-ethyl-4-hydroxy-5-(hydroxymethyl)-tetrahydrofuran-2-yl)-5-fluoropyrimidin-2(1H)-one |
| 83 | 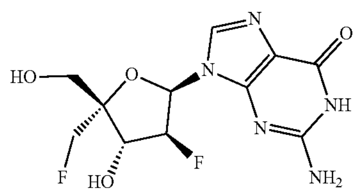 [SMILES: Nc1nc2c(ncn2[C@@H]2O[C@@](CO)(CF)[C@@H](O)[C@@H]2F)c(=O)[nH]1] | 2-amino-9-((2R,3S,4R,5R)-3-fluoro-5-(fluoromethyl)-4-hydroxy-5-(hydroxymethyl)tetrahydrofuran-2-yl)-1,9-dihydro-6H-purin-6-one |
| 84 | 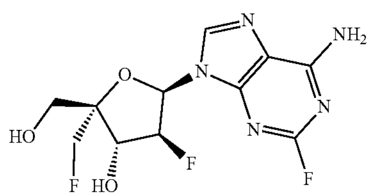 [SMILES: Nc1nc(F)nc2c1ncn2[C@@H]1O[C@@](CO)(CF)[C@@H](O)[C@@H]1F] | (2R,3R,4S,5R)-5-(6-amino-2-fluoro-9H-purin-9-yl)-4-fluoro-2-(fluoromethyl)-2-(hydroxymethyl)tetrahydrofuran-3-ol |
| 85 | 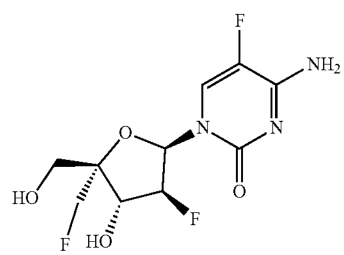 [SMILES: Nc1nc(=O)n([C@@H]2O[C@@](CO)(CF)[C@@H](O)[C@@H]2F)cc1F] | 4-amino-5-fluoro-1-((2R,3S,4R,5R)-3-fluoro-5-(fluoromethyl)-4-hydroxy-5-(hydroxymethyl)tetrahydrofuran-2-yl)pyrimidin-2(1H)-one |
| 86 | 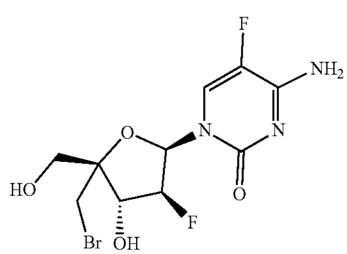 [SMILES: Nc1nc(=O)n([C@@H]2O[C@@](CO)(CBr)[C@@H](O)[C@@H]2F)cc1F] | 4-amino-1-((2R,3S,4R,5R)-5-(bromomethyl)-3-fluoro-4-hydroxy-5-(hydroxymethyl)-tetrahydrofuran-2-yl)-5-fluoropyrimidin-2(1H)-one |
| 87 | 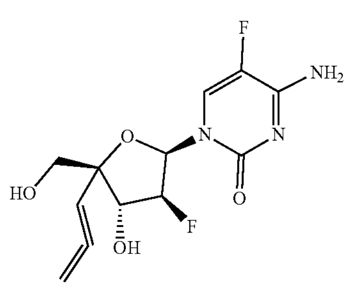 [SMILES: C=C=C[C@]1(CO)O[C@@H](n2cc(F)c(N)nc2=O)[C@@H](F)[C@@H]1O] | 4-amino-5-fluoro-1-((2R,3S,4R,5R)-3-fluoro-4-hydroxy-5-(hydroxymethyl)-5-(propa-1,2-dien-1-yl)tetrahydrofuran-2-yl)pyrimidin-2(1H)-one |

TABLE 1-A-continued

| Compound No. | Structure | Name |
|---|---|---|
| 88 | 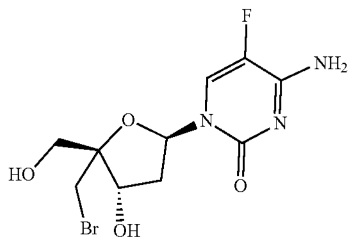 [SMILES: Nc1nc(=O)n([C@H]2C[C@H](O)[C@](CO)(CBr)O2)cc1F] | 4-amino-1-((2R,4S,5R)-5-(bromomethyl)-4-hydroxy-5-(hydroxymethyl)tetrahydrofuran-2-yl)-5-fluoropyrimidin-2(1H)-one |
| 89 | 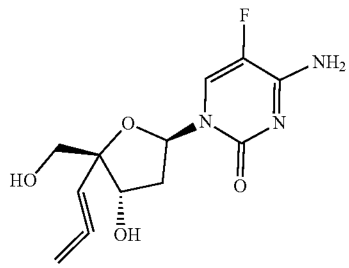 [SMILES: C=C=C[C@]1(CO)O[C@@H](n2cc(F)c(N)nc2=O)C[C@@H]1O] | 4-amino-5-fluoro-1-((2R,4S,5R)-4-hydroxy-5-(hydroxymethyl)-5-(propa-1,2-dien-1-yl)tetrahydrofuran-2-yl)pyrimidin-2(1H)-one |
| 90 | 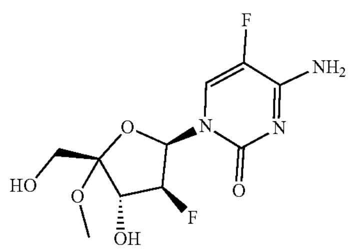 [SMILES: CO[C@]1(CO)O[C@@H](n2cc(F)c(N)nc2=O)[C@@H](F)[C@@H]1O] | 4-amino-5-fluoro-1-((2R,3S,4R,5R)-3-fluoro-4-hydroxy-5-(hydroxymethyl)-5-methoxytetrahydrofuran-2-yl)pyrimidin-2(1H)-one |
| 91 | 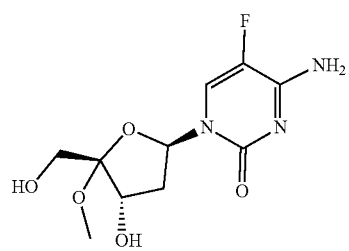 [SMILES: CO[C@]1(CO)O[C@@H](n2cc(F)c(N)nc2=O)C[C@@H]1O] | 4-amino-5-fluoro-1-((2R,4S,5R)-4-hydroxy-5-(hydroxymethyl)-5-methoxytetrahydrofuran-2-yl)pyrimidin-2(1H)-one |
| 92 | 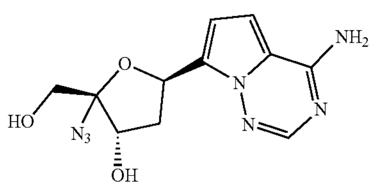 [SMILES: [N-]=[N+]=N[C@]1(CO)O[C@@H](c2ccc3c(N)ncnn23)C[C@@H]1O] | (2R,3S,5R)-5-(4-aminopyrrolo[2,1-f][1,2,4]triazin-7-yl)-2-azido-2-(hydroxymethyl)tetrahydrofuran-3-ol |
| 93 | 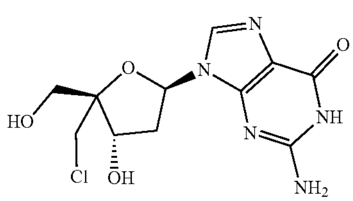 [SMILES: Nc1nc2c(ncn2[C@H]2C[C@H](O)[C@](CO)(CCl)O2)c(=O)[nH]1] | 2-amino-9-((2R,4S,5R)-5-(chloromethyl)-4-hydroxy-5-(hydroxymethyl)tetrahydrofuran-2-yl)-1,9-dihydro-6H-purin-6-one |
| 94 | 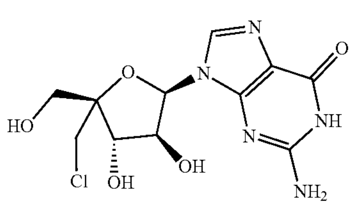 [SMILES: Nc1nc2c(ncn2[C@@H]2O[C@@](CO)(CCl)[C@@H](O)[C@@H]2O)c(=O)[nH]1] | 2-amino-9-((2R,3S,4S,5R)-5-(chloromethyl)-3,4-dihydroxy-5-(hydroxymethyl)tetrahydrofuran-2-yl)-1,9-dihydro-6H-purin-6-one |

TABLE 1-A-continued

| Compound No. | Structure | Name |
| --- | --- | --- |
| 95 | 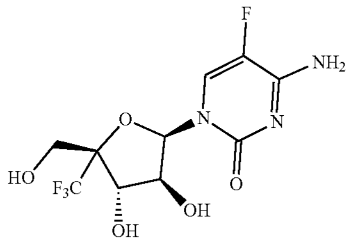 [SMILES: Nc1nc(=O)n([C@@H]2O[C@@](CO)(C(F)(F)F)[C@@H](O)[C@@H]2O)cc1F] | 4-amino-1-((2R,3S,4S,5R)-3,4-dihydroxy-5-(hydroxymethyl)-5-(trifluoromethyl)tetrahydrofuran-2-yl)-5-fluoropyrimidin-2(1H)-one |
| 96 | 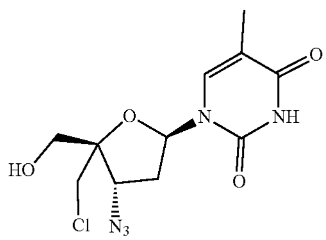 [SMILES: Cc1cn([C@H]2C[C@H](N=[N+]=[N-])[C@](CO)(CCl)O2)c(=O)[nH]c1=O] | 1-((2R,4S,5S)-4-azido-5-(chloromethyl)-5-(hydroxymethyl)-tetrahydrofuran-2-yl)-5-methylpyrimidine-2,4(1H,3H)-dione |
| 97 | 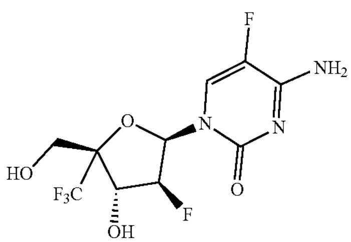 [SMILES: Nc1nc(=O)n([C@@H]2O[C@@](CO)(C(F)(F)F)[C@@H](O)[C@@H]2F)cc1F] | 4-amino-5-fluoro-1-((2R,3S,4R,5R)-3-fluoro-4-hydroxy-5-(hydroxymethyl)-5-(trifluoromethyl)tetrahydrofuran-2-yl)pyrimidin-2(1H)-one |
| 98 | 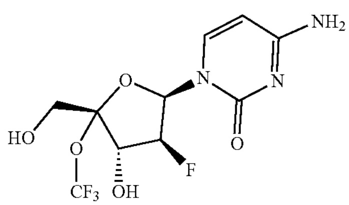 [SMILES: Nc1ccn([C@@H]2O[C@@](CO)(OC(F)(F)F)[C@@H](O)[C@@H]2F)c(=O)n1] | 4-amino-1-((2R,3S,4R,5S)-3-fluoro-4-hydroxy-5-(hydroxymethyl)-5-(trifluoromethoxy)tetrahydrofuran-2-yl)pyrimidin-2(1H)-one |
| 99 | 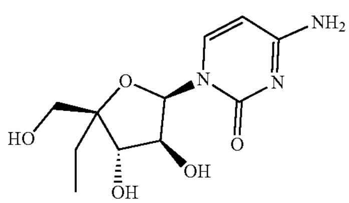 [SMILES: CC[C@]1(CO)O[C@@H](n2ccc(N)nc2=O)[C@@H](O)[C@@H]1O] | 4-amino-1-((2R,3S,4S,5R)-5-ethyl-3,4-dihydroxy-5-(hydroxymethyl)tetrahydrofuran-2-yl)pyrimidin-2(1H)-one |
| 100 | 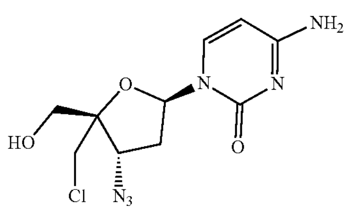 [SMILES: [N-]=[N+]=N[C@H]1C[C@H](n2ccc(N)nc2=O)O[C@@]1(CO)CCl] | 4-amino-1-((2R,4S,5S)-4-azido-5-(chloromethyl)-5-(hydroxymethyl)tetrahydrofuran-2-yl)pyrimidin-2(1H)-one |
| 101 | 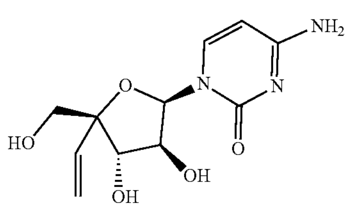 [SMILES: C=C[C@]1(CO)O[C@@H](n2ccc(N)nc2=O)[C@@H](O)[C@@H]1O] | 4-amino-1-((2R,3S,4S,5R)-3,4-dihydroxy-5-(hydroxymethyl)-5-vinyltetrahydrofuran-2-yl)pyrimidin-2(1H)-one |

TABLE 1-A-continued

| Compound No. | Structure | Name |
|---|---|---|
| 102 | [Structure image] | 4-amino-1-((2R,3S,4S,5R)-3,4-dihydroxy-5-(hydroxymethyl)-5-(prop-1-yn-1-yl)tetrahydrofuran-2-yl)pyrimidin-2(1H)-one |
| 103 | [Structure image] | 4-amino-1-((2R,4S,5S)-4-chloro-5-(chloromethyl)-5-(hydroxymethyl)tetrahydrofuran-2-yl)pyrimidin-2(1H)-one |
| 104 | [Structure image] | 4-amino-1-((2R,4S,5R)-5-(chloromethyl)-4-fluoro-5-(hydroxymethyl)tetrahydrofuran-2-yl)pyrimidin-2(1H)-one |
| 105 | [Structure image] | 4-amino-1-((2R,4S,5R)-5-(dichloromethyl)-4-hydroxy-5-(hydroxymethyl)tetrahydrofuran-2-yl)pyrimidin-2(1H)-one |
| 119 | [Structure image] | 4-amino-1-((2R,4R,5R)-5-(chloromethyl)-3,3-difluoro-4-hydroxy-5-(hydroxymethyl)tetrahydrofuran-2-yl)pyrimidin-2(1H)-one |

TABLE 1-B

| Compound | Structure |
|---|---|
| 2-TP | [Structure image] |
| 14-TP | [Structure image] |

TABLE 1-B-continued
| Compound | Structure |
|---|---|
| 25-TP | 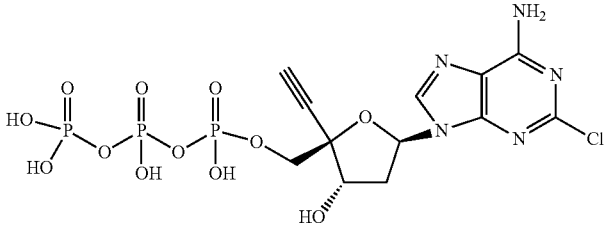 [SMILES: C#C[C@]1(COP(=O)(O)OP(=O)(O)OP(=O)(O)O)O[C@@H](n2cnc3c(N)nc(Cl)nc32)C[C@@H]1O] |
| 43-TP | 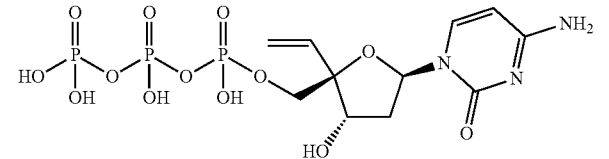 [SMILES: C=C[C@]1(COP(=O)(O)OP(=O)(O)OP(=O)(O)O)O[C@@H](n2ccc(N)nc2=O)C[C@@H]1O] |
| 44-TP | 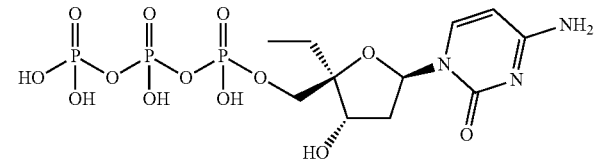 [SMILES: CC[C@]1(COP(=O)(O)OP(=O)(O)OP(=O)(O)O)O[C@@H](n2ccc(N)nc2=O)C[C@@H]1O] |
TABLE 1-C
| Compound | Structure |
|---|---|
| 120 | 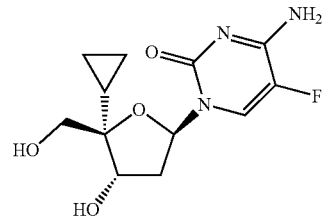 [SMILES: Nc1nc(=O)n([C@H]2C[C@H](O)[C@](CO)(C3CC3)O2)cc1F] |
| 121 | 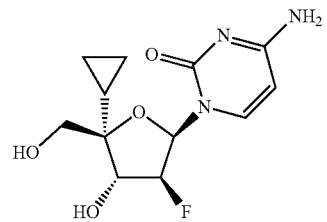 [SMILES: Nc1ccn([C@@H]2O[C@@](CO)(C3CC3)[C@@H](O)[C@@H]2F)c(=O)n1] |
| 122 | 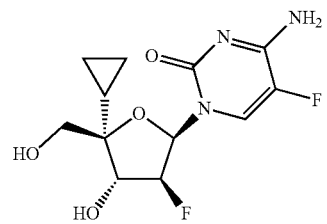 [SMILES: Nc1nc(=O)n([C@@H]2O[C@@](CO)(C3CC3)[C@@H](O)[C@@H]2F)cc1F] |

TABLE 1-C-continued

| Compound | Structure |
|---|---|
| 123 | (structure) |
| 124 | (structure) |
| 125 | (structure) |
| 126 | (structure) |
| 127 | (structure) |
| 128 | (structure) |
| 129 | (structure) |

TABLE 1-C-continued

| Compound | Structure |
|---|---|
| 130 | (structure) |
| 131 | (structure) |
| 132 | (structure) |
| 133 | (structure) |
| 134 | (structure) |
| 135 | (structure) |
| 136 | (structure) |

TABLE 1-C-continued

| Compound | Structure |
|---|---|
| 137 | 5'-chloromethyl, 2'-chloro, 5-fluorocytidine analog |
| 138 | 4'-carboxamide, 2'-fluoro, 5-fluorocytidine analog |
| 139 | 5'-aminomethyl, 2'-fluoro, 5-fluorocytidine analog |
| 140 | 4'-(chlorofluoromethyl), 2'-fluoro, 5-fluorocytidine analog |
| 141 | 4'-methylthio, 2'-fluoro, 5-fluorocytidine analog |
| 142 | 5'-chloromethyl-2'-deoxyguanosine analog |
| 143 | 4'-allyl-2'-deoxycytidine analog |

TABLE 1-C-continued

| Compound | Structure |
|---|---|
| 144 | 5'-chloro-5'-deoxy-2'-fluoro-thymidine analog (chloromethyl, hydroxymethyl, OH, F; thymine base) |
| 145 | 5'-fluoro analog (fluoromethyl, hydroxymethyl, OH, F; thymine base) |
| 146 | 5'-chloro analog with 5-chlorocytosine base |
| 147 | 5'-fluoro analog with 5-chlorocytosine base |
| 148 | 5'-fluoro analog with 5-trifluoromethyl-uracil base |
| 149 | 5'-chloro analog with 5-trifluoromethyl-cytosine base |

TABLE 1-C-continued

| Compound | Structure |
|---|---|
| 150 | 5-methylcytidine with 4'-fluoromethyl substituent |
| 151 | 2'-deoxy-5-trifluoromethyluridine with 4'-fluoromethyl substituent |
| 152 | 5-fluorouridine with 4'-chloromethyl substituent |
| 153 | 2'-deoxyuridine with 4'-fluoromethyl substituent |
| 154 | 2'-deoxy-2'-fluorocytidine with 4'-iodomethyl substituent |
| 155 | 2'-deoxy-2'-fluorocytidine with 4'-trifluoromethyl substituent |
| 156 | 2'-deoxy-2'-fluoro-5-methyluridine with 4'-ethyl substituent |

TABLE 1-C-continued

| Compound | Structure |
|---|---|
| 157 | 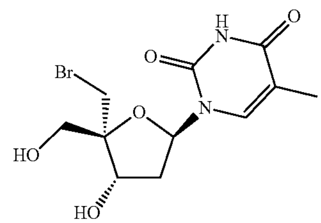 [SMILES: Cc1cn([C@H]2C[C@H](O)[C@](CO)(CBr)O2)c(=O)[nH]c1=O] |
| 158 | 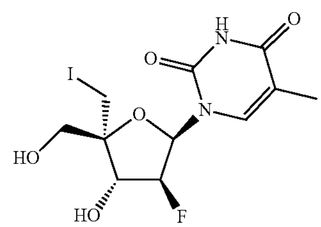 [SMILES: Cc1cn([C@@H]2O[C@@](CO)(CI)[C@@H](O)[C@@H]2F)c(=O)[nH]c1=O] |
| 159 | 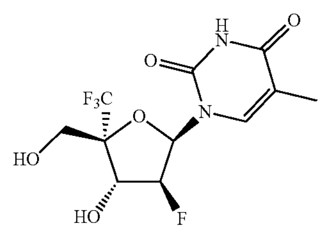 [SMILES: Cc1cn([C@@H]2O[C@@](CO)(C(F)(F)F)[C@@H](O)[C@@H]2F)c(=O)[nH]c1=O] |
| 160 | 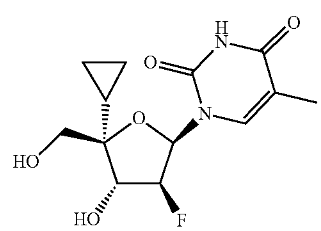 [SMILES: Cc1cn([C@@H]2O[C@@](CO)(C3CC3)[C@@H](O)[C@@H]2F)c(=O)[nH]c1=O] |
| 161 | 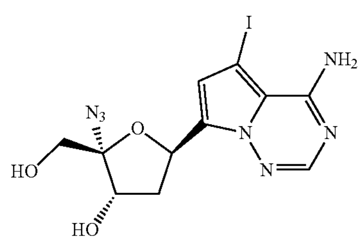 [SMILES: [N-]=[N+]=N[C@]1(CO)O[C@@H](c2cc(I)c3c(N)ncnn23)C[C@@H]1O] |
| 162 | 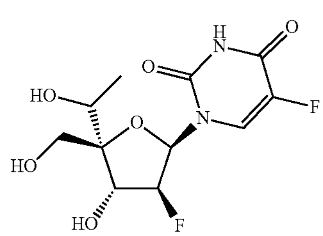 [SMILES: CC(O)[C@]1(CO)O[C@@H](n2cc(F)c(=O)[nH]c2=O)[C@@H](F)[C@@H]1O] |

TABLE 1-C-continued

| Compound | Structure |
|---|---|
| 163 | 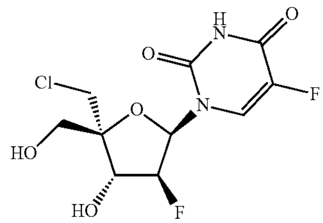 [SMILES: O=c1[nH]c(=O)n([C@@H]2O[C@@](CO)(CCl)[C@@H](O)[C@@H]2F)cc1F] |
| 164 | 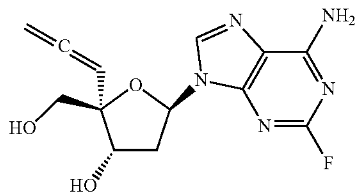 [SMILES: C=C=C[C@]1(CO)O[C@@H](n2cnc3c(N)nc(F)nc32)C[C@@H]1O] |
| 173 | 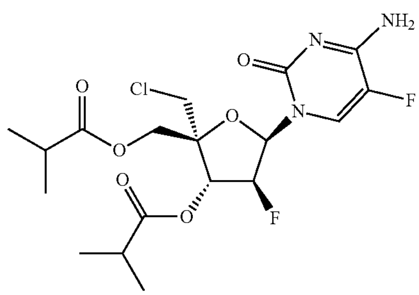 [SMILES: CC(C)C(=O)OC[C@@]1(CCl)O[C@@H](n2cc(F)c(N)nc2=O)[C@@H](F)[C@@H]1OC(=O)C(C)C] |
| 174 | 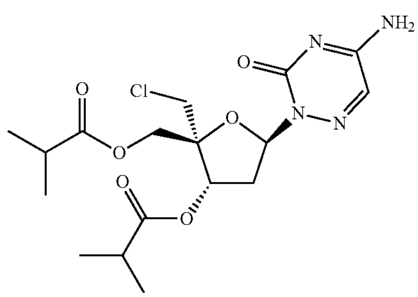 [SMILES: CC(C)C(=O)OC[C@@]1(CCl)O[C@@H](n2ncc(N)nc2=O)C[C@@H]1OC(=O)C(C)C] |
| 175 | 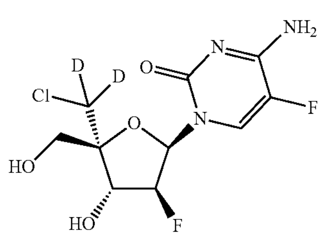 [SMILES: [2H]C([2H])(Cl)[C@]1(CO)O[C@@H](n2cc(F)c(N)nc2=O)[C@@H](F)[C@@H]1O] |
| 67-TP | 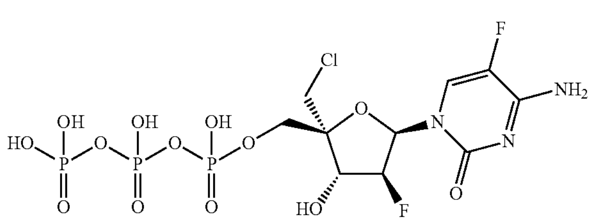 [SMILES: Nc1nc(=O)n([C@@H]2O[C@](CCl)(COP(=O)(O)OP(=O)(O)OP(=O)(O)O)[C@@H](O)[C@@H]2F)cc1F] |

TABLE 1-D

| Compound No. | Structure |
|---|---|
| 86-TP | 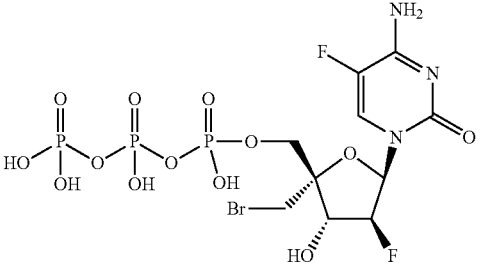 [SMILES: Nc1nc(=O)n([C@@H]2O[C@](CBr)(COP(=O)(O)OP(=O)(O)OP(=O)(O)O)[C@@H](O)[C@@H]2F)cc1F] |
| 176 | 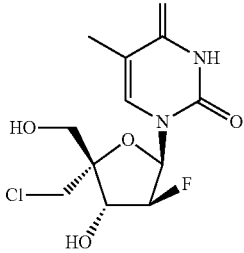 |
| 177 | 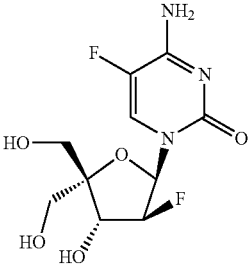 |
| 178 | 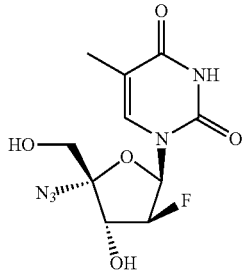 [SMILES: Cc1cn([C@@H]2O[C@@](CO)(N=[N+]=[N-])[C@@H](O)[C@@H]2F)c(=O)[nH]c1=O] |
| 179 | 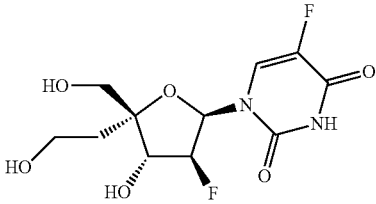 [SMILES: O=c1[nH]c(=O)n([C@@H]2O[C@@](CO)(CCO)[C@@H](O)[C@@H]2F)cc1F] |
| 180 | 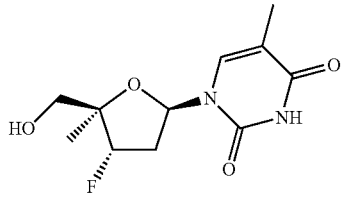 [SMILES: Cc1cn([C@H]2C[C@H](F)[C@@](C)(CO)O2)c(=O)[nH]c1=O] |

TABLE 1-D-continued

| Compound No. | Structure |
|---|---|
| 181 | 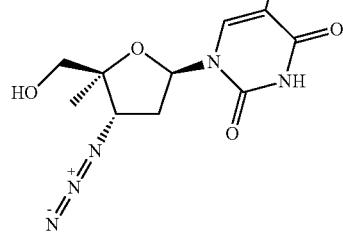 |
| 182 | 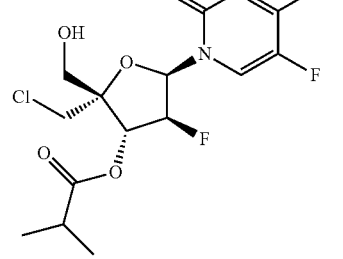 |
| 183 | 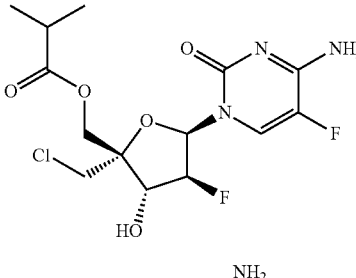 |
| 184 | 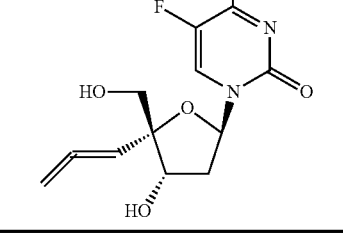 |

A twenty-second embodiment is a pharmaceutical composition comprising a compound according to Formula I as described in any of the embodiments above, or a pharmaceutically acceptable salt thereof, and a carrier, excipient, and/or vehicle. Another embodiment is a pharmaceutical composition comprising a compound as described in any of the embodiments above, or a pharmaceutically acceptable salt thereof, and a carrier, excipient, and/or vehicle. Another embodiment is a pharmaceutical composition comprising a compound as described in any of the embodiments herein, or a pharmaceutically acceptable salt thereof, and a carrier, excipient, and/or vehicle.

One aspect of any of the above embodiments excludes the compounds of Table 2 from the compounds of Formula I. Another aspect of any of the above embodiments excludes the compounds of Tables 2, 2-A, and 2-B from the compounds of Formula I.

The invention further provides herein, a compound according to Formula I-A:

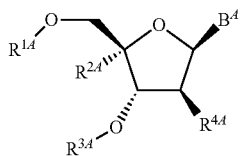

(I-A)

or a pharmaceutically acceptable salt thereof, wherein:
$R^{1A}$ is —C(O)$R^{5A}$, hydrogen, or —P(O)(OH)—OP(O)(OH)—OP(O)(OH)$_2$;
$R^{2A}$ is (i) halomethyl, $C_{1-3}$ aliphatic, or cyclopropyl, each of which optionally has one or more hydrogen replaced with deuterium, or (ii) —N$_3$;
$R^{3A}$ is —C(O)$R^{5A}$ or hydrogen;
$R^{4A}$ is halo, hydrogen, or —OH;
$R^{5A}$ represents independently for each occurrence $C_{1-20}$ aliphatic, $C_{1-20}$ haloaliphatic, —C(H)($R^{6A}$)—N($R^{7A}$)$_2$, phenyl, —CH$_2$-phenyl, or hydrogen; wherein each phenyl is substituted with m occurrences of $R^{10A}$;
$R^{6A}$ is $C_{1-6}$ alkyl or hydrogen, wherein said $C_{1-6}$ alkyl is optionally substituted with phenyl;
$R^{7A}$ represents independently for each occurrence hydrogen, $C_{1-6}$ alkyl, —C(O)CH$_3$, —C(O)OC(CH$_3$)$_3$, —C(O)O(CH$_2$)phenyl, or —C(O)O(CH$_2$)fluorenyl;
$R^{8A}$ is hydrogen, halo, —CH$_3$, or —CF$_3$;
$R^{9A}$ is halo, —CH$_3$, or —CF$_3$;
$R^{10A}$ represents independently for each occurrence $C_{1-6}$ alkyl, $C_{1-6}$ alkoxyl, $C_{1-6}$ haloalkyl,
$B^A$ is

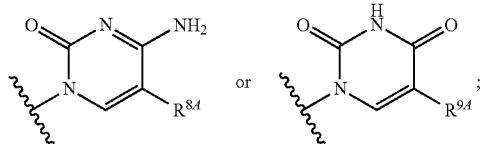

and
m is 0, 1, or 2;
provided that if $R^{4A}$ is hydrogen, then at least one of $R^{1A}$ and $R^{3A}$ is —C(O)$R^{5A}$; and
provided that if $R^{3A}$ is hydrogen, $R^{4A}$ is halo or —OH, and $R^{1A}$ is hydrogen or —P(O)(OH)—OP(O)(OH)—OP(O)(OH)$_2$, then $R^{8A}$ is halo, —CH$_3$, or —CF$_3$.

As described generally above, $R^{1A}$ is —C(O)$R^{5A}$, hydrogen, or —P(O)(OH)—OP(O)(OH)—OP(O)(OH)$_2$. In certain embodiments, $R^{1A}$ is hydrogen, or —P(O)(OH)—OP(O)(OH)—OP(O)(OH)$_2$. In certain embodiments, $R^{1A}$ is —C(O)$R^{5A}$ or —P(O)(OH)—OP(O)(OH)—OP(O)(OH)$_2$. In certain embodiments, $R^{1A}$ is —C(O)$R^{5A}$ or hydrogen. In certain embodiments, $R^{1A}$ is —C(O)$R^{5A}$. In certain embodiments, $R^{1A}$ is hydrogen. In certain embodiments, $R^{1A}$ is P(O)(OH)—OP(O)(OH)—OP(O)(OH)$_2$. In certain embodiments $R^{1A}$ is selected from those depicted in Tables 1, 1-A, 1-B, 1-C, and 1-D.

As described generally above, $R^{2A}$ is (i) halomethyl, $C_{1-3}$ aliphatic, or cyclopropyl, each of which optionally has one or more hydrogen replaced with deuterium, or (ii) —N$_3$. In certain embodiments, $R^{2A}$ is halomethyl. In certain embodiments, $R^{2A}$ is $C_{1-3}$ aliphatic. In certain embodiments, $R^{2A}$ is cyclopropyl. In certain embodiments, $R^{2A}$ is halomethyl which optionally has one or more hydrogen replaced with deuterium. In certain embodiments, $R^{2A}$ is $C_{1-3}$ aliphatic which optionally has one or more hydrogen replaced with deuterium. In certain embodiments, $R^{2A}$ is cyclopropyl which optionally has one or more hydrogen replaced with deuterium. In certain embodiments, $R^{2A}$ is —N$_3$. In certain embodiments, $R^{2A}$ is halomethyl, $C_{1-3}$ aliphatic, or cyclopropyl, each of which optionally has one or more hydrogen replaced with deuterium.

In certain embodiments, $R^{2A}$ is —CH$_2$F, —CH$_2$Br, or —CH$_2$Cl. In certain embodiments, $R^{2A}$ is —CH$_2$F. In certain embodiments, $R^{2A}$ is —CD$_2$F, —CD$_2$Br, or —CD$_2$Cl. In certain embodiments, $R^{2A}$ is —CD$_2$F. In certain embodiments $R^{2A}$ is selected from those depicted in Tables 1, 1-A, 1-B, 1-C, and 1-D.

As described generally above, $R^{3A}$ is —C(O)$R^{5A}$ or hydrogen. In certain embodiments, $R^{3A}$ is —C(O)$R^{5A}$. In certain embodiments, $R^{3A}$ is hydrogen. In certain embodiments $R^{3A}$ is selected from those depicted in Tables 1, 1-A, 1-B, 1-C, and 1-D.

As described generally above, $R^{4A}$ is halo, hydrogen, or —OH. In certain embodiments, $R^{4A}$ is halo. In certain embodiments, $R^{4A}$ is fluoro. In certain embodiments, $R^{4A}$ is hydrogen. In certain embodiments, $R^{4A}$ is —OH. In certain embodiments $R^{1A}$ is selected from those depicted in Tables 1, 1-A, 1-B, 1-C, and 1-D.

As described generally above, $R^{5A}$ represents independently for each occurrence $C_{1-20}$ aliphatic, $C_{1-20}$ haloaliphatic, —C(H)($R^{6A}$)—N($R^{7A}$)$_2$, phenyl, —CH$_2$-phenyl, or hydrogen; wherein each phenyl is substituted with m occurrences of $R^{10A}$. In certain embodiments, $R^{5A}$ represents independently for each occurrence $C_{1-20}$ aliphatic, $C_{1-20}$ haloaliphatic, —C(H)($R^{6A}$)—N($R^{7A}$)$_2$, phenyl, or —CH$_2$-phenyl; wherein each phenyl is substituted with m occurrences of $R^{10A}$. In certain embodiments, $R^{5A}$ represents independently for each occurrence $C_{1-20}$ aliphatic. In certain embodiments, $R^{5A}$ represents independently for each occurrence $C_{1-20}$ haloaliphatic. In certain embodiments, $R^{5A}$ represents independently for each occurrence —C(H)($R^{6A}$)—N($R^{7A}$)$_2$. In certain embodiments, $R^{5A}$ represents independently for each occurrence phenyl, wherein each phenyl is substituted with m occurrences of $R^{10A}$. In certain embodiments, $R^{5A}$ represents independently for each occurrence —CH$_2$-phenyl, wherein each phenyl is substituted with m occurrences of $R^{10A}$ In certain embodiments, $R^{5A}$ is hydrogen. In certain embodiments, $R^{5A}$ is $C_{1-20}$ aliphatic. In certain embodiments, $R^{5A}$ is $C_{1-20}$ haloaliphatic. In certain embodiments, $R^{5A}$ is —C(H)($R^{6A}$)—N($R^{7A}$)$_2$. In certain embodiments, $R^{5A}$ is phenyl, wherein each phenyl is substituted with m occurrences of $R^{10A}$. In certain embodiments, $R^{5A}$ is —CH$_2$-phenyl, wherein each phenyl is substituted with m occurrences of $R^{10A}$. In certain embodiments $R^{5A}$ is selected from those depicted in Tables 1, 1-A, 1-B, 1-C, and 1-D.

As described generally above, $R^{6A}$ is $C_{1-6}$ alkyl or hydrogen, wherein said $C_{1-6}$ alkyl is optionally substituted with phenyl. In certain embodiments $R^{6A}$ is $C_{1-6}$ alkyl, wherein said $C_{1-6}$ alkyl is optionally substituted with phenyl. In certain embodiments $R^{6A}$ hydrogen. In certain embodiments $R^{6A}$ is $C_{1-6}$ alkyl. In certain embodiments $R^{6A}$ is selected from those depicted in Tables 1, 1-A, 1-B, 1-C, and 1-D.

As described generally above, $R^{7A}$ represents independently for each occurrence hydrogen, $C_{1-6}$ alkyl, —C(O)CH$_3$, —C(O)OC(CH$_3$)$_3$, —C(O)O(CH$_2$)phenyl, or —C(O)O(CH$_2$)-fluorenyl. In certain embodiments $R^{7A}$ represents independently for each occurrence $C_{1-6}$ alkyl. In certain embodiments $R^{7A}$ is hydrogen. In certain embodiments $R^{7A}$ is $C_{1-6}$ alkyl. In certain embodiments $R^{7A}$ is —C(O)CH$_3$. In certain embodiments $R^{7A}$ is —C(O)O(CH$_2$)phenyl. In certain embodiments $R^{7A}$ is —C(O)O(CH$_2$)fluorenyl. In certain embodiments $R^{7A}$ represents independently for each occurrence $C_{1-6}$ alkyl, —C(O)CH$_3$, —C(O)OC(CH$_3$)$_3$, —C(O)O(CH$_2$)phenyl, or —C(O)O(CH$_2$)fluorenyl. In certain embodiments $R^{7A}$ is selected from those depicted in Tables 1, 1-A, 1-B, 1-C, and 1-D.

As described generally above, $R^{8A}$ is hydrogen, halo, —CH$_3$, or —CF$_3$. In certain embodiments, $R^{8A}$ is hydrogen, halo, —CH$_3$, or —CF$_3$. In certain embodiments, $R^{8A}$ is halo, —CH$_3$, or —CF$_3$. In certain embodiments, $R^{8A}$ is hydrogen, —CH$_3$, or —CF$_3$. In certain embodiments, $R^{8A}$ is hydrogen, halo, or —CF$_3$. In certain embodiments, $R^{8A}$ is hydrogen, halo, or —CH$_3$. In certain embodiments, $R^{8A}$ is hydrogen. In certain embodiments, $R^{8A}$ is halo. In certain embodiments, $R^{8A}$ is fluoro. In certain embodiments, $R^{8A}$ is —CH$_3$. In certain embodiments, $R^{8A}$ is —CF$_3$. In certain embodiments $R^{8A}$ is selected from those depicted in Tables 1, 1-A, 1-B, 1-C, and 1-D.

As described generally above, $R^{9A}$ is halo, —CH$_3$, or —CF$_3$. In certain embodiments $R^{9A}$ halo. In certain embodiments $R^{9A}$ is —CH$_3$. In certain embodiments $R^{9A}$ is —CF$_3$. In certain embodiments $R^{9A}$ is F, Br, or Cl. In certain embodiments $R^{9A}$ is selected from those depicted in Tables 1, 1-A, 1-B, 1-C, and 1-D.

As described generally above, $R^{10A}$ represents independently for each occurrence $C_{1-6}$ alkyl, $C_{1-6}$ alkoxyl, $C_{1-6}$ haloalkyl, or halo. In certain embodiments $R^{10A}$ represents independently for each occurrence $C_{1-6}$ alkyl. In certain embodiments $R^{10A}$ represents independently for each occurrence $C_{1-6}$ alkoxyl. In certain embodiments $R^{10A}$ represents independently for each occurrence $C_{1-6}$ haloalkyl. In certain embodiments $R^{10A}$ represents independently for each occurrence halo. In certain embodiments $R^{10A}$ is $C_{1-6}$ alkyl, $C_{1-6}$ alkoxyl, $C_{1-6}$ haloalkyl, or halo. In certain embodiments $R^{10A}$ is selected from those depicted in Tables 1, 1-A, 1-B, 1-C, and 1-D.

As described generally above, $B^A$ is

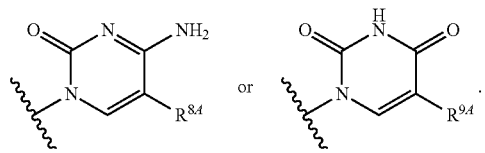

In certain embodiments, $B^A$ is

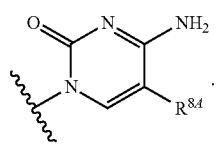

In certain in embodiments, $B^A$ is

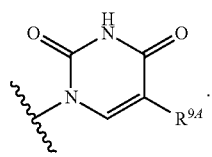

In certain embodiments $B^A$ is selected from those depicted in Tables 1, 1-A, 1-B, 1-C, and 1-D.

As defined generally above, m is 0, 1, or 2. In certain embodiments, m is 0. In certain embodiments, m is 1. In certain embodiments, m is 2. In certain embodiments, m is 1 or 2. In certain embodiments, m is 0 or 2. In certain embodiments, m is 0 or 2. In certain embodiments m is selected from those depicted in Tables 1, 1-A, 1-B, 1-C, and 1-D.

In certain embodiments, the compound of Formula II has the following formula or a pharmaceutically acceptable salt thereof:

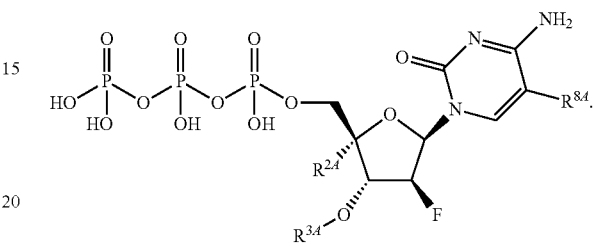

Another aspect of the disclosure provides a compound represented by Formula II:

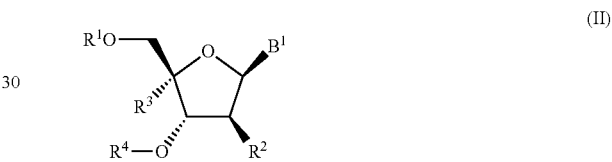

(II)

or a pharmaceutically acceptable salt thereof; wherein:
$R^1$ and $R^4$ represent independently —C(O)R$^5$ or hydrogen; provided that at least one of $R^1$ and $R^4$ is —C(O)R$^5$;
$R^2$ is halo, hydrogen, or —OH;
$R^3$ is halomethyl, $C_{1-3}$ aliphatic, or cyclopropyl, each of which optionally has one or more hydrogen replaced with deuterium;
$R^5$ represents independently for each occurrence $C_{1-20}$ aliphatic, $C_{1-20}$ haloaliphatic, —C(H)(R$^6$)—N(R$^7$)$_2$, phenyl, —CH$_2$-phenyl, or hydrogen; wherein each phenyl is substituted with m occurrences of $R^{10}$;
$R^6$ is $C_{1-6}$ alkyl or hydrogen, wherein said $C_{1-6}$ alkyl is optionally substituted with phenyl;
$R^7$ represents independently for each occurrence hydrogen, $C_{1-6}$ alkyl, —C(O)CH$_3$, —C(O)OC(CH$_3$)$_3$, —C(O)O(CH$_2$)phenyl, or —C(O)O(CH$_2$)fluorenyl;
$R^8$ is hydrogen, halo, —CH$_3$, or —CF$_3$;
$R^9$ is halo, —CH$_3$, or —CF$_3$;
$R^{10}$ represents independently for each occurrence $C_{1-6}$ alkyl, $C_{1-6}$ alkoxyl, $C_{1-6}$ haloalkyl, or halo;
$B^1$ is

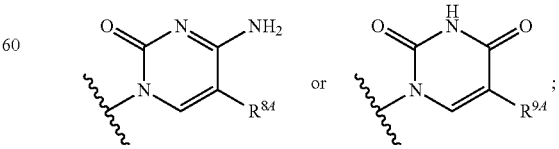

and
m is 0, 1, or 2.

The definitions of variables in Formula II above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is a compound of Formula II.

As defined generally above, $R^1$ and $R^4$ represent independently —$C(O)R^5$ or hydrogen; provided that at least one of $R^1$ and $R^4$ is —$C(O)R^5$.

In some embodiments, $R^1$ is —$C(O)R^5$, and $R^4$ is hydrogen. In some embodiments, $R^1$ is -hydrogen, and $R^4$ is $C(O)R^5$. In some embodiments, $R^1$ and $R^4$ represent independently —$C(O)R^5$. In some embodiments, $R^1$ and $R^4$ are —$C(O)R^5$.

As defined generally above, $R^2$ is halo, hydrogen, or —OH. In certain embodiments, $R^2$ is fluoro, hydrogen, or —OH. In some embodiments, $R^2$ is halo or hydrogen. In some embodiments, $R^2$ is fluoro or hydrogen. In some embodiments, $R^2$ is hydrogen or —OH. In some embodiments, $R^2$ is halo or —OH. In some embodiments, $R^2$ is fluoro or —OH.

In some embodiments, $R^2$ is halo. In certain embodiments, $R^2$ is fluoro. In some embodiments, $R^2$ is hydrogen. In some embodiments, $R^2$ is —OH.

As defined generally above, $R^3$ is halomethyl, $C_{1-3}$ aliphatic, or cyclopropyl, each of which optionally has one or more hydrogen replaced with deuterium. In certain embodiments, $R^3$ is halomethyl or $C_{1-3}$ aliphatic, each of which optionally has one or more hydrogen replaced with deuterium.

In certain embodiments, $R^3$ is halomethyl, $C_{1-3}$ aliphatic, or cyclopropyl, each of which has one or more hydrogen replaced with deuterium. In certain embodiments, $R^3$ is halomethyl or $C_{1-3}$ aliphatic, each of which has one or more hydrogen replaced with deuterium.

In certain embodiments, $R^3$ is halomethyl, $C_{1-3}$ aliphatic, or cyclopropyl. In some embodiments, $R^3$ is halomethyl or $C_{1-3}$ aliphatic. In some embodiments, $R^3$ is halomethyl or cyclopropyl. In some embodiments, $R^3$ is $C_{1-3}$ aliphatic or cyclopropyl. In some embodiments, $R^3$ is ethyl or cyclopropyl.

In some embodiments, $R^3$ is halomethyl which optionally has one or more hydrogen replaced with deuterium. In some embodiments, $R^3$ is halomethyl. In some embodiments, $R^3$ is —$CH_2Cl$, —$CH_2F$, —$CH_2Br$, —$CH_2I$, —$CHF_2$, or —$CF_3$. In some embodiments, $R^3$ is —$CH_2Cl$, —$CH_2F$, —$CH_2Br$, —$CH_2I$, or —$CF_3$. In some embodiments, $R^3$ is —$CH_2F$, —$CH_2Br$, —$CH_2I$, or —$CF_3$. In some embodiments, $R^3$ is —$CH_2Cl$, —$CH_2Br$, —$CH_2I$, or —$CF_3$. In some embodiments, $R^3$ is —$CH_2Cl$, —$CH_2F$, —$CH_2I$, or —$CF_3$. In some embodiments, $R^3$ is —$CH_2Cl$, —$CH_2F$, —$CH_2Br$, or —$CF_3$. In some embodiments, $R^3$ is —$CH_2Cl$, —$CH_2F$, —$CH_2Br$, or —$CH_2I$.

In some embodiments, $R^3$ is —$CH_2Br$, —$CH_2I$, or —$CF_3$. In some embodiments, $R^3$ is —$CH_2Cl$, —$CH_2I$, or —$CF_3$. In some embodiments, $R^3$ is —$CH_2Cl$, —$CH_2F$, or —$CF_3$. In some embodiments, $R^3$ is —$CH_2Cl$, —$CH_2F$, or —$CH_2Br$. In some embodiments, $R^3$ is —$CH_2F$, —$CH_2I$, or —$CF_3$. In some embodiments, $R^3$ is —$CH_2F$, —$CH_2Br$, or —$CF_3$. In some embodiments, $R^3$ is —$CH_2F$, —$CH_2Br$, or —$CH_2I$. In some embodiments, $R^3$ is —$CH_2Cl$, —$CH_2Br$, or —$CF_3$. In some embodiments, $R^3$ is —$CH_2Cl$, —$CH_2Br$, or —$CH_2I$.

In some embodiments, $R^3$ is —$CH_2Cl$, —$CH_2F$, or —$CH_2I$. In some embodiments, $R^3$ is —$CH_2F$, —$CHF_2$, or —$CF_3$.

In some embodiments, $R^3$ is —$CH_2I$ or —$CF_3$. In some embodiments, $R^3$ is —$CH_2Cl$ or —$CH_2F$. In some embodiments, $R^3$ is —$CH_2Cl$ or —$CF_3$. In some embodiments, $R^3$ is —$CH_2F$ or —$CH_2I$. In some embodiments, $R^3$ is —$CH_2Cl$ or —$CH_2Br$. In some embodiments, $R^3$ is —$CH_2Br$ or —$CH_2I$. In some embodiments, $R^3$ is —$CH_2Br$ or —$CF_3$. In some embodiments, $R^3$ is —$CH_2Cl$ or —$CH_2I$. In some embodiments, $R^3$ is —$CH_2F$ or —$CF_3$. In some embodiments, $R^3$ is —$CH_2F$ or —$CH_2Br$. In some embodiments, $R^3$ is —$CH_2F$ or —$CHF_2$. In some embodiments, $R^3$ is —$CHF_2$ or —$CF_3$.

In some embodiments, $R^3$ is —$CH_2Cl$. In some embodiments, $R^3$ is —$CH_2F$. In some embodiments, $R^3$ is —$CH_2Br$. In some embodiments, $R^3$ is —$CH_2I$. In some embodiments, $R^3$ is —$CHF_2$. In some embodiments, $R^3$ is —$CF_3$.

In some embodiments, $R^3$ is halomethyl which has one or more hydrogen replaced with deuterium. In some embodiments, $R^3$ is —$CD_2Cl$, —$CD_2F$, —$CD_2Br$, —$CD_2I$, or —$CDF_2$. In some embodiments, $R^3$ is —$CD_2Cl$ or —$CD_2F$. In some embodiments, $R^3$ is —$CD_2Cl$. In some embodiments, $R^3$ is —$CD_2F$. In some embodiments, $R^3$ is —$CD_2Br$. In some embodiments, $R^3$ is —$CD_2I$. In some embodiments, $R^3$ is —$CDF_2$.

In some embodiments, $R^3$ is $C_{1-3}$ aliphatic which optionally has one or more hydrogen replaced with deuterium. In some embodiments, $R^3$ is $C_{1-3}$ aliphatic which has one or more hydrogen replaced with deuterium. In some embodiments, $R^3$ is $C_{1-3}$ aliphatic. In some embodiments, $R^3$ is $C_{2-3}$ aliphatic. In some embodiments, $R^3$ is $C_{1-2}$ aliphatic. In some embodiments, $R^3$ is $C_{1-3}$ alkyl. In some embodiments, $R^3$ is $C_{2-3}$ alkyl. In some embodiments, $R^3$ is $C_{1-2}$ alkyl. In some embodiments, $R^3$ is —$CH_2CH_3$, —$C(H)=CH_2$, or —$C(H)=C=CH_2$. In some embodiments, $R^3$ is —$CH_2CH_3$. In some embodiments, $R^3$ is —$C(H)=CH_2$. In some embodiments, $R^3$ is —$C(H)=C=CH_2$.

In some embodiments, $R^3$ is cyclopropyl which optionally has one or more hydrogen replaced with deuterium. In some embodiments, $R^3$ is cyclopropyl which has one or more hydrogen replaced with deuterium. In some embodiments, $R^3$ is cyclopropyl.

As defined generally above, $R^5$ represents independently for each occurrence $C_{1-20}$ aliphatic, $C_{1-20}$ haloaliphatic, —$C(H)(R^6)$—$N(R^7)_2$, phenyl, —$CH_2$-phenyl, or hydrogen; wherein each phenyl is substituted with m occurrences of $R^{10}$.

In certain embodiments, $R^5$ represents independently for each occurrence $C_{1-20}$ aliphatic, $C_{1-20}$ haloaliphatic, phenyl, or hydrogen; wherein said phenyl is substituted with m occurrences of $R^{10}$. In certain embodiments, $R^5$ represents independently for each occurrence $C_{1-20}$ aliphatic, $C_{1-20}$ haloaliphatic, or hydrogen. In certain embodiments, $R^5$ represents independently for each occurrence —$C(H)(R^6)$—$N(R^7)_2$, phenyl, or —$CH_2$-phenyl; wherein each phenyl is substituted with m occurrences of $R^{10}$. In certain embodiments, $R^5$ represents independently for each occurrence —$C(H)(R^6)$—$N(R^7)_2$ or phenyl substituted with m occurrences of $R^{10}$.

In certain embodiments, $R^5$ is $C_{1-20}$ aliphatic, $C_{1-20}$ haloaliphatic, phenyl, or hydrogen; wherein said phenyl is substituted with m occurrences of $R^{10}$. In certain embodiments, $R^5$ is $C_{1-20}$ aliphatic, $C_{1-20}$ haloaliphatic, or hydrogen. In certain embodiments, $R^5$ is —$C(H)(R^6)$—$N(R^7)_2$, phenyl, or —$CH_2$-phenyl; wherein each phenyl is substituted with m occurrences of $R^{10}$. In certain embodiments, $R^5$ is phenyl or —$CH_2$-phenyl; wherein each phenyl is substituted with m occurrences of $R^{10}$. In certain embodiments, $R^5$ is —C(H)($R^6$)—N($R^7$)$_2$ or phenyl substituted with m occurrences of $R^{10}$.

In certain embodiments, $R^5$ represents independently for each occurrence $C_{1-20}$ aliphatic or $C_{1-20}$ haloaliphatic. In certain embodiments, $R^5$ represents independently for each occurrence $C_{1-8}$ aliphatic or $C_{1-8}$ haloaliphatic. In certain embodiments, $R^5$ represents independently for each occurrence $C_{10-20}$ aliphatic or $C_{10-20}$ haloaliphatic. In certain embodiments, $R^5$ represents independently for each occurrence $C_{1-20}$ alkyl or $C_{1-20}$ haloalkyl. In certain embodiments, $R^5$ represents independently for each occurrence $C_{1-8}$ alkyl or $C_{1-8}$ haloalkyl. In certain embodiments, $R^5$ represents independently for each occurrence $C_{10-20}$ alkyl or $C_{10-20}$ haloalkyl.

In certain embodiments, $R^5$ is $C_{1-20}$ aliphatic or $C_{1-20}$ haloaliphatic. In certain embodiments, $R^5$ is $C_{1-6}$ aliphatic or $C_{1-6}$ haloaliphatic. In certain embodiments, $R^5$ is $C_{10-20}$ aliphatic or $C_{10-20}$ haloaliphatic. In certain embodiments, $R^5$ is $C_{1-20}$ alkyl or $C_{1-20}$ haloalkyl. In certain embodiments, $R^5$ is $C_{1-6}$ alkyl or $C_{1-6}$ haloalkyl. In certain embodiments, $R^5$ is $C_{10-20}$ alkyl or $C_{10-20}$ haloalkyl.

In certain embodiments, $R^5$ represents independently for each occurrence $C_{1-20}$ aliphatic. In certain embodiments, $R^5$ represents independently for each occurrence $C_{1-6}$ aliphatic. In certain embodiments, $R^5$ represents independently for each occurrence $C_{10-20}$ aliphatic. In certain embodiments, $R^5$ represents independently for each occurrence $C_{1-20}$ alkyl. In certain embodiments, $R^5$ represents independently for each occurrence $C_{1-6}$ alkyl. In certain embodiments, $R^5$ represents independently for each occurrence $C_{10-20}$ alkyl.

In certain embodiments, $R^5$ is $C_{1-20}$ aliphatic. In certain embodiments, $R^5$ is $C_{1-6}$ aliphatic. In certain embodiments, $R^5$ is $C_{10-20}$ aliphatic. In certain embodiments, $R^5$ is $C_{1-20}$ alkyl. In certain embodiments, $R^5$ is $C_{1-6}$ alkyl. In certain embodiments, $R^5$ is $C_{1-5}$ alkyl. In certain embodiments, $R^5$ is $C_{10-20}$ alkyl.

In some embodiments, $R^5$ is —CH$_3$, —CH$_2$CH$_3$, —CH(CH$_3$)$_2$, —C(H)=CH$_2$, —CH$_2$C(H)=CH$_2$, —C≡CH, —(CH$_2$)$_3$CH$_3$, —(CH$_2$)$_3$C(H)=CH$_2$, —(CH$_2$)$_6$C(H)=CH$_2$, —(CH$_2$)$_3$C≡CH, —(CH$_2$)$_6$C≡CH, or cyclopropyl. In some embodiments, $R^5$ is —CH$_3$, —CH$_2$CH$_3$, —CH(CH$_3$)$_2$, —C(H)=CH$_2$, —CH$_2$C(H)=CH$_2$, or —C≡CH. In some embodiments, $R^5$ is —CH$_3$, —CH$_2$CH$_3$, or —CH(CH$_3$)$_2$. In some embodiments, $R^5$ is —C(H)=CH$_2$, —CH$_2$C(H)=CH$_2$, or —C≡CH. In some embodiments, $R^5$ is —CH$_3$. In some embodiments, $R^5$ is —CH$_2$CH$_3$. In some embodiments, $R^3$ is —CH(CH$_3$)$_2$. In some embodiments, $R^5$ is —C(H)=CH$_2$. In some embodiments, $R^5$ is —CH$_2$C(H)=CH$_2$. In some embodiments, $R^5$ is —C≡CH. In some embodiments, $R^5$ is —(CH$_2$)$_3$CH$_3$. In some embodiments, $R^5$ is —(CH$_2$)$_3$C(H)=CH$_2$. In some embodiments, $R^5$ is —(CH$_2$)$_6$C(H)=CH$_2$. In some embodiments, $R^5$ is —(CH$_2$)$_3$C≡CH. In some embodiments, $R^5$ is —(CH$_2$)$_6$C≡CH. In some embodiments, $R^5$ is cyclopropyl.

In certain embodiments, $R^5$ represents independently for each occurrence $C_{1-20}$ haloaliphatic. In certain embodiments, $R^5$ represents independently for each occurrence $C_{1-8}$ haloaliphatic. In certain embodiments, $R^5$ represents independently for each occurrence $C_{10-20}$ haloaliphatic. In certain embodiments, $R^5$ represents independently for each occurrence $C_{1-20}$ haloalkyl. In certain embodiments, $R^5$ represents independently for each occurrence $C_{1-8}$ haloalkyl. In certain embodiments, $R^5$ represents independently for each occurrence $C_{10-20}$ haloalkyl.

In certain embodiments, $R^5$ is $C_{1-20}$ haloaliphatic. In certain embodiments, $R^5$ is $C_{1-8}$ haloaliphatic. In certain embodiments, $R^5$ is $C_{10-20}$ haloaliphatic. In certain embodiments, $R^5$ is $C_{1-20}$ haloalkyl. In certain embodiments, $R^5$ is $C_{1-8}$ haloalkyl. In certain embodiments, $R^5$ is $C_{10-20}$ haloalkyl.

In some embodiments, $R^5$ represents independently for each occurrence —C(H)($R^6$)—N($R^7$)$_2$. In some embodiments, $R^5$ is —C(H)($R^6$)—N($R^7$)$_2$. In some embodiments, $R^5$ represents independently for each occurrence

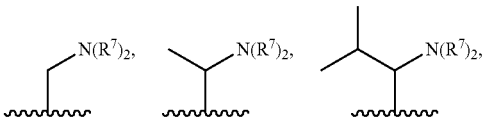

or

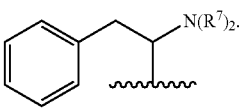

In some embodiments, $R^5$ is

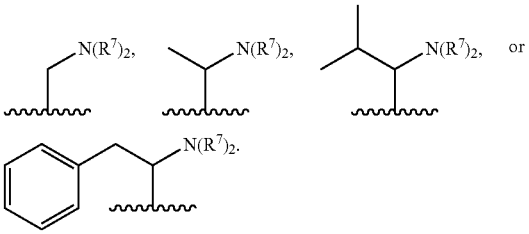

In some embodiments, $R^5$ is

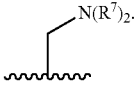

In some embodiments, $R^5$ is

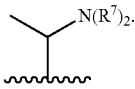

In some embodiments, $R^5$ is

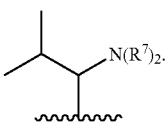

In some embodiments, $R^5$ is

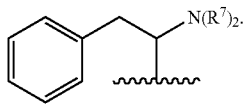

In some embodiments, $R^5$ represents independently for each occurrence

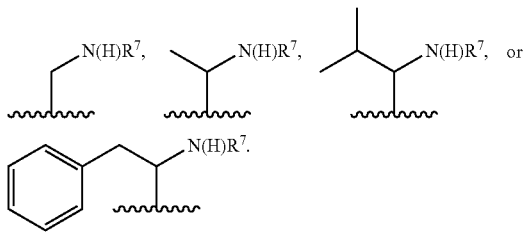

In some embodiments, $R^5$ is

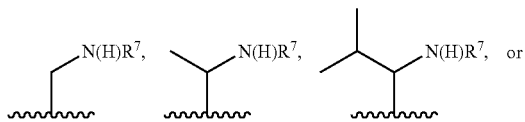

In some embodiments, $R^5$ is

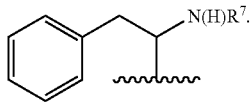

In some embodiments, $R^5$ is

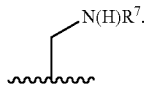

In some embodiments, $R^5$ is

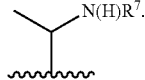

In some embodiments, $R^5$ is

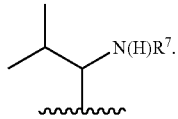

In some embodiments, $R^5$ is

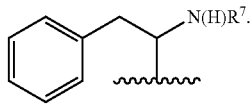

In some embodiments, $R^5$ represents independently for each occurrence phenyl substituted with m occurrences of $R^{10}$. In some embodiments, $R^5$ is phenyl substituted with m occurrences of $R^{10}$. In some embodiments, $R^5$ is phenyl.

In some embodiments, $R^5$ represents independently for each occurrence —$CH_2$-phenyl, wherein said phenyl is substituted with m occurrences of $R^{10}$. In some embodiments, $R^5$ is —$CH_2$-phenyl, wherein said phenyl is substituted with m occurrences of $R^{10}$. In some embodiments, $R^5$ is —$CH_2$-phenyl.

In some embodiments, $R^5$ is hydrogen.

As defined generally above, $R^6$ is $C_{1-6}$ alkyl or hydrogen, wherein said $C_{1-6}$ alkyl is optionally substituted with phenyl. In certain embodiments, $R^6$ is methyl, isopropyl, benzyl, or hydrogen. In certain embodiments, $R^6$ is $C_{1-6}$ alkyl optionally substituted with phenyl. In certain embodiments, $R^6$ is $C_{1-6}$ alkyl. In certain embodiments, $R^6$ is $C_{1-4}$ alkyl. In certain embodiments, $R^6$ is $C_{2-6}$ alkyl. In certain embodiments, $R^6$ is $C_{1-6}$ alkyl substituted with phenyl. In certain embodiments, $R^6$ is hydrogen.

As defined generally above, $R^7$ represents independently for each occurrence hydrogen, $C_{1-6}$ alkyl, —$C(O)CH_3$, —$C(O)OC(CH_3)_3$, —$C(O)O(CH_2)$phenyl, or —$C(O)O(CH_2)$-fluorenyl.

In certain embodiments, one occurrence of $R^7$ is hydrogen or $C_{1-6}$ alkyl, and the other occurrence of $R^7$ is hydrogen, $C_{1-6}$ alkyl, —$C(O)CH_3$, —$C(O)OC(CH_3)_3$, —$C(O)O(CH_2)$phenyl, or —$C(O)O(CH_2)$fluorenyl. In certain embodiments, one occurrence of $R^7$ is hydrogen or $C_{1-6}$ alkyl, and the other occurrence of $R^7$ is —$C(O)CH_3$, —$C(O)OC(CH_3)_3$, —$C(O)O(CH_2)$phenyl, or —$C(O)O(CH_2)$fluorenyl.

In certain embodiments, one occurrence of $R^7$ is hydrogen, and the other occurrence of $R^7$ is hydrogen, $C_{1-6}$ alkyl, —$C(O)CH_3$, —$C(O)OC(CH_3)_3$, —$C(O)O(CH_2)$phenyl, or —$C(O)O(CH_2)$-fluorenyl. In certain embodiments, one occurrence of $R^7$ is hydrogen, and the other occurrence of $R^7$ is —$C(O)CH_3$, —$C(O)OC(CH_3)_3$, —$C(O)O(CH_2)$phenyl, or —$C(O)O(CH_2)$fluorenyl.

In certain embodiments, $R^7$ represents independently for each occurrence hydrogen or $C_{1-6}$ alkyl. In certain embodiments, $R^7$ is hydrogen. In certain embodiments, $R^7$ represents independently for each occurrence $C_{1-6}$ alkyl.

As defined generally above, $R^8$ is hydrogen, halo, —$CH_3$, or —$CF_3$. In certain embodiments, $R^8$ is hydrogen or halo. In certain embodiments, $R^8$ is hydrogen or fluoro. In certain embodiments, $R^8$ is halo or —$CF_3$. In certain embodiments, $R^8$ is fluoro or —$CF_3$. In certain embodiments, $R^8$ is —$CH_3$ or —$CF_3$. In certain embodiments, $R^8$ is hydrogen. In certain embodiments, $R^8$ is halo. In certain embodiments, $R^8$ is fluoro. In certain embodiments, $R^8$ is —$CH_3$. In certain embodiments, $R^8$ is —$CF_3$.

As defined generally above, $R^9$ is halo, —$CH_3$, or —$CF_3$. In certain embodiments, $R^9$ is halo or —$CF_3$. In certain embodiments, $R^9$ is fluoro or —$CF_3$. In certain embodiments, $R^9$ is —$CH_3$ or —$CF_3$. In certain embodiments, $R^9$ is halo. In certain embodiments, $R^9$ is fluoro. In certain embodiments, $R^9$ is —$CH_3$. In certain embodiments, $R^9$ is —$CF_3$.

As defined generally above, $R^{10}$ represents independently for each occurrence $C_{1-6}$ alkyl, $C_{1-6}$ alkoxyl, $C_{1-6}$ haloalkyl, or halo. In certain embodiments, $R^{10}$ represents independently for each occurrence —$CH_3$, —$OCH_3$, —$CF_3$, or halo.

In certain embodiments, $R^{10}$ represents independently for each occurrence $C_{1-6}$ alkyl. In certain embodiments, $R^{10}$ is —$CH_3$. In certain embodiments, $R^{10}$ represents independently for each occurrence $C_{1-6}$ alkoxyl. In certain embodiments, $R^{10}$ is —$OCH_3$. In certain embodiments, $R^{10}$ represents independently for each occurrence $C_{1-6}$ haloalkyl. In certain embodiments, $R^{10}$ is —$CF_3$. In certain embodiments, $R^{10}$ represents independently for each occurrence halo.

As defined generally above, $B^1$ is

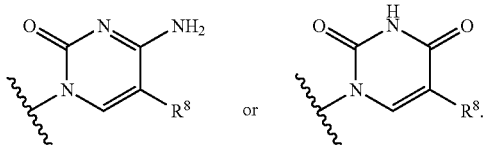

In some embodiments, $B^1$ is

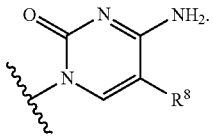

In some embodiments, $B^1$ is

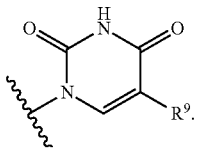

As defined generally above, m is 0, 1, or 2. In certain embodiments, m is 0. In certain embodiments, m is 1. In certain embodiments, m is 2. In certain embodiments, m is 0 or 1. In certain embodiments, m is 1 or 2.

The description above describes multiple embodiments relating to compounds of Formula II. The patent application specifically contemplates all combinations of the embodiments.

Another aspect of the disclosure provides a compound represented by Formula II-A:

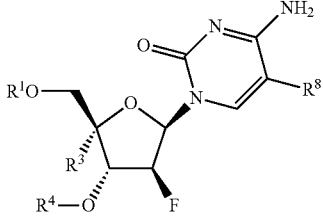

(II-A)

or a pharmaceutically acceptable salt thereof; wherein:
$R^1$ and $R^4$ are —$C(O)R^5$;
$R^3$ is halomethyl;
$R^5$ represents independently for each occurrence $C_{1-20}$ aliphatic, $C_{1-20}$ haloaliphatic, —$C(H)(R^6)$—$N(R^7)_2$, phenyl, or —$CH_2$-phenyl; wherein each phenyl is substituted with m occurrences of $R^{10}$;
$R^6$ is $C_{1-6}$ alkyl or hydrogen, wherein said $C_{1-6}$ alkyl is optionally substituted with phenyl;
$R^7$ represents independently for each occurrence hydrogen, $C_{1-6}$ alkyl, —$C(O)CH_3$, —$C(O)OC(CH_3)_3$, —$C(O)O(CH_2)$phenyl, or —$C(O)O(CH_2)$fluorenyl;
$R^8$ is halo or —$CF_3$;
$R^{10}$ represents independently for each occurrence $C_{1-6}$ alkyl, $C_{1-6}$ alkoxyl, $C_{1-6}$ haloalkyl, or halo; and
m is 0, 1, or 2.

As described generally above, $R^1$ and $R^4$ are —$C(O)R^5$. In certain embodiments $R^1$ and $R^4$ are selected from those depicted in Tables 1, 1-A, 1-B, 1-C, and 1-D.

As described generally above, $R^3$ is halomethyl. In certain embodiments $R^3$ is —$CH_2Cl$ or —$CH_2F$. In certain embodiments $R^3$ is —$CH_2Cl$. In certain embodiments $R^3$ is selected from those depicted in Tables 1, 1-A, 1-B, 1-C, and 1-D.

As described generally above, $R^5$ represents independently for each occurrence $C_{1-20}$ aliphatic, $C_{1-20}$ haloaliphatic, —$C(H)(R^{6A})$—$N(R^{7A})_2$, phenyl, —$CH_2$-phenyl, or hydrogen; wherein each phenyl is substituted with m occurrences of $R^{10A}$. In certain embodiments, $R^5$ represents independently for each occurrence $C_{1-20}$ aliphatic, $C_{1-20}$ haloaliphatic, —$C(H)(R^{6A})$—$N(R^{7A})_2$, phenyl, or —$CH_2$-phenyl; wherein each phenyl is substituted with m occurrences of $R^{10A}$. In certain embodiments, $R^5$ represents independently for each occurrence $C_{1-20}$ aliphatic. In certain embodiments, $R^5$ represents independently for each occurrence $C_{1-20}$ haloaliphatic. In certain embodiments, $R^5$ represents independently for each occurrence —$C(H)(R^{6A})$—$N(R^{7A})_2$. In certain embodiments, $R^5$ represents independently for each occurrence phenyl, wherein each phenyl is substituted with m occurrences of $R^{10A}$. In certain embodiments, $R^5$ represents independently for each occurrence —$CH_2$-phenyl, wherein each phenyl is substituted with m occurrences of $R^{10A}$. In certain embodiments, $R^5$ is hydrogen. In certain embodiments, $R^5$ is $C_{1-20}$ aliphatic. In certain embodiments, $R^5$ is $C_{1-20}$ haloaliphatic. In certain embodiments, $R^5$ is —$C(H)(R^{6A})$—$N(R^{7A})_2$. In certain embodiments, $R^5$ is phenyl, wherein each phenyl is substituted with m occurrences of $R^{10A}$. In certain embodiments, $R^5$ is —$CH_2$-phenyl, wherein each phenyl is substituted with m occurrences of $R^{10A}$. In certain embodiments $R^5$ is selected from those depicted in Tables 1, 1-A, 1-B, 1-C, and 1-D.

As described generally above, $R^6$ is $C_{1-6}$ alkyl or hydrogen, wherein said $C_{1-6}$ alkyl is optionally substituted with phenyl. In certain embodiments $R^6$ is $C_{1-6}$ alkyl, wherein said $C_{1-6}$ alkyl is optionally substituted with phenyl. In certain embodiments $R^6$ hydrogen. In certain embodiments $R^6$ is $C_{1-6}$ alkyl. In certain embodiments $R^6$ is selected from those depicted in Tables 1, 1-A, 1-B, 1-C, and 1-D.

As described generally above, $R^7$ represents independently for each occurrence hydrogen, $C_{1-6}$ alkyl, —$C(O)CH_3$, —$C(O)OC(CH_3)_3$, —$C(O)O(CH_2)$phenyl, or —$C(O)O(CH_2)$fluorenyl. In certain embodiments $R^7$ represents independently for each occurrence $C_{1-6}$ alkyl. In certain embodiments $R^7$ is hydrogen. In certain embodiments $R^7$ is $C_{1-6}$ alkyl. In certain embodiments $R^7$ is —$C(O)CH_3$. In certain embodiments $R^7$ is —$C(O)O(CH_2)$phenyl. In certain embodiments $R^7$ is —$C(O)O(CH_2)$fluorenyl. In certain embodiments $R^7$ represents independently for each occurrence $C_{1-6}$ alkyl, —$C(O)CH_3$, —$C(O)OC(CH_3)_3$, —$C(O)O(CH_2)$phenyl, or —$C(O)O(CH_2)$fluorenyl. In certain embodiments $R^7$ is selected from those depicted in Tables 1, 1-A, 1-B, 1-C, and 1-D.

As described generally above, $R^8$ is halo or —$CF_3$. In certain embodiments, $R^8$ is halo. In certain embodiments, $R^8$ is fluoro. In certain embodiments, $R^8$ is —$CF_3$. In certain embodiments, $R^8$ is selected from those depicted in Tables 1, 1-A, 1-B, 1-C, and 1-D.

As described generally above, $R^{10}$ represents independently for each occurrence $C_{1-6}$ alkyl, $C_{1-6}$ alkoxyl, $C_{1-6}$ haloalkyl, or halo. In certain embodiments $R^{10}$ represents independently for each occurrence $C_{1-6}$ alkyl. In certain embodiments $R^{10}$ represents independently for each occurrence $C_{1-6}$ alkoxyl. In certain embodiments $R^{10}$ represents independently for each occurrence $C_{1-6}$ haloalkyl. In certain embodiments $R^{10}$ represents independently for each occurrence halo. In certain embodiments $R^{10}$ is $C_{1-6}$ alkyl, $C_{1-6}$ alkoxyl, $C_{1-6}$ haloalkyl, or halo. In certain embodiments $R^{10}$ is selected from those depicted in Tables 1, 1-A, 1-B, 1-C, and 1-D.

As defined generally above, m is 0, 1, or 2. In certain embodiments, m is 0. In certain embodiments, m is 1. In certain embodiments, m is 2. In certain embodiments, m is 1 or 2. In certain embodiments, m is 0 or 2. In certain embodiments, m is 0 or 2. In certain embodiments m is selected from those depicted in Tables 1, 1-A, 1-B, 1-C, and 1-D.

Another aspect of the disclosure provides a compound represented by Formula III:

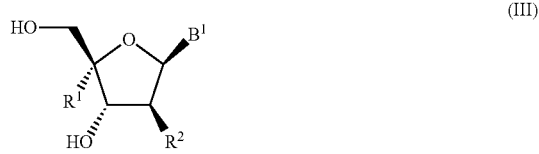

(III)

or a pharmaceutically acceptable salt thereof; wherein:
$R^1$ is —$CH_2Cl$, —$CH_2F$, —$CH_2Br$, —$CH_2I$, —$CF_3$, —$CH_2CH_3$, —$C(H)=CH_2$, —$C(H)=C=CH_2$, or cyclopropyl; each of which optionally has one or more hydrogen replaced with deuterium;
$R^2$ is fluoro or —OH;
$R^3$ is halo, —$CH_3$, or —$CF_3$; and
$B^1$ is

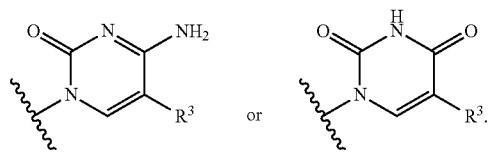

The definitions of variables in Formula III above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is a compound of Formula III.

As defined generally above, $R^1$ is —$CH_2Cl$, —$CH_2F$, —$CH_2Br$, —$CH_2I$, —$CF_3$, —$CH_2CH_3$, —$C(H)=CH_2$, —$C(H)=C=CH_2$, or cyclopropyl, each of which optionally has one or more hydrogen replaced with deuterium. In some embodiments, $R^1$ is —$CH_2Cl$, —$CH_2F$, —$CH_2Br$, —$CH_2I$, —$CH_2CH_3$, —$C(H)=CH_2$, —$C(H)=C=CH_2$, or cyclopropyl, each of which has one or more hydrogen replaced with deuterium.

In some embodiments, $R^1$ is —$CH_2Cl$, —$CH_2F$, —$CH_2Br$, —$CH_2I$, —$CF_3$, —$CH_2CH_3$, —$C(H)=CH_2$, —$C(H)=C=CH_2$, or cyclopropyl. In some embodiments, $R^1$ is —$CH_2Cl$, —$CH_2F$, —$CH_2Br$, —$CH_2I$, or —$CF_3$. In some embodiments, $R^1$ is —$CH_2CH_3$, —$C(H)=CH_2$, —$C(H)=C=CH_2$, or cyclopropyl.

In some embodiments, $R^1$ is —$CH_2F$, —$CH_2Br$, —$CH_2I$, or —$CF_3$. In some embodiments, $R^1$ is —$CH_2Cl$, —$CH_2Br$, —$CH_2I$, or —$CF_3$. In some embodiments, $R^1$ is —$CH_2Cl$, —$CH_2F$, —$CH_2I$, or —$CF_3$. In some embodiments, $R^1$ is —$CH_2Cl$, —$CH_2F$, —$CH_2Br$, or —$CF_3$. In some embodiments, $R^1$ is —$CH_2Cl$, —$CH_2F$, —$CH_2Br$, or —$CH_2I$.

In some embodiments, $R^1$ is —$CH_2Br$, —$CH_2I$, or —$CF_3$. In some embodiments, $R^1$ is —$CH_2Cl$, —$CH_2I$, or —$CF_3$. In some embodiments, $R^1$ is —$CH_2Cl$, —$CH_2F$, or —$CF_3$. In some embodiments, $R^1$ is —$CH_2Cl$, —$CH_2F$, or —$CH_2Br$. In some embodiments, $R^1$ is —$CH_2F$, —$CH_2I$, or —$CF_3$. In some embodiments, $R^1$ is —$CH_2F$, —$CH_2Br$, or —$CF_3$. In some embodiments, $R^1$ is —$CH_2F$, —$CH_2Br$, or —$CH_2I$. In some embodiments, $R^1$ is —$CH_2Cl$, —$CH_2Br$, or —$CF_3$. In some embodiments, $R^1$ is —$CH_2Cl$, —$CH_2Br$, or —$CH_2I$. In some embodiments, $R^1$ is —$CH_2Cl$, —$CH_2F$, or —$CH_2I$.

In some embodiments, $R^1$ is —$CH_2I$ or —$CF_3$. In some embodiments, $R^1$ is —$CH_2Cl$ or —$CH_2F$. In some embodiments, $R^1$ is —$CH_2Cl$ or —$CF_3$. In some embodiments, $R^1$ is —$CH_2F$ or —$CH_2I$. In some embodiments, $R^1$ is —$CH_2Cl$ or —$CH_2Br$. In some embodiments, $R^1$ is —$CH_2Br$ or —$CH_2I$. In some embodiments, $R^1$ is —$CH_2Br$ or —$CF_3$. In some embodiments, $R^1$ is —$CH_2Cl$ or —$CH_2I$. In some embodiments, $R^1$ is —$CH_2F$ or —$CF_3$. In some embodiments, $R^1$ is —$CH_2F$ or —$CH_2Br$.

In some embodiments, $R^1$ is —$CH_2Cl$. In some embodiments, $R^1$ is —$CH_2F$. In some embodiments, $R^1$ is —$CH_2Br$. In some embodiments, $R^1$ is —$CH_2I$. In some embodiments, $R^1$ is —$CF_3$.

In some embodiments, $R^1$ is —$CH_2Cl$, —$CH_2F$, —$CH_2Br$, —$CH_2I$, or —$CF_3$, each of which optionally has one or more hydrogen replaced with deuterium. In some embodiments, $R^1$ is —$CH_2Cl$, —$CH_2F$, —$CH_2Br$, or —$CH_2I$, each of which has one or more hydrogen replaced with deuterium. In some embodiments, $R^1$ is —$CD_2Cl$, —$CD_2F$, —$CD_2Br$, or —$CD_2I$. In some embodiments, $R^1$ is —$CD_2Cl$ or —$CD_2F$. In some embodiments, $R^1$ is —$CD_2Cl$. In some embodiments, $R^1$ is —$CD_2F$. In some embodiments, $R^1$ is —$CD_2Br$. In some embodiments, $R^1$ is —$CD_2I$.

In some embodiments, $R^1$ is —$CH_2CH_3$, —$C(H)=CH_2$, or —$C(H)=C=CH_2$. In some embodiments, $R^1$ is —$CH_2CH_3$ or cyclopropyl. In some embodiments, $R^1$ is —$C(H)=CH_2$, —$C(H)=C=CH_2$, or cyclopropyl. In some embodiments, $R^1$ is —$C(H)=CH_2$ or —$C(H)=C=CH_2$. In some embodiments, $R^1$ is —$CH_2CH_3$. In some embodiments, $R^1$ is —$C(H)=CH_2$. In some embodiments, $R^1$ is —$C(H)=C=CH_2$. In some embodiments, $R^1$ is cyclopropyl.

In some embodiments, $R^1$ is —$CH_2CH_3$, —$C(H)=CH_2$, —$C(H)=C=CH_2$, or cyclopropyl, each of which optionally has one or more hydrogen replaced with deuterium. In some embodiments, $R^1$ is —$CH_2CH_3$, —$C(H)=CH_2$, —$C(H)=C=CH_2$, or cyclopropyl, each of which has one or more hydrogen replaced with deuterium. In some embodiments, $R^1$ is —$CH_2CH_3$ which has one or more hydrogen replaced with deuterium. In some embodiments, $R^1$ is —$C(H)=CH_2$ which has one or more hydrogen replaced with deuterium. In some embodiments, $R^1$ is —C(H)=C=CH$_2$ which has one or more hydrogen replaced with deuterium. In some embodiments, $R^1$ is cyclopropyl which has one or more hydrogen replaced with deuterium.

As defined generally above, $R^2$ is fluoro or —OH. In some embodiments, $R^2$ is fluoro. In some embodiments, $R^2$ is —OH.

As defined generally above, $R^3$ is halo, —CH$_3$, or —CF$_3$. In some embodiments, $R^3$ is fluoro, chloro, —CH$_3$, or —CF$_3$. In some embodiments, $R^3$ is fluoro, —CH$_3$, or —CF$_3$.

In some embodiments, $R^3$ is —CH$_3$ or —CF$_3$. In some embodiments, $R^3$ is halo or —CF$_3$. In some embodiments, $R^3$ is halo or —CH$_3$.

In some embodiments, $R^3$ is halo. In some embodiments, $R^3$ is fluoro or chloro. In some embodiments, $R^3$ is fluoro. In some embodiments, $R^3$ is chloro. In some embodiments, $R^3$ is bromo. In some embodiments, $R^3$ is iodo.

In some embodiments, $R^3$ is —CH$_3$. In some embodiments, $R^3$ is —CF$_3$.

As defined generally above, $B^1$ is

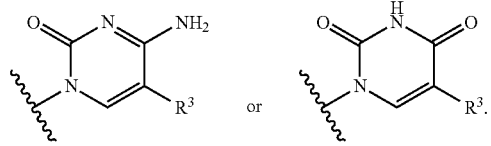

In some embodiments, $B^1$ is

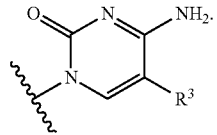

In some embodiments, $B^1$ is

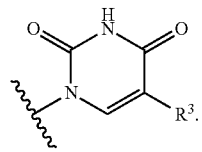

The description above describes multiple embodiments relating to compounds of Formula III. The patent application specifically contemplates all combinations of the embodiments.

The invention further provides compounds represented by Formula III-A:

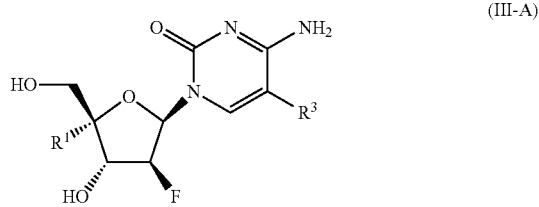

or a pharmaceutically acceptable salt thereof; wherein:
$R^1$ is —CH$_2$Cl, —CH$_2$Br, or —CH$_2$F; each of which optionally has one or more hydrogen replaced with deuterium; and
$R^3$ is halo or —CF$_3$.

In certain embodiments, the compound is a compound of Formula III-A.

As described generally above, $R^1$ is —CH$_2$Cl, —CH$_2$Br, or —CH$_2$F; each of which optionally has one or more hydrogen replaced with deuterium. In certain embodiments, $R^1$ is —CH$_2$Cl. In certain embodiments, $R^1$ is —CH$_2$Br. In certain embodiments, $R^1$ is —CH$_2$F. In certain embodiments, $R^1$ is —CH$_2$Cl or —CH$_2$F. In certain embodiments, $R^1$ is selected from those depicted in Tables 1, 1-A, 1-B, 1-C, and 1-D.

As described generally above, $R^3$ is halo or —CF$_3$. In certain embodiments, $R^3$ is halo. In certain embodiments, $R^3$ is —CF$_3$. In certain embodiments, $R^3$ is Cl, Br, or F. In certain embodiments, $R^3$ is F. In certain embodiments, $R^3$ is selected from those depicted in Tables 1, 1-A, 1-B, 1-C, and 1-D.

The invention further provides compounds represented by Formula III-B:

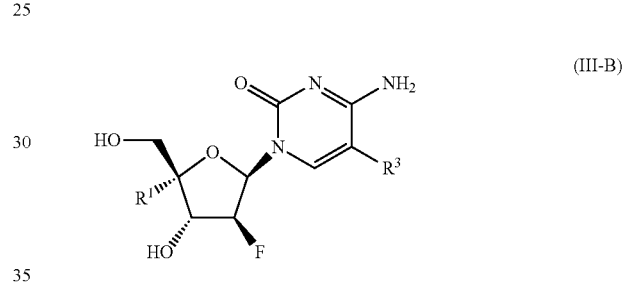

or a pharmaceutically acceptable salt thereof; wherein:
$R^1$ is —N$_3$; and
$R^3$ is halo or —CF$_3$.

In certain embodiments, the compound is a compound of Formula III-B.

As described generally above, $R^1$ is —N$_3$. In certain embodiments, $R^1$ is selected from those depicted in Tables 1, 1-A, 1-B, 1-C, and 1-D.

As described generally above, $R^3$ is halo or —CF$_3$. In certain embodiments, $R^3$ is halo. In certain embodiments, $R^3$ is —CF$_3$. In certain embodiments, $R^3$ is Cl, Br, or F. In certain embodiments, $R^3$ is F. In certain embodiments, $R^3$ is selected from those depicted in Tables 1, 1-A, 1-B, 1-C, and 1-D.

Another aspect of the disclosure provides a compound represented by Formula IV:

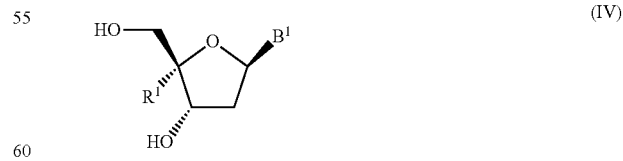

or a pharmaceutically acceptable salt thereof; wherein:
$R^1$ is —CH$_2$Cl, —CH$_2$F, —CH$_2$Br, —CH$_2$I, —CF$_3$, —CH$_2$CH$_3$, —C(H)=CH$_2$, —C(H)=C=CH$_2$, or cyclopropyl; each of which optionally has one or more hydrogen replaced with deuterium;
$R^2$ is hydrogen, halo, or —CF$_3$; and $B^1$ is

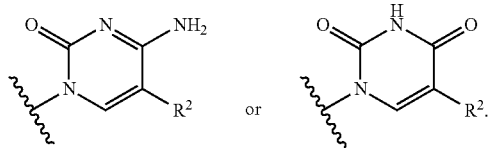

The definitions of variables in Formula IV above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is a compound of Formula IV.

As defined generally above, $R^1$ is —$CH_2Cl$, —$CH_2F$, —$CH_2Br$, —$CH_2I$, —$CF_3$, —$CH_2CH_3$, —$C(H)$=$CH_2$, —$C(H)$=$C$=$CH_2$, or cyclopropyl, each of which optionally has one or more hydrogen replaced with deuterium. In some embodiments, $R^1$ is —$CH_2Cl$, —$CH_2F$, —$CH_2Br$, —$CH_2I$, —$CH_2CH_3$, —$C(H)$=$CH_2$, —$C(H)$=$C$=$CH_2$, or cyclopropyl, each of which has one or more hydrogen replaced with deuterium.

In some embodiments, $R^1$ is —$CH_2Cl$, —$CH_2F$, —$CH_2Br$, —$CH_2I$, —$CF_3$, —$CH_2CH_3$, —$C(H)$=$CH_2$, —$C(H)$=$C$=$CH_2$, or cyclopropyl. In some embodiments, $R^1$ is —$CH_2Cl$, —$CH_2F$, —$CH_2Br$, —$CH_2I$, or —$CF_3$. In some embodiments, $R^1$ is —$CH_2CH_3$, —$C(H)$=$CH_2$, —$C(H)$=$C$=$CH_2$, or cyclopropyl.

In some embodiments, $R^1$ is —$CH_2F$, —$CH_2Br$, —$CH_2I$, or —$CF_3$. In some embodiments, $R^1$ is —$CH_2Cl$, —$CH_2Br$, —$CH_2I$, or —$CF_3$. In some embodiments, $R^1$ is —$CH_2Cl$, —$CH_2F$, —$CH_2I$, or —$CF_3$. In some embodiments, $R^1$ is —$CH_2Cl$, —$CH_2F$, —$CH_2Br$, or —$CF_3$. In some embodiments, $R^1$ is —$CH_2Cl$, —$CH_2F$, —$CH_2Br$, or —$CH_2I$.

In some embodiments, $R^1$ is —$CH_2Br$, —$CH_2I$, or —$CF_3$. In some embodiments, $R^1$ is —$CH_2Cl$, —$CH_2I$, or —$CF_3$. In some embodiments, $R^1$ is —$CH_2Cl$, —$CH_2F$, or —$CF_3$. In some embodiments, $R^1$ is —$CH_2Cl$, —$CH_2F$, or —$CH_2Br$. In some embodiments, $R^1$ is —$CH_2F$, —$CH_2I$, or —$CF_3$. In some embodiments, $R^1$ is —$CH_2F$, —$CH_2Br$, or —$CF_3$. In some embodiments, $R^1$ is —$CH_2F$, —$CH_2Br$, or —$CH_2I$. In some embodiments, $R^1$ is —$CH_2Cl$, —$CH_2Br$, or —$CF_3$. In some embodiments, $R^1$ is —$CH_2Cl$, —$CH_2Br$, or —$CH_2I$. In some embodiments, $R^1$ is —$CH_2Cl$, —$CH_2F$, or —$CH_2I$.

In some embodiments, $R^1$ is —$CH_2I$ or —$CF_3$. In some embodiments, $R^1$ is —$CH_2Cl$ or —$CH_2F$. In some embodiments, $R^1$ is —$CH_2Cl$ or —$CF_3$. In some embodiments, $R^1$ is —$CH_2F$ or —$CH_2I$. In some embodiments, $R^1$ is —$CH_2Cl$ or —$CH_2Br$. In some embodiments, $R^1$ is —$CH_2Br$ or —$CH_2I$. In some embodiments, $R^1$ is —$CH_2Br$ or —$CF_3$. In some embodiments, $R^1$ is —$CH_2Cl$ or —$CH_2I$. In some embodiments, $R^1$ is —$CH_2F$ or —$CF_3$. In some embodiments, $R^1$ is —$CH_2F$ or —$CH_2Br$.

In some embodiments, $R^1$ is —$CH_2Cl$. In some embodiments, $R^1$ is —$CH_2F$. In some embodiments, $R^1$ is —$CH_2Br$. In some embodiments, $R^1$ is —$CH_2I$. In some embodiments, $R^1$ is —$CF_3$.

In some embodiments, $R^1$ is —$CH_2Cl$, —$CH_2F$, —$CH_2Br$, —$CH_2I$, or —$CF_3$, each of which optionally has one or more hydrogen replaced with deuterium. In some embodiments, $R^1$ is —$CH_2Cl$, —$CH_2F$, —$CH_2Br$, or —$CH_2I$, each of which has one or more hydrogen replaced with deuterium. In some embodiments, $R^1$ is —$CD_2Cl$, —$CD_2F$, —$CD_2Br$, or —$CD_2I$. In some embodiments, $R^1$ is —$CD_2Cl$ or —$CD_2F$. In some embodiments, $R^1$ is —$CD_2Cl$. In some embodiments, $R^1$ is —$CD_2F$. In some embodiments, $R^1$ is —$CD_2Br$. In some embodiments, $R^1$ is —$CD_2I$.

In some embodiments, $R^1$ is —$CH_2CH_3$, —$C(H)$=$CH_2$, or —$C(H)$=$C$=$CH_2$. In some embodiments, $R^1$ is —$CH_2CH_3$ or cyclopropyl. In some embodiments, $R^1$ is —$C(H)$=$CH_2$, —$C(H)$=$C$=$CH_2$, or cyclopropyl. In some embodiments, $R^1$ is —$C(H)$=$CH_2$ or —$C(H)$=$C$=$CH_2$. In some embodiments, $R^1$ is —$CH_2CH_3$. In some embodiments, $R^1$ is —$C(H)$=$CH_2$. In some embodiments, $R^1$ is —$C(H)$=$C$=$CH_2$. In some embodiments, $R^1$ is cyclopropyl.

In some embodiments, $R^1$ is —$CH_2CH_3$, —$C(H)$=$CH_2$, —$C(H)$=$C$=$CH_2$, or cyclopropyl, each of which optionally has one or more hydrogen replaced with deuterium. In some embodiments, $R^1$ is —$CH_2CH_3$, —$C(H)$=$CH_2$, —$C(H)$=$C$=$CH_2$, or cyclopropyl, each of which has one or more hydrogen replaced with deuterium. In some embodiments, $R^1$ is —$CH_2CH_3$ which has one or more hydrogen replaced with deuterium. In some embodiments, $R^1$ is —$C(H)$=$CH_2$ which has one or more hydrogen replaced with deuterium. In some embodiments, $R^1$ is —$C(H)$=$C$=$CH_2$ which has one or more hydrogen replaced with deuterium. In some embodiments, $R^1$ is cyclopropyl which has one or more hydrogen replaced with deuterium.

As defined generally above, $R^2$ is hydrogen, halo, or —$CF_3$. In some embodiments, $R^2$ is hydrogen or —$CF_3$. In some embodiments, $R^2$ is halo or —$CF_3$. In some embodiments, $R^2$ is halo or hydrogen. In some embodiments, $R^2$ is fluoro or —$CF_3$. In some embodiments, $R^2$ is fluoro or hydrogen.

In some embodiments, $R^2$ is halo. In some embodiments, $R^2$ is fluoro or chloro. In some embodiments, $R^2$ is fluoro. In some embodiments, $R^2$ is chloro. In some embodiments, $R^2$ is bromo. In some embodiments, $R^2$ is iodo.

In some embodiments, $R^2$ is hydrogen. In some embodiments, $R^2$ is —$CF_3$.

As defined generally above, $B^1$ is

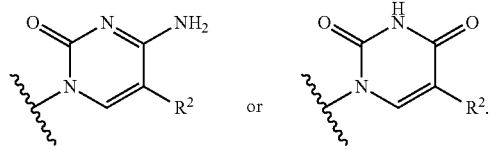

In some embodiments, $B^1$ is

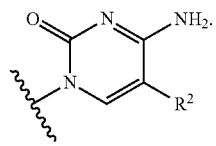

In some embodiments, $B^1$ is

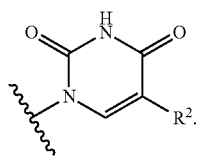

The description above describes multiple embodiments relating to compounds of Formula IV. The patent application specifically contemplates all combinations of the embodiments.

Another aspect of the disclosure provides a compound represented by Formula IV-A:

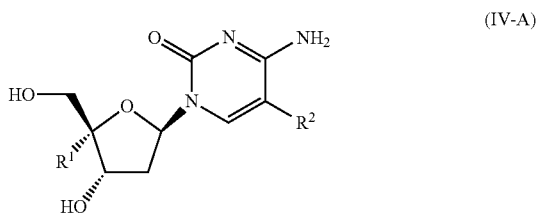

(IV-A)

or a pharmaceutically acceptable salt thereof; wherein:
$R^1$ is (i) —CH$_2$Cl, —CH$_2$F, or —CH$_2$Br, each of which optionally has one or more hydrogen replaced with deuterium, or (ii) —N$_3$; and
$R^2$ is hydrogen or halo.

In certain embodiments, the compound is a compound of Formula IV-A.

As described generally above, $R^1$ is (i) —CH$_2$Cl, —CH$_2$F, or —CH$_2$Br, each of which optionally has one or more hydrogen replaced with deuterium, or (ii) —N$_3$. In certain embodiments, $R^1$ is —CH$_2$Cl, —CH$_2$F, or —CH$_2$Br, each of which optionally has one or more hydrogen replaced with deuterium. In certain embodiments, $R^1$ is —N$_3$. In certain embodiments, $R^1$ is —CH$_2$Cl, —CH$_2$F, or —CH$_2$Br. In certain embodiments, $R^1$ is —CH$_2$Cl. In certain embodiments, $R^1$ is —CH$_2$F. In certain embodiments, $R^1$ is —CH$_2$Br. In certain embodiments, $R^1$ is selected from those depicted in Tables 1, 1-A, 1-B, 1-C, and 1-D.

As described generally above, $R^2$ is hydrogen or halo. In certain embodiments, $R^2$ is hydrogen. In certain embodiments, $R^2$ is halo. In certain embodiments, $R^2$ is Cl, Br, or F. In certain embodiments, $R^2$ is F. In certain embodiments, $R^2$ is selected from those depicted in Tables 1, 1-A, 1-B, 1-C, and 1-D.

Another aspect of the disclosure provides a compound represented by Formula IV-B:

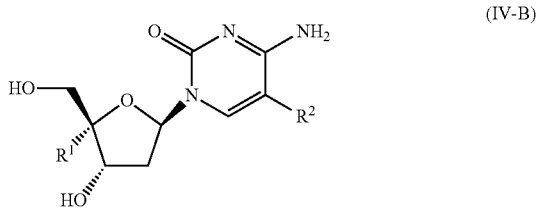

(IV-B)

or a pharmaceutically acceptable salt thereof; wherein:
$R^1$ is —CH$_2$Cl, —CH$_2$F, or —CH$_2$Br, each of which optionally has one or more hydrogen replaced with deuterium; and
$R^2$ is F.

In certain embodiments, the compound is a compound of Formula IV-B.

As described generally above, $R^1$ is —CH$_2$Cl, —CH$_2$F, or —CH$_2$Br, each of which optionally has one or more hydrogen replaced with deuterium. In certain embodiments, $R^1$ is —CH$_2$Cl. In certain embodiments, $R^1$ is —CH$_2$F. In certain embodiments, $R^1$ is —CH$_2$Br. In certain embodiments, $R^1$ is selected from those depicted in Tables 1, 1-A, 1-B, 1-C, and 1-D.

Another aspect of the disclosure provides a compound represented by Formula V:

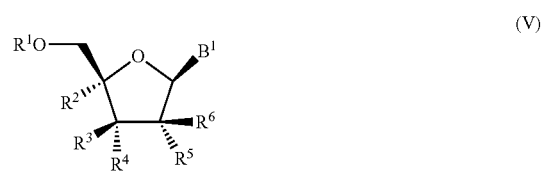

(V)

or a pharmaceutically acceptable salt thereof; wherein:
$B^1$ is

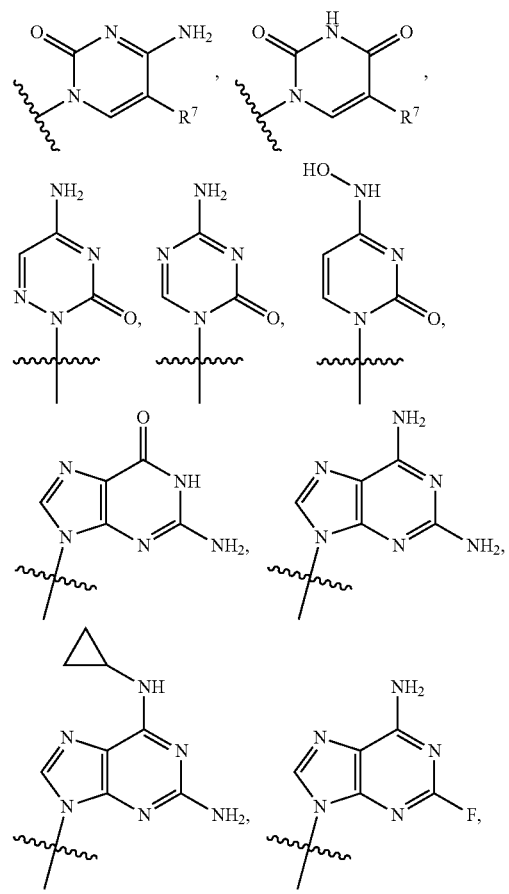

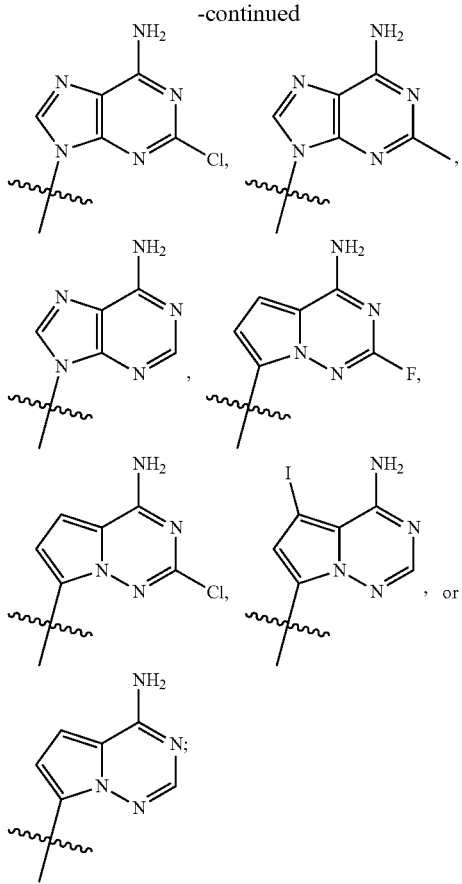

$R^1$ is —H, —C(O)$R^8$, or —P(O)(OH)—OP(O)(OH)—OP(O)(OH)$_2$;

$R^2$ is —H, $C_1$-$C_6$ aliphatic, $C_1$-$C_3$ haloaliphatic, $C_1$-$C_3$ hydroxyalkyl, —CH$_2$NH$_2$, —CH$_2$SH, —CH$_2$S—($C_1$-$C_3$ aliphatic), cyclopropyl, —CN, —C(O)NH$_2$, —N$_3$, —O—($C_1$-$C_3$ aliphatic), —O—($C_1$-$C_3$ haloaliphatic), —S—($C_1$-$C_3$ aliphatic), —F, or —Cl; wherein each of said $C_1$-$C_6$ aliphatic, $C_1$-$C_3$ haloaliphatic, and cyclopropyl optionally has one or more hydrogen replaced with deuterium;

$R^3$ is —H or —OH;

$R^4$ is —OH, —Cl, —OCH$_3$, —F, —N$_3$, or —OC(O)$R^8$;

$R^5$ is —H or —F;

$R^6$ is —H, —F, —Cl, $C_1$-$C_6$ aliphatic, $C_1$-$C_4$ haloaliphatic, —O—($C_1$-$C_4$ aliphatic), cyclopropyl, or —OH;

$R^7$ is hydrogen, halo, —CH$_3$, or —CF$_3$;

$R^8$ represents independently for each occurrence $C_{1-20}$ aliphatic, $C_{1-20}$ haloaliphatic, —C(H)($R^9$)—N($R^{10}$)$_2$, phenyl, —CH$_2$-phenyl, or hydrogen; wherein each phenyl is substituted with m occurrences of $R^{11}$;

$R^9$ is $C_{1-6}$ alkyl or hydrogen, wherein said $C_{1-6}$ alkyl is optionally substituted with phenyl;

$R^{10}$ represents independently for each occurrence hydrogen, $C_{1-6}$ alkyl, —C(O)CH$_3$, —C(O)OC(CH$_3$)$_3$, —C(O)O(CH$_2$)phenyl, or —C(O)O(CH$_2$)fluorenyl;

$R^{11}$ represents independently for each occurrence $C_{1-6}$ alkyl, $C_{1-6}$ alkoxyl, $C_{1-6}$ haloalkyl, or halo; and m is 0, 1, or 2.

The definitions of variables in Formula V above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is a compound of Formula V.

As defined generally above, $R^1$ is —H, —C(O)$R^8$, or —P(O)(OH)—OP(O)(OH)—OP(O)(OH)$_2$. In certain embodiments, $R^1$ is —H or —C(O)$R^8$. In certain embodiments, $R^1$ is —H or —C(O)C(H)(CH$_3$)$_2$. In certain embodiments, $R^1$ is —H or —P(O)(OH)—OP(O)(OH)—OP(O)(OH)$_2$. In certain embodiments, $R^1$ is —C(O)$R^8$ or —P(O)(OH)—OP(O)(OH)—OP(O)(OH)$_2$. In certain embodiments, $R^1$ is —H. In certain embodiments, $R^1$ is —C(O)$R^8$. In certain embodiments, $R^1$ is —P(O)(OH)—OP(O)(OH)—OP(O)(OH)$_2$.

As defined generally above, $R^2$ is —H, $C_1$-$C_6$ aliphatic, $C_1$-$C_3$ haloaliphatic, $C_1$-$C_3$ hydroxyalkyl, —CH$_2$NH$_2$, —CH$_2$SH, —CH$_2$S—($C_1$-$C_3$ aliphatic), cyclopropyl, —CN, —C(O)NH$_2$, —N$_3$, —O—($C_1$-$C_3$ aliphatic), —O—($C_1$-$C_3$ haloaliphatic), —S—($C_1$-$C_3$ aliphatic), —F, or —Cl; wherein each of said $C_1$-$C_6$ aliphatic, $C_1$-$C_3$ haloaliphatic, and cyclopropyl optionally has one or more hydrogen replaced with deuterium.

In some embodiments, $R^2$ is —H, $C_1$-$C_6$ aliphatic, $C_1$-$C_3$ haloaliphatic, $C_1$-$C_3$ hydroxyalkyl, —CH$_2$NH$_2$, —CH$_2$SH, —CH$_2$S—($C_1$-$C_3$ aliphatic), cyclopropyl, —CN, —C(O)NH$_2$, —N$_3$, —O—($C_1$-$C_3$ aliphatic), —O—($C_1$-$C_3$ haloaliphatic), —S—($C_1$-$C_3$ aliphatic), —F, or —Cl.

In certain embodiments, $R^2$ is $C_1$-$C_6$ aliphatic, $C_1$-$C_3$ haloaliphatic, $C_1$-$C_3$ hydroxyalkyl, —CH$_2$NH$_2$, —CH$_2$SH, —CH$_2$S—($C_1$-$C_3$ aliphatic), cyclopropyl, —CN, —C(O)NH$_2$, —N$_3$, —O—($C_1$-$C_3$ aliphatic), —O—($C_1$-$C_3$ haloaliphatic), —S—($C_1$-$C_3$ aliphatic), —F, or —Cl.

In certain embodiments, $R^2$ is —H, $C_1$-$C_6$ aliphatic, $C_1$-$C_3$ haloaliphatic, or cyclopropyl. In certain embodiments, $R^2$ is $C_1$-$C_6$ aliphatic, $C_1$-$C_3$ haloaliphatic, or cyclopropyl. In certain embodiments, $R^2$ is $C_1$-$C_6$ aliphatic or cyclopropyl. In certain embodiments, $R^2$ is $C_1$-$C_6$ aliphatic or $C_1$-$C_3$ haloaliphatic.

In certain embodiments, $R^2$ is $C_1$-$C_6$ aliphatic, $C_1$-$C_3$ haloaliphatic, or cyclopropyl, each of which optionally has one or more hydrogen replaced with deuterium. In certain embodiments, $R^2$ is $C_1$-$C_6$ aliphatic or cyclopropyl, each of which optionally has one or more hydrogen replaced with deuterium. In certain embodiments, $R^2$ is $C_1$-$C_6$ aliphatic or $C_1$-$C_3$ haloaliphatic, each of which optionally has one or more hydrogen replaced with deuterium.

In certain embodiments, $R^2$ is $C_1$-$C_6$ aliphatic, $C_1$-$C_3$ haloaliphatic, or cyclopropyl, each of which has one or more hydrogen replaced with deuterium. In certain embodiments, $R^2$ is $C_1$-$C_6$ aliphatic or cyclopropyl, each of which has one or more hydrogen replaced with deuterium. In certain embodiments, $R^2$ is $C_1$-$C_6$ aliphatic or $C_1$-$C_3$ haloaliphatic, each of which has one or more hydrogen replaced with deuterium.

In certain embodiments, $R^2$ is $C_1$-$C_3$ hydroxyalkyl, —CH$_2$NH$_2$, —CH$_2$SH, —CH$_2$S—($C_1$-$C_3$ aliphatic), —CN, —C(O)NH$_2$, —N$_3$, —O—($C_1$-$C_3$ aliphatic), —O—($C_1$-$C_3$ haloaliphatic), —S—($C_1$-$C_3$ aliphatic), —F, or —Cl. In certain embodiments, $R^2$ is $C_1$-$C_3$ hydroxyalkyl, —CH$_2$NH$_2$, or —CH$_2$SH. In certain embodiments, $R^2$ is —CH$_2$S—($C_1$-$C_3$ aliphatic), —O—($C_1$-$C_3$ aliphatic), —O—($C_1$-$C_3$ haloaliphatic), or —S—($C_1$-$C_3$ aliphatic). In certain embodiments, $R^2$ is —CN, —C(O)NH$_2$, or —N$_3$. In certain embodiments, $R^2$ is —F or —Cl.

In certain embodiments, $R^2$ is $C_1$-$C_3$ hydroxyalkyl, —O—($C_1$-$C_3$ aliphatic), or —O—($C_1$-$C_3$ haloaliphatic). In certain embodiments, $R^2$ is —$CH_2NH_2$, —CN, —C(O)$NH_2$, or —$N_3$. In certain embodiments, $R^2$ is —$CH_2SH$, —$CH_2S$—($C_1$-$C_3$ aliphatic), or —S—($C_1$-$C_3$ aliphatic).

In certain embodiments, $R^2$ is —H. In certain embodiments, $R^2$ is $C_1$-$C_6$ aliphatic which optionally has one or more hydrogen replaced with deuterium. In certain embodiments, $R^2$ is $C_1$-$C_6$ aliphatic which has one or more hydrogen replaced with deuterium. In certain embodiments, $R^2$ is $C_1$-$C_6$ aliphatic. In certain embodiments, $R^2$ is $C_1$-$C_3$ haloaliphatic which optionally has one or more hydrogen replaced with deuterium. In certain embodiments, $R^2$ is $C_1$-$C_3$ haloaliphatic which has one or more hydrogen replaced with deuterium. In certain embodiments, $R^2$ is $C_1$-$C_3$ haloaliphatic. In certain embodiments, $R^2$ is $C_1$-$C_3$ hydroxyalkyl. In certain embodiments, $R^2$ is —$CH_2NH_2$. In certain embodiments, $R^2$ is —$CH_2SH$. In certain embodiments, $R^2$ is —$CH_2S$—($C_1$-$C_3$ aliphatic). In certain embodiments, $R^2$ is cyclopropyl which optionally has one or more hydrogen replaced with deuterium. In certain embodiments, $R^2$ is cyclopropyl which has one or more hydrogen replaced with deuterium. In certain embodiments, $R^2$ is cyclopropyl. In certain embodiments, $R^2$ is —CN. In certain embodiments, $R^2$ is —C(O)$NH_2$. In certain embodiments, $R^2$ is —$N_3$. In certain embodiments, $R^2$ is —O—($C_1$-$C_3$ aliphatic). In certain embodiments, $R^2$ is —O—($C_1$-$C_3$ haloaliphatic). In certain embodiments, $R^2$ is —S—($C_1$-$C_3$ aliphatic). In certain embodiments, $R^2$ is —F. In certain embodiments, $R^2$ is —Cl.

In certain embodiments, $R^2$ is —$CH_3$, —$CF_3$, —$N_3$, —$OCH_3$, —$CH_2Cl$, —$CH_2F$, —$CHF_2$, —$CHCl_2$, —CHClF, —$CH_2CH_3$, —CH=$CH_2$, cyclopropyl, or —C≡CH. In certain embodiments, $R^2$ is —$N_3$, —$CH_3$, —$CH_2Cl$, —$CH_2F$, —CH=$CH_2$, or —C≡CH. In certain embodiments, $R^2$ is —$CH_2Cl$, —$CH_2F$ or —C≡CH. In certain embodiments, $R^2$ is —$CH_2Cl$ or —C≡CH. In certain embodiments, $R^2$ is —$CH_2Cl$ or —$CH_2F$.

In certain embodiments, $R^2$ is —$CH_3$, —$CH_2CH_3$, —CH=$CH_2$, cyclopropyl, or —C≡CH. In certain embodiments, $R^2$ is —$CH_2CH_3$, —CH=$CH_2$, cyclopropyl, or —C≡CH. In certain embodiments, $R^2$ is —$CH_2CH_3$, —CH=$CH_2$, or cyclopropyl. In certain embodiments, $R^2$ is —$CH_2CH_3$, —C(H)=$CH_2$, —C(H)=C=$CH_2$, or cyclopropyl. In some embodiments, $R^2$ is —$CH_2CH_3$, —C(H)=$CH_2$, or —C(H)=C=$CH_2$. In some embodiments, $R^2$ is —$CH_2CH_3$ or cyclopropyl. In some embodiments, $R^2$ is —C(H)=$CH_2$, —C(H)=C=$CH_2$, or cyclopropyl. In some embodiments, $R^2$ is —C(H)=$CH_2$ or —C(H)=C=$CH_2$.

In certain embodiments, $R^2$ is —$CF_3$, —$CH_2Cl$, —$CH_2F$, —$CHF_2$, —$CHCl_2$, or —CHClF. In certain embodiments, $R^2$ is —$CF_3$, —$CH_2Cl$, —$CH_2F$, or —$CHF_2$. In certain embodiments, $R^2$ is —$CF_3$, —$CH_2F$, or —$CHF_2$. In certain embodiments, $R^2$ is —$N_3$ or —$OCH_3$.

In certain embodiments, $R^2$ is —$CH_3$. In certain embodiments, $R^2$ is —$CF_3$. In certain embodiments, $R^2$ is —$N_3$. In certain embodiments, $R^2$ is —$OCH_3$. In certain embodiments, $R^2$ is —$CH_2Cl$. In certain embodiments, $R^2$ is —$CH_2F$. In certain embodiments, $R^2$ is —$CHF_2$. In certain embodiments, $R^2$ is —$CHCl_2$. In certain embodiments, $R^2$ is —CHClF. In certain embodiments, $R^2$ is —$CH_2CH_3$. In certain embodiments, $R^2$ is —CH=$CH_2$. In some embodiments, $R^2$ is —C(H)=C=$CH_2$. In certain embodiments, $R^2$ is cyclopropyl. In certain embodiments, $R^2$ is —C≡CH.

In some embodiments, $R^2$ is —$CH_2Cl$, —$CH_2F$, —$CH_2Br$, —$CH_2I$, or —$CF_3$, each of which optionally has one or more hydrogen replaced with deuterium. In some embodiments, $R^2$ is —$CH_2Cl$, —$CH_2F$, —$CH_2Br$, or —$CH_2I$, each of which has one or more hydrogen replaced with deuterium. In some embodiments, $R^2$ is —$CD_2Cl$, —$CD_2F$, —$CD_2Br$, or —$CD_2I$. In some embodiments, $R^2$ is —$CD_2Cl$ or —$CD_2F$. In some embodiments, $R^2$ is —$CD_2Cl$. In some embodiments, $R^2$ is —$CD_2F$. In some embodiments, $R^2$ is —$CD_2Br$. In some embodiments, $R^2$ is —$CD_2I$.

As defined generally above, $R^3$ is —H or —OH. In certain embodiments, $R^3$ is —H. In certain embodiments, $R^3$ is —OH.

As defined generally above, $R^4$ is —OH, —Cl, —$OCH_3$, —F, —$N_3$, or —OC(O)$R^8$. In certain embodiments, $R^4$ is —OH, —$OCH_3$, or —OC(O)$R^8$. In certain embodiments, $R^4$ is —OH or —$OCH_3$. In certain embodiments, $R^4$ is —OH or —OC(O)$R^8$. In certain embodiments, $R^4$ is —OH or —C(O)C(H)($CH_3$)$_2$. In certain embodiments, $R^4$ is —$OCH_3$ or —OC(O)$R^8$.

In certain embodiments, $R^4$ is —OH. In certain embodiments, $R^4$ is —Cl. In certain embodiments, $R^4$ is —$OCH_3$. In certain embodiments, $R^4$ is —F. In certain embodiments, $R^4$ is —$N_3$. In certain embodiments, $R^4$ is —OC(O)$R^8$. In certain embodiments, $R^4$ is —C(O)C(H)($CH_3$)$_2$.

As defined generally above, $R^5$ is —H or —F. In certain embodiments, $R^5$ is —H. In certain embodiments, $R^5$ is —F.

As defined generally above, $R^6$ is —H, —F, —Cl, $C_1$-$C_6$ aliphatic, $C_1$-$C_4$ haloaliphatic, —O—($C_1$-$C_4$ aliphatic), cyclopropyl, or —OH.

In certain embodiments, $R^6$ is —F or —Cl. In certain embodiments, $R^6$ is $C_1$-$C_6$ aliphatic, $C_1$-$C_4$ haloaliphatic, or cyclopropyl. In certain embodiments, $R^6$ is $C_1$-$C_6$ aliphatic or $C_1$-$C_4$ haloaliphatic. In certain embodiments, $R^6$ is $C_1$-$C_6$ aliphatic or cyclopropyl. In certain embodiments, $R^6$ is $C_1$-$C_4$ haloaliphatic or cyclopropyl. In certain embodiments, $R^6$ is —O—($C_1$-$C_4$ aliphatic) or —OH.

In certain embodiments, $R^6$ is —H, —F, —Cl, or —OH. In certain embodiments, $R^6$ is —H, —F, or —OH. In certain embodiments, $R^6$ is —H or —F. In certain embodiments, $R^6$ is —H or —OH. In certain embodiments, $R^6$ is —F or —OH.

In certain embodiments, $R^6$ is —H, —F, —$CH_3$, —$CH_2CH_3$, —$OCH_3$, —$OCH_2CH_3$, —CH=$CH_2$, —$CH_2F$, or —$CH_2Cl$.

In certain embodiments, $R^6$ is —H. In certain embodiments, $R^6$ is —F. In certain embodiments, $R^6$ is —Cl. In certain embodiments, $R^6$ is $C_1$-$C_6$ aliphatic. In certain embodiments, $R^6$ is —$CH_3$. In certain embodiments, $R^6$ is —$CH_2CH_3$. In certain embodiments, $R^6$ is —CH=$CH_2$. In certain embodiments, $R^6$ is $C_1$-$C_4$ haloaliphatic. In certain embodiments, $R^6$ is —$CH_2F$. In certain embodiments, $R^6$ is —$CH_2Cl$. In certain embodiments, $R^6$ is —O—($C_1$-$C_4$ aliphatic). In certain embodiments, $R^6$ is —$OCH_3$. In certain embodiments, $R^6$ is —$OCH_2CH_3$. In certain embodiments, $R^6$ is cyclopropyl. In certain embodiments, $R^6$ is —OH.

As defined generally above, $R^7$ is hydrogen, halo, —$CH_3$, or —$CF_3$. In certain embodiments, $R^7$ is hydrogen or halo. In certain embodiments, $R^7$ is hydrogen or fluoro. In certain embodiments, $R^7$ is halo or —$CF_3$. In certain embodiments, $R^7$ is fluoro or —$CF_3$. In certain embodiments, $R^7$ is —$CH_3$ or —$CF_3$. In certain embodiments, $R^7$ is hydrogen. In certain embodiments, $R^7$ is halo. In certain embodiments, $R^7$ is fluoro. In certain embodiments, $R^7$ is —$CH_3$. In certain embodiments, $R^7$ is —$CF_3$.

As defined generally above, $R^8$ represents independently for each occurrence $C_{1-20}$ aliphatic, $C_{1-20}$ haloaliphatic, —C(H)($R^9$)—N($R^{10}$)$_2$, phenyl, —$CH_2$-phenyl, or hydrogen; wherein each phenyl is substituted with m occurrences of $R^{11}$.

In certain embodiments, $R^8$ represents independently for each occurrence $C_{1-20}$ aliphatic, $C_{1-20}$ haloaliphatic, phenyl, or hydrogen; wherein said phenyl is substituted with m occurrences of $R^{11}$. In certain embodiments, $R^8$ represents independently for each occurrence $C_{1-20}$ aliphatic, $C_{1-20}$ haloaliphatic, or hydrogen. In certain embodiments, $R^8$ represents independently for each occurrence —C(H)($R^9$)—N($R^{10}$)$_2$, phenyl, or —CH$_2$-phenyl; wherein each phenyl is substituted with m occurrences of $R^{11}$. In certain embodiments, $R^8$ represents independently for each occurrence phenyl or —CH$_2$-phenyl, wherein each phenyl is substituted with m occurrences of $R^{11}$.

In certain embodiments, $R^8$ is $C_{1-20}$ aliphatic, $C_{1-20}$ haloaliphatic, phenyl, or hydrogen; wherein said phenyl is substituted with m occurrences of $R^{11}$. In certain embodiments, $R^8$ is $C_{1-20}$ aliphatic, $C_{1-20}$ haloaliphatic, or hydrogen. In certain embodiments, $R^8$ is —C(H)($R^9$)—N($R^{10}$)$_2$ or phenyl substituted with m occurrences of $R^{11}$.

In certain embodiments, $R^8$ represents independently for each occurrence $C_{1-20}$ aliphatic or $C_{1-20}$ haloaliphatic. In certain embodiments, $R^8$ represents independently for each occurrence $C_{1-8}$ aliphatic or $C_{1-8}$ haloaliphatic. In certain embodiments, $R^8$ represents independently for each occurrence $C_{10-20}$ aliphatic or $C_{10-20}$ haloaliphatic. In certain embodiments, $R^8$ represents independently for each occurrence $C_{1-20}$ alkyl or $C_{1-20}$ haloalkyl. In certain embodiments, $R^8$ represents independently for each occurrence $C_{1-8}$ alkyl or $C_{1-8}$ haloalkyl. In certain embodiments, $R^8$ represents independently for each occurrence $C_{10-20}$ alkyl or $C_{10-20}$ haloalkyl.

In certain embodiments, $R^8$ is $C_{1-20}$ aliphatic or $C_{1-20}$ haloaliphatic. In certain embodiments, $R^8$ is $C_{1-6}$ aliphatic or $C_{1-6}$ haloaliphatic. In certain embodiments, $R^8$ is $C_{10-20}$ aliphatic or $C_{10-20}$ haloaliphatic. In certain embodiments, $R^8$ is $C_{1-20}$ alkyl or $C_{1-20}$ haloalkyl. In certain embodiments, $R^8$ is $C_{1-6}$ alkyl or $C_{1-6}$ haloalkyl. In certain embodiments, $R^8$ is $C_{10-20}$ alkyl or $C_{10-20}$ haloalkyl.

In certain embodiments, $R^8$ represents independently for each occurrence $C_{1-20}$ aliphatic. In certain embodiments, $R^8$ represents independently for each occurrence $C_{1-6}$ aliphatic. In certain embodiments, $R^8$ represents independently for each occurrence $C_{10-20}$ aliphatic. In certain embodiments, $R^8$ represents independently for each occurrence $C_{1-20}$ alkyl. In certain embodiments, $R^8$ represents independently for each occurrence $C_{1-6}$ alkyl. In certain embodiments, $R^8$ represents independently for each occurrence $C_{10-20}$ alkyl.

In certain embodiments, $R^8$ is $C_{1-20}$ aliphatic. In certain embodiments, $R^8$ is $C_{1-6}$ aliphatic. In certain embodiments, $R^8$ is $C_{10-20}$ aliphatic. In certain embodiments, $R^8$ is $C_{1-20}$ alkyl. In certain embodiments, $R^8$ is $C_{1-6}$ alkyl. In certain embodiments, $R^8$ is $C_{10-20}$ alkyl.

In some embodiments, $R^8$ is —CH$_3$, —CH$_2$CH$_3$, —CH(CH$_3$)$_2$, —C(H)=CH$_2$, —CH$_2$C(H)=CH$_2$, —C≡CH, —CH$_2$CH$_3$, —C(H)=CH$_2$, —CH$_2$C(H)=CH$_2$, —C≡CH, —(CH$_2$)$_3$CH$_3$, —(CH$_2$)$_3$C(H)=CH$_2$, —(CH$_2$)$_6$C(H)=CH$_2$, —(CH$_2$)$_3$C≡CH, —(CH$_2$)$_6$C≡CH, or cyclopropyl. In some embodiments, $R^8$ is —CH$_3$, —CH$_2$CH$_3$, —CH(CH$_3$)$_2$, —C(H)=CH$_2$, —CH$_2$C(H)=CH$_2$, or —C≡CH. In some embodiments, $R^8$ is —CH$_3$, —CH$_2$CH$_3$, or —CH(CH$_3$)$_2$. In some embodiments, $R^8$ is —C(H)=CH$_2$, —CH$_2$C(H)=CH$_2$, or —C≡CH. In some embodiments, $R^8$ is —CH$_3$. In some embodiments, $R^8$ is —CH$_2$CH$_3$. In some embodiments, $R^3$ is —CH(CH$_3$)$_2$. In some embodiments, $R^8$ is —C(H)=CH$_2$. In some embodiments, $R^8$ is —CH$_2$C(H)=CH$_2$. In some embodiments, $R^8$ is —C≡CH. In some embodiments, $R^8$ is —(CH$_2$)$_3$CH$_3$. In some embodiments, $R^8$ is —(CH$_2$)$_3$C(H)=CH$_2$. In some embodiments, $R^8$ is —(CH$_2$)$_6$C(H)=CH$_2$. In some embodiments, $R^8$ is —(CH$_2$)$_3$C≡CH. In some embodiments, $R^8$ is —(CH$_2$)$_6$C≡CH. In some embodiments, $R^8$ is cyclopropyl.

In certain embodiments, $R^8$ represents independently for each occurrence $C_{1-20}$ haloaliphatic. In certain embodiments, $R^8$ represents independently for each occurrence $C_{1-6}$ haloaliphatic. In certain embodiments, $R^8$ represents independently for each occurrence $C_{10-20}$ haloaliphatic. In certain embodiments, $R^8$ represents independently for each occurrence $C_{1-20}$ haloalkyl. In certain embodiments, $R^8$ represents independently for each occurrence $C_{1-8}$ haloalkyl. In certain embodiments, $R^8$ represents independently for each occurrence $C_{10-20}$ haloalkyl.

In certain embodiments, $R^8$ is $C_{1-20}$ haloaliphatic. In certain embodiments, $R^8$ is $C_{1-8}$ haloaliphatic. In certain embodiments, $R^8$ is $C_{10-20}$ haloaliphatic. In certain embodiments, $R^8$ is $C_{1-20}$ haloalkyl. In certain embodiments, $R^8$ is $C_{1-8}$ haloalkyl. In certain embodiments, $R^8$ is $C_{10-20}$ haloalkyl.

In some embodiments, $R^8$ represents independently for each occurrence —C(H)($R^9$)—N($R^{10}$)$_2$. In some embodiments, $R^8$ is —C(H)($R^9$)—N($R^{10}$)$_2$. In some embodiments, $R^8$ represents independently for each occurrence

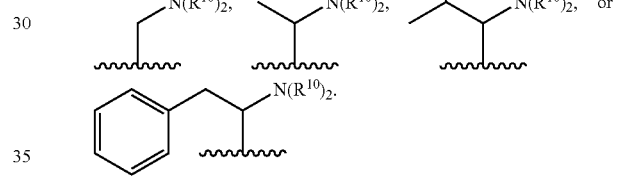

In some embodiments, $R^8$ is

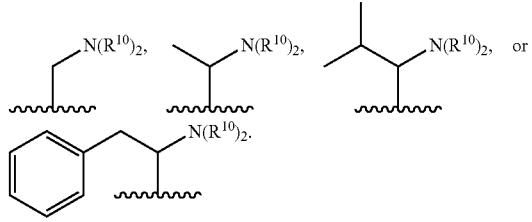

In some embodiments, $R^8$ is

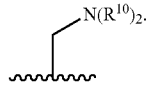

In some embodiments, $R^8$ is

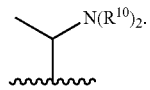

In some embodiments, $R^8$ is

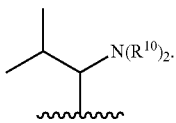

In some embodiments, $R^8$ is

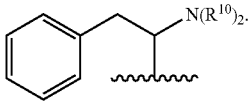

In some embodiments, $R^8$ represents independently for each occurrence

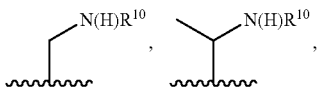

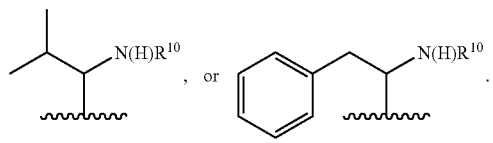

In some embodiments, $R^8$ is

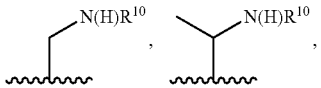

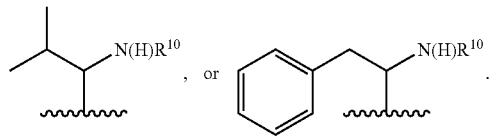

In some embodiments, $R^8$ is

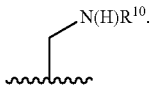

In some embodiments, $R^8$ is

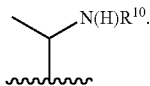

In some embodiments, $R^8$ is

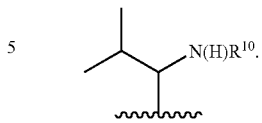

In some embodiments, $R^8$ is

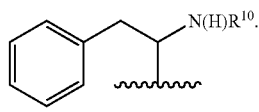

In some embodiments, $R^8$ represents independently for each occurrence phenyl substituted with m occurrences of $R^{11}$. In some embodiments, $R^8$ is phenyl substituted with m occurrences of $R^{11}$. In some embodiments, $R^8$ is phenyl.

In some embodiments, $R^8$ represents independently for each occurrence —$CH_2$-phenyl, wherein said phenyl is substituted with m occurrences of $R^{11}$. In some embodiments, $R^8$ is —$CH_2$-phenyl, wherein said phenyl is substituted with m occurrences of $R^{11}$. In some embodiments, $R^8$ is —$CH_2$-phenyl.

In some embodiments, $R^8$ is hydrogen.

As defined generally above, $R^9$ is $C_{1-6}$ alkyl or hydrogen, wherein said $C_{1-6}$ alkyl is optionally substituted with phenyl. In certain embodiments, $R^9$ is methyl, isopropyl, benzyl, or hydrogen. In certain embodiments, $R^9$ is $C_{1-6}$ alkyl optionally substituted with phenyl. In certain embodiments, $R^9$ is $C_{1-6}$ alkyl. In certain embodiments, $R^9$ is $C_{1-4}$ alkyl. In certain embodiments, $R^9$ is $C_{2-6}$ alkyl. In certain embodiments, $R^9$ is $C_{1-6}$ alkyl substituted with phenyl. In certain embodiments, $R^9$ is hydrogen.

As defined generally above, $R^{10}$ represents independently for each occurrence hydrogen, $C_{1-6}$ alkyl, —$C(O)CH_3$, —$C(O)OC(CH_3)_3$, —$C(O)O(CH_2)$phenyl, or —$C(O)O(CH_2)$-fluorenyl.

In certain embodiments, one occurrence of $R^{10}$ is hydrogen or $C_{1-6}$ alkyl, and the other occurrence of $R^{10}$ is hydrogen, $C_{1-6}$ alkyl, —$C(O)CH_3$, —$C(O)OC(CH_3)_3$, —$C(O)O(CH_2)$phenyl, or —$C(O)O(CH_2)$fluorenyl. In certain embodiments, one occurrence of $R^{10}$ is hydrogen or $C_{1-6}$ alkyl, and the other occurrence of $R^{10}$ is —$C(O)CH_3$, —$C(O)OC(CH_3)_3$, —$C(O)O(CH_2)$phenyl, or —$C(O)O(CH_2)$fluorenyl.

In certain embodiments, one occurrence of $R^{10}$ is hydrogen, and the other occurrence of $R^{10}$ is hydrogen, $C_{1-6}$ alkyl, —$C(O)CH_3$, —$C(O)OC(CH_3)_3$, —$C(O)O(CH_2)$phenyl, or —$C(O)O(CH_2)$fluorenyl. In certain embodiments, one occurrence of $R^{10}$ is hydrogen, and the other occurrence of $R^{10}$ is —$C(O)CH_3$, —$C(O)OC(CH_3)_3$, —$C(O)O(CH_2)$phenyl, or —$C(O)O(CH_2)$-fluorenyl.

In certain embodiments, $R^{10}$ represents independently for each occurrence hydrogen or $C_{1-6}$ alkyl. In certain embodiments, $R^{10}$ is hydrogen. In certain embodiments, $R^{10}$ represents independently for each occurrence $C_{1-6}$ alkyl.

As defined generally above, $R^{11}$ represents independently for each occurrence $C_{1-6}$ alkyl, $C_{1-6}$ alkoxyl, $C_{1-6}$ haloalkyl, or halo. In certain embodiments, $R^{11}$ represents independently for each occurrence —$CH_3$, —$OCH_3$, —$CF_3$, or halo.

In certain embodiments, $R^{11}$ represents independently for each occurrence $C_{1-6}$ alkyl. In certain embodiments, $R^{11}$ is —$CH_3$. In certain embodiments, $R^{11}$ represents independently for each occurrence $C_{1-6}$ alkoxyl. In certain embodiments, $R^{11}$ is —OCH$_3$. In certain embodiments, $R^{11}$ represents independently for each occurrence $C_{1-6}$ haloalkyl. In certain embodiments, $R^{11}$ is —CF$_3$. In certain embodiments, $R^{11}$ represents independently for each occurrence halo.

As defined generally above, $B^1$ is

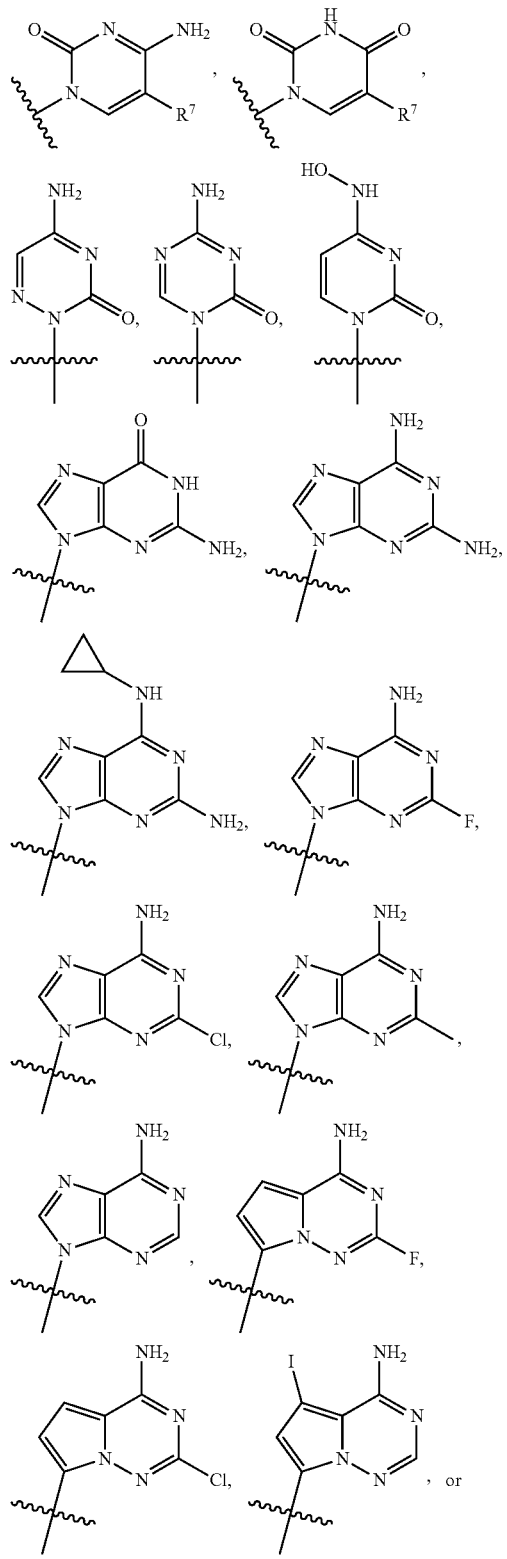

-continued

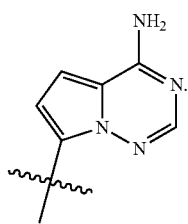

In certain embodiments, $B^1$ is

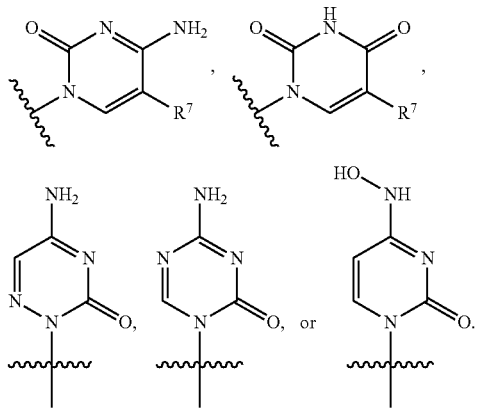

In certain embodiments, $B^1$ is

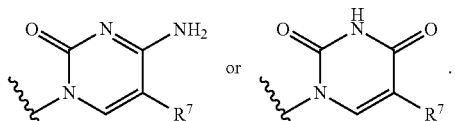

In certain embodiments, $B^1$ is

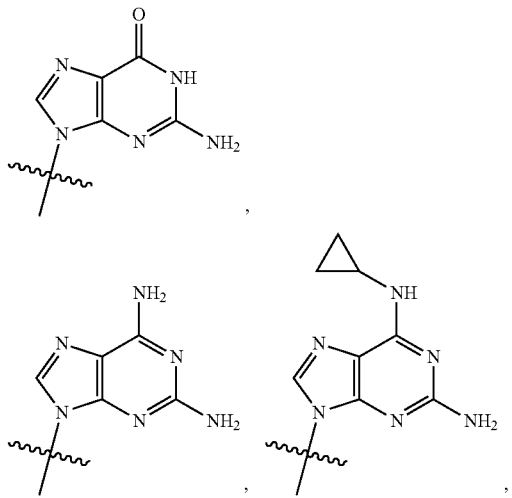

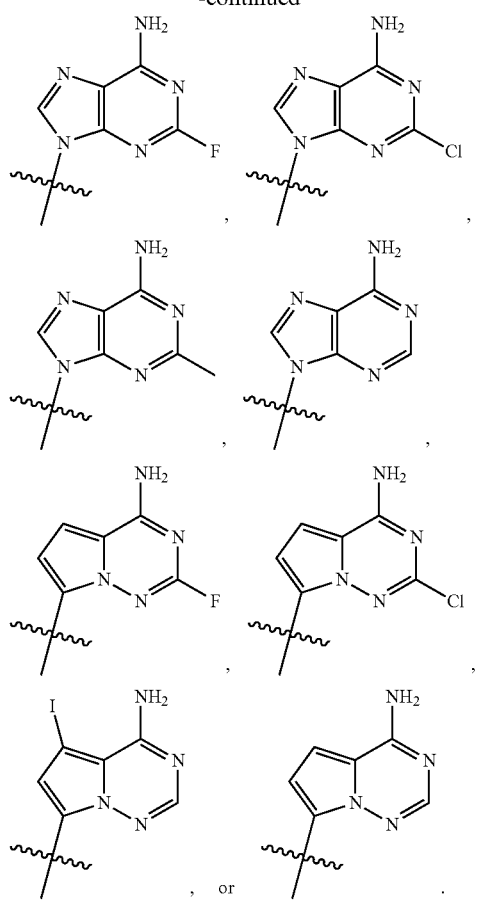
,
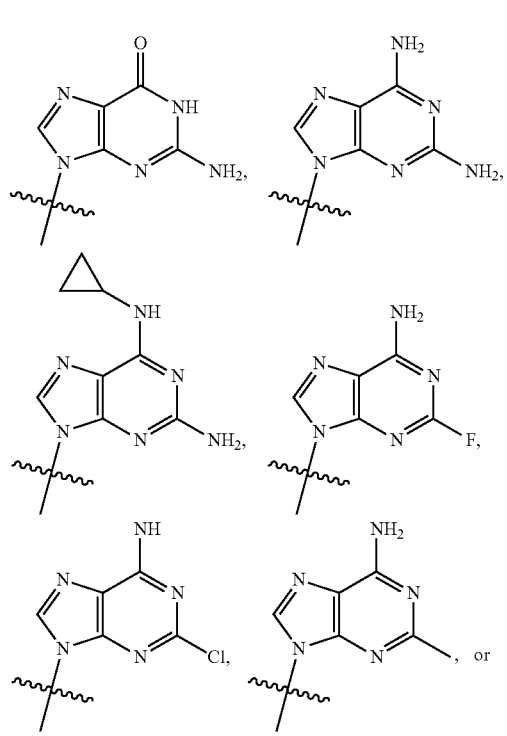
In certain embodiments, B¹ is
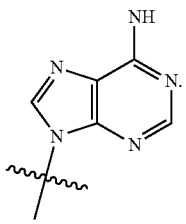
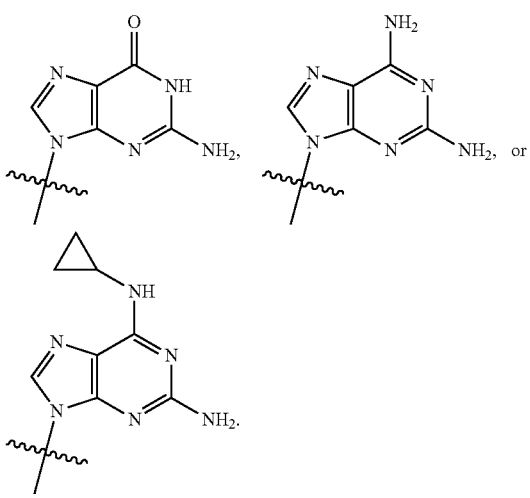
In certain embodiments, B¹ is
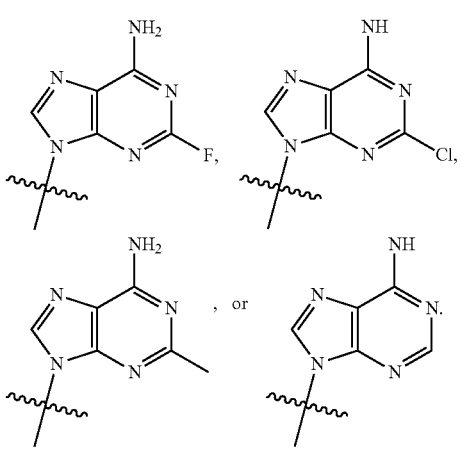
In certain embodiments, B¹ is
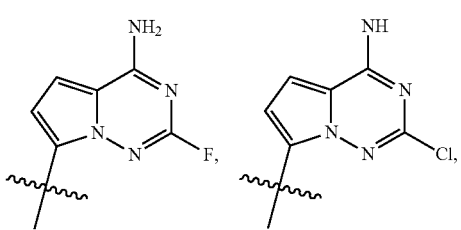

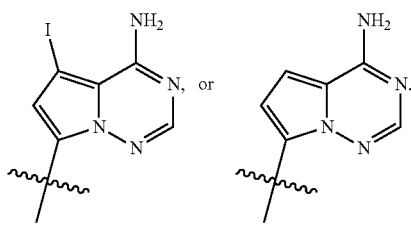
In certain embodiments, B¹ is
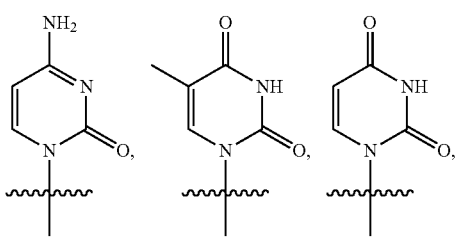
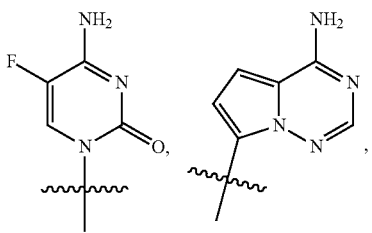
In certain embodiments, B¹ is
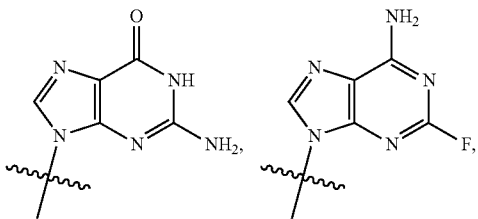
In certain embodiments, B¹ is
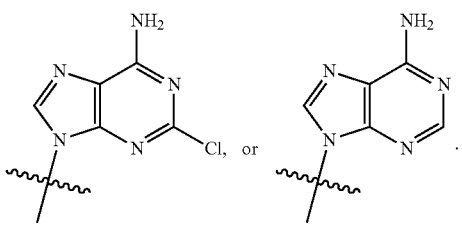
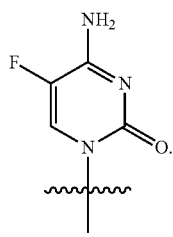
In certain embodiments, B¹ is
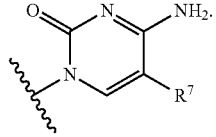
In certain embodiments, B¹ is
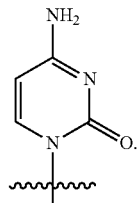
In certain embodiments, B¹ is
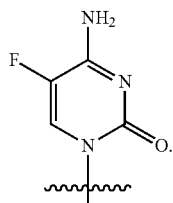
In certain embodiments, B¹ is
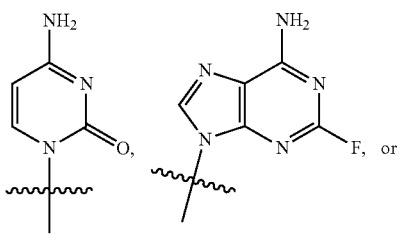
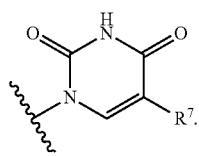

In certain embodiments, B¹ is
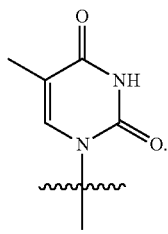 [SMILES: *n1cc(C)c(=O)[nH]c1=O]
In certain embodiments, B¹ is
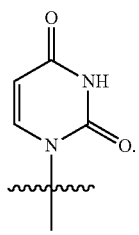
In certain embodiments, B¹ is
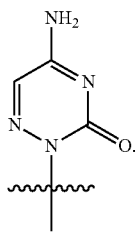 [SMILES: *n1ncc(N)nc1=O]
In certain embodiments, B¹ is
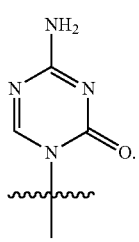 [SMILES: *n1cnc(N)nc1=O]
In certain embodiments, B¹ is
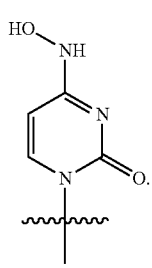
In certain embodiments, B¹ is
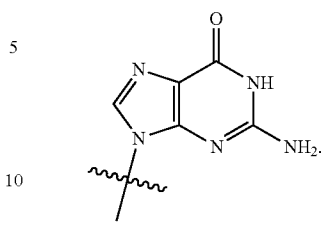
In certain embodiments, B¹ is
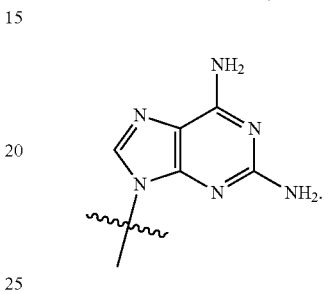
In certain embodiments, B¹ is
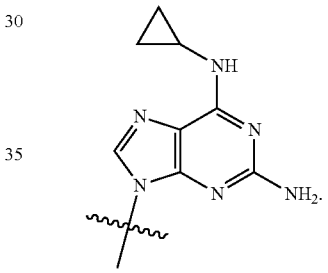
In certain embodiments, B¹ is
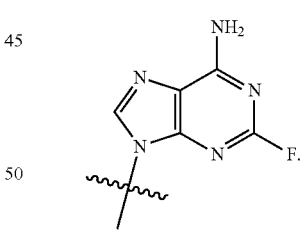
In certain embodiments, B¹
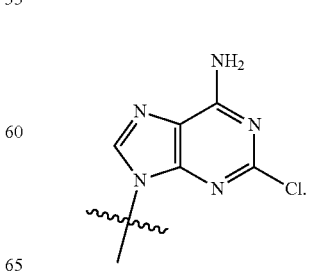

In certain embodiments, B¹ is

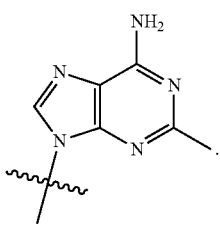 [SMILES: *n1cnc2c(N)nc(C)nc21]

In certain embodiments, B¹ is

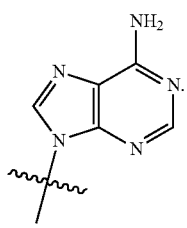 [SMILES: *n1cnc2c(N)ncnc21]

In certain embodiments, B¹ is

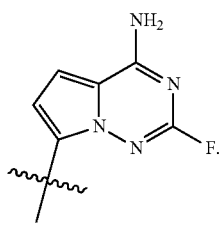 [SMILES: *c1ccc2c(N)nc(F)nn12]

In certain embodiments, B¹ is

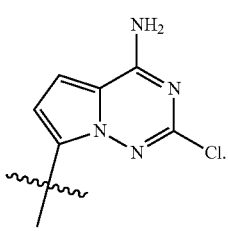 [SMILES: *c1ccc2c(N)nc(Cl)nn12]

In certain embodiments, B¹ is

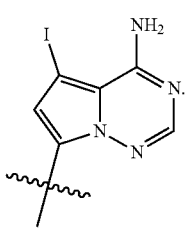 [SMILES: *c1cc(I)c2c(N)ncnn12]

In certain embodiments, B¹ is

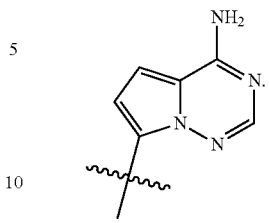

As defined generally above, m is 0, 1, or 2. In certain embodiments, m is 0. In certain embodiments, m is 1. In certain embodiments, m is 2. In certain embodiments, m is 0 or 1. In certain embodiments, m is 1 or 2.

The description above describes multiple embodiments relating to compounds of Formula V. The patent application specifically contemplates all combinations of the embodiments.

Another aspect of the disclosure provides a compound represented by Formula VI:

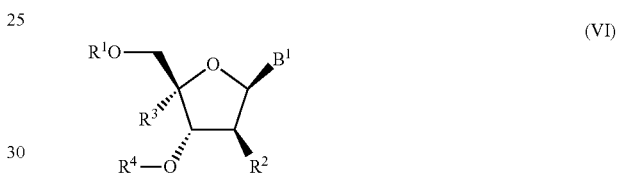

(VI)

or a pharmaceutically acceptable salt thereof; wherein:
$R^1$ and $R^4$ represent independently —C(O)R⁵ or hydrogen;
$R^2$ is halo, hydrogen, or —OH;
$R^3$ is halomethyl, $C_{1-3}$ aliphatic, or cyclopropyl, each of which optionally has one or more hydrogen replaced with deuterium;
$R^5$ represents independently for each occurrence $C_{1-20}$ aliphatic, $C_{1-20}$ haloaliphatic, —C(H)(R⁶)—N(R⁷)₂, phenyl, —CH₂-phenyl, or hydrogen; wherein each phenyl is substituted with m occurrences of $R^{10}$;
$R^6$ is $C_{1-6}$ alkyl or hydrogen, wherein said $C_{1-6}$ alkyl is optionally substituted with phenyl;
$R^7$ represents independently for each occurrence hydrogen, $C_{1-6}$ alkyl, C(O)OC(CH₃)₃, C(O)O(CH₂)phenyl, or C(O)O(CH₂)fluorenyl;
$R^8$ and $R^9$ each represent independently hydrogen, halo, —CH₃, or —CF₃;
$R^{10}$ represents independently for each occurrence $C_{1-6}$ alkyl, $C_{1-6}$ alkoxyl, $C_{1-6}$ haloalkyl, or halo;
B¹ is

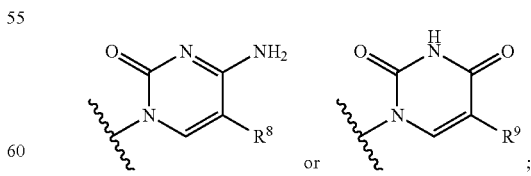

and
m is 0, 1, or 2.

The definitions of variables in Formula VI above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is a compound of Formula VI.

As defined generally above, $R^1$ and $R^4$ represent independently —C(O)$R^5$ or hydrogen. In certain embodiments, $R^1$ and $R^4$ are hydrogen.

In certain embodiments, $R^1$ is —C(O)$R^5$ or hydrogen. In certain embodiments, $R^1$ is —C(O)$R^5$. In certain embodiments, $R^1$ is hydrogen.

In certain embodiments, $R^4$ is —C(O)$R^5$ or hydrogen. In certain embodiments, $R^4$ is —C(O)$R^5$. In certain embodiments, $R^4$ is hydrogen.

As defined generally above, $R^8$ and $R^9$ each represent independently hydrogen, halo, —CH$_3$, or —CF$_3$.

In certain embodiments, $R^8$ is hydrogen, halo, —CH$_3$, or —CF$_3$. In certain embodiments, $R^8$ is hydrogen or halo. In certain embodiments, $R^8$ is hydrogen or fluoro. In certain embodiments, $R^8$ is halo or —CF$_3$. In certain embodiments, $R^8$ is fluoro or —CF$_3$. In certain embodiments, $R^8$ is —CH$_3$ or —CF$_3$. In certain embodiments, $R^8$ is hydrogen. In certain embodiments, $R^8$ is halo. In certain embodiments, $R^8$ is fluoro. In certain embodiments, $R^8$ is —CH$_3$. In certain embodiments, $R^8$ is —CF$_3$.

In certain embodiments, $R^9$ is hydrogen, halo, —CH$_3$, or —CF$_3$. In certain embodiments, $R^9$ is hydrogen or halo. In certain embodiments, $R^9$ is hydrogen or fluoro. In certain embodiments, $R^9$ is halo or —CF$_3$. In certain embodiments, $R^9$ is fluoro or —CF$_3$. In certain embodiments, $R^9$ is —CH$_3$ or —CF$_3$. In certain embodiments, $R^9$ is hydrogen. In certain embodiments, $R^9$ is halo. In certain embodiments, $R^9$ is fluoro. In certain embodiments, $R^9$ is —CH$_3$. In certain embodiments, $R^9$ is —CF$_3$.

In certain embodiments, the present invention provides a compound of Formula VI, wherein each of variables $R^2$, $R^3$, $R^5$, $R^6$, $R^7$, $R^{10}$, $B^1$, and m is as defined in the description of Formula II, above, and as described in embodiments herein, both singly and in combination. For example, in certain embodiments, $R^2$ is halo. In another example, in certain embodiments, $R^2$ is fluoro, and $R^3$ is halomethyl. In yet another example, in certain embodiments, $R^1$ and $R^4$ are hydrogen, $R^2$ is hydrogen, and $R^3$ is —CH$_2$F or —CH$_2$Cl.

The description above describes multiple embodiments relating to compounds of Formula VI. The patent application specifically contemplates all combinations of the embodiments.

II. METHODS OF TREATING MEDICAL DISORDERS AND/OR INHIBITING REVERSE TRANSCRIPTASES

It is contemplated that compounds in Section I above (e.g., a compound of Formula I, or a pharmaceutically acceptable salt thereof, as described above) or other compounds in Section III, below, provide therapeutic benefits to subjects suffering from cancer, autoimmune disorders, and/or neurological disorders.

Accordingly, one aspect of the disclosure provides a method of treating a disorder selected from the group consisting of cancer, an autoimmune disorder, and a neurological disorder. The method comprises administering to a subject in need thereof a therapeutically effective amount of a compound described herein (such as a compound of Formula I, II, III, IV, V, or VI, or other compound described in Section I or III), a pharmaceutically acceptable salt thereof, or a pharmaceutical composition of either of the foregoing, in order to treat the disorder. In certain embodiments, the particular compound is a compound described for any of the embodiments herein, in any and all combinations of the various embodiments, and aspects of embodiments, described.

Another aspect of the disclosure provides a method of treating a disorder selected from the group consisting of cancer, an autoimmune disorder, and a neurological disorder. The method comprises administering to a subject in need thereof a therapeutically effective amount of a compound of Formula I, a pharmaceutically acceptable salt thereof, or a pharmaceutical composition of either of the foregoing, in order to treat the disorder; wherein the compound of Formula I is as described for any of embodiment one through twenty-two above in any and all combination of the various embodiments, and aspects of embodiments, described.

Another aspect of the disclosure provides a method of treating a disorder selected from the group consisting of cancer, an autoimmune disorder, and a neurological disorder. The method comprises administering to a subject in need thereof a therapeutically effective amount of a compound described herein, such as a compound of Formula I or a compound in Table 1, 1-A, 1-B, 2, and/or 2-A, in order to treat the disorder. In certain embodiments, the particular compound is a compound described for any of the embodiments herein, in any and all combinations of the various embodiments, and aspects of embodiments, described.

Yet another aspect of the disclosure provides a method of treating a viral infection. The method comprises administering to a subject in need thereof a therapeutically effective amount of a compound described herein (such as a compound of Formula I, II, III, IV, V, or VI, or other compound described in Section I or III), a pharmaceutically acceptable salt thereof, or a pharmaceutical composition of either of the foregoing, in order to treat the viral infection. In certain embodiments, the particular compound is a compound described for any of the embodiments herein, in any and all combinations of the various embodiments, and aspects of embodiments, described.

In certain embodiments of each of the foregoing methods, the compound is a compound in Table 1, 1-A, 1-B, 1-C, I-D, 2, 2-A, 2-B, or 2-C, or a pharmaceutically acceptable salt thereof. In certain embodiments of each of the foregoing methods, the compound is a compound in Table 1, 1-A, 1-B, 1-C, 2, 2-A, 2-B, or 2-C, or a pharmaceutically acceptable salt thereof. In certain embodiments of each of the foregoing methods, the compound is a compound in Table 1, 1-A, 1-B, 1-C, I-D, 2, 2-A, 2-B, or 2-C. In certain embodiments, the compound is a compound in Table 1, 1-A, 1-B, 1-C, 2, 2-A, 2-B, or 2-C. In certain embodiments, the compound is a compound in Table 1, 1-A, 1-C, 2, 2-A, or 2-C, or a pharmaceutically acceptable salt thereof. In certain embodiments, the compound is a compound in Table 1, 1-A, 1-C, 2, 2-A, or 2-C. In certain embodiments, the compound is a compound in Table 1, 1-A, 1-B, 2, 2-A, or 2-B, or a pharmaceutically acceptable salt thereof. In certain embodiments, the compound is a compound in Table 1, 1-A, 1-B, 2, 2-A, or 2-B. In certain embodiments, the compound is a compound in Table 1, 1-A, 2, or 2-A, or a pharmaceutically acceptable salt thereof. In certain embodiments, the compound is a compound in Table 1, 1-A, 2, or 2-A. In certain embodiments, the compound is a compound in Table 1-B or 2-B, or a pharmaceutically acceptable salt thereof. In certain embodiments, the compound is a compound in Table 1-B or 2-B. In certain embodiments, the compound is a compound in Table 1 or Table 2, or a pharmaceutically acceptable salt thereof. In certain embodiments, the compound is a compound in Table 1 or Table 2.

In certain embodiments, the compound is administered in a pharmaceutical composition comprising the compound and a carrier, excipient, and/or vehicle, as further described in Section V, below.

In certain embodiments, the method further comprises administering an effective amount of one or more additional therapeutic agents, as further described in Section IV, below.

Cancer

In certain embodiments, the disorder is cancer. In certain embodiments, the cancer is a solid tumor or leukemia. In certain embodiments, the cancer is a solid tumor. In certain embodiments, the cancer is a carcinoma or melanoma. In certain embodiments, the cancer is a carcinoma. In certain embodiments, the cancer is a sarcoma. In certain embodiments, the cancer is a melanoma. In certain embodiments, the cancer is a lymphoma. In certain embodiments, the cancer is a leukemia.

In certain embodiments, the cancer is breast cancer, ovarian cancer, uterine cancer, cervical cancer, prostate cancer, testicular cancer, lung cancer, leukemia, head and neck cancer, oral cancer, esophageal cancer, stomach cancer, bile duct cancer, gallbladder cancer, bladder cancer, urinary tract cancer, colon cancer, rectal cancer, thyroid cancer, pancreatic cancer, kidney cancer, liver cancer, brain cancer, skin cancer, or eye cancer.

In certain embodiments, the cancer is breast cancer, ovarian cancer, uterine cancer, cervical cancer, prostate cancer, testicular cancer, lung cancer, leukemia, head and neck cancer, oral cancer, esophageal cancer, stomach cancer, bile duct cancer, gallbladder cancer, or bladder cancer.

In certain embodiments, the cancer has (i) expression of LINE1 RNA, LINE1 ORF1 polypeptide, and/or LINE1 ORF2 polypeptide; (ii) activity of LINE1 reverse transcriptase; (iii) expression of HERV-K RNA, and/or (iv) activity of HERV-K reverse transcriptase.

In certain embodiments, the cancer has (i) expression of LINE1 RNA, LINE1 ORF1 polypeptide, and/or LINE1 ORF2 polypeptide; and/or (ii) activity of LINE1 reverse transcriptase. In certain embodiments, the cancer has expression of LINE1 RNA, LINE1 ORF1 polypeptide, and/or LINE1 ORF2 polypeptide. In certain embodiments, the cancer has expression of LINE1 RNA. In certain embodiments, the cancer has expression of LINE1 ORF1 polypeptide. In certain embodiments, the cancer has expression of LINE1 ORF2 polypeptide. In certain embodiments, the cancer has activity of LINE1 reverse transcriptase.

In certain embodiments, the cancer has (i) expression of HERV-K RNA, and/or (ii) activity of HERV-K reverse transcriptase. In certain embodiments, the cancer has expression of HERV-K RNA. In certain embodiments, the cancer has activity of HERV-K reverse transcriptase.

In certain embodiments, the cancer has elevated (i) levels of LINE1 RNA, LINE1 ORF1 polypeptide, and/or LINE1 ORF2 polypeptide; (ii) activity of LINE1 reverse transcriptase; (iii) levels of HERV-K RNA, and/or (iv) activity of HERV-K reverse transcriptase.

In certain embodiments, the cancer has elevated (i) levels of LINE1 RNA, LINE1 ORF1 polypeptide, and/or LINE1 ORF2 polypeptide; and/or (ii) activity of LINE1 reverse transcriptase. In certain embodiments, the cancer has elevated levels of LINE1 RNA, LINE1 ORF1 polypeptide, and/or LINE1 ORF2 polypeptide. In certain embodiments, the cancer has elevated levels of LINE1 RNA. In certain embodiments, the cancer has elevated levels of LINE1 ORF1 polypeptide. In certain embodiments, the cancer has elevated levels of LINE1 ORF2 polypeptide. In certain embodiments, the cancer has elevated activity of LINE1 reverse transcriptase.

In certain embodiments, the cancer has elevated (i) levels of HERV-K RNA, and/or (ii) activity of HERV-K reverse transcriptase. In certain embodiments, the cancer has elevated levels of HERV-K RNA. In certain embodiments, the cancer has elevated activity of HERV-K reverse transcriptase.

In certain embodiments, the cancer is an epithelial cancer. In certain embodiments, the epithelial cancer is pancreatic cancer, colorectal cancer, breast cancer, prostate cancer, esophageal cancer, head and neck cancer, renal cancer, ovarian cancer, or lung cancer. In certain embodiments, the cancer is pancreatic cancer, colorectal cancer, breast cancer, prostate cancer, renal cancer, ovarian cancer, or lung cancer. In certain embodiments, the cancer is pancreatic cancer. In certain embodiments, the cancer is pancreatic adenocarcinoma. In certain embodiments, the cancer is colorectal cancer. In certain embodiments, the cancer comprises microsatellite instable (MSI) colorectal cancer or microsatellite stable (MSS) colorectal cancer. In certain embodiments, the cancer is breast cancer. In certain embodiments, the cancer is prostate cancer. In certain embodiments, the cancer is esophageal cancer. In certain embodiments, the cancer is head and neck cancer. In certain embodiments, the cancer is renal cancer. In certain embodiments, the cancer is ovarian cancer. In certain embodiments, the cancer is lung cancer. In certain embodiments, the lung cancer is non-small cell lung carcinoma or small cell lung carcinoma. In certain embodiments, the cancer is non-small cell lung carcinoma. In certain embodiments, the cancer is small cell lung carcinoma.

In certain embodiments, the cancer is a preneoplastic or early cancer lesion. In certain embodiments, the cancer is intraductal papillary mucinous neoplasm (IPMN), pancreatic intraepithelial neoplasia (PanIN), ductal carcinoma in situ (DCIS), or Barrett's Esophagus. In certain embodiments, the cancer intraductal papillary mucinous neoplasm (IPMN). In certain embodiments, the cancer is pancreatic intraepithelial neoplasia (PanIN). In certain embodiments, the cancer is ductal carcinoma in situ (DCIS). In certain embodiments, the cancer is Barrett's Esophagus.

In certain embodiments, the cancer has elevated levels of pericentrometric human satellite II (HSATII) RNA. In some embodiments, the cancer is a microsatellite instable (MSI) cancer. In some embodiments, the cancer is a microsatellite stable (MSS) cancer.

In aspects of any of the embodiments, the cancer is associated with long interspersed nuclear element-1 (LINE-1) reverse transcriptase (RT). In further aspects of these embodiments, the cancer is associated with high levels of LINE-1 RT activity.

In certain embodiments, the cancer is selected from B cell lymphomas (e.g., B cell chronic lymphocytic leukemia, B cell non-Hodgkin lymphoma, cutaneous B cell lymphoma, diffuse large B cell lymphoma), basal cell carcinoma, bladder cancer, blastoma, brain metastasis, breast cancer, Burkitt lymphoma, carcinoma (e.g., adenocarcinoma (e.g., of the gastroesophageal junction)), cervical cancer, colon cancer, colorectal cancer (colon cancer and rectal cancer), endometrial carcinoma, esophageal cancer, Ewing sarcoma, follicular lymphoma, gastric cancer, gastroesophageal junction carcinoma, gastrointestinal cancer, glioblastoma (e.g., glioblastoma multiforme, e.g., newly diagnosed or recurrent), glioma, head and neck cancer (e.g., head and neck squamous cell carcinoma), hepatic metastasis, Hodgkin's and non-Hodgkin's lymphoma, kidney cancer (e.g., renal cell carcinoma and Wilms' tumors), laryngeal cancer, leukemia (e.g., chronic myelocytic leukemia, hairy cell leukemia), liver cancer (e.g., hepatic carcinoma and hepatoma), lung cancer (e.g., non-small cell lung cancer and small-cell lung cancer), lymphoblastic lymphoma, lymphoma, mantle cell lymphoma, metastatic brain tumor, metastatic cancer, myeloma (e.g., multiple myeloma), neuroblastoma, ocular melanoma, oropharyngeal cancer, osteosarcoma, ovarian cancer, pancreatic cancer (e.g., pancreatic ductal adenocarcinoma), prostate cancer (e.g., hormone refractory (e.g., castration resistant), metastatic, metastatic hormone refractory (e.g., castration resistant, androgen independent)), renal cell carcinoma (e.g., metastatic), salivary gland carcinoma, sarcoma (e.g., rhabdomyosarcoma), skin cancer (e.g., melanoma (e.g., metastatic melanoma)), soft tissue sarcoma, solid tumor, squamous cell carcinoma, synovia sarcoma, testicular cancer, thyroid cancer, transitional cell cancer (urothelial cell cancer), uveal melanoma (e.g., metastatic), verrucous carcinoma, vulval cancer, and Waldenstrom macroglobulinemia.

In some embodiments, the cancer is a virus-associated cancer. As used herein, the term "virus-associated cancer" means any cancer in which a virus is known to play a role. For example, Epstein-Barr virus (EBV) has been reported to be associated with the endemic variant of Burkitt lymphoma and certain other lymphomas. Infection by human papilloma virus (HPV) is believed to be responsible for certain types of cervical and/or genital cancer. Human T-cell leukemia virus 1 (HTLV-1) has been reported to be linked adult T-cell leukemia/lymphoma (ATLL). Human T-cell leukemia virus 2 (HTLV-2) has been reported to be linked to cutaneous T-cell lymphoma. Human herpes virus 8 (HHV-8) is believed to cause Kaposi's sarcoma in patients with AIDS. In certain embodiments, the cancer is a cancer associated with EBV, HPV, HTLV-1, HTLV-2, or HHV-8. In certain embodiments, the cancer is Burkitt lymphoma, cervical cancer, genital cancer, adult T-cell leukemia/lymphoma, cutaneous T-cell lymphoma, or Kaposi's sarcoma.

In some embodiments, the cancer is a cancer other than a virus-associated cancer. In certain embodiments, the cancer is a cancer other than a cancer associated with EBV, HPV, HTLV-1, HTLV-2, or HHV-8. In certain embodiments, the cancer is a cancer other than Burkitt lymphoma, cervical cancer, genital cancer, adult T-cell leukemia/lymphoma, cutaneous T-cell lymphoma, or Kaposi's sarcoma. In one embodiment, the cancer is a tumor associated with Li_Fraumeni syndrome.

In some embodiments, the cancer is renal cell carcinoma, or kidney cancer, mesothelioma, hepatobiliary (hepatic and biliary duct), bone cancer, rhabdomyosarcoma, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, adrenocortical carcinoma, sarcoma of soft tissue, soft tissue and bone synovial sarcoma, cancer of the urethra, cancer of the penis, prostate cancer, testicular cancer, chronic or acute leukemia, chronic myeloid leukemia, acute myeloid leukemia, lymphocytic lymphomas, cancer of the bladder, cancer of the kidney or ureter, renal cell carcinoma, carcinoma of the renal pelvis, non-Hodgkin's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, squamous cell carcinoma of the head and neck (SCCHN); salivary gland cancer; neurofibromatosis-1 associated malignant peripheral nerve sheath tumors (MPNST); and medulloblastoma, or a combination of one or more of the foregoing cancers.

In some embodiments, the cancer is hepatocellular carcinoma (HCC). In some embodiments, the cancer is hepatoblastoma. In some embodiments, the cancer is colon cancer. In some embodiments, the cancer is rectal cancer. In some embodiments, the cancer is ovarian cancer, or ovarian carcinoma. In some embodiments, the cancer is ovarian epithelial cancer. In some embodiments, the cancer is fallopian tube cancer. In some embodiments, the cancer is papillary serous cystadenocarcinoma. In some embodiments, the cancer is uterine papillary serous carcinoma (UPSC). In some embodiments, the cancer is hepatocholangiocarcinoma. In some embodiments, the cancer is soft tissue and bone synovial sarcoma. In some embodiments, the cancer is rhabdomyosarcoma. In some embodiments, the cancer is osteosarcoma. In some embodiments, the cancer is anaplastic thyroid cancer. In some embodiments, the cancer is adrenocortical carcinoma. In some embodiments, the cancer is pancreatic cancer, or pancreatic ductal carcinoma. In some embodiments, the cancer is pancreatic adenocarcinoma. In some embodiments, the cancer is glioma. In some embodiments, the cancer is malignant peripheral nerve sheath tumors (MPNST). In some embodiments, the cancer is neurofibromatosis-1 associated MPNST. In some embodiments, the cancer is Waldenstrom's macroglobulinemia. In some embodiments, the cancer is medulloblastoma.

In certain embodiments, the cancer is a leukemia (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, or heavy chain disease. In one embodiment, the cancer is a solid tumor such as a sarcoma or carcinoma (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

In some embodiments, the cancer is glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, or retinoblastoma.

In some embodiments, the cancer is acoustic neuroma, astrocytoma (e.g. Grade I—Pilocytic Astrocytoma, Grade II—Low-grade Astrocytoma, Grade III—Anaplastic Astrocytoma, or Grade IV—Glioblastoma (GBM)), chordoma, CNS lymphoma, craniopharyngioma, brain stem glioma, ependymoma, mixed glioma, optic nerve glioma, subependymoma, medulloblastoma, meningioma, metastatic brain tumor, oligodendroglioma, pituitary tumors, primitive neuroectodermal (PNET) tumor, or schwannoma. In some embodiments, the cancer is a type found more commonly in children than adults, such as brain stem glioma, craniopharyngioma, ependymoma, juvenile pilocytic astrocytoma (JPA), medulloblastoma, optic nerve glioma, pineal tumor, primitive neuroectodermal tumors (PNET), or rhabdoid tumor.

Autoimmune Diseases and Disorders

In certain embodiments, the disorder is an autoimmune disorder. As used herein, the terms "autoimmune disorders" and "autoimmune diseases" are used interchangeably, and include those diseases and disorders which are traditionally classified as autoimmune disorders, as well as inflammatory disorders and immune disorders (excluding viral infections). The intention with the terms "autoimmune disease" and "autoimmune disorder" is to include all diseases and disorders which are driven by innate immune responses and adaptive immune responses which initiate some sort of innate immune inflammatory response. It is the applicant's intent to have the terms "autoimmune disease" and "autoimmune disorder" include the full scope of diseases and disorders which are driven by innate inflammation, with the exception of viral infections.

In certain embodiments, the invention provides for treatment of an autoimmune disorder. Traditional autoimmune disorders commonly occur when the immune system attacks normal cells and/or tissues in the body. Inflammatory disorders often present with chronic inflammation (among other symptoms) in the absence of infection. Autoimmune disorders also include symptoms which arise when the cellular immune system reacts against the body's autoantigens. There may also be autoimmune and/or inflammation manifestation associated with a range of primary immunodeficiency diseases. In further aspects of these embodiments, the autoimmune disease or disorder is associated with high levels of LINE-1 and/or HERV-K RNA protein expression.

One embodiment of the invention is a method of treating type I interferonopathies. In one aspect of this embodiment, the type I interferonopathy is a congenital disorder associated with type I interferon overexpression. In one aspect of this embodiment, the congenital type I interferonopathy is selected from Aicardi-Goutieres syndrome (AGS), Singleton-Merten syndrome, proteasome-associated autoinflammatory syndromes, chronic atypical neutrophilic dermatosis with lipodystrophy and elevated temperature (CANDLE), STING-associated vasculopathy with onset in infancy (SAVI), Japanese autoinflammatory syndrome with lipodystrophy (JASL), spondyloenchondrodysplasia (SPENCD), ISG15 deficiency, Ubiquitin-Specific Peptidase 18 deficiency (pseudo-TORCH syndrome), chronic atypical neurophilic dermatitis with lipodystrophy, DNA II deficiency, trichoheptoenteric syndrome 2, retinal vasculopathy with cerebral leukodystrophy, familial chilblain lupus, and X-linked reticulate pigmentary disorder (XLPDR). In another embodiment, the type I interferonopathy is an acquired disorder in the IFN system.

In one embodiment, the invention provides a method of treating an autoimmune disease which results in an overproduction of interferon. In one aspect of this embodiment, the interferon expressed includes type I interferon. In another aspect of this embodiment, the autoimmune disease is associated with elevated LINE-1 activity and/or expression. In another aspect of this embodiment, the autoimmune disease is associated with elevated HERV-K RNA activity and/or expression.

In certain embodiments, the autoimmune disorder is selected from the group consisting of achalasia, Addison's disease, adult Still's disease, agammaglobulinemia, alopecia areata, amyloidosis, ankylosing spondylitis, anti-GBM/anti-TBM nephritis, antiphospholipid syndrome, autoimmune angioedema, autoimmune dysautonomia, autoimmune encephalitis, autoimmune hepatitis, autoimmune inner ear disease (AIED), autoimmune myocarditis, autoimmune oophoritis, autoimmune orchitis, autoimmune pancreatitis, autoimmune retinopathy, autoimmune urticaria, axonal & neuronal neuropathy (AMAN), Balo disease, Behcet's disease, benign mucosal pemphigoid, bullous pemphigoid, Castleman disease (CD), celiac disease, Chagas disease, chronic inflammatory demyelinating polyneuropathy (CIDP), chronic recurrent multifactorial osteomyelitis (CRMO), Churg-Strauss syndrome or eosinophilic granulomatosis, cicatricial pemphigoid, Cogan's syndrome, cold agglutinin disease, complex regional pain syndrome (previously called reflex sympathetic dystrophy), congenital heart block, coxsackle myocarditis, CREST syndrome, Crohn's disease, cutaneous lupus erythematosus (CLE), dermatitis herpetiformis, dermatomyositis, Devic's disease (neuromyelitis optica), discoid lupus, Dressler's syndrome, endometriosis, eosinophilic esophagitis (EoE), eosinophilic fasciitis, erytherna nodosum, essential mixed cryoglobulinemia, Evans syndrome, fibromyalgia, fibrosing alveolitis, giant cell arteritis (temporal arteritis), giant cell myocarditis, glomerulonephritis, Goodpasture's syndrome, granulomatosis with polyangiitis, graft versus host disease, Graves' disease, Guillain-Barre syndrome, Hashimoto's thyroiditis, hemolytic anemia, Henoch-Schonlein purpura (HSP), herpes gestationis or pemphigold gestationis (PG), hidradenitis suppurativa (acne inversa), inflammatory bowel disease, IgA nephropathy, IgG4-related sclerosing disease, immune thrombocytopenic pupura (ITP), inclusion body myositis (IBM), interstitial cystitis (IC), juvenile arthritis, juvenile diabetes (type I diabetes), juvenile myositis (JM), Kawasaki disease, Lambert-Eaton syndrome, lichen planus, lichen sclerosus, ligneous conjunctivitis, linear IgA disease (LAD), lupus nephritis, lyme disease (chronic), Meniere's disease, microscopic polyangiitis (MPA), mixed connective tissue disease (MCTD), multifocal motor neuropathy, multiple sclerosis, myasthenia gravis, myelin oligodendrocyte glycoprotein antibody disorder, myositis, narcolepsy, neonatal lupus, neutropenia, ocular cicatricial pemphigoid, optic neuritis, palindromic rheumatism, pediatric autoimmune neuropsychiatric disorders associated with streptococcus infections (PANDAS), paraneoplastic cerebellar degeneration (PCD), paroxysmal nocturnal hemoglobinuria (PNH), pars planitis (peripheral uveitis), Parsonage-Turner syndrome, pemphigus, peripheral neuropathy, perivenous encephalomyelitis, pernicious anemia (PA), POEMS syndrome, polyarteritis rheumatica, polymyositis, postmyocardial infarction syndrome, postpericardiotomy syndrome, primary biliary cholangitis, primary sclerosing cholangitis, progesterone dermatitis, progressive hemifacial atrophy (Parry Romberg syndrome), psoriasis, psoriatic arthritis, pure red cell aplasia, pyoderma gangrenosum, Raynoud's phenomena, reactive arthritis, relapsing polychondritis, restless leg syndrome (RLS), retroperitoneal fibrosis, rheumatic fever, rheumatoid arthritis (RA), sarcoidosis, Schmidt syndrome (autoimmune polyendocrine syndrome type II), scleritis, scleroderma, Sjögren's disease, stiff person syndrome, Susac's syndrome, sympathetic ophthalmia, systemic lupus erythematosus (SLE), Takayasu's arteritis, thrombotic thrombocytopenic pupura, thyroid eye disease, Tolosa-Hunt syndrome, transverse myelitis, ulcerative colitis, undifferentiated connective tissue disease, uveitis, vasculitis, vitiligo, Vogt-Koyanagi-Harada disease, and warm autoimmune hemolytic anemia.

In certain embodiments, the autoimmune disorder is selected from Aicardi-Goutieres syndrome, rheumatoid arthritis, psoriasis, systemic lupus erythematosus (SLE), cutaneous lupus erythematosus (CLE), graft versus host disease, scleroderma, type I diabetes, dermatomyositis, inflammatory bowel disease, ulcerative colitis, Crohn's disease, vasculitis, and Sjögren's syndrome.

In certain embodiments, the autoimmune disorder is Aicardi-Goutieres syndrome (AGS). In another embodiment, the autoimmune disorder is systemic lupus erythematosus (SLE). In another embodiment, the autoimmune disease is lupus nephritis. In a further embodiment, the autoimmune disease is cutaneous lupus erythematosus (CLE). In another embodiment, the autoimmune disease is dermatomyositis.

In certain embodiments, the autoimmune disorder is a type 1 interferonopathy. In certain embodiments, the autoimmune disorder is type 1 diabetes, Aicardi-Goutieres syndrome (AGS), systemic lupus erythematosus (SLE), lupus nephritis, cutaneous lupus erythematosus (CLE), familial chilblain lupus, systemic sclerosis, STING-associated vasculopathy with onset in infancy (SAVI), Sjögren's syndrome, or dermatomyositis. In certain embodiments, the immune disorder is a type 1 interferonopathy, type 1 diabetes, Aicardi-Goutieres syndrome (AGS), systemic lupus erythematosus (SLE), lupus nephritis, cutaneous lupus erythematosus (CLE), dermatomyositis, or Sjogren's syndrome. In certain embodiments, the autoimmune disorder is systemic lupus erythematosus (SLE), lupus nephritis, cutaneous lupus erythematosus (CLE), or familial chilblain lupus. In certain embodiments, the immune disorder is systemic lupus erythematosus (SLE).

In certain embodiments, the autoimmune disorder is type 1 diabetes. In certain embodiments, the autoimmune disorder is familial chilblain lupus. In certain embodiments, the autoimmune disorder is systemic sclerosis. In certain embodiments, the autoimmune disorder is STING-associated vasculopathy with onset in infancy (SAVI). In certain embodiments, the autoimmune disorder is Sjögren's syndrome.

In certain embodiments, the autoimmune disorder is inflammatory bowel disease, Crohn's disease, or ulcerative colitis. In certain embodiments, the autoimmune disorder is inflammatory bowel disease. In certain embodiments, the autoimmune disorder is Crohn's disease. In certain embodiments, the autoimmune disorder is ulcerative colitis. In one embodiment, the autoimmune disorder is drug-induced colitis, such as colitis associated with the administration of checkpoint inhibitors to cancer patients.

In certain embodiments, the autoimmune disorder is osteoarthritis, nonalcoholic steatohepatitis (NASH), non-alcoholic fatty liver disease (NAFLD), cholestatic liver disease, sclerosing cholangitis, asthma, bronchitis, chronic obstructive pulmonary disease (COPD), pulmonary fibrosis, pulmonary hypertension, pericarditis, gout, or myositis.

In certain embodiments, the autoimmune disorder is Reiter's syndrome, exfoliative psoriatic dermatitis, pemphigus vulgaris, autoimmune uveitis, pulmonary hemosiderosis, amyloidosis, aphthous stomatitis, thyroiditis, gastritis, adrenalitis (Addison's disease), ovaritis, primary biliary cirrhosis, myasthenia gravis, gonadal failure, hypoparathyroidism, alopecia, malabsorption syndrome, pernicious anemia, hepatitis, hypopituitarism, diabetes insipidus, or sicca syndrome.

Neurological Disorders

In certain embodiments, the disorder is a neurological disorder. In certain embodiments, the neurological disorder is Alzheimer's disease, amyotrophic lateral sclerosis (ALS), multiple sclerosis, Parkinson's disease, Huntington's disease, peripheral neuropathy, age-related macular degeneration, Creutzfeldt-Jacob disease, stroke, prion disease, frontotemporal dementia, Pick's disease, progressive supranuclear palsy, spinocerebellar ataxias, Lewy body disease, dementia, multiple system atrophy, epilepsy, bipolar disorder, schizophrenia, an anxiety disorder, or major depression. In certain embodiments, the neurological disorder is Alzheimer's disease, amyotrophic lateral sclerosis (ALS), multiple sclerosis, Parkinson's disease, Huntington's disease, or dementia. In another embodiment, the neurological disorder is ALS or progressive supranuclear palsy.

In certain embodiments, the neurological disorder is peripheral neuropathy, age-related macular degeneration, Creutzfeldt-Jacob disease, stroke, prion disease, frontotemporal dementia, Pick's disease, progressive supranuclear palsy, spinocerebellar ataxias, Lewy body disease, dementia, multiple system atrophy, epilepsy, bipolar disorder, schizophrenia, an anxiety disorder, or major depression.

In certain embodiments, the neurological disorder is Alzheimer's disease. In other embodiments, the neurological disorder is amyotrophic lateral sclerosis (ALS). In another embodiment, the neurological disorder is multiple sclerosis. In a further embodiment, the neurological disorder is Parkinson's disease. In another embodiment, the neurological disorder is Huntington's disease. In another embodiment, the neurological disorder is dementia. In certain embodiments, the neurological disorder is age-related macular degeneration. In a further embodiment, the neurological disorder is progressive supranuclear palsy. In certain embodiments, the neurological disorder is stroke.

Viral Infection

In certain embodiments, the viral infection is an infection by human immunodeficiency viruses 1 or 2 (HIV-1 or HIV-2), human T-cell leukemia viruses 1 or 2 (HTLV-1 or HTLV-2), respiratory syncytial virus (RSV), human papilloma virus (HPV), adenovirus, hepatitis B virus (HBV), hepatitis C virus (HCV), Epstein-Barr virus (EBV), varicella zoster virus (VZV), cytomegalovirus (CMV), herpes simplex viruses 1 or 2 (HSV-1 or HSV-2), human herpes virus 8 (HHV-8, also known as Kaposi's sarcoma-associated virus), or a flavivirus selected from Yellow Fever virus, Dengue virus, Japanese Encephalitis, and West Nile virus.

In certain embodiments, the viral infection is an infection by human immunodeficiency viruses 1 or 2 (HIV-1 or HIV-2). In certain embodiments, the viral infection is an infection by human immunodeficiency virus 1 (HIV-1). In certain embodiments, the viral infection is an infection by human immunodeficiency virus 2 (HIV-2). In certain embodiments, the viral infection is an infection by human T-cell leukemia viruses 1 or 2 (HTLV-1 or HTLV-2). In certain embodiments, the viral infection is an infection by respiratory syncytial virus (RSV). In certain embodiments, the viral infection is an infection by human papilloma virus (HPV). In certain embodiments, the viral infection is an infection by adenovirus. In certain embodiments, the viral infection is an infection by hepatitis B virus (HBV). In certain embodiments, the viral infection is an infection by hepatitis C virus (HCV). In certain embodiments, the viral infection is an infection by Epstein-Barr virus (EBV). In certain embodiments, the viral infection is an infection by varicella zoster virus (VZV). In certain embodiments, the viral infection is an infection by cytomegalovirus (CMV). In certain embodiments, the viral infection is an infection by herpes simplex viruses 1 or 2 (HSV-1 or HSV-2). In certain embodiments, the viral infection is an infection by human herpes virus 8 (HHV-8, also known as Kaposi's sarcoma-associated virus). In certain embodiments, the viral infection is an infection by a flavivirus selected from Yellow Fever virus, Dengue virus, Japanese Encephalitis, and West Nile virus.

In certain embodiments, the viral infection is an infection by an adenovirus. In certain embodiments, the viral infection is an infection by a herpesvirus. In certain embodiments, the viral infection is an infection by a poxvirus. In certain embodiments, the viral infection is an infection by a parvovirus. In certain embodiments, the viral infection is an infection by a reovirus. In certain embodiments, the viral infection is an infection by a picornavirus. In certain embodiments, the viral infection is an infection by a rhinovirus or enterovirus. In certain embodiments, the viral infection is an infection by a togavirus. In certain embodiments, the viral infection is an infection by an orthomyxovirus. In certain embodiments, the viral infection is an infection by a rhabdovirus. In certain embodiments, the viral infection is an infection by a retrovirus. In certain embodiments, the viral infection is an infection by a hepadnavirus.

In certain embodiments, the viral infection is an infection by a coronavirus. In some embodiments, the coronavirus is an alpha, beta, gamma, or delta coronavirus. In certain embodiments, the viral infection is an infection by a coronavirus selected from 229E (alpha coronavirus), NL63 (alpha coronavirus), OC43 (beta coronavirus), HKU1 (beta coronavirus), MERS-CoV (beta coronavirus), SARS-CoV (beta coronavirus), and SARS-CoV-2 (coronavirus disease 2019, or COVID-19).

In certain embodiments, the viral infection is an infection by an influenza virus. In certain embodiments, the viral infection is an infection by a type A or type B influenza virus. In certain embodiments, the viral infection is an infection by an influenza virus selected from H5N1, H1N1, and H3N2.

In certain embodiments, the viral infection is an infection by a poliovirus. In certain embodiments, the viral infection is an infection by a type 1 poliovirus. In certain embodiments, the viral infection is an infection by a type 2 poliovirus. In certain embodiments, the viral infection is an infection by a type 3 poliovirus.

Subjects

In certain embodiments, the subject has (i) expression of LINE1 RNA, LINE1 ORF1 polypeptide, and/or LINE1 ORF2 polypeptide; (ii) activity of LINE1 reverse transcriptase; (iii) expression of HERV-K RNA, and/or (iv) activity of HERV-K reverse transcriptase.

In certain embodiments, the subject has (i) expression of LINE1 RNA, LINE1 ORF1 polypeptide, and/or LINE1 ORF2 polypeptide; and/or (ii) activity of LINE1 reverse transcriptase. In certain embodiments, the subject has (i) elevated expression of LINE1 RNA, LINE1 ORF1 polypeptide, and/or LINE1 ORF2 polypeptide; and/or (ii) elevated activity of LINE1 reverse transcriptase. In certain embodiments, the subject has expression of LINE1 RNA, LINE1 ORF1 polypeptide, and/or LINE1 ORF2 polypeptide. In certain embodiments, the subject has expression of LINE1 RNA. In certain embodiments, the subject has expression of LINE1 ORF1 polypeptide. In certain embodiments, the subject has expression of LINE1 ORF2 polypeptide. In certain embodiments, the subject has activity of LINE1 reverse transcriptase.

In certain embodiments, the subject has (i) expression of HERV-K RNA, and/or (ii) activity of HERV-K reverse transcriptase. In certain embodiments, the subject has expression of HERV-K RNA. In certain embodiments, the subject has activity of HERV-K reverse transcriptase.

In certain embodiments, the subject has elevated (i) levels of LINE1 RNA, LINE1 ORF1 polypeptide, and/or LINE1 ORF2 polypeptide; (ii) activity of LINE1 reverse transcriptase; (iii) levels of HERV-K RNA, and/or (iv) activity of HERV-K reverse transcriptase.

In certain embodiments, the subject has elevated (i) levels of LINE1 RNA, LINE1 ORF1 polypeptide, and/or LINE1 ORF2 polypeptide; and/or (ii) activity of LINE1 reverse transcriptase. In certain embodiments, the subject has elevated levels of LINE1 RNA, LINE1 ORF1 polypeptide, and/or LINE1 ORF2 polypeptide. In certain embodiments, the subject has elevated levels of LINE1 RNA. In certain embodiments, the subject has elevated levels of LINE1 ORF1 polypeptide. In certain embodiments, the subject has elevated levels of LINE1 ORF2 polypeptide. In certain embodiments, the subject has elevated activity of LINE1 reverse transcriptase.

In certain embodiments, the subject has elevated (i) levels of HERV-K RNA, and/or (ii) activity of HERV-K reverse transcriptase. In certain embodiments, the subject has elevated levels of HERV-K RNA. In certain embodiments, the subject has elevated activity of HERV-K reverse transcriptase.

In certain embodiments, the subject is a human. In certain embodiments, the subject is an adult human. In certain embodiments, the subject is a pediatric human. In certain embodiments, the subject is a companion animal. In certain embodiments, the subject is a canine, feline, or equine.

Uses of Compounds

Another aspect of the disclosure provides for the use of a compound described herein (such as a compound of Formula I, or other compounds in Section III) for treating a medical disorder, such as a medical disorder described herein.

Another aspect of the disclosure provides for the use of a compound described herein (such as a compound of Formula I, or other compounds in Section III) in the manufacture of a medicament. In certain embodiments, the medicament is for treating a disorder described herein, such as cancer, an autoimmune disorder, and/or a neurological disorder. In certain embodiments the disorder is aging, or a disease associated with aging.

Methods of Inhibiting LINE1 and/or HERV-K Reverse Transcriptase Activity in a Subject Another embodiment of the invention provides a method of inhibiting LINE1 reverse transcriptase activity in a subject suffering from a disorder selected from the group consisting of cancer, an autoimmune disorder, and a neurological disorder. The method comprises contacting a LINE1 reverse transcriptase with an effective amount of a compound of Formula I, in order to inhibit the activity of said LINE1 reverse transcriptase; wherein the compound of Formula I is as described in any of embodiments one through twenty-two, above. Additional compounds useful in the method are further described in Section III. In certain embodiments, the method includes administration of any compound in Table 1 and Table 2, or a pharmaceutically acceptable salt thereof, and/or a pharmaceutical composition comprising the same.

Another embodiment of the invention provides a method of a method of inhibiting LINE1 reverse transcriptase activity in a subject, the method comprising contacting a LINE1 reverse transcriptase with an effective amount of a compound according to Formula I, or a pharmaceutically acceptable salt thereof, or a composition comprising a compound according to Formula I, in order to inhibit the activity of said LINE1 reverse transcriptase.

In certain embodiments, the disorder is a disorder defined by one of the embodiments described above, such as cancer, an autoimmune disorder, and/or a neurological disorder. In certain embodiments the disorder is aging, or a disease associated with aging.

In certain embodiments, the method further comprises inhibiting HERV-K reverse transcriptase activity in the subject.

Another embodiment of the invention provides a method of inhibiting LINE1 reverse transcriptase activity in a subject suffering from a disorder selected from the group consisting of cancer, an autoimmune disorder, and a neurological disorder. The method comprises contacting a LINE1 reverse transcriptase with an effective amount of a compound described herein, such as a compound of Formula I or a compound in Table 1, 1-A, 1-B, 2, 2-A, or 2-B, in order to inhibit the activity of said LINE1 reverse transcriptase.

In certain embodiments, the disorder is a disorder defined by one of the embodiments described above, such as cancer, an autoimmune disorder, and/or a neurological disorder.

In certain embodiments, the method further comprises inhibiting HERV-K reverse transcriptase activity in the subject.

In certain embodiments, the particular compound is a compound described for any of the embodiments herein, in any and all combinations of the various embodiments, and aspects of embodiments, described. For example, in certain embodiments, the compound is a compound of Formula II, III, IV, V, or VI, or a pharmaceutically acceptable salt thereof. In certain embodiments, the compound is a compound in Table 1, 1-A, 1-B, 1-C, 2, 2-A, 2-B, or 2-C, or a pharmaceutically acceptable salt thereof. In certain embodiments, the compound is a compound in Table 1, 1-A, 1-B, 1-C, 1-D, 2, 2-A, 2-B, or 2-C, or a pharmaceutically acceptable salt thereof. In certain embodiments, the compound is a compound in Table 1, 1-A, 1-B, 1-C, 2, 2-A, 2-B, or 2-C. In certain embodiments, the compound is a compound in Table 1, 1-A, 1-B, 1-C, 1-D, 2, 2-A, 2-B, or 2-C. In certain embodiments, the compound is a compound in Table 1, 1-A, 1-C, 2, 2-A, or 2-C, or a pharmaceutically acceptable salt thereof. In certain embodiments, the compound is a compound in Table 1, 1-A, 1-C, 2, 2-A, or 2-C. In certain embodiments, the compound is a compound in Table 1, 1-A, 1-B, 2, 2-A, or 2-B, or a pharmaceutically acceptable salt thereof. In certain embodiments, the compound is a compound in Table 1, 1-A, 1-B, 2, 2-A, or 2-B. In certain embodiments, the compound is a compound in Table 1, 1-A, 2, or 2-A, or a pharmaceutically acceptable salt thereof. In certain embodiments, the compound is a compound in Table 1, 1-A, 2, or 2-A. In certain embodiments, the compound is a compound in Table 1-B or 2-B, or a pharmaceutically acceptable salt thereof. In certain embodiments, the compound is a compound in Table 1-B or 2-B. In certain embodiments, the compound is a compound in Table 1 or Table 2, or a pharmaceutically acceptable salt thereof. In certain embodiments, the compound is a compound in Table 1 or Table 2.

In certain embodiments, the compound is administered in a pharmaceutical composition comprising the compound and a carrier, excipient, and/or vehicle, as further described in Section V, below.

Another embodiment of the invention provides a method of inhibiting LINE1 reverse transcriptase activity. The method comprises contacting a LINE1 reverse transcriptase with a therapeutically effective amount of a compound described herein, such as a compound in Table 1, 1-A, or 1-B, in order to inhibit the activity of said LINE1 reverse transcriptase. In certain embodiments, the particular compound is a compound described for any of the embodiments herein, in any and all combinations of the various embodiments, and aspects of embodiments, described. For example, in certain embodiments, the compound is a compound of Formula I, II, III, IV, V, or VI, or a pharmaceutically acceptable salt thereof. In certain embodiments, the compound is a compound of Formula II, III, or IV, or a pharmaceutically acceptable salt thereof.

In certain embodiments, the compound is administered in a pharmaceutical composition comprising the compound and a carrier, excipient, and/or vehicle, as further described in Section V, below.

Another aspect of the disclosure provides a method of inhibiting HERV-K reverse transcriptase activity in a subject suffering from a disorder selected from the group consisting of cancer, an autoimmune disorder, and a neurological disorder. The method comprises contacting a HERV-K reverse transcriptase with an effective amount of a compound of Formula I, in order to inhibit the activity of said HERV-K reverse transcriptase; wherein the compound of Formula I is as described in any of embodiments one through twenty-two, above. Additional compounds useful in the method are further described in Section III. In certain embodiments, the method includes administration of any compound in Table 1 and Table 2, or a pharmaceutically acceptable salt thereof, and/or a pharmaceutical composition comprising the same.

Another aspect of the disclosure provides a method of inhibiting HERV-K reverse transcriptase activity in a subject, the method comprising contacting a HERV-K reverse transcriptase with an effective amount of a compound according to Formula I, or a pharmaceutically acceptable salt thereof, or the composition comprising a compound of Formula I, in order to inhibit the activity of said HERV-K reverse transcriptase.

In certain embodiments, the disorder is a disorder defined by one of the embodiments described in Section I, above, such as cancer, an autoimmune disorder, and/or a neurological disorder. In certain embodiments the disorder is aging, or a disease associated with aging.

In certain embodiments, the method further comprises inhibiting LINE1 reverse transcriptase activity in the subject.

Another embodiment of the invention provides a method of inhibiting HERV-K reverse transcriptase activity in a subject suffering from a disorder selected from the group consisting of cancer, an autoimmune disorder, and a neurological disorder. The method comprises contacting a HERV-K reverse transcriptase with an effective amount of a compound described herein, such as a compound of Formula I or a compound in Table 1, 1-A, 1-B, 2, or 2-A, in order to inhibit the activity of said HERV-K reverse transcriptase.

In certain embodiments, the disorder is a disorder defined by one of the embodiments described above, such as cancer, an autoimmune disorder, and/or a neurological disorder.

In certain embodiments, the method further comprises inhibiting LINE1 reverse transcriptase activity in the subject.

In certain embodiments, the particular compound is a compound described for any of the embodiments herein, in any and all combinations of the various embodiments, and aspects of embodiments, described. For example, in certain embodiments, the compound is a compound of Formula II, III, IV, V, or VI, or a pharmaceutically acceptable salt thereof. In certain embodiments, the compound is a compound in Table 1, 1-A, 1-B, 1-C, 2, 2-A, 2-B, or 2-C, or a pharmaceutically acceptable salt thereof. In certain embodiments, the compound is a compound in Table 1, 1-A, 1-B, 1-C, 1-D, 2, 2-A, 2-B, or 2-C, or a pharmaceutically acceptable salt thereof. In certain embodiments, the compound is a compound in Table 1, 1-A, 1-B, 1-C, 2, 2-A, 2-B, or 2-C. In certain embodiments, the compound is a compound in Table 1, 1-A, 1-B, 1-C, 1-D, 2, 2-A, 2-B, or 2-C. In certain embodiments, the compound is a compound in Table 1, 1-A, 1-C, 2, 2-A, or 2-C, or a pharmaceutically acceptable salt thereof. In certain embodiments, the compound is a compound in Table 1, 1-A, 1-C, 2, 2-A, or 2-C. In certain embodiments, the compound is a compound in Table 1, 1-A, 1-B, 2, 2-A, or 2-B, or a pharmaceutically acceptable salt thereof. In certain embodiments, the compound is a compound in Table 1, 1-A, 1-B, 2, 2-A, or 2-B. In certain embodiments, the compound is a compound in Table 1, 1-A, 2, or 2-A, or a pharmaceutically acceptable salt thereof. In certain embodiments, the compound is a compound in Table 1, 1-A, 2, or 2-A. In certain embodiments, the compound is a compound in Table 1-B or 2-B, or a pharmaceutically acceptable salt thereof. In certain embodiments, the compound is a compound in Table 1-B or 2-B. In certain embodiments, the compound is a compound in Table 1 or Table 2, or a pharmaceutically acceptable salt thereof. In certain embodiments, the compound is a compound in Table 1 or Table 2.

In certain embodiments, the compound is administered in a pharmaceutical composition comprising the compound and a carrier, excipient, and/or vehicle, as further described in Section V, below.

Another embodiment of the invention provides a method of inhibiting HERV-K reverse transcriptase activity. The method comprises contacting a HERV-K reverse transcriptase with a therapeutically effective amount of a compound described herein, such as a compound in Table 1, 1-A, or 1-B, in order to inhibit the activity of said HERV-K reverse transcriptase. In certain embodiments, the particular compound is a compound described for any of the embodiments herein, in any and all combinations of the various embodiments, and aspects of embodiments, described. For example, in certain embodiments, the compound is a compound of Formula I, II, III, IV, V, or VI, or a pharmaceutically acceptable salt thereof. In certain embodiments, the compound is a compound of Formula II, III, or IV, or a pharmaceutically acceptable salt thereof.

One aspect of the disclosure provides compounds having a superior combination of properties including potent inhibitory activity towards LINE1 reverse transcriptase, selectivity for inhibiting LINE1 reverse transcriptase, and superior physical properties that render the compounds well-suited for use as an orally administered medicine. Selectivity for inhibiting LINE1 reverse transcriptase can be characterized according to ability of the compounds to inhibit LINE1 reverse transcriptase while having substantially less inhibitory activity towards DNA polymerases (e.g., $\alpha$, $\beta$ and $\gamma$). In part because inhibition of DNA polymerases, such as DNA polymerase gamma, can result in toxicity in the form of mitotoxicity, compounds demonstrating potent inhibitory activity towards LINE1 reverse transcriptase while having substantially less inhibitory activity towards DNA polymerases are an important discovery and significant scientific advance. The potent inhibitory activity towards LINE1 reverse transcriptase in combination with low inhibitory activity towards DNA polymerases contributes to a high therapeutic index for subject compounds, thereby providing a superior performance profile for the compound in medical therapy. Experimental results herein demonstrate these benefits.

Another aspect of the disclosure provides compounds having a superior combination of properties including potent inhibitory activity towards LINE1 reverse transcriptase, selectivity for inhibiting LINE1 reverse transcriptase, potent inhibition of pathogenic interferon response in inflammatory tissues, and superior physical properties that render the compounds well-suited for use as an orally administered medicine. As described above, selectivity for inhibiting LINE1 reverse transcriptase can be characterized according to ability of the compounds to inhibit LINE1 reverse transcriptase while having substantially less inhibitory activity towards DNA polymerases (e.g., $\alpha$, $\beta$ and $\gamma$). In part because inhibition of DNA polymerase, such as DNA polymerase gamma, can result in toxicity in the form of mitotoxicity, compounds demonstrating potent inhibitory activity towards LINE1 reverse transcriptase while having substantially less inhibitory activity towards DNA polymerases (e.g., $\alpha$, $\beta$ and $\gamma$) are an important discovery and significant scientific advance. Compounds having potent inhibition of pathogenic interferon response in inflammatory tissues are useful for treating cancer, autoimmune disease (e.g., SLE and CLE), neurological disorders, aging, and diseases associated with aging. The potent inhibitory activity towards LINE1 reverse transcriptase in combination with low inhibitory activity towards DNA polymerases (e.g., $\alpha$, $\beta$ and $\gamma$) contributes to a high therapeutic index for subject compounds, thereby providing a superior performance profile for the compound in medical therapy.

Another aspect of the disclosure provides compounds having a superior combination of properties including potent inhibitory activity towards HERV-K reverse transcriptase, selectivity for inhibiting HERV-K reverse transcriptase, and superior physical properties that render the compounds well-suited for use as an orally administered medicine. Selectivity for inhibiting HERV-K reverse transcriptase can be characterized according to ability of the compounds to inhibit HERV-K reverse transcriptase while having substantially less inhibitory activity towards DNA polymerases (e.g., $\alpha$, $\beta$ and $\gamma$). In part because inhibition of DNA polymerases, such as DNA polymerase gamma, can result in toxicity in the form of mitotoxicity, compounds demonstrating potent inhibitory activity towards HERV-K reverse transcriptase while having substantially less inhibitory activity towards DNA polymerase are an important significant scientific advance. Compounds that are potent inhibitors of HERV-K reverse transcriptase are useful for treating HERV-K reverse transcriptase associated disorders. The potent inhibitory activity towards HERV-K reverse transcriptase in combination with low inhibitory activity towards DNA polymerases contributes to a high therapeutic index for subject compounds, thereby providing a superior performance profile for the compound in medical therapy.

In certain embodiments, the compound is administered in a pharmaceutical composition comprising the compound and a carrier, excipient, and/or vehicle, as further described in Section V, below.

Compounds may be tested for ability to inhibit LINE1 reverse transcriptase activity, for example, as described in the Examples. Compounds may be tested for ability to inhibit HERV-K reverse transcriptase activity, for example, as described in the Examples.

III. ADDITIONAL COMPOUNDS

The methods described in Section II above may be further characterized according to the compounds used in the methods. Additional exemplary compounds for use in the methods are described below, along with exemplary procedures for making the compounds.

In certain embodiments, the compound for use in the methods described above is a compound of Formula I found in Table 2:

TABLE 2

| Compound No. | Structure | Name |
|---|---|---|
| 23 | 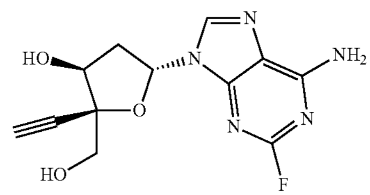 [SMILES: C#C[C@]1(CO)O[C@@H](n2cnc3c(N)nc(F)nc32)C[C@@H]1O] | (2R,3S,5R)-5-(6-amino-2-fluoro-9H-purin-9-yl)-2-ethynyl-2-(hydroxymethyl)tetrahydrofuran-3-ol |
| 24 | 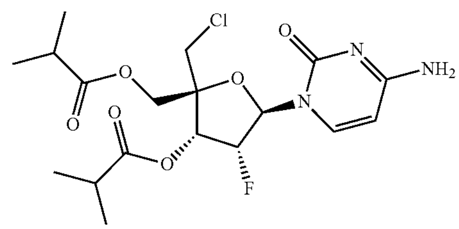 [SMILES: CC(C)C(=O)OC[C@@]1(CCl)O[C@@H](n2ccc(N)nc2=O)[C@H](F)[C@@H]1OC(=O)C(C)C] | (2R,3R,4R,5R)-5-(4-amino-2-oxopyrimidin-1(2H)-yl)-2-(chloromethyl)-4-fluoro-2-((isobutyryloxy)methyl)tetrahydrofuran-3-yl isobutyrate |
| 25 | 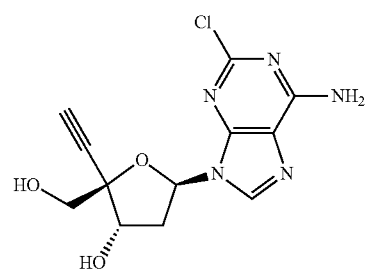 [SMILES: C#C[C@]1(CO)O[C@@H](n2cnc3c(N)nc(Cl)nc32)C[C@@H]1O] | (2R,3S,5R)-5-(6-amino-2-chloro-9H-purin-9-yl)-2-ethynyl-2-(hydroxymethyl)tetrahydrofuran-3-ol |
| 26 | 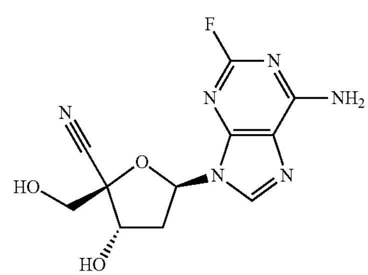 [SMILES: N#C[C@]1(CO)O[C@@H](n2cnc3c(N)nc(F)nc32)C[C@@H]1O] | (2R,3S,5R)-5-(6-amino-2-fluoro-9H-purin-9-yl)-3-hydroxy-2-(hydroxymethyl)tetrahydrofuran-2-carbonitrile |
| 27 | 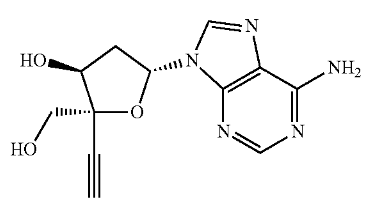 [SMILES: C#C[C@]1(CO)O[C@@H](n2cnc3c(N)ncnc32)C[C@@H]1O] | (2R,3S,5R)-5-(6-amino-9H-purin-9-yl)-2-ethynyl-2-(hydroxymethyl)tetrahydrofuran-3-ol |

TABLE 2-continued

| Compound No. | Structure | Name |
| --- | --- | --- |
| 28 | 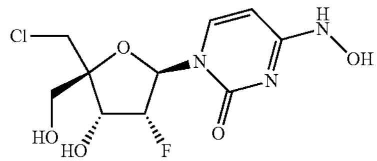 [SMILES: O=c1nc(NO)ccn1[C@@H]1O[C@@](CO)(CCl)[C@@H](O)[C@H]1F] | 1-((2R,3R,4R,5R)-5-(chloromethyl)-3-fluoro-4-hydroxy-5-(hydroxymethyl)tetrahydrofuran-2-yl)-4-(hydroxyamino)pyrimidin-2(1H)-one |
| 29 | 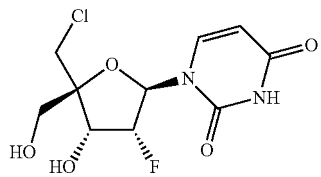 [SMILES: O=c1ccn([C@@H]2O[C@@](CO)(CCl)[C@@H](O)[C@H]2F)c(=O)[nH]1] | 1-((2R,3R,4R,5R)-5-(chloromethyl)-3-fluoro-4-hydroxy-5-(hydroxymethyl)tetrahydrofuran-2-yl)pyrimidine-2,4(1H,3H)-dione |
| 30 | 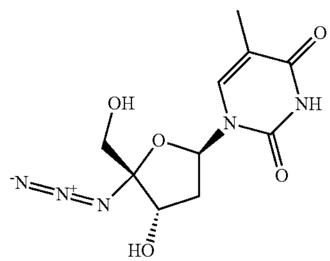 | 1-((2R,4S,5R)-5-azido-4-hydroxy-5-(hydroxymethyl)tetrahydrofuran-2-yl)-5-methylpyrimidine-2,4(1H,3H)-dione |
| 31 | 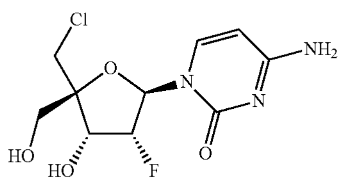 [SMILES: Nc1ccn([C@@H]2O[C@@](CO)(CCl)[C@@H](O)[C@H]2F)c(=O)n1] | 4-amino-1-((2R,3R,4R,5R)-5-(chloromethyl)-3-fluoro-4-hydroxy-5-(hydroxymethyl)tetrahydrofuran-2-yl)pyrimidin-2(1H)-one |
| 32 | 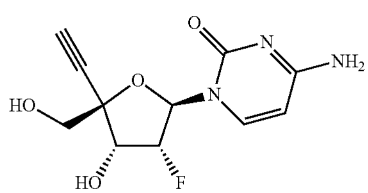 [SMILES: C#C[C@]1(CO)O[C@@H](n2ccc(N)nc2=O)[C@H](F)[C@@H]1O] | 4-amino-1-((2R,3R,4R,5R)-5-ethynyl-3-fluoro-4-hydroxy-5-(hydroxymethyl)tetrahydrofuran-2-yl)pyrimidin-2(1H)-one |
| 33 | 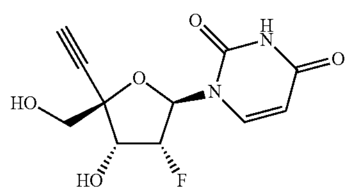 [SMILES: C#C[C@]1(CO)O[C@@H](n2ccc(=O)[nH]c2=O)[C@H](F)[C@@H]1O] | 1-((2R,3R,4R,5R)-5-ethynyl-3-fluoro-4-hydroxy-5-(hydroxymethyl)tetrahydrofuran-2-yl)pyrimidine-2,4(1H,3H)-dione |
| 34 | 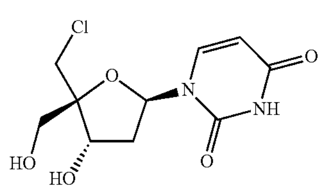 [SMILES: O=c1ccn([C@H]2C[C@H](O)[C@](CO)(CCl)O2)c(=O)[nH]1] | 1-((2R,4S,5R)-5-(chloromethyl)-4-hydroxy-5-(hydroxymethyl)tetrahydrofuran-2-yl)pyrimidine-2,4(1H,3H)-dione |
| 35 | 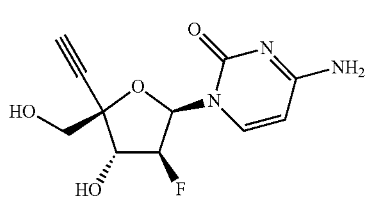 [SMILES: C#C[C@]1(CO)O[C@@H](n2ccc(N)nc2=O)[C@@H](F)[C@@H]1O] | 4-amino-1-((2R,3S,4R,5R)-5-ethynyl-3-fluoro-4-hydroxy-5-(hydroxymethyl)tetrahydrofuran-2-yl)pyrimidin-2(1H)-one |

TABLE 2-continued

| Compound No. | Structure | Name |
|---|---|---|
| 36 | 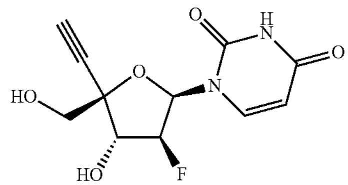 [SMILES: C#C[C@]1(CO)O[C@@H](n2ccc(=O)[nH]c2=O)[C@@H](F)[C@@H]1O] | 1-((2R,3S,4R,5R)-5-ethynyl-3-fluoro-4-hydroxy-5-(hydroxymethyl)tetrahydrofuran-2-yl)pyrimidine-2,4(1H,3H)-dione |
| 37 | 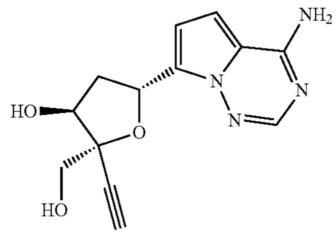 [SMILES: C#C[C@]1(CO)O[C@@H](c2ccc3c(N)ncnn23)C[C@@H]1O] | (2R,3S,5R)-5-(4-aminopyrrolo[2,1-f][1,2,4]triazin-7-yl)-2-ethynyl-2-(hydroxymethyl)tetrahydrofuran-3-ol |
| 38 | 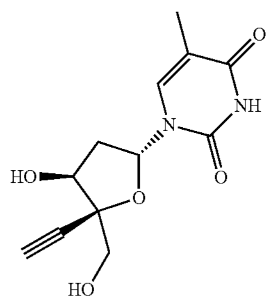 [SMILES: C#C[C@]1(CO)O[C@@H](n2cc(C)c(=O)[nH]c2=O)C[C@@H]1O] | 1-((2R,4S,5R)-5-ethynyl-4-hydroxy-5-(hydroxymethyl)tetrahydrofuran-2-yl)-5-methylpyrimidine-2,4(1H,3H)-dione |
| 39 | 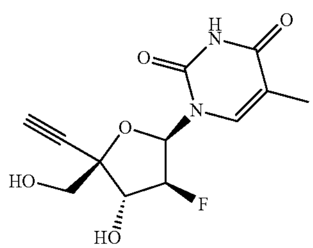 [SMILES: C#C[C@]1(CO)O[C@@H](n2cc(C)c(=O)[nH]c2=O)[C@@H](F)[C@@H]1O] | 1-((2R,3S,4R,5R)-5-ethynyl-3-fluoro-4-hydroxy-5-(hydroxymethyl)tetrahydrofuran-2-yl)-5-methylpyrimidine-2,4(1H,3H)-dione |
| 40 | 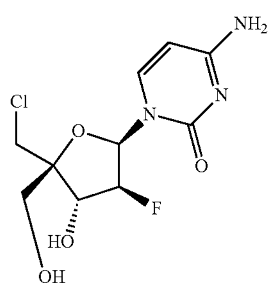 [SMILES: Nc1ccn([C@@H]2O[C@@](CO)(CCl)[C@@H](O)[C@@H]2F)c(=O)n1] | 4-amino-1-((2R,3S,4R,5R)-5-(chloromethyl)-3-fluoro-4-hydroxy-5-(hydroxymethyl)tetrahydrofuran-2-yl)pyrimidin-2(1H)-one |
| 41 | 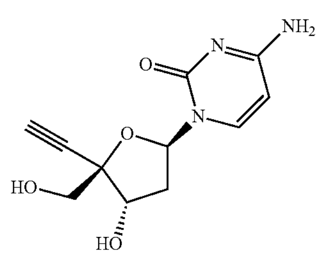 [SMILES: C#C[C@]1(CO)O[C@@H](n2ccc(N)nc2=O)C[C@@H]1O] | 4-amino-1-((2R,4S,5R)-5-ethynyl-4-hydroxy-5-(hydroxymethyl)tetrahydrofuran-2-yl)pyrimidin-2(1H)-one |

TABLE 2-continued

| Compound No. | Structure | Name |
|---|---|---|
| 42 | 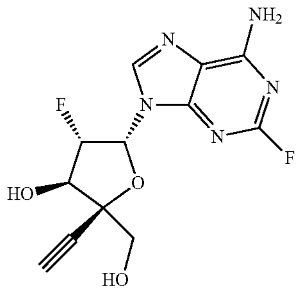 [SMILES: C#C[C@]1(CO)O[C@@H](n2cnc3c(N)nc(F)nc32)[C@@H](F)[C@@H]1O] | (2R,3R,4S,5R)-5-(6-amino-2-fluoro-9H-purin-9-yl)-2-ethynyl-4-fluoro-2-(hydroxymethyl)tetrahydrofuran-3-ol |
| 43 | 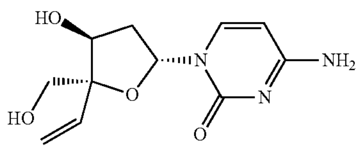 [SMILES: C=C[C@]1(CO)O[C@@H](n2ccc(N)nc2=O)C[C@@H]1O] | 4-amino-1-((2R,4S,5R)-4-hydroxy-5-(hydroxymethyl)-5-vinyltetrahydrofuran-2-yl)pyrimidin-2(1H)-one |
| 44 | 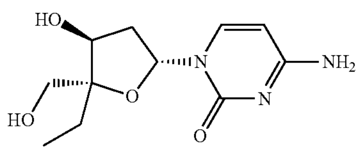 [SMILES: CC[C@]1(CO)O[C@@H](n2ccc(N)nc2=O)C[C@@H]1O] | 4-amino-1-((2R,4S,5R)-5-ethyl-4-hydroxy-5-(hydroxymethyl)tetrahydrofuran-2-yl)pyrimidin-2(1H)-one |
| 45 | 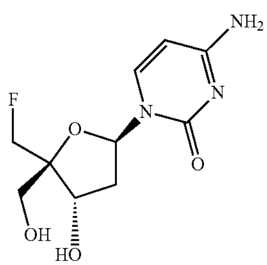 [SMILES: Nc1ccn([C@H]2C[C@H](O)[C@](CO)(CF)O2)c(=O)n1] | 4-amino-1-((2R,4S,5R)-5-(fluoromethyl)-4-hydroxy-5-(hydroxymethyl)tetrahydrofuran-2-yl)pyrimidin-2(1H)-one |
| 46 | 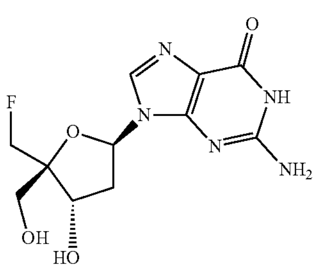 [SMILES: Nc1nc2c(ncn2[C@H]2C[C@H](O)[C@](CO)(CF)O2)c(=O)[nH]1] | 2-amino-9-((2R,4S,5R)-5-(fluoromethyl)-4-hydroxy-5-(hydroxymethyl)tetrahydrofuran-2-yl)-1,9-dihydro-6H-purin-6-one |
| 47 | 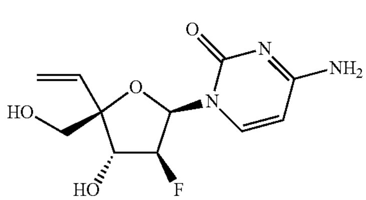 [SMILES: C=C[C@]1(CO)O[C@@H](n2ccc(N)nc2=O)[C@@H](F)[C@@H]1O] | 4-amino-1-((2R,3S,4R,5R)-3-fluoro-4-hydroxy-5-(hydroxymethyl)-5-vinyltetrahydrofuran-2-yl)pyrimidin-2(1H)-one |

TABLE 2-continued

| Compound No. | Structure | Name |
|---|---|---|
| 48 | 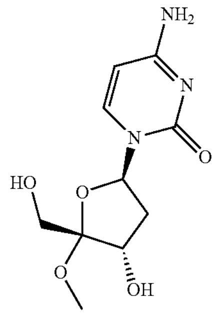 [SMILES: CO[C@]1(CO)O[C@@H](n2ccc(N)nc2=O)C[C@@H]1O] | 4-amino-1-((2R,4S,5R)-4-hydroxy-5-(hydroxymethyl)-5-methoxytetrahydrofuran-2-yl)pyrimidin-2(1H)-one |
| 49 | 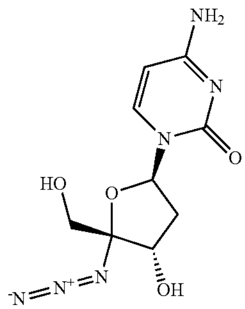 | 4-amino-1-((2R,4S,5R)-5-azido-4-hydroxy-5-(hydroxymethyl)tetrahydrofuran-2-yl)pyrimidin-2(1H)-one |
| 50 | 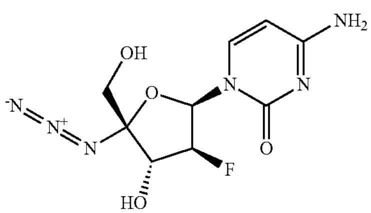 | 4-amino-1-((2R,3S,4R,5R)-5-azido-3-fluoro-4-hydroxy-5-(hydroxymethyl)tetrahydrofuran-2-yl)pyrimidin-2(1H)-one |
| 51 | 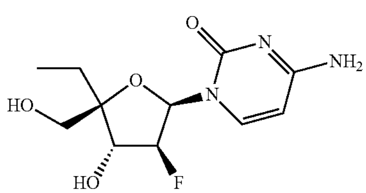 [SMILES: CC[C@]1(CO)O[C@@H](n2ccc(N)nc2=O)[C@@H](F)[C@@H]1O] | 4-amino-1-((2R,3S,4R,5R)-5-ethyl-3-fluoro-4-hydroxy-5-(hydroxymethyl)tetrahydrofuran-2-yl)pyrimidin-2(1H)-one |

In certain embodiments, the compound for use in the methods described above is a compound in Table 2, 2-A, 2-B, or 2-C, herein, or a pharmaceutically acceptable salt thereof. In certain embodiments, the compound for use in the methods described above is a compound in Table 2, 2-A, 2-B, or 2-C, herein. In certain embodiments, the compound for use in the methods described above is a compound in Table 2, 2-A, or 2-B, herein, or a pharmaceutically acceptable salt thereof. In certain embodiments, the compound for use in the methods described above is a compound in Table 2, 2-A, or 2-B, herein. In certain embodiments, the compound for use in the methods described above is a compound in Table 2 or 2-A, herein, or a pharmaceutically acceptable salt thereof. In certain embodiments, the compound for use in the methods described above is a compound in Table 2 or 2-A, herein. In certain embodiments, the compound for use in the methods described above is a compound in Table 2-A, below, or a pharmaceutically acceptable salt thereof. In certain embodiments, the compound for use in the methods described above is a compound in Table 2-A, below. In certain embodiments, the compound for use in the methods described above is a compound in Table 2-B, below, or a pharmaceutically acceptable salt thereof. In certain embodiments, the compound for use in the methods described above is a compound in Table 2-B, below. In certain embodiments, the compound for use in the methods described above is a compound in Table 2-C, below, or a pharmaceutically acceptable salt thereof. In certain embodiments, the compound for use in the methods described above is a compound in Table 2-C, below.

TABLE 2-A

| Compound | Structure | Name |
|---|---|---|
| 106 | 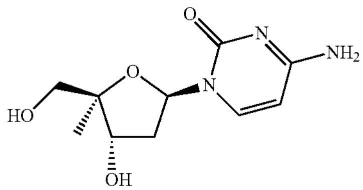 [SMILES: C[C@]1(CO)O[C@@H](n2ccc(N)nc2=O)C[C@@H]1O] | 4-amino-1-((2R,4S,5R)-4-hydroxy-5-(hydroxymethyl)-5-methyltetrahydrofuran-2-yl)pyrimidin-2(1H)-one |
| 107 | 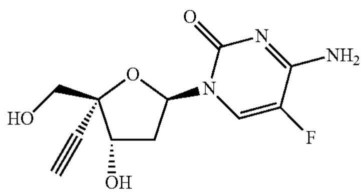 [SMILES: C#C[C@]1(CO)O[C@@H](n2cc(F)c(N)nc2=O)C[C@@H]1O] | 4-amino-1-((2R,4S,5R)-5-ethynyl-4-hydroxy-5-(hydroxymethyl)tetrahydrofuran-2-yl)-5-fluoropyrimidin-2(1H)-one |
| 108 | 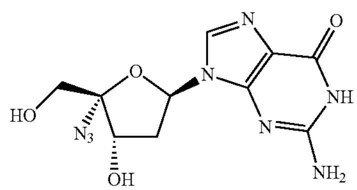 [SMILES: [N-]=[N+]=N[C@]1(CO)O[C@@H](n2cnc3c(=O)[nH]c(N)nc32)C[C@@H]1O] | 2-amino-9-((2R,4S,5R)-5-azido-4-hydroxy-5-(hydroxymethyl)tetrahydrofuran-2-yl)-1,9-dihydro-6H-purin-6-one |
| 109 | 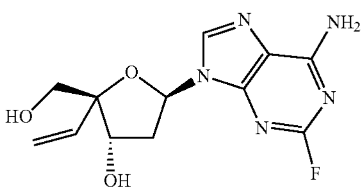 [SMILES: C=C[C@]1(CO)O[C@@H](n2cnc3c(N)nc(F)nc32)C[C@@H]1O] | (2R,3S,5R)-5-(6-amino-2-fluoro-9H-purin-9-yl)-2-(hydroxymethyl)-2-vinyltetrahydrofuran-3-ol |
| 110 | 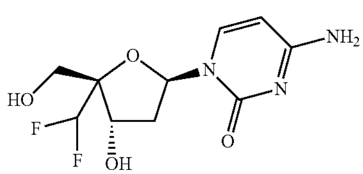 [SMILES: Nc1ccn([C@H]2C[C@H](O)[C@](CO)(C(F)F)O2)c(=O)n1] | 4-amino-1-((2R,4S,5R)-5-(difluoromethyl)-4-hydroxy-5-(hydroxymethyl)-tetrahydrofuran-2-yl)pyrimidin-2(1H)-one |
| 111 | 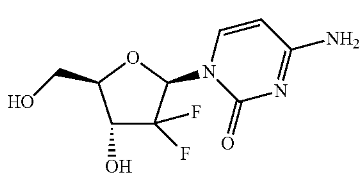 [SMILES: Nc1ccn([C@@H]2O[C@H](CO)[C@@H](O)C2(F)F)c(=O)n1] | 4-amino-1-((2R,4R,5R)-3,3-difluoro-4-hydroxy-5-(hydroxymethyl)tetrahydrofuran-2-yl)pyrimidin-2(1H)-one |
| 112 | 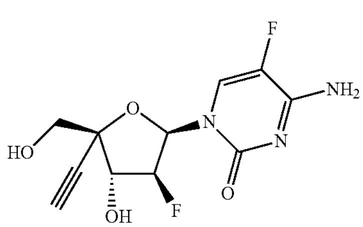 [SMILES: C#C[C@]1(CO)O[C@@H](n2cc(F)c(N)nc2=O)[C@@H](F)[C@@H]1O] | 4-amino-1-((2R,3S,4R,5R)-5-ethynyl-3-fluoro-4-hydroxy-5-(hydroxymethyl)-tetrahydrofuran-2-yl)-5-fluoropyrimidin-2(1H)-one |
| 113 | 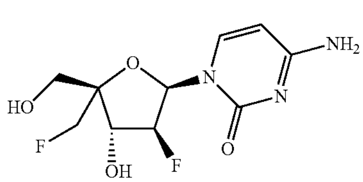 [SMILES: Nc1ccn([C@@H]2O[C@@](CO)(CF)[C@@H](O)[C@@H]2F)c(=O)n1] | 4-amino-1-((2R,3S,4R,5R)-3-fluoro-5-(fluoromethyl)-4-hydroxy-5-(hydroxymethyl)-tetrahydrofuran-2-yl)pyrimidin-2(1H)-one |

TABLE 2-A-continued

| Compound | Structure | Name |
|---|---|---|
| 114 | 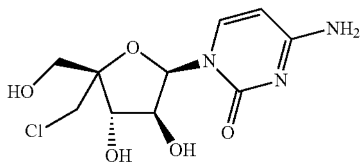 [SMILES: Nc1ccn([C@@H]2O[C@@](CO)(CCl)[C@@H](O)[C@@H]2O)c(=O)n1] | 4-amino-1-((2R,3S,4S,5R)-5-(chloromethyl)-3,4-dihydroxy-5-(hydroxymethyl)tetrahydrofuran-2-yl)pyrimidin-2(1H)-one |
| 115 | 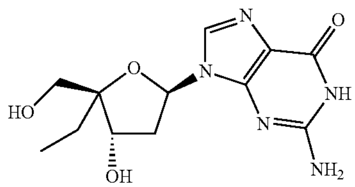 [SMILES: CC[C@]1(CO)O[C@@H](n2cnc3c(=O)[nH]c(N)nc32)C[C@@H]1O] | 2-amino-9-((2R,4S,5R)-5-ethyl-4-hydroxy-5-(hydroxymethyl)tetrahydrofuran-2-yl)-1,9-dihydro-6H-purin-6-one |
| 116 | 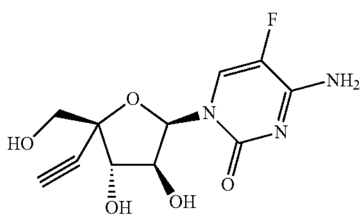 [SMILES: C#C[C@]1(CO)O[C@@H](n2cc(F)c(N)nc2=O)[C@@H](O)[C@@H]1O] | 4-amino-1-((2R,3S,4S,5R)-5-ethynyl-3,4-dihydroxy-5-(hydroxymethyl)tetrahydrofuran-2-yl)-5-fluoropyrimidin-2(1H)-one |
| 117 | 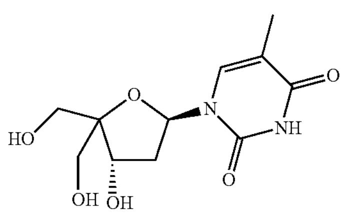 [SMILES: Cc1cn([C@H]2C[C@H](O)C(CO)(CO)O2)c(=O)[nH]c1=O] | 1-((2R,4S)-4-hydroxy-5,5-bis(hydroxymethyl)tetrahydrofuran-2-yl)-5-methylpyrimidine-2,4(1H,3H)-dione |
| 118 | 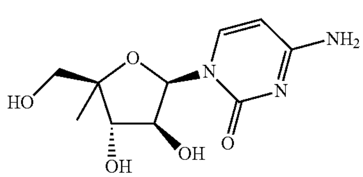 [SMILES: C[C@]1(CO)O[C@@H](n2ccc(N)nc2=O)[C@@H](O)[C@@H]1O] | 4-amino-1-((2R,3S,4S,5R)-3,4-dihydroxy-5-(hydroxymethyl)-5-methyltetrahydrofuran-2-yl)pyrimidin-2(1H)-one |

TABLE 2-B

| Compound | Structure |
|---|---|
| 35-TP | 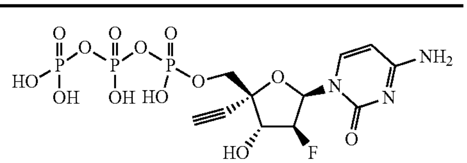 |
| 40-TP | 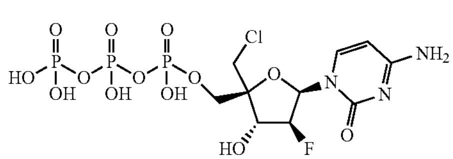 [SMILES: Nc1ccn([C@@H]2O[C@](CCl)(COP(=O)(O)OP(=O)(O)OP(=O)(O)O)[C@@H](O)[C@@H]2F)c(=O)n1] |

TABLE 2-C

| Compound | Structure |
|---|---|
| 165 | 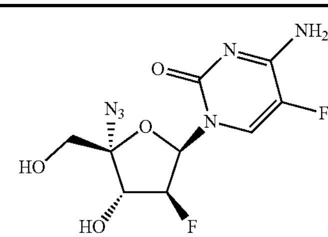 |
| 166 | 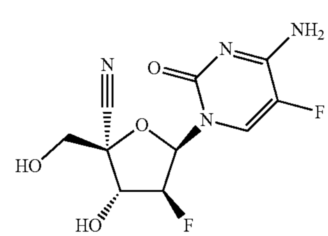 [SMILES: N#C[C@]1(CO)O[C@@H](n2cc(F)c(N)nc2=O)[C@@H](F)[C@@H]1O] |

TABLE 2-C-continued

| Compound | Structure |
|---|---|
| 167 | F₂HC, HO, HO, F (cytosine base with 5-F) |
| 168 | F₂HC, HO, HO, F (cytosine base) |
| 169 | Cl, HO, HO, OH (uracil base) |
| 170 | F, HO, HO, OH (uracil base) |
| 171 | Cl, HO, HO, F (uracil base) |
| 172 | Br, HO, HO, F (cytosine base) |

In certain embodiments, the compound is a compound of Formula I, or a pharmaceutically acceptable salt thereof. In certain embodiments, the compound of Formula I, or a pharmaceutically acceptable salt thereof, excludes all of the compounds listed in Table 2. In certain embodiments, the compound of Formula I, or a pharmaceutically acceptable salt thereof, excludes all of the compounds listed in Tables 2, 2-A, and 2-B. In certain embodiments, the compound of Formula I, or a pharmaceutically acceptable salt thereof, is a compound listed in Table 1, Table 1-A, or Table 1-B. In certain embodiments, the compound of Formula I, or a pharmaceutically acceptable salt thereof, is a compound listed in Table 1, Table 1-A, Table 1-B, or Table 1-C. In certain embodiments, the compound of Formula I, or a pharmaceutically acceptable salt thereof, is a compound listed in Table 1, Table 1-A, Table 1-B, Table 1-C, or Table 1-D. In certain embodiments, the compound of Formula I, or a pharmaceutically acceptable salt thereof, is a compound listed in Table 1. In any of these embodiments, the compound is a compound of Formula I.

IV. COMBINATION THERAPY

Another aspect of the disclosure provides for combination therapy. In certain embodiments, the methods described herein above further comprise administration of one or more additional therapeutic agents to treat medical disorders (e.g., according to the methods described in Section II). Accordingly, in some embodiments, a method of the invention further comprises administering an effective amount of one or more additional therapeutic agents.

Each of the methods described herein for treating disease using combination therapy may be further characterized according to the additional therapeutic agent used in the method. For example, in certain embodiments, the additional therapeutic agent is a second compound provided herein, or a pharmaceutically acceptable salt thereof. In certain embodiments, the additional therapeutic agent is a second compound provided herein.

In certain embodiments, the additional therapeutic agent is stavudine, a prodrug thereof, or a pharmaceutically acceptable salt of either of the foregoing. In certain embodiments, the additional therapeutic agent is stavudine, stampidine, or a pharmaceutically acceptable salt of either of the foregoing. In certain embodiments, the additional therapeutic agent is stavudine or stampidine.

In certain embodiments, the additional therapeutic agent is tenofovir, a prodrug thereof, or a pharmaceutically acceptable salt of either of the foregoing. In certain embodiments, the additional therapeutic agent is tenofovir, tenofovir alafenamide, tenofovir amibufenamide, tenofovir disoproxil, or tenofovir exalidex; or a pharmaceutically acceptable salt thereof. In certain embodiments, the additional therapeutic agent is tenofovir, tenofovir alafenamide, tenofovir amibufenamide, tenofovir disoproxil, or tenofovir exalidex.

In certain embodiments, the additional therapeutic agent is tenofovir, or a pharmaceutically acceptable salt thereof. In certain embodiments, the additional therapeutic agent is tenofovir. In certain embodiments, the additional therapeutic agent is tenofovir alafenamide, or a pharmaceutically acceptable salt thereof. In certain embodiments, the additional therapeutic agent is tenofovir alafenamide. In certain embodiments, the additional therapeutic agent is tenofovir amibufenamide, or a pharmaceutically acceptable salt thereof. In certain embodiments, the additional therapeutic agent is tenofovir amibufenamide. In certain embodiments, the additional therapeutic agent is tenofovir disoproxil, or a pharmaceutically acceptable salt thereof. In certain embodiments, the additional therapeutic agent is tenofovir disoproxil, or a fumarate, succinate, maleate, orotate, aspartate, or phosphate salt thereof. In certain embodiments, the additional therapeutic agent is tenofovir disoproxil, or a fumarate, succinate, or maleate salt thereof. In certain embodiments, the additional therapeutic agent is tenofovir disoproxil. In certain embodiments, the additional therapeutic agent is tenofovir exalidex, or a pharmaceutically acceptable salt thereof. In certain embodiments, the additional therapeutic agent is tenofovir exalidex, or a potassium salt thereof. In certain embodiments, the additional therapeutic agent is tenofovir exalidex.

In some embodiments, the present invention provides a method of treating a disclosed disease or condition comprising administering to a patient in need thereof an effective amount of a compound disclosed herein, or a pharmaceutically acceptable salt thereof, and co-administering simultaneously, separately or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

One or more other therapeutic agent may be administered separately from a compound or composition of the invention, as part of a multiple dosage regimen. Alternatively, one or more other therapeutic agents may be part of a single dosage form, mixed together with a compound of this invention in a single composition. If administered as a multiple dosage regime, one or more other therapeutic agent and a compound or composition of the invention may be administered simultaneously, sequentially or separately within a period of time from one another, for example within 1, 2, 3, 4, 5, 6, 7, 8, 9, 10, 11, 12, 13, 14, 15, 16, 17, 18, 19, 20, 21, 22, 23, or 24 hours from one another. In some embodiments, one or more other therapeutic agent and a compound or composition of the invention are administered as a multiple dosage regimen more than 24 hours apart.

The doses and dosage regimen of the active ingredients used in the combination therapy may be determined by an attending clinician. In certain embodiments, the compound described herein, such as a compound of Formula I, including other compounds in Section III, and the additional therapeutic agent(s) (e.g., the second, third, or fourth, or fifth anti-cancer agent, described below) are administered in doses commonly employed when such agents are used as monotherapy for treating the disorder. In other embodiments, the compound described herein, such as a compound of Formula I, including other compounds in Section III, and the additional therapeutic agent(s) (e.g., the second, third, or fourth, or fifth anti-cancer agent, described below) are administered in doses lower than the doses commonly employed when such agents are used as monotherapy for treating the disorder. In certain embodiments, the compound described herein, such as a compound of Formula I, including other compounds in Section III, and the additional therapeutic agent(s) (e.g. the second, third, or fourth, or fifth anti-cancer agent, described below) are present in the same pharmaceutical composition, which is suitable for oral administration.

In certain embodiments, the compound described herein, such as a compound of Formula I, including other compounds in Section III, and the additional therapeutic agent(s) (e.g., the second, third, or fourth, or fifth anti-cancer agent, described below) may act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

Another aspect of this invention is a kit comprising a therapeutically effective amount of a compound described herein, such as a compound of Formula I, including other compounds in Section III, a pharmaceutically acceptable carrier, adjuvant, or vehicle, and optionally at least one additional therapeutic agent listed below.

Cancer

Accordingly, another aspect of the disclosure provides a method of treating cancer in a patient. The method comprises administering to a subject in need thereof (i) a therapeutically effective amount of a compound of Formula I, including a compound selected from Table 1 or Table 2, or a pharmaceutically acceptable salt thereof, and (ii) a second anti-cancer agent, in order to treat the cancer. In certain embodiments, the method comprises administering to a subject in need thereof (i) a therapeutically effective amount of a compound described herein (such as a compound of Formula I, II, III, IV, V, or VI), or a pharmaceutically acceptable salt thereof, and (ii) a second anti-cancer agent, in order to treat the cancer.

In certain embodiments, the second anti-cancer agent is radiation therapy. In certain embodiments, the second anti-cancer agent is a therapeutic antibody. In certain embodiments, the therapeutic antibody targets one of the following: CD20, CD30, CD33, CD52, EpCAM, CEA, gpA33, a mucin, TAG-72, CAIX, PSMA, a folate-binding protein, a ganglioside, Le, VEGF, VEGFR, VEGFR2, integrin αVβ3, integrin α5 β1, EGFR, ERBB2, ERBB3, MET, IGF1R, EPHA3, TRAILR1, TRAILR2, RANKL, FAP, tenascin, CD19, KIR, NKG2A, CD47, CEACAM1, c-MET, VISTA, CD73, CD38, BAFF, interleukin-1 beta, B4GALNT1, interleukin-6, and interleukin-6 receptor. In certain embodiments, the therapeutic antibody targets VEGFR3 or TRAILR3.

In certain embodiments, the second anti-cancer agent is a therapeutic antibody selected from the group consisting of rituximab, ibritumomab tiuxetan, tositumomab, obinutuzumab, ofatumumab, brentuximab vedotin, gemtuzumab ozogamicin, alemtuzumab, IGN101, adecatumumab, labetuzumab, huA33, pemtumomab, oregovomab, minetumomab, cG250, J591, Mov18, farletuzumab, 3F8, ch14.18, KW-2871, hu3S193, gN311, bevacizumab, IM-2C6, pazopanib, sorafenib, axitinib, CDP791, lenvatinib, ramucirumab, etaracizumab, volociximab, cetuximab, panitumumab, nimotuzumab, 806, afatinib, erlotinib, gefitinib, osimertinib, vandetanib, trastuzumab, pertuzumab, MM-121, AMG 102, METMAB, SCH 900105, AVE1642, IMC-A12, MK-0646, R1507, CP 751871, KB004, IIIA-4, mapatumumab, HGS-ETR2, CS-1008, denosumab, sibrotuzumab, F19, 81C6, MEDI551, lirilumab, MEDI9447, daratumumab, belimumab, canakinumab, dinutuximab, siltuximab, and tocilizumab. In certain embodiments, the second anti-cancer agent is a therapeutic antibody selected from the group consisting of rituximab, ibritumomab tiuxetan, tositumomab, obinutuzumab, ofatumumab, brentuximab vedotin, gemtuzumab ozogamicin, alemtuzumab, IGN101, adecatumumab, labetuzumab, huA33, pemtumomab, oregovomab, minetumomab, cG250, J591, Mov18, farletuzumab, 3F8, ch14.18, KW-2871, hu3S193, IgN311, bevacizumab, IM-2C6, CDP791, ramucirumab, etaracizumab, volociximab, cetuximab, panitumumab, nimotuzumab, 806, trastuzumab, pertuzumab, MM-121, AMG 102, METMAB, SCH 900105, AVE1642, IMC-A12, MK-0646, R1507, CP 751871, KB004, IIIA-4, mapatumumab, HGS-ETR2, CS-1008, denosumab, sibrotuzumab, F19, 81C6, MEDI551, lirilumab, MEDI9447, daratumumab, belimumab, canakinumab, dinutuximab, siltuximab, and tocilizumab.

In certain embodiments, the second anti-cancer agent is a cytokine. In certain embodiments, the cytokine is IL-12, IL-15, GM-CSF, or G-CSF.

In certain embodiments, the second anti-cancer agent is sipuleucel-T, aldesleukin (a human recombinant interleukin-2 product having the chemical name des-alanyl-1, serine-125 human interleukin-2), dabrafenib (a kinase inhibitor having the chemical name N-{3-[5-(2-aminopyrimidin-4-yl)-2-tert-butyl-1,3-thiazol-4-yl]-2-fluorophenyl}-2,6-difluorobenzenesulfonamide), vemurafenib (a kinase inhibitor having the chemical name propane-1-sulfonic acid {3-[5-(4-chlorophenyl)-1H-pyrrolo[2,3-b]pyridine-3-carbonyl]-2,4-difluoro-phenyl}-amide), or 2-chloro-deoxyadenosine. In certain embodiments, the second anti-cancer agent is pazopanib, sorafenib, axitinib, lenvatinib, afatinib, erlotinib, gefitinib, osimertinib, or vandetanib.

In certain embodiments, the second anti-cancer agent is a placental growth factor, an antibody-drug conjugate, an oncolytic virus, or an anti-cancer vaccine. In certain embodiments, the second anti-cancer agent is a placental growth factor. In certain embodiments, the second anti-cancer agent is a placental growth factor comprising ziv-aflibercept. In certain embodiments, the second anti-cancer agent is an antibody-drug conjugate. In certain embodiments, the second anti-cancer agent is an antibody-drug conjugate selected from the group consisting of brentoxumab vedotin and trastuzumab emtransine.

In certain embodiments, the second anti-cancer agent is an oncolytic virus. In certain embodiments, the second anti-cancer agent is the oncolytic virus talimogene laherparepvec. In certain embodiments, the second anti-cancer agent is an anti-cancer vaccine. In certain embodiments, the second anti-cancer agent is an anti-cancer vaccine selected from the group consisting of a GM-CSF tumor vaccine, a STING/GM-CSF tumor vaccine, and NY-ESO-1. In certain embodiments, the second anti-cancer agent is a cytokine selected from IL-12, IL-15, GM-CSF, and G-CSF.

In certain embodiments, the second anti-cancer agent is an immune checkpoint inhibitor (also referred to as immune checkpoint blockers). Immune checkpoint inhibitors are a class of therapeutic agents that have the effect of blocking immune checkpoints. See, for example, Pardoll in *Nature Reviews Cancer* (2012) vol. 12, pages 252-264. In certain embodiments, the immune checkpoint inhibitor is an agent that inhibits one or more of (i) cytotoxic T-lymphocyte-associated antigen 4 (CTLA4), (ii) programmed cell death protein 1 (PD1), (iii) PDL1, (iv) LAB3, (v) B7-H3, (vi) B7-H4, and (vii) TIM3. In certain embodiments, the immune checkpoint inhibitor is ipilumumab. In certain embodiments, the immune checkpoint inhibitor is pembrolizumab. In certain embodiments, the immune checkpoint inhibitor is atezolizumab, cemiplimab, cemiplimab-rwlc, dostarlimab, durvalumab, or nivolumab.

In certain embodiments, the second anti-cancer agent is a monoclonal antibody that targets a non-checkpoint target (e.g., Herceptin). In certain embodiments, the second anti-cancer agent is a non-cytoxic agent (e.g., a kinase inhibitor).

In certain embodiments, the second anti-cancer agent is selected from mitomycin, ribomustin, vincristine, tretinoin, etoposide, cladribine, gemcitabine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, aminoglutethimide, amsacrine, proglumide, elliptinium acetate, ketanserin, doxifluridine, etretinate, isotretinoin, streptozocin, nimustine, vindesine, cytarabine, bicalutamide, vinorelbine, vesnarinone, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, colony stimulating factor-1, colony stimulating factor-2, denileukin diftitox, interleukin-2, leutinizing hormone releasing factor, interferon-alpha, interferon-2 alpha, interferon-beta, and interferon-gamma.

In certain embodiments, the second anti-cancer agent is paclitaxel, docetaxel, cisplatin, epirubicin, 5-fluorouracil, or capecitabine. In certain embodiments, the second anti-cancer agent is ixabepilone or eribulin. In certain embodiments, the second anti-cancer agent is ART558. In certain embodiments, the second anti-cancer agent is lapatinib, neratinib, or tucatinib. In certain embodiments, the second anti-cancer agent is fulvestrant. In certain embodiments, the second anti-cancer agent is anastrozole or exemestane. In certain embodiments, the second anti-cancer agent is MK2206. In certain embodiments, the second anti-cancer agent is dacomitinib, mobocertinib, necitumumab, or amivantamab. In certain embodiments, the second anti-cancer agent is pemetrexed. In certain embodiments, the second anti-cancer agent is brigatinib. In certain embodiments, the second anti-cancer agent is capmatinib or tepotinib. In certain embodiments, the second anti-cancer agent is entrectinib. In certain embodiments, the second anti-cancer agent is pralsetinib or selpercatinib. In certain embodiments, the second anti-cancer agent is ipilimumab. In certain embodiments, the second anti-cancer agent is sotorasib. In certain embodiments, the second anti-cancer agent is topotecan or irinotecan. In certain embodiments, the second anti-cancer agent is lurbinectedin, melphalan, or thiotepa. In certain embodiments, the second anti-cancer agent is trifluridine or tipiracil. In certain embodiments, the second anti-cancer agent is megestrol. In certain embodiments, the second anti-cancer agent is sunitinib. In certain embodiments, the second anti-cancer agent is lanreotide or lutetium. In certain embodiments, the second anti-cancer agent is belzutifan.

In certain embodiments, the second anti-cancer agent is an ALK Inhibitor, an ATR Inhibitor, an A2A Antagonist, a Base Excision Repair Inhibitor, a Bcr-Abl Tyrosine Kinase Inhibitor, a Bruton's Tyrosine Kinase Inhibitor, a CDC7 Inhibitor, a CHK1 Inhibitor, a Cyclin-Dependent Kinase Inhibitor, a DNA-PK Inhibitor, an Inhibitor of both DNA-PK and mTOR, a DNMT1 Inhibitor, a DNMT1 Inhibitor plus 2-chloro-deoxyadenosine, an HDAC Inhibitor, a Hedgehog Signaling Pathway Inhibitor, an IDO Inhibitor, a JAK Inhibitor, a mTOR Inhibitor, a MEK Inhibitor, a MELK Inhibitor, a MTH1 Inhibitor, a PARP Inhibitor, a Phosphoinositide 3-Kinase Inhibitor, an Inhibitor of both PARP1 and DHODH, a Proteasome Inhibitor, a Topoisomerase-II Inhibitor, a Tyrosine Kinase Inhibitor, a VEGFR Inhibitor, or a WEE1 Inhibitor.

In certain embodiments, the second anti-cancer agent is an ALK Inhibitor. In certain embodiments, the second anti-cancer agent is an ALK Inhibitor comprising ceritinib or crizotinib. In certain embodiments, the second anti-cancer agent is an ALK Inhibitor comprising lorlatinib. In certain embodiments, the second anti-cancer agent is an ATR Inhibitor. In certain embodiments, the second anti-cancer agent is an ATR Inhibitor comprising AZD6738 or VX-970. In certain embodiments, the second anti-cancer agent is an ATR Inhibitor comprising BAY1895344 or M4344. In certain embodiments, the second anti-cancer agent is an A2A Antagonist. In certain embodiments, the second anti-cancer agent is a Base Excision Repair Inhibitor comprising methoxyamine. In certain embodiments, the second anti-cancer agent is a Base Excision Repair Inhibitor, such as methoxyamine. In certain embodiments, the second anti-cancer agent is a Bcr-Abl Tyrosine Kinase Inhibitor. In certain embodiments, the second anti-cancer agent is a Bcr-Abl Tyrosine Kinase Inhibitor comprising dasatinib or nilotinib. In certain embodiments, the second anti-cancer agent is a Bruton's Tyrosine Kinase Inhibitor. In certain embodiments, the second anti-cancer agent is a Bruton's Tyrosine Kinase Inhibitor comprising ibrutinib. In certain embodiments, the second anti-cancer agent is a CDC7 Inhibitor. In certain embodiments, the second anti-cancer agent is a CDC7 Inhibitor comprising RXDX-103 or AS-141.

In certain embodiments, the second anti-cancer agent is a CHK1 Inhibitor. In certain embodiments, the second anti-cancer agent is a CHK1 Inhibitor comprising MK-8776, ARRY-575, or SAR-020106. In certain embodiments, the second anti-cancer agent is a CHK1 Inhibitor comprising AZD7762. In certain embodiments, the second anti-cancer agent is a Cyclin-Dependent Kinase Inhibitor. In certain embodiments, the second anti-cancer agent is a Cyclin-Dependent Kinase Inhibitor comprising palbociclib. In certain embodiments, the second anti-cancer agent is a Cyclin-Dependent Kinase Inhibitor comprising abemaciclib or ribociclib. In certain embodiments, the second anti-cancer agent is a DNA-PK Inhibitor. In certain embodiments, the second anti-cancer agent is a DNA-PK Inhibitor comprising MSC2490484A. In certain embodiments, the second anti-cancer agent is Inhibitor of both DNA-PK and mTOR. In certain embodiments, the second anti-cancer agent comprises CC-115.

In certain embodiments, the second anti-cancer agent is a DNMT1 Inhibitor. In certain embodiments, the second anti-cancer agent is a DNMT1 Inhibitor comprising decitabine, RX-3117, guadecitabine, NUC-8000, or azacytidine. In certain embodiments, the second anti-cancer agent comprises a DNMT1 Inhibitor and 2-chloro-deoxyadenosine. In certain embodiments, the second anti-cancer agent comprises ASTX-727.

In certain embodiments, the second anti-cancer agent is a HDAC Inhibitor. In certain embodiments, the second anti-cancer agent is a HDAC Inhibitor comprising OBP-801, CHR-3996, etinostate, resminostate, pracinostat, CG-200745, panobinostat, romidepsin, mocetinostat, belinostat, AR-42, ricolinostat, KA-3000, or ACY-241.

In certain embodiments, the second anti-cancer agent is a Hedgehog Signaling Pathway Inhibitor. In certain embodiments, the second anti-cancer agent is a Hedgehog Signaling Pathway Inhibitor comprising sonidegib or vismodegib. In certain embodiments, the second anti-cancer agent is an IDO Inhibitor. In certain embodiments, the second anti-cancer agent is an IDO Inhibitor comprising INCB024360. In certain embodiments, the second anti-cancer agent is a JAK Inhibitor. In certain embodiments, the second anti-cancer agent is a JAK Inhibitor comprising ruxolitinib or tofacitinib. In certain embodiments, the second anti-cancer agent is a mTOR Inhibitor. In certain embodiments, the second anti-cancer agent is a mTOR Inhibitor comprising everolimus or temsirolimus. In certain embodiments, the second anti-cancer agent is a MEK Inhibitor. In certain embodiments, the second anti-cancer agent is a MEK Inhibitor comprising cobimetinib or trametinib. In certain embodiments, the second anti-cancer agent is a MELK Inhibitor. In certain embodiments, the second anti-cancer agent is a MELK Inhibitor comprising ARN-7016, APTO-500, or OTS-167. In certain embodiments, the second anti-cancer agent is a MTH1 Inhibitor. In certain embodiments, the second anti-cancer agent is a MTH1 Inhibitor comprising (S)-crizotinib, TH287, or TH588.

In certain embodiments, the second anti-cancer agent is a PARP Inhibitor. In certain embodiments, the second anti-cancer agent is a PARP Inhibitor comprising MP-124, olaparib, BGB-290, talazoparib, veliparib, niraparib, E7449, rucaparib, or ABT-767. In certain embodiments, the second anti-cancer agent is a Phosphoinositide 3-Kinase Inhibitor. In certain embodiments, the second anti-cancer agent is a Phosphoinositide 3-Kinase Inhibitor comprising idelalisib. In certain embodiments, the second anti-cancer agent is a Phosphoinositide 3-Kinase Inhibitor comprising alpelisib. In certain embodiments, the second anti-cancer agent is an inhibitor of both PARP1 and DHODH (i.e., an agent that inhibits both poly ADP ribose polymerase 1 and dihydroorotate dehydrogenase).

In certain embodiments, the second anti-cancer agent is a Proteasome Inhibitor. In certain embodiments, the second anti-cancer agent is a Proteasome Inhibitor comprising bortezomib or carfilzomib. In certain embodiments, the second anti-cancer agent is a Topoisomerase-II Inhibitor. In certain embodiments, the second anti-cancer agent is a Topoisomerase-II Inhibitor comprising vosaroxin.

In certain embodiments, the second anti-cancer agent is a Tyrosine Kinase Inhibitor. In certain embodiments, the second anti-cancer agent is a Tyrosine Kinase Inhibitor comprising bosutinib, cabozantinib, imatinib or ponatinib. In certain embodiments, the second anti-cancer agent is a VEGFR Inhibitor. In certain embodiments, the second anti-cancer agent is a VEGFR Inhibitor comprising regorafenib. In certain embodiments, the second anti-cancer agent is a WEE1 Inhibitor. In certain embodiments, the second anti-cancer agent is a WEE1 Inhibitor comprising AZD1775.

In certain embodiments, the second anti-cancer agent is an agonist of OX40, CD137, CD40, GITR, CD27, HVEM, TNFRSF25, or ICOS. In certain embodiments, the second anti-cancer agent is an agonist of OX40, CD137, CD40, or GITR. In certain embodiments, the second anti-cancer agent is an agonist of CD27, HVEM, TNFRSF25, or ICOS.

In certain embodiments, the second anti-cancer agent is a second compound provided herein, or a pharmaceutically acceptable salt thereof. In certain embodiments, the second anti-cancer agent is a second compound provided herein.

In certain embodiments, the second anti-cancer agent is stavudine, a prodrug thereof, or a pharmaceutically acceptable salt of either of the foregoing. In certain embodiments, the second anti-cancer agent is stavudine, stampidine, or a pharmaceutically acceptable salt of either of the foregoing. In certain embodiments, the second anti-cancer agent is stavudine or stampidine.

In certain embodiments, the second anti-cancer agent is tenofovir, a prodrug thereof, or a pharmaceutically acceptable salt of either of the foregoing. In certain embodiments, the second anti-cancer agent is tenofovir, tenofovir alafenamide, tenofovir amibufenamide, tenofovir disoproxil, or tenofovir exalidex; or a pharmaceutically acceptable salt thereof. In certain embodiments, the second anti-cancer agent is tenofovir, tenofovir alafenamide, tenofovir amibufenamide, tenofovir disoproxil, or tenofovir exalidex.

In certain embodiments, the second anti-cancer agent is tenofovir, or a pharmaceutically acceptable salt thereof. In certain embodiments, the second anti-cancer agent is tenofovir. In certain embodiments, the second anti-cancer agent is tenofovir alafenamide, or a pharmaceutically acceptable salt thereof. In certain embodiments, the second anti-cancer agent is tenofovir alafenamide. In certain embodiments, the second anti-cancer agent is tenofovir amibufenamide, or a pharmaceutically acceptable salt thereof. In certain embodiments, the second anti-cancer agent is tenofovir amibufenamide. In certain embodiments, the second anti-cancer agent is tenofovir disoproxil, or a pharmaceutically acceptable salt thereof. In certain embodiments, the second anti-cancer agent is tenofovir disoproxil, or a fumarate, succinate, maleate, orotate, aspartate, or phosphate salt thereof. In certain embodiments, the second anti-cancer agent is tenofovir disoproxil, or a fumarate, succinate, or maleate salt thereof. In certain embodiments, the second anti-cancer agent is tenofovir disoproxil. In certain embodiments, the second anti-cancer agent is tenofovir exalidex, or a pharmaceutically acceptable salt thereof. In certain embodiments, the second anti-cancer agent is tenofovir exalidex, or a potassium salt thereof. In certain embodiments, the second anti-cancer agent is tenofovir exalidex.

In certain embodiments, the method further comprises administering to the subject a third anti-cancer agent. In certain embodiments, the method further comprises administering to the subject a fourth anti-cancer agent. In certain embodiments, the method further comprises administering to the subject a fifth anti-cancer agent.

In certain embodiments, the third anti-cancer agent is one of the second anti-cancer agents described above. In certain embodiments, the fourth anti-cancer agent is one of the second anti-cancer agents described above. In certain embodiments, the fifth anti-cancer agent is one of the second anti-cancer agents described above.

Autoimmune Disorders

Another aspect of the disclosure provides a method of treating an autoimmune disorder in a patient. The method comprises administering to a subject in need thereof (i) a therapeutically effective amount of a compound according to Formula I, including a compound selected from Table 1 or Table 2, or a pharmaceutically acceptable salt thereof, and (ii) a second therapeutic agent, in order to treat the autoimmune disorder. In certain embodiments, the method comprises administering to a subject in need thereof (i) a therapeutically effective amount of a compound described herein (such as a compound of Formula I, II, III, IV, V, or VI), or a pharmaceutically acceptable salt thereof, and (ii) a second therapeutic agent, in order to treat the autoimmune disorder.

In certain embodiments, the second therapeutic agent is a small molecule or a recombinant biologic agent. In certain embodiments, the second therapeutic agent is selected from acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®, Neoral®), tacrolimus, sirolimus, mycophenolate, leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-i" agents such as anakinra (Kineret®) and rilonacept (Arcalyst®), anti-T cell antibodies such as Thymoglobulin, IV Immunoglobulins (IVIg), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc© or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), anti-IL36 agents such as BI655130, Dihydroorotate dehydrogenase inhibitors such as IMU-838, anti-OX40 agents such as KHK-4083, microbiome agents such as RBX2660, SER-287, Narrow spectrum kinase inhibitors such as TOP-1288, anti-CD40 agents such as BI-655064 and FFP-104, guanylate cyclase agonists such as dolcanatide, sphingosine kinase inhibitors such as opaganib, anti-IL-12/IL-23 agents such as AK-101, Ubiquitin protein ligase complex inhibitors such as BBT-401, sphingosine receptors modulators such as BMS-986166, P38MAPK/PDE4 inhibitors such as CBS-3595, CCR9 antagonists such as CCX-507, FimH antagonists such as EB-8018, HIF-PH inhibitors such as FG-6874, HIF-1α stabilizer such as GB-004, MAP3K8 protein inhibitors such as GS-4875, LAG-3 antibodies such as GSK-2831781, RIP2 kinase inhibitors such as GSK-2983559, Farnesoid X receptor agonist such as MET-409, CCK2 antagonists such as PNB-001, IL-23 Receptor antagonists such as PTG-200, Purinergic P2X7 receptor antagonists such as SGM-1019, PDE4 inhibitors such as Apremilast, ICAM-1 inhibitors such as alicaforsen sodium, Anti-IL23 agents such as guselkumab, brazikumab and mirkizumab, ant-IL-15 agents such as AMG-714, TYK-2 inhibitors such as BMS-986165, NK Cells activators such as CNDO-201, RIP-1 kinase inhibitors such as GSK-2982772, anti-NKGD2 agents such as JNJ-4500, CXCL-10 antibodies such as JT-02, IL-22 receptor agonists such as RG-7880, GATA-3 antagonists such as SB-012, and Colony-stimulating factor-1 receptor inhibitors such as edicotinib.

In certain embodiments, the second therapeutic agent is pentoxifylline, propentofylline, torbafylline, cyclosporine, methotrexate, tamoxifen, forskolin and analogs thereof, tar derivatives, steroids, vitamin A and its derivatives, vitamin D and its derivatives, a cytokine, a chemokine, a stem cell growth factor, a lymphotoxin, an hematopoietic factor, a colony stimulating factor (CSF), erythropoietin, thrombopoietin, tumor necrosis factor-α (TNF), TNF-8, granulocyte-colony stimulating factor (G-CSF), granulocyte macrophage-colony stimulating factor (GM-CSF), interferon-α, interferon-β, interferon-7, interferon-k, stem cell growth factor designated "S1 factor", human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, mullerian-inhibiting substance, mouse gonadotropin-associated peptide, inhibin, activin, vascular endothelial growth factor, integrin, NGF-β, platelet-growth factor, TGF-α, TGF-β, insulin-like growth factor-I, insulin-like growth factor-II, macrophage-CSF (M-CSF), IL-1, IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, IL-25, LIF, FLT-3, angiostatin, thrombospondin, endostatin, or lymphotoxin.

In certain embodiments, the second therapeutic agent is a second compound provided herein, or a pharmaceutically acceptable salt thereof. In certain embodiments, the second therapeutic agent is a second compound provided herein.

In certain embodiments, the second therapeutic agent is stavudine, a prodrug thereof, or a pharmaceutically acceptable salt of either of the foregoing. In certain embodiments, the second therapeutic agent is stavudine, stampidine, or a pharmaceutically acceptable salt of either of the foregoing. In certain embodiments, the second therapeutic agent is stavudine or stampidine.

In certain embodiments, the second therapeutic agent is tenofovir, a prodrug thereof, or a pharmaceutically acceptable salt of either of the foregoing. In certain embodiments, the second therapeutic agent is tenofovir, tenofovir alafenamide, tenofovir amibufenamide, tenofovir disoproxil, or tenofovir exalidex; or a pharmaceutically acceptable salt thereof. In certain embodiments, the second therapeutic agent is tenofovir, tenofovir alafenamide, tenofovir amibufenamide, tenofovir disoproxil, or tenofovir exalidex.

In certain embodiments, the second therapeutic agent is tenofovir, or a pharmaceutically acceptable salt thereof. In certain embodiments, the second therapeutic agent is tenofovir. In certain embodiments, the second therapeutic agent is tenofovir alafenamide, or a pharmaceutically acceptable salt thereof. In certain embodiments, the second therapeutic agent is tenofovir alafenamide. In certain embodiments, the second therapeutic agent is tenofovir amibufenamide, or a pharmaceutically acceptable salt thereof. In certain embodiments, the second therapeutic agent is tenofovir amibufenamide. In certain embodiments, the second therapeutic agent is tenofovir disoproxil, or a pharmaceutically acceptable salt thereof. In certain embodiments, the second therapeutic agent is tenofovir disoproxil, or a fumarate, succinate, maleate, orotate, aspartate, or phosphate salt thereof. In certain embodiments, the second therapeutic agent is tenofovir disoproxil, or a fumarate, succinate, or maleate salt thereof. In certain embodiments, the second therapeutic agent is tenofovir disoproxil. In certain embodiments, the second therapeutic agent is tenofovir exalidex, or a pharmaceutically acceptable salt thereof. In certain embodiments, the second therapeutic agent is tenofovir exalidex, or a potassium salt thereof. In certain embodiments, the second therapeutic agent is tenofovir exalidex.

In certain embodiments, the method further comprises administering to the subject a third therapeutic agent. In certain embodiments, the method further comprises administering to the subject a fourth therapeutic agent. In certain embodiments, the method further comprises administering to the subject a fifth therapeutic agent.

In certain embodiments, the third therapeutic agent is one of the second therapeutic agents described above. In certain embodiments, the fourth therapeutic agent is one of the second therapeutic agents described above. In certain embodiments, the fifth therapeutic agent is one of the second therapeutic agents described above.

Viral Infection

Another aspect of the disclosure provides a method of treating an immune disorder that is a viral infection in a patient. The method comprises administering to a subject in need thereof (i) a therapeutically effective amount of a compound described herein (such as a compound of Formula I, II, III, IV, V, or VI), or a pharmaceutically acceptable salt thereof, and (ii) a second therapeutic agent, in order to treat the immune disorder that is a viral infection. In certain embodiments, the immune disorder is a viral infection other than an influenza viral infection.

In certain embodiments, the second therapeutic agent is an anti-HIV agent. In certain embodiments, the second therapeutic agent is a nucleoside reverse transcriptase inhibitor (NRTI), non-nucleoside reverse transcriptase inhibitor, protease inhibitor, or fusion inhibitor. In certain embodiments, the second therapeutic agent is 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), or the fusion inhibitor T20.

In certain embodiments, the second therapeutic agent is ddC, abacavir, ddI, ddA, 3TC, AZT, D4T, FTC, FddC, Fd4C, Atazanavir, Adefovir dipivoxyl, Tenofovir disoproxil, Etecavir, Indinavir, KHI-227.2-[3-[3-(S)-[[(Tetrahydrofuranyloxy)carbonyl]amino]-4-phenyl-2(R)-hydroxybutyl]]-N-(1,1-dimethylethyl)decahydro-3-isoquinolinecarboxamide, VB-11,328, KNI-174, Val-Val-Sta, CPG53820, HOEt-N2 aza-peptide isostere, 2,5-Diamino-N,N'-bis(N-benzyloxycarbonyluelyl)-1,6-diphenyl-3(S),4(S)-hexanediol BzOCValPhe[diCHOH(SS]PheValBzOC, 2,5,-Diamino-N, N'-bis(N-benzyloxycarbonyluelyl)-1,6-diphenyl-3(R),4(R)-hexanediol BzOCValPhe[diCHOH(RR]PheValBzOC, [bis(SATE)ddAMP], BILA 2186 BS, Agenerase, A-98881, A-83962, A-80987, (2-Naphthalcarbonyl)Asn[decarbonylPhe-hydroxyethyl]ProOtertButyl, A-81525, XM323, Tipranavir, SDZ PRI 053, SD146, Telinavir, (R)2QuinCOAsnPhe[CHOHCH2]PipCONHtBu, Saquinavir, R-87366, DMP 460, L685,434, L685,434-OEtNMe2, L689, 502, Lasinavir, Aluviran P9941, Palinavir, or Penicillin. In certain embodiments, the second therapeutic agent is ddC, abacavir, ddI, ddA, 3TC, AZT, D4T, FTC, FddC, or Fd4C.

In certain embodiments, the second therapeutic agent is tenofovir, a prodrug thereof, or a pharmaceutically acceptable salt of either of the foregoing. In certain embodiments, the second therapeutic agent is tenofovir, tenofovir alafenamide, tenofovir amibufenamide, tenofovir disoproxil, or tenofovir exalidex; or a pharmaceutically acceptable salt thereof. In certain embodiments, the second therapeutic agent is tenofovir, tenofovir alafenamide, tenofovir amibufenamide, tenofovir disoproxil, or tenofovir exalidex.

In certain embodiments, the second therapeutic agent is tenofovir, or a pharmaceutically acceptable salt thereof. In certain embodiments, the second therapeutic agent is tenofovir. In certain embodiments, the second therapeutic agent is tenofovir alafenamide, or a pharmaceutically acceptable salt thereof. In certain embodiments, the second therapeutic agent is tenofovir alafenamide. In certain embodiments, the second therapeutic agent is tenofovir amibufenamide, or a pharmaceutically acceptable salt thereof. In certain embodiments, the second therapeutic agent is tenofovir amibufenamide. In certain embodiments, the second therapeutic agent is tenofovir disoproxil, or a pharmaceutically acceptable salt thereof. In certain embodiments, the second therapeutic agent is tenofovir disoproxil, or a fumarate, succinate, maleate, orotate, aspartate, or phosphate salt thereof. In certain embodiments, the second therapeutic agent is tenofovir disoproxil, or a fumarate, succinate, or maleate salt thereof. In certain embodiments, the second therapeutic agent is tenofovir disoproxil. In certain embodiments, the second therapeutic agent is tenofovir exalidex, or a pharmaceutically acceptable salt thereof. In certain embodiments, the second therapeutic agent is tenofovir exalidex, or a potassium salt thereof. In certain embodiments, the second therapeutic agent is tenofovir exalidex.

In certain embodiments, the method further comprises administering to the subject a third therapeutic agent. In certain embodiments, the method further comprises administering to the subject a fourth therapeutic agent. In certain embodiments, the method further comprises administering to the subject a fifth therapeutic agent.

In certain embodiments, the third therapeutic agent is one of the second therapeutic agents described above. In certain embodiments, the fourth therapeutic agent is one of the second therapeutic agents described above. In certain embodiments, the fifth therapeutic agent is one of the second therapeutic agents described above.

Neurological Disorders

Another aspect of the disclosure provides a method of treating a neurological disorder in a patient. The method comprises administering to a subject in need thereof (i) a therapeutically effective amount of a compound according to Formula I, including a compound selected from Table 1 or Table 2, or a pharmaceutically acceptable salt thereof, and (ii) a second thereapeutic agent, in order to treat the neurological disorder. In certain embodiments, the method comprises administering to a subject in need thereof (i) a therapeutically effective amount of a compound described herein (such as a compound of Formula I, II, III, IV, V, or VI), or a pharmaceutically acceptable salt thereof, and (ii) a second therapeutic agent, in order to treat the neurological disorder.

In certain embodiments, the second therapeutic agent is a dopaminergic treatment, a cholinesterase inhibitor, an antipsychotic drug, deep brain stimulation (for example, to stop tremor and refractory movement disorders), riluzole, a caffein A2A receptor antagonist, pramipexole, or rasagilin.

In certain embodiments, the second therapeutic agent is a second compound provided herein, or a pharmaceutically acceptable salt thereof. In certain embodiments, the second therapeutic agent is a second compound provided herein.

In certain embodiments, the second therapeutic agent is stavudine, a prodrug thereof, or a pharmaceutically acceptable salt of either of the foregoing. In certain embodiments, the second therapeutic agent is stavudine, stampidine, or a pharmaceutically acceptable salt of either of the foregoing. In certain embodiments, the second therapeutic agent is stavudine or stampidine.

In certain embodiments, the second therapeutic agent is tenofovir, a prodrug thereof, or a pharmaceutically acceptable salt of either of the foregoing. In certain embodiments, the second therapeutic agent is tenofovir, tenofovir alafenamide, tenofovir amibufenamide, tenofovir disoproxil, or tenofovir exalidex; or a pharmaceutically acceptable salt thereof. In certain embodiments, the second therapeutic agent is tenofovir, tenofovir alafenamide, tenofovir amibufenamide, tenofovir disoproxil, or tenofovir exalidex.

In certain embodiments, the second therapeutic agent is tenofovir, or a pharmaceutically acceptable salt thereof. In certain embodiments, the second therapeutic agent is tenofovir. In certain embodiments, the second therapeutic agent is tenofovir alafenamide, or a pharmaceutically acceptable salt thereof. In certain embodiments, the second therapeutic agent is tenofovir alafenamide. In certain embodiments, the second therapeutic agent is tenofovir amibufenamide, or a pharmaceutically acceptable salt thereof. In certain embodiments, the second therapeutic agent is tenofovir amibufenamide. In certain embodiments, the second therapeutic agent is tenofovir disoproxil, or a pharmaceutically acceptable salt thereof. In certain embodiments, the second therapeutic agent is tenofovir disoproxil, or a fumarate, succinate, maleate, orotate, aspartate, or phosphate salt thereof. In certain embodiments, the second therapeutic agent is tenofovir disoproxil, or a fumarate, succinate, or maleate salt thereof. In certain embodiments, the second therapeutic agent is tenofovir disoproxil. In certain embodiments, the second therapeutic agent is tenofovir exalidex, or a pharmaceutically acceptable salt thereof. In certain embodiments, the second therapeutic agent is tenofovir exalidex, or a potassium salt thereof. In certain embodiments, the second therapeutic agent is tenofovir exalidex.

In certain embodiments, the method further comprises administering to the subject a third therapeutic agent. In certain embodiments, the method further comprises administering to the subject a fourth therapeutic agent. In certain embodiments, the method further comprises administering to the subject a fifth therapeutic agent.

In certain embodiments, the third therapeutic agent is one of the second therapeutic agents described above. In certain embodiments, the fourth therapeutic agent is one of the second therapeutic agents described above. In certain embodiments, the fifth therapeutic agent is one of the second therapeutic agents described above.

V. PHARMACEUTICAL COMPOSITIONS AND DOSING CONSIDERATIONS

As indicated above, the invention provides pharmaceutical compositions, which comprise a therapeutically-effective amount of one or more of the compounds described above, formulated together with one or more pharmaceutically acceptable carriers, adjuvant, and/or vehicle. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

In certain embodiments, the invention provides a pharmaceutical composition comprising a compound described herein (e.g., a compound of Formula I) and a pharmaceutically acceptable carrier. In certain embodiments, the invention provides a pharmaceutical composition comprising a compound described herein (e.g., a compound of Formula I), an additional therapeutic agent (e.g., a compound described in Section IV), and a pharmaceutically acceptable carrier.

The phrase "therapeutically effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, troches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

The invention further provides a unit dosage form (such as a tablet or capsule) comprising censavudine or a related compound described herein in a therapeutically effective amount for the treatment of a medical disorder described herein.

VI. ENUMERATED EMBODIMENTS

Additional aspects of the invention are described in the following enumerated embodiments:

Embodiment 1. A compound according to formula I:

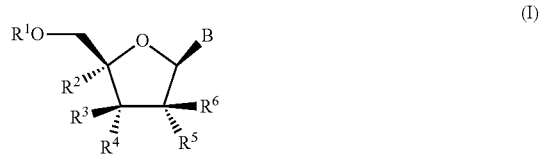

or a pharmaceutically acceptable salt thereof, wherein:
B is

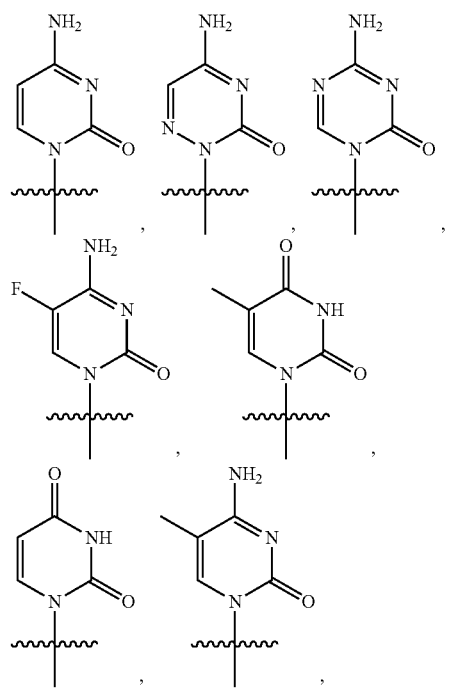

153

-continued

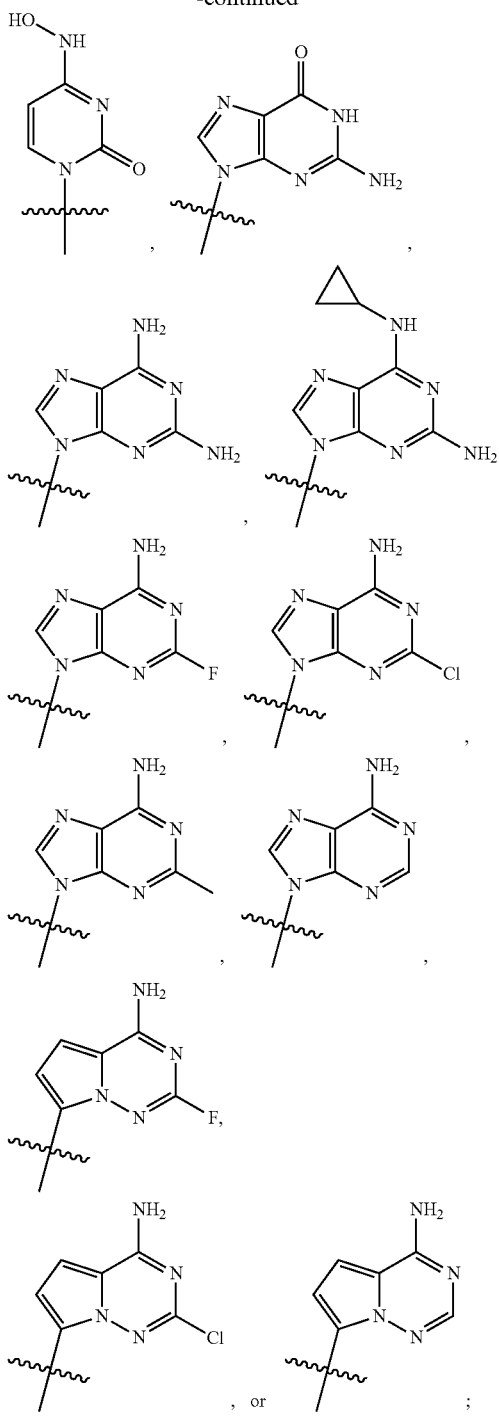

$R^1$ is —H

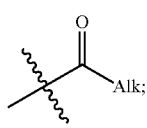

Alk is independently for each occurrence a $C_2$-$C_6$ aliphatic group;

154

$R^2$ is —H, $C_1$-$C_6$ aliphatic, $C_1$-$C_3$ haloaliphatic, $C_1$-$C_3$ hydroxyalkyl, cyclopropyl, —CN, —$N_3$, —O—($C_1$-$C_3$ aliphatic), —F, or —Cl;

$R^3$ is —H;

$R^4$ is —OH, —Cl, —OCH$_3$, —F, —$N_3$,

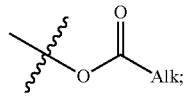

$R^5$ is —H or —F; and $R^6$ is —H, —F, —Cl, $C_1$-$C_6$ aliphatic, $C_1$-$C_4$ haloaliphatic, —O—($C_1$-$C_4$ aliphatic), cyclopropyl, or —OH.

Embodiment 2. The compound of embodiment 1, or a pharmaceutically acceptable salt thereof, wherein Alk is independently for each occurrence ethyl, propyl, isopropyl, sec-butyl, tert-butyl, or iso-butyl.

Embodiment 3. The compound of embodiment 1 or 2, or a pharmaceutically acceptable salt thereof, wherein $R^1$ is

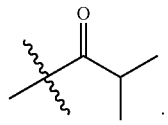 [SMILES: *C(=O)C(C)C]

Embodiment 4. The compound of any one of the preceding embodiments, or a pharmaceutically acceptable salt thereof, wherein $R^1$ is —H.

Embodiment 5. The compound of any one of the preceding embodiments, or a pharmaceutically acceptable salt thereof, wherein $R^5$ is —H.

Embodiment 6. The compound of any one of the preceding embodiments, or a pharmaceutically acceptable salt thereof, wherein $R^2$ is not —H.

Embodiment 7. The compound of any one of the preceding embodiments, or a pharmaceutically acceptable salt thereof, wherein $R^4$ is —OH.

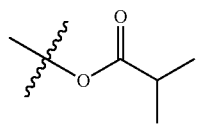

Embodiment 8. The compound of any one of the preceding embodiments, or a pharmaceutically acceptable salt thereof, wherein $R^6$ is —H, —F, —CH$_3$, —CH$_2$CH$_3$, —OCH$_3$, —OCH$_2$CH$_3$, —CH=CH$_2$, —CH$_2$F, or —CH$_2$Cl.

Embodiment 9. The compound of any one of the preceding embodiments, or a pharmaceutically acceptable salt thereof, wherein $R^6$ is —H or —F.

Embodiment 10. The compound of any one of the preceding embodiments, or a pharmaceutically acceptable salt thereof, wherein $R^6$ is —H.

Embodiment 11. The compound of any one of embodiments 1-9, or a pharmaceutically acceptable salt thereof, wherein $R^6$ is —F.

Embodiment 12. The compound of any one of the preceding embodiments, or a pharmaceutically acceptable salt thereof, wherein B is

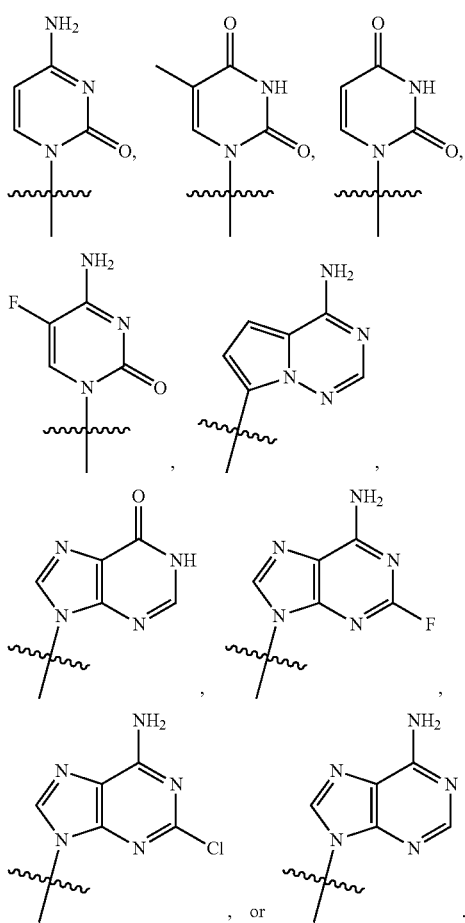

Embodiment 13. The compound of any one of the preceding embodiments, or a pharmaceutically acceptable salt thereof, wherein B is

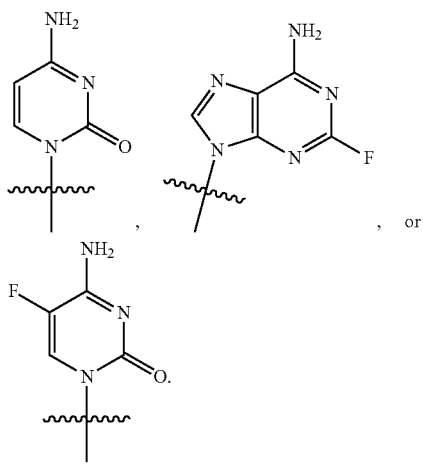

Embodiment 14. The compound of any one of the preceding embodiments, or a pharmaceutically acceptable salt thereof, wherein $R^2$ is —CH$_3$, —CF$_3$, —N$_3$, —OCH$_3$, —CH$_2$Cl, —CH$_2$F, —CHF$_2$, —CHCl$_2$, —CHClF, —CH$_2$CH$_3$, —CH=CH$_2$, cyclopropyl, or —C≡CH.

Embodiment 15. The compound of any one of embodiments 1-13, or a pharmaceutically acceptable salt thereof, wherein $R^2$ is —N$_3$, —CH$_3$, —CH$_2$Cl, —CH$_2$F, —CH=CH$_2$, or —C≡CH.

Embodiment 16. The compound of any one of embodiments 1-13, or a pharmaceutically acceptable salt thereof, wherein $R^2$ is —CH$_2$Cl, —CH$_2$F or —C≡CH.

Embodiment 17. The compound of any one of embodiments 1-13, or a pharmaceutically acceptable salt thereof, wherein $R^2$ is —CH$_2$Cl or —C≡CH.

Embodiment 18. The compound of any one of the preceding embodiments, or a pharmaceutically acceptable salt thereof, wherein $R^2$ is —CH$_2$Cl.

Embodiment 19. The compound of embodiment 1, or a pharmaceutically acceptable salt thereof, wherein:
$R^4$ is —OH;
$R^5$ is —H; and
$R^6$ is H.

Embodiment 20. The compound of embodiment 19, or a pharmaceutically acceptable salt thereof, wherein $R^2$ is —CH$_2$Cl.

Embodiment 21. The compound of embodiment 1, selected from the group consisting of:

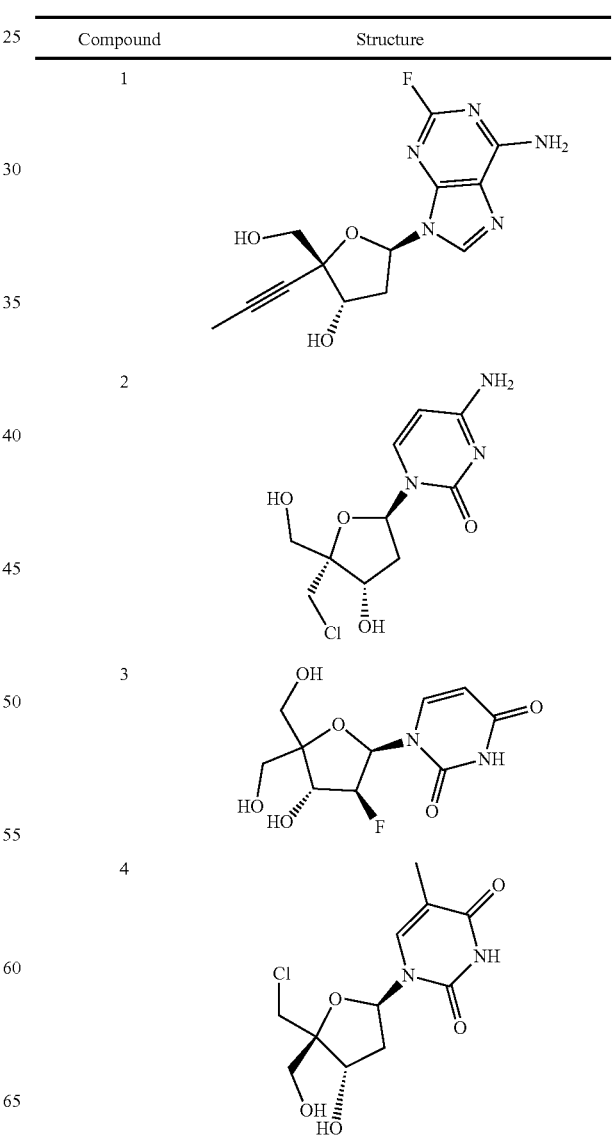

-continued

| Compound | Structure |
|---|---|
| 5 | (2-chloro-adenine nucleoside with ethynyl, HO, and F substituents on sugar) |
| 6 | (N-hydroxy cytosine nucleoside with CH2OH, CH2Cl, and OH on sugar) |
| 7 | (thymidine analog with CH2Cl and F on sugar) |
| 8 | (2-fluoroadenine nucleoside with CH2Cl and OH on sugar) |
| 9 | (thymidine analog with CH2OH, F, CH2Cl, OH on sugar) |
| 10 | (2-fluoroadenine nucleoside with two CH2OH and OH on sugar) |

-continued

| Compound | Structure |
|---|---|
| 11 | (cytosine with 5-methyl, CH2Cl, CH2OH, OH on sugar) |
| 12 | (cytosine nucleoside with CH2Cl, CH2OH, methyl, OH on sugar) |
| 13 | (cytosine nucleoside with CH2Cl, CH2OH, OH, OMe on sugar) |
| 14 | (5-fluorocytosine nucleoside with CH2Cl, CH2OH, OH on sugar) |
| 15 | (adenine nucleoside with CH2Cl, CH2OH, OH on sugar) |
| 16 | (cytosine nucleoside with CH2OH, cyclopropyl spiro, OH on sugar) |
| 17 | (cytosine nucleoside with CH2Cl, CH2OH, OH, ethynyl on sugar) |

| Compound | Structure |
|---|---|
| 18 | [structure: tetrahydrofuran with CH2Cl, HO, HO, and triazine-NH2 base] |
| 19 | [structure: sugar with HO, methyl, HO, and cytosine base] |
| 20 | [structure: sugar with HO, methyl, HO, ethynyl, and cytosine base] |
| 21 | [structure: sugar with OH, CF2F, HO, and cytosine-NH2 base] |
| 22 | [structure: sugar with CH2F, HO, HO, and 5-fluorocytosine base] | or a pharmaceutically acceptable salt thereof.

Embodiment 22. A compound in Table 1, 1-A, or 1-B herein, or a pharmaceutically acceptable salt thereof.

Embodiment 23. A pharmaceutical composition comprising a compound according to any one of embodiments 1-21, or a pharmaceutically acceptable salt thereof, and a carrier, excipient, and/or vehicle.

Embodiment 24. A pharmaceutical composition comprising a compound according to embodiment 22, or a pharmaceutically acceptable salt thereof, and a carrier, excipient, and/or vehicle.

Embodiment 25. A method of treating a disorder selected from the group consisting of cancer, an autoimmune disorder, and a neurological disorder, comprising administering to a subject in need thereof a therapeutically effective amount of a compound of Formula I according to any one of embodiments 1-21, or a pharmaceutically acceptable salt thereof, or the pharmaceutical composition of embodiment 23, in order to treat the disorder.

Embodiment 26. The method of embodiment 25, wherein the method further comprises administering an effective amount of an additional therapeutic agent.

Embodiment 27. A method of inhibiting LINE1 reverse transcriptase activity in a subject suffering from a disorder selected from the group consisting of cancer, an autoimmune disorder, and a neurological disorder, comprising contacting a LINE1 reverse transcriptase with an effective amount of a compound of Formula I according to any one of embodiments 1-21, or a pharmaceutically acceptable salt thereof, or the composition of embodiment 23, in order to inhibit the activity of said LINE1 reverse transcriptase.

Embodiment 28. The method of embodiment 27, wherein the method further comprises inhibiting HERV-K reverse transcriptase activity in the subject.

Embodiment 29. A method of inhibiting HERV-K reverse transcriptase activity in a subject suffering from a disorder selected from the group consisting of cancer, an autoimmune disorder, and a neurological disorder, comprising contacting a HERV-K reverse transcriptase with an effective amount of a compound of Formula I according to any one of embodiments 1-21, or a pharmaceutically acceptable salt thereof, or the composition of embodiment 23, in order to inhibit the activity of said HERV-K reverse transcriptase.

Embodiment 30. The method of any one of embodiments 25-29, wherein the compound is selected from the group consisting of:

| Compound | Structure |
|---|---|
| 1 | [structure: 2-fluoroadenine nucleoside with HO, ethynyl, HO] |
| 2 | [structure: cytidine analog with HO, CH2Cl, OH] |
| 3 | [structure: uridine analog with OH, HO, HO, F] |
| 4 | [structure: thymidine analog with Cl, OH, HO] |

-continued

| Compound | Structure |
|---|---|
| 5 | (structure: 2-chloro-adenine nucleoside with 4'-ethynyl, 4'-hydroxymethyl, 2'-fluoro ribose) |
| 6 | (structure: N-hydroxy cytosine nucleoside with 4'-hydroxymethyl, 4'-chloromethyl, 3'-hydroxy, 2'-deoxy sugar) |
| 7 | (structure: thymine nucleoside with 4'-chloromethyl, 3'-fluoro, 2'-deoxy sugar) |
| 8 | (structure: 2-fluoro-adenine nucleoside with 4'-chloromethyl, 3'-hydroxy, 2'-deoxy sugar) |
| 9 | (structure: thymine nucleoside with 4'-hydroxymethyl, 4'-chloromethyl, 3'-hydroxy, 2'-fluoro sugar) |
| 10 | (structure: 2-fluoro-adenine carbocyclic nucleoside with bis-hydroxymethyl cyclopentane) |

-continued

| Compound | Structure |
|---|---|
| 11 | (structure: 5-methyl-cytosine nucleoside with 4'-chloromethyl, 3'-hydroxy, 2'-deoxy sugar) |
| 12 | (structure: cytosine nucleoside with 4'-chloromethyl, 4'-hydroxymethyl, 3'-hydroxy, 2'-methyl sugar) |
| 13 | (structure: cytosine nucleoside with 4'-chloromethyl, 4'-hydroxymethyl, 3'-hydroxy, 2'-methoxy sugar) |
| 14 | (structure: 5-fluoro-cytosine nucleoside with 4'-chloromethyl, 4'-hydroxymethyl, 3'-hydroxy, 2'-deoxy sugar) |
| 15 | (structure: adenine nucleoside with 4'-chloromethyl, 4'-hydroxymethyl, 3'-hydroxy, 2'-deoxy sugar) |
| 16 | (structure: cytosine nucleoside with 4'-hydroxymethyl, 4'-cyclopropyl, 3'-hydroxy, 2'-deoxy sugar) |
| 17 | (structure: cytosine nucleoside with 4'-chloromethyl, 4'-hydroxymethyl, 3'-hydroxy, 2'-ethynyl sugar) |

163
-continued

| Compound | Structure |
|---|---|
| 18 | (chloromethyl-hydroxymethyl tetrahydrofuran linked to 5-amino-triazinone base) |
| 19 | (2'-methyl, 4'-methyl-hydroxymethyl nucleoside with cytosine) |
| 20 | (2'-ethynyl, 4'-methyl-hydroxymethyl nucleoside with cytosine) |
| 21 | (4'-CF3, 4'-hydroxymethyl nucleoside with cytosine) |
| 22 | (4'-fluoromethyl-hydroxymethyl nucleoside with 5-fluorocytosine) |
| 23 | (4'-ethynyl, 4'-hydroxymethyl nucleoside with 2-fluoroadenine) |
| 24 | (3'-F, 4'-chloromethyl, 5'-O-isobutyryl, 3'-O-isobutyryl cytidine) |

164
-continued

| Compound | Structure |
|---|---|
| 25 | (4'-ethynyl 2'-deoxy nucleoside with 2-chloroadenine) |
| 26 | (4'-cyano 2'-deoxy nucleoside with 2-fluoroadenine) |
| 27 | (4'-ethynyl, 4'-hydroxymethyl nucleoside with adenine) |
| 28 | (2'-F, 4'-chloromethyl-hydroxymethyl nucleoside with N4-hydroxy cytosine) |
| 29 | (2'-F, 4'-chloromethyl-hydroxymethyl nucleoside with uracil) |
| 30 | (3'-azido 2'-deoxy nucleoside with thymine) |
| 31 | (2'-F, 4'-chloromethyl-hydroxymethyl nucleoside with cytosine) |

-continued

| Compound | Structure |
|---|---|
| 32 | 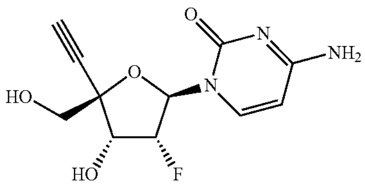 [SMILES: C#C[C@]1(CO)O[C@@H](n2ccc(N)nc2=O)[C@H](F)[C@@H]1O] |
| 33 | 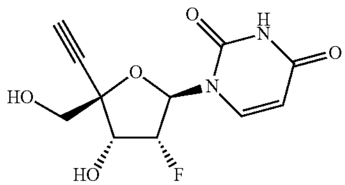 [SMILES: C#C[C@]1(CO)O[C@@H](n2ccc(=O)[nH]c2=O)[C@H](F)[C@@H]1O] |
| 34 | 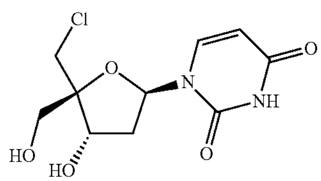 [SMILES: O=c1ccn([C@H]2C[C@H](O)[C@](CO)(CCl)O2)c(=O)[nH]1] |
| 35 | 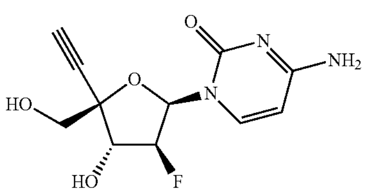 [SMILES: C#C[C@]1(CO)O[C@@H](n2ccc(N)nc2=O)[C@@H](F)[C@@H]1O] |
| 36 | 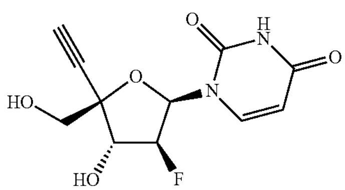 [SMILES: C#C[C@]1(CO)O[C@@H](n2ccc(=O)[nH]c2=O)[C@@H](F)[C@@H]1O] |
| 37 | 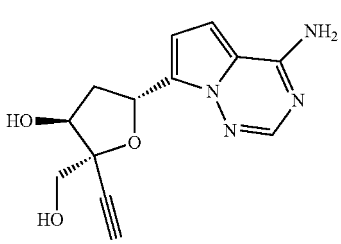 [SMILES: C#C[C@]1(CO)O[C@@H](c2ccc3c(N)ncnn23)C[C@@H]1O] |
| 38 | 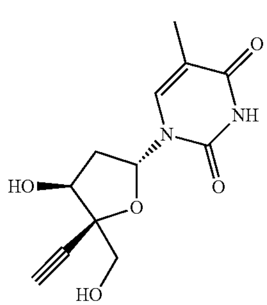 [SMILES: C#C[C@]1(CO)O[C@@H](n2cc(C)c(=O)[nH]c2=O)C[C@@H]1O] |

-continued

| Compound | Structure |
|---|---|
| 39 | 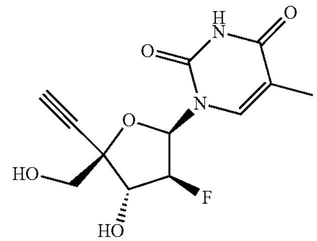 [SMILES: C#C[C@]1(CO)O[C@@H](n2cc(C)c(=O)[nH]c2=O)[C@@H](F)[C@@H]1O] |
| 40 | 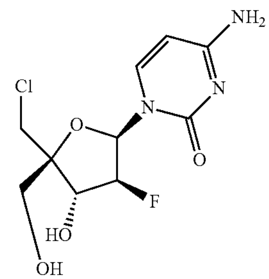 [SMILES: Nc1ccn([C@@H]2O[C@@](CO)(CCl)[C@@H](O)[C@@H]2F)c(=O)n1] |
| 41 | 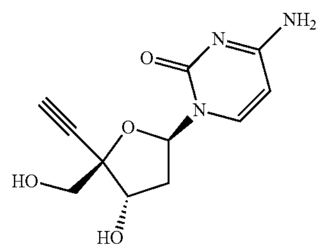 [SMILES: C#C[C@]1(CO)O[C@@H](n2ccc(N)nc2=O)C[C@@H]1O] |
| 42 | 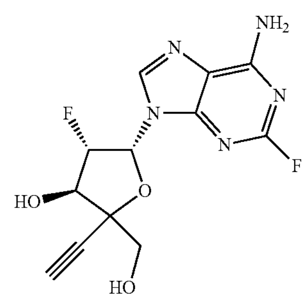 [SMILES: C#CC1(CO)O[C@@H](n2cnc3c(N)nc(F)nc32)[C@@H](F)[C@@H]1O] |
| 43 | 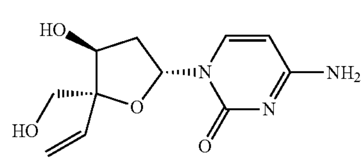 [SMILES: C=C[C@]1(CO)O[C@@H](n2ccc(N)nc2=O)C[C@@H]1O] |
| 44 | 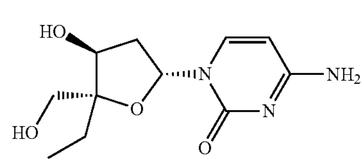 |

| Compound | Structure |
|---|---|
| 45 | (cytosine nucleoside analog with fluoromethyl and hydroxyl substituents on sugar) |
| 46 | (guanine nucleoside analog with fluoromethyl and hydroxyl substituents on sugar) |
| 47 | (cytosine nucleoside analog with vinyl, hydroxymethyl, hydroxyl, and fluoro substituents on sugar) |
| 48 | (cytosine nucleoside analog with hydroxymethyl, hydroxyl, and methoxy substituents on sugar) |
| 49 | (cytosine nucleoside analog with hydroxymethyl, azido, and hydroxyl substituents on sugar) |
| 50 | (cytosine nucleoside analog with hydroxymethyl, azido, hydroxyl, and fluoro substituents on sugar) |

| Compound | Structure |
|---|---|
| 51 | (cytosine nucleoside analog with ethyl, hydroxymethyl, hydroxyl, and fluoro substituents on sugar) | or a pharmaceutically acceptable salt thereof.

Embodiment 31. The method of any one of embodiments 25-30, wherein the disorder is cancer.

Embodiment 32. The method of embodiment 31, wherein the cancer is breast cancer, ovarian cancer, uterine cancer, cervical cancer, prostate cancer, testicular cancer, lung cancer, leukemia, head and neck cancer, oral cancer, esophageal cancer, stomach cancer, bile duct cancer, gallbladder cancer, bladder cancer, urinary tract cancer, colon cancer, rectal cancer, thyroid cancer, pancreatic cancer, kidney cancer, liver cancer, brain cancer, skin cancer, or eye cancer.

Embodiment 33. The method of any one of embodiments 25-30, wherein the disorder is an autoimmune disorder.

Embodiment 34. The method of embodiment 33, wherein the autoimmune disorder is selected from Aicardi-Goutieres syndrome, rheumatoid arthritis, psoriasis, systemic lupus erythematosus (SLE), cutaneous lupus erythematosus (CLE), graft versus host disease, scleroderma, type I diabetes, dermatomyositis, inflammatory bowel disease, ulcerative colitis, Crohn's disease, vasculitis, and Sjögren's syndrome.

Embodiment 35. The method of any one of embodiments 25-30, wherein the disorder is a neurological disorder.

Embodiment 36. The method of embodiment 35, wherein the neurological disorder is Alzheimer's disease, amyotrophic lateral sclerosis (ALS), multiple sclerosis, Parkinson's disease, Huntington's disease, peripheral neuropathy, age-related macular degeneration, Creutzfeldt-Jacob disease, stroke, prion disease, frontotemporal dementia, Pick's disease, progressive supranuclear palsy, spinocerebellar ataxias, Lewy body disease, dementia, multiple system atrophy, epilepsy, bipolar disorder, schizophrenia, an anxiety disorder, or major depression.

Embodiment 37. The method of any one of embodiments 25-36, wherein the subject has (i) elevated expression of LINE1 RNA, LINE1 ORF1 polypeptide, and/or LINE1 ORF2 polypeptide; and/or (ii) elevated activity of LINE1 reverse transcriptase.

Embodiment 38. The method of any one of embodiments 25-37, wherein the subject has (i) expression of HERV-K RNA and/or (ii) activity of HERV-K reverse transcriptase.

Embodiment 39. The method of any one of embodiments 25-38, wherein the subject is a human.

EXAMPLES

The invention now being generally described, will be more readily understood by reference to the following examples, which are included merely for purposes of illustration of certain aspects and embodiments of the present invention, and are not intended to limit the invention. Starting materials described herein can be obtained from commercial sources or may be readily prepared from commercially available materials using transformations known to those of skill in the art.

Example 1—Synthesis of Compound 44: 4-amino-1-((2R,4S,5R)-5-ethyl-4-hydroxy-5-(hydroxymethyl)tetrahydrofuran-2-yl)pyrimidin-2(1H)-one

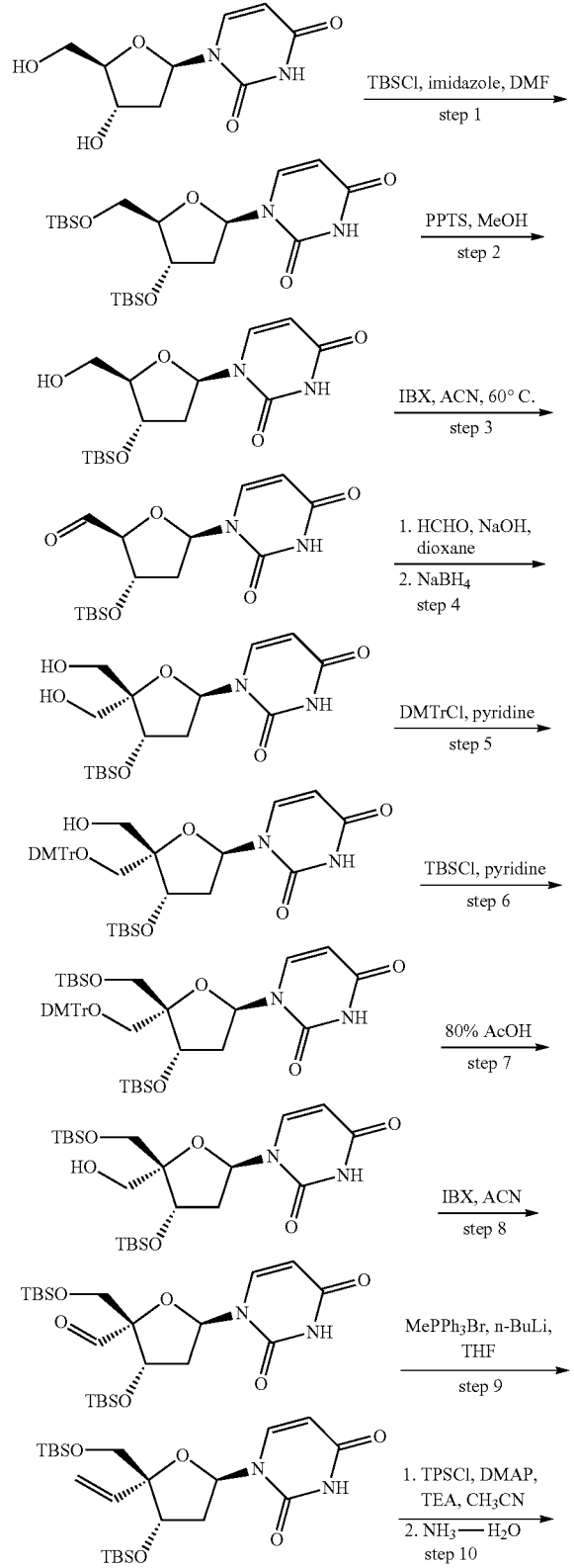

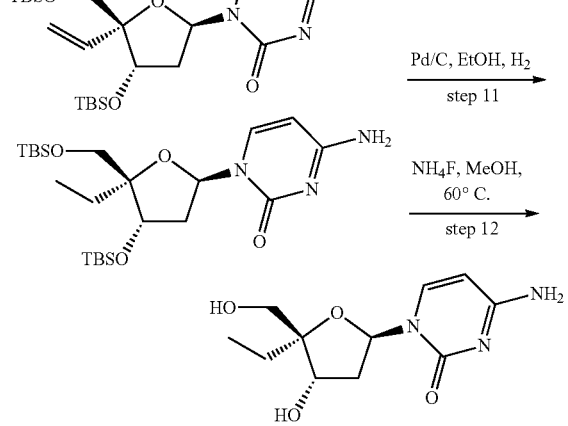

Step 1: To a stirred solution of 2'-deoxyuridine (50 g, 219.1) and imidazole (149.1 g, 2191.0 mmol) in pyridine (500 mL) was added TBSCl (99.1 g, 657.3 mmol) in portions at room temperature under nitrogen atmosphere. The mixture was stirred for 15 h at 80° C. LCMS showed the reaction was completed. The mixture was cooled to room temperature and diluted with EA, washed with brine and dried over anhydrous $Na_2SO_4$. The solids were filtered out, and the filtrate was combined and concentrated to afford 1-[(2R,4S,5R)-4-[(tert-butyldimethylsilyl) oxy]-5-{[(tert-butyldimethylsilyl) oxy] methyl} oxolan-2-yl]-3H-pyrimidine-2,4-dione (98 g, 215 mmol, crude) as light yellow oil. Product (ES, m/z): 457 (M+H⁺).

Step 2: To a stirred solution of 1-[(2R,4S,5R)-4-[(tert-butyldimethylsilyl) oxy]-5-{[(tert-butyldimethylsilyl) oxy] methyl} oxolan-2-yl]-3H-pyrimidine-2,4-dione (90 g, 197.1 mmol) in methanol (500 mL) was added PPTS (74.3 g, 295.5 mmol) in portions at room temperature under nitrogen atmosphere. The mixture was stirred for 15 h at 35° C. LCMS showed the reaction was completed. The mixture was concentrated under reduced pressure. The residue was diluted with EA, washed with the aqueous solution of citric acid and brine and dried over anhydrous $Na_2SO_4$. The solids were filtered out, the filtrate was combined and concentrated under reduced pressure to afford 1-[(2R,4S,5R)-4-[(tert-butyldimethylsilyl) oxy]-5-(hydroxymethyl) oxolan-2-yl]-3H-pyrimidine-2,4-dione (65 g, 190 mmol, crude) as white solid. Product (ES, m/z): 343 (M+H⁺).

Step 3: To a stirred solution of 1-[(2R,4S,5R)-4-[(tert-butyldimethylsilyl) oxy]-5-(hydroxymethyl) oxolan-2-yl]-3H-pyrimidine-2,4-dione (65 g, 189.7 mmol) in $CH_3CN$ (500 mL) was added IBX (159.4 g, 569.4 mmol). The mixture was stirred for 3 h at 60° C. LCMS showed the reaction was completed. The reaction was cooled to room temperature. The solids were filtered out, and the filtrate was concentrated to afford (2S,3S,5R)-3-[(tert-butyl-dimethylsilyl)oxy]-5-(2,4-dioxo-3H-pyrimidin-1-yl) oxolane-2-carbaldehyde (60 g, 176 mmol, crude) as an off-white solid. Product (ES, m/z): 341 (M+H⁺).

Step 4: To a stirred solution of (2S,3S,5R)-3-[(tert-butyldimethylsilyl) oxy]-5-(2,4-dioxo-3H-pyrimidin-1-yl) oxolane-2-carbaldehyde (60 g, 176.2 mmol) and formaldehyde (26.4 g, 881.1 mmol) in dioxane (500 mL) was added a solution of NaOH (21.1 g, 528.7 mmol) in water (50 mL) dropwise at room temperature under nitrogen atmosphere. The mixture was stirred for 15 h at room temperature.

LCMS showed the starting material was consumed, and then NaBH₄ (20 g, 528.7 mmol) was added at 0° C. The mixture was stirred for 30 min at 0° C., LCMS showed the reaction was completed. The reaction was quenched with aqueous NH₄Cl, and extracted with EA. The combined organics were washed with brine and dried over anhydrous Na₂SO₄. The solids were filtered out and the filtrate was concentrated. The residue was purified by silica gel column chromatography, eluted with methanol/dichloromethane (7/93) to afford 1-[(2R,4S)-4-[(tert-butyldimethylsilyl) oxy]-5,5-bis(hydroxymethyl)oxolan-2-yl]-3H-pyrimidine-2,4-dione (20 g, 53.7 mmol, 30.47%) as a white solid. Product (ES, m/z): 372 (M+H⁺).

Step 5: To a stirred solution of 1-[(2R,4S)-4-[(tert-butyldimethylsilyl) oxy]-5,5-bis(hydroxymethyl)oxolan-2-yl]-3H-pyrimidine-2,4-dione (20 g, 53.6 mmol) in pyridine (200 mL) was added 4,4'-(chloro(phenyl)methylene) bis (methoxybenzene) (18 g, 53.6 mmol) in portions at room temperature under nitrogen atmosphere. The mixture was stirred for 3 h at 30° C. LCMS showed the reaction was completed. The mixture was used in the next step without further purification. Product (ES, m/z): 675 (M+H⁺).

Step 6: To the above solution was added TBSCl (20 g, 133.3 mmol). The mixture was stirred for 15 h at 30° C. LCMS showed the reaction was completed. The mixture was diluted with EA, washed with the aqueous solution of citric acid and brine. The organic layer was dried over anhydrous Na₂SO₄. The solids were filtered out, and the filtrate was combined and concentrated under reduced pressure to afford 1-[(2R,4S,5R)-5-{[bis(4-methoxyphenyl) (phenyl)methoxy] methyl}-4-[(tert-butyldimethylsilyl) oxy]-5-{[(tert-butyldimethylsilyl) oxy]methyl} oxolan-2-yl]-3H-pyrimidine-2,4-dione (40 g, 50.7 mmol, crude) as yellow solid. Product (ES, m/z): 787 (M−H⁺)⁻.

Step 7: To a stirred solution of 1-[(2R,4S,5R)-5-{[bis(4-methoxyphenyl)(phenyl) methoxy] methyl}-4-[(tert-butyldimethylsilyl) oxy]-5-{[(tert-butyldimethylsilyl) oxy] methyl}oxolan-2-yl]-3H-pyrimidine-2,4-dione (40 g, 50.6 mmol) in CH₃CN (50 mL) was added 80% aqueous CH₃COOH (200 mL) dropwise at room temperature under nitrogen atmosphere. The mixture was stirred for 15 h at room temperature. LCMS showed the reaction was completed. The pH of the reaction was adjusted to 8 with aqueous solution of sodium bicarbonate, and extracted with EA. The combined organics were washed with brine and dried over by anhydrous Na₂SO₄. The solids were filtered out, and the filtrate was concentrated. The residue was purified by silica gel column chromatography, eluted with methanol/dichloromethane (3/97) to afford 1-[(2R,4S,5R)-4-[(tert-butyldimethylsilyl) oxy]-5-{[(tert-butyldimethylsilyl) oxy] methyl}-5-(hydroxymethyl) oxolan-2-yl]-3H-pyrimidine-2,4-dione (18 g, 37.0 mmol, 72.95%) as a light yellow solid. Product (ES, m/z): 487 (M+H⁺).

Step 8: A solution of 1-[(2R,4S,5R)-4-[(tert-butyldimethylsilyl) oxy]-5-{[(tert-butyldimethylsilyl) oxy] methyl}-5-(hydroxymethyl) oxolan-2-yl]-3H-pyrimidine-2,4-dione (18 g, 37.0 mmol) and IBX (31 g, 111.1 mmol) in acetonitrile (200 mL) was stirred for 2 h at 60° C. LCMS showed the reaction was completed. The reaction was cooled to room temperature, and the solids were filtered out. The filtrate was combined and concentrated under reduced pressure to afford (2R,3S,5R)-3-[(tert-butyldimethylsilyl) oxy]-2-{[(tert-butyldimethylsilyl) oxy]methyl}-5-(2,4-dioxo-3H-pyrimidin-1-yl) oxolane-2-carbaldehyde (17 g, 35.1 mmol, crude) as a white solid. Product (ES, m/z): 485 (M+H⁺).

Step 9: To a stirred solution of methyltriphenylphosphonium bromide (37.5 g, 105.2 mmol) in THF (200 mL) was added n-BuLi (42 mL, 105.2 mmol) dropwise at −78° C. under nitrogen atmosphere. The mixture was stirred for 30 min at 0° C., then (2R,3S,5R)-3-[(tert-butyldimethylsilyl) oxy]-2-{[(tert-butyldimethylsilyl) oxy] methyl}-5-(2,4-dioxo-3H-pyrimidin-1-yl) oxolane-2-carbaldehyde (17 g, 35.1 mmol) in THF (20 mL) was added. The mixture was stirred for 1.5 h at room temperature. LCMS showed the reaction was completed. The reaction was quenched with the solution of NH₄Cl, and extracted with EA. The combined organics were washed with brine and dried over anhydrous Na₂SO₄. The solids were filtered out, and the filtrate was combined and concentrated. The residue was purified by silica gel column chromatography, eluted with EA/PE (1/10) to afford 1-[(2R,4S,5R)-4-[(tert-butyldimethylsilyl) oxy]-5-{[(tert-butyldimethylsilyl) oxy] methyl}-5-ethenyloxolan-2-yl]-3H-pyrimidine-2,4-dione (15 g, 31.1 mmol, 88.60%) as an off-white solid. Product (ES, m/z): 483 (M+H⁺).

Step 10: To a stirred solution of 1-[(2R,4S,5R)-4-[(tert-butyldimethylsilyl) oxy]-5-{[(tert-butyldimethylsilyl) oxy] methyl}-5-ethenyloxolan-2-yl]-3H-pyrimidine-2,4-dione (15 g, 31.1 mmol) and DMAP (7.6 g, 62.1 mmol) in acetonitrile (200 mL) was added TEA (9.4 g, 93.2 mmol) and 2,4,6-triisopropylbenzenesulfonyl chloride (18.7 g, 62.1 mmol). The mixture was stirred for 1 h at room temperature. LCMS showed the reaction was completed. The reaction was quenched with NH₃—H₂O. The mixture was then diluted with EA, washed with brine and dried over anhydrous Na₂SO₄. The solids were filtered out, and the filtrate was combined and concentrated. The residue was purified by silica gel column chromatography, eluted with methanol/dichloromethane (7/93) to afford 4-amino-1-[(2R,4S,5R)-4-[(tert-butyldimethylsilyl) oxy]-5-{[(tert-butyldimethylsilyl) oxy] methyl}-5-ethenyloxolan-2-yl] pyrimidin-2-one (14 g, 29.1 mmol, 93.52%) as a light yellow solid. Product (ES, m/z): 482 (M+H⁺).

Step 11: To a stirred solution of 4-amino-1-[(2R,4S,5R)-4-[(tert-butyldimethylsilyl) oxy]-5-{[(tert-butyldimethylsilyl) oxy] methyl}-5-ethenyloxolan-2-yl] pyrimidin-2-one (13 g, 26.9 mmol, 1 equiv) in methanol (300 mL) was added Pd/C (2.5 g, w/w=20%). The mixture was stirred for 15 h at room temperature under H₂ atmosphere. LCMS showed the reaction was completed. The solids were filtered out, and the filtrate was combined and concentrated under reduced pressure to afford 4-amino-1-[(2R,4S,5R)-4-[(tert-butyldimethylsilyl) oxy]-5-{[(tert-butyldimethylsilyl) oxy] methyl}-5-ethyloxolan-2-yl] pyrimidin-2-one (10 g, 20.7 mmol, crude) as light yellow solid. LC-MS (ES, m/z): 484 (M+H⁺).

Step 12: To a stirred solution of 4-amino-1-[(2R,4S,5R)-4-[(tert-butyldimethylsilyl) oxy]-5-{[(tert-butyldimethylsilyl) oxy] methyl}-5-ethyloxolan-2-yl] pyrimidin-2-one (7 g, 14.4 mmol) in MeOH (300 mL) was added NH₄F (16.1 g, 434.0 mmol). The mixture was stirred for 15 h at 60° C. LCMS showed the reaction was completed. The reaction was cooled to room temperature. The solids were filtered, and the filter cake was washed with MeOH. The filtrate was concentrated under reduced pressure to afford crude product which was purified by prep-SFC with following conditions (Column: CHIRAL ART Amylose-SA, 7*25 cm, 10 μm; Mobile Phase A: CO₂, Mobile Phase B: MeOH (0.1% 2M NH₃-MeOH); Flow rate: 250 mL/min; Gradient: isocratic 50% B; Column Temperature (° C.): 35; Back Pressure (bar): 100; Wavelength: 220 nm; RT1(min): 3.998; Sample Solvent: MeOH-Preparative; Injection Volume: 2 mL; Number of Runs: 30) to afford 4-amino-1-[(2R,4S,5R)-5-ethyl-4-hydroxy-5-(hydroxymethyl) oxolan-2-yl] pyrimidin-2-one (1.0023 g, 3.9 mmol, 26.89%) as white solid. LC-MS (ES, m/z): 256 (M+H⁺), 99.1% purity. Conditions for the LCMS: (Column: Shim Pack Scepter C18, 33*3.0 mm, 3.0 μm; Mobile Phase A: Water/6.5 mM NH₄HCO₃, Mobile Phase B: ACN; Flow rate: 1.200 mL/min; Gradient: 10% B to 95% B in 1.2 min, 95% B to 95% B in 1.80 min, 95% B to 10% B in 1.82 min; Wavelength: 254/220 nm; RT1(min): 1.033). $^1$H NMR (300 MHz, DMSO-$d_6$) δ 7.86 (d, J=7.4 Hz, 1H), 7.11 (d, J=20.2 Hz, 2H), 6.08 (t, J=6.6 Hz, 1H), 5.70 (d, J=7.4 Hz, 1H), 5.05 (d, J=4.8 Hz, 1H), 4.96 (t, J=5.2 Hz, 1H), 4.23 (dt, J=5.8, 4.1 Hz, 1H), 3.41 (h, J=5.9, 5.4 Hz, 2H), 2.23-1.98 (m, 2H), 1.54 (ddq, J=28.8, 14.5, 7.3 Hz, 2H), 0.86 (t, J=7.5 Hz, 3H).

Example 2—Synthesis of Compound 14: 4-amino-1-((2R,4S,5R)-5-(chloromethyl)-4-hydroxy-5-(hydroxymethyl)tetrahydrofuran-2-yl)-5-fluoropyrimidin-2(1H)-one

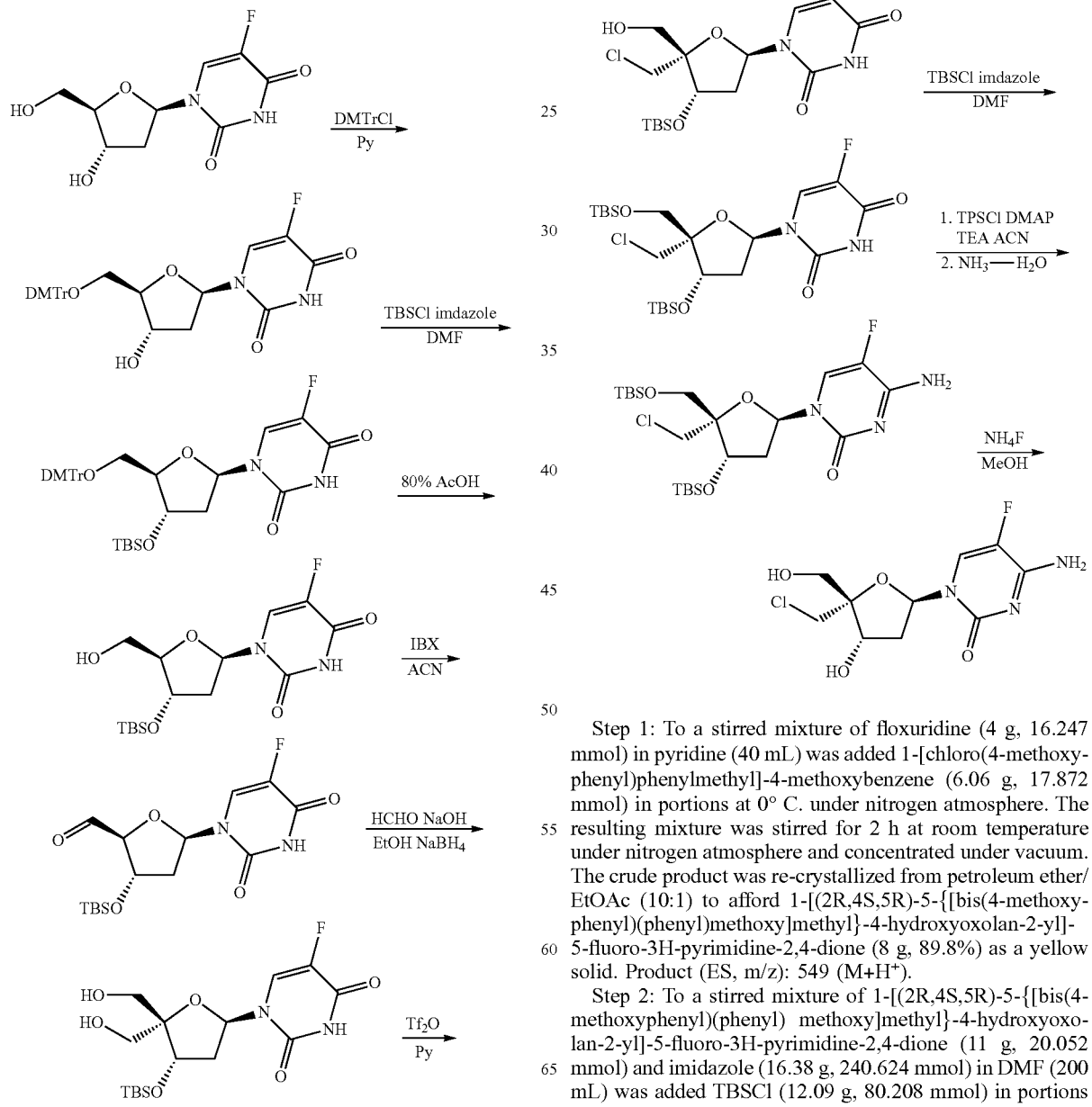

Step 1: To a stirred mixture of floxuridine (4 g, 16.247 mmol) in pyridine (40 mL) was added 1-[chloro(4-methoxyphenyl)phenylmethyl]-4-methoxybenzene (6.06 g, 17.872 mmol) in portions at 0° C. under nitrogen atmosphere. The resulting mixture was stirred for 2 h at room temperature under nitrogen atmosphere and concentrated under vacuum. The crude product was re-crystallized from petroleum ether/EtOAc (10:1) to afford 1-[(2R,4S,5R)-5-{[bis(4-methoxyphenyl)(phenyl)methoxy]methyl}-4-hydroxyoxolan-2-yl]-5-fluoro-3H-pyrimidine-2,4-dione (8 g, 89.8%) as a yellow solid. Product (ES, m/z): 549 (M+H⁺).

Step 2: To a stirred mixture of 1-[(2R,4S,5R)-5-{[bis(4-methoxyphenyl)(phenyl) methoxy]methyl}-4-hydroxyoxolan-2-yl]-5-fluoro-3H-pyrimidine-2,4-dione (11 g, 20.052 mmol) and imidazole (16.38 g, 240.624 mmol) in DMF (200 mL) was added TBSCl (12.09 g, 80.208 mmol) in portions at 0° C. under nitrogen atmosphere. The resulting mixture was stirred for 2 h at room temperature under nitrogen atmosphere and then quenched by the addition of saturated NaHCO₃ aqueous. The resulting mixture was extracted with EtOAc. The combined organics were washed with brine, dried over anhydrous Na₂SO₄, and concentrated under vacuum. This resulted in 1-[(2R,4S,5R)-5-{[bis(4-methoxyphenyl)(phenyl)methoxy]methyl}-4-[(tert-butyldimethylsilyl)oxy]oxolan-2-yl]-5-fluoro-3H-pyrimidine-2,4-dione (11 g, 82.76%) as a yellow solid. Product (ES, m/z): 663 (M+H⁺).

Step 3: A mixture of 1-[(2R,4S,5R)-5-1{[bis(4-methoxyphenyl)(phenyl)methoxy]methyl}-4-[(tert-butyldimethylsilyl)oxy]oxolan-2-yl]-5-fluoro-3H-pyrimidine-2,4-dione (8 g, 12.069 mmol) in AcOH (80 mL) was stirred overnight at room temperature. The reaction was quenched by the addition of saturated NaHCO₃ aqueous. The resulting mixture was extracted with EtOAc. The combined organics were washed with brine, dried over anhydrous Na₂SO₄, and concentrated under vacuum. This resulted in 1-[(2R,4S,5R)-4-[(tert-butyldimethylsilyl)oxy]-5-(hydroxymethyl) oxolan-2-yl]-5-fluoro-3H-pyrimidine-2,4-dione (4 g, 91.94%) as a white solid. Product (ES, m/z): 361 (M+H⁺).

Step 4: To a mixture of 1-[(2R,4S,5R)-4-[(tert-butyldimethylsilyl)oxy]-5-(hydroxymethyl)oxolan-2-yl]-5-fluoro-3H-pyrimidine-2,4-dione (5 g, 13.871 mmol) in ACN (100 mL), was added IBX (7.77 g, 27.742 mmol). The reaction mixture was stirred for 2 h at 60° C. The resulting mixture was filtered, and the filter cake was washed with acetonitrile. The filtrate was concentrated under vacuum. This resulted in (2S,3S,5R)-3-[(tert-butyldimethylsilyl)oxy]-5-(5-fluoro-2,4-dioxo-3H-pyrimidin-1-yl)oxolane-2-carbaldehyde (4.5 g, 90.51%) as a yellow solid. Product (ES, m/z): 359 (M+H⁺).

Step 5: To a stirred mixture of (2S,3S,5R)-3-[(tert-butyldimethylsilyl)oxy]-5-(5-fluoro-2,4-dioxo-3H-pyrimidin-1-yl)oxolane-2-carbaldehyde (5.0 g, 0.330 mmol) and NaOH aqueous (5 mL, 2M) in 1,4-dioxane (50 mL) was added formaldehyde (2.5 mL, 37%) dropwise at room temperature. The resulting mixture was stirred for 2 h at room temperature, then adjusted to pH 7 with AcOH. This was followed by the addition of EtOH (7.5 mL) and NaBH₄ (2.22 g, 58.586 mmol) at 0° C. The resulting mixture was stirred for 30 min at room temperature and quenched by the addition of saturated NH₄Cl aqueous. The resulting mixture was extracted with EtOAc. The combined organics were washed with brine, dried over anhydrous Na₂SO₄, and concentrated under vacuum. This resulted in 1-[(2R,4S)-4-[(tert-butyldimethylsilyl)oxy]-5,5-bis(hydroxymethyl)oxolan-2-yl]-5-fluoro-3H-pyrimidine-2,4-dione (4 g, 73.44%) as a white solid. Product (ES, m/z): 391 (M+H⁺).

Step 6: To a mixture of 1-[(2R,4S)-4-[(tert-butyldimethylsilyl)oxy]-5,5-bis(hydroxymethyl) oxolan-2-yl]-5-fluoro-3H-pyrimidine-2,4-dione (800 mg, 2.049 mmol) in pyridine (8 mL) was added Tf₂O (1213.83 mg, 4.303 mmol) at −30° C. under nitrogen atmosphere. The reaction mixture was stirred for 2 h at −30° C. under nitrogen atmosphere and then quenched by the addition of saturated NaHCO₃ aqueous. The resulting mixture was extracted with EtOAc. The combined organics were washed with brine, dried over anhydrous Na₂SO₄, and concentrated under vacuum. The residue was purified by silica gel column chromatography, eluted with petroleum ether/EtOAc (2:1) to afford [(3S,5R)-3-[(tert-butyldimethylsilyl)oxy]-5-(5-fluoro-2,4-dioxo-3H-pyrimidin-1-yl)-2-[(trifluoromethanesulfonyloxy)methyl] oxolan-2-yl]methyl trifluoromethanesulfonate (1.1 g, 82.02%) as a yellow solid. Product (ES, m/z): 655 (M+H⁺).

Step 7: A mixture of [(3S,5R)-3-[(tert-butyldimethylsilyl)oxy]-5-(5-fluoro-2,4-dioxo-3H-pyrimidin-1-yl)-2-[(trifluoromethanesulfonyloxy)methyl]oxolan-2-yl]methyl trifluoromethanesulfonate (800 mg, 1.222 mmol) and TEA (247.34 mg, 2.444 mmol) in THF (8 mL) was stirred overnight at room temperature under nitrogen atmosphere. Then to the above mixture was added lithium chloride (155.42 mg, 3.666 mmol). The resulting mixture was stirred for additional 2 h at 60° C. Desired product could be detected by LCMS. The crude resulting mixture was used in the next step directly without further purification. Product (ES, m/z): 391 (M+H⁺).

Step 8: The solution from previous step was diluted with H₂O (8 mL), followed by addition of NaOH (245.56 mg, 6.141 mmol). The reaction mixture was stirred overnight at room temperature and then quenched by the addition of saturated NH₄Cl aqueous. The resulting mixture was extracted with EtOAc. The combined organics were washed with brine, dried over anhydrous Na₂SO₄, and concentrated under vacuum. The residue was purified by silica gel column chromatography, eluted with petroleum ether/EtOAc (1:1) to afford 1-[(2R,4S,5R)-4-[(tert-butyldimethylsilyl)oxy]-5-(chloromethyl)-5-(hydroxymethyl)oxolan-2-yl]-5-fluoro-3H-pyrimidine-2,4-dione (600 mg, 71.70%) as a white solid. Product (ES, m/z): 409 (M+H⁺).

Step 9: To a stirred mixture of 1-[(2R,4S,5R)-4-[(tert-butyldimethylsilyl)oxy]-5-(chloromethyl)-5-(hydroxymethyl)oxolan-2-yl]-5-fluoro-3H-pyrimidine-2,4-dione (500 mg, 1.223 mmol) and imidazole (166.48 mg, 2.446 mmol) in DMF (10 mL) was added TBSCl (276.43 mg, 1.835 mmol) in portions at 0° C. under nitrogen atmosphere. The resulting mixture was stirred for 2 h at room temperature under nitrogen atmosphere and then quenched by the addition of saturated NaHCO₃ aqueous. The resulting mixture was extracted with EtOAc. The combined organics were washed with brine, dried over anhydrous Na₂SO₄, and concentrated under vacuum. This resulted in 1-[(2R,4S,5R)-4-[(tert-butyldimethylsilyl)oxy]-5-{[(tert-butyldimethylsilyl)oxy]methyl}-5-(chloromethyl)oxolan-2-yl]-5-fluoro-3H-pyrimidine-2,4-dione (600 mg, 93.79%) as a yellow solid. Product (ES, m/z): 523 (M+H⁺).

Step 10: To a stirred mixture of 1-[(2R,4S,5R)-4-[(tert-butyldimethylsilyl)oxy]-5-{[(tert-butyldimethylsilyl)oxy]methyl}-5-(chloromethyl)oxolan-2-yl]-5-fluoro-3H-pyrimidine-2,4-dione (500 mg, 0.956 mmol), DMAP (350.27 mg, 2.868 mmol), and TEA (290.12 mg, 2.868 mmol) in ACN (20 mL), was added 2,4,6-tris(propan-2-yl)benzene-1-sulfonyl chloride (868.31 mg, 2.868 mmol) at room temperature under nitrogen atmosphere. The resulting mixture was stirred for 2 h at room temperature under nitrogen atmosphere. Then to the above mixture was added dropwise NH₃·H₂O (10.00 mL). The resulting mixture was stirred for additional 1 h at room temperature and then concentrated under vacuum. The residue was purified by reverse-phase flash chromatography with the following conditions: column, C18 silica gel; mobile phase, ACN in water, 0% to 100% gradient in 15 min; detector, UV 254 nm. This resulted in 4-amino-1-[(2R,4S,5R)-4-[(tert-butyldimethylsilyl)oxy]-5-{[(tert-butyldimethylsilyl)oxy]methyl}-5-(chloromethyl)oxolan-2-yl]-5-fluoropyrimidin-2-one (400 mg, 80.15%) as a white solid. Product (ES, m/z): 522 (M+H⁺).

Step 11: To a mixture of 4-amino-1-[(2R,4S,5R)-4-[(tert-butyldimethylsilyl)oxy]-5-{[(tert-butyldimethylsilyl)oxy]methyl}-5-(chloromethyl)oxolan-2-yl]-5-fluoropyrimidin-2-one (400 mg, 0.766 mmol) in MeOH (4 mL) was added NH₄F (851.08 mg, 22.980 mmol). The reaction mixture was stirred overnight at 60° C. The resulting mixture was filtered, and the filter cake was washed with ethanol. The combined filtrate was concentrated under vacuum. The crude product was purified by Prep-HPLC with the following conditions: Column, XBridge Prep OBD C18 Column, 30*150 mm, 5 μm; mobile phase, Water (10 mmol/L NH₄HCO₃) and ACN (2% ACN up to 15% in 7 min); Detector, UV 254 nm. This resulted in 4-amino-1-[(2R,4S,5R)-5-(chloromethyl)-4-hydroxy-5-(hydroxymethyl)oxolan-2-yl]-5-fluoropyrimidin-2-one (71.4 mg, 31.58%) as a white solid. Compound 14 (ES, m/z): 294 (M+H⁺). ¹H NMR (400 MHz, DMSO-d₆) δ 8.02 (d, J=7.2 Hz, 1H), 7.77 (s, 1H), 7.53 (s, 1H), 6.22-6.18 (m, 1H), 5.45 (d, J=4.4 Hz, 1H), 5.30 (t, J=5.2 Hz, 1H), 4.38-4.36 (m, 1H), 3.78 (d, J=11.6 Hz, 1H), 3.71 (d, J=11.6 Hz, 1H), 3.66-3.56 (m, 2H), 2.24-2.17 (m, 2H).

Example 3—Synthesis of Compound 40: 4-amino-1-((2R,3S,4R,5R)-5-(chloromethyl)-3-fluoro-4-hydroxy-5-(hydroxymethyl)tetrahydrofuran-2-yl)pyrimidin-2(1H)-one

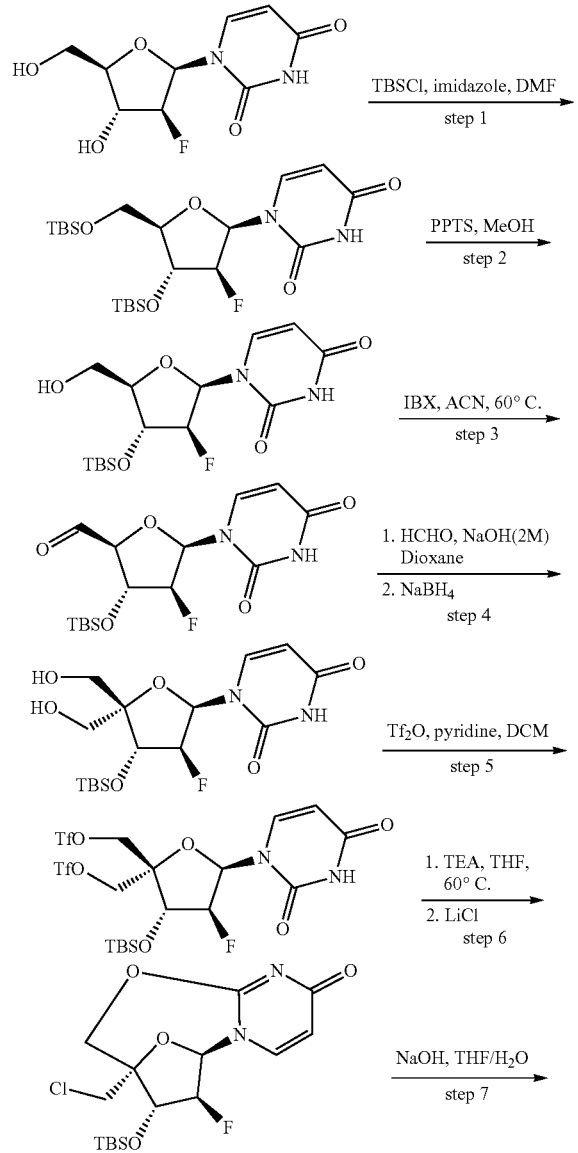

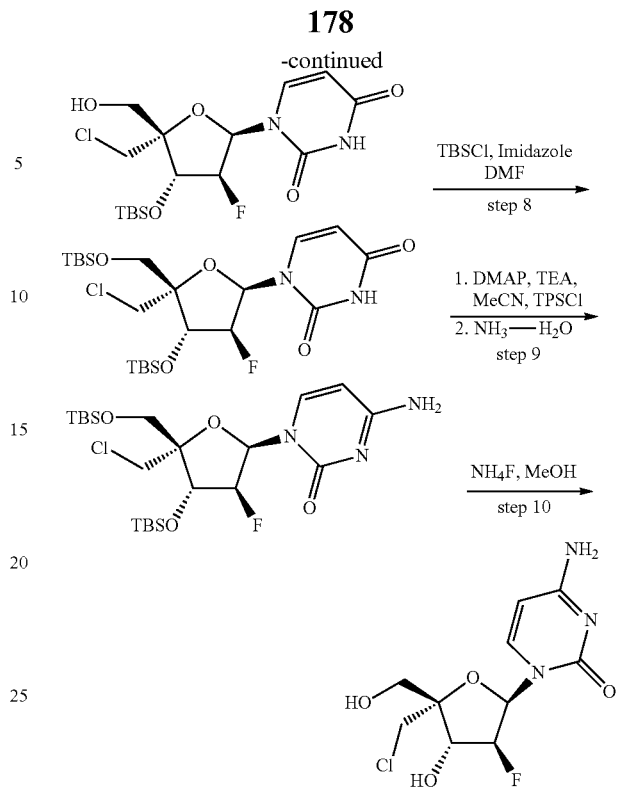

Step 1: To a stirred solution of 1-[(2R,3S,4R,5R)-3-fluoro-4-hydroxy-5-(hydroxymethyl) oxolan-2-yl]-3H-pyrimidine-2,4-dione (60 g, 243.7 mmol) and imidazole (166 g, 2437.1 mmol) in DMF (500 mL) was added TBSCl (110 g, 731.1 mmol) in portions at room temperature under nitrogen atmosphere. The mixture was stirred for 15 h at 80° C. LCMS showed the reaction was completed. The mixture was cooled to room temperature, diluted with EtOAc, washed with brine and dried over anhydrous Na₂SO₄. The solids were filtered out, and the filtrate was concentrated to afford 1-[(2R,3S,4R,5R)-4-[(tert-butyldimethylsilyl) oxy]-5-{[(tert-butyldimethylsilyl) oxy] methyl}-3-fluorooxolan-2-yl]-3H-pyrimidine-2,4-dione (110 g, 231.7 mmol, crude) as a white solid. Product (ES, m/z): 475 (M+H⁺).

Step 2: To a stirred solution of 1-[(2R,3S,4R,5R)-4-[(tert-butyldimethylsilyl) oxy]-5-{[(tert-butyldimethylsilyl) oxy] methyl}-3-fluorooxolan-2-yl]-3H-pyrimidine-2,4-dione (110 g, 231.7 mmol, 1 equiv) in MeOH (500 mL) was added PPTS (175 g, 695.1 mmol) in portions at room temperature under nitrogen atmosphere. The mixture was stirred for 15 h at 50° C. LCMS showed the reaction was completed. The mixture was cooled to room temperature and concentrated. The residue was diluted with EA, washed with brine, and dried over anhydrous Na₂SO₄. The solids were filtered out, and the filtrate was concentrated. The residue was purified by silica gel column chromatography, eluted with methanol/dichloromethane=3/97 to afford 1-[(2R,3S,4R,5R)-4-[(tert-butyldimethylsilyl) oxy]-3-fluoro-5-(hydroxymethyl) oxolan-2-yl]-3H-pyrimidine-2,4-dione (66 g, 183.3 mmol, 79.02%) as an off-white solid. Product (ES, m/z): 361 (M+H⁺).

Step 3: To a stirred solution of 1-[(2R,3S,4R,5R)-4-[(tert-butyldimethylsilyl)oxy]-3-fluoro-5-(hydroxymethyl) oxolan-2-yl]-3H-pyrimidine-2,4-dione (66 g, 183.3 mmol) in CH₃CN (500 mL) was added IBX (47 g, 166.4 mmol) in portions at room temperature under nitrogen atmosphere. The mixture was stirred for 5 h at 60° C. LCMS showed the reaction was completed. The mixture was cooled to room temperature. The solids were filtered out, and the filtrate was concentrated to afford (2S,3R,4S,5R)-3-[(tert-butyldimethylsilyl)oxy]-5-(2,4-dioxo-3H-pyrimidin-1-yl)-4-fluorooxolane-2-carbaldehyde (60 g, 167.5 mmol, crude) as a white solid. Product (ES, m/z): 359 (M+H$^+$).

Step 4: To a stirred solution of (2S,3R,4S,5R)-3-[(tert-butyldimethylsilyl) oxy]-5-(2,4-dioxo-3H-pyrimidin-1-yl)-4-fluorooxolane-2-carbaldehyde (60 g, 167.5 mmol) and HCHO (33 g, 1089.3 mmol, 6.5 equiv) in dioxane (1000 mL) was added a solution of NaOH (20 g, 502.7 mmol, 3 equiv) in water (50 mL) dropwise at 0° C. The resulting mixture was stirred for 1 h at room temperature. To the above mixture was added NaBH$_4$ (29 g, 754.1 mmol) in portions at 0° C. The resulting mixture was stirred for additional 30 min. The mixture was quenched with aqueous NH$_4$Cl. The resulting mixture was extracted with EA. The combined organic layers were washed with saturated salt water, and dried over anhydrous Na$_2$SO$_4$. After filtration, the filtrate was concentrated under reduced pressure. The residue was purified by silica gel column chromatography, eluted with DCM/MeOH (4.9% MeOH) to afford 1-[(2R,3S,4R)-4-[(tert-butyldimethylsilyl)oxy]-3-fluoro-5,5-bis(hydroxymethyl)oxolan-2-yl]-3H-pyrimidine-2,4-dione (35 g, 89.7 mmol, 53.55%) as a white solid. Product (ES, m/z): 391 (M+H$^+$).

Step 5: To a stirred solution of 1-[(2R,3S,4R)-4-[(tert-butyldimethylsilyl) oxy]-3-fluoro-5,5-bis(hydroxymethyl)oxolan-2-yl]-3H-pyrimidine-2,4-dione (31 g, 79.4 mmol) in DCM (500 mL) was added pyridine (31 g, 396.9 mmol) and triflic anhydride (49 g, 174.6 mmol) dropwise at −35° C. under nitrogen atmosphere. The mixture was stirred for 30 min at 0° C., LCMS showed the reaction was completed. The mixture was quenched with water and extracted with EA. The combined organics were washed with brine and dried over anhydrous Na$_2$SO$_4$. The solids were filtered out, and the filtrate was concentrated. The residue was purified by silica gel column chromatography, eluted with EA/PE (1/1) to afford [(3R,4S,5R)-3-[(tert-butyldimethylsilyl)oxy]-5-(2,4-dioxo-3H-pyrimidin-1-yl)-4-fluoro-2-[(trifluoromethane-sulfonyloxy)methyl]oxolan-2-yl]methyl trifluoromethanesulfonate (30 g, 45.8 mmol, 57.05%) as an off-white solid. Product (ES, m/z): 655 (M+H$^+$).

Step 6: To a stirred solution of [(3R,4S,5R)-3-[(tert-butyldimethylsilyl) oxy]-5-(2,4-dioxo-3H-pyrimidin-1-yl)-4-fluoro-2-[(trifluoromethanesulfonyloxy)methyl] oxolan-2-yl]methyl trifluoromethanesulfonate (30 g, 45.8 mmol) in THF (500 mL) was added TEA (46 g, 458.3 mmol) dropwise at room temperature under nitrogen atmosphere. The mixture was stirred for 15 h at 60° C. LCMS showed the starting material was consumed, and then lithium chloride (19 g, 458.3 mmol) was added. The resulting mixture was stirred for 2 h at 60° C., LCMS showed the reaction was completed. The mixture was used in the next reaction without further purification. Product (ES, m/z): 391 (M+H$^+$).

Step 7: To the above solution was slowly added a solution of NaOH (5.5 g, 136.6 mmol) in water (50 mL). The mixture was stirred for two days at room temperature. LCMS showed most of the starting material was consumed. The solids were filtered out, and the filtrate was combined and concentrated. The residue was diluted with EA, washed with brine and dried over anhydrous Na$_2$SO$_4$. The solids were filtered out, and the filtrate was concentrated. The residue was purified by silica gel column chromatography, eluted with methanol/dichloromethane (7/93) to afford 1-[(2R,3S,4R,5R)-4-[(tert-butyldimethylsilyl)oxy]-5-(chloromethyl)-3-fluoro-5-(hydroxymethyl) oxolan-2-yl]-3H-pyrimidine-2,4-dione (11 g, 26.9 mmol, 59.07%) as light yellow solid. Product (ES, m/z): 409 (M+H$^+$).

Step 8: To a stirred solution of 1-[(2R,3S,4R,5R)-4-[(tert-butyldimethylsilyl) oxy]-5-(chloromethyl)-3-fluoro-5-(hydroxymethyl) oxolan-2-yl]-3H-pyrimidine-2,4-dione (10 g, 24.4 mmol) and imidazole (17 g, 244.5 mmol) in dimethylformamide (200 mL) was added t-butyldimethylchlorosilane (11 g, 73.3 mmol) in portions at room temperature under nitrogen atmosphere. The mixture was stirred for 15 h at 80° C. LCMS showed the reaction was completed. The mixture was cooled to room temperature, diluted with EA, washed with brine, and dried over anhydrous Na$_2$SO$_4$. The solids were filtered out, and the filtrate was combined and concentrated. The residue was purified by silica gel column chromatography, eluted with methanol/dichloromethane (7/93) to afford 1-[(2R,3S,4R,5R)-4-[(tert-butyldimethylsilyl) oxy]-5-{[(tert-butyldimethylsilyl) oxy] methyl}-5-(chloromethyl)-3-fluorooxolan-2-yl]-3H-pyrimidine-2,4-dione (12 g, 23.0 mmol, 93.79%) as light yellow solid. Product (ES, m/z): 523 (M+H$^+$).

Step 9: To a stirred solution of 1-[(2R,3S,4R,5R)-4-[(tert-butyldimethylsilyl) oxy]-5-{[(tert-butyldimethylsilyl) oxy] methyl}-5-(chloromethyl)-3-fluorooxolan-2-yl]-3H-pyrimidine-2,4-dione (12 g, 22.9 mmol) and DMAP (5.6 g, 45.8 mmol) in CH$_3$CN (200 mL) was added TEA (7 g, 68.8 mmol) and 2,4,6-triisopropylbenzenesulfonyl chloride (14 g, 45.8 mmol) at room temperature under nitrogen atmosphere. The mixture was stirred for 15 h at 40° C. The starting material was consumed, and then NH$_3$·H$_2$O (50 mL) was added slowly. The resulting mixture was stirred for 1 h at room temperature. LCMS showed the reaction was completed. The mixture was diluted with EA, washed with brine, and dried over anhydrous Na$_2$SO$_4$. The solids were filtered out, and the filtrate was combined and concentrated. The residue was purified by silica gel column chromatography, eluted with methanol/dichloromethane (7/93) to afford 4-amino-1-[(2R,3S,4R,5R)-4-[(tert-butyldimethylsilyl) oxy]-5-{[(tert-butyldimethylsilyl) oxy] methyl}-5-(chloromethyl)-3-fluorooxolan-2-yl] pyrimidin-2-one (11 g, 21.1 mmol, 91.84%) as a light yellow solid. Product (ES, m/z): 522 (M+H$^+$).

Step 10: A mixture of 4-amino-1-[(2R,3S,4R,5R)-4-[(tert-butyldimethylsilyl) oxy]-5-{[(tert-butyldimethylsilyl) oxy] methyl}-5-(chloromethyl)-3-fluorooxolan-2-yl] pyrimidin-2-one (8 g, 15.4 mmol) and NH$_4$F (17 g, 461 mmol) in MeOH (200 mL) was stirred overnight at 60° C. under nitrogen atmosphere. The resulting mixture was cooled to room temperature and the solids were filtered out; the filter cake was washed with MeOH. The filtrate was combined and concentrated under reduced pressure. The crude product was purified by reverse flash (NH$_4$HCO$_3$) to afford 4-amino-1-[(2R,3S,4R,5R)-5-(chloromethyl)-3-fluoro-4-hydroxy-5-(hydroxymethyl) oxolan-2-yl] pyrimidin-2-one (2.5 g, 8.53 mmol, 55.38%) as a white solid. Compound 40 (ES, m/z): 294 (M+H$^+$), 98.6% purity. $^1$H NMR (400 MHz, DMSO-d$_6$) δ 7.63 (dd, J=7.5, 1.4 Hz, 1H), 7.24 (d, J=24.8 Hz, 2H), 6.25 (dd, J=17.9, 4.0 Hz, 1H), 6.15 (d, J=5.1 Hz, 1H), 5.74 (d, J=7.4 Hz, 1H), 5.34 (t, J=5.5 Hz, 1H), 5.09 (dt, J=53.0, 3.3 Hz, 1H), 4.42 (ddd, J=18.3, 5.2, 2.8 Hz, 1H), 3.97-3.69 (m, 2H), 3.66-3.50 (m, 2H).

Example 4—Synthesis of Compound 4: 1-((2R,4S, 5R)-5-(chloromethyl)-4-hydroxy-5-(hydroxymethyl) tetrahydrofuran-2-yl)-5-methylpyrimidine-2,4(1H, 3H)-dione

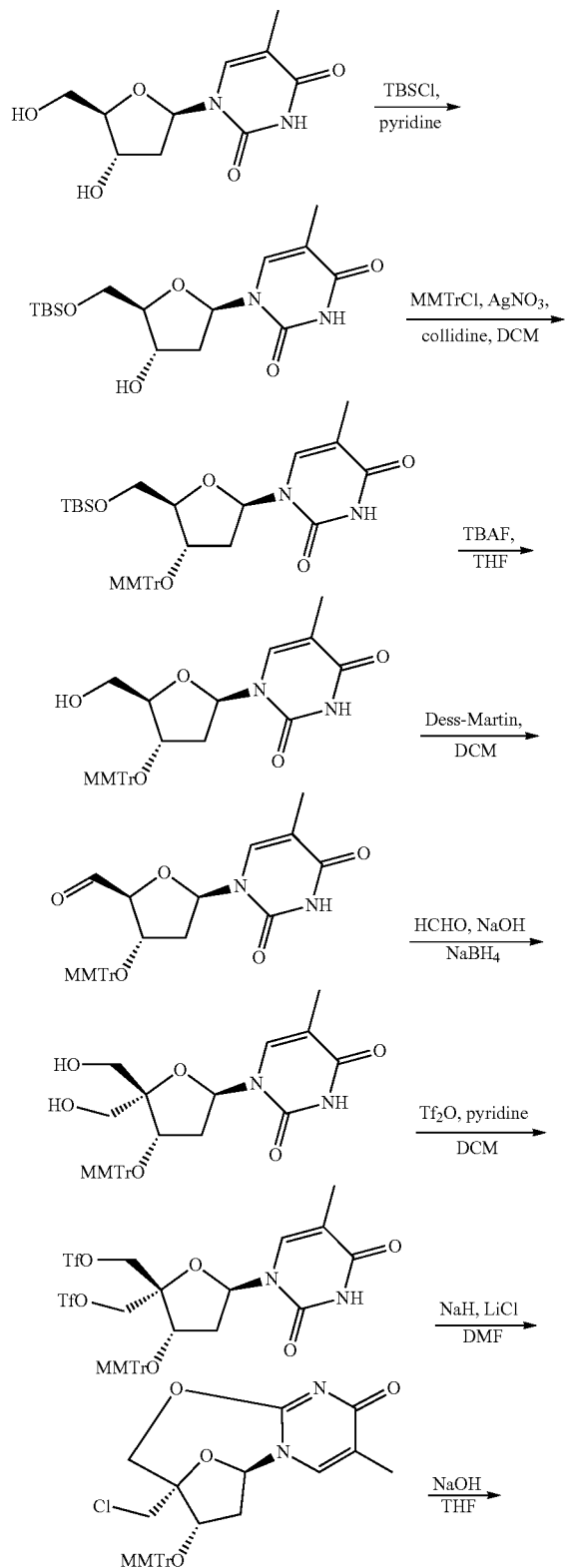

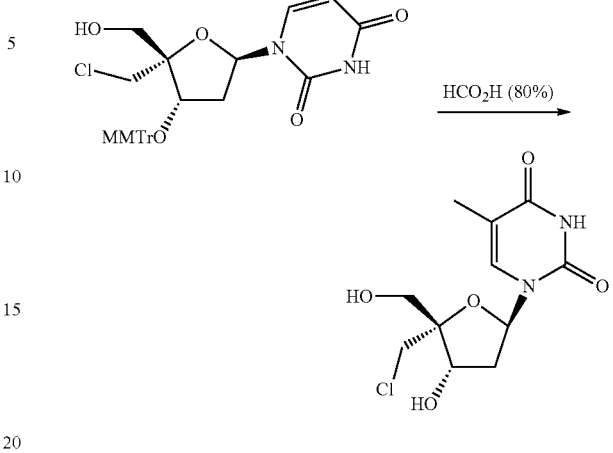

Step 1: A mixture of thymidine (5 g, 20.6 mmol) and tert-butylchlorodimethylsilane (3.4 g, 22.7 mmol) in pyridine (30 mL) was stirred for 3 h at room temperature. The resulting mixture was diluted with water (500 mL). The resulting mixture was extracted with ethyl acetate (3×300 mL). The combined organic layers were washed with brine (3×150 mL) and dried over anhydrous sodium sulfate. After filtration, the filtrate was concentrated under reduced pressure. The residue was applied on a silica gel column chromatography with dichloromethane/methyl alcohol (10/1) to afford 1-[(2R,4S,5R)-5-1{[(tert-butyldimethylsilyl) oxy] methyl}-4-hydroxyoxolan-2-yl]-5-methyl-3H-pyrimidine-2,4-dione (7 g, 19.6 mmol, 95.13%) as a white solid. LC-MS (ES, m/z): 357 [M+H]+.

Step 2: To a mixture of 1-[(2R,4S,5R)-5-{[(tert-butyldimethylsilyl) oxy] methyl}-4-hydroxyoxolan-2-yl]-5-methyl-3H-pyrimidine-2,4-dione (7 g, 19.6 mmol) and 2,4,6-trimethyl-pyridine (7.1 g, 58.9 mmol) in dichloromethane (50 mL) was added silver nitrate (6.6 g, 39.2 mmol) and 1-(chlorodiphenylmethyl)-4-methoxybenzene (6.6 g, 21.6 mmol) at 0° C., and the mixture was stirred overnight at room temperature. The mixture was acidified to pH 6 with hydrochloric acid (0.1M). The resulting mixture was extracted with ethyl acetate (3×200 mL). The combined organic layers were washed with brine (3×100 mL) and dried over anhydrous sodium sulfate. After filtration, the filtrate was concentrated under reduced pressure. The crude product was used directly in the next step without further purification. LC-MS (ES, m/z): 629 [M+H]+.

Step 3: A mixture of 1-[(2R,4S,5R)-5-{[(tert-butyldimethylsilyl) oxy] methyl}-4-[(4-methoxyphenyl) diphenylmethoxy] oxolan-2-yl]-5-methyl-3H-pyrimidine-2,4-dione (12 g, 19.1 mmol) and tetrabutylammonium fluoride (22.9 mL, 22.9 mmol, 1 M in THF) in tetrahydrofuran (300 mL) was stirred for 6 h at room temperature. The mixture was concentrated, and the residue was purified by silica gel column chromatography, eluted with petroleum ether/ethyl acetate (1:1) to afford 1-[(2R,4S,5R)-5-(hydroxymethyl)-4-[(4-methoxyphenyl) diphenylmethoxy] oxolan-2-yl]-5-methyl-3H-pyrimidine-2,4-dione (8 g, 15.5 mmol, 81.47%) as a light yellow solid. LC-MS (ES, m/z): 515 [M+H]+.

Step 4: A mixture of 1-[(2R,4S,5R)-5-(hydroxymethyl)-4-[(4-methoxyphenyl) diphenylmethoxy] oxolan-2-yl]-5-methyl-3H-pyrimidine-2,4-dione (8 g, 15.5 mmol) and Dess-Martin (6.5 g, 15.5 mmol) in dichloromethane (50 mL) was stirred overnight at room temperature under nitrogen atmosphere. The residue was purified by silica gel column chromatography, eluted with petroleum ether/ethyl acetate (1:1) to afford (2S,3S,5R)-3-[(4-methoxyphenyl) diphenylmethoxy]-5-(5-methyl-2,4-dioxo-3H-pyrimidin-1-yl) oxolane-2-carbaldehyde (6.8 g, 13.2 mmol, 85.33%) as an off-white solid. LC-MS (ES, m/z): 513 [M+H]+.

Step 5: A mixture of (2S,3S,5R)-3-[(4-methoxyphenyl) diphenylmethoxy]-5-(5-methyl-2,4-dioxo-3H-pyrimidin-1-yl) oxolane-2-carbaldehyde (6.8 g, 13.2 mmol) and HCHO (3.9 g, 132.8 mmol) in 1,4-dioxane (60 mL) and water (12 mL) was treated with caustic soda (1.1 g, 26.5 mmol) overnight at room temperature under nitrogen atmosphere followed by the addition of NaBH$_4$ (2.1 g, 53.1 mmol) in portions at room temperature. The resulting mixture was stirred for 1 h at room temperature under air atmosphere. The resulting mixture was diluted with water (200 mL). The resulting mixture was extracted with ethyl acetate (3×200 mL). The combined organic layers were washed with brine (3×100 mL) and dried over anhydrous sodium sulfate. After filtration, the filtrate was concentrated under reduced pressure. The residue was purified by silica gel column chromatography, eluted with dichloromethane/methyl alcohol (10:1) to afford 1-[(2R,4S)-5,5-bis(hydroxymethyl)-4-[(4-methoxyphenyl) diphenylmethoxy]oxolan-2-yl]-5-methyl-3H-pyrimidine-2,4-dione (3.5 g, 6.4 mmol, 48.44%) as a white solid. LC-MS (ES, m/z): 545 [M+H]+.

Step 6: To a mixture of 1-[(2R,4S)-5,5-bis(hydroxymethyl)-4-[(4-methoxyphenyl) diphenylmethoxy]oxolan-2-yl]-5-methyl-3H-pyrimidine-2,4-dione (3.5 g, 6.4 mmol) and pyridine (2.5 g, 32.1 mmol) in dichloromethane (50 mL) was added trifluoromethanesulfonic anhydride (3.6 g, 12. mmol) dropwise at −35° C., and the mixture was stirred for 2 h at room temperature under nitrogen atmosphere. The resulting mixture was diluted with water (200 mL). The resulting mixture was extracted with ethyl acetate (3×100 mL). The combined organic layers were washed with brine (3×100 mL) and dried over anhydrous sodium sulfate. After filtration, the filtrate was concentrated under reduced pressure. The residue was purified by silica gel column chromatography, eluted with PE/EA (1:1) to afford [(3S,5R)-3-[(4-methoxyphenyl) diphenylmethoxy]-5-(5-methyl-2,4-dioxo-3H-pyrimidin-1-yl)-2-[(trifluoromethanesulfonyloxy)methyl] oxolan-2-yl]methyl trifluoromethanesulfonate (2 g, 2.4 mmol, 38.48%) as a yellow solid. LC-MS (ES, m/z): 809 [M+H]+.

Step 7: A mixture of [(3S,5R)-3-[(4-methoxyphenyl)diphenylmethoxy]-5-(5-methyl-2,4-dioxo-3H-pyrimidin-1-yl)-2-[(trifluoromethanesulfonyloxy)methyl]oxolan-2-yl] methyl trifluoromethanesulfonate (2 g, 2.4 mmol) and sodium hydride (0.06 g, 2.4 mmol) in N,N-dimethylformamide (10 mL) was stirred for 4 h at room temperature under nitrogen atmosphere, before lithium chloride (0.31 g, 7.4 mmol) was added to the mixture and stirred for 1.5 h. The reaction was quenched by the addition of water (1 mL) at 0° C. The mixture was concentrated, and the residue was purified by silica gel column chromatography, eluted with dichloromethane/methanol (10:1) to afford (6R,8S,9R)-9-(chloromethyl)-8-((4-methoxyphenyl)diphenylmethoxy)-3-methyl-7,8,9,10-tetrahydro-2H,6H-6,9-epoxypyrimido[2,1-b][1,3]oxazocin-2-one (1 g, 1.8 mmol, 74.19%) as a white solid. LC-MS (ES, m/z): 545/547 [M+H]+.

Step 8: A mixture of (6R,8S,9R)-9-(chloromethyl)-8-((4-methoxyphenyl) diphenylmethoxy)-3-methyl-7,8,9,10-tetrahydro-2H,6H-6,9-epoxypyrimido[2,1-b][1,3]oxazocin-2-one (500 mg, 0.9 mmol) and sodium hydroxide (73.3 mg, 1.8 mmol) in tetrahydrofuran (10 mL) was stirred overnight at room temperature. The resulting mixture was concentrated under vacuum. The residue was purified by silica gel column chromatography, eluted with dichloromethane/methanol (10:1) to afford 1-[(2R,4S,5R)-5-(chloromethyl)-5-(hydroxymethyl)-4-[(4-methoxyphenyl) diphenylmethoxy] oxolan-2-yl]-5-methyl-3H-pyrimidine-2,4-dione (190 mg, 0.3 mmol, 36.78%) as a white solid. LC-MS (ES, m/z): 563/565 [M+H]+.

Step 9: A mixture of 1-[(2R,4S,5R)-5-(chloromethyl)-5-(hydroxymethyl)-4-[(4-methoxyphenyl) diphenylmethoxy] oxolan-2-yl]-5-methyl-3H-pyrimidine-2,4-dione (190 mg, 0.3 mmol) in formic acid (8 mL) and H$_2$O (2 mL) was stirred for 0.5 h at room temperature under nitrogen atmosphere. The mixture was concentrated, and the crude product (80 mg) was purified by Prep-HPLC with the following conditions (Column: XBridge Prep C18 OBD Column, 30*100 mm, 5 μm; Mobile Phase A: Water (10 mmol/L NH$_4$HCO$_3$), Mobile Phase B: ACN; Flow rate: 60 mL/min; Gradient: 20% B to 38% B in 10 min, 38% B; Wavelength: 254/220 nm; RT1(min): 9.98) to afford 1-[(2R,4S,5R)-5-(chloromethyl)-4-hydroxy-5-(hydroxymethyl) oxolan-2-yl]-5-methyl-3H-pyrimidine-2,4-dione (11.4 mg, 11.45%) as a white solid. LC-MS (ES, m/z): 291/293 [M+H]+. 98.5% purity. Conditions for the LCMS: (Column: Shim-pack ScepterC18, 33*3 mm, 3 μm; Mobile Phase A: Water/5 mM NH$_4$HCO$_3$, Mobile Phase B: Acetonitrile; Flow rate: 1.5000 mL/min; Gradient: 5% B to 30% B in 1.79 min, 30% B to 95% B in 0.40 min, 95% B to 95% B in 0.10 min, 95% B to 10% B in 0.30 min; Wavelength: 254 nm; RT1(min): 1.040). $^1$H NMR (400 MHz, DMSO-d$_6$) δ 11.24 (s, 1H), 7.63 (d, J=1.6 Hz, 1H), 6.26 (dd, J=8.2, 5.9 Hz, 1H), 5.48 (s, 1H), 5.25 (s, 1H), 4.41 (dd, J=6.2, 3.0 Hz, 1H), 3.84-3.70 (m, 2H), 3.59 (s, 2H), 2.33 (ddd, J=13.9, 8.3, 6.1 Hz, 1H), 2.20-2.06 (m, 1H), 1.79 (s, 3H).

Example 5—Synthesis of Compound 67

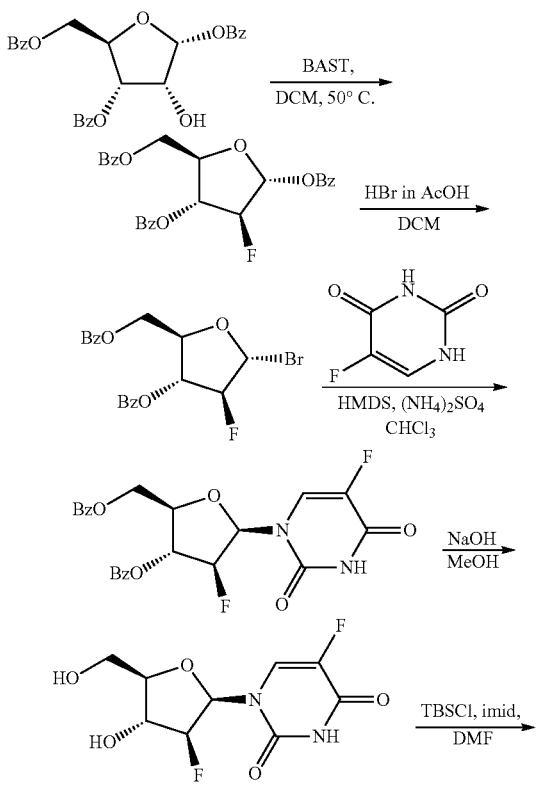

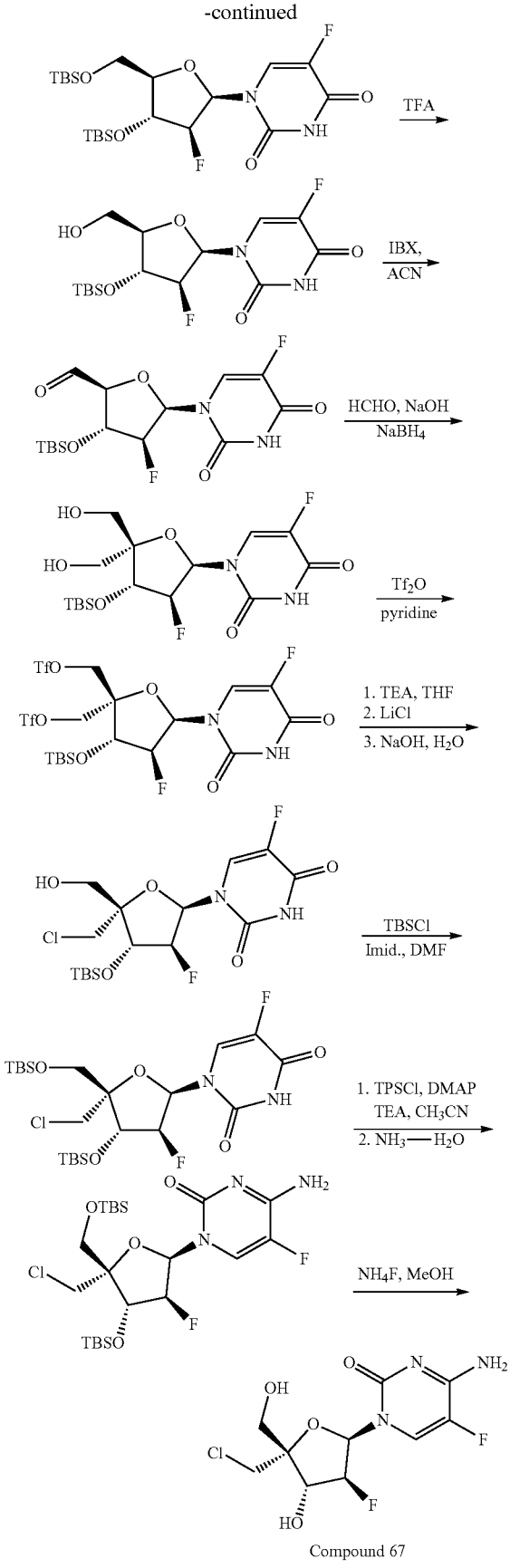

Compound 67

Step 1: To a solution of [(2R,3S,4R,5R)-3,5-bis(benzoyloxy)-4-hydroxyoxolan-2-yl]methyl benzoate (50 g, 108.1 mmol) in DCM (500 mL) was added BAST (47.8 g, 216.2 mmol) dropwise at 0° C. The resulting mixture was stirred for 2 days at 50° C., then cooled to 0° C. and quenched by the addition of water. The resulting solution was extracted with EtOAc. The combined organics were washed with saturated aqueous $NaHCO_3$, dried over anhydrous $Na_2SO_4$ and concentrated under vacuum. The residue was purified by silica gel column chromatography, eluted with petroleum ether/EtOAc (2:1) to afford [(2R,3R,4S,5R)-3,5-bis(benzoyloxy)-4-fluorooxolan-2-yl]methyl benzoate (40 g, 79.7%) as a white solid. LC-MS (ES, m/z): 343 (M-OBz)$^+$.

Step 2: To a solution of [(2R,3R,4S,5R)-3,5-bis(benzoyloxy)-4-fluorooxolan-2-yl]methyl benzoate (40 g, 86.1 mmol) in DCM (400 mL), was added HBr—AcOH (120 mL) dropwise. The resulting mixture was stirred overnight at room temperature and then quenched by the addition of water. The resulting solution was extracted with EtOAc. The combined organics were washed with saturated aqueous $NaHCO_3$, dried over anhydrous $Na_2SO_4$, and concentrated under vacuum. The residue was purified by silica gel column chromatography, eluted with petroleum ether/EtOAc (4:1) to afford [(2R,3R,4S,5R)-3-(benzoyloxy)-5-bromo-4-fluorooxolan-2-yl]methyl benzoate (35 g, 96.0%) as a brown yellow oil. LC-MS (ES, m/z): 343 (M-Br)+.

Step 3: To a stirred solution of fluorouracil (16.14 g, 124.0 mmol) in HMDS (160 mL), was added $(NH_4)_2SO_4$ (32.78 g, 248.1 mmol) in portions. The resulting mixture was stirred for 4 hours at 120° C., then cooled down to room temperature and concentrated under vacuum. To the above residue was added a solution of [(2R,3R,4S,5R)-3-(benzoyloxy)-5-bromo-4-fluorooxolan-2-yl]methyl benzoate (35 g, 82.697 mmol) in chloroform (350 mL). The resulting mixture was stirred overnight at 60° C. The resulting solution was cooled to room temperature, washed with brine, and concentrated under vacuum. The residue was purified by silica gel column chromatography, eluted with petroleum ether/EtOAc (5:1) to afford [(2R,3R,4S,5R)-3-(benzoyloxy)-4-fluoro-5-(5-fluoro-2,4-dioxo-3H-pyrimidin-1-yl)oxolan-2-yl]methyl benzoate (26 g, 66.6%) as a white solid. LC-MS (ES, m/z): 473 (M+H$^+$).

Step 4: To a stirred solution of [(2R,3R,4S,5R)-3-(benzoyloxy)-4-fluoro-5-(5-fluoro-2,4-dioxo-3H-pyrimidin-1-yl)oxolan-2-yl]methyl benzoate (26 g, 55.0 mmol) in MeOH (300 mL), was added NaOH (5.5 g, 137.6 mmol) in portions at room temperature under nitrogen atmosphere. The resulting mixture was stirred overnight at room temperature and concentrated under vacuum. The residue was purified by silica gel column chromatography, eluted with $CH_2Cl_2$/MeOH (15:1) to afford 5-fluoro-1-[(2R,3S,4R,5R)-3-fluoro-4-hydroxy-5-(hydroxymethyl)oxolan-2-yl]-3H-pyrimidine-2,4-dione (11 g, 75.7%) as a white solid. LC-MS (ES, m/z): 265 (M+H$^+$).

Step 5: To a stirred solution of 5-fluoro-1-[(2R,3S,4R,5R)-3-fluoro-4-hydroxy-5-(hydroxymethyl)oxolan-2-yl]-3H-pyrimidine-2,4-dione (20 g, 75.7 mmol) and imidazole (15.46 g, 227.1 mmol) in DMF (200 mL), was added TBSCl (28.53 g, 189.3 mmol) in portions at 0° C. under nitrogen atmosphere. The resulting mixture was stirred overnight at room temperature and then diluted with EtOAc (200 mL). The resulting solution was washed with brine, dried over anhydrous $Na_2SO_4$, and concentrated under vacuum. The residue was purified by silica gel column chromatography, eluted with petroleum ether/EtOAc (8:1) to afford 1-[(2R,3S,4R,5R)-4-[(tert-butyldimethylsilyl)oxy]-5-{[(tert-butyldimethylsilyl)oxy]methyl}-3-fluorooxolan-2-yl]-5- fluoro-3H-pyrimidine-2,4-dione (28 g, 75.1%) as a white solid. LC-MS (ES, m/z): 493 (M+H⁺).

Step 6: To a solution of 1-[(2R,3S,4R,5R)-4-[(tert-butyldimethylsilyl)oxy]-5-{[(tert-butyldimethylsilyl)oxy]methyl}-3-fluorooxolan-2-yl]-5-fluoro-3H-pyrimidine-2,4-dione (28 g, 57.1 mmol) in THF (300 mL), was added TFA (60 mL) dropwise at 0° C. under nitrogen atmosphere. The resulting mixture was stirred for 4 hours and then quenched by the addition of water. The resulting solution was extracted with EtOAc. The combined organics were washed with brine, dried over anhydrous $Na_2SO_4$ and concentrated under vacuum. The residue was purified by silica gel column chromatography, eluted with petroleum ether/EtOAc (5:1) to afford 1-[(2R,3S,4R,5R)-4-[(tert-butyldimethylsilyl)oxy]-3-fluoro-5-(hydroxymethyl)oxolan-2-yl]-5-fluoro-3H-pyrimidine-2,4-dione (15.3 g, 70.9%) as a white solid. LC-MS (ES, m/z): 379 (M+H⁺).

Step 7: To a solution of 1-[(2R,3S,4R,5R)-4-[(tert-butyldimethylsilyl)oxy]-3-fluoro-5-(hydroxymethyl)oxolan-2-yl]-5-fluoro-3H-pyrimidine-2,4-dione (15.3 g, 40.4 mmol) in acetonitrile (160 mL), was added IBX (22.64 g, 80.9 mmol). The mixture was stirred for 3 hours at 60° C., then cooled to room temperature. The resulting mixture was filtered, and the filter cake was washed with acetonitrile (3×100 mL). The filtrate was concentrated under vacuum to afford crude (2S,3R,4S,5R)-3-[(tert-butyldimethylsilyl)oxy]-4-fluoro-5-(5-fluoro-2,4-dioxo-3H-pyrimidin-1-yl) oxolane-2-carbaldehyde (12.9 g, 84.8%) as a white solid. The crude product was used in the next step directly without further purification. LC-MS (ES, m/z): 377 (M+H⁺).

Step 8: To a solution of (2S,3R,4S,5R)-3-[(tert-butyldimethylsilyl)oxy]-4-fluoro-5-(5-fluoro-2,4-dioxo-3H-pyrimidin-1-yl)oxolane-2-carbaldehyde (12.9 g, 34.3 mmol) in 1,4-dioxane (130 mL), was added HCHO aqueous (13 mL, 37%-40%) and NaOH aqueous (40 mL, 2 M, 80.0 mmol) dropwise at 0° C. The resulting mixture was stirred overnight at room temperature under nitrogen atmosphere and then adjusted to pH 7 with acetic acid. To the above mixture was added EtOH (39 mL) dropwise. That was followed by the addition of $NaBH_4$ (2.6 g, 68.5 mmol) in portions at 0° C. The resulting mixture was stirred for 4 hours at room temperature, then cooled to 0° C. and quenched by the addition of saturated aqueous $NH_4Cl$. The resulting solution was extracted with EtOAc. The combined organics were washed with brine, dried over anhydrous $Na_2SO_4$ and concentrated under vacuum. The residue was purified by silica gel column chromatography, eluted with petroleum ether/EtOAc (1:1) to afford 1-[(2R,3S,4R)-4-[(tert-butyldimethylsilyl)oxy]-3-fluoro-5,5-bis(hydroxymethyl)oxolan-2-yl]-5-fluoro-3H-pyrimidine-2,4-dione (6.7 g, 47.9%) as a white solid. LC-MS (ES, m/z): 409 (M+H⁺).

Step 9: To a stirred solution of 1-[(2R,3S,4R)-4-[(tert-butyldimethylsilyl)oxy]-3-fluoro-5,5-bis(hydroxymethyl)oxolan-2-yl]-5-fluoro-3H-pyrimidine-2,4-dione (10.0 g, 24.5 mmol 7.344 mmol) in pyridine (300 mL), was added $Tf_2O$ (17.3 g, 61.3 mmol) dropwise at −30° C. under nitrogen atmosphere. The resulting mixture was stirred for 2 hours at room temperature, then cooled to 0° C. and quenched by the addition of saturated aqueous of $NH_4Cl$. The resulting solution was extracted with EtOAc. The combined organics were washed with brine, dried over anhydrous $Na_2SO_4$ and concentrated under vacuum. The residue was purified by silica gel column chromatography, eluted with petroleum ether/EtOAc (5:1) to afford [(3R,4S,5R)-3-[(tert-butyldimethylsilyl)oxy]-4-fluoro-5-(5-fluoro-2,4-dioxo-3H-pyrimidin-1-yl)-2-[(trifluoromethanesulfonyloxy)-methyl]oxolan-2-yl]methyl trifluoromethanesulfonate (10.5 g, 63.75%) as a yellow solid. LC-MS (ES, m/z): 673 (M+H⁺).

Step 10: To a stirred solution of [(3R,4S,5R)-3-[(tert-butyldimethylsilyl)oxy]-4-fluoro-5-(5-fluoro-2,4-dioxo-3H-pyrimidin-1-yl)-2-[(trifluoromethanesulfonyloxy)methyl]oxolan-2-yl]methyl trifluoromethanesulfonate (10.2 g, 15.2 mmol) in THF (100 mL), was added TEA (15.3 g, 151.4 mmol) dropwise at room temperature under nitrogen atmosphere. The resulting mixture was stirred for 3 hours at 50° C. and then cooled to room temperature. To the above mixture was added LiCl (1.9 g, 45.5 mmol) in portions, and the resulting mixture was stirred overnight at 50° C. After cooling to room temperature, a solution of NaOH (1.2 g, 30.2 mmol) in water (40 mL) was added dropwise. The resulting mixture was stirred for additional 3 hours at room temperature, then extracted with EtOAc. The combined organics were washed with brine, dried over anhydrous $Na_2SO_4$ and concentrated under vacuum. The residue was purified by silica gel column chromatography, eluted with petroleum ether/EtOAc (2:1) to afford 1-((2R,3S,4R,5R)-4-((tert-butyldimethylsilyl)-oxy)-5-(chloromethyl)-3-fluoro-5-(hydroxymethyl) tetrahydrofuran-2-yl)-5-fluoropyrimidine-2,4(1H,3H)-dione (2.5 g, 40.4%) as a white solid. LC-MS (ES, m/z): 427 (M+H⁺).

Step 11: To a solution of 1-((2R,3S,4R,5R)-4-((tert-butyldimethylsilyl)oxy)-5-(chloromethyl)-3-fluoro-5-(hydroxymethyl)tetrahydrofuran-2-yl)-5-fluoropyrimidine-2,4 (1H,3H)-dione (2.5 g, 6.1 mmol) and imidazole (1.2 g, 17.5 mmol) in DMF (40 mL), was added TBSCl (1.32 g, 8.9 mmol) in portions at 0° C. The resulting mixture was stirred overnight and then quenched by the addition of water. The resulting solution was extracted with EtOAc. The combined organics were washed with brine, dried over anhydrous $Na_2SO_4$ and concentrated under vacuum. The residue was purified by silica gel column chromatography, eluted with petroleum ether/EtOAc (4:1) to afford 1-((2R,3S,4R,5R)-4-((tert-butyldimethylsilyl)oxy)-5-(((tert-butyldimethylsilyl)oxy)methyl)-5-(chloromethyl)-3-fluorotetrahydrofuran-2-yl)-5-fluoropyrimidine-2,4(1H,3H)-dione (1.5 g, 46.9%) as a white solid. LC-MS (ES, m/z): 541 (M+H⁺).

Step 12: To a stirred solution of 1-((2R,3S,4R,5R)-4-((tert-butyldimethylsilyl)oxy)-5-(((tert-butyldimethylsilyl)oxy)methyl)-5-(chloromethyl)-3-fluorotetrahydrofuran-2-yl)-5-fluoropyrimidine-2,4(1H,3H)-dione (1.5 g, 2.9 mmol) in $CH_3CN$ (30 mL), was added DMAP (701.5 mg, 5.75 mmol) and TEA (870.0 mg, 8.5 mmol) in portions at room temperature under nitrogen atmosphere. After stirred for 10 min at room temperature, 2,4,6-tris(propan-2-yl)benzene-1-sulfonyl chloride (1.7 g, 5.75 mmol) was added in portions. The resulting mixture was stirred for 0.5 h at room temperature, and that was followed by the dropwise addition of ammonia (2.5 mL). The resulting mixture was stirred overnight at room temperature and then quenched by the addition of water (20 mL). The resulting solution was extracted with EtOAc. The combined organics were washed with brine, dried over anhydrous $Na_2SO_4$ and concentrated under vacuum. The residue was purified by silica gel column chromatography, eluted with petroleum ether/EtOAc (1:1) to afford 4-amino-1-[(2R,3S,4R,5R)-4-[(tert-butyldimethylsilyl) oxy]-5-{[(tert-butyldimethylsilyl)oxy]methyl}-5-(chloromethyl)-3-fluorooxolan-2-yl]-5-fluoropyrimidin-2-one (810.0 mg, 42.2%) as a white solid. LC-MS (ES, m/z): 540 (M+H⁺).

Step 13: To a stirred solution of 4-amino-1-[(2R,3S,4R, 5R)-4-[(tert-butyldimethylsilyl)oxy]-5-{[(tert-butyldimethylsilyl)oxy]methyl}-5-(chloromethyl)-3-fluorooxolan-2- yl]-5-fluoropyrimidin-2-one (800.0 mg, 1.5 mmol) in MeOH (20 mL), was added NH$_4$F (267.9 mg, 7.2 mmol) in portions at room temperature under nitrogen atmosphere. The resulting mixture was stirred overnight at 60° C. and then cooled to room temperature. The precipitated solids were removed by filtration, and the filtrate was concentrated under vacuum. The crude product was purified by Prep-HPLC with the following conditions: Column: XBridge Shield RP18 OBD Column, 19*250 mm, 10 μm; Mobile Phase A: Water (10 mmol/L NH$_4$HCO$_3$), Mobile Phase B: ACN; Flow rate: 25 mL/min; Gradient: 5% B to 30% B in 6 min; Wavelength: 254 nm; RT1(min): 5.78. This resulted in 4-amino-1-[(2R,3S,4R,5R)-5-(chloromethyl)-3-fluoro-4-hydroxy-5-(hydroxymethyl)oxolan-2-yl]-5-fluoropyrimidin-2-one (111.2 mg, 23.8%) as a white solid. LC-MS (ES, m/z): 312 (M+H$^+$). $^1$H NMR (400 MHz, DMSO-d$_6$) δ 7.94 (d, J=6.8 Hz, 1H), 7.89-7.87 (m, 1H), 7.65 (brs, 1H), 6.25-6.20 (m, 1H), 6.17 (d, J=5.2 Hz, 1H), 5.47 (t, J=5.2 Hz, 1H), 5.23 (t, J=4.0 Hz, 0.5H), 5.09 (t, J=4.0 Hz, 0.5H), 4.47-4.40 (m, 1H), 3.89-3.86 (m, 1H), 3.71-3.68 (m, 1H), 3.64-3.59 (m, 2H).

Example 6—Synthesis of Compound 6: 1-((2R,4S,5R)-5-(chloromethyl)-4-hydroxy-5-(hydroxymethyl)tetrahydrofuran-2-yl)-4-(hydroxyamino)pyrimidin-2(1H)-one

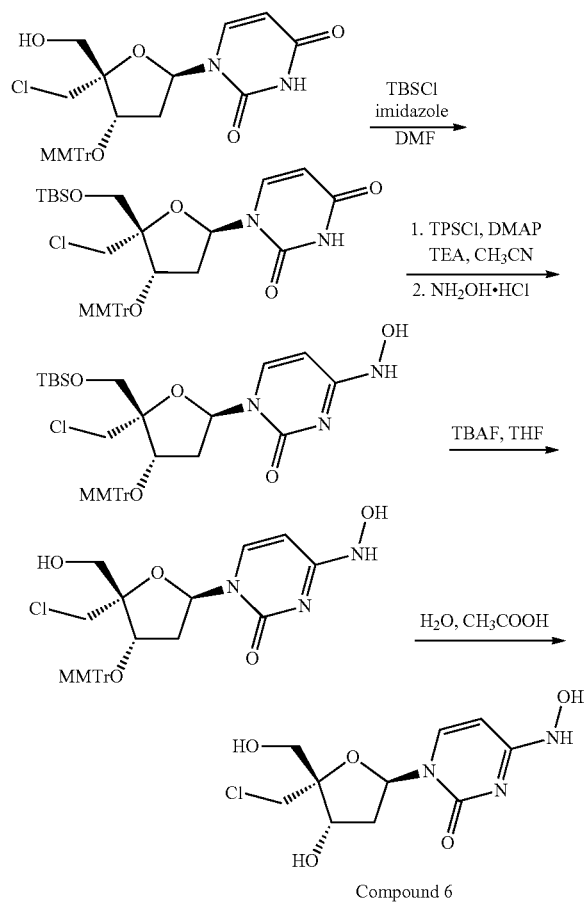

Compound 6

Step 1: To a stirred solution of 1-[(2R,4S,5R)-5-(chloromethyl)-5-(hydroxymethyl)-4-[(4-methoxyphenyl) diphenylmethoxy] oxolan-2-yl]-3H-pyrimidine-2,4-dione (500 mg, 0.9 mmol) in DMF (5.0 mL) was added t-butyldimethylchlorosilane (480 mg, 3.2 mmol) and imidazole (248 mg, 3.6 mmol) at room temperature. The resulting mixture was stirred for 2 h. Desired product could be detected by LCMS. The reaction was quenched by the addition of Water (10 mL) at room temperature and extracted with EtOAc (3×10 mL). The combined organic layers were dried over anhydrous Na$_2$SO$_4$. After filtration, the filtrate was concentrated under reduced pressure. The residue was purified by silica gel column chromatography, eluted with CH$_2$Cl$_2$/MeOH (10:1) to afford 1-[(2R,4S,5R)-5-{[(tert-butyldimethylsilyl) oxy]methyl}-5-(chloromethyl)-4-[(4-methoxyphenyl) diphenylmethoxy] oxolan-2-yl]-3H-pyrimidine-2,4-dione (400 mg, 0.60 mmol, 66%) as a yellow solid. LC-MS (ES, m/z): 663 (M+H$^+$).

Step 2: To a stirred solution of 1-[(2R,4S,5R)-5-{[(tert-butyldimethylsilyl) oxy]methyl}-5-(chloromethyl)-4-[(4-methoxyphenyl) diphenylmethoxy] oxolan-2-yl]-3H-pyrimidine-2,4-dione (380 mg, 0.6 mmol) in acetonitrile (5 mL) was added DMAP (139 mg, 1.1 mmol) and TEA (173 mg, 1.7 mmol), the reaction mixture was stirred for 10 mins at room temperature. 2,4,6-triisopropyl benzenesulfonyl chloride (347 mg, 1.1 mmol) was added. The mixture was stirred for 30 min at room temperature, and then DBU (261 mg, 1.7 mmol) and hydroxylamine hydrochloride (79 mg, 1.1 mmol) were added in portions. The mixture was stirred for 1 h at room temperature. LCMS showed the reaction was completed. The mixture was diluted with ethyl acetate (200 ml), washed with brine (2×100 ml), and dried over anhydrous sodium sulfate. The solids were filtered out and the filtration was concentrated. The residue was purified by Prep-TLC (methanol/dichloromehane=20/1) to afford 1-[(2R,4S,5R)-5-{[(tert-butyldimethylsilyl) oxy] methyl}-5-(chloromethyl)-4-[(4-methoxyphenyl) diphenylmethoxy] oxolan-2-yl]-4-(hydroxyamino) pyrimidin-2-one (350 mg, 0.51 mmol, 90%) as a yellow solid. LC-MS (ES, m/z): 678 (M+H$^+$).

Step 3: To a stirred solution of 1-[(2R,4S,5R)-5-{[(tert-butyldimethylsilyl) oxy]methyl}-5-(chloromethyl)-4-[(4-methoxyphenyl) diphenylmethoxy] oxolan-2-yl]-4-(hydroxyamino) pyrimidin-2-one (340 mg, 0.5 mmol) in tetrahydrofuran (5.0 mL) was added TBAF (1.0 mL, 1.00 mmol, 1M in THF) at room temperature. The resulting mixture was stirred for 2 h. Desired product could be detected by LCMS. The residue was purified by silica gel column chromatography, eluted with CH$_2$Cl$_2$/MeOH (10:1) to afford 1-[(2R,4S,5R)-5-(chloromethyl)-5-(hydroxymethyl)-4-[(4-methoxyphenyl) diphenylmethoxy] oxolan-2-yl]-4-(hydroxyamino) pyrimidin-2-one (80 mg, 0.14 mmol, 28%) as a yellow solid. LC-MS (ES, m/z): 564 (M+H$^+$).

Step 4: To a stirred solution of 1-[(2R,4S,5R)-5-(chloromethyl)-5-(hydroxymethyl)-4-[(4-methoxyphenyl) diphenylmethoxy] oxolan-2-yl]-4-(hydroxyamino) pyrimidin-2-one (70 mg, 0.1 mmol) was added acetic acid (4 mL) and H$_2$O (1 mL) at room temperature. The resulting mixture was stirred for 2 h. Desired product could be detected by LCMS. The resulting mixture was concentrated under vacuum and the residue was purified by reverse flash chromatography with the following conditions: Column: XBridge Prep OBD C18 Column, 30*150 mm, 5 μm; Mobile Phase A: Water (10 mmol/L NH$_4$HCO$_3$), Mobile Phase B: ACN; Flow rate: 60 mL/min; Gradient: 4% B to 25% B in 8 min, Wavelength: 254/220 nm; RT1(min): 6.05 to afford 1-[(2R,4S,5R)-5-(chloromethyl)-4-hydroxy-5-(hydroxymethyl) oxolan-2-yl]-4-(hydroxyamino) pyrimidin-2-one (10.3 mg, 0.035 mmol, 27%) as an off-white solid. LC-MS (ES, m/z): 292 (M+H$^+$); 98.5% purity. Conditions for the LCMS: (Column: Shimpack ScepterC18, 33*3.0 mm, 3.0 μm; Mobile Phase A: Water+5 mM $NH_4HCO_3$, Mobile Phase B: ACN; Flow rate: 1.5000 mL/min; Gradient: 5% B to 30% B in 1.1 min, 30% B to 95% B in 1.6 min, 95% B to 95% B in 1.9 min, 95% B to 10% B in 1.93 min; Wavelength: 254/220 nm; RT1 (min): 0.612). $^1$H NMR (300 MHz, DMSO-$d_6$) δ 9.98 (s, 1H), 7.00 (d, J=8.3 Hz, 1H), 6.24 (dd, J=8.6, 5.8 Hz, 1H), 5.59 (d, J=8.2 Hz, 1H), 5.44 (s, 1H), 5.17 (s, 1H), 4.37 (s, 1H), 3.75 (d, J=1.7 Hz, 2H), 3.63-3.43 (m, 2H), 2.38-2.15 (m, 1H), 2.13-1.97 (m, 1H).

Example 7—Synthesis of Compound 2: 4-amino-1-((2R,4S,5R)-5-(chloromethyl)-4-hydroxy-5-(hydroxymethyl)tetrahydrofuran-2-yl)pyrimidin-2(1H)-one

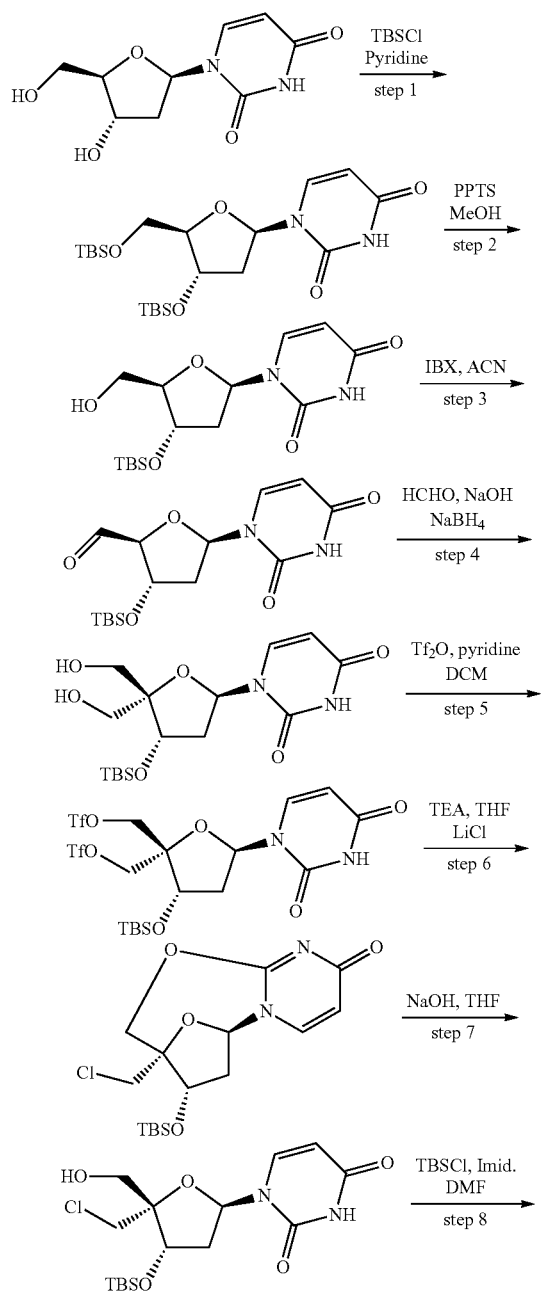

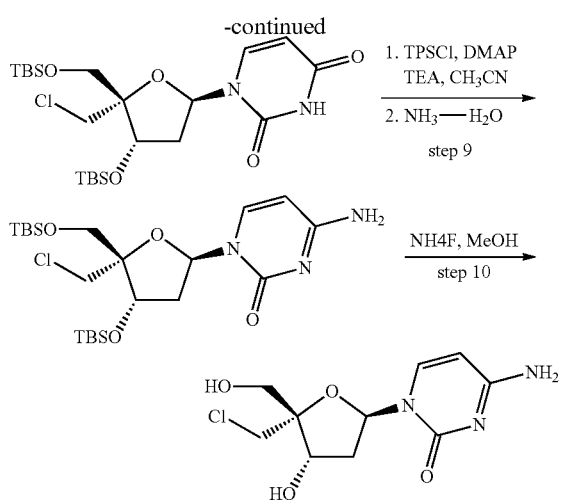

Step 1: A solution of 2'-deoxyuridine (40 g, 175.3 mmol, 1.0 equiv) and t-butyldimethylchlorosilane (106 g, 701.1 mmol, 4.0 equiv) in pyridine (800 mL) was stirred overnight at 60° C. under nitrogen atmosphere. The resulting mixture was diluted with water (500 mL). The resulting mixture was extracted with EtOAc (3×500 mL). The combined organic layers were washed with brine (3×250 mL), dried over anhydrous $Na_2SO_4$. After filtration, the filtrate was concentrated under reduced pressure. The residue was purified by silica gel column chromatography, eluted with PE/EA (2:1) to afford 1-[(2R,4S,5R)-4-[(tert-butyl-dimethylsilyl)oxy]-5-{[(tert-butyldimethylsilyl)oxy] methyl}oxolan-2-yl]-3H-pyrimidine-2,4-dione (73 g, 160 mmol, 91.1%) as a white solid. LC-MS (ES, m/z): 457 (M+H$^+$).

Step 2: A solution of 1-[(2R,4S,5R)-4-[(tert-butyldimethylsilyl)oxy]-5-{[(tert-butyldimethylsilyl)oxy] methyl}oxolan-2-yl]-3H-pyrimidine-2,4-dione (73 g, 159.8 mmol, 1 equiv) and PPTS (161 g, 639.3 mmol, 4 equiv) in MeOH (1.4 L) was stirred for 2 days at room temperature under air atmosphere. The resulting mixture was diluted with water (500 mL). The resulting mixture was extracted with EtOAc (3×500 mL). The combined organic layers were washed with brine (3×250 mL), dried over anhydrous $Na_2SO_4$. After filtration, the filtrate was concentrated under reduced pressure. The residue was purified by silica gel column chromatography, eluted with PE/EA (1:10) to afford 1-[(2R,4S,5R)-4-[(tert-butyl-dimethylsilyl)oxy]-5-(hydroxymethyl)oxolan-2-yl]-3H-pyrimidine-2,4-dione (28.7 g, 83.9 mmol, 52.4%) as a white solid. LC-MS (ES, m/z): 343 (M+H$^+$).

Step 3: A solution of 1-[(2R,4S,5R)-4-[(tert-butyldimethylsilyl)oxy]-5-(hydroxymethyl) oxolan-2-yl]-3H-pyrimidine-2,4-dione (28.7 g, 83.8 mmol, 1 equiv) and IBX (58.7 g, 209.5 mmol, 2.5 equiv) in acetonitrile (560 mL) was stirred for 2 h at 60° C. under air atmosphere. The resulting mixture was concentrated under reduced pressure. The residue was purified by silica gel column chromatography, eluted with $CH_2Cl_2$/MeOH (10:1) to afford (2S,3S,5R)-3-[(tert-butyldimethylsilyl) oxy]-5-(2,4-dioxo-3H-pyrimidin-1-yl)oxolane-2-carbaldehyde (27 g, 79.4 mmol, 94.6%) as a white solid. LC-MS (ES, m/z): 341 (M+H$^+$).

Step 4: A solution of (2S,3S,5R)-3-[(tert-butyldimethylsilyl)oxy]-5-(2,4-dioxo-3H-pyrimidin-1-yl)oxolane-2-carbaldehyde (27 g, 79.3 mmol, 1 equiv) and HCHO (23.8 g, 793.1 mmol, 10 equiv) in 1,4-dioxane (540 mL) was treated with sodium hydroxide (6.3 g, 158.6 mmol, 2 equiv) overnight at room temperature under nitrogen atmosphere followed by the addition of NaBH$_4$ (12 g, 317 mmol, 4 equiv) in portions at room temperature. The resulting mixture was stirred for 1 h at room temperature under air atmosphere. The resulting mixture was diluted with water (500 mL). The resulting mixture was extracted with EtOAc (3×500 mL). The combined organic layers were washed with brine (3×250 mL), dried over anhydrous Na$_2$SO$_4$. After filtration, the filtrate was concentrated under reduced pressure. The residue was purified by silica gel column chromatography, eluted with CH$_2$Cl$_2$/MeOH (10:1) to afford 1-[(2R,4S)-4-[(tert-butyldimethylsilyl)oxy]-5,5-bis(hydroxymethyl) oxolan-2-yl]-3H-pyrimidine-2,4-dione (14.8 g, 39.6 mmol, 50.1%) as a white solid. LC-MS (ES, m/z): 373 (M+H$^+$).

Step 5: To a stirred mixture of 1-[(2R,4S)-4-[(tert-butyldimethylsilyl)oxy]-5,5-bis(hydroxymethyl)oxolan-2-yl]-3H-pyrimidine-2,4-dione (12.5 g, 33.6 mmol, 1 equiv) in CH$_2$Cl$_2$ (150 mL) and pyridine (21.2 g, 268.5 mmol, 8 equiv) was added triflic anhydride (23.7 g, 83.9 mmol, 2.5 equiv) dropwise at −35° C. under nitrogen atmosphere. The mixture was stirred for 10 min at −35° C. Then return to room temperature and stirred for 1 h. The reaction was quenched with water at room temperature. The resulting mixture was extracted with dichloromethane. The combined organic layers were washed with sodium bicarbonate, dried over anhydrous sodium sulfate. After filtration, the filtrate was concentrated under reduced pressure. The residue was purified by silica gel column chromatography, eluted with PE/EA (30% EA) to afford [(3S,5R)-3-[(tert-butyldimethylsilyl) oxy]-5-(2,4-dioxo-3H-pyrimidin-1-yl)-2-[(trifluoromethanesulfonyloxy)methyl]oxolan-2-yl]methyl trifluoromethanesulfonate (12.8 g, 20.1 mmol, 59.9%) as a little yellow solid. LC-MS (ES, m/z): 637 (M+H$^+$).

Step 6: To a stirred solution of [(3S,5R)-3-[(tert-butyldimethylsilyl) oxy]-5-(2,4-dioxo-3H-pyrimidin-1-yl)-2-[(trifluoromethanesulfonyloxy)methyl]oxolan-2-yl]methyl trifluoromethane-sulfonate (12.8 g, 20.1 mmol, 1 equiv) in THF (150 mL) was added TEA (20 g, 201.1 mmol, 10 equiv) dropwise at room temperature under nitrogen atmosphere. The mixture was stirred for 16 h at 60° C. Then lithium chloride (4.3 g, 100.5 mmol, 5 equiv) was added, and the mixture was stirred at 60° C. for 2 h. The crude product was used in the next step directly without further purification. LC-MS (ES, m/z): 373 (M+H$^+$).

Step 7: To the above solution was added sodium hydroxide (2 g, 50 mmol, 2.5 equiv) in water (15 mL) dropwise at 0° C. under nitrogen atmosphere. The mixture was stirred for 2 h at room temperature. LCMS showed the reaction was completed. The resulting mixture was concentrated under vacuum. The resulting mixture was extracted with dichloromethane. The combined organic layers were washed with saturated aqueous solution of NH$_4$Cl, dried over anhydrous Na$_2$SO$_4$. After filtration, the filtrate was concentrated under reduced pressure. The residue was purified by silica gel column chromatography, eluted with CH$_2$Cl$_2$/MeOH to afford 1-[(2R,4S,5R)-4-[(tert-butyldimethylsilyl) oxy]-5-(chloromethyl)-5-(hydroxymethyl) oxolan-2-yl]-3H-pyrimidine-2,4-dione (3.7 g, 9.4 mmol) as an off-white solid. LC-MS (ES, m/z): 391 (M+H$^+$).

Step 8: To a stirred mixture of 1-[(2R,4S,5R)-4-[(tert-butyldimethylsilyl) oxy]-5-(chloromethyl)-5-(hydroxymethyl) oxolan-2-yl]-3H-pyrimidine-2,4-dione (3.7 g, 9.5 mmol, 1 equiv) in dimethylformamide (40 mL) and imidazole (3.2 g, 47.3 mmol, 5 equiv) was added t-butyldimethylchlorosilane (4.3 g, 28.4 mmol, 3 equiv) in portions at room temperature under nitrogen atmosphere. The mixture was stirred for 16 h at 60° C. The resulting mixture was extracted with EtOAc. The combined organic layers were washed with brine, dried over anhydrous sodium sulfate. After filtration, the filtrate was concentrated under reduced pressure. The residue was purified by silica gel column chromatography, eluted with PE/EA (40% EA) to afford 1-[(2R,4S,5R)-4-[(tert-butyldimethylsilyl) oxy]-5-{[(tert-butyldimethylsilyl) oxy] methyl}-5-(chloromethyl) oxolan-2-yl]-3H-pyrimidine-2,4-dione (3.2 g, 6.3 mmol, 66.9%) as an off-white solid. LC-MS (ES, m/z): 505 (M+H$^+$).

Step 9: To a stirred solution of 1-[(2R,4S,5R)-4-[(tert-butyldimethylsilyl) oxy]-5-{[(tert-butyldimethylsilyl) oxy] methyl}-5-(chloromethyl) oxolan-2-yl]-3H-pyrimidine-2,4-dione (3.2 g, 6.3 mmol, 1 equiv) in CH$_3$CN (30 mL) was added DMAP (1.5 g, 12.668 mmol, 2 equiv) and TEA (1.3 g, 12.668 mmol, 2 equiv), and the mixture was stirred for 10 min at room temperature under nitrogen atmosphere. To the above mixture was added 2,4,6-tris(propan-2-yl) benzene-1-sulfonyl chloride (3.84 g, 12.668 mmol, 2 equiv) at room temperature under nitrogen atmosphere. The mixture was stirred for 16 h at room temperature. Then NH$_3$·H$_2$O (0.44 g, 12.7 mmol, 2 equiv) was added and stirred at room temperature for 1 h. The resulting mixture was concentrated under vacuum. The residue was purified by silica gel column chromatography, eluted with PE/EA (50% EA) to afford 4-amino-1-[(2R,4S,5R)-4-[(tert-butyldimethylsilyl) oxy]-5-{[(tert-butyldimethylsilyl) oxy] methyl}-5-(chloromethyl) oxolan-2-yl] pyrimidin-2-one (2.6 g, 5.1 mmol, 79.8%) as an off-white solid. LC-MS (ES, m/z): 504 (M+H$^+$).

Step 10: To a stirred solution of 4-amino-1-[(2R,4S,5R)-4-[(tert-butyldimethylsilyl) oxy]-5-{[(tert-butyldimethylsilyl) oxy] methyl}-5-(chloromethyl) oxolan-2-yl] pyrimidin-2-one (2.6 g, 5.1 mmol, 1 equiv) in MeOH (50 mL) was added NH$_4$F (4.7 g, 126.4 mmol, 25 equiv) in portions at room temperature under nitrogen atmosphere. The mixture was stirred for 16 h at 60° C. The resulting mixture was filtered, and the filter cake was washed with EA. The filtrate was concentrated under reduced pressure. The residue was purified by silica gel column chromatography, eluted with CH$_2$Cl$_2$/MeOH (16% MeOH) to afford (1.2 g) crude product. The crude product (1.2 g) was purified by Prep-HPLC with the following conditions: Mobile Phase A: Water (0.01 M NH$_4$HCO$_3$), Mobile Phase B: ACN; Gradient: 100% A in 5 min; then up to 20% B in 20 min to afford 4-amino-1-[(2R,4S,5R)-5-(chloromethyl)-4-hydroxy-5-(hydroxymethyl) oxolan-2-yl] pyrimidin-2-one (831.5 mg, 3.0 mmol, 59.1%) as a white solid. LC-MS (ES, m/z): 276 (M+H$^+$); 99.1% purity. LCMS analytical conditions: Column: HALO AQ-C18 Column, 30*3.0 mm, 2 μm; Mobile Phase A: Water with 0.05% TFA, Mobile Phase B: Acetonitrile/0.05% TFA; Flow rate: 1.20 mL/min; Gradient: 0% B to 95% B in 1.3 min, 95% B to 95% B in 1.8 min, 95% B to 5% B in 1.83 min; Wavelength: 254/220 nm. $^1$H NMR (400 MHz, DMSO-d$_6$) δ 7.73 (dd, J=7.4, 1.1 Hz, 1H), 7.18 (s, 1H), 7.12 (s, 1H), 6.25 (dd, J=7.8, 6.0 Hz, 1H), 5.73 (dd, J=7.4, 1.6 Hz, 1H), 5.43 (d, J=4.4 Hz, 1H), 5.19 (d, J=4.7 Hz, 1H), 4.36 (q, J=4.2, 3.1 Hz, 1H), 3.82-3.70 (m, 2H), 3.63-3.48 (m, 2H), 2.25-2.09 (m, 2H).

Example 8—Synthesis of Compound 9: 1-((2R,3R, 4R,5R)-5-(chloromethyl)-3-fluoro-4-hydroxy-5-(hydroxymethyl)tetrahydrofuran-2-yl)-5-methylpyrimidine-2,4(1H,3H)-dione

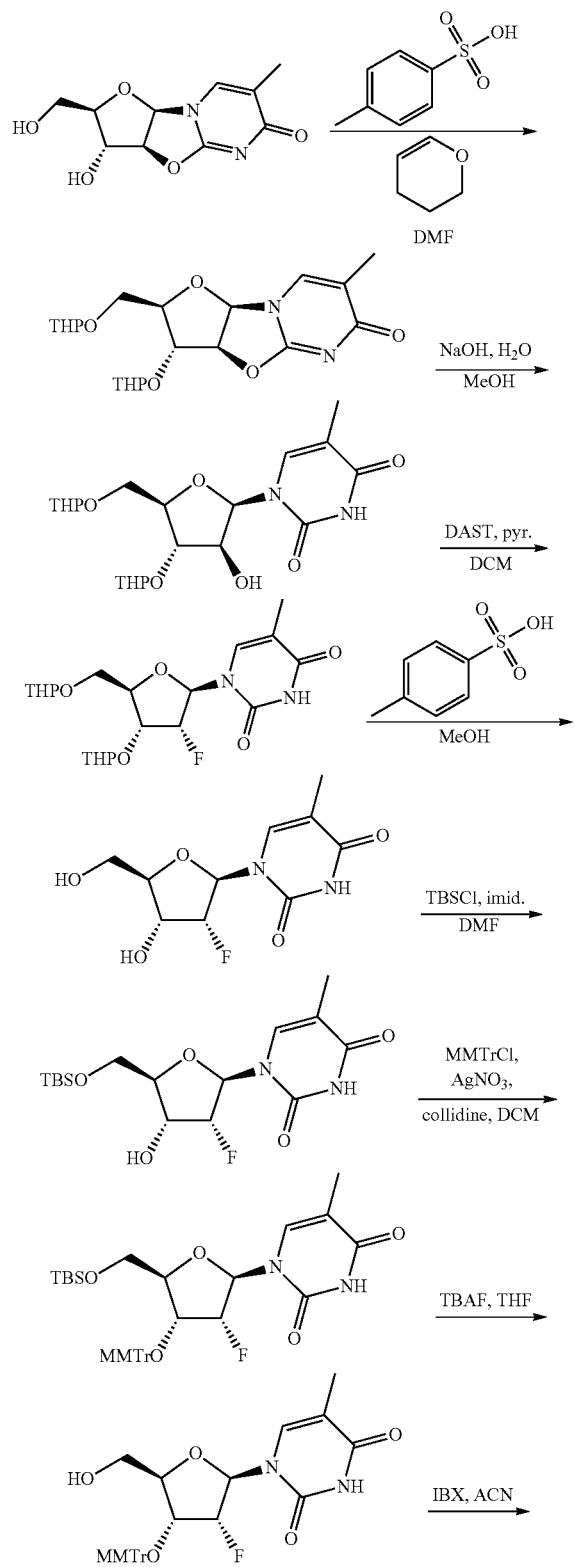

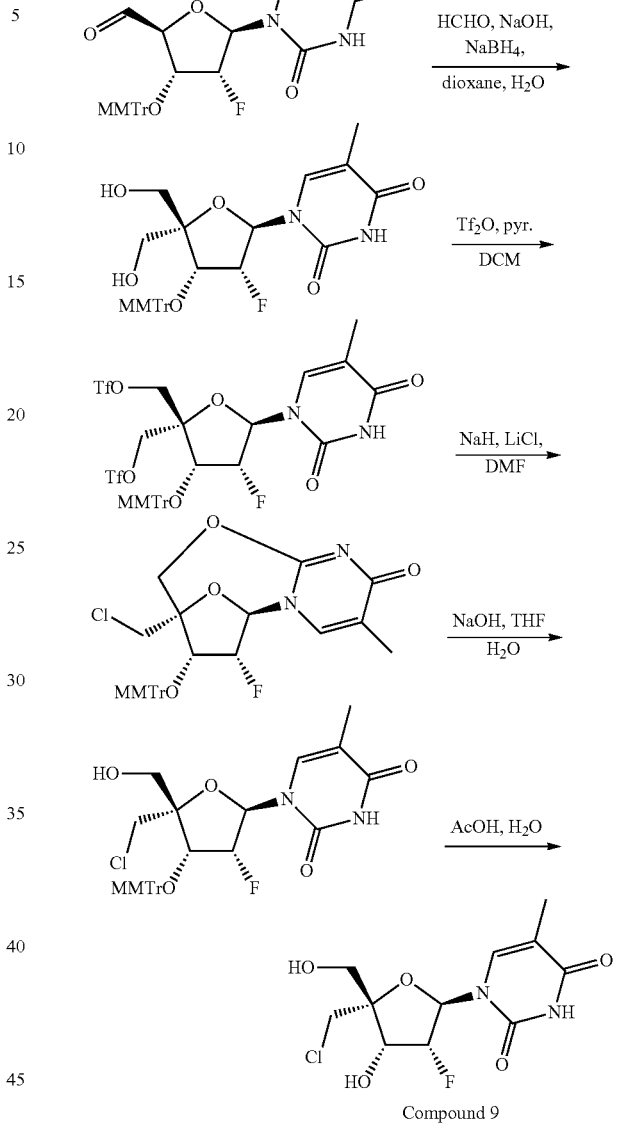

Compound 9

Step 1: To a stirred solution of (2R,4R,5R,6S)-5-hydroxy-4-(hydroxymethyl)-11-methyl-3,7-dioxa-1,9-diazatricyclo [6.4.0.0^{2,6}] dodeca-8,11-dien-10-one (10 g, 41.6 mmol) and dihydropyran (105 mL) in dimethyl formamide (200 ml) was added para-toluene sulfonate (7.8 g, 45.7 mmol) in portions at 0° C. under air atmosphere. The resulting mixture was stirred for overnight at room temperature under air atmosphere. The resulting mixture was diluted with water (500 mL). The resulting mixture was extracted with ethyl acetate (3×500 mL). The combined organic layers were washed with brine (3×250 mL), dried over anhydrous sodium sulfate. After filtration, the filtrate was concentrated under reduced pressure. The precipitated solids were collected by filtration and washed with hexane (3×200 mL). This resulted in (2R,4R,5R,6S)-11-methyl-5-(oxan-2-yloxy)-4-[(oxan-2-yloxy) methyl]-3,7-dioxa-1,9-diazatricyclo [6.4.0.0^{2,6}] dodeca-8,11-dien-10-one (15 g, 36.7 mmol, 88.22%) as a white solid. LC-MS (ES, m/z): 409 (M+H$^+$).

Step 2: A solution of (2R,4R,5R,6S)-11-methyl-5-(oxan-2-yloxy)-4-[(oxan-2-yloxy) methyl]-3,7-dioxa-1,9-diazatricyclo [6.4.0.0^{2,6}] dodeca-8,11-dien-10-one (15 g, 36.7 mmol) and caustic soda (4.4 g, 110.1 mmol) in methyl alcohol (300 ml) and water (110 ml) was stirred for overnight at room temperature under air atmosphere. The resulting mixture was concentrated under reduced pressure. The precipitated solids were collected by filtration and washed with ethyl acetate (3×200 mL). This resulted in 1-[(2R,3S,4S,5R)-3-hydroxy-4-(oxan-2-yloxy)-5-[(oxan-2-yloxy) methyl] oxolan-2-yl]-5-methyl-3H-pyrimidine-2,4-dione (15.5 g, 36.3 mmol, 98.97%) as a white solid. LC-MS (ES, m/z): 427 (M+H$^+$).

Step 3: To a stirred solution of 1-[(2R,3S,4S,5R)-3-hydroxy-4-(oxan-2-yloxy)-5-[(oxan-2-yloxy) methyl] oxolan-2-yl]-5-methyl-3H-pyrimidine-2,4-dione (15.5 g, 36.3 mmol) and pyridine (37 mL) in dichloromethane (300 ml) was added diethyl(trifluoro-lambda4-sulfanyl) amine (19.3 g, 119.9 mmol) dropwise at −60° C. under nitrogen atmosphere. The resulting mixture was stirred for overnight at 40° C. under nitrogen atmosphere. The resulting mixture was diluted with water (500 mL). The resulting mixture was extracted with ethyl acetate (3×500 mL). The combined organic layers were washed with brine (3×250 mL), dried over anhydrous sodium sulfate. After filtration, the filtrate was concentrated under reduced pressure. The crude product was used in the next step directly without further purification. LC-MS (ES, m/z): 429 (M+H$^+$).

Step 4: A solution of 1-[(2R,3R,4R,5R)-3-fluoro-4-(oxan-2-yloxy)-5-[(oxan-2-yloxy) methyl] oxolan-2-yl]-5-methyl-3H-pyrimidine-2,4-dione (15.5 g, 36.1 mmol) and para-toluene sulfonate (4.6 g, 27.1 mmol) in methyl alcohol (300 ml) was stirred for 2 h at room temperature under air atmosphere. The resulting mixture was diluted with water (500 mL). The resulting mixture was extracted with ethyl acetate (3×500 mL). The combined organic layers were washed with brine (3×250 mL), dried over anhydrous sodium sulfate. After filtration, the filtrate was concentrated under reduced pressure. The residue was purified by silica gel column chromatography, eluted with dichloromethane/methyl alcohol (10/1) to afford 1-[(2R,3R,4R,5R)-3-fluoro-4-hydroxy-5-(hydroxymethyl) oxolan-2-yl]-5-methyl-3H-pyrimidine-2,4-dione (9 g, 34.5 mmol, 95.60%) as a white solid. LC-MS (ES, m/z): 261 (M+H$^+$).

Step 5: To a stirred solution of 1-[(2R,3R,4R,5R)-3-fluoro-4-hydroxy-5-(hydroxymethyl) oxolan-2-yl]-5-methyl-3H-pyrimidine-2,4-dione (9 g, 34.5 mmol) and imidazole (14.1 g, 207.5 mmol) in dimethyl formamide (200 ml) was added t-butyldimethylchlorosilane (10.4 g, 69.1 mmol) in portions at room temperature under air atmosphere. The resulting mixture was stirred for 2 h at 80° C. under air atmosphere. The resulting mixture was diluted with water (500 mL). The resulting mixture was extracted with ethyl acetate (3×500 mL). The combined organic layers were washed with brine (3×250 mL), dried over anhydrous sodium sulfate. After filtration, the filtrate was concentrated under reduced pressure. The residue was purified by silica gel column chromatography, eluted with dichloromethane/methyl alcohol (10/1) to afford 1-[(2R,3R,4R,5R)-5-{[(tert-butyldimethylsilyl) oxy] methyl}-3-fluoro-4-hydroxyoxolan-2-yl]-5-methyl-3H-pyrimidine-2,4-dione (5.4 g, 14.4 mmol, 41.69%) as a white solid. LC-MS (ES, m/z): 375 (M+H$^+$).

Step 6: To a stirred solution of 1-[(2R,3R,4R,5R)-5-{[(tert-butyldimethylsilyl) oxy]methyl}-3-fluoro-4-hydroxyoxolan-2-yl]-5-methyl-3H-pyrimidine-2,4-dione (5.4 g, 14.4 mmol) and 2,4,6-collidine (10.4 g, 86.5 mmol) and argentio nitrate (9.8 g, 57.6 mmol) in dichloromethane (100 ml) was added 1-(chlorodiphenylmethyl)-4-methoxybenzene (8.9 g, 28.8 mmol) in portions at room temperature under air atmosphere. The resulting mixture was stirred for 2 h at room temperature under air atmosphere. The resulting mixture was diluted with water (500 mL). The resulting mixture was extracted with ethyl acetate (3×500 mL). The combined organic layers were washed with brine (3×250 mL), dried over anhydrous sodium sulfate. After filtration, the filtrate was concentrated under reduced pressure. The residue was purified by silica gel column chromatography, eluted with petroleum ether/ethyl acetate (2/1) to afford 1-[(2R,3R,4R,5R)-5-{[(tert-butyldimethylsilyl) oxy] methyl}-3-fluoro-4-[(4-methoxyphenyl) diphenylmethoxy] oxolan-2-yl]-5-methyl-3H-pyrimidine-2,4-dione (8.3 g, 12.8 mmol, 88.99%) as a white solid. LC-MS (ES, m/z): 647 (M+H$^+$).

Step 7: A solution of 1-[(2R,3R,4R,5R)-5-{[(tert-butyldimethylsilyl) oxy] methyl}-3-fluoro-4-[(4-methoxyphenyl) diphenylmethoxy] oxolan-2-yl]-5-methyl-3H-pyrimidine-2,4-dione (8.3 g, 12.8 mmol) and tetra-n-butylammonium fluoride (15.3 mL, 15.3 mmol, 1M in tetrahydrofuran) in tetrahydrofuran (160 ml) was stirred for overnight at room temperature under air atmosphere. The resulting mixture was concentrated under reduced pressure. The residue was purified by silica gel column chromatography, eluted with dichloromethane/methyl alcohol (10/1) to afford 1-[(2R,3R,4R,5R)-3-fluoro-5-(hydroxymethyl)-4-[(4-methoxyphenyl) diphenylmethoxy] oxolan-2-yl]-5-methyl-3H-pyrimidine-2,4-dione (6.2 g, 11.6 mmol, 90.73%) as a white solid. LC-MS (ES, m/z): 533 (M+H$^+$).

Step 8: A solution of 1-[(2R,3R,4R,5R)-3-fluoro-5-(hydroxymethyl)-4-[(4-methoxyphenyl) diphenylmethoxy] oxolan-2-yl]-5-methyl-3H-pyrimidine-2,4-dione (6.2 g, 11.6 mmol) and IBX (6.5 g, 23.2 mmol) in acetonitrile (120 ml) was stirred for 2 h at 60° C. under air atmosphere. The resulting mixture was concentrated under reduced pressure. The residue was purified by silica gel column chromatography, eluted with dichloromethane/methyl alcohol (10/1) to afford (2S,3R,4R,5R)-4-fluoro-3-[(4-methoxyphenyl) diphenylmethoxy]-5-(5-methyl-2,4-dioxo-3H-pyrimidin-1-yl) oxolane-2-carbaldehyde (6 g, 11.3 mmol, 97.14%) as a white solid. LC-MS (ES, m/z): 531 (M+H$^+$).

Step 9: A solution of (2S,3R,4R,5R)-4-fluoro-3-[(4-methoxyphenyl) diphenyl-methoxy]-5-(5-methyl-2,4-dioxo-3H-pyrimidin-1-yl) oxolane-2-carbaldehyde (6 g, 11.3 mmol) and HCHO (1.0 g, 33.9 mmol) in 1,4-dioxane (60 ml) added caustic soda (1.3 g, 33.9 mmol) in water (12 ml). The mixture was stirred for overnight at room temperature under nitrogen atmosphere followed by the addition of NaBH$_4$ (1.7 g, 45.2 mmol) in portions at room temperature. The resulting mixture was stirred for 1 h at room temperature under air atmosphere. The resulting mixture was diluted with water (200 mL). The resulting mixture was extracted with ethyl acetate (3×200 mL). The combined organic layers were washed with brine (3×100 mL), dried over anhydrous sodium sulfate. After filtration, the filtrate was concentrated under reduced pressure. The residue was purified by silica gel column chromatography, eluted with dichloromethane/methyl alcohol (10/1) to afford 1-[(2R,3R,4R)-3-fluoro-5,5-bis(hydroxymethyl)-4-[(4-methoxyphenyl) diphenylmethoxy] oxolan-2-yl]-5-methyl-3H-pyrimidine-2,4-dione (3.2 g, 5.68 mmol, 50.30%) as a white solid. LC-MS (ES, m/z): 563 (M+H$^+$).

Step 10: To a stirred solution of 1-[(2R,3R,4R)-3-fluoro-5,5-bis(hydroxymethyl)-4-[(4-methoxyphenyl) diphenylmethoxy] oxolan-2-yl]-5-methyl-3H-pyrimidine-2,4-dione (500 mg, 0.8 mmol) and pyridine (351 mg, 4.4 mmol) in dichloromethane (10 ml) was added triflic anhydride (752 mg, 2.6 mmol) dropwise at room temperature under air atmosphere. The resulting mixture was stirred for overnight at room temperature under air atmosphere. The resulting mixture was concentrated under reduced pressure. The residue was purified by Prep-TLC with dichloromethane/methyl alcohol (10/1) to afford [(3R,4R,5R)-4-fluoro-3-[(4-methoxyphenyl) diphenylmethoxy]-5-(5-methyl-2,4-dioxo-3H-pyrimidin-1-yl)-2-[(trifluoromethanesulfonyloxy) methyl] oxolan-2-yl] methyl trifluoromethanesulfonate (620 mg, 0.67 mmol, 84.38%) as a white solid. LC-MS (ES, m/z): 827 (M+H+).

Step 11: To a stirred solution of [(3R,4R,5R)-4-fluoro-3-[(4-methoxyphenyl) diphenylmethoxy]-5-(5-methyl-2,4-dioxo-3H-pyrimidin-1-yl)-2-[(trifluoromethanesulfonyloxy) methyl] oxolan-2-yl] methyl trifluoromethanesulfonate (800 mg, 0.9 mmol) and lithium chloride (123 mg, 2.9 mmol) in dimethyl formamide (16 ml) was added sodium hydride (23 mg, 0.9 mmol) in portions at room temperature under nitrogen atmosphere. The resulting mixture was stirred for 3 h at room temperature under nitrogen atmosphere. The resulting mixture was diluted with water (200 mL). The resulting mixture was extracted with ethyl acetate (3×200 mL). The combined organic layers were washed with brine (3×100 mL), dried over anhydrous sodium sulfate. After filtration, the filtrate was concentrated under reduced pressure. The residue was purified by Prep-TLC with dichloromethane/methyl alcohol (10/1) to afford (1R,10R,11R,12R)-10-(chloromethyl)-12-fluoro-11-[(4-methoxyphenyl) diphenylmethoxy]-4-methyl-8,13-dioxa-2,6-diazatricyclo [8.2.1.0{2,7}] trideca-3,6-dien-5-one (450 mg, 0.71 mmol, 82.59%) as a white solid. LC-MS (ES, m/z): 563 (M+H+).

Step 12: A solution of (1R,10R,11R,12R)-10-(chloromethyl)-12-fluoro-11-[(4-methoxyphenyl) diphenylmethoxy]-4-methyl-8,13-dioxa-2,6-diazatricyclo [8.2.1.0^{2,7}]trideca-3,6-dien-5-one (430 mg, 0.7 mmol) and caustic soda (61 mg, 1.5 mmol) in tetrahydrofuran (10 ml) and water (1 ml) was stirred for overnight at room temperature under air atmosphere. The resulting mixture was concentrated under reduced pressure. The residue was purified by Prep-TLC with dichloromethane/methyl alcohol (10:1) to afford 1-[(2R,3R,4R,5R)-5-(chloromethyl)-3-fluoro-5-(hydroxymethyl)-4-[(4-methoxyphenyl) diphenylmethoxy] oxolan-2-yl]-5-methyl-3H-pyrimidine-2,4-dione (350 mg, 0.51 mmol, 78.87%) as a white solid. LC-MS (ES, m/z): 581 (M+H+).

Step 13: A solution of 1-[(2R,3R,4R,5R)-5-(chloromethyl)-3-fluoro-5-(hydroxymethyl)-4-[(4-methoxyphenyl) diphenylmethoxy] oxolan-2-yl]-5-methyl-3H-pyrimidine-2,4-dione (330 mg, 0.5 mmol) and acetic acid (4 mL) in water (1 ml) was stirred for overnight at 60° C. under air atmosphere. The resulting mixture was concentrated under vacuum. The crude product was purified by Prep-HPLC with the following conditions (Column: XBridge Prep OBD C18 Column, 30*150 mm, 5 μm; Mobile Phase A: Water (10 mmol/L NH4HCO3), Mobile Phase B: ACN; Flow rate: 60 mL/min; Gradient: 8% B to 30% B in 8 min, 30% B; Wavelength: 254/220 nm; RT1(min): 6.26) to afford 1-[(2R,3R,4R,5R)-5-(chloromethyl)-3-fluoro-4-hydroxy-5-(hydroxymethyl) oxolan-2-yl]-5-methyl-3H-pyrimidine-2,4-dione (85.9 mg, 48.95%) as a white solid. LC-MS (ES, m/z): 309 (M+H+). 99.9% purity. Conditions for the LCMS: (Column: Ascentis Express C18 Column, 50*3.0 mm, 2.7 μm; Mobile Phase A: Water/0.05% TFA, Mobile Phase B: ACN/0.05% TFA; Flow rate: 1.5000 mL/min; Gradient: 5% B to 100% B in 1.10 min, 100% B to 100% B in 1.75 min, 100% B to 5% B in 1.80 min; Wavelength: 254/220 nm; RT1(min): 0.672). 1H NMR (400 MHz, DMSO-d6) δ 10.90 (s, 1H), 7.71 (d, J=1.4 Hz, 1H), 6.12 (dd, J=13.9, 5.3 Hz, 1H), 5.98 (d, J=5.4 Hz, 1H), 5.47 (t, J=5.1 Hz, 1H), 5.25 (dt, J=53.0, 5.2 Hz, 1H), 4.42 (dt, J=10.1, 4.9 Hz, 1H), 3.77 (s, 2H), 3.69 (dd, J=11.6, 3.9 Hz, 1H), 3.61 (dd, J=11.7, 3.7 Hz, 1H), 1.78 (d, J=1.2 Hz, 3H).

Example 9: Synthesis of Compound 10: ((3S,5R)-5-(6-amino-2-fluoro-9H-purin-9-yl)-3-hydroxytetrahydrofuran-2,2-diyl) dimethanol

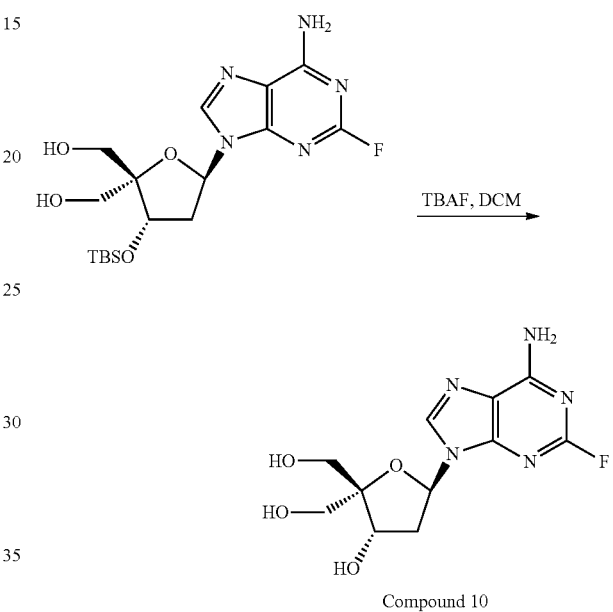

Compound 10

Step 1: To a stirred solution of [(3S,5R)-5-(6-amino-2-fluoropurin-9-yl)-3-[(tert-butyldimethylsilyl) oxy]-2-(hydroxymethyl) oxolan-2-yl] methanol (110 mg, 0.266 mmol) and TBAF (139.10 mg, 0.532 mmol) in DCM (3 mL) at room temperature under nitrogen atmosphere. The resulting mixture was stirred for additional 5 h at room temperature. Desired product could be detected by LCMS. The aqueous layer was extracted with EtOAc (3×30 mL). The organic extracts were concentrated under vacuum. The residue was purified by Prep-HPLC with the following conditions: Column: XBridge Prep OBD C18 Column, 30*150 mm, 5 μm; Mobile Phase A: Water (10 mmol/L NH4HCO3), Mobile Phase B: ACN; Flow rate: 60 mL/min; Gradient: 4% B to 15% B in 8 min, 15% B; Wavelength: 254/220 nm; RT1 (min): 6.1 to afford (3S,5R)-5-(6-amino-2-fluoropurin-9-yl)-2,2-bis(hydroxymethyl)oxolan-3-ol (11.4 mg, 0.04 mmol, 14.32%) as a white solid. LC-MS (ES, m/z): 300 (M+H+); 97.6% purity. Conditions for the LCMS: (Column: Shimpack Scepter C18, 50*3.0 mm, 3.0 μm; Mobile Phase A: Water/0.04% NH3·H2O, Mobile Phase B: Acetonitrile; Flow rate: 1.5000 mL/min; Gradient: 0% B to 95% B in 1.70 min, 100% B to 100% B in 0.60 min, 95% B to 10% B in 0.20 min; Wavelength: 254/220 nm; RT1(min): 1.009). 1H NMR (300 MHz, DMSO-d6) δ 8.32 (s, 1H), 7.83 (s, 2H), 6.26 (t, J=6.7 Hz, 1H), 5.19 (d, J=4.8 Hz, 1H), 4.90 (t, J=5.7 Hz, 1H), 4.47 (dt, J=16.5, 5.3 Hz, 2H), 3.65-3.48 (m, 4H), 2.75 (dt, J=13.3, 6.6 Hz, 1H), 2.36 (ddd, J=13.1, 6.4, 3.8 Hz, 1H).

201

Example 10: Synthesis of Compound 11: 4-amino-1-((2R,4S,5R)-5-(chloromethyl)-4-hydroxy-5-(hydroxymethyl)tetrahydrofuran-2-yl)-5-methylpyrimidin-2(1H)-one

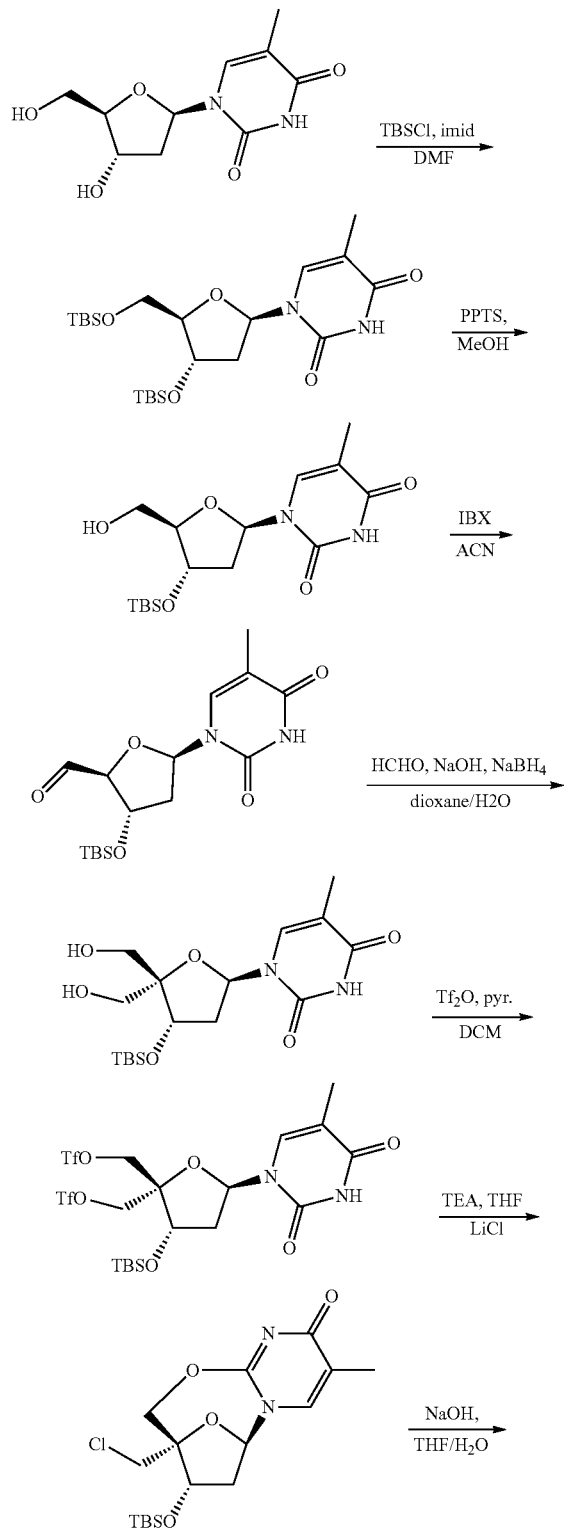

202

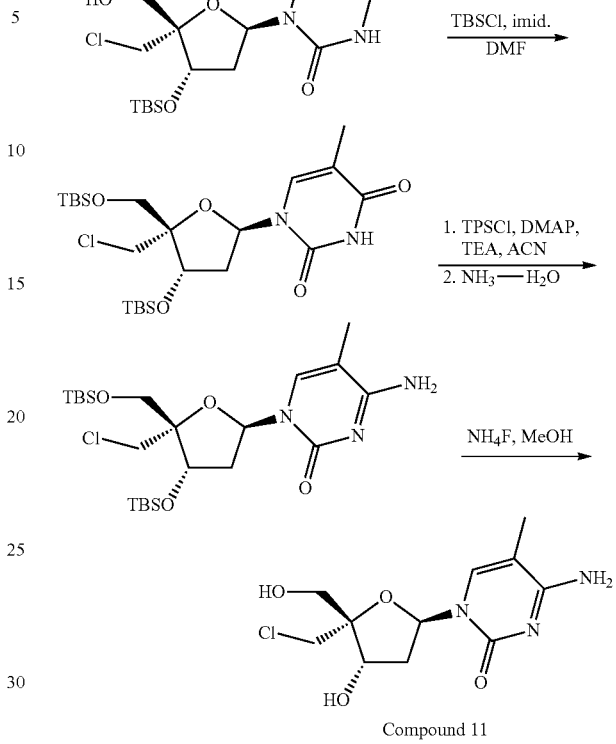

Compound 11

Step 1: To a stirred solution of thymidine (25 g, 103 mmol) and imidazole (35 g, 514 mmol) in DMF (300 mL) were added TBSCl (62 g, 411 mmol) in portions at room temperature. The resulting mixture was stirred for 2 h at room temperature, and then was diluted with EA (500 mL). The mixture was washed with water (5×500 mL), the organic layer was dried over anhydrous sodium sulfate, filtered and concentrated under vacuum. The residue was purified via silica gel chromatography (eluting with 30% EA in PE) to give 1-[(2R,4S,5R)-4-[(tert-butyldimethylsilyl) oxy]-5-{[(tert-butyldimethylsilyl) oxy] methyl} oxolan-2-yl]-5-methyl-3H-pyrimidine-2,4-dione (44.5 g, 94.5 mmol, 87.01%) as a white solid. LC-MS (ES, m/z): 471 (M+H$^+$).

Step 2: A solution of 1-[(2R,4S,5R)-4-[(tert-butyldimethylsilyl) oxy]-5-{[(tert-butyldimethylsilyl) oxy] methyl} oxolan-2-yl]-5-methyl-3H-pyrimidine-2,4-dione (44.5 g, 94.5 mmol) and PPTS (24 g, 95.5 mmol) in MeOH (500 mL) was stirred at 50° C. for 4 h. The resulting mixture was concentrated under vacuum. The residue was diluted with EA (500 mL), washed with water (3×500 mL) and sat. aq. NaHCO$_3$ until there is not any gas formed. The organic layer was dried over anhydrous sodium sulfate, filtered and concentrated under vacuum. The residue was purified via silica gel chromatography (eluting with 0% to 10% MeOH in DCM in 30 min) to give 1-[(2R,4S,5R)-4-[(tert-butyldimethylsilyl) oxy]-5-(hydroxymethyl) oxolan-2-yl]-5-methyl-3H-pyrimidine-2,4-dione (22.4 g, 62.8 mmol, 63.15%) as a white solid. LC-MS (ES, m/z): 357 (M+H$^+$).

Step 3: To a stirred solution of 1-[(2R,4S,5R)-4-[(tert-butyldimethylsilyl) oxy]-5-(hydroxymethyl)-5-methyl-3H-pyrimidine-2,4-dione (22.4 g, 62.8 mmol) in ACN (400 mL) was added IBX (35 g, 125 mmol). The resulting mixture was stirred at 60° C. for 1 h, and then cooled down to room temperature, filtered, and the filtrate was concentrated under vacuum to afford (2S,3S,5R)-3-[(tert-butyldimethylsilyl) oxy]-5-(5-methyl-2,4-dioxo-3H-pyrimidin-1-yl) oxolane-2-carbaldehyde (22.2 g, 63.2 mmol, 40.81%) as a white solid. LC-MS (ES, m/z): 355 (M+H$^+$).

Step 4: A solution of NaOH (7.6 g, 190 mmol) in H$_2$O (100 mL) was added to a mixture of (2S,3S,5R)-3-[(tert-butyldimethylsilyl) oxy]-5-(5-methyl-2,4-dioxo-3H-pyrimidin-1-yl) oxolane-2-carbaldehyde (22.4 g, 63.2 mmol), HCHO (19 g, 633 mmol) and 1,4-dioxane (500 mL). The resulting mixture was stirred for overnight at room temperature and then NaBH$_4$ (4.7 g, 124 mmol) was added in portions with an ice/water bath. The resulting mixture was stirred at room temperature for 1 h. The reaction was quenched with sat. aq. NH$_4$Cl, and then was poured into water (500 mL), the resulting mixture was extracted with EA (3×500 mL), the organic layers were combined, the pH value was adjusted to 5~6 by HOAc, washed with water, dried over anhydrous sodium sulfate, filtered and the organic layers were concentrated under vacuum to give 1-[(2R,4S)-4-[(tert-butyldimethylsilyl) oxy]-5,5-bis(hydroxymethyl) oxolan-2-yl]-5-methyl-3H-pyrimidine-2,4-dione (15.5 g, 46.76%) as a white solid. LC-MS (ES, m/z): 387 (M+H$^+$).

Step 5: To a stirred solution of 1-[(2R,4S)-4-[(tert-butyldimethylsilyl) oxy]-5,5-bis(hydroxymethyl)oxolan-2-yl]-5-methyl-3H-pyrimidine-2,4-dione (15.5 g, 40.2 mmol) in DCM (150 mL) and Pyridine (19 g, 240 mmol) was added Tf$_2$O (34 g, 121 mmol) was added dropwise at −30° C. The resulting mixture was stirred at −30° C. for 2 h. The reaction was quenched with water (100 mL). The mixture was extracted with DCM (3×200 mL), the combined organic layer was dried over anhydrous sodium sulfate, filtered and concentrated under vacuum. The residue was purified via silica gel chromatography (eluting with 0% to 50% EA in PE in 30 min) to give [(3S,5R)-3-[(tert-butyldimethylsilyl) oxy]-5-(5-methyl-2,4-dioxo-3H-pyrimidin-1-yl)-2-[(trifluoromethanesulfonyloxy)methyl] oxolan-2-yl] methyl trifluoromethanesulfonate (13.8 g, 21.2 mmol, 52.73%) as a white solid. LC-MS (ES, m/z): 651 (M+H$^+$).

Step 6: A solution of [(3S,5R)-3-[(tert-butyldimethylsilyl) oxy]-5-(5-methyl-2,4-dioxo-3H-pyrimidin-1-yl)-2-[(trifluoromethanesulfonyloxy)methyl] oxolan-2-yl] methyl trifluoromethanesulfonate (3.4 g, 5.2 mmol) and TEA (3.1 g, 31.4 mmol) in THF (150 mL) was stirred at 60° C. for 10 h and then LiCl (2.2 g, 52.4 mmol) was added, the mixture was stirred at 60° C. for 1 h. The mixture was used directly for the next step. LC-MS (ES, m/z): 387/389 (M+H$^+$).

Step 7: To the previous step solution was added a solution of NaOH (630 mg, 15.8 mmol) in H$_2$O (12.6 mL). The resulting mixture was stirred at room temperature for overnight. The mixture was partitioned between THF and H$_2$O. The pH value of organic layer was adjusted to 5~6 by HOAc. The resulting mixture was diluted with EA (300 mL), and then was washed with water (3×200 mL), the organic layer was dried over anhydrous sodium sulfate, filtered and concentrated under vacuum. the residue was purified via silica gel chromatography (eluting with 1:1 PE/EA) to give 1-[(2R,4S,5R)-4-[(tert-butyldimethylsilyl) oxy]-5-{[(tert-butyldimethylsilyl) oxy] methyl}-5-(chloromethyl) oxolan-2-yl]-5-methyl-3H-pyrimidine-2,4-dione (1.08 g, 2.67 mmol, 51.33% two steps) as a white solid. LC-MS (ES, m/z): 405/407 (M+H$^+$)

Step 8: To a stirred solution of 1-[(2R,4S,5R)-4-[(tert-butyldimethylsilyl) oxy]-5-(chloromethyl)-5-(hydroxymethyl) oxolan-2-yl]-5-methyl-3H-pyrimidine-2,4-dione (1.0 g, 2.6 mmol) and imidazole (1.7 g, 26.0 mmol) in DMF (10 mL) was added TBSCl (0.63 g, 4.1 mmol). The resulting mixture was stirred for 1 h at 60° C. The reaction was cooled to room temperature, poured into water (50 mL), extracted with EA (3×50 mL), the combined organic layer was dried over anhydrous sodium sulfate, filtered and concentrated under vacuum. The residue was purified via silica gel chromatography (eluting with 1/1 PE/EA) to give 1-[(2R,4S,5R)-4-[(tert-butyldimethylsilyl) oxy]-5-{[(tert-butyldimethylsilyl) oxy] methyl}-5-(chloromethyl) oxolan-2-yl]-5-methyl-3H-pyrimidine-2,4-dione (1.1 g, 2.1 mmol, 80.76%) as an off-white solid. LC-MS (ES, m/z): 519/521 (M+H$^+$).

Step 9: A solution of 1-[(2R,4S,5R)-4-[(tert-butyldimethylsilyl) oxy]-5-{[(tert-butyldimethylsilyl) oxy] methyl}-5-(chloromethyl) oxolan-2-yl]-5-methyl-3H-pyrimidine-2,4-dione (500 mg, 0.9 mmol), DMAP (235 mg, 1.9 mmol) and TEA (390 mg, 3.8 mmol) in acetonitrile (5 mL) was added 2,4,6-tris(propan-2-yl) benzene-1-sulfonyl chloride (875 mg, 2.9 mmol), the mixture was stirred for 15 h at room temperature. After that, NH$_3$·H$_2$O (3 mL) was added and stirred at room temperature for an additional 1 h. The resulting mixture was poured into water (50 mL), extracted with ethyl acetate (3×50 mL). The combined organic layers were washed with brine, dried over anhydrous sodium sulfate. After filtration, the filtrate was concentrated under reduced pressure. The residue was purified by silica gel column chromatography, eluted with dichloromethane/methyl alcohol (20/1) to afford 4-amino-1-[(2R,4S,5R)-4-[(tert-butyldimethylsilyl) oxy]-5-{[(tert-butyldimethylsilyl) oxy] methyl}-5-(chloromethyl) oxolan-2-yl]-5-methylpyrimidin-2-one (404 mg, 0.78 mmol, 86.82%) as a light yellow solid. LC-MS (ES, m/z): 518/520 (M+H$^+$).

Step 10: To a stirred solution of 4-amino-1-[(2R,4S,5R)-4-[(tert-butyldimethylsilyl) oxy]-5-{[(tert-butyldimethylsilyl) oxy] methyl}-5-(chloromethyl) oxolan-2-yl]-5-methyl-pyrimidin-2-one (360 mg, 0.7 mmol) in methanol (5 mL) was added NH$_4$F (772 mg, 20.9 mmol) at room temperature. The mixture was stirred for 16 h at room temperature. The resulting mixture was filtered, and the filter cake was washed with water (20 mL×3). The filtrate was concentrated under reduced pressure. The residue was purified by reverse phase chromatography (Column, C18 silica gel; Mobile phase A: water (containing 8 mmol/L NH$_4$HCO$_3$) and B: acetonitrile; Gradient: 0% to 35% B in 25 min; Detector, UV 254 nm) to afford 4-amino-1-[(2R,4S,5R)-5-(chloromethyl)-4-hydroxy-5-(hydroxymethyl) oxolan-2-yl]-5-methylpyrimidin-2-one (51.8 mg, 0.18 mmol, 24.45%) as an off-white solid. LC-MS (ES, m/z): 290/292 (M+H$^+$). 95.0% purity. Conditions for the LCMS: (Column: Kinetex EVO C18 Column, 33*3.0 mm, 2.6 m; Mobile Phase A: Water/5 mM NH$_4$HCO$_3$, Mobile Phase B: ACN; Flow rate: 1.5000 mL/min; Gradient: 2% B to 95% B in 1.2 min, 95% B to 95% B in 1.78 min, 95% B to 10% B in 1.83 min; Wavelength: 254/220 nm; RT1(min): 0.721). $^1$H-NMR (400 MHz, DMSO-d$_6$): δ (ppm) 7.55 (s, 1H), 7.31 (s, 1H), 6.81 (s, 1H), 6.27 (dd, J=8.0, 6.0 Hz, 1H), 5.42 (d, J=4.8 Hz, 1H), 5.21 (t, J=5.3 Hz, 1H), 4.39-4.36 (m, 1H), 3.81-3.69 (m, 2H), 3.57 (dd, J=5.0, 1.7 Hz, 2H), 2.22-2.14 (m, 2H), 1.90 (s, 3H).

Example 11—Synthesis of Compound 12: 4-amino-1-((2R,3S,4S,5R)-5-(chloromethyl)-4-hydroxy-5-(hydroxymethyl)-3-methyltetrahydrofuran-2-yl)pyrimidin-2(1H)-one
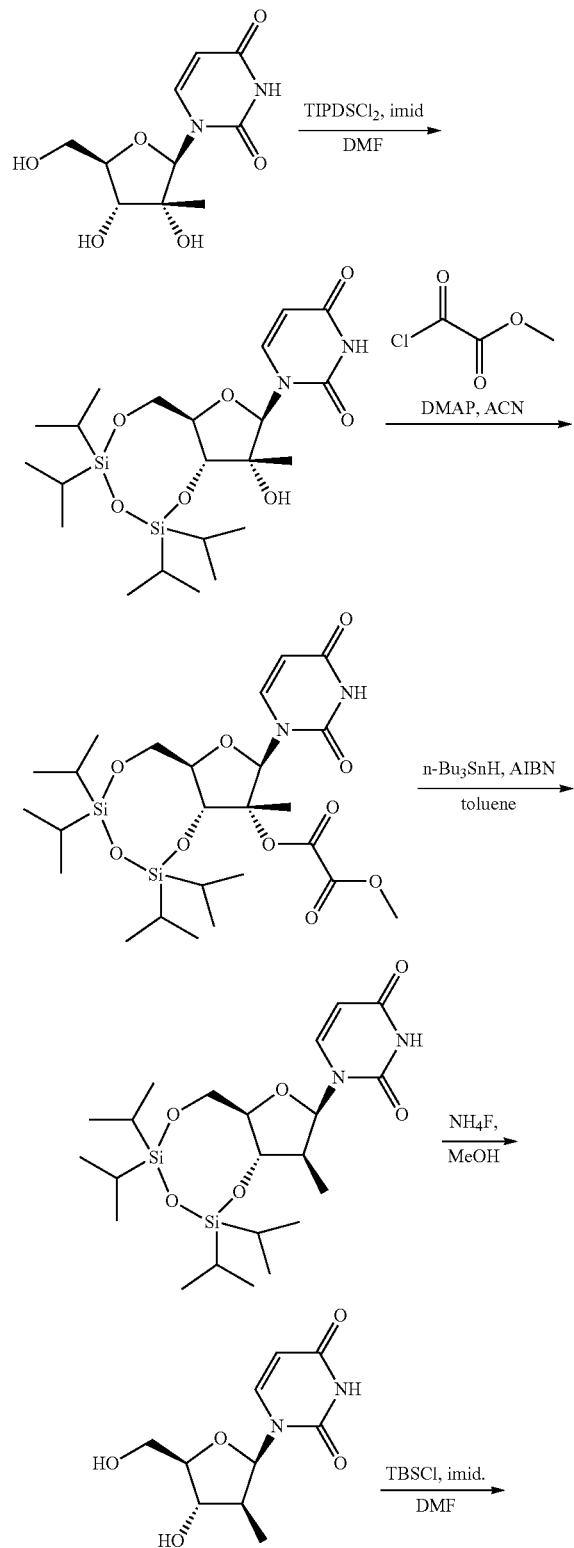
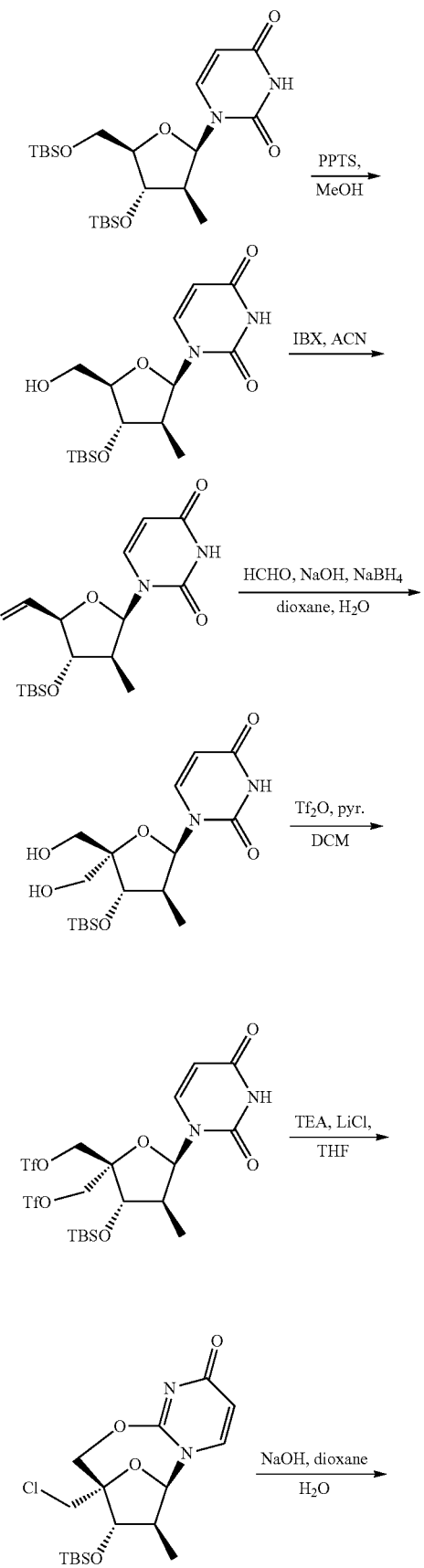

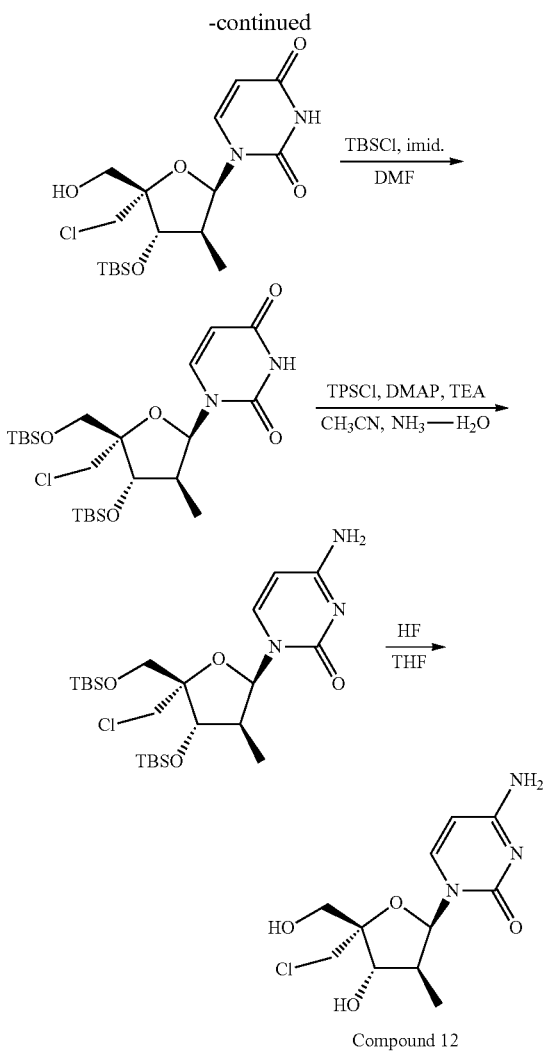

Compound 12

Step 1: To a stirred solution of 1-[(2R,3R,4R,5R)-3,4-dihydroxy-5-(hydroxymethyl)-3-methyloxolan-2-yl]-3H-pyrimidine-2,4-dione (40 g, 154.9 mmol) and imidazole (63.2 g, 929.4 mmol) in dimethyl formamide (500 mL) were added (chlorooxy)({[(chlorooxy)diisopropylsilyl]oxy}) diisopropylsilane (64.5 g, 185.8 mmol) dropwise at 0° C. under N₂ atmosphere. TLC showed the reaction was completed. The resulting mixture was extracted with ethyl acetate (2×500 mL). The combined organic layers were washed with water (100 mL), dried over anhydrous sodium sulfate. After filtration, the filtrate was concentrated under reduced pressure. The residue was purified by silica gel column chromatography, eluted with petroleum ether/ethyl acetate (2/1) to afford 1-[(6aR,8R,9R,9aR)-9-hydroxy-2,2,4,4-tetraisopropyl-9-methyl-tetrahydrofuro[3,2-f] [1,3,5,2,4] trioxadisilocin-8-yl]-3H-pyrimidine-2,4-dione (41 g, 83.8 mmol, 52.86%) as a white solid. LC-MS (ES, m/z): 501 (M+H⁺).

Step 2: A solution of 1-[(6aR,8R,9R,9aR)-9-hydroxy-2,2,4,4-tetraisopropyl-9-methyl-tetrahydrofuro[3,2-f] [1,3,5,2,4] trioxadisilocin-8-yl]-3H-pyrimidine-2,4-dione (41 g, 83.8 mmol) and methyl oxalochloridate (15.4 g, 125.8 mmol) and DMAP (20.4 g, 167.7 mmol) in ACN (500 mL) was stirred for 1 h at room temperature. Desired product could be detected by LCMS. The resulting mixture was extracted with ethyl acetate (3×500 mL). The combined organic layers were washed with brine (3×250 mL), dried over anhydrous sodium sulfate. After filtration, the filtrate was concentrated under reduced pressure. The residue was purified by silica gel column chromatography, eluted with petroleum ether/ethyl acetate (2:1) to afford (6aR,8R,9R,9aR)-8-(2,4-dioxo-3H-pyrimidin-1-yl)-2,2,4,4-tetraisopropyl-9-methyl-tetrahydrofuro[3,2-f] [1,3,5,2,4]trioxadisilocin-9-yl methyl oxalate (43 g, 73.2 mmol, 87.37%) as an off-white solid. LC-MS (ES, m/z): 587 (M+H⁺).

Step 3: To a stirred solution of (6aR,8R,9R,9aR)-8-(2,4-dioxo-3H-pyrimidin-1-yl)-2,2,4,4-tetraisopropyl-9-methyl-tetrahydrofuro[3,2-f] [1,3,5,2,4] trioxadisilocin-9-yl methyl oxalate (43 g, 73.2 mmol) in toluene (400 mL) was added AIBN (1.8 g, 10.9 mmol) and n-Bu3SnH (42.6 g, 146.5 mmol) under N₂ atmosphere. The resulting mixture was stirred for 2 h at 100° C. under N₂ atmosphere. LCMS showed the reaction was completed. The resulting mixture was concentrated under reduced pressure. The residue was purified by silica gel column chromatography, eluted with petroleum ether/ethyl acetate (2/1) to afford 1-[(6aR,8R,9S,9aS)-2,2,4,4-tetraisopropyl-9-methyl-tetrahydro-6H-furo[3,2-f] [1,3,5,2,4] trioxadisilocin-8-yl]-3H-pyrimidine-2,4-dione (29 g, 59.8 mmol, 81.64%) as a white solid. LC-MS (ES, m/z): 485 (M+H⁺).

Step 4: A solution of 1-[(6aR,8R,9S,9aS)-2,2,4,4-tetraisopropyl-9-methyl-tetrahydro-6H-furo[3,2-f] [1,3,5,2,4] trioxadisilocin-8-yl]-3H-pyrimidine-2,4-dione (29 g, 59.8 mmol) in methyl alcohol (300 mL) was treated with NH₄F (11.0 g, 299.1 mmol) for overnight at 60° C. under nitrogen atmosphere. Desired product could be detected by LCMS. The resulting mixture was concentrated under reduced pressure. The residue was purified by silica gel column chromatography, eluted with dichloromethane/methyl alcohol (10:1) to afford 1-[(2R,3S,4S,5R)-4-hydroxy-5-(hydroxymethyl)-3-methyloxolan-2-yl]-3H-pyrimidine-2,4-dione (14.4 g, 57.7 mmol, 99.37%) as an off-white solid. LC-MS (ES, m/z): 243 (M+H⁺).

Step 5: To a stirred solution of 1-[(2R,3S,4S,5R)-4-hydroxy-5-(hydroxymethyl)-3-methyloxolan-2-yl]-3H-pyrimidine-2,4-dione (14 g, 57.7 mmol) and imidazole (15.7 g, 231.1 mmol) in dimethyl formamide (300 mL) was added TBSCl (26.1 g, 173.3 mmol). The resulting mixture was stirred for 2 h at 60° C. LCMS showed the reaction was ok. The resulting mixture was extracted with ethyl acetate (3×300 mL). The combined organic layers were washed with brine, dried over anhydrous sodium sulfate. After filtration, the filtrate was concentrated under reduced pressure. The residue was purified by silica gel column chromatography, eluted with petroleum ether/ethyl acetate (2:1) to afford 1-[(2R,3S,4S,5R)-4-[(tert-butyldimethylsilyl) oxy]-5-{[(tert-butyldimethylsilyl) oxy] methyl}-3-methyloxolan-2-yl]-3H-pyrimidine-2,4-dione (19 g, 40.3 mmol, 69.83%) as a white solid. LC-MS (ES, m/z): 471 (M+H⁺).

Step 6: A solution of 1-[(2R,3S,4S,5R)-4-[(tert-butyldimethylsilyl) oxy]-5-{[(tert-butyldimethylsilyl) oxy] methyl}-3-methyloxolan-2-yl]-3H-pyrimidine-2,4-dione (19 g, 40.3 mmol) and PPTS (30.4 g, 121.0 mmol) in methyl alcohol (400 mL) was stirred for 3 h at 60° C. LCMS showed the reaction was complete. The resulting mixture was concentrated under vacuum. The residue was purified by silica gel column chromatography, eluted with petroleum ether/ethyl acetate (1:1) to afford 1-[(2R,3S,4S,5R)-4-[(tert-butyldimethylsilyl) oxy]-5-(hydroxymethyl)-3-methyloxolan-2-yl]-3H-pyrimidine-2,4-dione (9.5 g, 26.6 mmol, 66.03%) as a white solid. LC-MS (ES, m/z): 357 (M+H⁺).

Step 7: A solution of 1-[(2R,3S,4S,5R)-4-[(tert-butyldimethylsilyl) oxy]-5-(hydroxymethyl)-3-methyloxolan-2-yl]-

3H-pyrimidine-2,4-dione (9.5 g, 26.6 mmol) and IBX (14.9 g, 53.2 mmol) in acetonitrile (200 mL) was stirred for 2 h at 60° C. LCMS showed the reaction was complete. The resulting mixture was filtered; the filter cake was washed with acetonitrile (100 ml). The filtrate was concentrated under reduced pressure. This resulted in (2S,3S,4S,5R)-3-[(tert-butyldimethylsilyl) oxy]-5-(2,4-dioxo-3H-pyrimidin-1-yl)-4-methyloxolane-2-carbaldehyde (9 g, 25.3 mmol, 95.28%) as a yellow oil. LC-MS (ES, m/z): 355 (M+H$^+$).

Step 8: A solution of (2S,3S,4S,5R)-3-[(tert-butyldimethylsilyl) oxy]-5-(2,4-dioxo-3H-pyrimidin-1-yl)-4-methyloxolane-2-carbaldehyde (9 g, 25.3 mmol) in water (20 mL) and dioxane (200 mL) was treated with HCHO (4.5 g, 152.3 mmol) and caustic soda (2.2 g, 55.8 mmol) for 5 h at room temperature. Desired product could be detected by LCMS. To the above mixture was added NaBH$_4$ (3.8 g, 101.5 mmol). The resulting mixture was stirred for additional 1 h at room temperature. Desired product could be detected by LCMS. The reaction was quenched with sat. NH$_4$Cl (aq.) at room temperature. The aqueous layer was extracted with ethyl acetate (3×500 mL). After filtration, the filtrate was concentrated under reduced pressure. The residue was purified by silica gel column chromatography, eluted with dichloromethane/methyl alcohol (10:1) to afford 1-[(2R,3S,4S)-4-[(tert-butyldimethylsilyl) oxy]-5,5-bis(hydroxymethyl)-3-methyloxolan-2-yl]-3H-pyrimidine-2,4-dione (5.5 g, 14.3 mmol, 56.05%) as a white solid. LC-MS (ES, m/z): 387 (M+H$^+$).

Step 9: A solution of 1-[(2R,3S,4S)-4-[(tert-butyldimethylsilyl) oxy]-5,5-bis(hydroxymethyl)-3-methyloxolan-2-yl]-3H-pyrimidine-2,4-dione (3.5 g, 9.0 mmol) in dichloromethane (50 mL) was treated with pyridine (7.1 g, 90.5 mmol) for 5 min at room temperature under nitrogen atmosphere followed by the addition of Tf$_2$O (7.6 g, 27.1 mmol) dropwise at −35° C. Desired product could be detected by LCMS. The reaction was quenched with Water/Ice at −20° C. The aqueous layer was extracted with ethyl acetate (3×200 mL). The residue was purified by silica gel column chromatography, eluted with petroleum ether/ethyl acetate (2:1) to afford [(3S,4S,5R)-3-[(tert-butyldimethylsilyl) oxy]-5-(2,4-dioxo-3H-pyrimidin-1-yl)-4-methyl-2-[(trifluoromethanesulfonyloxy)methyl] oxolan-2-yl] methyl trifluoromethanesulfonate (1.5 g, 2.3 mmol, 25.46%) as an off-white solid. LC-MS (ES, m/z): 651 (M+H$^+$).

Step 10: A solution of [(3S,4S,5R)-3-[(tert-butyldimethylsilyl) oxy]-5-(2,4-dioxo-3H-pyrimidin-1-yl)-4-methyl-2-[(trifluoromethanesulfonyloxy)methyl] oxolan-2-yl] methyl trifluoromethanesulfonate (1.5 g, 2.3 mmol) in tetrahydrofuran (30 mL) was treated with TEA (2.3 g, 23.0 mmol) for overnight at 60° C. under nitrogen atmosphere, then into a solution were added LiCl (293 mg, 6.9 mmol) at 60° C. Desired product could be detected by LCMS. The resulting mixture was diluted with water (200 mL). The resulting mixture was extracted with ethyl acetate (3×200 mL). The combined organic layers were washed with brine (3×100 mL), dried over anhydrous sodium sulfate. After filtration, the filtrate was concentrated under reduced pressure. The resulting mixture was used in the next step directly without further purification. LC-MS (ES, m/z): 387 (M+H$^+$).

Step 11: A solution of (1R,10R,11S,12S)-11-[(tert-butyldimethylsilyl) oxy]-10-(chloromethyl)-12-methyl-8,13-dioxa-2,6-diazatricyclo [8.2.1.0ˆ{2,7}] trideca-3,6-dien-5-one (crude) in 1,4-dioxane (30 mL) and H$_2$O (15 mL) was treated with NaOH (465 mg, 11.6 mmol) for 2 h at room temperature under nitrogen atmosphere. Desired product could be detected by LCMS. The resulting mixture was diluted with water (200 mL). The resulting mixture was extracted with ethyl acetate (3×200 mL). The combined organic layers were washed with brine (3×100 mL), dried over anhydrous sodium sulfate. After filtration, the filtrate was concentrated under reduced pressure. The residue was purified by Prep-TLC (petroleum ether/ethyl acetate 1:1) to afford 1-[(2R,3S,4S,5R)-4-[(tert-butyldimethylsilyl) oxy]-5-(chloromethyl)-5-(hydroxymethyl)-3-methyloxolan-2-yl]-3H-pyrimidine-2,4-dione (470 mg, 1.16 mmol, 29.94%) as an off-white solid. LC-MS (ES, m/z): 405 (M+H$^+$).

Step 12: A solution of 1-[(2R,3S,4S,5R)-4-[(tert-butyldimethylsilyl) oxy]-5-(chloromethyl)-5-(hydroxymethyl)-3-methyloxolan-2-yl]-3H-pyrimidine-2,4-dione (350 mg, 0.8 mmol) in DMF (7 mL) was treated with imidazole (235 mg, 3.4 mmol) and tert-butyl(chloro)dimethylsilane (260 mg, 1.7 mmol) for overnight at room temperature under nitrogen atmosphere. Desired product could be detected by LCMS. The resulting mixture was diluted with water (100 mL). The aqueous layer was extracted with ethyl acetate (3×50 mL). The combined organic layer was concentrated under reduced pressure. The residue was purified by Prep-TLC (petroleum ether/ethyl acetate 1:1) to afford 1-[(2R,3S,4S,5R)-4-[(tert-butyldimethylsilyl) oxy]-5-{[(tert-butyldimethylsilyl) oxy] methyl}-5-(chloromethyl)-3-methyloxolan-2-yl]-3H-pyrimidine-2,4-dione (380 mg, 0.6 mmol, 84.68%) as an off-white solid. LC-MS (ES, m/z): 519 (M+H$^+$).

Step 13: A solution of 1-[(2R,3S,4S,5R)-4-[(tert-butyldimethylsilyl) oxy]-5-{[(tert-butyldimethylsilyl) oxy] methyl}-5-(chloromethyl)-3-methyloxolan-2-yl]-3H-pyrimidine-2,4-dione (360 mg, 0.6 mmol) in acetonitrile (5 mL) was treated with DMAP (169 mg, 1.3 mmol) and TEA (140 mg, 1.3 mmol) for 10 min at room temperature under nitrogen atmosphere, then a solution was added 2,4,6-tris (propan-2-yl) benzene-1-sulfonyl chloride (419 mg, 1.3 mmol) for 5 h at room temperature. Finally, a solution was added NH$_3$—H$_2$O (1 mL) for 15 min at room temperature. Desired product could be detected by LCMS. The resulting mixture was concentrated under reduced pressure. The residue was purified by Prep-TLC (petroleum ether/ethyl acetate 1:1) to afford 4-amino-1-[(2R,3S,4S,5R)-4-[(tert-butyldimethylsilyl) oxy]-5-{[(tert-butyldimethylsilyl) oxy] methyl}-5-(chloromethyl)-3-methyloxolan-2-yl] pyrimidin-2-one (280 mg, 0.54 mmol, 77.93%) as an off-white solid. LC-MS (ES, m/z): 518 (M+H$^+$).

Step 14: A solution of 4-amino-1-[(2R,3S,4S,5R)-4-[(tert-butyldimethylsilyl) oxy]-5-{[(tert-butyldimethylsilyl) oxy] methyl}-5-(chloromethyl)-3-methyloxolan-2-yl] pyrimidin-2-one (80 mg, 0.2 mmol) and HF (0.8 mL, 8.9 mmol, 70% in pyridine) in tetrahydrofuran (3 mL) was stirred for 2 h at room temperature. Desired product could be detected by LCMS. The resulting mixture was filtered; the filter cake was washed with methyl alcohol (3×5 mL). The filtrate was concentrated under reduced pressure. The crude product (40 mg) was purified by Prep-HPLC with the following conditions (Column: XBridge Prep OBD C18 Column, 30*150 mm, 5 μm; Mobile Phase A: Water (10 mmol/L NH$_4$HCO$_3$+ 0.1% NH$_3$·H$_2$O), Mobile Phase B: ACN; Flow rate: 60 mL/min; Gradient: 2% B to 19% B in 8 min, 19% B; Wavelength: 254/220 nm; RT1(min): 7.07) to afford 4-amino-1-[(2R,3S,4S,5R)-5-(chloromethyl)-4-hydroxy-5-(hydroxymethyl)-3-methyloxolan-2-yl] pyrimidin-2-one (26.4 mg, 58.19%) as an off-white solid.

LC-MS (ES, m/z): 290 (M+H$^+$); 98.5% purity. Conditions for the LCMS: (Column: HALO C18, 30*3.0 mm, 2.0 μm; Mobile Phase A: Water/0.05% TFA, Mobile Phase B: Acetonitrile/0.05% TFA; Flow rate: 1.2000 mL/min; Gradient: 5% B to 100% B in 1.3 min, 100% B to 100% B in 0.5 min, 100% B to 5% B in 0.03 min; Wavelength: 254/220 nm; RT1(min): 0.647). ¹H NMR (300 MHz, DMSO-d₆) δ 7.96 (d, J=7.4 Hz, 1H), 7.09 (d, J=21.6 Hz, 2H), 6.20 (d, J=8.0 Hz, 1H), 5.68 (d, J=7.4 Hz, 1H), 5.54 (d, J=5.0 Hz, 1H), 5.31 (t, J=5.1 Hz, 1H), 4.01 (dd, J=9.8, 5.0 Hz, 1H), 3.88 (d, J=12.1 Hz, 1H), 3.75 (dd, J=11.7, 5.2 Hz, 1H), 3.61 (d, J=12.1 Hz, 1H), 3.51 (dd, J=11.7, 5.1 Hz, 1H), 2.81-2.52 (m, 1H), 0.74 (d, J=7.0 Hz, 3H).
Example 12—Synthesis of Compound 13: 4-amino-1-((2R,3S,4S,5R)-5-(chloromethyl)-4-hydroxy-5-(hydroxymethyl)-3-methoxytetrahydrofuran-2-yl)pyrimidin-2(1H)-one
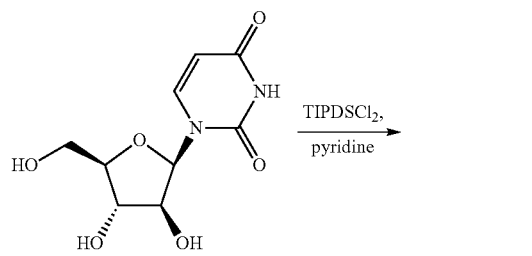
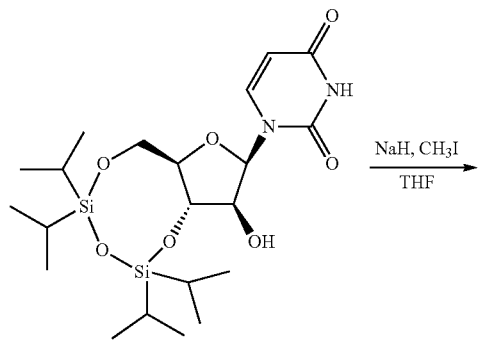
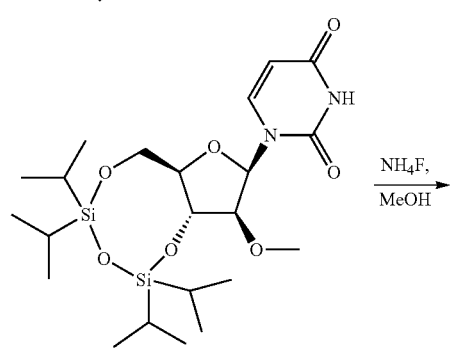
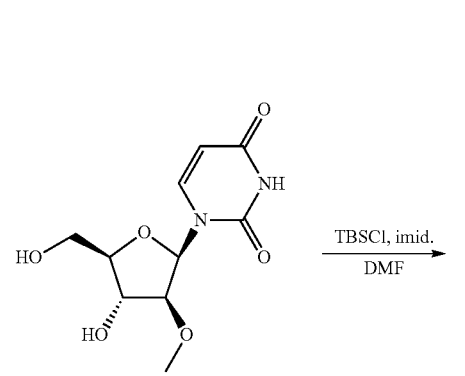
-continued
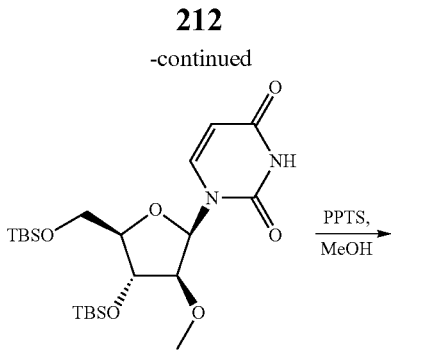
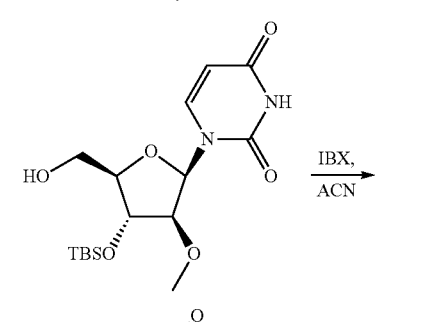
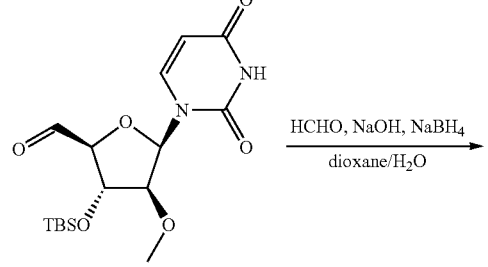
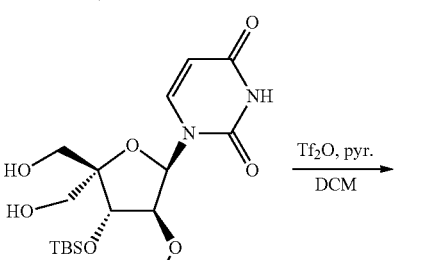
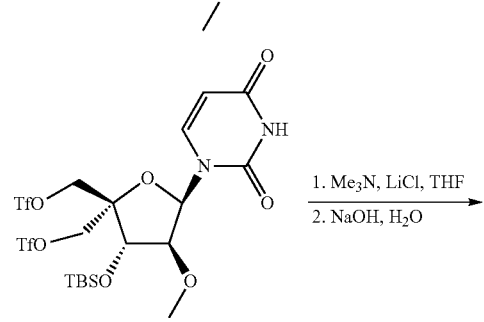
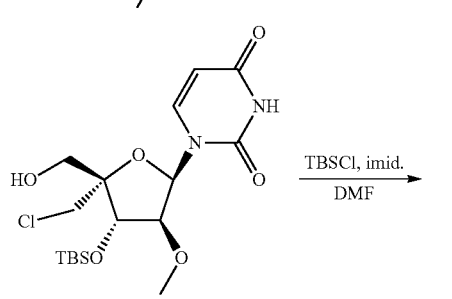

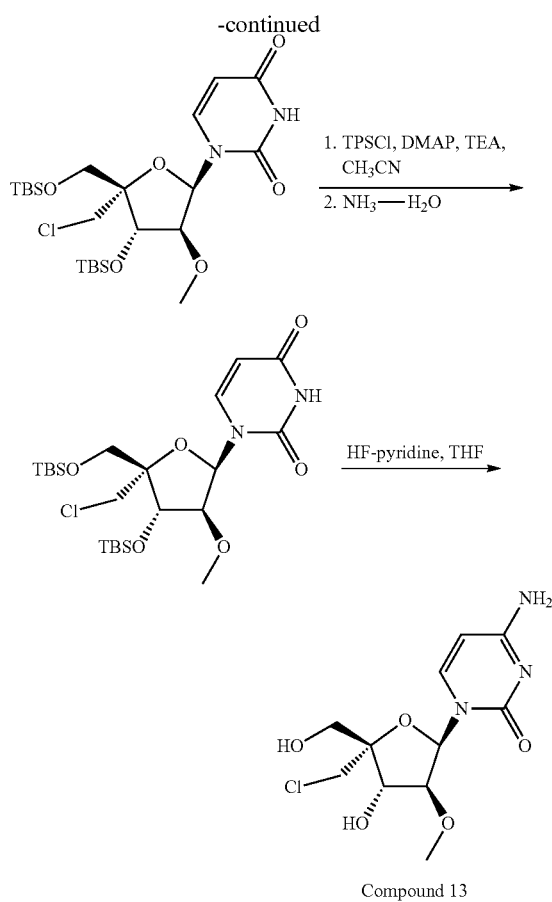

Compound 13

Step 1: To a stirred mixture of 1-[(2R,3S,4S,5R)-3,4-dihydroxy-5-(hydroxymethyl) oxolan-2-yl]-3H-pyrimidine-2,4-dione (1.5 g, 6.1 mmol) in pyridine (15 mL) were added chloro([[chlorobis(propan-2-yl) silyl] oxy]) bis(propan-2-yl) silane (2.3 g, 7.4 mmol) in portions at 0° C. under nitrogen atmosphere. The mixture was stirred for 2 hours at room temperature. The resulting mixture was concentrated under reduced pressure. The residue was purified by silica gel column chromatography, eluted with petroleum ether/ethyl acetate (3:2) to afford 1-[(6aR,8R,9S,9aS)-9-hydroxy-2,2,4,4-tetraisopropyl-tetrahydro-6H-furo[3,2-f][1,3,5,2,4]trioxadisilocin-8-yl]-3H-pyrimidine-2,4-dione (5.93 g, 12.2 mmol, 94.16%) as an off-white solid. LC-MS (ES, m/z): 487 (M+H⁺).

Step 2: To a stirred solution of 1-[(6aR,8R,9S,9aS)-9-hydroxy-2,2,4,4-tetraisopropyl-tetrahydro-6H-furo[3,2-f][1,3,5,2,4] trioxadisilocin-8-yl]-3H-pyrimidine-2,4-dione (5.0 g, 10.3 mmol) in tetrahydrofuran (200 mL) were added sodium hydride (493 mg, 20.5 mmol) and iodomethane (8.8 g, 61.6 mmol) in portions at 0° C. under nitrogen atmosphere. The mixture was stirred for 15 hours at room temperature. The reaction was quenched by the addition of water (50 mL) at 0° C. The resulting mixture was concentrated under reduced pressure. The resulting mixture was diluted with water and extracted with ethyl acetate (3×100 mL). The combined organic layers were washed with brine (2×200 mL), dried over anhydrous sodium sulfate. After filtration, the filtrate was concentrated under reduced pressure. The residue was purified by silica gel column chromatography, eluted with petroleum ether/ethyl acetate (1:1) to afford 1-((6aR,8R,9S,9aR)-2,2,4,4-tetraisopropyl-9-methoxytetrahydro-6H-furo[3,2-f][1,3,5,2,4]trioxadisilocin-8-yl)pyrimidine-2,4(1H,3H)-dione (2.69 g, 5.4 mmol, 52.29%) as a white solid. LC-MS (ES, m/z): 501 (M+H⁺).

Step 3: To a stirred solution of afford 1-((6aR,8R,9S,9aR)-2,2,4,4-tetraisopropyl-9-methoxytetrahydro-6H-furo[3,2-f][1,3,5,2,4]trioxadisilocin-8-yl)pyrimidine-2,4(1H,3H)-dione (21 g, 41.9 mmol) in methyl alcohol (250 mL) was added NH₄F (7.8 g, 209.7 mmol) in portions at room temperature under nitrogen atmosphere. The mixture was stirred for 15 hours at 60° C. The resulting mixture was concentrated under reduced pressure. The residue was purified by silica gel column chromatography, eluted with dichloromethane/methyl alcohol (10/1) to afford 1-[(2R,3S,4R,5R)-4-hydroxy-5-(hydroxymethyl)-3-methoxyoxolan-2-yl]-3H-pyrimidine-2,4-dione (9.6 g, 37.2 mmol, 88.65%) as an off-white solid. LC-MS (ES, m/z): 259 (M+H⁺).

Step 4: To a stirred solution of 1-[(2R,3S,4R,5R)-4-hydroxy-5-(hydroxymethyl)-3-methoxyoxolan-2-yl]-3H-pyrimidine-2,4-dione (10.5 g, 40.7 mmol) and imidazole (11.1 g, 162.6 mmol) in N,N-dimethyl formamide (150 mL) were added t-Butyldimethylchlorosilane (18.4 g, 122.0 mmol) in portions at room temperature under nitrogen atmosphere. The mixture was stirred for 15 hours at 80° C. The resulting mixture was diluted with water and extracted with ethyl acetate (3×300 mL). The combined organic layers were washed with brine (2×200 mL), dried over anhydrous sodium sulfate. After filtration, the filtrate was concentrated under reduced pressure. The residue was purified by silica gel column chromatography, eluted with petroleum ether/ethyl acetate (1/1) to afford 1-[(2R,3S,4R,5R)-4-[(tert-butyldimethylsilyl) oxy]-5-{[(tert-butyldimethylsilyl) oxy]methyl}-3-methoxyoxolan-2-yl]-3H-pyrimidine-2,4-dione (19.2 g, 39.4 mmol, 97.01%) as a light yellow oil. LC-MS (ES, m/z): 487 (M+H⁺).

Step 5: To a stirred solution of 1-[(2R,3S,4R,5R)-4-[(tert-butyldimethylsilyl) oxy]-5-{[(tert-butyldimethylsilyl) oxy]methyl}-3-methoxyoxolan-2-yl]-3H-pyrimidine-2,4-dione (19.2 g, 39.4 mmol) in methyl alcohol (500 mL) were added Pyridinium p-Toluenesulfonate (29.7 g, 118.3 mmol) in portions at room temperature under nitrogen atmosphere. The mixture was stirred for 4 hours at 60° C. The resulting mixture was concentrated under reduced pressure. The residue was purified by silica gel column chromatography, eluted with petroleum ether/ethyl acetate (3/7) to afford 1-[(2R,3S,4R,5R)-4-[(tert-butyldimethylsilyl) oxy]-5-(hydroxymethyl)-3-methoxyoxolan-2-yl]-3H-pyrimidine-2,4-dione (9.9 g, 26.6 mmol, 67.38%) as an off-white solid. LC-MS (ES, m/z): 373 (M+H⁺).

Step 6: To a stirred solution of 1-[(2R,3S,4R,5R)-4-[(tert-butyldimethylsilyl) oxy]-5-(hydroxymethyl)-3-methoxyoxolan-2-yl]-3H-pyrimidine-2,4-dione (4.9 g, 13.2 mmol) in acetonitrile (100 mL) were added 2-iodoxybenzoic acid (9.2 g, 32.9 mmol) in portions at room temperature under nitrogen atmosphere. The mixture was stirred for 2 hours at 60° C. The precipitated solids were collected by filtration and washed with acetonitrile (2×10 mL) to afford (2S,3S,4S,5R)-3-[(tert-butyldimethylsilyl) oxy]-5-(2,4-dioxo-3H-pyrimidin-1-yl)-4-methoxyoxolane-2-carbaldehyde (4.7 g, 12.7 mmol, 96.44%) as a white solid. LC-MS (ES, m/z): 371 (M+H⁺).

Step 7: To a stirred solution of (2S,3S,4S,5R)-3-[(tert-butyldimethylsilyl) oxy]-5-(2,4-dioxo-3H-pyrimidin-1-yl)-4-methoxyoxolane-2-carbaldehyde (4.7 g, 12.7 mmol) and formaldehyde (1.1 g, 38.1 mmol) in dioxane (80 mL) and water (16 mL) were added NaOH (1.5 g, 38 mmol) in portions at room temperature under nitrogen atmosphere. The mixture was stirred for 15 hours at room temperature.

Then the mixture was cooled to 0° C. and added sodium borohydride (1.9 g, 50.7 mmol). The mixture was stirred for 1 hour at room temperature. The resulting mixture was diluted with water and extracted with ethyl acetate (3×100 mL). The combined organic layers were washed with brine (2×200 mL), dried over anhydrous sodium sulfate. After filtration, the filtrate was concentrated under reduced pressure. The residue was purified by silica gel column chromatography, eluted with dichloromethane/methyl alcohol (10/1) to afford 1-[(2R,3S,4S)-4-[(tert-butyldimethylsilyl) oxy]-5,5-bis(hydroxymethyl)-3-methoxyoxolan-2-yl]-3H-pyrimidine-2,4-dione (2.15 g, 5.3 mmol, 42.10%) as a white solid. LC-MS (ES, m/z): 403 (M+H$^+$).

Step 8: To a stirred solution of 1-[(2R,3S,4S)-4-[(tert-butyldimethylsilyl) oxy]-5,5-bis(hydroxymethyl)-3-methoxyoxolan-2-yl]-3H-pyrimidine-2,4-dione (2.8 g, 7.0 mmol) and pyridine (2.8 g, 35.0 mmol) in dichloromethane (30 mL) were added trifluoromethanesulfonic anhydride (4.9 g, 17.5 mmol) dropwise at −35° C. under nitrogen atmosphere. The mixture was stirred for 2 hours at room temperature. The resulting mixture was diluted with water and extracted with ethyl acetate (3×200 mL). The combined organic layers were washed with brine (2×100 mL), dried over anhydrous sodium sulfate. After filtration, the filtrate was concentrated under reduced pressure. The residue was purified by silica gel column chromatography, eluted with petroleum ether/ethyl acetate (1/1) to afford [(3S,4S,5R)-3-[(tert-butyldimethylsilyl) oxy]-5-(2,4-dioxo-3H-pyrimidin-1-yl)-4-methoxy-2-[(trifluoromethanesulfonyloxy)methyl] oxolan-2-yl] methyl trifluoromethanesulfonate (3.55 g, 5.3 mmol, 76.01%) as a yellow oil. LC-MS (ES, m/z): 667 (M+H$^+$).

Step 9: To a stirred mixture of [(3S,4S,5R)-3-[(tert-butyldimethylsilyl) oxy]-5-(2,4-dioxo-3H-pyrimidin-1-yl)-4-methoxy-2-[(trifluoromethanesulfonyloxy)methyl] oxolan-2-yl]methyl trifluoromethanesulfonate (500 mg, 0.8 mmol) in tetrahydrofuran (10 mL) were added trimethylamine (759 mg, 7.5 mmol) dropwise at room temperature under nitrogen atmosphere. The mixture was stirred for 15 hours at 60° C. Then lithium chloride (127 mg, 3.0 mmol) was added. The mixture was stirred for 5 hours at 60° C. Then sodium hydroxide (90 mg, 2.3 mmol) and water (2 mL) was added at room temperature. The mixture was stirred for 15 hours at room temperature. The resulting mixture was diluted with water and extracted with ethyl acetate (3×100 mL). The combined organic layers were washed with brine (2×200 mL), dried over anhydrous sodium sulfate. After filtration, the filtrate was concentrated under reduced pressure. The residue was purified by silica gel column chromatography, eluted with dichloromethane/methyl alcohol (10/1) to afford 1-[(2R,3S,4S,5R)-4-[(tert-butyldimethylsilyl) oxy]-5-(chloromethyl)-5-(hydroxymethyl)-3-methoxyoxolan-2-yl]-3H-pyrimidine-2,4-dione (250 mg, 0.6 mmol, 79.18%) as a light yellow solid. LC-MS (ES, m/z): 421 (M+H$^+$).

Step 10: To a stirred solution of 1-[(2R,3S,4S,5R)-4-[(tert-butyldimethylsilyl) oxy]-5-(chloromethyl)-5-(hydroxymethyl)-3-methoxyoxolan-2-yl]-3H-pyrimidine-2,4-dione (1.0 g, 2.4 mmol) and imidazole (656 mg, 9.6 mmol) in N, N-dimethyl formamide (40 mL) was added t-Butyldimethylchlorosilane (726 mg, 4.8 mmol) in portions at room temperature under nitrogen atmosphere. The mixture was stirred for 18 hours at 60° C. The resulting mixture was diluted with water and extracted with ethyl acetate (3×30 mL). The combined organic layers were washed with brine (2×50 mL), dried over anhydrous sodium sulfate. After filtration, the filtrate was concentrated under reduced pressure. The residue was purified by silica gel column chromatography, eluted with petroleum ether/ethyl acetate (1/1) to afford 1-[(2R,3S,4S,5R)-4-[(tert-butyldimethylsilyl) oxy]-5-{[(tert-butyldimethylsilyl) oxy] methyl}-5-(chloromethyl)-3-methoxyoxolan-2-yl]-3H-pyrimidine-2,4-dione (760 mg, 1.4 mmol, 58.95%) as a light yellow solid. LC-MS (ES, m/z): 535 (M+H$^+$).

Step 11: To a stirred solution of 1-[(2R,3S,4S,5R)-4-[(tert-butyldimethylsilyl) oxy]-5-{[(tert-butyldimethylsilyl) oxy] methyl}-5-(chloromethyl)-3-methoxyoxolan-2-yl]-3H-pyrimidine-2,4-dione (760 mg, 1.4 mmol), DMAP (342 mg, 2.8 mmol), and trimethylamine (431 mg, 4.3 mmol) in acetonitrile (20 mL) were added 2,4,6-tris(propan-2-yl) benzene-1-sulfonyl chloride (860 mg, 2.8 mmol) in portions at room temperature under nitrogen atmosphere. The mixture was stirred for 15 hours at room temperature. Then ammonium hydroxide (10 mL) was added at room temperature under nitrogen atmosphere. The mixture was stirred for 1 hour. The resulting mixture was diluted with water and extracted with ethyl acetate (3×100 mL). The combined organic layers were washed with brine (2×200 mL), dried over anhydrous sodium sulfate. After filtration, the filtrate was concentrated under reduced pressure. The residue was purified by Prep-TLC with dichloromethane/methyl alcohol (10:1) to afford 4-amino-1-[(2R,3S,4S,5R)-4-[(tert-butyldimethylsilyl) oxy]-5-{[(tert-butyldimethylsilyl) oxy] methyl}-5-(chloromethyl)-3-methoxyoxolan-2-yl] pyrimidin-2-one (645 mg, 1.2 mmol, 85.03%) as a light yellow solid. LC-MS (ES, m/z): 534 (M+H$^+$ Step 12: To a stirred solution of 4-amino-1-[(2R,3S,4S,5R)-4-[(tert-butyldimethylsilyl) oxy]-5-{[(tert-butyldimethylsilyl) oxy] methyl}-5-(chloromethyl)-3-methoxyoxolan-2-yl]pyrimidin-2-one (200 mg, 0.4 mmol) in tetrahydrofuran (20 mL) were added HF-pyridine (4 mL) dropwise at room temperature under nitrogen atmosphere. The mixture was stirred for 48 hours at room temperature. The resulting mixture was filtered; the filter cake was washed with methyl alcohol (3×20 mL). The filtrate was concentrated under reduced pressure. The crude product (110 mg) was purified by Prep-HPLC with the following conditions (Column: XBridge Prep OBD C18 Column, 30*150 mm, 5 μm; Mobile Phase A: Water (10 mmol/L NH$_4$HCO$_3$+0.1% NH$_3$·H$_2$O), Mobile Phase B: ACN; Flow rate: 60 mL/min; Gradient: 2% B to 19% B in 8 min, 19% B; Wavelength: 254/220 nm; RT1(min): 6.25) to afford 4-amino-1-[(2R,3S,4S,5R)-5-(chloromethyl)-4-hydroxy-5-(hydroxymethyl)-3-methoxyoxolan-2-yl]pyrimidin-2-one (61.5 mg, 0.2 mmol, 53.52%) as an off-white solid. LC-MS (ES, m/z): 306 (M+H$^+$). 99.6% purity. Conditions for the LCMS: (Column: XBridge BEH Shield RP18, 30*4.6 mm, 2.5 μm particles; Mobile Phase A: Water/6.5 mM NH$_4$HCO$_3$, Mobile Phase B: Acetonitrile; Flow rate: 1.5000 mL/min; Gradient: 0% B to 95% B in 1.20 min, 95% B to 95% B in 0.58 min, 95% B to 10% B in 0.05 min; Wavelength: 254 nm; RT1(min): 0.765). $^1$H NMR (400 MHz, DMSO-d$_6$) δ 7.55 (d, J=7.4 Hz, 1H), 7.12 (d, J=38.0 Hz, 2H), 6.28 (d, J=5.1 Hz, 1H), 5.79 (d, J=5.0 Hz, 1H), 5.68 (d, J=7.5 Hz, 1H), 5.19 (t, J=5.4 Hz, 1H), 4.26 (t, J=4.4 Hz, 1H), 3.92 (dd, J=5.1, 3.9 Hz, 1H), 3.83 (d, J=11.6 Hz, 1H), 3.69 (d, J=11.6 Hz, 1H), 3.56 (d, J=4.9 Hz, 2H), 3.17 (s, 3H).

217
Example 13—Synthesis of Compound 15: (2R,3S,5R)-5-(6-amino-9H-purin-9-yl)-2-(chloromethyl)-2-(hydroxymethyl)tetrahydrofuran-3-ol
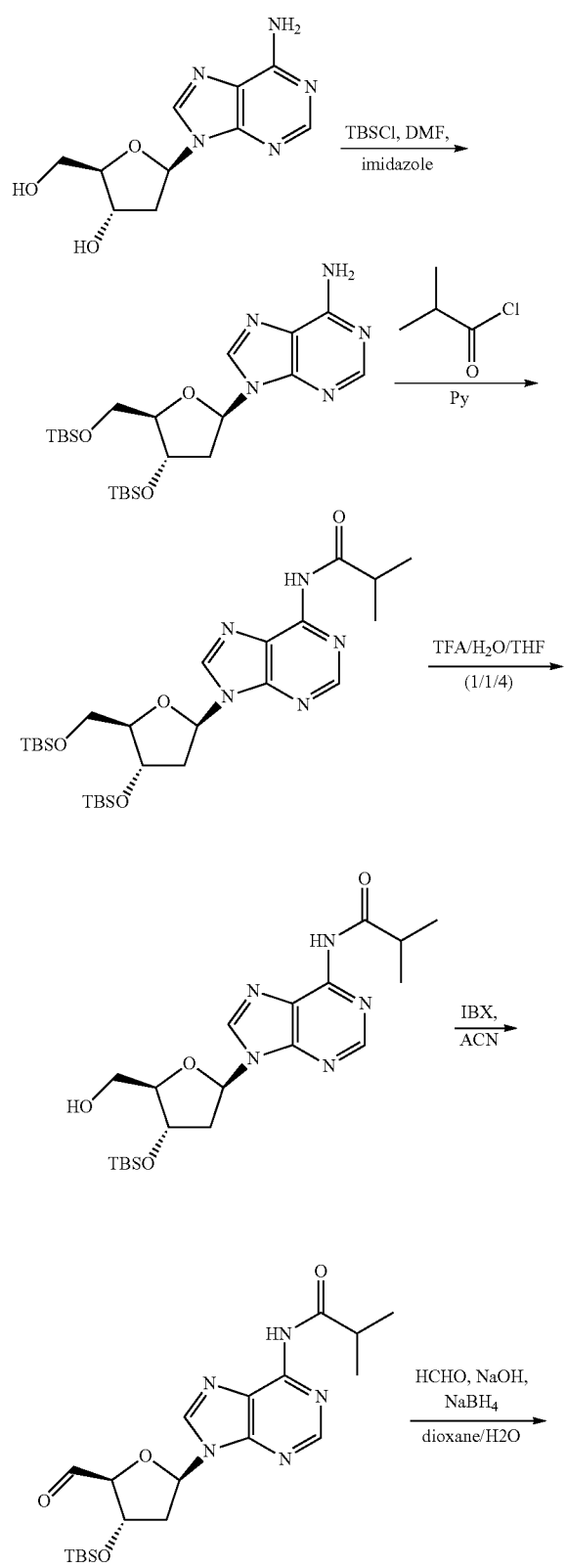
218
-continued
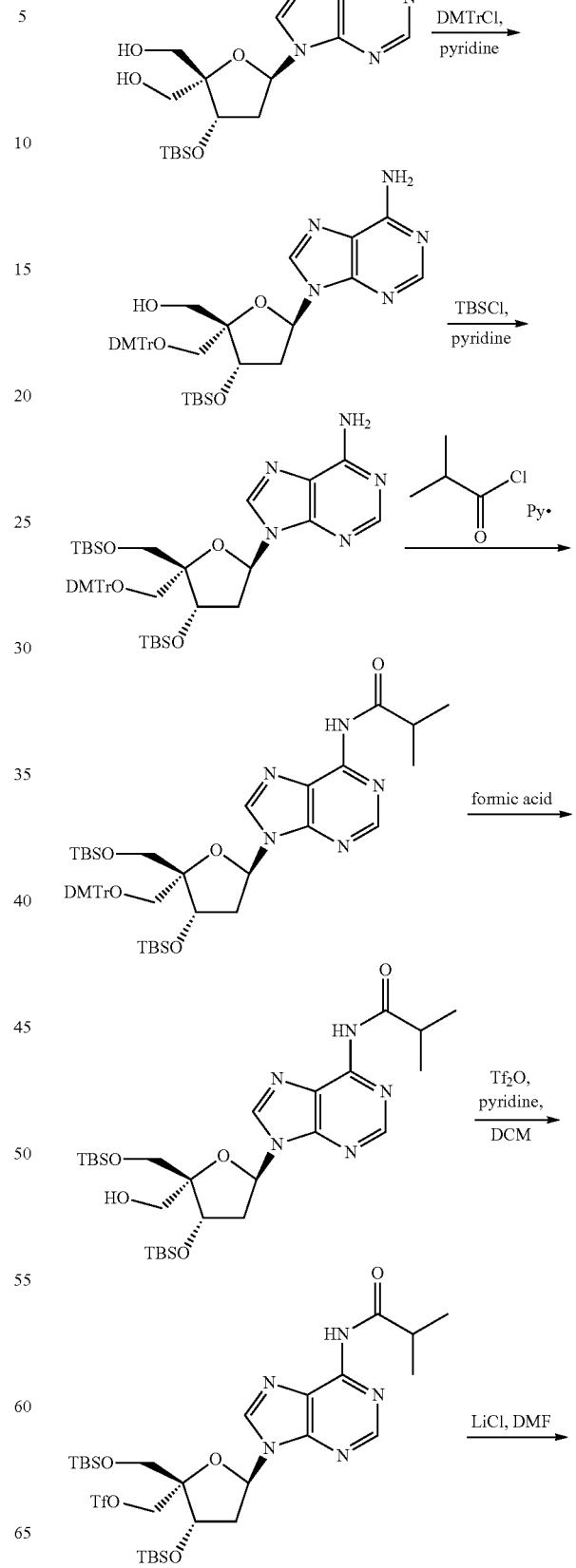

-continued

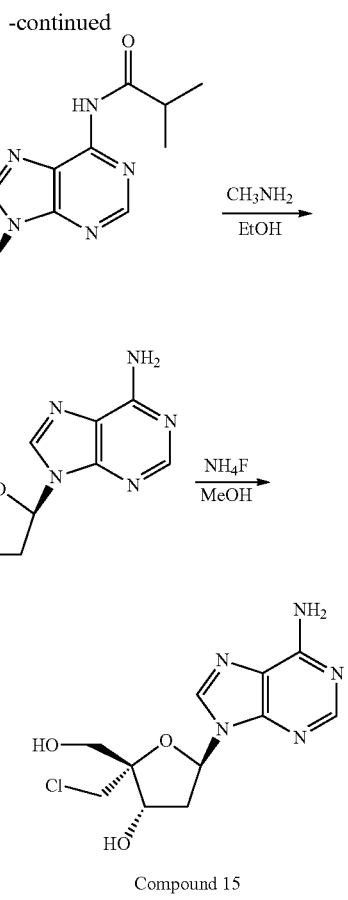

Compound 15

Step 1: A mixture of 2-deoxyadenosine (25 g, 99.5 mmol) and imidazole (40.6 g, 597.1 mmol) in DMF (100 mL) was added t-butyldimethylchlorosilane (44.8 g, 298.8 mmol) in portions at room temperature under air atmosphere. The resulting mixture was stirred for 2 h at room temperature under air atmosphere. The resulting mixture was diluted with water (500 mL). The resulting mixture was extracted with ethyl acetate (3×500 mL). The combined organic layers were washed with brine (3×250 mL), dried over anhydrous sodium sulfate. After filtration, the filtrate was concentrated under reduced pressure. The residue was purified by silica gel column chromatography, eluted with PE/EA (5:1) to afford 9-[(2R,4S,5R)-4-[(tert-butyldimethylsilyl) oxy]-5-{[(tert-butyldimethylsilyl) oxy] methyl} oxolan-2-yl] purin-6-amine (28 g, 58.3 mmol, 58.65%) as a white solid. LC-MS (ES, m/z): 480 [M+H$^+$].

Step 2: To a stirred mixture of 9-[(2R,4S,5R)-4-[(tert-butyldimethylsilyl) oxy]-5-{[(tert-butyldimethylsilyl) oxy] methyl} oxolan-2-yl] purin-6-amine (28 g, 58.3 mmol) in pyridine (100 mL) was added propanoyl chloride, 2-methyl (8.1 g, 75.8 mmol) dropwise at 0° C. under nitrogen atmosphere. The mixture was stirred for 30 min at 0° C. The reaction was quenched with water at room temperature. The resulting mixture was concentrated under reduced pressure. The residue was purified by silica gel column chromatography, eluted with dichlormethane/methyl alcohol (20/1) to afford N-{9-[(2R,4S,5R)-4-[(tert-butyldimethylsilyl) oxy]-5-{[(tert-butyldimethylsilyl) oxy] methyl} oxolan-2-yl] purin-6-yl}-2-methylpropanamide (24.5 g, 44.5 mmol, 76.35%) as an off-white solid. LC-MS (ES, m/z): 550 [M+H$^+$].

Step 3: To a stirred mixture of N-{9-[(2R,4S,5R)-4-[(tert-butyldimethylsilyl) oxy]-5-{[(tert-butyldimethylsilyl) oxy] methyl} oxolan-2-yl] purin-6-yl}-2-methylpropanamide (24.5 g, 44.5 mmol) in THF (200 mL) and H$_2$O (50 mL) was added TFA (50 mL) dropwise at 0° C. under nitrogen atmosphere. The mixture was stirred for 40 mins at 0° C. The resulting mixture was poured into water (300 mL), extracted with ethyl acetate (300 mL). The combined organic layers were washed with saturated sodium bicarbonate and then brine, dried over anhydrous sodium sulfate. After filtration, the filtrate was concentrated under reduced pressure. The residue was purified by silica gel column chromatography, eluted with petroleum ether/ethyl acetate (1/1) to afford N-{9-[(2R,4S,5R)-4-[(tert-butyldimethylsilyl) oxy]-5-(hydroxymethyl) oxolan-2-yl]purin-6-yl}-2-methylpropanamide (11.6 g, 26.6 mmol, 59.77%) as an off-white solid. LC-MS (ES, m/z): 436 [M+H$^+$].

Step 4: A mixture of N-{9-[(2R,4S,5R)-4-[(tert-butyldimethylsilyl) oxy]-5-(hydroxymethyl) oxolan-2-yl] purin-6-yl}-2-methylpropanamide (11.6 g, 26.6 mmol) and IBX (14.9 g, 53.2 mmol) in ACN (110 mL) was stirred for 1 h at 60° C. The mixture was cooled to room temperature, filtered, the filtrate was concentrated under vacuum. The residue was purified via silica gel chromatography (eluting with 1:5 ACN/EA) to give N-{9-[(2R,4S,5S)-4-[(tert-butyldimethylsilyl) oxy]-5-formyloxolan-2-yl] purin-6-yl}-2-methylpropanamide (9.1 g, 20.9 mmol, 78.81%) as a white solid. LC-MS4 (ES, m/z): 434 [M+H]$^+$.

Step 5: To a stirred solution of N-{9-[(2R,4S,5S)-4-[(tert-butyldimethylsilyl) oxy]-5-formyloxolan-2-yl] purin-6-yl}-2-methylpropanamide (9.1 g, 20.9 mmol) and HCHO (9.4 g, 314.7 mmol) in dioxane (90 mL) was added a solution of NaOH (2.5 g, 62.9 mmol) in water (9 mL). The mixture was stirred for 16 h at room temperature. Then NaBH$_4$ (1.6 g, 41.9 mmol) was added and stirred at 0° C. at 30 min. The reaction was quenched with sat. aq. NH$_4$Cl. The resulting mixture was diluted with water (100 mL), extracted with EA (5×100 mL), the pH of combined organic layer was adjusted to 5~6 with HOAc, washed with water (2×100 mL), dried over anhydrous sodium sulfate, filtered and concentrated under vacuum. The residue was purified via silica gel chromatography (eluting with 7% MeOH in DCM) to give N-{9-[(2R,4S)-4-[(tert-butyldimethylsilyl) oxy]-5,5-bis(hydroxymethyl)oxolan-2-yl] purin-6-yl}-2-methylpropanamide (2.68 g, 6.0 mmol, 27.42%) as a white solid. LC-MS (ES, m/z): 396 [M+H$^+$].

Step 6: A mixture of [(3S,5R)-5-(6-aminopurin-9-yl)-3-[(tert-butyldimethylsilyl) oxy]-2-(hydroxymethyl) oxolan-2-yl] methanol (2.4 g, 6.1 mmol) and 1-[chloro(4-methoxyphenyl) benzyl]-4-methoxybenzene (2.6 g, 7.8 mmol) in pyridine (20 mL) was stirred overnight at room temperature. The resulting mixture was diluted with ethyl acetate (100 mL) and washed with water (100 mL) and brine (100 mL). The organic layer was concentrated under vacuum. The residue was purified by silica gel column chromatography, eluted with CH$_2$Cl$_2$/MeOH (10:1) to afford [(2S,3S,5R)-5-(6-aminopurin-9-yl)-2-{[bis(4-methoxyphenyl) (phenyl) methoxy] methyl}-3-[(tert-butyldimethylsilyl) oxy] oxolan-2-yl] methanol (1.9 g, 2.7 mmol, 44.87%) as a yellow solid. LC-MS (ES, m/z): 698 [M+H]$^+$.

Step 7: A mixture of [(2S,3S,5R)-5-(6-aminopurin-9-yl)-2-{[bis(4-methoxyphenyl) (phenyl)methoxy] methyl}-3-[(tert-butyldimethylsilyl) oxy] oxolan-2-yl] methanol (1.9 g, 2.7 mmol) and imidazole (556 mg, 8.1 mmol) in DMF (20 mL) was added t-butyldimethylchlorosilane (613.3 mg, 4 mmol) in portions at room temperature under air atmosphere. The resulting mixture was stirred for 2 h at room temperature under air atmosphere. The resulting mixture was diluted with water (100 mL). The resulting mixture was extracted with ethyl acetate (3×100 mL). The combined organic layers were washed with brine (3×50 mL), dried over anhydrous sodium sulfate. After filtration, the filtrate was concentrated under reduced pressure. The resulting mixture was used in the next step directly without further purification. LC-MS (ES, m/z): 812 [M+H]⁺.

Step 8: 9-[(2R,4S,5R)-5-1{[bis(4-methoxyphenyl) (phenyl)methoxy] methyl}-4-[(tert-butyldimethylsilyl) oxy]-5-{[(tert-butyldimethylsilyl) oxy] methyl} oxolan-2-yl] purin-6-amine (2 g, 2.4 mmol) in Pyridine (20 mL) was added propanoyl chloride, 2-methyl (341.1 mg, 3.2 mmol) dropwise and stirred for 30 min at 0° C. The resulting mixture was concentrated under vacuum. The residue was purified by silica gel column chromatography, eluted with PE/EA (1:1) to afford N-{9-[(2R,4S,5R)-5-{[bis(4-methoxyphenyl) (phenyl)methoxy] methyl}-4-[(tert-butyldimethylsilyl) oxy]-5-{[(tert-butyldimethylsilyl) oxy] methyl} oxolan-2-yl] purin-6-yl}-2-methylpropanamide (1.02 g, 1.1 mmol, 46.95%) as a white solid. LC-MS (ES, m/z): 882[M+H]⁺.

Step 9: N-{9-[(2R,4S,5R)-5-1{[bis(4-methoxyphenyl) (phenyl)methoxy] methyl}-4-[(tert-butyldimethylsilyl) oxy]-5-{[(tert-butyldimethylsilyl) oxy] methyl} oxolan-2-yl] purin-6-yl}-2-methylpropanamide (1 g, 1.1 mmol) in a mixture of H₂O (2 mL) and formic acid (8 mL) was stirred at room temperature for 5 mins before quenching with MeOH. The resulting mixture was concentrated under vacuum. The residue was purified by silica gel column chromatography, eluted with PE/EA (1:1) to afford N-{9-[(2R,4S,5R)-4-[(tert-butyldimethylsilyl) oxy]-5-{[(tert-butyldimethylsilyl) oxy] methyl}-5-(hydroxymethyl) oxolan-2-yl] purin-6-yl}-2-methylpropanamide (600 mg, 1.1 mmol, 91.29%) as a white solid. LC-MS (ES, m/z): 580 [M+H⁺].

Step 10: To a stirred mixture of N-{9-[(2R,4S,5R)-4-[(tert-butyldimethylsilyl) oxy]-5-{[(tert-butyldimethylsilyl) oxy] methyl}-5-(hydroxymethyl) oxolan-2-yl] purin-6-yl1-2-methylpropanamide (590 mg, 1.1 mmol) and pyridine (241.4 mg, 3.1 mmol) in DCM (15) was added Tf₂O (287.1 mg, 1.1 mmol) dropwise at −30° C. then the mixture was stirred for 5 h. The reaction was quenched with water at room temperature. The resulting mixture was extracted with ethyl acetate (3×50 mL). The combined organic layers were washed with brine (3×50 mL), dried over anhydrous sodium sulfate. After filtration, the filtrate was concentrated under reduced pressure. The resulting mixture was concentrated under vacuum and was used in the next step without further purification. LC-MS (ES, m/z): 712 [M+H]⁺.

Step 11: A mixture of [(2S,3S,5R)-3-[(tert-butyldimethylsilyl) oxy]-2-{[(tert-butyldimethylsilyl) oxy] methyl}-5-[6-(2-methylpropanamido) purin-9-yl] oxolan-2-yl] methyl trifluoromethanesulfonate (600 mg, 0.8 mmol) and LiCl (107.1 mg, 2.5 mmol) in DMF (5 mL) was stirred for 3 h at room temperature. The resulting mixture was diluted with water (20 mL). The resulting mixture was extracted with ethyl acetate (3×100 mL). The combined organic layers were washed with brine (3×50 mL), dried over anhydrous sodium sulfate. After filtration, the filtrate was concentrated under reduced pressure. The resulting mixture was used in the next step directly without further purification. LC-MS (ES, m/z): 598/600 [M+H]⁺.

Step 12: A mixture of N-{9-[(2R,4S,5R)-4-[(tert-butyldimethylsilyl) oxy]-5-{[(tert-butyldimethylsilyl) oxy] methyl}-5-(chloromethyl) oxolan-2-yl] purin-6-yl}-2-methylpropanamide (580 mg, 0.9 mmol) in EtOH (10 mL) and methylamine (2M in THF, 5 mL) was stirred overnight at room temperature. The resulting mixture was used in the next step directly without further purification. LC-MS (ES, m/z): 528/530 [M+H]⁺.

Step 13: A mixture of 9-[(2R,4S,5R)-4-[(tert-butyldimethylsilyl) oxy]-5-{[(tert-butyldimethylsilyl) oxy] methyl}-5-(chloromethyl) oxolan-2-yl] purin-6-amine (300 mg, crude) and NH₄F (631 mg, 17.1 mmol) in MeOH (20 mL) was stirred for 2 days at 60° C. The mixture was allowed to cool down to room temperature before being concentrated under vacuum. The residue was purified by reverse flash chromatography with the following conditions: column, C18 silica gel; mobile phase, MeCN in Water (0.05% FA), 0% to 30% gradient in 30 min; detector, UV 254 nm to afford (2R,3S,5R)-5-(6-aminopurin-9-yl)-2-(chloromethyl)-2-(hydroxymethyl) oxolan-3-ol (11.3 mg, 0.07 mmol) as an off-white solid. LC-MS (ES, m/z): 300/302 [M+H]⁺ 97.8% purity. Conditions for the LCMS: (Column: XBridge Shield RP18, 50*4.6 mm, 3.5 μm; Mobile Phase A: Water/5 mM NH₄HCO₃, Mobile Phase B: Acetonitrile; Flow rate: 1.5000 mL/min; Gradient: 10% B to 95% B in 1.19 min, 95% B to 95% B in 0.58 min, 95% B to 10% B in 0.05 min; Wavelength: 254 nm; RT1(min): 0.661). ¹H NMR (400 MHz, DMSO-d₆) δ 8.35 (s, 1H), 8.14 (s, 1H), 7.32 (s, 2H), 6.41 (dd, J=8.3, 6.0 Hz, 1H), 5.54-5.35 (m, 2H), 4.59-4.52 (m, 1H), 3.81 (s, 2H), 3.66-3.59 (m, 2H), 3.05 (ddd, J=13.7, 8.4, 5.7 Hz, 1H), 2.35 (ddd, J=13.3, 6.1, 2.6 Hz, 1H).

Example 14—Synthesis of Compound 16: 4-amino-1-((2R,4S,5R)-5-cyclopropyl-4-hydroxy-5-(hydroxymethyl)tetrahydrofuran-2-yl)pyrimidin-2(1H)-one

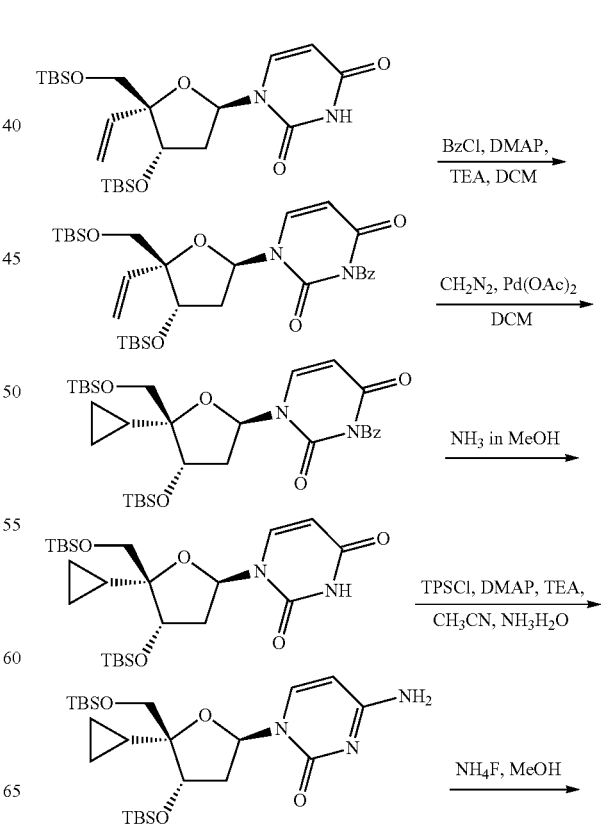

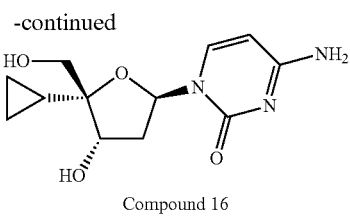

Compound 16

Step 1: To a stirred solution of 1-[(2R,4S,5R)-4-[(tert-butyldimethylsilyl) oxy]-5-{[(tert-butyldimethylsilyl) oxy] methyl}-5-ethenyloxolan-2-yl]-3H-pyrimidine-2,4-dione (1.2 g, 2.4 mmol, synthesis depicted in Example 1) and DMAP (607 mg, 4.9 mmol) and TEA (1.5 ml) in dichloromethane (20 ml) was added benzoyl chloride (698 mg, 4.9 mmol) dropwise at room temperature under nitrogen atmosphere. The resulting mixture was stirred for overnight at room temperature under nitrogen atmosphere. The resulting mixture was diluted with water (200 mL). The resulting mixture was extracted with ethyl acetate (3×200 mL). The combined organic layers were washed with brine (3×100 mL), dried over anhydrous sodium sulfate. After filtration, the filtrate was concentrated under reduced pressure. The residue was purified by silica gel column chromatography, eluted with petroleum ether/ethyl acetate (1:1) to afford 3-benzoyl-1-[(2R,4S,5R)-4-[(tert-butyldimethylsilyl) oxy]-5-{[(tert-butyldimethylsilyl) oxy]methyl}-5-ethenyloxolan-2-yl] pyrimidine-2,4-dione (1.2 g, 2 mmol, 82.26%) as a white solid. LC-MS (ES, m/z): 587 (M+H$^+$)

Step 2: To a stirred mixture of 3-benzoyl-1-[(2R,4S,5R)-4-[(tert-butyldimethylsilyl) oxy]-5-{[(tert-butyldimethylsilyl) oxy] methyl}-5-ethenyloxolan-2-yl] pyrimidine-2,4-dione (600 mg, 1.0 mmol) and (acetyloxy)palladio acetate (23 mg, 0.1 mmol) in dichloromethane (15 ml) was added diazomethane in ether (80 mL) dropwise at room temperature under nitrogen atmosphere. The resulting mixture was stirred for overnight at room temperature under nitrogen atmosphere. The resulting mixture was diluted with water (200 mL). The resulting mixture was extracted with dichloromethane (3×200 mL). The combined organic layers were washed with brine (3×100 mL), dried over anhydrous sodium sulfate. After filtration, the filtrate was concentrated under reduced pressure. The residue was purified by Prep-TLC with petroleum ether/ethyl acetate (1:1) to afford 3-benzoyl-1-[(2R,4S,5R)-4-[(tert-butyldimethylsilyl) oxy]-5-{[(tert-butyldimethylsilyl) oxy] methyl}-5-cyclopropyloxolan-2-yl] pyrimidine-2,4-dione (440 mg, 0.73 mmol, 71.62%) as a white solid. LC-MS (ES, m/z): 601 (M+H$^+$)

Step 3: A solution of 3-benzoyl-1-[(2R,4S,5R)-4-[(tert-butyldimethylsilyl) oxy]-5-{[(tert-butyldimethylsilyl) oxy] methyl}-5-cyclopropyloxolan-2-yl] pyrimidine-2,4-dione (200 mg, 0.3 mmol) and ammonia (4 mL, 7 M in methyl alcohol) was stirred for overnight at room temperature under nitrogen atmosphere. The resulting mixture was concentrated under vacuum. The residue was purified by Prep-TLC with petroleum ether/ethyl acetate (1:1) to afford 1-[(2R,4S,5R)-4-[(tert-butyldimethylsilyl) oxy]-5-{[(tert-butyldimethylsilyl) oxy] methyl}-5-cyclopropyloxolan-2-yl]-3H-pyrimidine-2,4-dione (90 mg, 0.1 mmol, 54.43%) as a white solid. LC-MS (ES, m/z): 497 (M+H$^+$)

Step 4: A solution of 1-[(2R,4S,5R)-4-[(tert-butyldimethylsilyl) oxy]-5-{[(tert-butyldimethylsilyl) oxy] methyl}-5-cyclopropyloxolan-2-yl]-3H-pyrimidine-2,4-dione (90 mg, 0.1 mmol) in acetonitrile (2 mL) was treated with DMAP (44 mg, 0.3 mmol) and TEA (36 mg, 0.3 mmol) for 30 min at room temperature under nitrogen atmosphere followed by the addition of 2,4,6-triisopropylbenzenesulfonyl chloride (109 mg, 0.3 mmol) in portions at room temperature. The resulting mixture was stirred for overnight at room temperature under nitrogen atmosphere. To the above mixture was added ammonium hydroxide (12 mg, 0.3 mmol) dropwise at room temperature. The resulting mixture was stirred for additional 1 h at room temperature. The resulting mixture was concentrated under vacuum. The residue was purified by Prep-TLC with dichloromethane/methyl alcohol (10:1) to afford 4-amino-1-[(2R,4S,5R)-4-[(tert-butyldimethylsilyl) oxy]-5-{[(tert-butyldimethylsilyl) oxy] methyl}-5-cyclopropyloxolan-2-yl]pyrimidin-2-one (80 mg, 0.1 mmol, 89.07%) as a white solid. LC-MS (ES, m/z): 496 (M+H$^+$)

Step 5: A mixture of 4-amino-1-[(2R,4S,5R)-4-[(tert-butyldimethylsilyl) oxy]-5-{[(tert-butyldimethylsilyl) oxy] methyl}-5-cyclopropyloxolan-2-yl] pyrimidin-2-one (80 mg, 0.1 mmol) and NH$_4$F (179 mg, 4.8 mmol) in methyl alcohol (5 ml) was stirred for 2 days at 60° C. under nitrogen atmosphere. The resulting mixture was concentrated under vacuum. The crude product was purified by Prep-HPLC with the following conditions (Column: XBridge Prep OBD C18 Column, 30*150 mm, 5 μm; Mobile Phase A: Water (10 mmol/L NH4HCO3+0.1% NH$_3$·H$_2$O), Mobile Phase B: ACN; Flow rate: 60 mL/min; Gradient: 2% B to 14% B in 8 min, 14% B; Wavelength: 254/220 nm; RT1(min): 7.52) to afford 4-amino-1-[(2R,4S,5R)-5-cyclopropyl-4-hydroxy-5-(hydroxymethyl) oxolan-2-yl] pyrimidin-2-one (17.6 mg, 0.066 mmol, 40.20%) as a white solid. LC-MS (ES, m/z): 268 (M+H$^+$) 98.5% purity. Conditions for the LCMS: (Column: Shim Pack Scepter C18 Column, 33*3.0 mm, 3.0 μm; Mobile Phase A: Water/6.5 mM NH4HCO3, Mobile Phase B: Acetonitrile; Flow rate: 1.2000 mL/min; Gradient: 10% B to 95% B in 1.20 min, 95% B to 95% B in 1.80 min, 95% B to 10% B in 1.82 min; Wavelength: 254/220 nm; RT1 (min): 0.512). $^1$H NMR (300 MHz, DMSO-d$_6$) δ 8.00 (d, J=7.4 Hz, 1H), 7.05 (d, J=15.9 Hz, 2H), 5.93 (dd, J=6.5, 5.1 Hz, 1H), 5.66 (d, J=7.4 Hz, 1H), 5.32-4.93 (m, 2H), 4.58-4.21 (m, 1H), 3.54-3.41 (m, 2H), 2.25-2.14 (m, 1H), 2.05 (dd, J=7.0, 5.3 Hz, 1H), 0.91 (td, J=8.3, 4.2 Hz, 1H), 0.47-0.05 (m, 4H).

Example 15—Synthesis of Compound 17: 4-amino-1-((2R,3S,4S,5R)-5-(chloromethyl)-3-ethynyl-4-hydroxy-5-(hydroxymethyl)tetrahydrofuran-2-yl) pyrimidin-2(1H)-one

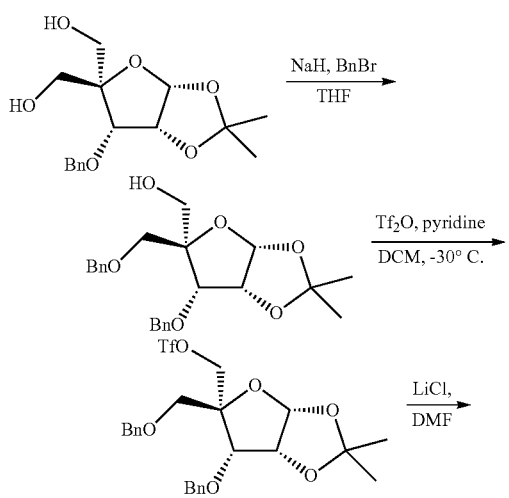

225
-continued
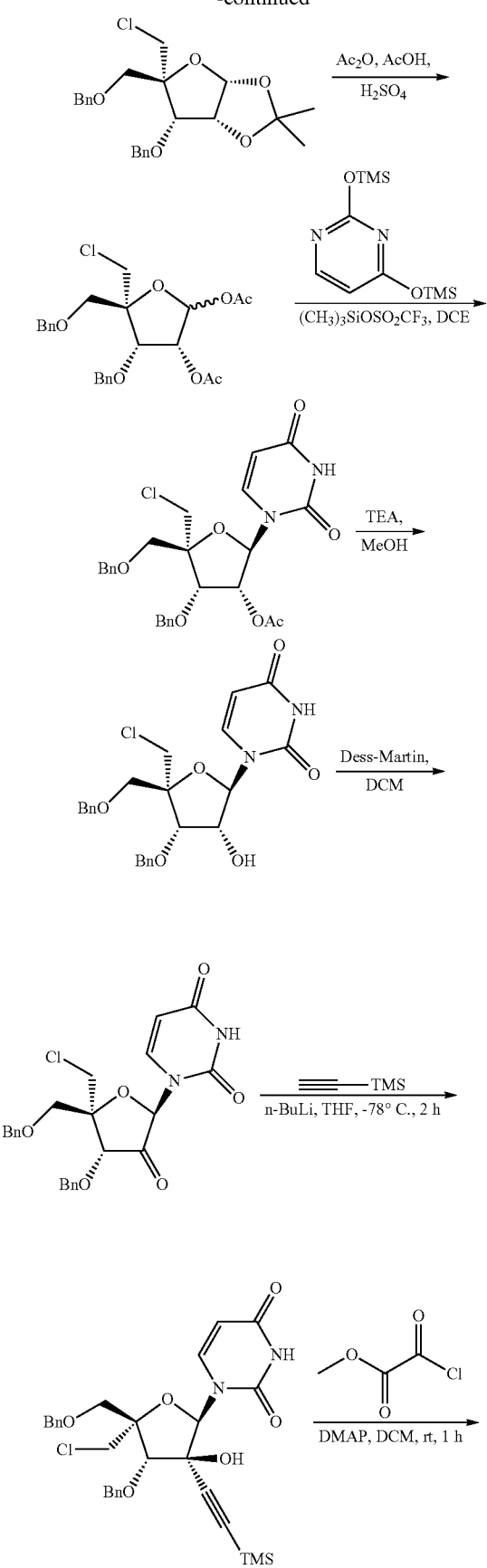
226
-continued
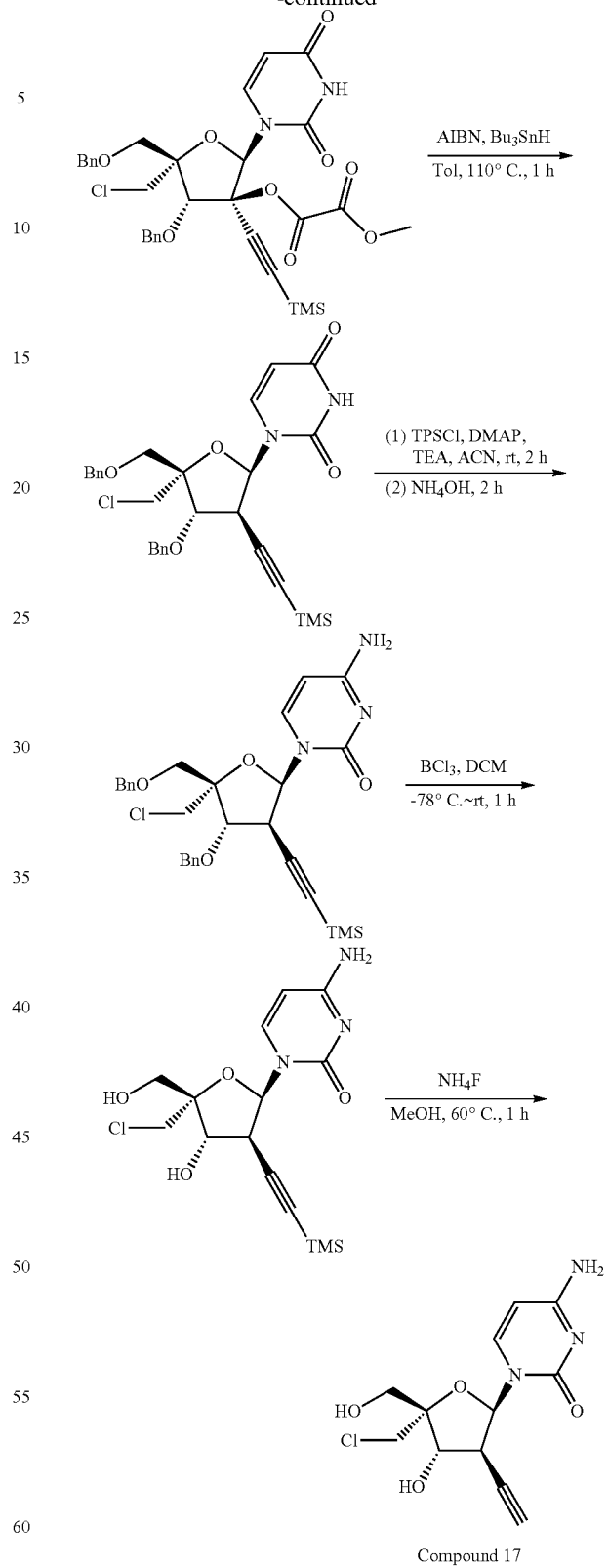
Compound 17
Step 1: A solution of ((3aR,6S,6aR)-6-(benzyloxy)-2,2-dimethyltetrahydrofuro[2,3-d][1,3]dioxole-5,5-diyl)dimethanol (20 g, 64.4 mmol) in THF (200 mL) was treated with NaH (2.5 g, 64.4 mmol, 60%) for 0.5 h at 0° C. under nitrogen atmosphere followed by the addition of BnBr (7.6 mL, 64.4 mmol) in portions at 0° C. The resulting mixture was stirred for additional overnight at room temperature. The reaction was quenched by the addition of Water (20 mL) at 0° C. The reaction was quenched by the addition of Water (20 mL) at 0° C. The resulting mixture was extracted with EtOAc (3×200 mL). The combined organic layers were washed with water (3×200 mL), dried over anhydrous $Na_2SO_4$. After filtration, the filtrate was concentrated under reduced pressure. The resulting mixture was concentrated under reduced pressure. The residue was purified by silica gel column chromatography, eluted with PE/EA (4:1) to afford ((3aR,5R,6S,6aR)-6-(benzyloxy)-5-((benzyloxy) methyl)-2,2-dimethyltetrahydrofuro[2,3-d][1,3]dioxol-5-yl) methanol (17 g, 42.4 mmol, 65.87%) as a white oil. LC-MS (ES, m/z): 418/420 [M+NH$_4$]$^+$.

Step 2: To a stirred solution of ((3aR,5R,6S,6aR)-6-(benzyloxy)-5-((benzyloxy)methyl)-2,2-dimethyltetrahydrofuro[2,3-d][1,3]dioxol-5-yl)methanol (17 g, 42.4 mmol) in DCM (200 mL) were added Tf$_2$O (20.3 g, 72.1 mmol) and pyridine (16.7 g, 212.2 mmol) in portions at −35° C. under nitrogen atmosphere. The resulting mixture was stirred for additional 1 h at −35° C. The resulting mixture was extracted with EtOAc (3×100 mL). The combined organic layers were washed with water (3×100 mL), dried over anhydrous $Na_2SO_4$. After filtration, the filtrate was concentrated under reduced pressure. The resulting mixture was concentrated under reduced pressure. The crude product mixture was used in the next step directly without further purification. This resulted in ((3aR,5S,6S,6aR)-6-(benzyloxy)-5-((benzyloxy) methyl)-2,2-dimethyltetrahydrofuro[2,3-d][1,3]dioxol-5-yl) methyl trifluoromethanesulfonate (22 g, 41.3 mmol, 97.32%) as a white solid. LC-MS (ES, m/z): 550/552 [M+NH$_4$]$^+$.

Step 3: To a stirred solution of ((3aR,5S,6S,6aR)-6-(benzyloxy)-5-((benzyloxy)methyl)-2,2-dimethyltetrahydrofuro[2,3-d][1,3]dioxol-5-yl)methyl trifluoromethanesulfonate (22 g, 41.3 mmol) in DMF (200 mL) was added LiCl (7 g, 165.2 mmol) in portions at 60° C. under nitrogen atmosphere. The resulting mixture was stirred for additional 2 h at 60° C. The resulting mixture was diluted with water (100 mL). The resulting mixture was extracted with EtOAc (3×100 mL). The combined organic layers were washed with Water (3×100 mL), dried over anhydrous $Na_2SO_4$. After filtration, the filtrate was concentrated under reduced pressure. The residue was purified by silica gel column chromatography, eluted with PE/EA (10:1) to afford (3aR,5R,6S,6aR)-6-(benzyloxy)-5-((benzyloxy)methyl)-5-(chloromethyl)-2,2-dimethyltetrahydrofuro[2,3-d][1,3]dioxole (9 g, 21.5 mmol, 52.00%) as a yellow oil. LC-MS (ES, m/z): 436/438 [M+NH$_4$]$^+$.

Step 4: To a stirred solution of (3aR,5R,6S,6aR)-6-(benzyloxy)-5-((benzyloxy)methyl)-5-(chloromethyl)-2,2-dimethyltetrahydrofuro[2,3-d][1,3]dioxole (9 g, 21.4 mmol) in AcOH (80 mL) were added Ac$_2$O (29.6 g, 290 mmol) and H$_2$SO$_4$ (252.8 mg, 2.5 mmol) in portions at 0° C. under nitrogen atmosphere. The resulting mixture was stirred for additional 2 h at room temperature. The residue was basified to pH 7 with saturated NaHCO$_3$(aq.). The resulting mixture was extracted with EtOAc (3×150 mL). The combined organic layers were washed with NaHCO$_3$ (3×100 mL), dried over anhydrous Na$_2$SO$_4$. After filtration, the filtrate was concentrated under reduced pressure. The residue was purified by silica gel column chromatography, eluted with PE/EA (4:1) to afford (3R,4S,5R)-2-(acetyloxy)-4-(benzyloxy)-5-[(benzyloxy)methyl]-5-(chloromethyl) oxolan-3-yl acetate (7.3 g, 15.8 mmol, 73.40%) as a yellow oil. LC-MS (ES, m/z): 480/482 [M+NH$_4$]$^+$.

Step 5: To a stirred solution of 2,4-bis[(trimethylsilyl)oxy]pyrimidine (7.3 g, 15.8 mmol) in DCE (243 mL) was added (3R,4S,5R)-2-(acetyloxy)-4-(benzyloxy)-5-[(benzyloxy) methyl]-5-(chloromethyl) oxolan-3-yl acetate (10.1 g, 21.3 mmol) and TMSOTf (5 mL) dropwise at 0° C. under N$_2$ atmosphere. The resulting mixture was stirred for 18 h at 35° C. under N$_2$ atmosphere. The reaction was quenched by the addition of NaHCO$_3$. The resulting mixture was extracted with EA (2×100 ml). The combined organic layers were washed with brine (100 mL), dried over anhydrous Na$_2$SO$_4$. After filtration, the filtrate was concentrated under reduced pressure to give (2R,3R,4S,5R)-4-(benzyloxy)-5-[(benzyloxy)methyl]-5-(chloromethyl)-2-(2,4-dioxo-3H-pyrimidin-1-yl) oxolan-3-yl acetate (7 g, 13.6 mmol, 89.9%) as a yellow oil. LC-MS (ES, m/z): 515/517 [M+H]$^+$.

Step 6: To a stirred solution of (2R,3R,4S,5R)-4-(benzyloxy)-5-[(benzyloxy)methyl]-5-(chloromethyl)-2-(2,4-dioxo-3H-pyrimidin-1-yl) oxolan-3-yl acetate (7 g, 13.5 mmol) in MeOH (25 mL) was added TEA (2.3 g, 230.7 mmol). The resulting mixture was stirred for 5 h at 60° C. The resulting mixture was concentrated under vacuum. The residue was purified by silica gel column chromatography, eluted with DCM/MeOH (10/1) to afford 1-[(2R,3R,4S,5R)-4-(benzyloxy)-5-[(benzyloxy)methyl]-5-(chloromethyl)-3-hydroxyoxolan-2-yl]-3H-pyrimidine-2,4-dione (5.3 g, 11.2 mmol, 82.6%) as a white solid. LC-MS (ES, m/z): 473/475 [M+H]$^+$.

Step 7: To a stirred solution of 1-[(2R,3R,4S,5R)-4-(benzyloxy)-5-[(benzyloxy) methyl]-5-(chloromethyl)-3-hydroxyoxolan-2-yl]-3H-pyrimidine-2,4-dione (5.3 g, 11.2 mmol) in DCM (50 mL) was added Dess-Martin (7.5 g, 17.8 mmol). The resulting mixture was stirred for 1 h at 30° C. LCMS showed the reaction was complete. The reaction was quenched with Na$_2$S2O3 at 0° C. The resulting mixture was extracted with EA (2×200 mL). The combined organic layers were washed with brine (100 mL), dried over anhydrous Na$_2$SO$_4$. After filtration, the filtrate was concentrated under reduced pressure to give 1-[(2R,4R,5R)-4-(benzyloxy)-5-[(benzyloxy)methyl]-5-(chloromethyl)-3-oxooxolan-2-yl]-3H-pyrimidine-2,4-dione (2.5 g, 5.3 mmol, 89.67%) as a yellow oil. LC-MS (ES, m/z): 471/473 [M+H]$^+$.

Step 8: To a stirred solution of trimethylsilylacetylene (312.9 mg, 3.19 mmol) in THF (15 mL) were added n-BuLi (1.27 mL, 3.19 mmol) dropwise at −78° C. under N$_2$ atmosphere. The resulting mixture was stirred for 0.5 h at −78° C. under N$_2$ atmosphere. To the above mixture was added 1-[(2R,4R,5R)-4-(benzyloxy)-5-[(benzyloxy) methyl]-5-(chloromethyl)-3-oxooxolan-2-yl]-3H-pyrimidine-2,4-dione (500 mg, 1.06 mmol) in THF (5 mL) dropwise at −78° C. The resulting mixture was stirred for additional 0.5 h at −78° C. LCMS showed the reaction was completed. The reaction was quenched by the addition of aqueous solution of NH$_4$Cl (5 mL) at −78° C. The resulting mixture was extracted with EA (2×50 mL). The combined organic layers were washed with brine (20 mL), dried over anhydrous Na$_2$SO$_4$. After filtration, the filtrate was concentrated under reduced pressure. The residue was purified by Prep-TLC (DCM/MeOH=12/1) to afford 1-[(2R,3S,4S,5R)-4-(benzyloxy)-5-[(benzyloxy)methyl]-5-(chloromethyl)-3-hydroxy-3-[2-(trimethylsilyl) ethynyl] oxolan-2-yl]-3H-pyrimidine-2,4-dione (359 mg, 0.63 mmol, 59.41%) as a yellow oil. LC-MS (ES, m/z): 569/571 [M+H]$^+$.

Step 9: To a stirred solution of 1-[(2R,3S,4S,5R)-4-(benzyloxy)-5-[(benzyloxy) methyl]-5-(chloromethyl)-3- hydroxy-3-[2-(trimethylsilyl) ethynyl] oxolan-2-yl]-3H-pyrimidine-2,4-dione (359 mg, 0.63 mmol) in DCM (5 mL) was added DMAP (154.1 mg, 1.26 mmol) and methyl oxalochloridate (115.9 mg, 0.95 mmol) dropwise at 0° C. The resulting mixture was stirred for 10 min at room temperature. LCMS showed the reaction was ok. The reaction was quenched with water (20 mL). The resulting mixture was extracted with DCM (2×20 mL). The combined organic layers were washed with brine (20 mL), dried over anhydrous $Na_2SO_4$. After filtration, the filtrate was concentrated under reduced pressure to give (2R,3S,4S,5R)-4-(benzyloxy)-5-[(benzyloxy)methyl]-5-(chloromethyl)-2-(2,4-dioxo-3H-pyrimidin-1-yl)-3-[2-(trimethylsilyl) ethynyl] oxolan-3-yl methyl oxalate (380 mg, 0.58 mmol, 91.95%) as a white solid. LC-MS (ES, m/z): 655/657 [M+H]$^+$.

Step 10: To a stirred solution of (2R,3S,4S,5R)-4-(benzyloxy)-5-[(benzyloxy)methyl]-5-(chloromethyl)-2-(2,4-dioxo-3H-pyrimidin-1-yl)-3-[2-(trimethylsilyl) ethynyl] oxolan-3-yl methyl oxalate (380 mg, 0.58 mmol) in toluene (6 mL) was added AIBN (28.5 mg, 0.17 mmol) and n-$Bu_3SnH$ (338.7 mg, 1.16 mmol) under $N_2$ atmosphere. The resulting mixture was stirred for 1 h at 100° C. under $N_2$ atmosphere. The resulting mixture was concentrated under vacuum. The residue was purified by Prep-TLC (DCM/MeOH) to afford 1-[(2R,3S,4S,5R)-4-(benzyloxy)-5-[(benzyloxy)methyl]-5-(chloromethyl)-3-[2-(trimethylsilyl) ethynyl] oxolan-2-yl]-3H-pyrimidine-2,4-dione (60 mg, 0.11 mmol, 14.21%) as a yellow oil. LC-MS9 (ES, m/z): 553/555 [M+H]$^+$.

Step 11: To a stirred solution of 1-[(2R,3S,4S,5R)-4-(benzyloxy)-5-[(benzyloxy)methyl]-5-(chloromethyl)-3-[2-(trimethylsilyl) ethynyl] oxolan-2-yl]-3H-pyrimidine-2,4-dione (60 mg, 0.11 mmol) in MeCN (2 mL) was added TEA (32.9 mg, 0.32 mmol), DMAP (26.5 mg, 0.22 mmol) and TPSCl (65.5 mg, 0.22 mmol). The resulting mixture was stirred for 18 h at room temperature. To the above mixture was added $NH_3 \cdot H_2O$ (19 mg, 0.54 mmol). The resulting mixture was stirred for additional 1 h at room temperature. LCMS showed the reaction was complete. The resulting mixture was concentrated under reduced pressure. The residue was purified by Prep-TLC (DCM/MeOH 12/1) to afford 4-amino-1-[(2R,3S,4S,5R)-4-(benzyloxy)-5-[(benzyloxy) methyl]-5-(chloromethyl)-3-[2-(trimethylsilyl) ethynyl] oxolan-2-yl]pyrimidin-2-one (50 mg, 0.09 mmol, 83.47%) as a yellow oil. LC-MS (ES, m/z): 552/554 [M+H]$^+$.

Step 12: To a stirred solution of 4-amino-1-[(2R,3S,4S,5R)-4-(benzyloxy)-5-[(benzyloxy)methyl]-5-(chloromethyl)-3-[2-(trimethylsilyl) ethynyl] oxolan-2-yl] pyrimidin-2-one (50 mg, 0.09 mmol) in DCM (5 mL) was added $BCl_3$ (0.9 mL, 0.9 mmol) dropwise at −78° C. under $N_2$ atmosphere. Then the reaction mixture was warmed to room temperature. LCMS showed the reaction was complete. The resulting mixture was concentrated under vacuum. The residue was purified by reverse flash chromatography with the following conditions: column, C18 silica gel; mobile phase, ACN; 10 mM $NH_4HCO_3$; 10% to 50% gradient in 10 min; detector, UV 254 nm. This resulted in 4-amino-1-[(2R, 3S,4S,5R)-5-(chloromethyl)-4-hydroxy-5-(hydroxymethyl)-3-[2-(trimethylsilyl) ethynyl] oxolan-2-yl] pyrimidin-2-one (20 mg, 0.05 mmol, 59.40%) as a white solid. LC-MS (ES, m/z): 372/374 [M+H]$^+$.

Step 13: To a stirred solution of 4-amino-1-[(2R,3S,4S,5R)-5-(chloromethyl)-4-hydroxy-5-(hydroxymethyl)-3-[2-(trimethylsilyl) ethynyl] oxolan-2-yl] pyrimidin-2-one (15 mg, 0.04 mmol) in MeOH (2 mL) was added $NH_4F$ (29.9 mg, 0.80 mmol). The resulting mixture was stirred for 36 h at 60° C. LCMS showed the reaction was complete. The resulting mixture was concentrated under vacuum. The crude product was purified by Prep-HPLC with the following conditions (Column: XBridge Prep OBD C18 Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 15% B to 28% B in 8 min, 28% B; Wavelength: 254/220 nm) to afford 4-amino-1-[(2R,3S, 4S,5R)-5-(chloromethyl)-3-ethynyl-4-hydroxy-5-(hydroxymethyl) oxolan-2-yl]pyrimidin-2-one (10.9 mg, 0.04 mmol, 89.00%) as a white solid. LC-MS (ES, m/z): 300/302 [M+H]$^+$. 98.7% purity. Conditions for the LCMS: (Column: HALO C18, 30*3 mm, 2.7 μm; Mobile Phase A: Water+ 0.05% TFA, Mobile Phase B: Acetonitrile; Flow rate: 1.5000 mL/min; Gradient: 5% B to 40% B in 1.90 min, 40% B to 100% B in 0.20 min, 100% B to 100% B in 0.50 min, 100% B to 5% B in 0.10 min; Wavelength: 210 nm; RT1(min): 0.668). $^1$H NMR (300 MHz, DMSO-$d_6$) δ 7.76 (d, J=7.4 Hz, 1H), 7.16 (s, 1H), 7.08 (s, 1H), 6.26 (d, J=7.2 Hz, 1H), 6.05 (d, J=5.3 Hz, 1H), 5.70 (d, J=7.4 Hz, 1H), 5.32 (t, J=5.3 Hz, 1H), 4.49-4.42 (m, 1H), 3.92 (d, J=11.9 Hz, 1H), 3.77-3.49 (m, 4H), 3.11 (d, J=2.6 Hz, 1H).

Example 16—Synthesis of Compound 18: 5-amino-2-((2R,4S,5R)-5-(chloromethyl)-4-hydroxy-5-(hydroxymethyl)tetrahydrofuran-2-yl)-1,2,4-triazin-3 (2H)-one

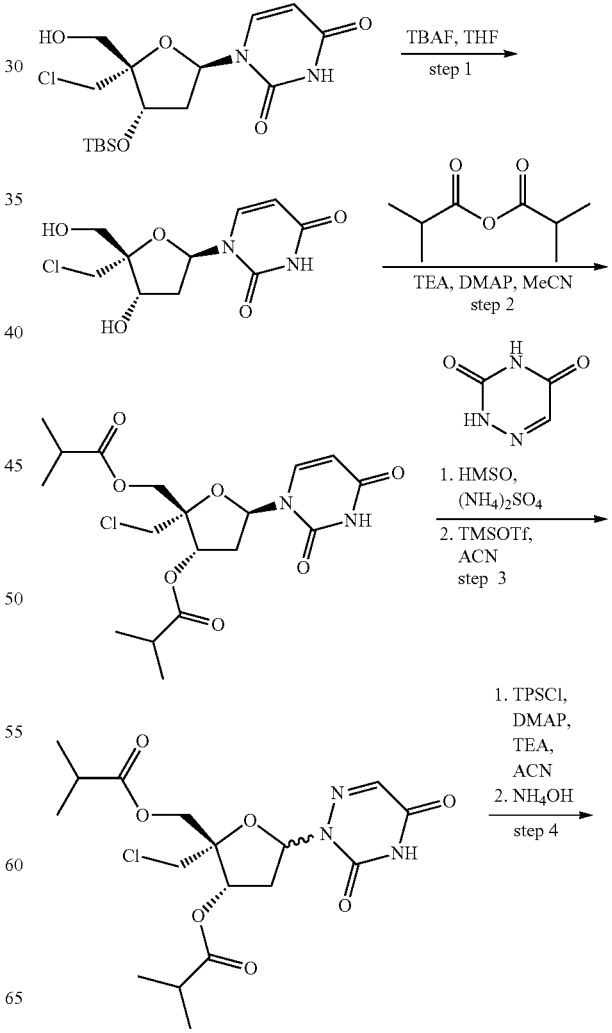

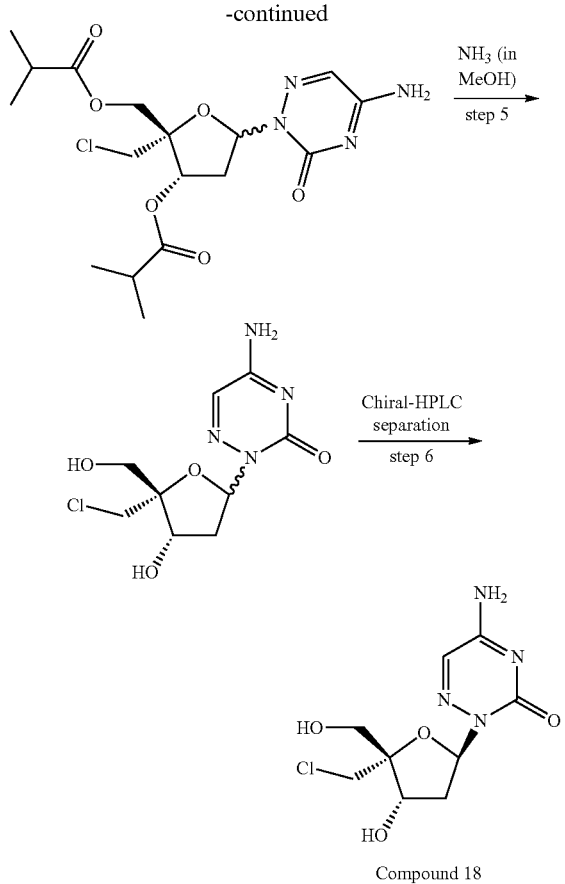

Compound 18

Step 1: To a solution of 1-[(2R,4S,5R)-4-[(tert-butyldimethylsilyl) oxy]-5-(chloromethyl)-5-(hydroxymethyl) oxolan-2-yl]-3H-pyrimidine-2,4-dione (1.8 g, 4.8 mmol) in tetrahydrofuran (16 mL) was added a solution of tetranbutylammonium fluoride in tetrahydrofuran (24 mL, 1.0 M) under nitrogen atmosphere. The mixture was stirred for 2 h at room temperature. The resulting mixture was concentrated under reduced pressure and purified by silica gel column chromatography, eluted with dichloromethane/methanol (10:1) to afford 1-[(2R,4S,5R)-5-(chloromethyl)-4-hydroxy-5-(hydroxymethyl) oxolan-2-yl]-3H-pyrimidine-2,4-dione (1.2 g, 4.3 mmol, 97%) as a white solid. LC-MS: (ES, m/z): 277/279 (M+H$^+$).

Step 2: To a solution of 1-[(2R,4S,5R)-5-(chloromethyl)-4-hydroxy-5-(hydroxymethyl) oxolan-2-yl]-3H-pyrimidine-2,4-dione (1.2 g, 4.3 mmol) in acetonitrile (50 mL) was added triethylamine (1.0 g, 10.1 mmol), 4-dimethylaminopyridine (61.8 mg, 0.5 mmol) under nitrogen atmosphere. Then was added 2-methylpropanoyl 2-methylpropanoate (3.2 g, 20.2 mmol) and stirred overnight at 40° C. The reaction was quenched by the addition of ice water. The resulting mixture was extracted with ethyl acetate. The combined organic layers were washed with aqueous sodium bicarbonate and sodium chloride solution, dried over anhydrous sodium sulfate. After filtration, the filtrate was concentrated under reduced pressure. The residue was purified by silica gel column chromatography, eluted with petroleum ether/ethyl acetate (1:3) to afford (2R,3S,5R)-2-(chloromethyl)-5-(2,4-dioxo-3,4-dihydropyrimidin-1(2H)-yl)-2-((isobutyryloxy)methyl) tetrahydrofuran-3-yl isobutyrate (1.5 g, 3.6 mmol, 83%) as a white solid. LC-MS: (ES, m/z): 417/419 (M+H$^+$).

Step 3: To a solution of azauracil (1.5 g, 13.0 mmol) in hexamethyldisilazane (20 mL) was added ammonium sulfate (19 mg, 0.1 mmol) under nitrogen atmosphere. The mixture was stirred overnight at 110° C. Hexamethyldisilazane was evaporated to give a crude product. To a solution of the crude product in acetonitrile (20 mL) was added (2R,3S,5R)-2-(chloromethyl)-5-(2,4-dioxo-3,4-dihydropyrimidin-1(2H)-yl)-2-((isobutyryloxy)methyl) tetrahydrofuran-3-yl isobutyrate (600 mg, 1.4 mmol) and trimethylsilyl trifluoromethanesulfonate (1.6 g, 7.2 mmol) under nitrogen atmosphere. The mixture was stirred overnight at 60° C. The reaction was quenched by the addition of aqueous sodium bicarbonate at 0° C. and extracted with ethyl acetate. The combined organic layers were washed with sodium chloride solution, dried over anhydrous sodium sulfate. After filtration, the filtrate was concentrated under reduced pressure. The residue was purified by silica gel column chromatography, eluted with dichloromethane/methanol (20:1) to afford (2R,3S)-2-(chloromethyl)-5-(3,5-dioxo-4,5-dihydro-1,2,4-triazin-2(3H)-yl)-2-((isobutyryloxy)methyl) tetrahydrofuran-3-yl isobutyrate (300 mg, 0.7 mmol, 50%) as a white semi-solid. LC-MS: (ES, m/z): 418/420 (M+H$^+$).

Step 4: To a solution of (2R,3S)-2-(chloromethyl)-5-(3,5-dioxo-4,5-dihydro-1,2,4-triazin-2(3H)-yl)-2-((isobutyryloxy)methyl) tetrahydrofuran-3-yl isobutyrate (300 mg, 0.7 mmol), 4-dimethylaminopyridine (175 mg, 1.4 mmol) and triethylamine (145 mg, 1.4 mmol) in acetonitrile (15 mL) was added 2,4,6-tris(propan-2-yl) benzene-1-sulfonyl chloride (435 mg, 1.4 mmol) under nitrogen atmosphere. The mixture was stirred overnight at 25° C. Then was added concentrated ammonium hydroxide (3 mL) and stirred 30 mins under nitrogen atmosphere. The resulting mixture was concentrated under reduced pressure. The residue was purified by silica gel column chromatography, eluted with dichloromethane/methanol (10:1) to afford [(2R,3S)-5-(5-amino-3-oxo-1,2,4-triazin-2-yl)-2-(chloromethyl)-3-[(2-methylpropanoyl) oxy] oxolan-2-yl] methyl 2-methylpropanoate (210 mg, 0.5 mmol, 70%) as a light yellow solid. LC-MS: (ES, m/z): 417/419 (M+H$^+$).

Step 5: To a solution of NH$_3$(g) in methanol (7 ml, 7.0 M) was added [(2R,3S)-5-(5-amino-3-oxo-1,2,4-triazin-2-yl)-2-(chloromethyl)-3-[(2-methylpropanoyl) oxy] oxolan-2-yl] methyl 2-methylpropanoate (210 mg, 0.5 mmol), the mixture was stirred overnight at 30° C. The resulting mixture was concentrated under reduced pressure. The crude product was purified by Prep-HPLC with the following conditions (Column: Xselect CSH C18 OBD Column 30*150 mm 5 μm, n; Mobile Phase A: Water (0.1% FA), Mobile Phase B: ACN; Flow rate: 60 mL/min; Gradient: 1% B to 4% B in 10 min, 4% B; Wavelength: 254 nm; RT1(min): 7.72) to afford 5-amino-2-[(4S,5R)-5-(chloromethyl)-4-hydroxy-5-(hydroxymethyl)tetrahydrofuran-2-yl]-1,2,4-triazin-3(2H)-one (65 mg, 0.2 mmol, 44%) as a light-yellow solid. LC-MS: (ES, m/z): 277/279 (M+H$^+$).

Step 6: The 5-amino-2-[(4S,5R)-5-(chloromethyl)-4-hydroxy-5-(hydroxymethyl) tetrahydrofuran-2-yl]-1,2,4-triazin-3(2H)-one (65 mg, 0.2 mmol) was purified by Prep-Chiral-HPLC with the following conditions (Column: CHIRALPAK IH, 2*25 cm, 5 μm; Mobile Phase A: Hex (0.5% 2M NH$_3$-MeOH), Mobile Phase B: EtOH—HPLC; Flow rate: 20 mL/min; Gradient: 20% B to 20% B in 23 min; Wavelength: 220/254 nm; RT1(min): 15.337; RT2(min): 19.203) to afford 5-amino-2-[(2R,4S,5R)-5-(chloromethyl)-4-hydroxy-5-(hydroxymethyl) oxolan-2-yl]-1,2,4-triazin-3-one (26.1 mg, 0.09 mmol, 18%) as an off-white solid. LC-MS: (ES, m/z): 277/279 (M+H$^+$). 99.0% purity.

Conditions for the LCMS: (Column: Shim-pack Scepter C18 Column, 30*3.0 mm, 3 m; Mobile Phase A: Water+5mMNH$_4$HCO$_3$, Mobile Phase B: Acetonitrile; Flow rate: 1.5000 mL/min; Gradient: 0% B to 95% B in 1.40 min, 95% B to 95% B in 1.80 min, 95% B to 10% B in 1.85 min; Wavelength: 254/220 nm; RT1(min): 0.711). $^1$H NMR (400 MHz, DMSO-d$_6$) δ 8.13-7.93 (m, 2H), 7.56 (s, 1H), 6.31 (dd, J=7.5, 6.1 Hz, 1H), 5.20 (d, J=7.0 Hz, 1H), 4.95 (t, J=5.7 Hz, 1H), 4.40 (q, J=6.9 Hz, 1H), 3.83-3.71 (m, 2H), 3.45 (d, J=5.6 Hz, 2H), 2.60 (dt, J=13.5, 7.5 Hz, 1H), 2.27 (dt, J=13.5, 6.2 Hz, 1H).

Example 17—Synthesis of Compound 19: 4-amino-1-((2R,3S,4S,5R)-4-hydroxy-5-(hydroxymethyl)-3,5-dimethyltetrahydrofuran-2-yl)pyrimidin-2(1H)-one

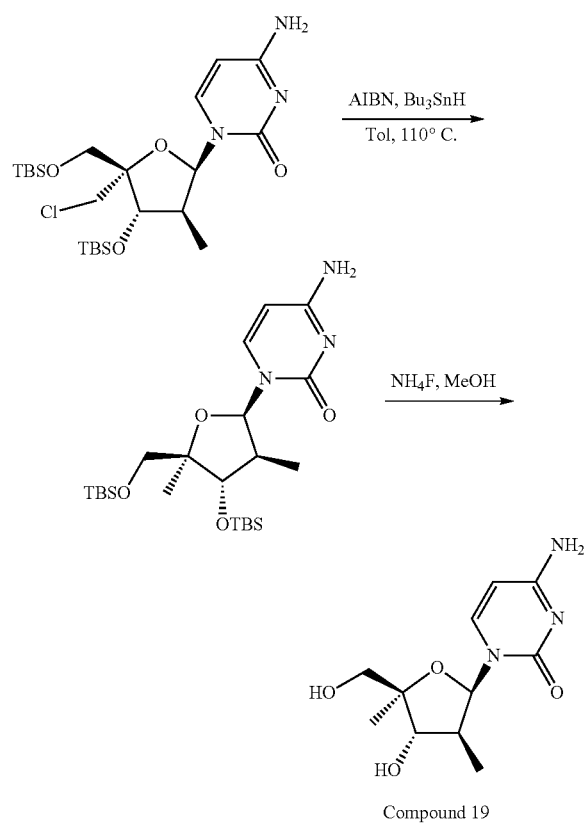

Compound 19

Step 1: A solution of 4-amino-1-((2R,3S,4S,5R)-4-((tert-butyldimethylsilyl)oxy)-5-(((tert-butyldimethylsilyl)oxy)methyl)-5-(chloromethyl)-3-methyltetrahydrofuran-2-yl)pyrimidin-2(1H)-one (10 mg, 0.02 mmol) in toluene (3 mL) was treated with AIBN (0.9 mg, 0.006 mmol) and n-Bu3SnH (16.7 mg, 0.06 mmol) at room temperature under nitrogen atmosphere. The resulting mixture was stirred for 4 h at 100° C. under nitrogen atmosphere. Desired product could be detected by LCMS. The resulting mixture was concentrated under reduced pressure. Then, the residue was purified by Prep-TLC with Petroleum ether/Ethyl acetate (1:1) to afford 4-amino-1-((2R,3S,4S,5R)-4-((tert-butyldimethylsilyl)oxy)-5-(((tert-butyldimethylsilyl)oxy)methyl)-3,5-dimethyltetrahydrofuran-2-yl)pyrimidin-2(1H)-one (60 mg, 0.12 mmol, 91.77%) as a yellow oil. LC-MS (ESI, m/z): 484 (M+H$^+$)

Step 2: To a stirred solution of 4-amino-1-((2R,3S,4S,5R)-4-((tert-butyldimethylsilyl) oxy)-5-(((tert-butyldimethylsilyl)oxy)methyl)-3,5-dimethyltetrahydrofuran-2-yl)pyrimidin-2(1H)-one (50 mg, 0.1 mmol) in methanol (2 mL) was added NH$_4$F (114.8 mg, 3.1 mmol) at room temperature under nitrogen atmosphere. The resulting mixture was stirred for 5.0 days at 60° C. under nitrogen atmosphere. Desired product could be detected by LCMS. The resulting mixture was concentrated under reduced pressure. The crude product was purified by Prep-HPLC with the following conditions (Column: XBridge Prep OBD C18 Column, 30*150 mm, 5 m; Mobile Phase A: Water (10 mmol/L NH$_4$HCO$_3$+0.1% NH$_3$·H$_2$O), Mobile Phase B: ACN; Flow rate: 60 mL/min; Gradient: 2% to 14% B in 8 min, 14% B; Wavelength: 254/220 nm; RT1(min): 5.88(min); Number of Runs: 0) to afford 4-amino-1-[(2R,3S,4S,5R)-4-hydroxy-5-(hydroxymethyl)-3,5-dimethyloxolan-2-yl] pyrimidin-2-one (8.3 mg, 0.03 mmol, 31.43%) as a white solid. LC-MS (ES, m/z): 256 (M+H$^+$) 99.9% purity. Conditions for the LCMS: (Column: Shim-pack Scepter C18 Column, 50*3.0 mm, 2.7 μm; Mobile PhaseA: Water/0.05% TFA, Mobile Phase B: ACN/0.05% TFA; Flow rate: 1.5000 mL/min; Gradient: 0 B to 100% B in 1.20 min, 100% B to 100% B in 0.62 min, 0% B to 0% B in 0.18 min; Wavelength: 254/220 nm; RT1(min): 0.353). $^1$H NMR (400 MHz, DMSO-d$_6$) δ 8.04 (d, J=7.3 Hz, 1H), 7.03 (d, J=32.9 Hz, 2H), 6.08 (d, J=7.9 Hz, 1H), 5.66 (d, J=7.4 Hz, 1H), 5.28-5.08 (m, 2H), 3.83-3.71 (m, 1H), 3.45 (m, 2H), 2.46 (s, 1H), 0.99 (s, 3H), 0.74 (d, J=6.8 Hz, 3H).

Example 18—Synthesis of Compound 20: 4-amino-1-((2R,3S,4S,5R)-3-ethynyl-4-hydroxy-5-(hydroxymethyl)-5-methyltetrahydrofuran-2-yl)pyrimidin-2(1H)-one

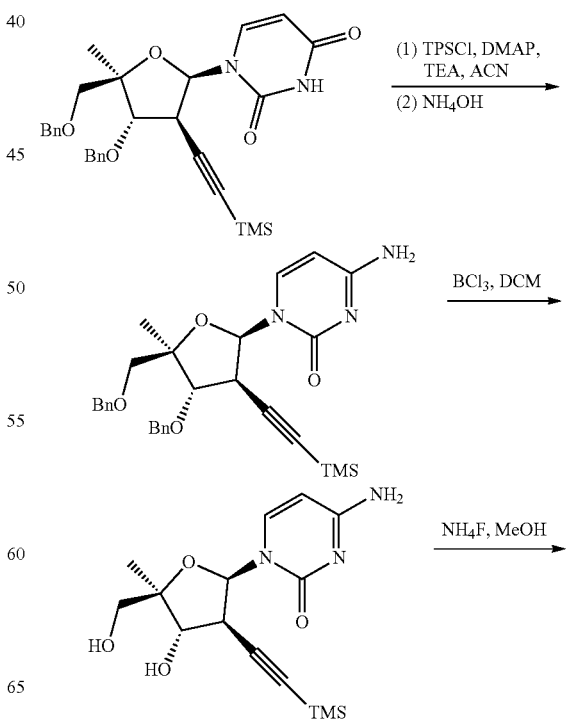

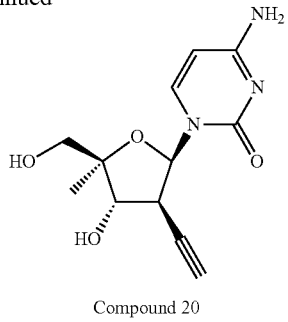

Compound 20

Step 1: A solution of 1-[(2R,3S,4S,5R)-4-(benzyloxy)-5-[(benzyloxy)methyl]-5-methyl-3-[2-(trimethylsilyl) ethynyl] oxolan-2-yl]-3H-pyrimidine-2,4-dione (100 mg, 0.2 mmol) in ACN (5 mL) was treated with DMAP (27.1 mg, 0.4 mmol) and TEA (39.2 mg, 0.4 mmol) for 10 min at room temperature under nitrogen atmosphere, then 2,4,6-tris(propan-2-yl) benzene-1-sulfonyl chloride (116.6 mg, 0.4 mmol) was added, the reaction was stirred for 5 h at room temperature. Finally, a solution of NH₄OH (0.5 mL) was added the resulting reaction mixture was stirred for 15 min at room temperature. Desired product could be detected by LCMS. The resulting mixture was concentrated under reduced pressure. The residue was purified by Prep-TLC with PE/EA (1:1) to afford 4-amino-1-[(2R,3S,4S,5R)-4-(benzyloxy)-5-[(benzyloxy)methyl]-5-methyl-3-[2-(trimethylsilyl) ethynyl] oxolan-2-yl] pyrimidin-2-one (80 mg, 0.2 mmol, 0.15%) as an off-white solid. LC-MS (ES, m/z): 518 (M+H⁺)

Step 2: A solution of 4-amino-1-[(2R,3S,4S,5R)-4-(benzyloxy)-5-[(benzyloxy)methyl]-5-methyl-3-[2-(trimethylsilyl) ethynyl] oxolan-2-yl] pyrimidin-2-one (80 mg, 0.2 mmol) in DCM (5 mL) was treated with boron trichloride (271.6 mg, 2.4 mmol) for 2 h at −78° C. under nitrogen atmosphere. Desired product could be detected by LCMS. The reaction was quenched by the addition of MeOH/TEA (2/1) at −20° C. The resulting mixture was concentrated under reduced pressure. The residue was purified by Prep-TLC with CH₂Cl₂/MeOH (10:1) to afford 4-amino-1-[(2R, 3S,4S,5R)-4-hydroxy-5-(hydroxymethyl)-5-methyl-3-[2-(trimethylsilyl) ethynyl] oxolan-2-yl] pyrimidin-2-one (35 mg, 0.1 mmol, 69.04%) as an off-white solid. LC-MS (ES, m/z): 338 (M+H⁺)

Step 3: A solution of 4-amino-1-[(2R,3S,4S,5R)-4-hydroxy-5-(hydroxymethyl)-5-methyl-3-[2-(trimethylsilyl) ethynyl] oxolan-2-yl] pyrimidin-2-one (35 mg, 0.1 mmol) and NH₄F (7.7 mg, 0.2 mmol) in methanol (4 mL) was stirred for overnight at 60° C. Desired products could be detected by LCMS. The resulting mixture was filtered; the filter cake was washed with MeOH (3×5 mL). The filtrate was concentrated under reduced pressure. The crude product (20 mg) was purified by Prep-HPLC with the following conditions (Column: XBridge Shield RP18 OBD Column, 19*250 mm, 10 μm; Mobile Phase A: Water (10 mmol/L NH₄HCO₃+0.1% NH₃—H₂O), Mobile Phase B: ACN; Flow rate: 25 mL/min; Gradient: 2% B to 8% B in 8 min, 8% B; Wavelength: 254/220 nm; RT1(min): 6.52) to afford 4-amino-1-[(2R,3S,4S,5R)-3-ethynyl-4-hydroxy-5-(hydroxymethyl)-5-methyloxolan-2-yl] pyrimidin-2-one (12.2 mg, 0.05 mmol, 43.46%) as an off-white solid. LC-MS (ES, m/z): 266 (M+H⁺); 98.0% purity.

Conditions for the LCMS: (Column: XSelect HSS T3, 30*2.1 mm, 2.5 μm; Mobile Phase A: Water+5 mM NH₄HCO₃, Mobile Phase B: Acetonitrile/0.05% TFA; Flow rate: 1.2000 mL/min; Gradient: 0% B to 50% B in 1.6 min, 50% B to 95% B in 0.4 min, 95% B to 95% B in 0.4 min, 95% B to 0% B in 0.4 min; Wavelength: 254/220 nm; RT1(min): 1.028)

¹H NMR (300 MHz, DMSO-d₆) δ 7.83 (d, J=7.4 Hz, 1H), 7.06 (d, J=26.4 Hz, 2H), 6.17 (d, J=7.5 Hz, 1H), 5.77-5.53 (m, 2H), 5.13 (t, J=5.4 Hz, 1H), 4.23 (dd, J=8.4, 5.6 Hz, 1H), 3.56-3.34 (m, 3H), 2.99 (d, J=2.5 Hz, 1H), 1.02 (s, 3H).

Example 19—Synthesis of Compound 22: 4-amino-5-fluoro-1-((2R,4S,5R)-5-(fluoromethyl)-4-hydroxy-5-(hydroxymethyl)tetrahydrofuran-2-yl)pyrimidin-2 (1H)-one

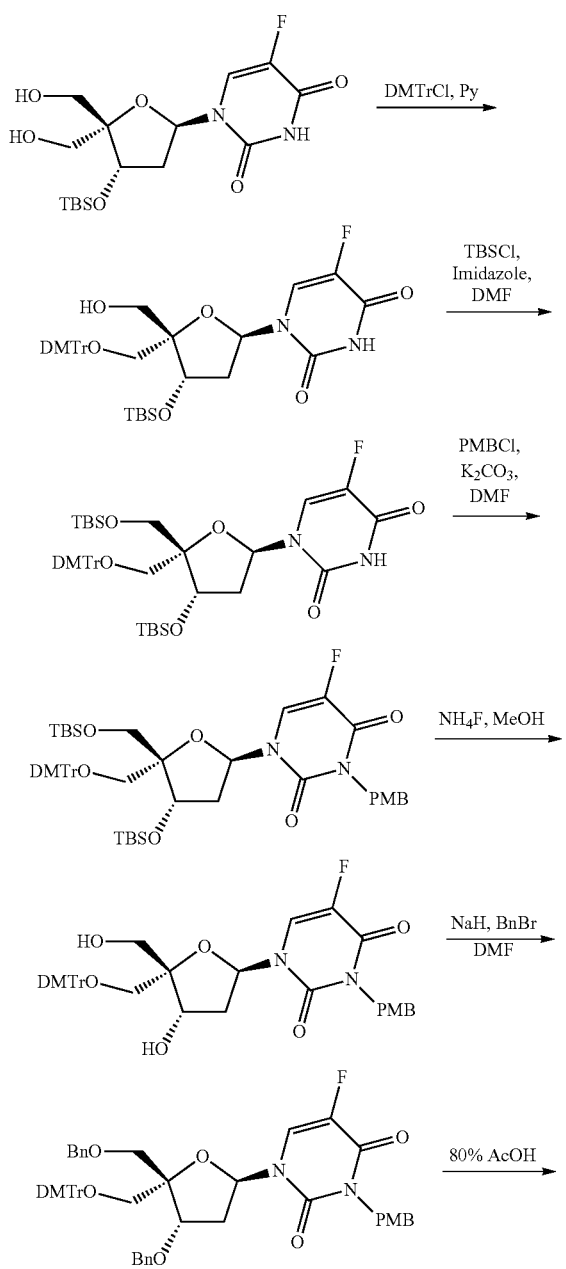

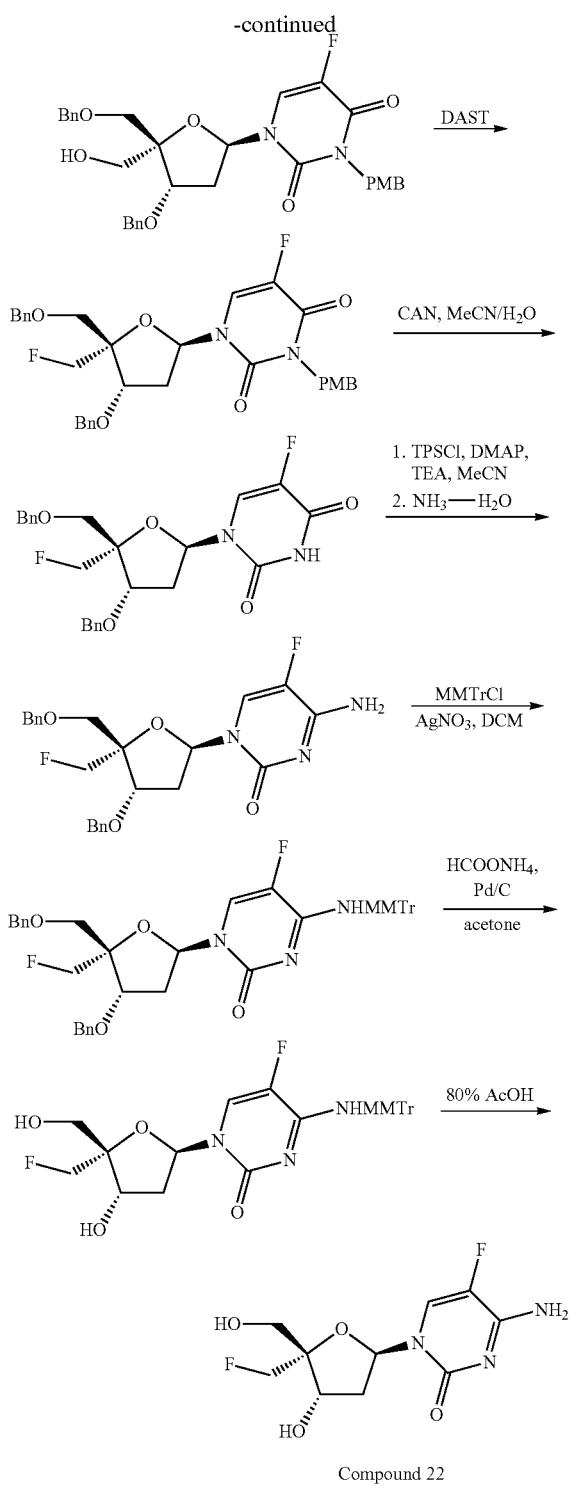

Compound 22

Step 1: To a solution of 1-[(2R,4S)-4-[(tert-butyldimethylsilyl)oxy]-5,5-bis(hydroxy-methyl)oxolan-2-yl]-5-fluoro-3H-pyrimidine-2,4-dione (20.0 g, 51.2 mmol) in pyridine (200 mL) was added 1-[chloro(4-methoxyphenyl)phenylmethyl]-4-methoxybenzene (17.35 g, 51.2 mmol) at 0° C. under an atmosphere of nitrogen. The resulting mixture was stirred for overnight at room temperature, then diluted with ethyl acetate (200 mL). The separated organic layer was washed with saturated NH$_4$Cl aqueous, dried over anhydrous Na$_2$SO$_4$ and concentrated under vacuum. The residue was purified by silica gel column chromatography, eluted with petroleum ether/ethyl acetate (8:1) to afford 1-[(2R,4S,5S)-5-{[bis(4-methoxyphenyl)(phenyl) methoxy]methyl}-4-[(tert-butyldimethylsilyl)oxy]-5-(hydroxymethyl) oxolan-2-yl]-5-fluoro-3H-pyrimidine-2,4-dione (30.5 g, 84.5%) as a white solid. LC-MS (ES, m/z): 693 (M+H$^+$).

Step 2: To a stirred solution of 1-[(2R,4S,5S)-5-{[bis(4-methoxyphenyl) (phenyl)methoxy]methyl}-4-[(tert-butyldimethylsilyl)oxy]-5-(hydroxymethyl)oxolan-2-yl]-5-fluoro-3H-pyrimidine-2,4-dione (30.0 g, 43.3 mmol) and imidazole (8.84 g, 129.9 mmol) in DMF (300 mL) was added TBSCl (7.83 g, 52.0 mmol) in portions at 0° C. under nitrogen atmosphere. The resulting mixture was stirred for overnight at room temperature and then diluted with ethyl acetate (300 mL). The separated organic layer was washed with brine, dried over anhydrous Na$_2$SO$_4$ and concentrated under vacuum. The residue was purified by silica gel column chromatography, eluted with petroleum ether/ethyl acetate (7:1) to afford 1-[(2R,4S,5R)-5-{[bis(4-methoxyphenyl) (phenyl)methoxy]methyl}-4-[(tert-butyldimethylsilyl)oxy]-5-{[(tert-butyldimethylsilyl)oxy]methyl}oxolan-2-yl]-5-fluoro-3H-pyrimidine-2,4-dione (29.8 g, 85.8%) as a white solid. LC-MS (ES, m/z): 807 (M+H$^+$).

Step 3: To a stirred solution of 1-[(2R,4S,5R)-5-{[bis(4-methoxyphenyl) (phenyl)methoxy]methyl}-4-[(tert-butyldimethylsilyl)oxy]-5-{[(tert-butyldimethylsilyl) oxy]methyl}oxolan-2-yl]-5-fluoro-3H-pyrimidine-2,4-dione (29.8 g, 37.2 mmol) and K$_2$CO$_3$ (10.27 g, 74.3 mmol) in DMF (300 mL), was added PMBCl (11.64 g, 74.3 mmol) dropwise at 0° C. under nitrogen atmosphere. The resulting mixture was stirred for overnight at room temperature and then quenched by the addition of saturated NaHCO$_3$ aqueous at 0° C. The resulting mixture was diluted with ethyl acetate (300 mL). The separated organic layer was washed with brine, dried over anhydrous Na$_2$SO$_4$ and concentrated under vacuum. The residue was purified by silica gel column chromatography, eluted with petroleum ether/ethyl acetate (10:1) to afford 1-[(2R,4S,5R)-5-{[bis(4-methoxyphenyl) (phenyl)methoxy]methyl}-4-[(tert-butyldimethylsilyl)oxy]-5-{[(tert-butyldimethylsilyl)oxy]methyl}oxolan-2-yl]-5-fluoro-3-[(4-methoxyphenyl)methyl]pyrimidine-2,4-dione (31.0 g, 87.0%) as a white solid. LC-MS (ES, m/z): 927 (M+H$^+$).

Step 4: To a stirred solution of 1-[(2R,4S,5R)-5-{[bis(4-methoxyphenyl) (phenyl)methoxy]methyl}-4-[(tert-butyldimethylsilyl)oxy]-5-{[(tert-butyldimethylsilyl) oxy]methyl}oxolan-2-yl]-5-fluoro-3-[(4-methoxyphenyl) methyl]pyrimidine-2,4-dione (30 g, 32.4 mmol) in MeOH (300 mL), was added NH$_4$F (6.0 g, 161.8 mmol) at room temperature under nitrogen atmosphere. The resulting mixture was stirred for overnight at 60° C., then cooled to room temperature and concentrated under vacuum. The residue was dissolved in ethyl acetate (300 mL). The resulting solution was washed with brine, dried over anhydrous Na$_2$SO$_4$ and concentrated under vacuum. The residue was purified by silica gel column chromatography, eluted with petroleum ether/ethyl acetate (5:1) to afford 1-[(2R,4S,5S)-5-{[bis(4-methoxyphenyl) (phenyl)methoxy]methyl}-4-hydroxy-5-(hydroxymethyl)oxolan-2-yl]-5-fluoro-3-[(4-methoxy-phenyl)methyl]pyrimidine-2,4-dione (18 g, 79.6%) as a white solid. LC-MS (ES, m/z): 699 (M+H$^+$).

Step 5: To a solution of 1-[(2R,4S,5S)-5-{[bis(4-methoxyphenyl)(phenyl)methoxy]methyl}-4-hydroxy-5-(hydroxymethyl)oxolan-2-yl]-5-fluoro-3-[(4-methoxyphenyl)methyl]pyrimidine-2,4-dione (18 g, 25.8 mmol) in DMF (200 mL) was added NaH (60% in oil, 3.08 g, 77.3 mmol) at 0° C. under nitrogen atmosphere. After stirred for 20 min, BnBr (9.69 g, 56.7 mmol) was added dropwise at 0° C. The resulting mixture was stirred for overnight at room temperature and then cooled to 0° C. and quenched by the addition of saturated NaHCO$_3$ aqueous. The resulting mixture was diluted with ethyl acetate (200 mL). The separated organic layer was washed with brine, dried over anhydrous Na$_2$SO$_4$ and concentrated under vacuum. The residue was purified by silica gel column chromatography, eluted with petroleum ether/ethyl acetate (10:1) to afford 1-[(2R,4S,5S)-4-(benzyloxy)-5-[(benzyloxy)methyl]-5-{[bis(4-methoxyphenyl)(phenyl)methoxy]methyl}oxolan-2-yl]-5-fluoro-3-[(4-methoxyphenyl)methyl]-pyrimidine-2,4-dione (15 g, 66.2%) as a white solid. LC-MS5 (ES, m/z): 879 (M+H$^+$).

Step 6: 1-[(2R,4S,5S)-4-(benzyloxy)-5-[(benzyloxy)methyl]-5-{[bis(4-methoxy-phenyl)(phenyl)methoxy]methyl}oxolan-2-yl]-5-fluoro-3-[(4-methoxyphenyl)methyl]pyrimidine-2,4-dione (15 g, 17.1 mmol) was dissolved in AcOH/H$_2$O (4:1, 150 mL). The reaction mixture was stirred for overnight at room temperature, then cooled to 0° C. and quenched by the addition of saturated NaHCO$_3$ aqueous. The resulting solution was extracted with ethyl acetate, washed with brine, dried over anhydrous Na$_2$SO$_4$ and concentrated under vacuum. The residue was purified by silica gel column chromatography, eluted with petroleum ether/ethyl acetate (5:1) to afford 1-[(2R,4S,5R)-4-(benzyloxy)-5-[(benzyloxy)methyl]-5-(hydroxymethyl)oxolan-2-yl]-5-fluoro-3-[(4-methoxyphenyl) methyl]pyrimidine-2,4-dione (7.1 g, 71.1%) as a white solid. LC-MS (ES, m/z): 577 (M+H$^+$).

Step 7: To a stirred solution of 1-[(2R,4S,5R)-4-(benzyloxy)-5-[(benzyloxy)methyl]-5-(hydroxymethyl)oxolan-2-yl]-5-fluoro-3-[(4-methoxyphenyl)methyl]pyrimidine-2,4-dione (7 g, 12.1 mmol) in toluene (70 mL), was added DAST (9.78 g, 60.7 mmol) dropwise at −78° C. under nitrogen atmosphere. The resulting mixture was stirred for overnight at 60° C., then cooled to 0° C. and quenched by the addition of saturated NaHCO$_3$ aqueous. The resulting solution was diluted with ethyl acetate (100 mL). The separated organic layer was washed with brine, dried over anhydrous Na$_2$SO$_4$ and concentrated under vacuum. The residue was purified by silica gel column chromatography, eluted with petroleum ether/ethyl acetate (5:1) to afford 1-[(2R,4S,5R)-4-(benzyloxy)-5-[(benzyloxy)methyl]-5-(fluoromethyl)oxolan-2-yl]-5-fluoro-3-[(4-methoxyphenyl)methyl]pyrimidine-2,4-dione (3.2 g, 42.7%) as a white solid. LC-MS (ES, m/z): 579 (M+H$^+$).

Step 8: To a solution of 1-[(2R,4S,5R)-4-(benzyloxy)-5-[(benzyloxy)methyl]-5-(fluoromethyl)oxolan-2-yl]-5-fluoro-3-[(4-methoxyphenyl)methyl]pyrimidine-2,4-dione (3.0 g, 5.2 mmol) in MeCN/H$_2$O (3:1, 50 mL), was added CAN (8.52 g, 15.6 mmol). The reaction mixture was stirred for overnight at room temperature under nitrogen atmosphere. The resulting mixture was diluted with ethyl acetate (100 mL). The separated organic layer was washed with brine, dried over anhydrous Na$_2$SO$_4$ and concentrated under vacuum. The residue was purified by reverse flash chromatography with the following conditions: column, C18 silica gel; mobile phase, MeCN in Water (10 mmol/L NH$_4$HCO$_3$), 10% to 80% gradient in 20 min; detector, UV 254 nm. This resulted in 1-[(2R,4S,5R)-4-(benzyloxy)-5-[(benzyloxy)methyl]-5-(fluoromethyl)oxolan-2-yl]-5-fluoro-3H-pyrimidine-2,4-dione (1.1 g, 42.1%) as a white solid. LC-MS (ES, m/z): 459 (M+H$^+$).

Step 9: To a stirred solution of 1-[(2R,4S,5R)-4-(benzyloxy)-5-[(benzyloxy)methyl]-5-(fluoromethyl)oxolan-2-yl]-5-fluoro-3H-pyrimidine-2,4-dione (1.0 g, 2.2 mmol), TEA (0.66 g, 6.5 mmol) and DMAP (0.53 g, 4.4 mmol) in MeCN (20 mL), was added TPSCl (1.32 g, 4.4 mmol) in portions at room temperature under nitrogen atmosphere. After being stirred for 30 min at room temperature, an ammonia solution (2 mL, 10.9 mmol) was added dropwise. The resulting mixture was stirred for additional overnight at room temperature and then diluted with ethyl acetate. The resulting solution was washed with saturated NH$_4$Cl aqueous, dried over anhydrous Na$_2$SO$_4$ and concentrated under vacuum. The residue was purified by reverse flash chromatography with the following conditions: column, C18 silica gel; mobile phase, MeCN in Water (10 mmol/L NH$_4$HCO$_3$), 40% to 100% gradient in 20 min; detector, UV 254 nm. This resulted in 4-amino-1-[(2R,4S,5R)-4-(benzyloxy)-5-[(benzyloxy)methyl]-5-(fluoromethyl)-oxolan-2-yl]-5-fluoropyrimidin-2-one (600 mg, 60.1%) as a white solid. LC-MS (ES, m/z): 458 (M+H$^+$).

Step 10: To a stirred solution of 4-amino-1-[(2R,4S,5R)-4-(benzyloxy)-5-[(benzyloxy)methyl]-5-(fluoromethyl)oxolan-2-yl]-5-fluoropyrimidin-2-one (600 mg, 1.3 mmol), AgNO$_3$ (445.6 mg, 2.6 mmol) and 2,4,6-collidine (317.9 mg, 2.6 mmol) in DCM (10 mL), was added 1-(chlorodiphenylmethyl)-4-methoxybenzene (405.0 mg, 1.3 mmol) in portions at room temperature under nitrogen atmosphere. The resulting mixture was stirred for overnight at room temperature and then diluted with ethyl acetate (50 mL). The separated organic layer was washed with saturated NH$_4$Cl aqueous, dried over anhydrous Na$_2$SO$_4$ and concentrated under vacuum. The residue was purified by silica gel column chromatography, eluted with petroleum ether/ethyl acetate (1:1) to afford 1-[(2R,4S,5R)-4-(benzyloxy)-5-[(benzyloxy)methyl]-5-(fluoromethyl)oxolan-2-yl]-5-fluoro-4-{[(4-methoxyphenyl)diphenyl methyl]amino}pyrimidin-2-one (500 mg, 52.2%) as a white solid. LC-MS (ES, m/z): 730 (M+H$^+$).

Step 11: To a stirred solution of 1-[(2R,4S,5R)-4-(benzyloxy)-5-[(benzyloxy)methyl]-5-(fluoromethyl)oxolan-2-yl]-5-fluoro-4-{[(4-methoxyphenyl)diphenylmethyl]amino}pyrimidin-2-one (500 mg, 0.7 mmol) and HCOONH$_4$ (0.86 g, 13.7 mmol) in acetone (10 mL), was added Pd/C (100 mg). The resulting mixture was stirred for overnight at 60° C., then cooled to room temperature. The solid was moved by filtration the filtrate was concentrated under vacuum. The residue was purified by silica gel column chromatography, eluted with petroleum ether/ethyl acetate (1:1) to afford 5-fluoro-1-[(2R,4S,5R)-5-(fluoromethyl)-4-hydroxy-5-(hydroxymethyl) oxolan-2-yl]-4-{[(4-methoxyphenyl)diphenylmethyl]amino}pyrimidin-2-one (100 mg, 26.6%) as a white solid. LC-MS (ES, m/z): 550 (M+H$^+$).

Step 12: A solution of 5-fluoro-1-[(2R,4S,5R)-5-(fluoromethyl)-4-hydroxy-5-(hydroxymethyl)oxolan-2-yl]-4-{[(4-methoxyphenyl)diphenylmethyl]amino}pyrimidin-2-one (100 mg, 0.2 mmol) in AcOH/H$_2$O (4:1, 5 mL) was stirred for overnight at room temperature under nitrogen atmosphere. The reaction was cooled to 0° C. and quenched by the addition of saturated NaHCO$_3$ aqueous. The resulting solution was extracted with ethyl acetate, washed with brine, dried over anhydrous Na$_2$SO$_4$ and concentrated under vacuum. The residue was purified by Prep-HPLC with the following conditions: Column: XBridge BEH C18 OBD Prep Column, 19*250 mm, 5 μm; Mobile Phase A: Water (10 mmol/L NH$_4$HCO$_3$), Mobile Phase B: ACN; Flow rate: 25 mL/min; Gradient: 2% B to 17% B in 8 min; Wavelength: 254 nm; RT1(min): 5.95. That resulted in 4-amino-5-fluoro-1-[(2R,4S,5R)-5-(fluoromethyl)-4-hydroxy-5-(hydroxymethyl)oxolan-2-yl]pyrimidin-2-one (7.3 mg, 14.4%) as a white solid. LC-MS-PH-ROF-RT-0453-0 (ES, m/z): 278 (M+H$^+$). $^1$H NMR (400 MHz, DMSO-d$_6$) δ 8.03 (d, J=7.2

Hz, 1H), 7.77 (brs, 1H), 7.53 (brs, 1H), 6.24-6.19 (m, 1H), 5.38 (d, J=4.8 Hz, 1H), 5.28 (t, J=5.2 Hz, 1H), 4.62-4.52 (m, 1H), 4.50-4.41 (m, 1H), 4.39-4.36 (m, 1H), 3.56 (s, 2H), 2.16 (t, J=6.0 Hz, 2H).

Example 20—Synthesis of Compound 8: (2R,3S,5R)-5-(6-amino-2-fluoro-9H-purin-9-yl)-2-(chloromethyl)-2-(hydroxymethyl)tetrahydrofuran-3-ol

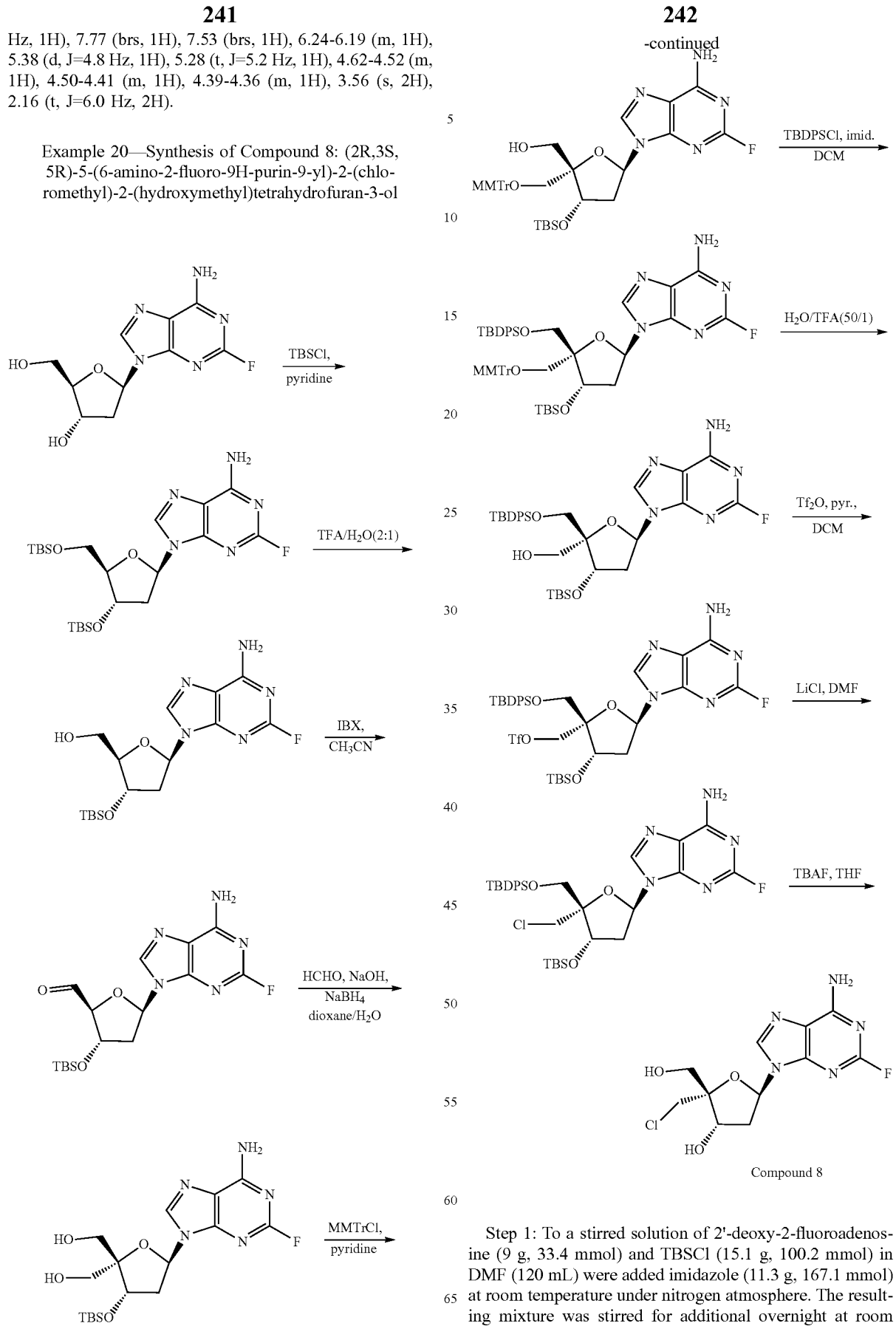

Compound 8

Step 1: To a stirred solution of 2'-deoxy-2-fluoroadenosine (9 g, 33.4 mmol) and TBSCl (15.1 g, 100.2 mmol) in DMF (120 mL) were added imidazole (11.3 g, 167.1 mmol) at room temperature under nitrogen atmosphere. The resulting mixture was stirred for additional overnight at room temperature. Desired product could be detected by LCMS.

The resulting mixture was extracted with EtOAc (3×500 mL). The combined organic layers were washed with brine (3×100 mL), dried over anhydrous $Na_2SO_4$. After filtration, the filtrate was concentrated under reduced pressure. The residue was purified by silica gel column chromatography, eluted with PE/EA (1:1) to afford 9-[(2R,4S,5R)-4-[(tert-butyldimethylsilyl) oxy]-5-{[(tert-butyl-dimethylsilyl)oxy] methyl} oxolan-2-yl]-2-fluoropurin-6-amine (15 g, 30.1 mmol, 90.15%) as a white solid. LC-MS (ES, m/z): 498 (M+H$^+$)

Step 2: A solution of 9-[(2R,4S,5R)-4-[(tert-butyldimethylsilyl) oxy]-5-{[(tert-butyldimethylsilyl) oxy] methyl} oxolan-2-yl]-2-fluoropurin-6-amine (13 g, 26.1 mmol) in TFA (50 mL), water (50 mL), and THF (100 mL) at 0° C. under nitrogen atmosphere was stirred for 1 h at 0° C. Desired products could be detected by LCMS. The resulting mixture was concentrated under vacuum. The residue was purified by reverse flash chromatography to afford [(2R,3S,5R)-5-(6-amino-2-fluoropurin-9-yl)-3-[(tert-butyldimethylsilyl) oxy] oxolan-2-yl] methanol (6.3 g, 16.4 mmol, 62.90%) as an off-white oil. LC-MS (ES, m/z): 384 (M+H$^+$).

Step 3: A solution of [(2R,3S,5R)-5-(6-amino-2-fluoropurin-9-yl)-3-[(tert-butyldimethylsilyl) oxy] oxolan-2-yl] methanol (6.3 g, 16.4 mmol) and IBX (18.4 g, 65.7 mmol) in ACN (70 mL) at room temperature under nitrogen atmosphere was stirred for 1.5 h at 60° C. Desired products could be detected by LCMS. The resulting mixture was extracted with EtOAc (2×300 mL). The combined organic layers were washed with $Na_2S_2O_3$, $NaHCO_3$, NaCl (2×200 mL), dried over anhydrous $Na_2SO_4$. After filtration, the filtrate was concentrated under reduced pressure. The residue was purified by reverse flash chromatography with the following conditions: column, C18 silica gel; mobile phase, MeCN in Water (0.1% $NH_3·H_2O$), 56% to 63% gradient in 10 min; detector, UV 254 nm to afford (2S,3S,5R)-5-(6-amino-2-fluoropurin-9-yl)-3-[(tert-butyldimethylsilyl) oxy] oxolane-2-carbaldehyde (2.7 g, 7.1 mmol, 41.99%) as an off-white solid. LC-MS (ES, m/z): 382 (M+H$^+$).

Step 4: To a stirred solution of (2S,3S,5R)-5-(6-amino-2-fluoropurin-9-yl)-3-[(tert-butyldimethylsilyl) oxy] oxolane-2-carbaldehyde (2.7 g, 7.1 mmol) and HCHO (4.3 g, 141.5 mmol) in 1,4-dioxane (40 mL) was added NaOH (0.6 g, 15.5 mmol) in $H_2O$ (4 ml) at room temperature under nitrogen atmosphere. The resulting mixture was stirred overnight at room temperature. To the above mixture was added $NaBH_4$ (1.7 g, 26.8 mmol) at 0° C. The resulting mixture was stirred for additional 1 h at 0° C. Desired products could be detected by LCMS. The resulting mixture was extracted with EtOAc (3×200 mL). The combined organic layers were washed with brine (3×100 mL), dried over anhydrous $Na_2SO_4$. After filtration, the filtrate was concentrated under reduced pressure. The residue was purified by silica gel column chromatography to afford [(3S,5R)-5-(6-amino-2-fluoropurin-9-yl)-3-[(tert-butyldimethylsilyl) oxy]-2-(hydroxymethyl) oxolan-2-yl] methanol (1.3 g, 3.1 mmol, 44.42%) as an off-white solid. LC-MS (ES, m/z): 414 (M+H$^+$).

Step 5: To a stirred solution of [(3S,5R)-5-(6-amino-2-fluoropurin-9-yl)-3-[(tert-butyldimethylsilyl) oxy]-2-(hydroxymethyl) oxolan-2-yl] methanol (1.3 g, 3.1 mmol) in pyridine (20 mL) was added 1-(chlorodiphenylmethyl)-4-methoxybenzene (1.4 g, 4.7 mmol) at room temperature under nitrogen atmosphere. The resulting mixture was stirred overnight at room temperature. Desired product could be detected by LCMS. The resulting mixture was extracted with EtOAc (3×100 mL). The combined organic layers were washed with brine (3×50 mL), dried over anhydrous $Na_2SO_4$. After filtration, the filtrate was concentrated under reduced pressure. The residue was purified by silica gel column chromatography, eluted with PE/EA (1:3) to afford [(2S,3S,5R)-5-(6-amino-2-fluoropurin-9-yl)-3-[(tert-butyldimethylsilyl) oxy]-2-{[(4-methoxyphenyl) diphenylmethoxy] methyl} oxolan-2-yl] methanol (750 mg, 1.08 mmol, 34.78%) as a yellow oil. LC-MS (ES, m/z): 686 (M+H$^+$).

Step 6: To a stirred solution of [(2S,3S,5R)-5-(6-amino-2-fluoropurin-9-yl)-3-[(tert-butyldimethylsilyl) oxy]-2-{1[(4-methoxyphenyl) diphenylmethoxy] methyl} oxolan-2-yl]methanol (600 mg, 0.8 mmol) and imidazole (178.6 mg, 2.6 mmol) in DCM (5 mL) was added TBDPSCl (360.6 mg, 1.3 mmol) at room temperature under nitrogen atmosphere. The resulting mixture was stirred for additional overnight at room temperature. Desired product could be detected by LCMS. The resulting mixture was extracted with EtOAc (3×100 mL). The combined organic layers were washed with brine (3×50 mL), dried over anhydrous $Na_2SO_4$. After filtration, the filtrate was concentrated under reduced pressure. The residue was purified by silica gel column chromatography, eluted with PE/EA (5:1) to afford 9-[(2R,4S,5R)-4-[(tert-butyldimethylsilyl) oxy]-5-{[(tert-butyldiphenylsilyl) oxy] methyl}-5-1{[(4-methoxyphenyl) diphenylmethoxy] methyl} oxolan-2-yl]-2-fluoropurin-6-amine (750 mg, 0.8 mmol, 92.76%) as a yellow oil. LC-MS (ES, m/z): 924 (M+H$^+$).

Step 7: To a stirred solution of 9-[(2R,4S,5R)-4-[(tert-butyldimethylsilyl) oxy]-5-{[(tert-butyldiphenylsilyl) oxy] methyl}-5-{1[(4-methoxyphenyl) diphenylmethoxy] methyl}oxolan-2-yl]-2-fluoropurin-6-amine (750 mg, 0.8 mmol) in DCM (15 mL) was added TFA (0.3 mL) at room temperature under nitrogen atmosphere. The resulting mixture was stirred for additional 30 min at room temperature. Desired product could be detected by LCMS. The resulting mixture was extracted with EtOAc (3×100 mL). The combined organic layers were washed with brine (3×50 mL), dried over anhydrous $Na_2SO_4$. After filtration, the filtrate was concentrated under reduced pressure. The residue was purified by silica gel column chromatography, eluted with PE/EA (1:1) to afford [(2R,3S,5R)-5-(6-amino-2-fluoropurin-9-yl)-3-[(tert-butyldimethylsilyl) oxy]-2-{[(tert-butyldiphenylsilyl) oxy] methyl} oxolan-2-yl]methanol (400 mg, 0.6 mmol, 75.61%) as an off-white solid. LC-MS (ES, m/z): 652 (M+H$^+$).

Step 8: To a stirred solution of [(2R,3S,5R)-5-(6-amino-2-fluoropurin-9-yl)-3-[(tert-butyldimethylsilyl) oxy]-2-{[(tert-butyldiphenylsilyl) oxy] methyl} oxolan-2-yl] methanol (400 mg, 0.6 mmol) and Pyridine (145.6 mg, 1.8 mmol) in DCM (5 mL) were added $Tf_2O$ (259.6 mg, 0.9 mmol) at 0° C. under nitrogen atmosphere. The resulting mixture was stirred for additional 10 min at 0° C. Desired products could be detected by LCMS. The resulting mixture was extracted with EtOAc (3×100 mL). The combined organic layers were washed with brine (3×50 mL), dried over anhydrous $Na_2SO_4$. After filtration, the filtrate was concentrated under reduced pressure. The crude product was used in the next step directly without further purification. LC-MS (ES, m/z): 784 (M+H$^+$).

Step 9: To a stirred solution of [(2S,3S,5R)-5-(6-amino-2-fluoropurin-9-yl)-3-[(tert-butyldimethylsilyl) oxy]-2-{[(tert-butyldiphenylsilyl) oxy] methyl} oxolan-2-yl] methyl trifluoromethanesulfonate (440 mg, 0.5 mmol) and LiCl (71.3 mg, 1.6 mmol) in DMF (5 mL) at room temperature under nitrogen atmosphere. The resulting mixture was stirred for additional overnight at room temperature. Desired product could be detected by LCMS. The residue was purified by reverse flash chromatography with the following conditions: column, C18 silica gel; mobile phase, MeCN in Water (0.1% NH₃—H₂O), 52% to 58% gradient in 10 min; detector, UV 254 nm to afford 9-[(2R,4S,5R)-4-[(tert-butyldimethylsilyl) oxy]-5-{[(tert-butyldiphenylsilyl) oxy] methyl}-5-(chloromethyl) oxolan-2-yl]-2-fluoropurin-6-amine (110 mg, 0.1 mmol, 29.24%) as an off-white solid. LC-MS (ES, m/z): 670 (M+H⁺).

Step 10: To a stirred solution of 9-[(2R,4S,5R)-4-[(tert-butyldimethylsilyl) oxy]-5-{[(tert-butyldiphenylsilyl) oxy] methyl}-5-(chloromethyl) oxolan-2-yl]-2-fluoropurin-6-amine (110 mg, 0.1 mmol) and TBAF (128.5 mg, 0.5 mmol) in DCM (3 mL) at room temperature under nitrogen atmosphere. The resulting mixture was stirred for additional overnight at room temperature. Desired product could be detected by LCMS. The residue was purified by reverse flash chromatography with the following conditions: Column: XBridge Prep OBD C18 Column, 30*150 mm, 5 μm; Mobile Phase A: Water (10 mmol/L NH₄HCO₃), Mobile Phase B: ACN; Flow rate: 60 mL/min; Gradient: 2% B to 20% B in 8 min, 20% B; Wavelength: 254/220 nm; RT1 (min): 7 to afford (2R,3S,5R)-5-(6-amino-2-fluoro-9H-purin-9-yl)-2-(chloromethyl)-2-(hydroxymethyl)tetrahydrofuran-3-ol (22.2 mg, 0.043 mmol, 42.58%) as a white solid. LC-MS (ES, m/z): 318 (M+H⁺); 99.9% purity. Conditions for the LCMS: (Column: XBridge Shield RP18, 50*4.6 mm, 3.5 μm; Mobile Phase A: Water/5 mM NH₄HCO₃, Mobile Phase B: Acetonitrile; Flow rate: 1.5000 mL/min; Gradient: 10% B to 95% B in 1.75 min, 95% B to 95% B in 1.05 min, 95% B to 10% B in 0.01 min; Wavelength: 254/220 nm; RT1(min): 1.040). ¹H NMR (300 MHz, DMSO-d₆) δ 8.32 (s, 1H), 7.84 (s, 2H), 6.30 (dd, J=7.9, 6.1 Hz, 1H), 5.53 (d, J=4.9 Hz, 1H), 5.13 (t, J=5.5 Hz, 1H), 4.55 (td, J=5.4, 3.0 Hz, 1H), 3.81 (s, 2H), 3.68-3.52 (m, 2H), 2.95 (ddd, J=13.6, 8.1, 5.8 Hz, 1H), 2.37 (ddd, J=13.4, 6.1, 3.0 Hz, 1H).

Example 21—Synthesis of Compound 55: 4-amino-1-[(2R,4S,5R)-4-hydroxy-5-(hydroxymethyl)-5-isopropyloxolan-2-yl] pyrimidin-2-one

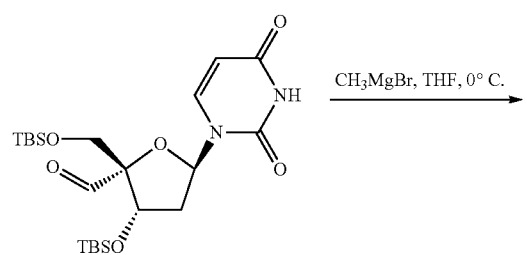

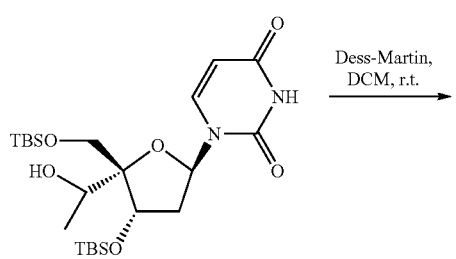

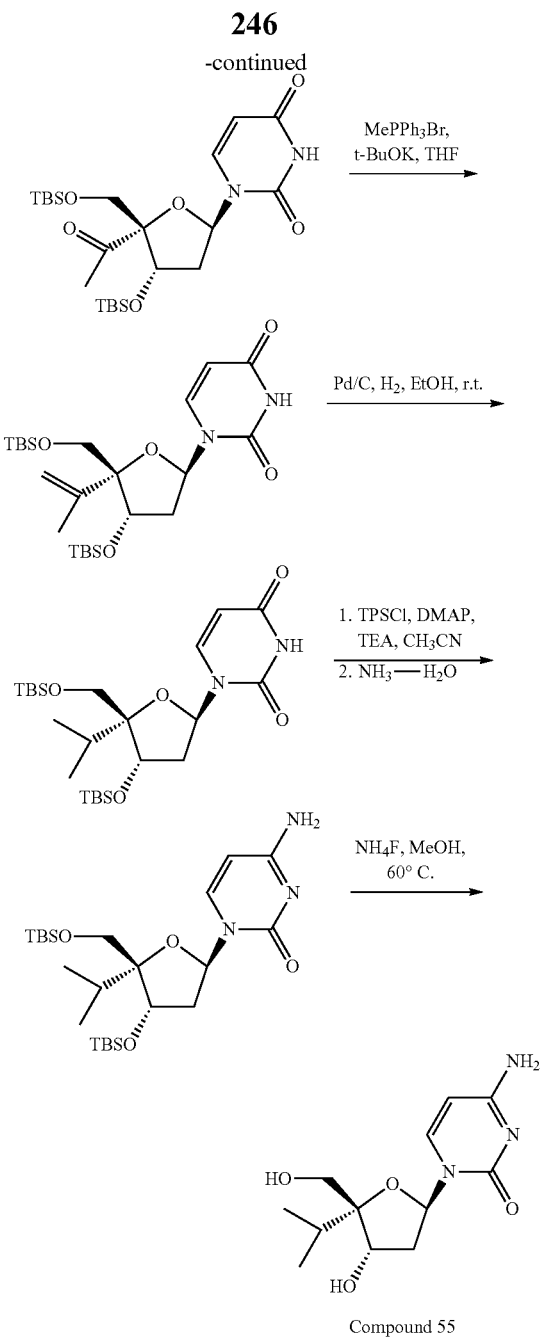

Compound 55

Step 1: To a solution of (2R,3S,5R)-3-[(tert-butyldimethylsilyl) oxy]-2-{[(tert-butyldimethylsilyl) oxy] methyl}-5-(2,4-dioxo-3H-pyrimidin-1-yl) oxolane-2-carbaldehyde (1 g, 2.2 mmol) in THF (10 mL) was added CH₃MgBr (7 mL, 59.1 mmol) at 0° C. under nitrogen atmosphere. The mixture was stirred 2 h at 0° C. The reaction was quenched by the addition of NH₄Cl (10 mL) at 0° C. The resulting mixture was extracted with ethyl acetate (3×20 mL). The combined organic layers were washed with brine (3×20 mL), dried over anhydrous Na₂SO₄. After filtration, the filtrate was concentrated under reduced pressure. This resulted in 1-[(2R,4S,5S)-4-[(tert-butyldimethylsilyl) oxy]-5-{[(tert-butyldimethylsilyl) oxy] methyl}-5-(1-hydroxyethyl) oxolan-2-yl]-3H-pyrimidine-2,4-dione (1 g, 2.2 mmol, crude) as a light yellow solid. LC-MS (ES, m/z): 501 (M+H⁺).

Step 2: To a solution of 1-[(2R,4S,5S)-4-[(tert-butyldimethylsilyl) oxy]-5-{[(tert-butyldimethylsilyl) oxy] methyl}-

5-(1-hydroxyethyl) oxolan-2-yl]-3H-pyrimidine-2,4-dione (1 g, 2.1 mmol) in dichlormethane (15 mL, 692.2 mmol) was added Dess-Martin (4.7 g, 10.9 mmol) under nitrogen atmosphere. The mixture was stirred for overnight at 30° C. The resulting mixture was concentrated, diluted with water and extracted with ethyl acetate (3×40 mL). The combined organic layers were washed with brine, dried over anhydrous Na$_2$SO$_4$. After filtration, the filtrate was concentrated under reduced pressure. The residue was purified by Prep-TLC (petroleum ether: ethyl acetate=3:1) to afford 1-[(2R,4S,5R)-5-acetyl-4-[(tert-butyldimethylsilyl) oxy]-5-{[(tert-butyldimethylsilyl) oxy] methyl} oxolan-2-yl]-3H-pyrimidine-2,4-dione (695 mg, 1.4 mmol, 63.44%) as a light yellow oil. LC-MS (ES, m/z): 499 (M+H$^+$).

Step 3: To a solution of methyltriphenylphosphaniumbromide (2.7 g, 7.5 mmol) in THF (10 mL) was added t-BuOK (0.8 g, 6.7 mmol) at 0° C. under nitrogen atmosphere. The mixture was stirred for 1 h at 0° C. To above mixture was added a solution of 1-[(2R,4S,5R)-5-acetyl-4-[(tert-butyldimethylsilyl) oxy]-5-{[(tert-butyldimethylsilyl) oxy] methyl} oxolan-2-yl]-3H-pyrimidine-2,4-dione (375 mg, 0.7 mmol) in THF (5 mL) at 0° C. The mixture was stirred for overnight at room temperature. The reaction was quenched by the addition of NH$_4$Cl at 0° C. The resulting mixture was extracted with dichloromethane. The combined organic layers were washed with brine, dried over anhydrous Na$_2$SO$_4$. After filtration, the filtrate was concentrated under reduced pressure. The residue was purified by silica gel column chromatography, eluted with petroleum ether: ethyl acetate (3:1) to afford 1-[(2R,4S,5R)-4-[(tert-butyldimethylsilyl) oxy]-5-{[(tert-butyldimethylsilyl) oxy] methyl}-5-(prop-1-en-2-yl) oxolan-2-yl]-3H-pyrimidine-2,4-dione (250 mg, 0.5 mmol, 66.93%) as an off-white oil. LC-MS (ES, m/z): 497 (M+H$^+$).

Step 4: To a solution of 1-[(2R,4S,5R)-5-acetyl-4-[(tert-butyldimethylsilyl) oxy]-5-{[(tert-butyldimethylsilyl) oxy] methyl} oxolan-2-yl]-3H-pyrimidine-2,4-dione (250 mg, 0.5 mmol) in EtOH (5 mL) was added Pd/C (33 mg, 10% Pd on carbon) under nitrogen atmosphere. The mixture was stirred for 2 h under hydrogen atmosphere at room temperature. The resulting mixture was filtered; the filter cake was washed with methanol (3×10 mL). The filtrate was concentrated under reduced pressure. This resulted in 1-[(2R,4S,5R)-4-[(tert-butyldimethylsilyl) oxy]-5-{[(tert-butyldimethylsilyl) oxy] methyl}-5-(prop-1-en-2-yl) oxolan-2-yl]-3H-pyrimidine-2,4-dione (250 mg, 0.5 mmol, crude) as a white solid. LC-MS (ES, m/z): 499 (M+H$^+$).

Step 5: To a solution of 1-[(2R,4S,5R)-4-[(tert-butyldimethylsilyl) oxy]-5-{[(tert-butyldimethylsilyl) oxy] methyl}-5-isopropyloxolan-2-yl]-3H-pyrimidine-2,4-dione (250 mg, 0.5 mmol) in CH$_3$CN (5 mL) was added DMAP (122 mg, 1.0 mmol), TEA (101 mg, 1.0 mmol) and 2,4,6-tris(propan-2-yl) benzene-1-sulfonyl chloride (303 mg, 1.0 mmol) and the mixture was stirred for overnight at room temperature under nitrogen atmosphere followed by the addition of NH$_3$·H$_2$O (1 mL) dropwise at room temperature. The resulting mixture was stirred for additional 30 min at room temperature. The resulting mixture was concentrated under reduced pressure. The residue was purified by silica gel column chromatography, eluted with petroleum ether/ethyl acetate (1:1) to afford 4-amino-1-[(2R,4S,5R)-4-[(tert-butyldimethylsilyl)oxy]-5-{[(tert-butyldimethylsilyl)oxy] methyl}-5-isopropyloxolan-2-yl]pyrimidin-2-one (150 mg, 0.3 mmol, 60.12%) as a white solid. LC-MS (ES, m/z): 498 (M+H$^+$).

Step 6: To a stirred solution of 4-amino-1-[(2R,4S,5R)-4-[(tert-butyldimethylsilyl) oxy]-5-{[(tert-butyldimethylsi-lyl) oxy] methyl}-5-isopropyloxolan-2-yl] pyrimidin-2-one (150 mg, 0.3 mmol) in MeOH (5 mL) was added NH$_4$F (669 mg, 18.0 mmol) in portions at room temperature under nitrogen atmosphere. The resulting mixture was stirred for overnight at 60° C. The resulting mixture was cooled to room temperature and concentrated under reduced pressure. The crude product was purified by Prep-HPLC with the following conditions (Column: XBridge Prep OBD C18 Column, 30*150 mm, 5 μm; Mobile Phase A: Water (10 mmol/L NH$_4$HCO$_3$+0.1% NH$_3$·H$_2$O), Mobile Phase B: ACN; Flow rate: 60 mL/min; Gradient: 3% B to 25% B in 8 min; Wavelength: 254/220 nm; RT1(min): 7.2) to afford 4-amino-1-[(2R,4S,5R)-4-hydroxy-5-(hydroxymethyl)-5-isopropyloxolan-2-yl] pyrimidin-2-one (17.9 mg, 0.06 mmol, 22.06%) as an off-white solid. LC-MS (ES, m/z): 270 (M+H$^+$) 97.6% purity. Conditions for the LCMS: (Column: Shim-pack ScepterC18 Column, 4.6*100 mm, 4.5 μm; Mobile Phase A: Water/5 mM NH4HCO3, Mobile Phase B: ACN; Flow rate: 1.50 mL/min; Gradient: 5% B to 95% B in 8 min, 95% B to 95% B in 10 min, 95% B to 10% B in 10.5 min; Wavelength: 254/220 nm; RT1(min): 2.500). $^1$H NMR (400 MHz, DMSO-d$_6$) δ 7.94 (dd, J=7.4, 1.5 Hz, 1H), 7.07 (d, J=25.0 Hz, 2H), 6.17 (dd, J=8.4, 5.8 Hz, 1H), 5.70 (dd, J=7.3, 1.5 Hz, 1H), 5.06 (dd, J=5.0, 1.5 Hz, 1H), 4.91 (t, J=5.0 Hz, 1H), 4.28 (td, J=5.2, 2.1 Hz, 1H), 3.52 (qd, J=11.6, 5.0 Hz, 2H), 2.27-1.91 (m, 3H), 0.93 (dd, J=9.1, 7.0 Hz, 6H).

Example 22: Synthesis of Compound 62: 4-amino-1-[(2R,4S,5R)-4-hydroxy-5-(hydroxymethyl)-5-(2,2,2-trifluoroethyl) oxolan-2-yl] pyrimidin-2-one

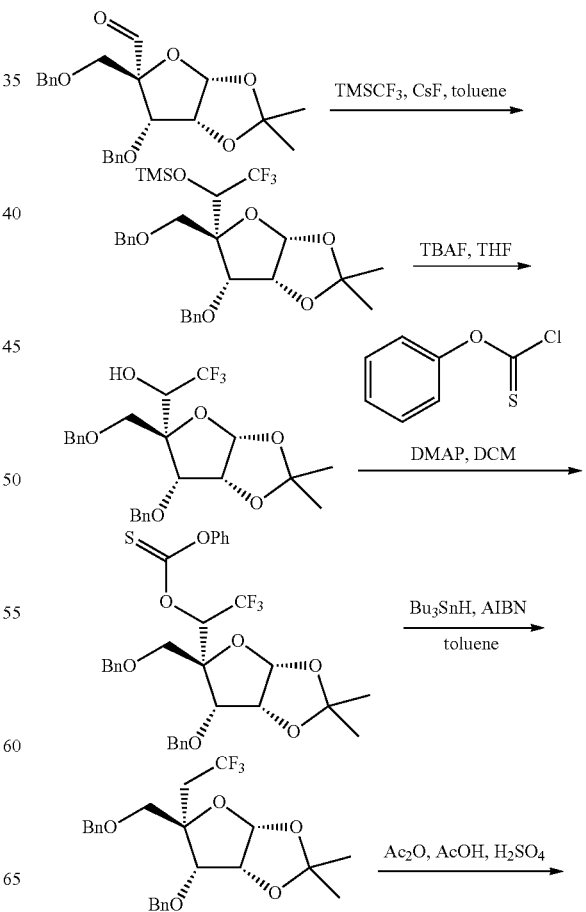

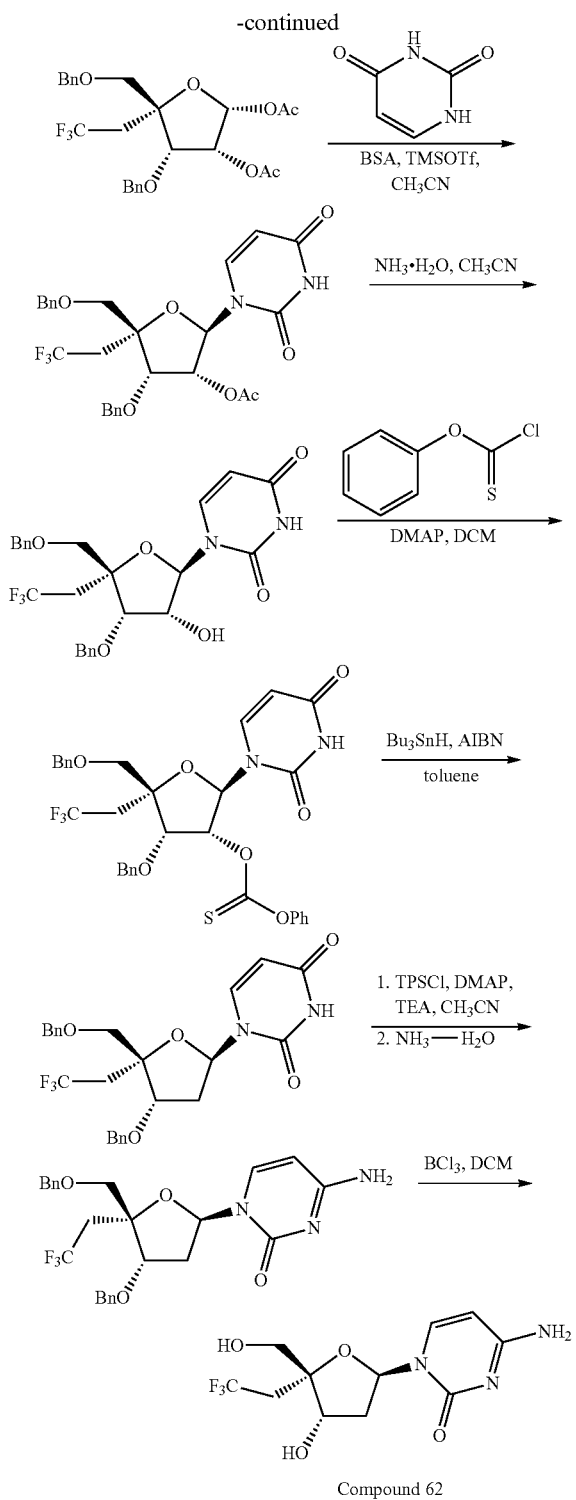

Compound 62

Step 1: To a stirred solution of (3aR,5R,6S,6aR)-6-(benzyloxy)-5-((benzyloxy) methyl)-2,2-dimethyltetrahydrofuro[2,3-d][1,3]dioxole-5-carbaldehyde (6.2 g, 15.6 mmol) and Cesium Fluoride (470 mg, 3.1 mmol) in toluene (150 mL) was added trifluoromethyl-trimethylsilane (8.9 g, 62.4 mmol) in portions at 0° C. under nitrogen atmosphere. The mixture was stirred for 18 hours at room temperature. The resulting mixture was diluted with water and extracted with ethyl acetate (3×100 mL). The combined organic layers were washed with brine (2×200 mL), dried over anhydrous sodium sulfate. After filtration, the filtrate was concentrated under reduced pressure to afford ((R)-1-((3aR,5R,6S,6aR)-6-(benzyloxy)-5-((benzyloxy) methyl)-2,2-dimethyltetrahydrofuro[2,3-d][1,3]dioxol-5-yl)-2,2,2-trifluoroethoxy)trimethylsilane (8.1 g, 15 mmol, crude) as a yellow oil. LC-MS (ES, m/z): 541 (M+H$^+$).

Step 2: To a stirred solution of ((R)-1-((3aR,5R,6S,6aR)-6-(benzyloxy)-5-((benzyloxy)methyl)-2,2-dimethyltetrahydrofuro[2,3-d][1,3]dioxol-5-yl)-2,2,2-trifluoroethoxy) trimethylsilane (8.5 g, 15.8 mmol) in tetrahydrofuran (100 mL) was added a solution of TBAF in THF (19.6 mL, 1.0 M) dropwise at room temperature under nitrogen atmosphere. The mixture was stirred for 20 minutes at room temperature. The resulting mixture was diluted with water and extracted with ethyl acetate (3×100 mL). The combined organic layers were washed with brine (2×200 mL), dried over anhydrous sodium sulfate. After filtration, the filtrate was concentrated under reduced pressure. The residue was purified by silica gel column chromatography, eluted with PE/EA (3/1) to afford (R)-1-((3aR,5S,6S,6aR)-6-(benzyloxy)-5-((benzyloxy)methyl)-2,2-dimethyltetrahydrofuro[2,3-d][1,3]dioxol-5-yl)-2,2,2-trifluoroethan-1-ol (7.2 g, 15.4 mmol, 97.19%) as a yellow oil. LC-MS (ES, m/z): 469 (M+H$^+$).

Step 3: To a stirred solution of (R)-1-((3aR,5S,6S,6aR)-6-(benzyloxy)-5-((benzyloxy)methyl)-2,2-dimethyltetrahydrofuro[2,3-d][1,3]dioxol-5-yl)-2,2,2-trifluoroethan-1-ol (7.2 g, 15.4 mmo) and DMAP (7.5 g, 61.5 mmol) in DCM (100 mL) was added phenyl chloromethanethioate (5.3 g, 30.7 mmol) dropwise at 0° C. under nitrogen atmosphere. The mixture was stirred for 2 hours at room temperature. The resulting mixture was diluted with water and extracted with ethyl acetate (3×100 mL). The combined organic layers were washed with brine (2×200 mL), dried over anhydrous sodium sulfate. After filtration, the filtrate was concentrated under reduced pressure. The residue was purified by silica gel column chromatography, eluted with PE/EA (4/1) to afford O—((R)-1-((3aR,5R,6S,6aR)-6-(benzyloxy)-5-((benzyloxy)methyl)-2,2-dimethyltetrahydrofuro[2,3-d][1,3]dioxol-5-yl)-2,2,2-trifluoroethyl) 0-phenyl carbonothioate (8.55 g, 14.2 mmol, 92.01%) as a light-yellow oil. LC-MS (ES, m/z): 605 (M+H$^+$).

Step 4: To a stirred solution of O—((R)-1-((3aR,5R,6S,6aR)-6-(benzyloxy)-5-((benzyloxy)methyl)-2,2-dimethyltetrahydrofuro[2,3-d][1,3]dioxol-5-yl)-2,2,2-trifluoroethyl) 0-phenyl carbonothioate (6.6 g, 10.8 mmol) and tributyltin (18.9 g, 65.0 mmol) in toluene (150 mL) was added AIBN (3.6 g, 21.7 mmol) at room temperature under nitrogen atmosphere. The mixture was stirred for 2 hours at 80° C. The resulting mixture was cooled to room temperature, diluted with water and extracted with ethyl acetate (3×100 mL). The combined organic layers were washed with brine (2×200 mL), dried over anhydrous sodium sulfate. After filtration, the filtrate was concentrated under reduced pressure. The residue was purified by silica gel column chromatography, eluted with PE/EtOAc (5/2) to afford (3aR,5R,6S,6aR)-6-(benzyloxy)-5-((benzyloxy)methyl)-2,2-dimethyl-5-(2,2,2-trifluoroethyl)tetrahydrofuro[2,3-d][1,3]dioxole (4 g, 8.8 mmol, 81.61%) as a light-yellow oil. LC-MS (ES, m/z): 453 (M+H$^+$).

Step 5: To a stirred solution of (3aR,5R,6S,6aR)-6-(benzyloxy)-5-((benzyloxy) methyl)-2,2-dimethyl-5-(2,2,2-trifluoroethyl)tetrahydrofuro[2,3-d][1,3]dioxole (5 g, 11.1 mmol) in acetic acid (80 mL) was added acetic anhydride (15.8 g, 154.7 mmol) and sulfuric acid (54 mg, 0.6 mmol) dropwise at 0° C. under nitrogen atmosphere. The mixture was stirred for 2 hours at room temperature. The resulting mixture was diluted with water and extracted with ethyl acetate (3×100 mL). The combined organic layers were washed with brine (2×200 mL), dried over anhydrous sodium sulfate. After filtration, the filtrate was concentrated under reduced pressure. The residue was purified by silica gel column chromatography, eluted with PE/EtOAc (4/1) to afford (2R,3R,4S,5R)-4-(benzyloxy)-5-((benzyloxy) methyl)-5-(2,2,2-trifluoroethyl) tetrahydrofuran-2,3-diyl diacetate (5.2 g, 10.5 mmol, 94.78%) as a light-yellow oil. LC-MS (ES, m/z): 497 (M+H$^+$).

Step 6: To a stirred solution of 1,2,3,4-tetrahydropyrimidine-2,4-dione (1.8 g, 15.7 mmol) in ACN (150 mL) was added (E)-(trimethylsilyl N-(trimethylsilyl) ethenecarboximidate) (8.5 g, 41.9 mmol) in portions at 0° C. under nitrogen atmosphere. The mixture was stirred for 2 hours at 80° C. The mixture was cooled to room temperature and a solution of (2R,3R,4S,5R)-4-(benzyloxy)-5-((benzyloxy) methyl)-5-(2,2,2-trifluoroethyl)tetrahydrofuran-2,3-diyl diacetate (5.2 g, 10.5 mmol) in ACN (50 mL) was added. Then trimethylsilyl triflate (3.7 g, 16.8 mmol) was added at room temperature under nitrogen atmosphere. The mixture was stirred for 15 hours at 80° C. The resulting mixture was cooled to room temperature, diluted with water and extracted with ethyl acetate (3×100 mL). The combined organic layers were washed with brine (2×200 mL), dried over anhydrous sodium sulfate. After filtration, the filtrate was concentrated under reduced pressure. The residue was purified by silica gel column chromatography, eluted with PE/EtOAc (2/1) to afford (2R,3R,4S,5R)-4-(benzyloxy)-5-((benzyloxy)methyl)-2-(2,4-dioxo-3,4-dihydropyrimidin-1 (2H)-yl)-5-(2,2,2-trifluoroethyl)tetrahydrofuran-3-yl acetate (3.94 g, 7.2 mmol, 68.58%) as a light-yellow solid. LC-MS (ES, m/z): 549 (M+H$^+$).

Step 7: To a stirred solution of NH$_3$(g) in MeOH (7 M, 50 mL) was added (2R,3R,4S,5R)-4-(benzyloxy)-5-((benzyloxy)methyl)-2-(2,4-dioxo-3,4-dihydropyrimidin-1(2H)-yl)-5-(2,2,2-trifluoroethyl)tetrahydrofuran-3-yl acetate (3.9 g, 7.2 mmol) at room temperature under nitrogen atmosphere. The mixture was stirred for 2 hours at room temperature and concentrated. The residue was purified by silica gel column chromatography, eluted with PE/EA (5/3) to afford 1-[(2R,3R,4S,5R)-4-(benzyloxy)-5-[(benzyloxy) methyl]-3-hydroxy-5-(2,2,2-trifluoroethyl) oxolan-2-yl]-3H-pyrimidine-2,4-dione (3.6 g, 7.1 mmol 98.95%) as a yellow solid. LC-MS (ES, m/z): 507 (M+H$^+$).

Step 8: To a stirred solution of 1-[(2R,3R,4S,5R)-4-(benzyloxy)-5-[(benzyloxy) methyl]-3-hydroxy-5-(2,2,2-trifluoroethyl) oxolan-2-yl]-3H-pyrimidine-2,4-dione (1.8 g, 3.6 mmol) and DMAP (1.7 g, 14.2 mmol) in DCM (30 mL) was added phenyl chloromethanethioate (1.2 g, 7.1 mmol) at 0° C. under nitrogen atmosphere. The mixture was stirred for 2 hours at room temperature. The resulting mixture was diluted with water and extracted with ethyl acetate (3×100 mL). The combined organic layers were washed with brine (2×200 mL), dried over anhydrous sodium sulfate. After filtration, the filtrate was concentrated under reduced pressure. The residue was purified by silica gel column chromatography, eluted with PE/EtOAc (4/1) to afford 1-[(2R,3R,4S,5R)-4-(benzyloxy)-5-[(benzyloxy)methyl]-3-[(phenoxymethanethioyl)oxy]-5-(2,2,2-trifluoroethyl) oxolan-2-yl]-3H-pyrimidine-2,4-dione (1.44 g, 2.2 mmol, 63.05%) as a light-yellow oil. LC-MS (ES, m/z): 643 (M+H$^+$).

Step 9: To a stirred solution of 1-[(2R,3R,4S,5R)-4-(benzyloxy)-5-[(benzyloxy) methyl]-3-[(phenoxymethanethioyl)oxy]-5-(2,2,2-trifluoroethyl) oxolan-2-yl]-3H-pyrimidine-2,4-dione (1.4 g, 2.2 mmol) and tributyltin (3.9 g, 13.4 mmol) in toluene (20 mL) was added AIBN (736 mg, 4.5 mmol) in portions at room temperature under nitrogen atmosphere. The mixture was stirred for 2 hours at 90° C. The resulting mixture was cooled to room temperature, diluted with water and extracted with ethyl acetate (3×100 mL). The combined organic layers were washed with brine (2×200 mL), dried over anhydrous sodium sulfate. After filtration, the filtrate was concentrated under reduced pressure. The residue was purified by silica gel column chromatography, eluted with PE/EtOAc (3/1) to afford 1-[(2R,4S,5R)-4-(benzyloxy)-5-[(benzyloxy)methyl]-5-(2,2,2-trifluoroethyl) oxolan-2-yl]-3H-pyrimidine-2,4-dione (880 mg, 1.8 mmol, 80.07%) as an off-white solid. LC-MS (ES, m/z): 491 (M+H$^+$).

Step 10: To a stirred solution of 1-[(2R,4S,5R)-4-(benzyloxy)-5-[(benzyloxy)methyl]-5-(2,2,2-trifluoroethyl) oxolan-2-yl]-3H-pyrimidine-2,4-dione (880 mg, 1.8 mmol) and TEA (545 mg, 5.4 mmol) in ACN (20 mL) was added 2,4,6-tris(propan-2-yl) benzene-1-sulfonyl chloride (1.1 g, 3.6 mmol) at room temperature under nitrogen atmosphere. The mixture was stirred for 15 hours at room temperature. Then ammonium hydroxide (4 mL) was added, and the mixture was stirred for 30 minutes at room temperature. The resulting mixture was diluted with water and extracted with ethyl acetate (3×100 mL). The combined organic layers were washed with brine (2×200 mL), dried over anhydrous sodium sulfate. After filtration, the filtrate was concentrated under reduced pressure. The residue was purified by silica gel column chromatography, eluted with DCM/MeOH (20/1) to afford 4-amino-1-[(2R,4S,5R)-4-(benzyloxy)-5-[(benzyloxy)methyl]-5-(2,2,2-trifluoroethyl) oxolan-2-yl] pyrimidin-2-one (730 mg, 1.5 mmol, 83.12%) as a yellow solid. LC-MS (ES, m/z): 490 (M+H$^+$).

Step 11: To a stirred solution of 4-amino-1-[(2R,4S,5R)-4-(benzyloxy)-5-[(benzyloxy)methyl]-5-(2,2,2-trifluoroethyl) oxolan-2-yl] pyrimidin-2-one (340 mg, 0.7 mmol) in DCM (20 mL) was added boron trichloride (10.4 mL, 10.4 mmol, 1.0 M in DCM) dropwise at −78° C. under nitrogen atmosphere. The mixture was stirred for 2 hours at room temperature. The reaction was quenched by the addition of solution TEA/MeOH (1/2) (50 mL) at 0° C. and then concentrated. The residue was purified by reverse flash chromatography with the following conditions: column, C18 silica gel; mobile phase, ACN in water, 0% to 25% gradient in 15 min; detector, UV 254 nm. The crude product was re-purified by Prep-HPLC with the following conditions (Column: XBridge Prep OBD C18 Column, 30*150 mm, 5 μm; Mobile Phase A: Water (10 mmol/L NH$_4$HCO$_3$+0.1% NH$_3$·H$_2$O), Mobile Phase B: ACN; Flow rate: 60 mL/min; Gradient: 4% B to 28% B in 8 min; Wavelength: 254/220 nm; RT1(min): 6.82) to afford 4-amino-1-[(2R,4S,5R)-4-hydroxy-5-(hydroxymethyl)-5-(2,2,2-trifluoroethyl) oxolan-2-yl]pyrimidin-2-one (93.6 mg, 0.3 mmol, 42.18%) as an off-white solid. LC-MS (ES, m/z): 310 (M+H$^+$). 96.8% purity. Conditions for the LCMS: (Column: Kinetex EVO C18, 30*3.0 mm, 2.6 m; Mobile Phase A: Water+ 5mMNH$_4$HCO3, Mobile Phase B: Acetonitrile; Flow rate: 1.50 mL/min; Gradient: 0% B to 95% B in 1.20 min, 95% B hold for 0.58 min, 95% B to 10% B in 0.05 min; Wavelength: 254 nm; RT1(min): 0.619). $^1$H NMR (400 MHz, DMSO-d$_6$) δ 7.79 (d, J=7.5 Hz, 1H), 7.14 (d, J=22.2 Hz, 2H), 6.19 (t, J=6.7 Hz, 1H), 5.72 (d, J=7.4 Hz, 1H), 5.40 (d, J=84.0 Hz, 2H), 4.35 (t, J=5.1 Hz, 1H), 3.65-3.45 (m, 2H), 2.66 (dq, J=15.6, 12.6 Hz, 1H), 2.48-2.29 (m, 1H), 2.25-1.98 (m, 2H).

Example 23—Synthesis of Compound 112: 4-amino-1-((2R,3S,4R,5R)-5-ethynyl-3-fluoro-4-hydroxy-5-(hydroxymethyl)tetrahydrofuran-2-yl)-5-fluoropyrimidin-2(1H)-one

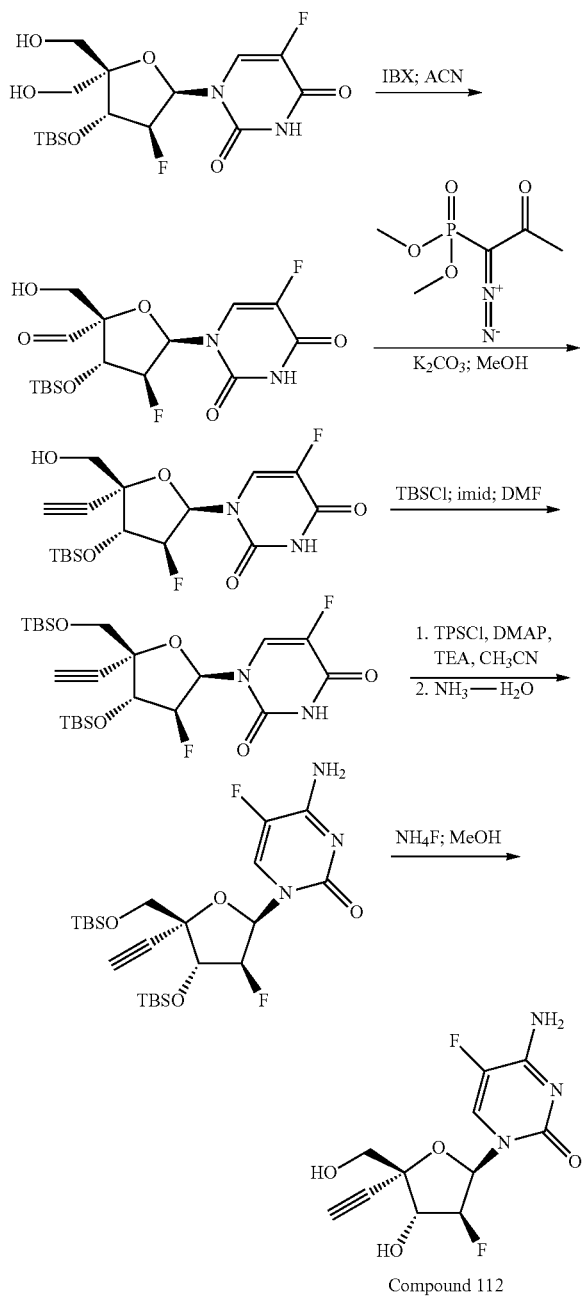

Compound 112

Step 1: To a stirred solution of 1-[(2R,3S,4R)-4-[(tert-butyldimethylsilyl)oxy]-3-fluoro-5,5-bis(hydroxymethyl)oxolan-2-yl]-5-fluoro-3H-pyrimidine-2,4-dione (1.5 g, 3.7 mmol) in ACN (20 mL) was added IBX (1.23 g, 4.4 mmol) in portions at room temperature under nitrogen atmosphere. The resulting mixture was stirred for 2 h at 60° C., then cooled room temperature and remove the solid by filtration. The filter cake was washed with MeCN and the combined filtrate was concentrated under vacuum to afford crude (2R,3R,4S,5R)-3-(((tert-butyldimethylsilyl)oxy)-4-fluoro-5-(5-fluoro-2,4-dioxo-3,4-dihydropyrimidin-1(2H)-yl)-2-(hydroxymethyl)tetrahydrofuran-2-carbaldehyde (~1.3 g), which was used in the next step directly without further purification. LC-MS (ES, m/z): 407 (M+H$^+$).

Step 2: To a stirred solution of dimethyl (1-diazo-2-oxopropyl)phosphonate (665.5 mg, 3.5 mmol) in ACN (10 mL), was added K$_2$CO$_3$ (870.5 mg, 6.3 mmol) in portions at room temperature under nitrogen atmosphere. This was followed by the addition of a solution of (2R,3R,4S,5R)-3-[(tert-butyldimethylsilyl)oxy]-4-fluoro-5-(5-fluoro-2,4-di-oxo-3H-pyrimidin-1-yl)-2-(hydroxymethyl)oxolane-2-carb-aldehyde (1.28 g, 3.1 mmol) in MeOH (10 mL) dropwise at room temperature. The resulting mixture was stirred for overnight at room temperature and then quenched by the addition of water. The resulting solution was extracted with EtOAc, washed with brine, dried over anhydrous Na$_2$SO$_4$ and concentrated under vacuum. The residue was purified by silica gel column chromatography, eluted with petroleum ether/EtOAc (1:1) to afford 1-((2R,3S,4R,5R)-4-((tert-butyldimethylsilyl)oxy)-5-ethynyl-3-fluoro-5-(hydroxymethyl) tetrahydrofuran-2-yl)-5-fluoropyrimidine-2,4(1H, 3H)-dione (410 mg, 27.7% over two steps) as a white solid. LC-MS (ES, m/z): 403 (M+H$^+$).

Step 3: To a stirred solution of 1-((2R,3S,4R,5R)-4-((tert-butyldimethylsilyl)oxy)-5-ethynyl-3-fluoro-5-(hydroxymethyl)tetrahydrofuran-2-yl)-5-fluoropyrimidine-2,4(1H, 3H)-dione (410 mg, 1.0 mmol) and imidazole (208.1 mg, 3.1 mmol) in DMF (10 mL), was added TBSCl (230.3 mg, 1.5 mmol) in portions at 0° C. under nitrogen atmosphere. The resulting mixture was stirred for additional 3 hours at room temperature and then quenched by the addition of water. The resulting solution was extracted with EtOAc, washed with brine, dried over anhydrous Na$_2$SO$_4$ and concentrated under vacuum. The residue was purified by silica gel column chromatography, eluted with petroleum ether/EtOAc (2:1) to afford 1-((2R,3S,4R,5R)-4-((tert-butyldimethylsilyl)oxy)-5-(((tert-butyldimethylsilyl)oxy)methyl)-5-ethynyl-3-fluoro-tetra-hydrofuran-2-yl)-5-fluoropyrimidine-2,4(1H,3H)-dione (280 mg, 53.2%) as a white solid. LC-MS (ES, m/z): 517 (M+H$^+$).

Step 4: To a stirred solution of 1-((2R,3S,4R,5R)-4-((tert-butyldimethylsilyl)oxy)-5-(((tert-butyldimethylsilyl)oxy)methyl)-5-ethynyl-3-fluorotetrahydrofuran-2-yl)-5-fluoropyrimidine-2,4(1H,3H)-dione (230 mg, 0.5 mmol), TEA (146.9 mg, 1.5 mmol) and DMAP (118.2 mg, 1.0 mmol) in CH$_3$CN (5 mL), was added 2,4,6-tris(propan-2-yl)benzene-1-sulfonyl chloride (293.1 mg, 1.0 mmol) in portions at room temperature under nitrogen atmosphere. After stirred for 0.5 hour at room temperature, to the mixture was added ammonia (0.5 mL) dropwise. The resulting mixture was stirred overnight at room temperature and quenched by the addition of water. The resulting solution was extracted with EtOAc, washed with brine, dried over anhydrous Na$_2$SO$_4$ and concentrated under vacuum. The residue was purified by Prep-TLC (petroleum ether/EtOAc=1:1) to afford 4-amino-1-((2R,3S,4R,5R)-4-((tert-butyldimethyl-silyl)oxy)-5-(((tert-butyldimethylsilyl)oxy)methyl)-5-ethynyl-3-fluoro-tetrahydrofuran-2-yl)-5-fluoropyrimidin-2(1H)-one (130 mg, 52.1%) as a white solid. LC-MS (ES, m/z): 516 (M+H$^+$).

Step 5: To a stirred solution of 4-amino-1-((2R,3S,4R,5R)-4-((tert-butyldimethyl-silyl)oxy)-5-(((tert-butyldimethylsilyl)oxy)methyl)-5-ethynyl-3-fluorotetrahydrofuran-2-yl)-5-fluoropyrimidin-2(1H)-one (110 mg, 0.3 mmol) in MeOH (5 mL), was added NH$_4$F (140.0 mg, 3.8 mmol). The resulting mixture was stirred overnight at 60° C., then cooled to room temperature and concentrated under vacuum.

The crude product was purified by Prep-HPLC with the following conditions: Column: X Bridge Shield RP18 OBD Column, 19*250 mm, 10 μm; Mobile Phase A: Water (10 mmol/L NH$_4$HCO$_3$), Mobile Phase B: ACN; Flow rate: 25 mL/min; Gradient: 3% B to 3% B in 2 min, 3% B to 15% B in 7.5 min, 15% B; Wavelength: 254 nm; RT1: 7.07 min. This resulted in 4-amino-1-((2R,3S,4R,5R)-5-ethynyl-3-fluoro-4-hydroxy-5-(hydroxymethyl)tetrahydrofuran-2-yl)-5-fluoropyrimidin-2(1H)-one (57.1 mg, 78.9%) as a white solid. LC-MS (ES, m/z): 288 (M+H$^+$). $^1$H NMR (400 MHz, DMSO-d$_6$) δ 7.96-7.90 (m, 2H), 7.70 (brs, 1H), 6.22 (s, 1H), 6.16 (d, J=7.2 Hz, 1H), 5.61 (d, J=6.4 Hz, 1H), 5.17-5.04 (m, 1H), 4.39-4.33 (m, 1H), 3.72-3.68 (m, 2H), 3.61-3.57 (m, 1H).

Example 24: Synthesis of Compound 76

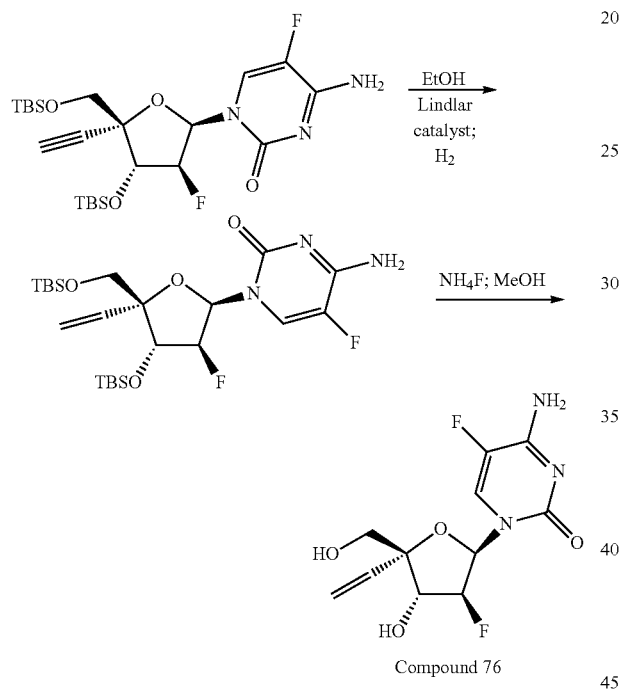

Compound 76

Step 1: To a solution of 4-amino-1-[(2R,3S,4R,5R)-4-[(tert-butyldimethylsilyl)oxy]-5-{[(tert-butyldimethylsilyl)oxy]methyl}-5-ethynyl-3-fluorooxolan-2-yl]-5-fluoropyrimidin-2-one (1.0 g, 1.9 mmol) in 20 mL EtOH, was added Lindlar catalyst (400.4 mg, 1.9 mmol) under nitrogen atmosphere. The mixture was sparged with nitrogen, placed under an atmosphere of hydrogen gas (balloon), then stirred overnight at room temperature. The solids were removed by filtration and the filtrate was concentrated under vacuum. The residue was purified by silica gel column chromatography, eluted with petroleum ether/EtOAc (2:1) to afford 4-amino-1-[(2R,3S,4R,5R)-4-[(tert-butyldimethylsilyl)oxy]-5-{[(tert-butyldimethylsilyl)oxy]methyl}-5-ethenyl-3-fluorooxolan-2-yl]-5-fluoropyrimidin-2-one (800 mg, 79.69%) as a white solid. LC-MS (ES, m/z): 518 (M+H$^+$).

Step 2: To a stirred solution of 4-amino-1-[(2R,3S,4R,5R)-4-[(tert-butyldimethylsilyl) oxy]-5-{[(tert-butyldimethylsilyl)oxy]methyl}-5-ethenyl-3-fluorooxolan-2-yl]-5-fluoro-pyrimidin-2-one (800 mg, 1.5 mmol) in MeOH, was added NH$_4$F (858.4 mg, 23.2 mmol). The resulting mixture was stirred overnight at 60° C., then cooled to room temperature and remove the solid by filtration. The filter cake was washed with MeOH and the combined filtrate was concentrated under vacuum. The residue was purified by reversed-phase flash chromatography with the following conditions: column, C18 silica gel; mobile phase, MeCN in water (0.1% TFA), 5% to 20% gradient in 15 min; UV detection at 254 nm. This resulted in 4-amino-1-[(2R,3S,4R,5R)-5-ethenyl-3-fluoro-4-hydroxy-5-(hydroxymethyl)oxolan-2-yl]-5-fluoropyrimidin-2-one (300 mg, purity: 90%) as a yellow solid. 100 mg crude solid was further purified by Prep-HPLC with the following conditions: Column, XBridge Shield RP18 OBD Column, 19*250 mm, 10 μm; Mobile Phase A: Water (10 mmol/L NH$_4$HCO$_3$), Mobile Phase B: ACN; Flow rate: 25 mL/min; Gradient: 3% B to 20% B in 6.5 min, 20% B; Wavelength: 254 nm. After lyophilization overnight, the desired 4-amino-1-[(2R,3S,4R,5R)-5-ethenyl-3-fluoro-4-hydroxy-5-(hydroxymethyl)oxolan-2-yl]-5-fluoropyrimidin-2-one (56.3 mg) was obtained as a white solid. LC-MS (ES, m/z): 290 (M+H$^+$). $^1$H NMR (400 MHz, DMSO-d$_6$) δ 8.17 (d, J=7.2 Hz, 1H), 7.88 (s, 1H), 7.64 (s, 1H), 6.14-6.11 (m, 1H), 6.04 (d, J=5.2 Hz, 1H), 5.97-5.90 (m, 1H), 5.53 (t, J=5.6 Hz, 1H), 5.41-5.32 (m, 1H), 5.26-5.23 (m, 1H), 5.03-5.00 (m, 0.5H), 4.89-4.87 (m, 0.5H), 4.48-4.42 (m, 1H), 3.55-3.51 (m, 1H), 3.39-3.36 (m, 1H).

Example 25—Synthesis of Compound 77: 4-amino-1-[(2R,3S,4R,5R)-5-ethyl-3-fluoro-4-hydroxy-5-(hydroxymethyl)oxolan-2-yl]-5-fluoropyrimidin-2-one

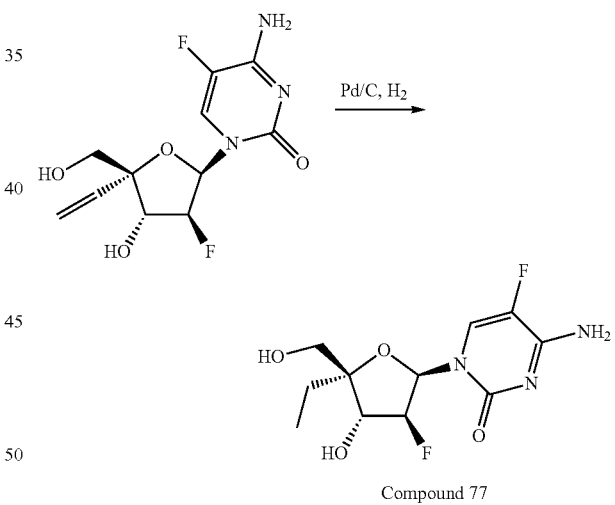

Compound 77

Step 1: To a solution of 4-amino-1-[(2R,3S,4R,5R)-5-ethenyl-3-fluoro-4-hydroxy-5-(hydroxymethyl)oxolan-2-yl]-5-fluoropyrimidin-2-one (200 mg, 0.7 mmol) in 5 mL MeOH was added Pd/C (10%, 100 mg) under nitrogen atmosphere. The mixture was degassed with with nitrogen, placed under an atmosphere of hydrogen gas (balloon), then stirred overnight at room temperature. The solids were removed by filtration and the filtrate was concentrated under vacuum. The crude product was purified by Prep-HPLC with the following conditions: Column: X Bridge Shield RP18 OBD Column, 19*250 mm, 10 μm; Mobile Phase A: water (10 mmol/L NH$_4$HCO$_3$), Mobile Phase B: ACN; Flow rate: 25 mL/min; Gradient: 5% B to 30% B in 6 min, 30% B; Wavelength: 254 nm. After lyophilization overnight, 4-amino-1-[(2R,3S,4R,5R)-5-ethyl-3-fluoro-4-hydroxy-5-(hydroxymethyl)oxolan-2-yl]-5-fluoropyrimidin-2-one (51.6 mg, 25.6%) was obtained as a white solid. LC-MS (ES, m/z): 292 (M+H⁺). ¹H NMR (400 MHz, DMSO-$d_6$) δ 8.07 (d, J=6.8 Hz, 1H), 7.84 (s, 1H), 7.60 (s, 1H), 6.12-6.04 (m, 1H), 5.81 (d, J=4.4 Hz, 1H), 5.25 (brs, 1H), 5.16 (s, 0.5H), 5.03 (s, 0.5H), 4.34-4.29 (m, 1H), 3.58-3.52 (m, 1H), 3.42-3.40 (m, 1H), 1.65-1.61 (m, 1H), 1.59-1.48 (m, 1H), 0.86 (t, J=7.6 Hz, 3H).

Example 26—Synthesis of Compound 65: 4-amino-1-[(2R,4S,5R)-5-(difluoromethyl)-4-hydroxy-5-(hydroxymethyl)oxolan-2-yl]-5-fluoropyrimidin-2-one

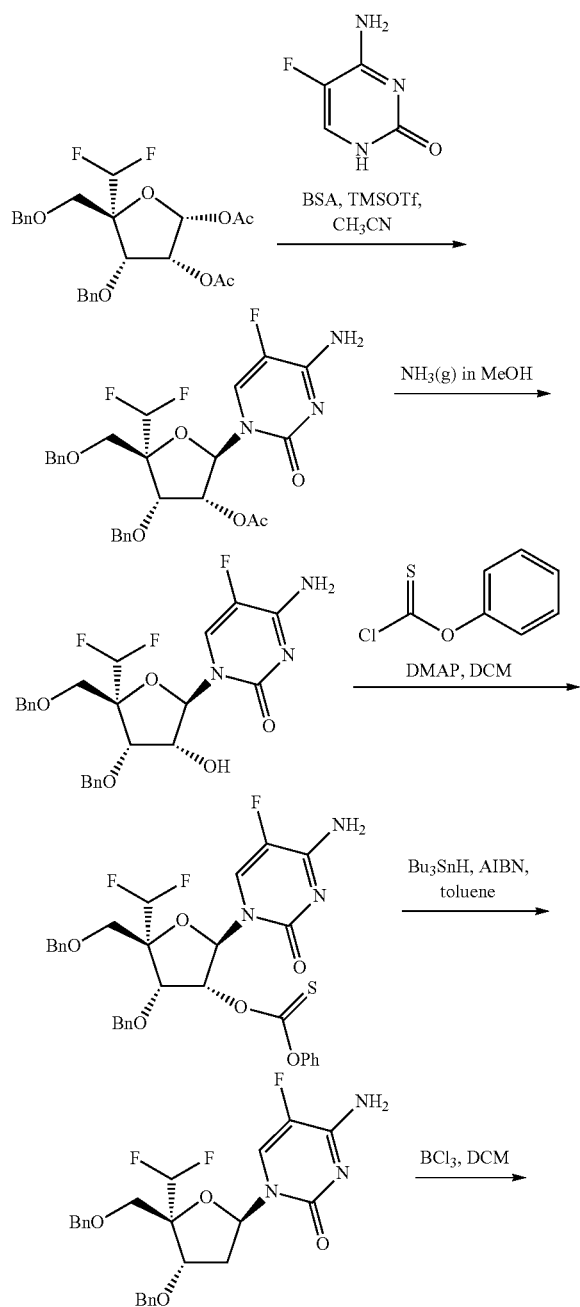

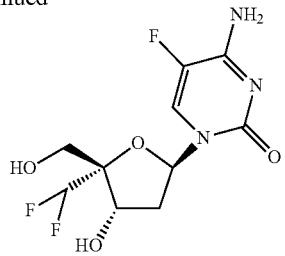

Compound 65

Step 1: To a stirred mixture of 5-fluorocytosine (2 g, 16.1 mmol) in ACN (50 mL) was added (E)-(trimethylsilyl N-(trimethylsilyl) ethenecarboximidate) (8.8 g, 43.0 mmol) in portions at room temperature under nitrogen atmosphere. The resulting mixture was stirred for 2 h at 80° C. Then to above mixture were added (2R,3R,4S,5R)-2-(acetyloxy)-4-(benzyloxy)-5-[(benzyloxy)methyl]-5-(difluoromethyl) oxolan-3-yl acetate (5 g, 10.7 mmol) and TMSOTf (4.8 g, 21.5 mmol) at 0° C. under nitrogen atmosphere. The resulting mixture was stirred for additional 3 h at 80° C. The reaction was cooled to room temperature and quenched with sat. NH₄Cl (aq.) at 0° C. The resulting mixture was extracted with ethyl acetate (3×40 mL). The combined organic layers were washed with brine (3×40 mL), dried over anhydrous Na₂SO₄. After filtration, the filtrate was concentrated under reduced pressure. The residue was purified by silica gel column chromatography, eluted with dichloromethane/methanol (10:1) to afford (2R,3R,4S,5R)-2-(4-amino-5-fluoro-2-oxopyrimidin-1(2H)-yl)-4-(benzyloxy)-5-((benzyloxy)methyl)-5-(difluoromethyl)tetrahydrofuran-3-yl acetate (2.8 g, 5.2 mmol, 60.94%) as a white solid. LC-MS (ES, m/z): 534 (M+H⁺).

Step 2: To a solution of NH₃(g) in MeOH (20 mL, 7.0 M) was added (2R,3R,4S,5R)-2-(4-amino-5-fluoro-2-oxopyrimidin-1(2H)-yl)-4-(benzyloxy)-5-((benzyloxy)methyl)-5-(difluoromethyl)tetrahydrofuran-3-yl acetate (2.8 g, 5.2 mmol) at room temperature. The resulting mixture was stirred for overnight at room temperature. The resulting mixture was concentrated under reduced pressure. The residue was purified by silica gel column chromatography, eluted with dichloromethane/methanol (10:1) to afford 4-amino-1-[(2R,3R,4S,5R)-4-(benzyloxy)-5-[(benzyloxy)methyl]-5-(difluoromethyl)-3-hydroxyoxolan-2-yl]-5-fluoropyrimidin-2-one (2.2 g, 4.5 mmol, 85.29%) as a white solid. LC-MS (ES, m/z): 492 (M+H⁺).

Step 3: To a stirred mixture of 4-amino-1-[(2R,3R,4S,5R)-4-(benzyloxy)-5-[(benzyloxy)methyl]-5-(difluoromethyl)-3-hydroxyoxolan-2-yl]-5-fluoropyrimidin-2-one (500 mg, 1.0 mmol) in dichloromethane (5 mL) were added phenyl chloromethanethioate (210 mg, 1.2 mmol) and DMAP (497 mg, 4.0 mmol) at room temperature under nitrogen atmosphere. The resulting mixture was stirred for 2 h at room temperature. The resulting mixture was concentrated under reduced pressure. The residue was purified by silica gel column chromatography, eluted with dichloromethane/methanol (10:1) to afford 4-amino-1-[(2R,3R,4S,5R)-4-(benzyloxy)-5-[(benzyloxy)methyl]-5-(difluoromethyl)-3-[(phenoxy-methanethioyl)oxy] oxolan-2-yl]-5-fluoropyrimidin-2-one (340 mg, 0.5 mmol, 53.25%) as a white solid. LC-MS (ES, m/z): 628 (M+H⁺).

Step 4: To a stirred solution of 4-amino-1-[(2R,3R,4S,5R)-4-(benzyloxy)-5-[(benzyloxy)methyl]-5-(difluoromethyl)-3-[(phenoxymethanethioyl)oxy] oxolan-2-yl]-5-fluoropyrimidin-2-one (340 mg, 0.5 mmol) in toluene (8 mL) were added AIBN (178 mg, 1.0 mmol) and tributylstannane (942 mg, 3.2 mmol) at room temperature under nitrogen atmosphere. The resulting mixture was stirred for 2 h at 90° C. The resulting mixture was cooled to room temperature and concentrated under reduced pressure. The residue was purified by silica gel column chromatography, eluted with dichloromethane/methanol (10:1) to afford 4-amino-1-[(2R,4S,5R)-4-(benzyloxy)-5-[(benzyloxy)methyl]-5-(difluoromethyl) oxolan-2-yl]-5-fluoropyrimidin-2-one (180 mg, 0.4 mmol, 69.88%) as a white solid. LC-MS (ES, m/z): 476 (M+H⁺).

Step 5: To a stirred mixture of 4-amino-1-[(2R,4S,5R)-4-(benzyloxy)-5-[(benzyloxy)methyl]-5-(difluoromethyl) oxolan-2-yl]-5-fluoropyrimidin-2-one (180 mg, 0.3 mmol) in DCM (5 mL) was added boron trichloride (0.9 mL, 1.0 M in DCM) dropwise at −78° C. under nitrogen atmosphere. The resulting mixture was stirred for 2 h at −78° C. The reaction was quenched by the addition of methanol at −78° C. The resulting mixture was concentrated under reduced pressure. The crude product was purified by Prep-HPLC with the following conditions (Column: XBridge Shield RP18 OBD Column, 19*250 mm, 10 μm; Mobile Phase A: Water (10 mmol/L NH₄HCO₃), Mobile Phase B: ACN; Flow rate: 25 mL/min; Gradient: 5% B to 16% B in 3 min, 16% B to 19% B in 7 min; Wavelength: 254 nm) to afford 4-amino-1-[(2R,4S,5R)-5-(difluoromethyl)-4-hydroxy-5-(hydroxymethyl)oxolan-2-yl]-5-fluoropyrimidin-2-one (15 mg, 0.05 mmol, 13.42%) as an off-white solid. LC-MS (ES, m/z): 296 (M+H⁺). 98.1% purity. Conditions for the HPLC: (Column: Shim-pack ScepterC18 Column, 4.6*100 mm, 4.5 μm; Mobile Phase A: Water/5 mM NH₄HCO₃, Mobile Phase B: ACN; Flow rate: 1.50 mL/min; Gradient: 5% B to 95% B in 8 min, 95% B to 95% B in 10 min, 95% B to 10% B in 10.5 min; Wavelength: 254/220 nm; RT1(min): 2.500). ¹H NMR (400 MHz, DMSO-d₆) δ 8.22-7.96 (m, 1H), 7.86 (d, J=31.0 Hz, 1H), 7.68-7.45 (m, 1H), 6.43-6.25 (m, 1H), 6.08 (t, J=54.6 Hz, 1H), 5.80-5.53 (m, 1H), 5.49-5.37 (m, 1H), 4.77-4.34 (m, 1H), 3.85-3.44 (m, 2H), 2.22 (t, J=6.2 Hz, 2H).

Example 27—Synthesis of Compound 63: 2-amino-9-[(2R,3S,4R,5R)-5-ethenyl-3-fluoro-4-hydroxy-5-(hydroxymethyl) oxolan-2-yl]-1H-purin-6-one

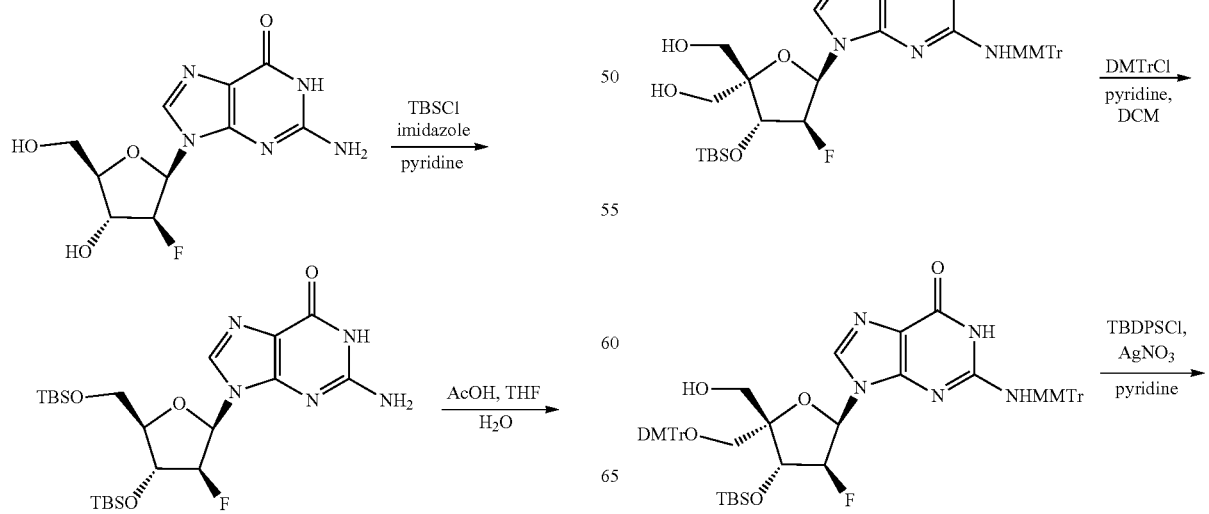

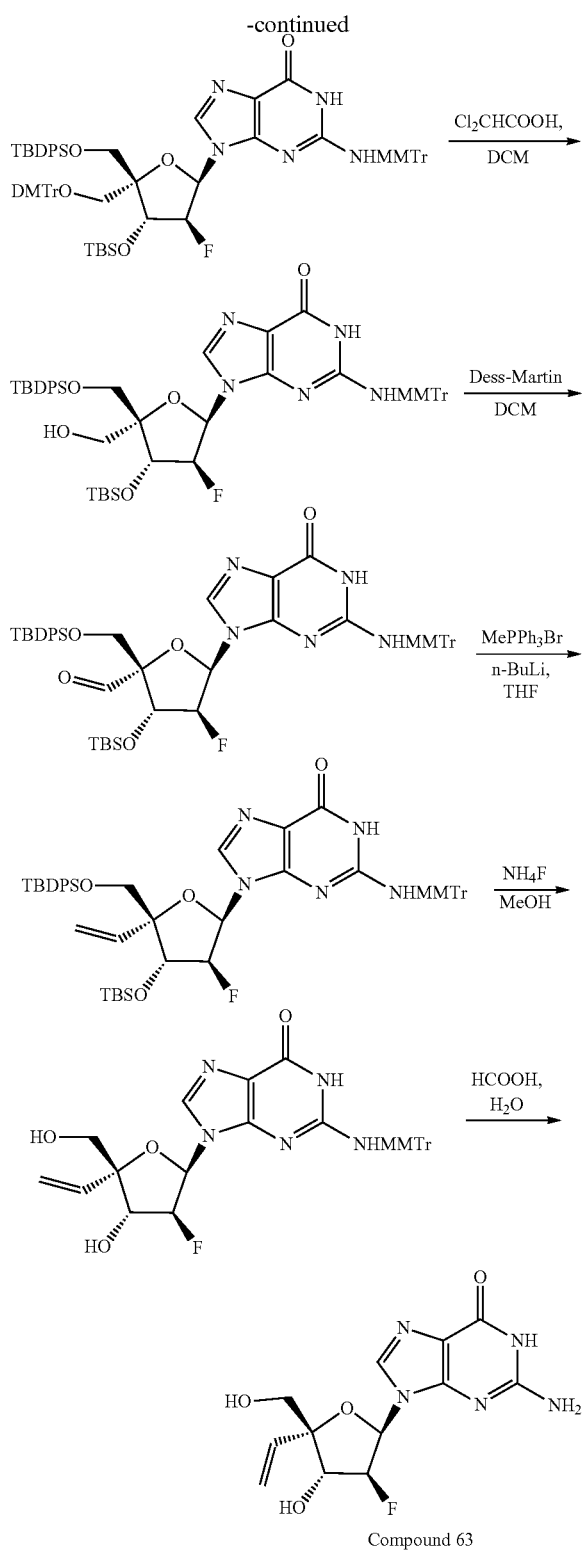

Compound 63

Step 1: To a stirred solution of 2-amino-9-[(2R,3S,4R,5R)-3-fluoro-4-hydroxy-5-(hydroxymethyl) oxolan-2-yl]-1H-purin-6-one (13 g, 45.5 mmol) and imidazole (23 g, 341.8 mmol) in pyridine (250 ml) was added TBSCl (17 g, 113.9 mmol) in portions at room temperature under nitrogen atmosphere. The resulting mixture was stirred for overnight at room temperature under nitrogen atmosphere. The resulting mixture was diluted with water (1000 mL). The resulting mixture was extracted with ethyl acetate (3×500 mL). The combined organic layers were washed with brine (3×500 mL), dried over anhydrous sodium sulfate. After filtration, the filtrate was concentrated under reduced pressure. The residue was purified by silica gel column chromatography, eluted with petroleum ether/ethyl acetate (1:1) to afford 2-amino-9-[(2R,3S,4R,5R)-4-[(tert-butyldimethylsilyl) oxy]-5-{[(tert-butyldimethylsilyl) oxy] methyl}-3-fluorooxolan-2-yl]-1H-purin-6-one (23 g, 44.8 mmol, 98.23%) as a white solid. LC-MS (ES, m/z): 514 (M+H$^+$).

Step 2: A solution of 2-amino-9-[(2R,3S,4R,5R)-4-[(tert-butyldimethylsilyl) oxy]-5-{[(tert-butyldimethylsilyl) oxy] methyl}-3-fluorooxolan-2-yl]-1H-purin-6-one (23 g, 44.7 mmol) and AcOH (210 mL) in THF (105 ml) and H$_2$O (70 mL) was stirred for overnight at 60° C. under nitrogen atmosphere. The resulting mixture was diluted with water (500 mL). The resulting mixture was extracted with ethyl acetate (3×500 mL). The combined organic layers were washed with brine (3×500 mL), dried over anhydrous sodium sulfate. After filtration, the filtrate was concentrated under reduced pressure. The residue was purified by silica gel column chromatography, eluted with petroleum ether/ethyl acetate (1:1) to afford 2-amino-9-[(2R,3S,4R,5R)-4-[(tert-butyldimethylsilyl) oxy]-3-fluoro-5-(hydroxymethyl) oxolan-2-yl]-1H-purin-6-one (17 g, 42.6 mmol, 95.05%) as a white solid. LC-MS (ES, m/z): 400 (M+H$^+$).

Step 3: A solution of 2-amino-9-[(2R,3S,4R,5R)-4-[(tert-butyldimethylsilyl) oxy]-3-fluoro-5-(hydroxymethyl) oxolan-2-yl]-1H-purin-6-one (17 g, 42.5 mmol) in pyridine (300 ml) was treated with Ac$_2$O (6.5 g, 63.8 mmol) for overnight at room temperature under nitrogen atmosphere followed by the addition of 1-(chlorodiphenylmethyl)-4-methoxybenzene (39.4 g, 127.6 mmol) and AgNO$_3$ (21.6 g, 127.6 mmol) in portions at room temperature. The resulting mixture was stirred for overnight at room temperature under nitrogen atmosphere. The resulting mixture was diluted with water (500 mL). The resulting mixture was extracted with ethyl acetate (3×500 mL). The combined organic layers were washed with brine (3×500 mL), dried over anhydrous sodium sulfate. After filtration, the filtrate was concentrated under reduced pressure. The residue was purified by silica gel column chromatography, eluted with dichloromethane/methanol (20:1) to afford [(2R,3R,4S,5R)-3-[(tert-butyldimethylsilyl) oxy]-4-fluoro-5-(2-{[(4-methoxyphenyl) diphenyl methyl] amino}-6-oxo-1H-purin-9-yl) oxolan-2-yl] methyl acetate (23.8 g, 33.3 mmol, 78.35%) as a yellow solid. LC-MS (ES, m/z): 714 (M+H$^+$).

Step 4: To a solution of NH$_3$(g) in MeOH (238 mL, 7 M) was added [(2R,3R,4S,5R)-3-[(tert-butyldimethylsilyl) oxy]-4-fluoro-5-(2-{[(4-methoxyphenyl) diphenyl methyl] amino}-6-oxo-1H-purin-9-yl) oxolan-2-yl] methyl acetate (24 g, 33.3 mmol) and stirred for overnight at room temperature under nitrogen atmosphere. The resulting mixture was concentrated under reduced pressure. The residue was purified by silica gel column chromatography, eluted with dichloromethane/methanol (20:1) to afford 9-[(2R,3S,4R,5R)-4-[(tert-butyldimethylsilyl) oxy]-3-fluoro-5-(hydroxymethyl) oxolan-2-yl]-2-{[(4-methoxyphenyl) diphenyl methyl] amino}-1H-purin-6-one (10.4 g, 15.4 mmol, 46.43%) as a yellow solid. LC-MS (ES, m/z): 672 (M+H$^+$).

Step 5: A mixture of 9-[(2R,3S,4R,5R)-4-[(tert-butyldimethylsilyl) oxy]-3-fluoro-5-(hydroxymethyl) oxolan-2-yl]-2-{[(4-methoxyphenyl) diphenyl methyl] amino}-1H-purin-6-one (10 g, 15.4 mmol) and IBX (5.6 g, 20.1 mmol) in acetonitrile (200 ml) was stirred for 2 h at 60° C. under nitrogen atmosphere. The resulting mixture was cooled to room temperature, filtered and the filter cake was washed with acetonitrile (3×200 mL). The filtrate was concentrated under reduced pressure. The crude product was used in the next step directly without further purification. LC-MS (ES, m/z): 670 (M+H$^+$).

Step 6: To a solution of (2S,3R,4S,5R)-3-[(tert-butyldimethylsilyl) oxy]-4-fluoro-5-(2-{[(4-methoxyphenyl) diphenyl methyl] amino}-6-oxo-1H-purin-9-yl) oxolane-2-carbaldehyde (10 g, 15.5 mmol) in dioxane (200 ml) and H$_2$O (40 mL) was added paraformaldehyde (5.5 g, 62.1 mmol) and NaOH (931 mg, 23.2 mmol) and stirred for overnight at room temperature under nitrogen atmosphere followed by the addition of NaBH$_4$ (3.5 g, 93.1 mmol) in portions at 0° C. The resulting mixture was stirred for 1 h at room temperature under nitrogen atmosphere. The resulting mixture was quenched with ice water (500 mL). The resulting mixture was extracted with ethyl acetate (3×500 mL). The combined organic layers were washed with brine (3×500 mL), dried over anhydrous sodium sulfate. After filtration, the filtrate was concentrated under reduced pressure. The residue was purified by silica gel column chromatography, eluted with dichloromethane/methanol (20:1) to afford 9-[(2R,3S,4R)-4-[(tert-butyldimethylsilyl) oxy]-3-fluoro-5,5-bis(hydroxymethyl)oxolan-2-yl]-2-{[(4-methoxyphenyl) diphenyl methyl] amino}-1H-purin-6-one (6.5 g, 9.2 mmol, 59.65%) as a yellow solid. LC-MS (ES, m/z): 702 (M+H$^+$).

Step 7: A solution of 9-[(2R,3S,4R)-4-[(tert-butyldimethylsilyl) oxy]-3-fluoro-5,5-bis(hydroxymethyl)oxolan-2-yl]-2-{[(4-methoxyphenyl) diphenylmethyl] amino}-1H-purin-6-one (1.3 g, 1.8 mmol) and 1-[chloro(4-methoxyphenyl) phenyl methyl]-4-methoxybenzene (627 mg, 1.8 mmol) in dichloromethane (20 ml) and pyridine (5 mL) was stirred for 2 h at room temperature under nitrogen atmosphere. The resulting mixture was diluted with water (100 mL). The resulting mixture was extracted with dichloromethane (3×100 mL). The combined organic layers were washed with brine (3×100 mL), dried over anhydrous sodium sulfate. After filtration, the filtrate was concentrated under reduced pressure. The residue was purified by silica gel column chromatography, eluted with dichloromethane/methanol (25:1) to afford 9-[(2R,3S,4R,5S)-5-{[bis(4-methoxyphenyl) (phenyl)methoxy] methyl}-4-[(tert-butyldimethylsilyl) oxy]-3-fluoro-5-(hydroxymethyl) oxolan-2-yl]-2-{1[(4-methoxyphenyl) diphenyl methyl] amino}-1H-purin-6-one (1 g, 0.9 mmol, 53.76%) as a yellow solid. LC-MS (ES, m/z): 1004 (M+H$^+$).

Step 8: To a stirred mixture of 9-[(2R,3S,4R,5S)-5-{[bis(4-methoxyphenyl) (phenyl)methoxy] methyl}-4-[(tert-butyldimethylsilyl) oxy]-3-fluoro-5-(hydroxymethyl) oxolan-2-yl]-2-{1[(4-methoxyphenyl) diphenylmethyl] amino}-1H-purin-6-one (950 mg, 0.9 mmol) and AgNO$_3$ (321 mg, 1.8 mmol) in pyridine (20 ml) was added TBDP-SCl (520 mg, 1.8 mmol) dropwise at room temperature under nitrogen atmosphere. The resulting mixture was stirred for 2 h at room temperature under nitrogen atmosphere. The resulting mixture was diluted with water (100 mL) and extracted with ethyl acetate (3×100 mL). The combined organic layers were washed with brine (3×100 mL), dried over anhydrous sodium sulfate. After filtration, the filtrate was concentrated under reduced pressure. The residue was purified by silica gel column chromatography, eluted with dichloromethane/methanol (40:1) to afford 9-[(2R,3S,4R,5R)-5-{[bis(4-methoxyphenyl) (phenyl) methoxy] methyl}-4-[(tert-butyldimethylsilyl) oxy]-5-{[(tert-butyldiphenylsilyl) oxy] methyl}-3-fluorooxolan-2-yl]-2-{1[(4-methoxyphenyl) diphenyl methyl]amino}-1H-purin-6-one (1.1 g, 0.8 mmol, 93.58%) as a white solid. LC-MS (ES, m/z): 1243 (M+H$^+$).

Step 9: To a stirred solution of 9-[(2R,3S,4R,5R)-5-{[bis (4-methoxyphenyl) (phenyl)methoxy] methyl}-4-[(tert-butyldimethylsilyl) oxy]-5-{[(tert-butyldiphenylsilyl) oxy] methyl}-3-fluorooxolan-2-yl]-2-{1[(4-methoxyphenyl) diphenyl methyl] amino}-1H-purin-6-one (1.1 g, 0.8 mmol) in dichloromethane (15 ml) was added dichloroacetic acid (0.5 mL) dropwise at −78° C. under nitrogen atmosphere. The resulting mixture was stirred for 2 h at −10° C. under nitrogen atmosphere. The resulting mixture was quenched with ice water (100 mL). The resulting mixture was extracted with dichloromethane (3×100 mL). The combined organic layers were washed with brine (3×100 mL), dried over anhydrous sodium sulfate. After filtration, the filtrate was concentrated under reduced pressure. The residue was purified by silica gel column chromatography, eluted with dichloromethane/methanol (30:1) to afford 9-[(2R,3S,4R, 5R)-4-[(tert-butyldimethylsilyl) oxy]-5-{[(tert-butyldiphenylsilyl) oxy] methyl}-3-fluoro-5-(hydroxymethyl) oxolan-2-yl]-2-{1[(4-methoxyphenyl) diphenylmethyl] amino}-1H-purin-6-one (400 mg, 0.4 mmol, 48.06%) as a white solid. LC-MS (ES, m/z): 940 (M+H$^+$).

Step 10: To a solution of 9-[(2R,3S,4R,5R)-4-[(tert-butyldimethylsilyl) oxy]-5-{[(tert-butyldiphenylsilyl) oxy] methyl}-3-fluoro-5-(hydroxymethyl) oxolan-2-yl]-2-{[(4-methoxyphenyl) diphenyl methyl] amino}-1H-purin-6-one (350 mg, 0.3 mmol) in dichloromethane (10 ml) was added Dess-Martin (394 mg, 0.9 mmol) in portions and stirred for 4 h at room temperature under nitrogen atmosphere. The resulting mixture was filtered and the filter cake was washed with dichloromethane (3×10 mL). The filtrate was concentrated under reduced pressure. The crude product was used in the next step directly without further purification. LC-MS (ES, m/z): 938 (M+H$^+$).

Step 11: To a solution of methyltriphenylphosphanium bromide (371 mg, 1.0 mmol) in tetrahydrofuran (10 ml) was added n-BuLi (0.1 ml, 1.0 mmol, 2.5 M in THF) and stirred for 1 h at −78° C. under nitrogen atmosphere. Then a solution of (2R,3R,4S,5R)-3-[(tert-butyldimethylsilyl) oxy]-2-{[(tert-butyldiphenylsilyl) oxy] methyl}-4-fluoro-5-(2-{[(4-methoxyphenyl) diphenyl methyl] amino}-6-oxo-1H-purin-9-yl) oxolane-2-carbaldehyde (325 mg, 0.3 mmol) in tetrahydrofuran (10 ml) was added dropwise at 0° C. The resulting mixture was stirred for overnight at room temperature under nitrogen atmosphere. The resulting mixture was quenched with ice water (100 mL). The resulting mixture was extracted with ethyl acetate (3×100 mL). The combined organic layers were washed with brine (3×100 mL), dried over anhydrous sodium sulfate. After filtration, the filtrate was concentrated under reduced pressure. The residue was purified by Prep-TLC (dichloromethane/methanol 20:1) to afford 9-[(2R,3S,4R,5R)-4-[(tert-butyldimethylsilyl) oxy]-5-{[(tert-butyldiphenylsilyl) oxy] methyl}-5-ethenyl-3-fluorooxolan-2-yl]-2-{1[(4-methoxyphenyl) diphenyl methyl] amino}-1H-purin-6-one (200 mg, 0.2 mmol, 61.67%) as a white solid. LC-MS (ES, m/z): 936 (M+H$^+$).

Step 12: A mixture of 9-[(2R,3S,4R,5R)-4-[(tert-butyldimethylsilyl) oxy]-5-{[(tert-butyldiphenylsilyl) oxy] methyl}-5-ethenyl-3-fluorooxolan-2-yl]-2-{1[(4-methoxyphenyl) diphenylmethyl] amino}-1H-purin-6-one (180 mg, 0.1 mmol) and NH$_4$F (167 mg, 4.5 mmol) in methanol (5 ml) was stirred for overnight at 60° C. under nitrogen atmosphere. The resulting mixture was cooled to room temperature, filtered and the filter cake was washed with methanol (3×5 mL). The filtrate was concentrated under reduced pressure. The residue was purified by Prep-TLC (dichloromethane/methanol 10:1) to afford 9-[(2R,3S,4R,5R)-5-ethenyl-3-fluoro-4-hydroxy-5-(hydroxymethyl) oxolan-2-yl]-2-{1[(4-methoxyphenyl) diphenyl methyl] amino}-1H-purin-6-one (60 mg, 0.1 mmol, 53.48%) as a white solid. LC-MS-PH-ROF-RT-0503-12 (ES, m/z): 584 (M+H$^+$).

Step 13: A solution of 9-[(2R,3S,4R,5R)-5-ethenyl-3-fluoro-4-hydroxy-5-(hydroxymethyl) oxolan-2-yl]-2-{[(4-methoxyphenyl) diphenyl methyl] amino}-1H-purin-6-one (55 mg, 0.1 mmol) in HCOOH (0.8 mL) and water (0.2 ml) was stirred for 2 h at room temperature under nitrogen atmosphere. The resulting mixture was concentrated under vacuum. The crude product was purified by Prep-HPLC with the following conditions (Column: XBridge Prep OBD C18 Column, 30*150 mm, 5 μm; Mobile Phase A: Water (10 mmol/L NH$_4$HCO$_3$+0.1% NH$_3$·H$_2$O), Mobile Phase B: ACN; Flow rate: 60 mL/min; Gradient: 3% B to 16% B in 8 min; Wavelength: 254/220 nm; RT1(min): 6.92) to afford 2-amino-9-[(2R,3S,4R,5R)-5-ethenyl-3-fluoro-4-hydroxy-5-(hydroxymethyl) oxolan-2-yl]-1H-purin-6-one (7.7 mg, 26.01%) as a white solid. LC-MS (ES, m/z): 312 (M+H$^+$). 99.1% purity. Conditions for the LCMS: (Column: Kinetex EVO C18-100A, 30*3.0 mm, 2.6 μm; Mobile Phase A: Water/6.5 mM NH$_4$HCO$_3$, Mobile Phase B: Acetonitrile; Flow rate: 1.2000 mL/min; Gradient: 5% B to 95% B in 1.20 min, 95% B to 95% B in 1.80 min, 95% B to 10% B in 1.82 min; Wavelength: 254/220 nm; RT1(min): 0.310). $^1$H NMR (300 MHz, DMSO-d$_6$) δ 9.68 (s, 1H), 7.92 (s, 1H), 6.52 (s, 2H), 6.26-5.85 (m, 3H), 5.48-4.91 (m, 4H), 4.67 (d, J=21.1 Hz, 1H), 3.53 (s, 1H), 3.44-3.37 (m, 1H).

Example 28—Synthesis of Compound 68: 2-amino-9-((2R,3S,4R,5R)-5-ethyl-3-fluoro-4-hydroxy-5-(hydroxymethyl)tetrahydrofuran-2-yl)-1,9-dihydro-6H-purin-6-one

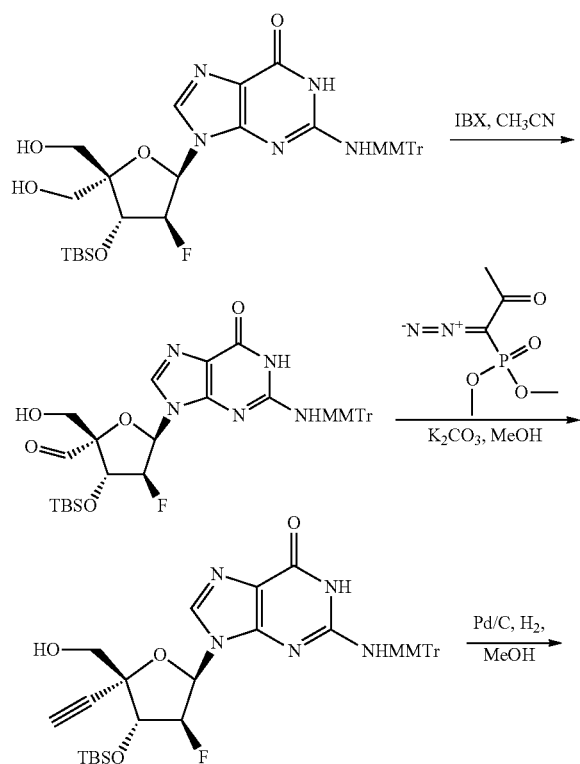

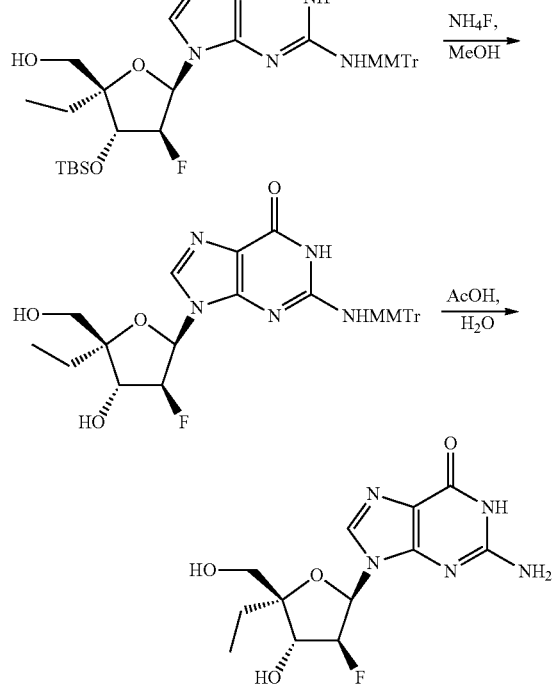

Compound 68

Step 1: To a mixture of 9-[(2R,3S,4R)-4-[(tert-butyldimethylsilyl) oxy]-3-fluoro-5,5-bis(hydroxymethyl)oxolan-2-yl]-2-{1[(4-methoxyphenyl) diphenyl methyl] amino}-1H-purin-6-one (1 g, 1.4 mmol) in acetonitrile (100 ml) was added IBX (598 mg, 2.1 mmol) in portions and stirred for overnight at room temperature under nitrogen atmosphere. The resulting mixture was filtered; the filter cake was washed with acetonitrile (3×20 mL). The filtrate was concentrated under reduced pressure. The crude product was used in the next step directly without further purification. LC-MS (ES, m/z): 700 (M+H$^+$).

Step 2: To a stirred mixture of (2R,3R,4S,5R)-3-[(tert-butyldimethylsilyl) oxy]-4-fluoro-2-(hydroxymethyl)-5-(2-{1[(4-methoxyphenyl) diphenyl methyl] amino}-6-oxo-1H-purin-9-yl) oxolane-2-carbaldehyde (1 g, 1.4 mmol) and K$_2$CO$_3$ (592 mg, 4.2 mmol) in methanol (20 ml) was added dimethyl (1-diazo-2-oxopropyl)phosphonate (549 mg, 2.8 mmol) at room temperature under nitrogen atmosphere and stirred for overnight at room temperature under nitrogen atmosphere. The resulting mixture was concentrated under reduced pressure. The residue was purified by silica gel column chromatography, eluted with dichloromethane/methanol (20:1) to afford 9-[(2R,3S,4R,5R)-4-[(tert-butyldimethylsilyl) oxy]-5-ethynyl-3-fluoro-5-(hydroxymethyl) oxolan-2-yl]-2-{1[(4-methoxyphenyl) diphenyl methyl] amino}-1H-purin-6-one (380 mg, 0.5 mmol, 38.22%) as a white solid. LC-MS (ES, m/z): 696 (M+H$^+$).

Step 3: A mixture of 9-[(2R,3S,4R,5R)-4-[(tert-butyldimethylsilyl) oxy]-5-ethynyl-3-fluoro-5-(hydroxymethyl) oxolan-2-yl]-2-{1[(4-methoxyphenyl) diphenylmethyl] amino}-1H-purin-6-one (370 mg, 0.5 mmol) and Pd/C (37 mg, 0.3 mmol, 10% on carbon) in methanol (10 ml) was stirred for overnight at room temperature under hydrogen atmosphere. The resulting mixture was filtered; the filter cake was washed with methanol (3×10 mL). The filtrate was concentrated under reduced pressure. This resulted in 9-[(2R,3S,4R,5R)-4-[(tert-butyldimethylsilyl) oxy]-5-ethyl-3-fluoro-5-(hydroxymethyl) oxolan-2-yl]-2-{[(4-methoxyphenyl) diphenylmethyl] amino}-1H-purin-6-one (350 mg, 0.5 mmol, crude) as a white solid. LC-MS (ES, m/z): 700 (M+H$^+$).

Step 4: A mixture of 9-[(2R,3S,4R,5R)-4-[(tert-butyldimethylsilyl) oxy]-5-ethyl-3-fluoro-5-(hydroxymethyl) oxolan-2-yl]-2-{1[(4-methoxyphenyl) diphenylmethyl] amino}-1H-purin-6-one (340 mg, 0.4 mmol) and NH$_4$F (422 mg, 11.4 mmol) in methanol (10 ml) was stirred for overnight at 60° C. under nitrogen atmosphere. The resulting mixture was cooled to room temperature, filtered; the filter cake was washed with methanol (3×10 mL). The filtrate was concentrated under reduced pressure. The residue was purified by Prep-TLC (dichloromethane/methanol 10:1) to afford 9-[(2R,3S,4R,5R)-5-ethyl-3-fluoro-4-hydroxy-5-(hydroxymethyl) oxolan-2-yl]-2-{1[(4-methoxyphenyl) diphenyl methyl] amino}-1H-purin-6-one (140 mg, 0.2 mmol, 49.21%) as a white solid. LC-MS (ES, m/z): 586 (M+H$^+$).

Step 5: A solution of 9-[(2R,3S,4R,5R)-5-ethyl-3-fluoro-4-hydroxy-5-(hydroxymethyl) oxolan-2-yl]-2-{1[(4-methoxyphenyl) diphenylmethyl] amino}-1H-purin-6-one (130 mg, 0.2 mmol) in acetic acid (1.6 mL) and water (0.4 ml) was stirred for overnight at room temperature under nitrogen atmosphere. The resulting mixture was concentrated under vacuum. The crude product was purified by Prep-HPLC with the following conditions (Column: XBridge Shield RP18 OBD Column, 19*250 mm, 10 μm; Mobile Phase A: Water (10 mmol/L NH$_4$HCO$_3$), Mobile Phase B: ACN; Flow rate: 25 mL/min; Gradient: 5% B to 30% B in 6 min; Wavelength: 254 nm) to afford 2-amino-9-((2R,3S,4R,5R)-5-ethyl-3-fluoro-4-hydroxy-5-(hydroxymethyl)tetrahydrofuran-2-yl)-1,9-dihydro-6H-purin-6-one (30.1 mg, 0.1 mmol, 42.94%) as a white solid. LC-MS (ES, m/z): 314 (M+H$^+$). 99.2% purity. Conditions for the HPLC: (Column: Xselect HSS T3, 100*4.6 mm, 3.5 μm; Mobile Phase A: water/0.05% TFA, Mobile Phase B: MeOH; Flow rate: 1.2000 mL/min; Gradient: 5% B to 95% B in 8.00 min, 95% B to 95% B in 10.00 min, 90% B to 10% B in 10.50 min; Wavelength: 254/220 nm; RT1(min): 3.78). $^1$H NMR (400 MHz, DMSO-d$_6$) δ 8.23 (s, 1H), 7.85 (s, 1H), 6.55 (s, 2H), 6.15 (dd, J=13.7, 4.7 Hz, 1H), 5.89 (s, 1H), 5.20 (dt, J=53.4, 4.7 Hz, 2H), 4.54 (dd, J=19.7, 4.4 Hz, 1H), 3.49 (q, J=11.8 Hz, 2H), 1.60 (ddq, J=43.7, 14.9, 7.5 Hz, 2H), 0.89 (t, J=7.5 Hz, 3H).

Example 29—Synthesis of Compound 69: 2-amino-9-((2R,4S,5R)-4-hydroxy-5-hydroxymethyl)-5-vinyltetrahydrofuran-2-yl)-1,9-dihydro-6H-purin-6-one

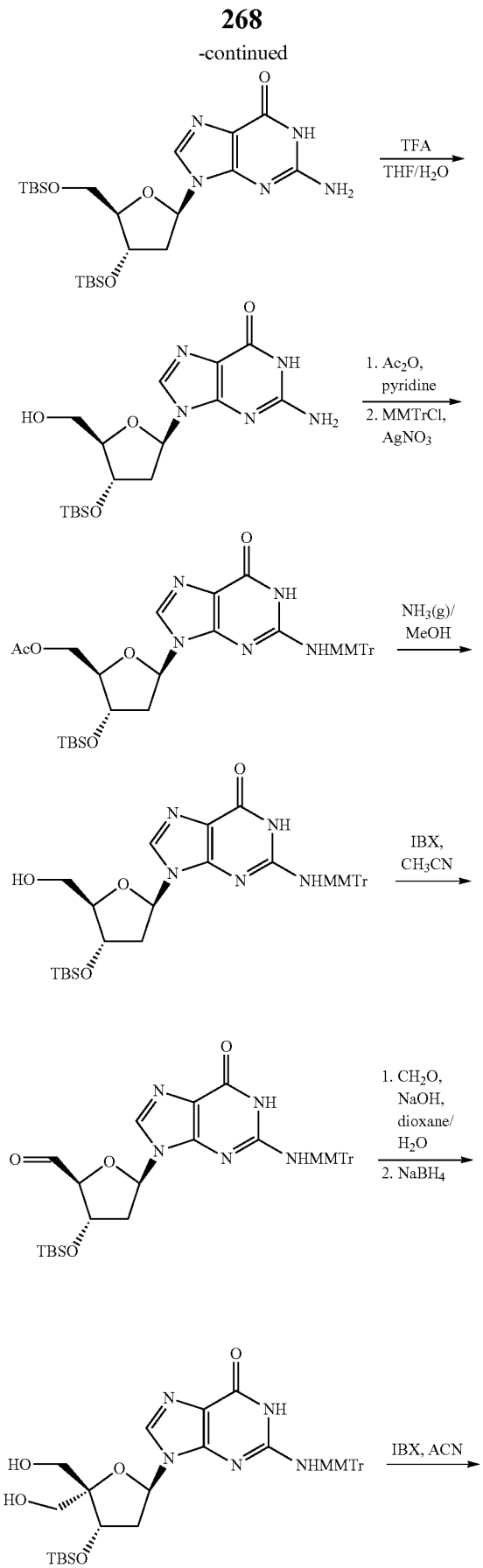

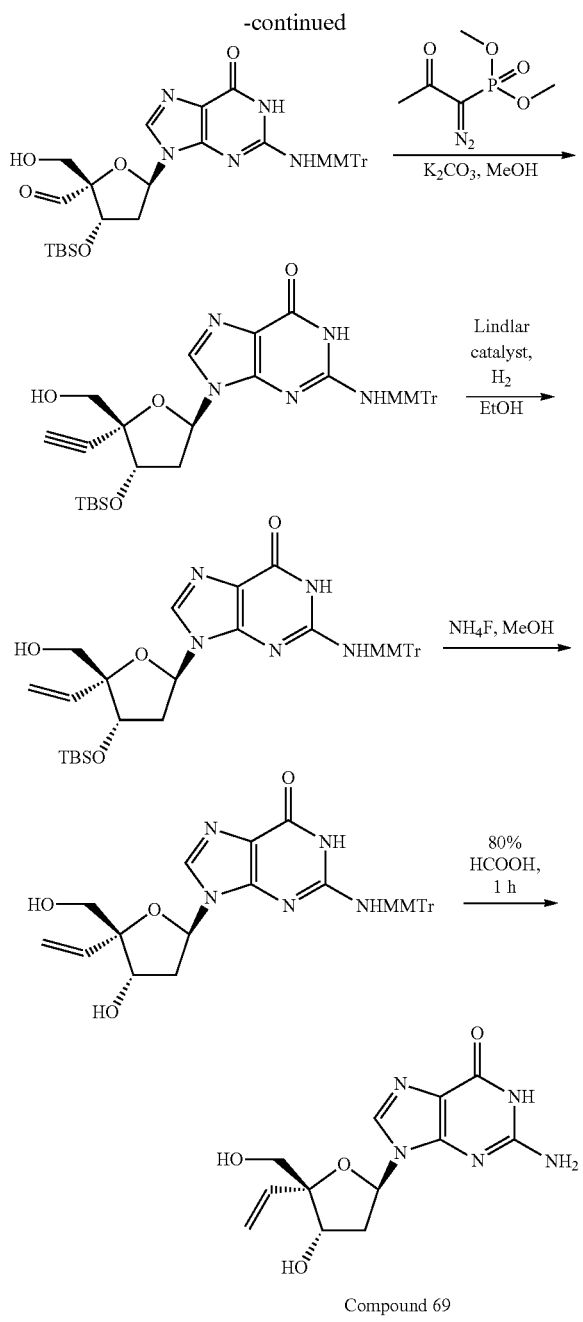

Compound 69

Step 1: To a stirred solution of 2-deoxyguanosine (20 g, 74.8 mmol) and imidazole (20.4 g, 299.3 mmol) in pyridine (300 mL) were added TBSCl (45.1 g, 299.3 mmol) in portions at room temperature under nitrogen atmosphere. The solution was stirred at room temperature for 12 h. The resulting mixture was concentrated under vacuum, diluted with water and extracted with ethyl acetate (3×300 mL). The combined organic layers were washed with brine (2×300 mL), dried over anhydrous sodium sulfate. After filtration, the filtrate was concentrated under reduced pressure. This resulted in 2-amino-9-[(2R,4S,5R)-4-[(tert-butyldimethylsilyl) oxy]-5-{[(tert-butyldimethylsilyl) oxy] methyl} oxolan-2-yl]-1H-purin-6-one (36 g, 72.7 mmol, crude) as a white solid. LC-MS (ES, m/z): 496 (M+H$^+$).

Step 2: Into a 1 L round-bottom flask were added 2-amino-9-[(2R,4S,5R)-4-[(tert-butyldimethylsilyl)oxy]-5-{[(tert-butyldimethylsilyl)oxy]methyl}oxolan-2-yl]-1H-purin-6-one (30 g, 48.4 mmol) in THF (200 mL) and H$_2$O (100 mL), then TFA (100 mL) was added at 0° C. and stirred for 1 h. The resulting mixture was concentrated under vacuum. The mixture was diluted with water and extracted with ethyl acetate (3×300 mL). The combined organic layers were washed with brine (2×300 mL), dried over anhydrous sodium sulfate. After filtration, the filtrate was concentrated under reduced pressure. The residue was purified by silica gel column chromatography, eluted with CH$_2$Cl$_2$/MeOH (20:1) to afford 2-amino-9-[(2R,4S,5R)-4-[(tert-butyldimethylsilyl) oxy]-5-(hydroxymethyl) oxolan-2-yl]-1H-purin-6-one (13 g, 34.1 mmol, 63.3%) as a yellow solid. LC-MS (ES, m/z): 382 (M+H$^+$).

Step 3: A mixture of 2-amino-9-[(2R,4S,5R)-4-[(tert-butyldimethylsilyl) oxy]-5-(hydroxymethyl) oxolan-2-yl]-1H-purin-6-one (13 g, 34.1 mmol) and Ac$_2$O (5.2 g, 51.1 mmol) in pyridine (200 mL) was stirred for 6 h at room temperature under nitrogen atmosphere. To the above mixture was added AgNO$_3$ (17.4 g, 102.2 mmol) and 1-(chlorodiphenylmethyl)-4-methoxybenzene (31.6 g, 102.2 mmol) at room temperature. The resulting mixture was stirred for additional 6 h at room temperature. Then ice water was added to quench the reaction. The resulting mixture was concentrated under vacuum. The resulting mixture was diluted with ethyl acetate (300 mL) and washed with brine (3×100 mL), dried over anhydrous sodium sulfate. After filtration, the filtrate was concentrated under reduced pressure. This resulted in [(2R,3S,5R)-3-[(tert-butyldimethylsilyl) oxy]-5-(2-{1[(4-methoxyphenyl) diphenylmethyl] amino}-6-oxo-1H-purin-9-yl) oxolan-2-yl] methyl acetate (25 g, 25.1 mmol, crude) as a yellow solid. LC-MS (ES, m/z): 696 (M+H$^+$).

Step 4: Into a 500 mL round-bottom flask were added [(2R,3S,5R)-3-[(tert-butyldimethylsilyl) oxy]-5-(2-{1[(4-methoxyphenyl) diphenylmethyl] amino}-6-oxo-1H-purin-9-yl) oxolan-2-yl] methyl acetate (25 g, 25.1 mmol) in MeOH (150 mL), then a solution of NH$_3$(g) in MeOH (105.0 mL, 7.0 M) was added and stirred at room temperature for 2 h. The resulting mixture was concentrated under vacuum. The residue was purified by silica gel column chromatography, eluted with CH$_2$Cl$_2$/MeOH (15:1) to afford 9-[(2R,4S,5R)-4-[(tert-butyldimethylsilyl) oxy]-5-(hydroxymethyl) oxolan-2-yl]-2-{1[(4-methoxyphenyl) diphenylmethyl] amino}-1H-purin-6-one (7 g, 10.7 mmol, 40.4%) as a yellow solid. LC-MS (ES, m/z): 654 (M+H$^+$).

Step 5: Into a 250 mL round-bottom flask were added 9-[(2R,4S,5R)-4-[(tert-butyldimethylsilyl) oxy]-5-(hydroxymethyl) oxolan-2-yl]-2-{1[(4-methoxyphenyl) diphenylmethyl] amino}-1H-purin-6-one (7 g, 10.7 mmol) and IBX (9 g, 32.1 mmol) in CH$_3$CN (100 mL) at room temperature. The mixture was stirred for 2 h at 60° C. under nitrogen atmosphere and then cooled to room temperature. The precipitated solids were filtrated and washed with CH$_3$CN (3×50 mL). The resulting filtrate was concentrated under vacuum. This resulted in (2S,3S,5R)-3-[(tert-butyldimethylsilyl) oxy]-5-(2-{1[(4-methoxyphenyl) diphenylmethyl] amino}-6-oxo-1H-purin-9-yl) oxolane-2-carbaldehyde (4.7 g, 7.2 mmol, crude) as a white solid. LC-MS (ES, m/z): 652 (M+H$^+$).

Step 6: A solution of (2S,3S,5R)-3-[(tert-butyldimethylsilyl) oxy]-5-(2-{1[(4-methoxyphenyl) diphenylmethyl] amino}-6-oxo-1H-purin-9-yl) oxolane-2-carbaldehyde (4.7 g, 7.2 mmol) and paraformaldehyde (1.1 g, 36.1 mmol) in dioxane (60 mL) and H$_2$O (6 mL) was stirred for 12 h at room temperature under nitrogen atmosphere. To the above mixture was added NaBH$_4$ (0.8 g, 21.6 mmol) in portions at 0° C. and stirred for additional 1 h at 0° C. The reaction was quenched with sat. NH₄Cl (aq.) at 0° C. The resulting mixture was extracted with EtOAc (3×100 mL). The combined organic layers were washed with brine (2×100 mL), dried over anhydrous Na₂SO₄. After filtration, the filtrate was concentrated under reduced pressure. The residue was purified by silica gel column chromatography, eluted with CH₂Cl₂/MeOH (10:1) to afford 9-[(2R,4S)-4-[(tert-butyldimethylsilyl) oxy]-5,5-bis(hydroxymethyl)oxolan-2-yl]-2-{[(4-methoxyphenyl) diphenylmethyl] amino}-1H-purin-6-one (1.5 g, 2.12 mmol, 28.6%) as an off-white solid. LC-MS (ES, m/z): 684 (M+H⁺).

Step 7: A solution of 9-[(2R,4S)-4-[(tert-butyldimethylsilyl)oxy]-5,5-bis(hydroxymethyl)oxolan-2-yl]-2-{[(4-methoxyphenyl)diphenylmethyl]amino}-1H-purin-6-one (700 mg, 1.02 mmol) and IBX (1146.5 mg, 4.1 mmol) in ACN (10 mL) was stirred for 12 h at room temperature under nitrogen atmosphere. The resulting mixture was filtered; the filter cake was washed with ACN (3×10 mL). The filtrate was concentrated under reduced pressure. This resulted in (2R,3S,5R)-3-[(tert-butyldimethylsilyl) oxy]-2-(hydroxymethyl)-5-(2-{[(4-methoxyphenyl) diphenylmethyl] amino}-6-oxo-1H-purin-9-yl) oxolane-2-carbaldehyde (700 mg, 0.001 mmol, crude) as a white solid. LC-MS (ES, m/z): 682 (M+H⁺).

Step 8: A mixture of (2R,3S,5R)-3-[(tert-butyldimethylsilyl)oxy]-2-(hydroxymethyl)-5-(2-{[(4-methoxyphenyl)diphenylmethyl]amino}-6-oxo-1H-purin-9-yl)oxolane-2-carbaldehyde (700 mg, 1.02 mmol), K₂CO₃ (425.6 mg) and dimethyl (1-diazo-2-oxopropyl)phosphonate (394.4 mg, 2.05 mmol) in MeOH (10 mL) was stirred for 2 h at 0° C. under nitrogen atmosphere. The resulting mixture was concentrated under vacuum. The residue was purified by Prep-TLC (CH₂Cl₂/MeOH 15:1) to afford 9-[(2R,4S,5R)-4-[(tert-butyldimethylsilyl)oxy]-5-ethynyl-5-(hydroxymethyl) oxolan-2-yl]-2-{[(4-methoxyphenyl) diphenylmethyl] amino}-1H-purin-6-one (420 mg, 0.6 mmol, 54.9%) as a yellow solid. LC-MS (ES, m/z): 678 (M+H⁺).

Step 9: A mixture of 9-[(2R,4S,5R)-4-[(tert-butyldimethylsilyl) oxy]-5-ethynyl-5-(hydroxymethyl) oxolan-2-yl]-2-{[(4-methoxyphenyl) diphenylmethyl] amino}-1H-purin-6-one (420 mg, 0.6 mmol) and Lindlar catalyst (12.8 mg, 0.06 mmol) in EtOH (5 mL) was stirred for 12 h at room temperature under hydrogen atmosphere. LCMS showed the reaction was completed. The solids were filtered out and then filtration was concentrated under vacuum. The residue was purified by Prep-TLC (CH₂Cl₂/MeOH 15:1) to afford 9-[(2R,4S,5R)-4-[(tert-butyldimethylsilyl) oxy]-5-ethenyl-5-(hydroxymethyl) oxolan-2-yl]-2-{[(4-methoxyphenyl) diphenylmethyl] amino}-1H-purin-6-one (410 mg, 0.6 mmol, 87.6%) as a yellow solid. LC-MS (ES, m/z): 680 (M+H⁺).

Step 10: A solution of 9-[(2R,4S,5R)-4-[(tert-butyldimethylsilyl)oxy]-5-ethenyl-5-(hydroxymethyl)oxolan-2-yl]-2-{[(4-methoxyphenyl)diphenylmethyl]amino}-1H-purin-6-one (400 mg, 0.6 mmol) and NH₄F (653 mg, 17.6 mmol) in MeOH (10 mL) was stirred for 4 h at 60° C. under nitrogen atmosphere. The resulting mixture was cooled to room temperature and concentrated under vacuum. The residue was purified by Prep-TLC (CH₂Cl₂/MeOH 10:1) to afford 9-[(2R,4S,5R)-5-ethenyl-4-hydroxy-5-(hydroxymethyl) oxolan-2-yl]-2-{[(4-methoxyphenyl) diphenylmethyl] amino}-1H-purin-6-one (150 mg, 0.25 mmol, 40.6%) as a white solid. LC-MS (ES, m/z): 566 (M+H⁺).

Step 11: A mixture of 9-[(2R,4S,5R)-5-ethenyl-4-hydroxy-5-(hydroxymethyl) oxolan-2-yl]-2-{1[(4-methoxyphenyl) diphenylmethyl] amino}-1H-purin-6-one (70 mg, 0.1 mmol) in AcOH (2 mL) and H₂O (0.5 mL) was stirred for 24 h at room temperature under nitrogen atmosphere. The resulting mixture was concentrated under vacuum. The crude product was purified by Prep-HPLC with the following conditions (2 #SHIMADZU (HPLC-01)): Column, XBridge Shield RP18 OBD Column, 19*250 mm, 10 μm; mobile phase, Water (10 mmol/L NH₄HCO₃) and ACN (5% ACN up to 20% in 5.5 min; UV detection at 254 nm. The product-containing fractions were combined and lyophilized overnight to give 2-amino-9-[(2R,4S,5R)-5-ethenyl-4-hydroxy-5-(hydroxymethyl) oxolan-2-yl]-1H-purin-6-one (13 mg, 0.04 mmol, 35.71%) as a white solid. LC-MS (ES, m/z): 294 (M+H⁺). Conditions for the LCMS: (Column: HALO C18, 30*3 mm, 3 μm; Mobile Phase A: water/0.05% TFA, Mobile Phase B: ACN/0.05% TFA; Flow rate: 1.50 mL/min; Gradient: 5% B to 100% B in 1.20 min, 100% B to 100% B in 1.80 min, 100% B to 5% B in 1.82 min, 5% B to 5% B in 2.00 min; Wavelength: 254 nm). ¹H NMR (400 MHz, DMSO-d₆) δ 10.67 (s, 1H), 7.98 (s, 1H), 6.50 (s, 2H), 6.16-6.08 (m, 1H), 5.97 (dd, J=17.3, 10.9 Hz, 1H), 5.42-5.08 (m, 4H), 4.59 (q, J=6.0 Hz, 1H), 3.51 (dd, J=11.8, 5.6 Hz, 1H), 3.42 (dd, J=11.8, 4.9 Hz, 1H), 2.46 (dt, J=12.0, 5.7 Hz, 1H), 2.21 (dt, J=13.3, 6.9 Hz, 1H).

Example 30—Synthesis of Compound 64: (2R,3S,5R)-5-(6-amino-2-fluoro-9H-purin-9-yl)-2-ethyl-2-(hydroxymethyl)tetrahydrofuran-3-ol

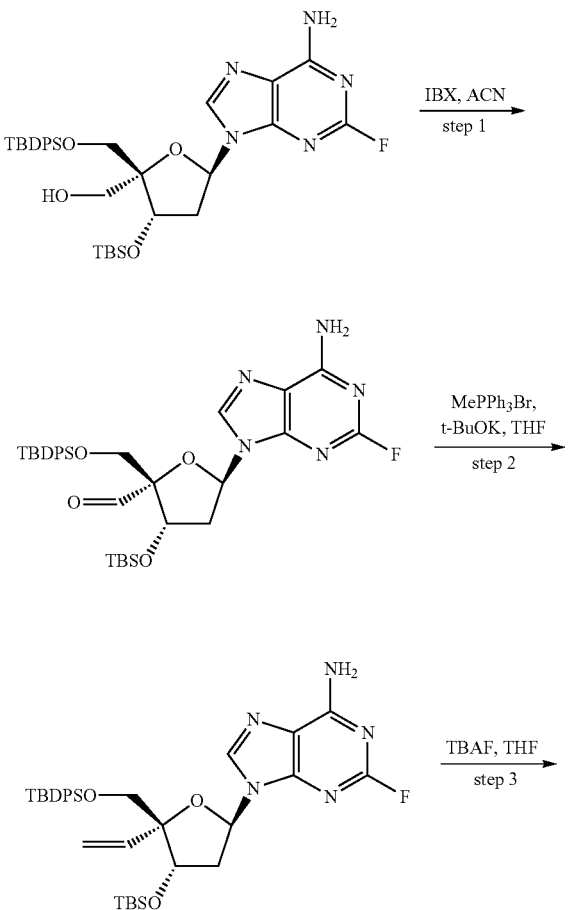

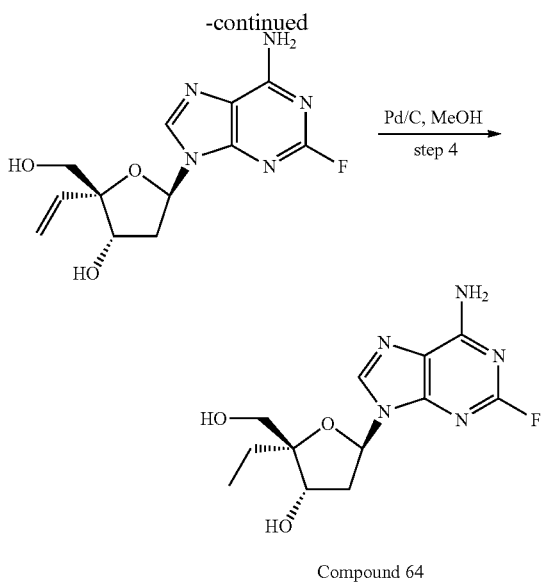

Compound 64

Step 1: To a stirred solution of [(2R,3S,5R)-5-(6-amino-2-fluoropurin-9-yl)-3-[(tert-butyldimethylsilyl) oxy]-2-{[(tert-butyldiphenylsilyl) oxy] methyl} oxolan-2-yl] methanol (1 g, 1.5 mmol) in ACN (20 mL) was added IBX (1.2 g, 4.5 mmol) in portions at room temperature under nitrogen atmosphere. The resulting mixture was stirred for 2 h at 60° C. under nitrogen atmosphere. The resulting mixture was filtered; the filter cake was washed with ACN. The filtrate was concentrated under reduced pressure to afford (2R,3S,5R)-5-(6-amino-2-fluoropurin-9-yl)-3-[(tert-butyldimethylsilyl)oxy]-2-{[(tert-butyldiphenylsilyl) oxy] methyl} oxolane-2-carbaldehyde (940 mg, 1.4 mmol, crude) as a white solid. The crude product was used in the next step directly without further purification. LC-MS: (ES, m/z): 650 (M+H$^+$).

Step 2: To a stirred solution of tert-butoxypotassium (568 mg, 5.1 mmol) in tetrahydrofuran (5 mL) was added methyltriphenylphosphonium bromide (2.1 g, 5.7 mmol) in portions at room temperature under nitrogen atmosphere. The resulting mixture was stirred for 1 h at room temperature under nitrogen atmosphere. To the above mixture was added a solution of (2R,3S,5R)-5-(6-amino-2-fluoropurin-9-yl)-3-[(tert-butyldimethylsilyl) oxy]-2-{[(tert-butyldiphenylsilyl) oxy] methyl} oxolane-2-carbaldehyde (940 mg, 1.4 mmol) in tetrahydrofuran (5 mL) dropwise at room temperature. The mixture was stirred for 15 h at room temperature. The resulting mixture was quenched with ice water and extracted with EA. The combined organic layers were washed with brine and dried over anhydrous Na$_2$SO$_4$. After filtration, the filtrate was concentrated under reduced pressure. The residue was purified by silica gel column chromatography, eluted with petroleum ether/ethyl acetate (1/1) to afford 9-[(2R,4S,5R)-4-[(tert-butyldimethylsilyl) oxy]-5-{[(tert-butyldiphenylsilyl) oxy] methyl}-5-ethenyloxolan-2-yl]-2-fluoropurin-6-amine (570 mg, 0.88 mmol, 60.83%) as a white solid. LC-MS: (ES, m/z): 648 (M+H$^+$).

Step 3: To a stirred solution of 9-[(2R,4S,5R)-4-[(tert-butyldimethylsilyl) oxy]-5-{[(tert-butyldiphenylsilyl) oxy] methyl}-5-ethenyloxolan-2-yl]-2-fluoropurin-6-amine (520 mg, 0.81 mmol) in tetrahydrofuran (10 mL) was added a solution of TBAF in THF (1.2 mL, 1.0 M) dropwise at room temperature under nitrogen atmosphere. The resulting mixture was stirred for 15 h at room temperature under nitrogen atmosphere. The resulting mixture was concentrated under reduced pressure. The residue was purified by Prep-TLC (dichloromethane/methanol=10/1) to afford crude product and further purified by silica gel column chromatography, eluted with dichloromethane/methanol (5/1). The residue was purified by reverse flash chromatography with the following conditions: column, C18 silica gel; mobile phase, NaHCO$_3$ (5 M) in ACN, 10% to 50% gradient in 15 min; detector, UV 254 nm to afford (2R,3S,5R)-5-(6-amino-2-fluoro-9H-purin-9-yl)-2-(hydroxymethyl)-2-vinyltetrahydrofuran-3-ol (180 mg, 0.6 mmol, 74.07%) as an off-white solid. LC-MS: (ES, m/z): 296 (M+H$^+$).

Step 4: To a stirred solution of (2R,3S,5R)-5-(6-amino-2-fluoro-9H-purin-9-yl)-2-(hydroxymethyl)-2-vinyltetrahydrofuran-3-ol (180 mg, 0.6 mmol) in methanol (5 mL) was added 10% Pd on carbon (36 mg) at room temperature under nitrogen atmosphere. The resulting mixture was stirred for 1 h at room temperature under hydrogen atmosphere. The resulting mixture was filtered; the filter cake was washed with MeOH. The filtrate was concentrated under reduced pressure. The crude product was purified by Prep-HPLC with the following conditions: Column: SunFire Prep C18 OBD Column, 19×150 mm, 5 ums; Mobile Phase A: Water (0.1% NH$_4$HCO$_3$+0.1% NH$_3$—H$_2$O), Mobile Phase B: ACN; Flow rate: 60 mL/min; Gradient: 30 B to 60 B in 7 min; Detector, UV 254/210 nm; The product-containing fractions were collected and evaporated partially under reduced pressure on rotary evaporator and lyophilized overnight to result (2R,3S,5R)-5-(6-amino-2-fluoropurin-9-yl)-2-ethyl-2-(hydroxymethyl) oxolan-3-ol (91.5 mg, 0.31 mol, 51.69%) as a white solid. LC-MS: (Negative mode, ES, m/z): 296 [M–H]$^+$. 98.9% purity (M+H$^+$). Conditions for the LCMS: (Column: Kinetex EVO C18, 33*3 mm, 2.6 µm; Mobile Phase A: Water/5 mM NH$_4$HCO$_3$, Mobile Phase B: Acetonitrile; Flow rate: 1.5000 mL/min; Gradient: 10% B to 95% B in 1.20 min, 95% B to 95% B in 1.78 min, 95% B to 10% B in 1.83 min; Wavelength: 254 nm; RT1(min): 0.539). $^1$H NMR (400 MHz, DMSO-d$_6$) δ 8.33 (s, 1H), 7.83 (s, 2H), 6.19 (dd, J=7.5, 6.2 Hz, 1H), 5.17 (d, J=4.9 Hz, 1H), 4.92 (t, J=5.6 Hz, 1H), 4.45-4.36 (m, 1H), 3.50 (dd, J=11.5, 5.3 Hz, 1H), 3.41 (dd, J=11.5, 6.0 Hz, 1H), 2.81 (ddd, J=13.4, 7.6, 5.9 Hz, 1H), 2.28 (ddd, J=13.3, 6.2, 3.4 Hz, 1H), 1.60 (ddq, J=29.0, 14.6, 7.3 Hz, 2H), 0.88 (t, J=7.5 Hz, 3H). $^{19}$F NMR (376 MHz, DMSO-d$_6$) δ –15.15).

Example 31—Synthesis of Compound 72: 4-amino-5-fluoro-1-((2R,3S,4S,5R)-5-(fluoromethyl)-3,4-dihydroxy-5-(hydroxymethyl)tetrahydrofuran-2-yl) pyrimidin-2(1H)-one

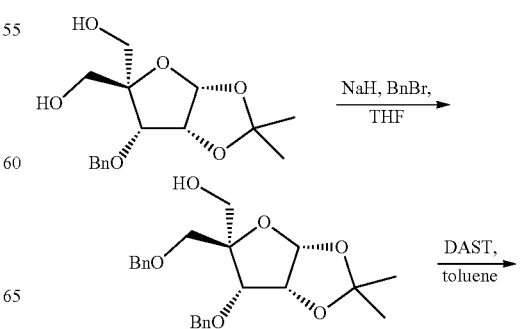

-continued

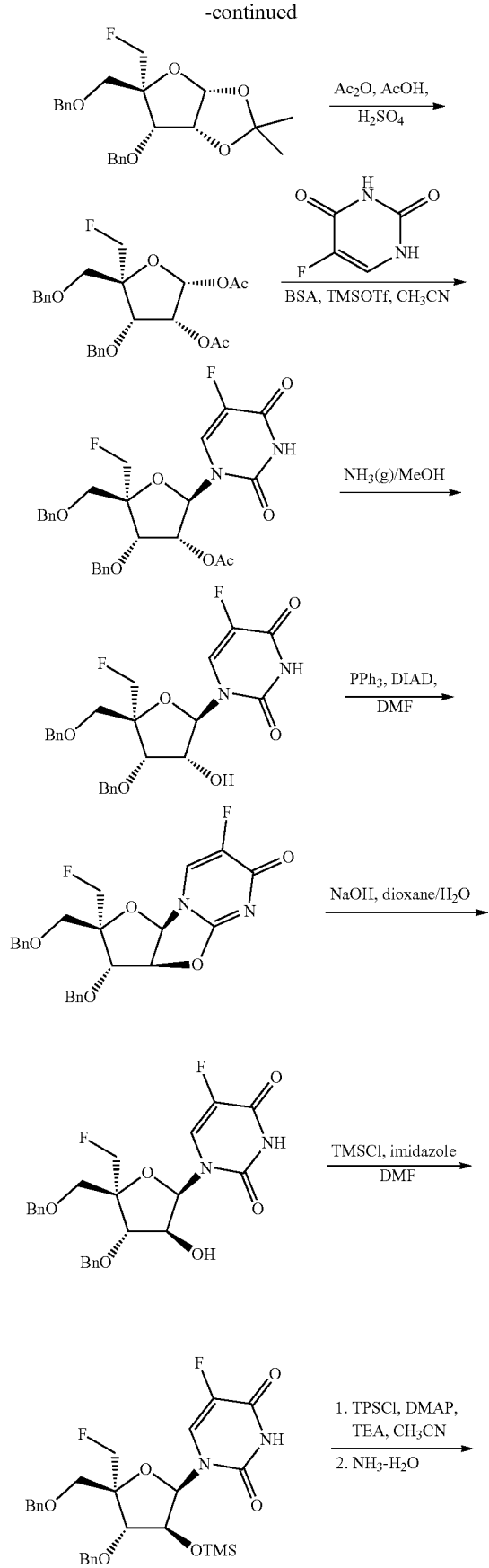

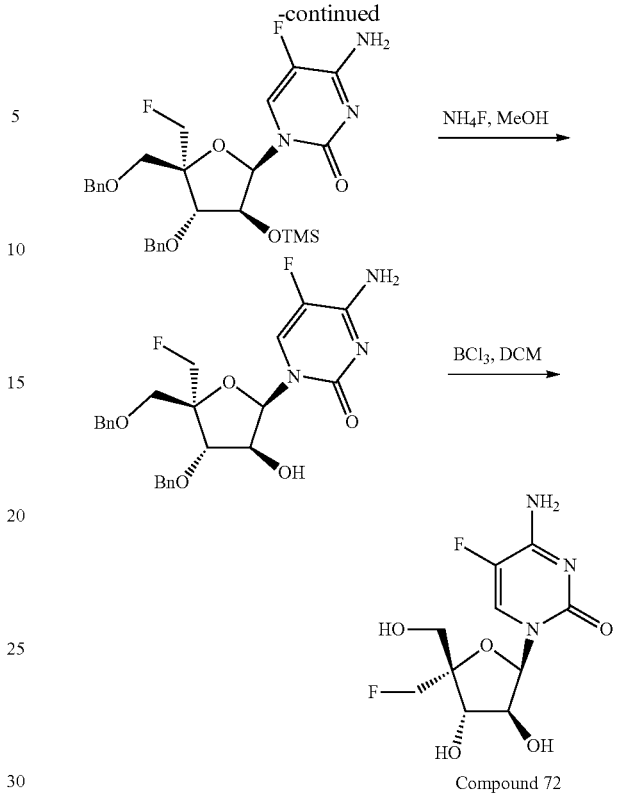

Compound 72

Step 1: To a stirred solution of ((3aR,6S,6aR)-6-(benzyloxy)-2,2-dimethyl-tetrahydrofuro[2,3-d][1,3]dioxole-5,5-diyl)dimethanol (40 g, 128.9 mmol) in tetrahydrofuran (1000 mL) was added NaH (5.2 g, 128.9 mmol) in portions in 15 minutes at 0° C. under nitrogen atmosphere. The mixture was stirred for 15 minutes at 0° C. Then benzyl bromide (22 g, 128.9 mmol) in tetrahydrofuran (100 mL) was added and stirred for 15 minutes at 20° C. The reaction was quenched by the addition of saturated NH₄Cl (1000 mL) at 0° C. The resulting mixture was extracted with ethyl acetate (3×1000 mL). The combined organic layers were washed with brine (2×200 mL), dried over anhydrous sodium sulfate. After filtration, the filtrate was concentrated under reduced pressure. The residue was purified by silica gel column chromatography, eluted with PE/EA (4/1) to afford ((3aR,5R,6S,6aR)-6-(benzyloxy)-5-((benzyloxy)methyl)-2,2-dimethyltetrahydrofuro[2,3-d][1,3]dioxol-5-yl)methanol (29.5 g, 73.8 mmol, 57.15%) as a yellow oil. LC-MS (ES, m/z): 401 (M+H⁺).

Step 2: To a stirred solution of ((3aR,5R,6S,6aR)-6-(benzyloxy)-5-((benzyloxy)methyl)-2,2-dimethyltetrahydrofuro[2,3-d][1,3]dioxol-5-yl)methanol (5 g, 12.4 mmol) in toluene (200 mL) was added DAST (4 g, 25 mmol) in portions in 15 minutes at 0° C. under nitrogen atmosphere. The mixture was stirred for 5 minutes at 60° C. The reaction was cooled to room temperature, quenched by the addition of saturated NaHCO₃(aq) (300 mL) at 0° C. The resulting mixture was diluted with water and extracted with ethyl acetate (3×100 mL). The combined organic layers were washed with brine (2×200 mL), dried over anhydrous sodium sulfate. After filtration, the filtrate was concentrated under reduced pressure. The residue was purified by silica gel column chromatography, eluted with PE/EA (4/1) to afford (3aR,5R,6S,6aR)-6-(benzyloxy)-5-((benzyloxy)methyl)-5-(fluoromethyl)-2,2-dimethyltetrahydrofuro[2,3- d] [1,3]dioxole (3.91 g, 9.7 mmol, 77.81%) as a dark yellow oil. LC-MS (ES, m/z): 403 (M+H⁺).

Step 3: To a stirred solution of (3aR,5R,6S,6aR)-6-(benzyloxy)-5-((benzyloxy) methyl)-5-(fluoromethyl)-2,2-dimethyltetrahydrofuro[2,3-d][1,3]dioxole (3.9 g, 9.7 mmol) in acetic acid (100 mL) was added acetic anhydride (13.9 g, 136 mmol) and sulfuric acid (0.5 mL) dropwise in 5 minutes at 0° C. under nitrogen atmosphere. The mixture was stirred for 2 hours at room temperature. The resulting mixture was diluted with water and extracted with ethyl acetate (3×100 mL). The combined organic layers were washed with brine (2×200 mL), dried over anhydrous sodium sulfate. After filtration, the filtrate was concentrated under reduced pressure. The residue was purified by silica gel column chromatography, eluted with PE/EtOAc (3/1) to afford (2R,3R,4S,5R)-4-(benzyloxy)-5-((benzyloxy)methyl)-5-(fluoromethyl)tetrahydrofuran-2,3-diyl diacetate (2.91 g, 6.5 mmol, 67.09%) as a light-yellow oil. LC-MS (ES, m/z): 447 (M+H⁺).

Step 4: To a stirred solution of fluorouracil (857 mg, 6.6 mmol) in ACN (30 mL) was added (E)-(trimethylsilyl N-(trimethylsilyl) ethenecarboximidate) (3.6 g, 17.6 mmol) in portions at 0° C. under nitrogen atmosphere. The mixture was stirred for 1 hours at 80° C. The mixture was cooled to room temperature and (2R,3R,4S,5R)-4-(benzyloxy)-5-((benzyloxy)methyl)-5-(fluoromethyl)tetrahydrofuran-2,3-diyl diacetate (2 g, 4.4 mmol) in ACN (30 mL) was added. Then trimethylsilyl triflate (1.6 g, 7 mmol) was added at room temperature under nitrogen atmosphere. The mixture was stirred for 2 hours at 80° C. The resulting mixture was cooled to room temperature, diluted with water and extracted with ethyl acetate (3×100 mL). The combined organic layers were washed with brine (2×200 mL), dried over anhydrous sodium sulfate. After filtration, the filtrate was concentrated under reduced pressure. The residue was purified by silica gel column chromatography, eluted with PE/EtOAc (3/2) to afford (2R,3R,4S,5R)-4-(benzyloxy)-5-((benzyloxy)methyl)-2-(5-fluoro-2,4-dioxo-3,4-dihydropyrimidin-1(2H)-yl)-5-(fluoromethyl)tetrahydrofuran-3-yl acetate (900 mg, 1.7 mmol, 39.69%) as an off-white solid. LC-MS (ES, m/z): 517 (M+H⁺).

Step 5: To a stirred solution of NH₃(g) in MeOH (10 mL, 7.0 M) was added (2R,3R,4S,5R)-4-(benzyloxy)-5-((benzyloxy)methyl)-2-(5-fluoro-2,4-dioxo-3,4-dihydropyrimidin-1(2H)-yl)-5-(fluoromethyl)tetrahydrofuran-3-yl acetate (895 mg, 1.7 mmol) at room temperature under nitrogen atmosphere. The mixture was stirred for 2 hours at room temperature. The resulting mixture was concentrated under reduced pressure. The residue was purified by Prep-TLC (PE/EtOAc=1/2) to afford 1-[(2R,3R,4S,5R)-4-(benzyloxy)-5-[(benzyloxy)methyl]-5-(fluoromethyl)-3-hydroxyoxolan-2-yl]-5-fluoro-3H-pyrimidine-2,4-dione (610 mg, 1.3 mmol, 74.20%) as a light yellow solid. LC-MS (ES, m/z): 475 (M+H⁺).

Step 6: To a stirred solution of 1-[(2R,3R,4S,5R)-4-(benzyloxy)-5-[(benzyloxy)methyl]-5-(fluoromethyl)-3-hydroxyoxolan-2-yl]-5-fluoro-3H-pyrimidine-2,4-dione (630 mg, 1.3 mmol) and triphenylphosphine (1.1 g, 4 mmol) in dimethylformamide (10 mL) was added DIAD (805 mg, 4 mmol) in portions at 0° C. under nitrogen atmosphere. The mixture was stirred for 15 hours at room temperature. The resulting mixture was diluted with water and extracted with ethyl acetate (3×100 mL). The combined organic layers were washed with brine (2×200 mL), dried over anhydrous sodium sulfate. After filtration, the filtrate was concentrated under reduced pressure. The residue was purified by Prep-TLC (EtOAc) to afford (2R,4R,5S,6S)-5-(benzyloxy)-4-[(benzyloxy)methyl]-11-fluoro-4-(fluoromethyl)-3,7-dioxa-1,9-diazatricyclo [6.4.0.0^{2,6}] dodeca-8,11-dien-10-one (crude, 1.49 g, 3.3 mmol) as a light yellow solid. LC-MS (ES, m/z): 457 (M+H⁺).

Step 7: To a stirred solution of (2R,4R,5S,6S)-5-(benzyloxy)-4-[(benzyloxy)methyl]-11-fluoro-4-(fluoromethyl)-3,7-dioxa-1,9-diazatricyclo [6.4.0.0^{2,6}] dodeca-8,11-dien-10-one (1.5 g, 3.2 mmol) in dioxane (20 mL) and water (4 mL) was added NaOH (381 mg, 9.5 mmol) in portions at room temperature under nitrogen atmosphere. The mixture was stirred for 2 hours at room temperature. The resulting mixture was diluted with water and extracted with ethyl acetate (3×100 mL). The combined organic layers were washed with brine (2×200 mL), dried over anhydrous sodium sulfate. After filtration, the filtrate was concentrated under reduced pressure. The residue was purified by Prep-TLC (EtOAc) to afford 1-[(2R,3S,4S,5R)-4-(benzyloxy)-5-[(benzyloxy)methyl]-5-(fluoromethyl)-3-hydroxyoxolan-2-yl]-5-fluoro-3H-pyrimidine-2,4-dione (440 mg, 0.9 mmol, 29.19%) as a light yellow solid. LC-MS (ES, m/z): 475 (M+H⁺).

Step 8: To a stirred solution of 1-[(2R,3S,4S,5R)-4-(benzyloxy)-5-[(benzyloxy) methyl]-5-(fluoromethyl)-3-hydroxyoxolan-2-yl]-5-fluoro-3H-pyrimidine-2,4-dione (420 mg, 0.9 mmol) and imidazole (181 mg, 2.7 mmol) in dimethylformamide (10 mL) was added chlorotrimethylsilane (144 mg, 1.3 mmol) at 0° C. under nitrogen atmosphere. The mixture was stirred for 2 hours at room temperature. The resulting mixture was diluted with water and extracted with ethyl acetate (3×100 mL). The combined organic layers were washed with brine (2×200 mL), dried over anhydrous sodium sulfate. After filtration, the filtrate was concentrated under reduced pressure. The residue was purified by Prep-TLC (PE/EtOAc=1/1) to afford 1-[(2R,3S,4S,5R)-4-(benzyloxy)-5-[(benzyloxy)methyl]-5-(fluoromethyl)-3-[(trimethylsilyl)oxy]oxolan-2-yl]-5-fluoro-3H-pyrimidine-2,4-dione (370 mg, 0.7 mmol, 76.46%) as a light yellow oil. LC-MS (ES, m/z): 547 (M+H⁺).

Step 9: To a stirred solution of 1-[(2R,3S,4S,5R)-4-(benzyloxy)-5-[(benzyloxy)methyl]-5-(fluoromethyl)-3-[(trimethylsilyl)oxy] oxolan-2-yl]-5-fluoro-3H-pyrimidine-2,4-dione (350 mg, 0.6 mmol) and TEA (194 mg, 1.9 mmol) in ACN (12 mL) was added 2,4,6-tris(propan-2-yl) benzene-1-sulfonyl chloride (388 mg, 1.2 mmol) at room temperature under nitrogen atmosphere. The mixture was stirred for 2 hours at room temperature. Then ammonium hydroxide (2 mL) was added and the mixture was stirred for 1 hour at room temperature. The resulting mixture was diluted with water and extracted with ethyl acetate (3×100 mL). The combined organic layers were washed with brine (2×200 mL), dried over anhydrous sodium sulfate. After filtration, the filtrate was concentrated under reduced pressure. The residue was purified by Prep-TLC (DCM/MeOH=10/1) to afford 4-amino-1-[(2R,3S,4S,5R)-4-(benzyloxy)-5-[(benzyloxy)methyl]-5-(fluoromethyl)-3-[(trimethylsilyl)oxy]oxolan-2-yl]-5-fluoropyrimidin-2-one (246 mg, 0.5 mmol, 70.41%) as a light yellow solid. LC-MS (ES, m/z): 546 (M+H⁺).

Step 10: To a stirred solution of 4-amino-1-[(2R,3S,4S,5R)-4-(benzyloxy)-5-[(benzyloxy)methyl]-5-(fluoromethyl)-3-[(trimethylsilyl)oxy] oxolan-2-yl]-5-fluoropyrimidin-2-one (236 mg, 0.4 mmol) in methanol (10 mL) was added NH₄F (480 mg, 13.0 mmol) at room temperature under nitrogen atmosphere. The mixture was stirred for 2 hours at room temperature. The resulting mixture was concentrated under reduced pressure. The residue was purified by silica gel column chromatography, eluted with DCM/

MeOH (20/1) to afford 4-amino-1-[(2R,3S,4S,5R)-4-(benzyloxy)-5-[(benzyloxy)methyl]-5-(fluoromethyl)-3-hydroxyoxolan-2-yl]-5-fluoropyrimidin-2-one (195 mg, 0.4 mmol, 95.22%) as an off-white solid. LC-MS (ES, m/z): 474 (M+H$^+$).

Step 11: To a stirred solution of 4-amino-1-[(2R,3S,4S,5R)-4-(benzyloxy)-5-[(benzyloxy)methyl]-5-(fluoromethyl)-3-hydroxyoxolan-2-yl]-5-fluoropyrimidin-2-one (170 mg, 0.4 mmol) in DCM (12 mL) was added boron trichloride (7.2 mL, 7.2 mmol, 1.0 M in DCM) dropwise at −78° C. under nitrogen atmosphere. The mixture was stirred for 2 hours at 0° C. The reaction was quenched by the addition of TEA/MeOH (40 mL, 1/2) at 0° C. The resulting mixture was concentrated under reduced pressure. The residue was purified by reverse flash chromatography with the following conditions: column, C18 silica gel; mobile phase, ACN in water, 0% to 15% gradient in 15 min; UV detection at 254 nm. The crude product was re-purified by Prep-HPLC with the following conditions (Column: XBridge Shield RP18 OBD Column, 19*250 mm, 10 μm; Mobile Phase A: water (10 mmol/L NH$_4$HCO$_3$), Mobile Phase B: ACN; Flow rate: 25 mL/min; Gradient: 3% B to 20% B in 6 min; Wavelength: 254 nm). The product-containing fraction was lyophilized overnight to afford the product (48.7 mg, 0.2 mmol, 44.78%) as an off-white solid. LC-MS (ES, m/z): 294 (M+H$^+$). 96.8% purity. Conditions for the LCMS: (Column: Atlantis HILIC Silica, 100*4.6 mm, 3 μm; Mobile Phase A: 20 mmol Ammonium Acetate, Mobile Phase B: Acetonitrile; Flow rate: 1.20 mL/min; Gradient: 95% B to 95% B in 1.00 min, 95% B to 50% B in 6.00 min; Wavelength: 254 nm). $^1$H NMR (400 MHz, DMSO-d$_6$) δ 7.75 (t, J=9.4 Hz, 2H), 7.49 (s, 1H), 6.09 (s, 1H), 5.64 (d, J=16.0 Hz, 2H), 5.28 (s, 1H), 4.69-4.33 (m, 2H), 4.09 (s, 2H), 3.58 (q, J=11.3 Hz, 2H).

Example 32—Synthesis of Compound 73: 4-amino-1-((2R,3S,4S,5R)-5-(chloromethyl)-3,4-dihydroxy-5-(hydroxymethyl)tetrahydrofuran-2-yl)-5-fluoropyrimidin-2(1H)-one

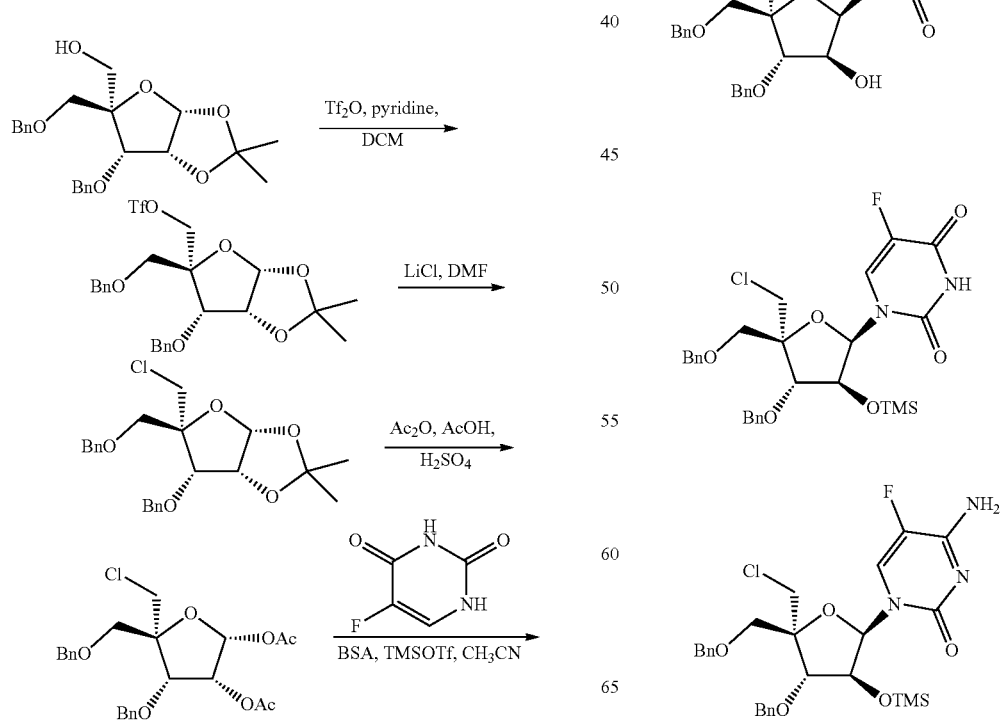

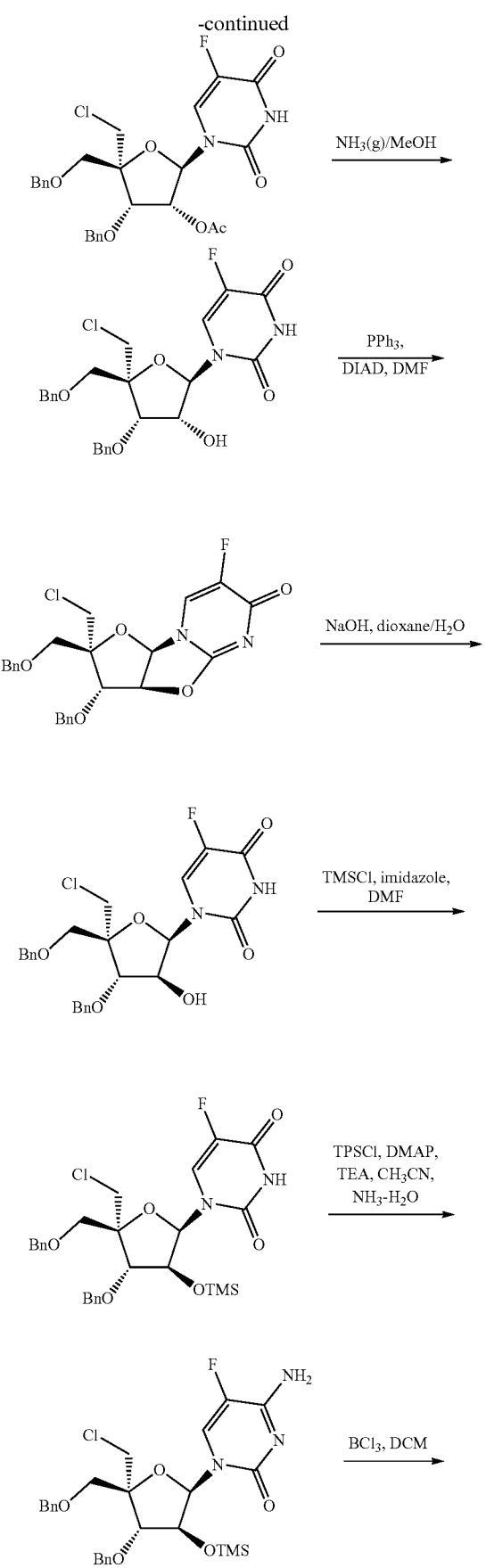

-continued

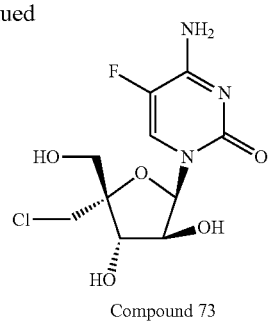

Compound 73

Step 1: A solution of ((3aR,5R,6S,6aR)-6-(benzyloxy)-5-((benzyloxy)methyl)-2,2-dimethyltetrahydrofuro[2,3-d][1,3]dioxol-5-yl)methanol (1 g, 2.5 mmol) and pyridine (1.0 g, 12.5 mmol) in DCM (20 mL) was treated with Tf$_2$O (1.2 g, 4.2 mmol) for 2 h at −35° C. under nitrogen atmosphere. The reaction was quenched by the addition of saturated NH$_4$Cl solution. The resulting mixture was extracted with DCM. The combined organic layers were washed with brine, dried over anhydrous sodium sulfate. After filtration, the filtrate was concentrated under reduced pressure. The crude product was used in the next step directly without further purification. LC-MS (ES, m/z): 550 (M+NH$_4$+).

Step 2: To a solution of ((3aR,5S,6S,6aR)-6-(benzyloxy)-5-((benzyloxy)methyl)-2,2-dimethyltetrahydrofuro[2,3-d][1,3]dioxol-5-yl)methyl trifluoromethanesulfonate (1.5 g, 2.8 mmol) in DMF (15 mL) was add LiCl (0.5 g, 11.2 mmol). The mixture was stirred for 2 h at 60° C. under nitrogen atmosphere. The mixture was cooled to room temperature and diluted with water. The aqueous layer was extracted with EtOAc (3×30 mL). The resulting mixture was concentrated under reduced pressure. The residue was purified by silica gel column chromatography, eluted with PE/EA (5:1) to afford (3aR,5R,6S,6aR)-6-(benzyloxy)-5-((benzyloxy)methyl)-5-(chloromethyl)-2,2-dimethyltetrahydrofuro[2,3-d][1,3]dioxole (900 mg, 2.1 mmol, 76.2%) as an off-white solid. LC-MS (ES, m/z): 436/438 (M+NH$_4$+).

Step 3: To a solution of (3aR,5R,6S,6aR)-6-(benzyloxy)-5-((benzyloxy)methyl)-5-(chloromethyl)-2,2-dimethyltetrahydrofuro[2,3-d][1,3]dioxole (900 mg, 2 mmol) in AcOH (11.6 g) was added Ac$_2$O (3 g, 29 mmol) and H$_2$SO$_4$ (13.7 μL, 0.2 mmol) dropwise and the mixture was stirred for 3 h at room temperature under nitrogen atmosphere. The mixture was quenched with saturated NaHCO$_3$(aq) and extracted with EtOAc. The resulting mixture was concentrated under reduced pressure. The crude product was used in the next step directly without further purification. LC-MS (ES, m/z): 480/482 (M+NH$_4$+).

Step 4: A solution of (2R,3R,4S,5R)-4-(benzyloxy)-5-((benzyloxy)methyl)-5-(chloromethyl)tetrahydrofuran-2,3-diyl diacetate (1 g, 2.1 mmol) in ACN (20 mL) was treated with (E)-(trimethylsilyl N-(trimethylsilyl) ethenecarboximidate) (1.7 g, 8.6 mmol) for 30 min at 80° C. under nitrogen atmosphere followed by the addition of fluorouracil (0.4 g, 3.0 mmol) and TMSOTf (0.8 g, 3.5 mmol) dropwise. The mixture was stirred at 80° C. for another 2 hours. Then cooled to room temperature and quenched with ice water. The aqueous layer was extracted with EtOAc. The resulting mixture was concentrated under reduced pressure. The residue was purified by silica gel column chromatography, eluted with PE/EtOAc (3:1) to afford (2R,3R,4S,5R)-4-(benzyloxy)-5-((benzyloxy)methyl)-5-(chloromethyl)-2-(5-fluoro-2,4-dioxo-3,4-dihydropyrimidin-1(2H)-yl)tetrahydrofuran-3-yl acetate (600 mg, 1.1 mmol, 52.1%) as an off-white solid. LC-MS (ES, m/z): 533/535 (M+H$^+$).

Step 5: To a solution of NH$_3$(g) in MeOH (10 mL, 7.0 M) was added (2R,3R,4S,5R)-4-(benzyloxy)-5-((benzyloxy)methyl)-5-(chloromethyl)-2-(5-fluoro-2,4-dioxo-3,4-dihydropyrimidin-1(2H)-yl)tetrahydrofuran-3-yl acetate (600 mg, 1.1 mmol). The mixture was stirred for 2 h at 60° C. under nitrogen atmosphere. The resulting mixture was cooled to room temperature and concentrated under reduced pressure. The residue was purified by Prep-TLC (PE/EtOAc=2:1) to afford 1-[(2R,3R,4S,5R)-4-(benzyloxy)-5-[(benzyloxy)methyl]-5-(chloromethyl)-3-hydroxyoxolan-2-yl]-5-fluoro-3H-pyrimidine-2,4-dione (400 mg, 0.81 mmol, 72.3%) as an off-white solid. LC-MS (ES, m/z): 491/493 (M+H$^+$).

Step 6: A solution of 1-[(2R,3R,4S,5R)-4-(benzyloxy)-5-[(benzyloxy)methyl]-5-(chloromethyl)-3-hydroxyoxolan-2-yl]-5-fluoro-3H-pyrimidine-2,4-dione (400 mg, 0.8 mmol) in DMF (5 mL) was treated with PPh$_3$ (641 mg, 2.4 mmol) and DIAD (494 mg, 2.4 mmol) for overnight at room temperature under nitrogen atmosphere. The mixture was diluted with water and extracted with EtOAc. The resulting mixture was concentrated under reduced pressure. The residue was purified by Prep-TLC (CH$_2$Cl$_2$/MeOH 10:1) to afford (2R,4R,5S,6S)-5-(benzyloxy)-4-[(benzyloxy)methyl]-4-(chloromethyl)-11-fluoro-3,7-dioxa-1,9-diazatricyclo [6.4.0.0ˆ{2,6}] dodeca-8,11-dien-10-one (1.1 g, 2.3 mmol, crude) as an off-white solid (include PPh$_3$). The crude product was used in the next step directly. LC-MS (ES, m/z): 473/475 (M+H$^+$).

Step 7: To a solution of (2R,4R,5S,6S)-5-(benzyloxy)-4-[(benzyloxy)methyl]-4-(chloromethyl)-11-fluoro-3,7-dioxa-1,9-diazatricyclo [6.4.0.0ˆ{2,6}] dodeca-8,11-dien-10-one (1.1 g, 2.3 mmol) in 1,4-dioxane (10 mL) and H$_2$O (2 mL) was added NaOH (0.3 g, 6.9 mmol) and the mixture was stirred for overnight at room temperature under nitrogen atmosphere. The mixture was diluted with water and extracted with EtOAc. The resulting mixture was concentrated under reduced pressure. The residue was purified by Prep-TLC (PE/EtOAc=1:1) to afford 1-[(2R,3S,4S,5R)-4-(benzyloxy)-5-[(benzyloxy)methyl]-5-(chloromethyl)-3-hydroxyoxolan-2-yl]-5-fluoro-3H-pyrimidine-2,4-dione (1 g, 2.0 mmol, 87.6%) as an off-white solid (include PPh$_3$). The crude product was used in the next step directly. LC-MS (ES, m/z): 491/493 (M+H$^+$).

Step 8: A solution of 1-[(2R,3S,4S,5R)-4-(benzyloxy)-5-[(benzyloxy)methyl]-5-(chloromethyl)-3-hydroxyoxolan-2-yl]-5-fluoro-3H-pyrimidine-2,4-dione (1 g, 2 mmol) in DMF (10 mL) was treated with TMSCl (332 mg, 3.0 mmol) and Imidazole (416 mg, 6 mmol) for overnight at room temperature under nitrogen atmosphere. The mixture was diluted with water and extracted with EtOAc. The resulting mixture was concentrated under reduced pressure. The residue was purified by Prep-TLC (PE/EtOAc=3:1) to afford 1-[(2R,3S,4S,5R)-4-(benzyloxy)-5-[(benzyloxy)methyl]-5-(chloromethyl)-3-[(trimethylsilyl)oxy] oxolan-2-yl]-5-fluoro-3H-pyrimidine-2,4-dione (100 mg, 0.18 mmol, 8.7%) as an off-white solid. LC-MS (ES, m/z): 563/565 (M+H$^+$).

Step 9: A solution of 1-[(2R,3S,4S,5R)-4-(benzyloxy)-5-[(benzyloxy)methyl]-5-(chloromethyl)-3-[(trimethylsilyl) oxy] oxolan-2-yl]-5-fluoro-3H-pyrimidine-2,4-dione (100 mg, 0.2 mmol) in ACN (2 mL) was treated with DMAP (43.4 mg, 0.4 mmol) and TEA (53.9 mg, 0.5 mmol) for 10 min at room temperature under nitrogen atmosphere, then 2,4,6-tris(propan-2-yl) benzene-1-sulfonyl chloride (107.5 mg, 0.4 mmol) was added and stirred for 5 h at room temperature. Finally, NH$_3$·H$_2$O (0.1 mL, 2.5 mmol) was added and stirred for 15 min at room temperature. The resulting mixture was concentrated under reduced pressure. The residue was purified by Prep-TLC (PE/EtOAc=1:1) to afford 4-amino-1-[(2R,3S,4S,5R)-4-(benzyloxy)-5-[(benzyloxy)methyl]-5-(chloromethyl)-3-[(trimethylsilyl)oxy] oxolan-2-yl]-5-fluoropyrimidin-2-one (90 mg, 0.16 mmol, 90%) as an off-white solid. LC-MS (ES, m/z): 562/564 (M+H⁺).

Step 10: A solution of 4-amino-1-[(2R,3S,4S,5R)-4-(benzyloxy)-5-[(benzyloxy) methyl]-5-(chloromethyl)-3-[(trimethylsilyl)oxy] oxolan-2-yl]-5-fluoropyrimidin-2-one (100 mg, 0.2 mmol) in DCM (3 mL) was treated with boron trichloride (2.7 mL, 2.7 mmol, 1.0 M in DCM) for 2 h at −78° C. under nitrogen atmosphere. The reaction was quenched by the addition of MEOH/TEA (5 mL, 1/1) at −20° C. and concentrated. The crude product was purified by Prep-HPLC with the following conditions (Column: XBridge Shield RP18 OBD Column, 19*250 mm, 10 μm; Mobile Phase A: water (10 mmol/L NH$_4$HCO$_3$), Mobile Phase B: ACN; Flow rate: 25 mL/min; Gradient: 3% B to 20% B in 6 min; Wavelength: 254 nm) to afford 4-amino-1-[(2R,3S,4S,5R)-5-(chloromethyl)-3,4-dihydroxy-5-(hydroxymethyl)oxolan-2-yl]-5-fluoropyrimidin-2-one (31.4 mg, 0.10 mmol, 56.9%) as a white solid. LC-MS (ES, m/z): 310/312 (M+H⁺); 99.9% purity. Conditions for the LCMS: (Column: Shim-pack Scepter C18, 33*3.0 mm; Mobile Phase A: Water/5 mM NH$_4$HCO$_3$, Mobile Phase B: Acetonitrile; Flow rate: 1.5000 mL/min; Gradient: 0% B to 95% B in 1.7 min, 95% B to 95% B in 1.1 min, 95% B to 10% B in 0.03 min; Wavelength: 254/220 nm). $^1$H NMR (400 MHz, DMSO-d$_6$) δ 7.77 (d, J=7.6 Hz, 2H), 7.49 (s, 1H), 6.09 (s, 1H), 5.69 (d, J=21.1 Hz, 2H), 5.27 (s, 1H), 4.10 (d, J=19.6 Hz, 2H), 3.81 (d, J=11.4 Hz, 1H), 3.68 (d, J=14.9 Hz, 3H).

Example 33—Synthesis of Compound 70: 2-amino-9-((2R,3S,4R,5R)-5-(chloromethyl)-3-fluoro-4-hydroxy-5-(hydroxymethyl)-tetrahydrofuran-2-yl)-1,9-dihydro-6H-purin-6-one

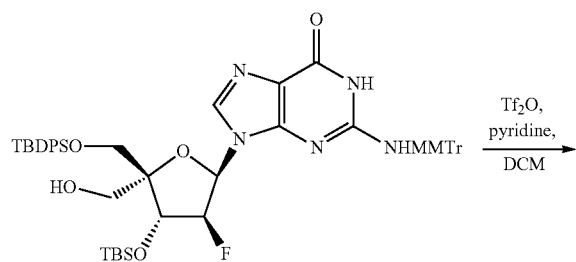

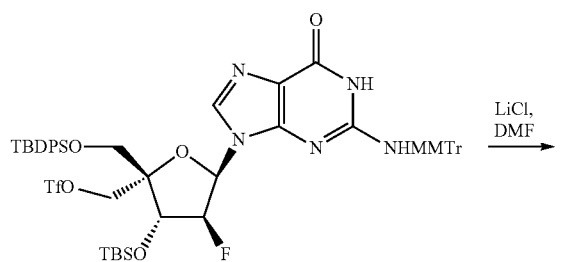

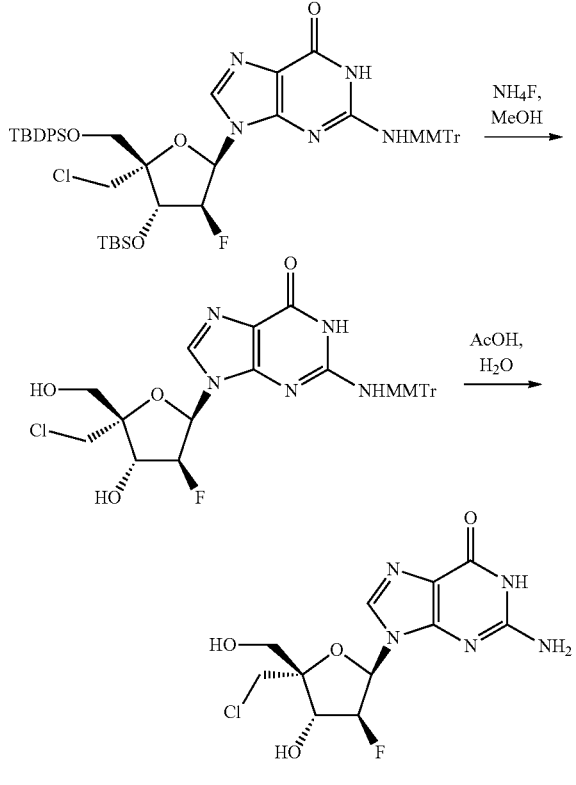

Compound 70

Step 1: To a stirred solution of 9-[(2R,3S,4R,5R)-4-[(tert-butyldimethylsilyl) oxy]-5-{[(tert-butyldiphenylsilyl) oxy] methyl}-3-fluoro-5-(hydroxymethyl) oxolan-2-yl]-2-{[(4-methoxyphenyl) diphenyl methyl] amino}-1H-purin-6-one (450 mg, 0.4 mmol) and pyridine (189 mg, 2.3 mmol) in dichloromethane (10 ml) was added Tf$_2$O (229 mg, 0.8 mmol) dropwise at 0° C. under nitrogen atmosphere. The resulting mixture was stirred for overnight at room temperature under nitrogen atmosphere. The resulting mixture was diluted with water (100 mL). The resulting mixture was extracted with dichloromethane (3×100 mL). The combined organic layers were washed with brine (3×100 mL), dried over anhydrous sodium sulfate. After filtration, the filtrate was concentrated under reduced pressure. The crude product was used in the next step directly without further purification. LC-MS (ES, m/z): 1072 (M+H⁺).

Step 2: A mixture of ((2S,3R,4S,5R)-3-((tert-butyldimethylsilyl)oxy)-2-(((tert-butyldiphenylsilyl)oxy)methyl)-4-fluoro-5-(2-(((4-methoxyphenyl)diphenylmethyl)amino)-6-oxo-1,6-dihydro-9H-purin-9-yl)tetrahydrofuran-2-yl) methyl trifluoromethanesulfonate (450 mg, 0.4 mmol) and LiCl (71 mg, 1.6 mmol) in dimethyl formamide (10 ml) was stirred for overnight at room temperature under nitrogen atmosphere. The resulting mixture was diluted with water (100 mL). The resulting mixture was extracted with ethyl acetate (3×100 mL). The combined organic layers were washed with brine (3×100 mL), dried over anhydrous sodium sulfate. After filtration, the filtrate was concentrated under reduced pressure. The crude product was used in the next step directly without further purification. LC-MS (ES, m/z): 958 (M+H⁺).

Step 3: A mixture of 9-[(2R,3S,4R,5R)-4-[(tert-butyldimethylsilyl) oxy]-5-{[(tert-butyldiphenylsilyl) oxy] methyl}-5-(chloromethyl)-3-fluorooxolan-2-yl]-2-{1[(4-methoxyphenyl) diphenylmethyl] amino}-1H-purin-6-one (450 mg, 0.4 mmol) and NH₄F (408 mg, 11.0 mmol) in methanol (10 ml) was stirred for overnight at 60° C. under nitrogen atmosphere. The resulting mixture was cooled to room temperature, filtered and the filter cake was washed with methanol (3×10 mL). The filtrate was concentrated under reduced pressure. The residue was purified by Prep-TLC (dichloromethane/methanol 10:1) to afford 9-[(2R,3S,4R,5R)-5-(chloromethyl)-3-fluoro-4-hydroxy-5-(hydroxymethyl) oxolan-2-yl]-2-{1[(4-methoxyphenyl) diphenyl methyl]amino}-1H-purin-6-one (130 mg, 0.2 mmol, 45.70%) as a white solid. LC-MS (ES, m/z): 606 (M+H⁺).

Step 4: A solution of 9-[(2R,3S,4R,5R)-5-(chloromethyl)-3-fluoro-4-hydroxy-5-(hydroxymethyl) oxolan-2-yl]-2-{1[(4-methoxyphenyl) diphenyl methyl] amino}-1H-purin-6-one (120 mg, 0.1 mmol) in acetic acid (1.6 mL) and water (0.4 ml) was stirred for overnight at room temperature under nitrogen atmosphere. The resulting mixture was concentrated under vacuum. The crude product was purified by Prep-HPLC with the following conditions (Column: XBridge Shield RP18 OBD Column, 19*250 mm, 10 μm; Mobile Phase A: Water (10 mmol/L NH₄HCO₃), Mobile Phase B: ACN; Flow rate: 25 mL/min; Gradient: 5% B to 30% B in 7 min; Wavelength: 254 nm) to afford 2-amino-9-[(2R,3S,4R,5R)-5-(chloromethyl)-3-fluoro-4-hydroxy-5-(hydroxymethyl) oxolan-2-yl]-1H-purin-6-one (25.9 mg, 0.1 mmol, 37.87%) as a white solid. LC-MS (ES, m/z): 334 (M+H⁺). 96.6% purity. Conditions for the HPLC: (Column: Xbridge RP18, 100*4.6 mm, 3.5 μm; Mobile Phase A: H₂O+0.1% TFA, Mobile Phase B: MeOH; Flow rate: 1.2000 mL/min; Gradient: 5% B to 95% B in 8.00 min, 95% B to 95% B in 10.00 min, 90% B to 10% B in 10.50 min; Wavelength: 254/220 nm). ¹H NMR (400 MHz, DMSO-d₆) δ 8.09 (s, 1H), 7.82 (d, J=2.8 Hz, 1H), 6.57 (s, 2H), 6.38-6.19 (m, 2H), 5.30 (dt, J=53.1, 4.3 Hz, 2H), 4.65 (d, J=18.8 Hz, 1H), 3.88 (d, J=12.0 Hz, 1H), 3.76 (d, J=11.9 Hz, 1H), 3.61 (t, J=11.9 Hz, 2H).

Example 34—Synthesis of Compound 74: 4-amino-5-fluoro-1-((2R,4S,5R)-4-hydroxy-5-(hydroxymethyl)-5-vinyltetrahydrofuran-2-yl)pyrimidin-2(1H)-one

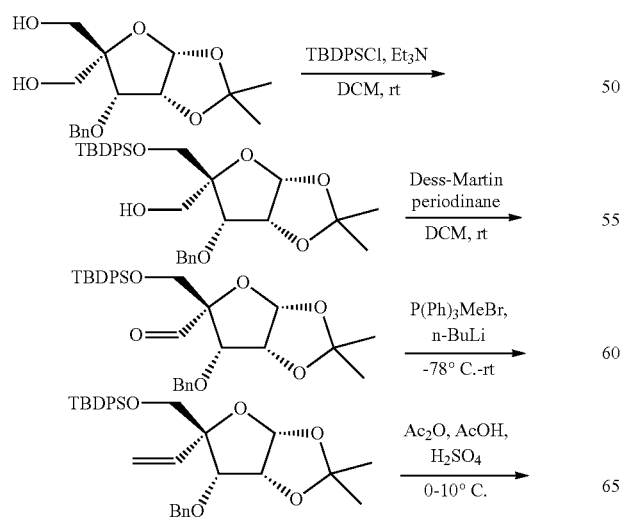

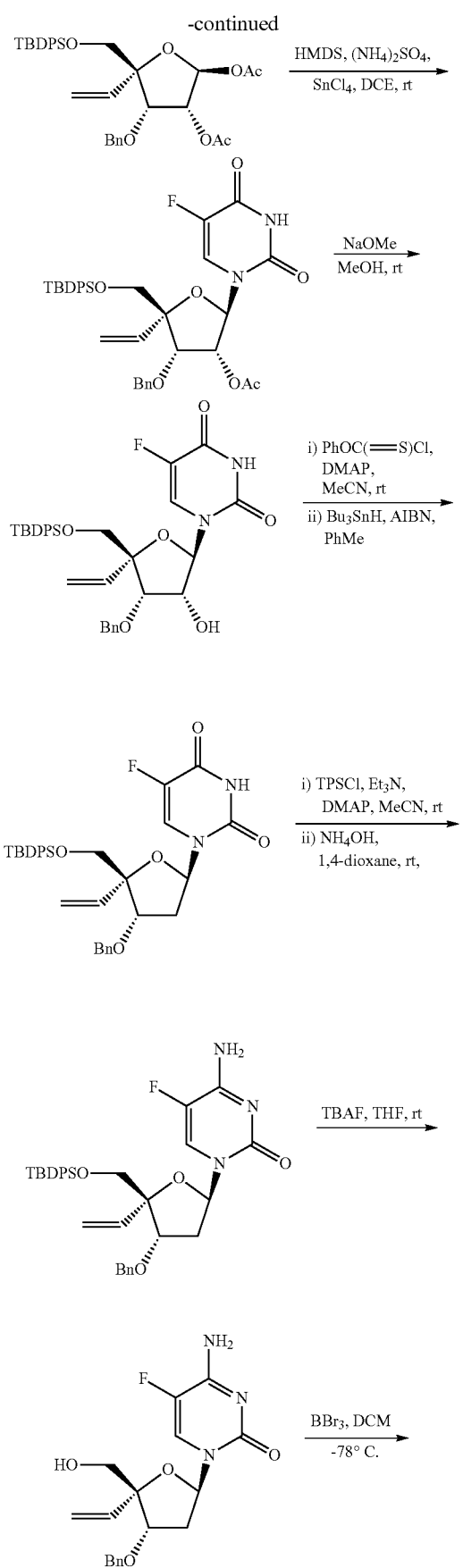

-continued

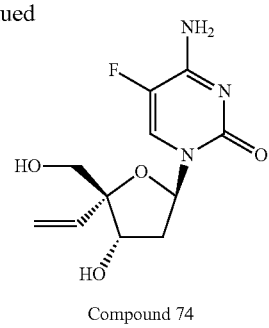

Compound 74

Step 1: To a solution of 3-O-benzyl-4-(hydroxymethyl-1, 2-O-isopropylidene)-alpha-d-erythropentofuranose (18 g, 58.1 mmol) in anhydrous DCM (280 mL), Et$_3$N (24.2 mL, 174.1 mmol) and tert-butyl-chloro-diphenylsilane (42.3 mL, 162.4 mmol) were sequentially added at rt under nitrogen atmosphere and stirred for 18 h. After completion, the reaction mixture was quenched by addition of sat. NaHCO$_3$ (20 mL) and extracted with DCM (2×30 mL). The organic layers were combined, dried with sodium sulfate and filtered. The filtrate was evaporated in vacuo to afford the crude residue, which was purified by column chromatography over silica gel (Gradient: 0-40% EtOAc in hexanes) to afford isomer 2b (20.4 g, 64.1% yield, white solid): $^1$H NMR (400 MHz, DMSO-d$_6$) δ 7.63-7.54 (m, 4H), 7.49-7.22 (m, 11H), 5.73 (d, J=3.7 Hz, 1H), 4.83 (dd, J=5.2, 3.7 Hz, 1H), 4.69 (d, J=12.2 Hz, 1H), 4.49 (d, J=12.2 Hz, 1H), 4.34 (d, J=5.1 Hz, 1H), 4.23 (dd, J=6.7, 5.0 Hz, 1H), 3.83 (dd, J=11.9, 5.0 Hz, 1H), 3.73 (d, J=10.8 Hz, 1H), 3.63-3.51 (m, 2H), 1.50 (s, 3H), 1.29 (s, 3H), 0.90 (s, 9H).

Step 2: To a solution of [(5R,6S,6aR)-6-benzyloxy-5-[[tert-butyl(diphenyl)silyl]oxymethyl]-2,2-dimethyl-6,6a-dihydro-3aH-furo[2,3-d][1,3]dioxol-5-yl]methanol 2b (20.4 g, 37.2 mmol) in anhydrous DCM (75 mL), was added Dess-Martin periodinane (18.9 g, 44.6 mmol) and the mixture was stirred under nitrogen atmosphere at rt for 6 h. Completion of the reaction was followed by TLC (30% EtOAc in hexanes). The reaction was quenched by addition of sat. NaHCO$_3$ solution (200 mL). The layers were separated and the aqueous layer was extracted with DCM (3×100 mL). The organic layers were combined, dried with sodium sulfate and filtered and then concentrated in vacuo. Crude residue was purified by column chromatography over silica gel (Gradient: 0-100% EtOAc in hexanes) to afford (3aR,5R,6S,6aR)-6-(benzyloxy)-5-(((tert-butyldiphenylsilyl)oxy)methyl)-2,2-dimethyl-tetrahydrofuro[2,3-d][1,3]dioxole-5-carbaldehyde (18.3 g, 90% yield) as a white solid. $^1$H NMR (400 MHz, CDCl$_3$) δ 9.90 (s, 1H), 7.65-7.55 (m, 4H), 7.47-7.28 (m, 11H), 5.87 (d, J=3.3 Hz, 1H), 4.74 (d, J=12.2 Hz, 1H), 4.70-4.58 (m, 2H), 4.54 (d, J=4.4 Hz, 1H), 3.88 (d, J=11.5 Hz, 1H), 3.79 (d, J=11.5 Hz, 1H), 1.62 (s, 3H), 1.37 (s, 3H), 0.98 (s, 9H).

Step 3: Methyl triphenyl phosphonium bromide (20.2 g, 56.4 mmol) was suspended in anhydrous THF (188 mL) under argon and cooled down to 0° C. n-Butyllithium solution (2.5 M in hexanes, 18.8 mL, 47 mmol) was then carefully added at 0° C. The solution turned yellow, and the mixture was stirred at this temperature for 10 min, then warmed up and stirred at rt for 1 h. The solution was then further cooled down to −78° C. and (3aR,5R,6S,6aR)-6-(benzyloxy)-5-(((tert-butyldiphenylsilyl)oxy)methyl)-2,2-dimethyltetrahydrofuro[2,3-d][1,3]dioxole-5-carbaldehyde (10.3 g, 18.8 mmol) was added as a solution in anhydrous THF (30 mL) at this temperature. The stirring was continued at −78° C. for 30 min under nitrogen, after which the reaction mixture was allowed to warm to rt and stirred for an additional 16 h. The mixture was quenched with sat. NH$_4$Cl solution (200 mL) and stirred for 5 mins. The mixture was then extracted with EtOAc (3×100 mL). The organic layers were combined, dried with sodium sulfate, filtered and concentrated in vacuo. The crude residue was purified via column chromatography over silica gel (Gradient: 0-40% EtOAc in hexanes) to afford [(5R,6S,6aR)-6-benzyloxy-2,2-dimethyl-5-vinyl-6,6a-dihydro-3aH-furo[2,3-d][1,3]dioxol-5-yl]methoxy-tert-butyl-diphenyl-silane (9.12 g, 89% yield) as a colorless gum. $^1$H NMR (400 MHz, CDCl$_3$) δ 7.68-7.57 (m, 4H), 7.46-7.27 (m, 11H), 6.17 (dd, J=17.6, 11.1 Hz, 1H), 5.81 (d, J=3.8 Hz, 1H), 5.45 (dd, J=17.6, 1.9 Hz, 1H), 5.18 (dd, J=11.0, 1.9 Hz, 1H), 4.83 (d, J=12.4 Hz, 1H), 4.71-4.59 (m, 2H), 4.45 (d, J=4.9 Hz, 1H), 3.57-3.46 (m, 2H), 1.55 (s, 3H), 1.32 (s, 3H), 0.98 (s, 9H).

Step 4: To a cold solution of [(5R,6S,6aR)-6-benzyloxy-2,2-dimethyl-5-vinyl-6,6a-dihydro-3aH-furo[2,3-d][1,3]dioxol-5-yl]methoxy-tert-butyl-diphenyl-silane (5 g, 9.2 mmol) in a mixture of acetic acid (84 mL) and acetic anhydride (9.3 mL, 98.9 mmol), was added concentrated sulfuric acid (80.7 µL, 1.5 mmol) and the mixture was stirred at 0-10° C. until completion. After 2 h, the mixture was carefully neutralized with cold sat. NaHCO$_3$ (1.2 L) and pH was brought to 6-7. The aqueous layer was then extracted with EtOAc (5×500 mL). The organic extracts were combined, dried with sodium sulfate and filtered. The filtrate was concentrated in vacuo and the crude residue was purified over silica gel via column chromatography (Gradient; 0-30% EtOAc in hexanes) to afford both anomers as colorless gummy solids. Major anomer, (2S,3R,4S,5R)-4-(benzyloxy)-5-(((tert-butyldiphenylsilyl)oxy)methyl)-5-vinyltetrahydrofuran-2,3-diyl diacetate, (3.4 g, 64%); $^1$H NMR (400 MHz, CDCl$_3$) δ 7.64 (tt, J=5.9, 1.5 Hz, 4H), 7.44-7.28 (m, 11H), 6.26 (s, 1H), 5.98 (dd, J=17.4, 11.0 Hz, 1H), 5.47 (dd, J=17.3, 1.8 Hz, 1H), 5.34 (d, J=4.9 Hz, 1H), 5.18 (dd, J=11.0, 1.8 Hz, 1H), 4.71-4.62 (m, 2H), 4.53 (d, J=11.6 Hz, 1H), 3.67-3.58 (m, 2H), 2.05 (s, 3H), 1.85 (s, 3H), 1.05 (s, 9H). Minor anomer, (2R,3R,4S,5R)-4-(benzyloxy)-5-(((tert-butyldiphenylsilyl) oxy)methyl)-5-vinyltetrahydrofuran-2,3-diyl diacetate, (392 mg, 7%); $^1$H NMR (400 MHz, CDCl$_3$) δ 7.63 (ddt, J=11.3, 6.6, 1.6 Hz, 4H), 7.49-7.29 (m, 11H), 6.46 (d, J=4.6 Hz, 1H), 5.91 (dd, J=17.4, 11.1 Hz, 1H), 5.43-5.32 (m, 2H), 5.17 (dd, J=11.0, 1.7 Hz, 1H), 4.68-4.51 (m, 2H), 4.46 (d, J=6.2 Hz, 1H), 3.52 (s, 2H), 2.10 (s, 3H), 2.06 (s, 3H), 1.05 (s, 9H).

Step 5: A stirred mixture of 5-fluorouracil (1.7 g, 12.9 mmol) and (NH$_4$)$_2$SO$_4$ (77.7 mg, 0.6 mmol) in HMDS (21 mL, 100 mmol) was heated to reflux at 130° C. under nitrogen for 3 h. The mixture was then cooled to rt, HMDS was evaporated off and the mixture put on high vacuum for 30 mins. The mixture was then cooled down to 0° C., and to this mixture, a solution of (2S,3R,4S,5R)-4-(benzyloxy)-5-(((tert-butyldiphenylsilyl)oxy)methyl)-5-vinyltetrahydrofuran-2,3-diyl diacetate (3.46 g, 5.88 mmol) in anhydrous DCE (29 mL) was added under nitrogen. After stirring for 5 mins, Tin(IV)chloride (1.4 mL, 11.8 mmol) was added and the mixture was allowed to warm to rt overnight. The mixture was carefully quenched with sat. NaHCO$_3$ solution (20 mL), and then extracted with EtOAc (4×100 mL). The organic layers were combined, dried with sodium sulfate, filtered and concentrated in vacuo. The crude residue was purified by column chromatography over silica gel (Gradient: 0-50% EtOAc in DCM) to afford [(2R,3R,4S,5R)-4-benzyloxy-5-[[tert-butyl(diphenyl)silyl]oxymethyl]-2-(5- fluoro-2,4-dioxo-pyrimidin-1-yl)-5-vinyl-tetrahydrofuran-3-yl] acetate (2.7 g, 69.7% yield) as a white solid. $^1$H NMR (400 MHz, CDCl$_3$) δ 8.25 (d, J=4.7 Hz, 1H), 7.87 (d, J=5.7 Hz, 1H), 7.64 (ddd, J=6.7, 3.3, 1.6 Hz, 4H), 7.48-7.29 (m, 9H), 7.23 (dd, J=7.4, 2.0 Hz, 2H), 6.16 (dd, J=4.4, 1.7 Hz, 1H), 5.80 (dd, J=17.4, 10.9 Hz, 1H), 5.42 (dd, J=17.4, 1.4 Hz, 1H), 5.33 (dd, J=6.1, 4.3 Hz, 1H), 5.22 (dd, J=10.9, 1.4 Hz, 1H), 4.57 (d, J=11.2 Hz, 1H), 4.50-4.37 (m, 2H), 3.67 (q, J=11.7 Hz, 2H), 2.06 (s, 3H), 1.11 (s, 9H).

Step 6: A solution of [(2R,3R,4S,5R)-4-benzyloxy-5-[[tert-butyl(diphenyl)silyl]oxymethyl]-2-(5-fluoro-2,4-dioxo-pyrimidin-1-yl)-5-vinyl-tetrahydrofuran-3-yl] acetate (2.53 g, 3.84 mmol) and sodium methoxide (1.23 mL, 5.4 mmol, 25% wt solution in MeOH) in anhydrous methanol (60 mL) was stirred at rt for 3.5 h. The reaction mixture was neutralized with 10% w/v aq. tartaric acid (10 mL) (pH=5) and the mixture was extracted with DCM (3×100 mL). The organic extracts were combined, dried with sodium sulfate, filtered and concentrated in vacuo. The crude residue was purified by column chromatography over silica gel (Gradient: 0-50% EtOAc in DCM) to afford 1-[(2R,3R,4S,5R)-4-benzyloxy-5-[[tert-butyl (diphenyl)silyl]oxymethyl]-3-hydroxy-5-vinyl-tetrahydrofuran-2-yl]-5-fluoro-pyrimidine-2,4-dione (2.05 g, 86.5% yield) as a white solid. $^1$H NMR (400 MHz, CDCl$_3$) δ 8.36 (d, J=13.0 Hz, 1H), 7.85 (d, J=5.8 Hz, 1H), 7.66-7.59 (m, 4H), 7.49-7.34 (m, 9H), 7.31-7.27 (m, 2H), 5.99 (dd, J=4.5, 1.7 Hz, 1H), 5.81 (dd, J=17.3, 10.9 Hz, 1H), 5.47 (dd, J=17.3, 1.4 Hz, 1H), 5.26 (dd, J=10.9, 1.4 Hz, 1H), 4.56 (t, J=0.6 Hz, 2H), 4.28 (d, J=6.1 Hz, 1H), 4.24 (dd, J=6.1, 4.5 Hz, 1H), 3.74-3.63 (m, 2H), 2.77 (s, 1H), 1.10 (s, 9H).

Step 7: To a solution of 1-[(2R,3R,4S,5R)-4-benzyloxy-5-[[tert-butyl(diphenyl)silyl]oxymethyl]-3-hydroxy-5-vinyl-tetrahydrofuran-2-yl]-5-fluoro-pyrimidine-2,4-dione (2.05 g, 3.32 mmol) in anhydrous MeCN (25 mL), was added DMAP (2.4 g, 19.94 mmol) and phenyl chloro thionoformate (0.7 mL, 4.99 mmol), and the mixture was stirred for 1 h at rt. The mixture was then quickly concentrated to remove the solvent, re-diluted with DCM (20 mL) and washed with aq. 5% citric acid (5 mL) and water (5 mL). The organic layer was then dried with sodium sulfate, filtered and concentrated in vacuo. The obtained crude mixture 1-[(2R,3R,4S,5R)-4-benzyloxy-5-[[tert-butyl (diphenyl)silyl]oxymethyl]-3-phenoxycarbothioyloxy-5-vinyl-tetrahydrofuran-2-yl]-5-fluoro-pyrimidine-2,4-dione (2.5 g, 3.3 mmol) was dissolved in anhydrous toluene (30 mL). To this solution was added n-Bu3SnH (4.5 mL, 16.6 mmol) and catalytic amount of AIBN (109.1 mg, 0.66 mmol), and the mixture was refluxed for 1 h. The mixture was then cooled to rt, and evaporated to remove the solvent. The crude residue was purified by column chromatography over silica gel (Gradient: 0-80% EtOAc in hexanes) to afford 1-[(2R,4S,5R)-4-benzyloxy-5-[[tert-butyl(diphenyl)silyl]oxymethyl]-5-vinyl-tetrahydrofuran-2-yl]-5-fluoro-pyrimidine-2,4-dione (810.2 mg, 41% yield over two steps) as a white solid. $^1$H NMR (400 MHz, CDCl$_3$) δ 8.13 (d, J=4.7 Hz, 1H), 8.02 (d, J=5.8 Hz, 1H), 7.67-7.56 (m, 4H), 7.47-7.30 (m, 9H), 7.27 (d, J=2.0 Hz, 2H), 6.20 (ddd, J=7.2, 3.8, 1.7 Hz, 1H), 5.87 (dd, J=17.3, 10.9 Hz, 1H), 5.47 (dd, J=17.3, 1.6 Hz, 1H), 5.26 (dd, J=10.9, 1.6 Hz, 1H), 4.60-4.41 (m, 3H), 3.73 (s, 2H), 2.46 (dt, J=13.6, 7.5 Hz, 1H), 2.20 (ddd, J=13.5, 7.1, 3.8 Hz, 1H), 1.08 (s, 9H).

Step 8: 2,4,6-Triisopropyl-benzenesulfonyl chloride (1.22 g, 4.02 mmol) and DMAP (491.1 mg, 4.02 mmol) were added to a 100 mL RB flask, followed by a solution of 1-[(2R,4S,5R)-4-benzyloxy-5-[[tert-butyl(diphenyl)silyl]oxymethyl]-5-vinyl-tetrahydrofuran-2-yl]-5-fluoro-pyrimidine-2,4-dione (805 mg, 1.34 mmol) in anhydrous MeCN (25 mL). Et$_3$N (0.57 mL, 4.02 mmol) was then added. The reaction mixture was stirred for 4 h at rt after which starting material had been completely consumed. Ammonia solution (28% w/v, 25 mL, 39.69 mmol) was added to the orange reaction mixture and mixture stirred for 3 h at rt. The mixture turned a cloudy, light yellow after a few minutes of stirring. The mixture was then evaporated to remove the ammonia and MeCN from the previous step. The resulting residue was extracted with DCM (3×30 mL). The organic layers were combined, dried with sodium sulfate, filtered and concentrated in vacuo. The crude residue was purified by column chromatography over silica gel (Gradient: 0-5% MeOH in DCM) to afford 4-amino-1-[(2R,4S,5R)-4-benzyloxy-5-[[tert-butyl(diphenyl)silyl]oxymethyl]-5-vinyl-tetrahydrofuran-2-yl]-5-fluoro-pyrimidin-2-one (606.1 mg, 76.4% yield) as an off-white solid. $^1$H NMR (400 MHz, DMSO-d$_6$) δ 7.88 (d, J=6.7 Hz, 1H), 7.77 (s, 1H), 7.69-7.56 (m, 4H), 7.53 (s, 1H), 7.46-7.20 (m, 11H), 6.10 (ddd, J=6.3, 3.6, 1.2 Hz, 1H), 5.90 (dd, J=17.3, 10.9 Hz, 1H), 5.39 (dd, J=17.3, 2.0 Hz, 1H), 5.23 (dd, J=10.8, 2.0 Hz, 1H), 4.66-4.37 (m, 3H), 3.68 (d, J=11.2 Hz, 1H), 3.68 (d, J=11.2 Hz, 1H), 2.32 (ddd, J=13.3, 7.2, 4.0 Hz, 1H), 2.23 (dt, J=13.3, 7.6 Hz, 1H), 0.98 (s, 9H). $^{19}$F NMR (376 MHz, DMSO-d$_6$) δ −166.76, −166.77, −166.78.

Step 9: To a solution of 4-amino-1-[(2R,4S,5R)-4-benzyloxy-5-[[tert-butyl(diphenyl)silyl]oxymethyl]-5-vinyl-tetrahydrofuran-2-yl]-5-fluoro-pyrimidin-2-one (600.mg, 1 mmol) in anhydrous THF (4 mL), was added tetrabutylammonium fluoride solution (1.0 M in THF, 1.5 mL, 1.5 mmol) at rt under nitrogen and the mixture was stirred for 16 h. The mixture was concentrated in vacuo and the crude residue was purified by column chromatography over silica gel (0-20% MeOH in DCM) to afford 4-amino-1-[(2R,4S,5R)-4-benzyloxy-5-(hydroxymethyl)-5-vinyl-tetrahydrofuran-2-yl]-5-fluoro-pyrimidin-2-one (326.2 mg, 90.2% yield) as a white solid. $^1$H NMR (400 MHz, DMSO-d$_6$) δ 8.28 (d, J=7.3 Hz, 1H), 7.70 (s, 1H), 7.47 (s, 1H), 7.39-7.21 (m, 5H), 6.02 (dt, J=6.3, 3.1 Hz, 1H), 5.93 (dd, J=17.3, 10.8 Hz, 1H), 5.48 (t, J=5.0 Hz, 1H), 5.36 (dd, J=17.4, 2.1 Hz, 1H), 5.21 (dd, J=10.9, 2.1 Hz, 1H), 4.53 (s, 2H), 4.37 (t, J=7.2 Hz, 1H), 3.61 (dd, J=11.9, 5.1 Hz, 1H), 3.44 (d, J=4.9 Hz, 1H), 2.19 (dd, J=7.2, 5.5 Hz, 2H).

Step 10: To a −78° C. solution of 4-amino-1-[(2R,4S,5R)-4-benzyloxy-5-(hydroxy-methyl)-5-vinyl-tetrahydrofuran-2-yl]-5-fluoro-pyrimidin-2-one (80 mg, 0.22 mmol) in anhydrous DCM (10 mL), BBr$_3$ solution (1.0 M in DCM, 0.5 mL, 0.5000 mmol) was added and the mixture stirred for 6 h at −78° C. The mixture was quenched with 2:1 mixture of pyridine: methanol (10 mL) at −78° C. and allowed to stir for 30 minutes. The mixture was brought to rt and evaporated in vacuo to remove the solvent, with thorough co-evaporation with toluene (3 times) and DCM (3 times) to remove traces of pyridine. The crude residue was then purified by column chromatography over silica gel (Gradient: 0-30% MeOH in EtOAc) to afford 4-amino-5-fluoro-1-[(2R,4S,5R)-4-hydroxy-5-(hydroxymethyl)-5-vinyl-tetrahydrofuran-2-yl]pyrimidin-2-one (Compound 74) (12.2 mg, 20.3% yield) as a white solid. $^1$H NMR (400 MHz, DMSO-d$_6$) δ 8.31 (d, J=7.4 Hz, 1H), 7.67 (s, 1H), 7.44 (s, 1H), 5.96 (d, J=6.0 Hz, 1H), 5.88 (dd, J=17.3, 10.9 Hz, 1H), 5.39 (s, 1H), 5.32 (dd, J=17.4, 2.2 Hz, 1H), 5.24 (d, J=4.7 Hz, 1H), 5.18 (dd, J=10.9, 2.2 Hz, 1H), 4.40 (t, J=6.2 Hz, 1H), 3.56 (dd, J=11.6, 4.5 Hz, 1H), 3.38 (d, J=4.5 Hz, 1H), 2.15-1.98 (m, 2H). $^{19}$F NMR (376 MHz, DMSO-d$_6$) δ −167.85, −167.86, −167.87, −167.88; HPLC: >99%; HRMS: calcd. for [2M+Na]$^+$ 565.1833, found 565.1830.

Example 35—Synthesis of Compound 75: 4-amino-1-((2R,3S,4S,5R)-3,4-dihydroxy-5-(hydroxymethyl)-5-vinyltetrahydrofuran-2-yl)-5-fluoropyrimidin-2(1H)-one

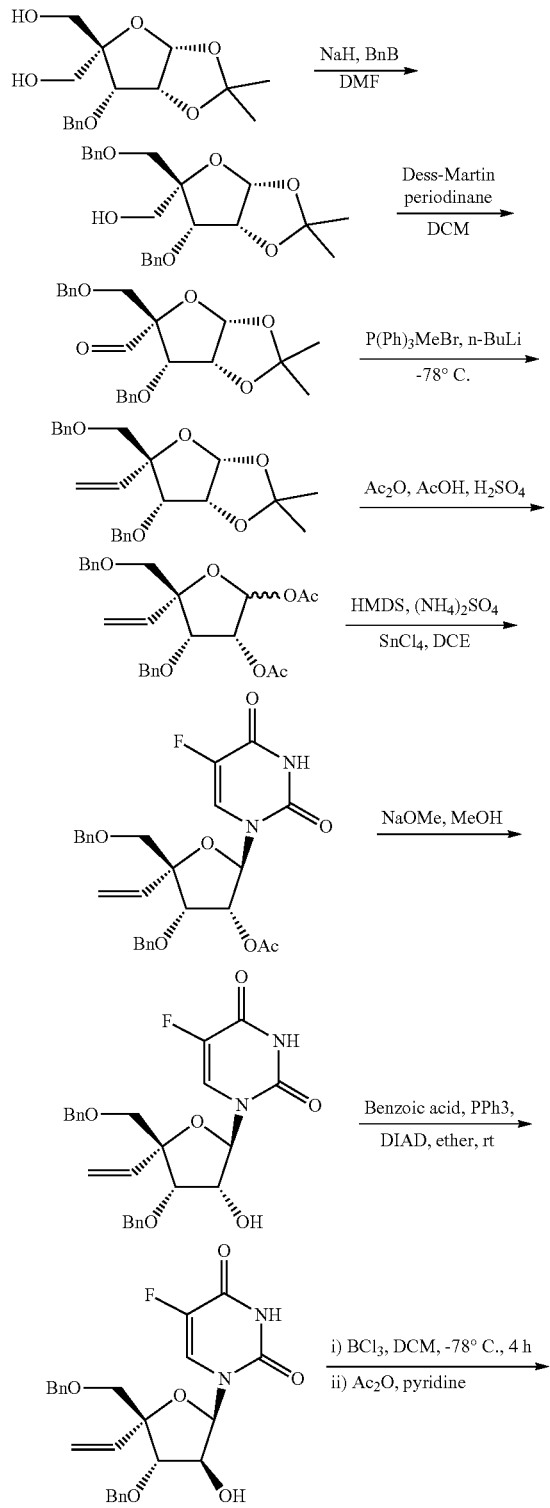

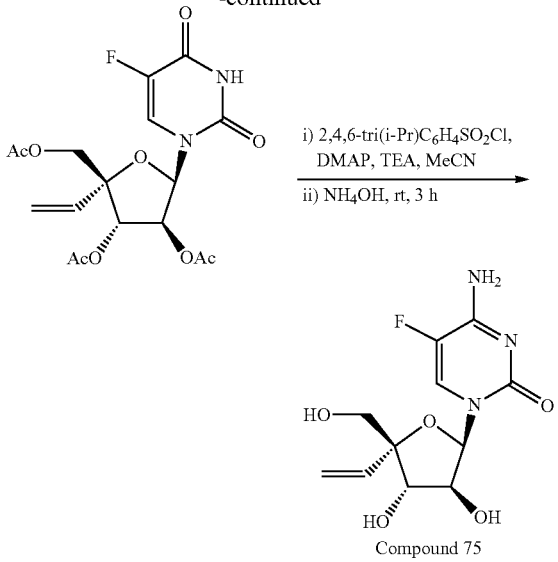

Compound 75

Step 1: To a solution of 3-O-benzyl-4-(hydroxymethyl-1,2-O-isopropylidene)-alpha-d-erythropentofuranose (12.7 g, 41.1 mmol) in anhydrous DMF (60 mL) was added sodium hydride (60% dispersion in mineral oil, 1.97 g, 49.3 mmol) at 0° C. The reaction was stirred at 0° C. for 15 min then warmed to room temperature. After the mixture was stirred at room temperature for 30 min, benzyl bromide (5.13 mL, 43.1 mmol) was added drop-wise. The mixture was stirred at room temperature for 3 h. The reaction was quenched with ice-cold H$_2$O (100 mL) and extracted with EtOAc (4×100 mL). The combined organic extracts were dried over anhydrous Na$_2$SO$_4$, filtered, and concentrated in vacuo. The crude was purified by column chromatography on silica gel (Gradient: 0-30% EtOAc in hexanes) to give ((3aR,5R,6S,6aR)-6-(benzyloxy)-5-((benzyloxy)methyl)-2,2-dimethyl-tetrahydrofuro[2,3-d][1,3]dioxol-5-yl)methanol (10.2 g, 62% yield) as a light yellow solid. $^1$H NMR (400 MHz, CDCl$_3$) δ 7.36-7.24 (m, 10H), 5.78 (d, J=3.9 Hz, 1H), 4.78 (d, J=11.8 Hz, 1H), 4.64 (dd, J=5.3, 3.9 Hz, 1H), 4.56-4.43 (m, 3H), 4.27 (d, J=5.3 Hz, 1H), 3.93 (d, J=11.9 Hz, 1H), 3.83 (d, J=11.9 Hz, 1H), 3.62-3.51 (m, 2H), 2.36 (s, 1H), 1.63 (s, 3H), 1.34 (d, J=0.7 Hz, 3H).

Step 2: To a solution of ((3aR,5R,6S,6aR)-6-(benzyloxy)-5-((benzyloxy)methyl)-2,2-dimethyltetrahydrofuro[2,3-d][1,3]dioxol-5-yl)methanol (10.2 g, 25.5 mmol) in anhydrous DCM (40 mL) was added Dess-Martin periodinane (12.9 g, 30.6 mmol) and the mixture was stirred at room temperature for 6 h. The reaction was quenched with aqueous saturated NaHCO$_3$ solution (100 mL). The organic layer was separated and the aqueous layer was extracted with DCM (2×100 mL). The combined organic extracts were washed with brine (250 mL), dried over anhydrous Na$_2$SO$_4$, filtered, and concentrated in vacuo. The crude was purified by column chromatography on silica gel (Gradient: 0-20% EtOAc in hexanes) to give (3aR,5R,6S,6aR)-6-(benzyloxy)-5-((benzyloxy)methyl)-2,2-dimethyltetrahydrofuro[2,3-d][1,3]dioxole-5-carbaldehyde (9.49 g, 93% yield) as a colorless oil. $^1$H-NMR (400 MHz, CDCl$_3$) δ 9.91 (s, 1H), 7.37-7.27 (m, 8H), 7.25-7.21 (m, 2H), 5.84 (d, J=3.4 Hz, 1H), 4.71 (d, J=12.2 Hz, 1H), 4.62-4.57 (m, 2H), 4.49 (q, J=12.0 Hz, 2H), 4.37 (d, J=4.5 Hz, 1H), 3.71-3.58 (m, 2H), 1.60 (s, 3H), 1.35 (d, J=0.7 Hz, 3H).

Step 3: To a cooled (0° C.) mixture of methyl triphenyl phosphonium bromide (22.9 g, 64.3 mmol) in anhydrous THF (60 mL) under argon was added n-butyllithium (1.6 M in hexanes, 32.7 mL, 52.4 mmol). After the mixture was stirred for 5 min, the ice bath was removed and stirring was continued at room temperature for 1 h. The orange-yellow reaction mixture was then cooled to −78° C., and a solution of (3aR,5R,6S,6aR)-6-(benzyloxy)-5-((benzyloxy)methyl)-2,2-dimethyltetrahydrofuro[2,3-d][1,3]dioxole-5-carbaldehyde (9.49 g, 23.82 mmol) in THF (15 mL) was added. Stirring was continued for 30 minutes before being warmed to room temperature. After stirring overnight, the reaction mixture was quenched at 0° C. with aqueous saturated NH$_4$Cl solution (50 mL) and extracted with EtOAc (3×100 mL). The combined organic extracts were dried over anhydrous Na$_2$SO$_4$, filtered, and concentrated in vacuo. The crude was purified by column chromatography on silica gel (Gradient: 0-10% EtOAc in hexanes) to give (3aR,5R,6S,6aR)-6-(benzyloxy)-5-((benzyloxy)methyl)-2,2-dimethyl-5-vinyltetrahydrofuro[2,3-d][1,3]dioxole (7.1 g, 17.9 mmol, 75% yield) as a colorless oil. $^1$H NMR (400 MHz, CDCl$_3$) δ 7.38-7.21 (m, 10H), 6.20 (dd, J=17.6, 11.1 Hz, 1H), 5.76 (d, J=3.9 Hz, 1H), 5.52 (dd, J=17.6, 1.9 Hz, 1H), 5.25 (dd, J=11.1, 1.8 Hz, 1H), 4.77 (d, J=12.3 Hz, 1H), 4.62-4.55 (m, 2H), 4.52 (d, J=12.1 Hz, 1H), 4.41 (d, J=12.1 Hz, 1H), 4.25 (d, J=5.0 Hz, 1H), 3.33 (d, J=1.5 Hz, 2H), 1.53 (s, 3H), 1.31-1.27 (m, 3H).

Step 4: To a cooled solution of give (3aR,5R,6S,6aR)-6-(benzyloxy)-5-((benzyloxy)methyl)-2,2-dimethyl-5-vinyltetra-hydrofuro[2,3-d][1,3]dioxole (7.1 g, 17.9 mmol) in acetic acid (140 mL) was added acetic anhydride (18.2 mL, 192.9 mmol) and sulfuric acid (0.16 mL, 2.9 mmol). The reaction was stirred at 0-10° C. (cold water bath) for 2 h. The reaction was neutralized (pH=7) with aqueous saturated NaHCO$_3$ solution (200 mL), then extracted with EtOAc (3×200 mL). The combined organic extracts were washed with brine (350 mL), dried over anhydrous Na$_2$SO$_4$, filtered, and concentrated in vacuo. The crude was purified by column chromatography on silica gel (Gradient: 0-10% EtOAc in hexanes) to give (3R,4S,5R)-4-(benzyloxy)-5-((benzyloxy)methyl)-5-vinyltetrahydrofuran-2,3-diyl diacetate (5.9 g, 75% yield) as a white solid. $^1$H NMR (400 MHz, CDCl$_3$) δ 7.35-7.26 (m, 8H), 7.26-7.23 (m, 2H), 6.19 (d, J=0.5 Hz, 1H), 5.98 (dd, J=17.4, 11.0 Hz, 1H), 5.49 (dd, J=17.4, 1.7 Hz, 1H), 5.28 (dd, J=4.8, 0.6 Hz, 1H), 5.24 (dd, J=11.0, 1.7 Hz, 1H), 4.65 (d, J=12.0 Hz, 1H), 4.51-4.47 (m, 3H), 4.39 (d, J=11.9 Hz, 1H), 3.41 (d, J=1.8 Hz, 2H), 2.05 (s, 3H), 1.86 (s, 3H).

Step 5: A mixture of 5-fluorouracil (3.8 g, 29.6 mmol) and ammonium sulfate (177 mg, 1.34 mmol) in hexamethyldisilazane (47.8 mL, 227.9 mmol) was heated to reflux (130° C.) under argon for 3 h. The mixture was cooled to room temperature and the solvent was removed. To this crude was added a solution of (3R,4S,5R)-4-(benzyloxy)-5-((benzyloxy)methyl)-5-vinyltetrahydrofuran-2,3-diyl diacetate (5.9 g, 13.4 mmol) in anhydrous DCE (60 mL) at 0° C. under argon, followed by addition of tin(IV) chloride (3.1 mL, 26.9 mmol). The mixture was warmed to room temperature and stirred overnight. The reaction was diluted with saturated aqueous NaHCO$_3$ (250 mL) and extracted with EtOAc (3×300 mL). The combined organic extracts were washed with brine, dried over anhydrous Na$_2$SO$_4$, filtered, and concentrated in vacuo. The crude was purified by column chromatography on silica gel (Gradient: 0-40% EtOAc in hexanes) to give (2R,3R,4S,5R)-4-(benzyloxy)-5-((benzyloxy)methyl)-2-(5-fluoro-2,4-dioxo-3,4-dihydropyrimidin-1 (2H)-yl)-5-vinyltetrahydrofuran-3-yl acetate (6.1 g, 89% yield) as a white solid. LCMS: m/z=511 [M+H]$^+$. $^1$H NMR (400 MHz, CDCl$_3$) δ 8.93 (d, J=33.1 Hz, 1H), 8.07 (d, J=6.4 Hz, 1H), 7.39-7.26 (m, 9H), 7.25 (d, J=1.5 Hz, 1H), 6.16 (dd, J=3.7, 1.6 Hz, 1H), 5.90 (dd, J=17.4, 11.0 Hz, 1H), 5.46 (dd, J=17.4, 1.3 Hz, 1H), 5.32-5.25 (m, 2H), 4.60 (d, J=11.7 Hz, 1H), 4.50 (d, J=11.4 Hz, 1H), 4.43 (d, J=5.7 Hz, 1H), 4.40 (d, J=5.5 Hz, 1H), 4.38 (d, J=5.8 Hz, 1H), 3.50 (d, J=10.6 Hz, 1H), 3.43 (d, J=10.6 Hz, 1H), 2.06 (s, 3H).

Step 6: To a solution of 11 g (6.1 g, 11.9 mmol) in anhydrous methanol (60 mL) was added sodium methoxide (25% in methanol, 4.4 mL, 19.2 mmol) under argon and the reaction mixture was stirred at room temperature for 2.5 h. Upon completion indicated by TLC, the reaction was neutralized (pH=5) with concentrated aqueous tartaric acid (20 mL, 2 g/20 mL), water (50 mL) was added, and the mixture was extracted with DCM (3×100 mL). The combined organic extracts were dried over anhydrous Na$_2$SO$_4$, filtered, and concentrated in vacuo. The crude was purified by column chromatography on silica gel (Gradient: 0-30% EtOAc in DCM) to give 1-((2R,3R,4S,5R)-4-(benzyloxy)-5-((benzyloxy)methyl)-3-hydroxy-5-vinyltetrahydrofuran-2-yl)-5-fluoropyrimidine-2,4(1H,3H)-dione 12 g (5.3 g, 95% yield) as a white solid. LCMS: m/z=469 [M+H]$^+$. $^1$H NMR (400 MHz, CDCl$_3$) δ 8.88 (d, J=4.8 Hz, 1H), 8.03 (d, J=6.4 Hz, 1H), 7.39-7.30 (m, 8H), 7.29-7.26 (m, 2H), 6.03-5.99 (m, 1H), 5.92 (dd, J=17.3, 10.9 Hz, 1H), 5.51 (dd, J=17.3, 1.3 Hz, 1H), 5.31 (dd, J=11.0, 1.3 Hz, 1H), 4.67-4.58 (m, 2H), 4.55 (d, J=11.3 Hz, 1H), 4.47 (d, J=11.3 Hz, 1H), 4.27-4.23 (m, 2H), 3.52 (d, J=2.1 Hz, 2H).

Step 7: To a cooled solution of triphenylphosphine (1.1 g, 4.27 mmol) in anhydrous diethyl ether (20 mL) under argon was added diisopropyl azodicarboxylate (0.84 mL, 4.27 mmol) and the reaction was stirred at 0° C. for 30 minutes. To this yellow slurry suspension was added a cooled solution of 1-((2R,3R,4S,5R)-4-(benzyloxy)-5-((benzyloxy)methyl)-3-hydroxy-5-vinyltetrahydrofuran-2-yl)-5-fluoropyrimidine-2,4(1H,3H)-dione (1 g, 2.13 mmol) and benzoic acid (521 mg, 4.27 mmol) in anhydrous diethyl ether (20 mL) at 0° C. The mixture was warmed to room temperature and stirred for 16 h. After the reaction mixture was concentrated in vacuo, a solution of NaOH (316 mg) in MeOH (40 mL) was added and the reaction mixture was stirred overnight at 50° C. The reaction was cooled to room temperature and the excess solvent was removed. 1N HCl solution (50 mL) was added and the mixture was extracted with EtOAc (3×60 mL). The combined organic extracts were dried over anhydrous Na$_2$SO$_4$, filtered, and concentrated in vacuo. The crude was purified by column chromatography on silica gel (Gradient: 0-45% EtOAc in hexanes) to give 1-((2R,3S,4S, 5R)-4-(benzyloxy)-5-((benzyloxy)methyl)-3-hydroxy-5-vinyltetrahydrofuran-2-yl)-5-fluoropyrimidine-2,4(1H,3H)-dione (680 mg, 68% yield) as a white solid. LCMS: m/z=469 [M+H]$^+$. $^1$H NMR (400 MHz, DMSO-d$_6$) δ 11.84 (s, 1H), 7.93 (d, J=7.1 Hz, 1H), 7.40-7.24 (m, 10H), 6.08 (dd, J=6.3, 1.8 Hz, 1H), 6.04-5.92 (m, 2H), 5.44 (dd, J=17.2, 1.8 Hz, 1H), 5.28 (dd, J=10.8, 1.8 Hz, 1H), 4.72 (d, J=12.1 Hz, 1H), 4.62 (d, J=12.0 Hz, 1H), 4.50 (q, J=11.7 Hz, 2H), 4.28 (q, J=6.4 Hz, 1H), 4.20 (d, J=7.2 Hz, 1H), 3.62 (d, J=10.7 Hz, 1H), 3.50 (d, J=10.7 Hz, 1H).

Step 8: To a solution of 1-((2R,3S,4S,5R)-4-(benzyloxy)-5-((benzyloxy)methyl)-3-hydroxy-5-vinyltetrahydrofuran-2-yl)-5-fluoropyrimidine-2,4(1H,3H)-dione (666 mg, 1.42 mmol) in anhydrous DCM (17 mL) was added boron tribromide (1.0 M in DCM, 7.1 mL, 7.11 mmol) at −78° C. under argon and the mixture was stirred for 4 h at the same temperature. To the solution was added a mixture of pyridine (3 mL) and methanol (4.4 mL) and the mixture was stirred for 1 h at −78° C. Excess solvent was removed and the residue was co-evaporated with pyridine twice and then dissolved in pyridine (20 mL). Acetic anhydride (2.0 mL, 21.3 mmol) was added to the light-yellow solution and stirred at room temperature for 18 h. The reaction was evaporated and the residue was partitioned between EtOAc (60 mL) and H$_2$O (50 mL). The organic layer was separated and the aqueous layer was extracted with EtOAc (2×50 mL). The combined organic extracts were dried over anhydrous Na$_2$SO$_4$, filtered, and concentrated in vacuo. The crude was purified by column chromatography on silica gel (Gradient: 0-25% EtOAc in DCM) to give (2R,3S,4S,5R)-2-(acetoxymethyl)-5-(5-fluoro-2,4-dioxo-3,4-dihydropyrimidin-1 (2H)-yl)-2-vinyltetrahydrofuran-3,4-diyl diacetate (262 mg, 44% yield) as a light-yellow solid. LCMS: m/z=415 [M+H]$^+$. $^1$H NMR (400 MHz, DMSO-d$_6$) δ 12.00 (s, 1H), 8.02 (d, J=7.0 Hz, 1H), 6.24 (d, J=6.0 Hz, 1H), 5.89 (dd, J=17.3, 10.9 Hz, 1H), 5.57 (d, J=5.9 Hz, 1H), 5.51 (dd, J=17.3, 1.4 Hz, 1H), 5.40 (dd, J=10.8, 1.4 Hz, 1H), 5.31 (t, J=5.9 Hz, 1H), 4.34 (d, J=12.0 Hz, 1H), 4.24 (d, J=11.9 Hz, 1H), 2.09 (s, 3H), 2.05 (s, 3H), 1.98 (s, 3H).

Step 9: To a solution of (2R,3S,4S,5R)-2-(acetoxymethyl)-5-(5-fluoro-2,4-dioxo-3,4-dihydropyrimidin-1(2H)-yl)-2-vinyltetrahydrofuran-3,4-diyl diacetate (260 mg, 0.63 mmol), 2,4,6-triisopropylbenzenesulfonyl chloride (570 mg, 1.88 mmol), and 4-(dimethylamino)pyridine (230 mg, 1.88 mmol) in anhydrous acetonitrile (10 mL) was added triethylamine (0.26 mL, 1.88 mmol) under argon. The reaction was stirred at room temperature 17 h. Ammonium hydroxide (28% aqueous, 15 mL) was added and the reaction was stirred at room temperature for 3 h. The excess solvent was removed and the crude was purified by column chromatography twice on silica gel (Gradient: 0-10% MeOH in DCM). The solids were co-evaporated with 5% MeOH in DCM five times then re-suspended in 5% MeOH in DCM, collected by vacuum filtration, washed with DCM, and dried under high vacuum to give 4-amino-1-((2R,3S,4S,5R)-3,4-dihydroxy-5-(hydroxymethyl)-5-vinyltetrahydrofuran-2-yl)-5-fluoropyrimidin-2(1H)-one (Compound 75) (37 mg, 20% yield) as an ivory solid. $^1$H NMR (400 MHz, DMSO-d$_6$) δ 8.04 (d, J=7.4 Hz, 1H), 7.66 (s, 1H), 7.44 (s, 1H), 6.04 (dd, J=6.1, 2.2 Hz, 1H), 5.94 (dd, J=17.4, 10.9 Hz, 1H), 5.48 (dd, J=11.9, 5.4 Hz, 2H), 5.39-5.30 (m, 2H), 5.18 (dd, J=10.9, 2.2 Hz, 1H), 4.11 (dd, J=6.9, 5.1 Hz, 1H), 3.99 (q, J=6.2 Hz, 1H), 3.53 (dd, J=11.8, 5.6 Hz, 1H), 3.34 (dd, J=11.8, 5.1 Hz, 1H). HRMS (m/z): calc'd for C$_{11}$H$_{14}$FN$_3$O$_5$ (2M+Na)$^+$ 597.1730; found 597.1732. HPLC purity=99%.

Example 36—Synthesis of Compounds 57 and 60: 4-amino-1-((2R,4S,5R)-4-hydroxy-5-(hydroxymethyl)-5-propyltetrahydrofuran-2-yl)pyrimidin-2 (1H)-one

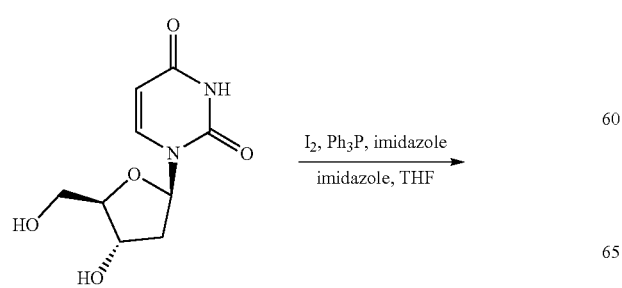

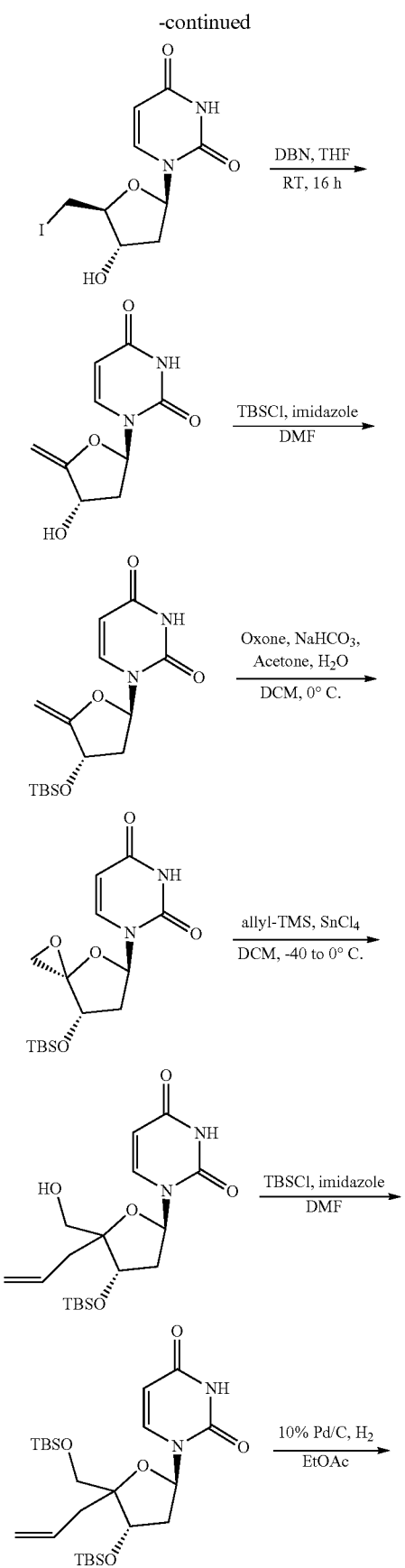

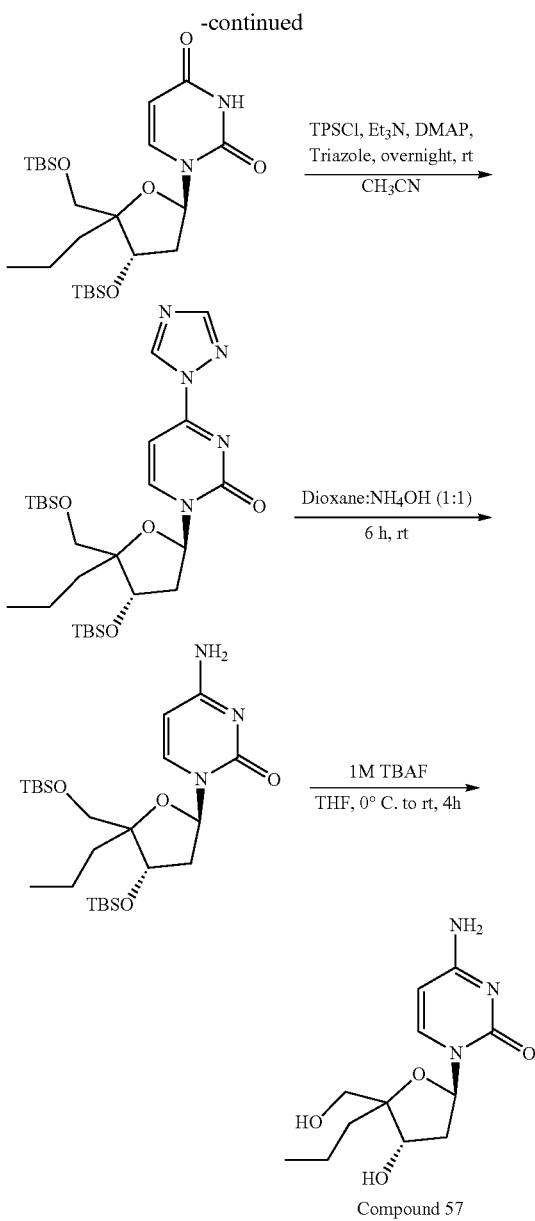

Compound 57

Step 1: To a stirred solution of 1-((2R,4S,5R)-4-hydroxy-5-(hydroxymethyl)-tetrahydrofuran-2-yl)pyrimidine-2,4(1H,3H)-dione (10 g, 43.8 mmol) in THF (100 ml) was added imidazole (5.97 g, 87.64 mmol) followed by triphenyl phosphate (17.24 g, 65.73 mmol) at rt and stirred for 15 min. To this 12 (8.34 g, 65.73 mmol) was added in a portion wise manner at 0° C. and after stirring the reaction mixture at rt for 6 h, the reaction progress was monitored by TLC. After completion, the reaction mass was concentrated and resulting residue was diluted with ice water and quenched with sodium bi-sulphate solution, extracted with Ethyl acetate. The combines organic fractions were washed with water and brine, then dried over sodium sulphate, filtered, and concentrated to get crude product which was purified by combi-flash eluting with 3% Methanol in DCM to afford desired product (4.2 g, 28%) as white color solid. LC-MS (ES, m/z): 336.90 (M−H).

Step 2: To a stirred solution of 1-((2R,4S,5S)-4-hydroxy-5-(iodomethyl) tetrahydrofuran-2-yl)pyrimidine-2,4(1H,3H)-dione (6 g, 17.75 mmol) in THF (100 ml) was added DBN (6.61 g, 53.24 mmol) at rt and after stirring the reaction mixture at 60° C. for 6 h, the reaction progress was monitored by TLC. After completion, the reaction mixture was concentrated to get crude product which was purified by combi-flash chromatography eluting with 3% Methanol in DCM to afford desired product (2.1 g, 56%) as off-white solid. LC-MS (ES, m/z): 210.80 (M+H⁺).

Step 3: To a stirred solution of 1-((2R,4S)-4-hydroxy-5-methylenetetrahydrofuran-2-yl)pyrimidine-2,4(1H,3H)-dione (9.0 g, 42.818 mmol) in DMF (90 ml) was added imidazole (8.74 g, 128.455 mmol) at rt and stirred for 15 min. To this TBSCl (12.907 g, 85.637 mmol) was added and after stirring the reaction mixture at rt for 4 h, the reaction progress was monitored by TLC. After completion, the reaction mass was diluted with ice water and extracted with ethyl acetate. The combined organic fractions were washed with water and brine, then dried over sodium sulphate, filtered, and concentrated to get crude product which was purified by combi flash chromatography eluting with 1% Methanol in DCM to afford desired product (5.2 g, 37%) as off-white solid. LC-MS (ES, m/z): 324.90 (M+H⁺).

Step 4: To a stirred solution of 1-((2R,4S)-4-((tert-butyldimethylsilyl)oxy)-5-methylenetetrahydrofuran-2-yl)pyrimidine-2,4(1H,3H)-dione (2.500 g, 7.705 mmol) in DCM (40 ml) was added NaHCO₃ (9.709 g, 115.58 mmol) and acetone (17.901 g, 308.214 mmol) at 0° C. and stirred for 15 min. To this Oxone (16.579 g, 53.937 mmol) in water (75 ml) was added dropwise at 0° C. and after stirring the reaction mixture at 0° C. for 2 h, the reaction progress was monitored by TLC. After completion, the reaction mass was diluted with cold DCM and washed with cold sodium thiosulphate solution, ice water and cold brine, then dried over sodium sulphate, filtered, and concentrated to get crude product (2.7 g) as pale-yellow solid which was used as such for the next step without purification. LC-MS (ES, m/z): 340.95 (M+H⁺).

Step 5: To a stirred solution of 1-((3S,5R,7S)-7-((tert-butyldimethylsilyl)oxy)-1,4-dioxaspiro[2.4]heptan-5-yl)pyrimidine-2,4(1H,3H)-dione (2.5 g, 7.343 mmol) in DCM (40 ml) was added Ally trimethyl silane (3.356 g, 29.373 mmol) and stirred for 15 min. To this SnCl₄ (7.652 g, 29.373 mmol) was added in a drop wise manner at −40° C. and after stirring the reaction mixture for 2 h at 0° C., the reaction progress was monitored by TLC. After completion, the reaction mixture was quenched with NaHCO₃ solution, extracted with DCM. The combines organic fractions were washed with water and brine, then dried over sodium sulphate, filtered and concentrated to get crude product as pale-yellow solid which was purified by combi flash chromatography eluting with 1.2% Methanol in DCM to afford desired product (0.85 g, 30%) as white solid. LC-MS (ES, m/z): 380.85 (M−H).

Step 6: To a stirred solution of 1-((2R,4S,5R)-5-allyl-4-((tert-butyldimethylsilyl)oxy)-5-(hydroxymethyl)tetrahydrofuran-2-yl)pyrimidine-2,4(1H,3H)-dione (0.840 g, 2.196 mmol) in DMF (8 mL) was added imidazole (0.448 g, 6.588 mmol) at rt and stirred for 15 min. To this TBDMS-Cl (0.662 g, 4.392 mmol) was added and after stirring at rt for 4 h, the reaction progress was monitored by TLC. After completion, the reaction mixture was diluted with ice water and extracted with Ethyl acetate. The combines organic fractions were washed with water and brine, then dried over sodium sulphate, filtered, and concentrated to get crude product as foam type solid which was purified by combi-flash chromatography eluting with 30% EtOAc in Hexane to afford desired product (0.820 g, 75%) as a white solid. LC-MS (ES, m/z): 495.10 (M–H).

Step 7: To a stirred solution of 1-((2R,4S,5R)-5-allyl-4-((tert-butyldimethylsilyl)oxy)-5-(((tert-butyldimethylsilyl)oxy)methyl)tetrahydrofuran-2-yl)pyrimidine-2,4(1H,3H)-dione (0.4 g, 0.805 mmol) in Ethyl acetate (20 mL) was added 10% Pd/C (40 mg, 10% wt/wt) at rt. After stirring the reaction mixture for 2 h at rt under hydrogen balloon pressure, the reaction progress was monitored by TLC. After completion reaction mixture was filtered over celite, filtrate was concentrated to get crude product which was purified by Combi-flash chromatography eluting with 30% EtOAc in Hexane to afford desired product (0.310 g, 73%) as white solid. LC-MS (ES, m/z): 540.20 (M+41' MeCN adduct).

Step 8: To a stirred solution of 1-((2R,4S,5R)-4-((tert-butyldimethylsilyl)oxy)-5-(((tert-butyldimethylsilyl)oxy)methyl)-5-propyl tetrahydrofuran-2-yl)pyrimidine-2,4(1H,3H)-dione (0.380 g, 0.762 mmol) in $CH_3CN$ (7 ml) was added $Et_3N$ (0.308 g, 3.047 mmol) and DMAP (0.186 g, 1.524 mmol) at rt and stirred for 15 min. To this TPSCl (0.461 g, 1.524 mmol) was added in a portion wise manner at 0° C. and stirred for 2 h at rt. Followed by 1,2,4-Triazole (0.263 g, 3.809 mmol) added at 0° C. and stirring was continued for 2 h at rt. The reaction progress was monitored by TLC and LCMS. After completion, the reaction mixture was diluted with ice water and Ethyl acetate. Organic layer was separated, and aqueous layer was washed with 2×20 mL EtOAc. Combined organics were washed with water and brine, then dried over sodium sulphate, filtered, and concentrated to get crude product which was purified by Combiflash chromatography eluting with 30% EtOAc in Hexane to afford desired product (0.310 g, 73%) as colorless gummy liquid. LC-MS (ES, m/z): 550.15 $(M+H^+)$.

Step 9: To a stirred solution of 1-((2R,4S,5R)-4-((tert-butyldimethylsilyl)oxy)-5-(((tert-butyldimethylsilyl)oxy)methyl)-5-propyl tetrahydrofuran-2-yl)-4-(1H-1,2,4-triazol-1-yl)pyrimidin-2(1H)-one (0.300 g, 0.545 mmol) in 1,4-Dioxane (2 mL) was added ammonia solution (2 mL) and stirred for 15 min at rt and then heated to 30° C. for 4 h. The reaction progress was monitored by TLC and LCMS. After completion, the reaction mixture was concentrated to get crude product as pale-yellow liquid which was purified by Combiflash chromatography eluting with 4% MeOH in DCM to afford desired product (0.190 g) as colorless sticky liquid. LC-MS (ES, m/z): 498.20 $(M+H^+)$.

Step 10: To a stirred solution of 4-amino-1-((2R,4S,5R)-4-((tert-butyldimethylsilyl) oxy)-5-(((tert-butyldimethylsilyl)oxy)methyl)-5-propyl tetrahydrofuran-2-yl)pyrimidin-2(1H)-one (0.170 g, 0.341 mmol) in THF (3 mL) was added TBAF (2.05 ml, 2.049 mmol) at 0° C. After stirring the reaction mixture at 0° C. to rt for 4 h, the reaction progress was monitored by TLC. After completion, the reaction mass was concentrated under vacuum. The crude was purified by prep-HPLC with following conditions: Column: X SELECT (250 mm×20.0 mm), 5.0µ; Mobile Phase: A: 0.02% $NH_4OH$ in WATER, B: ACN, Flow rate: 18.0 ml/min, Gradient program: Time/% B: 0/5,2/10,8/20 to afford 29 mg of Compound 57 which was subjected further for chiral prep-purification with following conditions: Column: Chiralpak IH, 250 mmλ21 mm, 5 µm; Mobile Phase: n-Hexane(A) and Ammonia in IPA:MeOH, 1:1(B); Flow rate:15 ml; Isocratic: 75 (A):25(B); Diluents: EtOH: DCM, 3:1.2 ml; Injection Volume-0.5 ml; Run Time-15 min; Instrument Make and Model: Agilent-1260 Infinity. This afforded 4-amino-1-((2R,4S,5R)-4-hydroxy-5-(hydroxymethyl)-5-propyltetrahydrofuran-2-yl)pyrimidin-2(1H)-one (10 mg, 11% as white solid) (Compound 60). LC-MS (ES, m/z): $[M+H]^+$=269.85, $^1H$ NMR (400 MHz, DMSO-$d_6$) δ 7.84 (d, J=7.4 Hz, 1H), 7.16-6.99 (m, 2H), 6.10-6.05 (m, 1H), 5.69 (d, J=7.4 Hz, 1H), 5.04 (d, J=4.9 Hz, 1H), 4.97-4.93 (m, 1H), 4.25-4.19 (m, 1H), 3.47-3.36 (m, 2H), 2.19-2.12 (m, 1H), 2.08-2.00 (m, 1H), 1.58-1.45 (m, 2H), 1.41-1.28 (m, 2H), 0.87 (t, J=7.2 Hz, 3H).

Example 37—Synthesis of Compound 61: 4-amino-1-((2R,4S,5R)-5-azido-4-hydroxy-5-(hydroxymethyl)tetrahydrofuran-2-yl)-5-fluoropyrimidin-2(1H)-one

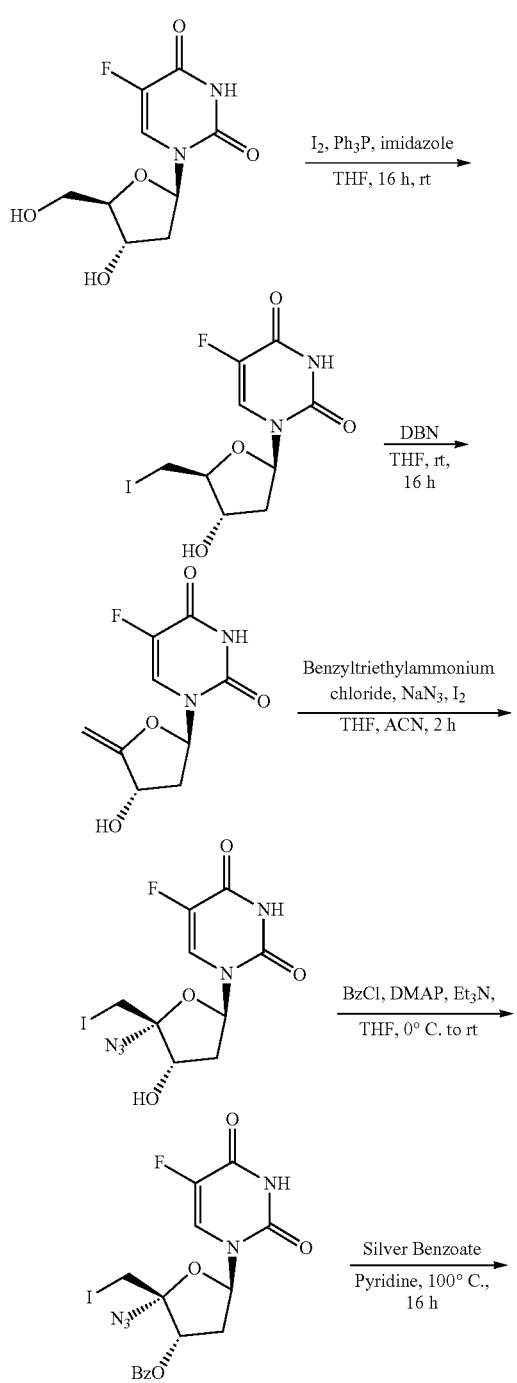

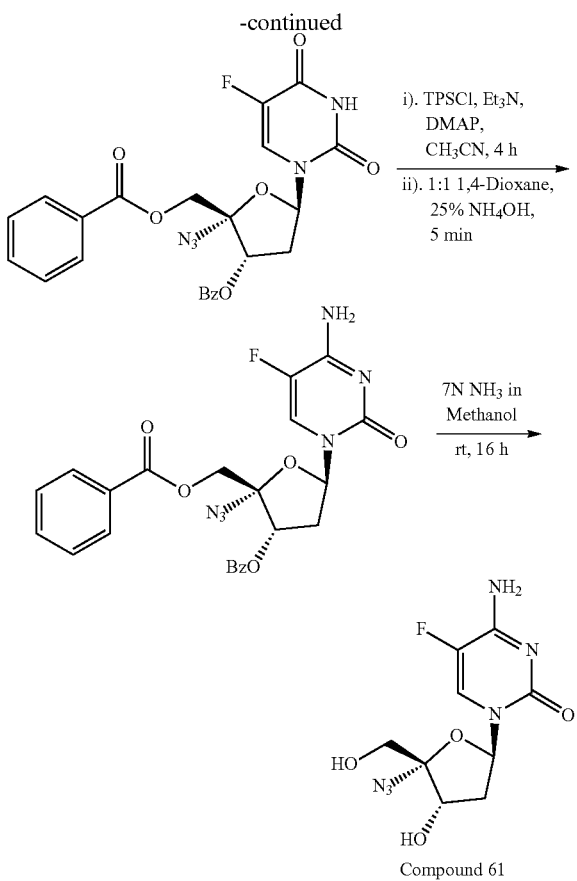

Compound 61

Step 1: To a solution of 5-fluoro-1-((2R,4S,5R)-4-hydroxy-5-(hydroxymethyl) tetrahydrofuran-2-yl)pyrimidine-2,4(1H,3H)-dione (14 g, 56.87 mmol) and imidazole (7.74 g, 113.73 mmol) in dry THF (160 mL) was added triphenylphosphine (22.37 g, 85.30 mmol), the reaction mixture was stirred for 15 min, after that iodine (21.64 g, 85.30 mmol) was added portion wise at 0° C. After stirring the reaction mixture at rt for 16 h, the reaction progress was monitored by TLC. The reaction mixture was filtered, washed with THF (50 mL). The filtrate was concentrated under reduced pressure to afford crude compound. The crude material was dissolved in DCM (500 mL), washed with water (200 mL) and aqueous layer was extracted with DCM (200 mL). The combined organics were washed with water (300 mL), brine (300 mL), dried over anhydrous $Na_2SO_4$, filtered and concentrated under reduced pressure to afforded crude compound. The crude residue was purified by combi-flash column chromatography, eluted with 10% MeOH in DCM to afford 5-fluoro-1-((2R,4S,5S)-4-hydroxy-5-(iodomethyl) tetrahydrofuran-2-yl)pyrimidine-2,4(1H,3H)-dione (9 g, 44.46%) as white solid. (ES, m/z): 356.75 (M+H$^+$).

Step 2: To a solution of 5-fluoro-1-((2R,4S,5S)-4-hydroxy-5-(iodomethyl) tetrahydrofuran-2-yl)pyrimidine-2,4 (1H,3H)-dione (8 g, 22.47 mmol) in THF (80 mL) was added DBN (11.10 mL, 89.86 mmol) at rt. After stirring the reaction mixture at 60° C. for 2 h, the reaction progress was monitored by TLC. After completion, the reaction mixture was concentrated under reduced pressure to afford crude compound. The crude product was purified by combi-flash chromatography eluting with 4% MeOH in DCM to afford desired product (3.6 g, 70.31%) as white solid. (ES, m/z): 226.90 (M−1).

Step 3: Sodium azide (538.47 mg, 8.28 mmol) was added to a solution of Benzyl triethylammonium chloride (1.89 g, 8.28 mmol) in MeCN (12 mL) and the mixture was stirred at rt for 2 h. Resulting suspension was passed through a syringe with syringe filter into a suspension of 5-fluoro-1-((2R,4S)-4-hydroxy-5-methylenetetrahydrofuran-2-yl)pyrimidine-2,4(1H,3H)-dione (630 mg, 2.76 mmol) in THF (10 mL) at rt. To this mixture was added iodine (701.01 mg, 2.76 mmol) in THF (5 mL) and the mixture was stirred for another 2 h. The reaction progress was monitored by TLC and LCMS. After completion, the reaction mixture was concentrated under reduced pressure to afford crude compound. The crude residue was purified by combi-flash chromatography eluting with 4% MeOH in DCM to afford 1-((2R,4S,5S)-5-azido-4-hydroxy-5-(iodomethyl)tetrahydrofuran-2-yl)-5-fluoropyrimidine-2,4(1H,3H)-dione (600 mg, 55.04%) as white solid. (ES, m/z): 395.75 (M−H).

Step 4: To a stirred solution of 1-((2R,4S,5S)-5-azido-4-hydroxy-5-(iodomethyl) tetrahydrofuran-2-yl)-5-fluoropyrimidine-2,4(1H,3H)-dione (600 mg, 1.51 mmol), DMAP (18.45 mg, 0.15 mmol) and $Et_3N$ (0.420 mL, 3.0219 mmol) in THF (20 mL) was added benzoyl chloride (0.210 mL, 1.8131 mmol) drop wise at 0° C. After stirring the reaction mixture at rt for 2 h, the reaction progress was monitored by TLC. After completion the reaction mixture was concentrated under reduced pressure to afforded crude compound. The crude residue was purified by combi-flash chromatography eluted with 4% MeOH in DCM to afford (2S,3S,5R)-2-azido-5-(5-fluoro-2,4-dioxo-3,4-dihydropyrimidin-1(2H)-yl)-2-(iodomethyl)tetrahydrofuran-3-yl benzoate (360 mg, 47.61%) as white solid. (ES, m/z): 499.85 (M−H).

Step 5: A mixture of (2S,3S,5R)-2-azido-5-(5-fluoro-2,4-dioxo-3,4-dihydropyrimidin-1(2H)-yl)-2-(iodomethyl)tetrahydrofuran-3-yl benzoate (300 mg, 0.60 mmol) and silver benzoate (1.37 g, 5.99 mmol) in pyridine (3 mL) was heated at 100° C. for 16 h. The reaction progress was monitored by TLC and LCMS. After completion, the reaction mixture was concentrated under reduced pressure to afforded crude compound. The crude residue was purified by combi-flash chromatography eluted with 6% MeOH in DCM to afford (2R,3S,5R)-2-azido-2-((benzoyloxy) methyl)-5-(5-fluoro-2,4-dioxo-3,4-dihydropyrimidin-1(2H)-yl)tetrahydrofuran-3-yl benzoate (260 mg, 87.83%) as white solid. (ES, m/z): 493.95 (M−H).

Step 6: To a stirred solution of (2R,3S,5R)-2-azido-2-((benzoyloxy)methyl)-5-(5-fluoro-2,4-dioxo-3,4-dihydropyrimidin-1(2H)-yl)tetrahydrofuran-3-yl benzoate (0.02 g, 0.04 mmol) in MeCN (1.0 ml) were added $Et_3N$ (0.022 ml, 0.160 mmol), DMAP (0.009 g, 0.08 mmol) and TPSCl (0.024 g, 0.080 mmol) at to 0° C. and after stirring the reaction mixture at rt for 4 h, $NH_4OH$:1,4-Dioxane (0.01 ml) was added to it and stirred for 15 min at rt. The reaction progress was monitored by TLC. After completion, the reaction mixture was concentrated and dried under vacuum. The crude material was purified by Prpep-TLC elutting with 5% MeoH in DCM to afford (2R,3S,5R)-5-(4-amino-5-fluoro-2-oxopyrimidin-1(2H)-yl)-2-azido-2-((benzoyloxy) methyl)tetrahydrofuran-3-yl benzoate (0.018 g, 91.0%) as white solid. (ES, m/z): 494.8 (M+H$^+$).

Step 7: A solution of (2R,3S,5R)-5-(4-amino-5-fluoro-2-oxopyrimidin-1(2H)-yl)-2-azido-2-((benzoyloxy)methyl) tetrahydrofuran-3-yl benzoate, 7 (0.046 g; 0.093 mmol) in 7N Methanolic ammonia (2.0 ml) was stirred at rt for 16 h and then the reaction progress was monitored by TLC. After completion, the reaction mixture was concentrated and dried under vacuum. The crude product was purified by prep-HPLC with following conditions: Mobile Phase: A: 0.02%

NH₄OH in water; B: MeCN; Column: X SELECT (250 mm×20.0 mm), 5.0μ; Flow rate: 15 ml/min; Gradient program: Time/% B: 0/5,2/10,8/25 to afford 4-amino-1-((2R,4S,5R)-5-azido-4-hydroxy-5-(hydroxymethyl)tetrahydrofuran-2-yl)-5-fluoropyrimidin-2(1H)-one (8.5 mg, 32%) as white solid. (ES, m/z): (M+H⁺)=286.90; ¹H NMR (400 MHz, DMSO-d₆) δ 7.99 (d, J=7.2 Hz, 1H), 7.87-7.81 (m, 1H), 7.63-7.57 (m, 1H), 6.30-6.25 (m, 1H), 5.73 (d, J=5.6 Hz, 1H), 5.64 (t, J=5.7 Hz, 1H), 4.45-4.39 (m, 1H), 3.68-3.56 (m, 2H), 2.28-2.22 (m, 2H).

Example 38—Synthesis of Compound 66: 4-amino-5-fluoro-1-((2R,4S,5R)-4-hydroxy-5-(hydroxymethyl)-5-(trifluoromethyl)tetrahydrofuran-2-yl)pyrimidin-2(1H)-one

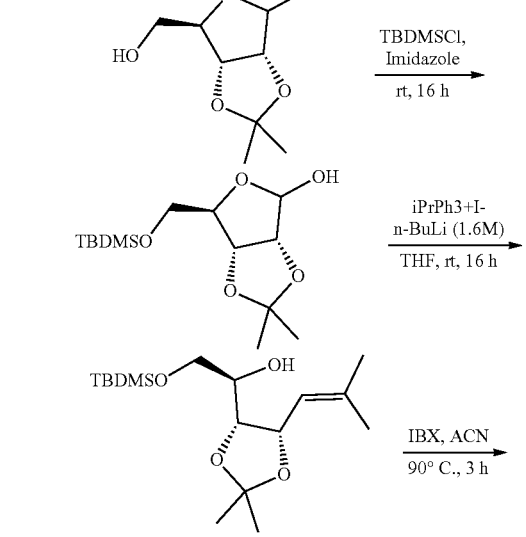

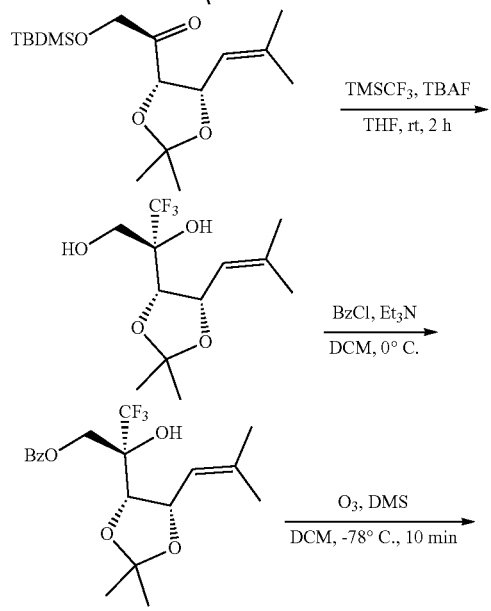

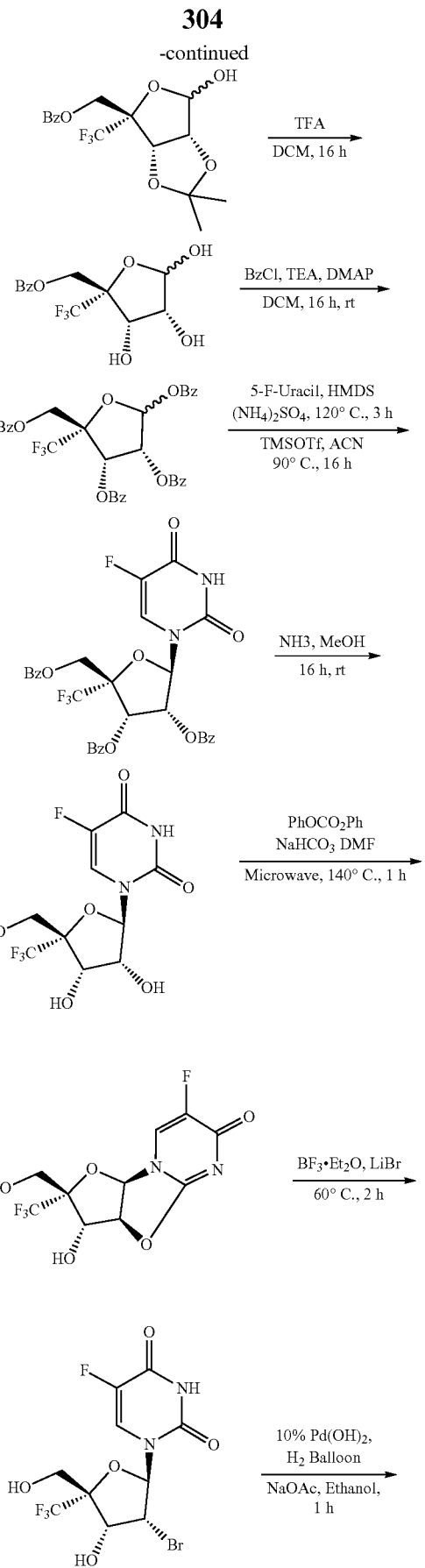

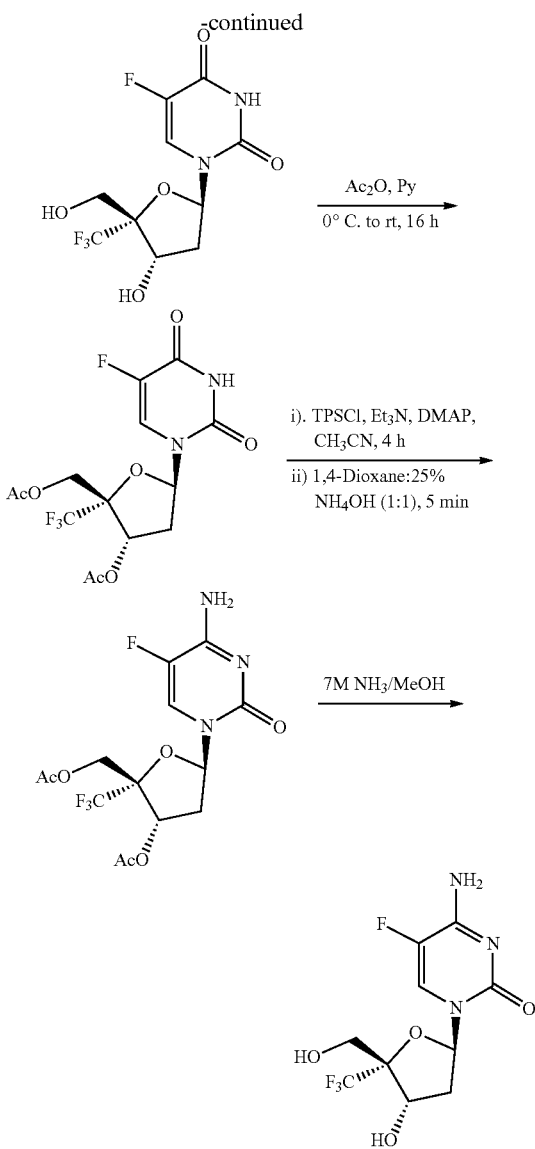

Step 1: To a stirred suspension of D-Ribose (50 g, 333.1 mmol) in acetone (500 mL) was added C. H₂SO₄ (1.8 mL, 33.31 mmol) and after stirring the reaction mixture at rt for 16 h, The reaction progress was monitored by TLC. After completion, solid NaHCO₃ was added to the reaction mixture and stirred for 1 h. The obtained solid was filtered through celite bed and filtrate was dried over Na₂SO₄ and concentrated under reduced pressure. The crude material was purified by column (60-120 Silica gel) chromatography eluting with 80% Ethyl acetate in Hexane to obtain (3aR, 6R,6aR)-6-(hydroxymethyl)-2,2-dimethyltetrahydrofuro[3, 4-d][1,3]dioxol-4-ol (52 g, 82.0%) as colourless oil.

Step 2: To a stirred solution of (3aR,6R,6aR)-6-(hydroxymethyl)-2,2-dimethyl-tetrahydrofuro[3,4-d][1,3]dioxol-4-ol (62 g, 325.9 mmol) in DCM (500 mL) was added Imidazole (33.2 g, 488.8 mmol) and cooled it to 0° C. and then a solution of TBDMSCl (49.1 g, 325.9 mmol) in DCM (100 mL) was added dropwise. After stirring the reaction mixture at rt for 16 h, the reaction progress was monitored by TLC. The reaction mixture was partitioned between DCM and aqueous sodium bicarbonate solution. Organic layer was separated, washed with brine, dried over Na₂SO₄ and concentrated under reduced pressure. The crude material was purified by Combiflash column chromatography eluting with 10-15% Ethyl acetate in Hexane to afford (3aR,6R,6aR)-6-(((tert-butyldimethylsilyl)oxy)methyl)-2,2-dimethyltetrahydrofuro[3,4-d][1,3]dioxol-4-ol (62 g, 62.4%) as colourless oil.

Step 3: To a stirred suspension of of Isopropyltriphenylphosphinium iodide (2.8 g, 6.570 mmol) in THF (15 mL) was added n-BuLi (1.6 M in n-Hexane) (4.1 mL, 6.57 mmol) dropwise at 0° C. and the reaction mixture was stirred at rt for 1 h. Then a solution of (3aR,6R,6aR)-6-(((tert-butyldimethylsilyl) oxy) methyl)-2,2-dimethyltetrahydrofuro[3,4-d] [1,3]dioxol-4-ol (1 g; 3.285 mmol) in THF (5 mL) was added dropwise at 0° C. into the above reaction mixture. After stirring the reaction mixture at rt for 16 h, the reaction progress was monitored by TLC. The reaction mixture was quenched with sat NaHCO₃ and resulted solid was filtered through celite bed. The filtrate was diluted with diethyl ether and washed with water and brine, dried over Na₂SO₄ and concentrated under vacuum. The crude material was purified by Combiflash column chromatography eluting with 10% Ethyl acetate in Hexane to afford desired product (0.46 g, 42.3%) as colourless oil and 0.25 g of (R)-2-((tert-butyldimethylsilyl)oxy)-1-((4R,5S)-2,2-dimethyl-5-(2-methylprop-1-en-1-yl)-1,3-dioxolan-4-yl)ethan-1-ol was recovered.

Step 4: To a stirred solution of (R)-2-((tert-butyldimethylsilyl) oxy)-1-((4R,5S)-2,2-dimethyl-5-(2-methylprop-1-en-1-yl)-1,3-dioxolan-4-yl) ethan-1-ol (12 g, 36.30 mmol) in MeCN (100 mL) was added IBX (15.2 g, 54.46 mmol) at rt and then the reaction mixture was refluxed for 3 h and the reaction progress was monitored by TLC. The reaction mixture was filtered through celite bed and the filtarate was concentrated under reduced pressure. The crude material was purified by Combiflash column chromatographuy eluting with 10% Ethyl acetate in Hexane to afford 2-((tert-butyldimethylsilyl)oxy)-1-((4S,5S)-2,2-dimethyl-5-(2-methylprop-1-en-1-yl)-1,3-dioxolan-4-yl)ethan-1-one (9 g, 75.4%) as colourless oil.

Step 5: To a stirred solution of 2-((tert-butyldimethylsilyl) oxy)-1-((4S,5S)-2,2-dimethyl-5-(2-methylprop-1-en-1-yl)-1,3-dioxolan-4-yl) ethan-1-one (6.3 g, 19.17 mmol) and TMSCF₃ (3.4 mL, 23.01 mmol) in THF (100 mL) was added TBAF (23 mL, 23.01 mmol) at 0° C. and after stirring the reaction mixture at 0° C. for 30 min and then at rt for 2 h, the reaction progress was monitored by TLC. After completion, the reaction mixture was concentrated and resulting residue was partitioned in DCM and aqueous sodium bicarbonate. Organic layer was separated, washed with brine, dried over Na₂SO₄ and concentrated under reduced pressure. The crude material was purified by Combiflash column chromatography eluting with 30-40% EA in Hexane to afford (R)-2-((4S,5S)-2,2-dimethyl-5-(2-methylprop-1-en-1-yl)-1,3-dioxolan-4-yl)-3,3,3-trifluoropropane-1,2-diol (4 g, 73.4%) as yellow oil.

Step 6: To a stirred solution of (R)-2-((4S,5S)-2,2-dimethyl-5-(2-methylprop-1-en-1-yl)-1,3-dioxolan-4-yl)-3,3,3-trifluoropropane-1,2-diol (0.18 g, 0.633 mmol) in DCM (10 mL) were added Et₃N (0.097 mL, 0.696 mmol), DMAP (10 mg) and Benzoyl Chloride (0.074 mL, 0.633 mmol) 0° C. and after stirring the reaction mixture at rt for 16 h, the reaction progress was monitored by TLC. The reaction mixture was partitioned between DCM and aqueous sodium bicarbonate. Organic layer was separated, washed with brine, dried over Na₂SO₄ and concentrated under reduced pressure. The crude material was purified Combiflash column chromatography eluting with 30-40% Ethyl acetate in Hexane to obtain (R)-2-((4S,5S)-2,2-dimethyl-5-(2-methylprop-1-en-1-yl)-1,3-dioxolan-4-yl)-3,3,3-trifluoro-2-hydroxypropyl benzoate (0.18 g, 73.2%) as yellow oil.

Step 7: A stirred solution of (R)-2-((4S,5S)-2,2-dimethyl-5-(2-methylprop-1-en-1-yl)-1,3-dioxolan-4-yl)-3,3,3-trifluoro-2-hydroxypropyl benzoate (4 g, 10.30 mmol) in DCM (200 mL) was cooled to −78° C. and $O_3$ gas) was bubbled into it until the mixture turned to blue colour. To the above reaction mixture oxygen was bubbled and ozonide was quenched with an excess of DMS (4.0 mL) and after stirring the reaction mixture at rt for 16 h, the reaction progress was monitored by TLC. After completion, the reaction mixture was concentrated and the crude material was purified by conbiflash column chromatography eluting with 30-40% Ethyl acetate in Hexane to afford ((3aS,4R,6aR)-6-hydroxy-2,2-dimethyl-4-(trifluoromethyl) tetrahydrofuro[3,4-d][1,3]dioxol-4-yl)methyl benzoate (3.6 g, 96.4%) as colourless liquid. (ES, m/z): 380.0 (M+18).

Step 8: ((3aS,4R,6aR)-6-hydroxy-2,2-dimethyl-4-(trifluoromethyl) tetrahydrofuro[3,4-d][1,3]dioxol-4-yl) methyl benzoate (3.6 g, 9.94 mmol) was dissolved in TFA (18 mL) & Water (2 mL) at 0° C. and after stirring the reaction mixture at rt for 16 h, the reaction progress was monitored by TLC. After completion, the reaction mixture was concentrated and resulting residue was co-distilled with toluene twice and used as such for the next step without purification (3.2 g, 99.9%). (ES, m/z): 320.7 (M−H).

Step 9: To a stirred solution of ((2R,3S,4R)-3,4,5-trihydroxy-2-(trifluoromethyl) tetrahydrofuran-2-yl)methyl benzoate (3.2 g, 9.93 mmol) in DCM (100 mL) were added $Et_3N$ (6.9 mL, 49.65 mmol), DMAP (6 g, 49.65 mmol) and Benzoyl Chloride (5.8 ml, 49.65 mmol) at 0° C. After stirring the reaction mixture at rt for 16 h, the reaction progress was monitored by TLC. After completion, the reaction mixture was portioned between DCM and aqueous sodium bicarbonate. Organic layer was separated, washed with brine, dried over $Na_2SO_4$ and concentered under vacuum to afford crude material. The crude product was purified by Combiflash column chromatography eluting with 30-40% ethyl acetate in Hexane to obtain the desired product (4 g, 66.4%). (ES, m/z): 652 (M+18).

Step 10: A suspension of 5-fluoroUracil (1.3 g, 10.40 mmol) and ammonium sulfate (60 mg) in HMDS (17.5 mL, 84.15 mmol) was heated at 120° C. for 2 h, when the reaction mixture becomes clear solution, it was concentrated and the residue was dissolved in MeCN (40 ml) and the resulting solution was added to a solution of (3R,4S,5R)-5-((benzoyloxy)methyl)-5-(trifluoromethyl) tetrahydrofuran-2,3,4-triyl tribenzoate, 10 (3.0 g; 4.728 mmol) in MeCN (10 mL) at rt. TMSOTf (6.1 mL, 33.09 mmol) was added to the above reaction mixture at rt and after heating the reaction mixture at 90° C. for 16 h, the reaction progress was monitored by TLC. After completion, the reaction mixture was quenched with sat. $NaHCO_3$ and the resulting mixture was extracted with EtOAc (3×15 mL). Combined organics were washed once with cold water, dried over $Na_2SO_4$ and concentrated under reduced pressure to afford crude material which was purified by Combiflash column chromatography eluting with 30% ethyl acetate in n-Hexane to afford ((2R,3S,4R,5R)-2-((benzoyloxy)methyl)-5-(5-fluoro-2,4-dioxo-3,4-dihydropyrimidin-1(2H)-yl)-2-(trifluoromethyl)tetrahydrofuran-3,4-diyl dibenzoate (1.4 g, 46.0%) as white solid and 1 g of (3R,4S,5R)-5-((benzoyloxy)methyl)-5-(trifluoromethyl) tetrahydrofuran-2,3,4-triyl tribenzoate was recovered. (ES, m/z): 642.7 (M+H⁺).

Step 11: A solution of (2R,3S,4R,5R)-2-((benzoyloxy) methyl)-5-(5-fluoro-2,4-dioxo-3,4-dihydropyrimidin-1 (2H)-yl)-2-(trifluoromethyl) tetrahydrofuran-3,4-diyl dibenzoate (1.4 g, 2.18 mmol) in 7N Methanolic ammonia (20 mL) was stirred at rt for 16 h and the reaction progress was monitored by TLC. The reaction mixture was concentrated and dried under vacuum. The crude material was purified by Combiflash column chromatography eluting with 8% MeOH in DCM to obtain 1-((2R,3R,4S,5R)-3,4-dihydroxy-5-(hydroxymethyl)-5-(trifluoromethyl)tetrahydrofuran-2-yl)-5-fluoropyrimidine-2,4(1H,3H)-dione (0.6 g, 83.4%) as colourless sticky solid. (ES, m/z): M+1=330.8.

Step 12: To a stirred solution of 1-((2R,3R,4S,5R)-3,4-dihydroxy-5-(hydroxymethyl)-5-(trifluoromethyl) tetrahydrofuran-2-yl)-5-fluoropyrimidine-2,4(1H,3H)-dione (0.3 g, 0.91 mmol) in DMF (2.0 mL) were added Diphenyl Carbonate (0.2 g, 0.99 mmol) and $NaHCO_3$(0.019 g, 0.227 mmol) at rt. The reaction mixture was stirred for 1 h at 140° C. in MW and the reaction progress was monitored by TLC. After completion, the reaction mixture was concentrated and dried under vacuum to afford desired product (0.45 g) as white solid. The crude material was used as such for the next step. (ES, m/z): M+1=312.8.

Step 13: To a stirred solution of (2R,3S,3aS,9aR)-7-fluoro-3-hydroxy-2-(hydroxymethyl)-2-(trifluoromethyl)-2,3,3a,9a-tetrahydro-6H-furo[2',3':4,5]oxazolo[3,2-a]pyrimidin-6-one (0.35 g, 1.12 mmol) in 1,4-Dioxane (20 mL) were added LiBr (0.12 g, 1.46 mmol) and $BF_3·Et_2O$ (0.15 ml, 1.233 mmol) at rt and After stirring the reaction mixture at 60° C. for 16 h, the reaction progress was monitored by TLC. The reaction mixture was concentrated to afford crude material which was purified by Combiflash column chromatography eluting with 8% MeOH in DCM to obtain 1-((2R,3R,4R,5R)-3-bromo-4-hydroxy-5-(hydroxymethyl)-5-(trifluoromethyl)tetrahydrofuran-2-yl)-5-fluoropyrimidine-2,4(1H,3H)-dione (0.35 g, 79.4%) as white solid. (ES, m/z): M+1=394.7.

Step 14: A stirred solution of 1-((2R,3R,4R,5R)-3-bromo-4-hydroxy-5-(hydroxymethyl)-5-(trifluoromethyl) tetrahydrofuran-2-yl)-5-fluoropyrimidine-2,4(1H,3H)-dione (0.18 g; 0.458 mmol) in Ethanol (10.0 mL) was degassed with Argon for 5 mins and Pd (OH)$_2$ (0.04 g) followed by NaOAc (0.056 g; 0.687 mmol) was added into it. After stirring the reaction mixture under $H_2$ gas atmosphere at rt for 2 h, the reaction progress was monitored by TLC. After completion, the reaction mass was filtered through celite bed, and the filtrate was concentrated under reduced pressure to get crude product. The crude material was purified Combiflash column chromatography eluting with 8% MeOH in DCM to obtain 5-fluoro-1-((2R,4S,5R)-4-hydroxy-5-(hydroxymethyl)-5-(trifluoromethyl)tetrahydrofuran-2-yl)pyrimidine-2,4(1H,3H)-dione (0.12 g, 83.4%) as colorless sticky material. (ES, m/z): M+1=314.7.

Step 15: To a stirred solution of 5-fluoro-1-((2R,4S,5R)-4-hydroxy-5-(hydroxymethyl)-5-(trifluoromethyl) tetrahydrofuran-2-yl) pyrimidine-2,4(1H,3H)-dione (0.12 g, 0.382 mmol) in pyridine (5.0 mL) was added acetic anhydride (0.1 mL, 1.146 mmol) at rt. After stirring the reaction mixture at rt for 16 h, the reaction progress was monitored by TLC. After completion, the reaction mixture was concentrated under reduced pressure and resulting residue was partioned between EtOAc and aqueous sodium bicarbonate. Organic layer was separated, washed with brine, dried over $Na_2SO_4$ and concentrated under reduced pressure to afford crude compound which was purified by Combiflash column chromatography eluting with 20% Ethyl acetate in Hexane to obtain of ((2R,3S,5R)-3-acetoxy-5-(5-fluoro-2,4-dioxo-3,4- dihydro-pyrimidin-1(2H)-yl)-2-(trifluoromethyl)tetrahydrofuran-2-yl)methyl acetate (0.12 g, 78.8%) as white solid. (ES, m/z): M+1=398.8.

Step 16: To a stirred solution of ((2R,3S,5R)-3-acetoxy-5-(5-fluoro-2,4-dioxo-3,4-dihydropyrimidin-1(2H)-yl)-2-(trifluoromethyl)tetrahydrofuran-2-yl)methyl acetate (0.035 g, 0.087 mmol) in MeCN (1.0 mL) were added Et$_3$N (0.048 mL, 0.348 mmol), DMAP (0.021 g, 0.174 mmol) and TPSCl (0.053 g, 0.175 mmol) at 0° C. and the reaction mixture was stirred at rt for 4 h. Then NH$_4$OH:1,4-Dioxane (0.2 ml) was added to RM and stirred for 15 min at rt. The reaction progress was monitored by TLC. After completion, the reaction mixture was concentrated and dried under vacuum. The crude material was purified by Prep-TLC was eluting with 100% EtOAc to afford ((2R,3S,5R)-3-acetoxy-5-(4-amino-5-fluoro-2-oxopyrimidin-1(2H)-yl)-2-(trifluoromethyl)tetrahydrofuran-2-yl)methyl acetate (0.025 g; 72.3%) as yellow solid. (ES, m/z): M+1=397.45.

Step 17: A solution of ((2R,3S,5R)-3-acetoxy-5-(4-amino-5-fluoro-2-oxopyrimidin-1(2H)-yl)-2-(trifluoromethyl) tetrahydrofuran-2-yl) methyl acetate (0.125 g, 0.314 mmol) in 7N Methanolic ammonia (2.0 mL) was stirred at rt for 16 h and the reaction progress was monitored by TLC and LCMS. After completion, the reaction mixture was concentrated and dried under vacuum. The crude compound was purified by prep-HPLC with following conditions: Mobile Phase: A=0.02% NH$_4$OH IN WATER; B=MeCN; Column: X SELECT (250 mm×20.0 mm), 5.0p; Flow rate: 18 ml/min; Gradient program: Time/% B: 0/5,2/10,8/30 to afford 4-amino-5-fluoro-1-((2R,4S,5R)-4-hydroxy-5-(hydroxymethyl)-5-(trifluoromethyl)tetrahydrofuran-2-yl)pyrimidin-2(1H)-one (20 mg, 20%) as white solid. (ES, m/z): M+1=313.95; $^1$H NMR (400 MHz, DMSO-d$_6$) δ 7.97 (d, J=7.0 Hz, 1H), 7.90-7.82 (m, 1H), 7.65-7.58 (m, 1H), 6.35-6.29 (m, 1H), 5.80-5.73 (m, 1H), 5.65-5.57 (m, 1H), 4.73-4.66 (m, 1H), 3.76-3.64 (m, 2H), 2.39-2.18 (m, 2H).

Example 39—Synthesis of Compound 7: 1-((2R,4S,5R)-5-(chloromethyl)-4-fluoro-5-(hydroxymethyl)tetrahydrofuran-2-yl)-5-methylpyrimidine-2,4(1H,3H)-dione

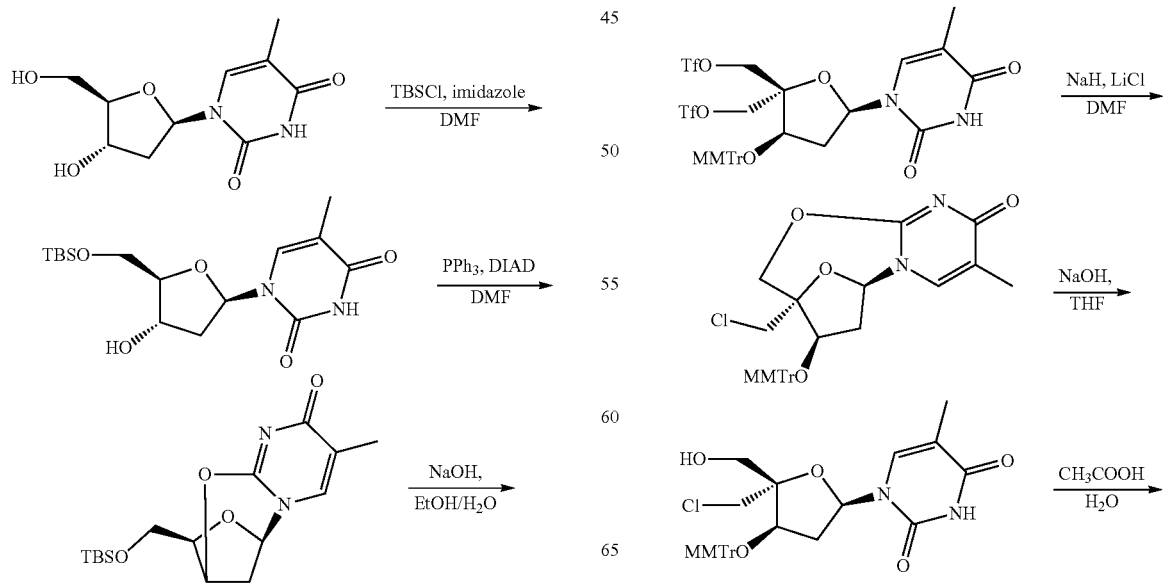

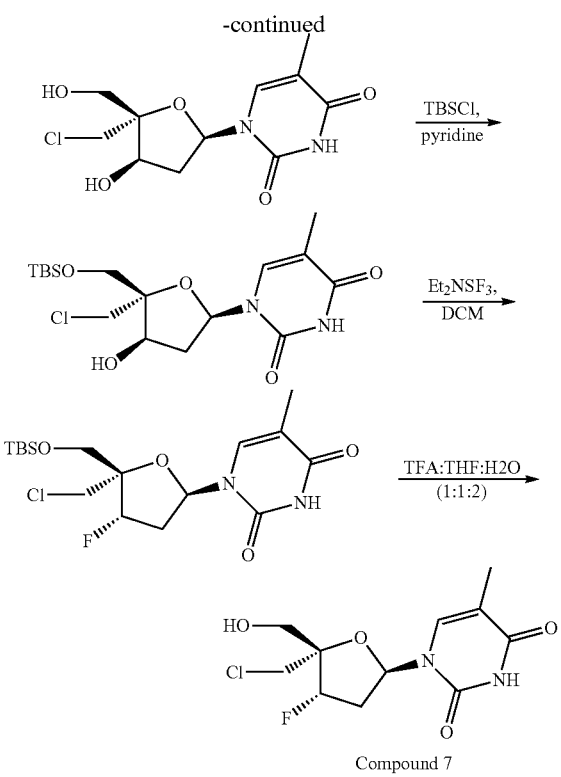

Compound 7

Step 1: To a solution of thymidine (14.2 g, 58.6 mmol) in DMF (150 mL) was added imidazole (11.9 g, 175.8 mmol) under nitrogen atmosphere. Then was added tert-butyldimethylsilyl chloride (9.7 g, 64.4 mmol) at 0° C. After stirring for 2 h at room temperature under nitrogen atmosphere. Desired product could be detected by LCMS. The resulting mixture was extracted with ethyl acetate (3×100 mL). The combined organic layers were washed with saturated salt solution (3×100 mL), dried over anhydrous sodium sulfate. After filtration, the filtrate was concentrated under reduced pressure. The residue was purified by silica gel column chromatography, eluted with dichloromethane/methanol (20/1) to afford 1-[(2R,4S,5R)-5-1{[(tert-butyldimethylsilyl) oxy] methyl}-4-hydroxyoxolan-2-yl]-5-methyl-3H-pyrimidine-2,4-dione (15.5 g, 43.4 mmol, 74.17%) as a light yellow oil. LC-MS (ES, m/z): 357 [M+H]+.

Step 2: To a solution of 1-[(2R,4S,5R)-5-{[(tert-butyldimethylsilyl) oxy] methyl}-4-hydroxyoxolan-2-yl]-5-methyl-3H-pyrimidine-2,4-dione (15.5 g, 43.4 mmol) in N,N-Dimethylformamide (200 mL) was added PPh₃ (34.2 g, 130.4 mmol) under nitrogen atmosphere. Then was added diisopropyl azodicarboxylate (26.3 g, 130.4 mmol) under water ice. After stirring for 1.5 h at room temperature under nitrogen atmosphere. Desired product could be detected by LCMS. The resulting mixture was extracted with ethyl acetate (3×100 mL). The combined organic layers were washed with saturated salt solution (3×100 mL), dried over anhydrous sodium sulfate. After filtration, the filtrate was concentrated under reduced pressure. The residue was purified by silica gel column chromatography, eluted with dichloromethane/methanol (20/1) to afford (1R,10R)-10-{[(tert-butyldimethylsilyl) oxy] methyl}-4-methyl-8,11-dioxa-2,6-diazatricyclo [7.2.1.0^{2,7}] dodeca-3,6-dien-5-one (14.5 g, 42.8 mmol, 98.53%) as a light yellow oil. LC-MS (ES, m/z): 339 [M+H]+.

Step 3: To a solution of (1R,10R)-10-{[(tert-butyldimethylsilyl) oxy] methyl}-4-methyl-8,11-dioxa-2,6-diazatricyclo [7.2.1.0{2,71}] dodeca-3,6-dien-5-one (14.5 g, 42.8 mmol) in ethanol (140 mL) and water (14 mL) was added sodium hydroxide (3.4 g, 85.6 mmol) under nitrogen atmosphere. After stirring for 2 h at 45° C. under a nitrogen atmosphere desired product could be detected by LCMS. The resulting mixture was concentrated under reduced pressure. The residue was purified by reverse flash chromatography with the following conditions: (column, silica gel; mobile phase, MeCN in water, 10% to 20% gradient in 15 min; detector, UV 254 nm) to afford 1-[(2R,4R,5R)-4-hydroxy-5-(hydroxymethyl) oxolan-2-yl]-5-methyl-3H-pyrimidine-2,4-dione (7.6 g, 31.3 mmol, 73.24%) as a white solid. LC-MS (ES, m/z): 243 [M+H]+.

Step 4: To a solution of 1-[(2R,4R,5R)-4-hydroxy-5-(hydroxymethyl) oxolan-2-yl]-5-methyl-3H-pyrimidine-2,4-dione (6.5 g, 26.8 mmol) in dimethylformamide (40 mL) was added imidazole (5.48 g, 80.5 mmol) and tert-butyldimethylsilyl chloride (4.4 g, 29.5 mmol) under nitrogen atmosphere at water ice. After stirring overnight at room temperature under nitrogen atmosphere desired product could be detected by LCMS. The resulting mixture was purified by reverse flash chromatography with the following conditions: (column, silica gel; mobile phase, MeCN in water, 10% to 80% gradient in 15 min; detector, UV 254 nm) to afford 1-[(2R,4R,5R)-5-{[(tert-butyldimethylsilyl) oxy] methyl}-4-hydroxyoxolan-2-yl]-5-methyl-3H-pyrimidine-2,4-dione (8.5 g, 23.8 mmol, 88.86%) as a white solid. LC-MS (ES, m/z): 357 [M+H]+.

Step 5: To a solution of 1-[(2R,4R,5R)-5-{[(tert-butyldimethylsilyl) oxy] methyl}-4-hydroxyoxolan-2-yl]-5-methyl-3H-pyrimidine-2,4-dione (8.5 g, 23.8 mmol) in dichloromethane (80 mL) was added 2,4,6-trimethylpyridine (11.5 g, 95.3 mmol) and silver nitrate (16.2 g, 95.3 mmol) under nitrogen atmosphere. Then was added 1-(chlorodiphenylmethyl)-4-methoxybenzene (36.8 g, 119.2 mmol) under water ice. After stirring overnight at room temperature under a nitrogen atmosphere. Desired product could be detected by LCMS. The resulting mixture was extracted with dichloromethane (3×100 mL). The combined organic layers were washed with saturated salt solution (3×100 mL), dried over anhydrous sodium sulfate. After filtration, the filtrate was concentrated under reduced pressure to afford 1-[(2R,4R,5R)-5-{[(tert-butyldimethylsilyl) oxy] methyl}-4-[(4-methoxyphenyl) diphenylmethoxy] oxolan-2-yl]-5-methyl-3H-pyrimidine-2,4-dione (14 g, 22.2 mmol, 93.37%) as a light yellow oil. LC-MS (ES, m/z): 629 [M+H]+.

Step 6: To a solution of 1-[(2R,4R,5R)-5-{[(tert-butyldimethylsilyl) oxy] methyl}-4-[(4-methoxyphenyl) diphenylmethoxy] oxolan-2-yl]-5-methyl-3H-pyrimidine-2,4-dione (14 g, 22.2 mmol) in tetrahydrofuran (140 mL) was added tetrabutylammonium fluoride (44.5 mL, 44.526 mmol, 1 M in THF) under nitrogen atmosphere. After stirring overnight at room temperature under a nitrogen atmosphere desired product could be detected by LCMS. The resulting mixture was concentrated and purified by silica gel column chromatography, eluted with dichloromethane/methanol (20/1) to afford 1-[(2R,4R,5R)-5-(hydroxymethyl)-4-[(4-methoxyphenyl) diphenylmethoxy] oxolan-2-yl]-5-methyl-3H-pyrimidine-2,4-dione (11 g, 21.3 mmol, 96.02%) as a light yellow solid. LC-MS (ES, m/z): 515 [M+H]+.

Step 7: A mixture of 1-[(2R,4R,5R)-5-(hydroxymethyl)-4-[(4-methoxyphenyl) diphenylmethoxy]oxolan-2-yl]-5-methyl-3H-pyrimidine-2,4-dione (11 g, 21.3 mmol) and IBX (23.9 g, 85.5 mmol) in acetotronile (20 mL) was stirred for 0.5 h at 60° C. The resulting mixture was filtered; the filter cake was washed with acetonitrile (3×100 mL). The filtrate was concentrated under reduced pressure. The residue was purified by silica gel column chromatography, eluted with PE/EA (1/1) to afford (2S,3R,5R)-3-[(4-methoxyphenyl) diphenylmethoxy]-5-(5-methyl-2,4-dioxo-3H-pyrimidin-1-yl) oxolane-2-carbaldehyde (10 g, 19.5 mmol, 91.27%) as a white solid. LC-MS (ES, m/z): 513 [M+H]$^+$.

Step 8: A mixture of (2S,3R,5R)-3-[(4-methoxyphenyl) diphenylmethoxy]-5-(5-methyl-2,4-dioxo-3H-pyrimidin-1-yl)oxolane-2-carbaldehyde (10 g, 19.5 mmol) and HCHO (4.8 g, 126.9 mmoL) in dioxane (100 mL) was added NaOH 1.5 g, 39.1 mmol) in H$_2$O (20 mL), the mixture was stirred for 15 hours at room temperature and then NaBH$_4$ (3.3 g, 87.7 mmol) was added and stirred for 20 mins at 0° C. The resulting mixture was concentrated under vacuum. The resulting mixture was extracted with ethyl acetate (3×100 mL). The combined organic layers were washed with saturated salt solution (3×100 mL), dried over anhydrous sodium sulfate. After filtration, the filtrate was concentrated under reduced pressure. The residue was purified by silica gel column chromatography, eluted with dichloromethane/methanol (10/) to afford 1-[(2R,4R)-5,5-bis(hydroxymethyl)-4-[(4-methoxyphenyl) diphenylmethoxy] oxolan-2-yl]-5-methyl-3H-pyrimidine-2,4-dione (5.6 g, 9.5 mmol, 52.71%) as a white solid. LC-MS (ES, m/z): 545 [M+H]$^+$.

Step 9: A mixture of 1-[(2R,4R)-5,5-bis(hydroxymethyl)-4-[(4-methoxyphenyl) diphenylmethoxy] oxolan-2-yl]-5-methyl-3H-pyrimidine-2,4-dione (5.2 g, 9.5 mmol) and pyridine (3.7 g, 47.9 mmo) in DCM (50 mL) was added Tf$_2$O (5.41 g, 19.1 mmol) at −30° C. and stirred for 1.5 h at room temperature. The mixture was quenched with water (10 mL) and washed with saturated NaHCO$_3$ solution. The residue was purified by silica gel column chromatography, eluted with PE/EA (1/1) to afford [(3R,5R)-3-[(4-methoxyphenyl) diphenylmethoxy]-5-(5-methyl-2,4-dioxo-3H-pyrimidin-1-yl)-2-[(trifluoromethanesulfonyloxy) methyl] oxolan-2-yl] methyl trifluoromethane-sulfonate (4 g, 4.9 mmol, 51.60%) as an off-white solid. LC-MS (ES, m/z): 809 [M+H]$^+$.

Step 10: A solution of [(3R,5R)-3-[(4-methoxyphenyl) diphenylmethoxy]-5-(5-methyl-2,4-dioxo-3H-pyrimidin-1-yl)-2-[(trifluoromethanesulfonyloxy)methyl] oxolan-2-yl] methyl trifluoromethanesulfonate (3.5 g, 4.3 mmol) and NaH (0.10 g, 4.3 mmol) in DMF (20 mL) was added LiCl (1.1 g, 25.9 mmoL) stirred for 2 h at room temperature. The resulting mixture was extracted with ethyl acetate (3×100 mL). The combined organic layers were washed with saturated salt solution (3×100 mL), dried over anhydrous sodium sulfate. After filtration, the filtrate was concentrated under reduced pressure. The residue was purified by silica gel column chromatography, eluted with PE/EA (1/1) to afford (1R,10R,11R)-10-(chloromethyl)-11-[(4-methoxyphenyl) diphenylmethoxy]-4-methyl-8,13-dioxa-2,6-diazatricyclo [8.2.1.0{2,7}] trideca-3,6-dien-5-one (1.2 g, 2.2 mmol, 50.87%) as a white solid. LC-MS (ES, m/z): 545/547 [M+H]$^+$.

Step 11: A mixture of (1R,10R,11R)-10-(chloromethyl)-11-[(4-methoxyphenyl) diphenylmethoxy]-4-methyl-8,13-dioxa-2,6-diazatricyclo [8.2.1.0{2,7}] trideca-3,6-dien-5-one (1.2 g, 2.2 mmol) in THF was added NaOH (0.18 g, 4.4 mmol) in water (2 mL), the mixture was stirred overnight at room temperature. The resulting mixture was concentrated under vacuum. The residue was purified by silica gel column chromatography, eluted with DCM/MeOH (10/1) to afford 1-[(2R,4R,5R)-5-(chloromethyl)-5-(hydroxymethyl)-4-[(4-methoxyphenyl) diphenylmethoxy] oxolan-2-yl]-5-methyl-3H-pyrimidine-2,4-dione (750 mg, 1.3 mmol, 60.50%) as a white solid. LC-MS (ES, m/z): 563/565 [M+H]$^+$.

Step 12: A mixture of 1-[(2R,4R,5R)-5-(chloromethyl)-5-(hydroxymethyl)-4-[(4-methoxyphenyl) diphenylmethoxy] oxolan-2-yl]-5-methyl-3H-pyrimidine-2,4-dione (750 mg, 1.3 mmol) and CH$_3$COOH (8 mL) in H$_2$O (2 mL) was stirred for 2 h at room temperature. The resulting mixture was concentrated under vacuum. The residue was purified by silica gel column chromatography, eluted with CH$_2$Cl$_2$/MeOH (10/1) to afford 1-[(2R,4R,5R)-5-(chloromethyl)-4-hydroxy-5-(hydroxymethyl) oxolan-2-yl]-5-methyl-3H-pyrimidine-2,4-dione (350 mg, 1.2 mmol, 90.39%) as a white solid. LC-MS (ES, m/z): 291/293 [M+H]$^+$.

Step 13: A mixture of 1-[(2R,4R,5R)-5-(chloromethyl)-4-hydroxy-5-(hydroxymethyl) oxolan-2-yl]-5-methyl-3H-pyrimidine-2,4-dione (280 mg, 0.9 mmol) and TBSCl (159.6 mg, 1.1 mmol, 1.1) in pyridine (5 mL) was stirred for 1 h at room temperature. The resulting mixture was concentrated under vacuum. The residue was purified by silica gel column chromatography, eluted with CH$_2$Cl$_2$/MeOH (10/1) to afford 1-[(2R,4R,5R)-5-{[(tert-butyldimethylsilyl) oxy]methyl}-5-(chloromethyl)-4-hydroxyoxolan-2-yl]-5-methyl-3H-pyrimidine-2,4-dione (310 mg, 0.7 mmol, 79.48%) as a white solid. LC-MS (ES, m/z): 405/407 [M+H]$^+$.

Step 14: A solution of 1-[(2R,4R,5R)-5-{[(tert-butyldimethylsilyl) oxy] methyl}-5-(chloromethyl)-4-hydroxyoxolan-2-yl]-5-methyl-3H-pyrimidine-2,4-dione (310 mg, 0.7 mmol) in DCM (5 mL) was added DAST (3.1 mL, 3.1 mmol, 1 M in DCM) dropwise at 0° C. stirred for 10 min at room temperature. The residue was purified by Prep-TLC with CHCl$_2$/MeOH (10/1) to afford 1-[(2R,4S,5R)-5-1{[(tert-butyldimethylsilyl) oxy] methyl}-5-(chloromethyl)-4-fluorooxolan-2-yl]-5-methyl-3H-pyrimidine-2,4-dione (35 mg, 0.075, 11.24%) as a white solid. LC-MS (ES, m/z): 407/409 [M+H]$^+$.

Step 15: A mixture of 1-[(2R,4S,5R)-5-{[(tert-butyldimethylsilyl) oxy] methyl}-5-(chloromethyl)-4-fluorooxolan-2-yl]-5-methyl-3H-pyrimidine-2,4-dione (30 mg, 0.07 mmol) and TFA (0.7 mL) in THF (2.1 mL) and H$_2$O (0.7 mL) was stirred for overnight at room temperature under nitrogen atmosphere. The residue was purified by Prep-TLC with CH$_2$Cl$_2$/MeOH (10/1) to afford 1-((2R,4S,5R)-5-(chloromethyl)-4-fluoro-5-(hydroxymethyl) tetrahydrofuran-2-yl)-5-methylpyrimidine-2,4(1H,3H)-dione (10.9 mg, 0.035 mmol, 50.32%) as a white solid. LC-MS (ES, m/z): 293/295 [M+H]$^+$. 99.6% purity. Conditions for the LCMS: (Column: Luna Omega, 50*3 mm, 3 μm; Mobile Phase A: Water/0.09% FA, Mobile Phase B: Acetonitrile/0.1% FA; Flow rate: 1.5000 mL/min; Gradient: 20% B to 50% B in 1.89 min, 50% B to 100% B in 0.10 min, 100% B to 100% B in 0.70 min, 100% B to 5% B in 0.05 min; Wavelength: 254 nm; RT1(min): 0.842). $^1$H NMR (300 MHz, DMSO-d$_6$) δ 7.66 (d, J=1.6 Hz, 1H), 6.31 (dd, J=8.4, 6.5 Hz, 1H), 5.43-5.25 (m, 1H), 3.82-3.63 (m, 4H), 2.56-2.55 (m, 1H), 2.49 (d, J=6.3 Hz, 1H), 1.81 (d, J=1.3 Hz, 3H).

Example 40—Synthesis of Compound 3: 1-((2R,3S,4R)-3-fluoro-4-hydroxy-5,5-bis(hydroxymethyl)tetrahydrofuran-2-yl)pyrimidine-2,4(1H,3H)-dione

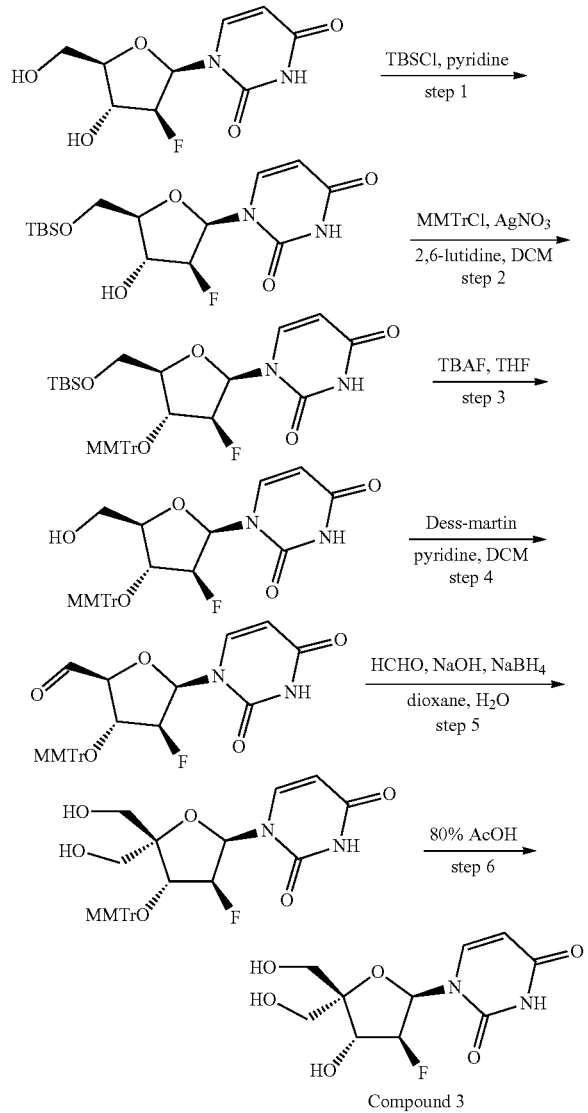

Step 1: To a stirred mixture of 1-[(2R,3S,4R,5R)-3-fluoro-4-hydroxy-5-(hydroxymethyl) oxolan-2-yl]-3H-pyrimidine-2,4-dione (4 g, 16.3 mmol) in pyridine (25 mL) was added t-butyldimethylchlorosilane (2.7 g, 17.9 mmol) in portions at room temperature under nitrogen atmosphere. The mixture was stirred for 3 hours at room temperature. The resulting mixture was diluted with water and extracted with ethyl acetate. The combined organic layers were washed with brine, dried over anhydrous sodium sulfate. After filtration, the filtrate was concentrated under reduced pressure to afford 1-[(2R,3S,4R,5R)-5-{[(tert-butyldimethyl-silyl)oxy] methyl}-3-fluoro-4-hydroxyoxolan-2-yl]-3H-pyrimidine-2,4-dione (5.34 g, 14.8 mmol, 91.18%) as an off-white solid. LC-MS: (ES, m/z): 361 (M+H$^+$).

Step 2: To a stirred mixture of 1-[(2R,3S,4R,5R)-5-{[(tert-butyldimethylsilyl) oxy]methyl}-3-fluoro-4-hydroxyoxolan-2-yl]-3H-pyrimidine-2,4-dione (5.3 g, 14.8 mmol), silver nitrate (5.1 g, 29.6 mmol) and 2,6-lutidine (4.8 g, 44.4 mmol) in dichloromethane (20 mL) was added 1-(chlorodiphenylmethyl)-4-methoxybenzene (5 g, 16.3 mmol) in portions at 0° C. under nitrogen atmosphere. The mixture was stirred for 15 hours at room temperature. The resulting mixture was filtered; the filter cake was washed with dichloromethane. The filtrate was diluted with aqueous hydrochloric acid (1 M) and brine. The resulting mixture was filtered; the filter cake was washed with dichloromethane. The combined organic layers were washed with brine, dried over anhydrous sodium sulfate. After filtration, the filtrate was concentrated under reduced pressure to afford 1-[(2R,3S,4R,5R)-5-{[(tert-butyl-dimethylsilyl)oxy]methyl}-3-fluoro-4-[(4-methoxyphenyl) diphenylmethoxy] oxolan-2-yl]-3H-pyrimidine-2,4-dione (8.84 g, 13.9 mmol, 94.30%) as a yellow solid. LC-MS: (ES, m/z): 633 (M+H$^+$).

Step 3: To a stirred mixture of 1-[(2R,3S,4R,5R)-5-{[(tert-butyldimethylsilyl) oxy]methyl}-3-fluoro-4-[(4-methoxyphenyl) diphenylmethoxy] oxolan-2-yl]-3H-pyrimidine-2,4-dione (8.84 g, 14.0 mmol) in tetrahydrofuran (60 mL) was added a solution of tetrabutylammonium fluoride in tetrahydrofuran (16.8 mL, 1.0 M) dropwise at room temperature under nitrogen atmosphere. The mixture was stirred for 15 hours at room temperature. The resulting mixture was concentrated under reduced pressure. The residue was purified by silica gel column chromatography, eluted with dichloromethane/methanol (20/1) to afford 1-[(2R,3S,4R,5R)-3-fluoro-5-(hydroxymethyl)-4-[(4-methoxyphenyl)diphenylmethoxy]oxolan-2-yl]-3H-pyrimidine-2,4-dione (6.3 g, 12.2 mmol, 86.94%) as a yellow solid. LC-MS: (ES, m/z): 519 (M+H$^+$).

Step 4: To a stirred mixture of 1-[(2R,3S,4R,5R)-3-fluoro-5-(hydroxymethyl)-4-[(4-methoxyphenyl) diphenylmethoxy] oxolan-2-yl]-3H-pyrimidine-2,4-dione (6.3 g, 12.2 mmol) in dichloromethane (100 mL) was added pyridine (3.4 g, 43.0 mmol) and Dess-martin (6.7 g, 15.8 mmol) at 0° C. under nitrogen atmosphere. The mixture was stirred for 15 hours at room temperature. The reaction was quenched by the addition of 4% aqueous sodium thiosulfate and 4% aqueous sodium carbonate at room temperature. The resulting mixture was filtered; the filter cake was washed with dichloromethane. The resulting mixture was diluted with water and extracted with dichloromethane. The combined organic layers were washed with brine, dried over anhydrous sodium sulfate. After filtration, the filtrate was concentrated under reduced pressure. The residue was purified by silica gel column chromatography, eluted with dichloromethane/methanol (20/1) to afford (2S,3R,4S,5R)-5-(2,4-dioxo-3H-pyrimidin-1-yl)-4-fluoro-3-[(4-methoxyphenyl) diphenylmethoxy] oxolane-2-carbaldehyde (5.72 g, 11.1 mmol, 91.20%) as a yellow solid. LC-MS: (ES, m/z): 517 (M+H$^+$).

Step 5: To a stirred mixture of (2S,3R,4S,5R)-5-(2,4-dioxo-3H-pyrimidin-1-yl)-4-fluoro-3-[(4-methoxyphenyl) diphenylmethoxy] oxolane-2-carbaldehyde (5.7 g, 11.1 mmol) in dioxane (50 mL) and water (5 mL) was added formaldehyde (998 mg, 33.3 mmol) and sodium hydroxide (1.3 g, 33.3 mmol) at room temperature under nitrogen atmosphere. The mixture was stirred for 15 hours at room temperature. The mixture was allowed to cool down to 0° C. and sodium borohydride (1.7 g, 44.4 mmol) was added. The mixture was stirred for 30 minutes at room temperature. The reaction was quenched with saturated ammonium chloride solution at room temperature. The resulting mixture was diluted with water and extracted with ethyl acetate. The combined organic layers were washed with brine, dried over anhydrous sodium sulfate. After filtration, the filtrate was concentrated under reduced pressure. The residue was purified by silica gel column chromatography, eluted with dichloromethane/methanol (20/1) to afford 1-[(2R,3S,4R)-3-fluoro-5,5-bis(hydroxymethyl)-4-[(4-methoxyphenyl)diphenylmethoxy]oxolan-2-yl]-3H-pyrimidine-2,4-dione (2.35 g, 4.3 mmol, 38.78%) as an off-white solid. LC-MS: (ES, m/z): 549 (M+H$^+$).

Step 6: A solution of 1-[(2R,3S,4R)-3-fluoro-5,5-bis(hydroxymethyl)-4-[(4-methoxyphenyl)diphenylmethoxy]oxolan-2-yl]-3H-pyrimidine-2,4-dione (170 mg, 0.3 mmol) in water (1 mL) and acetic acid (4 mL) was stirred for 16 hours at room temperature. The resulting mixture was concentrated under reduced pressure. The residue was purified by Prep-TLC with dichloromethane/methanol (10:1). The crude product was purified by Prep-HPLC with the following conditions (Column: XBridge Prep C18 OBD Column, 30*100 mm, 5 μm; Mobile Phase A: water (10 mmol/L NH$_4$HCO$_3$), Mobile Phase B: ACN; Flow rate: 60 mL/min; Gradient: 2% B to 2% B in 2 min, 2% B to 7% B in 9 min, 7% B; Wavelength: 254/220 nm; RT1(min): 3.65). The product-containing fractions were collected and evaporated partially under reduced pressure on rotary evaporator and lyophilized overnight to afford 1-[(2R,3S,4R)-3-fluoro-4-hydroxy-5,5-bis(hydroxymethyl)oxolan-2-yl]-3H-pyrimidine-2,4-dione (10.8 mg, 0.04 mmol, 12.40%) as an off-white solid. LC-MS: (ES, m/z): 277 (M+H$^+$). 98.3% purity (M+H$^+$).

Conditions for the LCMS: (Column: Ascentis Express C18, 50*3.0 mm; 2.7 μm; Mobile Phase A: Water/0.05% TFA, Mobile Phase B: ACN/0.05% TFA; Flow rate: 1.2000 mL/min; Gradient: 2% B to 100% B in 0.80 min, 100% B to 100% B in 0.65 min, 100% B to 2% B in 0.05 min; Wavelength: 254 nm; RT1(min): 0.579). $^1$H NMR (400 MHz, DMSO-d$_6$) δ 10.51 (s, 1H), 7.89 (d, J=8.1 Hz, 1H), 6.32 (t, J=6.6 Hz, 1H), 5.93 (s, 1H), 5.66 (d, J=8.1 Hz, 1H), 5.31 (dt, J=57.0, 6.0 Hz, 2H), 4.98 (s, 1H), 4.38 (dd, J=27.9, 5.9 Hz, 1H), 3.58 (d, J=11.4 Hz, 1H), 3.45 (q, J=12.0 Hz, 2H), 3.29 (d, J=11.4 Hz, 1H).

Example 41—Synthesis of Compound 5: (2R,3R,4S,5R)-5-(6-amino-2-chloro-9H-purin-9-yl)-2-ethynyl-4-fluoro-2-(hydroxymethyl)tetrahydrofuran-3-ol

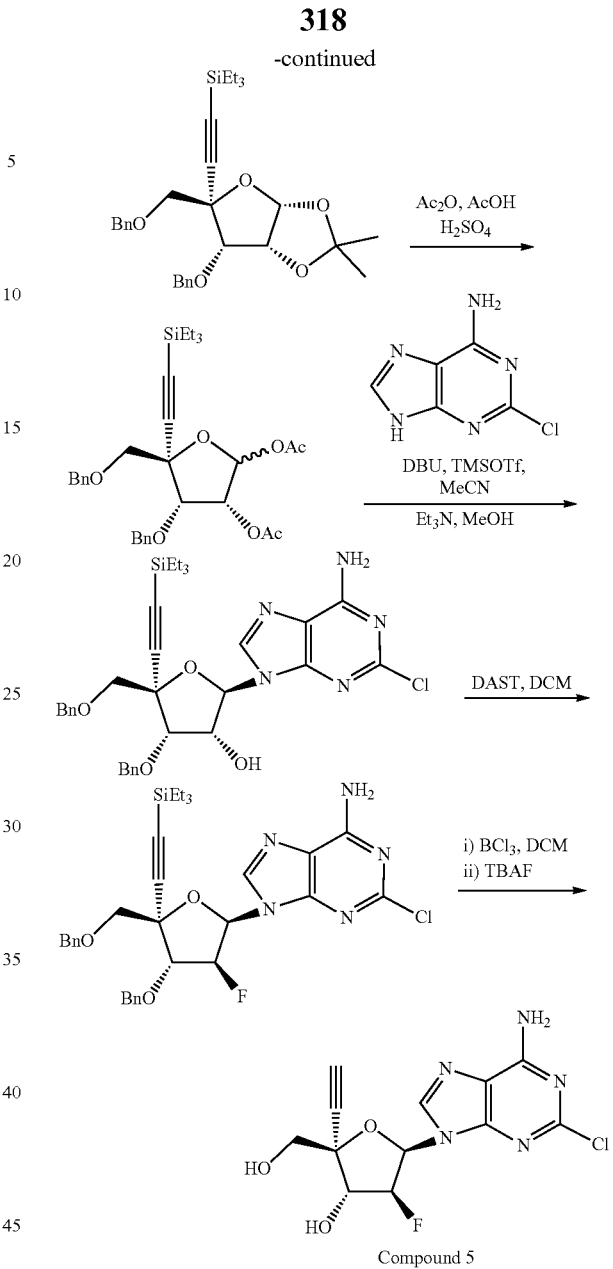

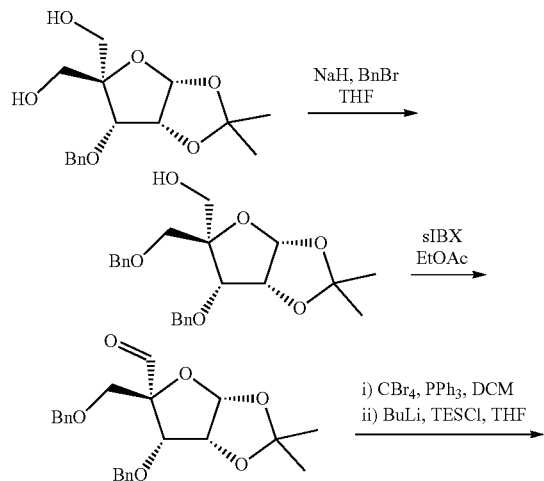

Step 1: To a stirred suspension of sodium hydride (3.22 g of a 60% dispersion in mineral oil, 80.6 mmol) in tetrahydrofuran (230 mL) at 0° C. under argon was added ((3aR,6S,6aR)-6-(benzyloxy)-2,2-dimethyltetrahydrofuro[2,3-d][1,3]dioxole-5,5-diyl)dimethanol (25 g, 80.6 mmol) portionwise over 15 min. The resulting white suspension was stirred at 0° C. for 15 min then a solution of benzyl bromide (9.58 mL, 80.6 mmol) in tetrahydrofuran (20 mL) was added over 10 min. The resulting white suspension was stirred at 20° C. for 18 h. The reaction mixture was quenched by addition of ammonium chloride saturated solution (250 mL). The resulting mixture was diluted with ethyl acetate (300 mL) and the layers were separated. The aqueous was extracted with ethyl acetate (300 mL) and the combined organics were dried over magnesium sulfate, filtered, and concentrated under reduced pressure to give the crude product as a yellow oil. Purification by dry flash chromatography on silica and eluting with heptane-ethyl acetate (9:1) to (4:1) to (2:1) to (1:1) followed by rotary evaporation gave two batches of mixed fractions. Mixed fractions were re-purified by normal phase silica chromatography (Isolera, 120 g SiliaSep cartridge, 2-60% ethyl acetate with heptane over 12 column volumes) to give ((3aR,5R,6S,6aR)-6-(benzyloxy)-5-((benzyloxy)methyl)-2,2-dimethyltetrahydrofuro[2,3-d][1,3]dioxol-5-yl)methanol (19.2 g, 59%) a yellow oil. $^1$H NMR (CDCl$_3$, 400 MHz): 7.36-7.22 (m, 10H), 5.78 (d, 1H), 4.77 (d, 1H), 4.64 (dd, 1H), 4.56-4.46 (m, 3H), 4.27 (d, 1H), 3.92 (dd, 1H), 3.82 (dd, 1H), 3.59 (d, 1H), 3.53 (d, 1H), 1.62 (s, 3H), 1.34 (s, 3H), 1H not observed. UPLC-MS (basic, 2-95%, 1.2 min, BEH C18): 99.7%, Rt=0.96 min, [M+Na]$^+$423.2.

Step 2: A stirred suspension of ((3aR,5R,6S,6aR)-6-(benzyloxy)-5-((benzyloxy) methyl)-2,2-dimethyltetrahydrofuro[2,3-d][1,3]dioxol-5-yl)methanol (10.3 g, 25.7 mmol) and 2-iodoxybenzoic acid (24.0 g of a 45 wt. % mixture, stabilized with benzoic acid and isophthalic acid, 38.6 mmol) in ethyl acetate (100 mL) was heated at 60° C. for 24 h under argon. The resulting suspension was cooled to room temperature. The suspension was filtered through a pad of celite rinsing the filter cake with ethyl acetate (3×100 mL). The filtrate was washed with sodium hydrogen carbonate (2×100 mL of a saturated aqueous solution) and brine (100 mL), dried over magnesium sulfate, filtered, and concentrated under reduced pressure to give the crude product. Material was combined with a second batch (22.1 mmol) and purified by silica chromatography (Isolera, 120 g SiliaSep cartridge, 2-30% ethyl acetate with heptane over 13 column volumes) to give a yellow oil which contained IBX impurities. The material was dissolved in ethyl acetate (100 mL) and washed with sodium hydrogen carbonate (2×100 mL of a saturated aqueous solution) and brine (100 mL), dried over magnesium sulfate, filtered and concentrated under reduced pressure to give (3aR,5R,6S,6aR)-6-(benzyloxy)-5-((benzyloxy)methyl)-2,2-dimethyltetrahydrofuro[2,3-d][1,3]dioxole-5-carbaldehyde (12.4 g, 65%) as a pale yellow oil. $^1$H NMR (CDCl$_3$, 400 MHz): 9.90 (s, 1H), 7.37-7.20 (m, 10H), 5.83 (d, 1H), 4.70 (d, 1H), 4.61-4.56 (m, 2H), 4.48 (q, 2H), 4.36 (d, 1H), 3.67 (d, 1H), 3.60 (d, 1H), 1.59 (s, 3H), 1.34 (s, 3H). UPLC-MS (basic, 2-95%, 1.2 min, BEH C18): 87.2%, Rt=1.03 min. Mass ion not observed.

Step 3(i): To a stirred solution of (3aR,5R,6S,6aR)-6-(benzyloxy)-5-((benzyloxy) methyl)-2,2-dimethyltetrahydrofuro[2,3-d][1,3]dioxole-5-carbaldehyde (2.00 g, 5.02 mmol, 1 eq) in dichloromethane (42 mL) at 0° C. was added carbon tetrabromide (3.32 g, 10.0 mmol, 2 eq) followed by triphenylphosphine (5.27 g, 20.1 mmol, 4 eq). The reaction mixture was stirred for 1 h at 0° C. Triethylamine (4.5 mL, 30.1 mmol, 6 eq) was added and mixture was added to heptane (210 mL). Precipitate was filtered and solvent was evaporated under reduced pressure. Material was purified by passing through silica plug with heptane:ethyl acetate (2:1, 300 mL) and concentrated under reduced pressure to give (3aR,5R,6S,6aR)-6-(benzyloxy)-5-((benzyloxy)methyl)-5-(2,2-dibromovinyl)-2,2-dimethyltetrahydrofuro[2,3-d][1,3]dioxole (2.41 g, 87%) as a yellow oil. $^1$H NMR (CDCl$_3$, 400 MHz): 7.37-7.22 (m, 10H), 7.11 (s, 1H), 5.75 (d, 1H), 4.71 (d, 1H), 4.61 (s, 1H), 4.57 (s, 1H), 4.52 (t, 1H), 4.42 (d, 1H), 4.20 (d, 1H), 3.82 (d, 1H), 3.40 (d, 1H), 1.58 (s, 3H), 1.29 (s, 3H). UPLC-MS (Long basic, 50-95%, BEH C18): 89.7%, Rt=0.96 min. Mass ion not observed.

Step 3(ii): To a stirred solution of (3aR,5R,6S,6aR)-6-(benzyloxy)-5-((benzyloxy) methyl)-5-(2,2-dibromovinyl)-2,2-dimethyltetrahydrofuro[2,3-d][1,3]dioxole (1.80 g, 3.25 mmol, 1 eq) in tetrahydrofuran (36 mL) at −78° C. under argon was added n-butyllithium (1.6M in heptane) (5.07 mL, 8.11 mmol, 2.5 eq) slowly and mixture was stirred at −78° C. for 30 min. Chlorotriethylsilane (0.65 mL, 3.90 mmol, 1.2 eq) was added and mixture was warmed to room temperature and stirred for 15 min. Mixture was diluted with water (50 mL) and extracted with ethyl acetate (3×70 mL). The organic layers were combined, dried over magnesium sulfate, filtered, concentrated under reduced pressure and combined with a second batch of crude product obtained from 500 mg of (3aR,5R,6S,6aR)-6-(benzyloxy)-5-((benzyloxy) methyl)-5-(2,2-dibromovinyl)-2,2-dimethyltetrahydrofuro[2,3-d][1,3]dioxole to give (((3aR,5R,6S,6aR)-6-(benzyloxy)-5-((benzyloxy)methyl)-2,2-dimethyltetrahydrofuro[2,3-d][1,3]dioxol-5-yl)ethynyl)triethylsilane (2.10 g, 99%) as a yellow oil. $^1$H NMR (CDCl$_3$, 400 MHz): 7.41-7.35 (m, 2H), 7.34-7.20 (m, 8H), 5.70 (d, 1H), 4.74 (d, 1H), 4.67-4.61 (m, 2H), 4.56 (d, 1H), 4.47 (d, 1H), 4.22 (d, 1H), 3.70 (d, 1H), 3.57 (d, 1H), 1.72 (s, 3H), 1.33 (s, 3H), 0.97 (t, 9H), 0.59 (q, 6H). UPLC-MS (Short basic, 50-95%, BEH C18): Rt=1.24 min.

Step 4: To a stirred solution of (((3aR,5R,6S,6aR)-6-(benzyloxy)-5-((benzyloxy) methyl)-2,2-dimethyltetrahydrofuro[2,3-d][1,3]dioxol-5-yl)ethynyl)triethylsilane (2.10 g, 4.13 mmol) in acetic anhydride (5.3 mL) and acetic acid (21.2 mL) at room temperature was added sulfuric acid (26.6 μL). The resulting solution was stirred at room temperature for 4 h then poured into ethyl acetate (100 mL), heptane (100 mL) and water (200 mL). The organic layers were separated and the organics were washed with water (2×150 mL), sodium hydrogen carbonate (2×150 mL of a saturated aqueous solution) and brine (150 mL), dried over magnesium sulfate, filtered and concentrated to give crude product (2.05 g). Starting material present. Crude material was subjected to the same conditions and stirred overnight. Mixture was poured into ethyl acetate (100 mL), heptane (100 mL) and water (200 mL). The organic layers were separated and the organics were washed with water (2×150 mL), sodium hydrogen carbonate (2×150 mL of a saturated aqueous solution) and brine (150 mL), dried over magnesium sulfate, filtered and concentrated to give (3R,4S,5R)-4-(benzyloxy)-5-((benzyloxy) methyl)-5-((triethylsilyl)ethynyl)tetrahydrofuran-2,3-diyl diacetate (1.78 g) as a pale yellow oil which was used in the next step without further purification.

Step 5: To a stirred suspension of 2-chloro-9H-purine-6-amine (1.05 g, 6.20 mmol, 1.5 eq) in acetonitrile (15 mL) were successively added 1,8-diazabicyclo[5.4.0]undec-7-ene (1.23 mL, 8.26 mmol, 2 eq) and trimethylsilyltrifluoromethane sulfonate (4.5 mL, 24.8 mmol, 6 eq) at room temperature, and the mixture was stirred at 60° C. for 20 min. To the resulting yellow solution was added the solution of (3R,4S,5R)-4-(benzyloxy)-5-((benzyloxy)methyl)-5-((triethylsilyl)ethynyl)tetrahydrofuran-2,3-diyl diacetate (1.78 g, 4.13 mmol, 1 eq) in acetonitrile (15 mL) over 5 min. After 30 min of stirring at 60° C., the mixture was poured into ice-water (100 mL) and extracted with EtOAc (3×100 mL). The extract was washed with brine, dried over magnesium sulfate, filtered and concentrated in vacuo to give the crude product, which was then dissolved in methanol (41 mL). To the solution was added triethylamine (10.4 mL) at room temperature and the mixture was stirred at 60° C. for 18 h. The mixture was concentrated in vacuo and diluted with ethyl acetate (100 mL). The solution was washed with water (50 mL×3) and brine (50 mL), dried over magnesium sulfate, and concentrated under reduced pressure. The residue was purified by normal phase silica chromatography (Isolera, 40 g SiliaSep cartridge, 2-80% ethyl acetate with heptane over 15 column volumes) to give (2R,3R,4S,5R)-2-(6-amino-2-chloro-9H-purin-9-yl)-4-(benzyloxy)-5-((benzyloxy)methyl)-5-((triethylsilyl)ethynyl)tetrahydrofuran-3-ol (996 mg, 39% over three steps) as an off-white solid. ¹H NMR (CDCl₃, 400 MHz): 8.02 (s, 1H), 7.42-7.24 (m, 10H), 6.13 (d, 1H), 5.94 (brs, 1H), 4.96 (d, 1H), 4.72-4.65 (m, 2H), 4.55 (q, 2H), 4.43 (d, 1H), 3.83 (d, 1H), 3.71 (d, 1H), 3.24 (brs, 1H), 0.98 (t, 9H), 0.61 (q, 6H). UPLC-MS (Long basic, 50-95%, BEH C8): 94.5%, RT=0.97 min, [M+H]⁺ 620.3.

Step 6: A solution of (2R,3R,4S,5R)-2-(6-amino-2-chloro-purin-9-yl)-4-benzyloxy-5-(benzyloxymethyl)-5-(2-triethylsilylethynyl)tetrahydrofuran-3-ol (500 mg, 806 µmol) and pyridine (383 mg, 4.83 mmol, 391 µL) in dichloromethane (10 mL) under argon was cooled to −78° C. and DAST (520 mg, 3.23 mmol, 426 µL) added. The reaction was allowed to warm to rt over 3 hours then stirred at room temperature for 16 hours. The reaction was cooled to 0° C. and quenched with sat NaHCO₃ (30 ml). The DCM layer was collected through a phase separator and the aqueous further extracted with DCM (2×10 ml). The DCM layer was concentrated to a brown gum. Material purified by normal phase chromatography (Biotage Isolera, 25 g Silicycle cartridge; eluent 0-80% ethyl acetate in heptane) to give 9-[(2R,3S,4R,5R)-4-benzyloxy-5-(benzyloxymethyl)-3-fluoro-5-(2-triethylsilylethynyl) tetrahydrofuran-2-yl]-2-chloro-purin-6-amine (238 mg, 383 µmol, 47% yield, 100% purity) as a white solid. ¹H NMR (400 MHz, CDCl₃): δ [ppm]=8.26 (s, 1H), 7.44-7.31 (m, 10H), 6.63 (dd, 1H), 5.45 (dt, 1H), 4.74 (dd, 2H), 4.65-4.57 (m, 3H), 3.83 (dd, 1H), 3.73 (d, 1H), 1.02 (t, 9H), 0.66 (q, 6H), 2H not observed. ¹⁹F NMR (376 MHz, CDCl₃): δ [ppm]=−196.9−−197.1 (m, 1F). UPLC-MS: (BEH C18 Long Base 50-95%) Rt=2.68 min (100%), MS (ESIpos): m/z=[M+H]⁺ 622.2.

Step 7(i): A solution of 9-[(2R,3S,4R,5R)-4-benzyloxy-5-(benzyloxymethyl)-3-fluoro-5-(2-triethylsilylethynyl) tetrahydrofuran-2-yl]-2-chloro-purin-6-amine (287 mg, 461 µmol) in dichloromethane (10 mL) under argon was cooled to −78° C. and boron trichloride (1 M, 4.61 mL) added slowly. The reaction was stirred at −78° C. for 3.5 hours, then at −30° C. for 30 minutes. The reaction was cooled to −78° C. and quenched with a cooled mixture of methanol (6 ml) and triethylamine (3 ml), then allowed to warm. The mixture was concentrated to a slurry and purified by reverse phase chromatography (Biotage Isolera, 60 g Biotage C18 cartridge; gradient 25-85% (acetonitrile+0.1% NH₄OH) in (water+0.1% NH₄OH) over 9CV). The product fractions were combined and freeze dried to give (2R,3R,4S,5R)-5-(6-amino-2-chloro-purin-9-yl)-4-fluoro-2-(hydroxymethyl)-2-(2-triethylsilylethynyl) tetrahydrofuran-3-ol (152 mg, 308 µmol, 67% yield, 89.7% purity). ¹H NMR (400 MHz, CDCl₃): δ [ppm]=8.86 (s, 1H), 6.60 (dd, 1H), 5.46-5.30 (m, 1H), 4.87 (d, 1H), 4.04 (d, 1H), 3.95 (d, 1H), 1.04 (t, 9H), 0.69 (q, 6H), 4H not observed. ¹⁹F NMR (376 MHz, CDCl₃): δ [ppm]=−200.2. nUPLC-MS: (BEH C18 Short Base 2-95%) Rt=0.95 min (89.7%), MS (ESIpos): m/z=[M+H]⁺ 442.1.

Step 7(ii): To a solution of (2R,3R,4S,5R)-5-(6-amino-2-chloro-purin-9-yl)-4-fluoro-2-(hydroxymethyl)-2-(2-triethylsilylethynyl)tetrahydrofuran-3-ol (150 mg, 339 µmol) in Tetrahydrofuran (2 mL) at room temp. was added TBAF (177 mg, 509 µmol, 197 µL, 75% purity). The reaction was stirred for 2 hours, the purified by reverse phase chromatography (Biotage Isolera, 60 g Biotage C18 cartridge; gradient 2-40% (acetonitrile+0.1% NH₄OH) in (water+0.1% NH₄OH) over 8CV) and the product fractions freeze dried to give (2R,3R,4S,5R)-5-(6-amino-2-chloro-purin-9-yl)-2-ethynyl-4-fluoro-2-(hydroxymethyl)tetrahydrofuran-3-ol (98 mg, 299 µmol, 88% yield, 100% purity) as a white solid. ¹H NMR (400 MHz, DMSO-d₆): δ [ppm]=8.25 (d, 1H), 7.90 (s, 2H), 6.40 (dd, 1H), 6.29 (d, 1H), 5.50 (t, 1H), 5.39 (dt, 1H), 4.65 (dt, 1H), 3.72-3.61 (m, 3H). ¹⁹F NMR (376 MHz, DMSO-d₆): δ [ppm]=−199.2 (ddd, 1F). UPLC-MS: (CSH C18 Long Acid 2-50%) Rt=1.15 min (100%), MS (ESIpos): m/z=[M+H]⁺ 328.0.

Example 42—Synthesis of Compound 27: (2R,3S,5R)-5-(6-amino-9H-purin-9-yl)-2-ethynyl-2-(hydroxymethyl)tetrahydrofuran-3-ol

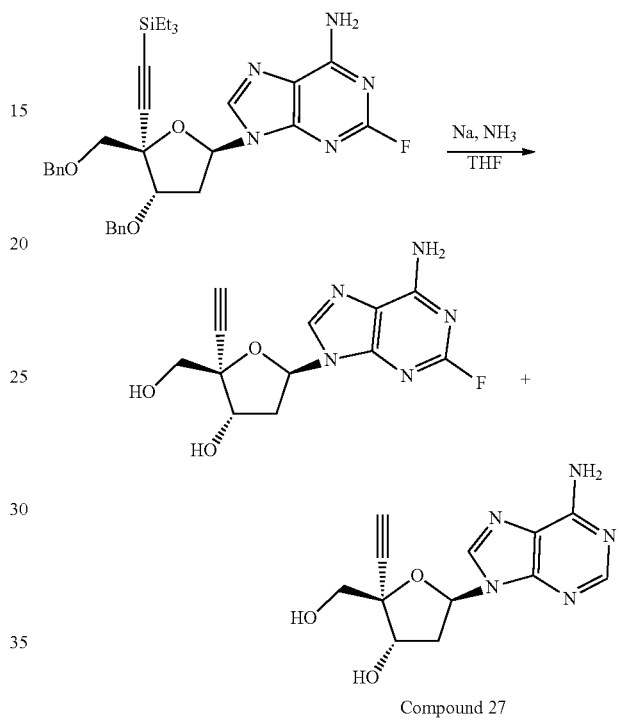

Compound 27

Step 1: To a solution of 9-((2R,4S,5R)-4-(benzyloxy)-5-((benzyloxy)methyl)-5-((triethylsilyl)ethynyl)tetrahydrofuran-2-yl)-2-fluoro-9H-purin-6-amine (340 mg, 578 µmol) (Synthesis shown in Example 41) in tetrahydrofuran (2 mL) at −78° C. was added ammonia (15 ml), followed portionwise by sodium (66.5 mg, 2.89 mmol). The reaction was stirred for 10 minutes the quenched at 0° C. with ammonium chloride (155 mg, 5 eq). The mixture was stirred overnight at room temperature, then slurried in methanol, filtered and concentrated. The residue was purified by reverse phase chromatography (Biotage Isolera, 30 g Biotage C18 cartridge; gradient 0-20% (acetonitrile+0.1% NH₄OH) in (water+0.1% NH₄OH) over 10CV) and the product fractions freeze dried to give 2 products as white solids:

(2R,3S,5R)-5-(6-Amino-2-fluoro-9H-purin-9-yl)-2-ethynyl-2-(hydroxymethyl) tetrahydrofuran-3-ol (30 mg, 102 µmol, 18% yield, 85.3% purity).). UPLC-MS: (BEH C18 Short Base 2-20%) Rt=0.69 min (85.3%), MS (ESIneg): m/z=[M−H]⁻. 292.0. ¹H NMR (400 MHz, MeOD-d₃): δ 8.25 (s, 1H), 6.33 (dd, 1H), 4.71 (t, 1H), 3.86-3.73 (m, 3H), 2.76 (ddd, 1H), 2.59 (td, 1H).

(2R,3S,5R)-5-(6-Amino-9H-purin-9-yl)-2-ethynyl-2-(hydroxymethyl)tetrahydrofuran-3-ol (52 mg, 189 µmol, 94.7% purity). UPLC-MS: (BEH C18 Long Base 2-95%) Rt=0.94 min (94.7%), MS (ESIpos): m/z=[M+H]⁺ 276.2. ¹H NMR (400 MHz, MeOD-d₃): δ 8.33 (s, 1H), 8.19 (s, 1H), 6.46 (dd, 1H), 4.73 (t, 1H), 3.83 (dd, 2H), 2.83 (ddd, 1H), 2.63-2.57 (m, 1H), 1.89 (s, 1H).

Example 43—Synthesis of Compound 173: (2R,3R, 4S,5R)-5-(4-amino-5-fluoro-2-oxopyrimidin-1(2H)-yl)-2-(chloromethyl)-4-fluoro-2-((isobutyryloxy) methyl) tetrahydrofuran-3-yl isobutyrate

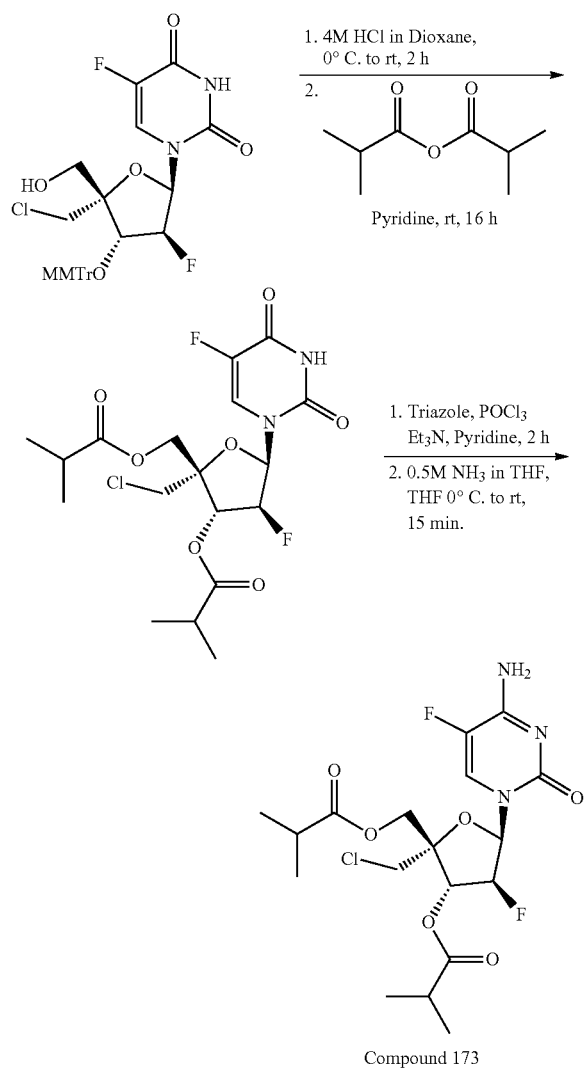

Compound 173

Step 1: To a stirred solution of 1-((2R,3S,4R,5R)-5-(chloromethyl)-3-fluoro-5-(hydroxymethyl)-4-((4-methoxyphenyl) diphenylmethoxy) tetrahydrofuran-2-yl)-5-fluoropyrimidine-2,4(1H,3H)-dione (20 g, 34.19 mmol) in DCM (100 mL) was added 4M HCl in 1,4-dioxane (150 mL) at 0° C. and stirred for 2 h at 0° C. to rt. The reaction progress was monitored by TLC. After completion, the reaction mixture was concentrated and co-distilled with toluene. The resulting residue was dissolved in pyridine (100 mL), followed by addition at rt of isobutyric anhydride (12.4 mL, 75.21 mmol). After stirring the reaction mixture at rt for 16 h, the reaction mixture was concentrated to afford the crude product, which was purified by Combiflash eluting with 20% EtOAc in hexane to afford (2R,3R,4S,5R)-2-(chloromethyl)-4-fluoro-5-(5-fluoro-2,4-dioxo-3,4-dihydropyrimidin-1(2H)-yl)-2-((isobutyryloxy)methyl)tetrahydrofuran-3-yl isobutyrate (3.9 g, 25.19%) as a pale-yellow solid. LC-MS (ES, m/z): 451.00 (M−1).

Step 2: To a stirred solution of 1,2,4-triazole (4.9 g, 71.55 mmol, 9 Eq.) in pyridine (15 mL) was added $POCl_3$ (1.18 mL, 15.90 mmol, 2 Eq.) at 0° C. Then $Et_3N$ (10 mL, 71.55 mmol, 9 Eq.) was added, and the mixture was stirred at 0° C. for 30 min. To this, (2R,3R,4S,5R)-2-(chloromethyl)-4-fluoro-5-(5-fluoro-2,4-dioxo-3,4-dihydropyrimidin-1(2H)-yl)-2-((isobutyryloxy)methyl) tetrahydrofuran-3-yl isobutyrate (3.6 g, 7.95 mmol, 1 Eq.) in pyridine (15 mL) was added at 0° C. and stirred at rt for 2 h. The reaction mixture was concentrated to dryness and co-distilled with toluene. The resulting residue was dissolved in DCM (30 mL), washed with brine solution, dried over $Na_2SO_4$, and concentrated to dryness. The resulting material was dissolved in THF (10 mL), 0.5M $NH_3$ in THF (30 mL) was added, and the mixture was stirred at 0° C. to rt for 15 min. The reaction progress was monitored by TLC. After completion, the reaction mixture was diluted with ice water and ethyl acetate (50 mL each). The organic later was separated, washed with water and brine, dried over sodium sulfate, filtered, and concentrated. The crude product was purified by Combiflash chromatography eluting with 0.9% MeOH in DCM. The resulting material was re-crystallized using MTBE to afford desired product (1.7 g, 47.35%) as a white solid. LC-MS (ES, m/z): 449.95 (M−1). $^1$H NMR (400 MHz, DMSO-$d_6$) δ=7.98 (br s, 1H), 7.79-7.71 (m, 2H), 6.34 (br dd, J=3.2, 17.1 Hz, 1H), 5.66 (dd, J=2.2, 19.4 Hz, 1H), 5.48-5.29 (m, 1H), 4.48-4.35 (m, 2H), 4.00 (d, J=12.0 Hz, 1H), 3.85 (d, J=11.9 Hz, 1H), 2.73-2.55 (m, 2H), 1.18-1.09 (m, 12H).

Example 44—Synthesis of Compound 53: [(2R,3S,5R)-5-(4-amino-2-oxopyrimidin-1-yl)-2-ethenyl-3-[(2-methylpropanoyl) oxy] oxolan-2-yl] methyl 2-methylpropanoate

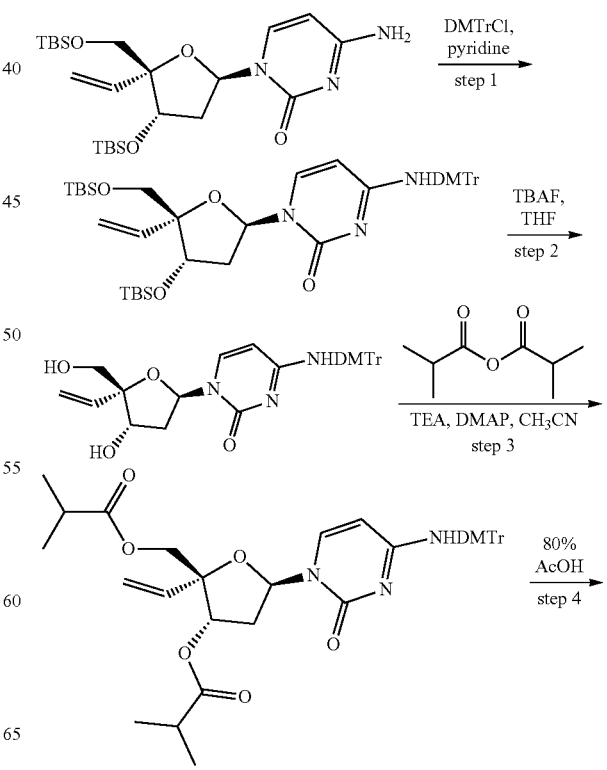

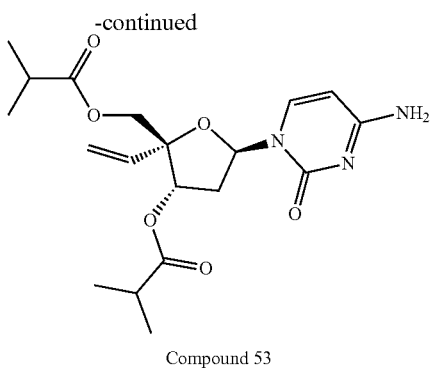

Compound 53

Step 1: A solution of 4-amino-1-[(2R,4S,5R)-4-[(tert-butyldimethylsilyl)oxy]-5-{[(tert-butyldimethylsilyl)oxy]methyl}-5-ethenyloxolan-2-yl]pyrimidin-2-one (1 g, 2.1 mmol) and DMTr-Cl (0.9 g, 3.1 mmol) in pyridine (10 mL) was stirred for 12 hrs at room temperature under nitrogen atmosphere. The resulting mixture was concentrated under vacuum. The residue was dissolved in EtOAc. The resulting solution was washed with brine, dried over anhydrous $Na_2SO_4$. After filtration, the filtrate was concentrated under reduced pressure, which resulted in 4-{[bis(4-methoxyphenyl) (phenyl)methyl] amino}-1-[(2R,4S,5R)-4-[(tert-butyldimethylsilyl) oxy]-5-{[(tert-butyldimethylsilyl) oxy] methyl}-5-ethenyloxolan-2-yl]pyrimidin-2-one (2 g, 1.7 mmol, 86.02%) as a yellow solid. LC-MS (ES, m/z): 784 $(M+H)^+$.

Step 2: A solution of 4-{[bis(4-methoxyphenyl) (phenyl)methyl] amino}-1-[(2R,4S,5R)-4-[(tert-butyldimethylsilyl)oxy]-5-{[(tert-butyldimethylsilyl) oxy] methyl}-5-ethenyloxolan-2-yl] pyrimidin-2-one (1.9 g, 1.7 mmol) and TBAF (0.5 g, 2.03 mmol) in THF was stirred for 2 h at room temperature under nitrogen atmosphere. The resulting mixture was concentrated under reduced pressure. The residue was dissolved in water. The resulting mixture was extracted with EtOAc. The combined organic layers were washed with brine and dried over anhydrous $Na_2SO_4$. After filtration, the filtrate was concentrated under reduced pressure, which resulted in 4-{[bis(4-methoxyphenyl) (phenyl)methyl] amino}-1-[(2R,4S,5R)-5-ethenyl-4-hydroxy-5-(hydroxymethyl) oxolan-2-yl] pyrimidin-2-one (1 g, 1.8 mmol, 90.2%) as an off-white solid. LC-MS (ES, m/z): 556 $(M+H)^+$.

Step 3: To a stirred solution of 4-{[bis(4-methoxyphenyl)(phenyl)methyl]amino}-1-[(2R,4S,5R)-5-ethenyl-4-hydroxy-5-(hydroxymethyl)oxolan-2-yl]pyrimidin-2-one (1 g, 1.8 mmol), TEA (0.4 g, 3.6 mmol) and DMAP (21.9 mg, 0.2 mmol) in $CH_3CN$ was added isobutyric anhydride (1.1 g, 7.2 mmol) dropwise at 0° C. The resulting mixture was stirred for 4 h at room temperature under nitrogen atmosphere. The resulting mixture was concentrated under vacuum. The mixture was diluted with ethyl acetate and washed with brine, dried over anhydrous sodium sulfate. After filtration, the filtrate was concentrated under reduced pressure. The residue was purified by silica gel column chromatography, eluted with $CH_2Cl_2$/MeOH (15:1) to afford [(2R,3S,5R)-5-(4-{[bis(4-methoxyphenyl) (phenyl)methyl] amino}-2-oxopyrimidin-1-yl)-2-ethenyl-3-[(2-methylpropanoyl) oxy] oxolan-2-yl] methyl 2-methylpropanoate (900 mg, 1.26 mmol, 66.8%) as a yellow solid. LC-MS (ES, m/z): 696 $(M+H)^+$.

Step 4: A solution of [(2R,3S,5R)-5-(4-{[bis(4-methoxyphenyl) (phenyl)methyl]amino}-2-oxopyrimidin-1-yl)-2-ethenyl-3-[(2-methylpropanoyl) oxy] oxolan-2-yl] methyl 2-methylpropanoate (100 mg, 0.14 mmol) in AcOH (4 mL) and $H_2O$ (1 mL) was stirred for 2 h at room temperature under nitrogen atmosphere. The resulting mixture was concentrated under vacuum. The crude product was purified with following condition: (Column: XBridge Prep OBD C18 Column, 30*150 mm, 5 μm; Mobile Phase A: Water (10 mmol/L $NH_4HCO_3$+0.1% $NH_3·H_2O$), Mobile Phase B: ACN; Flow rate: 60 mL/min; Gradient: 34% B to 44% B in 8 min; Wavelength: 254/220 nm). The product-containing fractions were collected and lyophilized overnight to afford [(2R,3S,5R)-5-(4-amino-2-oxopyrimidin-1-yl)-2-ethenyl-3-[(2-methylpropanoyl) oxy] oxolan-2-yl] methyl 2-methylpropanoate (45 mg, 0.11 mmol, 76.9%) as a white solid. LC-MS (ES, m/z): 394 $(M+H)^+$. LCMS conditions: (HALO C18, 30*3.0 mm, 2.7 μm; Mobile Phase A: Water (0.05% TFA), Mobile Phase B: Acetonitrile (0.05% TFA); Flow rate: 1.5000 mL/min; Gradient: 5% B to 70% B in 1.90 min, 70% B to 100% B in 2.05 min, 100% B to 100% B in 2.60 min, 100% B to 5% B in 2.70 min; Wavelength: 254/220 nm). $^1H$ NMR (400 MHz, DMSO-$d_6$) δ 7.67 (d, J=6.9 Hz, 1H), 7.22 (d, J=13.0 Hz, 2H), 6.19 (t, J=6.4 Hz, 1H), 5.77 (q, J=10.3, 9.6 Hz, 2H), 5.49-5.30 (d, J=10.8 Hz, 3H), 4.17 (d, J=3.5 Hz, 2H), 2.57 (dt, J=14.3, 7.1 Hz, 2H), 2.39 (q, J=6.8 Hz, 1H), 2.33-2.23 (m, 1H), 1.45-1.05 (m, 12H).

Example 45—Synthesis of Compound 58: ((2R,3S,5R)-5-(4-amino-5-fluoro-2-oxopyrimidin-1(2H)-yl)-2-(chloromethyl)-2-((isobutyryloxy)methyl)tetrahydrofuran-3-yl isobutyrate)

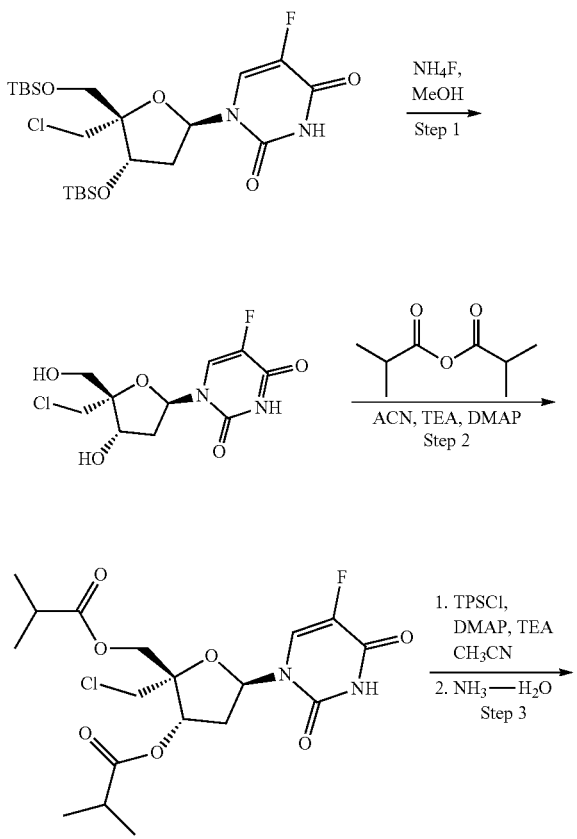

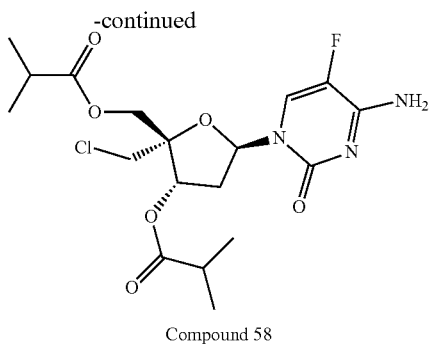

Compound 58

Step 1: To a stirred solution of 1-[(2R,4S,5R)-4-[(tert-butyldimethylsilyl)oxy]-5-{[(tert-butyldimethylsilyl)oxy]methyl}-5-(chloromethyl)oxolan-2-yl]-5-fluoro-3H-pyrimidine-2,4-dione (600 mg, 1.15 mmol) in MeOH (15 mL) was added NH$_4$F (637.1 mg, 17.2 mmol) in portions at room temperature under nitrogen atmosphere. The resulting mixture was stirred for overnight at 60° C., then cooled to room temperature and removed the solid by filtration. The filter cake was washed with MeOH and the filtrate was concentrated under vacuum. The residue was purified by reversed-phase flash chromatography with the following conditions: column, C18 silica gel; mobile phase, MeCN in Water (0.1% TFA), 5% to 30% gradient in 10 min; detector, UV 254 nm. This resulted in 1-[(2R,4S,5R)-5-(chloromethyl)-4-hydroxy-5-(hydroxymethyl)oxolan-2-yl]-5-fluoro-3H-pyrimidine-2,4-dione (300 mg, 88.8%) as a white solid. LC-MS (ES, m/z): 295 (M+H)$^+$.

Step 2: To a stirred solution of 1-[(2R,4S,5R)-5-(chloromethyl)-4-hydroxy-5-(hydroxymethyl)oxolan-2-yl]-5-fluoro-3H-pyrimidine-2,4-dione (300 mg, 1.0 mmol), TEA (206.0 mg, 2.0 mmol) and DMAP (248.8 mg, 2.0 mmol) in MeCN was added 2-methylpropanoyl 2-methylpropanoate (402.7 mg, 2.5 mmol) dropwise at 0° C. under nitrogen atmosphere. The resulting mixture was stirred for 3 hours at room temperature and then quenched by the addition of water. The resulting solution was extracted with EtOAc, washed with brine, dried over anhydrous Na$_2$SO$_4$ and concentrated under vacuum. The residue was purified by silica gel column chromatography, eluted with petroleum ether/EtOAc (5:1) to afford [(2R,3S,5R)-2-(chloromethyl)-5-(5-fluoro-2,4-dioxo-3H-pyrimidin-1-yl)-3-[(2-methylpropanoyl)oxy]oxolan-2-yl]methyl 2-methylpropanoate (400 mg, 90.4%) as a white solid. LC-MS (ES, m/z): 435 (M+H)$^+$.

Step 3: To a stirred solution of [(2R,3S,5R)-2-(chloromethyl)-5-(5-fluoro-2,4-dioxo-3H-pyrimidin-1-yl)-3-[(2-methylpropanoyl)oxy]oxolan-2-yl]methyl 2-methylpropanoate (400 mg, 0.9 mmol), TEA (279.2 mg, 2.8 mmol) and DMAP (224.76 mg, 1.840 mmol) in CH$_3$CN (10 mL) was added 2,4,6-tris(propan-2-yl)benzene-1-sulfonyl chloride (557.2 mg, 1.8 mmol) in portions at room temperature under nitrogen atmosphere. The resulting mixture was stirred for 30 min at room temperature. This was followed by the addition of ammonia (1 mL) dropwise. The resulting mixture was stirred for additional 4 hours at room temperature and the quenched by the addition of water. The resulting solution was extracted with EtOAc, washed with brine, dried over anhydrous Na$_2$SO$_4$ and concentrated under vacuum. The crude product was purified by Prep-HPLC with the following conditions: Column: XBridge Shield RP18 OBD Column, 30*150 mm, 5 μm; Mobile Phase A: Water (10 mmol/L NH$_4$HCO$_3$), Mobile Phase B: ACN; Flow rate: 60 mL/min; Gradient: 28% B to 50% B in 8 min, 50% B; Wavelength: 220 nm; RT1(min): 7.62 min. The product-containing fractions were collected and lyophilized overnight to afford [(2R,3S,5R)-5-(4-amino-5-fluoro-2-oxopyrimidin-1-yl)-2-(chloromethyl)-3-[(2-methylpropanoyl)oxy]oxolan-2-yl]methyl 2-methylpropanoate (102 mg, 25.6%) as a white solid. LC-MS (ES, m/z): 434 (M+H)$^+$. $^1$H NMR (400 MHz, DMSO-d$_6$) δ 7.91 (s, 1H), 7.87 (d, J=7.2 Hz, 1H), 7.67 (brs, 1H), 6.24 (t, J=6.8 Hz, 1H), 5.51-5.48 (m, 1H), 4.32 (dd, J=16.0, 11.6 Hz, 2H), 3.92-3.89 (m, 1H), 3.81-3.79 (m, 1H), 2.69-2.58 (m, 3H), 2.40-2.36 (m, 1H), 1.18-1.12 (m, 12H).

Example 46—Synthesis of Compound 52: [(2R,3S,5R)-5-(4-amino-2-oxopyrimidin-1-yl)-2-ethyl-3-[(2-methylpropanoyl) oxy] oxolan-2-yl] methyl 2-methylpropanoate

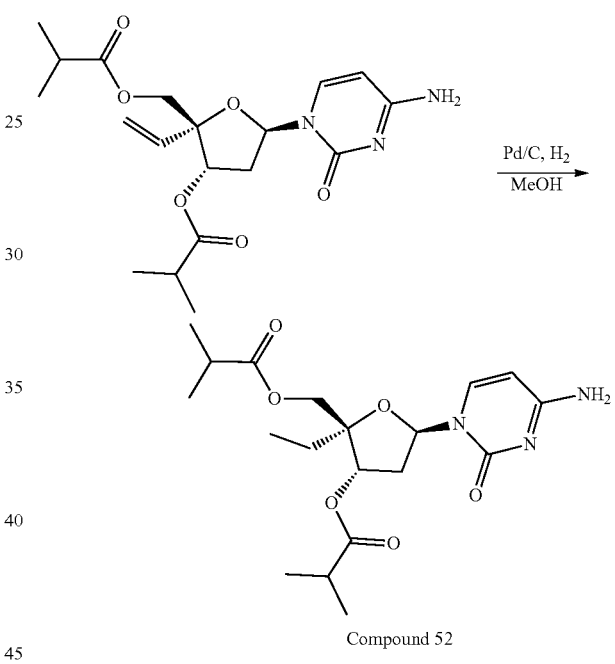

Compound 52

A solution of [(2R,3S,5R)-5-(4-amino-2-oxopyrimidin-1-yl)-2-ethenyl-3-[(2-methylpropanoyl) oxy] oxolan-2-yl] methyl 2-methylpropanoate (200 mg, 0.5 mmol) and Pd/C (20 mg, 10% Pd on carbon) in MeOH (5 mL) was stirred for 12 h at room temperature under hydrogen atmosphere. The resulting mixture was filtered; the filter cake was washed with MeOH and the filtrate was concentrated under reduced pressure. The crude product was purified by Prep-HPLC with the following conditions (Column: XBridge Prep OBD C18 Column, 30*150 mm, 5 μm; Mobile Phase A: Water (10 mmol/L NH$_4$HCO$_3$+0.1% NH$_3$·H$_2$O), Mobile Phase B: ACN; Flow rate: 60 mL/min; Gradient: 34% B to 44% B in 8 min; Wavelength: 254/220 nm). The product-containing fractions were collected and lyophilized overnight to afford [(2R,3S,5R)-5-(4-amino-2-oxopyrimidin-1-yl)-2-ethyl-3-[(2-methylpropanoyl) oxy] oxolan-2-yl] methyl 2-methylpropanoate (88.9 mg, 42.81%) as a white solid. LC-MS (ES, m/z): 396.2 (M+H)$^+$. LCMS conditions: (HALO C18, 30*3.0 mm, 2.7 μm; Mobile Phase A: Water+0.05% TFA, Mobile Phase B: Acetonitrile+0.05% TFA; Flow rate: 1.5000 mL/min; Gradient: 20% B to 70% B in 1.90 min, 70% B to 100% B in 2.00 min, 100% B to 100% B in 2.60 min, 100% B to 5% B in 2.70 min; Wavelength: 254/220 nm). $^1$H NMR (300 MHz, DMSO-d$_6$) δ 7.62 (d, J=7.4 Hz, 1H), 7.20 (d, J=11.9 Hz, 2H), 6.12 (t, J=6.8 Hz, 1H), 5.74 (d, J=7.4 Hz, 1H), 5.36 (dd, J=6.5, 3.4 Hz, 1H), 4.12 (d, J=2.8 Hz, 2H), 2.69-2.52 (m, 2H), 2.48-2.24 (m, 2H), 1.69 (p, J=7.4 Hz, 1H), 1.55 (dq, J=14.6, 7.2 Hz, 1H), 1.11 (td, J=7.3, 2.7 Hz, 12H), 0.88 (t, J=7.4 Hz, 3H).

Example 47—Synthesis of Compound 161 and Compound 92: (2R,3S,5R)-5-(4-amino-5-iodopyrrolo[2,1-f][1,2,4]triazin-7-yl)-2-azido-2-(hydroxymethyl)tetrahydrofuran-3-ol & (2R,3S,5R)-5-(4-aminopyrrolo[2,1-f][1,2,4]triazin-7-yl)-2-azido-2-(hydroxymethyl) tetrahydrofuran-3-ol Step 1: A mixture of N-[7-[(2R,4S,5R)-4-hydroxy-5-(hydroxymethyl) tetrahydrofuran-2-yl]pyrrolo[2,1-f][1,2,4]triazin-4-yl]benzamide (4.23 g, 11.9 mmol), imidazole (975 mg, 14.3 mmol), and triphenylphosphine (3.75 g, 14.3 mmol) in anhydrous THF (50 mL) was cooled in an ice bath, and a solution of iodine (3.63 g, 14.3 mmol) in anhydrous THF (10 mL) was added dropwise over 10 min. The reaction mixture was stirred at 0° C. for 10 min then warmed to room temperature and stirred for 18 h. The reaction mixture was diluted with DCM (300 mL) and washed with 0.5 M Na$_2$S$_2$O$_3$ in sat. aq. NaHCO$_3$(200 mL). The aqueous layer was washed with DCM and the combined organic layers were dried over anhydrous Na$_2$SO$_4$, filtered, and concentrated in vacuo. The crude oil was purified by column chromatography over silica gel (Gradient: 0-100% EtOAc in hexanes) to give N-(7-((2R,4S,5S)-4-hydroxy-5-(iodom-

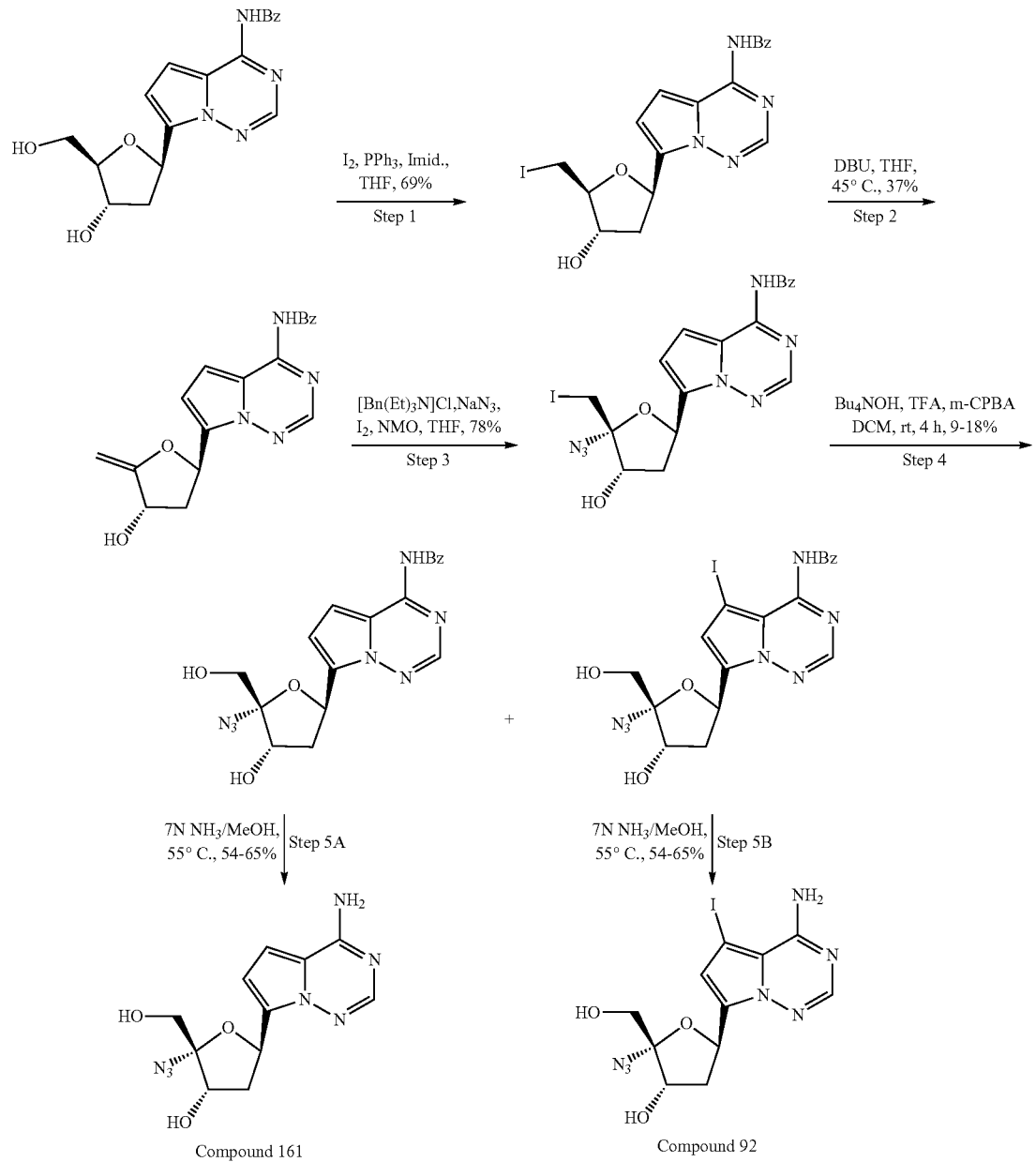

ethyl) tetrahydrofuran-2-yl)pyrrolo[2,1-f][1,2,4]triazin-4-yl)benzamide (3.84 g, 69% yield) as a yellow solid. LCMS (m/z): 465.8 [M+H]$^+$; $^1$H NMR (400 MHz, DMSO-d$_6$) δ 8.17 (d, J=77.1 Hz, 3H), 7.63 (d, J=7.5 Hz, 1H), 7.54 (t, J=7.5 Hz, 2H), 7.14 (s, 1H), 6.96 (s, 1H), 5.67 (s, 1H), 5.38 (d, J=4.0 Hz, 1H), 4.24 (s, 1H), 3.89 (td, J=6.0, 2.1 Hz, 1H), 3.40 (dd, J=10.3, 6.3 Hz, 1H), 3.34 (s, 1H), 2.36 (td, J=11.8, 10.1, 5.5 Hz, 1H), 2.21 (dd, J=12.8, 5.7 Hz, 1H).

Step 2: To a solution of N-(7-((2R,4S,5S)-4-hydroxy-5-(iodomethyl) tetrahydrofuran-2-yl)pyrrolo[2,1-f][1,2,4]triazin-4-yl)benzamide (3.96 g, 8.53 mmol) in anhydrous THF (25 mL) was added 2,3,4,6,7,8,9,10-octahydropyrimido[1,2-a]azepine (3.13 mL, 22.69 mmol) and the reaction was stirred at room temperature 16 h then heated to 45° C. and stirred for 6 h. The reaction mixture was concentrated in vacuo and the crude was purified by column chromatography over silica gel twice (Gradient: 0-5% MeOH in DCM) to give N-(7-((2R,4S)-4-hydroxy-5-methylenetetrahydrofuran-2-yl)pyrrolo[2,1-f][1,2,4]triazin-4-yl)benzamide (1.06 g, 37% yield) as a light-yellow solid. LCMS (m/z): 337 [M+H]$^+$; $^1$H NMR (400 MHz, DMSO-d$_6$) δ 11.28 (s, 1H), 8.19 (d, J=99.5 Hz, 3H), 7.64 (t, J=7.3 Hz, 1H), 7.54 (t, J=7.6 Hz, 2H), 7.13 (s, 1H), 6.94 (s, 1H), 5.95 (s, 1H), 5.49 (d, J=4.7 Hz, 1H), 4.72-4.62 (m, 1H), 4.17 (s, 1H), 4.06 (s, 1H), 2.48-2.40 (m, 1H), 2.28 (ddd, J=12.8, 6.2, 3.3 Hz, 1H).

Step 3: To a stirred solution of benzyltriethylammonium chloride (1.04 g, 4.58 mmol) in anhydrous MeCN (20 mL) was added sodium azide (298 mg, 4.58 mmol). The mixture was sonicated for 20 min and then stirred under argon at room temperature for 16 h. The solution was filtered and added via syringe to a solution of N-(7-((2R,4S)-4-hydroxy-5-methylenetetrahydrofuran-2-yl)pyrrolo[2,1-f][1,2,4]triazin-4-yl)benzamide (700 mg, 2.08 mmol) in anhydrous THF (8 mL). Morpholine, 4-methyl- (0.55 mL, 4.99 mmol) was added and the resulting solution was cooled to 0° C., then a solution of iodine (1.05 g, 4.16 mmol) in THF (8 mL) was added dropwise over 30 min. Stirring was continued in ice bath for 4 h, then N-acetyl cysteine was added until the evolution of gas was no longer observable (to destroy excess azide), followed by addition of saturated aqueous Na$_2$S$_2$O$_3$ (15 mL) until the solution was light-yellow. The solvent was removed in vacuo and the residue was diluted with H$_2$O (80 mL) and extracted with EtOAc (3×100 mL). The combined organic extracts were dried over anhydrous Na$_2$SO$_4$, filtered, and concentrated in vacuo. The crude was purified by column chromatography over silica gel (Gradient: 0-25% EtOAc in hexanes) to give N-(7-((2R,4S,5S)-5-azido-4-hydroxy-5-(iodomethyl)tetrahydrofuran-2-yl)pyrrolo[2,1-f][1,2,4]triazin-4-yl)benzamide (825 mg, 78% yield) as a yellow solid. LCMS (m/z): 506.8 [M+H$^1$H NMR (400 MHz, DMSO-d$_6$) δ 11.26 (s, 1H), 8.20 (d, J=123.8 Hz, 3H), 7.69-7.49 (m, 3H), 7.10 (d, J=39.3 Hz, 2H), 6.09 (d, J=5.1 Hz, 1H), 5.91 (s, 1H), 4.59-4.51 (m, 1H), 3.61-3.51 (m, 2H), 2.63 (dt, J=13.6, 7.1 Hz, 1H), 2.41 (dt, J=12.7, 6.3 Hz, 1H).

Step 4: To a solution of tetrabutylammonium hydroxide (19 mL, 39.19 mmol) in a round-bottom flask was added TFA (3 mL) to adjust the pH to 4.0. N-(7-((2R,4S,5S)-5-azido-4-hydroxy-5-(iodomethyl)tetrahydrofuran-2-yl)pyrrolo[2,1-f][1,2,4]triazin-4-yl)benzamide (825 mg, 1.63 mmol) in anhydrous DCM (20 mL) was added to the solution, followed by 3-chloroperbenzoic acid (1.83 g, 8.16 mmol) which was added in three portions at hourly intervals. After vigorous stirring for additional 3.5 h, the reaction was quenched with saturated aqueous Na$_2$S$_2$O$_3$ solution. The organic layer was separated and washed with saturated aqueous NaHCO$_3$ and brine, dried over anhydrous Na$_2$SO$_4$, filtered, and concentrated in vacuo. The crude was purified by column chromatography over silica gel (Gradient: 0-5% MeOH in DCM) to give N-(7-((2R,4S,5R)-5-azido-4-hydroxy-5-(hydroxymethyl)tetrahydrofuran-2-yl)pyrrolo[2,1-f][1,2,4]triazin-4-yl)benzamide (114 mg, 18% yield) and N-(7-((2R,4S,5R)-5-azido-4-hydroxy-5-(hydroxymethyl) tetrahydrofuran-2-yl)-5-iodopyrrolo[2,1-f][1,2,4]triazin-4-yl)benzamide (74 mg, 9% yield) as yellow solids.

N-(7-((2R,4S,5R)-5-azido-4-hydroxy-5-(hydroxymethyl) tetrahydrofuran-2-yl)pyrrolo[2,1-f][1,2,4]triazin-4-yl)benzamide: LCMS (m/z): 396 [M+H]$^+$; $^1$H NMR (400 MHz, DMSO-d$_6$)) δ 11.28 (s, 1H), 8.57-7.99 (m, 3H), 7.74-7.53 (m, 3H), 7.11 (d, J=46.6 Hz, 2H), 5.89 (s, 1H), 5.68 (d, J=5.6 Hz, 1H), 5.35 (t, J=6.2 Hz, 1H), 4.48 (q, J=6.2 Hz, 1H), 3.65 (dd, J=11.9, 6.2 Hz, 1H), 3.56 (dd, J=11.9, 6.2 Hz, 1H), 2.48 (d, J=6.4 Hz, 1H), 2.41 (q, J=6.5 Hz, 1H).

N-(7-((2R,4S,5R)-5-azido-4-hydroxy-5-(hydroxymethyl) tetrahydrofuran-2-yl)-5-iodopyrrolo[2,1-f][1,2,4]triazin-4-yl)benzamide: LC/MS (ESI, m/z): [M+H]$^+$=522; $^1$H NMR (400 MHz, DMSO-d$_6$) δ 13.22 (s, 1H), 8.51-7.84 (m, 3H), 7.64-7.49 (m, 3H), 7.13 (s, 1H), 5.71 (s, 1H), 5.63 (d, J=5.6 Hz, 1H), 5.33 (t, J=6.1 Hz, 1H), 4.39 (d, J=6.3 Hz, 1H), 3.60 (dd, J=12.0, 6.3 Hz, 1H), 3.52 (dd, J=11.9, 6.1 Hz, 1H), 2.36 (d, J=16.4 Hz, 2H).

Step 5A: A solution of N-(7-((2R,4S,5R)-5-azido-4-hydroxy-5-(hydroxymethyl) tetrahydrofuran-2-yl)-5-iodopyrrolo[2,1-f][1,2,4]triazin-4-yl)benzamide (67 mg, 0.13 mmol) in MeOH (1.5 mL) was added 7N methanolic ammonia solution (0.55 mL, 3.86 mmol) and the reaction was heated at 55° C. overnight. The excess solvent was removed in vacuo and the crude was purified by column chromatography over silica gel (Gradient: 0-5% MeOH in DCM) to give (2R,3S,5R)-5-(4-amino-5-iodopyrrolo[2,1-f][1,2,4]triazin-7-yl)-2-azido-2-(hydroxymethyl) tetrahydrofuran-3-ol (35 mg, 65% yield) as an ivory solid. $^1$H NMR (400 MHz, DMSO-d$_6$) δ 7.90 (s, 1H), 6.99 (s, 1H), 5.72 (t, J=7.1 Hz, 1H), 5.58 (d, J=5.6 Hz, 1H), 5.29 (t, J=6.2 Hz, 1H), 4.37 (q, J=6.1 Hz, 1H), 3.57 (dd, J=11.9, 6.3 Hz, 1H), 3.49 (dd, J=11.8, 6.2 Hz, 1H), 2.38-2.24 (m, 2H); HPLC purity: 98.9%; HRMS (m/z): calc'd for C$_{11}$H$_{12}$IN$_7$O$_3$(M+H)$^+$ 418.0125; found 418.0126.

Step 5B: A solution of N-(7-((2R,4S,5R)-5-azido-4-hydroxy-5-(hydroxymethyl) tetrahydrofuran-2-yl)pyrrolo[2,1-][1,2,4]triazin-4-yl)benzamide (111 mg, 0.28 mmol) in MeOH (2 mL) was added 7N methanolic ammonia solution (1.2 mL, 8.42 mmol) and the reaction was heated at 55° C. overnight. The excess solvent was removed in vacuo and the crude was purified by column chromatography over silica gel (Gradient: 0-6% MeOH in DCM) to (2R,3S,5R)-5-(4-aminopyrrolo[2,1-f][1,2,4]triazin-7-yl)-2-azido-2-(hydroxymethyl)tetrahydrofuran-3-ol (45 mg, 54% yield) as a yellow solid. $^1$H NMR (400 MHz, DMSO-d$_6$) δ 7.85 (s, 1H), 7.70 (s, 2H), 6.84 (d, J=4.5 Hz, 1H), 6.71 (d, J=4.4 Hz, 1H), 5.77-5.72 (m, 1H), 5.56 (d, J=5.6 Hz, 1H), 5.26 (t, J=6.2 Hz, 1H), 4.41 (q, J=6.1 Hz, 1H), 3.57 (dd, J=11.9, 6.2 Hz, 1H), 3.48 (dd, J=11.9, 6.2 Hz, 1H), 2.43 (dt, J=13.3, 6.9 Hz, 1H), 2.28 (ddd, J=12.8, 7.5, 5.7 Hz, 1H); HPLC purity: 98%; HRMS (m/z): calc'd for C$_{11}$H$_{13}$N$_7$O$_3$ (M+H)$^+$ 292.1158; found 292.1156.

Example 48—Synthesis of Compound 25: ({[(2R, 3S,5R)-5-(6-amino-2-chloropurin-9-yl)-2-ethynyl-3-hydroxyoxolan-2-yl] methoxy (hydroxy) phosphoryl} oxy (hydroxy) phosphoryl) oxyphosphonic acid TEA salt

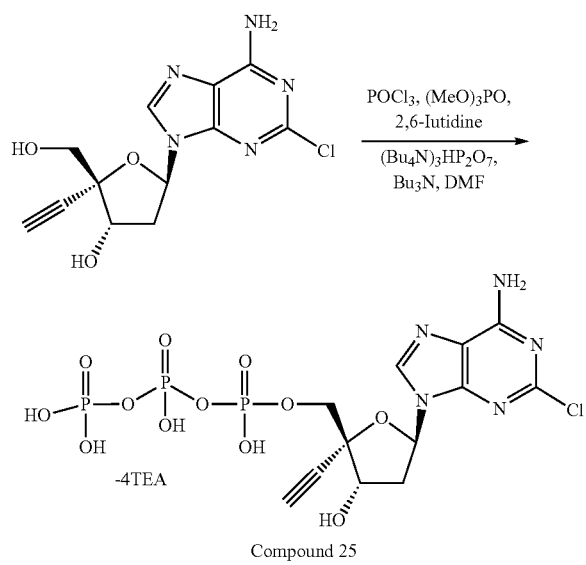

Compound 25

Step 1: To a solution of stavudine (50 mg, 0.21 mmol) in (MeO)$_3$PO (2 mL) was added POCl$_3$ (342 mg, 2.1 mmol) at 0° C. After stirring 10 min, 2,6-lutidine (17 mg, 0.22 mmol) was added. The mixture was stirred for 2 h at room temperature under N$_2$ atmosphere. Then a solution of (Bu$_4$N)$_3$HP$_2$O$_7$ (728 mg, 0.82 mmol) and Bu$_3$N (149 mg, 0.82 mmol) in DMF (3 mL) were added to the above solution. The mixture was stirred for 15 h at room temperature. The mixture was quenched with TEAB (1M, buffer) at 0° C. The mixture was diluted with water and washed with DCM (7×20 mL). The aqueous phase was combined and concentrated under reduced pressure. The residue was purified by ion exchange column with the following conditions (Column: HiTrap DEAE Sepharose FF, 5 mL; Mobile Phase A: Water, Mobile Phase B: Water (0.5M TEAB); Flow rate: 5 mL/min; Gradient: to 25% B in 15 min; Wavelength: 254 nm; RT1(min): 12) to afford 27 mg crude product. The crude product was purified by Prep-HPLC with the following conditions (Column: Atlantis Prep T$_3$ OBD Column, 19*250 mm 10 m; Mobile Phase A: Water (20 mM TEAB), Mobile Phase B: ACN; Flow rate: 25 mL/min; Gradient: to 15% B in 8 min; Wavelength: 254 nm; RT1(min): 6.5). The fraction was collected and concentrated under vacuum, the residue was re-dissolved in CH$_3$CN and H$_2$O, and then was lyophilized to afford ((2R,3S,5R)-5-(6-amino-2-chloro-9H-purin-9-yl)-2-ethynyl-3-hydroxytetrahydrofuran-2-yl)methyl tetrahydrogen triphosphate TEA salt (3.9 mg, 7 mmol, 3.2%) as a white solid. LCMS (ES, m/z): 548/550 [M−H]$^−$, 95.1% purity. Conditions for the LCMS: (Column: XSelect HSS T3, 100*4.6 mm, 3.5 μm; Mobile Phase A: 20 mM TEAA+ H$_2$O, Mobile Phase B: ACN; Flow rate: 1.50 mL/min; Gradient: 0% B to 30% B in 6 min, 30% B to 95% B in 2 min; Wavelength: 254/220 nm; RT1(min): 3.665). $^1$H NMR (400 MHz, D$_2$O) δ 8.34 (s, 1H), 6.29 (dd, J=7.1, 4.4 Hz, 1H), 4.83 (d, J=7.5 Hz, 1H), 4.11 (ddd, J=59.8, 11.4, 5.0 Hz, 2H), 3.03 (q, J=7.5 Hz, 24H), 2.63 (ddp, J=21.4, 14.1, 7.3 Hz, 2H), 1.11 (t, J=7.4 Hz, 36H). $^{31}$P NMR (162 MHz, D$_2$O) δ −6.64 (d, J=21.2 Hz), −12.05 (d, J=19.7 Hz), −22.41 (t, J=20.0 Hz).

Example 49—Synthesis of Compound 174: (2R,3S, 5R)-5-(5-amino-3-oxo-1,2,4-triazin-2(3H)-yl)-2-(chloromethyl)-2-((isobutyryloxy) methyl) tetrahydrofuran-3-yl isobutyrate

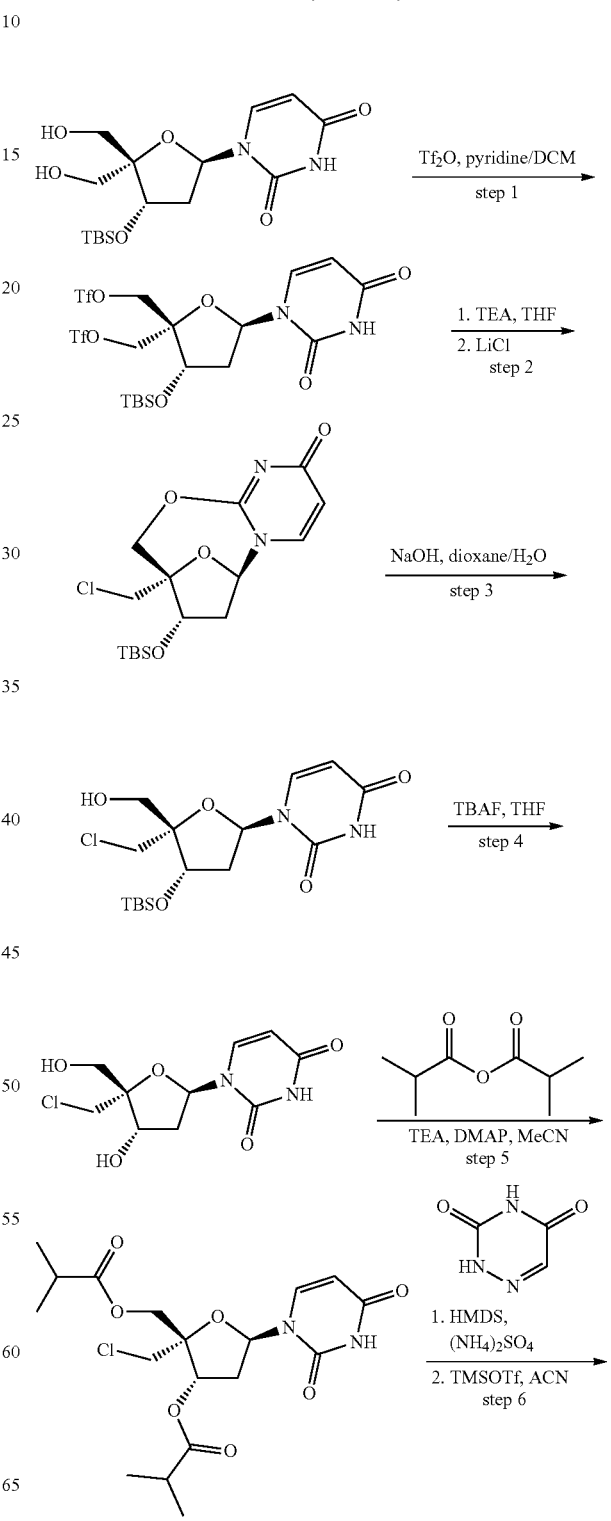

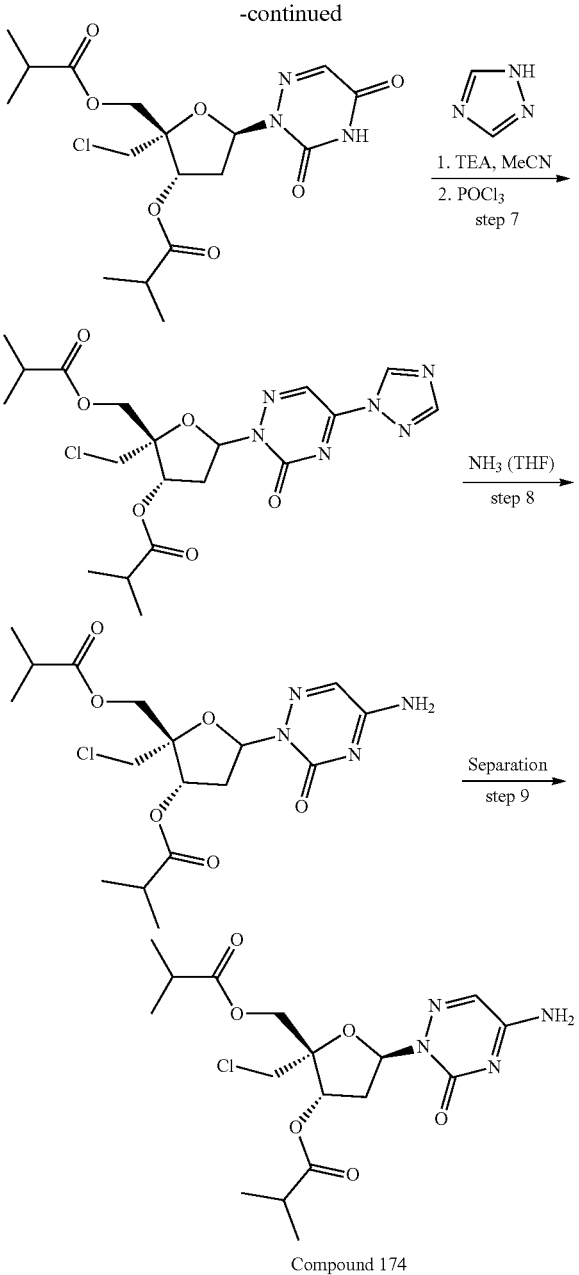

Compound 174

Step 1: To a solution of 1-((2R,4S)-4-((tert-butyldimethylsilyl) oxy)-5,5-bis(hydroxy-methyl)tetrahydrofuran-2-yl) pyrimidine-2,4(1H,3H)-dione (4.71 g, 12.62 mmol) in DCM (150 mL) was added pyridine (5 g, 63.12 mmol) under $N_2$ atmosphere. To the solution was then added $Tf_2O$ (7.82 g, 27.83 mmol) at −35° C. and the reaction was stirred for 1 h. The reaction was quenched by the addition of ice water at 0° C. The resulting mixture was extracted with EtOAc (3×300 mL). The combined organic layers were washed with brine and dried over anhydrous $Na_2SO_4$. After filtration the filtrate was concentrated under reduced pressure. The residue was purified by silica gel column chromatography, eluted with PE/EtOAc (1:1) to afford ((3S,5R)-3-((tert-butyldimethylsilyl) oxy)-5-(2,4-dioxo-3,4-dihydropyrimidin-1(2H)-yl)tetrahydrofuran-2,2-diyl)bis(methylene)bis (trifluoromethanesulfonate) (5.42 g, 8.48 mmol, 67.1%) as a light-yellow solid. LC-MS (ES, m/z): 637 [M+H]⁺.

Step 2: To a solution of ((3S,5R)-3-((tert-butyldimethylsilyl) oxy)-5-(2,4-dioxo-3,4-dihydropyrimidin-1(2H)-yl) tetrahydrofuran-2,2-diyl) bis (methylene) bis (trifluoromethanesulfonate) (5.42 g, 8.51 mmol) in THF (100 mL) was added TEA (13.8 g, 127.22 mmol) under $N_2$ atmosphere. The mixture was stirred for 2 days at 60° C. Then to the reaction was added LiCl (7.23 g, 169.61 mmol). After stirring for 1 day at 60° C., the resulting mixture was cooled to room temperature, concentrated under reduced pressure. The residue was purified by silica gel column chromatography, eluted with PE/EtOAc (1:2) to afford (6R,8S,9R)-8-((tert-butyldimethylsilyl) oxy)-9-(chloromethyl)-7,8,9,10-tetrahydro-2H,6H-6,9-epoxypyrimido[2,1-b] [1,3] oxazocin-2-one (2.82 g, 7.51 mmol, 88.2%) as a light-yellow solid. LC-MS (ES, m/z): 373/375 [M+H]⁺.

Step 3: To a solution of (6R,8S,9R)-8-((tert-butyldimethylsilyl) oxy)-9-(chloromethyl)-7,8,9,10-tetrahydro-2H,6H-6,9-epoxypyrimido[2,1-b] [1,3] oxazocin-2-one (2.82 g, 7.51 mmol) in 1,4-dioxane (50 mL) and water (5 mL) was added NaOH (1.22 g, 30 mmol) under $N_2$ atmosphere. The mixture was stirred for 2 h at room temperature. The mixture was neutralized to pH~7 with saturated $NH_4Cl$ solution, and the resulting mixture was extracted with EtOAc (3×100 mL). The combined organic layers were washed with brine and dried over anhydrous $Na_2SO_4$. After filtration the filtrate was concentrated under reduced pressure. The residue was purified by silica gel column chromatography, eluting with PE/EtOAc (1:3) to afford 1-((2R,4S,5R)-4-((tert-butyldimethylsilyl) oxy)-5-(chloromethyl)-5-(hydroxymethyl) tetrahydrofuran-2-yl) pyrimidine-2,4(1H,3H)-dione (1.33 g, 3.31 mmol, 43.1%) as a light-yellow solid. LC-MS (ES, m/z): 391/393 [M+H]⁺.

Step 4: To a solution of 1-((2R,4S,5R)-4-((tert-butyldimethylsilyl) oxy)-5-(chloromethyl)-5-(hydroxymethyl) tetrahydrofuran-2-yl) pyrimidine-2,4(1H,3H)-dione (1.82 g, 4.81 mmol) in THF (16 mL) was added TBAF (33 mL, 33 mmol, 1 M in THF) under $N_2$ atmosphere. The mixture was stirred for 2 h at room temperature. The resulting mixture was concentrated under reduced pressure and the residue was purified by silica gel column chromatography, eluting with DCM/MeOH (10:1) to afford 1-((2R,4S,5R)-5-(chloromethyl)-4-hydroxy-5-(hydroxymethyl) tetrahydrofuran-2-yl) pyrimidine-2,4(1H,3H)-dione (1.22 g, 4.31 mmol, 97.1%) as a white solid. LC-MS (ES, m/z): 277/279 [M+H]⁺.

Step 5: To a solution of 1-((2R,4S,5R)-5-(chloromethyl)-4-hydroxy-5-(hydroxymethyl) tetrahydrofuran-2-yl) pyrimidine-2,4(1H,3H)-dione (1.42 g, 5.11 mmol) in ACN (50 mL) was added TEA (1 g, 10.12 mmol) and DMAP (62 mg, 0.53 mmol) under $N_2$ atmosphere. To the reaction was then added 2-methylpropanoyl 2-methylpropanoate (3.23 g, 20.21 mmol) and the reaction was stirred overnight at 40° C. The reaction was quenched by the addition of ice water, and the resulting mixture was extracted with EtOAc (3×100 mL). The combined organic layers were washed with saturated $NaHCO_3$ solution and brine, and dried over anhydrous $Na_2SO_4$. After filtration the filtrate was concentrated under reduced pressure. The residue was purified by silica gel column chromatography, eluting with petroleum ether/EtOAc (1:3) to afford (2R,3S,5R)-2-(chloromethyl)-5-(2,4-dioxo-3,4-dihydropyrimidin-1(2H)-yl)-2-((isobutyryloxy) methyl) tetrahydrofuran-3-yl isobutyrate (1.72 g, 4.11 mmol, 83.2%) as a white solid. LC-MS (ES, m/z): 417/419 [M+H]⁺.

Step 6: To a solution of 1,2,4-triazine-3,5(2H,4H)-dione (1.52 g, 13 mmol) in HMDS (20 mL) was added $(NH_4)_2SO_4$ (19 mg, 0.11 mmol) under $N_2$ atmosphere. The mixture was stirred overnight at 110° C. The mixture was evaporated to give a crude product. To a solution of the crude product in ACN (20 mL) was added (2R,3S,5R)-2-(chloromethyl)-5-(2,4-dioxo-3,4-dihydropyrimidin-1(2H)-yl)-2-((isobutyryloxy) methyl) tetrahydrofuran-3-yl isobutyrate (600 mg, 1.42 mmol) and TMSOTf (1.64 g, 7.22 mmol) under N₂ atmosphere. The mixture was stirred overnight at 60° C. The reaction was cooled to room temperature, quenched by the addition of saturated NaHCO₃ solution at 0° C. and extracted with EtOAc (3×50 mL). The combined organic layers were washed with brine, and dried over anhydrous Na₂SO₄. After filtration the filtrate was concentrated under reduced pressure. The residue was purified by silica gel column chromatography, eluting with DCM/MeOH (20:1) to afford (2R,3S)-2-(chloromethyl)-5-(3,5-dioxo-4,5-dihydro-1,2,4-triazin-2(3H)-yl)-2-((isobutyryloxy) methyl) tetrahydrofuran-3-yl isobutyrate (300 mg, 0.72 mmol, 50.1%) as a white semi-solid. LC-MS (ES, m/z): 418/420 [M+H]⁺.

Step 7: To a solution of (2R,3S)-2-(chloromethyl)-5-(3,5-dioxo-4,5-dihydro-1,2,4-triazin-2(3H)-yl)-2-((isobutyryloxy) methyl) tetrahydrofuran-3-yl isobutyrate (140 mg, 0.32 mmol) in ACN (5 mL) was added 1,2,4-triazole (1.51 g, 21.82 mmol) under N₂ atmosphere followed by the addition of TEA (194 mg, 1.92 mmol) dropwise at 0° C. Then was added POCl₃ (1 g, 6.72 mmol) and stirred 24 h at room temperature. The reaction was quenched by the addition of ice water at 0° C. The resulting mixture was extracted with EtOAc (3×50 mL). The combined organic layers were washed with brine, dried over anhydrous Na₂SO₄, filtered and the filtrate was concentrated to afford (2R,3S)-2-(chloromethyl)-2-((isobutyryloxy)methyl)-5-(3-oxo-5-(1H-1,2,4-triazol-1-yl)-1,2,4-triazin-2(3H)-yl)tetrahydrofuran-3-yl isobutyrate (140 mg, 0.38 mmol, 89.1%) as a light-yellow oil. LC-MS (ES, m/z): 469/471 [M+H]⁺.

Step 8: A solution of (2R,3S)-2-(chloromethyl)-2-((isobutyryloxy)methyl)-5-(3-oxo-5-(1H-1,2,4-triazol-1-yl)-1,2,4-triazin-2(3H)-yl)tetrahydrofuran-3-yl isobutyrate (140 mg, 0.32 mmol) in 0.5M NH₃ in THF (30 mL, 15 mmol) was stirred for 24 h at room temperature. The resulting mixture was concentrated under reduced pressure. The residue was purified by Prep-TLC with DCM/MeOH (10:1) to afford (2R,3S)-5-(5-amino-3-oxo-1,2,4-triazin-2(3H)-yl)-2-(chloromethyl)-2-((isobutyryloxy)methyl)tetrahydrofuran-3-yl isobutyrate (80 mg, 0.21 mmol, 64.2%) as a yellow solid. LC-MS (ES, m/z): 417/419 [M+H⁺.

Step 9: The (2R,3S)-5-(5-amino-3-oxo-1,2,4-triazin-2(3H)-yl)-2-(chloromethyl)-2-((isobutyryloxy) methyl) tetrahydrofuran-3-yl isobutyrate (50 mg, 0.12 mmol) was separated by Prep-HPLC with the following conditions (Column: XBridge Prep OBD C18 Column, 30*150 mm, 5 μm; Mobile Phase A: Water (10 mmol/L NH₄HCO₃+0.1% NH₃—H₂O), Mobile Phase B: ACN; Flow rate: 60 mL/min; Gradient: 40% B to 50% B in 8 min, Wavelength: 254/220 nm; RT1(min): 6.83). The fraction was collected and concentrated under vacuum, the residue was re-dissolved in CH₃CN and H₂O, and then was lyophilized to afford (2R, 3S,5R)-5-(5-amino-3-oxo-1,2,4-triazin-2(3H)-yl)-2-(chloromethyl)-2-((isobutyryloxy)methyl) tetrahydrofuran-3-yl isobutyrate (3.9 mg, 0.01 mmol, 8%) as an off-white solid. LC-MS (ES, m/z): 417/419 [M+H]⁺, 99.7% purity. Conditions for the LCMS: (Column: Kinetex EVO C18 Column, 30*3.0 mm, 2.6 μm; Mobile Phase A: Water+5 mM NH₄HCO₃, Mobile Phase B: ACN; Flow rate: 1.50 mL/min; Gradient: 10% B to 95% B in 1.20 min, 95% B to 95% B in 1.78 min, 95% B to 10% B in 1.83 min; Wavelength: 254/220 nm; RT1(min): 0.988). ¹H NMR (400 MHz, DMSO-d₆) δ 8.11-8.06 (m, 1H), 7.96 (s, 1H), 7.53 (s, 1H), 6.52 (m, J=7.3, 4.8 Hz, 1H), 5.52 (m, J=6.4 Hz, 1H), 4.15 (m, J=11.5 Hz, 2H), 3.84-3.77 (d, J=11.7 Hz, 2H), 2.73 (m, J=13.7, 7.0, 4.9 Hz, 1H), 2.67-2.53 (m, 1H), 2.56-2.47 (m, 1H), 2.41 (m, J=13.5, 7.4, 5.8 Hz, 1H), 1.13-1.07 (m, J=7.0, 1.8 Hz, 12H).

Example 50—Synthesis of Compound 21: 4-amino-1-((2R,4S,5R)-4-hydroxy-5-(hydroxymethyl)-5-(trifluoromethyl)tetrahydrofuran-2-yl)pyrimidin-2(1H)-one

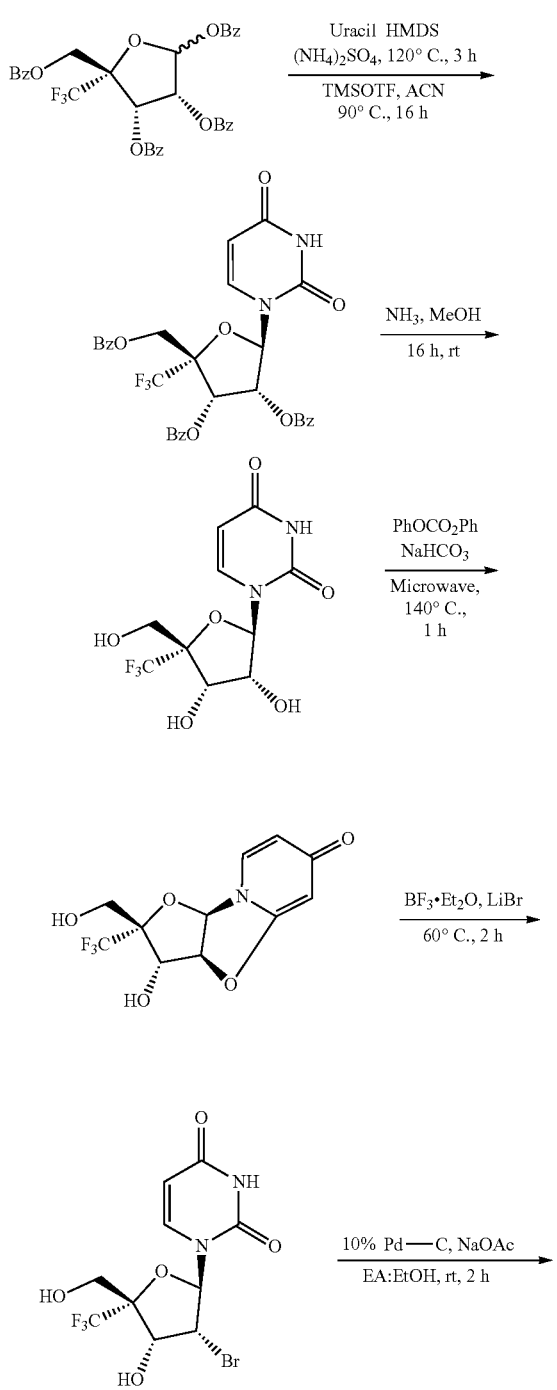

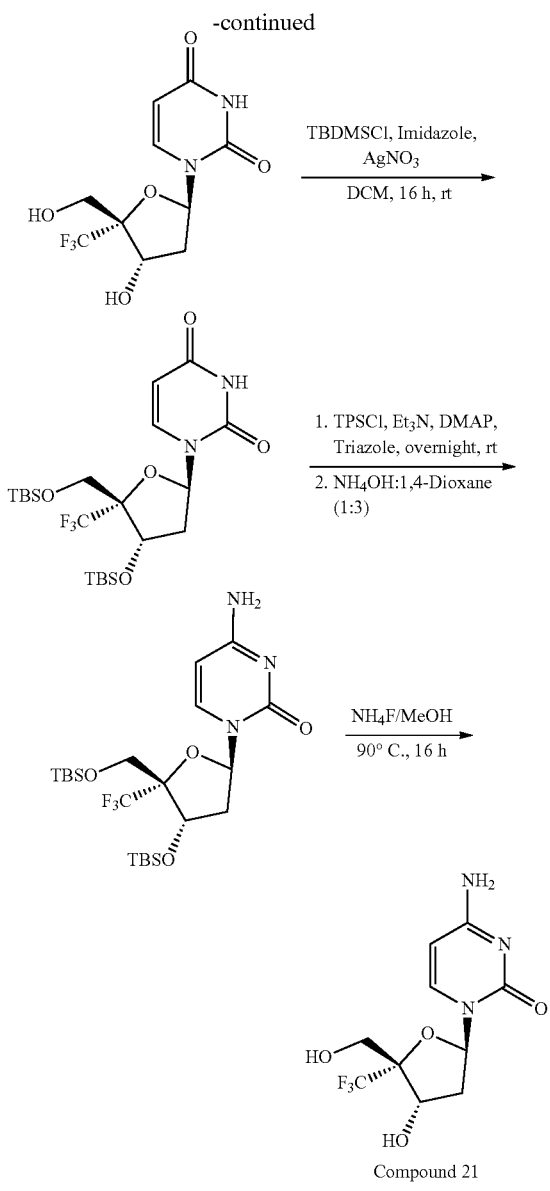

Compound 21

Step 1: A suspension of Uracil (0.46 g; 4.160 mmol) and ammonium sulfate (10 mg) in HMDS (7.0 mL; 33.65 mmol) was heated to 120° C. for 2 h at which time, the reaction mixture became a clear solution. The reaction was then concentrated and the residue was dissolved in acetonitrile (15.0 mL). To this solution was then added a solution (3R,4S,5R)-5-((benzoyloxy)methyl)-5-(trifluoromethyl) tetrahydrofuran-2,3,4-triyl tribenzoate (1.2 g, 1.891 mmol) in acetonitrile (5.0 mL) followed by TMSOTf (1.7 mL, 9.46 mmol) at rt. The reaction mixture was then heated at 90° C. for 16 h, at which time the reaction was complete as determined by TLC and LCMS. The reaction mixture was then quenched with sat. NaHCO₃ solution and the aqueous layer was extracted with EtOAc (15 mL×3). The combined organics were washed once with cold water, dried over Na₂SO₄. The solvent was removed under reduced pressure and the resulting residue was purified by MPLC (Combi-Flash Siliasep 12 g column, eluting with 20% EtOAc in n-Hexane to obtain the titled product (0.5 g, 42.3%). LC-MS (ES, m/z): 625.0 (M+1).

Step 2: A solution of (2R,3S,4R,5R)-2-((benzoyloxy)methyl)-5-(2,4-dioxo-3,4-dihydropyrimidin-1(2H)-yl)-2-(trifluoromethyl)tetrahydrofuran-3,4-diyl dibenzoate (0.75 g, 1.200 mmol) in 7N methanolic ammonia (16.0 mL) was stirred at rt for 16 h. The reaction was monitored by TLC and LCMS and after completion, the reaction mixture was concentrated and dried under vacuum. The resulting residue was purified by MPLC (CombiFlash Siliasep 40 g column) eluting with 8% MeOH in DCM to obtain the desired product (0.35 g, 93.4%). LC-MS (ES, m/z): 312.8 (M+1).

Step 3: To a stirred solution of 1-((2R,3R,4S,5R)-3,4-dihydroxy-5-(hydroxymethyl)-5-(trifluoromethyl) tetrahydrofuran-2-yl) pyrimidine-2,4(1H,3H)-dione (0.28 g, 0.896 mmol) in DMF (2.0 mL) were added diphenyl carbonate (0.21 g, 0.986 mmol) followed by NaHCO₃ (0.018 g, 0.224 mmol) at rt. The reaction mixture was heated at 140° C. for 1 h using a microwave reactor. The reaction mixture was concentrated and the resulting residue was purified by MPLC (CombiFlash Siliasep 40 g column) eluting with 8% MeOH in DCM to obtain the desired product (0.21 g; 79.6%). LC-MS-APSL-0574-051-P1 (ES, m/z): 294.7 (M+1).

Step 4: To a stirred solution of (2R,3S,3aS,9aR)-3-hydroxy-2-(hydroxymethyl)-2-(trifluoromethyl)-2,3,3a,9a-tetrahydro-6H-furo[2',3':4,5]oxazolo[3,2-a]pyrimidin-6-one (0.21 g, 0.714 mmol) in 1,4-Dioxane (10.0 mL) were added LiBr (0.080 g; 0.928 mmol) and BF₃·Et₂O (0.096 mL; 0.785 mmol) at rt. The reaction mixture was stirred at 60° C. for 2 h, at which time TLC and LCMS showed a complete reaction. The reaction mixture was concentrated and the resulting residue was purified by MPLC (CombiFlash, Siliasep 40 g column) eluting with 8% MeOH in DCM to obtain the desired product (0.19 g; 70.9%). LC-MS (ES, m/z): 376.7 (M+1).

Step 5: A solution of 1-((2R,3R,4R,5R)-3-bromo-4-hydroxy-5-(hydroxymethyl)-5-(trifluoromethyl) tetrahydrofuran-2-yl) pyrimidine-2,4(1H,3H)-dione (0.19 g, 0.506 mmol) in methanol (10.0 mL) was degassed with Argon for 5 mins. To the solution was added 10% Pd/C (0.075 g) followed by NaOAc (0.062 g, 0.759 mmol) at rt. The reaction mixture was stirred under H₂ gas (1 atm) at rt for 2 h and the reaction progress was monitored by TLC and LCMS. The reaction mixture was filtered through a celite bed, and the filtrate was concentrated under reduced pressure to get crude product (0.13 g, 86.7%). LC-MS (ES, m/z): 340.8 (M+45_formate adduct).

Step 6: To a stirred solution of 1-((2R,4S,5R)-4-hydroxy-5-(hydroxymethyl)-5-(trifluoromethyl) tetrahydrofuran-2-yl) pyrimidine-2,4(1H,3H)-dione (0.13 g, 0.438 mmol) in DMF (10 mL) were added imidazole (0.29 g, 4.380 mmol), TBDMSCl (0.66 g, 4.380 mmol) and AgNO₃ (0.14 g, 0.876 mmol) at rt. The reaction mixture was stirred at 80° C. for 2 h, at which time the reaction was shown to be complete by TLC and LCMS. The reaction mixture was diluted with EtOAc and aqueous sodium bicarbonate. The organic layer was separated, washed with brine, dried over Na₂SO₄ and concentrated. The resulting residue was purified by MPLC (CombiFlash, Siliasep 40 g column) eluting with 10-15% EtOAc in n-Hexane to obtain the desired product (0.15 g, 65.2%). LC-MS (ES, m/z): 524.9 (M+1).

Step 7: To a stirred solution of 1-((2R,4S,5R)-4-((tert-butyldimethylsilyl)oxy)-5-(((tert-butyldimethylsilyl)oxy)methyl)-5-(trifluoromethyl)tetrahydrofuran-2-yl)pyrimidine-2,4(1H,3H)-dione (0.1 g, 0.190 mmol) in acetonitrile (5.0 mL) were added Et₃N (0.053 mL, 0.381 mmol), DMAP (0.046 g; 0.381 mmol) and TPSCl (0.115 g; 0.381 mmol) at 0° C. The reaction mixture was stirred at rt for 2 h, at which time the reaction was complete by TLC and LCMS. To the reaction was then added aq. ammonia (0.4 ml) and the reaction was stirred at rt for 2 h. The reaction mixture was concentrated and the resulting residue was purified by MPLC (CombiFlash, Siliasep 40 g column) eluting with 4% MeOH in DCM to obtain the desired product (0.08 g, 80.3%). LC-MS (ES, m/z): 524.1 (M+1).

Step 8: To a stirred solution of 4-amino-1-((2R,4S,5R)-4-((tert-butyl-dimethylsilyl)oxy)-5-(((tert-butyldimethylsilyl) oxy) methyl)-5-(trifluoromethyl) tetrahydrofuran-2-yl) pyrimidin-2(1H)-one (0.135 g, 0.257 mmol) in methanol (10.0 mL) was added $NH_4F$ (0.095 g, 2.58 mmol) at rt. The reaction mixture was stirred at 90° C. at which time TLC and LCMS showed a complete reaction. The reaction mass was filtered through a celite bed, and the filtrate was concentrated. The resulting residue was purified by Prep-HPLC by following conditions: Mobile Phase: A=0.02% $NH_4OH$ IN water; B=MeCN; Column: X SELECT (250 mm×20.0 mm), 5.0p; Flow: 18 ml/min; Gradient Program: Time % B 0/5, 2/10, 8/30 to afford the desired product (0.026 g, 21.6%). LC-MS-APSL-0574-062-P1 (ES, m/z): 295.9 (M+1). $^1H$ NMR (400 MHz, DMSO-$d_6$) δ 7.71 (d, J=7.5 Hz, 1H), 7.24 (br s, 1H), 7.20 (br s, 1H), 6.37 (t, J=6.7 Hz, 1H), 5.75 (d, J=7.5 Hz, 2H), 5.56-5.43 (m, 1H), 4.69 (br t, J=5.9 Hz, 1H), 3.74-3.62 (m, 2H), 2.24 (t, J=6.5 Hz, 2H).

Example 51—Synthesis of Compound 14: ((2R,3S, 5R)-5-(4-amino-5-fluoro-2-oxopyrimidin-1(2H)-yl)-2-(chloromethyl)-3-hydroxytetrahydrofuran-2-yl) methyl tetrahydrogen triphosphate TEA Salt mg crude product. The crude product was re-purified by Prep-HPLC with the following conditions (Column: XSelect CSH Prep C18 OBD Column, 19*250 mm, 5 μm; Mobile Phase A: Water (50 mM TEAB), Mobile Phase B: ACN; Flow rate: 25 mL/min; Gradient: 2% B to 25% B in 7 min; Wavelength: 254/220 nm; $RT_1$(min): 5.7). The fraction was collected and concentrated under vacuum, the residue was re-dissolved in $CH_3CN$ and $H_2O$, and then was lyophilized to afford ((2R,3S,5R)-5-(4-amino-5-fluoro-2-oxopyrimidin-1(2H)-yl)-2-(chloromethyl)-3-hydroxytetrahydrofuran-2-yl) methyl tetrahydrogen triphosphate TEA salt (11 mg, 0.01 mmol, 8.3%) as a white solid. LC-MSO (ES, m/z): 532/534 [M−H]⁻, 96.6% purity. Conditions for the LCMS: (Column: EVO C18, 150 mm, 4.6 mm; Mobile Phase A: 20 mmol TEA, Mobile Phase B: ACN; Flow rate: 1.20 mL/min; Gradient: 0% B to 95% B in 6 min, 95% B to 95% B hold for 7.9 min; Wavelength: 254/220 nm; RT1(min): 2.358). $^1H$ NMR (400 MHz, $D_2O$) δ 7.94 (d, J=6.1 Hz, 1H), 6.33-6.07 (m, 1H), 4.698-4.735 (m, 1H), 4.29-3.92 (m, 2H), 3.82-3.67 (m, 2H), 3.05 (q, J=7.3 Hz, 24H), 2.38 (dd, J=11.7, 6.1 Hz, 2H), 1.13 (t, J=7.3 Hz, 36H). $^{31}P$ NMR (162 MHz, $D_2O$) δ −7.61, −11.81, −22.75.

Example 52—Synthesis of Compound 54: 4-amino-1-[(2R,4S,5R)-5-(chloromethyl)-5-(hydroxymethyl)-4-methoxyoxolan-2-yl]-3,4-dihydropyrimidin-2-one

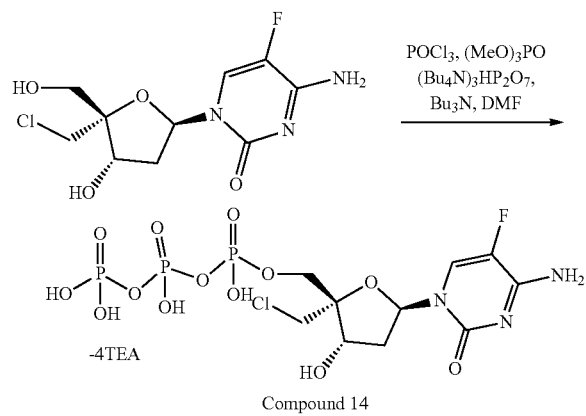

Compound 14

To a solution of 4-amino-1-((2R,4S,5R)-5-(chloromethyl)-4-hydroxy-5-(hydroxymethyl)tetrahydrofuran-2-yl)-5-fluoropyrimidin-2(1H)-one (40 mg, 0.21 mmol) in (MeO)$_3$PO (3 mL) was added $POCl_3$ (667 mg, 4.41 mmol) at 0° C. The mixture was stirred for 2 h at room temperature under $N_2$ atmosphere. Then a solution of $(Bu_4N)_3HP_2O_7$ (3.93 g, 4.35 mmol) and $Bu_3N$ (0.6 mL) in DMF (5 mL) were added to the above solution. The mixture was stirred for 15 h at room temperature. The mixture was quenched with TEAB buffer (1M) at 0° C. The mixture was diluted with water and washed with DCM (7×40 mL). The aqueous phase was combined and concentrated under reduced pressure. The residue was purified by ion exchange column with the following conditions (Column: HiTrap DEAE Sepharose FF, 5 mL; Mobile Phase A: Water, Mobile Phase B: Water (0.5M TEAB); Flow rate: 5 mL/min; Gradient: 0% to 50% B in 10 min; Wavelength: 254/220 nm; $RT_1$(min): 6.3) to afford 40

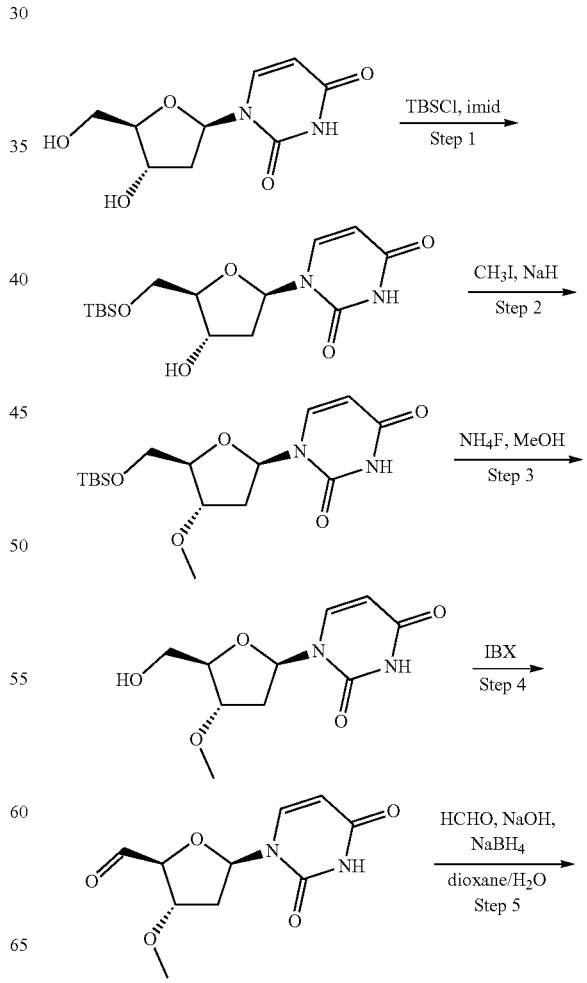

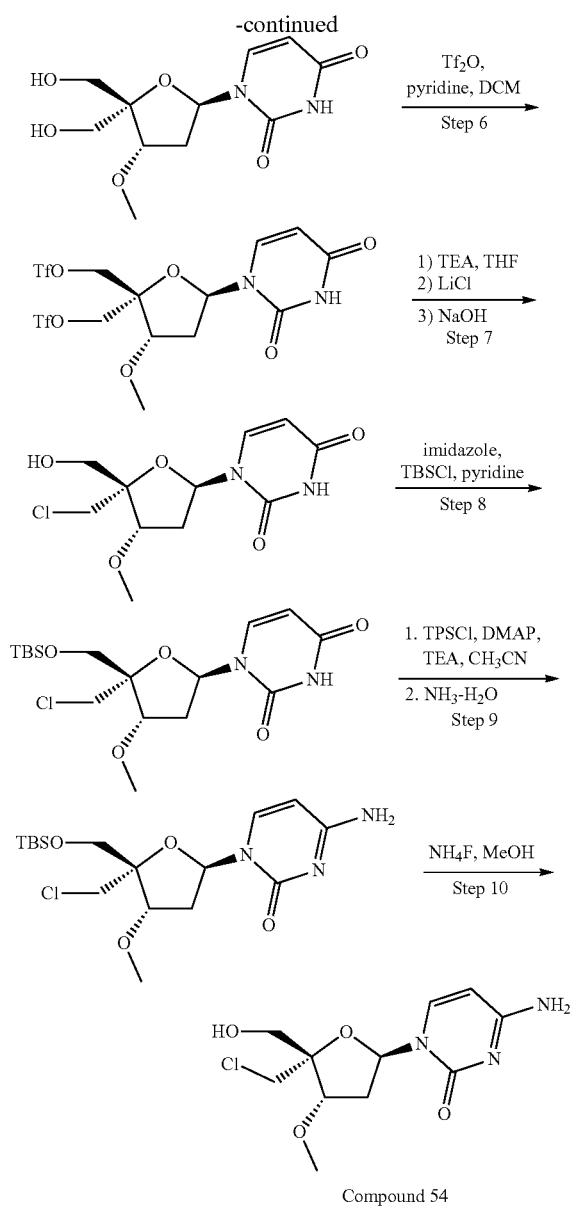

Step 1: To a stirred solution of 2'-deoxyuridine (10 g, 43.82 mmol) and imidazole (5.9 g, 87.64 mmol) in DMF (100 mL) was added TBSCl (6.6 g, 43.82 mmol) in portions at 0° C. under a nitrogen atmosphere. The resulting mixture was then stirred for 16 h at room temperature under nitrogen atmosphere. The reaction was diluted with EtOAc (20 mL), and the resulting mixture was washed with brine (3×20 mL), and dried over anhydrous $Na_2SO_4$. After filtration the filtrate was concentrated under reduced pressure to afford 1-[(2R,4S,5R)-5-{[(tert-butyldimethylsilyl) oxy] methyl}-4-hydroxyoxolan-2-yl]-3H-pyrimidine-2,4-dione (12.0 g, crude) as a yellow oil. The crude product was used in the next step directly without further purification. LC-MS (ES, m/z): 343 $(M+H)^+$.

Step 2: To a stirred solution of 1-[(2R,4S,5R)-5-{[(tert-butyldimethylsilyl) oxy]methyl}-4-hydroxyoxolan-2-yl]-3H-pyrimidine-2,4-dione (12.0 g, crude) in THF (200 mL) was added NaH (1.7 g, 70.1 mmol) at 0° C. under nitrogen atmosphere. The mixture was stirred for 10 minutes at 0° C. Then $CH_3I$ (14.9 g, 105.12 mmol) was added in portions. The mixture was stirred for 16 hours at room temperature and quenched by the addition of ice water (100 mL). The resulting mixture was extracted with EtOAc (2×50 mL). The combined organic layers were washed with brine (3×50 mL), dried over anhydrous $Na_2SO_4$. After filtration the filtrate was concentrated under reduced pressure. The residue was purified by silica gel column chromatography, eluting with PE/EtOAc (1:1) to afford 1-[(2R,4S,5R)-5-{[(tert-butyldimethylsilyl) oxy] methyl}-4-methoxyoxolan-2-yl]-3H-pyrimidine-2,4-dione (8.0 g, 22.44 mmol, 51.3% yield in two steps) as a white oil. LC-MS (ES, m/z): 357 $(M+H)^+$.

Step 3: A solution of 1-[(2R,4S,5R)-5-{[(tert-butyldimethylsilyl) oxy] methyl}-4-methoxyoxolan-2-yl]-3H-pyrimidine-2,4-dione (8.0 g, 22.44 mmol) and $NH_4F$ (16.6 g, 448.82 mmol) in MeOH (100 mL) was stirred for 16 h at room temperature under nitrogen atmosphere. The resulting mixture was filtered; and the filter cake was washed with MeOH (2×20 mL). The combined filtrate was concentrated under reduced pressure to afford 1-[(4S)-5-(hydroxymethyl)-4-methoxyoxolan-2-yl]-3H-pyrimidine-2,4-dione (5.0 g, crude) as a white solid which was used in the next step directly without further purification. LC-MS (ES, m/z): 243 $(M+H)^+$.

Step 4: To a solution of 1-[(2R,4S,5R)-5-(hydroxymethyl)-4-methoxyoxolan-2-yl]-3H-pyrimidine-2,4-dione (5.0 g, crude) in ACN (50 mL), was added IBX (11.6 g, 41.28 mmol). The mixture was stirred for 2 h at 80° C. under nitrogen atmosphere. The resulting mixture was filtered; the filter cake was washed with ACN (2×20 mL). The combined filtrate was concentrated under reduced pressure to afford (3S)-5-(2,4-dioxo-3H-pyrimidin-1-yl)-3-methoxyoxolane-2-carbaldehyde (3.0 g, crude) as a white solid which was used in the next step directly without further purification. LC-MS (ES, m/z): 241 $(M+H)^+$.

Step 5: To a stirred solution of (2S,3S,5R)-5-(2,4-dioxo-3H-pyrimidin-1-yl)-3-methoxyoxolane-2-carbaldehyde (3.0 g, crude) in 1,4-dioxane (60 mL), was added NaOH aq. (12.5 mL, 2M). This was followed by the addition of HCHO (5 mL, 37% in water) dropwise at room temperature under nitrogen atmosphere. The mixture was stirred for 15 h at room temperature and then cooled to 0° C. To the above mixture was added $NaBH_4$ (0.9 g, 24.97 mmol) in portions over 5 min at 0° C. The resulting mixture was stirred for 2 h at room temperature and then quenched by the addition of sat. $NH_4Cl$ (aq.) at 0° C. The resulting mixture was extracted with EtOAc (3×60 mL). The combined organic layers were washed with brine (2×100 mL), and dried over anhydrous $Na_2SO_4$. After filtration the filtrate was concentrated under reduced pressure. The residue was purified by silica gel column chromatography, eluting with PE/EtOAc (1:1) to afford 1-[(2R,4S)-5,5-bis(hydroxymethyl)-4-methoxyoxolan-2-yl]-3H-pyrimidine-2,4-dione; methane (300 mg, 1.10 mmol, 7.9% yield in three steps) as a white solid. LC-MS (ES, m/z): 273 $(M+H)^+$.

Step 6: To a stirred solution of 1-[(2R,4S)-5,5-bis(hydroxymethyl)-4-methoxyoxolan-2-yl]-3H-pyrimidine-2,4-dione (300 mg, 1.10 mmol) in pyridine (5 mL) was added $Tf_2O$ (621.0 mg, 2.20 mmol) dropwise at −30° C. under nitrogen atmosphere. The resulting mixture was stirred for 1 h at room temperature and quenched by the addition of water (10 mL). The resulting mixture was extracted with DCM (2×10 mL). The combined organic layers were washed with brine (2×20 mL) and dried over anhydrous $Na_2SO_4$. After filtration the filtrate was concentrated under reduced pressure. The residue was purified by Prep-TLC (PE/EtOAc 1:1) to afford [(3S,5R)-5-(2,4-dioxo-3H-pyrimidin-1-yl)-3- methoxy-2-[(trifluoromethanesulfonyloxy) methyl] oxolan-2-yl] methyl trifluoromethanesulfonate (300 mg, 0.56 mmol, 50.8%) as a yellow oil. LC-MS (ES, m/z): 537 (M+H)+.

Step 7: To a solution of [(3S,5R)-5-(2,4-dioxo-3H-pyrimidin-1-yl)-3-methoxy-2-[(trifluoromethanesulfonyloxy) methyl]oxolan-2-yl]methyl trifluoromethanesulfonate (300 mg, 0.56 mmol) in THF (3 mL), was added Et₃N (566.0 mg, 5.60 mmol). The mixture was stirred for 3 h at room temperature. To the above mixture was added LiCl (46 mg, 1.12 mmol) and the resulting mixture was stirred overnight at room temperature. This was followed by the addition of a solution of NaOH (82.0 mg, 2.08 mmol) in water (1 mL). The resulting mixture was stirred for additional 3 h at room temperature and concentrated under vacuum. The residue was purified by silica gel column chromatography, eluting with DCM/MeOH (50:1) to afford 3-acetyl-1-[(2R,4S,5R)-5-(chloromethyl)-5-(hydroxymethyl)-4-methoxyoxolan-2-yl]urea (120 mg, 0.42 mmol, 75.0%) as a yellow solid. LC-MS (ES, m/z): 291/293 (M+H)+.

Step 8: To a stirred solution of 3-acetyl-1-[(2R,4S,5R)-5-(chloromethyl)-5-(hydroxymethyl)-4-methoxyoxolan-2-yl] urea (120.0 mg, 0.42 mmol) and imidazole (56.2 mg, 0.81 mmol) in DMF (5 mL) was added TBSCl (123.0 mg, 0.81 mmol) in portions at room temperature under a nitrogen atmosphere. The resulting mixture was stirred for 3 h at room temperature and diluted with EtOAc (10 mL). The resulting solution was washed with brine (3×10 mL) and concentrated under reduced pressure. The residue was purified by silica gel chromatography, eluting with PE/EtOAc (1:1) to afford 1-[(2R,4S,5R)-5-{[(tert-butyl-dimethylsilyl) oxy] methyl}-5-(chloromethyl)-4-methoxyoxolan-2-yl]-3H-pyrimidine-2,4-dione (150.0 mg, 0.12 mmol, 89.9%) as a yellow oil. LC-MS (ES, m/z): 405/407 (M+H)+.

Step 9: To a stirred solution of 1-[(2R,4S,5R)-5-{[(tert-butyldimethylsilyl) oxy]methyl}-5-(chloromethyl)-4-methoxyoxolan-2-yl]-3H-pyrimidine-2,4-dione (150.0 mg, 0.36 mmol) and DMAP (135.0 mg, 10.8 mmol) in MeCN (3 mL) were added Et₃N (111.0 mg, 1.08 mmol) and TPSCl (336.0 mg, 1.08 mmol) in portions at room temperature under nitrogen atmosphere. The resulting mixture was stirred for 2 h at room temperature under nitrogen atmosphere. To the above mixture was added NH₃·H₂O (129.0 mg, 3.69 mmol) dropwise at room temperature. The resulting mixture was stirred for 4 h at room temperature and concentrated under reduced pressure. The residue was purified by silica gel column chromatography, eluting with PE/EtOAc (1:1) to afford 4-amino-1-[(2R,4S,5R)-5-{[(tert-butyldimethylsilyl) oxy]methyl}-5-(chloromethyl)-4-methoxyoxolan-2-yl]-3,4-dihydropyrimidin-2-one (80.0 mg, 0.20 mmol, 53.3%) as a white solid. LC-MS (ES, m/z): 404/406 (M+H)+.

Step 10: A solution of 4-amino-1-[(2R,4S,5R)-5-{[(tert-butyldimethylsilyl) oxy]methyl}-5-(chloromethyl)-4-methoxyoxolan-2-yl]-3,4-dihydropyrimidin-2-one (80.0 mg, 0.20 mmol) and NH₄F (72.0 mg, 2.00 mmol) in MeOH (2 mL) was stirred for 1 day at room temperature under nitrogen atmosphere. The resulting mixture was concentrated under reduced pressure. The residue was purified by Prep-HPLC with the following conditions: Column: XBridge Shield RP18 OBD Column, 30×150 mm, 5 µm; Mobile Phase A: Water (10 mmol/L NH₄HCO₃), Mobile Phase B: ACN; Flow rate: 60 mL/min; Gradient: 2% B to 20% B in 8 min; Wavelength: 254/210 nm. The product-containing fractions were combined and evaporated partially to remove the solvents, then lyophilized overnight to afford 4-amino-1-[(2R,4S,5R)-5-(chloromethyl)-5-(hydroxymethyl)-4-methoxyoxolan-2-yl]-3,4-dihydropyrimidin-2-one (35.8 mg, 0.12 mmol, 62.4%) as a white solid. LC-MS (ES, m/z): 290/292 (M+H)+, 99.2% purity. Conditions for the HPLC: (Column: Shim-pack Scepter C18-120, 33*3.0 mm, 3.0 µm; Mobile Phase A: Water/5 mM NH₄HCO₃, Mobile Phase B: Acetonitrile; Flow rate: 1.5000 mL/min; Gradient: 10% B to 95% B in 1.19 min, 95% B to 95% B in 0.6 min, 95% B to 10% B in 0.02 min; Wavelength: 254/220 nm; RT1(min): 0.564). ¹H NMR (400 MHz, DMSO-d₆) δ 7.76 (d, J=7.6 Hz, 1H), 7.19 (d, J=25.6 Hz, 2H), 6.16 (t, J=6.9 Hz, 1H), 5.74 (d, J=7.6 Hz, 1H), 5.29 (t, J=5.2 Hz, 1H), 4.06 (dd, J=6.0, 3.4 Hz, 1H), 3.78-3.70 (m, 2H), 3.63-3.55 (m, 2H), 3.30 (s, 3H), 2.41-2.37 (m, 1H), 2.18-2.11 (m, 1H).

Example 53—Synthesis of Compound 56: 1-((2R, 4S)-5-allyl-4-hydroxy-5-(hydroxymethyl)tetrahydrofuran-2-yl)-4-aminopyrimidin-2(1H)-one

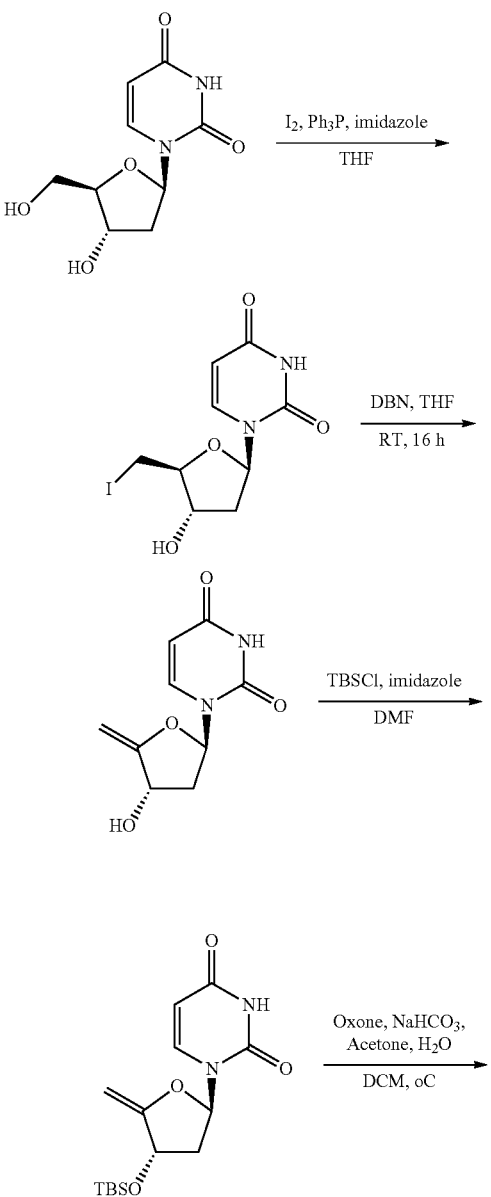

-continued

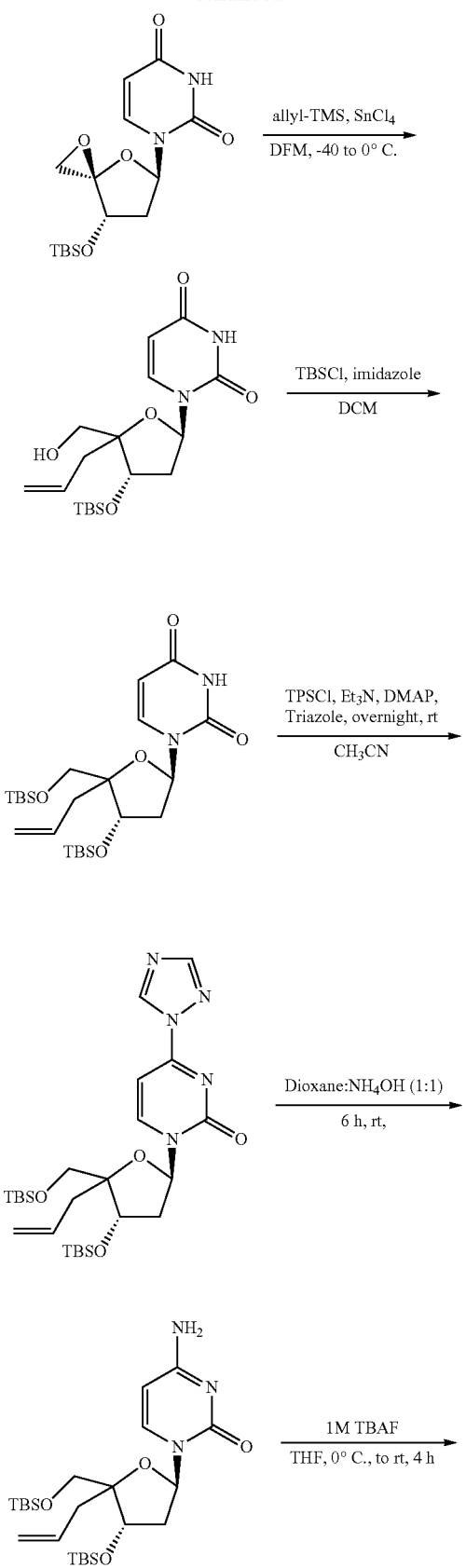

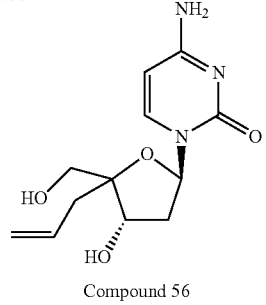

Compound 56

Step 1: To a stirred solution of 1-((2R,4S,5R)-4-hydroxy-5-(hydroxymethyl) tetrahydrofuran-2-yl) pyrimidine-2,4(1H,3H)-dione (10.00 g, 43.82 mmol) in THF (100 mL) was added imidazole (5.96 g, 87.64 mmol) and TPP (17.24 g, 65.73 mmol) at rt. The reaction was stirred for 15 min. and was then treated with 12 (8.34 g, 65.73 mmol), added in a portionwise manner at 0° C. After stirring the reaction mixture at rt for 16 h, TLC showed a complete reaction. The reaction mixture was filtered, and the filter cake washed with THF (50 mL). The filtrate was concentrated under reduced pressure to afford crude compound. The crude material was dissolved in DCM (500 mL), washed with water (200 mL) and the aqueous layer was extracted with DCM (200 mL). The combined organics were washed with water (300 mL), brine (300 mL), dried over anhydrous $Na_2SO_4$, filtered, and concentrated under reduced pressure to afforded crude compound. The crude residue was purified by CombiFlash column chromatography by eluting with 10% MeOH in DCM to afford the desired product (4.2 g, 28%) as white solid. LC-MS (ES, m/z): 336.90 (M−H).

Step 2: To a stirred solution of 1-((2R,4S,5S)-4-hydroxy-5-(iodomethyl) tetrahydrofuran-2-yl) pyrimidine-2,4(1H,3H)-dione (19.80 g 159.76 mmol) in THF (180 mL) was added DBN (19.80 g, 159.76 mmol) at rt. The reaction mixture was stirred at 60° C. for 6 h at which time TLC and LCMS showed a complete reaction. The reaction mixture was concentrated, and the resulting residue was purified by CombiFlash chromatography by eluting with 3% MeOH in DCM to afford the desired product (10.0 g; 55.5%) as off-white solid. LC-MS (ES, m/z): 210.8 (M+H)⁺.

Step 3: To a stirred solution of 1-((2R,4S)-4-hydroxy-5-methylene-tetrahydrofuran-2-yl)pyrimidine-2,4(1H,3H)-dione (9.0 g, 42.818 mmol) in DMF (90 mL) was added imidazole (8.744 g, 128.455 mmol) followed by TBDMS-Cl (12.907 g, 85.637 mmol) at rt. The reaction mixture at rt for 4 h, at which time TLC and LCMS showed the reaction to be complete. The reaction mixture was diluted with ice water and extracted with EtOAc. The combined organic fractions were washed with water and brine, then dried over sodium sulphate, filtered, and concentrated. The residue was purified by CombiFlash column chromatography by eluting with 1% methanol in DCM to afford 5.2 g, (Yield: 37%) of 1-((2R,4S)-4-((tert-butyldimethylsilyl)oxy)-5-methylenetetrahydrofuran-2-yl)pyrimidine-2,4(1H,3H)-dione. LC-MS (ES, m/z): 324.90 (M+H)⁺.

Step 4: To a stirred solution of 1-((2R,4S)-4-((tert-butyldimethylsilyl)oxy)-5-methylenetetrahydrofuran-2-yl)pyrimidine-2,4(1H,3H)-dione (2.50 g, 7.70 mmol) in DCM (40 mL) was added $NaHCO_3$ (9.71 g, 115.58 mmol) and acetone (17.90 g, 308.21 mmol). The reaction was cooled to 0° C. and was stirred for 15 min. To this cold solution was added Oxone (16.58 g, 53.94 mmol) in water (75 mL) dropwise. The reaction was stirred for 2 hr at 0° C. at which time TLC and LCMS showed a complete reaction. The reaction was diluted with cold DCM and washed with cold sodium thiosulphate solution, ice water and cold brine. The organics were dried over sodium sulphate, filtered, and concentrated to get the titled compound as pale-yellow solid (2.7 g). LC-MS (ES, m/z): 340.95 (M+H).

Step 5: To a stirred solution of 1-((3S,5R,7S)-7-((tert-butyldimethylsilyl)oxy)-1,4-dioxaspiro[2.4]heptan-5-yl)pyrimidine-2,4(1H,3H)-dione (2.50 g, 7.34 mmol) in DCM (40 mL) was added allytrimethyl silane (3.36 g, 29.373 mmol). The reaction was stirred for 15 min and then cooled to −40° C. To this cooled solution was then added SnCl$_4$ (7.65 g, 29.37 mmol) in a dropwise manner at −40° C. The reaction was stirred for 2 hr at 0° C. at which time TLC and LCMS showed a complete reaction. The reaction was quenched with NaHCO$_3$ solution, and extracted with DCM. The combined organics were washed with water and brine, and dried over sodium sulphate. The solution was filtered and concentrated. The residue was purified by CombiFlash chromatography eluting with 1.2% Methanol in DCM to afford 0.85 g, (30%) of the titled product as pale-yellow solid. LC-MS (ES, m/z): 380.85 (M−H).

Step 6: To a stirred solution of 1-((2R,4S,5R)-5-allyl-4-((tert-butyldimethylsilyl) oxy)-5-(hydroxymethyl)tetrahydrofuran-2-yl)pyrimidine-2,4(1H,3H)-dione (0.840 g, 2.196 mmol) in DMF (8 mL), was added imidazole (0.448 g, 6.588 mmol) followed by TBDMS-Cl (0.662 g, 4.392 mmol) at rt. The reaction was stirred at rt for 4 hr at which time TLC and LCMS showed a complete reaction. The reaction mixture was diluted with ice water and extracted with EtOAc. The combined organics were washed with water and brine, then dried over sodium sulphate. The solution was filtered and concentrated. The residue was purified by CombiFlash chromatography eluting with 30% EtOAc in Hexane to afford 0.82 g, (75%) of the titled compound as solid foam. LC-MS (ES, m/z): 495.10 (M−H).

Step 7: To a stirred solution of 1-((2R,4S,5R)-5-allyl-4-((tert-butyl-dimethylsilyl)oxy)-5-(((tert-butyldimethylsilyl)oxy)methyl) tetrahydrofuran-2-yl)pyrimidine-2,4(1H,3H)-dione (0.300 g, 0.604 mmol) in MeCN (7 mL) was added Et3N (0.244 g, 2.415 mmol) and DMAP (0.148 g, 1.208 mmol) at rt. The reaction was stirred for 15 min and cooled to 0° C. The reaction was treated with TPS-Cl (0.37 g, 1.21 mmol) added in a portionwise manner at 0° C. and stirring was continued at rt for 2 h. The reaction was cooled to 0° C. and treated with 1,2,4-Triazole (0.209 g, 3.019 mmol) and stirred at rt for 2 h at which time TLC and LCMS showed a complete reaction. The reaction was diluted with ice water and extracted with EtOAc. The combined organics were washed with water and brine, then dried over sodium sulphate. The solution was filtered and concentrated. The residue was purified by CombiFlash chromatography by eluting with 40% EtOAc in n-Hexane to afford 0.26 g, (73%) of the titled compound as an off-white solid. LC-MS (ES, m/z): 570.20 (M+Na).

Step 8: To a stirred solution of 1-((2R,4S,5R)-5-allyl-4-((tert-butyldimethylsilyl) oxy)-5-(((tert-butyldimethylsilyl) oxy) methyl) tetrahydrofuran-2-yl)-4-(1H-1,2,4-triazol-1-yl)pyrimidin-2(1H)-one (0.210 g, 0.383 mmol) in 1,4-Dioxane (2 mL) added ammonia solution (2 mL). The reaction was stirred for 15 min at rt then heated to 30° C. for 4 h. at which time TLC and LCMS showed complete reaction. The reaction mass was concentrated to afford the titled compound as a pale-yellow liquid (0.210 g). LC-MS (ES, m/z): 496.10 (M+1).

Step 9: To a stirred solution of 1-((2R,4S,5R)-5-allyl-4-((tert-butyldimethylsilyl) oxy)-5-(((tert-butyldimethylsilyl) oxy)methyl) tetrahydrofuran-2-yl)-4-aminopyrimidin-2 (1H)-one (0.195 g, 0.393 mmol) in THF (3 mL) was added TBAF (1M in THF) (2.36 mL, 2.36 mmol). The reaction mixture was stirred at rt for 4 h at which time TLC and HPLC shows a complete reaction. The reaction mixture was concentrated, and residue was purified by prep-HPLC under the following conditions: mobile phase: A=0.02% NH$_4$OH in water, B=CH$_3$CN, Column: X SELECT (250 mm×20.0 mm), 5.0μ Flow: 18.0 mL/min, Gradient: Time/% B:0/5,2/10,8/20. The above obtained material was repurified by prep-HPLC by following same conditions as above to afford 10 mg of the titled compound as a white solid. LC-MS (ES, m/z): 267.80 (M+1). $^1$H NMR (400 MHz, DMSO-d$_6$) δ 7.86 (d, J=7.5 Hz, 1H), 7.15-7.00 (m, 2H), 6.11 (t, J=6.5 Hz, 1H), 5.86 (br d, J=7.3 Hz, 1H), 5.69 (d, J=7.3 Hz, 1H), 5.18 (d, J=4.8 Hz, 1H), 5.09-4.98 (m, 3H), 4.27 (br d, J=6.0 Hz, 1H), 3.40 (t, J=5.5 Hz, 2H), 2.41-2.30 (m, 1H), 2.28-2.14 (m, 2H), 2.06 (td, J=6.7, 13.2 Hz, 1H).

Example 54—Synthesis of Compound 59: 4-amino-1-[(2R,4R,5R)-5-(chloromethyl)-4-hydroxy-5-(hydroxymethyl) oxolan-2-yl] pyrimidin-2-one

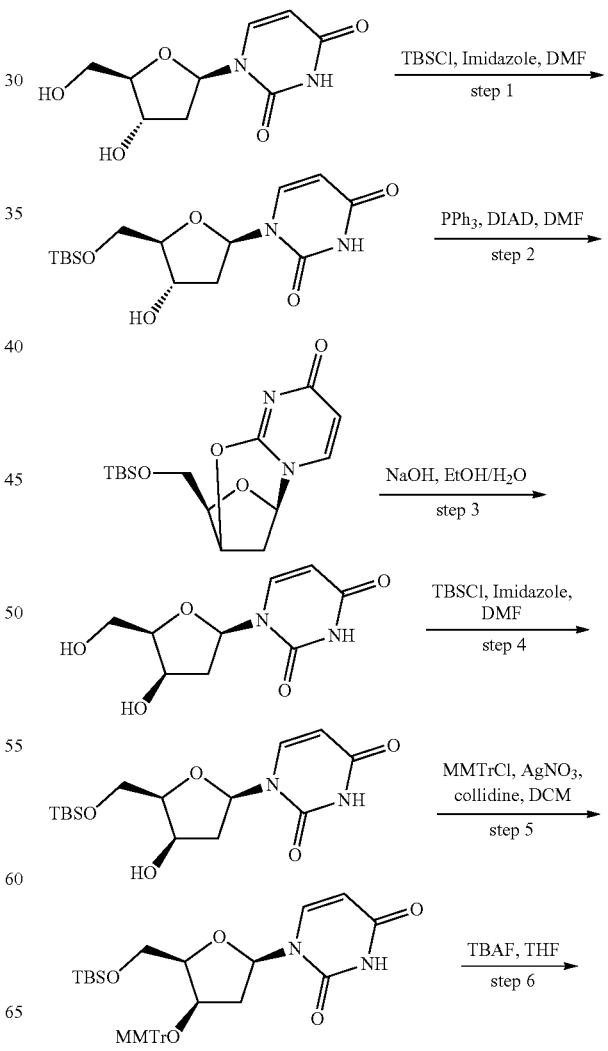

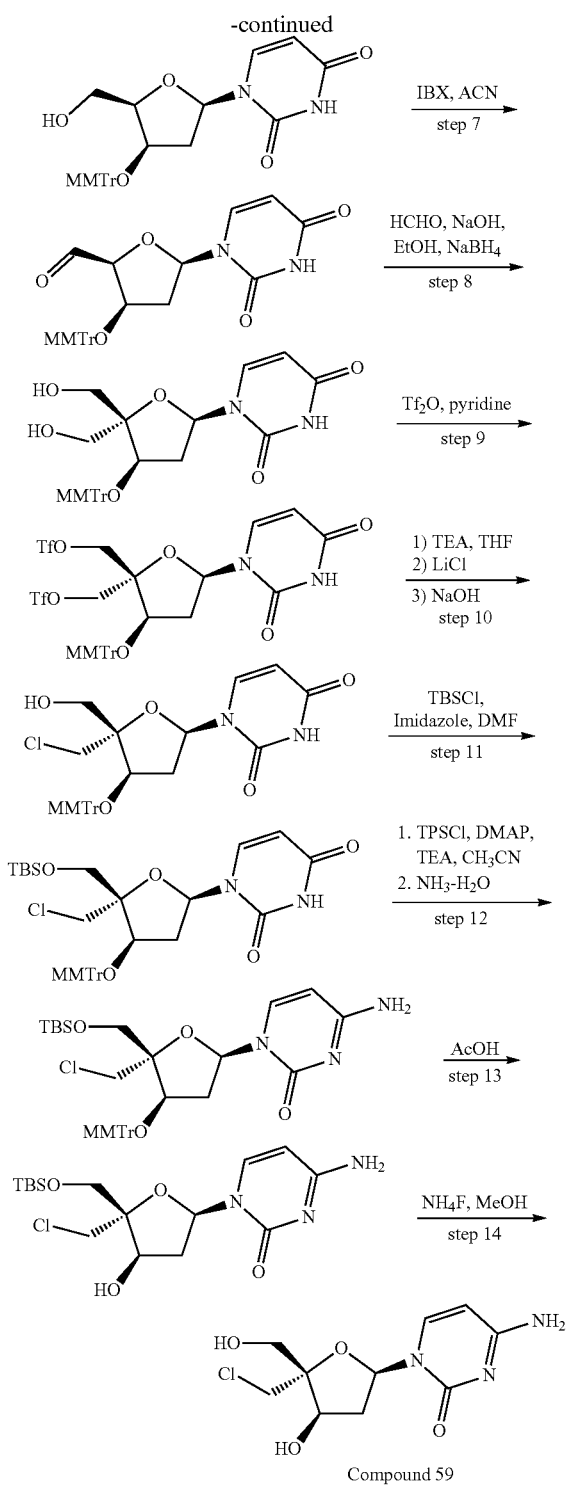

Compound 59

Step 1: To a stirred solution of 2'-deoxyuridine (40.0 g, 175.28 mmol) and imidazole (17.9 g, 262.92 mmol) in DMF (800 mL) was added TBSCl (26.4 g, 175.28 mmol) in portions at 0° C. under nitrogen atmosphere. The resulting mixture was stirred for 2 h at room temperature under nitrogen atmosphere. The reaction was quenched by the addition of 100 mL of sat. NaHCO$_3$(aq.) at 0° C. The resulting mixture was extracted with EtOAc (3×500 mL). The combined organic layers were washed with brine (2×500 mL) and dried over anhydrous Na$_2$SO$_4$. After filtration the filtrate was concentrated under reduced pressure. The residue was purified by silica gel column chromatography, eluting with PE/EtOAc (1:1) to afford 1-[(2R,4S,5R)-5-1{[(tert-butyldimethylsilyl) oxy] methyl}-4-hydroxyoxolan-2-yl]-3H-pyrimidine-2,4-dione (50.0 g, 146.0 mmol, 83.3%) as a white solid. LC-MS (ES, m/z): 343 (M+H)$^+$.

Step 2: To a stirred solution of 1-[(2R,4S,5R)-5-{[(tert-butyldimethylsilyl) oxy]methyl}-4-hydroxyoxolan-2-yl]-3H-pyrimidine-2,4-dione (50.0 g, 146.00 mmol) and PPh$_3$ (114.9 g, 437.99 mmol) in DMF (500 mL) was added DIAD (88.6 g, 438.00 mmol) dropwise at 0° C. under nitrogen atmosphere. The resulting mixture was stirred overnight at room temperature under nitrogen atmosphere. The reaction was quenched by the addition of water (220 mL) at 0° C. The resulting solution was extracted with EtOAc (3×200 mL). The combined organic layers were washed with brine (2×200 mL) and dried over anhydrous Na$_2$SO$_4$. After filtration the filtrate was concentrated under reduced pressure. The residue was purified by silica gel column chromatography, eluting with CHCl$_2$/MeOH (30:1) to afford (1R,10R)-10-{[(tert-butyldimethylsilyl) oxy] methyl}-8,11-dioxa-2,6-diazatricyclo [7.2.1.0^{2,7}]dodeca-3,6-dien-5-one (35.0 g, 107.8 mmol, 73.9%) as a light-yellow solid. LC-MS (ES, m/z): 325 (M+H)$^+$.

Step 3: To a stirred solution of (1R,10R)-10-{[(tert-butyldimethylsilyl) oxy]methyl}-8,11-dioxa-2,6-diazatricyclo [7.2.1.0^{2,7}] dodeca-3,6-dien-5-one (35.0 g, 107.9 mmol) in H$_2$O (70 mL) and EtOH (350 mL) was added 1M aq. NaOH (220 mL, 220.0 mmol) dropwise at 0° C. The resulting mixture was stirred overnight at 60° C. and then cooled to room temperature. The resulting mixture was neutralized to pH 7 with AcOH (aq.) and concentrated under reduced pressure. The residue was purified by silica gel column chromatography, eluted with DCM/MeOH (30:1) to afford 1-[(2R,4R,5R)-4-hydroxy-5-(hydroxymethyl) oxolan-2-yl]-3H-pyrimidine-2,4-dione (20.0 g, 87.6 mmol, 81.2%) as a white solid. LC-MS (ES, m/z): 229 (M+H)$^+$.

Step 4: To a stirred solution of 1-[(2R,4R,5R)-4-hydroxy-5-(hydroxymethyl) oxolan-2-yl]-3H-pyrimidine-2,4-dione (20.0 g, 87.64 mmol) and imidazole (8.9 g, 131.46 mmol) in DMF (400 mL) was added TBSCl (13.2 g, 87.64 mmol) in portions at 0° C. under nitrogen atmosphere. The resulting mixture was stirred for 2 h at room temperature under nitrogen atmosphere and then quenched by the addition of sat. NaHCO$_3$(aq.) (50 mL) at 0° C. The resulting mixture was extracted with EtOAc (3×200 mL). The combined organic layers were washed with brine (2×200 mL) and dried over anhydrous Na$_2$SO$_4$. After filtration the filtrate was concentrated under reduced pressure. The residue was purified by silica gel column chromatography, eluting with PE/EtOAc (1:1) to afford 1-[(2R,4R,5R)-5-{[(tert-butyldimethylsilyl) oxy] methyl}-4-hydroxyoxolan-2-yl]-3H-pyrimidine-2,4-dione (25.0 g, 73.0 mmol, 83.3%) as a white solid. LC-MS (ES, m/z): 343 (M+H)$^+$.

Step 5: To a stirred solution of 1-[(2R,4R,5R)-5-{[(tert-butyldimethylsilyl) oxy]methyl}-4-hydroxyoxolan-2-yl]-3H-pyrimidine-2,4-dione (25.0 g, 73.00 mmol) and AgNO$_3$ (24.7 g, 146.00 mmol) in DCM (600 mL) were added s-collidine (88.0 g, 730.00 mmol) and MMTrCl (98.7 g, 292.00 mmol) in portions at 0° C. under nitrogen atmosphere. The resulting mixture was stirred overnight at room temperature under nitrogen atmosphere. The resulting mixture was filtered; the filter cake was washed with DCM (3×300 mL). The combined organic layers were washed with brine (2×300 mL), NaHCO$_3$(aq.) (100 ml) and dried over anhydrous Na$_2$SO$_4$. After filtration the filtrate was concentrated under reduced pressure to afford 1-[(2R,4R, 5R)-5-{[(tert-butyldimethylsilyl) oxy] methyl}-4-[(4-methoxyphenyl) diphenylmethoxy] oxolan-2-yl]-3H-pyrimidine-2,4-dione (35.0 g, crude). The crude product was used in the next step directly without further purification. LC-MS (ES, m/z): 615 (M+H)$^+$.

Step 6: To a stirred solution of 1-[(2R,4R,5R)-5-{[(tert-butyldimethylsilyl) oxy]methyl}-4-[(4-methoxyphenyl) diphenylmethoxy] oxolan-2-yl]-3H-pyrimidine-2,4-dione (35.0 g, crude) in THF (350 mL), was added TBAF (17.8 g, 68.31 mmol) in portions at room temperature. The resulting mixture was stirred overnight at room temperature. The resulting mixture was concentrated under reduced pressure. The residue was diluted with brine (100 mL). The resulting mixture was extracted with EtOAc (3×200 mL) and dried over anhydrous Na$_2$SO$_4$. After filtration the filtrate was concentrated under reduced pressure. The residue was purified by silica gel column chromatography, eluting with PE/EtOAc (1:2) to afford 1-[(2R,4R,5R)-5-(hydroxymethyl)-4-[(4-methoxyphenyl)diphenylmethoxy] oxolan-2-yl]-3H-pyrimidine-2,4-dione (20.0 g, 40.0 mmol, 54.8% yield in two steps) as a white solid. LC-MS (ES, m/z): 499 (M−H)$^-$.

Step 7: To a stirred solution of 1-[(2R,4R,5R)-5-(hydroxymethyl)-4-[(4-methoxyphenyl) diphenylmethoxy] oxolan-2-yl]-3H-pyrimidine-2,4-dione (20.0 g, 39.96 mmol) in ACN (40 mL) was added IBX (22.4 g, 79.91 mmol) in portions at room temperature under nitrogen atmosphere. The resulting mixture was stirred for 2 h at 60° C. under nitrogen atmosphere. The mixture was allowed to cool down to room temperature. The resulting mixture was filtered; the filter cake was washed with acetonitrile (3×5 mL). The combined filtrate was concentrated under vacuum to give (2S,3R,5R)-5-(2,4-dioxo-3H-pyrimidin-1-yl)-3-[(4-methoxyphenyl) diphenylmethoxy] oxolane-2-carbaldehyde (18.0 g, crude) as a white solid. The crude product was used in the next step directly without further purification. LC-MS (ES, m/z): 499 (M+H)$^+$.

Step 8: To a stirred solution of (2S,3R,5R)-5-(2,4-dioxo-3H-pyrimidin-1-yl)-3-[(4-methoxyphenyl) diphenylmethoxy] oxolane-2-carbaldehyde (18.0 g, crude) in 1,4-dioxane (150 mL) were added HCHO (9 mL, 37% in water) and NaOH aq. (40 mL, 2M) dropwise at room temperature. The resulting mixture was degassed three times with nitrogen, and then stirred overnight at room temperature under a nitrogen atmosphere. To the above mixture was added NaBH$_4$ (5.8 g, 151.65 mmol) in portions over 5 min at 0° C. The resulting mixture was stirred for additional 1 h at room temperature. The reaction was quenched by the addition of sat. NH$_4$Cl (aq.) (200 mL) at 0° C. The resulting mixture was extracted with EtOAc (3×200 mL). The combined organic layers were washed with brine (2×200 mL), dried over anhydrous Na$_2$SO$_4$. After filtration the filtrate was concentrated under reduced pressure. The residue was purified by silica gel column chromatography, eluting with CH$_2$Cl$_2$/MeOH (20:1) to afford 1-[(2R,4R)-5,5-bis(hydroxymethyl)-4-[(4-methoxyphenyl) diphenylmethoxy] oxolan-2-yl]-3H-pyrimidine-2,4-dione (12.6 g, 23.76 mmol, 34.0% yield in two steps) as a white solid. LC-MS (ES, m/z): 529 (M−H)$^-$.

Step 9: To a solution of 1-[(2R,4R)-5,5-bis(hydroxymethyl)-4-[(4-methoxy-phenyl)diphenylmethoxy] oxolan-2-yl]-3H-pyrimidine-2,4-dione (5.0 g, 9.42 mmol) in pyridine (40 mL), was added Tf$_2$O (8.0 g, 28.27 mmol) at −30° C. The resulting mixture was stirred for 2 h at room temperature under nitrogen atmosphere and quenched by the addition of sat. NaHCO$_3$(aq.) (200 mL) at 0° C. The resulting mixture was extracted with EtOAc (2×200 mL). The combined organic layers were washed with brine (2×200 mL), and dried over anhydrous Na$_2$SO$_4$. After filtration the filtrate was concentrated under reduced pressure. The residue was purified by silica gel column chromatography, eluting with CH$_2$Cl$_2$/MeOH (20:1) to afford [(3R,5R)-5-(2,4-dioxo-3H-pyrimidin-1-yl)-3-[(4-methoxyphenyl) diphenylmethoxy]-2-[(trifluoromethanesulfonyloxy)methyl] oxolan-2-yl] methyl trifluoromethanesulfonate (4.0 g, 5.0 mmol, 53.41%) as a yellow solid. LC-MS (ES, m/z): 795 (M+H)$^+$.

Step 10: To a stirred solution of [(3R,5R)-5-(2,4-dioxo-3H-pyrimidin-1-yl)-3-[(4-methoxyphenyl) diphenylmethoxy]-2-[(trifluoromethanesulfonyloxy)methyl] oxolan-2-yl]methyl trifluoromethanesulfonate (4.0 g, 5.03 mmol) in THF (40 mL) was added TEA (5.1 g, 50.33 mmol) in portions at room temperature under nitrogen atmosphere. The resulting mixture was stirred for 3 h at room temperature. To the above mixture was added LiCl (493.0 mg, 11.63 mmol) and the resulting mixture was stirred overnight at room temperature. To the resulting mixture was added a solution of NaOH (226.0 mg, 5.65 mmol) in water (3 mL). The resulting mixture was stirred for additional 3 h at room temperature. After completion, 20 mL of water was added and extracted with EtOAc (3×60 mL). The organic layers were washed with brine, and dried over anhydrous Na$_2$SO$_4$. After filtration the filtrate was concentrated under reduced pressure. The residue was purified by silica gel chromatography, eluting with PE/EtOAc (1:1) to afford 1-[(2R,4R,5R)-5-(chloromethyl)-5-(hydroxymethyl)-4-[(4-methoxyphenyl) diphenylmethoxy] oxolan-2-yl]-3H-pyrimidine-2,4-dione (600.0 mg, 1.1 mmol, 21.7%). LC-MS (ES, m/z): 549/551 (M+H)$^+$.

Step 11: To a stirred solution of 1-[(2R,4R,5R)-5-(chloromethyl)-5-(hydroxymethyl)-4-[(4-methoxyphenyl) diphenylmethoxy] oxolan-2-yl]-3H-pyrimidine-2,4-dione (600.0 mg, 1.12 mmol) and imidazole (112.0 mg, 1.64 mmol) in DMF (12 mL) was added TBSCl (165.0 mg, 1.12 mmol) in portions at 0° C. under nitrogen atmosphere. The resulting mixture was stirred for 2 h at room temperature under nitrogen atmosphere and quenched by the addition of sat. NaHCO$_3$(aq.) (100 mL) at 0° C. The resulting solution was extracted with EtOAc (2×100 mL). The combined organic layers were washed with brine (2×100 mL), and dried over anhydrous Na$_2$SO$_4$. After filtration the filtrate was concentrated under reduced pressure. The residue was purified by silica gel column chromatography, eluting with CH$_2$Cl$_2$/MeOH (20:1) to afford 1-[(2R,4R,5R)-5-1{[(tert-butyldimethylsilyl) oxy] methyl}-5-(chloro-methyl)-4-[(4-methoxyphenyl) diphenylmethoxy] oxolan-2-yl]-3H-pyrimidine-2,4-dione (700.0 mg, 1.1 mmol, 96.57%) as a white solid. LC-MS (ES, m/z): 663/665 (M+H)$^+$.

Step 12: To a stirred solution of 1-[(2R,4R,5R)-5-{[(tert-butyldimethylsilyl) oxy]methyl}-5-(chloromethyl)-4-[(4-methoxyphenyl) diphenylmethoxy] oxolan-2-yl]-3H-pyrimidine-2,4-dione (600.0 mg, 0.91 mmol) and DMAP (332.0 mg, 2.72 mmol) in ACN (24 mL) were added TEA (275.0 mg, 2.72 mmol) and TPSCl (822.0 mg, 2.72 mmol) in portions at room temperature. The resulting mixture was stirred for 2 h at room temperature. To the above mixture was added NH$_3$·H$_2$O (12 mL, 0.71 mmol) dropwise at room temperature. The resulting mixture was stirred for additional 1 h at room temperature. The resulting mixture was concentrated under reduced pressure. The residue was purified by silica gel column chromatography, eluting with CH$_2$Cl$_2$/MeOH (10:1) to afford 4-amino-1-[(2R,4R,5R)-5-{[(tert-butyldimethylsilyl) oxy] methyl}-5-(chloromethyl)-4-[(4-methoxyphenyl) diphenyl-methoxy]oxolan-2-yl] pyrimidin-2-one (400.0 mg, 0.6 mmol, 66.77%) as a light-yellow solid. LC-MS (ES, m/z): 662/664 (M+H)$^+$.

Step 13: A solution of 4-amino-1-[(2R,4R,5R)-5-{[(tert-butyldimethylsilyl) oxy]methyl}-5-(chloromethyl)-4-[(4-methoxyphenyl) diphenylmethoxy] oxolan-2-yl] pyrimidin-2-one (400.0 mg, 0.60 mmol) in acetic acid (8 mL, 80%) was stirred for 1 h at 50° C. under nitrogen atmosphere. The mixture was allowed to cool down to room temperature and neutralized to pH 7 with saturated $NaHCO_3$(aq.). The resulting mixture was extracted with EtOAc (3×100 mL). The combined organic layers were washed with brine (3×100 mL), dried over anhydrous $Na_2SO_4$. After filtration the filtrate was concentrated under reduced pressure. The residue was purified by silica gel column chromatography, eluting with $CH_2Cl_2$/MeOH (10:1) to afford 4-amino-1-[(2R,4R,5R)-5-{[(tert-butyldimethylsilyl) oxy] methyl}-5-(chloromethyl)-4-hydroxyoxolan-2-yl] pyrimidin-2-one (200.0 mg, 0.51 mmol, 84.92%) as a white solid. LC-MS (ES, m/z): 390/392 (M+H)⁺.

Step 14: To a stirred solution of 4-amino-1-[(2R,4R,5R)-5-{[(tert-butyldimethylsilyl) oxy] methyl}-5-(chloromethyl)-4-hydroxyoxolan-2-yl] pyrimidin-2-one (200.0 mg, 0.51 mmol) in MeOH (2 mL) was added $NH_4F$ (200.0 mg, 5.40 mmol) in portions at room temperature. The resulting mixture was stirred overnight at room temperature. The resulting mixture was filtered; and the filter cake was washed with MeOH (3×5 mL). The filtrate was concentrated under reduced pressure. The residue was purified by Prep-HPLC with the following conditions: Column: XBridge Prep OBD C18 Column, 30×150 mm, 5 μm; Mobile Phase A: water (10 mmol/L $NH_4HCO_3$), Mobile Phase B: ACN; Flow rate: 60 mL/min; Gradient: 2% B to 16% B in 8 min; Wavelength: 254/220 nm. The product-containing fractions were combined and evaporated partially to remove the solvents, then lyophilized overnight to afford 4-amino-1-[(2R,4R,5R)-5-(chloromethyl)-4-hydroxy-5-(hydroxymethyl) oxolan-2-yl]pyrimidin-2-one (59.6 mg, 0.2 mmol, 42.15%) as a white solid. LC-MS 276/278 (M+H)⁺. 99.2% purity. Conditions for the HPLC: (Column: Atlantis T3, 100*4.6 mm, 3.5 μm; Mobile Phase A: Water/0.05% TFA, Mobile Phase B: MeOH; Flow rate: 1.0000 mL/min; Gradient: 3% B to 95% B in 8.00 min, 95% B to 95% B in 2.00 min, 90% B to 10% B in 0.50 min; Wavelength: 254/220 nm; RT1(min): 3.54). ¹H NMR (400 MHz, DMSO-d₆) δ 7.89 (d, J=7.6 Hz, 1H), 7.17 (brs, 1H), 7.10 (brs, 1H), 6.16-6.13 (m, 1H), 5.75 (d, J=7.6 Hz, 1H), 5.50-5.49 (m, 1H), 4.81-4.79 (m, 1H), 4.27-4.25 (m, 1H), 3.78-3.64 (m, 4H), 2.82-2.75 (m, 1H), 1.88-1.86 (m, 1H).

Example 55—Synthesis of Compound 44: (([(2R,3S,5R)-5-(4-amino-2-oxopyrimidin-1-yl)-2-ethyl-3-hydroxyoxolan-2-yl] methoxy(hydroxy) phosphoryloxy (hydroxy) phosphoryl) oxyphosphonic acid; tetrakis(triethylamine)

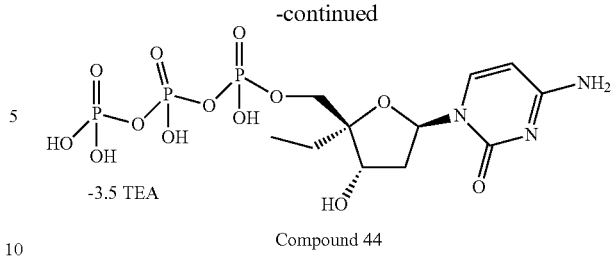

Compound 44

To a stirred solution of 4-amino-1-[(2R,4S,5R)-5-ethyl-4-hydroxy-5-(hydroxymethyl) oxolan-2-yl] pyrimidin-2-one (40 mg, 0.21 mmol) in (MeO)₃PO (4 mL) was added POCl₃ (480 mg, 3.22 mmol) dropwise at 0° C. under $N_2$ atmosphere. The resulting mixture was stirred for 2 h at room temperature. Then a solution of $(Bu_4N)_3HP_2O_7$ (2.82 g, 3.21 mmol) and $Bu_3N$ (580 mg, 3.11 mmol) in DMF (4 mL) were added dropwise at 0° C. under $N_2$ atmosphere. The resulting mixture was stirred for 18 h at room temperature under $N_2$ atmosphere. The mixture was quenched with TEAB buffer (1M) at 0° C., diluted with water and washed with DCM (7×40 mL). The aqueous phase was combined and concentrated under reduced pressure. The residue was purified by ion exchange column with the following conditions (Column: HiTrap DEAE Sepharose FF, 5 mL; Mobile Phase A: Water, Mobile Phase B: Water (0.5M TEAB); Flow rate: 5 mL/min mL/min; Gradient: 60% B to 80% B in 15 min; Wavelength: 254 nm/220 nm; RT1(min): 8.7) to afford the crude product. The crude product was purified by Prep-HPLC with the following conditions (Column: YMC Triart C18 ExRs 5 m, 20*250 mm; Mobile Phase A: Water (50 mM TEAB), Mobile Phase B: ACN; Flow rate: 25 mL/min; Gradient: 3% B to 20% B in 10 min; Wavelength: 254/220 nm; RT1(min): 8.8). The fraction containing product was collected and concentrated under vacuum, the residue was re-dissolved in $CH_3CN$ and $H_2O$, and then was lyophilized to afford ((2R,3S,5R)-5-(4-amino-2-oxopyrimidin-1(2H)-yl)-2-ethyl-3-hydroxytetrahydrofuran-2-yl) methyl tetrahydrogen triphosphate TEA Salt (17.2 mg, 0.02 mmol, 11.9%) as a white solid. LCMS (ES, m/z): 494 [M−H]⁻, 98.3% purity. Conditions for the LCMS: (Column: Kinetex EVO, 100*4.6 mm, 2.6 μm; Mobile Phase A: 20 mM TEAA, Mobile Phase B: ACN; Flow rate: 1.20 mL/min; Gradient: 0% B to 95% B in 8.00 min; Wavelength: 254/220 nm; RT1(min): 3.382). ¹H NMR (400 MHz, D₂O) δ 7.90 (d, J=7.8 Hz, 1H), 6.13 (d, J=6.9 Hz, 1H), 6.02 (d, J=7.6 Hz, 1H), 4.56 (t, J=6.4 Hz, 1H), 3.19-2.80 (m, 21H), 2.30 (p, J=8.2, 7.8 Hz, 2H), 1.58 (ddd, J=44.3, 14.7, 7.5 Hz, 2H), 1.15 (tt, J=7.4, 1.6 Hz, 31H), 0.85 (t, J=7.6 Hz, 3H). 31P NMR (162 MHz, D₂O) δ −9.91 (d, J=20.7 Hz), −11.52 (d, J=20.1 Hz), −23.17 (t, J=19.8 Hz).

Example 56—Synthesis of Compound 44: ((2R,3S,5R)-5-(4-amino-2-oxopyrimidin-1(2H)-yl)-3-hydroxy-2-vinyltetrahydrofuran-2-yl)methyl tetrahydrogen triphosphate TEA salt

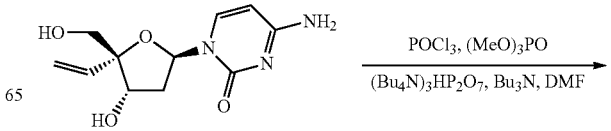

-continued

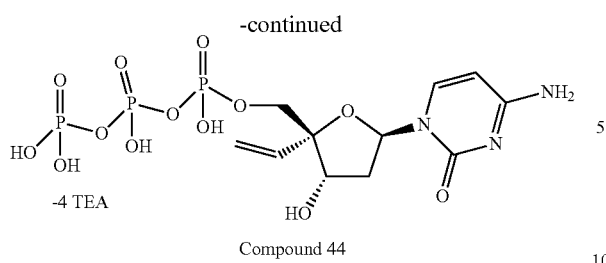

Compound 44

To a stirred solution of 4-amino-1-[(2R,4S,5R)-5-ethenyl-4-hydroxy-5-(hydroxymethyl) oxolan-2-yl] pyrimidin-2-one (50 mg, 0.21 mmol) in (MeO)$_3$PO (6 mL) was added POCl$_3$ (605 mg, 3.92 mmol) dropwise at 0° C. under N$_2$ atmosphere. The resulting mixture was stirred for 2 h at room temperature under N$_2$ atmosphere. To the above solution, (Bu$_4$N)$_3$HP$_2$O$_7$ (3.6 g, 3.92 mmol) and Bu$_3$N (1.2 mL) in DMF (4 mL) were added dropwise at 0° C. under N$_2$ atmosphere. The resulting mixture was stirred for 14 h at room temperature under N$_2$ atmosphere. The mixture was basified to pH 11 with TEAB buffer (1M) at 0° C. The resulting mixture was washed with DCM (7×40 mL). The aqueous solution was concentrated under vacuum. The residue was purified by ion-exchange column with the following conditions (Column: HiTrap DEAE Sepharose FF, 5 mL; Mobile Phase A: Water, Mobile Phase B: Water (0.5M TEAB); Flow rate: 5 mL/min; Gradient: 2% B to 50% B in 15 min, Wavelength: 254/220 nm; RT1(min): 6.7) to afford 50 mg crude product. The crude product (50 mg) was re-purified by Prep-HPLC with the following conditions (Column: YMC-Actus Triart C18 ExRS, 20*250 mm, 5 μm; Mobile Phase A: water (50 mM TEAB), Mobile Phase B: ACN; Flow rate: 25 mL/min; Gradient: 2% B to 20% B in 10 min, Wavelength: 254/220 nm; RT1(min): 6.8). The fractions containing product were collected and concentrated under vacuum, the residue was re-dissolved in CH$_3$CN and H$_2$O, and then was lyophilized to afford ((2R,3S,5R)-5-(4-amino-2-oxopyrimidin-1(2H)-yl)-3-hydroxy-2-vinyltetrahydrofuran-2-yl)methyl tetrahydrogen triphosphate TEA salt (16 mg, 18 μmol, 8.7%) as a white solid. LC-MS (ES, m/z): 492 [M–H]$^+$, 97.1% purity. Conditions for the HPLC: (Column: Kinetex EVO, 100*4.6 mm, 2.6 μm; Mobile Phase A: 20 mM TEAA, Mobile Phase B: Acetonitrile; Flow rate: 1.20 mL/min; Gradient: 0% B to 0% B in 1.0 min, 0% B to 95% B in 7.0 min; Wavelength: 254 nm; RT1(min): 3.487). $^1$H NMR (300 MHz, D$_2$O) δ 8.03 (d, J=7.6 Hz, 1H), 6.21 (t, J=5.5 Hz, 1H), 6.05 (d, J=7.6 Hz, 1H), 5.88 (dd, J=17.4, 10.9 Hz, 1H), 5.43 (dd, J=17.4, 1.4 Hz, 1H), 5.33 (dd, J=10.9, 1.4 Hz, 1H), 4.72 (d, J=7.8 Hz, 1H), 4.19 (dd, J=11.5, 5.6 Hz, 1H), 3.86 (dd, J=11.5, 3.8 Hz, 1H), 3.08 (q, J=7.3 Hz, 24H), 2.32-2.21 (m, 2H), 1.16 (t, J=7.3 Hz, 36H). $^{31}$P NMR (121 MHz, D$_2$O) δ -6.40 (d, J=21.0 Hz), -11.70 (d, J=19.7 Hz), -22.55 (t, J=20.5 Hz).

Example 57—Synthesis of Compound 119: 4-amino-1-((2R,4R,5R)-5-(chloromethyl)-3,3-difluoro-4-hydroxy-5-(hydroxymethyl)tetrahydrofuran-2-yl)pyrimidin-2(1H)-one

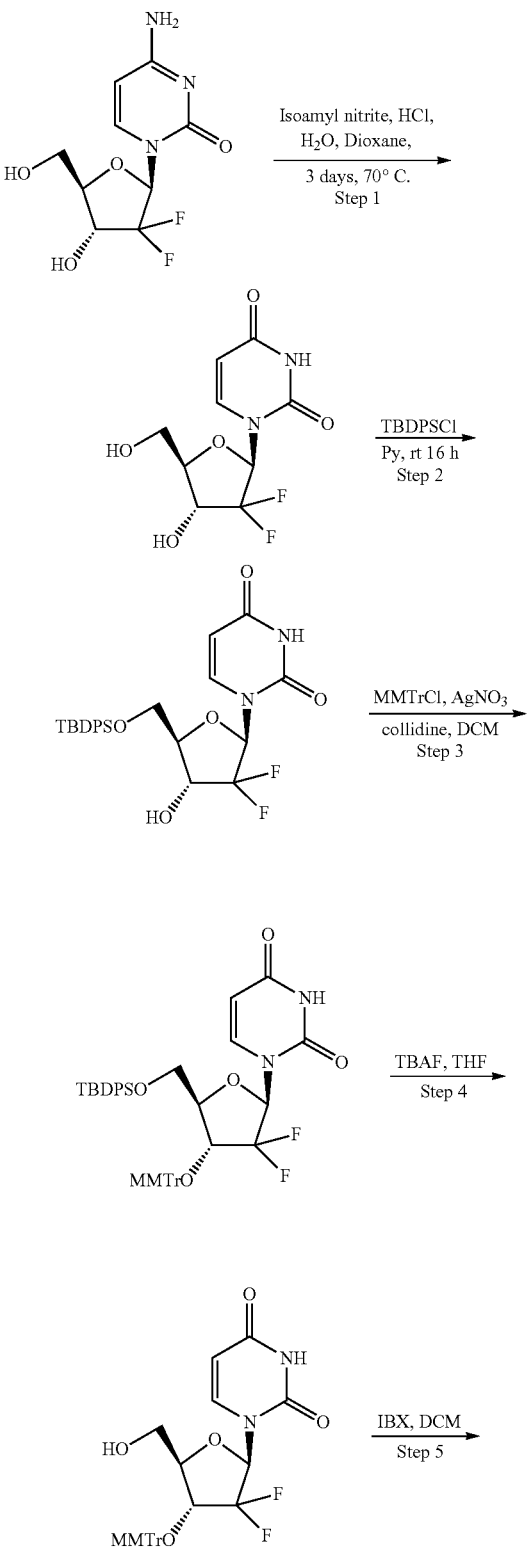

-continued

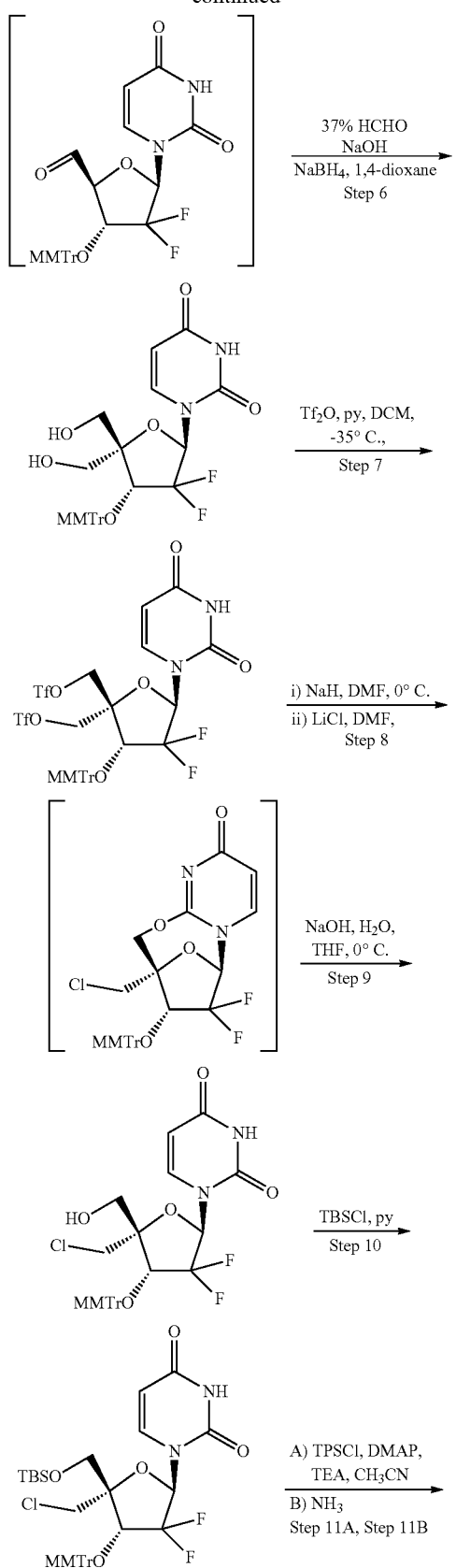

-continued

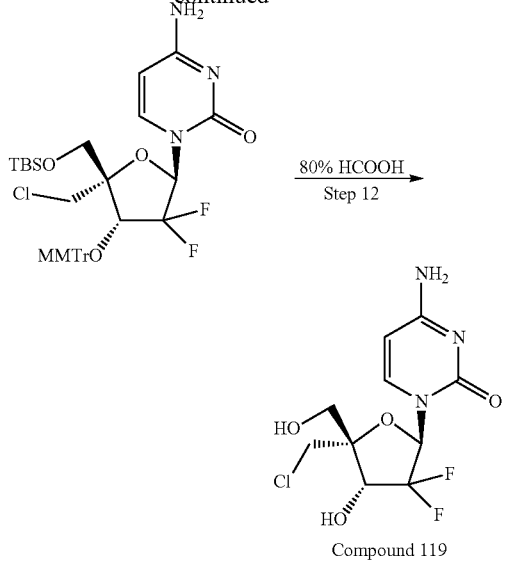

Compound 119

Step 1: To a stirred solution of 4-amino-1-((2R,4R,5R)-3,3-difluoro-4-hydroxy-5-(hydroxymethyl) tetrahydrofuran-2-yl)pyrimidin-2(1H)-one (13 g, 49.39 mmol) in 1,4-Dioxane (65 mL) and water (80 mL) was added 1N HCl (6.5 mL) and the reaction was stirred at rt for 15 min. To this iso-amyl nitrite (57.86 g, 493.92 mmol) was added. The reaction was stirred at 70° C. for 16 hr at which time TLC and LSMS showed a complete reaction. The reaction mixture was concentrated and resulting residue was triturated with n-Hexane and dried under vacuum to afford the desired compound (13.1 g, crude) as white solid. LC-MS (ES, m/z): 264.80 (M+H).

Step 2: To a stirred solution of 1-((2R,4R,5R)-3,3-difluoro-4-hydroxy-5-(hydroxymethyl)tetrahydrofuran-2-yl) pyrimidine-2,4(1H,3H)-dione (12.8 g, 48.45 mmol) in pyridine (150 mL) was added TBDPSCl (14.649 g, 53.297 mmol) at 0° C. The reaction was stirred at rt for 4 hr at which time TLC and LCMS showed a complete reaction. The reaction mixture was concentrated, diluted with ice water (250 mL) and extracted with EtOAc (2×250 mL). The combined organics were washed with water (100 mL), then brine (100 mL), and dried over sodium sulphate. The mixture was filtered, and the filtrate concentrated. The residue was purified by CombiFlash column chromatography by eluting 40% EtOAc in n-Hexane to afford the desired product (10.8 g, 51%) as an off-white solid. LC-MS (ES, m/z): 502.85 (M+H).

Step 3: To a stirred solution of 1-((2R,4R,5R)-5-(((tert-butyldiphenylsilyl) oxy)methyl)-3,3-difluoro-4-hydroxytetrahydrofuran-2-yl) pyrimidine-2,4(1H,3H)-dione (10.80 g, 21.489 mmol) in DCM (100 mL) was added AgNO$_3$ (4.02 g, 23.64 mmol) followed by 2,4,6-Collidine (2.864 g, 23.638 mmol) at rt. After stirring for 15 min, MMTr-Cl (7.30 g, 23.638 mmol) was added in a portionwise manner at 0° C. After stirring for 6 hr, TLC and LCMS showed a complete reaction. The reaction mixture was diluted with ice water (250 mL), and extracted with DCM (2×250 mL). The combined organics were washed with water (100 mL) and brine (100 mL), and then dried over sodium sulphate. The mixture was then filtered, and the filtrate concentrated. The residue was purified by CombiFlash column chromatography by eluting with 40% EtOAc in n-Hexane to afford the desired product (12.7 g, 76%) as an off-white solid. LC-MS (ES, m/z): 772.85 (M−H).

Step 4: To a stirred solution of 1-((2R,4R,5R)-5-(((tert-butyldiphenylsilyl)oxy) methyl)-3,3-difluoro-4-((4-methoxyphenyl)diphenylmethoxy) tetrahydrofuran-2-yl)pyrimidine-2,4(1H,3H)-dione (12.50 g, 16.13 mmol) in THF (100 mL) was added TBAF (1M in THF) (64.5 mL, 64.52 mmol). After stirring the reaction mixture at rt for 4 h, TLC and LCMS showed a complete reaction. The reaction mixture was diluted with ice water (250 mL) and resulting mixture was extracted with EtOAc (2×250 mL). The combined organics were washed with water (100 mL) and brine (100 mL), then dried over sodium sulphate. The mixture was filtered, and concentrated. The residue was purified by CombiFlash column chromatography by eluting with 40% EtOAc in Hexane to afford the desired product (7.6 g, 87%) as an off-white solid. LC-MS (ES, m/z): 535.00 (M−H).

Steps 5 and 6: To a stirred solution of 1-((2R,4R,5R)-3,3-difluoro-5-(hydroxymethyl)-4-((4-methoxyphenyl)diphenylmethoxy) tetrahydrofuran-2-yl)pyrimidine-2,4(1H,3H)-dione (3.0 g, 5.59 mmol) in $CH_3CN$ (30 mL) was added IBX (1.879 g, 6.710 mmol) at rt. The reaction was stirred at 90° C. for 2 h, at which time TLC and LCMS showed a complete reaction. The reaction mixture was filtered, and the filtrate was concentrated to dryness to afford the crude aldehyde. The aldehyde was dissolved in 1,4-dioxane (30 mL) and treated with HCHO (1.82 mL, 22.37 mmol) followed by 2M NaOH (5.6 mL, 11.18 mmol). The reaction was then stirred for 2 h at rt. To the reaction was then added, $NaBH_4$ (1.269 g, 33.549 mmol) at 0° C. The reaction was stirred for 30 min at rt at which time the TLC and LCMS showed complete reaction. The reaction mixture was diluted with brine (100 mL) and extracted with DCM (2×100 mL). The combined organics were washed with water and brine and dried over sodium sulphate. The mixture was filtered, concentrated, and resulting residue was purified by CombiFlash column chromatography by eluting with 70% EtOAc in n-Hexane to afford the desired product (0.95 g, 29%) as off-white solid. LC-MS (ES, m/z): 566.85 (M+H).

Step 7: To a stirred solution of 1-((2R,4R)-3,3-difluoro-5,5-bis(hydroxymethyl)-4-((4-methoxyphenyl) diphenylmethoxy)tetrahydrofuran-2-yl)pyrimidine-2,4(1H,3H)-dione (0.550 g, 0.97 mmol) in DCM (10 mL) was added pyridine (0.768 g, 9.71 mmol). The reaction was stirred for 15 min, cooled to −30° C. and treated with $Tf_2O$ (0.603 g, 2.136 mmol). The reaction was stirred at −30° C. for 1 hr at which time TLC and LCMS showed a complete reaction. The reaction mass was quenched with water (150 mL) at −30° C., stirred for 10 min at 0° C., and then extracted with DCM (2×150 mL). The combined organics were washed with water and brine, and then dried over sodium sulphate. The mixture was filtered and concentrated and resulting residue was purified by CombiFlash column chromatography by eluting with 25% EtOAc in n-Hexane to afford the desired product (0.95 g, 29%) as off-white solid. LC-MS (ES, m/z): 830.70 (M+H).

Steps 8 and 9: To a stirred solution of ((3R,5R)-5-(2,4-dioxo-3,4-dihydropyrimidin-1(2H)-yl)-4,4-difluoro-3-((4-methoxyphenyl)diphenylmethoxy) tetrahydrofuran-2,2-diyl)bis (methylene)bis(trifluoromethanesulfonate) (0.60 g, 0.72 mmol) in DMF (5 mL) was added NaH (0.031 g, 0.795 mmol) at 0° C. The reaction was stirred at 0° C. for 1 h at which time TLC and LCMS showed a complete reaction. The reaction was then treated LiCl (0.092 g, 2.17 mmol) and stirred at rt for 4 h. To the reaction was then added 1M NaOH (1.1 mL, 1.083 mmol) in dropwise manner at 0° C. The reaction was stirred for 1 h at which time TLC and LCMS showed a complete reaction. The reaction mixture was quenched with water (100 mL), stirred for 10 min, and extracted with EtOAc (2×100 mL). The combined organic fractions were washed with water (50 mL) and brine (50 mL), then dried over sodium sulphate. The mixture was filtered, and the filtrate concentrated under reduced pressure. The residue was purified by CombiFlash column chromatography by eluting with 55% EtOAc in n-Hexane to afford the desired product (0.31 g, 73%) as off-white solid. LC-MS (ES, m/z): 583.15 (M−H).

Step 10: To a stirred solution of 1-((2R,4R,5R)-5-(chloromethyl)-3,3-difluoro-5-(hydroxymethyl)-4-((4-methoxyphenyl)diphenylmethoxy) tetrahydrofuran-2-yl)pyrimidine-2,4(1H,3H)-dione (0.30 g, 0.513 mmol) in DMF (3 mL) was added imidazole (0.105 g, 1.54 mmol) followed by TBDMS-Cl (0.155 g, 1.026 mmol) at rt. The reaction was stirred for 6 h at rt at which time TLC and LCMS showed complete reaction. The reaction mixture was diluted with ice water (100 mL) and extracted with EtOAc (2×100 mL). The combined organics were washed with water and brine, then dried over sodium sulphate. The mixture was filtered, concentrated, and resulting residue purified by CombiFlash column chromatography by eluting 55% EtOAc in n-Hexane to afford the desired product (0.270 g, 75%) as an off-white solid. LC-MS (ES, m/z): 696.75 (M−1).

Step 11A: To a stirred solution of 1-((2R,4R,5R)-5-(((tert-butyldimethylsilyl) oxy)methyl)-5-(chloromethyl)-3,3-difluoro-4-((4-methoxyphenyl) diphenylmethoxy) tetrahydrofuran-2-yl)pyrimidine-2,4(1H,3H)-dione (0.200 g, 0.286 mmol) in $CH_3CN$ (5 mL) was added $Et_3N$ (0.116 g, 1.14 mmol), DMAP (0.070 g, 0.572 mmol) followed by TPS-Cl (0.173 g, 0.572 mmol) at 0° C. The reaction was stirred at rt for 2 h and then cooled to 0° C. To the reaction was then added 1H-1,2,4-triazole (0.079 g, 1.144 mmol) and the reactions was stirred for 2 h at rt. at which time TLC and LCMS showed a complete reaction. The reaction was diluted with ice water (100 mL) and extracted with EtOAc (2×100 mL). The combined organics were washed with water and brine, then dried over sodium sulphate. The mixture was filtered and concentrated. The residue was purified by CombiFlash column chromatography by eluting with 55% EtOAc in n-Hexane to afford the desired product (0.175 g, 81%) as gummy liquid. LC-MS (ES, m/z): 749.85 (M−1).

Step 11B: To a stirred solution of 1-((2R,4R,5R)-5-(((tert-butyldimethylsilyl) oxy)methyl)-5-(chloromethyl)-3,3-difluoro-4-((4-methoxyphenyl)diphenylmethoxy) tetrahydrofuran-2-yl)-4-(1H-1,2,4-triazol-1-yl)pyrimidin-2(1H)-one (0.170 g, 0.226 mmol) in 1,4-Dioxane (2 mL) was added ammonia solution (2 mL) and stirred at rt for 15 min then heated to 30° C. for 2 h. The reaction progress was shown to be complete by TLC and LCMS. Reaction was concentrated washed with hexane, and dried to afford the desired compound (13.1 g, crude) as off-white solid. LC-MS (ES, m/z): 697.80 (M+H).

Step 12: A stirred solution of 4-amino-1-((2R,4R,5R)-5-(((tert-butyldimethylsilyl) oxy) methyl)-5-(chloromethyl)-3,3-difluoro-4-((4-methoxyphenyl)diphenylmethoxy) tetrahydrofuran-2-yl)pyrimidin-2(1H)-one (0.160 g, 0.229 mmol) in 80% HCOOH (1.6 mL) was stirred at 0° C. to rt for 16 h at which time TLC and LCMS showed a complete reaction. The reaction mixture was concentrated and residue purified by Prep-HPLC using the following conditions: Mobile Phase: A=0.01% HCOOH in water, B=MeCN; Column: X SELECT (250 mm×20.0 mm), 5.0μ; Flow: 18.0 mL/min; Gradient Program: Time/% B:0/5,2/10,8/25 to afford the desired product (10 mg, 10%) as a white solid. LC-MS (ES, m/z): 311.60 (M+H). $^1H$ NMR (400 MHz, DMSO-$d_6$) δ=7.64 (d, J=7.6 Hz, 1H), 7.42-7.36 (m, 2H), 6.64 (br d, J=5.9 Hz, 1H), 6.29 (t, J=8.7 Hz, 1H), 5.79 (d, J=7.6 Hz, 1H), 5.50-5.44 (m, 1H), 4.50-4.41 (m, 1H), 3.87-3.82 (m, 1H), 3.76 (s, 1H), 3.74-3.69 (m, 1H), 3.57 (br d, J=11.2 Hz, 1H).
Example 58—Synthesis of Compound 71: 4-amino-1-((2R,4S,5R)-5-(chloromethyl)-4-hydroxy-5-(hydroxymethyl)tetrahydrofuran-2-yl)-5-(trifluoromethyl)pyrimidin-2(1H)-one
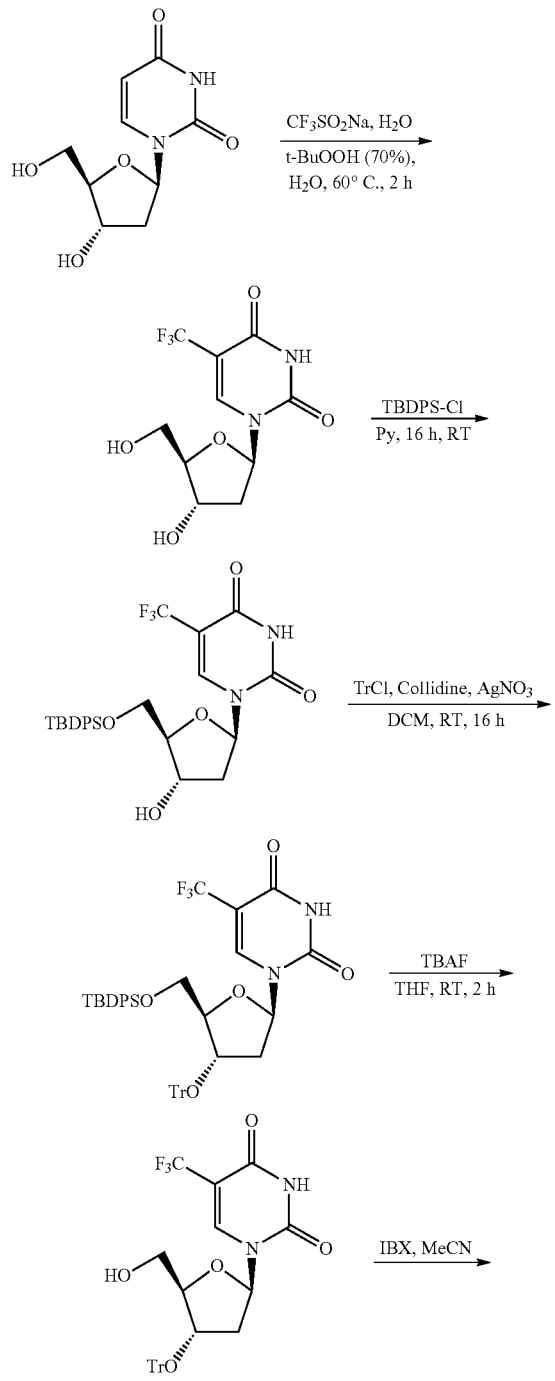
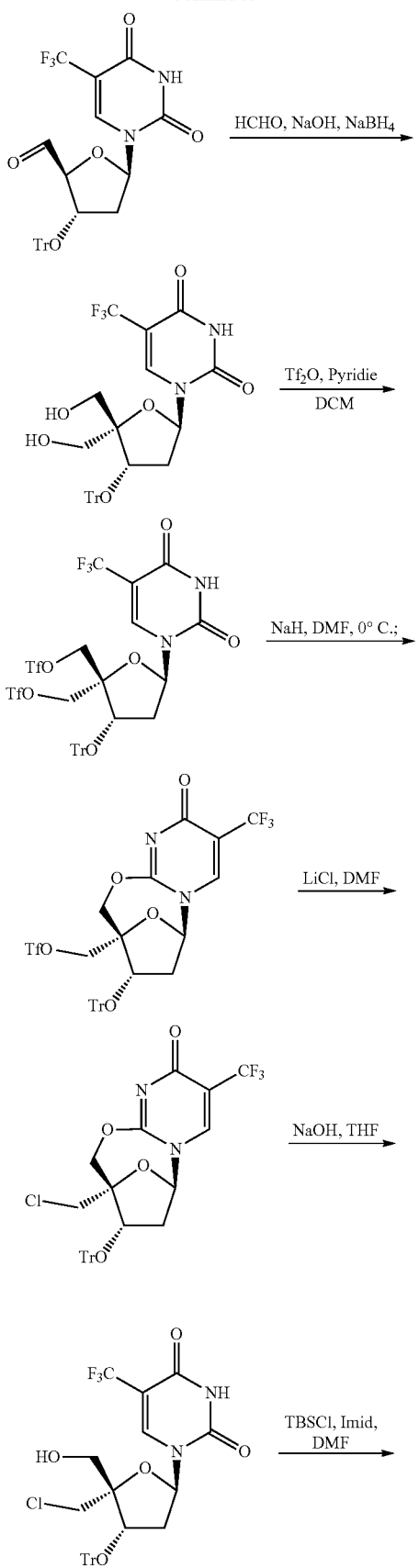

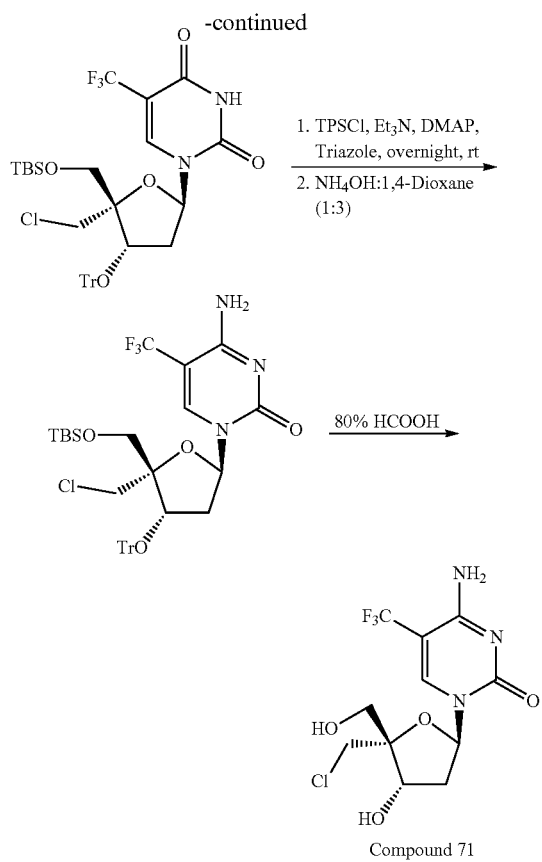

Compound 71

Step 1: To a stirred solution of CF$_3$SO$_2$Na (20.51 g, 131.46 mmol) in water (100 mL) under N$_2$ was added 1-((2R,4S,5R)-4-hydroxy-5-(hydroxymethyl)tetrahydrofuran-2-yl)pyrimidine-2,4-(1H,3H)dione (20.0 g, 87.64 mmol). The reaction mixture was cooled to −5° C. to 5° C. and t-BuOOH (70% aqueous solution, 34 mL, 23.68 g, 262.92 mmol) was added slowly over a period of 20 min. (13-15° C. exotherm). The reaction mixture was allowed to warm to 20-30° C. and then heated to 70° C. for 2 h. After 2 h, a pale-yellow heterogeneous mass was formed. The reaction mixture was concentrated and resulting residue was purified by CombiFlash using 80 g column and the product by eluting with 70% EtOAc in n-hexane to afford the desired product (8 g, 30.80%) as a white solid. LC-MS (ES, m/z): 294.75 (M−H).

Step 2: To a stirred solution of 1-((2R,4S,5R)-4-hydroxy-5-(hydroxymethyl) tetrahydrofuran-2-yl)-5-(trifluoromethyl)pyrimidine-2,4(1H,3H)-dione (6.8 g, 16.88 mmol) in pyridine (50 mL) was added TBDPSCl (6.8 g, 17.732 mmol) at rt. The reaction was stirred for 16 hr at rt at which time TLC and LCMS showed a complete reaction. The reaction mixture was evaporated under high vacuum and the residue was partitioned between EtOAc and water. The organic layer was separated, dried over Na$_2$SO$_4$ and concentrated. The residue was purified by CombiFlash column chromatography by using 80 g column by eluting with 40% EtOAc in n-hexane to afford the desired product (6.8 g, 75.35%) as an off-white solid. LC-MS (ES, m/z): 532.85 (M−H).

Step 3: To a stirred solution of 1-((2R,4S,5R)-5-(((tert-butyldiphenylsilyl) oxy)methyl)-4-hydroxytetrahydrofuran-2-yl)-5-(trifluoromethyl)pyrimidine-2,4(1H,3H)-dione (1.5 g, 2.81 mmol) in DCM (10 mL) was added collidine (0.4 mL, 3.09 mmol), AgNO$_3$ (0.52 g, 3.085 mmol) and then Trityl Chloride (0.86 g, 3.085 mmol) at rt. The reaction was stirred for 16 h at rt at which time TLC and LCMS showed a complete reaction. The reaction mixture was concentrated and residue was partitioned between EtOAc and water. The organic layer was separated, dried over Na$_2$SO$_4$, concentrated and the crude material was purified by CombiFlash using 40 g column by eluting with 45% EtOAc in n-Hexane to obtain the desired product (2.0 g, 91.79%) as an off-white solid. LC-MS (ES, m/z): 774.95 (M−H).

Step 4: To a stirred solution of 1-((2R,4S,5R)-5-(((tert-butyldiphenylsilyl) oxy)methyl)-4-(trityloxy)tetrahydrofuran-2-yl)-5-(trifluoromethyl)pyrimidine-2,4(1H,3H)-dione (2.0 g, 2.57 mmol) in THF (20 mL) was added TBAF (1M in THF) (10.30 mL, 10.30 mmol) at rt. The reaction was stirred for 4 h at rt at which time TLC and LCMS showed a complete reaction. The reaction mixture was evaporated and the resulting residue was partitioned between EtOAc and water. The organic layer was separated, dried over Na$_2$SO$_4$, and concentrated. The resulting residue was purified by CombiFlash column by eluting with 45% EtOAc in n-Hexane to afford the desired product (1 g, 72.14%) as an off-white solid. LC-MS (ES, m/z): 536.75 (M−H).

Step 5: To a stirred solution of 11-((2R,4S,5R)-5-(hydroxymethyl)-4-(trityloxy) tetrahydrofuran-2-yl)-5-(trifluoromethyl)pyrimidine-2,4(1H,3H)-dione, (0.45 g, 0.835 mmol) in ACN (10.0 mL) was added IBX (0.28 g, 1.00 mmol) at rt. The reaction was stirred for 2 h at 90° C. at which time TLC and LCMS showed a complete reaction. The reaction mixture was filtered and the filtrate concentrated to afford the crude aldehyde. The aldehyde was dissolved in 1,4-dioxane (5 mL) and treated with formaldehyde (0.45 mL) followed by 1N NaOH (1.0 mL) at rt. The reaction was stirred for 12 h at which time TLC and LCMS showed a complete reaction. The reaction mixture was cooled to 0° C. and NaBH$_4$ (0.12 g, 3.34 mmol) was added portionwise. The reaction was stirred for 1 h at rt at which time TLC and LCMS showed a complete reaction. The reaction mixture was concentrated, and the resulting residue was partitioned between EtOAc (50 mL) and water (100 mL). The organic layer was separated, dried over Na$_2$SO$_4$, and concentrated under reduced pressure. The resulting residue was triturated with n-pentane and stirred for 15 minutes. The pentane layer was decanted, and the solid obtained was dried under vacuum to afford the desired product (0.4 g, 84.25%) as an off-white solid. LC-MS (ES, m/z): 566.80 (M−H).

Step 6: To a stirred solution of 1-((2R,4S)-4-((tert-butyldimethylsilyl)oxy)-5,5-bis(hydroxymethyl)tetrahydrofuran-2-yl)-5-(trifluoromethyl)pyrimidine-2,4(1H,3H)-dione (1.4 g, 2.462 mmol) in DCM (20 mL) was added pyridine (1.9 mL, 24.62 mmol) followed by Tf$_2$O (0.9 mL, 5.41 mmol) at −30° C. The reaction was stirred at same temperature for 2 hours, at which time TLC showed a complete reaction. The reaction mixture was quenched with ice-cold water and then partitioned between EtOAc (30 mL) and water (5 mL). The organic layer was separated, dried over Na$_2$SO$_4$, and concentrated, and the resulting residue was purified by CombiFlash using 12 g column by eluting with 35% EtOAc in n-hexane to afford the desired product (1.0 g, 48.78%) as an off-white solid. LC-MS (ES, m/z): 830.10 (M−H).

Step 7: To a solution of ((3S,5R)-5-(2,4-dioxo-5-(trifluoromethyl)-3,4-dihydropyrimidin-1(2H)-yl)-3-(trityloxy)tetrahydrofuran-2,2-diyl)bis(methylene) bis(trifluoromethanesulfonate) (1 g, 1.2 mmol) in DMF (10 mL) was added NaH (0.034 g, 1.4 mmol) at 0° C. The reaction was stirred at 0° C. for 2 h, at which time TLC showed a complete reaction. The reaction was then treated with LiCl (0.15 g, 3.6 mmol)

and stirring was continued at rt for 2 h. The reaction mixture was quenched with ice-cold water and then partitioned between EtOAc and water. The organic layer was separated, dried over Na₂SO₄ and concentrated under reduced pressure to get the desired crude compound (1.0 g, crude). LC-MS (ES, m/z): 568.85 (M−H).

Step 8: To a solution of (6R,8S,9R)-9-(chloromethyl)-3-(trifluoromethyl)-8-(trityloxy)-7,8,9,10-tetrahydro-2H,6H-6,9-epoxypyrimido[2,1-b][1,3]oxazocin-2-one (1 g, 1.2 mmol) in THF (10 mL) was added 1N NaOH (1.4 mL, 0.1.4 mmol at rt. The reaction was stirred at rt for 1 hr at which time TLC and LCMS showed a complete reaction. The reaction mixture was quenched with ice-cold water and then partitioned between EtOAc and water. The organic layer was separated, dried over Na₂SO₄, concentrated under reduced pressure to get the desired crude compound. The crude product was purified by CombiFlash using 24 g column eluting with 35% EtOAc in n-Hexane to afford the desired product (0.38 g, 53.99%) as an off-white solid. LC-MS (ES, m/z): 584.65 (M−H).

Step 9: To a solution of 1-((2R,4S,5R)-5-(chloromethyl)-5-(hydroxymethyl)-4-(trityloxy)tetrahydrofuran-2-yl)-5-(trifluoromethyl)pyrimidine-2,4(1H,3H)-dione (160 mg, 0.272 mmol) in DMF (2 mL) was added imidazole (55 mg, 0.817 mmol), TBSCl (82 mg, 0.545 mmol) followed by silver nitrate (93 mg, 0.544 mmol) at 0° C. The reaction was stirred at rt for 12 h at which time TLC and LCMS showed a complete reaction. The reaction mixture was quenched with ice-cold water and then partitioned between EtOAc and water. The organic layer was separated, dried over Na₂SO₄, concentrated and the resulting residue was purified by CombiFlash column chromatography eluting with 35% EtOAc in n-Hexane to afford the desired product (100 mg, 52.20%) as an off-white solid. LC-MS (ES, m/z): 699.05 (M−H).

Step 10: To a solution of 1-((2R,4S,5R)-5-(((tert-butyldimethylsilyl)oxy)methyl)-5-(chloromethyl)-4-(trityloxy)tetrahydrofuran-2-yl)-5-(trifluoromethyl)pyrimidine-2,4(1H, 3H)-dione (80 mg, 0.114 mmol) in ACN (2 mL) was added TEA (0.06 mL, 0.456 mmol), DMAP (69 mg, 0.228 mmol) and then TPSCl (17 mg, 0.057 mmol) at 0° C. The reaction was then stirred at rt for 2 h and treated with NH₄OH:1,4-Dioxane (1 mL). The reaction progress was monitored by TLC and LCMS. After completion, the reaction mixture was concentrated and resulting residue was purified by prep-TLC by eluting with 50% EtOAc in n-Hexane to afford the desired product (20 mg, 25.05%) as an off-white solid. LC-MS (ES, m/z): 697.95 (M−H).

Step 11: To a solution of 4-amino-1-((2R,4S,5R)-5-(((tert-butyldimethylsilyl) oxy)methyl)-5-(chloromethyl)-4-(trityloxy)tetrahydrofuran-2-yl)-5-(trifluoromethyl)pyrimidin-2 (1H)-one (70 mg, 0.009 mmol) in DCM (2 mL) was added 80% Formic acid (0.7 mL) at 0° C. The reaction was stirred for 6 h at rt, while being monitored by TLC and LCMS. After completion, the reaction mixture was concentrated and resulting residue was purified by prep-HPLC under the following conditions: Mobile Phase: A=0.02% 0.1% HCOOH in water B=ACN; Column: X SELECT (250 mm×20.0 mm), 5.0μ Flow: 15 mL/min Gradient Programmer: Time/% B: 0/5,2/10,8/40 to afford the desired product (0.6 mg, 19%) as a white solid. LC-MS (ES, m/z): 343.90 (M+H). 1H NMR (400 MHz, DMSO-d₆) δ 8.59 (s, 1H), 7.96-7.83 (m, 1H), 7.13-6.99 (m, 1H), 6.14 (t, J=6.3 Hz, 1H), 5.53-5.39 (m, 2H), 4.41-4.35 (m, 1H), 3.81 (d, J=11.4 Hz, 1H), 3.69 (d, J=11.4 Hz, 2H), 3.57 (d, J=11.4 Hz, 1H), 2.44-2.36 (m, 1H), 2.29-2.20 (m, 1H).

Example 59—Synthesis of Compound 116: 4-amino-1-((2R,3S,4S,5R)-5-ethynyl-3,4-dihydroxy-5-(hydroxymethyl) tetrahydrofuran-2-yl)-5-fluoropyrimidin-2(1H)-one

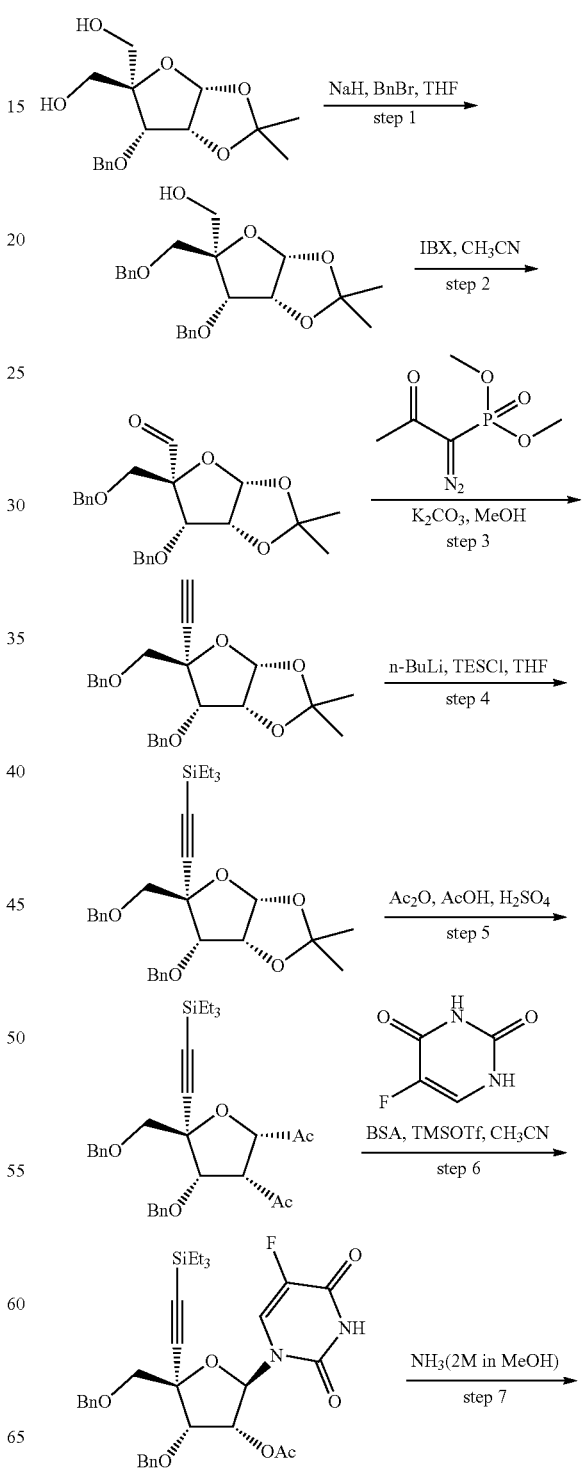

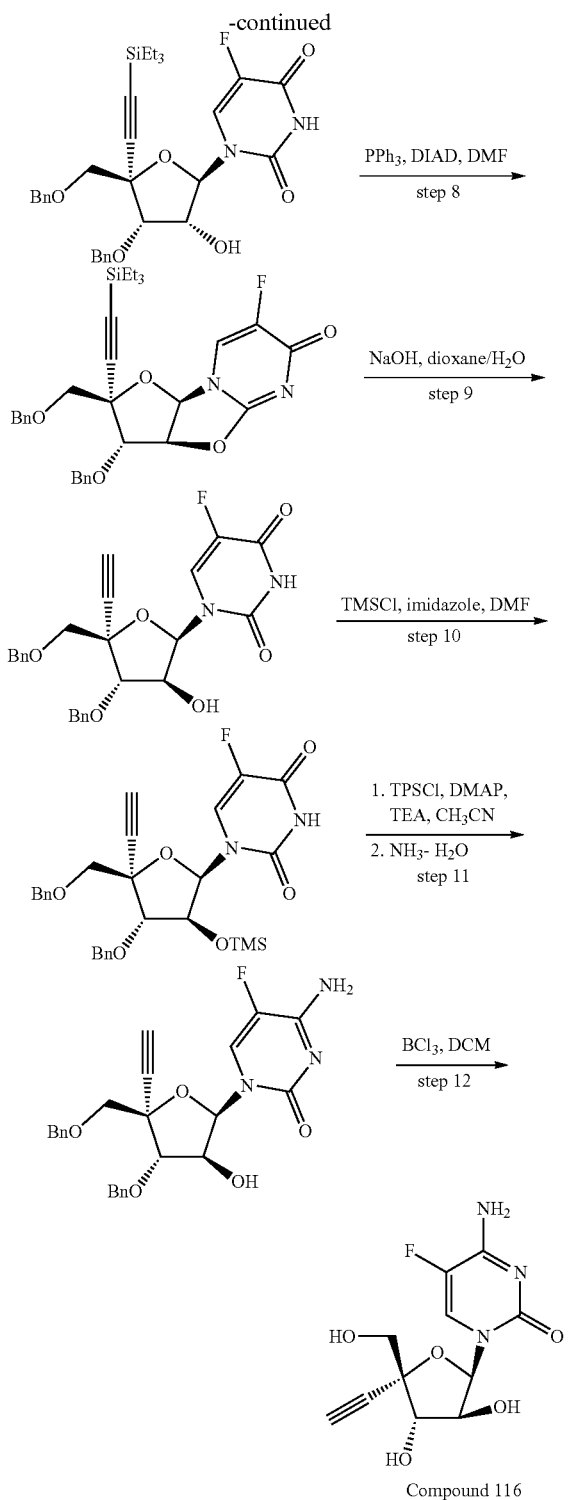

Compound 116

Step 1: To a solution of [(3aR,6S,6aR)-6-(benzyloxy)-5-(hydroxymethyl)-2,2-dimethyl-dihydro-3aH-furo [2,3-d][1,3]dioxol-5-yl] methanol (30 g, 96.61 mmol) in THF (300 mL) was added NaH (3.86 g, 96.61 mmol, 60% in oil) at 0° C. under N₂ atmosphere. The reaction mixture was stirred for 30 mins. To the above solution, benzyl bromide (16 g, 96.61 mmol) was added and the mixture was allowed to warm to room temperature and stirred overnight. The reaction mixture was quenched by ice water and extracted with EtOAc (3×500 mL). The combined organic layers were dried over anhydrous Na₂SO₄. After filtration the filtrate was concentrated under reduced pressure. The residue was purified by silica gel column chromatography, eluting with EtOAc/Petroleum ether (1:5) to afford [(3aR,5R,6S,6aR)-6-(benzyloxy)-5-[(benzyloxy) methyl]-2,2-dimethyl-dihydro-3aH-furo[2,3-d][1,3]dioxol-5-yl]methanol (28 g, 69.83 mmol, 72.1%) as an off-white solid. LC-MS (ES, m/z): 418 [M+NH₄]⁺.

Step 2: To a stirred solution of [(3aR,5R,6S,6aR)-6-(benzyloxy)-5-[(benzyloxy) methyl]-2,2-dimethyl-dihydro-3aH-furo[2,3-d][1,3]dioxol-5-yl] methanol (28 g, 69.83 mmol) in ACN (300 mL) was added IBX (29 g, 104.81 mmol) at room temperature under a N₂ atmosphere. The resulting mixture was stirred for 12 h at 60° C. and cooled to room temperature. The solid in the reaction mixture was filtered out and the filtrate was concentrated under reduced pressure. The residue was purified by silica gel column chromatography, eluting with EtOAc/Petroleum ether (1:3) to afford (3aR,5R,6S,6aR)-6-(benzyloxy)-5-[(benzyloxy) methyl]-2,2-dimethyl-dihydro-3aH-furo[2,3-d][1,3]dioxole-5-carbaldehyde (20 g, 50.13 mmol, 71.2%) as a yellow oil. LC-MS (ES, m/z): 416 [M+NH₄]⁺.

Step 3: To a stirred solution of (3aR,5R,6S,6aR)-6-(benzyloxy)-5-[(benzyloxy) methyl]-2,2-dimethyl-dihydro-3aH-furo[2,3-d][1,3]dioxole-5-carbaldehyde (20 g, 50.13 mmol) and K₂CO₃ (21 g, 150.39 mmol) in CH₃OH (200 mL) was added dimethyl (1-diazo-2-oxopropyl)phosphonate (19 g, 100.26 mmol) at 0° C. The resulting mixture was stirred for 1 h at room temperature. The solid in the reaction mixture was filtered out and the filtrate was concentrated under reduced pressure. The residue was purified by silica gel column chromatography, eluting with EtOAc/Petroleum ether (1:4) to afford (3aR,5R,6S,6aR)-6-(benzyloxy)-5-[(benzyloxy)methyl]-5-ethynyl-2,2-dimethyl-dihydro-3aH-furo[2,3-d] [1,3]dioxole (16 g, 40.61 mmol, 80.1%) as a yellow solid. LC-MS (ES, m/z): 412 [M+NH₄]⁺.

Step 4: To a stirred solution of (3aR,5R,6S,6aR)-6-(benzyloxy)-5-[(benzyloxy) methyl]-5-ethynyl-2,2-dimethyl-dihydro-3aH-furo[2,3-d][1,3]dioxole (16 g, 40.61 mmol) in THF (160 mL) was added n-butyllithium (41 mL, 101.52 mmol, 2.5 M in hexane) at −78° C. under a N₂ atmosphere. The reaction was stirred for 30 mins at −78° C. Then TESCl (9 g, 60.91 mmol) in THF (2 mL) was added dropwise at −78° C. The resulting mixture was stirred for further 30 mins at −78° C. The reaction was quenched by the addition of ice water (100 mL) at 0° C., then the resulting mixture was extracted with EtOAc (3×250 mL). The combined organic layers were dried over anhydrous Na₂SO₄. After filtration the filtrate was concentrated under reduced pressure. The residue was purified by silica gel column chromatography, eluted with EtOAc/Petroleum ether (1:5) to afford {2-[(3aR,5R,6S,6aR)-6-(benzyloxy)-5-[(benzyloxy) methyl]-2,2-dimethyl-dihydro-3aH-furo[2,3-d][1,3]dioxol-5-yl] ethynyl}triethylsilane (9.5 g, 18.7 mmol, 46.2%) as a yellow oil. LC-MS (ES, m/z): 526 [M+NH₄]⁺.

Step 5: To a stirred solution of {2-[(3aR,5R,6S,6aR)-6-(benzyloxy)-5-[(benzyloxy) methyl]-2,2-dimethyl-dihydro-3aH-furo[2,3-d][1,3]dioxol-5-yl] ethynyl}triethylsilane (4 g, 7.6 mmol) in AcOH (40 mL) was added Ac₂O (10 g, 106.12 mmol) and concentrated H₂SO₄ (1.54 g, 1.53 mmol) at 0° C. The resulting mixture was stirred for 2 h at room temperature. The reaction was quenched by the addition of saturated Na₂S₂O₃ (100 mL, aq.) at 0° C. The resulting mixture was extracted with EtOAc (3×200 mL). The combined organic layers were dried over anhydrous Na₂SO₄. After filtration the filtrate was concentrated under reduced pressure to afford (2R,3R,4S,5R)-2-(acetyloxy)-4-(benzyloxy)-5-[(benzyloxy) methyl]-5-[2-(triethylsilyl) ethynyl] oxolan-3-yl acetate (4.3 g, crude) as a yellow oil. The crude product was directly used in the next step without further purification. LC-MS (ES, m/z): 570 [M+NH$_4$]$^+$.

Step 6: To a stirred solution of fluorouracil (1 g, 1.75 mmol) in ACN (40 mL) was added (E)-(trimethylsilyl N-(trimethylsilyl) ethenecarboximidate) (6 g, 31.12 mmol) at 0° C. The reaction was stirred for 30 mins at 80° C. and then cooled to 0° C. (2R,3R,4S,5R)-2-(acetyloxy)-4-(benzyloxy)-5-[(benzyloxy) methyl]-5-[2-(triethylsilyl) ethynyl] oxolan-3-yl acetate (4.3 g, 7.79 mmol) and TMSOTf (2 g, 12.41 mmol) were added. The reaction mixture was stirred at 80° C. for 2 h. The resulting mixture was cooled to room temperature, diluted with water and extracted with EtOAc (3×100 mL). The combined organic layers were dried over anhydrous Na$_2$SO$_4$. After filtration the filtrate was concentrated under reduced pressure. The residue was purified by silica gel column chromatography, eluting with EtOAc/Petroleum ether (1:7) to afford (2R,3R,4S,5R)-4-(benzyloxy)-5-[(benzyloxy)methyl]-2-(5-fluoro-2,4-dioxo-3H-pyrimidin-1-yl)-5-[2-(triethylsilyl)ethynyl]oxolan-3-yl acetate (3.5 g, 5.62 mmol, 72.1%) as a yellow solid. (ES, m/z): 623 [M+H]$^+$.

Step 7: To a solution of NH$_3$ (g) (35 mL, 2M in MeOH), (2R,3R,4S,5R)-4-(benzyloxy)-5-[(benzyloxy) methyl]-2-(5-fluoro-2,4-dioxo-3H-pyrimidin-1-yl)-5-[2-(triethylsilyl) ethynyl] oxolan-3-yl acetate (3.5 g, 5.62 mmol) was added. The mixture was stirred for 3 h at room temperature. The resulting mixture was concentrated under vacuum. The residue was purified by silica gel column chromatography, eluted with EtOAc/Petroleum ether (1:3) to afford 1-[(2R,3R,4S,5R)-4-(benzyloxy)-5-[(benzyloxy)methyl]-3-hydroxy-5-[2-(triethylsilyl) ethynyl] oxolan-2-yl]-5-fluoro-3H-pyrimidine-2,4-dione (1.3 g, 2.24 mmol, 41.1%) as a yellow solid. LC-MS (ES, m/z): 581 [M+H]$^+$.

Step 8: To a stirred solution of 1-[(2R,3R,4S,5R)-4-(benzyloxy)-5-[(benzyloxy) methyl]-3-hydroxy-5-[2-(triethylsilyl) ethynyl] oxolan-2-yl]-5-fluoro-3H-pyrimidine-2,4-dione (1.3 g, 2.24 mmol) in DMF (10 mL) was added PPh$_3$ (1.8 g, 6.72 mmol) and DIAD (1.4 g, 6.72 mmol) at 0° C. under N$_2$ atmosphere. The resulting mixture was stirred overnight at room temperature. The resulting mixture was diluted with water and extracted with EtOAc (3×80 mL). The combined organic layers were dried over anhydrous Na$_2$SO$_4$. After filtration the filtrate was concentrated under reduced pressure. The residue was purified by silica gel column chromatography, eluting with EtOAc/Petroleum ether (3:2) to afford (2R,4R,5S,6S)-5-(benzyloxy)-4-[(benzyloxy) methyl]-11-fluoro-4-[2-(triethylsilyl) ethynyl]-3,7-dioxa-1,9-diazatricyclo [6.4.0.0^{2,6}] dodeca-8,11-dien-10-one (900 mg, 1.61 mmol, 68.1%) as a yellow solid. LC-MS (ES, m/z): 563 [M+H]$^+$.

Step 9: To a stirred solution of (2R,4R,5S,6S)-5-(benzyloxy)-4-[(benzyloxy) methyl]-11-fluoro-4-[2-(triethylsilyl) ethynyl]-3,7-dioxa-1,9-diazatricyclo [6.4.0.0^{2,6}]dodeca-8,11-dien-10-one (800 mg, 1.42 mmol) in water (7 mL) and dioxane (7 mL) was added NaOH (227 mg, 5.67 mmol) at room temperature. The resulting mixture was stirred for 2 h at room temperature. The resulting mixture was extracted with EtOAc (3×10 mL). The combined organic layers were dried over anhydrous Na$_2$SO$_4$. After filtration the filtrate was concentrated under reduced pressure. The residue was purified by silica gel column chromatography, eluting with EtOAc/Petroleum ether (1:1) to afford 1-[(2R,3S,4S,5R)-4-(benzyloxy)-5-[(benzyloxy) methyl]-5-ethynyl-3-hydroxyoxolan-2-yl]-5-fluoro-3H-pyrimidine-2,4-dione (450 mg, 0.96 mmol, 67.2%) as a yellow solid. LC-MS (ES, m/z): 467 [M+H]$^+$.

Step 10: To a stirred solution of 1-[(2R,3S,4S,5R)-4-(benzyloxy)-5-[(benzyloxy) methyl]-5-ethynyl-3-hydroxyoxolan-2-yl]-5-fluoro-3H-pyrimidine-2,4-dione (450 mg, 0.96 mmol) in DMF (10 mL) was added imidazole (197 mg, 2.88 mmol) and TMSCl (157 mg, 1.44 mmol) under N$_2$ atmosphere. The resulting mixture was stirred for 2 h at room temperature. The resulting mixture was quenched with ice water and extracted with EtOAc (3×40 mL). The combined organic layers were dried over anhydrous Na$_2$SO$_4$. After filtration the filtrate was concentrated under reduced pressure. The residue was purified by silica gel column chromatography, eluting with EtOAc/Petroleum ether (2:3) to afford 1-[(2R,3S,4S,5R)-4-(benzyloxy)-5-[(benzyloxy) methyl]-5-ethynyl-3-[(trimethylsilyl) oxy] oxolan-2-yl]-5-fluoro-3H-pyrimidine-2,4-dione (450 mg, 0.84 mmol, 86.3%) as a yellow solid. LC-MS (ES, m/z): 539 [M+H]$^+$.

Step 11: To a stirred solution of 1-[(2R,3S,4S,5R)-4-(benzyloxy)-5-[(benzyloxy) methyl]-5-ethynyl-3-[(trimethylsilyl) oxy] oxolan-2-yl]-5-fluoro-3H-pyrimidine-2,4-dione (150 mg, 0.28 mmol) in ACN (5 mL) was added DMAP (68 mg, 0.56 mmol) and TEA (64 mg, 0.56 mmol) at room temperature. The reaction mixture was stirred for 10 min. To the above solution, 2,4,6-tris(propan-2-yl) benzene-1-sulfonyl chloride (168 mg, 0.56 mmol) was added. The resulting mixture was stirred for 12 h at room temperature. Then concentrated ammonium hydroxide (2 mL) was added and stirred for 30 min. The resulting mixture was diluted with water and extracted with EtOAc (3×30 mL). The combined organic layers were dried over anhydrous Na$_2$SO$_4$. After filtration the filtrate was concentrated under reduced pressure. The residue was purified by silica gel column chromatography, eluting with DCM/MeOH (5:1) to afford 4-amino-1-[(2R,3S,4S,5R)-4-(benzyloxy)-5-[(benzyloxy) methyl]-5-ethynyl-3-[(trimethylsilyl) oxy] oxolan-2-yl]-5-fluoropyrimidin-2-one (100 mg, 0.21 mmol, 66.2%) as a yellow solid. LC-MS (ES, m/z): 466 [M+H]$^+$.

Step 12: To a stirred solution of 4-amino-1-[(2R,3S,4S,5R)-4-(benzyloxy)-5-[(benzyloxy)methyl]-5-ethynyl-3-hydroxyoxolan-2-yl]-5-fluoropyrimidin-2-one (100 mg, 0.21 mmol) in DCM (5 mL) was added BCl3 (3 mL, 3.15 mmol, 1M in hexane)) dropwise at −78° C. under N$_2$ atmosphere. The mixture was allowed to warm to room temperature and stirred for 2 h. The reaction was quenched by the addition of MeOH (10 mL) and TEA (5 mL) at −78° C. and stirred for 10 min. The resulting mixture was concentrated under reduced pressure. The residue was purified by Prep-HPLC with the following conditions (Column: XBridge Shield RP18 OBD Column, 19*250 mm, 10 μm; Mobile Phase A: Water (10 mmol/L NH$_4$HCO$_3$), Mobile Phase B: ACN; Flow rate: 25 mL/min; Gradient: 3% B to 20% B in 6 min, Wavelength: 254 nm; RT1(min): 5.85). The fraction was collected and concentrated under vacuum, the residue was re-dissolved in CH$_3$CN and H$_2$O, and then was lyophilized to afford 4-amino-1-[(2R,3S,4S,5R)-5-ethynyl-3,4-dihydroxy-5-(hydroxymethyl) oxolan-2-yl]-5-fluoropyrimidin-2-one (24.4 mg, 85 mol, 39.1%) as an off-white solid. LC-MS (ES, m/z): 286 [M+H]$^+$. 99.1% purity. Conditions for the LCMS: (Column: Atlantis T3, 100*4.6 mm, 3 μm; Mobile Phase A: water+5 mM TFA, Mobile Phase B: ACN; Flow rate: 1.20 mL/min; Gradient: 0% B to 95% B in 8 min, 95% B to 95% B in 10 min, 95% B to 10% B in 10.5 min; Wavelength: 254/220 nm; RT1(min): 2.24). $^1$H NMR (400 MHz, DMSO-d$_6$) δ 7.78 (d, J=6.5 Hz, 2H), 7.53 (s, 1H), 6.09 (d, J=6.0 Hz, 1H), 5.74 (d, J=5.3 Hz, 1H), 5.65 (d, J=5.3 Hz, 1H), 5.52 (d, J=6.5 Hz, 1H), 4.19 (d, J=6.5 Hz, 1H), 3.99 (d, J=6.0 Hz, 1H), 3.62 (dd, J=13.8, 5.3 Hz, 2H), 3.54 (d, J=2.9 Hz, 1H).

Example 60—Synthesis of Compound 78: 4-amino-1-((2R,3S,4S,5R)-5-ethyl-3,4-dihydroxy-5-(hydroxymethyl) tetrahydrofuran-2-yl)-5-fluoropyrimidin-2(1H)-one

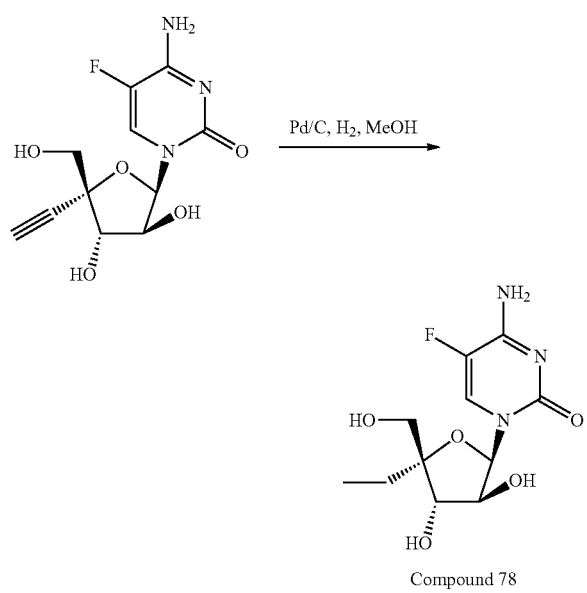

Compound 78

To a stirred solution of 4-amino-1-[(2R,3S,4S,5R)-5-ethynyl-3,4-dihydroxy-5-(hydroxymethyl) oxolan-2-yl]-5-fluoropyrimidin-2-one (60 mg, 0.21 mmol) in MeOH (5 mL) was added Pd/C (6 mg, 10% Pd on carbon) at room temperature under $N_2$ atmosphere. The resulting mixture was stirred for 1 h under $H_2$ atmosphere. The reaction mixture was filtered out and the filtrate was concentrated under reduced pressure. The residue was purified by Prep-HPLC with the following conditions (Column: XBridge Shield RP18 OBD Column, 19*250 mm, 10 μm; Mobile Phase A: Water (10 mmol/L $NH_4HCO_3$), Mobile Phase B: ACN; Flow rate: 25 mL/min; Gradient: 3% B to 20% B in 6 min, Wavelength: 254 nm; RT1(min): 5.28). The fraction was collected and concentrated under vacuum, the residue was re-dissolved in $CH_3CN$ and $H_2O$, and then was lyophilized overnight to afford 4-amino-1-[(2R,3S,4S,5R)-5-ethyl-3,4-dihydroxy-5-(hydroxymethyl)oxolan-2-yl]-5-fluoropyrimidin-2-one (18.6 mg, 64 μmol, 30.1%) as an off-white solid. LC-MS (ES, m/z): 290 [M+H]$^+$, purity: 95.2%. Conditions for the LCMS: (Column: Atlantis T3, 100*4.6 mm, 3 μm; Mobile Phase A: Water+5 mM TFA, Mobile Phase B: ACN; Flow rate: 1.20 mL/min; Gradient: 0% B to 95% B in 8 min, 95% B to 95% B in 10 min, 95% B to 10% B in 10.5 min; Wavelength: 254/220 nm; RT1 (min): 3.67). $^1$H NMR (400 MHz, DMSO-d$_6$) δ 7.95-7.88 (m, 1H), 7.67 (s, 1H), 7.44 (s, 1H), 5.97 (d, J=4.9 Hz, 1H), 5.53-5.47 (m, 1H), 5.34 (d, J=4.4 Hz, 1H), 5.12 (s, 1H), 4.08 (s, 1H), 3.98 (s, 1H), 3.51 (s, 2H), 1.61 (d, J=16.0 Hz, 1H), 1.49 (d, J=12.1 Hz, 1H), 0.86 (d, J=7.7 Hz, 3H).

Example 61—Synthesis of Compound 79: (2R,3S,5R)-5-(4-aminopyrrolo[2,1-f] [1,2,4]triazin-7-yl)-2-(fluoromethyl)-2-(hydroxymethyl) tetrahydrofuran-3-ol

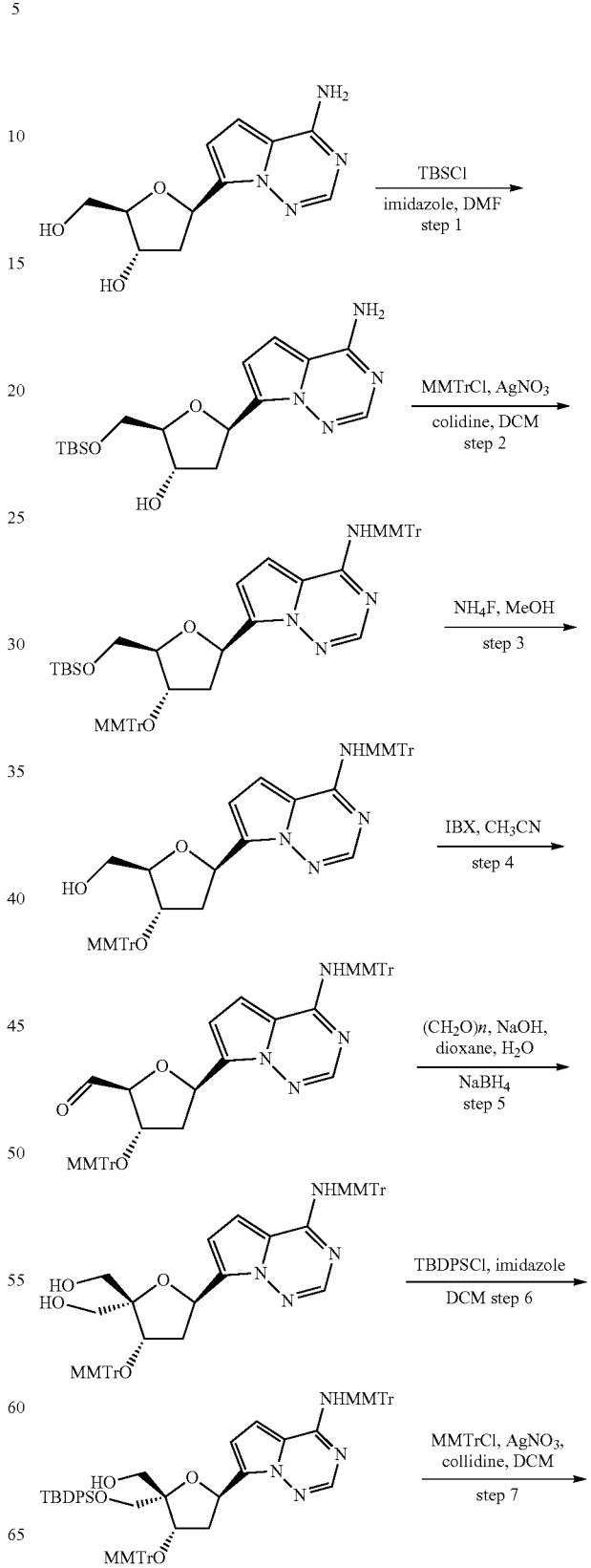

-continued

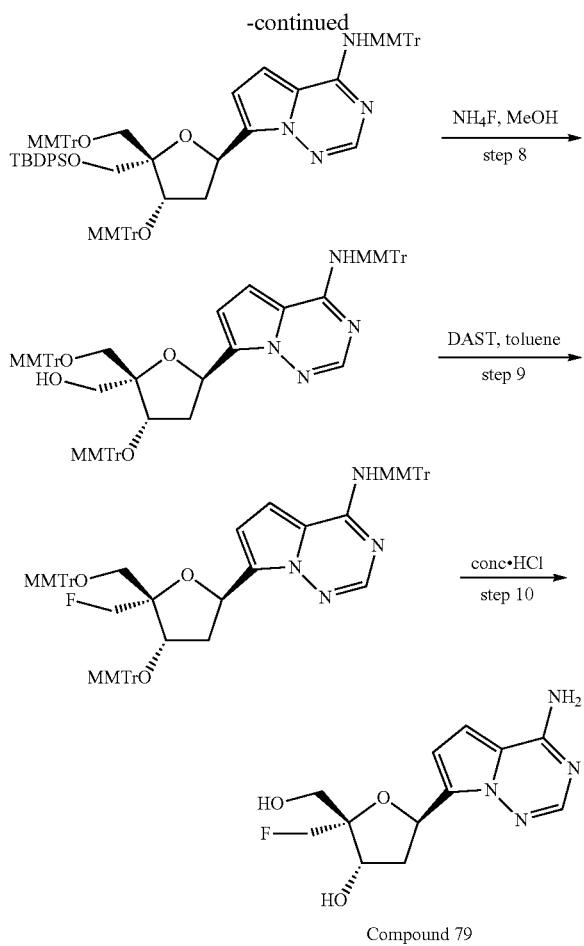

Compound 79

Step 1: To a stirred solution of (2R,3S,5R)-5-(4-aminopyrrolo[2,1-f] [1,2,4]triazin-7-yl)-2-(hydroxymethyl) tetrahydrofuran-3-ol (2.7 g, 10.81 mmol) and imidazole (2.2 g, 32.31 mmol) in DMF (50 mL) was added TBSCl (1.8 g, 11.92 mmol) at room temperature under N₂ atmosphere. The mixture was stirred for 15 hours at 60° C. The resulting mixture was diluted with water and extracted with EtOAc (3×100 mL). The combined organic layers were washed with brine, and dried over anhydrous Na₂SO₄. After filtration the filtrate was concentrated under reduced pressure. The residue was purified by silica gel column chromatography, eluting with PE/EtOAc (2/1) to afford (2R,3S,5R)-5-(4-aminopyrrolo[2,1-f] [1,2,4] triazin-7-yl)-2-(((tert-butyldimethylsilyl) oxy) methyl) tetrahydrofuran-3-ol (3.6 g, 9.91 mmol, 91.5%) as a light-yellow solid. LC-MS (ES, m/z): 365 [M+H]⁺.

Step 2: To a solution of (2R,3S,5R)-5-(4-aminopyrrolo[2,1-f] [1,2,4] triazin-7-yl)-2-(((tert-butyldimethylsilyl) oxy) methyl) tetrahydrofuran-3-ol (1.8 g, 4.93 mmol) in DCM (50 mL) was added 2,4,6-trimethylpyridine (3.6 g, 29.61 mmol) and AgNO₃ (4.2 g, 24.72 mmol) under N₂ atmosphere. Then was added MMTrCl (7.6 g, 24.71 mmol) under ice-water. After stirring overnight at room temperature under N₂ atmosphere, the resulting mixture was diluted with water and extracted with EA. The combined organic layers were washed with saturated NH₄Cl solution and then washed with citric acid, dried over anhydrous Na₂SO₄. After filtration the filtrate was concentrated under reduced pressure. The residue was purified by silica gel column chromatography, eluting with PE/EtOAc (4:1) to afford 7-((2R,4S,5R)-5-(((tert-butyldimethylsilyl) oxy) methyl)-4-((4-methoxyphenyl) diphenylmethoxy) tetrahydrofuran-2-yl)-N-((4-methoxyphenyl) diphenylmethyl) pyrrolo[2,1-f] [1,2,4] triazin-4-amine (4.2 g, 4.6 mmol, 93.5%) as a light-yellow solid. LC-MS (ES, m/z): 909 [M+H]⁺.

Step 3: To a solution of 7-((2R,4S,5R)-5-(((tert-butyldimethylsilyl) oxy) methyl)-4-((4-methoxyphenyl) diphenylmethoxy) tetrahydrofuran-2-yl)-N-((4-methoxyphenyl) diphenylmethyl) pyrrolo[2,1-f] [1,2,4] triazin-4-amine (4.2 g, 4.6 mmol) in MeOH (100 mL) was added NH₄F (5.1 g, 138.6 mmol) under N₂ atmosphere. After stirring overnight at 60° C. under N₂ atmosphere. The resulting mixture was concentrated and the residue was purified by silica gel column chromatography, eluting with PE/EA (3:1) to afford ((2R,3S,5R)-3-((4-methoxyphenyl) diphenylmethoxy)-5-(4-(((4-methoxyphenyl) diphenylmethyl) amino) pyrrolo[2,1-f] [1,2,4]triazin-7-yl) tetrahydrofuran-2-yl) methanol (3 g, 3.81 mmol, 81.7%) as a light-yellow solid. LC-MS (ES, m/z): 795 [M+H]⁺.

Step 4: To a solution of ((2R,3S,5R)-3-((4-methoxyphenyl) diphenylmethoxy)-5-(4-(((4-methoxyphenyl) diphenylmethyl) amino) pyrrolo[2,1-f] [1,2,4] triazin-7-yl) tetrahydrofuran-2-yl) methanol (3 g, 3.81 mmol) in ACN (50 mL) was added IBX (2.1 g, 7.52 mmol) under N₂ atmosphere. After stirring for 1 h at 60° C. under N₂ atmosphere. The resulting mixture was filtered and the filter cake was washed with ACN. The filtrate was concentrated under reduced pressure to afford (2S,3S,5R)-3-((4-methoxyphenyl) diphenylmethoxy)-5-(4-(((4-methoxyphenyl) diphenylmethyl) amino) pyrrolo[2,1-f] [1,2,4] triazin-7-yl) tetrahydrofuran-2-carbaldehyde (2.8 g, 3.52 mmol, 93.6%) as a light-yellow solid. LC-MS (ES, m/z): 793 [M+H]⁺.

Step 5: To a solution of (2S,3S,5R)-3-((4-methoxyphenyl) diphenylmethoxy)-5-(4-(((4-methoxyphenyl) diphenylmethyl) amino) pyrrolo[2,1-f] [1,2,4] triazin-7-yl) tetrahydrofuran-2-carbaldehyde (3.4 g, 9.61 mmol) in 1,4-dioxane (100 mL) and H₂O (10 mL) was added paraformaldehyde (1.4 g, 47.92 mmol) and NaOH (343 mg, 8.6 mmol) under N₂ atmosphere. The reaction was stirred overnight at room temperature. Then was added NaBH₄ (487 mg, 12.93 mmol) at 0° C. After stirring for 2 h at room temperature under N₂ atmosphere. The resulting mixture was diluted with water and extracted with EtOAc (3×100 mL). The combined organic layers were washed with saturated NH₄Cl solution, dried over anhydrous Na₂SO₄. After filtration the filtrate was concentrated under reduced pressure. The residue was purified by silica gel column chromatography, eluting with PE/EtOAc (1/1) to afford ((3S,5R)-3-((4-methoxyphenyl) diphenylmethoxy)-5-(4-(((4-methoxyphenyl) diphenylmethyl) amino) pyrrolo[2,1-f] [1,2,4] triazin-7-yl) tetrahydrofuran-2,2-diyl) dimethanol (1.96 g, 2.41 mmol, 52.9%) as a white solid. LC-MS (ES, m/z): 825 [M+H]⁺.

Step 6: To a solution of ((3S,5R)-3-((4-methoxyphenyl) diphenylmethoxy)-5-(4-(((4-methoxyphenyl) diphenylmethyl) amino) pyrrolo[2,1-f] [1,2,4] triazin-7-yl) tetrahydrofuran-2,2-diyl) dimethanol (2.3 g, 2.81 mmol) and imidazole (570 mg, 8.42 mmol) in DCM (50 mL) was added TBDPSCl (919 mg, 3.43 mmol) under N₂ atmosphere at 0° C. After stirring overnight at room temperature under N₂ atmosphere, the resulting mixture was concentrated under reduced pressure and the residue was purified by silica gel column chromatography, eluting with PE/EA (1/1) to afford ((2S,3S,5R)-2-(((tert-butyldiphenylsilyl) oxy) methyl)-3-((4-methoxyphenyl) diphenylmethoxy)-5-(4-(((4-methoxyphenyl) diphenylmethyl) amino) pyrrolo[2,1-f] [1,2,4]triazin-7-yl) tetrahydrofuran-2-yl) methanol (1.58 g, 1.52 mmol, 53.3%) as a white solid. LC-MS (ES, m/z): 1063 [M+H]⁺.

Step 7: To a solution of ((2S,3S,5R)-2-(((tert-butyldiphenylsilyl) oxy) methyl)-3-((4-methoxyphenyl) diphenylmethoxy)-5-(4-(((4-methoxyphenyl) diphenylmethyl) amino) pyrrolo[2,1-f] [1,2,4] triazin-7-yl) tetrahydrofuran-2-yl) methanol (1.6 g, 1.5 mmol) in DCM (30 mL) was added 2,4,6-trimethylpyridine (540 mg, 4.5 mmol) and AgNO₃ (505 mg, 3.11 mmol) under N₂ atmosphere. Then MMTrCl (688 mg, 2.2 mmol) was added under 0° C. After stirring overnight at room temperature under N₂ atmosphere. The resulting mixture was diluted with water, extracted with DCM. The combined organic layers were washed with saturated NH₄Cl solution and citric acid, dried over anhydrous Na₂SO₄. After filtration the filtrate was concentrated under reduced pressure and the residue was purified by silica gel column chromatography, eluting with PE/EtOAc (5/1) to afford 7-((2R,4S,5S)-5-(((tert-butyldiphenylsilyl) oxy) methyl)-4-((4-methoxyphenyl) diphenylmethoxy)-5-(((4-methoxyphenyl) diphenylmethoxy) methyl) tetrahydrofuran-2-yl)-N-((4-methoxyphenyl) diphenylmethyl) pyrrolo [2,1-f] [1,2,4] triazin-4-amine (1.9 g, 1.41 mmol, 95.7%) as a light-yellow solid. LC-MS (ES, m/z): 1336 [M+H]⁺.

Step 8: To a solution of 7-((2R,4S,5S)-5-(((tert-butyldiphenylsilyl) oxy) methyl)-4-((4-methoxyphenyl) diphenylmethoxy)-5-(((4-methoxyphenyl) diphenylmethoxy) methyl) tetrahydrofuran-2-yl)-N-((4-methoxyphenyl) diphenylmethyl) pyrrolo[2,1-f] [1,2,4] triazin-4-amine (1.9 g, 1.52 mmol) in MeOH (100 mL) was added NH₄F (1.6 g, 43.83 mmol) at room temperature under N₂ atmosphere. After stirring overnight at 60° C. under N₂ atmosphere the resulting mixture was cooled to room temperature and concentrated. The residue was purified by silica gel column chromatography, eluting with PE/EA (1/1) to afford ((2R, 3S,5R)-3-((4-methoxyphenyl) diphenylmethoxy)-2-(((4-methoxyphenyl) diphenylmethoxy) methyl)-5-(4-(((4-methoxyphenyl) diphenylmethyl) amino) pyrrolo[2,1-f] [1,2,4]triazin-7-yl) tetrahydrofuran-2-yl) methanol (1.47 g, 1.31 mmol, 91.8%) as a white solid. LC-MS (ES, m/z): 1097 [M+H]⁺.

Step 9: A solution of ((2R,3S,5R)-3-((4-methoxyphenyl) diphenylmethoxy)-2-(((4-methoxyphenyl) diphenylmethoxy) methyl)-5-(4-(((4-methoxyphenyl) diphenylmethyl) amino) pyrrolo[2,1-f] [1,2,4] triazin-7-yl) tetrahydrofuran-2-yl) methanol (440 mg, 0.42 mmol) and DAST (194 mg, 1.21 mmol) in toluene (5 mL) was stirred for 2 hours at 0° C. under N₂ atmosphere. The reaction was quenched by the addition of saturated NaHCO₃ solution at 0° C. The resulting mixture was diluted with water and extracted with EtOAc (3×30 mL). The combined organic layers were washed with brine and dried over anhydrous Na₂SO₄. After filtration the filtrate was concentrated under reduced pressure. The residue was purified by Prep-TLC (PE/EtOAc=2/1) to afford 7-((2R,4S,5R)-5-(fluoromethyl)-4-((4-methoxyphenyl) diphenylmethoxy)-5-(((4-methoxyphenyl) diphenylmethoxy) methyl) tetrahydrofuran-2-yl)-N-((4-methoxyphenyl) diphenylmethyl) pyrrolo[2,1-f] [1,2,4] triazin-4-amine (355 mg, 0.32 mmol, 80.5%) as a light-yellow solid. LC-MS (ES, m/z): 1099 [M+H]⁺.

Step 10: A solution of 7-((2R,4S,5R)-5-(fluoromethyl)-4-((4-methoxyphenyl) diphenylmethoxy)-5-(((4-methoxyphenyl) diphenylmethoxy) methyl) tetrahydrofuran-2-yl)-N-((4-methoxyphenyl) diphenylmethyl) pyrrolo[2,1-f] [1,2,4] triazin-4-amine (300 mg, 0.27 mmol) in concentrated hydrochloric acid (10 mL) was stirred for 6 hours at 0° C. under N₂ atmosphere. The reaction was quenched by the addition of MeOH (20 mL) at 0° C. The resulting mixture was concentrated under reduced pressure. The residue was purified by Prep-TLC (DCM/MeOH=10/1) to afford crude product. The crude product was purified by Prep-HPLC with the following conditions (Column: XBridge Shield RP18 OBD Column, 19*250 mm, 10 m; Mobile Phase A: water (10 mmol/L NH₄HCO₃), Mobile Phase B: ACN; Flow rate: 25 mL/min; Gradient: 5% B to 10% B in 2 min, 10% B to 20% B in 7 min, Wavelength: 254 nm; RT1(min): 6.82). The fraction was collected and concentrated under vacuum, the residue was re-dissolved in CH₃CN and H₂O, and then was lyophilized to afford (2R,3S,5R)-5-(4-aminopyrrolo[2,1-f] [1,2,4] triazin-7-yl)-2-(fluoromethyl)-2-(hydroxymethyl) tetrahydrofuran-3-ol (5.6 mg, 0.02 mmol, 6.9%) as an off-white solid. LC-MS (ES, m/z): 283 [M+H]⁺, 95.5% purity. Conditions for the LC-MS: (Column: Shim-pack Scepter C18, 33*3.0 mm; Mobile Phase A: Water/5 mM NH₄HCO₃, Mobile Phase B: Acetonitrile; Flow rate: 1.50 mL/min; Gradient: 10% B to 95% B in 1.20 min, 95% B to 95% B in 0.60 min, 95% B to 10% B in 0.02 min; Wavelength: 254 nm; RT1(min): 0.417). ¹H NMR (400 MHz, DMSO-d₆) δ 7.85 (s, 1H), 7.69 (s, 2H), 6.84 (d, J=4.4 Hz, 1H), 6.64 (d, J=4.4 Hz, 1H), 5.41 (d, J=4.3 Hz, 1H), 5.27 (d, J=11.6 Hz, 1H), 4.81 (t, J=5.9 Hz, 1H), 3.93 (s, 1H), 3.88-3.72 (m, 2H), 3.66-3.46 (m, 2H), 2.38-2.19 (m, 1H), 1.83 (dd, J=13.6, 3.1 Hz, 1H).

Example 62—Synthesis of Compound 80: (2R,3R, 4S,5R)-5-(6-amino-2-fluoropurin-9-yl)-2-ethenyl-4-fluoro-2-(hydroxymethyl)oxolan-3-ol

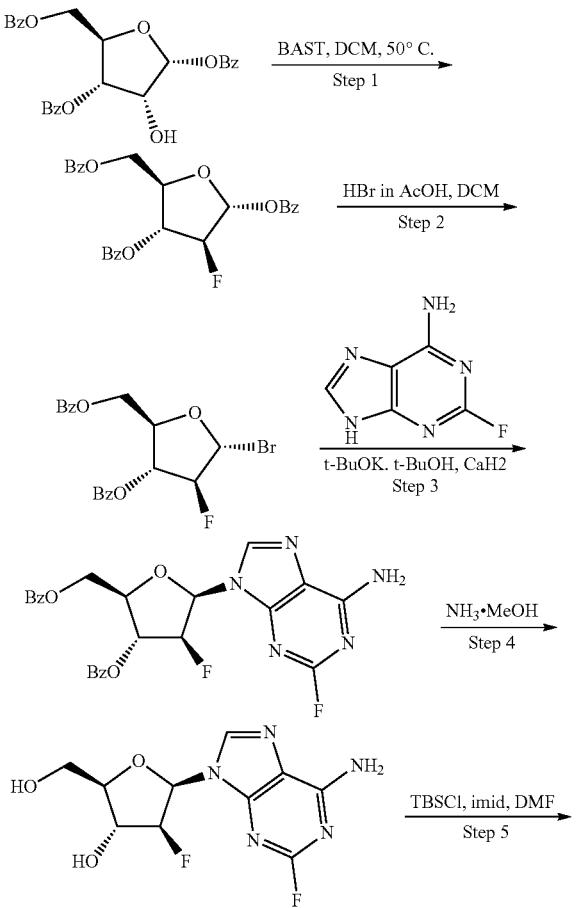

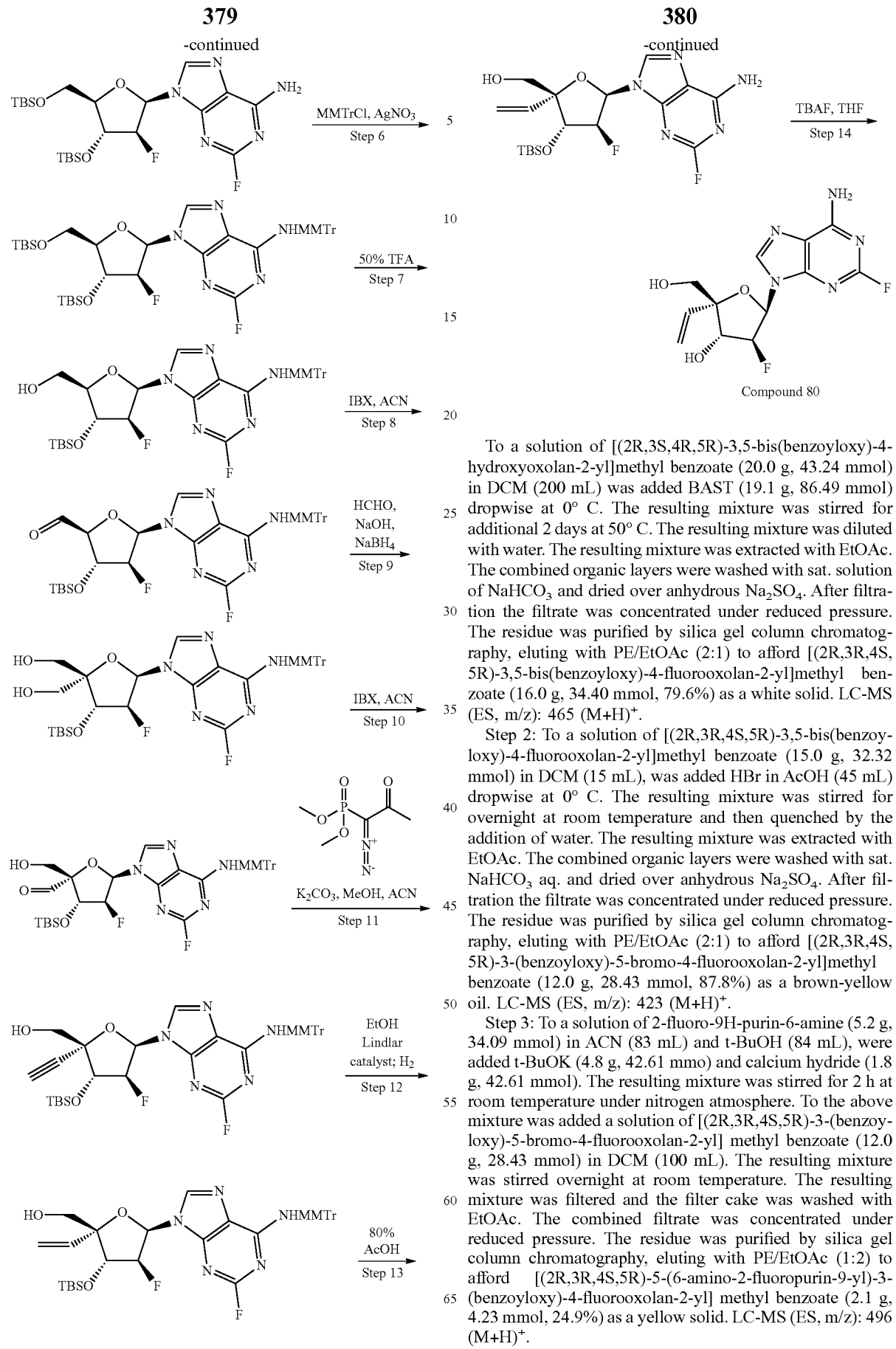

Compound 80

To a solution of [(2R,3S,4R,5R)-3,5-bis(benzoyloxy)-4-hydroxyoxolan-2-yl]methyl benzoate (20.0 g, 43.24 mmol) in DCM (200 mL) was added BAST (19.1 g, 86.49 mmol) dropwise at 0° C. The resulting mixture was stirred for additional 2 days at 50° C. The resulting mixture was diluted with water. The resulting mixture was extracted with EtOAc. The combined organic layers were washed with sat. solution of NaHCO$_3$ and dried over anhydrous Na$_2$SO$_4$. After filtration the filtrate was concentrated under reduced pressure. The residue was purified by silica gel column chromatography, eluting with PE/EtOAc (2:1) to afford [(2R,3R,4S,5R)-3,5-bis(benzoyloxy)-4-fluorooxolan-2-yl]methyl benzoate (16.0 g, 34.40 mmol, 79.6%) as a white solid. LC-MS (ES, m/z): 465 (M+H)$^+$.

Step 2: To a solution of [(2R,3R,4S,5R)-3,5-bis(benzoyloxy)-4-fluorooxolan-2-yl]methyl benzoate (15.0 g, 32.32 mmol) in DCM (15 mL), was added HBr in AcOH (45 mL) dropwise at 0° C. The resulting mixture was stirred for overnight at room temperature and then quenched by the addition of water. The resulting mixture was extracted with EtOAc. The combined organic layers were washed with sat. NaHCO$_3$ aq. and dried over anhydrous Na$_2$SO$_4$. After filtration the filtrate was concentrated under reduced pressure. The residue was purified by silica gel column chromatography, eluting with PE/EtOAc (2:1) to afford [(2R,3R,4S,5R)-3-(benzoyloxy)-5-bromo-4-fluorooxolan-2-yl]methyl benzoate (12.0 g, 28.43 mmol, 87.8%) as a brown-yellow oil. LC-MS (ES, m/z): 423 (M+H)$^+$.

Step 3: To a solution of 2-fluoro-9H-purin-6-amine (5.2 g, 34.09 mmol) in ACN (83 mL) and t-BuOH (84 mL), were added t-BuOK (4.8 g, 42.61 mmo) and calcium hydride (1.8 g, 42.61 mmol). The resulting mixture was stirred for 2 h at room temperature under nitrogen atmosphere. To the above mixture was added a solution of [(2R,3R,4S,5R)-3-(benzoyloxy)-5-bromo-4-fluorooxolan-2-yl] methyl benzoate (12.0 g, 28.43 mmol) in DCM (100 mL). The resulting mixture was stirred overnight at room temperature. The resulting mixture was filtered and the filter cake was washed with EtOAc. The combined filtrate was concentrated under reduced pressure. The residue was purified by silica gel column chromatography, eluting with PE/EtOAc (1:2) to afford [(2R,3R,4S,5R)-5-(6-amino-2-fluoropurin-9-yl)-3-(benzoyloxy)-4-fluorooxolan-2-yl] methyl benzoate (2.1 g, 4.23 mmol, 24.9%) as a yellow solid. LC-MS (ES, m/z): 496 (M+H)$^+$.

Step 4: A solution of [(2R,3R,4S,5R)-5-(6-amino-2-fluoropurin-9-yl)-3-(benzoyloxy)-4-fluorooxolan-2-yl] methyl benzoate (2.1 g, 4.23 mmol) in NH$_3$ (g) in MeOH (80 mL) was stirred for 6 h at room temperature. The mixture was adjusted to pH 7 with conc. HCl. The resulting mixture was concentrated under vacuum. The crude product was purified by reverse phase flash with the following conditions: C18 column; Mobile Phase A: Water (0.1% TFA), Mobile Phase B: ACN; Flow rate: 100 mL/min; Gradient: 0% B to 50% in 15 min, UV detection at 254 nm. This resulted in (2R,3R,4S,5R)-5-(6-amino-2-fluoropurin-9-yl)-4-fluoro-2-(hydroxymethyl) oxolan-3-ol (1.0 g, 3.48 mmol, 82.1%) as a light-yellow solid. LC-MS (ES, m/z): 287 (M+H)$^+$.

Step 5: To a solution of (2R,3R,4S,5R)-5-(6-amino-2-fluoropurin-9-yl)-4-fluoro-2-(hydroxymethyl) oxolan-3-ol (1.0 g, 3.48 mmol) and imidazole (2.8 g, 41.78 mmol) in DMF (10 mL), was added TBSCl (2.1 g, 13.92 mmol) in portions at 0° C. The resulting mixture was stirred overnight at room temperature and quenched by the addition of water. The resulting mixture was extracted with EtOAc. The combined organic layers were washed with brine and dried over anhydrous Na$_2$SO$_4$. After filtration the filtrate was concentrated under reduced pressure. The residue was purified by silica gel column chromatography, eluting with PE/EtOAc (2:1) to afford 9-[(2R,3S,4R,5R)-4-[(tert-butyldimethylsilyl) oxy]-5-{[(tert-butyldimethylsilyl) oxy] methyl}-3-fluorooxolan-2-yl]-2-fluoropurin-6-amine (1.6 g, 3.10 mmol, 89.1%) as a light-yellow solid. LC-MS (ES, m/z): 516 (M+H)$^+$.

Step 6: To a solution of 9-[(2R,3S,4R,5R)-4-[(tert-butyldimethylsilyl) oxy]-5-{[(tert-butyldimethylsilyl) oxy] methyl}-3-fluorooxolan-2-yl]-2-fluoropurin-6-amine (1.6 g, 3.10 mmol) in DCM (16 mL), were added 2,4,6-collidine (1.1 g, 9.30 mmol) and AgNO$_3$ (1.1 g, 6.20 mmol) at 0° C. under nitrogen atmosphere. This was followed by the addition of 1-(chlorodiphenylmethyl)-4-methoxybenzene (1.9 g, 6.20 mmol) in portions at 0° C. The resulting mixture was stirred overnight at room temperature. The resulting mixture was filtered and the filter cake was washed with EtOAc. The combined filtrate was concentrated under reduced pressure. The residue was purified by silica gel column chromatography, eluting with PE/EtOAc (5:1) to afford 9-[(2R,3S,4R,5R)-4-[(tert-butyldimethylsilyl) oxy]-5-{[(tert-butyldimethylsilyl)oxy] methyl}-3-fluorooxolan-2-yl]-2-fluoro-N-[(4-methoxyphenyl) diphenylmethyl]purin-6-amine (2.2 g, 2.79 mmol, 89.9%) as a light-yellow oil. LC-MS (ES, m/z): 788 (M+H)$^+$.

Step 7: To a solution of 9-[(2R,3S,4R,5R)-4-[(tert-butyldimethylsilyl) oxy]-5-{[(tert-butyldimethylsilyl) oxy] methyl}-3-fluorooxolan-2-yl]-2-fluoro-N-[(4-methoxyphenyl) diphenylmethyl] purin-6-amine (2.2 g, 2.79 mmol) in THF (10 mL) was added a solution of TFA (3 mL, 40.38 mmol) in H$_2$O (3 mL) dropwise at 0° C. The resulting mixture was stirred for 2 h at 0° C. The mixture was adjusted to pH 7 with saturated aq. NaHCO$_3$. The resulting mixture was extracted with EtOAc. The combined organic layers were washed with brine, and dried over anhydrous Na$_2$SO$_4$. After filtration the filtrate was concentrated under reduced pressure. The residue was purified by silica gel column chromatography, eluting with PE/EtOAc (1:1) to afford [(2R,3R,4S,5R)-3-[(tert-butyldimethylsilyl) oxy]-4-fluoro-5-(2-fluoro-6-{[(4-methoxyphenyl) diphenylmethyl] amino} purin-9-yl) oxolan-2-yl] methanol (1.6 g, 2.37 mmol, 85.0%) as a white solid. LC-MS (ES, m/z): 674 (M+H)$^+$.

Step 8: To a solution of [(2R,3R,4S,5R)-3-[(tert-butyldimethylsilyl) oxy]-4-fluoro-5-(2-fluoro-6-{[(4-methoxyphenyl) diphenylmethyl] amino} purin-9-yl) oxolan-2-yl] methanol (1.6 g, 2.37 mmol) in ACN (16 mL), was added IBX (1331.4 mg, 4.75 mmol) in portions. The resulting mixture was stirred for 4 h at 60° C. The resulting mixture was filtered; the filter cake was washed with acetonitrile. The combined filtrate was concentrated under reduced pressure. This resulted in (2S,3R,4S,5R)-3-[(tert-butyldimethylsilyl) oxy]-4-fluoro-5-(2-fluoro-6-{[(4-methoxyphenyl) diphenylmethyl] amino} purin-9-yl) oxolane-2-carbaldehyde (1.4 g, crude) as a light-yellow oil. The crude product was used in the next step directly without further purification. LC-MS (ES, m/z): 672 (M+H)$^+$.

Step 9: To a mixture of (2S,3R,4S,5R)-3-[(tert-butyldimethylsilyl) oxy]-4-fluoro-5-(2-fluoro-6-{[(4-methoxyphenyl) diphenylmethyl] amino} purin-9-yl) oxolane-2-carbaldehyde (1.4 g, crude) in 1,4-dioxane (20 mL), was added HCHO (1 mL, 37% in water). The resulting mixture was stirred overnight at room temperature under nitrogen atmosphere. To the above mixture was added NaBH$_4$ (323.7 mg, 8.74 mmol) in portions at 0° C. The resulting mixture was stirred for additional 2 h at room temperature and then quenched by the addition of sat. NH$_4$Cl (aq.) at 0° C. The resulting mixture was extracted with EtOAc. The combined organic layers were washed with brine, and dried over anhydrous Na$_2$SO$_4$. After filtration the filtrate was concentrated under reduced pressure. The residue was purified by silica gel column chromatography, eluting with PE/EtOAc (1:2) to afford [(3R,4S,5R)-3-[(tert-butyldimethyl silyl) oxy]-4-fluoro-5-(2-fluoro-6-{1[(4-methoxyphenyl) diphenylmethyl] amino} purin-9-yl)-2-(hydroxymethyl) oxolan-2-yl] methanol (600.0 mg, 0.85 mmol, 35.9% yield in two steps) as a white solid. LC-MS (ES, m/z): 704 (M+H)$^+$.

Step 10: To a solution of [(3R,4S,5R)-3-[(tert-butyldimethylsilyl) oxy]-4-fluoro-5-(2-fluoro-6-{[(4-methoxyphenyl) diphenylmethyl] amino} purin-9-yl)-2-(hydroxymethyl) oxolan-2-yl] methanol (600.0 mg, 0.85 mmol) in ACN (8 mL) was added IBX (286.8 mg, 1.02 mmol). The resulting mixture was stirred for 4 h at 65° C. under nitrogen atmosphere. The resulting mixture was cooled to room temperature and filtered. The filter cake was washed with acetonitrile. The combined filtrate was concentrated under reduced pressure. This resulted in (2R,3R,4S,5R)-3-[(tert-butyldimethylsilyl) oxy]-4-fluoro-5-(2-fluoro-6-{[(4-methoxyphenyl) diphenylmethyl] amino} purin-9-yl)-2-(hydroxymethyl) oxolane-2-carbaldehyde (550 mg, crude) as a light-yellow oil. The crude product was used in the next step directly without further purification. LC-MS (ES, m/z): 702 (M+H)$^+$.

Step 11: To a mixture of dimethyl (1-diazo-2-oxopropyl) phosphonate (165.7 mg, 0.86 mmol) in ACN (5 mL), was added K$_2$CO$_3$ (216.4 mg, 1.56 mmol). The resulting mixture was stirred for 30 min at 0° C. under nitrogen atmosphere. To the above mixture was added a solution of (2R,3R,4S,5R)-3-[(tert-butyldimethylsilyl) oxy]-4-fluoro-5-(2-fluoro-6-{[(4-methoxyphenyl) diphenylmethyl] amino} purin-9-yl)-2-(hydroxymethyl) oxolane-2-carbaldehyde (550 mg, crude) in MeOH (5 mL) dropwise at 0° C. The resulting mixture was stirred overnight at room temperature and then concentrated under vacuum. The residue was purified by silica gel column chromatography, eluting with PE/EtOAc (1:2) to afford [(2R,3R,4S,5R)-3-[(tert-butyldimethylsilyl) oxy]-2-ethynyl-4-fluoro-5-(2-fluoro-6-{[(4-methoxyphenyl)diphenylmethyl] amino} purin-9-yl) oxolan-2-yl] methanol (220.0 mg, 0.31 mmol, 36.9% yield in two steps) as a light-yellow solid. LC-MS (ES, m/z): 698 (M+H)$^+$.

Step 12: To a solution of [(2R,3R,4S,5R)-3-[(tert-butyldimethylsilyl) oxy]-2-ethynyl-4-fluoro-5-(2-fluoro-6-{[(4- methoxyphenyl) diphenylmethyl] amino} purin-9-yl) oxolan-2-yl] methanol (220.0 mg, 0.31 mmol) in EtOH (5 mL) was added Lindlar catalyst (65.7 mg, 0.31 mmol) in portions at room temperature. The flask was evacuated and flushed three times with nitrogen, followed by flushing with hydrogen. The mixture was stirred 1 h at room temperature under an atmosphere of hydrogen (balloon). The resulting mixture was filtered; the filter cake was washed with ethanol. The combined filtrate was concentrated under reduced pressure. This resulted in [(2R,3R,4S,5R)-3-[(tert-butyldimethylsilyl) oxy]-2-ethenyl-4-fluoro-5-(2-fluoro-6-{1[(4-methoxyphenyl) diphenylmethyl] amino} purin-9-yl) oxolan-2-yl] methanol (200 mg, crude) as a colorless oil. The crude product was used in the next step directly without further purification. LC-MS (ES, m/z): 700 (M+H)+.

Step 13: A solution of [(2R,3R,4S,5R)-3-[(tert-butyldimethylsilyl) oxy]-4-fluoro-5-(2-fluoro-6-{1[(4-methoxyphenyl) diphenylmethyl] amino} purin-9-yl)-2-(prop-1-en-2-yl) oxolan-2-yl] methanol (200 mg, crude) in AcOH (3 mL, 80%) was stirred for overnight at 0° C. under nitrogen atmosphere. The resulting mixture was diluted with water. The resulting mixture was extracted with EtOAc. The combined organic layers were washed with sat. solution of NaHCO$_3$ and dried over anhydrous Na$_2$SO$_4$. After filtration the filtrate was concentrated under reduced pressure. The residue was purified by silica gel column chromatography, eluting with CH$_2$Cl$_2$/MeOH (10:1) to afford [(2R,3R,4S,5R)-5-(6-amino-2-fluoropurin-9-yl)-3-[(tert-butyldimethylsilyl) oxy]-2-ethenyl-4-fluorooxolan-2-yl] methanol (100.0 mg, 0.23 mmol, 74.2% yield in two steps) as a light-yellow oil. LC-MS (ES, m/z): 428 (M+H)+.

Step 14: To a solution of [(2R,3R,4S,5R)-5-(6-amino-2-fluoropurin-9-yl)-3-[(tert-butyldimethylsilyl) oxy]-4-fluoro-2-(prop-1-en-2-yl) oxolan-2-yl] methanol (100.0 mg, 0.23 mmol) in THF (2 mL), was added TBAF (1 mL, 1N in THF) dropwise. The resulting mixture was stirred overnight at room temperature and then concentrated under vacuum. The residue was purified by silica gel column chromatography, eluting with CH$_2$Cl$_2$/MeOH (10:1) to afford (2R,3R,4S,5R)-5-(6-amino-2-fluoropurin-9-yl)-2-ethenyl-4-fluoro-2-(hydroxymethyl) oxolan-3-ol (60 mg, crude) as a light-yellow oil. The crude product was further purified by Prep-HPLC with the following conditions Column: SunFire C18 OBD Prep Column, 19×250 mm, 5 μm; Mobile Phase A: Water (0.1% FA), Mobile Phase B: ACN; Flow rate: 25 mL/min; Gradient: 40% B to 60% B in 6 min; Wavelength: 254/210 nm. The product-containing fractions were combined and evaporated partially to remove the solvents, then lyophilized overnight to afford (2R,3R,4S,5R)-5-(6-amino-2-fluoropurin-9-yl)-2-ethenyl-4-fluoro-2-(hydroxymethyl) oxolan-3-ol (16.3 mg, 0.05 mmol, 22.23%) as a white solid. LC-MS (ES, m/z): 314 (M+H)+; 99.5% purity. Conditions for the HPLC: (Column: Shim-pack Scepter C18, 33*3.0 mm, 3.5 μm; Mobile Phase A: water/0.05% NH$_4$CO$_3$, Mobile Phase B: ACN; Flow rate: 1.2000 mL/min; Gradient: 10% B to 10% B in 0.01 min, 10% B to 40% B in 1.69 min, 40% B to 95% B in 0.5 min; 95% B to 95% B in 0.5 min; 95% B to 10% B in 0.03 min; Wavelength: 254/220 nm; RT1(min): 0.812). $^1$H NMR (400 MHz, DMSO-d$_6$) δ 8.36 (d, J=1.2 Hz, 1H), 7.91 (brs, 2H), 6.36 (t, J=6.4 Hz, 1H), 6.11 (d, J=5.2 Hz, 1H), 5.98 (dd, J=17.6, 10.8 Hz, 1H), 5.49-5.44 (m, 1H), 5.38 (t, J=5.6 Hz, 1H), 5.30-5.23 (m, 1H), 5.11 (t, J=6.4 Hz, 1H), 4.79-4.71 (m, 1H), 3.61-3.56 (m, 1H), 3.46-3.41 (m, 1H).

Example 63—Synthesis of Compound 81: (2R,3R,4S,5R)-5-(6-amino-2-fluoropurin-9-yl)-2-ethyl-4-fluoro-2-(hydroxymethyl)oxolan-3-ol

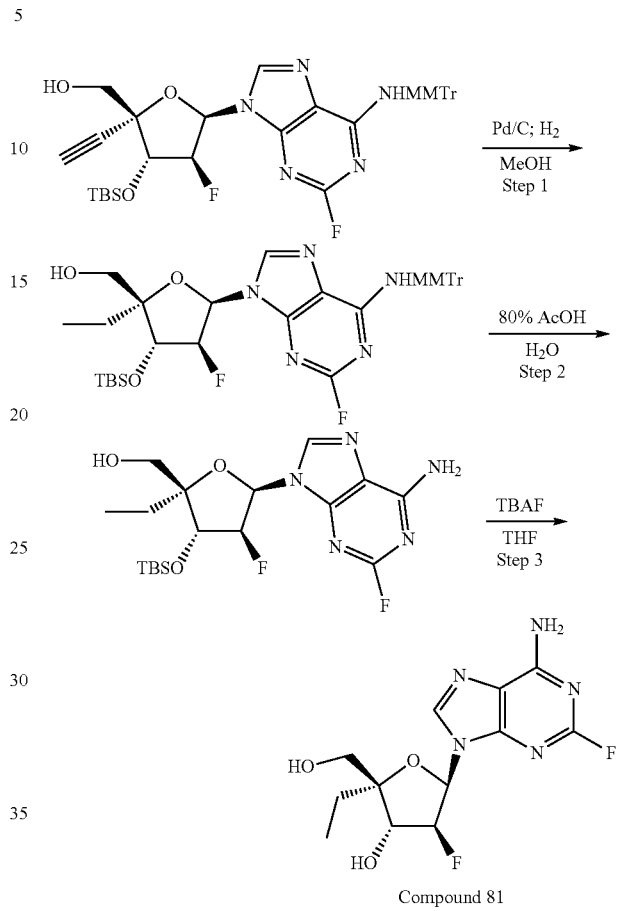

Compound 81

Step 1: To a solution of [(2R,3R,4S,5R)-3-[(tert-butyldimethylsilyl) oxy]-2-ethynyl-4-fluoro-5-(2-fluoro-6-{1[(4-methoxyphenyl) diphenylmethyl] amino} purin-9-yl) oxolan-2-yl] methanol (200.0 mg, 0.28 mmol) in EtOH (2 mL) was added Pd/C (20 mg, 10%) under nitrogen atmosphere. The flask was evacuated and flushed three times with nitrogen, followed by flushing with hydrogen. The mixture was stirred 2 h at room temperature under an atmosphere of hydrogen (balloon). The resulting mixture was filtered; the filter cake was washed with ethanol. The combined filtrate was concentrated under reduced pressure. This resulted in [(2R,3R,4S,5R)-3-[(tert-butyldimethylsilyl) oxy]-2-ethyl-4-fluoro-5-(2-fluoro-6-{[(4-methoxy phenyl)diphenylmethyl] amino} purin-9-yl) oxolan-2-yl] methanol (190 mg, crude) as a colorless oil. The crude product was used in the next step directly without further purification. LC-MS (ES, m/z): 702 (M+H)+.

Step 2: A solution of [(2R,3R,4S,5R)-3-[(tert-butyldimethylsilyl) oxy]-2-ethyl-4-fluoro-5-(2-fluoro-6-{1[(4-methoxyphenyl) diphenylmethyl] amino} purin-9-yl) oxolan-2-yl]methanol (180.0 mg, 0.26 mmol) in AcOH (3 mL, 80% in water) was stirred overnight at room temperature under nitrogen atmosphere. The resulting mixture was diluted with water. The resulting mixture was extracted with EtOAc. The combined organic layers were washed with saturated aq. NaHCO$_3$, dried over anhydrous Na$_2$SO$_4$. After filtration the filtrate was concentrated under reduced pressure. This resulted in [(2R,3R,4S,5R)-5-(6-amino-2-fluoropurin-9-yl)-3-[(tert-butyldimethylsilyl) oxy]-2-ethyl-4-fluorooxolan-2-yl] methanol (100.0 mg, 0.23 mmol, 81.3% yield in two steps) as a colorless oil. LC-MS (ES, m/z): 430 (M+H)+.

Step 3: To a solution of [(2R,3R,4S,5R)-5-(6-amino-2-fluoropurin-9-yl)-3-[(tert-butyldimethylsilyl) oxy]-2-ethyl-4-fluorooxolan-2-yl] methanol (100.0 mg, 0.23 mmol) in THF (2 mL), was added TBAF (0.4 mL, 1N in THF) dropwise at 0° C. The resulting mixture was stirred for overnight at room temperature and then concentrated under vacuum. The residue was purified by silica gel column chromatography, eluted with CH$_2$Cl$_2$/MeOH (10:1) to afford crude (2R,3R,4S,5R)-5-(6-amino-2-fluoropurin-9-yl)-2-ethyl-4-fluoro-2-(hydroxymethyl)oxolan-3-ol (100 mg, crude) as a light-yellow solid. The crude product was further purified by prep-HPLC with the following conditions: Column: SunFire C18 OBD Prep Column, 19*250 mm, 5 μm; Mobile Phase A: Water (0.1% FA), Mobile Phase B: ACN; Flow rate: 25 mL/min; Gradient: 40% B to 60% B in 6 min; Wavelength: 254/210 nm. The product-containing fractions were combined and evaporated partially to remove the solvents, then lyophilized overnight to afford (2R,3R,4S,5R)-5-(6-amino-2-fluoropurin-9-yl)-2-ethyl-4-fluoro-2-(hydroxymethyl) oxolan-3-ol (17.3 mg, 0.05 mmol, 23.43%) as a white solid. LC-MS (ES, m/z): 316 (M+H). 99.4% purity. Conditions for the HPLC: (Column: Shim-pack Scepter C18, 33*3.0 mm, 3.5 μm; Mobile Phase A: water/0.05% NH$_4$CO$_3$, Mobile Phase B: ACN; Flow rate: 1.2000 mL/min; Gradient: 5% B to 95% B in 1.19 min, 95% B to 95% B in 0.6 min, 90% B to 5% B in 0.02 min; Wavelength: 254/220 nm; RT1(min): 0.517). $^1$H NMR (400 MHz, DMSO-d$_6$) δ 8.29 (d, J=2.0 Hz, 1H), 7.88 (brs, 2H), 6.32-6.28 (m, 1H), 5.88 (d, J=5.6 Hz, 1H), 5.38 (t, J=5.2 Hz, 0.5H), 5.25 (t, J=5.2 Hz, 0.5H), 5.14 (t, J=5.6 Hz, 1H), 4.64-4.58 (m, 1H), 3.56-3.53 (m, 1H), 3.50-3.46 (m, 1H), 1.69-1.56 (m, 2H), 0.90 (t, J=7.6 Hz, 3H).

Example 64—Synthesis of Compound 83: 2-amino-9-((2R,3S,4R,5R)-3-fluoro-5-(fluoromethyl)-4-hydroxy-5-(hydroxymethyl) tetrahydrofuran-2-yl)-1,9-dihydro-6H-purin-6-one

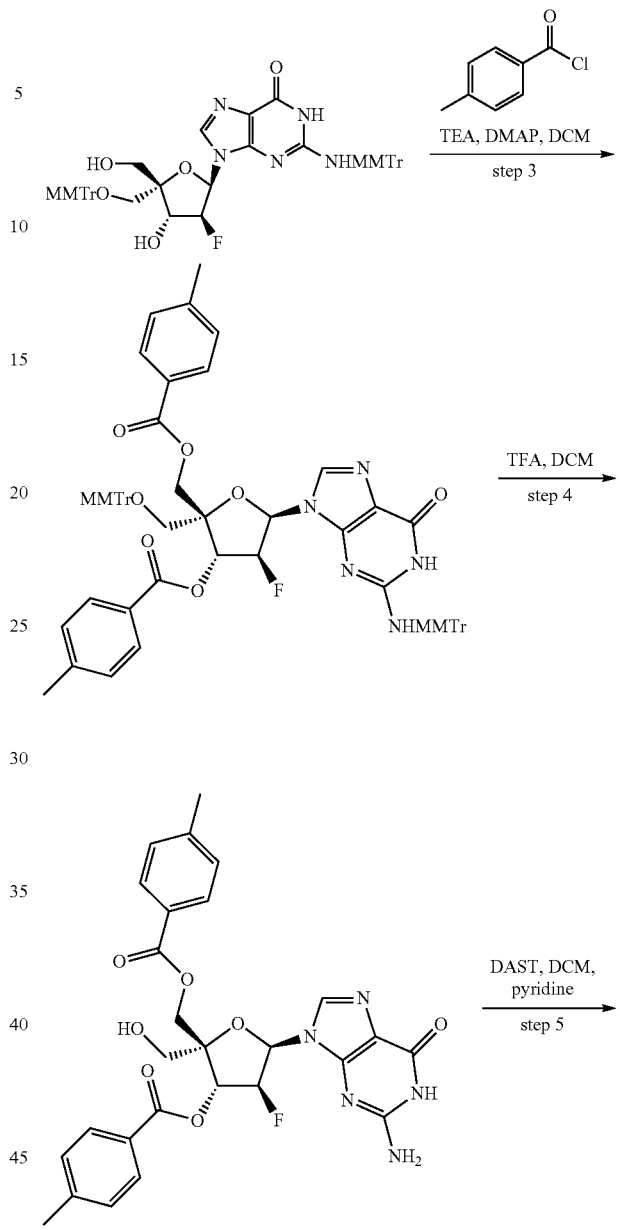

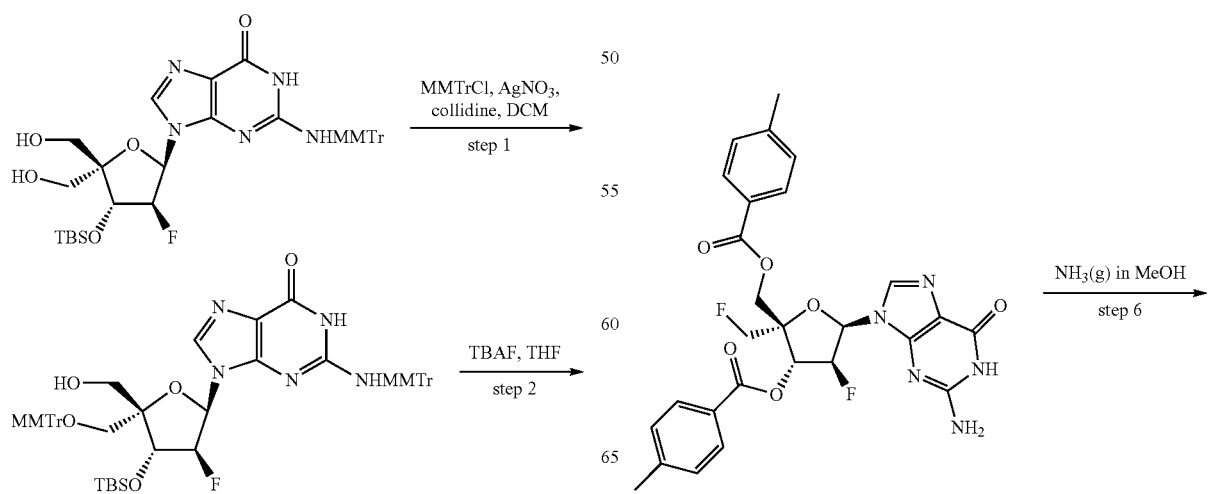

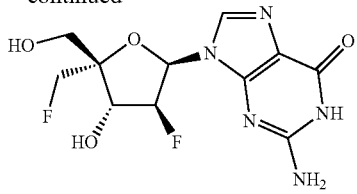

Compound 83

Step 1: To a stirred mixture of 9-((2R,3S,4R)-4-((tert-butyldimethylsilyl) oxy)-3-fluoro-5,5-bis(hydroxymethyl) tetrahydrofuran-2-yl)-2-(((4-methoxyphenyl) diphenylmethyl) amino)-1,9-dihydro-6H-purin-6-one (2.51 g, 3.51 mmol), 2,4,6-collidine (1.2 g, 10.53 mmol) and AgNO$_3$ (1.2 g, 7.02 mmol) in DCM (25 mL) was added MMTrCl (1.2 g, 3.86 mmol) in portions at room temperature under N$_2$ atmosphere. The resulting mixture was stirred for 2 h at room temperature under N$_2$ atmosphere. The resulting mixture was diluted with water and extracted with DCM (3×100 mL). The combined organic layers were washed with brine, and dried over by anhydrous Na$_2$SO$_4$. After filtration the filtrate was concentrated under reduced pressure. The resulting mixture was used in the next step directly without further purification. LC-MS (ES, m/z): 974 [M+H]$^+$.

Step 2: To a solution of TBAF (10 mL, 3.82 mmol, 1M in THF) in THF (25 mL) was added 9-((2R,3S,4R,5S)-4-((tert-butyldimethylsilyl) oxy)-3-fluoro-5-(hydroxymethyl)-5-(((4-methoxyphenyl) diphenylmethoxy) methyl) tetrahydrofuran-2-yl)-2-(((4-methoxyphenyl) diphenylmethyl) amino)-1,9-dihydro-6H-purin-6-one (2.5 g, 2.51 mmol). The mixture was stirred for 2 h at room temperature under N$_2$ atmosphere and concentrated. The residue was purified by silica gel column chromatography, eluting with EtOAc/ Petroleum ether (1:1) to afford 9-((2R,3S,4R,5S)-3-fluoro-4-hydroxy-5-(hydroxymethyl)-5-(((4-methoxyphenyl) diphenylmethoxy) methyl) tetrahydrofuran-2-yl)-2-(((4-methoxyphenyl) diphenylmethyl) amino)-1,9-dihydro-6H-purin-6-one (1.6 g, 1.82 mmol, 72.5%) as a yellow solid. LC-MS (ES, m/z): 860 [M+H]$^+$.

Step 3: To a stirred solution of 9-((2R,3S,4R,5S)-3-fluoro-4-hydroxy-5-(hydroxymethyl)-5-(((4-methoxyphenyl) diphenylmethoxy) methyl) tetrahydrofuran-2-yl)-2-(((4-methoxyphenyl) diphenylmethyl) amino)-1,9-dihydro-6H-purin-6-one (1.6 g, 1.82 mmol), TEA (1.6 g, 16.73 mmol) and DMAP (340 mg, 2.74 mmol) in DCM (15 mL) was added 4-methyl-benzoyl chloride (862 mg, 5.52 mmol) at room temperature under N$_2$ atmosphere. The resulting mixture was stirred for 2 h at room temperature under N$_2$ atmosphere. The resulting mixture was diluted with water and extracted with DCM (3×80 mL). The combined organic layers were washed with brine, and dried over anhydrous Na$_2$SO$_4$. After filtration the filtrate was concentrated under reduced pressure. The residue was purified by silica gel column chromatography, eluting with EtOAc/Petroleum ether (1:1) to afford (2R,3R,4S,5R)-4-fluoro-2-(((4-methoxyphenyl) diphenylmethoxy) methyl)-5-(2-(((4-methoxyphenyl) diphenylmethyl) amino)-6-oxo-1,6-dihydro-9H-purin-9-yl)-2-(((4-methylbenzoyl) oxy) methyl) tetrahydrofuran-3-yl 4-methylbenzoate (870 mg, 0.72 mmol, 42.7%) as a yellow solid. LC-MS (ES, m/z): 1096 [M+H]$^+$.

Step 4: A solution of (2R,3R,4S,5R)-4-fluoro-2-(((4-methoxyphenyl) diphenylmethoxy) methyl)-5-(2-(((4-methoxyphenyl) diphenylmethyl) amino)-6-oxo-1,6-dihydro-9H-purin-9-yl)-2-(((4-methylbenzoyl) oxy) methyl) tetrahydrofuran-3-yi 4-methyl benzoate (870 mg, 0.72 mmol) and TFA (0.3 mL) in DCM (9 mL) was stirred for 2 h at room temperature under N$_2$ atmosphere. The resulting mixture was concentrated under vacuum. The residue was purified by reversed-phase flash chromatography with the following conditions: C18 column; mobile phase, ACN and water (10 mmol/L NH$_4$HCO$_3$), 65% to 75% gradient in 5 min; UV detections at 254 nm. This resulted in (2R,3R,4S,5R)-5-(2-amino-6-oxo-1,6-dihydro-9H-purin-9-yl)-4-fluoro-2-(hydroxymethyl)-2-(((4-methylbenzoyl) oxy) methyl) tetrahydrofuran-3-yl 4-methylbenzoate (250 mg, 0.42 mmol, 57.1%) as a white solid. LC-MS (ES, m/z): 552 [M+H]$^+$.

Step 5: To a stirred solution of (2R,3R,4S,5R)-5-(2-amino-6-oxo-1,6-dihydro-9H-purin-9-yl)-4-fluoro-2-(hydroxymethyl)-2-(((4-methylbenzoyl) oxy) methyl) tetrahydrofuran-3-yl 4-methylbenzoate (100 mg, 0.14 mmol) in DCM (2 mL) and pyridine (0.3 mL) was added DAST (87 mg, 0.51 mmol) at room temperature under N$_2$ atmosphere. The resulting mixture was stirred overnight at 40° C. under N$_2$ atmosphere. The resulting mixture was quenched with water and extracted with DCM (3×50 mL). The combined organic layers were washed with brine and dried over anhydrous Na$_2$SO$_4$. After filtration the filtrate was concentrated under reduced pressure. The residue was purified by reversed-phase flash chromatography with the following conditions: C18 column; mobile phase, ACN and water (10 mmol/L NH$_4$HCO$_3$), 75% to 85% gradient in 5 min; UV detection at 254 nm. This resulted in [(2R,3R,4S,5R)-5-(2-amino-6-oxo-1H-purin-9-yl)-4-fluoro-2-(fluoromethyl)-3-(4-methylbenzoyloxy) oxolan-2-yl] methyl 4-methylbenzoate (30 mg, 0.05 mmol, 29.9%) as a white solid. LC-MS (ES, m/z): 554 [M+H]$^+$.

Step 6: To a solution of NH$_3$ (g) in MeOH (1 mL, 7 M) was added (2R,3R,4S,5R)-5-(2-amino-6-oxo-1,6-dihydro-9H-purin-9-yl)-4-fluoro-2-(fluoromethyl)-2-(((4-methylbenzoyl) oxy) methyl) tetrahydrofuran-3-yl 4-methylbenzoate (30 mg, 0.05 mmol). The reaction was stirred overnight at room temperature under N$_2$ atmosphere. The resulting mixture was concentrated under reduced pressure. The crude product was purified by Prep-HPLC with the following conditions (Column: XBridge Shield RP18 OBD Column, 19*250 mm, 10 μm; Mobile Phase A: water (10 mmol/L NH$_4$HCO$_3$), Mobile Phase B: ACN; Flow rate: 25 mL/min; Gradient: 5% B to 25% B in 6 min; Wavelength: 254 nm; RT1(min): 5.7). The fraction was collected and concentrated under vacuum. The residue was re-dissolved in CH$_3$CN and H$_2$O and lyophilized to afford 2-amino-9-((2R,3S,4R,5R)-3-fluoro-5-(fluoromethyl)-4-hydroxy-5-(hydroxymethyl) tetrahydrofuran-2-yl)-1,9-dihydro-6H-purin-6-one (2.4 mg, 7 μmol, 13.6%) as a white solid. LC-MS (ES, m/z): 318 [M+H]$^+$, 97.6% purity. Conditions for the HPLC: (Column: HALO C18, 100*4.6 mm; Mobile Phase A: H$_2$O+0.1% TFA, Mobile Phase B: ACN+0.1% TFA; Flow rate: 1.20 mL/min; Gradient: 0% B to 95% B in 8 min, 95% B to 95% B in 10 min, 95% B to 10% B in 10.5 min; Wavelength: 254/220 nm; RT1(min): 2.45). $^1$H NMR (400 MHz, DMSO-d$_6$) δ 7.81 (d, J=2.2 Hz, 1H), 6.54 (s, 2H), 6.30-6.17 (m, 2H), 5.36-5.06 (m, 2H), 4.73-4.64 (m, 1H), 4.64-4.42 (m, 2H), 3.62 (dd, J=11.9, 5.5 Hz, 1H), 3.53 (dd, J=11.4, 5.3 Hz, 1H).

Example 65—Synthesis of Compound 84: (2R,3R,4S,5R)-5-(6-amino-2-fluoropurin-9-yl)-4-fluoro-2-(fluoromethyl)-2-(hydroxymethyl) oxolan-3-ol)

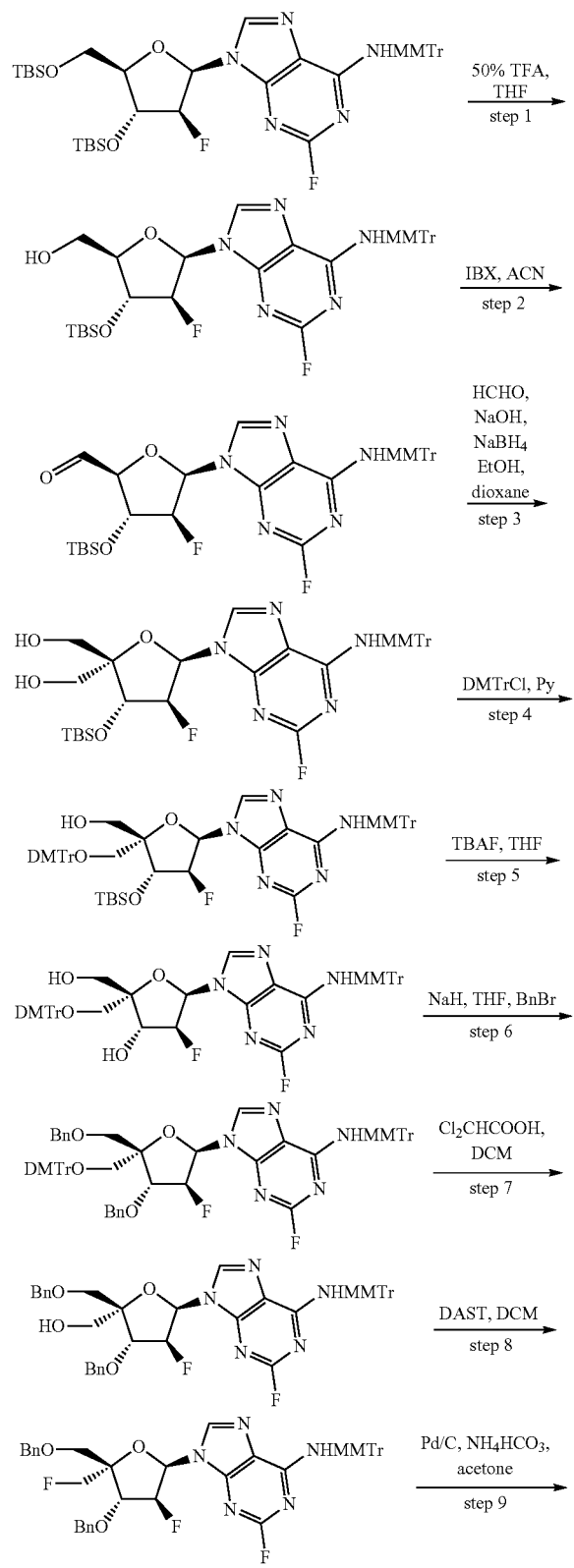

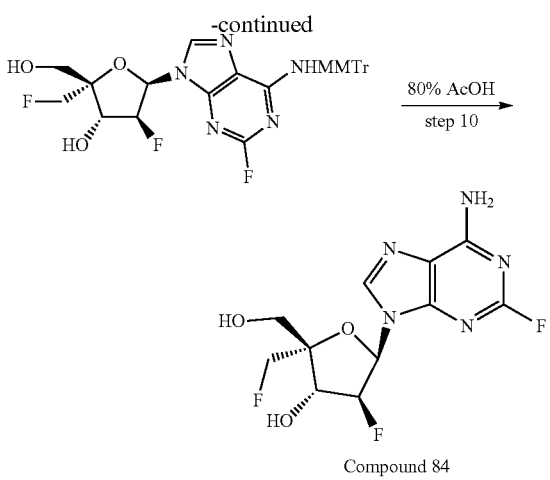

Compound 84

Step 1: To a stirred solution of 9-[(2R,3S,4R,5R)-4-[(tert-butyldimethylsilyl) oxy]-5-{[(tert-butyldimethylsilyl) oxy]methyl}-3-fluorooxolan-2-yl]-2-fluoro-N-[(4-methoxyphenyl) diphenylmethyl] purin-6-amine (2.0 g, 2.54 mmol) in THF (8 mL) was added TFA (8 mL, 50% in water) dropwise at 0° C. under nitrogen atmosphere. The resulting mixture was stirred for 1 h at 0° C. and then quenched by the addition of sat. NaHCO$_3$(aq.) (50 mL) at 0° C. The resulting mixture was extracted with EtOAc (3×100 mL). The combined organic layers were washed with brine (3×100 mL) and dried over anhydrous Na$_2$SO$_4$. After filtration the filtrate was concentrated under reduced pressure. The residue was purified by silica gel column chromatography, eluted with PE/EtOAc (1:1) to afford [(2R,3R,4S,5R)-3-[(tert-butyldimethylsilyl) oxy]-4-fluoro-5-(2-fluoro-6-{[(4-methoxyphenyl) diphenylmethyl] amino}purin-9-yl) oxolan-2-yl] methanol (1.5 g, 2.2 mmol, 87.7%) as a white solid. LC-MS (ES, m/z): 674 (M+H)$^+$.

Step 2: To a solution of [(2R,3R,4S,5R)-3-[(tert-butyldimethylsilyl) oxy]-4-fluoro-5-(2-fluoro-6-{[(4-methoxyphenyl) diphenylmethyl] amino} purin-9-yl) oxolan-2-yl] methanol (1.5 g, 2.23 mmol) in ACN (30 mL) was added IBX (11.2 g, 4.45 mmol). The resulting mixture was stirred for 2 h at 65° C. under nitrogen atmosphere and cooled down to room temperature. The resulting mixture was filtered; the filter cake was washed with MeCN (3×10 mL). The combined filtrate was concentrated under reduced pressure. This resulted in (2S,3R,4S,5R)-3-[(tert-butyldimethylsilyl) oxy]-4-fluoro-5-(2-fluoro-6-{[(4-methoxyphenyl) diphenylmethyl] amino} purin-9-yl) oxolane-2-carbaldehyde (1.4 g, crude) as a white solid. The crude product was used in the next step directly without further purification. LC-MS (ES, m/z): 672 (M+H)$^+$.

Step 3: To a stirred solution of (2S,3R,4S,5R)-3-[(tert-butyldimethylsilyl) oxy]-4-fluoro-5-(2-fluoro-6-{1[(4-methoxyphenyl) diphenylmethyl] amino} purin-9-yl) oxolane-2-carbaldehyde (1.4 g, crude) and HCHO (0.7 mL, 37% in water) in 1,4-dioxane (14 mL) was added NaOH aq. (2.8 mL, 2M) in portions at room temperature. The resulting mixture was degassed three times with nitrogen, and then stirred for overnight at room temperature under a nitrogen atmosphere. To the above mixture was added NaBH$_4$ (331.0 mg, 8.75 mmol) in portions at 0° C. The resulting mixture was stirred for additional 30 min at room temperature and then quenched by the addition of sat. NH$_4$Cl aq. (200 mL) at 0° C. The resulting solution was extracted with EtOAc (2×200 mL). The combined organic layers were washed with brine (2×200 mL), dried over anhydrous Na$_2$SO$_4$. After filtration the filtrate was concentrated under reduced pressure. The residue was purified by silica gel column chromatography, eluted with PE/EtOAc (1:1) to afford [(3R,4S,5R)-3-[(tert-butyldimethylsilyl) oxy]-4-fluoro-5-(2-fluoro-6-{1[(4-methoxyphenyl) diphenylmethyl] amino} purin-9-yl)-2-(hydroxymethyl) oxolan-2-yl]methanol (1.0 g, 1.4 mmol, 64.1% yield in two steps) as a white solid. LC-MS (ES, m/z): 704 (M+H)$^+$.

Step 4: To a stirred solution of [(3R,4S,5R)-3-[(tert-butyldimethylsilyl) oxy]-4-fluoro-5-(2-fluoro-6-{1[(4-methoxyphenyl) diphenylmethyl] amino} purin-9-yl)-2-(hydroxymethyl) oxolan-2-yl] methanol (1.0 g, 1.42 mmol) in pyridine (20 mL) was added DMTrCl (480.0 mg, 1.56 mmol) in portions at 0° C. under nitrogen atmosphere. The resulting mixture was stirred for overnight at room temperature under nitrogen atmosphere and quenched by the addition of MeOH (1 mL) at 0° C. The resulting mixture was concentrated under reduced pressure. The residue was purified by silica gel column chromatography, eluted with PE/EtOAc (2:1) to afford [(2S,3R,4S,5R)-2-{[bis(4-methoxyphenyl) (phenyl)methoxy] methyl}-3-[(tert-butyldimethylsilyl) oxy]-4-fluoro-5-(2-fluoro-6-{1[(4-methoxyphenyl) diphenylmethyl] amino}purin-9-yl) oxolan-2-yl] methanol (900.0 mg, 0.9 mmol, 62.9%) as a light-yellow solid. LC-MS (ES, m/z): 1006 (M+H)$^+$.

Step 5: To a stirred solution of [(2S,3R,4S,5R)-2-{[bis(4-methoxyphenyl) (phenyl)methoxy] methyl}-3-[(tert-butyldimethylsilyl) oxy]-4-fluoro-5-(2-fluoro-6-{[(4-methoxyphenyl) diphenylmethyl] amino} purin-9-yl) oxolan-2-yl] methanol (900.0 mg, 0.89 mmol) in THF (9 mL) was added TBAF (470.0 mg, 1.79 mmol) in portions at room temperature under nitrogen atmosphere. The resulting mixture was stirred for 2 h at room temperature and quenched by the addition of water (100 mL). The resulting mixture was extracted with EtOAc (3×100 mL). The combined organic layers were washed with brine (2×100 mL), dried over anhydrous Na$_2$SO$_4$. After filtration the filtrate was concentrated under reduced pressure. The residue was purified by silica gel column chromatography, eluted with PE/EtOAc (1:1) to afford (2S,3R,4S,5R)-2-{[bis(4-methoxyphenyl)(phenyl)methoxy] methyl}-4-fluoro-5-(2-fluoro-6-{[(4-methoxyphenyl)diphenylmethyl]amino} purin-9-yl)-2-(hydroxymethyl) oxolan-3-ol (700.0 mg, 0.8 mmol, 87.7%) as a light-yellow solid. LC-MS (ES, m/z): 892 (M+H)$^+$.

Step 6: (2S,3R,4S,5R)-2-{[bis(4-methoxyphenyl) (phenyl)methoxy] methyl}-4-fluoro-5-(2-fluoro-6-{1[(4-methoxyphenyl) diphenylmethyl] amino} purin-9-yl)-2-(hydroxymethyl) oxolan-3-ol (700.0 mg, 0.79 mmol) in THF (14 mL) was added NaH (38 mg, 60% in oil, 1.57 mmol) at 0° C. under nitrogen atmosphere. After stirred 10 min, BnBr (268.0 mg, 1.57 mmol) was added dropwise at 0° C. under nitrogen atmosphere. The resulting mixture was stirred for overnight at room temperature under nitrogen atmosphere and quenched by the addition of sat. NH$_4$Cl aq. (100 mL) at 0° C. The resulting solution was extracted with EtOAc (3×100 mL). The combined organic layers were washed with brine (2×100 mL), dried over anhydrous Na$_2$SO$_4$. After filtration the filtrate was concentrated under reduced pressure. The residue was purified by silica gel column chromatography, eluted with PE/EtOAc (1:1) to afford 9-[(2R,3S,4R,5S)-4-(benzyloxy)-5-[(benzyloxy)methyl]-5-{[bis(4-methoxyphenyl) (phenyl)methoxy] methyl}-3-fluorooxolan-2-yl]-2-fluoro-N-[(4-methoxyphenyl) diphenylmethyl]purin-6-amine (710.0 mg, 0.6 mmol, 83.19%) as a light-yellow solid. LC-MS (ES, m/z): 1072 (M+H)$^+$.

Step 7: To a stirred solution of 9-[(2R,3S,4R,5S)-4-(benzyloxy)-5-[(benzyloxy)methyl]-5-{[bis(4-methoxyphenyl) (phenyl)methoxy] methyl}-3-fluorooxolan-2-yl]-2-fluoro-N-[(4-methoxyphenyl) diphenylmethyl] purin-6-amine (700.0 mg, 0.65 mmol) in CH$_2$Cl$_2$ (10 mL) was added a solution of Cl$_2$CHCOOH (0.35 mL) in CH$_2$Cl$_2$ (3.5 mL) dropwise at −78° C. under nitrogen atmosphere. The resulting mixture was stirred for 30 min at 0° C. under nitrogen atmosphere and quenched by the addition of sat. NaHCO$_3$ (aq.) (100 mL) at 0° C. The resulting solution was extracted with CH$_2$Cl$_2$ (3×100 mL). The combined organic layers were washed with brine (2×100 mL) and dried over anhydrous Na$_2$SO$_4$. After filtration the filtrate was concentrated under reduced pressure. The residue was purified by silica gel column chromatography, eluted with PE/EtOAc (1:1) to afford [(2R,3R,4S,5R)-3-(benzyloxy)-2-[(benzyloxy) methyl]-4-fluoro-5-(2-fluoro-6-{1[(4-methoxyphenyl) diphenylmethyl] amino}purin-9-yl) oxolan-2-yl] methanol (305.0 mg, 0.4 mmol, 59.69%) as a white solid. LC-MS (ES, m/z): 770 (M+H)$^+$.

Step 8: To a stirred solution of [(2R,3R,4S,5R)-3-(benzyloxy)-2-[(benzyloxy)methyl]-4-fluoro-5-(2-fluoro-6-{1[(4-methoxyphenyl) diphenylmethyl] amino}purin-9-yl) oxolan-2-yl] methanol (300.0 mg, 0.39 mmol) in DCM (30 mL) was added DAST (628.0 mg, 3.90 mmol) in portions at −78° C. under nitrogen atmosphere. The resulting mixture was stirred for overnight at 0° C. under nitrogen atmosphere and then quenched by the addition of sat. NaHCO$_3$ aq. (50 mL) at 0° C. The resulting solution was extracted with EtOAc (2×100 mL). The combined organic layers were washed with brine (2×100 mL) and dried over anhydrous Na$_2$SO$_4$. After filtration the filtrate was concentrated under reduced pressure. The residue was purified by silica gel column chromatography, eluted with PE/EtOAc (1:2) to afford 9-[(2R,3S,4R,5R)-4-(benzyloxy)-5-[(benzyloxy) methyl]-3-fluoro-5-(fluoromethyl) oxolan-2-yl]-2-fluoro-N-[(4-methoxyphenyl) diphenylmethyl] purin-6-amine (250.0 mg, 0.30 mmol, 83.14%) as a light-yellow solid. LC-MS (ES, m/z): 772 (M+H)$^+$.

Step 9: To a stirred solution of 9-[(2R,3S,4R,5R)-4-(benzyloxy)-5-[(benzyloxy)methyl]-3-fluoro-5-(fluoromethyl) oxolan-2-yl]-2-fluoro-N-[(4-methoxyphenyl) diphenylmethyl] purin-6-amine (250.0 mg, 0.32 mmol) and NH$_4$HCO$_3$ (919.0 mg, 14.58 mmol) in acetone (5 mL) was added Pd/C (345.0 mg, 3.24 mmol) under nitrogen atmosphere. The resulting mixture was stirred for overnight at 60° C. The resulting mixture was cooled to room temperature and filtered; the filter cake was washed with MeOH (5×5 mL). The combined filtrate was concentrated under reduced pressure. The residue was purified by silica gel column chromatography, eluted with CH$_2$Cl$_2$/MeOH (10:1) to afford (2R,3R,4S,5R)-4-fluoro-5-(2-fluoro-6-{1[(4-methoxyphenyl) diphenylmethyl] amino} purin-9-yl)-2-(fluoromethyl)-2-(hydroxymethyl)oxolan-3-ol (170.0 mg, 0.3 mmol, 88.72%) as a light-yellow solid. LC-MS (ES, m/z): 592 (M+H)$^+$.

Step 10: A solution of (2R,3R,4S,5R)-4-fluoro-5-(2-fluoro-6-{[(4-methoxyphenyl) diphenylmethyl] amino} purin-9-yl)-2-(fluoromethyl)-2-(hydroxymethyl) oxolan-3-ol (170.0 mg, 0.29 mmol) in AcOH (4 mL, 80%) was stirred for overnight at room temperature. The mixture was neutralized to pH 7 with saturated NaHCO$_3$ (aq.). The resulting mixture was concentrated under reduced pressure. The crude product was purified by Prep-HPLC with the following conditions: Column: SunFire Prep C18 OBD Column, 19*150 mm, 5 μm; Mobile Phase A: Water (0.1% FA), Mobile Phase B: ACN; Flow rate: 20 mL/min; Gradient: 65% B to 90% B in 5.3 min; Wavelength: 210/254 nm; RT1(min): 5.3. This resulted in (2R,3R,4S,5R)-5-(6-amino-2-fluoropurin-9-yl)-4-fluoro-2-(fluoromethyl)-2-(hydroxymethyl) oxolan-3-ol (27.7 mg, 0.1 mmol, 25.67%) as a white solid. LC-MS (ES, m/z): 320 (M+H$^+$). 99.5% purity. Conditions for the HPLC: (Column: Luna Omega PS C18, 30*2.1 mm, 3.5 μm; Mobile Phase A: water/0.1% FA, Mobile Phase B: ACN/0.1% FA; Flow rate: 1.2000 mL/min; Gradient: 5% B to 100% B in 1.2.00 min, 100% B to 100% B in 0.6 min, 100% B to 5% B in 0.2 min; Wavelength: 254/220 nm; RT1(min): 0.43). $^1$H NMR (400 MHz, DMSO-d$_6$) δ 8.25 (d, J=1.2 Hz, 1H), 7.91 (brs, 2H), 6.41-6.37 (m, 1H), 6.23 (d, J=5.2 Hz, 1H), 5.37-5.24 (m, 1H), 5.29 (t, J=5.6 Hz, 1H), 4.77-4.69 (m, 1H), 4.63-4.58 (m, 1H), 4.47 (d, J=10.0 Hz, 1H), 3.70-3.66 (m, 1H), 3.61-3.57 (m, 1H).

Example 66—Synthesis of Compound 85: 4-amino-5-fluoro-1-[(2R,3S,4R,5R)-3-fluoro-5-(fluoromethyl)-4-hydroxy-5-(hydroxymethyl) oxolan-2-yl] pyrimidin-2-one

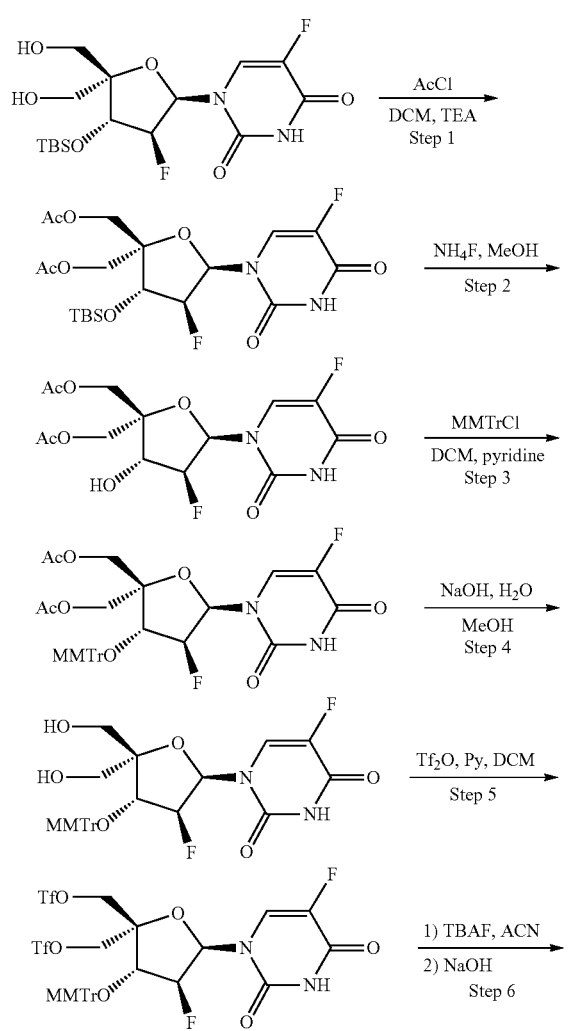

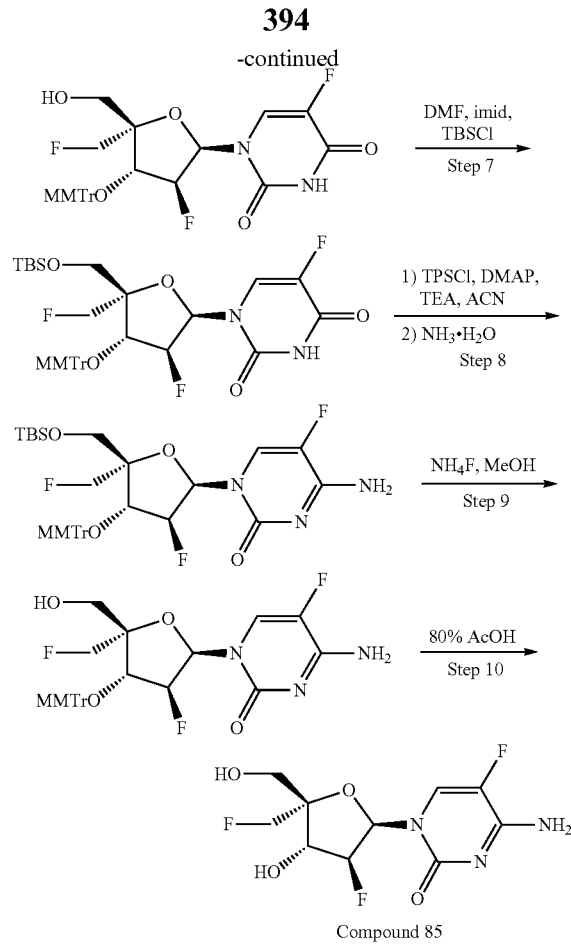

Compound 85

Step 1: To a stirred solution of 1-[(2R,3S,4R)-4-[(tert-butyldimethylsilyl) oxy]-3-fluoro-5,5-bis(hydroxymethyl) oxolan-2-yl]-5-fluoro-3H-pyrimidine-2,4-dione (1.0 g, 2.45 mmol) and TEA (740.0 mg, 7.34 mmol) in DCM (10 mL), was added and acetyl chloride (480.0 mg, 6.12 mmol) in portions at 0° C. under nitrogen atmosphere. The resulting mixture was stirred for 2 h at 0° C. under nitrogen atmosphere. The resulting mixture was diluted with DCM. The organic layer was washed with brine and dried over anhydrous Na$_2$SO$_4$. After filtration the filtrate was concentrated under reduced pressure. The residue was purified by silica gel column chromatography, eluting with PE/EtOAc (10:1) to afford [(3R,4S,5R)-2-[(acetyloxy)methyl]-3-[(tert-butyldimethylsilyl) oxy]-4-fluoro-5-(5-fluoro-2,4-dioxo-3H-pyrimidin-1-yl) oxolan-2-yl]mEtOAc (1.0 g, 2.03 mmol, 82.93%) as a yellow solid. LC-MS (ES, m/z): 493 (M+H)$^+$.

Step 2: To a stirred solution of [(3R,4S,5R)-2-[(acetyloxy) methyl]-3-[(tert-butyldimethylsilyl)oxy]-4-fluoro-5-(5-fluoro-2,4-dioxo-3H-pyrimidin-1-yl)oxolan-2-yl]mEtOAc (1.0 g, 2.03 mmol) in MeOH (10 mL), was added NH$_4$F (230.0 mg, 6.09 mmol) under nitrogen atmosphere. The resulting mixture was stirred overnight at 60° C. under nitrogen atmosphere. The mixture was allowed to cool down to room temperature and concentrated under reduced pressure. The residue was purified by silica gel column chromatography, eluting with PE/EtOAc (4:1) to afford [(3R,4S,5R)-2-[(acetyloxy)methyl]-4-fluoro-5-(5-fluoro-2,4-dioxo-3H-pyrimidin-1-yl)-3-hydroxyoxolan-2-yl] mEtOAc) (800.0 mg, 2.12 mmol) as a yellow solid. LC-MS (ES, m/z): 379 (M+H)$^+$.

Step 3: To a stirred solution of [(3R,4S,5R)-2-[(acetyloxy)methyl]-4-fluoro-5-(5-fluoro-2,4-dioxo-3H-pyrimidin-1-yl)-3-hydroxyoxolan-2-yl] mEtOAc (800.0 mg, 2.12 mmol) and pyridine (5 mL, 6.35 mmol) in DCM (8 mL), was added 1-(chlorodiphenylmethyl)-4-methoxybenzene (784.0 mg, 2.54 mmol) in portions at room temperature under nitrogen atmosphere. The resulting mixture was stirred overnight at room temperature under nitrogen atmosphere and quenched by the addition of sat. NH$_4$Cl (aq.). The resulting mixture was extracted with DCM. The combined organic layers were washed with brine, and dried over anhydrous Na$_2$SO$_4$. After filtration the filtrate was concentrated under reduced pressure. The residue was purified by silica gel column chromatography, eluting with PE/EtOAc (8:1) to afford [(3R,4S,5R)-2-[(acetyloxy)methyl]-4-fluoro-5-(5-fluoro-2,4-dioxo-3H-pyrimidin-1-yl)-3-[(4-methoxyphenyl) diphenylmethoxy] oxolan-2-yl] mEtOAc (1.0 g, 1.54 mmol, 72.68%) as a yellow solid. LC-MS (ES, m/z): 651 (M+H)$^+$.

Step 4: To a stirred solution of [(3R,4S,5R)-2-[(acetyloxy)methyl]-4-fluoro-5-(5-fluoro-2,4-dioxo-3H-pyrimidin-1-yl)-3-[(4-methoxyphenyl) diphenylmethoxy] oxolan-2-yl] mEtOAc (1.0 g, 1.54 mmol) in MeOH (10 mL) were added a solution of NaOH (180.0 mg, 4.61 mmol) in H$_2$O (5 mL) dropwise. The resulting mixture was stirred for 3 h at room temperature and then concentrated under reduced pressure. The residue was purified by reversed-phase flash chromatography with the following conditions: C18 column; Mobile phase A: water (0.1% NH$_3$·H$_2$O) and B: CH$_3$CN; Gradient: 5% to 100% B in 20 min; UV detection at 254/220 nm. This resulted in 5-fluoro-1-[(2R,3S,4R)-3-fluoro-5,5-bis(hydroxymethyl)-4-[(4-methoxyphenyl) diphenylmethoxy] oxolan-2-yl]-3H-pyrimidine-2,4-dione (700.0 mg, 1.24 mmol, 80.39%) as a white solid. LC-MS (ES, m/z): 567 (M+H)$^+$.

Step 5: To a stirred solution of 5-fluoro-1-[(2R,3S,4R)-3-fluoro-5,5-bis(hydroxymethyl)-4-[(4-methoxyphenyl) diphenylmethoxy] oxolan-2-yl]-3H-pyrimidine-2,4-dione (700.0 mg, 1.24 mmol) in DCM (7 mL) was added pyridine (293.0 mg, 3.71 mmol) dropwise at room temperature. This was followed by the addition of Tf$_2$O (871.0 mg, 3.09 mmol) dropwise at −30° C. The resulting mixture was stirred for additional 2 h at 0° C. and then quenched by the addition of sat. NaHCO$_3$(aq.) at 0° C. The resulting mixture was extracted with EtOAc. The combined organic layers were washed with water and dried over anhydrous Na$_2$SO$_4$. After filtration the filtrate was concentrated under reduced pressure. The residue was purified by silica gel column chromatography, eluting with PE/EtOAc (5:1) to afford [(3R,4S,5R)-4-fluoro-5-(5-fluoro-2,4-dioxo-3H-pyrimidin-1-yl)-3-[(4-methoxyphenyl) diphenylmethoxy]-2-[(trifluoromethanesulfonyloxy)methyl] oxolan-2-yl] methyl trifluoromethanesulfonate (710 mg, 0.84 mmol, 68.20%) as a yellow solid. (ES, m/z): 831 (M+H)$^+$.

Step 6: To a solution of [(3R,4S,5R)-4-fluoro-5-(5-fluoro-2,4-dioxo-3H-pyrimidin-1-yl)-3-[(4-methoxyphenyl) diphenylmethoxy]-2-[(trifluoromethanesulfonyloxy) methyl]oxolan-2-yl]methyl trifluoromethanesulfonate (700.0 mg, 0.84 mmol) in ACN (7 mL) was added TBAF (331.0 mg, 1.26 mmol). The resulting mixture was stirred for 12 h at room temperature under nitrogen atmosphere. To the above mixture was added aq. NaOH (1M, 20 mL, 20.00 mmol) dropwise. The resulting mixture was stirred for additional 1 h at room temperature and quenched by the addition of sat. NH$_4$Cl (aq.) at 0° C. The resulting mixture was extracted with EtOAc. The combined organic layers were washed with water and dried over anhydrous Na$_2$SO$_4$. After filtration the filtrate was concentrated under reduced pressure. The residue was purified by silica gel column chromatography, eluting with CH$_2$Cl$_2$/MeOH (10:1) to afford 5-fluoro-1-[(2R,3S,4R,5R)-3-fluoro-5-(fluoromethyl)-5-(hydroxymethyl)-4-[(4-methoxyphenyl) diphenylmethoxy] oxolan-2-yl]-3H-pyrimidine-2,4-dione (405.0 mg, 0.84 mmol, 83.49%) as a white solid. LC-MS (ES, m/z): 569 (M+H)$^+$.

Step 7: To a stirred solution of 5-fluoro-1-[(2R,3S,4R,5R)-3-fluoro-5-(fluoromethyl)-5-(hydroxymethyl)-4-[(4-methoxyphenyl) diphenylmethoxy] oxolan-2-yl]-3H-pyrimidine-2,4-dione (400.0 mg, 0.70 mmol) and imidazole (144.0 mg, 2.11 mmol) in DMF (4 mL), was added t-butyldimethylchlorosilane (117.0 mg, 0.77 mmol) at 0° C. under nitrogen atmosphere. The resulting mixture was stirred overnight at room temperature under nitrogen atmosphere and diluted with EtOAc. The organic layer was washed with brine and dried over anhydrous Na$_2$SO$_4$. After filtration the filtrate was concentrated under reduced pressure. The residue was purified by reversed-phase flash chromatography with the following conditions: C18 column; Mobile phase A: water (containing 0.1% NH$_3$·H$_2$O) and B: CH$_3$CN; Gradient: 10% to 100% B in 20 min; UV detection at 254/220 nm. This resulted in 1-[(2R,3S,4R,5R)-5-{[(tert-butyldimethylsilyl) oxy] methyl}-3-fluoro-5-(fluoromethyl)-4-[(4-methoxyphenyl) diphenylmethoxy] oxolan-2-yl]-5-fluoro-3H-pyrimidine-2,4-dione (380.0 mg, 0.70 mmol, 79.10%) as a white solid. LC-MS (ES, m/z): 683 (M+H)$^+$.

Step 8: To a solution of 1-[(2R,3S,4S,5R)-4-[(tert-butyldimethylsilyl) oxy]-5-{[(tert-butyldimethylsilyl) oxy] methyl}-5-(fluoromethyl)-3-fluorooxolan-2-yl]-5-fluoro-3H-pyrimidine-2,4-dione (380.0 mg, 0.70 mmol) in ACN (4 mL) were added DMAP (172.0 mg, 1.40 mmol) and TEA (213.0 mg, 2.11 mmol). This was followed by the addition of 2,4,6-tris(propan-2-yl) benzene-1-sulfonyl chloride (425.0 mg, 1.40 mmol) in portions. The resulting mixture was stirred for 2 h at room temperature. Then to the above mixture was added NH$_3$·H$_2$O (2 mL) dropwise. The resulting mixture was stirred for additional 3 h at room temperature and then concentrated under reduced pressure. The residue was purified by Prep-TLC (PE/EtOAc=5:1) to afford 4-amino-1-[(2R,3S,4R,5R)-4-[(tert-butyldimethylsilyl) oxy]-5-{[(tert-butyldimethylsilyl) oxy] methyl}-5-(fluoromethyl)-3-fluorooxolan-2-yl]-5-fluoropyrimidin-2-one (200.0 mg, 0.29 mmol, 52.73%) as a white solid. LC-MS (ES, m/z): 682 (M+H)$^+$.

Step 9: To a stirred solution of 4-amino-1-[(2R,3S,4R,5R)-5-{[(tert-butyldimethylsilyl) oxy] methyl}-3-fluoro-5-(fluoromethyl)-4-[(4-methoxyphenyl) diphenylmethoxy] oxolan-2-yl]-5-fluoropyrimidin-2-one (200.0 mg, 0.29 mmol) in MeOH (2 mL), was added NH$_4$F (33.0 mg, 0.88 mmol) in portions at room temperature. The resulting mixture was stirred for overnight at 60° C. under nitrogen atmosphere. The resulting mixture was cooled to room temperature and concentrated under reduced pressure. The residue was purified by reversed-phase flash chromatography with the following conditions: C18 column; Mobile phase A: water (0.1% NH$_3$·H$_2$O) and B: CH$_3$CN; Gradient: 10% to 100% B in 10 min; UV detection at 254/220 nm. This resulted in 4-amino-5-fluoro-1-[(2R,3S,4R,5R)-3-fluoro-5-(fluoromethyl)-5-(hydroxymethyl)-4-[(4-methoxyphenyl) diphenylmethoxy] oxolan-2-yl]pyrimidin-2-one (100.0 mg, 0.18 mmol, 60.07%) as a white solid. LC-MS (ES, m/z): 568 (M+H)$^+$.

Step 10: A solution of 4-amino-5-fluoro-1-[(2R,3S,4R,5R)-3-fluoro-5-(fluoromethyl)-5-(hydroxymethyl)-4-[(4-methoxyphenyl) diphenylmethoxy] oxolan-2-yl]pyrimidin-2-one (100.0 mg, 0.18 mmol) in AcOH (1 mL) was stirred for overnight at room temperature and then concentrated under reduced pressure. The residue was purified by Prep-HPLC with the following conditions: Column: XBridge Shield RP18 OBD Column, 19*250 mm, 10 μm; Mobile Phase A: Water (10 mmol/L NH₄HCO₃), Mobile Phase B: ACN; Flow rate: 25 mL/min; Gradient: 5% B to 18% B in 6 min; Wavelength: 254 nm; RT1(min): 4.87. This resulted in 4-amino-5-fluoro-1-[(2R,3S,4R,5R)-3-fluoro-5-(fluoromethyl)-4-hydroxy-5-(hydroxymethyl) oxolan-2-yl] pyrimidin-2-one (34.0 mg, 0.12 mmol, 40.84%) as a white solid. LC-MS (ES, m/z): 296 (M+H)⁺. 95.0% purity. Conditions for the HPLC: (Column: Atlantis T3 3 m 4.6*100 mm; Mobile Phase A: water/0.05% TFA, Mobile Phase B: ACN/0.05% TFA; Flow rate: 1.2000 mL/min; Gradient: 5% B to 95% B in 8.00 min, 5% B to 95% B in 2.00 min, 90% B to 10% B in 0.50 min; Wavelength: 254 nm; RT1(min): 2.22). ¹H NMR (400 MHz, DMSO-d₆) δ 8.03-8.00 (m, 3H), 6.22-6.17 (m, 2H), 5.09 (d, J=53.2 Hz, 1H), 4.67 (d, J=10.0 Hz, 1H), 4.59-4.54 (m, 1H), 4.46 (d, J=4.0 Hz, 1H), 4.42-4.40 (m, 1H), 3.61-3.51 (m, 2H).

Example 67—Synthesis of Compound 95: 4-amino-1-((2R,3S,4S,5R)-3,4-dihydroxy-5-(hydroxymethyl)-5-(trifluoromethyl)tetrahydrofuran-2-yl)-5-fluoropyrimidin-2(1H)-one

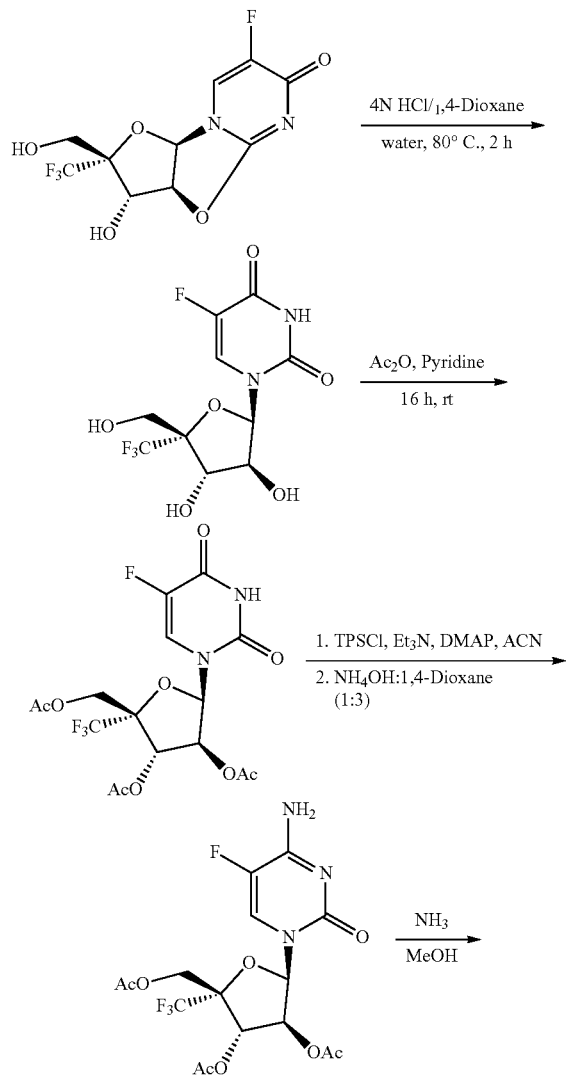

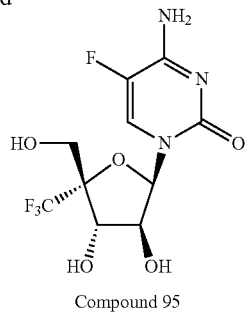

Compound 95

Step 1: To a mixture of 4N HCl in 1,4 Dioxane (2.0 mL) and H₂O (2.0 mL) at 0° C. was added (2R,3S,3aS,9aR)-7-fluoro-3-hydroxy-2-(hydroxymethyl)-2-(trifluoromethyl)-2,3,3a,9a-tetrahydro-6H-furo [2',3':4,5] oxazolo[3,2-a]pyrimidin-6-one (0.4 g, 1.28 mmol). The reaction was heated at 80° C. for 2 hr at which time TLC and LCMS showed a complete reaction. The reaction mixture was concentrated and resulting residue was purified by Combi-Flash column chromatography by eluting with 5% MeOH in DCM to afford the desired product (0.28 g, 66.2%) as white solid. LC-MS (ES, m/z): 331.1 (M+H).

Step 2: To a stirred solution of 1-((2R,3S,4S,5R)-3,4-dihydroxy-5-(hydroxymethyl)-5-(trifluoromethyl) tetrahydrofuran-2-yl)-5-fluoropyrimidine-2,4(1H,3H)-dione (0.28 g, 0.848 mmol) in pyridine (10 mL) was added acetic anhydride (0.4 mL, 4.24 mmol). The reaction was stirred for 16 h at which time TLC and LCMS showed a complete reaction. The reaction mixture was concentrated and diluted with EtOAc washed with solution of aqueous sodium bicarbonate and brine (10 mL). After drying over Na₂SO₄, the solutions was concentrated, and the resulting residue was purified by CombiFlash column chromatography by eluting with 20% EtOAc in n-Hexane to afford the desired product (0.22 g, 56%) as white solid. LC-MS (ES, m/z): 454.9 (M−H).

Step 3: To a stirred solution of (2R,3S,4S,5R)-2-(acetoxymethyl)-5-(5-fluoro-2,4-dioxo-3,4-dihydropyrimidin-1(2H)-yl)-2-(trifluoromethyl)tetrahydrofuran-3,4-diyl diacetate (0.15 g, 0.328 mmol) in acetonitrile (5 mL) were added TEA (0.18 mL, 1.312 mmol), DMAP (0.08 g, 0.656 mmol) and then TPSCl (0.19 g, 0.657 mmol) at 0° C. After stirring the reaction mixture at rt for 4 h, NH₄OH:1,4-Dioxane (0.6 mL) was added to above reaction mixture and stirred at rt for 15 min. The reaction progress was monitored by TLC and LCMS. After completion, the reaction mixture was concentrated and resulting residue was purified by Prep TLC, using 100% EtOAc as eluent to afford desired product (0.12 g, 80%) as white solid. LC-MS (ES, m/z): 456.1 (M+H).

Step 4: To a stirred solution of (2R,3S,4S,5R)-2-(acetoxymethyl)-5-(4-amino-5-fluoro-2-oxopyrimidin-1(2H)-yl)-2-(trifluoromethyl) tetrahydrofuran-3,4-diyl diacetate (0.08 g, 0.175 mmol) in MeOH (0.3 mL) was added 7N NH₃ in MeOH (2 mL). The reaction was stirred for 4 h at rt. The reaction mixture was concentrated and resulting residue was purified by Prep HPLC by following below conditions; Mobile Phase: A=0.02% NH₄OH in water, B=CH₃CN, Column: waters X BRIDGE (250 mm×20.0 mm), 5.0μ, Flow: 15.0 mL/min, Gradient Program: Time/% B:0/5, 2/10, 8/30) to afford the desired product (0.025 g, 43%) as white solid. LC-MS (ES, m/z): 330.05 (M+H). ¹H NMR (400 MHz, DMSO-d₆) δ=7.78 (d, J=7.2 Hz, 2H), 7.56 (br s, 1H), 6.22 (dd, J=1.9, 5.7 Hz, 1H), 6.05 (d, J=5.4 Hz, 1H), 5.85 (d, J=5.3 Hz, 1H), 5.68 (t, J=5.6 Hz, 1H), 4.38 (t, J=5.3 Hz, 1H), 4.24 (q, J=5.3 Hz, 1H), 3.79-3.68 (m, 2H).
Example 68—Synthesis of Compound 88: 4-amino-1-((2R,4S,5R)-5-(bromomethyl)-4-hydroxy-5-(hydroxymethyl)tetrahydrofuran-2-yl)-5-fluoropyrimidin-2(1H)-one
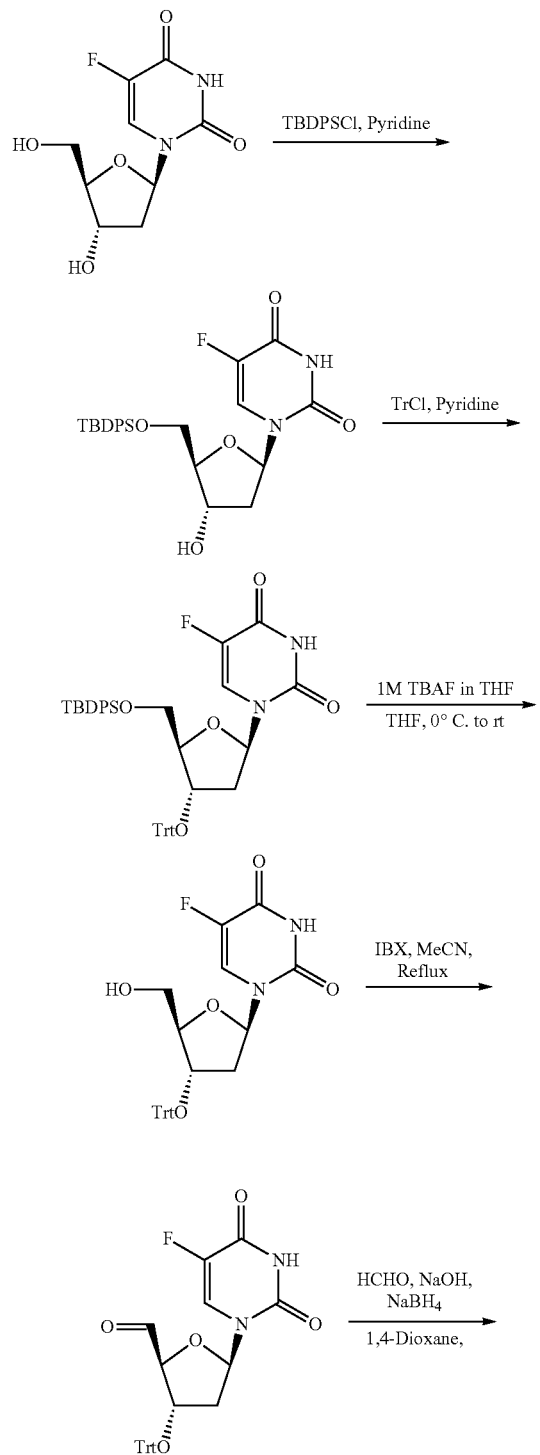
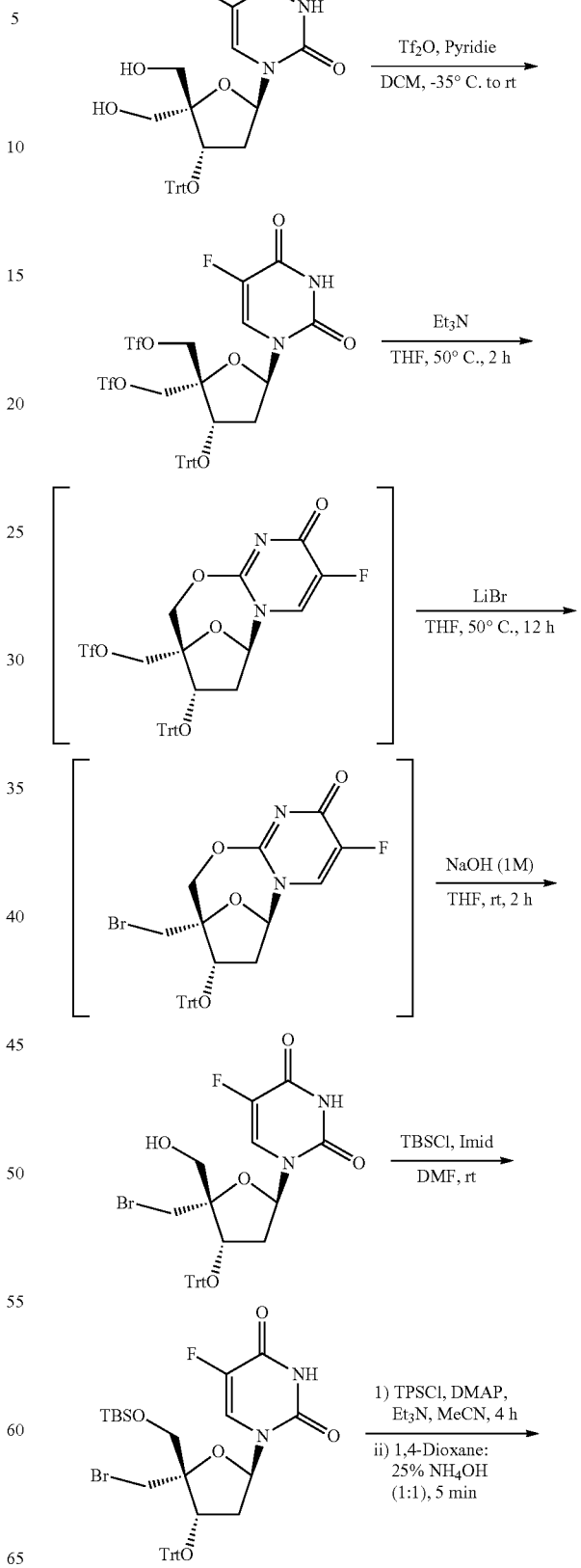

-continued

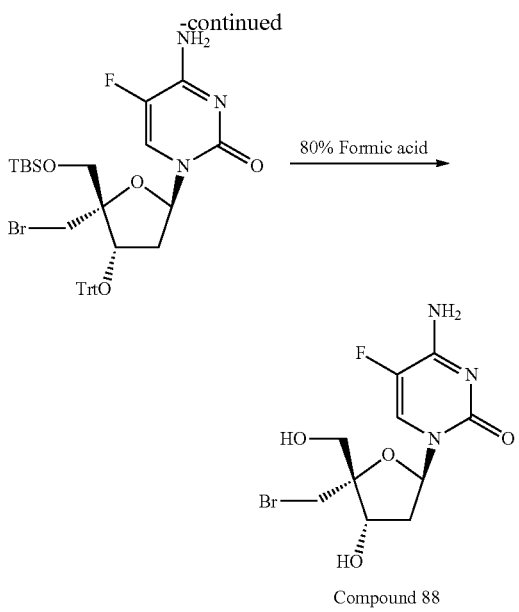

Compound 88

Step 1: To a solution of 5-fluoro-1-((2R,4S,5R)-4-hydroxy-5-(hydroxymethyl) tetrahydrofuran-2-yl)pyrimidine-2,4(1H,3H)-dione (20.0 g, 81.238 mmol) in pyridine (400 mL) was added TBDPSCl (23.44 mL, 85.299 mmol) at rt. The reaction was stirred at rt for 16 h at which time TLC and LCMS showed a complete reaction. After completion, the reaction mixture was evaporated and resulting residue was partitioned between EtOAc and water. The organic layer was separated, dried over $Na_2SO_4$, concentrated and the crude product was purified by CombiFlash column by eluting with 40% EtOAc in n-Hexane to obtain the desired product (30 g, 76.20%) as off-white solid. LC-MS (ES, m/z): 484.80 (M+H$^+$).

Step 2: To a stirred solution of 1-((2R,4S,5R)-5-(((tert-butyldiphenylsilyl) oxy)methyl)-4-hydroxytetrahydrofuran-2-yl)-5-(trifluoromethyl)pyrimidine-2,4(1H,3H)-dione (0.5 g, 1.031 mmol) in DCM (10 mL) was added collidine (0.14 mL, 1.13 mmol), $AgNO_3$ (0.19 g, 1.134 mmol) followed by Trityl Chloride (0.31 g, 1.13 mmol) at rt. The reaction was stirred for 16 h at rt at which time TLC and LCMS showed a complete reaction. The reaction mixture was evaporated and resulting residue was partitioned between EtOAc and water. The organic layer was separated and dried over $Na_2SO_4$, concentrated and the crude product was purified by CombiFlash column by eluting with 30% EtOAc in n-Hexane to afford the desired product (0.7 g, 93.40%) as an off-white solid. LC-MS (ES, m/z): 724.80 (M−1).

Step 3: To a stirred solution of 1-((2R,4S,5R)-5-(((tert-butyldiphenylsilyl) oxy)methyl)-4-(trityloxy)tetrahydro-furan-2-yl)-5-fluoropyrimidine-2,4(1H,3H)-dione (200 mg, 0.275 mmol) in THF (4 mL) was added TBAF (1.1 mL, 1.10 mmol) at 0° C. The reaction was stirred at rt for 4 h at which time TLC and LCMS showed a complete reaction. The reaction mixture was evaporated and the residue was partitioned with EtOAc (50 mL) and water. The organic layer was separated, dried over $Na_2SO_4$, concentrated and the crude product was purified by CombiFlash using 12 g column by eluting with 55% EtOAc in n-Hexane to obtain the desired product (60 mg, 44.66%) as an off-white solid. LC-MS (ES, m/z): 486.75 (M−1).

Steps 4 and 5: To a solution of 5-fluoro-1-((2R,4S,5R)-5-(hydroxymethyl)-4-(trityloxy)tetrahydrofuran-2-yl)pyrimidine-2,4(1H,3H)-dione (2.7 g, 5.53 mmol) in ACN (50.0 mL) was added IBX (1.85 g, 6.63 mmol) at rt. The reaction was stirred for at 85° C. for 2 h, cooled to rt and filtered. The filtrate was concentrated to afford crude aldehyde material. The aldehyde was dissolved in 1,4-dioxane (50 mL) and treated with formaldehyde (2.7 mL) followed by 2N NaOH (5.4 mL) at rt. The reaction was stirred for 16 h at rt. The reaction was cooled to 0° C. and treated with $NaBH_4$ (0.84 g, 22.11 mmol). The reaction was then stirred at rt for 1 h. The reaction mixture was evaporated under high vacuum to get the desired crude compound. The crude product was purified by CombiFlash by eluting with 5% MeOH in DCM to obtain the desired product (1.4 g, 48.85%) as an off-white solid. LC-MS (ES, m/z): 517.20 (M−1).

Step 6: To a stirred solution of 1-((2R,4S)-5,5-bis(hydroxymethyl)-4-(trityloxy)tetrahydrofuran-2-yl)-5-fluoropyrimidine-2,4(1H,3H)-dionetrifluoromethyl) pyrimidine-2,4(1H,3H)-dione (0.1 g, 0.175 mmol) in DCM (2 mL) was added pyridine (0.31 mL, 3.85 mmol) followed by $Tf_2O$ (0.15 mL, 0.848 mmol) at −30° C. The reaction was stirred at rt for 2 h. To the reaction mixture ice-cold water was added and the mixture extracted twice with DCM. The organic layer was separated, dried over $Na_2SO_4$, concentrated and the crude material was purified by CombiFlash column by eluting with 35% EtOAc in n-Hexane to obtain the desired product (0.16 g, 53.09%) as an off-white solid. LC-MS (ES, m/z): 780.95 (M−1).

Steps 7, 8, and 9: To a stirred solution of ((3S,5R)-5-(5-fluoro-2,4-dioxo-3,4-dihydropyrimidin-1(2H)-yl)-3-(trityloxy)tetrahydrofuran-2,2-diyl)bis(methylene) bis(trifluoromethanesulfonate) (150 mg, 0.19 mmol) in THF (4 mL) was added $Et_3N$ (0.26 mL, 1.916 mmol) at rt. The reaction was stirred at 50° C. for 3 h, cooled to 0° C. and treated with LiBr (49 mg, 0.573 mmol). The reaction was stirred for 12 h at 50° C. cooled to 0° C. and 1N NaOH (0.57 mL. 0.573 mmol) was added slowly. After stirring the reaction mixture at rt for for 2 h the reaction mixture was partitioned between ice-cold water and DCM 20 mL each. The organic layer was separated, dried over $Na_2SO_4$ and to afford the desired product (110 mg, crude) as an off-white solid. LC-MS (ES, m/z): 579.00 (M−1).

Step 10: To a stirred solution of 1-((2R,4S,5R)-5-(bromomethyl)-5-(hydroxy-methyl)-4-(trityloxy)tetrahydrofuran-2-yl)-5-fluoropyrimidine-2,4(1H,3H)-dione (0.6 g, 1.03 mmol) in DMF (12 mL) was added imidazole (0.35 g, 5.15 mmol), TBSCl (0.46 g, 3.095 mmol) and followed by silver nitrate (0.35 g, 2.062 mmol) at 0° C. The reaction was stirred at rt for 48 h. The reaction mixture was quenched with ice-cold water and then partitioned between EtOAc and water (20 mL each). The organic layer was separated, dried over $Na_2SO_4$, concentrated and crude product was purified by CombiFlash column by eluting with at 45% EtOAc in n-Hexane to afford the product (0.42 g, 58.55%) as pale-yellow sticky. LC-MS (ES, m/z): 695.10 (M+1).

Steps 11 and 12: To a stirred solution of 1-((2R,4S,5R)-5-(bromomethyl)-5-(((tert-butyldimethylsilyl)oxy)methyl)-4-(trityloxy)tetrahydrofuran-2-yl)-5-fluoropyrimidine-2,4(1H,3H)-dione (50 mg, 0.071 mmol) in ACN (2 mL) was added $Et_3N$ (0.03 mL, 0.29 mmol) and DMAP (17 mg, 0.143 mmol) and then TPSCl (43 mg, 0.143 mmol) at 0° C. The reaction was stirred for 2 h at rt and treated with Triazole (19 mg, 0.287 mmol). After stirring for another 2 h $NH_4OH$:1, 4-Dioxane (0.5 mL) was added to the above reaction mixture and stirred for 2 hours. The reaction mixture was quenched with ice-cold water and then partitioned with EtOAc (20 mL) and water (5 mL). The organic layer was separated, aq. layer was washed with EtOAc (2×10 mL). The combined organics were dried over Na$_2$SO$_4$ and organic layer was concentrated under reduced pressure to get the desired crude compound. Crude compound was purified by prep TLC by eluting with 100% EtOAc in n-Hexane to afford the desired product (20 mg, 40.54%) as an off-white solid. LC-MS (ES, m/z): 694.20 (M+1).

Step 13: A stirred solution of 4-amino-1-((2R,4S,5R)-5-(bromomethyl)-5-(((tert-butyldimethylsilyl)oxy)methyl)-4-(trityloxy)tetrahydrofuran-2-yl)-5-fluoropyrimi-din-2(1H)-one (150 mg, 0.215 mmol) in DCM (3 mL) was treated with 80% Formic acid (0.4 mL) at 0° C. After stirring the reaction mixture at rt for 12 h, the reaction mixture was concentrated and resulting residue was purified by prep-HPLC by following below conditions: Mobile Phase: A: 0.02% NH$_4$OH. in water; B: MeCN; Column: X SELECT (250 mm×20.0 mm), 5.0p; Flow rate: 15 mL/min; Gradient program: Time/% B: 0/5,2/10,8/30 to afford the desired product (9 mg, 12.17%) as white solid. LC-MS (ES, m/z): 338.0 (M+1). $^1$H NMR (400 MHz, DMSO-d$_6$) δ=8.01 (d, J=7.2 Hz, 1H), 7.81-7.47 (m, 2H), 6.22-6.17 (m, 1H), 5.45 (d, J=4.8 Hz, 1H), 5.31 (t, J=5.1 Hz, 1H), 4.39-4.35 (m, 1H), 3.70-3.63 (m, 2H), 3.61-3.56 (m, 2H), 2.28-2.15 (m, 2H).

Example 69—Synthesis of Compound 121: 4-amino-1-[(2R,3S,4R,5R)-5-cyclopropyl-3-fluoro-4-hydroxy-5-(hydroxymethyl) oxolan-2-yl] pyrimidin-2-one

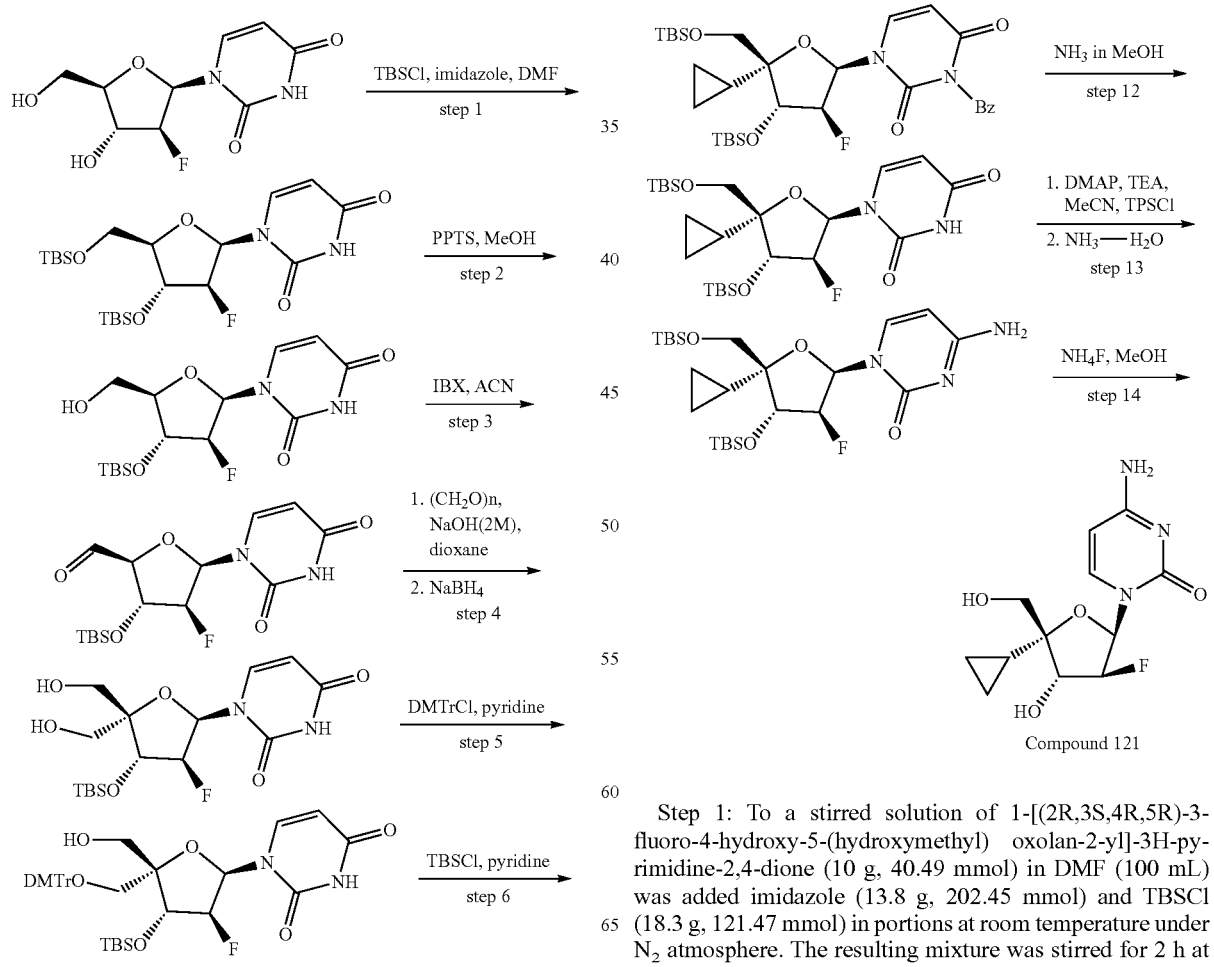

Step 1: To a stirred solution of 1-[(2R,3S,4R,5R)-3-fluoro-4-hydroxy-5-(hydroxymethyl) oxolan-2-yl]-3H-pyrimidine-2,4-dione (10 g, 40.49 mmol) in DMF (100 mL) was added imidazole (13.8 g, 202.45 mmol) and TBSCl (18.3 g, 121.47 mmol) in portions at room temperature under N$_2$ atmosphere. The resulting mixture was stirred for 2 h at 80° C. under N$_2$ atmosphere. The resulting mixture was cooled to room temperature, diluted with water and extracted with EtOAc (3×300 mL). The combined organic layers were washed with brine and dried over anhydrous $Na_2SO_4$. After filtration the filtrate was concentrated under reduced pressure to afford crude product (22 g, crude) which was used in the next step directly without further purification. LC-MS (ES, m/z): 475 $[M+H]^+$.

Step 2: To a stirred solution of 1-[(2R,3S,4R,5R)-4-[(tert-butyldimethylsilyl) oxy]-5-{[(tert-butyldimethylsilyl) oxy] methyl}-3-fluorooxolan-2-yl]-3H-pyrimidine-2,4-dione (22 g, 46.32 mmol) in MeOH (300 mL) was added PPTS (34.9 g, 138.96 mmol) in portions at room temperature under $N_2$ atmosphere. The resulting mixture was stirred for 15 h at 50° C. under $N_2$ atmosphere. The resulting mixture was concentrated under vacuum and diluted with water. The resulting mixture was extracted with EtOAc (3×200 mL). The combined organic layers were washed with brine and dried over anhydrous $Na_2SO_4$. After filtration the filtrate was concentrated under reduced pressure to afford 1-[(2R,3S,4R,5R)-4-[(tert-butyldimethylsilyl) oxy]-3-fluoro-5-(hydroxymethyl) oxolan-2-yl]-3H-pyrimidine-2,4-dione (11.8 g, crude) as a white solid. LC-MS (ES, m/z): 361 $[M+H]^+$.

Step 3: To a stirred solution of 1-[(2R,3S,4R,5R)-4-[(tert-butyldimethylsilyl) oxy]-3-fluoro-5-(hydroxymethyl) oxolan-2-yl]-3H-pyrimidine-2,4-dione (11.8 g, 32.69 mmol) in ACN (100 mL) was added IBX (27.3 g, 98.07 mmol) in portions at room temperature under $N_2$ atmosphere. The resulting mixture was stirred for 2 h at 60° C. under $N_2$ atmosphere. The resulting mixture was cooled to room temperature and filtered; the filter cake was washed with ACN. The filtrate was concentrated under reduced pressure to afford (2S,3R,4S,5R)-3-[(tert-butyldimethylsilyl) oxy]-5-(2,4-dioxo-3H-pyrimidin-1-yl)-4-fluorooxolane-2-carbaldehyde (10.2 g, crude) as a white solid. LC-MS (ES, m/z): 359 $[M+H]^+$.

Step 4: To a stirred solution of (2S,3R,4S,5R)-3-[(tert-butyldimethylsilyl) oxy]-5-(2,4-dioxo-3H-pyrimidin-1-yl)-4-fluorooxolane-2-carbaldehyde (10.2 g, 28.41 mmol) and paraformaldehyde (4.3 g, 142.05 mmol) in dioxane (100 mL) was added NaOH (2.3 g, 56.82 mmol) in water (10 mL) dropwise at room temperature. The resulting mixture was stirred for 15 h at room temperature. To the above mixture was added $NaBH_4$ (3.2 g, 85.23 mmol) in portions at 0° C. The resulting mixture was stirred for additional 30 mins at room temperature. The reaction was quenched with saturated $NH_4Cl$ (aq.) at 0° C. The resulting mixture was extracted with EtOAc (3×200 mL). The combined organic layers were washed with brine, and dried over anhydrous $Na_2SO_4$. After filtration the filtrate was concentrated under reduced pressure. The residue was purified by silica gel column chromatography, eluting with DCM/MeOH (10:1) to afford 1-[(2R,3S,4R)-4-[(tert-butyldimethylsilyl) oxy]-3-fluoro-5,5-bis(hydroxymethyl)oxolan-2-yl]-3H-pyrimidine-2,4-dione (5.2 g, 13.3 mmol, 46.8%) as a white solid. LC-MS (ES, m/z): 391 $[M+H]^+$.

Step 5: To a stirred solution of 1-[(2R,3S,4R)-4-[(tert-butyldimethylsilyl) oxy]-3-fluoro-5,5-bis(hydroxymethyl) oxolan-2-yl]-3H-pyrimidine-2,4-dione (3 g, 7.67 mmol) in pyridine (50 mL) was added DMTrCl (3.9 g, 11.51 mmol) in portions at 0° C. under $N_2$ atmosphere. The resulting mixture was stirred for 3 h at room temperature under $N_2$ atmosphere. The resulting mixture was used in the next step directly without further purification. LC-MS (ES, m/z): 693 $[M+H]^+$.

Step 6: To the above mixture was added TBSCl (3.4 g, 22.56 mmol) in portions at room temperature. The resulting mixture was stirred for additional 15 h at 60° C. The resulting mixture was cooled to room temperature and concentrated under vacuum. The residue was purified by silica gel column chromatography, eluting with DCM/MeOH (10:1) to afford 1-[(2R,3S,4R,5R)-5-1{[bis(4-methoxyphenyl) (phenyl)methoxy] methyl}-4-[(tert-butyldimethylsilyl) oxy]-5-{[(tert-butyldimethylsilyl) oxy] methyl}-3-fluorooxolan-2-yl]-3H-pyrimidine-2,4-dione (2.2 g, 2.73 mmol, 36.1%) as a yellow solid. LC-MS-PH (ES, m/z): 807 $[M+H]^+$.

Step 7: A solution of 1-[(2R,3S,4R,5R)-5-{[bis(4-methoxyphenyl) (phenyl)methoxy] methyl}-4-[(tert-butyldimethylsilyl) oxy]-5-{[(tert-butyldimethylsilyl) oxy] methyl}-3-fluorooxolan-2-yl]-3H-pyrimidine-2,4-dione (2.2 g, 2.73 mmol) in AcOH (16 mL) and water (4 mL) was stirred for 2 h at room temperature. The resulting mixture was concentrated under vacuum. The residue was purified by silica gel column chromatography, eluting with DCM/MeOH (10:1) to afford 1-[(2R,3S,4R,5R)-4-[(tert-butyldimethylsilyl) oxy]-5-{[(tert-butyldimethylsilyl) oxy] methyl}-3-fluoro-5-(hydroxymethyl) oxolan-2-yl]-3H-pyrimidine-2,4-dione (1.2 g, 2.38 mmol, 87.2%) as a yellow solid. LC-MS (ES, m/z): 505 $[M+H]^+$.

Step 8: To a stirred solution of 1-[(2R,3S,4R,5R)-4-[(tert-butyldimethylsilyl) oxy]-5-{[(tert-butyldimethylsilyl) oxy] methyl}-3-fluoro-5-(hydroxymethyl) oxolan-2-yl]-3H-pyrimidine-2,4-dione (820 mg, 1.62 mmol) in ACN (15 mL) was added IBX (1.3 g, 4.86 mmol) in portions at room temperature under $N_2$ atmosphere. The resulting mixture was stirred for 2 h at 60° C. under $N_2$ atmosphere. The resulting mixture was cooled to room temperature and filtered; the filter cake was washed with ACN. The filtrate was concentrated under reduced pressure to afford (2R,3R,4S,5R)-3-[(tert-butyldimethylsilyl)oxy]-2-{[(tert-butyldimethylsilyl) oxy] methyl}-5-(2,4-dioxo-3H-pyrimidin-1-yl)-4-fluorooxolane-2-carbaldehyde (680 mg, 1.35 mmol, 83.3%) as a white solid. LC-MS (ES, m/z): 503 $[M+H]^+$.

Step 9: To a stirred mixture of bromo(methyl)triphenyl-lambda5-phosphane (3.2 g, 9.06 mmol) in THF (30 mL) was added n-BuLi (3 mL, 7.55 mmol, 2.5 M in THF) dropwise at −78° C. under $N_2$ atmosphere. The resulting mixture was stirred for 1 h at room temperature under $N_2$ atmosphere. To the above mixture was added (2R,3R,4S,5R)-3-[(tert-butyldimethylsilyl) oxy]-2-{[(tert-butyldimethylsilyl) oxy] methyl}-5-(2,4-dioxo-3H-pyrimidin-1-yl)-4-fluorooxolane-2-carbaldehyde (760 mg, 1.51 mmol) in THF (10 mL) dropwise at room temperature. The resulting mixture was stirred for additional 15 h at room temperature. The reaction was quenched with ice water at 0° C. The resulting mixture was extracted with EtOAc (3×100 mL). The combined organic layers were washed with brine and dried over anhydrous $Na_2SO_4$. After filtration the filtrate was concentrated under reduced pressure. The residue was purified by Prep-TLC (DCM/MeOH 10:1) to afford 1-[(2R,3S,4R,5R)-4-[(tert-butyldimethylsilyl) oxy]-5-{[(tert-butyldimethylsilyl) oxy] methyl}-5-ethenyl-3-fluorooxolan-2-yl]-3H-pyrimidine-2,4-dione (600 mg, 1.19 mmol, 79.3%) as a yellow solid. LC-MS (ES, m/z): 501 $[M+H]^+$.

Step 10: To a stirred solution of 1-[(2R,3S,4R,5R)-4-[(tert-butyldimethylsilyl) oxy]-5-{[(tert-butyldimethylsilyl) oxy] methyl}-5-ethenyl-3-fluorooxolan-2-yl]-3H-pyrimidine-2,4-dione (590 mg, 1.18 mmol) and DMAP (143 mg, 1.18 mmol) in DCM (10 mL) was added TEA (357 mg, 3.54 mmol) and benzoyl chloride (248 mg, 1.77 mmol) dropwise at room temperature under $N_2$ atmosphere. The resulting mixture was stirred for 2 h at room temperature under $N_2$ atmosphere. The resulting mixture was extracted with DCM (3×50 mL). The combined organic layers were washed with brine and dried over anhydrous Na$_2$SO$_4$. After filtration the filtrate was concentrated under reduced pressure. The residue was purified by Prep-TLC (DCM/MeOH 20:1) to afford 3-benzoyl-1-[(2R,3S,4R,5R)-4-[(tert-butyldimethylsilyl) oxy]-5-{[(tert-butyldimethylsilyl)oxy] methyl}-5-ethenyl-3-fluorooxolan-2-yl] pyrimidine-2,4-dione (500 mg, 0.83 mmol, 70.2%) as a white solid. LC-MS (ES, m/z): 605 [M+H]$^+$.

Step 11: To a stirred solution of 3-benzoyl-1-[(2R,3S,4R,5R)-4-[(tert-butyldimethylsilyl)oxy]-5-{[(tert-butyldimethylsilyl)oxy]methyl}-5-ethenyl-3-fluorooxolan-2-yl]pyrimidine-2,4-dione (500 mg, 0.83 mmol) in DCM (10 mL) was added Pd(OAc)$_2$ (18 mg, 0.08 mmol) at room temperature under N$_2$ atmosphere. To the above mixture was added CH$_2$N$_2$ ether solution (100 mL) dropwise at 0° C. The resulting mixture was stirred for additional 15 h at room temperature. The resulting mixture was filtered; the filter cake was washed with DCM. The filtrate was concentrated under reduced pressure. The resulting mixture was washed with brine and dried over anhydrous Na$_2$SO$_4$. After filtration the filtrate was concentrated under reduced pressure. The residue was purified by Prep-TLC (EtOAc/Petroleum ether 5:1) to afford 3-benzoyl-1-[(2R,3S,4R,5R)-4-[(tert-butyldimethylsilyl)oxy]-5-{[(tert-butyldimethylsilyl)oxy] methyl}-5-cyclopropyl-3-fluorooxolan-2-yl] pyrimidine-2,4-dione (310 mg, 0.5 mmol, 60.6%) as a yellow solid. LC-MS (ES, m/z): 619 [M+H]$^+$.

Step 12: To a solution of NH$_3$(g) in MeOH (6 mL, 7M), 3-benzoyl-1-[(2R,3S,4R,5R)-4-[(tert-butyldimethylsilyl) oxy]-5-{[(tert-butyldimethylsilyl) oxy] methyl}-5-cyclopropyl-3-fluorooxolan-2-yl] pyrimidine-2,4-dione (310 mg, 0.5 mmol) was added. The mixture was stirred for 2 h at room temperature under N$_2$ atmosphere. The resulting mixture was concentrated under vacuum. The residue was purified by Prep-TLC (DCM/MeOH 20:1) to afford 1-[(2R,3S,4R,5R)-4-[(tert-butyldimethylsilyl) oxy]-5-{[(tert-butyldimethylsilyl) oxy]methyl}-5-cyclopropyl-3-fluorooxolan-2-yl]-3H-pyrimidine-2,4-dione (240 mg, 0.47 mmol, 93.1%) as a white solid. LC-MS (ES, m/z): 515 [M+H]$^+$.

Step 13: To a stirred solution of 1-[(2R,3S,4R,5R)-4-[(tert-butyldimethylsilyl) oxy]-5-{[(tert-butyldimethylsilyl) oxy] methyl}-5-cyclopropyl-3-fluorooxolan-2-yl]-3H-pyrimidine-2,4-dione (220 mg, 0.43 mmol) in ACN (5 mL) was added DMAP (104 mg, 0.86 mmol) and TEA (86 mg, 0.86 mmol) at room temperature under N$_2$ atmosphere. The resulting mixture was stirred for 10 min at room temperature under N$_2$ atmosphere. To the above mixture was added TPSCl (258 mg, 0.86 mmol) in portions and stirred for additional 15 h at room temperature. To the above mixture was added concentrated ammonium hydroxide (2 mL) at room temperature. The resulting mixture was stirred for 30 min at room temperature. The resulting mixture was concentrated under vacuum. The residue was purified by Prep-TLC (DCM/MeOH 10:1) to afford 4-amino-1-[(2R,3S,4R,5R)-4-[(tert-butyldimethylsilyl)oxy]-5-{[(tert-butyldimethylsilyl)oxy] methyl}-5-cyclopropyl-3-fluorooxolan-2-yl] pyrimidin-2-one (220 mg, 0.43 mmol, 100%) as a white solid. LC-MS (ES, m/z): 514 [M+H]$^+$.

Step 14: To a stirred solution of 4-amino-1-[(2R,3S,4R,5R)-4-[(tert-butyldimethylsilyl) oxy]-5-{[(tert-butyldimethylsilyl) oxy] methyl}-5-cyclopropyl-3-fluorooxolan-2-yl] pyrimidin-2-one (220 mg, 0.43 mmol) in MeOH (6 mL) was added NH$_4$F (475 mg, 12.9 mmol) in portions at room temperature under N$_2$ atmosphere. The resulting mixture was stirred for 48 h at 60° C. under N$_2$ atmosphere. The resulting mixture was cooled to room temperature and filtered; the filter cake was washed with MeOH. The filtrate was concentrated under reduced pressure. The crude product was purified by Prep-HPLC with the following conditions (Column: SunFire Prep C18 OBD Column, 19*150 mm, 5 μm; Mobile Phase A: Water (10 mmol/L NH$_4$HCO$_3$+0.1% NH$_3$—H$_2$O), Mobile Phase B: ACN; Flow rate: 60 mL/min; Gradient: 50% B to 70% B in 6 min, Wavelength: 254/210 nm; RT1(min): 6.35). The fraction was collected and concentrated under vacuum, the residue was re-dissolved in CH$_3$CN and H$_2$O, and then was lyophilized to afford 4-amino-1-[(2R,3S,4R,5R)-5-cyclopropyl-3-fluoro-4-hydroxy-5-(hydroxymethyl) oxolan-2-yl] pyrimidin-2-one (42.4 mg, 0.15 mmol, 34.7%) as a white solid. LC-MS (ES, m/z): 286 [M+H]$^+$, 96.3% purity. Conditions for the LCMS: (Column: Shim-pack Scepter C18, 33*3.0 mm, 2.7 μm; Mobile Phase A: Water/5 mM NH$_4$HCO$_3$, Mobile Phase B: ACN; Flow rate: 1.50 mL/min; Gradient: 10% B to 95% B in 1.2 min, 95% B to 95% B in 0.60 min, 95% B to 10% B in 0.02 min; Wavelength: 254/220 nm; RT1(min): 2.828). $^1$H NMR (400 MHz, DMSO-d$_6$) δ 7.92 (d, J=7.5 Hz, 1H), 7.19 (d, J=28.5 Hz, 2H), 6.10 (dd, J=9.0, 5.5 Hz, 1H), 5.88 (s, 1H), 5.69 (d, J=7.5 Hz, 1H), 5.35 (d, J=5.2 Hz, 1H), 5.11 (dt, J=54.3, 5.6 Hz, 1H), 4.47 (dd, J=22.0, 5.7 Hz, 1H), 3.48 (d, J=4.1 Hz, 2H), 1.02 (tt, J=8.5, 5.6 Hz, 1H), 0.46-0.38 (m, 1H), 0.37-0.28 (m, 1H), 0.24 (d, J=5.2 Hz, 2H).

Example 70—Synthesis of Compound 120: 4-amino-1-[(2R,4S,5R)-5-cyclopropyl-4-hydroxy-5-(hydroxymethyl) oxolan-2-yl]-5-fluoropyrimidin-2-one

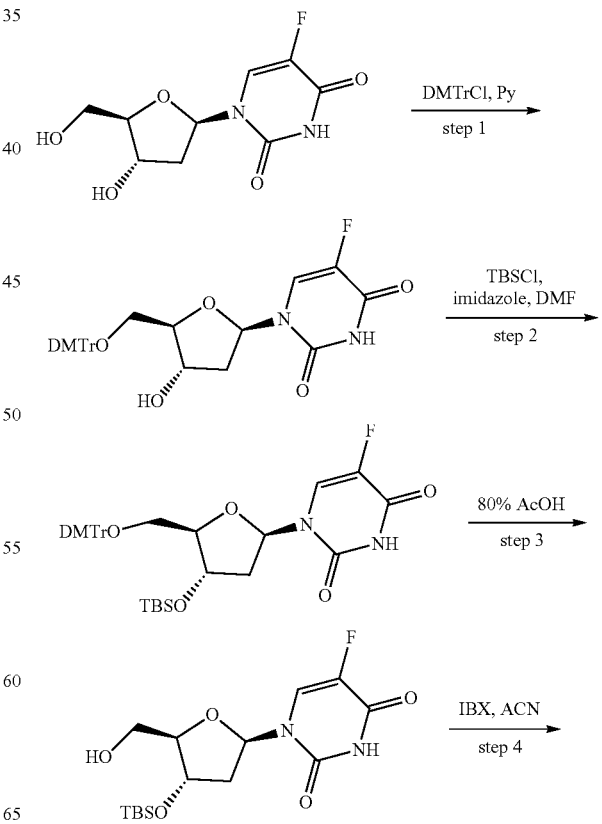

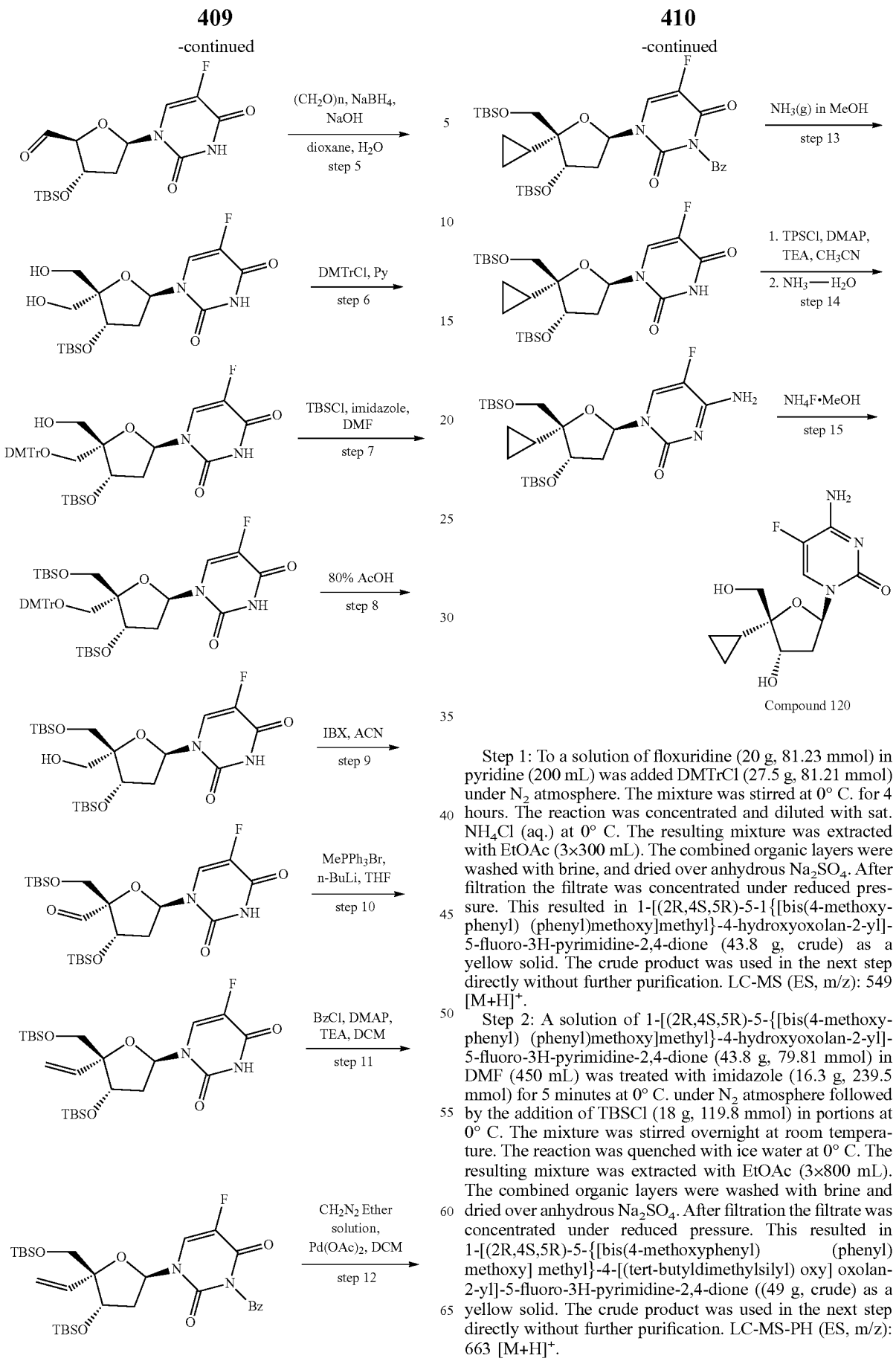

Step 1: To a solution of floxuridine (20 g, 81.23 mmol) in pyridine (200 mL) was added DMTrCl (27.5 g, 81.21 mmol) under N₂ atmosphere. The mixture was stirred at 0° C. for 4 hours. The reaction was concentrated and diluted with sat. NH₄Cl (aq.) at 0° C. The resulting mixture was extracted with EtOAc (3×300 mL). The combined organic layers were washed with brine, and dried over anhydrous Na₂SO₄. After filtration the filtrate was concentrated under reduced pressure. This resulted in 1-[(2R,4S,5R)-5-1{[bis(4-methoxyphenyl) (phenyl)methoxy]methyl}-4-hydroxyoxolan-2-yl]-5-fluoro-3H-pyrimidine-2,4-dione (43.8 g, crude) as a yellow solid. The crude product was used in the next step directly without further purification. LC-MS (ES, m/z): 549 [M+H]⁺.

Step 2: A solution of 1-[(2R,4S,5R)-5-{[bis(4-methoxyphenyl) (phenyl)methoxy]methyl}-4-hydroxyoxolan-2-yl]-5-fluoro-3H-pyrimidine-2,4-dione (43.8 g, 79.81 mmol) in DMF (450 mL) was treated with imidazole (16.3 g, 239.5 mmol) for 5 minutes at 0° C. under N₂ atmosphere followed by the addition of TBSCl (18 g, 119.8 mmol) in portions at 0° C. The mixture was stirred overnight at room temperature. The reaction was quenched with ice water at 0° C. The resulting mixture was extracted with EtOAc (3×800 mL). The combined organic layers were washed with brine and dried over anhydrous Na₂SO₄. After filtration the filtrate was concentrated under reduced pressure. This resulted in 1-[(2R,4S,5R)-5-{[bis(4-methoxyphenyl) (phenyl)methoxy] methyl}-4-[(tert-butyldimethylsilyl) oxy] oxolan-2-yl]-5-fluoro-3H-pyrimidine-2,4-dione ((49 g, crude) as a yellow solid. The crude product was used in the next step directly without further purification. LC-MS-PH (ES, m/z): 663 [M+H]⁺.

Step 3: A solution of 1-[(2R,4S,5R)-5-{[bis(4-methoxyphenyl) (phenyl)methoxy]methyl}-4-[(tert-butyldimethylsilyl) oxy] oxolan-2-yl]-5-fluoro-3H-pyrimidine-2,4-dione (49 g, 73.91 mmol) in water (100 mL) and AcOH (400 mL) was stirred overnight at room temperature under $N_2$ atmosphere. The mixture was concentrated and neutralized to pH 7 with saturated $NaHCO_3$(aq.). The resulting mixture was extracted with EtOAc (3×500 mL). The combined organic layers were washed with brine and dried over anhydrous $Na_2SO_4$. After filtration the filtrate was concentrated under reduced pressure. The residue was purified by silica gel column chromatography, eluting with (EtOAc/Petroleum ether 5:1) to afford 1-[(2R,4S,5R)-4-[(tert-butyldimethylsilyl) oxy]-5-(hydroxymethyl) oxolan-2-yl]-5-fluoro-3H-pyrimidine-2,4-dione (17.2 g, 47.71 mmol, 64.6%) as a yellow solid. LC-MS (ES, m/z): 361 [M+H]$^+$.

Step 4: To a solution of 1-[(2R,4S,5R)-4-[(tert-butyldimethylsilyl) oxy]-5-(hydroxymethyl) oxolan-2-yl]-5-fluoro-3H-pyrimidine-2,4-dione (17.2 g, 47.71 mmol) in ACN (200 mL) was added IBX (26.7 g, 95.42 mmol) at room temperature under $N_2$ atmosphere. The mixture was stirred at 60° C. for 4 hours. The resulting mixture was cooled to room temperature and filtered; the filter cake was washed with ACN. The filtrate was concentrated under reduced pressure to afford (2S,3S,5R)-3-[(tert-butyldimethylsilyl) oxy]-5-(5-fluoro-2-oxo-3,4-dihydropyrimidin-1-yl) oxolane-2-carbaldehyde (16.8 g, crude) as a yellow solid. The crude product was used in the next step directly without further purification. LC-MS (ES, m/z): 359 [M+H]$^+$.

Step 5: A solution of (2S,3S,5R)-3-[(tert-butyldimethylsilyl)oxy]-5-(5-fluoro-2,4-dioxo-3H-pyrimidin-1-yl) oxolane-2-carbaldehyde (16.8 g, 44.8 mmol) in 1,4-dioxane (160 mL) was treated with paraformaldehyde (13.1 g, 436.92 mmol) and NaOH (2.62 g, 64 mmol) in water (32 mL). The reaction was stirred overnight at room temperature under $N_2$ atmosphere. To the above mixture was added $NaBH_4$ (3.43 g, 89.31 mmol) in portions over 5 minutes at 0° C. The resulting mixture was stirred for additional 1 hour at room temperature. The reaction was quenched with sat. $NH_4Cl$ (aq.) at 0° C. The resulting mixture was extracted with EtOAc (3×300 mL). The combined organic layers were washed with water, dried over anhydrous $Na_2SO_4$. After filtration the filtrate was concentrated under reduced pressure. The residue was purified by silica gel column chromatography, eluting with (EtOAc/Petroleum ether 1/1) to afford 1-[(2R,4S)-4-[(tert-butyldimethylsilyl) oxy]-5,5-bis (hydroxymethyl)oxolan-2-yl]-5-fluoro-3H-pyrimidine-2,4-dione (5.52 g, 14.12 mmol, 31.5%) as a white solid. LC-MS (ES, m/z): 391 [M+H]$^+$.

Step 6: To a stirred solution of 1-[(2R,4S)-4-[(tert-butyldimethylsilyl) oxy]-5,5-bis(hydroxymethyl)oxolan-2-yl]-5-fluoro-3H-pyrimidine-2,4-dione (5.52 g, 14.12 mmol) in pyridine (50 mL) was added DMTrCl (5.72 g, 16.93 mmol) in portions at 0° C. under $N_2$ atmosphere. The resulting mixture was stirred overnight at room temperature. The reaction was concentrated and quenched with sat. $NH_4Cl$ (aq.) at 0° C. The resulting mixture was extracted with EtOAc (3×150 mL). The combined organic layers were washed with brine and dried over anhydrous $Na_2SO_4$. After filtration the filtrate was concentrated under reduced pressure to afford 1-[(2R,4S,5S)-5-1{[bis(4-methoxyphenyl) (phenyl)methoxy] methyl}-4-[(tert-butyldimethylsilyl) oxy]-5-(hydroxymethyl) oxolan-2-yl]-5-fluoro-3H-pyrimidine-2,4-dione (10.8 g, 15.64 mmol, 99.7%) as a yellow solid. The crude product was used in the next step directly without further purification. LC-MS-PH (ES, m/z): 693 [M+H]$^+$.

Step 7: To a stirred solution of imidazole (3.22 g, 46.83 mmol) and 1-[(2R,4S,5S)-5-{[bis(4-methoxyphenyl) (phenyl)methoxy] methyl}-4-[(tert-butyldimethylsilyl) oxy]-5-(hydroxymethyl) oxolan-2-yl]-5-fluoro-3H-pyrimidine-2,4-dione (10.8 g, 15.64 mmol) in DMF (100 mL) was added TBSCl (3.54 g, 23.42 mmol) in portions at 0° C. under $N_2$ atmosphere. The resulting mixture was stirred overnight at room temperature under $N_2$ atmosphere. The reaction was quenched with ice water at 0° C. The resulting mixture was extracted with EtOAc (3×200 mL). The combined organic layers were washed with brine and dried over anhydrous $Na_2SO_4$. After filtration the filtrate was concentrated under reduced pressure. This resulted in 1-[(2R,4S,5R)-5-1{[bis (4-methoxyphenyl) (phenyl)methoxy] methyl}-4-[(tert-butyldimethylsilyl) oxy]-5-{[(tert-butyldimethylsilyl) oxy] methyl} oxolan-2-yl]-5-fluoro-3H-pyrimidine-2,4-dione (13.2 g, crude) as a yellow solid. The crude product was used in the next step directly without further purification. LC-MS (ES, m/z): 807 [M+H]$^+$.

Step 8: A solution of 1-[(2R,4S,5R)-5-{[bis(4-methoxyphenyl) (phenyl)methoxy]methyl}-4-[(tert-butyldimethylsilyl) oxy]-5-{[(tert-butyldimethylsilyl) oxy] methyl} oxolan-2-yl]-5-fluoro-3H-pyrimidine-2,4-dione (13.2 g, 16.14 mmol) in water (26 mL) and AcOH (104 mL) was stirred overnight at room temperature under $N_2$ atmosphere. The mixture was concentrated and neutralized to pH 7 with saturated $NaHCO_3$ (aq.). The resulting mixture was extracted with EtOAc (3×500 mL). The combined organic layers were washed with brine and dried over anhydrous $Na_2SO_4$. After filtration the filtrate was concentrated under reduced pressure. The residue was purified by silica gel column chromatography, eluting with (EtOAc/Petroleum ether 1/1) to afford 1-[(2R,4S,5R)-4-[(tert-butyldimethylsilyl) oxy]-5-{[(tert-butyldimethylsilyl) oxy] methyl}-5-(hydroxymethyl) oxolan-2-yl]-5-fluoro-3H-pyrimidine-2,4-dione (5 g, 9.91 mmol, 61.5%) as a white solid. LC-MS (ES, m/z): 505 [M+H]$^+$.

Step 9: To a stirred solution of 1-[(2R,4S,5R)-4-[(tert-butyldimethylsilyl) oxy]-5-{[(tert-butyldimethylsilyl) oxy] methyl}-5-(hydroxymethyl) oxolan-2-yl]-5-fluoro-3H-pyrimidine-2,4-dione (5 g, 9.91 mmol) in ACN (50 mL) was added IBX (8.33 g, 29.72 mmol) in portions at room temperature under $N_2$ atmosphere. The resulting mixture was stirred 3 hours at 60° C. under $N_2$ atmosphere. The resulting mixture was cooled to room temperature and filtered; the filter cake was washed with ACN. The filtrate was concentrated under reduced pressure to afford (2R,3S,5R)-3-[(tert-butyldimethylsilyl) oxy]-2-{[(tert-butyldimethylsilyl) oxy] methyl}-5-(5-fluoro-2,4-dioxo-3H-pyrimidin-1-yl) oxolane-2-carbaldehyde (5 g, crude) as a yellow solid. The crude product was used in the next step directly without further purification. LC-MS (ES, m/z): 503 [M+H]$^+$.

Step 10: A solution of methyltriphenylphosphanium bromide (3.91 g, 10.92 mmol) in THF (40 mL) was treated with n-BuLi (4 mL, 10.92 mmol, 2.5 M in hexane) for 5 minutes at 0° C. under $N_2$ atmosphere followed by the addition of (2R,3S,5R)-3-[(tert-butyldimethylsilyl) oxy]-2-{[(tert-butyldimethylsilyl) oxy] methyl}-5-(5-fluoro-2,4-dioxo-3H-pyrimidin-1-yl) oxolane-2-carbaldehyde (5 g, 9.92 mmol) in THF (50 mL) dropwise at 0° C. under $N_2$ atmosphere. The resulting mixture was stirred for 2 hours at 0° C. under $N_2$ atmosphere. The reaction was quenched with ice water at 0° C. The resulting mixture was extracted with EtOAc (3×200 mL). The combined organic layers were washed with brine and dried over anhydrous $Na_2SO_4$. After filtration the filtrate was concentrated under reduced pressure. The residue was purified by silica gel column chromatography, eluting with (EtOAc/Petroleum ether 5/1) to afford 1-[(2R,4S,5R)-4-[(tert-butyldimethylsilyl)oxy]-5-{[(tert-butyldimethylsilyl) oxy]methyl}-5-ethenyloxolan-2-yl]-5-fluoro-3H-pyrimidine-2,4-dione (2 g, 3.99 mmol, 40.2%) as a yellow solid. LC-MS (ES, m/z): 501 [M+H]+.

Step 11: To a stirred solution of 1-[(2R,4S,5R)-4-[(tert-butyldimethylsilyl) oxy]-5-{[(tert-butyldimethylsilyl) oxy]methyl}-5-ethenyloxolan-2-yl]-5-fluoro-3H-pyrimidine-2,4-dione (2 g, 3.99 mmol) in DCM (20 mL) were added TEA (1.2 g, 11.73 mmol), DMAP (1.5 g, 11.73 mmol) and benzoyl chloride (842 mg, 5.87 mmol) in sequence at 0° C. under $N_2$ atmosphere. The resulting mixture was stirred overnight at room temperature under $N_2$ atmosphere. The resulting mixture was diluted with DCM (3×100 mL). The combined organic layers were washed with brine and dried over anhydrous $Na_2SO_4$. After filtration the filtrate was concentrated under reduced pressure. The residue was purified by silica gel column chromatography, eluting with (EtOAc/Petroleum ether 10/1) to afford 3-benzoyl-1-[(2R,4S,5R)-4-[(tert-butyldimethylsilyl) oxy]-5-{[(tert-butyldimethylsilyl) oxy] methyl}-5-ethenyloxolan-2-yl]-5-fluoropyrimidine-2,4-dione (700 mg, 1.16 mmol, 28.9%) as a white solid. LC-MS (ES, m/z): 605 [M+H]+.

Step 12: To a stirred solution of 3-benzoyl-1-[(2R,4S,5R)-4-[(tert-butyldimethylsilyl) oxy]-5-{[(tert-butyldimethylsilyl) oxy] methyl}-5-ethenyloxolan-2-yl]-5-fluoropyrimidine-2,4-dione (700 mg, 1.16 mmol) in DCM (20 mL) was added Pd(OAc)$_2$ (26 mg, 0.11 mmol) at room temperature under $N_2$ atmosphere. To the above mixture was added $CH_2N_2$ ether solution (20 mL) dropwise at 0° C. The resulting mixture was stirred for additional 15 hours at room temperature. The resulting mixture was filtered; the filter cake was washed with DCM. The filtrate was concentrated under reduced pressure. The resulting mixture was washed with water, and dried over anhydrous $Na_2SO_4$. After filtration the filtrate was concentrated under reduced pressure. The residue was purified by Prep-TLC (EtOAc/Petroleum ether 5/1) to afford 3-benzoyl-1-[(2R,4S,5R)-4-[(tert-butyldimethylsilyl)oxy]-5-{[(tert-butyldimethylsilyl) oxy] methyl}-5-cyclopropyloxolan-2-yl]-5-fluoropyrimidine-2,4-dione (540 mg, 0.87 mmol, 75.4%) as a yellow solid. (ES, m/z): 619 [M+H]+.

Step 13: To a solution of $NH_3$(g) in MeOH (10 mL, 7 M), 3-benzoyl-1-[(2R,4S,5R)-4-[(tert-butyldimethylsilyl) oxy]-5-{[(tert-butyldimethylsilyl) oxy] methyl}-5-cyclopropyloxolan-2-yl]-5-fluoropyrimidine-2,4-dione (540 mg, 0.87 mmol) was added. The mixture was stirred for 2 hours at room temperature. The resulting mixture was concentrated under vacuum. The residue was purified by Prep-TLC (DCM/MeOH 15/1) to afford 1-[(2R,4S,5R)-4-[(tert-butyldimethylsilyl)oxy]-5-{[(tert-butyldimethylsilyl)oxy] methyl}-5-cyclopropyloxolan-2-yl]-5-fluoro-3H-pyrimidine-2,4-dione (340 mg, 0.66 mmol, 77.1%) as a white solid. LC-MS (ES, m/z): 515 [M+H]+.

Step 14: To a stirred mixture of 1-[(2R,4S,5R)-4-[(tert-butyldimethylsilyl) oxy]-5-{[(tert-butyldimethylsilyl) oxy] methyl}-5-cyclopropyloxolan-2-yl]-5-fluoro-3H-pyrimidine-2,4-dione (320 mg, 0.66 mmol), DMAP (152 mg, 1.32 mmol) and TEA (189 mg, 1.85 mmol) in ACN (10 mL) was added TPSCl (377 mg, 1.32 mmol) in portions at room temperature under $N_2$ atmosphere. The mixture was stirred for 15 hours at room temperature. Then conc. ammonium hydroxide (5 mL) was added and the mixture was stirred for 1 hour at room temperature. The resulting mixture was concentrated under reduced pressure. The residue was purified by Prep-TLC (DCM/MeOH 8/1) to afford 4-amino-1-[(2R,4S,5R)-4-[(tert-butyldimethylsilyl)oxy]-5-{[(tert-butyldimethylsilyl) oxy] methyl}-5-cyclopropyloxolan-2-yl]-5-fluoropyrimidin-2-one (300 mg, 0.58 mmol, 93.9%) as an off-white solid. LC-MS (ES, m/z): 514 [M+H]+.

Step 15: To a stirred mixture of 4-amino-1-[(2R,4S,5R)-4-[(tert-butyldimethylsilyl) oxy]-5-{[(tert-butyldimethylsilyl) oxy] methyl}-5-cyclopropyloxolan-2-yl]-5-fluoropyrimidin-2-one (300 mg, 0.58 mmol) in MeOH (14 mL) was added $NH_4F$ (649 mg, 17.4 mmol) in portions at room temperature under $N_2$ atmosphere. The mixture was stirred for 15 hours at 60° C. The resulting mixture was cooled to room temperature and concentrated under reduced pressure. The residue was purified by Prep-TLC (DCM/MeOH=8:1) to afford crude product. The crude product was purified by Prep-HPLC with the following conditions (Column: Xselect CSH C18 OBD Column 30*150 mm 5 m, n; Mobile Phase A: Water (10 mmol/L $NH_4HCO_3$), Mobile Phase B: ACN; Flow rate: 60 mL/min; Gradient: 2% B to 15% B in 7 min, Wavelength: 220 nm; RT1(min): 7.63). The fraction was collected and concentrated under vacuum, the residue was re-dissolved in $CH_3CN$ and $H_2O$, and then was lyophilized to afford 4-amino-1-[(2R,4S,5R)-5-cyclopropyl-4-hydroxy-5-(hydroxymethyl) oxolan-2-yl]-5-fluoropyrimidin-2-one (14.5 mg, 0.05 mmol, 8.4%) as an off-white solid. LC-MS (ES, m/z): 286 [M+H]+, 96.2% purity. Conditions for the LCMS: (Column: HALO C18, 100*4.6 mm, 2.7 μm; Mobile Phase A: $H_2O$+0.1% TFA, Mobile Phase B: ACN+0.1% TFA; Flow rate: 1.20 mL/min; Gradient: 0% B to 95% B in 8.00 min, 95% B to 95% B in 2.00 min, 95% B to 10% B in 0.50 min; Wavelength: 254 nm; RT1(min): 2.85). $^1$H NMR (400 MHz, DMSO-d$_6$) δ 8.37 (d, J=7.4 Hz, 1H), 7.56 (d, J=93.1 Hz, 2H), 5.86 (ddd, J=6.4, 4.2, 1.9 Hz, 1H), 5.33 (t, J=4.8 Hz, 1H), 5.15 (d, J=4.9 Hz, 1H), 4.41 (q, J=6.9 Hz, 1H), 3.63-3.43 (m, 2H), 2.28-1.99 (m, 2H), 0.89 (td, J=8.2, 4.2 Hz, 1H), 0.45-0.35 (m, 1H), 0.26 (q, J=6.0, 5.5 Hz, 2H), 0.18-0.08 (m, 1H).

Example 71—Synthesis of Compound 94: 2-amino-9-[(2R,3S,4S,5R)-5-(chloromethyl)-3,4-dihydroxy-5-(hydroxymethyl) oxolan-2-yl]-1H-purin-6-one

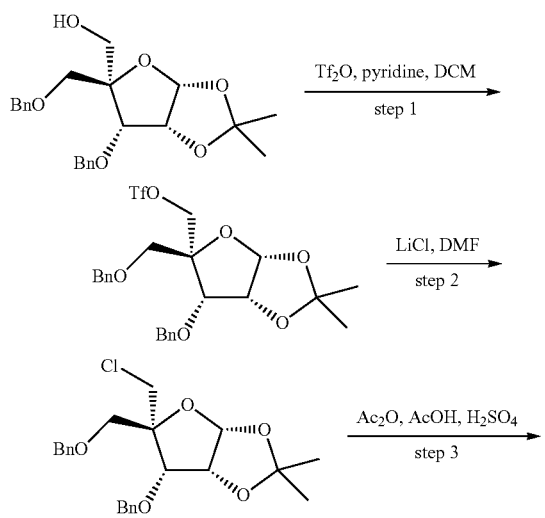

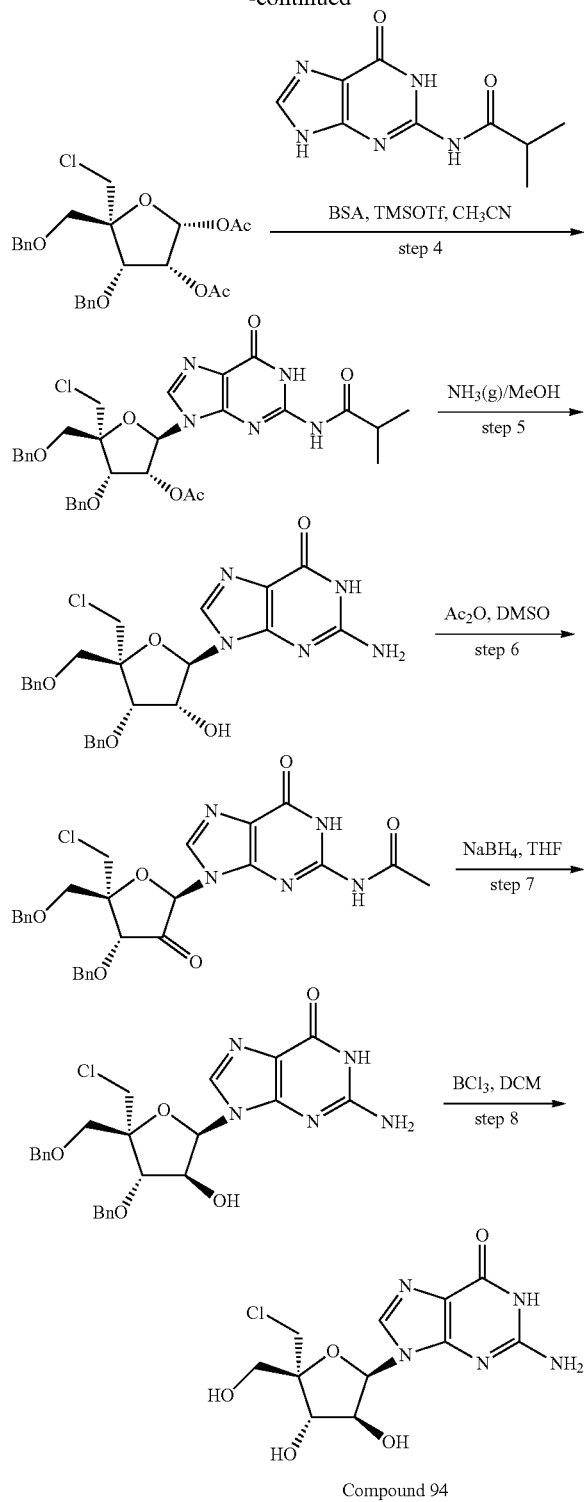

Compound 94 with EtOAc (3×300 mL). The combined organic layers were washed with brine and dried over anhydrous Na₂SO₄. After filtration the filtrate was concentrated under reduced pressure. The residue was purified by silica gel column chromatography, eluting with EtOAc/Petroleum ether (3/1) to afford [(3aR,5S,6S,6aR)-6-(benzyloxy)-5-[(benzyloxy) methyl]-2,2-dimethyl-dihydro-3aH-furo[2,3-d][1,3]dioxol-5-yl] methyl trifluoromethanesulfonate (10.4 g, 19.51 mmol, 97.8%) as a light-yellow oil. LC-MS (ES, m/z): 550 $[M+NH_4]^+$.

Step 2: To a stirred mixture of [(3aR,5S,6S,6aR)-6-(benzyloxy)-5-[(benzyloxy)methyl]-2,2-dimethyl-dihydro-3aH-furo[2,3-d][1,3]dioxol-5-yl] methyl trifluoromethanesulfonate (10.4 g, 19.51 mmol) in DMF (100 mL) was added LiCl (8.3 g, 197.62 mmol) at room temperature under N₂ atmosphere. The mixture was stirred for 2 hours at 60° C. The resulting mixture was concentrated under reduced pressure. The resulting mixture was diluted with water and extracted with EtOAc (3×300 mL). The combined organic layers were washed with brine, and dried over anhydrous Na₂SO₄. After filtration the filtrate was concentrated under reduced pressure. The residue was purified by silica gel column chromatography, eluting with EtOAc/Petroleum ether (3/1) to afford crude product. The crude product was purified by reversed-phase flash chromatography with the following conditions: C18 column; mobile phase, water and ACN, 5% to 100% gradient in 20 min; UV detection at 254 nm. This afforded (3aR,5R,6S,6aR)-6-(benzyloxy)-5-[(benzyloxy)methyl]-5-(chloromethyl)-2,2-dimethyl-dihydro-3aH-furo[2,3-d][1,3]dioxole (5.1 g, 12.21 mmol, 62.4%) as a light-yellow oil. LC-MS (ES, m/z): 436/438 $[M+NH_4]^+$.

Step 3: To a stirred mixture of (3aR,5R,6S,6aR)-6-(benzyloxy)-5-[(benzyloxy)methyl]-5-(chloromethyl)-2,2-dimethyl-dihydro-3aH-furo[2,3-d][1,3]dioxole (5.1 g, 12.21 mmol) in AcOH (60 mL) was added Ac₂O (17.4 g, 170.78 mmol) and concentrated H₂SO₄ (1 mL) dropwise at 0° C. under N₂ atmosphere. The mixture was stirred for 2 hours at room temperature. The resulting mixture was concentrated under reduced pressure and quenched with ice water. The residue was adjusted to pH 8 with saturated NaHCO₃(aq.). The resulting mixture was extracted with EtOAc (3×200 mL). The combined organic layers were washed with brine and dried over anhydrous Na₂SO₄. After filtration the filtrate was concentrated under reduced pressure. The residue was purified by silica gel column chromatography, eluting with PE/EA (2/1) to afford (2R,3R,4S,5R)-2-(acetyloxy)-4-(benzyloxy)-5-[(benzyloxy)methyl]-5-(chloromethyl) oxolan-3-yl acetate (4.4 g, 9.51 mmol, 78.1%) as a light-yellow oil. LC-MS (ES, m/z): 480/482 $[M+NH_4]^+$.

Step 4: To a stirred solution of 2-Methyl-N-(6-oxo-1,9-dihydropurin-2-yl) propanamide (1.7 g, 7.71 mmol) in ACN (30 mL) were added (E)-(trimethylsilyl N-(trimethylsilyl) ethanimidate) (4.2 g, 20.52 mmol) at room temperature under N₂ atmosphere. The mixture was stirred for 1 hour at 80° C. The mixture was cooled to room temperature, then TMSOTf (1.8 g, 8.2 mmol) and (2R,3R,4S,5R)-2-(acetyloxy)-4-(benzyloxy)-5-[(benzyloxy)methyl]-5-(chloromethyl) oxolan-3-yl acetate (2.4 g, 5.21 mmol) in ACN (10 mL) was added dropwise under nitrogen. The mixture was stirred for 15 hours at 80° C. The resulting mixture was cooled to room temperature, diluted with water and extracted with EtOAc (3×100 mL). The combined organic layers were washed with brine and dried over anhydrous Na₂SO₄. After filtration the filtrate was concentrated under reduced pressure. The residue was purified by silica gel column chromatography, eluting with DCM/MeOH (10/1) to afford ((2R,3R,4S,5R)-4-(benzyloxy)-5-((benzyloxy)

Step 1: To a stirred solution of [(3aR,5R,6S,6aR)-6-(benzyloxy)-5-[(benzyloxy) methyl]-2,2-dimethyl-dihydro-3aH-furo[2,3-d][1,3]dioxol-5-yl] methanol (8 g, 19.91 mmol) and pyridine (6.3 g, 79.87 mmol) in DCM (150 mL) was added Tf₂O (7.3 g, 25.88 mmol) at −35° C. under N₂ atmosphere. The mixture was stirred for 2 hours at 0° C. The resulting mixture was concentrated under reduced pressure. The resulting mixture was diluted with water and extracted methyl)-5-(chloromethyl)-2-(2-isobutyramido-6-oxo-1,6-dihydro-9H-purin-9-yl)tetrahydrofuran-3-yl acetate (2.9 g, 4.62 mmol, 89.2%) as a white solid. LC-MS (ES, m/z): 624/626 [M+H]+.

Step 5: To a solution of NH3 (g) in MeOH (15 mL, 2M) was added (2R,3R,4S,5R)-4-(benzyloxy)-5-((benzyloxy)methyl)-5-(chloromethyl)-2-(2-isobutyramido-6-oxo-1,6-dihydro-9H-purin-9-yl)tetrahydrofuran-3-yl acetate (1.2 g, 1.91 mmol) at room temperature and stirred for 15 hours under N2 atmosphere. The resulting mixture was concentrated under reduced pressure. The residue was purified by silica gel column chromatography, eluting with DCM/MeOH (10/1) to afford 2-amino-9-[(2R,3R,4S,5R)-4-(benzyloxy)-5-[(benzyloxy)methyl]-5-(chloromethyl)-3-hydroxyoxolan-2-yl]-1H-purin-6-one (860 mg, 1.72 mmol, 88.4%) as an off-white solid. LC-MS (ES, m/z): 512/514 [M+H]+.

Step 6: To a stirred mixture of 2-amino-9-[(2R,3R,4S,5R)-4-(benzyloxy)-5-[(benzyloxy)methyl]-5-(chloromethyl)-3-hydroxyoxolan-2-yl]-1H-purin-6-one (860 mg, 1.72 mmol) in DMSO (24 mL) was added Ac2O (17 mL) at room temperature under N2 atmosphere. The mixture was stirred for 2 hours at room temperature. The reaction was quenched by the addition of sat. NH4Cl (aq.) at 0° C. The resulting mixture extracted with EtOAc (3×100 mL). The combined organic layers were washed with brine and dried over anhydrous Na2SO4. After filtration the filtrate was concentrated under reduced pressure. The residue was purified by Prep-TLC (DCM/MeOH=10/1) to afford N-{9-[(2R,4R,5R)-4-(benzyloxy)-5-[(benzyloxy)methyl]-5-(chloromethyl)-3-oxooxolan-2-yl]-6-oxo-1H-purin-2-yl} acetamide (490 mg, 0.91 mmol, 52.2%) as a yellow solid. LC-MS (ES, m/z): 552/554 [M+H]+.

Step 7: To a stirred solution of N-{9-[(2R,4R,5R)-4-(benzyloxy)-5-[(benzyloxy) methyl]-5-(chloromethyl)-3-oxooxolan-2-yl]-6-oxo-1H-purin-2-yl} acetamide (490 mg, 0.91 mmol) in THF (25 mL) was added NaBH4 (168 mg, 4.42 mmol) under N2 atmosphere at 0° C. The mixture was stirred for 2 hours at 0° C. The reaction was quenched by the addition of sat. NH4Cl (aq.) at 0° C. The resulting mixture was extracted with EtOAc. The combined organic layers were washed with brine and dried over anhydrous Na2SO4. After filtration the filtrate was concentrated under reduced pressure. The residue was purified by Prep-TLC (DCM:MeOH=10:1) to afford 300 mg crude product. The crude product was purified by Prep-chiral-HPLC with following conditions (Column: SunFire Prep C18 OBD Column, 19*150 mm, 5 μm; Mobile Phase A: Water (10 mmol/L NH4HCO3+0.1% NH3·H2O), Mobile Phase B: ACN; Flow rate: 60 mL/min; Gradient: 40% B to 60% B in 6.34 min, Wavelength: 254/210 nm; RT1(min): 6). The fraction was collected and concentrated under vacuum, the residue was re-dissolved in CH3CN and H2O, and then was lyophilized to afford 2-amino-9-[(2R,3S,4S,5R)-4-(benzyloxy)-5-[(benzyloxy)methyl]-5-(chloromethyl)-3-hydroxyoxolan-2-yl]-1H-purin-6-one (45 mg, 0.09 mmol, 9.9%) as an off-white solid. LC-MS (ES, m/z): 512/514 [M+H]+.

Step 8: To a stirred solution of 2-amino-9-[(2R,3S,4S,5R)-4-(benzyloxy)-5-[(benzyloxy)methyl]-5-(chloromethyl)-3-hydroxyoxolan-2-yl]-1H-purin-6-one (60 mg, 0.12 mmol) in DCM (30 mL) was added BCl3 (1.8 mL, 1.82 mmol, 1M in hexane) at −78° C. under N2 atmosphere. The reaction mixture was stirred at room temperature for 1 hour. The reaction was quenched by a solution of MeOH/TEA=2:1 at 0° C. The resulting mixture was concentrated under reduced pressure and purified by Prep-HPLC with the following conditions (Column: XBridge Prep Phenyl OBD Column, 19*250 mm, 5 μm; Mobile Phase A: water (10 mmol/L NH4HCO3+0.1% NH3·H2O), Mobile Phase B: ACN; Flow rate: 20 mL/min; Gradient: 3% B to 9% B in 7 min, Wavelength: 254/210 nm; RT1(min): 6.35). The fraction was collected and concentrated under vacuum, the residue was re-dissolved in CH3CN and H2O and lyophilized overnight to afford 2-amino-9-[(2R,3S,4S,5R)-5-(chloromethyl)-3,4-dihydroxy-5-(hydroxymethyl) oxolan-2-yl]-1H-purin-6-one (23.6 mg, 0.07 mmol, 60.2%) as an off-white solid. LC-MS (ES, m/z): 332/334 [M+H]+, 99.1% purity. Conditions for the LCMS: (Column: HALO C18, 100*4.6 mm, 2.7 μm; Mobile Phase A: H2O+0.1% TFA, Mobile Phase B: ACN+0.1% TFA; Flow rate: 1.20 mL/min; Gradient: 0% B to 95% B in 8.00 min, 95% B to 95% B in 2.00 min, 95% B to 10% B in 0.50 min; Wavelength: 254 nm; RT1(min): 2.51). 1H NMR (400 MHz, DMSO-d6) δ 7.92 (s, 1H), 6.44 (s, 2H), 6.03 (d, J=5.2 Hz, 1H), 5.59 (m, 2H), 5.00 (s, 1H), 4.40 (t, J=5.3 Hz, 1H), 4.32 (d, J=5.2 Hz, 1H), 3.78 (s, 2H), 3.73-3.61 (m, 2H).

Example 72—Synthesis of Compound 86: 4-amino-1-[(2R,3S,4R,5R)-5-(bromomethyl)-3-fluoro-4-hydroxy-5-(hydroxymethyl) oxolan-2-yl]-5-fluoropyrimidin-2-one

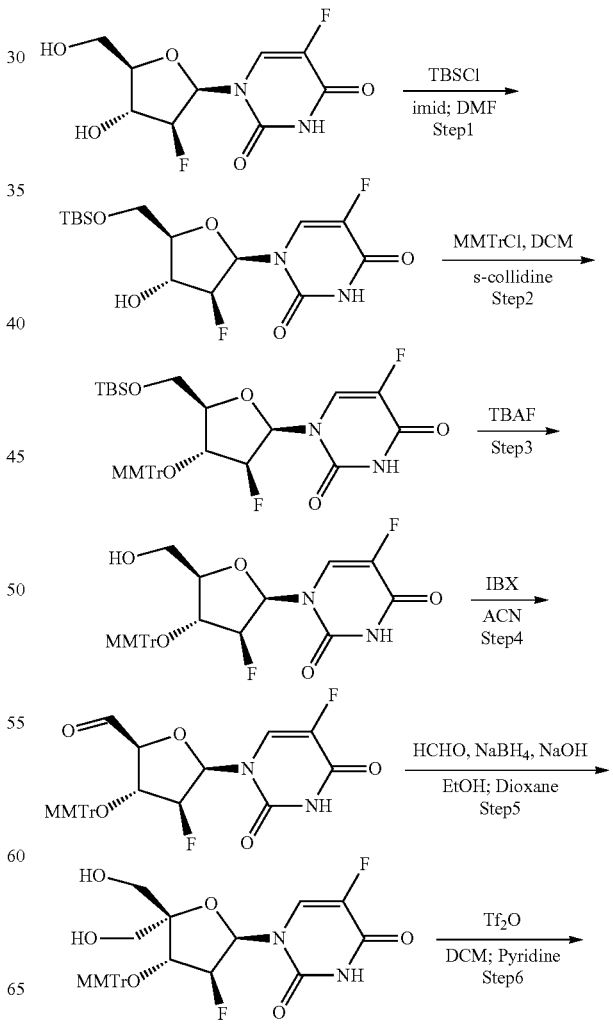

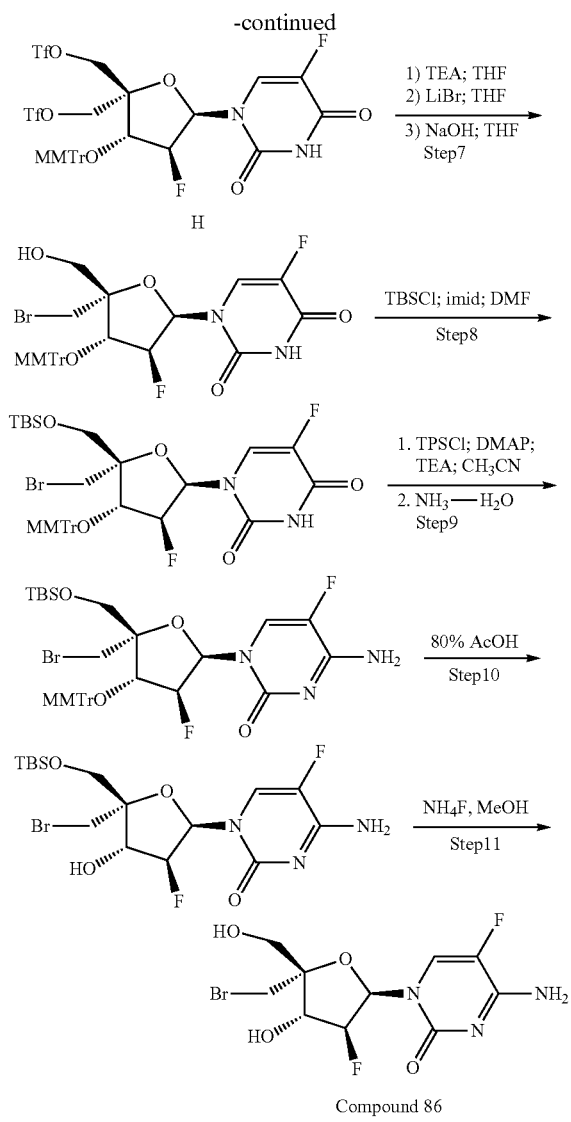

Compound 86

Step 1: To a solution of 5-fluoro-1-[(2R,3S,4R,5R)-3-fluoro-4-hydroxy-5-(hydroxymethyl) oxolan-2-yl]-3H-pyrimidine-2,4-dione (20.0 g, 75.70 mmol) in DMF (400 mL), was added imid (12.8 g, 189.26 mmol) under nitrogen atmosphere. This was followed by the addition of TBSCl (22.8 g, 151.41 mmol) in portions at 0° C. The resulting mixture was stirred overnight and quenched by the addition of ice-water (400 mL) at 0° C. The resulting solution was extracted with EtOAc (3×100 ml). The combined organic layers were washed with brine and dried over anhydrous $Na_2SO_4$. After filtration the filtrate was concentrated under reduced pressure. The residue was purified by silica gel column chromatography, eluting with PE/EtOAc (1:1) to afford 1-[(2R,3S,4R,5R)-5-{[(tert-butyldimethylsilyl) oxy] methyl}-3-fluoro-4-hydroxyoxolan-2-yl]-5-fluoro-3H-pyrimidine-2,4-dione (15.0 g, 39.63 mmol, 52.36%) as a white solid. LC-MS-PH (ES, m/z): 379 $(M+H)^+$.

Step 2: To a solution of 1-[(2R,3S,4R,5R)-5-{[(tert-butyldimethylsilyl) oxy]methyl}-3-fluoro-4-hydroxyoxolan-2-yl]-5-fluoro-3H-pyrimidine-2,4-dione (15.0 g, 39.63 mmol) in DCM (150 mL), was added 2,4,6-trimethylpyridine (14.4 g, 118.90 mmol) under nitrogen atmosphere. This was followed by the addition of 1-(chlorodiphenylmethyl)-4-methoxybenzene (24.4 g, 79.27 mmol) in portions at 0° C. The resulting mixture was stirred overnight at room temperature and then quenched by the addition of ice-water (150 mL) at 0° C. The resulting mixture was extracted with $CH_2Cl_2$ (3×100 ml). The combined organic layers were washed with Citric acid aqueous solution, dried over anhydrous $Na_2SO_4$ and concentrated under vacuum. The residue was purified by silica gel column chromatography, eluting with PE/EtOAc (2:1) to afford 1-[(2R,3S,4R,5R)-5-1{[(tert-butyldimethylsilyl) oxy] methyl}-3-fluoro-4-[(4-methoxyphenyl) diphenylmethoxy] oxolan-2-yl]-5-fluoro-3H-pyrimidine-2,4-dione (21.0 g, 32.26 mmol, 81.41%) as a white solid. LC-MS (ES, m/z): 651 $(M+H)^+$.

Step 3: To a solution of 1-[(2R,3S,4R,5R)-5-{[(tert-butyldimethylsilyl) oxy]methyl}-3-fluoro-4-[(4-methoxyphenyl) diphenylmethoxy] oxolan-2-yl]-5-fluoro-3H-pyrimidine-2,4-dione (21.0 g, 32.26 mmol) in THF (210 mL), was added TBAF (16.9 g, 64.53 mmol). The resulting mixture was stirred for 3 h at room temperature under nitrogen atmosphere and quenched by the addition of aq. HCl (1M, 100 ml) at 0° C. The resulting mixture was extracted with EtOAc (3×70 ml). The combined organic layers were washed with brine and dried over anhydrous $Na_2SO_4$. After filtration the filtrate was concentrated under reduced pressure. The residue was purified by silica gel column chromatography, eluting with PE/EtOAc (1:1) to afford 5-fluoro-1-[(2R,3S,4R,5R)-3-fluoro-5-(hydroxymethyl)-4-[(4-methoxyphenyl) diphenylmethoxy] oxolan-2-yl]-3H-pyrimidine-2,4-dione (15.0 g, 27.95 mmol, 86.64%) as a white solid. LC-MS (ES, m/z): 537 $(M+H)^+$.

Step 4: To a solution of 5-fluoro-1-[(2R,3S,4R,5R)-3-fluoro-5-(hydroxymethyl)-4-[(4-methoxyphenyl) diphenylmethoxy] oxolan-2-yl]-3H-pyrimidine-2,4-dione (15.0 g, 27.95 mmol) in ACN (150 mL) was added IBX (15.7 g, 55.91 mmol). The resulting mixture was stirred for 2 h at 60° C. under nitrogen atmosphere. The resulting mixture was filtered; the filter cake was washed with acetonitrile. The combined filtrate was concentrated under vacuum to give (2S,3R,4S,5R)-4-fluoro-5-(5-fluoro-2,4-dioxo-3H-pyrimidin-1-yl)-3-[(4-methoxyphenyl) diphenylmethoxy] oxolane-2-carbaldehyde (14 g, crude). The crude product was used in the next step directly without further purification. LC-MS (ES, m/z): 535 $(M+H^+)$.

Step 5: To a solution of (2S,3R,4S,5R)-4-fluoro-5-(5-fluoro-2,4-dioxo-3H-pyrimidin-1-yl)-3-[(4-methoxyphenyl) diphenylmethoxy] oxolane-2-carbaldehyde (14.0 g, crude) in 1,4-dioxane (140 mL), was added HCHO (28 mL, 37% in water) at 0° C. under nitrogen atmosphere. This was followed by the addition of aq. NaOH (28 mL, 2M) dropwise at 0° C. The resulting mixture was stirred overnight at room temperature under a nitrogen atmosphere. To the above mixture was added $NaBH_4$ (4.2 g, 110.53 mmol) in portions at 0° C. The resulting mixture was stirred for additional 1 h at room temperature and quenched by the addition of saturated aq. $NH_4Cl$ at 0° C. The resulting mixture was extracted with EtOAc (3×200 ml). The combined organic layers were washed with brine and dried over anhydrous $Na_2SO_4$. After filtration the filtrate was concentrated under reduced pressure. The residue was purified by silica gel column chromatography, eluting with PE/EtOAc (3:2) to afford 5-fluoro-1-[(2R,3S,4R)-3-fluoro-5,5-bis(hydroxymethyl)-4-[(4-methoxyphenyl) diphenylmethoxy] oxolan-2-yl]-3H-pyrimidine-2,4-dione (6.0 g, 1.06 mmol, 37.9% yield in two steps) as a white solid. LC-MS (ES, m/z): 567 $(M+H)^+$.

Step 6: To a solution of 5-fluoro-1-[(2R,3S,4R)-3-fluoro-5,5-bis(hydroxymethyl)-4-[(4-methoxyphenyl) diphenylmethoxy] oxolan-2-yl]-3H-pyrimidine-2,4-dione (1.5 g, 2.64 mmol) in DCM (15 mL) was added pyridine (1.6 g, 21.18 mmol) at room temperature under nitrogen atmosphere. This was followed by the addition of triflic anhydride (1.9 g, 6.62 mmol) dropwise at −30° C. under nitrogen atmosphere. The resulting mixture was stirred for 2 h at room temperature under nitrogen atmosphere and quenched by the addition of aq. NaHCO$_3$ at 0° C. The resulting mixture was extracted with EtOAc (3×100 ml). The combined organic layers were washed with brine, dried over anhydrous Na$_2$SO$_4$ and concentrated under vacuum. The residue was purified by silica gel column chromatography, eluting with PE/EtOAc (1:1) to afford [(3R,4S,5R)-4-fluoro-5-(5-fluoro-2,4-dioxo-3H-pyrimidin-1-yl)-3-[(4-methoxyphenyl) diphenylmethoxy]-2-[(trifluoromethanesulfonyloxy)methyl] oxolan-2-yl]methyl trifluoromethanesulfonate (2.1 g, 2.52 mmol, 95.49%) as a white solid. LC-MS (ES, m/z): 831 (M+H)$^+$.

Step 7: To a solution of [(3R,4S,5R)-4-fluoro-5-(5-fluoro-2,4-dioxo-3H-pyrimidin-1-yl)-3-[(4-methoxyphenyl) diphenylmethoxy]-2-[(trifluoromethanesulfonyloxy) methyl] oxolan-2-yl] methyl trifluoromethanesulfonate (2.1 g, 2.52 mmol) in THF (21 mL) was added TEA (2.5 g, 25.28 mmol). The resulting mixture was stirred for 2 h at room temperature under nitrogen atmosphere. To the above mixture was added LiBr (0.65 g, 7.49 mmol) and the resulting mixture was stirred for overnight at room temperature. To the resulting mixture was added a solution of NaOH (0.2 g, 4.90 mmol) in water (2 mL). The mixture was stirred for addition 2 h at room temperature and quenched by the addition of ice-water at 0° C. The resulting mixture was extracted with EtOAc (3×200 ml). The combined organic layers were washed with brine and dried over anhydrous Na$_2$SO$_4$. After filtration the filtrate was concentrated under reduced pressure. The residue was purified by silica gel chromatography, eluting with PE/EtOAc (1:1) to afford 1-[(2R,3S,4R,5R)-5-(bromomethyl)-3-fluoro-5-(hydroxymethyl)-4-[(4-methoxyphenyl) diphenylmethoxy] oxolan-2-yl]-5-fluoro-3H-pyrimidine-2,4-dione (950.0 mg, 1.50 mmol, 59.7%) as a yellow solid. LC-MS (ES, m/z): 629/631 (M+H)$^+$.

Step 8: To a solution of 1-[(2R,3S,4R,5R)-5-(bromomethyl)-3-fluoro-5-(hydroxymethyl)-4-[(4-methoxyphenyl) diphenylmethoxy] oxolan-2-yl]-5-fluoro-3H-pyrimidine-2,4-dione (950.0 mg, 1.50 mmol) in DMF (10 mL), was added imid (256.0 mg, 3.77 mmol). The resulting mixture was stirred for 2 h at room temperature under nitrogen atmosphere. This was followed by the addition of t-butyldimethylchlorosilane (341.0 mg, 2.26 mmol) in portions at 0° C. The resulting mixture was stirred for overnight at room temperature and quenched by the addition of water. The resulting mixture was extracted with EtOAc (3×100 ml). The combined organic layers were washed with brine and dried over anhydrous Na$_2$SO$_4$. After filtration the filtrate was concentrated under reduced pressure. The residue was purified by silica gel column chromatography, eluting with PE/EtOAc (2:1) to afford 1-[(2R,3S,4R,5R)-5-(bromomethyl)-5-1{[(tert-butyldimethylsilyl) oxy] methyl}-3-fluoro-4-[(4-methoxyphenyl) diphenylmethoxy] oxolan-2-yl]-5-fluoro-3H-pyrimidine-2,4-dione (955.0 mg, 1.27 mmol, 84.64%) as a white solid. LC-MS (ES, m/z): 743/745 (M+H).$^+$ Step 9: To a solution of 1-[(2R,3S,4R,5R)-5-(bromomethyl)-5-{[(tert-butyldimethylsilyl) oxy] methyl}-3-fluoro-4-[(4-methoxyphenyl) diphenylmethoxy] oxolan-2-yl]-5-fluoro-3H-pyrimidine-2,4-dione (950.0 mg, 1.27 mmol), TEA (387.0 mg, 3.83 mmol) and DMAP (468.0 mg, 3.83 mmol) in CH$_3$CN (10 mL), was added 2,4,6-tris(propan-2-yl) benzene-1-sulfonyl chloride (1.2 g, 3.83 mmol) at 0° C. The reaction mixture was stirred for 3 h at room temperature under nitrogen atmosphere. To the above mixture was added NH$_3$·H$_2$O (20 mL) dropwise. The resulting mixture was stirred for additional 1 h at room temperature and concentrated under reduced pressure. The residue was purified by silica gel column chromatography, eluting with PE/EtOAc (1:1) to afford 4-amino-1-[(2R,3S,4R,5R)-5-(bromomethyl)-5-{[(tert-butyldimethylsilyl) oxy] methyl}-3-fluoro-4-[(4-methoxyphenyl) diphenylmethoxy] oxolan-2-yl]-5-fluoropyrimidin-2-one (720.0 mg, 0.94 mmol, 75.89%) as a white solid. LC-MS (ES, m/z): 742/744 (M+H$^+$).

Step 10: A solution of 4-amino-1-[(2R,3S,4R,5R)-5-(bromomethyl)-5-{[(tert-butyldimethylsilyl) oxy] methyl}-3-fluoro-4-[(4-methoxyphenyl) diphenylmethoxy] oxolan-2-yl]-5-fluoropyrimidin-2-one (700.0 mg, 0.94 mmol) in AcOH (7 mL, 80% in water) was stirred overnight at room temperature under nitrogen atmosphere. The reaction was quenched by the addition of water/ice at 0° C. The resulting mixture was extracted with EtOAc (3×100 ml). The combined organic layers were washed with brine and dried over anhydrous Na$_2$SO$_4$. After filtration the filtrate was concentrated under reduced pressure. The residue was purified by Prep-TLC (CH$_2$Cl$_2$/MeOH 8:1) to afford 4-amino-1-[(2R,3S,4R,5R)-5-(bromomethyl)-5-{[(tert-butyldimethylsilyl) oxy] methyl}-3-fluoro-4-hydroxyoxolan-2-yl]-5-fluoropyrimidin-2-one (225.0 mg, 0.43 mmol, 50.75%) as a white solid. LC-MS (ES, m/z): 470/472 (M+H$^+$).

Step 11: To a solution of 4-amino-1-[(2R,3S,4R,5R)-5-(bromomethyl)-5-{[(tert-butyldimethylsilyl) oxy] methyl}-3-fluoro-4-hydroxyoxolan-2-yl]-5-fluoropyrimidin-2-one (200.0 mg, 0.42 mmol) in MeOH (4 mL), was added NH$_4$F (400.0 mg, 10.80 mmol). The resulting mixture was stirred overnight at room temperature under nitrogen atmosphere and then concentrated under reduced pressure. The crude product was purified by prep-HPLC with the following conditions: Column: C18; Mobile Phase A: Water (10 mmol/L NH$_4$HCO$_3$), Mobile Phase B: ACN; Flow rate: 100 mL/min; Gradient: 10% B to 50% in 15 min; detector: UV 254 nm. The product-containing fractions were combined and evaporated partially to remove the solvents, then lyophilized overnight to afford 4-amino-1-[(2R,3S,4R,5R)-5-(bromomethyl)-3-fluoro-4-hydroxy-5-(hydroxymethyl) oxolan-2-yl]-5-fluoropyrimidin-2-one (59.2 mg, 0.16 mmol, 39.10%) as a white solid. LC-MS (ES, m/z): 356/358 (M+H$^+$). 99.0% purity.

Conditions for the HPLC: (Column: Shim-pack Scepter C18, 33*3 mm, 3.0 μm; Mobile Phase A: Water/5 mM NH$_4$HCO$_3$, Mobile Phase B: Acetonitrile; Flow rate: 1.5000 mL/min; Gradient: 10% B to 95% B in 1.20 min, 95% B to 95% B in 0.60 min, 95% B to 10% B in 0.02 min; Wavelength: 254/220 nm; RT1(min): 0.460). $^1$H NMR (400 MHz, DMSO-d$_6$) δ 7.93 (d, J=6.8 Hz, 1H), 7.88 (brs, 1H), 6.64 (brs, 1H), 6.25-6.24 (m, 1H), 6.21-6.17 (m, 1H), 5.47 (t, J=5.6 Hz, 1H), 5.26 (t, J=3.2 Hz, 0.5H), 5.11 (t, J=3.2 Hz, 0.5H), 4.48-4.42 (m, 1H), 3.78 (d, J=11.2 Hz, 1H), 3.71-3.66 (m, 1H), 3.62-3.57 (m, 2H).

Example 73—Synthesis of Compound 129: 4-amino-5-fluoro-1-((2R,3S,4R,5R)-3-fluoro-4-hydroxy-5-(hydroxymethyl)-5-(iodomethyl)tetrahydrofuran-2-yl)pyrimidin-2(1H)-one

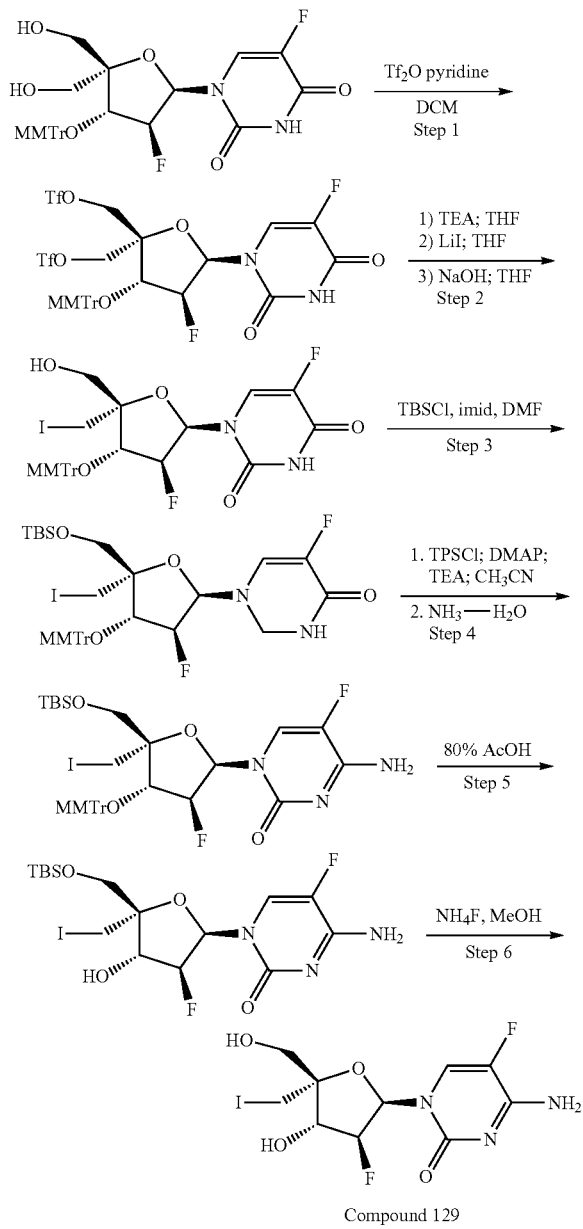

Compound 129

Step 1: To a solution of 5-fluoro-1-[(2R,3S,4R)-3-fluoro-5,5-bis(hydroxymethyl)-4-[(4-methoxyphenyl) diphenylmethoxy] oxolan-2-yl]-3H-pyrimidine-2,4-dione (2.0 g, 3.53 mmol) in DCM (20 mL) was added pyridine (2.2 g, 28.24 mmol) under nitrogen atmosphere. This was followed by the addition of triflic anhydride (2.5 g, 8.82 mmol) dropwise at −30° C. under nitrogen atmosphere. The resulting mixture was stirred for 2 h at room temperature and quenched by the addition of NaHCO₃ aq. (20 ml) at 0° C. The resulting mixture was extracted with EtOAc (3×70 ml). The combined organic layers were washed with brine, and dried over anhydrous Na₂SO₄. After filtration the filtrate was concentrated under reduced pressure. The residue was purified by silica gel column chromatography, eluting with PE/EtOAc (3:1) to afford [(3R,4S,5R)-4-fluoro-5-(5-fluoro-2,4-dioxo-3H-pyrimidin-1-yl)-3-[(4-methoxyphenyl) diphenylmethoxy]-2-[(trifluoromethanesulfonyloxy)methyl] oxolan-2-yl] methyl trifluoromethanesulfonate (2.0 g, 2.40 mmol, 68.2%) as a yellow solid. LC-MS (ES, m/z): 831 (M+H)⁺.

Step 2: To a solution of [(3R,4S,5R)-4-fluoro-5-(5-fluoro-2,4-dioxo-3H-pyrimidin-1-yl)-3-[(4-methoxyphenyl) diphenylmethoxy]-2-[(trifluoromethanesulfonyloxy) methyl]oxolan-2-yl] methyl trifluoromethanesulfonate (2.0 g, 2.40 mmol) in THF (20 mL) was added TEA (2.4 g, 24.08 mmol). The resulting mixture was stirred for 2 h at room temperature under nitrogen atmosphere. To the above mixture was added LiI (946.0 mg, 7.07 mmol) and the resulting mixture was stirred overnight at room temperature. To the resulting mixture was added a solution of NaOH (182.0 mg, 4.55 mmol) in water (2 mL). The resulting mixture was stirred for additional 3 h at room temperature and diluted with water (20 mL). The resulting solution was extracted with EtOAc (3×50 mL). The organic layers were washed with brine and dried over anhydrous Na₂SO₄. After filtration the filtrate was concentrated under reduced pressure. The residue was purified by silica gel chromatography, eluting with PE/EtOAc (1:1) to afford 5-fluoro-1-[(2R,3S,4R,5R)-3-fluoro-5-(hydroxymethyl)-5-(iodomethyl)-4-[(4-methoxyphenyl) diphenylmethoxy] oxolan-2-yl]-3H-pyrimidine-2,4-dione (1.2 g, 1.77 mmol, 73.6%) as a yellow solid. LC-MS (ES, m/z): 677 (M+H⁺).

Step 3: To a solution of 5-fluoro-1-[(2R,3S,4R,5R)-3-fluoro-5-(hydroxymethyl)-5-(iodomethyl)-4-[(4-methoxyphenyl) diphenylmethoxy] oxolan-2-yl]-3H-pyrimidine-2,4-dione (1.2 g, 1.77 mmol) in DMF (12 mL) was added imid (301.0 mg, 4.43 mmol). This was followed by the addition of TBSCl (401.0 mg, 2.66 mmol) in portions at 0° C. under nitrogen atmosphere. The resulting mixture was stirred for 2 h at room temperature under nitrogen atmosphere and then quenched by the addition of water. The resulting mixture was extracted with EtOAc (3×50 ml). The combined organic layers were washed with brine, and dried over anhydrous Na₂SO₄. After filtration the filtrate was concentrated under reduced pressure. The residue was purified by silica gel column chromatography, eluting with PE/EtOAc (2:1) to afford 1-[(2R,3S,4R,5R)-5-{[(tert-butyldimethylsilyl) oxy]methyl}-3-fluoro-5-(iodomethyl)-4-[(4-methoxyphenyl) diphenylmethoxy] oxolan-2-yl]-5-fluoro-3H-pyrimidine-2,4-dione (810.0 mg, 1.01 mmol, 57.03%) as a white solid. LC-MS (ES, m/z): 791 (M+H)⁺.

Step 4: To a solution of 1-[(2R,3S,4R,5R)-5-{[(tert-butyldimethylsilyl) oxy]methyl}-3-fluoro-5-(iodomethyl)-4-[(4-methoxyphenyl) diphenylmethoxy] oxolan-2-yl]-5-fluoro-3H-pyrimidine-2,4-dione (800.0 mg, 1.01 mmol) in CH₃CN (10 mL) was added DMAP (370.0 mg, 3.03 mmol) and TEA (307.1 mg, 3.04 mmol) under nitrogen atmosphere. This was followed by the addition of 2,4,6-tris(propan-2-yl)benzene-1-sulfonyl chloride (919.0 mg, 3.03 mmol) in portions at room temperature. The resulting mixture was stirred for 4 h at room temperature under nitrogen atmosphere. To the above mixture was added NH₃·H₂O (10 mL) dropwise. The resulting mixture was stirred for additional 1 h at room temperature and concentrated under reduced pressure. The residue was purified by silica gel column chromatography, eluting with PE/EtOAc (2:1) to afford 4-amino-4-amino-1-((2R,3S,4R,5R)-5-(((tert-butyldimethylsilyl)oxy)methyl)-3-fluoro-5-(iodomethyl)-4-((4-methoxyphenyl)diphenylmethoxy)tetrahydrofuran-2-yl)-5-fluoropyrimidin-2(1H)- one (705.0 mg, 0.88 mmol, 87.61%) as a white solid. LC-MS (ES, m/z): 790 (M+H)+.

Step 5: A solution of 4-amino-1-[(2R,3S,4R,5R)-5-1{[(tert-butyldimethylsilyl) oxy] methyl}-3-fluoro-5-(iodomethyl)-4-[(4-methoxyphenyl) diphenylmethoxy] oxolan-2-yl]-5-fluoropyrimidin-2-one (700.0 mg, 0.88 mmol) in AcOH (15 mL, 80% in water) was stirred overnight at room temperature under nitrogen atmosphere. The reaction was quenched by the addition of ice-water at 0° C. The resulting mixture was extracted with EtOAc (3×50 ml). The combined organic layers were washed with saturated aq. NaHCO$_3$ and dried over anhydrous Na$_2$SO$_4$. After filtration the filtrate was concentrated under reduced pressure. The residue was purified by silica gel column chromatography, eluting with CH$_2$Cl$_2$/MeOH (50:1) to afford 4-amino-1-[(2R,3S,4R,5R)-5-1{[(tert-butyldimethylsilyl) oxy] methyl}-3-fluoro-4-hydroxy-5-(iodomethyl) oxolan-2-yl]-5-fluoropyrimidin-2-one (405.0 mg, 0.77 mmol, 87.22%) as a white solid. LC-MS-ROF (ES, m/z): 518 (M+H+). Step 6: To a solution of 4-amino-1-[(2R,3S,4R,5R)-5-{[(tert-butyldimethylsilyl) oxy] methyl}-3-fluoro-4-hydroxy-5-(iodomethyl) oxolan-2-yl]-5-fluoropyrimidin-2-one (400.0 mg, 0.77 mmol) in MeOH (4 mL) was added NH$_4$F (800.0 mg, 21.60 mmol). The reaction mixture was stirred overnight at 60° C. The resulting mixture was cooled to room temperature and concentrated under reduced pressure. The crude product was purified by Prep-HPLC with the following conditions: Column: XBridge Prep OBD C18 Column, 30*150 mm, 5 μm; Mobile Phase A: water (10 mmol/L NH$_4$HCO$_3$), Mobile Phase B: ACN; Flow rate: 60 mL/min; Gradient: 5% B to 15% B in 7 min; Wavelength: 254/220 nm. The product-containing fractions were combined and evaporated partially to remove the solvents, then lyophilized overnight to afford 4-amino-5-fluoro-1-((2R,3S,4R,5R)-3-fluoro-4-hydroxy-5-(hydroxymethyl)-5-(iodomethyl)tetrahydrofuran-2-yl)pyrimidin-2(1H)-one 4, (51.0 mg, 0.13 mmol. 15.92%) as a white solid. LC-MS (ES, m/z): 404 (M+H+). 97.3% purity. Conditions for the HPLC: (Column: Shim-pack Scepter C18, 33*3 mm, 3.0 μm; Mobile Phase A: Water/5 mM NH$_4$HCO$_3$, Mobile Phase B: Acetonitrile; Flow rate: 1.5000 mL/min; Gradient: 10% B to 95% B in 1.20 min, 95% B to 95% B in 0.60 min, 95% B to 10% B in 0.02 min; Wavelength: 254/220 nm; RT1(min): 0.495. $^1$H NMR (400 MHz, DMSO-d$_6$) δ 7.92 (d, J=6.8 Hz, 1H), 7.88 (brs, 1H), 7.64 (brs, 1H), 6.21-6.20 (m, 1H), 6.18-6.14 (m, 1H), 5.45 (t, J=5.2 Hz, 1H), 5.29 (t, J=4.4 Hz, 0.5H), 5.16 (t, J=4.4 Hz, 0.5H), 4.47-4.40 (m, 1H), 3.73-3.70 (m, 1H), 3.59-3.52 (m, 2H), 3.34-3.32 (m, 1H).

Example 74—Synthesis of Compound 139: 4-amino-1-[(2R,3S,4R,5R)-5-(aminomethyl)-3-fluoro-4-hydroxy-5-(hydroxymethyl) oxolan-2-yl]-5-fluoropyrimidin-2-one

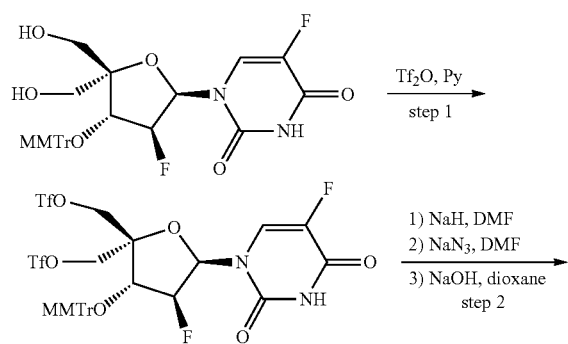

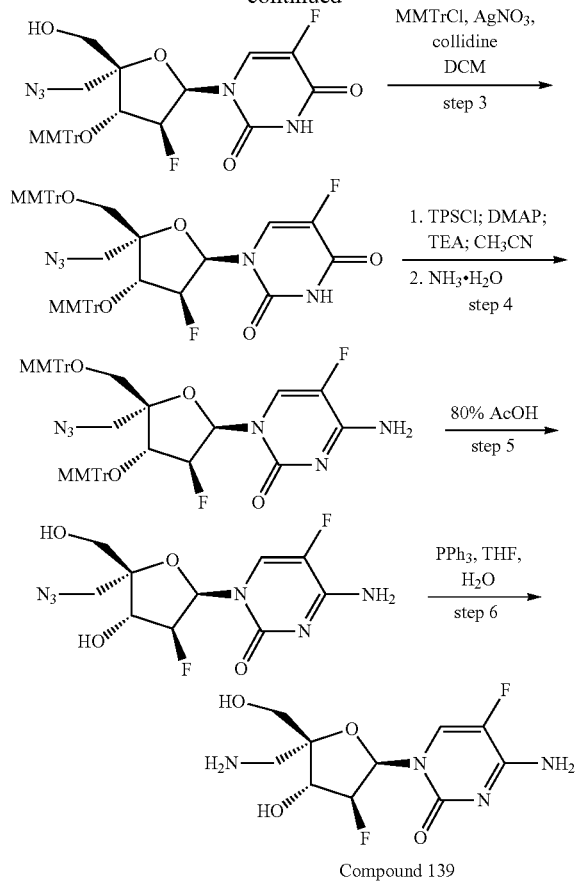

Compound 139

Step 1: To a stirred solution of 5-fluoro-1-[(2R,3S,4R)-3-fluoro-5,5-bis(hydroxymethyl)-4-[(4-methoxyphenyl) diphenylmethoxy] oxolan-2-yl]-3H-pyrimidine-2,4-dione (3.0 g, 5.30 mmol) in Pyridine (30 mL) was added triflic anhydride (3.7 g, 13.24 mmol) dropwise at −30° C. under nitrogen atmosphere. The resulting mixture was stirred for 2 h at room temperature under nitrogen atmosphere and quenched by the addition of sat. NaHCO$_3$ aq. (300 mL) at 0° C. The resulting mixture was extracted with EtOAc (2×300 mL). The combined organic layers were washed with brine (2×300 mL), and dried over anhydrous Na$_2$SO$_4$. After filtration the filtrate was concentrated under reduced pressure. The residue was purified by silica gel column chromatography, eluting with PE/EtOAc (1:1) to afford [(3R,4S,5R)-4-fluoro-5-(5-fluoro-2,4-dioxo-3H-pyrimidin-1-yl)-3-[(4-methoxyphenyl) diphenylmethoxy]-2-[(trifluoromethanesulfonyloxy)methyl] oxolan-2-yl] methyl trifluoromethanesulfonate (3.1 g, 3.73 mmol, 68.2%) as a brown solid. LC-MS (ES, m/z): 831 (M+H+).

Step 2: To a stirred solution of [(3R,4S,5R)-4-fluoro-5-(5-fluoro-2,4-dioxo-3H-pyrimidin-1-yl)-3-[(4-methoxyphenyl) diphenylmethoxy]-2-[(trifluoromethanesulfonyloxy)methyl] oxolan-2-yl] methyl trifluoromethanesulfonate (3.0 g, 3.61 mmol) in DMF (30 mL) was added NaH (152.2 mg, 60% in mineral oil, 3.97 mmol) in portions at 0° C. under nitrogen atmosphere. The resulting mixture was stirred for 2 h at room temperature under nitrogen atmosphere. To the above mixture was added azido sodium (1.2 g, 17.63 mmol) and the resulting mixture was stirred overnight at room temperature. This was followed by the addition of NaOH aq. (3.5 mL, 2M). The resulting mixture was stirred overnight at room temperature. The resulting mixture was diluted with EtOAc (300 mL). The resulting solution was washed with brine (3×300 mL) and dried over anhydrous $Na_2SO_4$. After filtration the filtrate was concentrated under reduced pressure. The residue was purified by silica gel column chromatography, eluting with PE/EtOAc (1:1) to afford 1-[(2R,3S,4R,5R)-5-(azidomethyl)-3-fluoro-5-(hydroxymethyl)-4-[(4-methoxyphenyl) diphenylmethoxy] oxolan-2-yl]-5-fluoro-3H-pyrimidine-2,4-dione (1.2 g, 2.03 mmol, 56.2%) as a light-yellow solid. LC-MS (ES, m/z): 592 (M+H$^+$).

Step 3: To a stirred solution of 1-[(2R,3S,4R,5R)-5-(azidomethyl)-3-fluoro-5-(hydroxymethyl)-4-[(4-methoxyphenyl) diphenylmethoxy] oxolan-2-yl]-5-fluoro-3H-pyrimidine-2,4-dione (1.2 g, 2.03 mmol), $AgNO_3$ (1.0 g, 6.08 mmol) and S-collidine (740.0 mg, 6.08 mmol) in DCM (24 mL) was added 1-(chlorodiphenylmethyl)-4-methoxybenzene (1.3 g, 4.06 mmol) in portions at 0° C. under nitrogen atmosphere. The resulting mixture was stirred overnight at room temperature under nitrogen atmosphere and quenched by the addition of ice-water (150 mL) at 0° C. The resulting mixture was extracted with $CH_2Cl_2$ (3×100 ml). The combined organic layers were washed with Citric acid aqueous solution, dried over anhydrous $Na_2SO_4$ and concentrated under vacuum. After filtration the filtrate was concentrated under reduced pressure. The residue was purified by silica gel column chromatography, eluting with PE/EtOAc (3:1) to afford 1-[(2R,3S,4R,5R)-5-(azidomethyl)-3-fluoro-4-[(4-methoxyphenyl) diphenylmethoxy]-5-{1[(4-methoxyphenyl) diphenylmethoxy] methyl} oxolan-2-yl]-5-fluoro-3H-pyrimidine-2,4-dione (1.3 g, 1.51 mmol, 74.18%) as a yellow solid. LC-MS (ES, m/z): 864 (M+H$^+$).

Step 4: To a stirred solution of 1-[(2R,3S,4R,5R)-5-(azidomethyl)-3-fluoro-4-[(4-methoxyphenyl) diphenylmethoxy]-5-{[(4-methoxyphenyl) diphenylmethoxy] methyl} oxolan-2-yl]-5-fluoro-3H-pyrimidine-2,4-dione (1.3 g, 1.51 mmol) and DMAP (552.0 mg, 4.52 mmol) in $CH_3CN$ (42 mL) were added TEA (457.0 mg, 4.52 mmol) and TPSCl (1.4 g, 4.52 mmol) in portions at room temperature. The resulting mixture was stirred for 2 h at room temperature. To the above mixture was added $NH_3 \cdot H_2O$ (26.0 mL) dropwise at room temperature. The resulting mixture was stirred for additional 1 h at room temperature and concentrated under reduced pressure. The residue was purified by silica gel column chromatography, eluting with $CH_2Cl_2$/MeOH (30:1) to afford 4-amino-1-[(2R,3S,4R,5R)-5-(azidomethyl)-3-fluoro-4-[(4-methoxyphenyl) diphenylmethoxy]-5-{[(4-methoxyphenyl) diphenylmethoxy] methyl} oxolan-2-yl]-5-fluoropyrimidin-2-one (1.0 g, 1.16 mmol, 77.01%) as a light-yellow solid. LC-MS (ES, m/z): 861 (M−H$^-$).

Step 5: A solution of 4-amino-1-[(2R,3S,4R,5R)-5-(azidomethyl)-3-fluoro-4-[(4-methoxyphenyl) diphenylmethoxy]-5-{[(4-methoxyphenyl) diphenylmethoxy] methyl} oxolan-2-yl]-5-fluoropyrimidin-2-one (1.0 g, 1.16 mmol) in AcOH (10 mL, 80%) was stirred overnight at room temperature. The resulting mixture was concentrated under reduced pressure. The residue was purified by reversed-phase flash chromatography with the following conditions: C18 column; Mobile phase A: water (10 mmol/L $NH_4HCO_3$) and B: $CH_3CN$; Gradient: 10% to 60% B in 15 min; UV detection at 254/220 nm. This afforded in 4-amino-1-[(2R,3S,4R,5R)-5-(azidomethyl)-3-fluoro-4-hydroxy-5-(hydroxymethyl) oxolan-2-yl]-5-fluoropyrimidin-2-one (250 mg, 0.79 mmol, 67.75%) as a white solid. LC-MS (ES, m/z): 319 (M+H$^+$).

Step 6: To a stirred solution of 4-amino-1-[(2R,3S,4R,5R)-5-(azidomethyl)-3-fluoro-4-hydroxy-5-(hydroxymethyl) oxolan-2-yl]-5-fluoropyrimidin-2-one (250.0 mg, 0.79 mmol) in $H_2O$ (0.3 mL) and THF (3 mL), was added $PPh_3$ (1236.3 mg, 4.72 mmol) in portions at room temperature under nitrogen atmosphere. The resulting mixture was stirred overnight at room temperature under nitrogen atmosphere and concentrated under reduced pressure. The residue was purified by Prep-HPLC with the following conditions: Column: XBridge Prep Amide OBD Column, 19×150 mm, 5 μm; Mobile Phase A: Water (10 mmol/L $NH_4HCO_3$), Mobile Phase B: ACN; Flow rate: 25 mL/min; Gradient: 50% B to 90% B in 7 min; Wavelength: 254/220 nm. This afforded 4-amino-1-[(2R,3S,4R,5R)-5-(aminomethyl)-3-fluoro-4-hydroxy-5-(hydroxymethyl) oxolan-2-yl]-5-fluoropyrimidin-2-one (18.1 mg, 0.06 mmol, 7.88%) as a white solid. LC-MS (ES, m/z): 293 (M+H$^+$). 98.9% purity. $^1$H NMR (400 MHz, Methanol-d$_4$) δ 8.05 (d, J=6.4 Hz, 1H), 6.34-6.29 (m, 1H), 5.25-5.24 (m, 0.5H), 5.12-5.11 (m, 0.5H), 4.47-4.42 (m, 1H), 3.71 (s, 2H), 3.09 (d, J=14.0 Hz, 1H), 3.00 (d, J=14.0 Hz, 1H).

Example 75—Synthesis of Compound 138: (2R,3R,4S,5R)-5-(4-amino-5-fluoro-2-oxopyrimidin-1-yl)-4-fluoro-3-hydroxy-2-(hydroxymethyl) oxolane-2-carboxamide

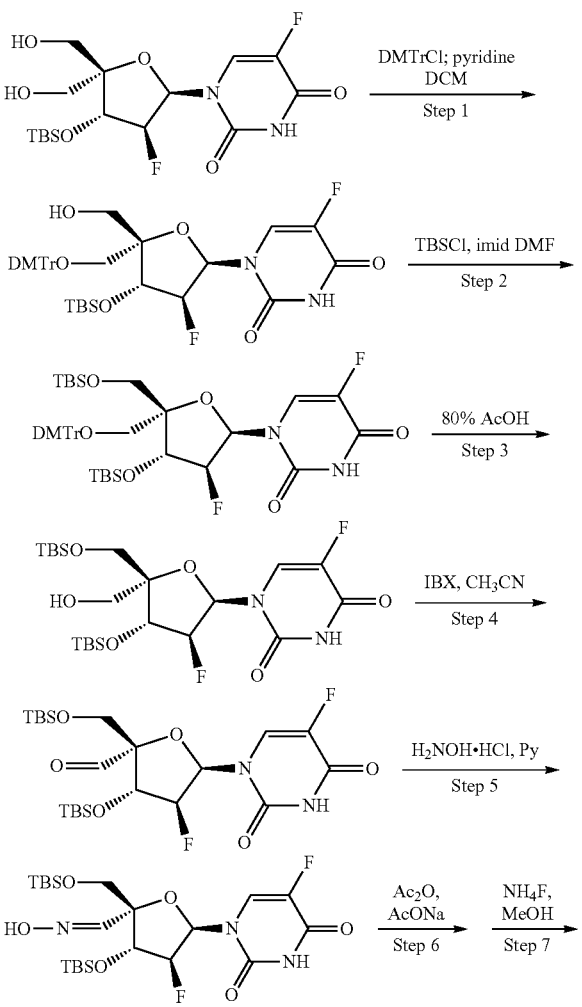

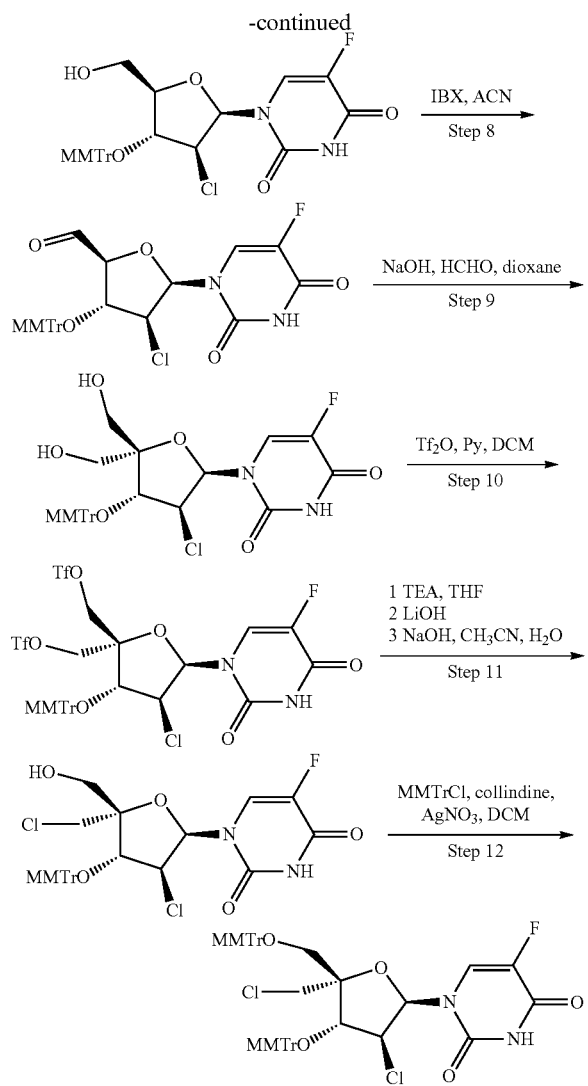

Step 1: To a solution of 1-[(2R,3S,4R)-4-[(tert-butyldimethylsilyl) oxy]-3-fluoro-5,5-bis(hydroxymethyl)oxolan-2-yl]-5-fluoro-3H-pyrimidine-2,4-dione (4.0 g, 9.79 mmol) and pyridine (8 mL) in DCM (32 mL, was added 1-[chloro (4-methoxyphenyl)phenylmethyl]-4-methoxybenzene (4.0 g, 11.75 mmol) in portions at 0° C. The resulting mixture was stirred overnight at room temperature and then quenched by the addition of water (50 mL). The resulting mixture was extracted with EtOAc. The combined organic layers were washed with brine, and dried over anhydrous Na$_2$SO$_4$. After filtration the filtrate was concentrated under reduced pressure. The residue was purified by silica gel column chromatography, eluting with PE/EtOAc (1:1) to afford 1-[(2R,3S,4R,5S)-5-{[bis(4-methoxyphenyl)(phenyl) methoxy]methyl}-4-[(tert-butyldimethylsilyl)oxy]-3-fluoro-5-(hydroxymethyl)oxolan-2-yl]-5-fluoro-3H-pyrimidine-2,4-dione (5.5 g, 7.73 mmol, 79.01%) as a yellow solid. LC-MS (ES, m/z): 711 (M+H$^+$).

Step 2: To a solution of 1-[(2R,3S,4R,5S)-5-{[bis(4-methoxyphenyl)(phenyl) methoxy]methyl}-4-[(tert-butyldimethylsilyl)oxy]-3-fluoro-5-(hydroxymethyl)oxolan-2-yl]-5-fluoro-3H-pyrimidine-2,4-dione (5.5 g, 7.73 mmol) in DMF (55 mL) was added imid (1.6 g, 23.21 mmol). This was followed by the addition of TBSCl (1.8 g, 11.60 mmol) dropwise at 0° C. The resulting mixture was stirred for 3 h at room temperature under nitrogen atmosphere and then quenched by the addition of sat. NaHCO$_3$(aq.) at 0° C. The resulting mixture was extracted with EtOAc. The combined organic layers were washed with brine and dried over anhydrous Na$_2$SO$_4$. After filtration the filtrate was concentrated under reduced pressure. This resulted in -crude [(2R, 3S,4R,5R)-5-1{[bis(4-methoxyphenyl) (phenyl)methoxy] methyl}-4-[(tert-butyldimethylsilyl) oxy]-5-{[(tert-butyldimethylsilyl) oxy] methyl}-3-fluorooxolan-2-yl]-5-fluoro-3H-pyrimidine-2,4-dione (6.0 g, 7.27 mmol, 93.98%) as a light-yellow solid. LC-MS (ES, m/z): 823 (M–H$^-$).

Step 3: A solution of 1-[(2R,3S,4R,5R)-5-{[bis(4-methoxyphenyl) (phenyl)methoxy] methyl}-4-[(tert-butyldimethylsilyl) oxy]-5-{[(tert-butyldimethylsilyl) oxy] methyl}-3-fluorooxolan-2-yl]-5-fluoro-3H-pyrimidine-2,4-dione (6.0 g, 7.27 mmol) in AcOH (60 mL, 80% in water) was stirred overnight at room temperature under nitrogen atmosphere. The reaction mixture was concentrated under reduced pressure. The residue was diluted with water and adjusted to pH 7 with saturated NaHCO$_3$(aq.). The resulting mixture was extracted with EtOAc. The combined organic layers were washed with brine and dried over anhydrous Na$_2$SO$_4$. After filtration the filtrate was concentrated under reduced pressure. The residue was purified by silica gel column chromatography, eluting with PE/EtOAc (2:1) to afford 1-[(2R,3S,4R,5R)-4-[(tert-butyldimethylsilyl) oxy]-5-{[(tert-butyldimethylsilyl) oxy] methyl}-3-fluoro-5-(hydroxymethyl) oxolan-2-yl]-5-fluoro-3H-pyrimidine-2,4-dione (2.8 g, 5.35 mmol, 73.66%) as a light-yellow oil. LC-MS (ES, m/z): 523 (M+H$^+$).

Step 4: To a solution of 1-[(2R,3S,4R,5R)-4-[(tert-butyldimethylsilyl)oxy]-5-{[(tert-butyldimethylsilyl)oxy] methyl}-3-fluoro-5-(hydroxymethyl)oxolan-2-yl]-5-fluoro-3H-pyrimidine-2,4-dione (2.8 g, 5.35 mmol) in ACN (28 mL), was added IBX (3.0 g, 10.71 mmol). The resulting solution was stirred for 3 h at 80° C. under nitrogen atmosphere. The resulting mixture was cooled to room temperature and filtered, the filter cake was washed with acetonitrile. The combined filtrate was concentrated under reduced pressure. This afforded crude (2R,3R,4S,5R)-3-[(tert-butyldimethylsilyl) oxy]-2-{[(tert-butyldimethylsilyl) oxy]methyl}-4-fluoro-5-(5-fluoro-2,4-dioxo-3H-pyrimidin-1-yl) oxolane-2-carbaldehyde (2.6 g, 4.99 mmol) as a light-yellow oil. (ES, m/z): 521 (M+H$^+$).

Step 5: To a solution of (2R,3R,4S,5R)-3-[(tert-butyldimethylsilyl) oxy]-2-{[(tert-butyldimethylsilyl) oxy] methyl}-4-fluoro-5-(5-fluoro-2,4-dioxo-3H-pyrimidin-1-yl) oxolane-2-carbaldehyde (2.6 g, 4.99 mmol) in pyridine (26 mL), was added hydroxylamine hydrochloride (0.7 g, 9.98 mmol). The resulting mixture was stirred overnight at room temperature and quenched by the addition of water. The resulting mixture was extracted with EtOAc. The combined organic layers were washed with brine and dried over anhydrous Na$_2$SO$_4$. After filtration the filtrate was concentrated under reduced pressure. The residue was purified by silica gel column chromatography, eluting with PE/EtOAc (1:1) to afford 1-[(2R,3S,4R,5R)-4-[(tert-butyldimethylsilyl) oxy]-5-{[(tert-butyldimethylsilyl) oxy] methyl}-3-fluoro-5-[(hydroxyimino)methyl] oxolan-2-yl]-5-fluoro-3H-pyrimidine-2,4-dione (1.7 g, 3.17 mmol, 63.55%) as a light-yellow solid. LC-MSPH (ES, m/z): 536 (M+H$^+$).

Step 6: To a solution of 1-[(2R,3S,4R,5R)-4-[(tert-butyldimethylsilyl)oxy]-5-{[(tert-butyldimethylsilyl)oxy] methyl}-3-fluoro-5-[(hydroxyimino)methyl]oxolan-2-yl]-5-fluoro-3H-pyrimidine-2,4-dione (1.0 g, 1.87 mmol) in Ac$_2$O (15 mL), was added AcONa (612.5 mg, 7.46 mmol). The resulting mixture was stirred for 4 h at 120° C., then cooled to room temperature and quenched by the addition of water. The resulting mixture was extracted with EtOAc. The combined organic layers were washed with brine and dried over anhydrous Na$_2$SO$_4$. After filtration the filtrate was concentrated under reduced pressure. The residue was purified by silica gel column chromatography, eluting with PE/EtOAc (1:1) to afford (2R,3R,4S,5R)-3-[(tert-butyldimethylsilyl)oxy]-2-{[(tert-butyldimethylsilyl) oxy]methyl}-4-fluoro-5-(5-fluoro-2,4-dioxo-3H-pyrimidin-1-yl) oxolane-2-carbonitrile (510.0 mg, 0.96 mmol, 51.74%) as a light-yellow solid. LC-MS (ES, m/z): 518 (M+H$^+$).

Step 7: To a solution of (2R,3R,4S,5R)-3-[(tert-butyldimethylsilyl) oxy]-2-{[(tert-butyldimethylsilyl) oxy]methyl}-4-fluoro-5-(5-fluoro-2,4-dioxo-3H-pyrimidin-1-yl) oxolane-2-carbonitrile (500.0 mg, 0.96 mmol) in DMSO (5 mL) was added K$_2$CO$_3$ (400.4 mg, 2.89 mmol) at 0° C. The resulting mixture was stirred for 20 min at 0° C. To the above mixture was added H$_2$O$_2$(1.5 mL, 30% in water) dropwise at 0° C. The resulting mixture was stirred for additional 4 h at room temperature and quenched by the addition of water. The resulting solution was extracted with EtOAc. The combined organic layers were washed with brine and dried over anhydrous Na$_2$SO$_4$. After filtration the filtrate was concentrated under reduced pressure. The residue was purified by silica gel column chromatography, eluting with PE/EtOAc (1:1) to afford (2R,3R,4S,5R)-3-[(tert-butyldimethylsilyl) oxy]-2-{[(tert-butyldimethylsilyl) oxy]methyl}-4-fluoro-5-(5-fluoro-2,4-dioxo-3H-pyrimidin-1-yl) oxolane-2-carboxamide (310.0 mg, 0.56 mmol, 57.98%) as a white solid. LC-MS (ES, m/z): 536 (M+H$^+$).

Step 8: To a solution of (2R,3R,4S,5R)-3-[(tert-butyldimethylsilyl) oxy]-2-{[(tert-butyldimethylsilyl) oxy]methyl}-4-fluoro-5-(5-fluoro-2,4-dioxo-3H-pyrimidin-1-yl) oxolane-2-carboxamide (300.0 mg, 0.56 mmol), DMAP (273.7 mg, 2.24 mmol) and TEA (340.0 mg, 3.36 mmol) in ACN (5 mL), was added 2,4,6-triisopropylbenzenesulfonyl chloride (678.4 mg, 2.24 mmol) in portions at 0° C. The resulting mixture was stirred for 4 h at room temperature. This was followed by the addition of NH$_3$·H$_2$O (6 mL), then the mixture was stirred for additional 2 h at room temperature. The resulting mixture was concentrated under vacuum. The residue was purified by silica gel column chromatography, eluting with CH$_2$Cl$_2$/MeOH (10:1) to afford (2R,3R,4S,5R)-5-(4-amino-5-fluoro-2-oxopyrimidin-1-yl)-3-[(tert-butyldimethylsilyl) oxy]-2-{[(tert-butyl dimethylsilyl)oxy]methyl}-4-fluorooxolane-2-carboxamide (220.0 mg, 0.37 mmol, 73.47%) as a light-yellow solid. LC-MS (ES, m/z): 535 (M+H$^+$).

Step 9: To a solution of (2R,3R,4S,5R)-5-(4-amino-5-fluoro-2-oxopyrimidin-1-yl)-3-[(tert-butyldimethylsilyl) oxy]-2-{[(tert-butyldimethylsilyl) oxy] methyl}-4-fluorooxolane-2-carboxamide (180.0 mg, 0.33 mmol) in MeOH (5 mL), was added NH$_4$F (409.0 mg, 11.05 mmol). The resulting mixture was stirred overnight at 60° C., then cooled to room temperature and concentrated under reduced pressure. The residue was dissolved in EtOH (20 mL). The resulting mixture was filtered, the filter cake was washed with EtOH. The filtrate was concentrated under reduced pressure. The residue was purified by Prep-HPLC with the following conditions: Column: C18; Mobile Phase A: Water (10 mmol/L NH$_4$HCO$_3$), Mobile Phase B: ACN; Flow rate: 100 mL/min; Gradient: 0% B to 30% B in 18 min, detector: UV 254 nm. This afforded (2R,3R,4S,5R)-5-(4-amino-5-fluoro-2-oxopyrimidin-1-yl)-4-fluoro-3-hydroxy-2-(hydroxymethyl) oxolane-2-carboxamide (27.9 mg, 0.09 mmol, 27.06%) as a white solid. LC-MS (ES, m/z): 307 (M+H$^+$) 96.5% purity. Conditions for the HPLC: (Column: Atlantis T3 3 m, 100*4.6 mm, 3.5 µm; Mobile Phase A: water/0.05% TFA, Mobile Phase B: MeOH; Flow rate: 1.2000 mL/min; Gradient: 0% B to 95% B in 7.99 min, 95% B to 95% B in 2.00 min, 95% B to 10% B in 0.5 min; Wavelength: 254/220 nm; RT1(min): 2.53). $^1$H NMR (400 MHz, DMSO-d$_6$) δ 8.03 (d, J=7.2, 1H), 7.85 (brs, 1H), 7.60 (brs, 1H), 7.46 (s, 1H), 7.21 (s, 1H), 6.26-6.20 (m, 1H), 6.04 (d, J=4.8 Hz, 1H), 5.22-5.19 (m, 1H), 5.02 (t, J=1.2 Hz, 0.5H), 4.88 (t, J=1.2 Hz, 0.5H), 4.14 (dd, J=12.6, 4.0 Hz, 1H), 3.91 (dd, J=11.8, 6.8 Hz, 1H), 3.55-3.52 (m, 1H).

Example 76—Synthesis of Compound 135: 4-amino-5-fluoro-1-[(2R,3S,4R,5R)-3-fluoro-4-hydroxy-5-(hydroxymethyl)-5-[(methylsulfanyl)methyl] oxolan-2-yl] pyrimidin-2-one

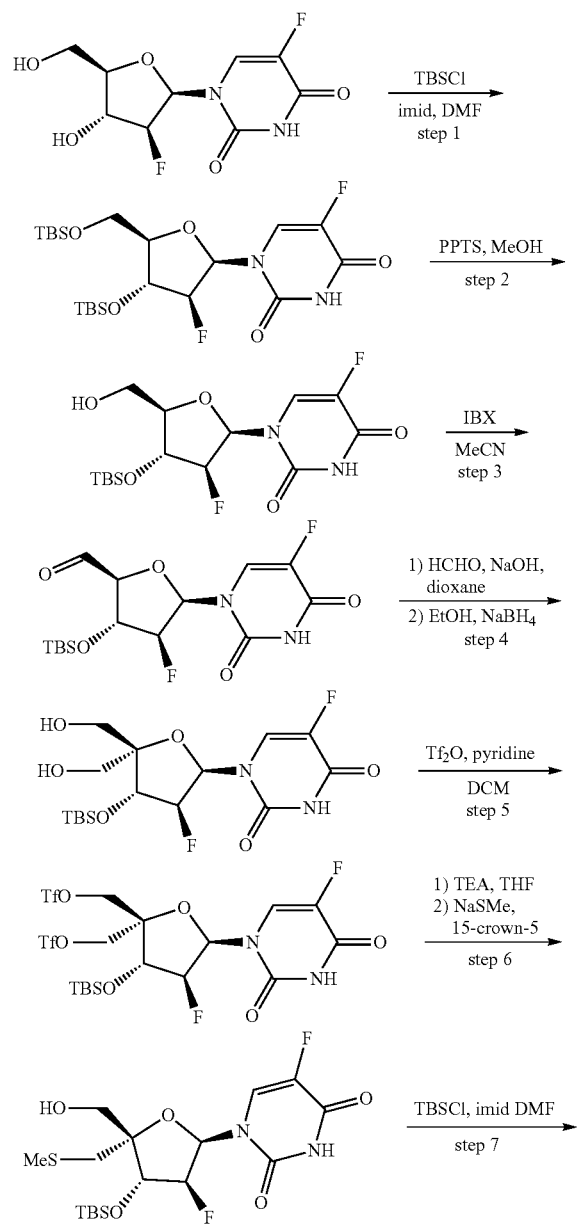

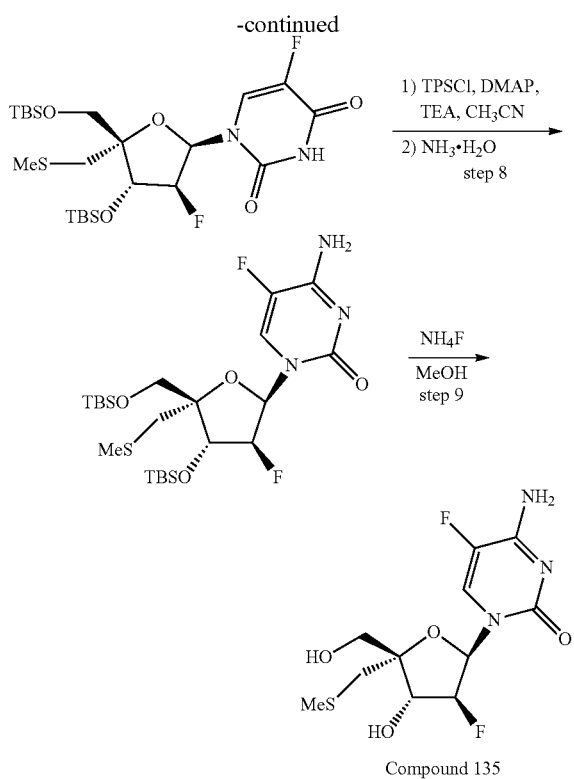

Compound 135

Step 1: To a stirred solution of 5-fluoro-1-[(2R,3S,4R,5R)-3-fluoro-4-hydroxy-5-(hydroxymethyl) oxolan-2-yl]-3H-pyrimidine-2,4-dione (12.0 g, 45.42 mmol) and imid (15.5 g, 227.12 mmol) in DMF (120 mL) was added TBSCl (34.2 g, 227.12 mmol) in portions at 0° C. under nitrogen atmosphere. The resulting mixture was stirred overnight at room temperature under nitrogen atmosphere and quenched by the addition of water at 0° C. The resulting mixture was extracted with EtOAc. The combined organic layers were washed with brine and dried over anhydrous Na₂SO₄. After filtration the filtrate was concentrated under reduced pressure to afford 1-[(2R,3S,4R,5R)-4-[(tert-butyldimethylsilyl) oxy]-5-{[(tert-butyldimethylsilyl) oxy] methyl}-3-fluorooxolan-2-yl]-5-fluoro-3H-pyrimidine-2,4-dione (18 g, crude) as a white solid. The crude product was used in the next step directly without further purification. LC-MS (ES, m/z): 493 (M+H⁺).

Step 2: To a stirred solution of 1-[(2R,3S,4R,5R)-4-[(tert-butyldimethylsilyl) oxy]-5-{[(tert-butyldimethylsilyl) oxy] methyl}-3-fluorooxolan-2-yl]-5-fluoro-3H-pyrimidine-2,4-dione (18 g, crude) in MeOH (180 mL) was added PPTS (17.9 g, 71.04 mmol) in portions at room temperature. The reaction mixture was stirred for 3 h at 60° C., then cooled to room temperature and quenched by the addition of sat. NaHCO₃(aq.) at 0° C. The resulting solution was extracted with EtOAc. The combined organic layers were washed with brine and dried over anhydrous Na₂SO₄. After filtration the filtrate was concentrated under reduced pressure. The residue was purified by silica gel column chromatography, eluting with PE/EtOAc (1:1) to afford 1-[(2R,3S,4R,5R)-4-[(tert-butyl-dimethylsilyl)oxy]-3-fluoro-5-(hydroxymethyl) oxolan-2-yl]-5-fluoro-3H-pyrimidine-2,4-dione (11.9 g, 31.44 mmol, 69.3% yield in two steps) as a white solid. LC-MS (ES, m/z): 379 (M+H⁺).

Step 3: To a stirred solution of 1-[(2R,3S,4R,5R)-4-[(tert-butyldimethylsilyl) oxy]-3-fluoro-5-(hydroxymethyl) oxolan-2-yl]-5-fluoro-3H-pyrimidine-2,4-dione (11.9 g, 31.44 mmol) in acetonitrile (120 mL) was added IBX (17.6 g, 62.89 mmol) in portions at room temperature. The resulting mixture was stirred for 3 h at 65° C. The resulting mixture was cooled to room temperature filtered and the filter cake was washed with acetonitrile. The combined filtrate was concentrated under reduced pressure to afford (2S,3R,4S,5R)-3-[(tert-butyldimethylsilyl) oxy]-4-fluoro-5-(5-fluoro-2,4-dioxo-3H-pyrimidin-1-yl) oxolane-2-carbaldehyde (11 g, crude) as a white solid. The crude product was used in the next step directly without further purification. LC-MS (ES, m/z): 377 (M+H⁺).

Step 4: To a solution of (2S,3R,4S,5R)-3-[(tert-butyldimethylsilyl) oxy]-4-fluoro-5-(5-fluoro-2,4-dioxo-3H-pyrimidin-1-yl) oxolane-2-carbaldehyde (11 g, crude) in 1,4-dioxane (110 mL), was added HCHO (22.00 mL, 37% in water) and aq. NaOH (2M, 22.1 mL, 44.13 mmol) dropwise. The resulting mixture was stirred overnight at room temperature under a nitrogen atmosphere. To the above mixture was added NaBH₄(4.6 g, 122.73 mmol) in portions at 0° C. The resulting mixture was stirred for additional 30 min at room temperature and quenched by the addition of sat. NH₄Cl (aq.) at 0° C. The resulting solution was extracted with EtOAc. The combined organic layers were washed with brine and dried over anhydrous Na₂SO₄. After filtration the filtrate was concentrated under reduced pressure. The residue was purified by silica gel column chromatography, eluting with CH₂Cl₂/MeOH (20:1) to afford 1-[(2R,3S,4R)-4-[(tert-butyldimethylsilyl) oxy]-3-fluoro-5,5-bis(hydroxymethyl) oxolan-2-yl]-5-fluoro-3H-pyrimidine-2,4-dione (5.6 g, 13.73 mmol, 43.6% yield in two steps) as a white solid. LC-MS (ES, m/z): 409 (M+H⁺).

Step 5: To a stirred solution of 1-[(2R,3S,4R)-4-[(tert-butyldimethylsilyl) oxy]-3-fluoro-5,5-bis(hydroxymethyl) oxolan-2-yl]-5-fluoro-3H-pyrimidine-2,4-dione (3.0 g, 7.34 mmol) and pyridine (4.7 g, 58.75 mmol) in DCM (30 mL) was added triflic anhydride (5.2 g, 18.36 mmol) dropwise at −30° C. under nitrogen atmosphere. The resulting mixture was stirred for 2 h at room temperature under nitrogen atmosphere and quenched by the addition of sat. NaHCO₃ (aq.) at 0° C. The resulting mixture was extracted with EtOAc. The combined organic layers were washed with brine and dried over anhydrous Na₂SO₄. After filtration the filtrate was concentrated under reduced pressure. The residue was purified by silica gel column chromatography, eluting with PE/EtOAc (5:1) to afford [(3R,4S,5R)-3-[(tert-butyldimethylsilyl) oxy]-4-fluoro-5-(5-fluoro-2,4-dioxo-3H-pyrimidin-1-yl)-2-[(trifluoromethanesulfonyloxy) methyl] oxolan-2-yl] methyl trifluoromethane-sulfonate (4.3 g, 6.39 mmol, 87.05%) as a white solid. LC-MS-PH-R (ES, m/z): 673 (M+H⁺).

Step 6: To a stirred solution of [(3R,4S,5R)-3-[(tert-butyldimethylsilyl) oxy]-4-fluoro-5-(5-fluoro-2,4-dioxo-3H-pyrimidin-1-yl)-2-[(trifluoromethanesulfonyloxy) methyl]oxolan-2-yl] methyl trifluoromethanesulfonate (4.3 g, 6.39 mmol) in THF (45 mL), was added TEA (6.5 g, 63.93 mmol) under nitrogen atmosphere. The resulting mixture was stirred for 2 h at 60° C. under nitrogen atmosphere. After cooling the reaction to 0° C., (methylsulfanyl)sodium (2.6 g, 36.75 mmol) and 15-crown-5 (1.6 g, 7.35 mmol) was added under nitrogen atmosphere. The resulting mixture was stirred overnight at room temperature under nitrogen atmosphere and quenched by the addition of water. The resulting mixture was extracted with EtOAc. The combined organic layers were washed with brine and dried over anhydrous Na₂SO₄. After filtration the filtrate was concentrated under reduced pressure. The residue was purified by silica gel column chromatography, eluting with PE/EtOAc (2:1) to afford 1-[(2R,3S,4R,5R)-4-[(tert-butyldimethylsilyl) oxy]-3-fluoro-5-(hydroxymethyl)-5-[(methylsulfanyl) methyl] oxolan-2-yl]-5-fluoro-3H-pyrimidine-2,4-dione (840.0 mg, 1.92 mmol, 30.0%) as a yellow solid. LC-MS (ES, m/z): 439 (M+H$^+$).

Step 7: To a stirred solution of 1-[(2R,3S,4R,5R)-4-[(tert-butyldimethylsilyl) oxy]-3-fluoro-5-(hydroxymethyl)-5-[(methylsulfanyl)methyl] oxolan-2-yl]-5-fluoro-3H-pyrimidine-2,4-dione (823.0 mg, 1.88 mmol) and imid (447.2 mg, 6.57 mmol) in DMF (9 mL), was added TBSCl (707.1 mg, 4.69 mmol) in portions at 0° C. under nitrogen atmosphere. The resulting mixture was stirred for 3 h at room temperature under nitrogen atmosphere and quenched by the addition of water at room temperature. The resulting mixture was extracted with EtOAc. The combined organic layers were washed with brine and dried over anhydrous $Na_2SO_4$. After filtration the filtrate was concentrated under reduced pressure. The residue was purified by silica gel column chromatography, eluting with PE/EtOAc (3:1) to afford 1-[(2R,3S,4R,5R)-4-[(tert-butyldimethylsilyl) oxy]-5-{[(tert-butyldimethylsilyl) oxy] methyl}-3-fluoro-5-[(methylsulfanyl)methyl] oxolan-2-yl]-5-fluoro-3H-pyrimidine-2,4-dione (710.0 mg, 1.27 mmol, 67.48%) as a yellow oil. LC-MS-PH (ES, m/z): 553 (M+H$^+$).

Step 8: To a stirred solution of 1-[(2R,3S,4R,5R)-4-[(tert-butyldimethylsilyl) oxy]-5-{[(tert-butyldimethylsilyl) oxy] methyl}-3-fluoro-5-[(methylsulfanyl)methyl] oxolan-2-yl]-5-fluoro-3H-pyrimidine-2,4-dione (385.0 mg, 0.70 mmol), DMAP (510.5 mg, 4.18 mmol) and TEA (422.8 mg, 4.18 mmol) in $CH_3CN$ (16 mL), was added 2,4,6-tris(propan-2-yl) benzene-1-sulfonyl chloride (1.3 g, 4.18 mmol) in portions at room temperature. The resulting mixture was stirred for 5 h at room temperature. To the above mixture was added $NH_3$—$H_2O$ (7.7 mL) at room temperature. The resulting mixture was stirred for additional 2 h at room temperature. The resulting mixture was extracted with EtOAc. The combined organic layers were washed with brine and dried over anhydrous $Na_2SO_4$. After filtration the filtrate was concentrated under reduced pressure. The residue was purified by Prep-TLC ($CH_2Cl_2$/MeOH 10:1) to afford 4-amino-1-[(2R,3S,4R,5R)-4-[(tert-butyldimethylsilyl) oxy]-5-{[(tert-butyldimethylsilyl) oxy]methyl}-3-fluoro-5-[(methylsulfanyl)methyl] oxolan-2-yl]-5-fluoro-pyrimidin-2-one (264.0 mg, 0.48 mmol, 68.69%) as a white solid. LC-MS (ES, m/z): 552 (M+H$^+$).

Step 9: To a solution of 4-amino-1-[(2R,3S,4R,5R)-4-[(tert-butyldimethylsilyl) oxy]-5-{[(tert-butyldimethylsilyl) oxy] methyl}-3-fluoro-5-[(methylsulfanyl)methyl] oxolan-2-yl]-5-fluoropyrimidin-2-one (264.0 mg, 0.48 mmol) in methanol (3 mL), was added $NH_4F$ (1.1 g, 28.62 mmol). The resulting solution was stirred for 43 h at 60° C. The resulting mixture was cooled to room temperature and concentrated under reduced pressure. The crude product was purified by Prep-HPLC with the following conditions: Column, XBridge Shield RP18 OBD Column, 30×150 mm, 5 μm; mobile phase, water (10 mmol/L $NH_4HCO_3$+0.1% $NH_3$—$H_2O$) and ACN (11% ACN up to 17% in 7 min); UV detection at 254/220 nm. The product-containing fractions were combined and evaporated partially to remove the solvents, then lyophilized overnight to afford 4-amino-5-fluoro-1-[(2R,3S,4R,5R)-3-fluoro-4-hydroxy-5-(hydroxymethyl)-5-[(methylsulfanyl)methyl] oxolan-2-yl] pyrimidin-2-one (58.4 mg, 0.18 mmol, 20.91%) as a white solid. LC-MS (ES, m/z): 324 (M+H$^+$). 98.8% purity. Conditions for the HPLC: (Column: Shim-pack Scepter C18, 33*3.0 mm, 3.0 μm; Mobile Phase A: water/5 mM $NH_4HCO_3$, Mobile Phase B: Acetonitrile; Flow rate: 1.5000 mL/min; Gradient: 10% B to 95% B in 1.20 min, 95% B to 95% B in 0.60 min, 95% B to 10% B in 0.06 min; Wavelength: 254/220 nm; RT1(min): 0.453). $^1$H NMR (400 MHz, DMSO-d$_6$) δ 8.08 (d, J=7.2 Hz, 1H), 7.84 (brs, 1H), 7.60 (brs, 1H), 6.23-6.19 (m, 1H), 6.02 (d, J=4.0 Hz, 1H), 5.42 (d, J=5.2 Hz, 1H), 5.31 (t, J=4.4 Hz, 0.5H), 5.17 (t, J=4.4 Hz, 0.5H), 4.41-4.35 (m, 1H), 3.69-3.66 (m, 1H), 3.53-3.50 (m, 1H), 2.85-2.82 (m, 1H), 2.59-2.55 (m, 1H), 2.08 (s, 3H).

Example 77—Synthesis of Compound 163: 1-[(2R, 3S,4R,5R)-5-(chloromethyl)-3-fluoro-4-hydroxy-5-(hydroxymethyl) oxolan-2-yl]-5-fluoro-3H-pyrimidine-2,4-dione

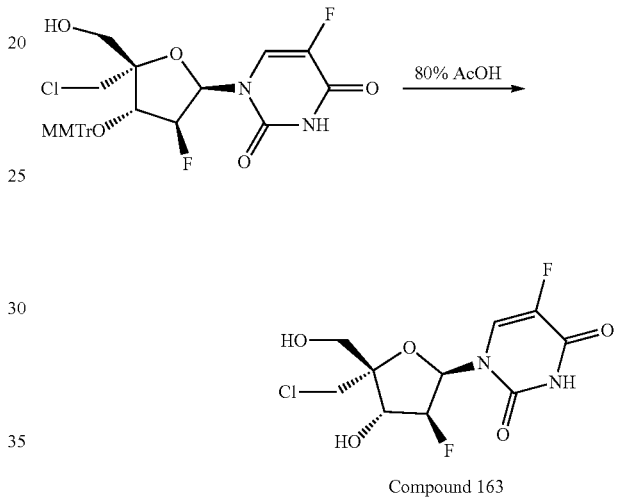

Compound 163

A solution of 1-[(2R,3S,4R,5R)-5-(chloromethyl)-3-fluoro-5-(hydroxymethyl)-4-[(4-methoxyphenyl) diphenylmethoxy] oxolan-2-yl]-5-fluoro-3H-pyrimidine-2,4-dione (50 mg, 0.08 mmol) in AcOH (4 mL) and water (2 mL) was stirred overnight at room temperature under $N_2$ atmosphere. The resulting mixture was concentrated under reduced pressure. The crude product was purified by Prep-HPLC with the following conditions (Column: XBridge Shield RP18 OBD Column, 30*150 mm, 5 μm; Mobile Phase A: Water (10 mmol/L $NH_4HCO_3$+0.1% $NH_3$·$H_2O$), Mobile Phase B: ACN; Flow rate: 60 mL/min; Gradient: 5% B to 8% B in 9 min, Wavelength: 254/210 nm; RT1(min): 8.75). The fraction was collected and concentrated under vacuum, the residue was re-dissolved in $CH_3CN$ and $H_2O$, and then was lyophilized to afford 1-[(2R,3S,4R,5R)-5-(chloromethyl)-3-fluoro-4-hydroxy-5-(hydroxymethyl)oxolan-2-yl]-5-fluoro-3H-pyrimidine-2,4-dione (20.3 mg, 65 μmol, 72.1%) as an off-white solid. LC-MS (ES, m/z): 313/315 [M+H]$^+$, 95.1% purity. Conditions for the LCMS: (Column: Atlantis T3 3 m 4.6*100 mm; Mobile Phase A: $H_2O$+0.1% TFA, Mobile Phase B: ACN+0.1% TFA; Flow rate: 1.20 mL/min; Gradient: 0% B to 95% B in 8 min, 95% B to 95% B in 2 min, 95% B to 10% B in 0.5 min; Wavelength: 254; RT1(min): 3.38). $^1$H NMR (400 MHz, Methanol-d$_4$) δ 8.04 (dd, J=6.7, 2.1 Hz, 1H), 6.37 (ddd, J=14.6, 4.4, 1.6 Hz, 1H), 5.24 (dt, J=53.3, 4.0 Hz, 1H), 4.54 (dd, J=19.5, 3.5 Hz, 1H), 3.95-3.70 (m, 4H).

Example 78—Synthesis of Compound 162: 5-fluoro-1-[(2R,3S,4R,5S)-3-fluoro-4-hydroxy-5-(1-hydroxyethyl)-5-(hydroxymethyl)oxolan-2-yl]-3H-pyrimidine-2,4-dione

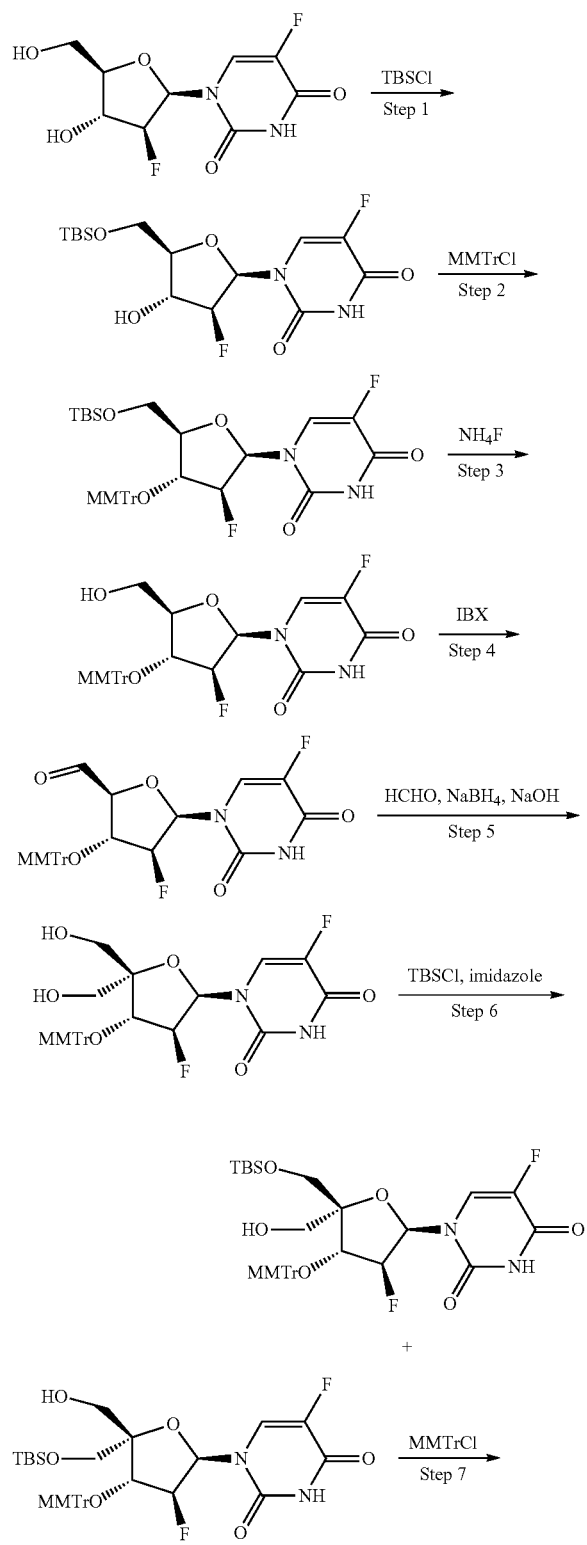

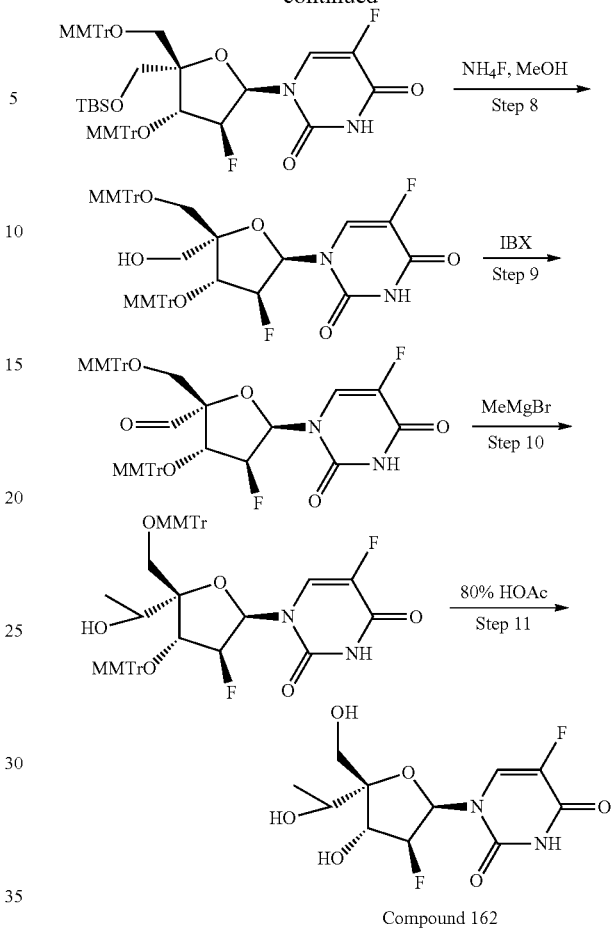

Compound 162

Step 1: To a stirred solution of 5-fluoro-1-[(2R,3S,4R,5R)-3-fluoro-4-hydroxy-5-(hydroxymethyl)oxolan-2-yl]-3H-pyrimidine-2,4-dione (11.0 g, 41.6 mmol) and imidazole (14.2 g, 208 mmol) in DMF (150 mL) was added t-butyldimethylchlorosilane (7.53 g, 49.9 mmol) at room temperature. The reaction was then was stirred for 4 h at room temperature. The reaction mixture was poured into water (300 mL), and extracted with EtOAc (3×100 mL). The combined organic layers were dried over anhydrous $Na_2SO_4$. After filtration the filtrate was concentrated under reduced pressure. The residue was purified by silica gel column chromatography, eluting with PE/EtOAc (4:1) to afford 1-[(2R,3S,4R,5R)-5-([(tert-butyldimethylsilyl)oxy]methyl-3-fluoro-4-hydroxyoxolan-2-yl]-5-fluoro-3H-pyrimidine-2,4-dione (11.2 g, 29.6 mmol, 71.08%) as a white solid. LC-MS (ES, m/z): 379 $[M+H]^+$.

Step 2: To a stirred solution of 1-[(2R,3S,4R,5R)-5-([(tert-butyldimethylsilyl) oxy]methyl-3-fluoro-4-hydroxyoxolan-2-yl]-5-fluoro-3H-pyrimidine-2,4-dione (11.2 g, 29.6 mmol) and 2,4,6-collidine (7.17 g, 59.2 mmol) in DCM (100 mL) was added 1-(chlorodiphenylmethyl)-4-methoxybenzene (18.3 g, 59.2 mmol) at room temperature. The reaction was then stirred overnight at room temperature. The resulting mixture was poured into water (100 mL) and extracted with DCM (3×100 mL). The combined organic layers were dried over anhydrous $Na_2SO_4$. After filtration the filtrate was concentrated under reduced pressure to give 1-[(2R,3S,4R,5R)-5-([(tert-butyldimethylsilyl)oxy]methyl-3-fluoro-4-[(4-methoxyphenyl)diphenylmethoxy]oxolan-2-yl]-5-fluoro- 3H-pyrimidine-2,4-dione (15.0 g, crude). The crude product was used in the next step directly without further purification. LC-MS (ES, m/z): 651 [M+H]$^+$.

Step 3: To a stirred solution of 1-[(2R,3S,4R,5R)-5-([[(tert-butyldimethylsilyl)oxy]methyl-3-fluoro-4-[(4-methoxyphenyl)diphenylmethoxy]oxolan-2-yl]-5-fluoro-3H-pyrimidine-2,4-dione (15.0 g, crude) in MeOH (150 mL) was added NH$_4$F (4.27 g, 115 mmol) at room temperature. The resulting mixture was stirred overnight at 60° C. The reaction mixture was allowed to cool down to room temperature, diluted with water (500 mL) and extracted with EtOAc (3×300 mL). The combined organic layers were dried over anhydrous Na$_2$SO$_4$. After filtration the filtrate was concentrated under reduced pressure. The residue was purified by silica gel column chromatography, eluting with PE/EtOAc (3:1) to afford 5-fluoro-1-[(2R,3S,4R,5R)-3-fluoro-5-(hydroxymethyl)-4-[(4-methoxyphenyl)diphenylmethoxy]oxolan-2-yl]-3H-pyrimidine-2,4-dione (11.3 g, 21.1 mmol, 71.2% yield in two steps) as a yellow solid. LC-MS (ES, m/z): 537 [M+H]$^+$.

Step 4: To a stirred solution of 5-fluoro-1-[(2R,3S,4R,5R)-3-fluoro-5-(hydroxymethyl)-4-[(4-methoxyphenyl)diphenylmethoxy]oxolan-2-yl]-3H-pyrimidine-2,4-dione (6.00 g, 11.2 mmol) in MeCN (60.0 mL) was added IBX (3.76 g, 13.4 mmol) at room temperature. The reaction was then stirred for 1 h at 75° C. The resulting mixture was allowed to cool down to room temperature, filtered, and the filter cake was washed with MeCN. The filtrate was concentrated under reduced pressure to give (2S,3R,4S,5R)-4-fluoro-5-(5-fluoro-2,4-dioxo-3H-pyrimidin-1-yl)-3-[(4-methoxyphenyl) diphenylmethoxy]oxolane-2-carbaldehyde (6.00 g, crude). The crude product was used in the next step directly without further purification. LC-MS (ES, m/z): 535 [M+H]$^+$.

Step 5: To a stirred solution of (2S,3R,4S,5R)-4-fluoro-5-(5-fluoro-2,4-dioxo-3H-pyrimidin-1-yl)-3-[(4-methoxyphenyl)diphenylmethoxy]oxolane-2-carbaldehyde (6.00 g, crude) and formalin (6.00 mL, 37%) in 1,4-dioxane (60.0 mL) was added a solution of NaOH in H$_2$O (12.0 mL, 24.0 mmol, 2N) at room temperature. The resulting mixture was stirred overnight at room temperature. To the above mixture was added EtOH (20.0 mL), followed by the addition of NaBH$_4$ (1.27 g, 33.7 mmol) in portions at 0° C. The resulting mixture was stirred for 4 h at room temperature, then cooled to 0° C. and quenched by the addition of saturated aqueous of NH$_4$Cl. The resulting solution was extracted with EtOAc (3×200 mL), washed with brine (2×300 mL), dried over anhydrous Na$_2$SO$_4$, filtered and concentrated under vacuum. The residue was purified by silica gel column chromatography, eluting with PE/EA (1:1) to afford 5-fluoro-1-[(2R,3S,4R)-3-fluoro-5,5-bis(hydroxymethyl)-4-[(4-methoxyphenyl)diphenylmethoxy]oxolan-2-yl]-3H-pyrimidine-2,4-dione (2.10 g, 3.71 mmol, 33.02% yield in two steps) as a white solid. LC-MS (ES, m/z): 567 [M+H]$^+$.

Step 6: To a stirred solution of 5-fluoro-1-[(2R,3S,4R)-3-fluoro-5,5-bis(hydroxy-methyl)-4-[(4-methoxyphenyl)diphenylmethoxy]oxolan-2-yl]-3H-pyrimidine-2,4-dione (2.10 g, 3.71 mmol) in pyridine (25.0 mL) was added TBSCl (670 mg, 4.45 mmol) at room temperature. The reaction was then stirred for 4 h at room temperature. The reaction mixture was quenched by water (100 mL) and extracted with EtOAc (3×100 mL). The combined organic layers were dried over anhydrous Na$_2$SO$_4$. After filtration the filtrate was concentrated under reduced pressure. The residue was purified by silica gel column chromatography, eluting with PE/EtOAc (3:1) to afford 1-[(2R,3S,4R,5S)-5-([[(tert-butyldimethylsilyl)oxy]methyl-3-fluoro-5-(hydroxymethyl)-4-[((4-methoxyphenyl)diphenylmethoxy]oxolan-2-yl]-5-fluoro-3H-pyrimidine-2,4-dione (480 mg, 0.71 mmol, 19.02%) as a white solid and 1-((2R,3S,4R,5S)-5-(((tert-butyldimethylsilyl)oxy)methyl)-3-fluoro-5-(hydroxymethyl)-4-((4-methoxyphenyl) diphenylmethoxy)tetrahydrofuran-2-yl)-5-fluoropyrimidine-2,4(1H,3H)-dione (480 mg, 0.71 mmol, 19.02%) as a white solid. LC-MS (ES, m/z): 681 [M+H]$^+$ and LC-MS (ES, m/z): 681 [M+H]$^+$.

Step 7: To a stirred solution of 1-[(2R,3S,4R,5S)-5-([[(tert-butyldimethylsilyl)oxy]methyl-3-fluoro-5-(hydroxymethyl)-4-[(4-methoxyphenyl)diphenylmethoxy]oxolan-2-yl]-5-fluoro-3H-pyrimidine-2,4-dione (480 mg, 0.71 mmol) and 2,4,6-collidine (256 mg, 2.11 mmol) in DCM (5.00 mL) was added 1-(chlorodiphenylmethyl)-4-methoxybenzene (653 mg, 2.11 mmol) at room temperature. The resulting mixture was stirred overnight at room temperature. The reaction mixture was diluted by water (10 mL) and extracted with DCM (3×10 mL). The combined organic layers were dried over anhydrous Na$_2$SO$_4$. After filtration the filtrate was concentrated under reduced pressure to give 1-[(2R,3S,4R,5S)-5-([[(tert-butyldimethylsilyl)oxy]methyl-3-fluoro-4-[(4-methoxyphenyl)diphenylmethoxy]-5-([[(4-methoxyphenyl)diphenylmethoxy]methyloxolan-2-yl]-5-fluoro-3H-pyrimidine-2,4-dione (600 mg, crude). The crude product was used in the next step directly without further purification. LC-MS-PH (ES, m/z): 953 [M+H]$^+$.

Step 8: To a stirred solution of 1-[(2R,3S,4R,5S)-5-([[(tert-butyldimethylsilyl)oxy]methyl-3-fluoro-4-[(4-methoxyphenyl)diphenylmethoxy]-5-([[(4-methoxyphenyl) diphenylmethoxy]methyloxolan-2-yl]-5-fluoro-3H-pyrimidine-2,4-dione (600 mg, crude) in MeOH (10.0 mL) was added NH$_4$F (233 mg, 6.29 mmol) at room temperature. The resulting mixture was stirred overnight at 60° C. under nitrogen atmosphere. The reaction mixture was allowed to cool down to room temperature, and then was diluted by water (30 mL), and extracted with DCM (3×30 mL). The combined organic layers were dried over anhydrous Na$_2$SO$_4$. After filtration the filtrate was concentrated under reduced pressure. The residue was purified by silica gel column chromatography, eluting with PE/EtOAc (2:1) to afford 5-fluoro-1-[(2R,3S,4R,5R)-3-fluoro-5-(hydroxymethyl)-4-[(4-methoxyphenyl)diphenylmethoxy]-5-([[(4-methoxyphenyl) diphenylmethoxy]methyloxolan-2-yl]-3H-pyrimidine-2,4-dione (450 mg, 0.5 mmol, 75.9% yield in two steps) as a white solid. LC-MS-PH (ES, m/z): 839 [M+H]$^+$.

Step 9: To a stirred solution of 5-fluoro-1-[(2R,3S,4R,5R)-3-fluoro-5-(hydroxymethyl)-4-[(4-methoxyphenyl)diphenylmethoxy]-5-([[(4-methoxyphenyl) diphenylmethoxy]methyloxolan-2-yl]-3H-pyrimidine-2,4-dione (200 mg, 0.24 mmol) and in MeCN (2.00 mL) was added IBX (100 mg, 0.36 mmol) at room temperature. The resulting mixture was stirred for 2 h at room temperature. The resulting mixture was filtered, and the filter cake was washed with MeCN. The filtrate was concentrated under reduced pressure to give (2R,3R,4S,5R)-4-fluoro-5-(5-fluoro-2,4-dioxo-3H-pyrimidin-1-yl)-3-[(4-methoxyphenyl) diphenylmethoxy]-2-([[(4-methoxyphenyl)diphenyl methoxy]methyloxolane-2-carbaldehyde (180 mg, crude). The resulting mixture was used in the next step directly without further purification. LC-MS (ES, m/z): 837 [M+H]$^+$.

Step 10: To a stirred solution of (2R,3R,4S,5R)-4-fluoro-5-(5-fluoro-2,4-dioxo-3H-pyrimidin-1-yl)-3-[(4-methoxyphenyl)diphenylmethoxy]-2-([[(4-methoxyphenyl)diphenylmethoxy]methyloxolane-2-carbaldehyde (180 mg, 0.22 mmol) in THF (3.00 mL) was added a solution of bromo(methyl)magnesium in THF (0.9 mL, 0.90 mmol, 1M) dropwise at −78° C. under nitrogen atmosphere. The resulting mixture was stirred for 1 h at −78° C. under nitrogen atmosphere. The reaction mixture was quenched by water (10 mL) and extracted with EtOAc (3×10 mL). The combined organic layers were dried over anhydrous Na$_2$SO$_4$. After filtration the filtrate was concentrated under reduced pressure to give 5-fluoro-1-[(2R,3S,4R,5S)-3-fluoro-5-(1-hydroxyethyl)-4-[(4-methoxyphenyl)diphenylmethoxy]-5-([(4-methoxyphenyl)diphenyl-methoxy]methyloxolan-2-yl]-3H-pyrimidine-2,4-dione (100 mg, crude). The crude product was used in the next step directly without further purification. LC-MS (ES, m/z): 853 [M+H]$^+$.

Step 11: To a stirred solution of 5-fluoro-1-[(2R,3S,4R,5S)-3-fluoro-5-(1-hydroxyethyl)-4-[(4-methoxyphenyl)diphenylmethoxy]-5-([(4-methoxyphenyl)diphenyl-methoxy]methyloxolan-2-yl]-3H-pyrimidine-2,4-dione (100 mg, crude) in AcOH (0.80 mL) was added H$_2$O (0.20 mL) at room temperature. The resulting mixture was stirred overnight at 60° C. The resulting mixture was concentrated under vacuum. The residue was purified via reverse phase chromatography with the following conditions (Column: X-Select Prep OBD C18 Column, 30×150 mm, 5 µm; Mobile Phase A: water (0.1% FA), Mobile Phase B: ACN; Flow rate: 60 mL/min mL/min; Gradient: 30% B to 50% B in 7 min; Wavelength: 254 nm/220 nm nm). The product-containing fraction was collected and concentrated under vacuum to remove most of the solvent, and then was lyophilized to afford 5-fluoro-1-[(2R,3S,4R,5S)-3-fluoro-4-hydroxy-5-(1-hydroxyethyl)-5-(hydroxymethyl)oxolan-2-yl]-3H-pyrimidine-2,4-dione (6.4 mg, 0.02 mmol, 8.7% yield in 3 steps) as a white solid. LC-MS (ES, m/z): 309 [M+H]$^+$, 99.08% purity. Conditions for the HPLC: (Column: X-bridge RP18 3.5 m, 100×4.6 mm, 2.2 µm; Mobile Phase A: water/5 mM NH$_4$HCO$_3$, Mobile Phase B: MeOH; Flow rate: 1.00 mL/min; Gradient: 0% B to 60% B in 6.00 min, 60% B to 95% B in 2.00 min, hold 95% in 1.5 min, 95% B to 0% B in 0.2 min; Wavelength: 254 nm; RT1(min): 2.83, RT2(min): 3.04). $^1$H NMR (400 MHz, DMSO-d$_6$) δ 11.20 (s, 1H), 8.31-8.25 (m, 1H), 6.30-6.25 (m, 1H), 5.95-5.80 (m, 1H), 5.61-5.23 (m, 2H), 4.96-4.92 (m, 1H), 4.73-4.41 (m, 1H), 3.82-3.76 (m, 1H), 3.66-3.45 (m, 2H), 1.18-0.99 (m, 3H).

Example 79—Synthesis of Compound 137: 4-amino-1-[(2R,3S,4R,5R)-3-chloro-5-(chloromethyl)-4-hydroxy-5-(hydroxymethyl)oxolan-2-yl]-5-fluoropyrimidin-2-one

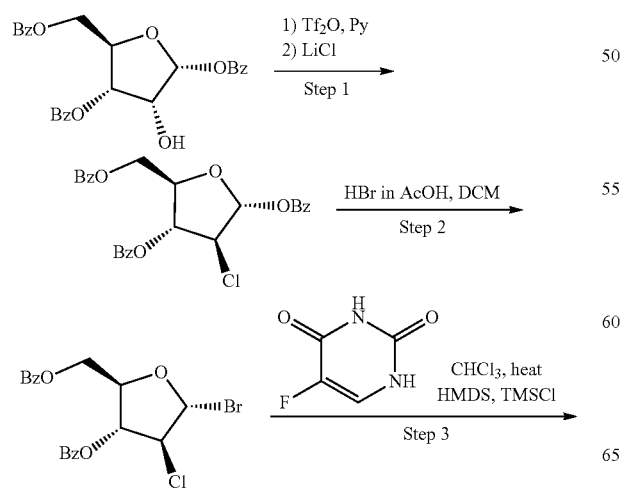

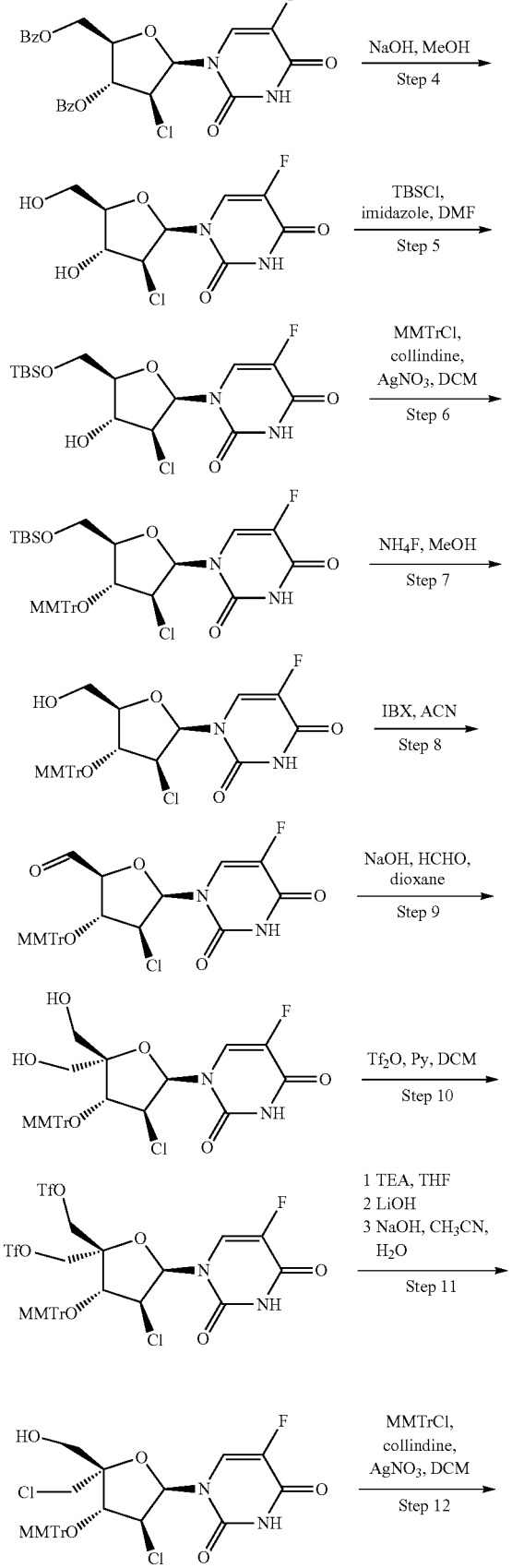

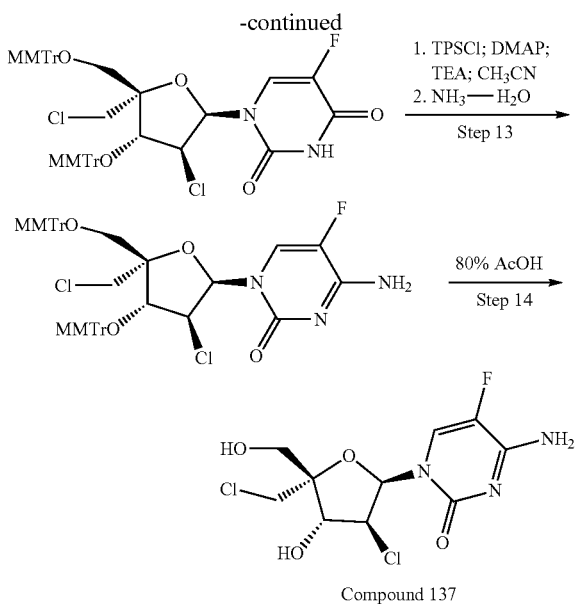

Compound 137

Step 1: To a solution of [(2R,3S,4R,5R)-3,5-bis(benzoyloxy)-4-hydroxyoxolan-2-yl]methyl benzoate (80.0 g, 0.17 mol) in DCM (400 mL) was added pyridine (41.1 g, 5.19 mol) at 0° C. After stirring for 15 min at 0° C., Tf₂O (58.6 g, 0.21 mol) was added to the above mixture at 0° C. After stirring for an additional 45 min at 0° C., the resulting mixture was diluted with DCM (200 mL). The resulting mixture was washed with saturated NaHCO₃ aqueous (3×400 mL), dried over anhydrous Na₂SO₄. After filtration the filtrate was concentrated under reduced pressure. The residue was diluted with NMP (400 mL) and then LiCl (36.7 g, 0.87 mol) was added to the above mixture at room temperature. After stirring overnight at room temperature, the resulting mixture was diluted with water (1 L). The resulting mixture was extracted with EtOAc (3×1.0 L) and dried over anhydrous Na₂SO₄. After filtration the filtrate was concentrated under reduced pressure. The residue was purified by silica gel column chromatography, eluting with PE/EtOAc (5:1) to afford [(2R,3R,4S,5R)-3,5-bis(benzoyloxy)-4-chlorooxolan-2-yl]methyl benzoate (64.0 g, 0.13 mol, 76.9%) as a yellow oil. LC-MS (ES, m/z): 359/361 [M-OBz]⁺.

Step 2: To a solution of [(2R,3R,4S,5R)-3,5-bis(benzoyloxy)-4-chlorooxolan-2-yl]methyl benzoate (64.0 g, 0.13 mol) in DCM (640 mL) was added a solution of HBr in AcOH (220 mL, 33%) cooled in an ice/water bath. After stirring overnight at room temperature, the resulting mixture was washed with water (2×300 mL) and saturated aqueous NaHCO₃(2×300 mL), and dried over anhydrous Na₂SO₄. After filtration, the resulting mixture was concentrated under vacuum to afford [(2R,3R,4S,5R)-3-(benzoyloxy)-5-bromo-4-chlorooxolan-2-yl]methyl benzoate (64.0 g, crude) as a yellow oil. (ES, m/z): 439/441[M−H]⁻.

Step 3: To a solution of fluorouracil (28.4 g, 0.22 mol) in HMDS (100 mL) was added TMSCl (15.8 g, 0.15 mol) at room temperature. After stirring for 4 h at 120° C., the resulting mixture was cooled down to room temperature, and then was concentrated under vacuum. To the residue was added a solution of [(2R,3R,4S,5R)-3-(benzoyloxy)-5-bromo-4-chlorooxolan-2-yl]methyl benzoate (64.0 g, crude) in CHCl₃ (640 mL). After stirring overnight at 60° C., the mixture was allowed to cool down to room temperature, and quenched by the addition of MeOH (20 mL) at 0° C. The resulting mixture was concentrated under reduced pressure. The residue was purified by trituration with ACN/water (1:10) and MeOH, filtered, the collected solid was dried in air to afford [(2R,3R,4S,5R)-3-(benzoyloxy)-4-chloro-5-(5-fluoro-2,4-dioxo-3H-pyrimidin-1-yl)oxolan-2-yl]methyl benzoate (50.0 g, 0.10 mol, 78.8% yield in 2 steps) as a white solid. LC-MS (ES, m/z): 489/491[M+H]⁺.

Step 4: To a mixture of [(2R,3R,4S,5R)-3-(benzoyloxy)-4-chloro-5-(5-fluoro-2,4-dioxo-3H-pyrimidin-1-yl)oxolan-2-yl]methyl benzoate (50.0 g, 0.10 mol) in MeOH (100 mL) was added NaOH (8.20 g, 205 mmol). After stirring for 1 h at room temperature the resulting mixture was filtered and the filtrate was concentrated under reduced pressure. The residue was purified by silica gel column chromatography, eluting with CH₂Cl₂/MeOH (10:1) to afford 1-[(2R,3S,4R,5R)-3-chloro-4-hydroxy-5-(hydroxymethyl)oxolan-2-yl]-5-fluoro-3H-pyrimidine-2,4-dione (20.0 g, 0.7 mol 69.7%) as a white solid. LC-MS (ES, m/z): 281/283[M+H]⁺.

Step 5: To a mixture of 1-[(2R,3S,4R,5R)-3-chloro-4-hydroxy-5-(hydroxymethyl)oxolan-2-yl]-5-fluoro-3H-pyrimidine-2,4-dione (20.0 g, 0.07 mol) in DMF (200 mL) was added imidazole (97.0 g, 714 mmol) and TBSCl (16.1 g, 107 mmol). After stirring for 30 min at room temperature, the reaction was quenched with MeOH (50.0 mL) at 0° C. The resulting mixture was diluted with water (400 mL). The resulting mixture was extracted with EtOAc (3×300 mL). The combined organic layers were dried over anhydrous Na₂SO₄. After filtration and the filtrate was concentrated under reduced pressure. The residue was purified by silica gel column chromatography, eluting with PE/EtOAc (1:1) to afford 1-[(2R,3S,4R,5R)-5-{[(tert-butyldimethylsilyl)oxy]methyl}-3-chloro-4-hydroxyoxolan-2-yl]-5-fluoro-3H-pyrimidine-2,4-dione (20.0 g, 50.7 mmol, 71.1%) as a white solid. LC-MS (ES, m/z): 395/397 [M+H]⁺.

Step 6: A mixture of 1-[(2R,3S,4R,5R)-5-{[(tert-butyldimethylsilyl)oxy]methyl}-3-chloro-4-hydroxyoxolan-2-yl]-5-fluoro-3H-pyrimidine-2,4-dione (14.0 g, 35.5 mmol), 1-(chlorodiphenylmethyl)-4-methoxybenzene (32.8 g, 106 mmol), AgNO₃ (6.00 g, 35.5 mmol) and 2,4,6-trimethylpyridine (8.60 g, 70.9 mmol) in DCM (140 mL) was stirred for 4 h at room temperature. The resulting mixture was filtered, and the filter cake was washed with DCM. The resulting mixture was diluted with water (200 mL) and extracted with DCM (3×200 mL). The combined organic layers were dried over anhydrous Na₂SO₄. After filtration the filtrate was concentrated under reduced pressure to afford 1-[(2R,3S,4R,5R)-5-{[(tert-butyldimethylsilyl) oxy]methyl}-3-chloro-4-[(4-methoxyphenyl)diphenylmethoxy]oxolan-2-yl]-5-fluoro-3H-pyrimidine-2,4-dione (25.0 g crude) as a light orange oil. LC-MS (ES, m/z): 667/669 [M+H]⁺.

Step 7: A mixture of 1-[(2R,3S,4R,5R)-5-{[(tert-butyldimethylsilyl)oxy]methyl}-3-chloro-4-[(4-methoxyphenyl)diphenylmethoxy]oxolan-2-yl]-5-fluoro-3H-pyrimidine-2,4-dione (25.0 g, crude) and NH₄F (8.00 g, 216 mmol) in MeOH (250 mL) was stirred overnight at 60° C. The mixture was allowed to cool down to room temperature, filtered, the filter cake was washed with MeOH. The combined organic layers were concentrated under reduced pressure to remove most of the solvent, and then was purified by silica gel column chromatography, eluting with DCM/MeOH (10/1) to afford 1-[(2R,3S,4R,5R)-3-chloro-5-(hydroxymethyl)-4-[(4-methoxyphenyl)diphenyl-methoxy]oxolan-2-yl]-5-fluoro-3H-pyrimidine-2,4-dione (13.0 g, 23.5 mmol, 66.2% yield in two steps) as a light-yellow solid. LC-MS (ES, m/z): 553/555 [M+H]⁺. Step 8: To a mixture of 1-[(2R,3S,4R,5R)-3-chloro-5-(hydroxymethyl)-4-[(4-methoxyphenyl) diphenylmethoxy]oxolan-2-yl]-5-fluoro-3H-pyrimidine-2,4-dione (4.00 g, 7.24 mmol) in ACN (40.0 mL) was added IBX (2.60 g, 9.28 mmol) at room temperature. After stirring for 2 h at 75° C., the resulting mixture was filtered and the filter cake was washed with MeCN. The filtrate was concentrated under vacuum to give (2S,3R,4S,5R)-4-chloro-5-(5-fluoro-2,4-dioxo-3H-pyrimidin-1-yl)-3-[(4-methoxyphenyl)diphenylmethoxy]oxolane-2-carbaldehyde (4.00 g, crude) as a yellow oil. The crude product was used in the next step directly without further purification. LC-MS (ES, m/z): 551/553[M+H]$^+$.

Step 9: To a solution of (2S,3R,4S,5R)-4-chloro-5-(5-fluoro-2,4-dioxo-3H-pyrimidin-1-yl)-3-[(4-methoxyphenyl)diphenylmethoxy]oxolane-2-carbaldehyde (4.00 g, crude) in dioxane (40.0 mL) were added NaOH (0.88 g, 22.0 mmol) and paraformaldehyde (0.88 g, 29.3 mmol). The resulting mixture was degassed three times with nitrogen, and then stirred overnight at room temperature under a nitrogen atmosphere. To the above mixture was added NaBH$_4$ (1.64 g, 43.3 mmol) in portions over 5 min at 0° C. The resulting mixture was stirred for an additional 1 h at room temperature. The reaction was quenched by the addition of saturated NH$_4$Cl aqueous (20 mL) at 0° C. The resulting mixture was extracted with EtOAc (3×20 mL). The combined organic layers were dried over anhydrous Na$_2$SO$_4$. After filtration the filtrate was concentrated under reduced pressure. The residue was purified by silica gel column chromatography, eluting with PE/EtOAc (1:1) to afford 1-[(2R,3S,4R)-3-chloro-5,5-bis(hydroxymethyl)-4-[(4-methoxyphenyl)diphenylmethoxy]oxolan-2-yl]-5-fluoro-3H-pyrimidine-2,4-dione (2.00 g, 3.43 mmol, 47.2% yield in two steps) as a white solid. LC-MS (ES, m/z): 583/585[M+H]$^+$.

Step 10: To a solution of 1-[(2R,3S,4R)-3-chloro-5,5-bis(hydroxymethyl)-4-[(4-methoxyphenyl) diphenylmethoxy] oxolan-2-yl]-5-fluoro-3H-pyrimidine-2,4-dione (2.00 g, 3.43 mmol) and pyridine (0.54 g, 6.86 mmol) in DCM (20.0 mL) was added Tf$_2$O (2.42 g, 8.57 mmol) at 0° C. After stirring for 2 h at room temperature. The resulting mixture was diluted with water (20 mL). The resulting mixture was extracted with DCM (3×40 mL). The combined organic layers were dried over Na$_2$SO$_4$. After filtration the filtrate was concentrated under reduced pressure to afford [(3R,4S,5R)-4-chloro-5-(5-fluoro-2,4-dioxo-3H-pyrimidin-1-yl)-3-[(4-methoxyphenyl)diphenylmethoxy]-2-[(trifluoromethane-sulfonyloxy)methyl]oxolan-2-yl]methyl trifluoromethanesulfonate (2.00 g, 2.36 mmol, 68.8%) as a light-yellow oil. The crude product was used in the next step directly without further purification. LC-MS (ES, m/z): 847/849[M+H]$^+$.

Step 11: To a mixture of [(3R,4S,5R)-4-chloro-5-(5-fluoro-2,4-dioxo-3H-pyrimidin-1-yl)-3-[(4-methoxyphenyl)diphenylmethoxy]-2-[(trifluoromethanesulfonyloxy)methyl]oxolan-2-yl]methyl trifluoromethanesulfonate (2.00 g, 2.36 mmol) in THF (20.0 mL) was added TEA (2.39 g, 23.6 mmol) dropwise at room temperature. The resulting mixture was stirred for 3 h at room temperature. To the above mixture was added LiCl (0.50 g, 11.8 mmol) and the resulting mixture was stirred overnight at room temperature. To the resulting mixture was added a solution of NaOH (0.19 g, 4.72 mmol) in water (2.00 mL). The resulting mixture was stirred for an additional 3 h at room temperature. The resulting mixture was diluted with water (20 mL), then extracted with EtOAc (3×50 mL). The organic layers were washed with brine and dried over anhydrous Na$_2$SO$_4$. After filtration the filtrate was concentrated under reduced pressure. The residue was purified by silica gel chromatography, eluting with PE/EA (1:1) to afford 1-[(2R,3S,4R,5R)-3-chloro-5-(chloromethyl)-5-(hydroxymethyl)-4-[(4-methoxyphenyl)diphenylmethoxy]oxolan-2-yl]-5-fluoro-3H-pyrimidine-2,4-dione (1.00 g, 1.66 mmol, 69.4%) as a light-yellow oil. LC-MS (ES, m/z): 601/603[M+H]$^+$.

Step 12: A mixture of 1-[(2R,3S,4R,5R)-3-chloro-5-(chloromethyl)-5-(hydroxymethyl)-4-[(4-methoxyphenyl) diphenylmethoxy]oxolan-2-yl]-5-fluoro-3H-pyrimidine-2,4-dione (1.00 g, 1.66 mmol), AgNO$_3$ (0.28 g, 1.66 mmol) and 2,4,6-trimethylpyridine (0.40 g, 3.32 mmol) in DCM (20.0 mL) was stirred for 2 h at room temperature. The mixture was filtered and washed with DCM (10 mL). The filtrate was concentrated under vacuum. The residue was purified by silica gel chromatography, eluting with PE/EA (1:1) to afford 1-[(2R,3S,4R,5R)-3-chloro-5-(chloromethyl)-4-[(4-methoxyphenyl)diphenylmethoxy]-5-{1[(4-methoxyphenyl) diphenyl-methoxy]methyl}oxolan-2-yl]-5-fluoro-3H-pyrimidine-2,4-dione (1.00 g, 1.14 mmol, 67.4%) as a light-yellow oil. LC-MS (ES, m/z): 873/875[M+H]$^+$.

Step 13: To a stirred mixture of 1-[(2R,3S,4R,5R)-3-chloro-5-(chloromethyl)-4-[(4-methoxyphenyl)diphenylmethoxy]-5-{[(4-methoxyphenyl)diphenylmethoxy]methyl}oxolan-2-yl]-5-fluoro-3H-pyrimidine-2,4-dione (1.00 g, 1.14 mmol) in MeCN (10.0 mL) were added DMAP (0.28 g, 2.28 mmol) and TEA (0.35 g, 3.42 mmol) at room temperature. After stirring for 10 min at room temperature, 2,4,6-tris(propan-2-yl)benzene-1-sulfonyl chloride (0.69 g, 2.28 mmol) was added. The resulting mixture was stirred for 12 h at room temperature, and treated with ammonia (1.00 mL, 30%) dropwise. The resulting mixture was stirred overnight at room temperature and then quenched by the addition of water (10 mL). The resulting mixture was extracted with EtOAc (3×20 mL), washed with brine, dried over anhydrous Na$_2$SO$_4$, filtered and concentrated under vacuum. The residue was purified by silica gel column chromatography, eluting with PE/EA (1:1) to afford 4-amino-1-[(2R,3S,4R,5R)-3-chloro-5-(chloromethyl)-4-[(4-methoxyphenyl)diphenylmethoxy]-5-{[(4-methoxyphenyl)diphenyl methoxy]methyl}oxolan-2-yl]-5-fluoropyrimidin-2-one (0.4 g, 0.46 mmol, 41.7%) as a light-yellow solid. LC-MS (ES, m/z): 872/874 [M+H]$^+$.

Step 14: A solution of 4-amino-1-[(2R,3S,4R,5R)-3-chloro-5-(chloromethyl)-4-[(4-methoxyphenyl)diphenylmethoxy]-5-{[(4-methoxyphenyl)diphenylmethoxy] methyl}oxolan-2-yl]-5-fluoropyrimidin-2-one (0.40 g, 0.46 mmol) in AcOH (4.00 mL)/THF (1.00 mL) was stirred for 12 h at 60° C. The mixture was allowed to cool down to room temperature and concentrated under vacuum. The residue was purified by Prep-HPLC with the following conditions: Column: XBridge Shield RP18 OBD Column, 30×150 mm, 5 μm; Mobile Phase A: water (10 mmol/L NH$_4$HCO$_3$+0.1% NH$_3$·H$_2$O), Mobile Phase B: ACN; Flow rate: 60 mL/min; Gradient: 11% to 16% B in 9 min, 16% B; Wavelength: 254/210 nm. The product-containing fractions were combined and evaporated partially to remove the solvents, then lyophilized overnight to afford 4-amino-1-[(2R,3S,4R,5R)-3-chloro-5-(chloromethyl)-4-hydroxy-5-(hydroxymethyl)oxolan-2-yl]-5-fluoropyrimidin-2-one (34.9 mg, 0.11 mmol, 23.0%) as a white solid. LC-MS (ES, m/z): 328/330 [M+H]$^+$. 99.2% purity. Conditions for the LCMS: (Column: HALO C18, 30×3.0 mm; 2.0 μm; Mobile Phase A: water/0.05% TFA, Mobile Phase B: ACN/0.05% TFA; Flow rate: 1.50 mL/min; Gradient: 5% B to 95% B in 1.2 min, 95% B to 95% B in 0.6 min, 95% B to 5% B in 0.02 min; Wavelength: 254 nm; RT1(min): 0.524). $^1$H NMR (400 MHz, DMSO-d$_6$) δ 8.11 (d, J=7.2 Hz, 1H), 7.87 (br s, 1H), 7.75 (br s, 1H), 6.34-6.29 (m, 2H), 5.59 (t, J=5.2 Hz, 1H), 4.80 (t, J=6.4 Hz, 1H), 4.46-4.45 (m, 1H), 3.97 (d, J=12.0 Hz, 1H), 3.79-3.74 (m, 1H), 3.73 (d, J=13.6 Hz, 1H), 3.58-3.33 (m, 1H).

Example 80—Synthesis of Compound 122: 4-amino-1-[(2R,3S,4R,5R)-5-cyclopropyl-3-fluoro-4-hydroxy-5-(hydroxymethyl) oxolan-2-yl]-5-fluoropyrimidin-2-one

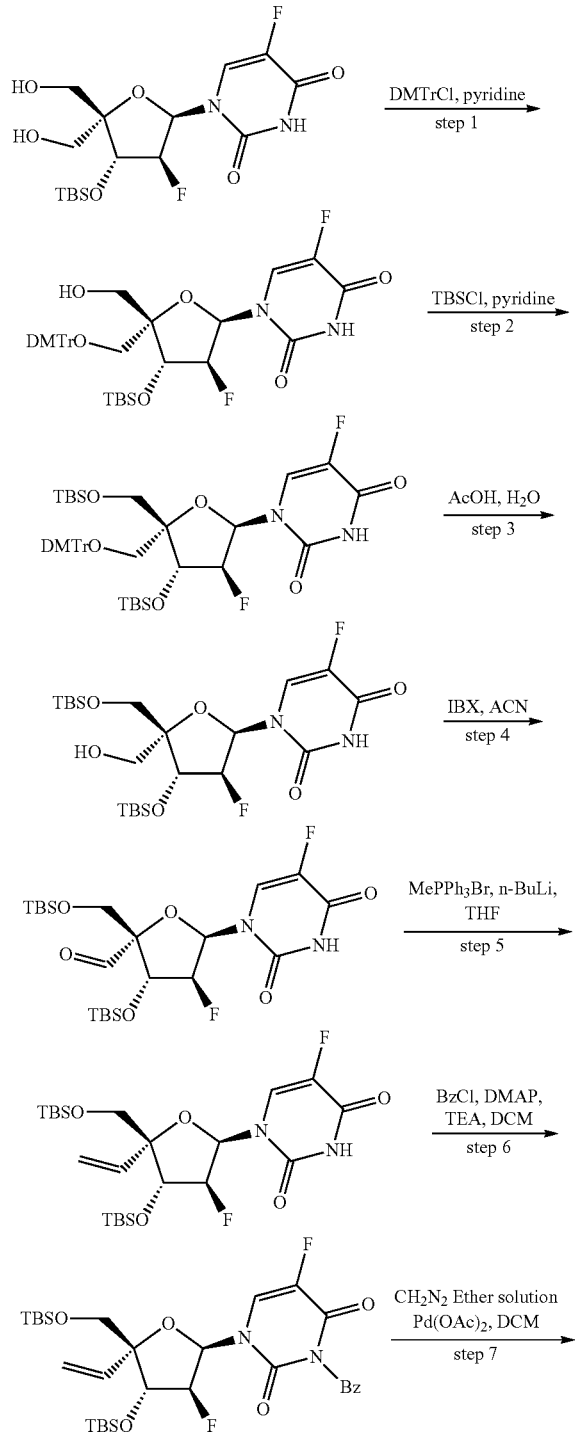

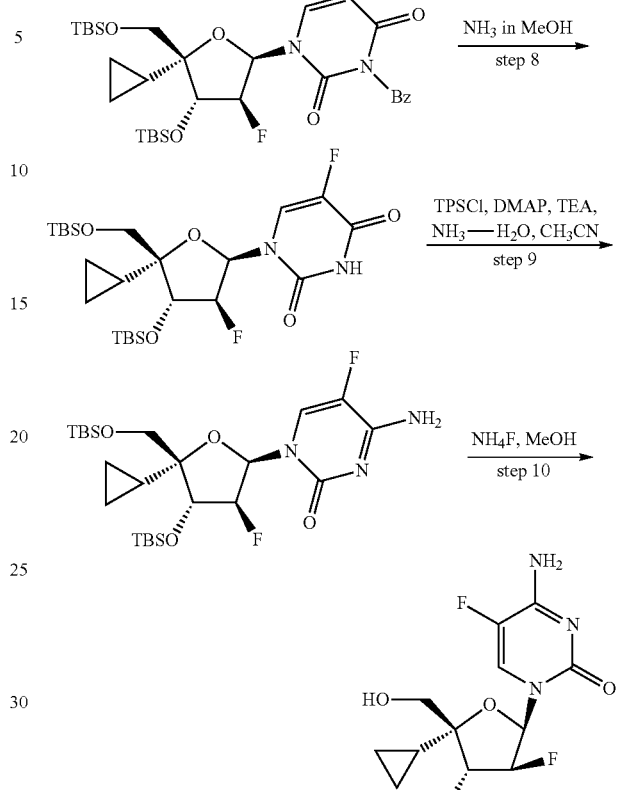

Step 1: To a solution of 1-[(2R,3S,4R)-4-[(tert-butyldimethylsilyl) oxy]-3-fluoro-5,5-bis(hydroxymethyl)oxolan-2-yl]-5-fluoro-3H-pyrimidine-2,4-dione (6.0 g, 14.61 mmol) in pyridine (60 mL) was added DMTrCl (6.4 g, 18.99 mmol) in portions at room temperature under $N_2$ atmosphere. The mixture was stirred overnight at room temperature. The resulting mixture was used in the next step directly without further purification. LC-MS (ES, m/z): 711 [M+H]$^+$.

Step 2: To the above solution was added TBSCl (3.8 g, 25.35 mmol) in portions at room temperature under $N_2$ atmosphere. The mixture was stirred overnight at room temperature. The resulting mixture was diluted with water and extracted with EtOAc (3×250 mL). The combined organic layers were washed with brine and dried over anhydrous $Na_2SO_4$. After filtration the filtrate was concentrated under reduced pressure. The crude product (12 g) was used in the next step directly without further purification. LC-MS (ES, m/z): 825 [M+H]$^+$.

Step 3: A solution of 1-[(2R,3S,4R,5R)-5-{[bis(4-methoxyphenyl)(phenyl) methoxy]methyl}-4-[(tert-butyldimethylsilyl)oxy]-5-{[(tert-butyldimethylsilyl)oxy]methyl}-3-fluorooxolan-2-yl]-5-fluoro-3H-pyrimidine-2,4-dione (12.0 g, 14.5 mmol) in AcOH (96 mL) and water (24 mL) was stirred overnight at room temperature under $N_2$ atmosphere. The resulting mixture was concentrated under vacuum. The residue was purified by silica gel column chromatography, eluting with DCM/MeOH (20:1) to afford 1-[(2R,3S,4R,5R)-4-[(tert-butyldimethylsilyl)oxy]-5-{[(tert-butyldimethylsilyl)oxy]methyl}-3-fluoro-5-(hydroxymethyl) oxolan-2-yl]-5-fluoro-3H-pyrimidine-2,4-dione (4.5 g, 8.6 mmol, 59.2%) as a white solid. LC-MS (ES, m/z): 523 [M+H]$^+$.

Step 4: A mixture of 1-[(2R,3S,4R,5R)-4-[(tert-butyldimethylsilyl) oxy]-5-{[(tert-butyldimethylsilyl) oxy] methyl}-3-fluoro-5-(hydroxymethyl) oxolan-2-yl]-5-fluoro-3H-pyrimidine-2,4-dione (4.5 g, 8.6 mmol) and IBX (7.2 g, 25.81 mmol) in ACN (45 mL) was stirred for 2 h at 60° C. under $N_2$ atmosphere. The resulting mixture was cooled to room temperature and filtered; the filter cake was washed with ACN (3×45 mL). The filtrate was concentrated under reduced pressure. The crude product (4.5 g, crude) was used in the next step directly without further purification. LC-MS (ES, m/z): 521 [M+H]$^+$.

Step 5: To a stirred solution of methyltriphenylphosphanium bromide (9.2 g, 25.91 mmol) in THF (45 mL) was added n-BuLi (10 mL, 25.9 mmol, 2.5 M in hexane) dropwise at −78° C. under $N_2$ atmosphere. The resulting mixture was stirred for 2 h at −50° C. under $N_2$ atmosphere. To the above mixture was added (2R,3R,4S,5R)-3-[(tert-butyldimethylsilyl)oxy]-2-{[(tert-butyl-dimethylsilyl)oxy]methyl}-4-fluoro-5-(5-fluoro-2,4-dioxo-3H-pyrimidin-1-yl)oxolane-2-carbaldehyde (4.5 g, 8.64 mmol) in THF (15 mL) at −50° C. under $N_2$ atmosphere. The resulting mixture was stirred overnight at room temperature. The resulting mixture was quenched with ice water and extracted with EtOAc (3×150 mL). The combined organic layers were washed with brine and dried over anhydrous $Na_2SO_4$. After filtration the filtrate was concentrated under reduced pressure. The residue was purified by silica gel column chromatography, eluting with DCM/MeOH (20:1) to afford 1-[(2R,3S,4R,5R)-4-[(tert-butyldimethylsilyl) oxy]-5-{[(tert-butyldimethylsilyl) oxy] methyl}-5-ethenyl-3-fluorooxolan-2-yl]-5-fluoro-3H-pyrimidine-2,4-dione (2.6 g, 5.01 mmol, 58%) as a white solid. LC-MS (ES, m/z): 519 [M+H]$^+$.

Step 6: To a stirred solution of 1-[(2R,3S,4R,5R)-4-[(tert-butyldimethylsilyl) oxy]-5-{[(tert-butyldimethylsilyl) oxy] methyl}-5-ethenyl-3-fluorooxolan-2-yl]-5-fluoro-3H-pyrimidine-2,4-dione (2.6 g, 5.01 mmol), DMAP (612 mg, 5.01 mmol) and TEA (1.5 g, 15.03 mmol) in DCM (25 mL) was added benzoyl chloride (1 g, 7.52 mmol) dropwise at room temperature under $N_2$ atmosphere. The resulting mixture was stirred overnight. The mixture was quenched with water and extracted with DCM (3×150 mL). The combined organic layers were washed with brine and dried over anhydrous $Na_2SO_4$. After filtration the filtrate was concentrated under reduced pressure. The residue was purified by silica gel column chromatography, eluting with DCM/MeOH (20:1) to afford 3-benzoyl-1-[(2R,3S,4R,5R)-4-[(tert-butyldimethylsilyl) oxy]-5-{[(tert-butyldimethylsilyl) oxy] methyl}-5-ethenyl-3-fluorooxolan-2-yl]-5-fluoropyrimidine-2,4-dione (2.1 g, 3.21 mmol, 67.3%) as a white solid. LC-MS (ES, m/z): 623 [M+H]$^+$.

Step 7: To a stirred mixture of 3-benzoyl-1-[(2R,3S,4R,5R)-4-[(tert-butyldimethylsilyl) oxy]-5-{[(tert-butyldimethylsilyl) oxy] methyl}-5-ethenyl-3-fluorooxolan-2-yl]-5-fluoropyrimidine-2,4-dione (720 mg, 1.16 mmol) and Pd(OAc)$_2$ (25 mg, 0.11 mmol) in DCM (10 mL) was added $CH_2N_2 \cdot Et_2O$ solution (60 mL) dropwise at room temperature under $N_2$ atmosphere. The resulting mixture was stirred overnight at room temperature under $N_2$ atmosphere. The resulting mixture was concentrated under reduced pressure. The residue was purified by Prep-TLC (DCM/MeOH 20:1) to afford 3-benzoyl-1-[(2R,3S,4R,5R)-4-[(tert-butyldimethylsilyl) oxy]-5-{[(tert-butyldimethylsilyl) oxy] methyl}-5-cyclopropyl-3-fluorooxolan-2-yl]-5-fluoropyrimidine-2,4-dione (620 mg, 0.97 mmol, 84.2%) as a white solid. LC-MS (ES, m/z): 637 [M+H]$^+$.

Step 8: To a solution of $NH_3(g)$ in MeOH (10 mL, 7 M), 3-benzoyl-1-[(2R,3S,4R,5R)-4-[(tert-butyldimethylsilyl) oxy]-5-{[(tert-butyldimethylsilyl) oxy] methyl}-5-cyclopropyl-3-fluorooxolan-2-yl]-5-fluoropyrimidine-2,4-dione (620 mg, 0.97 mmol) was added. The mixture was stirred overnight at room temperature under $N_2$ atmosphere. The resulting mixture was concentrated under reduced pressure. The residue was purified by Prep-TLC (DCM/MeOH 20:1) to afford 1-[(2R,3S,4R,5R)-4-[(tert-butyldimethylsilyl)oxy]-5-{[(tert-butyldimethylsilyl)oxy]methyl}-5-cyclopropyl-3-fluorooxolan-2-yl]-5-fluoro-3H-pyrimidine-2,4-dione (440 mg, 0.83 mmol, 84.8%) as a white solid. LC-MS (ES, m/z): 533 [M+H]$^+$.

Step 9: A solution of 1-[(2R,3S,4R,5R)-4-[(tert-butyldimethylsilyl) oxy]-5-{[(tert-butyldimethylsilyl) oxy] methyl}-5-cyclopropyl-3-fluorooxolan-2-yl]-5-fluoro-3H-pyrimidine-2,4-dione (440 mg, 0.83 mmol), DMAP (201 mg, 1.66 mmol) and TEA (167 mg, 1.66 mmol) in ACN (5 mL) was treated with 2,4,6-TPSCl (500 mg, 1.66 mmol) and stirred for 2 h at room temperature under $N_2$ atmosphere followed by the addition of concentrated ammonium hydroxide (2 mL) at room temperature. The resulting mixture was stirred for 30 mins at room temperature under $N_2$ atmosphere. The resulting mixture was diluted with water and extracted with EtOAc (3×50 mL). The combined organic layers were washed with brine and dried over anhydrous $Na_2SO_4$. After filtration the filtrate was concentrated under reduced pressure. The residue was purified by Prep-TLC (DCM/MeOH 10:1) to afford 4-amino-1-[(2R,3S,4R,5R)-4-[(tert-butyldimethylsilyl) oxy]-5-{[(tert-butyldimethylsilyl) oxy] methyl}-5-cyclopropyl-3-fluorooxolan-2-yl]-5-fluoropyrimidin-2-one (430 mg, 0.81 mmol, 97.9%) as a white solid. LC-MS (ES, m/z): 532 [M+H]$^+$.

Step 10: A mixture of 4-amino-1-[(2R,3S,4R,5R)-4-[(tert-butyldimethylsilyl) oxy]-5-{[(tert-butyldimethylsilyl) oxy] methyl}-5-cyclopropyl-3-fluorooxolan-2-yl]-5-fluoropyrimidin-2-one (430 mg, 0.81 mmol) and $NH_4F$ (703 mg, 20.25 mmol) in MeOH (20 mL) was stirred for 2 days at 60° C. under $N_2$ atmosphere. The resulting mixture was cooled to room temperature and concentrated under reduced pressure. The crude product was purified by Prep-HPLC with the following conditions (Column: XBridge Shield RP18 OBD Column, 30*150 mm, 5 μm; Mobile Phase A: water (10 mmol/L $NH_4HCO_3$+0.1% $NH_3 \cdot H_2O$), Mobile Phase B: ACN; Flow rate: 60 mL/min; Gradient: 13% B to 18% B in 9 min; Wavelength: 254/210 nm; RT1(min): 8.55). The fraction was collected and concentrated under vacuum, the residue was re-dissolved in $CH_3CN$ and $H_2O$ and lyophilized to afford 4-amino-1-[(2R,3S,4R,5R)-5-cyclopropyl-3-fluoro-4-hydroxy-5-(hydroxymethyl) oxolan-2-yl]-5-fluoropyrimidin-2-one (53.8 mg, 0.18 mmol, 21.9%) as a white solid. LC-MS (ES, m/z): 304 [M+H]$^+$, 99.9% purity. Conditions for the LCMS: (Column: Shim-pack Scepter C18, 33*3.0 mm; Mobile Phase A: Water/5 mM $NH_4HCO_3$, Mobile Phase B: Acetonitrile; Flow rate: 1.50 mL/min; Gradient: 10% B to 40% B in 1.70 min, 40% B to 95% B in 2.30 min, 95% B to 95% B in 2.80 min, 95% B to 10% B in 2.83 min; Wavelength: 254/220 nm; RT1(min): 0.572). $^1$H NMR (400 MHz, DMSO-d$_6$) δ 8.35 (d, J=7.4 Hz, 1H), 7.69 (d, J=91.9 Hz, 2H), 6.06 (td, J=6.0, 1.9 Hz, 1H), 5.94 (d, J=4.9 Hz, 1H), 5.55 (t, J=4.8 Hz, 1H), 5.18 (dt, J=54.6, 6.3 Hz, 1H), 4.49 (dt, J=23.1, 5.5 Hz, 1H), 3.62-3.44 (m, 2H), 1.06-0.94 (m, 1H), 0.49-0.17 (m, 4H).

Example 81—Synthesis of Compound 131: 4-amino-1-[(2R,3S,4R,5R)-5(E)-(2-chloroethenyl)-3-fluoro-4-hydroxy-5-(hydroxymethyl) oxolan-2-yl]-5-fluoropyrimidin-2-one

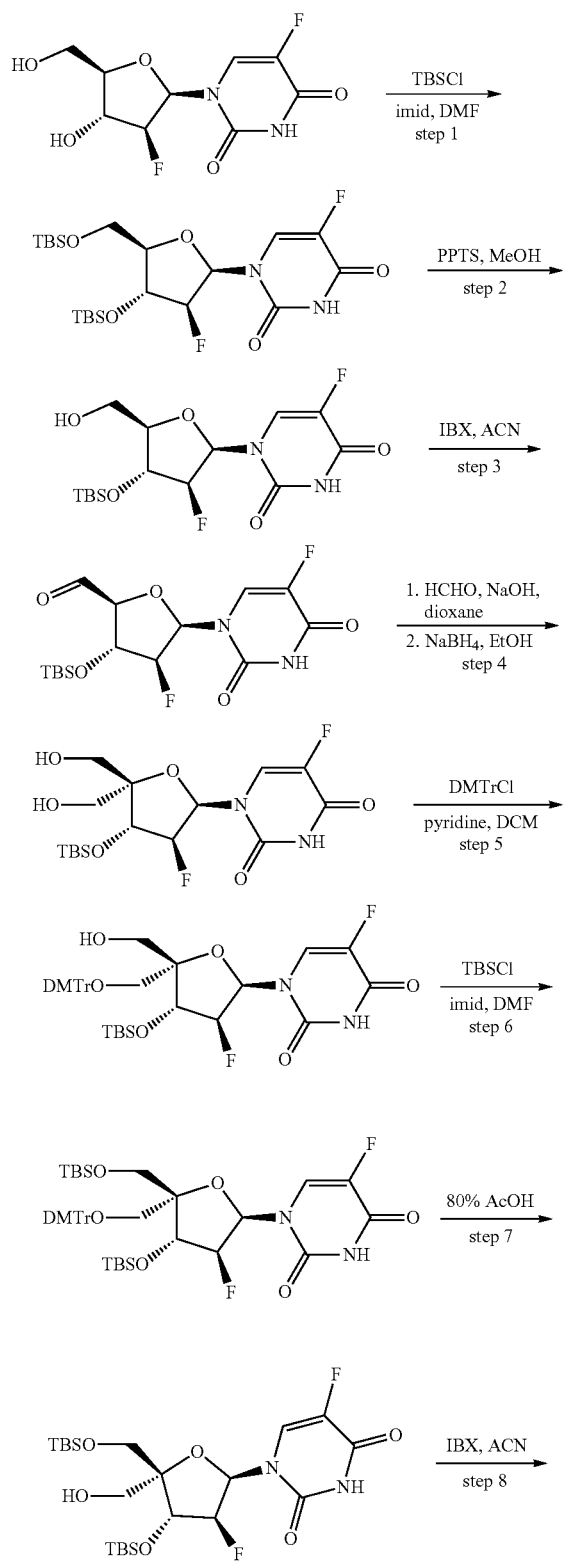

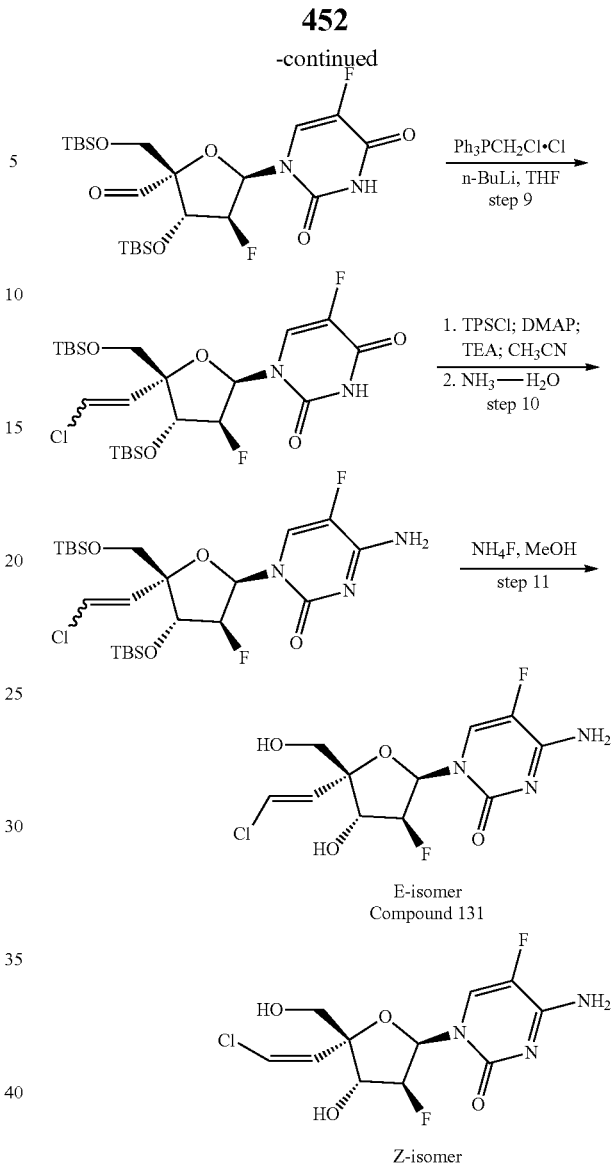

Step 1: To a stirred solution of 5-fluoro-1-[(2R,3S,4R,5R)-3-fluoro-4-hydroxy-5-(hydroxymethyl) oxolan-2-yl]-3H-pyrimidine-2,4-dione (25.0 g, 94.63 mmol) and imid (32.2 g, 473.16 mmol) in DMF (250 mL) was added t-butyldimethylchlorosilane (71.3 g, 473.16 mmol) in portions at 0° C. under nitrogen atmosphere. The resulting mixture was stirred for 3 h at room temperature under nitrogen atmosphere and quenched by the addition of water at 0° C. The resulting mixture was extracted with EtOAc. The combined organic layers were washed with brine and dried over anhydrous $Na_2SO_4$. After filtration the filtrate was concentrated under reduced pressure. The residue was purified by silica gel column chromatography, eluting with PE/EtOAc (10:1) to afford 1-[(2R,3S,4R,5R)-4-[(tert-butyldimethylsilyl) oxy]-5-{[(tert-butyldimethylsilyl) oxy]methyl}-3-fluorooxolan-2-yl]-5-fluoro-3H-pyrimidine-2,4-dione (36.0 g, 73.17 mmol, 77.2%) as a light-yellow solid. LC-MS (ES, m/z): 493 (M+H)⁺.

Step 2: To a stirred solution of 1-[(2R,3S,4R,5R)-4-[(tert-butyldimethylsilyl) oxy]-5-{[(tert-butyldimethylsilyl) oxy]methyl}-3-fluorooxolan-2-yl]-5-fluoro-3H-pyrimidine-2,4-dione (34.0 g, 69.01 mmol) in MeOH (340 mL) was added PPTS (34.7 g, 138.01 mmol) at room temperature. The resulting mixture was stirred for 3 h at 60° C., then cooled to 0° C. temperature and quenched by the addition of sat. NaHCO₃ (aq.) at 0° C. The resulting mixture was extracted with EtOAc. The combined organic layers were washed with brine and dried over anhydrous Na₂SO₄. After filtration the filtrate was concentrated under reduced pressure. The residue was purified by silica gel column chromatography, eluting with PE/EtOAc (5:1) to afford 1-[(2R,3S,4R,5R)-4-[(tert-butyldimethylsilyl) oxy]-3-fluoro-5-(hydroxymethyl) oxolan-2-yl]-5-fluoro-3H-pyrimidine-2,4-dione (22.0 g, 58.13 mmol, 84.2%) as a yellow solid. LC-MS (ES, m/z): 379 (M+H)⁺.

Step 3: To a stirred solution of 1-[(2R,3S,4R,5R)-4-[(tert-butyldimethylsilyl) oxy]-3-fluoro-5-(hydroxymethyl) oxolan-2-yl]-5-fluoro-3H-pyrimidine-2,4-dione (22.0 g, 58.13 mmol) in ACN (220 mL) was added IBX (32.6 g, 116.26 mmol) at room temperature. The resulting mixture was stirred for 5 h at 80° C. The resulting mixture was cooled to room temperature and filtered, the filter cake was washed with acetonitrile. The combined filtrate was concentrated under reduced pressure. This resulted in (2S,3R,4S,5R)-3-[(tert-butyldimethylsilyl) oxy]-4-fluoro-5-(5-fluoro-2,4-dioxo-3H-pyrimidin-1-yl) oxolane-2-carbaldehyde (20.6 g, crude) as a white solid. The crude product was used in the next step directly without further purification. LC-MS (ES, m/z): 377 (M+H)⁺.

Step 4: To a solution of (2S,3R,4S,5R)-3-[(tert-butyldimethylsilyl) oxy]-4-fluoro-5-(5-fluoro-2,4-dioxo-3H-pyrimidin-1-yl) oxolane-2-carbaldehyde (20.6 g, crude) in 1,4-dioxane (200 mL), were added HCHO (41.0 mL, 37% in water) and NaOH (aq.) (2M, 41.0 mL, 82.00 mmol). The resulting mixture was stirred overnight at room temperature under a nitrogen atmosphere. To the above mixture was added NaBH₄ (8.7 g, 229.84 mmol) in portions at 0° C. The resulting mixture was stirred for an additional 30 min at room temperature and quenched by the addition of sat. NH₄Cl aq. at 0° C. The resulting mixture was extracted with EtOAc. The combined organic layers were washed with brine and dried over anhydrous Na₂SO₄. After filtration the filtrate was concentrated under reduced pressure. The residue was purified by silica gel column chromatography, eluting with CH₂Cl₂/MeOH (20:1) to afford 1-[(2R,3S,4R)-4-[(tert-butyldimethylsilyl) oxy]-3-fluoro-5,5-bis(hydroxymethyl) oxolan-2-yl]-5-fluoro-3H-pyrimidine-2,4-dione (11.5 g, 28.19 mmol, 31.3% yield in two steps) as a white solid. LC-MS (ES, m/z): 409 (M+H)⁺.

Step 5: To a stirred solution of 1-[(2R,3S,4R)-4-[(tert-butyldimethylsilyl) oxy]-3-fluoro-5,5-bis(hydroxymethyl) oxolan-2-yl]-5-fluoro-3H-pyrimidine-2,4-dione (6.0 g, 14.69 mmol) in pyridine (48 mL) and DCM (12 mL) was added DMTrCl (5.5 g, 16.16 mmol) in portions at 0° C. under nitrogen atmosphere. The resulting mixture was stirred overnight at room temperature under nitrogen atmosphere and quenched by the addition of MeOH at room temperature. The resulting mixture was concentrated under reduced pressure. The residue was diluted with water (100 mL) and extracted with EtOAc. The combined organic layers were washed with brine and dried over anhydrous Na₂SO₄. After filtration the filtrate was concentrated under reduced pressure. The residue was purified by silica gel column chromatography, eluting with PE/EtOAc (3:1) to afford 1-[(2R,3S,4R,5S)-5-{[bis(4-methoxyphenyl) (phenyl)methoxy] methyl}-4-[(tert-butyldimethylsilyl) oxy]-3-fluoro-5-(hydroxymethyl) oxolan-2-yl]-5-fluoro-3H-pyrimidine-2,4-dione (8.0 g, 11.27 mmol, 76.6%) as a yellow solid. LC-MS (ES, m/z): 711 (M+H)⁺.

Step 6: To a stirred solution of 1-[(2R,3S,4R,5S)-5-{[bis(4-methoxyphenyl) (phenyl)methoxy] methyl}-4-[(tert-butyldimethylsilyl) oxy]-3-fluoro-5-(hydroxymethyl) oxolan-2-yl]-5-fluoro-3H-pyrimidine-2,4-dione (7.5 g, 10.55 mmol) and imid (2.2 g, 31.65 mmol) in DMF (80 mL) was added TBSCl (3.2 g, 21.10 mmo) in portions at 0° C. under nitrogen atmosphere. The resulting mixture was stirred for 2 h at room temperature under nitrogen atmosphere and then quenched by the addition of water at 0° C. The resulting mixture was extracted with EtOAc. The combined organic layers were washed with brine and dried over anhydrous Na₂SO₄. After filtration the filtrate was concentrated under reduced pressure. This resulted in 1-[(2R,3S,4R,5R)-5-{[bis(4-methoxyphenyl) (phenyl)methoxy] methyl}-4-[(tert-butyldimethylsilyl) oxy]-5-{[(tert-butyldimethylsilyl) oxy] methyl}-3-fluorooxolan-2-yl]-5-fluoro-3H-pyrimidine-2,4-dione (7.6 g, crude) as a yellow solid. The crude product was used in the next step directly without further purification. LC-MS (ES, m/z): 825 (M+H)⁺.

Step 7: A solution of 1-[(2R,3S,4R,5R)-5-{[bis(4-methoxyphenyl) (phenyl)methoxy] methyl}-4-[(tert-butyldimethylsilyl) oxy]-5-{[(tert-butyldimethylsilyl) oxy] methyl}-3-fluorooxolan-2-yl]-5-fluoro-3H-pyrimidine-2,4-dione (7.6 g, crude) in AcOH (150 mL, 80% in water) was stirred for overnight at room temperature. The mixture was concentrated under reduce pressure and the residue was dilute with water. The solution was adjusted to pH 7 with saturated NaHCO₃(aq.). The resulting mixture was extracted with EtOAc. The combined organic layers were washed with brine and dried over anhydrous Na₂SO₄. After filtration the filtrate was concentrated under reduced pressure. The residue was purified by silica gel column chromatography, eluting with PE/EtOAc (3:1) to afford 1-[(2R,3S,4R,5R)-4-[(tert-butyldimethylsilyl) oxy]-5-{[(tert-butyldimethylsilyl) oxy] methyl}-3-fluoro-5-(hydroxymethyl) oxolan-2-yl]-5-fluoro-3H-pyrimidine-2,4-dione (3.6 g, 6.90 mmol, 65.3% yield two steps) as a yellow solid. LC-MS (ES, m/z): 523 (M+H)⁺.

Step 8: To a stirred solution of 1-[(2R,3S,4R,5R)-4-[(tert-butyldimethylsilyl) oxy]-5-{[(tert-butyldimethylsilyl) oxy] methyl}-3-fluoro-5-(hydroxymethyl) oxolan-2-yl]-5-fluoro-3H-pyrimidine-2,4-dione (1.5 g, 2.87 mmol) in ACN (15 mL) was added IBX (1.0 g, 3.73 mmol) at room temperature. The resulting mixture was stirred for 3 h at 75° C. under. The resulting mixture was cooled to room temperature and filtered, the filter cake was washed with acetonitrile. The combined filtrate was concentrated under reduced pressure. This resulted in (2R,3R,4S,5R)-3-[(tert-butyldimethylsilyl) oxy]-2-{[(tert-butyldimethylsilyl) oxy] methyl}-4-fluoro-5-(5-fluoro-2,4-dioxo-3H-pyrimidin-1-yl) oxolane-2-carbaldehyde (1.5 g, crude) as a white solid. The crude product was used in the next step directly without further purification. LC (ES, m/z): 521 (M+H)⁺.

Step 9: To a stirred solution of chloro(chloromethyl) triphenyl-lambda5-phosphane (2.8 g, 8.07 mmol) in THF (20 mL) was added n-BuLi (2.5M in hexanes, 3.8 mL, 9.41 mmol) dropwise at −78° C. under nitrogen atmosphere. The resulting mixture was stirred for 50 min at −78° C. under nitrogen atmosphere. This was followed by the addition of (2R,3R,4S,5R)-3-[(tert-butyldimethylsilyl) oxy]-2-{[(tert-butyldimethylsilyl) oxy] methyl}-4-fluoro-5-(5-fluoro-2,4-dioxo-3H-pyrimidin-1-yl) oxolane-2-carbaldehyde (1.4 g, crude) at −78° C. under nitrogen atmosphere. The resulting mixture was stirred overnight at room temperature and quenched by the addition of sat. NH₄Cl (aq.) at 0° C. The resulting mixture was extracted with EtOAc. The combined organic layers were washed with brine and dried over anhydrous Na₂SO₄. After filtration the filtrate was concentrated under reduced pressure. The residue was purified by silica gel column chromatography, eluting with PE/EtOAc (3:1) to afford 1-[(2R,3S,4R,5R)-4-[(tert-butyldimethylsilyl) oxy]-5-{[(tert-butyldimethylsilyl) oxy] methyl}-5-(2-chloroethenyl)-3-fluorooxolan-2-yl]-5-fluoro-3H-pyrimidine-2,4-dione (810.0 mg, 1.46 mmol, 57.8%) as a light-yellow solid. LC-MS (ES, m/z): 553/555 (M+H)⁺.

Step 10: To a stirred solution of 1-[(2R,3S,4R,5R)-4-[(tert-butyldimethylsilyl) oxy]-5-{[(tert-butyldimethylsilyl) oxy] methyl}-5-(2-chloroethenyl)-3-fluorooxolan-2-yl]-5-fluoro-3H-pyrimidine-2,4-dione (810.0 mg, 1.46 mmol) and TEA (445.0 mg, 4.39 mmol) in CH₃CN (32 mL) were added DMAP (536.0 mg, 4.39 mmol) and 2,4,6-tris(propan-2-yl)benzene-1-sulfonyl chloride (2.2 g, 7.32 mmol) at room temperature. The resulting mixture was stirred for 2 h at room temperature. To the above mixture was added NH₃·H₂O (16.2 mL, 415.95 mmol) dropwise at room temperature. The resulting mixture was stirred for additional 1 h at room temperature. The mixture was neutralized to pH 7 with aq. HCl (1M). The resulting mixture was extracted with EtOAc. The combined organic layers were washed with brine and dried over anhydrous Na₂SO₄. After filtration the filtrate was concentrated under reduced pressure. The residue was purified by silica gel column chromatography, eluting with CH₂Cl₂/MeOH (10:1) to afford 4-amino-1-[(2R,3S,4R,5R)-4-[(tert-butyldimethylsilyl) oxy]-5-{[(tert-butyldimethylsilyl) oxy] methyl}-5-(2-chloroethenyl)-3-fluorooxolan-2-yl]-5-fluoropyrimidin-2-one (730.0 mg, 1.32 mmol, 90.28%) as a light-yellow solid. LC-MS (ES, m/z): 552/554 (M+H)⁺.

Step 11: To a solution of 4-amino-1-[(2R,3S,4R,5R)-4-[(tert-butyldimethylsilyl) oxy]-5-{[(tert-butyldimethylsilyl) oxy] methyl}-5-(2-chloroethenyl)-3-fluorooxolan-2-yl]-5-fluoropyrimidin-2-one (180.0 mg, 0.33 mmol) in MeOH (2 mL) was added NH₄F (360.0 mg, 9.72 mmol). The resulting mixture was stirred overnight at 60° C. under a N₂ atmosphere. The resulting mixture was cooled to room temperature and concentrated under reduced pressure. The crude product was purified by Prep-HPLC with the following conditions: Column: XBridge Shield RP18 OBD Column, 30*150 mm, 5 μm; Mobile Phase A: water (10 mmol/L NH₄HCO₃+0.1% NH₃·H₂O), Mobile Phase B: ACN; Flow rate: 60 mL/min; Gradient: 11% B to 16% B in 9 min; Wavelength: 254/210 nm; RT1(min): 6.68, RT2(min): 8.68. The product-containing fractions were combined and evaporated partially to remove the solvents, then lyophilized overnight to afford 4-amino-1-[(2R,3S,4R,5R)-5(E)-(2-chloroethenyl)-3-fluoro-4-hydroxy-5-(hydroxymethyl) oxolan-2-yl]-5-fluoropyrimidin-2-one (9.5 mg, 0.03 mmol, 8.99%) as a white solid and 4-amino-1-[(2R,3S,4R,5R)-5-(2-chloroethenyl)-3-fluoro-4-hydroxy-5(Z)-(hydroxymethyl) oxolan-2-yl]-5-fluoropyrimidin-2-one (20.3 mg, 0.06 mmol, 19.22%). Compound 131: LC-MS (ES, m/z): 324/326 (M+H)⁺. 99.8% purity. Compound 132: LC-MS (ES, m/z): 324/326 (M+H)⁺. 99.9% purity. Conditions for the LCMS: (Column: Shim-pack Scepter C18, 33*3.0 mm, 3.0 μm; Mobile Phase A: Water/5 mM NH₄HCO₃, Mobile Phase B: Acetonitrile; Flow rate: 1.5000 mL/min; Gradient: 10% B to 95% B in 1.20 min, 95% B to 95% B in 0.60 min, 95% B to 10% B in 0.02 min; Wavelength: 254 nm; RT1(min): 0.49).

Compound 131: ¹H NMR (400 MHz, DMSO-d₆) δ 8.09 (d, J=7.2 Hz, 1H), 7.87 (brs, 1H), 7.63 (brs, 1H), 6.53 (d, J=13.2 Hz, 1H), 6.19-6.14 (m, 2H), 6.06 (d, J=13.2 Hz, 1H), 5.56 (t, J=5.2 Hz, 1H), 5.09 (t, J=5.2 Hz, 0.5H), 4.96 (t, J=5.2 Hz, 0.5H), 4.45-4.40 (m, 1H), 3.58-3.53 (m, 1H), 3.49-3.45 (m, 1H).

Compound 132: ¹H NMR (400 MHz, DMSO-d₆) δ 8.05 (d, J=7.2 Hz, 1H), 7.89 (brs, 1H), 7.64 (brs, 1H), 6.52 (d, J=8.0 Hz, 1H), 6.21-6.20 (m, 1H), 6.11-6.08 (m, 1H), 6.00 (d, J=8.0 Hz, 1H), 5.55-5.53 (m, 1H), 5.08 (t, J=5.2 Hz, 0.5H), 4.94 (t, J=5.2 Hz, 0.5H), 4.48-4.41 (m, 1H), 3.77-3.73 (m, 1H), 3.54-3.50 (m, 1H).

Example 82—Synthesis of Compound 123: 4-amino-5-fluoro-1-((2R,3S,4R,5R)-3-fluoro-5-((Z)-2-fluorovinyl)-4-hydroxy-5-(hydroxymethyl)tetrahydrofuran-2-yl)pyrimidin-2(1H)-one

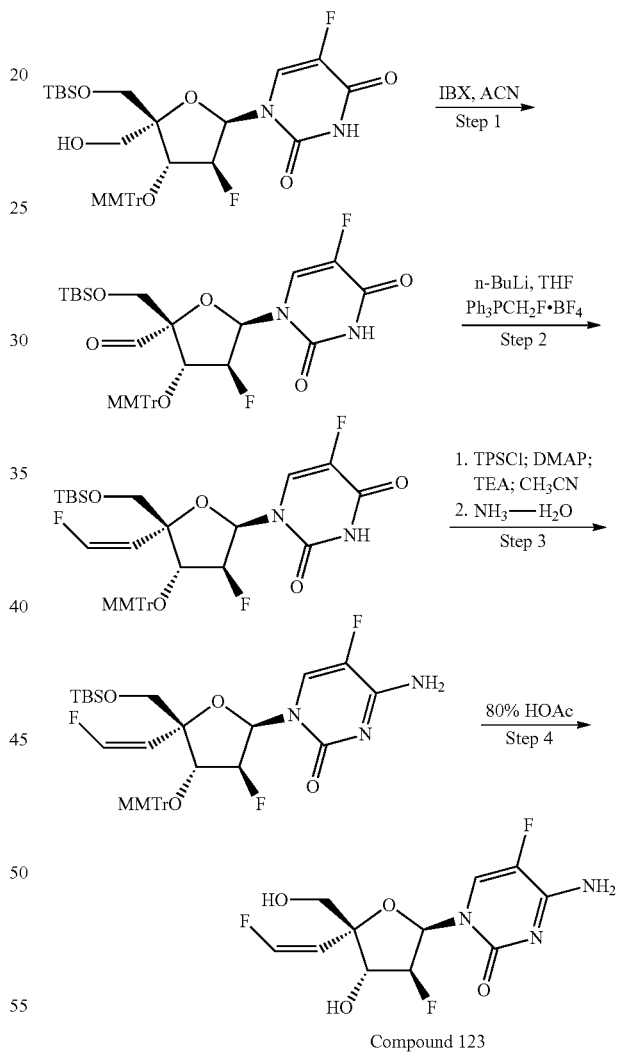

Compound 123

Step 1: A mixture of 1-[(2R,3S,4R,5R)-5-1{[(tert-butyldimethylsilyl)oxy]methyl}-3-fluoro-5-(hydroxymethyl)-4-[(4-methoxyphenyl)diphenylmethoxy]oxolan-2-yl]-5-fluoro-3H-pyrimidine-2,4-dione (487 mg, 0.72 mmol) and IBX (260 mg, 0.93 mmol) in anhydrous ACN (7.00 mL) was stirred for 1 h at 75° C. The mixture was cooled down to room temperature, filtered, the filter cake was washed with ACN. The filtrate was concentrated under reduced pressure. The residue was purified by silica gel column chromatography, eluted with DCM/Hexane (3/1) to afford (2R,3R,4S,5R)-2-{[(tert-butyldimethylsilyl)oxy]methyl}-4-fluoro-5-(5-fluoro-2,4-dioxo-3H-pyrimidin-1-yl)-3-[(4-methoxyphenyl)diphenylmethoxy]oxolane-2-carbaldehyde (390 mg, 0.58 mmol, 80%) as a yellow solid. LC-MS (ES, m/z): 677 [M−H]⁻.

Step 2: To a solution of (fluoromethyl)triphenylphosphanium tetrafluoroboranuide (878 mg, 2.30 mmol) in anhydrous THF (5.80 mL) was added, dropwise, a solution of n-BuLi in hexane (0.90 mL, 2.5 M) at −70° C. under nitrogen atmosphere. The reaction was stirred at −70° C. for 50 min. A solution of (2R,3R,4S,5R)-2-{[(tert-butyldimethyl-silyl)oxy]methyl}-4-fluoro-5-(5-fluoro-2,4-dioxo-3H-pyrimidin-1-yl)-3-[(4-methoxyphenyl) diphenylmethoxy]oxolane-2-carbaldehyde (390 mg, 0.58 mmol) in anhydrous THF (2.00 mL) was added at −70° C., and the reaction was stirred at 0° C. for 3 h and then at room temperature overnight. The reaction was quenched with sat. NH₄Cl aqueous (10 mL), the resulting mixture was extracted with EtOAc (3×10 mL). The combined organic layers were dried over anhydrous Na₂SO₄, filtered and concentrated under vacuum. The residue was purified by Prep-TLC (PE/EtOAc 2:1) to afford 1-((2R,3S,4R,5R)-5-(((tert-butyldimethylsilyl)oxy)methyl)-3-fluoro-5-((Z)-2-fluorovinyl)-4-((4-methoxyphenyl)diphenylmethoxy) tetrahydrofuran-2-yl)-5-fluoropyrimidine-2,4(1H,3H)-dione (150 mg, 0.2 mmol, 37%) as a colorless oil. LC-MS (ES, m/z): m/z 693 [M−H]⁻.

Step 3: To a solution of 1-((2R,3S,4R,5R)-5-(((tert-butyldimethylsilyl)oxy) methyl)-3-fluoro-5-((Z)-2-fluorovinyl)-4-((4-methoxyphenyl)diphenylmethoxy)tetrahydrofuran-2-yl)-5-fluoropyrimidine-2,4(1H,3H)-dione (130 mg, 0.19 mmol) in CH₃CN (3.00 mL), DMAP (45 mg, 0.37 mmol) and TEA (56 mg, 0.56 mmol) were added at room temperature. The mixture was degassed three times with nitrogen and stirred for 10 min at room temperature. To this mixture TPSCl (113 mg, 0.38 mmol) was added. The resulting mixture was stirred at room temperature until the starting material was consumed completely, and then NH₃·H₂O (4.00 mL, 30%) was added, and stirred at room temperature until the intermediate was completely converted to the desired product. The reaction mixture was concentrated under reduced pressure. The residue was diluted with water (10 mL) and extracted with EtOAc (3×10 mL). The organic layer was dried over anhydrous Na₂SO₄, filtered and concentrated under reduced pressure. The residue was purified by Prep-TLC (PE/EtOAc=1/2) to give 4-amino-1-((2R,3S,4R,5R)-5-(((tert-butyldimethylsilyl)oxy) methyl)-3-fluoro-5-((Z)-2-fluorovinyl)-4-((4-methoxyphenyl) diphenylmethoxy)tetrahydrofuran-2-yl)-5-fluoropyrimidin-2(1H)-one (80 mg, 0.11 mmol, 61%) as an off-white solid. LC-MS (ES, m/z): m/z 694 [M+H]⁺.

Step 4: A solution of 4-amino-1-((2R,3S,4R,5R)-5-(((tert-butyldimethylsilyl)oxy) methyl)-3-fluoro-5-((Z)-2-fluorovinyl)-4-((4-methoxyphenyl) diphenylmethoxy)tetrahydrofuran-2-yl)-5-fluoropyrimidin-2(1H)-one (70 mg, 0.10 mmol) in AcOH (8.0 mL, 80%) was stirred for 4 days at room temperature under nitrogen atmosphere. The resulting mixture was concentrated under vacuum. The residue was purified firstly via reverse phase chromatography with the following conditions (Column: Cis silica gel; Mobile phase A: water (containing 0.05% FA) and B: CH₃CN; Gradient: 0% to 20% B in 15 min; Detector: 254/220 nm). The product containing fraction was collected and concentrated under vacuum to give ~40 mg crude product. The crude product was re-purified by Prep-HPLC under the following conditions (Column: X-Select Prep OBD C18 Column, 30×150 mm, 5 μm; Mobile Phase A: water (0.05% FA), Mobile Phase B: ACN; Flow rate: 60 mL/min mL/min; Gradient: 30% B to 50% B in 7 min; wavelength: 254 nm/220 nm nm). The product-containing fraction was collected and concentrated under reduce pressure to remove some solvents and then lyophilized overnight to afford 4-amino-5-fluoro-1-((2R,3S,4R,5R)-3-fluoro-5-((Z)-2-fluorovinyl)-4-hydroxy-5-(hydroxymethyl)tetrahydrofuran-2-yl)pyrimidin-2(1H)-one (13.4 mg, 0.04 mmol, 28%) as a colorless oil. LC-MS (ES, m/z): 308 [M+H]⁺. 97.4% purity. HPLC conditions: (Column: Xselect HSS T3, 100×4.6 mm, 3.5 μm; Mobile Phase A: water/0.05% TFA, Mobile Phase B: MeOH; Flow rate: 1.20 mL/min; Gradient: 0% B to 60% B in 8.00 min, 60% B to 95% B in 2.00 min, 95% B to 10% B in 0.5 min; wavelength: 254 nm; RT1(min): 4.21). ¹H NMR (400 MHz, DMSO-d₆) δ 8.09 (d, J=7.2 Hz, 1H), 7.87 (br s, 1H), 7.63 (br s, 1H), 6.77 (dd, J=84, 5.6 Hz, 1H), 6.15-6.08 (m, 2H), 5.58 (br s, 1H), 5.14-4.91 (m, 2H), 4.99 (dd, J=48.4, 5.6 Hz, 1H), 4.44 (dd, J=23.6, 5.2 Hz, 1H), 3.68 (d, J=12.0 Hz, 1H), 3.58 (d, J=12.4 Hz, 1H).

Example 83—Synthesis of Compound 164: (2R,3S,5R)-5-(6-amino-2-fluoropurin-9-yl)-2-(hydroxymethyl)-2-(propa-1,2-dien-1-yl) oxolan-3-ol

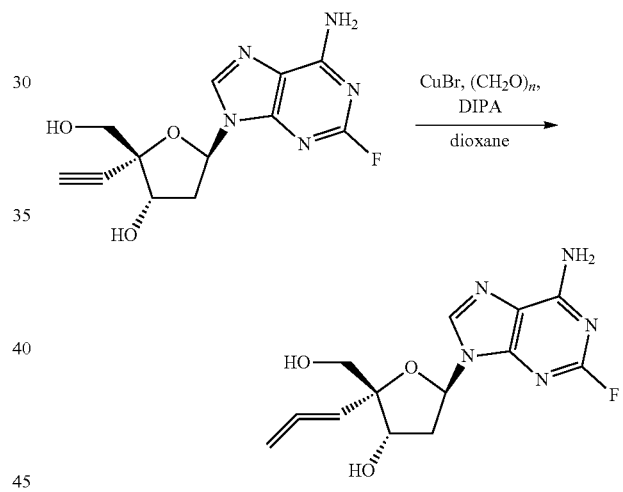

Step 1: To a stirred solution of (2R,3S,5R)-5-(6-amino-2-fluoropurin-9-yl)-2-ethynyl-2-(hydroxymethyl) oxolan-3-ol (150.0 mg, 0.51 mmol) in 1,4-dioxane (1.5 mL) were added CuBr (36.7 mg, 0.26 mmol), POM (30.9 mg, 0.34 mmol) and DIPA (129.4 mg, 1.28 mmol) at room temperature. The resulting mixture was stirred for 2 h at 140° C. The reaction was cooled to room temperature and quenched by the addition of sat. NH₄Cl aq. at 0° C. The resulting mixture was extracted with EtOAc, washed with brine and dried over anhydrous Na₂SO₄. After filtration the filtrate was concentrated under reduced pressure. The crude product was purified by Prep-HPLC with the following conditions: Column, XBridge Prep OBD C18 Column, 30*150 mm, 5 μm; mobile phase, water (10 mmol/L NH₄HCO₃) and ACN (10% ACN up to 14% in 6.5 min); UV detection at 254 nm. The product-containing fractions were combined and evaporated partially to remove the solvents, then lyophilized overnight to afford (2R,3S,5R)-5-(6-amino-2-fluoropurin-9-yl)-2-(hydroxymethyl)-2-(propa-1,2-dien-1-yl) oxolan-3-ol (32.4 mg, 0.11 mmol, 20.59%) as a white solid. LC-MS (ES, m/z): 308 (M+H)⁺. 99.9% purity. Conditions for the HPLC: (Column: Shim-pack Scepter C18, 33*3.0 mm, 3.0 μm; Mobile Phase A: water/5 mM NH$_4$HCO$_3$, Mobile Phase B: Acetonitrile; Flow rate: 1.5000 mL/min; Gradient: 10% B to 40% B in 1.69 min, 40% B to 95% B in 0.60 min, 95% B to 95% B in 0.50 min, 95% B to 10% B in 0.03 min; Wavelength: 254/220 nm; RT1(min): 0.783). $^1$H NMR (400 MHz, DMSO-d$_6$) δ 8.33 (s, 1H), 7.82 (brs, 2H), 6.19 (dd, J=7.2, 4.8 Hz, 1H), 5.40-5.36 (m, 2H), 5.14 (t, J=6.0 Hz, 1H), 5.02-4.91 (m, 2H), 4.63 (q, J=5.2 Hz, 1H), 3.56-3.53 (m, 2H), 2.61-2.56 (m, 1H), 2.39-2.32 (m, 1H).

Example 84—Synthesis of Compound 90: 4-amino-5-fluoro-1-((2R,3S,4R,5R)-3-fluoro-4-hydroxy-5-(hydroxymethyl)-5-methoxytetrahydrofuran-2-yl)pyrimidin-2(1H)-one

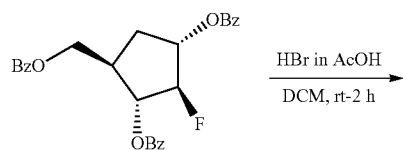
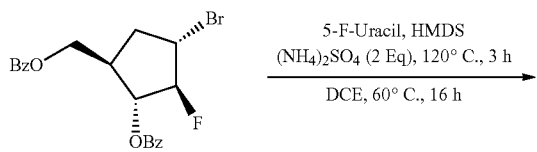
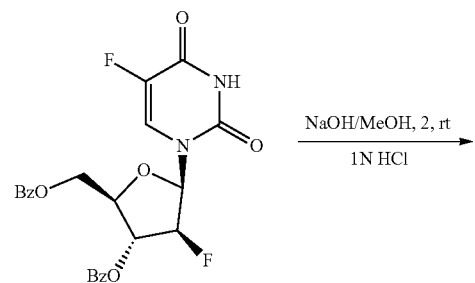
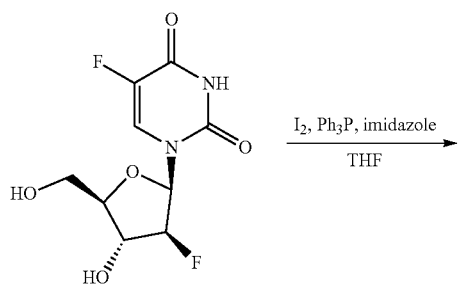
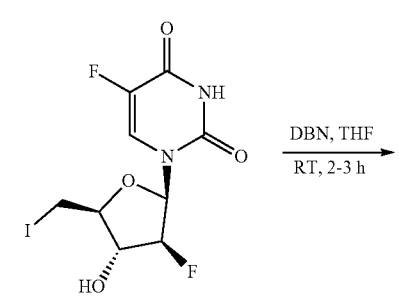
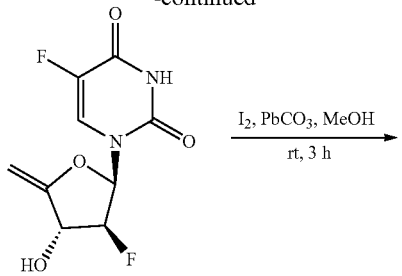
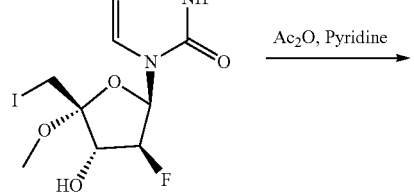
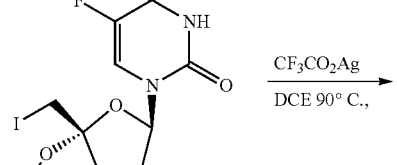
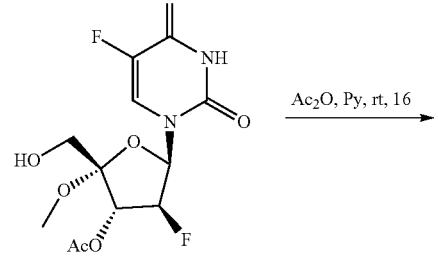
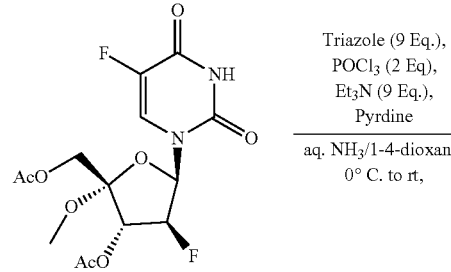
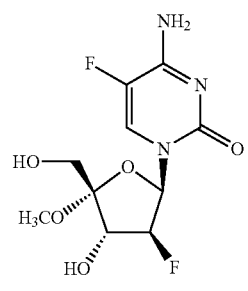

Compound 90

Step 1: To a stirred solution of (2R,3S,4R,5R)-5-((benzoyloxy)methyl)-3-fluorotetrahydrofuran-2,4-diyl dibenzoate (100 g, 215.308 mmol) in DCM (1000 mL) was added HBr in Acetic acid (300 mL) in a drop wise manner at 0° C. After stirring the reaction for 2 h, TLC showed complete reaction. After completion, the reaction mixture was diluted with ice water (500 mL) and DCM (500 mL) made basic with NaHCO$_3$ solution and extracted with DCM (3×500 mL). The combined organics were washed with water (3×500 mL) and brine (2×500 mL), then dried over sodium sulphate, filtered, and concentrated to get the titled compound (48g) as white foam type sticky solid which was used as such for the next step without purification. LC-MS (ES, m/z): 423.90 (M+1).

Step 2: To a stirred solution of 5-fluorouracil (50 g, 384.378 mmol) in HMDS (500 mL) was added ammonium sulfate (101.58 g, 768.757 mmol). The resulting reaction mixture was stirred at 120° C. for 3 h, then cooled to room temperature and concentrated under vacuum. To the above residue was added a solution of ((2R,3R,4S,5R)-3-(benzoyloxy)-5-bromo-4-fluorotetrahydrofuran-2-yl) methyl benzoate (89.47 g, 211.408 mmol) in DCE (700 mL). The resulting reaction mixture was stirred at 80° C. for 16 h. The reaction mixture was partitioned between brine solution (500 mL) and DCM (500 mL). The organic layer was separated, and the combined organics were washed with water (2×500 mL) and brine (2×500 mL), dried over sodium sulphate, filtered, and concentrated to get a crude product. The crude product was dissolved in DCM (250 mL) and to this n-hexane (750 mL) was added while stirring. The obtained solid was filtered and washed with hexane and dried under vacuum to get desired product (80 g, 80.11%) as white solid. LC-MS (ES, m/z): 473.2 (M+1).

Step 3: To a stirred solution of ((2R,3R,4S,5R)-3-(benzoyloxy)-4-fluoro-5-(5-fluoro-2,4-dioxo-3,4-dihydropyrimidin-1(2H)-yl) tetrahydrofuran-2-yl) methyl benzoate (10 g, 21.1685 mmol) in MeOH (100 mL) was added NaOH (2.11 g, 52.92 mmol) in a portion wise manner at rt. The resulting mixture was stirred at rt for 16 h. The reaction progress was monitored and after completion, it was neutralized with 1N HCl and later concentrated under vacuum to get the crude material (6.0 g) as white solid which was used as such for the next step. LC-MS (ES, m/z): 265.10 (M+1).

Step 4: To a stirred solution 5-fluoro-1-((2R,3S,4R,5R)-3-fluoro-4-hydroxy-5-(hydroxymethyl)tetrahydrofuran-2-yl)pyrimidine-2,4(1H,3H)-dione (5 g, 18.93 mmol) and imidazole (2.57 g, 37.853 mmol) in THF (100 mL) was added triphenylphosphine (7.44 g, 28.3897 mmol) at rt and the reaction mixture was stirred for 15 min; after that iodine (7.20 g, 28.39 mmol) was added in a portionwise manner at 0° C. After stirring the reaction mixture at rt for 16 h, the mixture was filtered and washed with THF (50 mL). The filtrate was concentrated under reduced pressure to afford crude compound. The crude material was dissolved in DCM (500 mL), washed with water (200 mL) and aqueous layer was extracted with DCM (200 mL). The combined organics were washed with water (300 mL), brine (300 mL), dried over anhydrous Na$_2$SO$_4$, filtered, and concentrated under reduced pressure to afforded crude compound. The crude material was purified by CombiFlash column chromatography, eluting with 10% MeOH in DCM to afford the desired product (2.5 g, 35.31%) as white solid. LC-MS (ES, m/z): 374.65 (M+H).

Step 5: To a stirred solution of 5-fluoro-1-((2R,3S,4R,5S)-3-fluoro-4-hydroxy-5-(iodomethyl) tetrahydrofuran-2-yl) pyrimidine-2,4(1H,3H)-dione (1.7 g, 4.54 mmol) in THF (30 mL) was added DBN (2.24 mL, 18.18 mmol) at rt. The resulting clear solution was stirred at rt for 16 h After completion, the reaction mixture was concentrated under reduced pressure to afford the crude compound. The crude product was purified by CombiFlash chromatography eluting with 4% MeOH in DCM to afford desired product (0.9 g, 81.81%) as white solid. LC-MS (ES, m/z): 244.95 (M−1).

Step 6: To a stirred solution of 5-fluoro-1-((2R,3S,4R)-3-fluoro-4-hydroxy-5-methylenetetrahydrofuran-2-yl) pyrimidine-2,4(1H,3H)-dione (100 mg, 0.4062 mmol) in MeOH (2 mL) was added PbCO$_3$ (217.09 mg, 0.8124 mmol) followed by iodine (230.58 mg, 0.8124 mmol) in MeOH (1 mL) at 0° C. After stirring the resulting reaction mixture at rt for 16 h, the reaction mixture was concentrated, and the resulting residue was purified by CombiFlash chromatography eluting with 4% MeOH in DCM to afford the desired product (150 mg) as white solid. LC-MS (ES, m/z): 403.0 (M−1).

Step 7: To a stirred solution of 5-fluoro-1-((2R,3S,4R,5S)-3-fluoro-4-hydroxy-5-(iodomethyl)-5-methoxytetrahydrofuran-2-yl) pyrimidine-2,4(1H,3H)-dione (0.50 g, 1.23 mmol) in Pyridine (10 mL) added acetic anhydride (0.442 mL, 4.33 mmol) in a dropwise manner at ice cold condition and stirred at rt for 4 h. The reaction mixture was concentrated and resulting residue was purified by CombiFlash chromatography eluted with 4% MeOH in DCM to afford the desired product (450 mg, 85.70%) as a white solid. LC-MS (ES, m/z): 446.25 (M+H).

Step 8: To a stirred solution of (2S,3R,4S,5R)-4-fluoro-5-(5-fluoro-2,4-dioxo-3,4-dihydropyrimidin-1(2H)-yl)-2-(iodomethyl)-2-methoxytetrahydrofuran-3-yl acetate (0.300 g, 0.673 mmol) in DCE (10 mL) was added silver trifluoroacetate (1.48 g, 6.73 mmol) at 0° C. and stirred at rt for 16 h. The reaction progress was monitored by TLC analysis and LCMS. After completion, the reaction mixture was concentrated under reduced pressure to afford the crude compound (300 mg) as white solid. LC-MS (ES, m/z): 336.61 (M+H)$^+$.

Step 9: To a stirred solution of (2R,3R,4S,5R)-4-fluoro-5-(5-fluoro-2,4-dioxo-3,4-dihydropyrimidin-1(2H)-yl)-2-(hydroxymethyl)-2-methoxytetrahydrofuran-3-yl acetate (0.20 g, 0.595 mmol) in pyridine (5 mL) was added acetic anhydride (0.243 mL, 2.38 mmol) in a dropwise manner at 0° C. and stirred at rt for 16 h. After completion, the reaction mixture was concentrated and resulting residue was purified by CombiFlash chromatography eluted with 4% MeOH in DCM to afford the desired product (200 mg, 88.82%) as a white solid. LC-MS (ES, m/z): 376.90 (M−1).

Step 10: To a solution of triazole (0.33 g, 4.76 mmol) in pyridine (3 mL) was added phosphorus oxychloride (0.162 g, 1.058 mmol) at 0° C. After 5 min triethylamine (0.481 g, 4.761 mmol) was added dropwise manner at 0° C., the above solution was stirred for 30 min at the same temp. The uracil derivative (0.20 g, 0.53 mmol) dissolved in dry pyridine (2 mL) and was added to the above reaction mixture at 0° C. in a drop wise manner. The reaction was stirred at 0° C. for 2.5 h. The reaction mixture was concentrated and co-evaporated with toluene (2×20 mL). The crude product was dissolved with DCM (100 mL) and washed twice with brine (60 mL). The aqueous layer was extracted with DCM (30 mL). Combined organic layers were dried over anhydrous Na$_2$SO$_4$, filtered, and evaporated. The resulting residue was dissolved in 1,4-dioxane (20 mL), cooled to 0° C. and aqueous ammonia 25% (20 mL) were added. The resulting solution was stirred at rt for 2 h and the reaction progress was monitored by TLC and LCMS. After completion, the solution was evaporated and co-evaporated with toluene (3×20 mL). The crude product was purified by prep-HPLC by following below conditions. Mobile Phase: A: 0.02% NH$_4$OH in water; B: MeCN; Column: X SELECT (250 mm×20.0 mm), 5.0μ; Flow rate: 15 mL/min; Gradient program: Time/% B: 0/5, 2/10, 8/25 to afford desired product (8.5 mg, 32%) as a white solid. LC-MS (ES, m/z): 294.1 (M+1). ¹H NMR (400 MHz, DMSO-d$_6$) δ=8.13-7.78 (m, 3H), 6.25-6.19 (m, 1H), 5.30-5.10 (m, 1H), 4.42-4.32 (m, 1H), 3.76-3.70 (m, 1H), 3.50 (dd, J=10.4, 11.3 Hz, 2H), 3.27 (s, 3H).
Example 85—Synthesis of Compound 58: 1-((2R, 3S,4R,5R)-5-(chloromethyl)-3-fluoro-4-hydroxy-5-(hydroxymethyl)tetrahydrofuran-2-yl)-5-methylpyrimidine-2,4(1H,3H)-dione
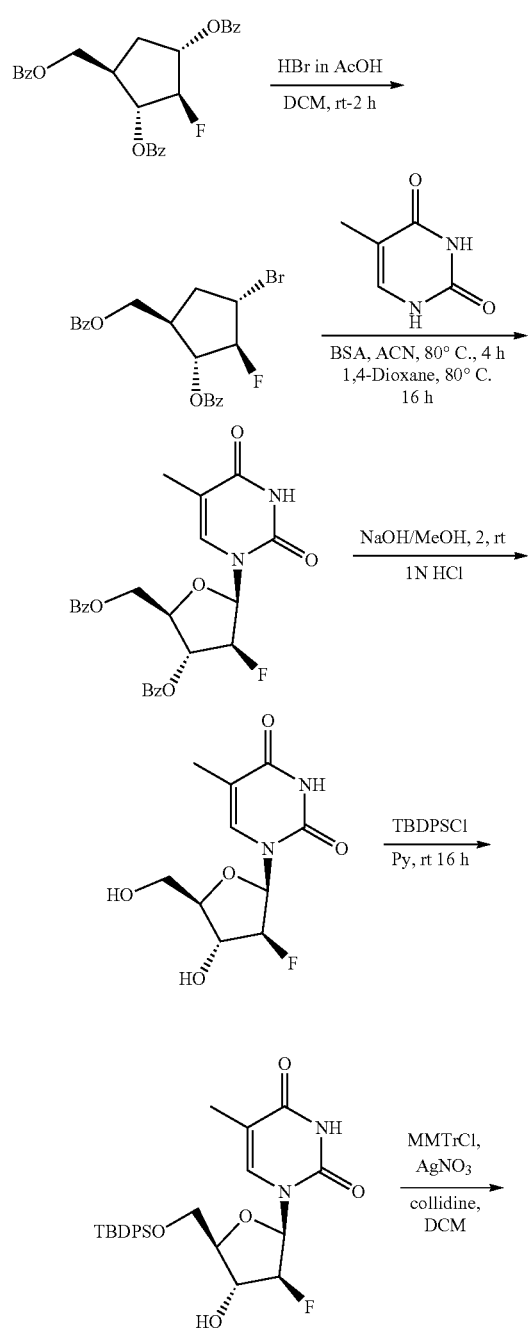
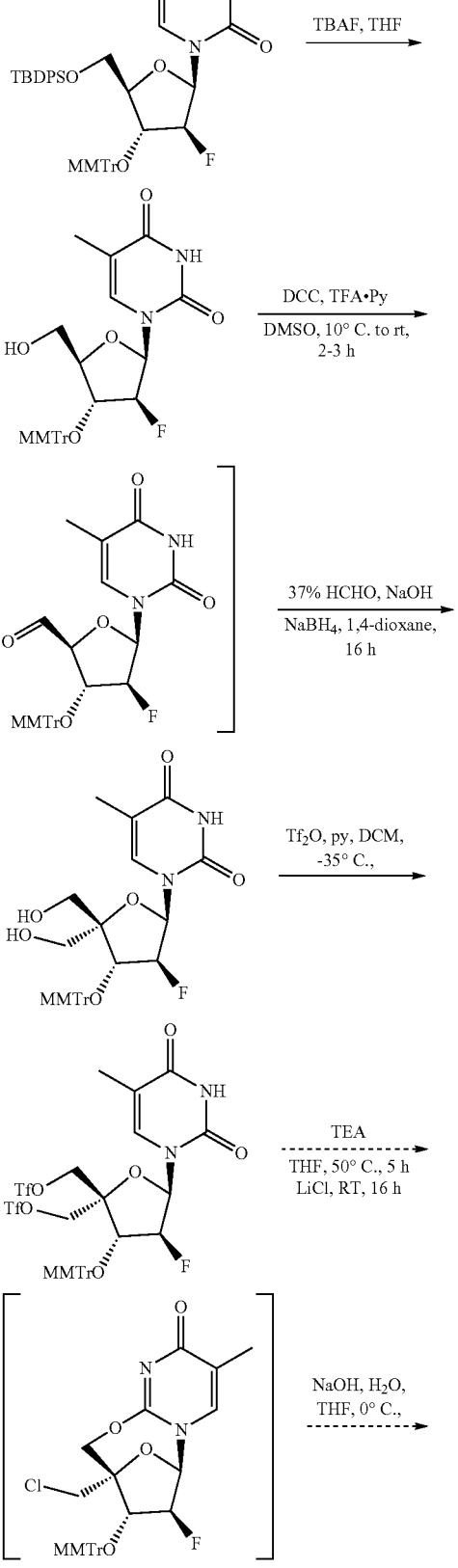

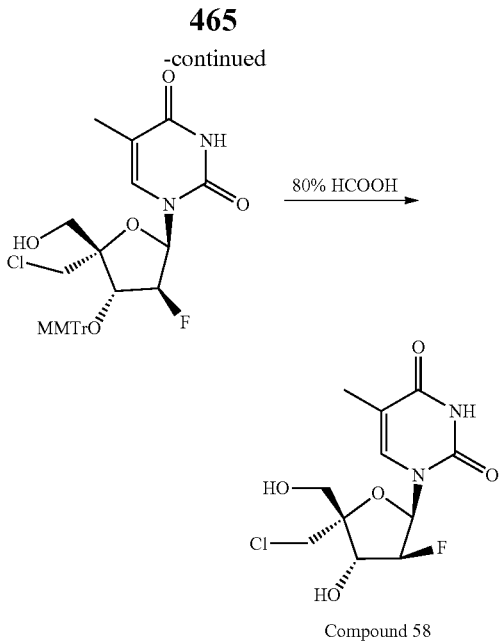

Compound 58

Step 1: To a stirred solution of (2R,3S,4R,5R)-5-((benzoyloxy)methyl)-3-fluorotetrahydrofuran-2,4-diyl di-benzoate (6 g, 12.92 mmol) in DCM (60 mL) was added HBr in AcOH (18 mL) in a dropwise manner at 0° C. The reaction was stirred for 2 h at 0° C. The reaction mixture was quenched with ice and then extracted with DCM (150 mL). The combined organics were washed with water (2×100 mL), saturated NaHCO₃ solution (2×100 mL), dried over Na₂SO₄, filtered, and concentrated under reduced pressure to afford crude compound. LC-MS (ES, m/z): 423.90 (M+2).

Step 2: A stirred solution of Thymine (3 g, 23.7887 mmol) and BSA (12.79 mL, 52.3352 mmol) in ACN (30 mL) was heated at 80° C. for 4 h, then cooled to room temperature and concentrated under vacuum. To the above residue was added a solution of ((2R,3R,4S,5R)-3-(benzoyloxy)-5-bromo-4-fluorotetrahydrofuran-2-yl)methyl benzoate (5.53 g, 13.08 mmol) in 1,4-Dioxane (40 mL) at 0° C. The reaction was stirred for 16 h at 80° C. After completion, the reaction mixture was cooled to room temperature and extracted with water and DCM. The organic layer was separated, dried over Na₂SO₄, filtered, and concentrated under reduced pressure to afforded crude compound. The crude product was recrystallized from DCM and n-Hexane to afford the desired product (5.6 g, 50.26%) as white solid. LC-MS (ES, m/z): 469.2 (M+1).

Step 3: To a stirred solution of ((2R,3R,4S,5R)-3-(benzoyloxy)-4-fluoro-5-(5-methyl-2,4-dioxo-3,4-dihydropyrimidin-1(2H)-yl) tetrahydrofuran-2-yl) methyl benzoate (28 g, 59.78 mmol) in MeOH (300 mL) was added NaOH (5.97 g, 149.432 mmol) in a portionwise manner at 0° C. under nitrogen atmosphere. After stirring the reaction mixture at rt for 16 the reaction mixture was neutralized with 1N HCl and concentrated under vacuum to get crude material (15.1 g) as white solid used as such for the next step. LC-MS (ES, m/z): 261.15 (M+H).

Step 4: To a stirred solution of 1-((2R,3S,4R,5R)-3-fluoro-4-hydroxy-5-(hydroxymethyl) tetrahydrofuran-2-yl)-5-methylpyrimidine-2,4(1H,3H)-dione (15.1 g, 58.03 mmol) in pyridine (150 mL) was added TBDPSCl (19.74 mL, 75.44 mmol) at 0° C. After stirring the reaction mixture at rt for 16 h the reaction was concentrated at low pressure and diluted with ice water (500 mL) and EtOAc (500 mL). The organic layer was separated, washed with water (3×500 mL) and brine (2×500 mL), dried over sodium sulphate, filtered, and concentrated and resulting residue was purified by CombiFlash chromatography by eluting with 30% EtOAc in Hexane to afford desired product (19.3 g, 66.71%) as white solid which was used as such for the next step. LC-MS (ES, m/z): 499.2 (M+H).

Step 5: To a stirred solution of 1-((2R,3S,4R,5R)-5-(((tert-butyldiphenylsilyl) oxy)methyl)-3-fluoro-4-hydroxytetrahydrofuran-2-yl)-5-methylpyrimidine-2,4(1H,3H)-dione (22 g, 44.1208 mmol) in DCM (300 mL) was added collidine (6.89 mL, 52.94 mmol) followed by AgNO₃ (8.99 g, 52.95 mmol) and MMTrCl (16.34 g, 52.95 mmol) at 0° C. After stirring the reaction mixture at rt for 16 h, the reaction mixture quenched with methanol and stirred for 20 min. The reaction mixture was concentrated and resulting residue purified by CombiFlash chromatography by eluting with 30% EtOAc in Hexane to afford the desired product (23 g, 67.64%) as white solid. LC-MS (ES, m/z): 771.40 (M+1).

Step 6: To a stirred solution of 1-((2R,3S,4R,5R)-5-(((tert-butyldiphenylsilyl)oxy) methyl)-3-fluoro-4-((4-methoxyphenyl)diphenylmethoxy)tetrahydrofuran-2-yl)-5-methylpyrimidine-2,4(1H,3H)-dione (24.5 g, 31.7781 mmol) in THF (250 mL) was added TBAF (79.44 mL, 79.4453 mmol) at 0° C. The resulting reaction mixture was stirred at RT for 16 h and the reaction progress was monitored by TLC and LCMS. After completion, the reaction mass was concentrated and diluted with ice water (500 mL) and EtOAc (500 mL). The organic later was separated, washed with water (3×500 mL) and brine (2×500 mL), dried over sodium sulphate, filtered, and concentrated. The crude product was purified by CombiFlash chromatography by eluting with 30% EtOAc in Hexane to afford the desired product (14 g, 82.74%) as white solid which was used as such for the next step. LC-MS (ES, m/z): 533.15 (M+1).

Step 7: To a stirred solution of 1-((2R,3S,4R,5R)-3-fluoro-5-(hydroxymethyl)-4-((4-methoxyphenyl)diphenylmethoxy)tetrahydrofuran-2-yl)-5-methylpyrimidine-2,4 (1H,3H)-dione (13 g, 24.41 mmol) in DMSO (130 mL) was added DCC (15.10 g, 73.23 mmol) followed by TFA. Py (4.71 g, 24.41 mmol) at 0° C. The resulting reaction mixture was stirred at rt for 2 and, the reaction mixture was diluted with water and EtOAc at rt. The obtained solids were filtered washed with EtOAc. The filtrate was extracted with EtOAc, organic layer was washed with water, brine, dried over anhydrous Na₂SO₄, filtered, and concentrated under reduced pressure to obtain crude aldehyde (13 g) which was used as such for the next step.

Step 8: To a stirred solution of (2S,3R,4S,5R)-4-fluoro-3-((4-methoxyphenyl) diphenylmethoxy)-5-(5-methyl-2,4-dioxo-3,4-dihydropyrimidin-1(2H)-yl)tetrahydrofuran-2-carbaldehyde (13 g, 24.5028 mmol) in Dioxane (130 mL) was added 37% HCHO (13 mL) followed by the addition of 2N NaOH solution (26 mL). After stirring, the reaction mixture at rt for 16 h, NaBH₄ (2.31 g, 61.26 mmol) was added at 0° C. and stirring was continued of another at RT for 1 h. The reaction progress was monitored by TLC and LCMS. After completion, the reaction mixture quenched with NH₄Cl solution at 0° C. and resulting mixture was extracted with EtOAc (500 mL). The combined organics were washed with water (3×500 mL) and brine (2×500 mL), then dried over sodium sulphate, filtered, and concentrated. The crude product was purified by CombiFlash chromatography by eluting with 30% EtOAc in Hexane to afford desired product (10 g, 76.92%) as white solid which was used as such for the next step. LC-MS (ES, m/z): 561.10 (M−1).

Step 9: To a stirred solution of 1-((2R,3S,4R)-3-fluoro-5,5-bis(hydroxymethyl)-4-((4-methoxyphenyl)diphenylmethoxy)tetrahydrofuran-2-yl)-5-methylpyrimidine-2,4(1H,3H)-dione (3.5 g, 6.22 mmol) in DCM (50 mL) was added pyridine (2.5 mL, 31.11 mmol) followed by the addition of triflic anhydride (3.15 mL, 18.66 mmol) at −35° C. The resulting reaction mixture was stirred at rt for 2 h. The reaction mixture quenched with NaHCO$_3$ solution and extracted with EtOAc (300 mL). The combined organics were washed with water (3×200 mL) and brine (2×200 mL), then dried over sodium sulphate, filtered, and concentrated. The crude product was purified by CombiFlash chromatography by eluting with 30% EtOAc in Hexane to afford the desired product (2.0 g, 38.91%) as white solid which was used as such for the next step. LC-MS (ES, m/z): 826.7 (M+1).

Step 10: To a stirred solution of ((3R,4S,5R)-4-fluoro-3-((4-methoxyphenyl) diphenylmethoxy)-5-(5-methyl-2,4-dioxo-3,4-dihydropyrimidin-1(2H)-yl)tetrahydrofuran-2,2-diyl)bis(methylene) bis(trifluoromethanesulfonate) (2 g, 2.42 mmol) in THF (30 mL) was added Et$_3$N (3.36 mL, 24.2 mmol) at rt. After stirring the reaction mixture at 50° C. for 5 h, the reaction mixture was cooled to rt and then LiCl (307.6 mg, 7.26 mmol) was added and stirring was continued at rt for 16 h. After completion, the reaction mixture was concentrated under reduced pressure to afford the desired product (1.5 g) as a white solid which was used as such for the next step. LC-MS (ES, m/z): 563.2 (M+H).

Step 11: To a stirred solution of (6R,7S,8R,9R)-9-(chloromethyl)-7-fluoro-8-((4-methoxyphenyl)diphenylmethoxy)-3-methyl-7,8,9,10-tetrahydro-2H,6H-6,9-epoxypyrimido[2,1-b][1,3]oxazocin-2-one (1.5 g, 2.6642 mmol) in THF (30 mL) was added 1N NaOH solution (6.66 mL, 6.66 mmol) at 0° C. The resulting reaction mixture was stirred at RT for 3 h and the reaction progress was monitored by TLC and LCMS. The reaction mixture was quenched with NH$_4$Cl solution at 0° C. and extracted with EtOAc (300 mL). The combined organics were washed with water (3×200 mL) and brine (2×200 mL), dried over sodium sulphate, filtered, concentrated and the resulting residue was purified by CombiFlash chromatography by eluting with 30% EtOAc in Hexane to afford the desired product (0.8 g, 51.94%) as white solid. LC-MS (ES, m/z): 578.95 (M−1).

Step 12: To a stirred solution of 1-((2R,3S,4R,5R)-5-(chloromethyl)-3-fluoro-5-(hydroxymethyl)-4-((4-methoxyphenyl) diphenyl methoxy) tetrahydrofuran-2-yl)-5-methylpyrimidine-2,4(1H,3H)-dione (200 mg, 0.344 mmol) in DCM (4 mL) was added 80% HCOOH (2 mL) at 0° C. The resulting reaction mixture was stirred at rt for 3 h and the reaction was concentrated and the residue was purified by prep-HPLC by the following conditions: Mobile Phase: A=0.1% HCOOH IN water, B=CAN; Column: Gemini NX (250 mm×21.2 mm), 5.0µ; Flow: 18 mL/min; Gradient program: Time/% B: 0/10,2/20,8/40 to afford desired product (30 mg, 29.12%) as white solid. LC-MS (ES, m/z): 309.0 (M+1). $^1$H NMR (400 MHz, DMSO-d$_6$) δ=11.48-11.38 (m, 1H), 7.60 (s, 1H), 6.26 (dd, J=4.8, 14.2 Hz, 1H), 6.19 (d, J=5.1 Hz, 1H), 5.46 (t, J=5.4 Hz, 1H), 5.29-5.12 (m, 1H), 4.55-4.45 (m, 1H), 3.87 (d, J=11.9 Hz, 1H), 3.70 (d, J=11.7 Hz, 1H), 3.67-3.56 (m, 2H), 1.78 (d, J=0.9 Hz, 3H).

Example 86—Synthesis of Compound 91: 4-amino-5-fluoro-1-((2R,4S,5R)-4-hydroxy-5-(hydroxymethyl)-5-methoxytetrahydrofuran-2-yl)pyrimidin-2(1H)-one

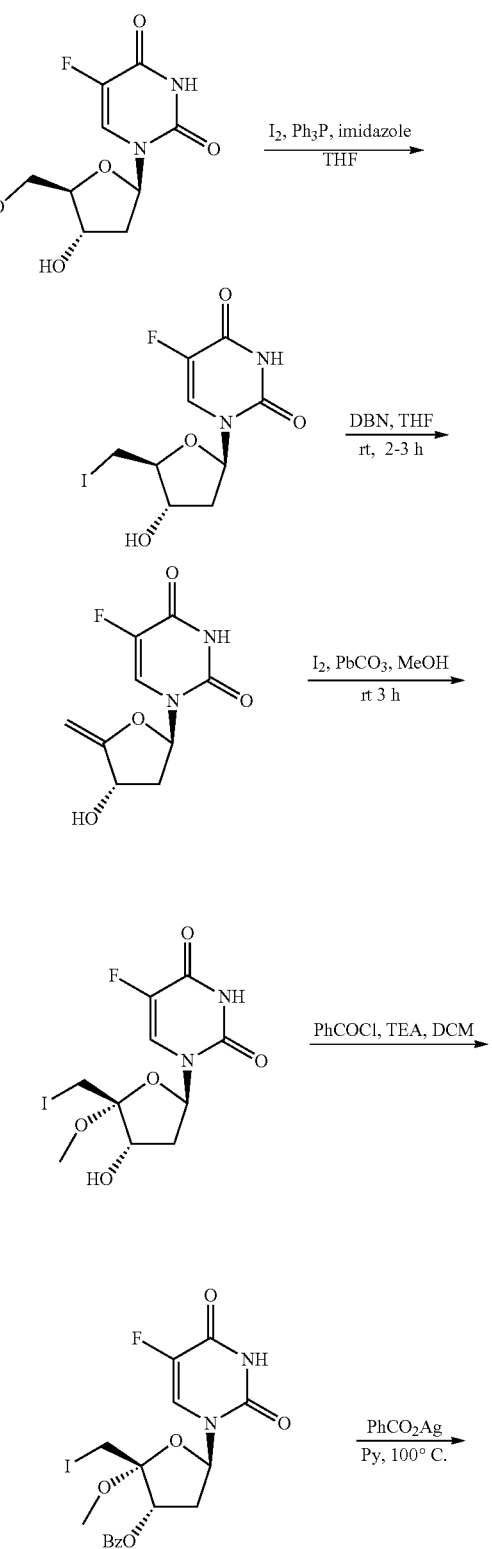

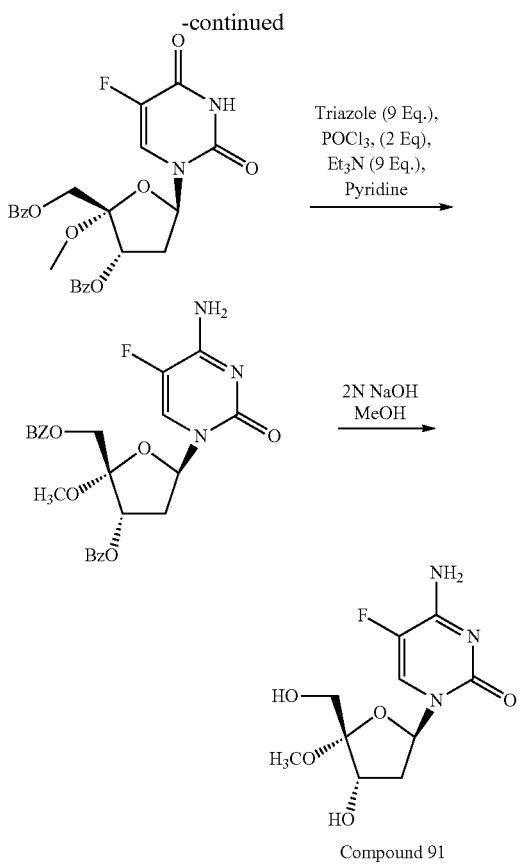

Compound 91

Step 1: To a stirred solution of 5-fluoro-1-((2R,4S,5R)-4-hydroxy-5-(hydroxymethyl)tetrahydrofuran-2-yl)pyrimidine-2,4(1H,3H)dione (10 g, 40.619 mmol in THF (100 mL), was imidazole (5.6 g, 101.54 mmol) at 0° C., followed by triphenylphosphine (16 g, 60.928 mmol), and iodine (7.73 g, 60.928 mmol). The reaction mixture was stirred for 16 h at room temperature and then the reaction mixture was partitioned between water (100 mL) and EtOAc (250 mL). The organics were separated and dried over Na$_2$SO$_4$. The solution was filtered and the solvent was removed under reduced pressure to afforded crude compound. The crude residue was purified by CombiFlash column chromatography, eluting with 20-30% EtOAc in Hexane to afford desired product as white solid (6.3 g). LC-MS (ES, m/z): 356.90 (M+H)$^+$.

Step 2: To a stirred solution of 5-fluoro-1-((2R,4S,5S)-4-hydroxy-5-(iodomethyl) tetrahydrofuran-2-yl)pyrimidine-2,4(1H,3H)-dione (6.3 g, 17.692 mmol) in THF (100 mL) was added DBN (6.59 g, 53.076 mmol). The reaction was stirred for 6 h at rt. And concentrated to afford the crude product as a brown liquid. The crude residue was purified by CombiFlash column chromatography, eluting with 3% MeOH in DCM to afford desired product as brown liquid (3 g). LC-MS (ES, m/z): 227.0 (M–H).

Step 3: A stirred solution of 5-fluoro-1-((2R,4S)-4-hydroxy-5-methylene-tetrahydrofuran-2-yl)pyrimidine-2,4 (1H,3H)-dione (2 g, 8.77 mmol) in methanol (20 mL) was purged with argon. The reaction was treated with PbCO$_3$ (4.68 g, 13.14 mmol) followed by Iodine (4.5 g, 13.14 mmol) at rt. The reaction was stirred for 6 h at rt. The reaction mixture was diluted with ice water (50 mL) and quenched with sodium bisulfite solution (20 mL), and extracted with EtOAc (3*100 mL). The combined extracts were washed with water and brine, then dried over sodium sulphate, filtered, and concentrated to afford the crude product as brown solid. (0.7 g). LC-MS (ES, m/z): 384.90 (M–H).

Step 4: To a stirred solution of 5-fluoro-1-((2R,4S,5S)-4-hydroxy-5-(iodomethyl)-5-methoxytetrahydrofuran-2-yl)pyrimidine-2,4(1H,3H)-dione (0.7 g, 1.8129 mmol) in DCM (5 mL) was added pyridine (0.6 mL, 5.44 mmol). The reaction was stirred for 15 min. and to this BzCl (0.3 mL, 1.99 mmol) was added at 0° C. and stirring was continued at rt for 2 h. The reaction progress was monitored by TLC and LCMS. After completion, the reaction mixture was diluted with ice water (25 mL) extracted with DCM (2×75 mL). The combined organic fractions were washed with water and brine, then dried over sodium sulphate, filtered, concentrated, and resulting residue was purified by CombiFlash column chromatography eluting with 70% EtOAc in n-Hexane to afford the desired product as brown solid (0.3 g). LC-MS (ES, m/z): 489.20 (M–H).

Step 5: To a stirred solution of (2S,3S,5R)-5-(5-fluoro-2,4-dioxo-3,4-dihydropyrimidin-1(2H)-yl)-2-(iodomethyl)-2-methoxytetrahydrofuran-3-yl benzoate (0.65 g, 1.32 mmol) in pyridine (5 mL) was added silver benzoate (1.82 g, 7.96 mmol) at rt. After stirring the reaction mixture at 110° C. for 4 h, the reaction mixture was diluted with ice water (10 mL), extracted with EtOAc (2×50 mL). The combined organic fractions were washed with water and brine, then dried over sodium sulphate, filtered, concentrated, and resulting residue was purified by CombiFlash column chromatography eluting with 55% EtOAc in n-Hexane to afford the desired product (0.55 g, 85.67%) as brown solid. LC-MS (ES, m/z): 483.30 (M–H).

Step 6: To a stirred solution of 1,2,4-Triazole (0.257 g, 3.716 mmol) in pyridine (4 mL) was added POCl$_3$ (0.127 g, 0.826 mmol) at 0° C. To this Et$_3$N (0.376 g, 3.72 mmol) was added and stirred for 30 min at the same temp. To this ((2R,3S,5R)-3-(benzoyloxy)-5-(5-fluoro-2,4-dioxo-3,4-dihydropyrimidin-1(2H)-yl)-2-methoxytetrahydrofuran-2-yl) methyl benzoate (0.250 g, 0.413 mmol) in pyridine (4 mL) was added at 0° C. and stirred at rt for 2 h. The reaction progress was monitored by TLC and after completion, the reaction mixture was concentrated to dryness and co-distilled with Toluene. The crude was dissolved in DCM and washed with Brine solution, dried over Na$_2$SO$_4$, and concentrated. The above crude material was dissolved in aq. NH$_4$OH:1,4-Dioxane (1:3) (4 mL) at 0° C. and after stirring the reaction mixture at rt for 2 h, the reaction mixture was concentrated and resulting residue was purified by Prep-TLC purification by eluting with 5% MeOH in DCM to afford the desired product (0.150 g, 58.59%) as white solid. LC-MS (ES, m/z): 482.05 (M–H).

Step 7: To a stirred solution of (2R,3S,5R)-5-(4-amino-5-fluoro-2-oxopyrimidin-1(2H)-yl)-2-((benzoyloxy) methyl)-2-methoxytetrahydrofuran-3-yl benzoate (0.150 g, 0.3103 mmol) in MeOH (5 mL) was added 2M NaOH (0.5 mL). The reaction was stirred for 15 min and the pH adjusted to ~5. The reaction mixture was concentrated. The resulting residue was purified by chiral prep purification by following below conditions; column: Regis (S,S) Whelk-O1, 250 mm×21.1 mm, 5 µm; mobile phase: n-Hexane(A) and EtOH (B); Flow: 15 mL; gradient: Time; Solvent (B) 0/30, 10/50; diluents: EtOH: DCM, 3:1, 5 mL; Injection volume-0.750 mL; run Time-15 min to afford the desired compound (8 mg, 9.41%) as white solid. LC-MS (ES, m/z): 276.10 (M+1). $^1$H NMR (400 MHz, DMSO-d$_6$) δ=8.22-8.01 (m, 1H), 7.80-7.37 (m, 2H), 6.04-6.01 (m, 1H), 5.39-5.31 (m, 1H), 4.91 (br d, J=6.7 Hz, 1H), 4.39-4.29 (m, 1H), 3.74-3.66 (m, 1H), 3.51-3.43 (m, 1H), 3.28 (s, 3H), 2.31-2.20 (m, 1H), 2.08 (ddd, J=2.5, 8.1, 13.1 Hz, 1H).

Example 87—Synthesis of Compound 177: 4-amino-5-fluoro-1-((2R,3S,4R)-3-fluoro-4-hydroxy-5,5-bis(hydroxymethyl)tetrahydrofuran-2-yl)pyrimidin-2(1H)-one

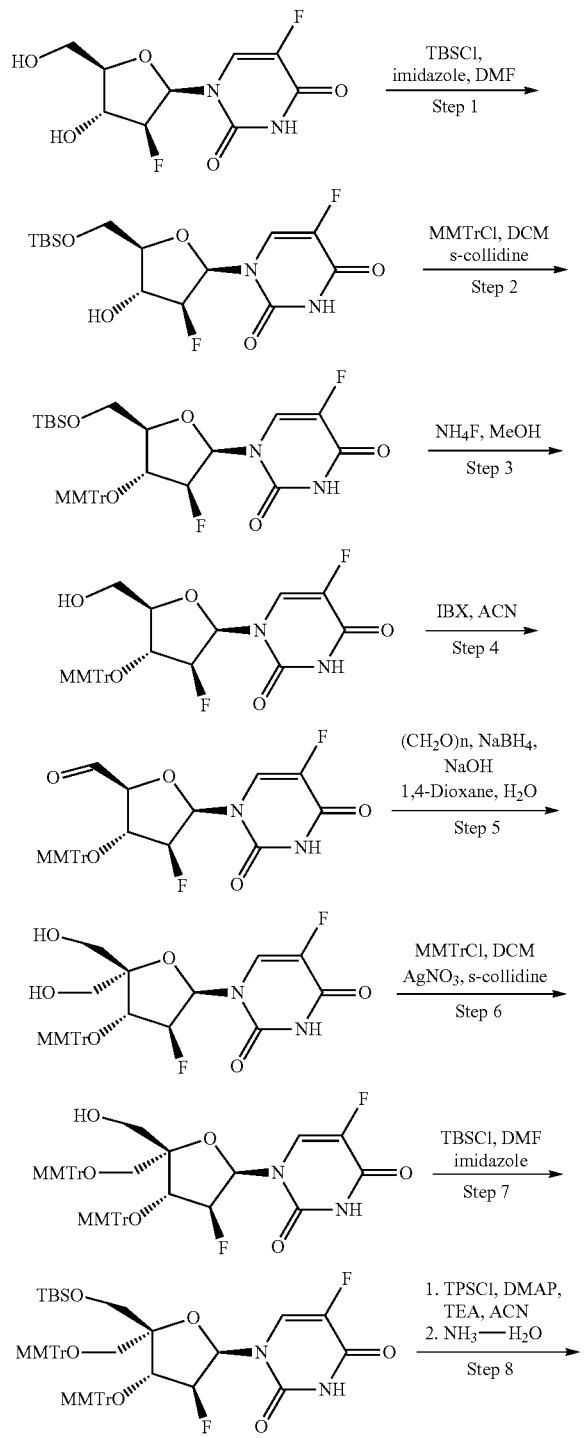

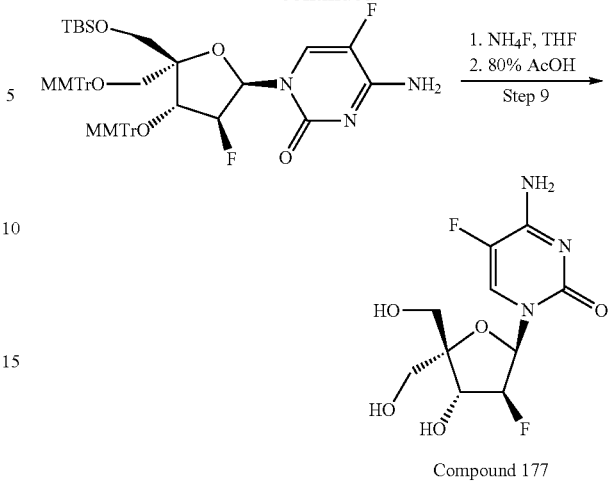

Compound 177

Step 1: To a stirred solution of imidazole (7.7 g, 114 mmol) and 5-fluoro-1-((2R,3S,4R,5R)-3-fluoro-4-hydroxy-5-(hydroxymethyl) tetrahydrofuran-2-yl) pyrimidine-2,4 (1H,3H)-dione (10 g, 37.9 mmol) in DMF (100 mL) was added TBSCl (6.9 g, 45.4 mmol) in portions at 0° C. under $N_2$ atmosphere. The reaction was stirred for 4 h at room temperature. The resulting mixture was diluted with water and extracted with EtOAc (3×200 mL). The combined organic layers were washed with brine and dried over anhydrous $Na_2SO_4$. After filtration the filtrate was concentrated under reduced pressure to afford the product (10.6 g, crude) which was used in the next step directly without further purification. LCMS (ES, m/z): 379 [M+H]$^+$.

Step 2: To a stirred solution of 1-((2R,3S,4R,5R)-5-(((tert-butyldimethylsilyl) oxy) methyl)-3-fluoro-4-hydroxytetrahydrofuran-2-yl)-5-fluoropyrimidine-2,4(1H,3H)-dione (10.6 g, 28 mmol) in DCM (100 mL) were added s-collidine (10.2 g, 84 mmol) and MMTrCl (17.3 g, 56.1 mmol) in portions at 0° C. under $N_2$ atmosphere. The reaction was stirred overnight at room temperature. The resulting mixture was diluted with water and extracted with DCM (3×100 mL). The combined organic layers were washed with brine and dried over anhydrous $Na_2SO_4$. After filtration the filtrate was concentrated under reduced pressure to afford the product (15 g, crude) which was used in the next step directly without further purification. LCMS (ES, m/z): 651 [M+H]$^+$.

Step 3: A solution of $NH_4F$ (3.4 g, 92.4 mmol) and 1-((2R,3S,4R,5R)-5-(((tert-butyldimethylsilyl) oxy) methyl)-3-fluoro-4-((4-methoxyphenyl) diphenylmethoxy) tetrahydrofuran-2-yl)-5-fluoropyrimidine-2,4(1H,3H)-dione (15 g, 23.1 mmol) in MeOH (150 mL) was stirred overnight at 45° C. under $N_2$ atmosphere. The resulting mixture was cooled to room temperature. The resulting mixture was filtered and the filter cake was washed with EA. The filtrate was concentrated under reduced pressure to afford the product (10.2 g, crude) which was used in the next step directly without further purification. (ES, m/z): 537 [M+H]$^+$.

Step 4: To a stirred solution of 5-fluoro-1-((2R,3S,4R,5R)-3-fluoro-5-(hydroxymethyl)-4-((4-methoxyphenyl) diphenylmethoxy) tetrahydrofuran-2-yl) pyrimidine-2,4(1H,3H)-dione (10.2 g, 19.1 mmol) in ACN (98 mL) was added IBX (10.2 g, 36.5 mmol) in portions at room temperature under $N_2$ atmosphere. The resulting mixture was stirred overnight at 50° C. The resulting mixture was cooled to room temperature. The resulting mixture was filtered and the filter cake was washed with ACN. The filtrate was concentrated under reduced pressure to afford the product (9.8 g, crude) which was used in the next step directly without further purification. LCMS (ES, m/z): 535 [M+H]⁺.

Step 5: To a solution of (2S,3R,4S,5R)-4-fluoro-5-(5-fluoro-2,4-dioxo-3,4-dihydropyrimidin-1(2H)-yl)-3-((4-methoxyphenyl) diphenylmethoxy) tetrahydrofuran-2-carbaldehyde (9.8 g, 18.3 mmol) in 1,4-dioxane (98 mL) was added paraformaldehyde (2.8 g, 91.6 mmol) in portions at 0° C. under N₂ atmosphere. Then NaOH (2.2 g, 55 mmol) in H₂O (9.8 mL) was added at 0° C. under N₂ atmosphere. The resulting mixture was stirred overnight at room temperature under N₂ atmosphere. Then was added NaBH₄ (2.1 g, 55 mmol) at 0° C. under N₂ atmosphere. The resulting mixture was stirred for additional 30 min at room temperature under N₂ atmosphere. The resulting mixture was quenched with water at 0° C. and extracted with EtOAc (3×300 mL). The combined organic layers were washed with brine and dried over anhydrous Na₂SO₄. After filtration the filtrate was concentrated under reduced pressure. The residue was purified by silica gel column chromatography, eluting with DCM/MeOH (15:1) to afford 5-fluoro-1-((2R,3S,4R)-3-fluoro-5,5-bis(hydroxymethyl)-4-((4-methoxyphenyl) diphenylmethoxy) tetrahydrofuran-2-yl) pyrimidine-2,4(1H,3H)-dione (9.8 g, 17.3 mmol, 94.3%) as a yellow solid. LCMS (ES, m/z): 567 [M+H]⁺.

Step 6: To a stirred solution of 5-fluoro-1-((2R,3S,4R)-3-fluoro-5,5-bis(hydroxymethyl)-4-((4-methoxyphenyl) diphenylmethoxy) tetrahydrofuran-2-yl) pyrimidine-2,4(1H,3H)-dione (9.8 g, 17.3 mmol) in DCM (98 mL) was added AgNO₃ (5.9 g, 34.6 mmol) and s-collidine (8.4 g, 69.2 mmol) at room temperature under N₂ atmosphere. Then was added MMTrCl (8 g, 25.9 mmol) at 0° C. under N₂ atmosphere. The resulting mixture was stirred overnight at 40° C. under N₂ atmosphere. The resulting mixture was cooled to room temperature. The resulting mixture was diluted with water and extracted with DCM (3×100 mL). The combined organic layers were washed with brine and dried over anhydrous Na₂SO₄. After filtration the filtrate was concentrated under reduced pressure. The residue was purified by silica gel column chromatography, eluting with PE/EA (4:1) to afford 5-fluoro-1-((2R,3S,4R,5S)-3-fluoro-5-(hydroxymethyl)-4-((4-methoxyphenyl) diphenylmethoxy)-5-(((4-methoxyphenyl) diphenylmethoxy) methyl) tetrahydrofuran-2-yl) pyrimidine-2,4(1H,3H)-dione (4 g, 4.81 mmol, 27.6%) as a yellow solid. LCMS (ES, m/z): 839 [M+H]⁺.

Step 7: To a stirred solution of 5-fluoro-1-((2R,3S,4R,5S)-3-fluoro-5-(hydroxymethyl)-4-((4-methoxyphenyl) diphenylmethoxy)-5-(((4-methoxyphenyl) diphenylmethoxy) methyl) tetrahydrofuran-2-yl) pyrimidine-2,4(1H,3H)-dione (4 g, 4.81 mmol) in DMF (40 mL) were added TBSCl (1.4 g, 9.62 mmol) and imidazole (1.6 g, 24.1 mmol) in portions at room temperature under N₂ atmosphere. The resulting mixture was stirred overnight at 80° C. under N₂ atmosphere. The resulting mixture was cooled to room temperature. The resulting mixture was diluted with water and extracted with EtOAc (3×200 mL). The combined organic layers were washed with brine and dried over anhydrous Na₂SO₄. After filtration the filtrate was concentrated under reduced pressure. The residue was purified by silica gel column chromatography, eluting with PE/EA (2:1) to afford 1-((2R,3S,4R,5R)-5-(((tert-butyl-dimethylsilyl) oxy) methyl)-3-fluoro-4-((4-methoxyphenyl) diphenylmethoxy)-5-(((4-methoxyphenyl) diphenylmethoxy) methyl) tetrahydrofuran-2-yl)-5-fluoropyrimidine-2,4(1H,3H)-dione (4.3 g, 4.52 mmol, 94.6%) as a white solid. LCMS-PH (ES, m/z): 953 [M+H]⁺.

Step 8: To a stirred solution of 1-((2R,3S,4R,5R)-5-(((tert-butyldimethylsilyl) oxy) methyl)-3-fluoro-4-((4-methoxyphenyl) diphenylmethoxy)-5-(((4-methoxyphenyl) diphenylmethoxy) methyl) tetrahydrofuran-2-yl)-5-fluoropyrimidine-2,4(1H,3H)-dione (800 mg, 840 μmol) in ACN (11 mL) was added DMAP (615 mg, 5.04 mmol) and TEA (509 mg, 5.04 mmol) at room temperature under N₂ atmosphere. The resulting mixture was stirred for 10 min. Then TPSCl (763 mg, 2.52 mmol) was added and the reaction was stirred for 15 h at room temperature under N₂ atmosphere. Then conc. NH₃·H₂O (2 mL) was added and the reaction was stirred for 30 min at room temperature under N₂ atmosphere. The resulting mixture was diluted with water and extracted with EtOAc (3×50 mL). The combined organic layers were washed with brine and dried over anhydrous Na₂SO₄. After filtration the filtrate was concentrated under reduced pressure. The residue was purified by silica gel column chromatography, eluting with PE/EtOAc (2:1) to afford 4-amino-1-((2R,3S,4R,5R)-5-(((tert-butyldimethylsilyl) oxy) methyl)-3-fluoro-4-((4-methoxyphenyl) diphenylmethoxy)-5-(((4-methoxyphenyl) diphenylmethoxy) methyl) tetrahydrofuran-2-yl)-5-fluoropyrimidin-2(1H)-one (530 mg, 0.56 mmol, 66.3%) as a white solid. LCMS (ES, m/z): 952 [M+H]⁺.

Step 9: To a stirred solution of 4-amino-1-((2R,3S,4R,5R)-5-(((tert-butyldimethylsilyl) oxy) methyl)-3-fluoro-4-((4-methoxyphenyl) diphenylmethoxy)-5-(((4-methoxyphenyl) diphenylmethoxy) methyl) tetrahydrofuran-2-yl)-5-fluoropyrimidin-2(1H)-one (160 mg, 168 μmol) in MeOH (2 mL) was added NH₄F (187 mg, 5.04 mmol) at room temperature under N₂ atmosphere. The resulting mixture was stirred overnight at 60° C. The resulting mixture was cooled to room temperature and the resulting mixture was filtered. The filter cake was washed with EtOAc. The filtrate was concentrated under reduced pressure to afford the crude product. To the above residue was added AcOH (0.8 mL) and H₂O (0.2 mL) at room temperature under N₂ atmosphere. The resulting mixture was stirred for 1 h at 40° C. under N₂ atmosphere. The resulting mixture was cooled to room temperature. The mixture was concentrated under reduced pressure to afford the crude product. The crude product was purified by Prep-HPLC with the following conditions (Column: XBridge Prep OBD C18 Column, 30*150 mm, 5 μm; Mobile Phase A: water (10 mmol/L NH₄HCO₃), Mobile Phase B: ACN; Flow rate: 60 mL/min; Gradient: 71% B to 76% B in 9 min; Wavelength: 254 nm/220 nm; RT1(min): 8.9). The fraction was collected and concentrated under vacuum, the residue was re-dissolved in CH₃CN and H₂O, and then was lyophilized to afford 4-amino-5-fluoro-1-((2R,3S,4R)-3-fluoro-4-hydroxy-5,5-bis(hydroxymethyl)tetrahydrofuran-2-yl) pyrimidin-2(1H)-one (23.6 mg, 81 μmol, 50.3%) as an off-white solid. LCMS (ES, m/z): 294 [M+H]⁺, 99.8% purity. Conditions for the HPLC: (Column: Atlantis HILIC Silica, 100*4.6 mm; 3.0 μm; Mobile Phase A: Water/5 mM NH₄HCO₃, Mobile Phase B: MeOH; Flow rate: 1.20 mL/min; Gradient: 0% B to 95% B in 5.00 min, 95% B to 95% B in 2.00 min, 95% B to 0% B in 0.30 min; Wavelength: 254 nm; RT1(min): 3.367). ¹H NMR (400 MHz, DMSO-d₆) δ 8.11 (d, J=7.2 Hz, 1H), 7.93-7.38 (m, 2H), 6.28 (ddd, J=7.8, 5.8, 2.0 Hz, 1H), 5.83 (s, 1H), 5.25 (dt, J=57.0, 5.7 Hz, 2H), 4.92 (t, J=5.5 Hz, 1H), 4.37 (dd, J=27.5, 5.6 Hz, 1H), 3.57 (dd, J=11.5, 5.1 Hz, 1H), 3.52-3.39 (m, 2H), 3.27 (dd, J=11.7, 4.4 Hz, 1H).

Example 88—Synthesis of Compound 178: 1-((2R, 3S,4R,5R)-5-azido-3-fluoro-4-hydroxy-5-(hydroxymethyl)tetrahydrofuran-2-yl)-5-methylpyrimidine-2,4(1H,3H)-dione

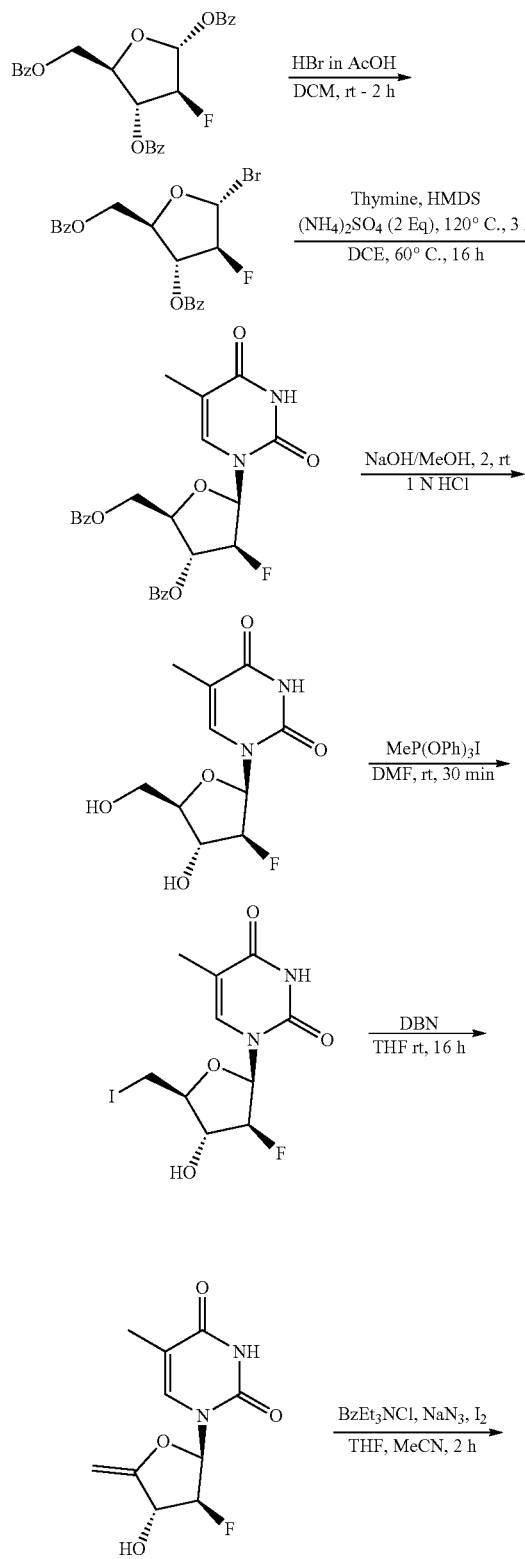

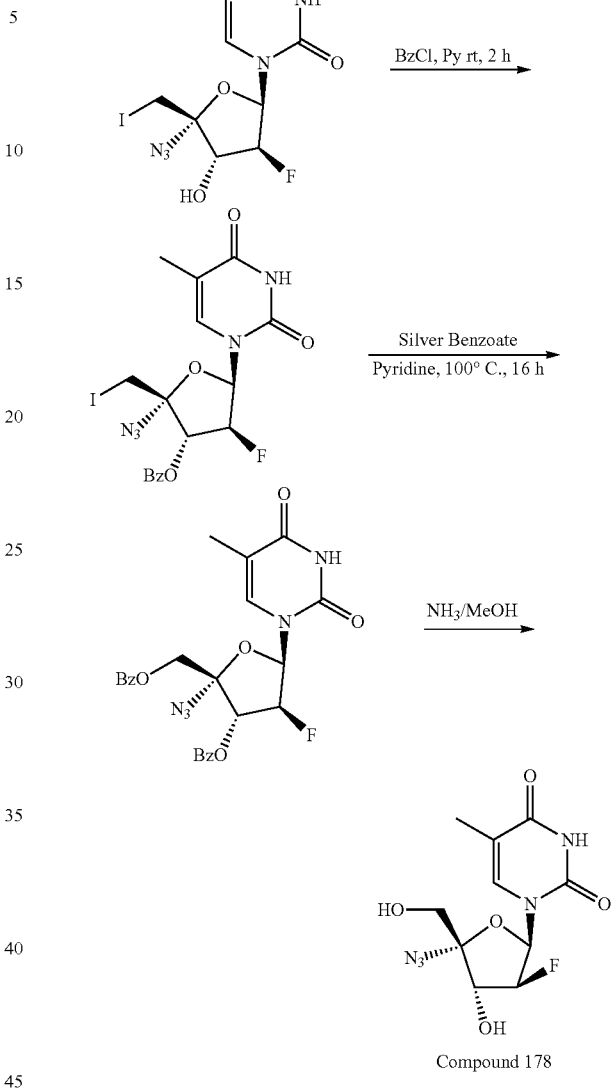

Compound 178

Step 1: To a stirred solution of (2R,3S,4R,5R)-5-((benzoyloxy)methyl)-3-fluorotetrahydrofuran-2,4-diyl dibenzoate (30 g, 64.59 mmol) in DCM (300 mL) was added HBr in acetic acid dropwise (90 mL) at 0° C. The reaction mixture stirred for 2 h at room temperature. Completion of the reaction was monitored by TLC. The crude material was dissolved in DCM (500 mL), washed with water (200 mL) and aqueous layer was extracted with DCM (200 mL). The combined organics were washed with water (300 mL), brine (300 mL), and sodium bicarbonate (300 mL), dried over anhydrous $Na_2SO_4$, filtered, and concentrated under reduced pressure to afforded crude ((2R,3R,4S,5R)-3-(benzoyloxy)-5-bromo-4-fluorotetrahydrofuran-2-yl)methyl benzoate (27 g) as white foam/sticky solid which was used as such for the next step.

Step 2: To a stirred solution of thymine (15 g, 118.94 mmol) in acetonitrile (150.0 mL) was added BSA (290 mL, 1189 mmol) at room temperature. The reaction mixture was stirred for 4 h at 100° C. The clear reaction mixture was concentrated to dryness and resulting residue was dissolved in 1-4 Dioxane (150.0 mL) and added to a solution of ((2R,3R,4S,5R)-3-(benzoyloxy)-5-bromo-4-fluorotetrahydrofuran-2-yl)methyl benzoate (25 g, 59.47 mmol) at 0° C. The reaction mixture stirred for 16 h at 80° C. Completion of the reaction was monitored by TLC. The reaction mixture was partitioned between brine solution (500 mL) and DCM (500 mL). The organic layer was separated, and combined organics were washed with water (2×500 mL) and brine (2×500 mL), dried over sodium sulphate, filtered, and concentrated. The crude product was dissolved in DCM (250 mL), added to hexane (750 mL), and stirred. A precipitate formed which was isolated by filtration and washed with hexane. The solid was dried under vacuum to afford the desired product. (25 g, 90.25%) as off-white solid. LC-MS (ES, m/z): 469.2 (M+1).

Step 3: To a stirred solution ((2R,3R,4S,5R)-3-(benzoyloxy)-4-fluoro-5-(5-methyl-2,4-dioxo-3,4-dihydropyrimidin-1(2H)-yl)tetrahydrofuran-2-yl)methyl benzoate (29.0 g, 4.27 mmol) in methanol (300 mL) was added sodium hydroxide (4.2 g, 10.68 mmol) at 0° C.) in portions at room temperature under nitrogen atmosphere. The resulting mixture was stirred for 2 h at room temperature and neutralized with 1N HCl and concentrated under vacuum to afford the desired product (17 g) as off-white solid. LC-MS (ES, m/z): 260.90 (M+H).

Step 4: To a stirred solution of 1-((2R,3S,4R,5R)-3-fluoro-4-hydroxy-5-(hydroxymethyl)tetrahydrofuran-2-yl)-5-methylpyrimidine-2,4(1H,3H)-dione (10 g, 38.44 mmol) in DMF (100 mL) was added MeP(OPh)$_3$I (34 g, 76.89 mmol). The reaction mixture was stirred for 30 min at room temperature and 2.0 mL of methanol was added at rt. The reaction mixture was stirred for 10 min at rt. Completion of the reaction was monitored by TLC. After completion, the reaction mixture was concentrated under reduced pressure. The crude product was purified by CombiFlash chromatography eluting with 4% MeOH in DCM to afford the desired product (3.0 g, 21.09%) as white solid. LC-MS (ES, m/z): 370.95 (M+1).

Step 5: To a stirred solution of 1-((2R,3S,4R,5S)-3-fluoro-4-hydroxy-5-(iodomethyl)tetrahydrofuran-2-yl)-5-methylpyrimidine-2,4(1H,3H)-dione (3.0 g, 8.098 mmol) in THF (30 mL) was added DBN (3.0 mL, 24.24 mmol) at 0° C. The reaction mixture was stirred for 16 h at room temperature. Completion of the reaction was monitored by TLC. After completion, the reaction mixture was concentrated under reduced pressure. The crude product was purified by CombiFlash chromatography eluting with 60% EtOAc in n-Hexane to afford the desired product (900 mg, 45.91%) as white solid. LC-MS (ES, m/z): 243 (M+1).

Step 6: To a stirred solution of benzyl triethylammonium Chloride (2.5 g, 11.15 mmol) was added sodium azide (725 mg, 11.15 mmol) in acetonitrile (10.0 mL) at 0° C. The reaction mixture was stirred for 2 h at room temperature. Then the reaction was treated with 1-((2R,3S,4R)-3-fluoro-4-hydroxy-5-methylenetetrahydrofuran-2-yl)-5-methylpyrimidine-2,4(1H,3H)-dione (900 mg, 3.71 mmol) at 0° C. followed by iodine (941 mg, 3.71 mmol) in THF (5.0 mL) at 0° C. The reaction mixture was stirred for 2 h at room temperature. Completion of the reaction was monitored by TLC. After completion, the reaction mixture was concentrated under reduced pressure. The crude residue was purified by CombiFlash chromatography eluting with 4% MeOH in DCM to afford the desired product (700 mg, 46%) as white solid. LC-MS (ES, m/z): 411.90 (M+2).

Step 7: To a stirred solution of 1-((2R,3S,4R,5S)-5-azido-3-fluoro-4-hydroxy-5-(iodomethyl)tetrahydrofuran-2-yl)-5-methylpyrimidine-2,4(1H,3H)-dione (900 mg, 2.18 mmol) in pyridine (10 mL) was added benzoyl chloride (0.5 mL, 4.37 mmol) at 0° C. The reaction mixture was stirred for 2 h at room temperature. Completion of the reaction was monitored by TLC. After completion the reaction mixture was concentrated under reduced pressure. The crude residue was purified by CombiFlash chromatography eluted with 4% MeOH in DCM to afford desired product (800 mg, 71.42%) as white solid. LC-MS (ES, m/z): 514.10 (M–H).

Step 8: To a stirred solution of (2S,3R,4S,5R)-2-azido-4-fluoro-2-(iodomethyl)-5-(5-methyl-2,4-dioxo-3,4-dihydropyrimidin-1(2H)-yl)tetrahydrofuran-3-yl benzoate (800 mg, 1.55 mmol) in pyridine (10 mL) was added silver benzoate (3.5 g, 15.53 mmol) at room temperature. The reaction mixture stirred for 16 h at 90° C. Completion of the reaction was monitored by TLC. After completion, the reaction mixture was concentrated under reduced pressure. The crude residue was purified by CombiFlash chromatography eluted with 6% MeOH in DCM to afford desired compound (400 mg, 50%) as white solid. LC-MS (ES, m/z): 508.1 (M–H).

Step 9: A solution of (2R,3R,4S,5R)-2-azido-2-((benzoyloxy)methyl)-4-fluoro-5-(5-methyl-2,4-dioxo-3,4-dihydropyrimidin-1(2H)-yl)tetrahydrofuran-3-yl benzoate (100 mg, 0.19 mmol) in 7N methanol in ammonia (2.0 mL) was stirred at rt for 2 h and the reaction progress was monitored by TLC and LCMS. After completion, the reaction mixture was concentrated and dried under vacuum. The crude product was purified by prep-HPLC using the following conditions: Mobile Phase: A: 0.02% NH$_4$OH in water; B: MeCN; Column: X SELECT (250 mm×20.0 mm), 5.0μ; Flow rate: 15 mL/min; Gradient program: Time/% B: 0/5, 2/10, 8/25 to afford the desired product (22 mg, 37%) as white solid. LC-MS (ES, m/z): 301.85 (M+1). $^1$H NMR (400 MHz, DMSO-d$_6$) δ=11.56-11.43 (m, 1H), 7.51 (s, 1H), 6.47 (br d, J=5.0 Hz, 1H), 6.35 (dd, J=5.9, 10.1 Hz, 1H), 5.82 (br t, J=5.6 Hz, 1H), 5.35-5.15 (m, 1H), 4.56-4.46 (m, 1H), 3.83-3.73 (m, 2H), 1.79 (s, 3H).

Example 89—Synthesis of Compound 130:
4-amino-1-[(2R,3S,4R,5R)-5-(2-chloroethyl)-3-fluoro-4-hydroxy-5-(hydroxymethyl) oxolan-2-yl]-5-fluoropyrimidin-2-one

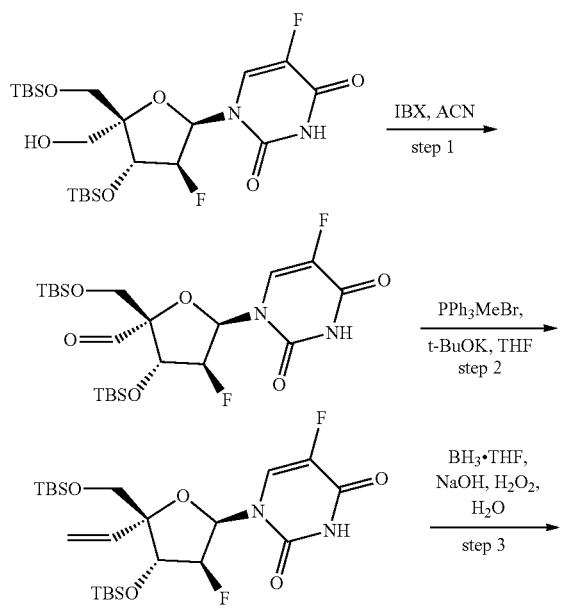

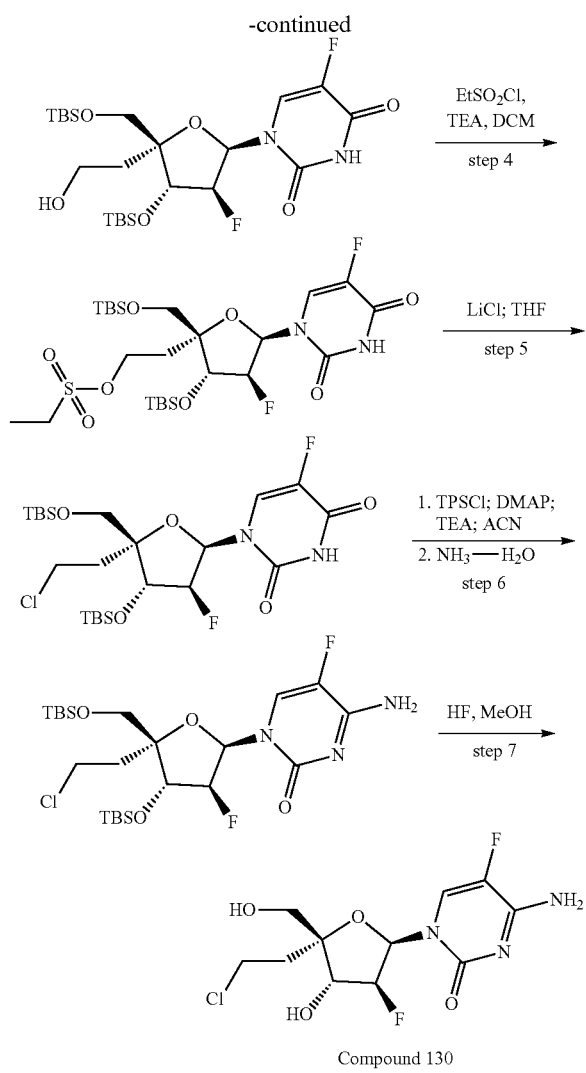

Compound 130

Step 1: To a stirred solution of 1-[(2R,3S,4R,5R)-4-[(tert-butyldimethylsilyl) oxy]-5-{[(tert-butyldimethylsilyl) oxy] methyl}-3-fluoro-5-(hydroxymethyl) oxolan-2-yl]-5-fluoro-3H-pyrimidine-2,4-dione (1.9 g, 3.64 mmol) in ACN (38 mL) was added IBX (1.3 g, 4.73 mmol). The resulting mixture was stirred for 2 h at 75° C. and then cooled to room temperature. The resulting mixture was filtered and the filter cake was washed with acetonitrile. The combined filtrate was concentrated under reduced pressure. This resulted in (2R,3R,4S,5R)-3-[(tert-butyldimethylsilyl) oxy]-2-{[(tert-butyldimethylsilyl) oxy] methyl}-4-fluoro-5-(5-fluoro-2,4-dioxo-3H-pyrimidin-1-yl) oxolane-2-carbaldehyde (1.8 g, crude) as a white solid. LC-MS (ES, m/z): 521 (M+H⁺).

Step 2: A solution of bromo(methyl)triphenyl-lambda5-phosphane (3.7 g, 10.37 mmol) and potassium t-butoxide (1.2 g, 10.37 mmol) in THF (36 mL) was stirred for 1 h at 60° C. under nitrogen atmosphere. To the above mixture was added (2R,3R,4S,5R)-3-[(tert-butyldimethylsilyl) oxy]-2-{[(tert-butyldimethylsilyl) oxy] methyl}-4-fluoro-5-(5-fluoro-2,4-dioxo-3H-pyrimidin-1-yl) oxolane-2-carbaldehyde (1.8 g, crude) in portions at room temperature. The resulting mixture was stirred for an additional 30 min at room temperature and then quenched by the addition of sat. NH₄Cl aq. at 0° C. The resulting mixture was extracted with EtOAc. The combined organic layers were washed with brine and dried over anhydrous Na₂SO₄. After filtration the filtrate was concentrated under reduced pressure. The crude product was purified by reverse phase flash with the following conditions: Column: C18; Mobile Phase A: Water (10 mmol/L NH₄HCO₃), Mobile Phase B: ACN; Flow rate: 100 mL/min; Gradient: 10% B to 80% in 20 min; UV detection at 254 nm. This resulted in 1-[(2R,3S,4R,5R)-4-[(tert-butyldimethylsilyl) oxy]-5-{[(tert-butyldimethylsilyl) oxy] methyl}-5-ethenyl-3-fluorooxolan-2-yl]-5-fluoro-3H-pyrimidine-2,4-dione (1.1 g, 2.12 mmol, 61.34%) as a yellow solid. LC-MS (ES, m/z): 519 (M+H⁺).

Step 3: To a solution of 1-[(2R,3S,4R,5R)-4-[(tert-butyldimethylsilyl) oxy]-5-{[(tert-butyldimethylsilyl) oxy] methyl}-5-ethenyl-3-fluorooxolan-2-yl]-5-fluoro-3H-pyrimidine-2,4-dione (1.1 g, 2.12 mmol) in THF (20 mL), was added BH₃-THF (1M, 6.4 mL, 6.40 mmol) at 0° C. under nitrogen atmosphere. The resulting mixture was stirred for 1 h at room temperature under nitrogen atmosphere. To the above mixture was added H₂O (1.0 mL, 61.06 mmol) dropwise at 0° C. The resulting mixture was stirred for additional 15 min at 0° C. Then to the above mixture, aq. NaOH (2.1 mL, 6.30 mmol, 3 mol/L) was added dropwise at 0° C. The resulting mixture was stirred for an additional 15 min at 0° C. This was followed by the addition of H₂O₂ (2.1 mL, 27.20 mmol, 30%) dropwise at 0° C. The resulting mixture was stirred for an additional 2 h at room temperature and then quenched by the addition of sat. NH₄Cl aq. at 0° C. The resulting mixture was extracted with EtOAc. The combined organic layers were washed with brine and dried over anhydrous Na₂SO₄. After filtration the filtrate was concentrated under reduced pressure. The residue was purified by Prep-TLC (PE/EtOAc=3:1) to afford 1-[(2R,3S,4R,5R)-4-[(tert-butyldimethylsilyl) oxy]-5-{[(tert-butyldimethylsilyl) oxy] methyl}-3-fluoro-5-(2-hydroxyethyl) oxolan-2-yl]-5-fluoro-3H-pyrimidine-2,4-dione (450.0 mg, 0.84 mmol, 39.54%) as a yellow solid. LC-MS (ES, m/z): 537 (M+H⁺).

Step 4: To a stirred solution of 1-[(2R,3S,4R,5R)-4-[(tert-butyldimethylsilyl) oxy]-5-{[(tert-butyldimethylsilyl) oxy] methyl}-3-fluoro-5-(2-hydroxyethyl) oxolan-2-yl]-5-fluoro-3H-pyrimidine-2,4-dione (450.0 mg, 0.84 mmol) and TEA (212.0 mg, 2.10 mmol) in DCM (5 mL) was added ethanesulfonyl chloride (162.0 mg, 1.26 mmol) dropwise at 0° C. under nitrogen atmosphere. The resulting mixture was stirred for 1 h at room temperature under nitrogen atmosphere and then concentrated under reduced pressure. This resulted in 2-[(2R,3R,4S,5R)-3-[(tert-butyldimethylsilyl) oxy]-2-{[(tert-butyldimethylsilyl) oxy] methyl}-4-fluoro-5-(5-fluoro-2,4-dioxo-3H-pyrimidin-1-yl) oxolan-2-yl] ethyl ethanesulfonate (500 mg, crude) as a brown solid. LC-MS (ES, m/z): 629 (M+H⁺).

Step 5: To a stirred solution of 2-[(2R,3R,4S,5R)-3-[(tert-butyldimethylsilyl) oxy]-2-{[(tert-butyldimethylsilyl) oxy] methyl}-4-fluoro-5-(5-fluoro-2,4-dioxo-3H-pyrimidin-1-yl) oxolan-2-yl] ethyl ethanesulfonate (500 mg, crude) in THF (5 mL) was added LiCl (337.0 mg, 7.95 mmol). The resulting mixture was stirred overnight at 50° C., then cooled to room temperature and quenched by the addition of water. The resulting mixture was extracted with EtOAc. The combined organic layers were washed with brine and dried over anhydrous Na₂SO₄. After filtration the filtrate was concentrated under reduced pressure. The residue was purified by Prep-TLC (CH₂Cl₂/MeOH=30:1) to afford 1-[(2R,3S,4R,5R)-4-[(tert-butyldimethylsilyl) oxy]-5-{[(tert-butyldimethylsilyl) oxy] methyl}-5-(2-chloroethyl)-3- fluorooxolan-2-yl]-5-fluoro-3H-pyrimidine-2,4-dione (300.0 mg, 0.54 mmol, 67.96%) as a yellow solid. LC-MS (ES, m/z): 555/557 (M+H⁺).

Step 6: To a stirred solution of 1-[(2R,3S,4R,5R)-4-[(tert-butyldimethylsilyl) oxy]-5-{[(tert-butyldimethylsilyl) oxy] methyl}-5-(2-chloroethyl)-3-fluorooxolan-2-yl]-5-fluoro-3H-pyrimidine-2,4-dione (300.0 mg, 0.54 mmol) and TEA (164.0 mg, 1.62 mmol) in ACN (12 mL) were added DMAP (198.0 mg, 1.62 mmol) and 2,4,6-tris(propan-2-yl) benzene-1-sulfonyl chloride (818.0 mg, 2.70 mmol) under a nitrogen atmosphere. The resulting mixture was stirred for 2 h at room temperature. To the above mixture was added NH$_3$·H$_2$O (6.0 mL) dropwise at room temperature. The resulting mixture was stirred for an additional 1 h at room temperature and then concentrated under reduced pressure. The residue was purified by Prep-TLC (CH$_2$Cl$_2$/MeOH=10:1) to afford 4-amino-1-[(2R,3S,4R,5R)-4-[(tert-butyldimethylsilyl) oxy]-5-{[(tert-butyldimethylsilyl) oxy] methyl}-5-(2-chloroethyl)-3-fluorooxolan-2-yl]-5-fluoropyrimidin-2-one (280.0 mg, 0.51 mmol, 93.50%) as a yellow solid. LC-MS (ES, m/z): 554/556 (M+H⁺).

Step 7: To a stirred solution of 4-amino-1-[(2R,3S,4R,5R)-4-[(tert-butyldimethylsilyl) oxy]-5-{[(tert-butyldimethylsilyl) oxy] methyl}-5-(2-chloroethyl)-3-fluorooxolan-2-yl]-5-fluoropyrimidin-2-one (50 mg, 0.09 mmol) in MeOH (0.5 mL) was added aqueous HF (0.5 mL, 14.62 mmol, 50%) dropwise at 0° C. under a nitrogen atmosphere. The resulting mixture was purified by reversed-phase flash chromatography with the following conditions: column, C18 silica gel; mobile phase A: Water (0.1% TFA), mobile phase B: MeCN, 0% B to 50% gradient in 15 min; UV detection at 254 nm. The product-containing fractions were combined and evaporated partially to remove the solvents, then lyophilized overnight to afford 4-amino-1-[(2R,3S,4R,5R)-5-(2-chloroethyl)-3-fluoro-4-hydroxy-5-(hydroxymethyl) oxolan-2-yl]-5-fluoropyrimidin-2-one (4.6 mg, 0.01 mmol, 14.98%) as a white solid. LC-MS (ES, m/z): 326/328 (M+H⁺). Conditions for the LCMS: (Column: Shim-pack Scepter C18, 30*3.0 mm, 2.0 m; Mobile Phase A: water/0.05% TFA, Mobile Phase B: ACN/0.05% TFA; Flow rate: 1.5000 mL/min; Gradient: 5% B to 40% B in 1.70 min, 40% B to 100% B in 0.60 min, 100% B to 100% B in 0.50 min, 100% B to 5% B in 0.03 min; Wavelength: 254 nm; RT1(min): 0.71). ¹H NMR (400 MHz, Methanol-d$_4$) δ 8.24 (d, J=6.8 Hz, 1H), 6.24-6.19 (m, 1H), 5.22 (t, J=3.6 Hz, 0.5H), 5.09 (t, J=3.6 Hz, 0.5H), 4.45-4.40 (m, 1H), 3.75-3.65 (m, 4H), 2.32-2.18 (m, 2H).

Example 90—Synthesis of Compound 175: 4-amino-1-((2R,3S,4R,5R)-5-(chloromethyl-d2)-3-fluoro-4-hydroxy-5-(hydroxymethyl)tetrahydrofuran-2-yl)-5-fluoropyrimidin-2(1H)-one

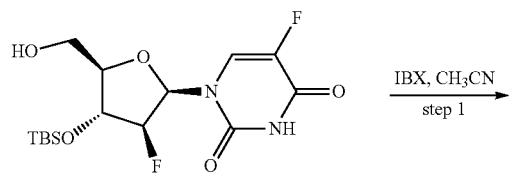

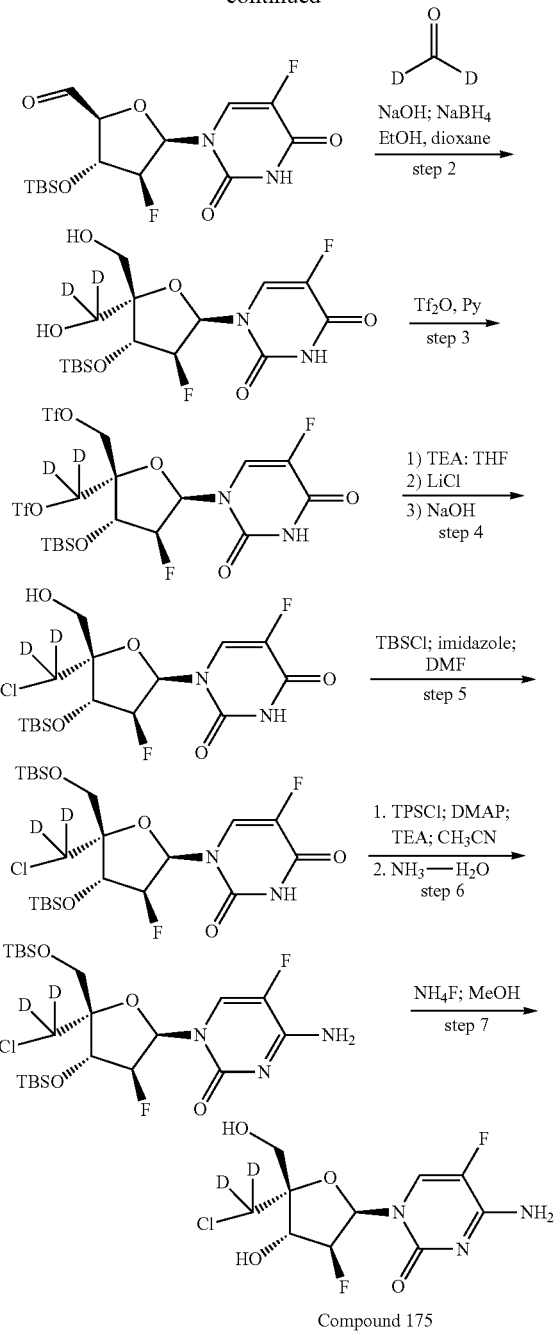

Compound 175

Step 1: To a stirred solution of 1-[(2R,3S,4R,5R)-4-[(tert-butyldimethylsilyl) oxy]-3-fluoro-5-(hydroxymethyl) oxolan-2-yl]-5-fluoro-3H-pyrimidine-2,4-dione (3.0 g, 7.93 mmol) in ACN (60 mL) was added IBX (4.4 g, 15.85 mmol) in portions at room temperature. The resulting mixture was stirred for 2 h at 70° C. under a nitrogen atmosphere. The mixture was allowed to cool down to room temperature and filtered. The filter cake was washed with MeCN (5×10 mL). The combined filtrate was concentrated under reduced pressure. This resulted in (2S,3R,4S,5R)-3-[(tert-butyldimethylsilyl) oxy]-4-fluoro-5-(5-fluoro-2,4-dioxo-3H-pyrimidin-1-yl) oxolane-2-carbaldehyde (2.9 g, crude) as a white solid. The crude product was used in the next step directly without further purification. LC-MS (ES, m/z): 377 (M+H⁺).

Step 2: To a stirred solution of (2S,3R,4S,5R)-3-[(tert-butyldimethylsilyl) oxy]-4-fluoro-5-(5-fluoro-2,4-dioxo-3H-pyrimidin-1-yl) oxolane-2-carbaldehyde (2.9 g, 7.70 mmol) and formaldehyde-d$_2$ (3 mL, 37% in water) in 1,4-dioxane (30 mL) was added aq. NaOH (6 mL, 2M) dropwise. The resulting mixture was stirred overnight at room temperature. To the above mixture were added EtOH (9 mL) and NaBH$_4$ (1.22 g, 32.36 mmol) in portions at 0° C. The resulting mixture was stirred for additional 1 h at room temperature and then quenched by the addition of sat. NH$_4$Cl (aq.) (200 mL) at 0° C. The resulting mixture was extracted with EtOAc (3×200 mL). The combined organic layers were washed with brine (3×200 mL), dried over anhydrous Na$_2$SO$_4$. After filtration the filtrate was concentrated under reduced pressure. The residue was purified by silica gel column chromatography, eluting with PE/EtOAc (1:1) to afford 1-((2R,3S,4R,5S)-4-((tert-butyldimethylsilyl)oxy)-3-fluoro-5-(hydroxymethyl)-5-(hydroxymethyl-d$_2$)tetrahydrofuran-2-yl)-5-fluoropyrimidine-2,4(1H,3H)-dione (1.5 g, 3.62 mmol, 46.1% yield in two steps) as a white solid. LC-MS (ES, m/z): 411 (M+H$^+$).

Step 3: To a stirred solution of 1-((2R,3S,4R,5S)-4-((tert-butyldimethylsilyl)oxy)-3-fluoro-5-(hydroxymethyl)-5-(hydroxymethyl-d$_2$)tetrahydrofuran-2-yl)-5-fluoropyrimidine-2,4(1H,3H)-dione (1.5 g, 3.62 mmol) in pyridine (12 mL) was added Tf$_2$O (2.55 g, 9.05 mmol) dropwise at –30° C. under a nitrogen atmosphere. The resulting mixture was stirred for 2 h at room temperature under a nitrogen atmosphere and quenched by the addition of sat. NaHCO$_3$(aq.) (200 mL) at 0° C. The resulting mixture was extracted with EtOAc (2×200 mL). The combined organic layers were washed with brine (2×200 mL) and dried over anhydrous Na$_2$SO$_4$. After filtration the filtrate was concentrated under reduced pressure. The residue was purified by silica gel column chromatography, eluting with PE/EtOAc (1:1) to afford ((2S,3R,4S,5R)-3-((tert-butyldimethylsilyl)oxy)-4-fluoro-5-(5-fluoro-2,4-dioxo-3,4-dihydropyrimidin-1(2H)-yl)-2-((((trifluoromethyl)sulfonyl)oxy)methyl) tetrahydrofuran-2-yl)methyl-d$_2$ trifluoromethanesulfonate (1.7 g, 2.52 mmol, 86.2%) as a brown solid. LC-MS (ES, m/z): 675 (M+H$^+$).

Step 4: To a stirred solution of ((2S,3R,4S,5R)-3-((tert-butyldimethylsilyl)oxy)-4-fluoro-5-(5-fluoro-2,4-dioxo-3,4-dihydropyrimidin-1(2H)-yl)-2-((((trifluoromethyl)sulfonyl)oxy)methyl)tetrahydrofuran-2-yl)methyl-d$_2$ trifluoromethanesulfonate (1.7 g, 2.52 mmol) in THF (17 mL) was added TEA (2.55 g, 25.20 mmol) dropwise at room temperature. The resulting mixture was stirred for 3 h at room temperature. To the above mixture was added LiCl (1.3 g, 2.48 mmol) and the resulting mixture was stirred for overnight at room temperature. This was followed by addition of a solution of NaOH (195.0 mg, 4.87 mmol) in water (2 mL) at room temperature. The resulting mixture was stirred for an additional 3 h at room temperature and then quenched by the addition of water (20 mL). The resulting solution was extracted with EtOAc (3×50 mL). The organic layers were washed with brine, and dried over anhydrous Na$_2$SO$_4$. After filtration the filtrate was concentrated under reduced pressure. The residue was purified by silica gel chromatography, eluting with CH$_2$Cl$_2$/MeOH (20:1) to afford 1-((2R,3S,4R,5R)-4-((tert-butyldimethylsilyl)oxy)-5-(chloromethyl-d$_2$)-3-fluoro-5-(hydroxymethyl)tetrahydrofuran-2-yl)-5-fluoropyrimidine-2,4(1H,3H)-dione (705.0 mg, 1.64 mmol, 67.48%) as a brown-yellow solid. LC-MS (ES, m/z): 429 (M+H$^+$).

Step 5: To a stirred solution of 1-((2R,3S,4R,5R)-4-((tert-butyldimethylsilyl)oxy)-5-(chloromethyl-d$_2$)-3-fluoro-5-(hydroxymethyl)tetrahydrofuran-2-yl)-5-fluoropyrimidine-2,4(1H,3H)-dione (700.0 mg, 1.64 mmol) and imidazole (159.0 mg, 3.34 mmol) in DMF (10 mL) was added TBSCl (991.0 mg, 6.56 mmol) in portions at 0° C. under a nitrogen atmosphere. The resulting mixture was stirred for overnight at room temperature under a nitrogen atmosphere and then quenched by the addition of sat. NaHCO$_3$ aq. (100 mL) at 0° C. The resulting mixture was extracted with EtOAc (2×100 mL). The combined organic layers were washed with brine (2×50 mL), dried over anhydrous Na$_2$SO$_4$. After filtration the filtrate was concentrated under reduced pressure. The residue was purified by silica gel column chromatography, eluting with PE/EtOAc (2:1) to afford 1-((2R,3S,4R,5R)-4-((tert-butyldimethylsilyl)oxy)-5-(((tert-butyldimethylsilyl)oxy)methyl)-5-(chloromethyl-d$_2$)-3-fluorotetrahydrofuran-2-yl)-5-fluoropyrimidine-2,4(1H,3H)-dione (510.0 mg, 0.92 mmol, 78.9%) as a yellow solid. LC-MS-PH (ES, m/z): 543 (M+H$^+$).

Step 6: To a stirred solution of 1-((2R,3S,4R,5R)-4-((tert-butyldimethylsilyl)oxy)-5-(((tert-butyldimethylsilyl)oxy)methyl)-5-(chloromethyl-d$_2$)-3-fluorotetrahydrofuran-2-yl)-5-fluoropyrimidine-2,4(1H,3H)-dione (500.0 mg, 0.92 mmol) and TEA (279.0 mg, 2.760 mmol) in CH$_3$CN (20 mL) were added DMAP (337.0 mg, 2.76 mmol) and TPSCl (1394.0 mg, 4.60 mmol) in portions at room temperature. The resulting mixture was stirred overnight at room temperature. To the above mixture was added NH$_3$·H$_2$O (10 mL) dropwise at room temperature. The resulting mixture was stirred for additional 1 h at room temperature and then quenched by the addition of water (100 mL). The resulting mixture was extracted with EtOAc (3×100 mL). The combined organic layers were washed with brine (2×100 mL) and dried over anhydrous Na$_2$SO$_4$. After filtration the filtrate was concentrated under reduced pressure. The residue was purified by silica gel column chromatography, eluting with CH$_2$Cl$_2$/MeOH (10:1) to afford 4-amino-1-((2R,3S,4R,5R)-4-((tert-butyl-dimethylsilyl)oxy)-5-(((tert-butyldimethylsilyl) oxy)methyl)-5-(chloromethyl-d$_2$)-3-fluoro-tetrahydrofuran-2-yl)-5-fluoropyrimidin-2(1H)-one (400.0 mg, 0.74 mmol, 80.4%) as a yellow solid. LC-MS (ES, m/z): 542 (M+H$^+$).

Step 7: To a stirred solution of 4-amino-1-((2R,3S,4R,5R)-4-((tert-butyldimethylsilyl)oxy)-5-(((tert-butyldimethylsilyl)oxy)methyl)-5-(chloromethyl-d$_2$)-3-fluorotetrahydrofuran-2-yl)-5-fluoropyrimidin-2(1H)-one (400.0 mg, 0.74 mmol) in MeOH (8.00 mL) was added NH$_4$F (800.0 mg, 21.60 mmol) in portions at room temperature. The resulting mixture was stirred overnight at room temperature. The resulting mixture was filtered; the filter cake was washed with EtOH (5×5 mL). The combine filtrate was concentrated under reduced pressure. The residue was purified by Prep-HPLC flash chromatography with the following conditions: Column: XBridge Prep OBD C18 Column, 30*150 mm, 5 μm; Mobile Phase A: Water (10 mmol/L NH$_4$HCO$_3$), Mobile Phase B: ACN; Flow rate: 100 mL/min; Gradient: 10% B to 70% B in 20 min; Wavelength: 254 nm/220 nm. The product-containing fractions were combined and evaporated partially to remove the solvents, then lyophilized overnight to afford 4-amino-1-((2R,3S,4R,5R)-5-(chloromethyl-d$_2$)-3-fluoro-4-hydroxy-5-(hydroxymethyl) tetrahydrofuran-2-yl)-5-fluoropyrimidin-2(1H)-one (48.2 mg, 0.15 mmol, 20.21%) as a white solid. LC-MS (ES, m/z): 314 (M+H$^+$); 99.9% purity. Conditions for the HPLC: (Column: XBridge Shield RP C18, 100*4.6 mm, 2.2 μm; Mobile Phase A: Water/5 mM NH$_4$HCO$_3$, Mobile Phase B: ACN; Flow rate: 1.5000 mL/min; Gradient: 0% B to 30% B in 10.00 min, 30% B to 95% B in 2.00 min, 95% B to 95%

B in 1.7 min, 95% B to 95% B in 0.3 min; Wavelength: 254/220 nm; RT1(min): 4.63). $^1$H NMR (400 MHz, DMSO-$d_6$) δ 7.94 (d, J=7.2 Hz, 1H), 7.89 (brs, 1H), 7.64 (brs, 1H), 6.25-6.20 (m, 1H), 6.19 (d, J=4.8 Hz, 1H), 5.48-5.43 (m, 1H), 5.23 (t, J=4.0 Hz, 0.5H), 5.09 (t, J=4.0 Hz, 0.5H), 4.47-4.40 (m, 1H), 3.65-3.61 (m, 2H).
Example 91—Synthesis of Compound 125: 4-amino-5-fluoro-1-((2R,3S,4R,5R)-3-fluoro-5-(2-fluoroethyl)-4-hydroxy-5-(hydroxymethyl) tetrahydrofuran-2-yl) pyrimidin-2(1H)-one
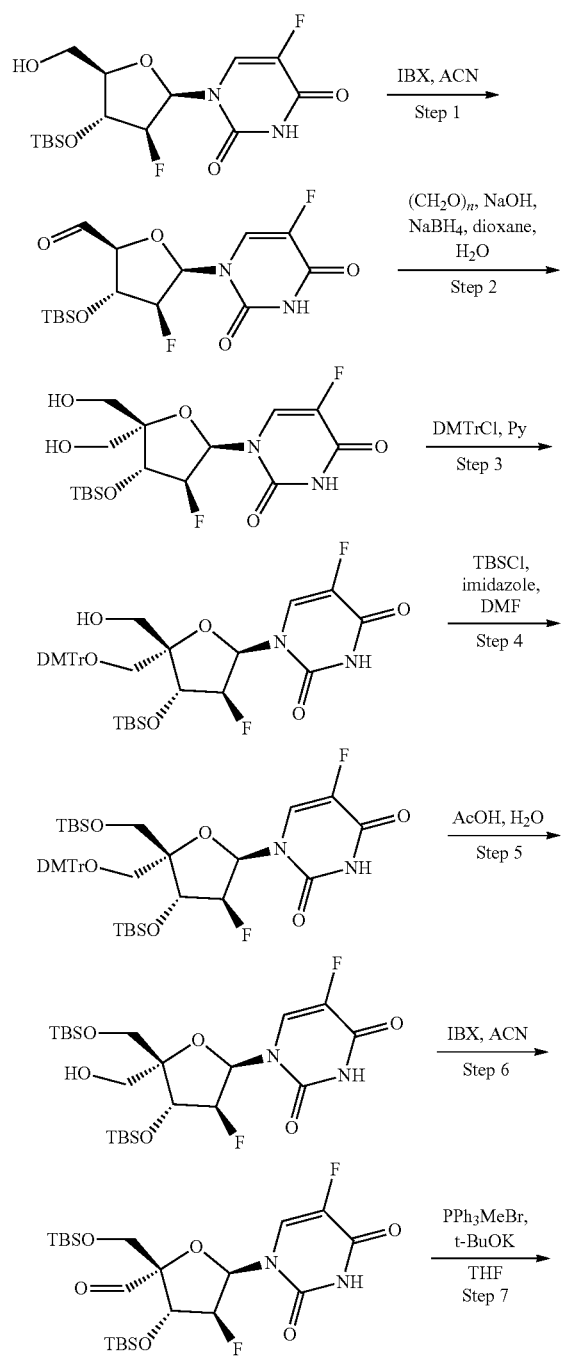
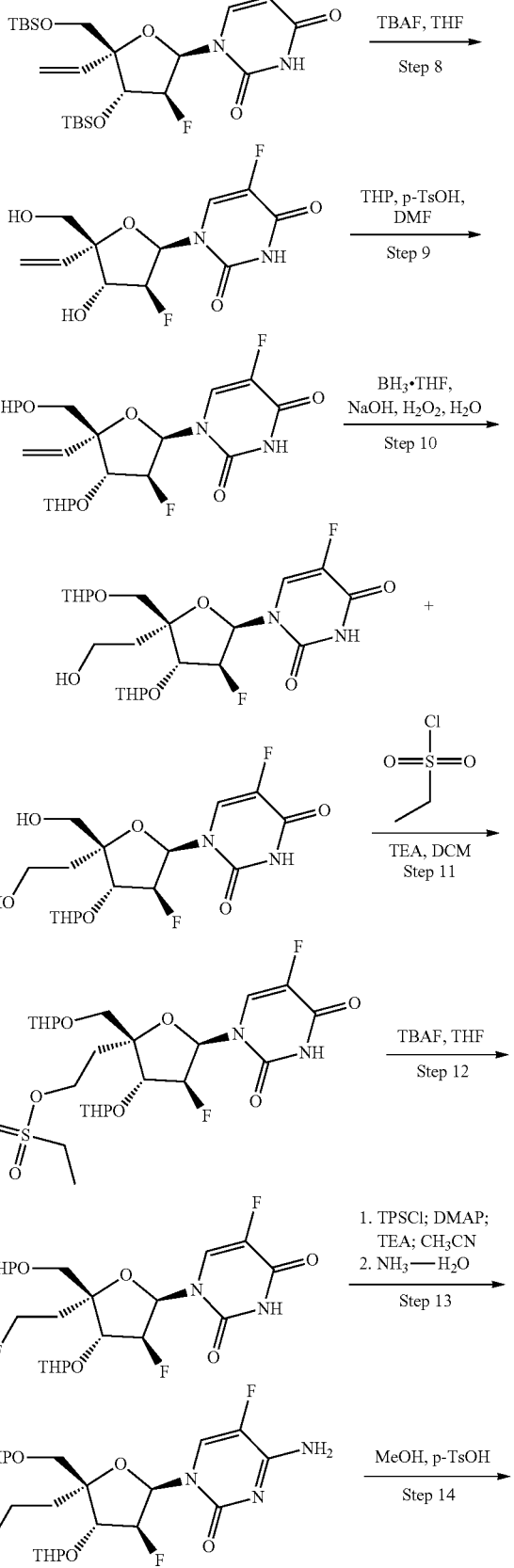

-continued

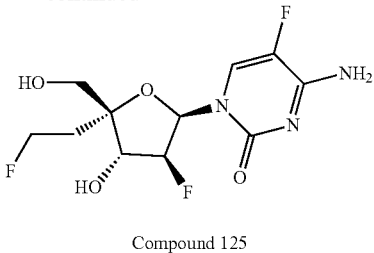 [SMILES: Nc1nc(=O)n([C@@H]2O[C@@](CO)(CCF)[C@@H](O)[C@@H]2F)cc1F]

Compound 125

Step 1: To a stirred solution of 1-((2R,3S,4R,5R)-4-((tert-butyldimethylsilyl) oxy)-3-fluoro-5-(hydroxymethyl) tetrahydrofuran-2-yl)-5-fluoropyrimidine-2,4(1H,3H)-dione (20 g, 52.9 mmol) in ACN (300 mL) was added IBX (37 g, 132.1 mmol) at room temperature under a $N_2$ atmosphere. The resulting mixture was stirred for 2 h at 60° C. and was allowed to cool down to room temperature. The resulting mixture was filtered and the filter cake was washed with ACN. The filtrate was concentrated under reduced pressure to afford the product (12 g, crude) which was used in the next step directly without further purification. LC-MS (ES, m/z): 377 [M+H]$^+$.

Step 2: To a stirred solution of (2S,3R,4S,5R)-3-((tert-butyldimethylsilyl) oxy)-4-fluoro-5-(5-fluoro-2,4-dioxo-3,4-dihydropyrimidin-1(2H)-yl) tetrahydrofuran-2-carbaldehyde (12 g, 31.9 mmol) and paraformaldehyde (4.8 g, 159 mmol) in dioxane (150 mL) was added NaOH (3.8 g, 95.6 mmol) in $H_2O$ (15 mL) dropwise at 0° C. under $N_2$ atmosphere. The resulting mixture was stirred for 15 h at room temperature. To the above mixture was added NaBH$_4$ (3.6 g, 95.6 mmol) in portions at 0° C. under a $N_2$ atmosphere. The resulting mixture was stirred for additional 1 h at room temperature. The reaction was quenched with sat. NH$_4$Cl solution at 0° C. and extracted with EtOAc (3×300 mL). The combined organic layers were washed with brine and dried over anhydrous Na$_2$SO$_4$. After filtration the filtrate was concentrated under reduced pressure. The residue was purified by silica gel column chromatography, eluting with DCM/MeOH (10:1) to afford 1-((2R,3S,4R)-4-((tert-butyldimethylsilyl) oxy)-3-fluoro-5,5-bis(hydroxymethyl) tetrahydrofuran-2-yl)-5-fluoropyrimidine-2,4(1H,3H)-dione (6.5 g, 15.9 mmol, 44.9%) as a yellow solid. LC-MS (ES, m/z): 409 [M+H]$^+$.

Step 3: A solution of 1-((2R,3S,4R)-4-((tert-butyldimethylsilyl) oxy)-3-fluoro-5,5-bis(hydroxymethyl)tetrahydrofuran-2-yl)-5-fluoropyrimidine-2,4(1H,3H)-dione (6.5 g, 15.9 mmol) and DMTrCl (5.4 g, 17.5 mmol) in pyridine (100 mL) was stirred for 12 h at room temperature under a $N_2$ atmosphere. The resulting mixture was concentrated under vacuum. Then the residue was diluted with water and extracted with EtOAc (3×100 mL). The resulting mixture was washed with brine. The organic layer was dried over anhydrous Na$_2$SO$_4$. After filtration the filtrate was concentrated under reduced pressure. The residue was purified by silica gel column chromatography, eluting with DCM/MeOH (10:1) to afford 1-((2R,3S,4R,5S)-5-((bis(4-methoxyphenyl) (phenyl)methoxy) methyl)-4-((tert-butyldimethylsilyl) oxy)-3-fluoro-5-(hydroxymethyl) tetrahydrofuran-2-yl)-5-fluoropyrimidine-2,4(1H,3H)-dione (9.4 g, 13.3 mmol, 75.1%) as a yellow solid. LC-MS (ES, m/z): 709 [M−H]$^-$.

Step 4: To a stirred mixture of 1-((2R,3S,4R,5S)-5-((bis (4-methoxyphenyl) (phenyl)methoxy) methyl)-4-((tert-butyldimethylsilyl) oxy)-3-fluoro-5-(hydroxymethyl) tetrahydrofuran-2-yl)-5-fluoropyrimidine-2,4(1H,3H)-dione (7.5 g, 10.6 mmol) and imidazole (3.6 g, 52.7 mmol) in DMF (60 mL) was added TBSCl (3.9 g, 26.4 mmol) in portions at room temperature under a $N_2$ atmosphere. The mixture was stirred for 16 h at 60° C. and then the mixture was cooled to room temperature. The resulting mixture was diluted with water and extracted with EtOAc (3×200 mL). The combined organic layers were washed with brine and dried over anhydrous Na$_2$SO$_4$. After filtration the filtrate was concentrated under reduced pressure. The residue was purified by silica gel column chromatography, eluting with PE/EtOAc (1:1) to afford 1-((2R,3S,4R,5R)-5-((bis(4-methoxyphenyl) (phenyl)methoxy) methyl)-4-((tert-butyldimethylsilyl) oxy)-5-(((tert-butyldimethylsilyl) oxy) methyl)-3-fluorotetrahydrofuran-2-yl)-5-fluoropyrimidine-2,4(1H,3H)-dione (6.1 g, 7.39 mmol, 69.5%) as a light-yellow solid. LC-MS (ES, m/z): 825 [M+H]$^+$.

Step 5: A solution of 1-((2R,3S,4R,5R)-5-((bis(4-methoxyphenyl) (phenyl)methoxy) methyl)-4-((tert-butyldimethylsilyl) oxy)-5-(((tert-butyldimethylsilyl) oxy) methyl)-3-fluorotetrahydrofuran-2-yl)-5-fluoropyrimidine-2,4(1H,3H)-dione (6.1 g, 7.39 mmol) in water (8 mL) and AcOH (32 mL) was stirred for 16 h at room temperature under a $N_2$ atmosphere. The resulting mixture was concentrated under reduced pressure. The residue was purified by silica gel column chromatography, eluting with PE/EtOAc (2:1) to afford 1-((2R,3S,4R,5R)-4-((tert-butyldimethylsilyl) oxy)-5-(((tert-butyldimethylsilyl) oxy) methyl)-3-fluoro-5-(hydroxymethyl) tetrahydrofuran-2-yl)-5-fluoropyrimidine-2,4(1H,3H)-dione (2.2 g, 4.21 mmol, 57.4%) as a yellow solid. LC-MS (ES, m/z): 523 [M+H]$^+$.

Step 6: To a stirred mixture of 1-((2R,3S,4R,5R)-4-((tert-butyldimethylsilyl) oxy)-5-(((tert-butyldimethylsilyl) oxy) methyl)-3-fluoro-5-(hydroxymethyl) tetrahydrofuran-2-yl)-5-fluoropyrimidine-2,4(1H,3H)-dione (2.2 g, 4.21 mmol) in ACN (20 mL) was added IBX (3.5 g, 12.6 mmol) in portions at room temperature under a $N_2$ atmosphere. The mixture was stirred for 2 h at 60° C. The mixture was cooled to room temperature. The resulting mixture was filtered; the filter cake was washed with ACN. The filtrate was concentrated under reduced pressure to afford the product (2.1 g, crude) which was used in the next step directly without further purification. LC-MS (ES, m/z): 521 [M+H]$^+$.

Step 7: To a stirred mixture of PPh$_3$MeBr (4.5 g, 12.7 mmol) in THF (30 mL) was added t-BuOK (1.4 g, 12.7 mmol) in portions at 0° C. under $N_2$ atmosphere. The mixture was stirred for 1 h at room temperature. Then (2R,3R,4S,5R)-3-((tert-butyldimethylsilyl) oxy)-2-(((tert-butyldimethylsilyl) oxy) methyl)-4-fluoro-5-(5-fluoro-2,4-dioxo-3,4-dihydropyrimidin-1(2H)-yl) tetrahydrofuran-2-carbaldehyde (2.2 g, 4.22 mmol) was added at 0° C. and the mixture was stirred for an additional 15 h at room temperature. The resulting mixture was quenched with water at 0° C. and extracted with EtOAc (3×100 mL). The combined organic layers were washed with brine and dried over anhydrous Na$_2$SO$_4$. After filtration the filtrate was concentrated under reduced pressure. The residue was purified by silica gel column chromatography, eluting with PE/EtOAc (2:1) to afford 1-((2R,3S,4R,5R)-4-((tert-butyldimethylsilyl) oxy)-5-(((tert-butyldimethylsilyl) oxy) methyl)-3-fluoro-5-vinyltetrahydrofuran-2-yl)-5-fluoropyrimidine-2,4(1H,3H)-dione (1.3 g, 2.51 mmol, 59.3%) as an off-white solid. LC-MS (ES, m/z): 519 [M+H]$^+$.

Step 8: To a stirred solution of 1-((2R,3S,4R,5R)-4-((tert-butyldimethylsilyl) oxy)-5-(((tert-butyldimethylsilyl) oxy) methyl)-3-fluoro-5-vinyltetrahydrofuran-2-yl)-5-fluoropyrimidine-2,4(1H,3H)-dione (1.3 g, 2.51 mmol) in THF (10 mL) was added TBAF (5 mL, 5 mmol, 1.0 M in THF) dropwise at room temperature under a $N_2$ atmosphere. The resulting mixture was stirred for 1 h at room temperature. The resulting mixture was diluted with water and extracted with EtOAc (3×50 mL). The combined organic layers were washed with brine, and dried over anhydrous $Na_2SO_4$. After filtration the filtrate was concentrated under reduced pressure. The residue was purified by silica gel column chromatography, eluting with DCM/MeOH (10:1) to afford 5-fluoro-1-((2R,3S,4R,5R)-3-fluoro-4-hydroxy-5-(hydroxymethyl)-5-vinyltetrahydrofuran-2-yl) pyrimidine-2,4 (1H,3H)-dione (728 mg, 2.51 mmol, 99.9%) as a white solid. LC-MS (ES, m/z): 291 [M+H]$^+$.

Step 9: To a stirred solution of 5-fluoro-1-((2R,3S,4R,5R)-3-fluoro-4-hydroxy-5-(hydroxymethyl)-5-vinyltetrahydrofuran-2-yl) pyrimidine-2,4(1H,3H)-dione (800 mg, 2.75 mmol) and THP (8 mL) in DMF (10 mL) was added p-TsOH (512 mg, 2.91 mmol) in portions at 0° C. under $N_2$ atmosphere. The resulting mixture was stirred for 4 h at room temperature under a $N_2$ atmosphere. The mixture was neutralized to pH 7 with TEA. The resulting mixture was diluted with water and extracted with EtOAc (3×50 mL). The combined organic layers were washed with sat. $NaHCO_3$ solution, dried over anhydrous $Na_2SO_4$. After filtration the filtrate was concentrated under reduced pressure. The residue was purified by Prep-TLC (PE/EA=1:1) to afford 5-fluoro-1-((2R,3S,4R,5R)-3-fluoro-4-((tetrahydro-2H-pyran-2-yl) oxy)-5-(((tetrahydro-2H-pyran-2-yl) oxy) methyl)-5-vinyltetrahydrofuran-2-yl) pyrimidine-2,4(1H, 3H)-dione (850 mg, 1.86 mmol, 67.3%) as a white solid. LC-MS (ES, m/z): 457 [M−H]$^−$.

Step 10: To a stirred solution of 5-fluoro-1-((2R,3S,4R,5R)-3-fluoro-4-((tetrahydro-2H-pyran-2-yl) oxy)-5-(((tetrahydro-2H-pyran-2-yl) oxy) methyl)-5-vinyltetrahydrofuran-2-yl) pyrimidine-2,4(1H,3H)-dione (200 mg, 440 µmol) in THF (8 mL) was added $BH_3$-THF (1.3 mL, 1.32 mmol, 1.0 M in THF) dropwise at 0° C. under a $N_2$ atmosphere. The resulting mixture was stirred for 2 h at room temperature. To the above mixture was added water (2 mL) dropwise at 0° C. The resulting mixture was stirred for additional 10 min at 0° C. To the above mixture was added NaOH solution (1 mL, 3.0 M in $H_2O$) dropwise at 0° C. The resulting mixture was stirred for additional 2 min at 0° C. To the above mixture was added $H_2O_2$(928 mg, 8.19 mmol, 30% in $H_2O$) dropwise at 0° C. The resulting mixture was stirred for additional 2 h at room temperature. The mixture was quenched with sat. $Na_2S_2O_3$ solution at 0° C. and extracted with EtOAc (3×50 mL). The combined extracts were dried over anhydrous $Na_2SO_4$. After filtration the filtrate was concentrated under reduced pressure. The residue was purified by Prep-TLC (DCM/MeOH=10:1) to afford 5-fluoro-1-((2R,3S,4R,5R)-3-fluoro-5-(2-hydroxyethyl)-4-((tetrahydro-2H-pyran-2-yl) oxy)-5-(((tetrahydro-2H-pyran-2-yl) oxy) methyl) tetrahydrofuran-2-yl) pyrimidine-2,4(1H,3H)-dione (275 mg, 578 µmol, 33.1%) and 5-fluoro-1-((2R,3S,4R,5R)-3-fluoro-5-(2-hydroxyethyl)-5-(hydroxymethyl)-4-((tetrahydro-2H-pyran-2-yl) oxy) tetrahydrofuran-2-yl) pyrimidine-2,4(1H,3H)-dione (370 mg, 944 µmol, 35.5%) as white solid. LC-MS (ES, m/z): 477 [M+H]$^+$. LC-MS (ES, m/z): 393 [M+H]$^+$.

Step 11: To a stirred solution of 5-fluoro-1-((2R,3S,4R,5R)-3-fluoro-5-(2-hydroxyethyl)-4-((tetrahydro-2H-pyran-2-yl) oxy)-5-(((tetrahydro-2H-pyran-2-yl) oxy) methyl) tetrahydrofuran-2-yl) pyrimidine-2,4(1H,3H)-dione (275 mg, 578 µmol) in DCM (10 mL) was added TEA (146 mg, 1.45 mmol) and ethanesulfonyl chloride (111 mg, 867 µmol) dropwise at 0° C. under a $N_2$ atmosphere. The resulting mixture was stirred for 1 h at room temperature under a $N_2$ atmosphere. The resulting mixture was concentrated under reduced pressure. The residue was purified by Prep-TLC (EA) to afford 2-((2R,3R,4S,5R)-4-fluoro-5-(5-fluoro-2,4-dioxo-3,4-dihydropyrimidin-1(2H)-yl)-3-((tetrahydro-2H-pyran-2-yl) oxy)-2-(((tetrahydro-2H-pyran-2-yl) oxy) methyl) tetrahydrofuran-2-yl) ethyl ethanesulfonate (270 mg, 470 µmol, 96.4%) as a white solid. LC-MS-P (ES, m/z): 567 [M−H]$^−$.

Step 12: To a stirred solution of 2-((2R,3R,4S,5R)-4-fluoro-5-(5-fluoro-2,4-dioxo-3,4-dihydropyrimidin-1(2H)-yl)-3-((tetrahydro-2H-pyran-2-yl) oxy)-2-(((tetrahydro-2H-pyran-2-yl) oxy) methyl) tetrahydrofuran-2-yl) ethyl ethanesulfonate (270 mg, 470 µmol) in THF (8 mL) was added TBAF (1.9 mL, 1.88 mmol, 1.0 M in THF) dropwise at room temperature under a $N_2$ atmosphere. The resulting mixture was stirred for 15 h at room temperature under a $N_2$ atmosphere. The resulting mixture was diluted with water and extracted with EtOAc (3×50 mL). The combined organic layers were washed with brine and dried over anhydrous $Na_2SO_4$. After filtration the filtrate was concentrated under reduced pressure. The residue was purified by Prep-TLC (DCM/MeOH=10:1) to afford 5-fluoro-1-((2R,3S,4R,5R)-3-fluoro-5-(2-fluoroethyl)-4-((tetrahydro-2H-pyran-2-yl) oxy)-5-(((tetrahydro-2H-pyran-2-yl) oxy) methyl) tetrahydrofuran-2-yl) pyrimidine-2,4(1H,3H)-dione (260 mg, 540 µmol, 96.1%) as a white solid. LC-MS (ES, m/z): 477 [M−H]$^−$.

Step 13: To a stirred solution of 5-fluoro-1-((2R,3S,4R,5R)-3-fluoro-5-(2-fluoroethyl)-4-((tetrahydro-2H-pyran-2-yl) oxy)-5-(((tetrahydro-2H-pyran-2-yl) oxy) methyl) tetrahydrofuran-2-yl) pyrimidine-2,4(1H,3H)-dione (260 mg, 540 µmol) in ACN (8 mL) was added TEA (109 mg, 1.08 mmol) and DMAP (132 mg, 1.08 mmol) at room temperature under a $N_2$ atmosphere. The resulting mixture was stirred for 10 min at room temperature. To the above mixture was added TPSCl (329 mg, 1.08 mmol) at room temperature. The resulting mixture was stirred for additional 15 h at room temperature. To the above mixture was added conc. $NH_3$·$H_2O$ solution (1 mL) dropwise at room temperature. The resulting mixture was stirred for additional 30 min at room temperature. The resulting mixture was concentrated under reduced pressure. The residue was purified by Prep-TLC (DCM/MeOH=10:1) to afford 4-amino-5-fluoro-1-((2R,3S,4R,5R)-3-fluoro-5-(2-fluoroethyl)-4-((tetrahydro-2H-pyran-2-yl) oxy)-5-(((tetrahydro-2H-pyran-2-yl) oxy) methyl) tetrahydrofuran-2-yl) pyrimidin-2(1H)-one (240 mg, 503 µmol, 92.5%) as a white solid. LC-MS (ES, m/z): 478 [M+H]$^+$.

Step 14: To a stirred solution of 4-amino-5-fluoro-1-((2R,3S,4R,5R)-3-fluoro-5-(2-fluoroethyl)-4-((tetrahydro-2H-pyran-2-yl) oxy)-5-(((tetrahydro-2H-pyran-2-yl) oxy) methyl) tetrahydrofuran-2-yl) pyrimidin-2(1H)-one (240 mg, 503 µmol) in MeOH (6 mL) was added p-TsOH (207 mg, 1.01 mmol) in portions at room temperature under a $N_2$ atmosphere. The resulting mixture was stirred for 3 h at room temperature under $N_2$ atmosphere. The resulting mixture was concentrated under reduced pressure and purified by Prep-TLC (DCM/MeOH=10:1) to afford the crude product. The crude product was purified by Prep-HPLC with the following conditions (Column: Xbridge Phenyl OBD Column, 19*150 mm, 5 m; Mobile Phase A: Water (10 mmol/L $NH_4HCO_3$), Mobile Phase B: ACN; Flow rate: 20 mL/min; Gradient: 8% B to 25% B in 20 min; RT1(min): 9.89). The fraction was collected and concentrated under vacuum, the residue was re-dissolved in $CH_3CN$ and $H_2O$, and then was lyophilized to afford 4-amino-5-fluoro-1-((2R,3S,4R,5R)-3- fluoro-5-(2-fluoroethyl)-4-hydroxy-5-(hydroxymethyl) tetrahydrofuran-2-yl) pyrimidin-2(1H)-one (8 mg, 26 μmol, 4.3%) as a white solid. LC-MS (ES, m/z): 310 [M+H]+, 98.9% purity. Conditions for the HPLC: (XBridge Shield RP C18, 100*4.6 mm, 3.5 μm; Mobile Phase A: Water/5 mM NH$_4$HCO$_3$, Mobile Phase B: Acetonitrile; Flow rate: 1.50 mL/min; Gradient: 0% B to 30% B in 10.00 min, 30% B to 95% B in 2.00 min, 95% B to 95% B in 1.70 min; Wavelength: 254 nm; RT1(min): 4.381). $^1$H NMR (400 MHz, DMSO-d$_6$) δ 8.05 (d, J=7.2 Hz, 1H), 7.84 (s, 1H), 7.60 (s, 1H), 6.10 (ddd, J=13.4, 4.8, 1.9 Hz, 1H), 6.05-5.95 (m, 1H), 5.40-5.30 (m, 1H), 5.12 (dt, J=53.4, 4.4 Hz, 1H), 4.72-4.46 (m, 2H), 4.43-4.30 (m, 1H), 3.56 (dd, J=12.3, 5.1 Hz, 1H), 3.45 (dd, J=11.9, 5.3 Hz, 1H), 2.18-1.84 (m, 2H).

Example 92—Synthesis of Compound 179:
5-fluoro-1-((2R,3S,4R,5R)-3-fluoro-4-hydroxy-5-(2-hydroxyethyl)-5-(hydroxymethyl) tetrahydrofuran-2-yl) pyrimidine-2,4(1H,3H)-dione

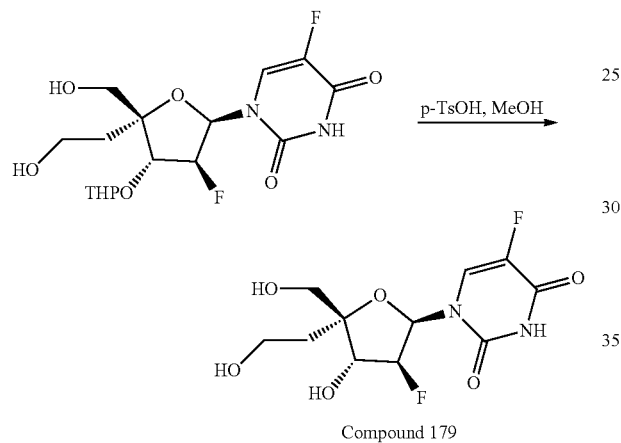

Compound 179

To a stirred solution of 5-fluoro-1-((2R,3S,4R,5R)-3-fluoro-5-(2-hydroxyethyl)-5-(hydroxymethyl)-4-((tetrahydro-2H-pyran-2-yl) oxy) tetrahydrofuran-2-yl) pyrimidine-2,4(1H,3H)-dione (370 mg, 944 μmol) in MeOH (10 mL) was added p-TsOH (243 mg, 1.42 mmol) in portions at room temperature under a N$_2$ atmosphere. The resulting mixture was stirred for 3 h at room temperature under a N$_2$ atmosphere. The mixture was concentrated and purified by Prep-TLC (DCM/MeOH=5:1) to afford the crude product. The crude product was purified by Prep-HPLC with the following conditions (Column: Xbridge Phenyl OBD Column, 19*150 mm, 5 μm; Mobile Phase A: Water (10 mmol/L NH$_4$HCO$_3$), Mobile Phase B: ACN; Flow rate: 20 mL/min; Gradient: 8% B to 25% B in 20 min; Wavelength: 254 nm; RT1(min): 9.89). The fraction was collected and concentrated under vacuum, the residue was re-dissolved in CH$_3$CN and H$_2$O, and then was lyophilized to afford 5-fluoro-1-((2R,3S,4R,5R)-3-fluoro-4-hydroxy-5-(2-hydroxyethyl)-5-(hydroxymethyl) tetrahydrofuran-2-yl) pyrimidine-2,4(1H,3H)-dione (20.1 mg, 65 μmol, 6.8%) as a white solid. LC-MS (ES, m/z): 309 [M+H]+, 97.6% purity. Conditions for the HPLC: (Atlantis T3, 100*4.6 mm, 3 μm; Mobile Phase A: H$_2$O+0.05% TFA, Mobile Phase B: can+ 0.05% TFA; Flow rate: 1.50 mL/min; Gradient: 0% B to 95% B in 8.00 min, 95% B to 95% B in 2.00 min, 95% B to 10% B in 0.50 min; Wavelength: 254 nm; RT1(min): 2.48). $^1$H NMR (400 MHz, DMSO-d$_6$) δ 9.34 (d, J=212.2 Hz, 1H), 8.23 (dd, J=7.2, 2.4 Hz, 1H), 6.11 (ddd, J=10.8, 5.2, 1.8 Hz, 1H), 5.90 (s, 1H), 5.41 (s, 1H), 5.17 (dt, J=53.9, 5.1 Hz, 1H), 4.58 (s, 1H), 4.37 (dd, J=23.0, 4.9 Hz, 1H), 3.65-3.57 (m, 1H), 3.53 (t, J=6.8 Hz, 2H), 3.43 (d, J=12.0 Hz, 1H), 1.82-1.61 (m, 2H).

Example 93—Synthesis of Compound 96: 1-((2R, 4S,5S)-4-azido-5-(chloromethyl)-5-(hydroxymethyl) tetrahydrofuran-2-yl)-5-methylpyrimidine-2,4(1H, 3H)-dione

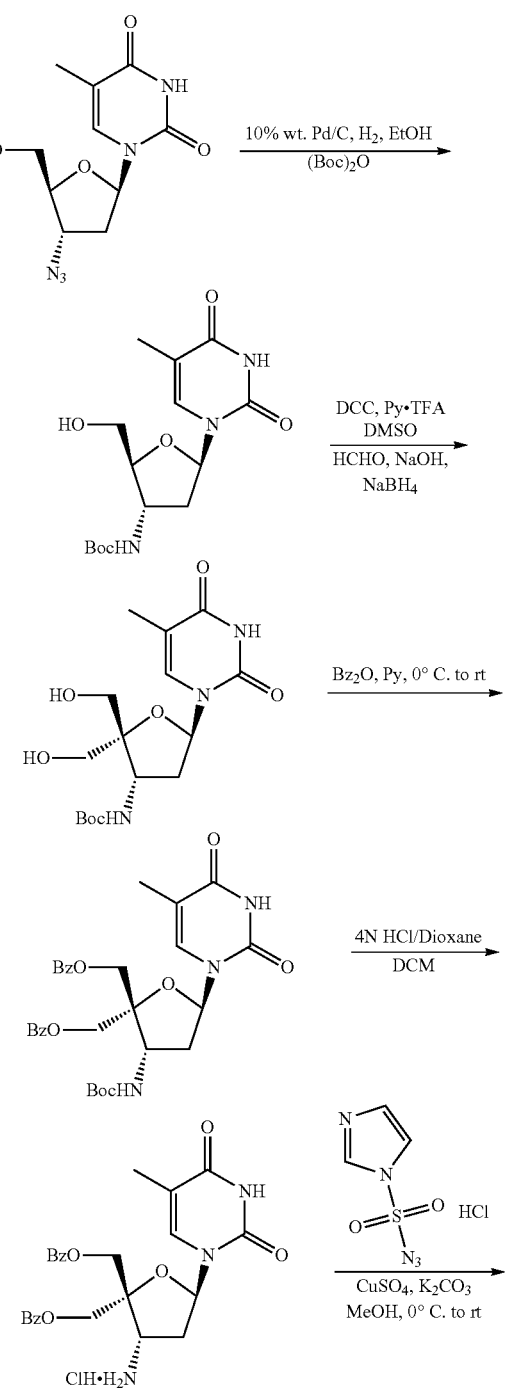

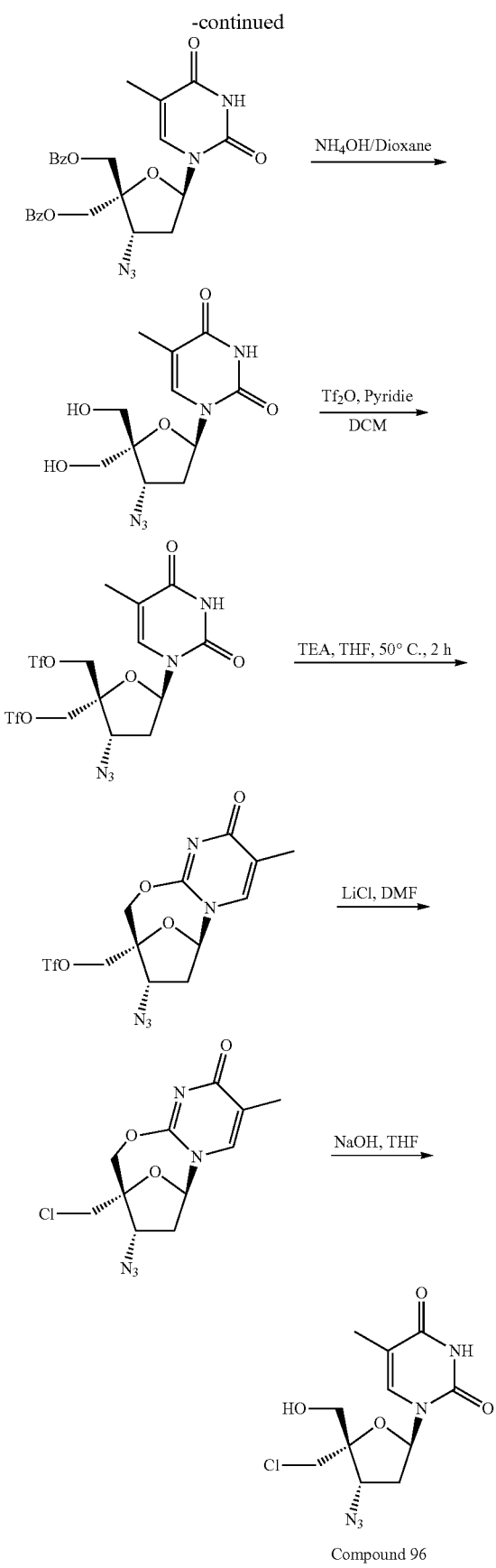

Compound 96

Step 1: To a stirred solution of 1-((2R,4S,5S)-4-azido-5-(hydroxymethyl) tetrahydrofuran-2-yl)-5-methylpyrimidine-2,4(1H,3H)-dione (50 g, 187.09 mmol) in ethanol (250 mL) was added boc anhydride (94 mL, 411.5 mmol) followed by 10% wt. Pd/C (5.0 g) at 0° C. After stirring the reaction mixture under hydrogen atmosphere (60 psi) at rt for 16 h in autoclave (1 L). the reaction mixture was filtered through a celite bed and the celite bed was washed with ethanol. The filtrate was concentrated under reduced pressure to afford desired product (35 g, 54.80%) as off-white solid. LC-MS (ES, m/z): 386.2 (M+45).

Step 2: To a solution of tert-butyl ((2S,3S,5R)-2-(hydroxymethyl)-5-(5-methyl-2,4-dioxo-3,4-dihydropyrimidin-1(2H)-yl)tetrahydrofuran-3-yl)carbamate (20 g, 58.58 mmol) in MeCN (200 mL), IBX (50 g, 175.7 mmol) was added and the reaction was stirred at 90° C. for 2 h. The reaction progress was monitored by TLC. After completion, the reaction mixture was filtered, and the filtrate was concentrated to afford crude aldehyde material which was used as such for the next step. The crude aldehyde material was diluted with 1,4-Dioxane (200 mL) and formaldehyde (20 mL, 585.8 mmol) followed by addition of 2N NaOH (40 mL, 234.3 mmol) at 0° C. and stirred for 12 hours at rt. The reaction progress was monitored by TLC. After completion, sodium borohydride (4.5 g, 117.7 mmol) was added in portion wise manner and stirred for 1 hour. The reaction progress was monitored by TLC and LCMS. After completion, the reaction mixture was quenched with ammonium chloride and then partitioned with EtOAc (250 mL) and water (100 mL). The organic layer was separated, and aq. layer was extracted with EtOAc (2×100 mL) and combined organics were dried over $Na_2SO_4$, concentrated, and the residue was purified by CombiFlash column chromatography by eluting with 65% EtOAc in n-Hexane to afford the desired product (13 g, 59.75%) as white solid. LC-MS (ES, m/z): 372.10 (M+H).

Step 3: To a solution of tert-butyl ((3S,5R)-2,2-bis(hydroxymethyl)-5-(5-methyl-2,4-dioxo-3,4-dihydropyrimidin-1(2H)-yl)tetrahydrofuran-3-yl)carbamate (13 g, 35.00 mmol) in DCM (150 mL) was added pyridine (13 mL, 175.0 mmol) and the reaction was stirred for 15 min. To the above reaction mixture, BzCl (9.38 mL, 87.50 mmol) was added at 0° C. and stirring was continued at rt for 2 h. The reaction progress was monitored by TLC and LCMS. After completion, the reaction mixture was partitioned between water (100 mL) and DCM (250 mL). The organic layer was separated, dried over $Na_2SO_4$, concentrated, and resulting residue was purified by CombiFlash column chromatography by eluting with 38% EtOAc in n-Hexane to afford the desired product (18 g, 88.72%) as white solid. LC-MS (ES, m/z): 580.15 (M+H).

Step 4: To a solution of ((3S,5R)-3-((tert-butoxycarbonyl)amino)-5-(5-methyl-2,4-dioxo-3,4-dihydropyrimidin-1 (2H)-yl)tetrahydrofuran-2,2-diyl)bis(methylene) dibenzoate (18 g, 31.05 mmol) in DCM (50 mL) was added 4N HCl in dioxane (50 mL, 93.16 mmol) at 0° C. After stirring the reaction mixture at rt for 4 h, the reaction mixture was concentrated under reduced pressure and co-distilled with ether to remove the excess HCl gas. The residue was triturated with n-Hexane to afford the crude compound as pale pink solid (16 g) which was used as such for the next step. LC-MS (ES, m/z): 480.15 (M+H).

Step 5: To a solution of ((3S,5R)-3-amino-5-(5-methyl-2,4-dioxo-3,4-dihydropyrimidin-1(2H)-yl)tetrahydrofuran-2,2-diyl)bis(methylene) di-benzoate (12.5 g, 26.06 mmol) in methanol (120 mL) was added potassium carbonate (8.4 g, 65.17 mmol) followed by $CuSO_4 0.5 \cdot H_2O$ (620 mg, 2.606 mmol) and then 1H-imidazole-1-sulfonyl azide. HCl (7.6 g, 39.10 mmol) at 0° C. After stirring the reaction mixture at rt for 5 h, the reaction mixture was partitioned between water (100 mL) and DCM (250 mL). The organic layer was separated, dried over Na$_2$SO$_4$, concentrated and the residue was purified by CombiFlash column chromatography by eluting with 35% EtOAc in n-Hexane to afford the desired product (6 g, 48.98%) as off-white solid. LC-MS (ES, m/z): 504.05 (M−H).

Step 6: To a stirred solution of ((3S,5R)-3-azido-5-(5-methyl-2,4-dioxo-3,4-dihydropyrimidin-1(2H)-yl)tetrahydrofuran-2,2-diyl)bis(methylene) di-benzoate (6 g, 11.86 mmol) in methanol (10 mL) was added methanolic ammonia (15 mL, 35.60 mmol) at 0° C. After stirring the reaction mixture at rt for 16 h, the reaction mixture was concentrated and the residue was purified by CombiFlash column chromatography by eluting with 60% EtOAc in n-Hexane to afford the desired product (2.45 g, 69.41%) as an off-white solid. LC-MS (ES, m/z): 295.90 (M−H).

Step 7: To a solution of 1-((2R,4S)-4-azido-5,5-bis(hydroxymethyl) tetrahydrofuran-2-yl)-5-methylpyrimidine-2,4(1H,3H)-dione (0.5 g, 1.68 mmol) in DCM (5 mL) was added pyridine (0.667 mL, 8.409 mmol) and after cooling to −35° C., triflic anhydride (0.852 mL, 5.045 mmol) was added in a dropwise manner. The reaction was then stirred for 2 hr at −35° C. The reaction mixture was quenched with saturated sodium bicarbonate and extracted with EtOAc, the organic layer was washed with brine, and dried over Na$_2$SO$_4$, organic layer was concentrated under reduced pressure and the residue was purified by CombiFlash column chromatography by eluting with 55% EtOAc in n-Hexane to afford the desired product (0.5 g, 52.97%) as an off-white solid. LC-MS (ES, m/z): 559.90 (M−H).

Step 8: To a stirred solution of ((3S,5R)-3-azido-5-(5-methyl-2,4-dioxo-3,4-dihydropyrimidin-1(2H)-yl)tetrahydrofuran-2,2-diyl)bis(methylene)bis(trifluoromethanesulfonate) (250 mg, 0.426 mmol) in THF (5 mL) was added Et$_3$N (0.6 mL, 4.260 mmol) at rt under nitrogen atmosphere. After stirring the reaction mixture at 50° C. for 3 hours. The reaction mixture was cooled to room temperature and to this LiCl (60 mg, 1.28 mmol) was added in portions. The reaction mixture was stirred at rt for 16 h and the reaction progress was monitored by TLC and LCMS. After completion, a solution of 1N NaOH (0.5 mL, 1.07 mmol) was added dropwise. After stirring the reaction mixture at for 3 h, the reaction mixture was extracted with EtOAc, washed with brine, dried over anhydrous Na$_2$SO$_4$, concentrated under vacuum and the residue was purified by prep-HPLC by using these conditions; mobile Phase: A=0.1% HCOOH IN water B=MeCN; column: Waters X BRIDGE (150 mm×20.0 mm), 5.0µ; flow: 15 mL/min gradient program: Time % B: 0/20, 2/30, 8/60 to afford the desired product (6 mg, 4.26% (overall yield for 3 steps)) as off-white solid. LC-MS (ES, m/z): 316.1 (M−H). $^1$H NMR (400 MHz, DMSO-d$_6$) δ=11.32 (br s, 1H), 7.61 (s, 1H), 6.17 (t, J=6.3 Hz, 1H), 5.45 (t, J=5.2 Hz, 1H), 4.71 (t, J=7.6 Hz, 1H), 3.84-3.72 (m, 2H), 3.68-3.55 (m, 2H), 2.59-2.54 (m, 1H), 2.47-2.40 (m, 1H), 1.83-1.75 (m, 3H).

Example 94—Synthesis of Compound 180: 1-((2R, 4S,5R)-4-fluoro-5-(hydroxymethyl)-5-methyltetrahydrofuran-2-yl)-5-methylpyrimidine-2,4(1H,3H)-dione

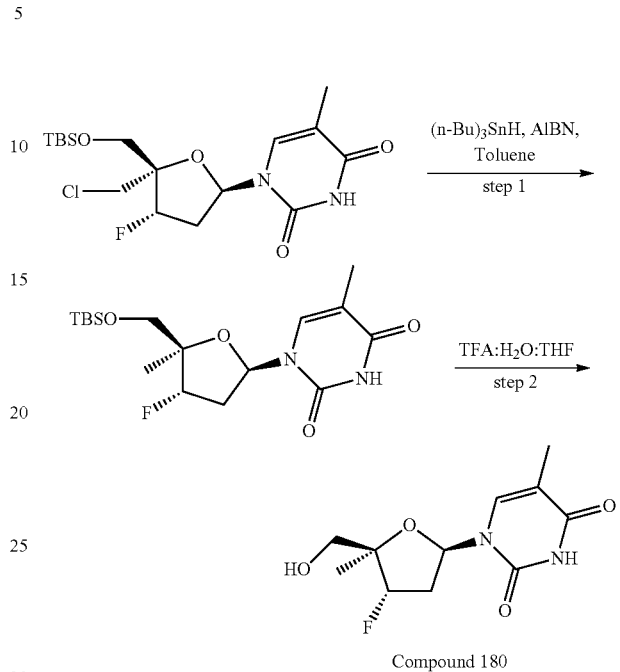

Compound 180

Step 1: To a stirred solution of 1-((2R,4S,5R)-5-(((tert-butyldimethylsilyl) oxy) methyl)-5-(chloromethyl)-4-fluorotetrahydrofuran-2-yl)-5-methylpyrimidine-2,4(1H,3H)-dione (47 mg, 116 µmol) in Toluene (2 mL) was added AIBN (38 mg, 232 µmol) and n-Bu3SnH (202 mg, 696 µmol) at room temperature under a N$_2$ atmosphere. The reaction mixture was stirred for 3 h at 100° C. The resulting mixture was cooled to room temperature, concentrated under reduced pressure and purified by Prep-TLC (PE/EtOAc=1:1) to afford 1-((2R,4S,5R)-5-(((tert-butyldimethylsilyl) oxy) methyl)-4-fluoro-5-methyltetrahydrofuran-2-yl)-5-methylpyrimidine-2,4(1H,3H)-dione (31 mg, 83 µmol, 72.1%) as a white solid. LC-MS (ES, m/z): 373 [M+H]$^+$.

Step 2: To a stirred solution of 1-((2R,4S,5R)-5-(((tert-butyldimethylsilyl) oxy) methyl)-4-fluoro-5-methyltetrahydrofuran-2-yl)-5-methylpyrimidine-2,4(1H,3H)-dione (31 mg, 83 µmol) in THF (4 mL) and H$_2$O (1.2 mL) was added TFA (0.8 mL). The reaction was stirred for 16 h at room temperature under a N$_2$ atmosphere. The resulting mixture was concentrated under reduced pressure and purified by Prep-HPLC with the following conditions (Column: X-Select Prep OBD C18 Column, 30*150 mm, 5 µm; Mobile Phase A: Water (0.1% FA), Mobile Phase B: 20 mm NaOH+ 10% ACN; Flow rate: 60 mL/min; Gradient: 30% B to 50% B in 7 min; Wavelength: 254 nm/220 nm; RT1(min): 6.56). The fraction was collected and concentrated under vacuum, the residue was re-dissolved in CH$_3$CN and H$_2$O, and then was lyophilized to afford 1-((2R,4S,5R)-4-fluoro-5-(hydroxymethyl)-5-methyltetrahydrofuran-2-yl)-5-methylpyrimidine-2,4(1H,3H)-dione (2.7 mg, 10 µmol, 12.5%) as an off-white solid. LC-MS (ES, m/z): 259 [M+H]$^+$, 99.7% purity. Conditions for the LCMS: (Column: Shim-pack Scepter C18 Column, 33*3.0 mm, 3.0 µm; Mobile Phase A: water/5 mM NH$_4$HCO$_3$, Mobile Phase B: Acetonitrile; Flow rate: 1.50 mL/min; Gradient: 10% B to 95% B in 1.20 min, 95% B to 95% B in 0.60 min, 95% B to 10% B in 0.02 min;

Wavelength: 254/220 nm; RT1(min): 0.517). $^1$H NMR (400 MHz, DMSO-$d_6$) δ 11.34 (s, 1H), 7.78-7.74 (m, 1H), 6.20 (t, J=7.4 Hz, 1H), 5.34 (t, J=5.1 Hz, 1H), 5.27-5.03 (m, 1H), 3.48 (dd, J=5.2, 1.8 Hz, 2H), 2.46 (s, 1H), 2.43-2.37 (m, 1H), 1.78 (d, J=1.2 Hz, 3H), 1.17 (d, J=4.4 Hz, 3H).

Example 95—Synthesis of Compound 86-TP: ((2R, 3R,4S,5R)-5-(4-amino-5-fluoro-2-oxopyrimidin-1 (2H)-yl)-2-(bromomethyl)-4-fluoro-3-hydroxytetrahydrofuran-2-yl) methyl tetrahydrogen triphosphate; tetrakis(triethylamine)

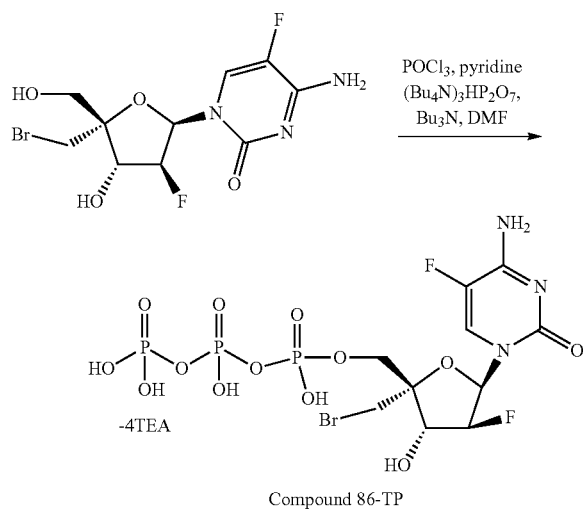

Compound 86-TP

To a stirred solution of 4-amino-1-((2R,3S,4R,5R)-5-(bromomethyl)-3-fluoro-4-hydroxy-5-(hydroxymethyl) tetrahydrofuran-2-yl)-5-fluoropyrimidin-2(1H)-one (30 mg, 84 mol) in pyridine (2 mL) was added POCl$_3$ (194 mg, 1.27 mmol) dropwise at 0° C. under N$_2$ atmosphere. The mixture was stirred for 20 min at 0° C., then the solution of (Bu$_4$N)$_3$HP$_2$O$_7$(1.1 g, 1.27 mmol) and Bu$_3$N (312 mg, 1.68 mmol) in DMF (2 mL) was added at 0° C. under an N$_2$ atmosphere. The reaction was stirred for 3 h at room temperature. The reaction was quenched with TEAB buffer (1.0 M in H$_2$O) at 0° C. and washed with DCM (7×10 mL). The aqueous phase was combined and concentrated under reduced pressure to give crude product. The crude product was purified by ion-exchange column purification with following conditions (Column: HiTrap DEAE Sepharose FF, 5 mL; Mobile Phase A: Water, Mobile Phase B: water (0.5 M TEAB); Flow rate: 5 mL/min; Gradient: 60% B to 80% B in 15 min; Wavelength: 254 nm/246 nm; RT1(min): 8.7) to afford the crude product. The crude product was purified by Prep-HPLC with the following conditions (Column: YMC Triart C18 ExRs 5 m, 20*250 mm; Mobile Phase A: water (50 mM TEAB), Mobile Phase B: ACN; Flow rate: 25 mL/min; Gradient: 3% B to 20% B in 10 min; Wavelength: 254 nm/220 nm; RT1(min): 8.8). The fraction was collected and concentrated under vacuum, the residue was re-dissolved in CH$_3$CN and H$_2$O, and then was lyophilized to afford ((2R,3R,4S,5R)-5-(4-amino-5-fluoro-2-oxopyrimidin-1(2H)-yl)-2-(bromomethyl)-4-fluoro-3-hydroxytetrahydrofuran-2-yl) methyl tetrahydrogen triphosphate TEA salt (2.9 mg, 5 μmol, 6.1%) as an off-white solid. LCMS (ES, m/z): 594/596 [M−H]$^−$, 95.4% purity. Conditions for the LCMS: (Column: Xselect HSS T3, 100*4.6 mm, 3.5 μm; Mobile Phase A: 20 mM TEAA, Mobile Phase B: Acetonitrile; Flow rate: 1.50 mL/min; Gradient: 0% B to 30% B in 6.00 min, 30% B to 95% B in 2.00 min, 95% B to 95% B in 2.00 min, 95% B to 0% B in 0.20 min; Wavelength: 254/220 nm; RT1(min): 2.555). $^1$H NMR (400 MHz, D$_2$O) δ 8.02 (d, J=6.3 Hz, 1H), 6.38 (dd, J=11.0, 5.3 Hz, 1H), 5.38 (dt, J=53.1, 5.1 Hz, 1H), 4.83 (dd, J=24.1, 4.9 Hz, 1H), 4.18 (ddd, J=34.1, 11.2, 4.6 Hz, 2H), 3.66 (q, J=11.8 Hz, 2H), 2.90 (q, J=7.3 Hz, 26H), 1.11 (q, J=7.1 Hz, 39H). $^{31}$P NMR (162 MHz, D$_2$O) δ −9.21, −11.85 (d, J=20.7 Hz), −22.81.

Example 96—Synthesis of Compound 181: 1-[(2R, 4S,5S)-4-azido-5-(hydroxymethyl)-5-methyloxolan-2-yl]-5-methyl-3H-pyrimidine-2,4-dione

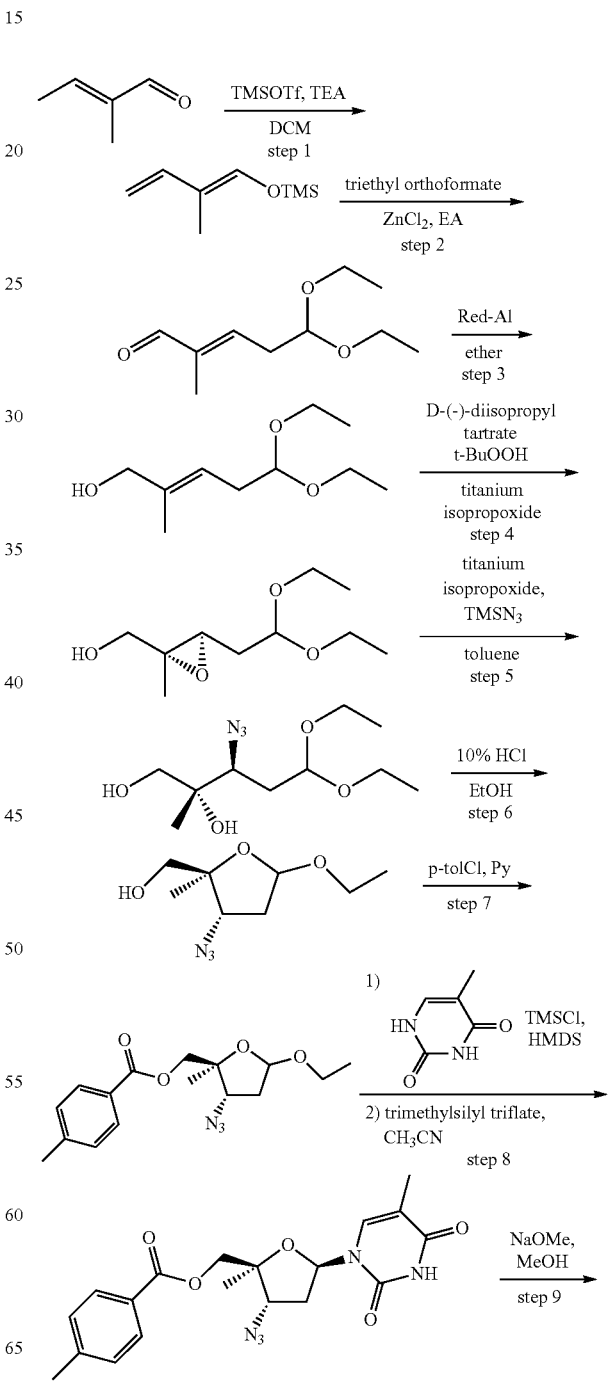

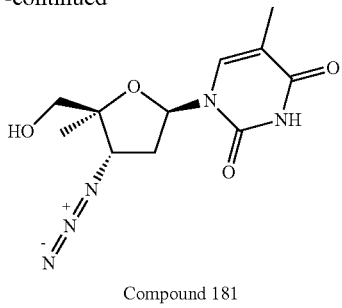

Compound 181

Step 1: To a stirred solution of trans-2-methyl-2-butenal (20.0 g, 237.76 mmol) and TEA (36.1 g, 356.65 mmol) in DCM (300 mL) was added TMSOTf (58.1 g, 261.55 mmol) dropwise at 0° C. The mixture was stirred for 4 h at 0° C. and then overnight at room temperature. The reaction was quenched by the addition of sat. NaHCO₃(aq.) at 0° C. The resulting mixture was washed with sat. NH₄Cl (aq.) and sat. NaHCO₃(aq.), and dried over anhydrous Na₂SO₄. After filtration the filtrate was concentrated under reduced pressure. The crude product was purified by distillation under reduced pressure and the fraction was collected at 68-72° C. resulting in trimethyl({[(1E)-2-methylbuta-1,3-dien-1-yl]oxy})silane (22.5 g, 144.23 mmol, 60.55%) as a light-yellow oil. GC-MS (ES, m/z): 156 (M).

Step 2: To a stirred mixture of (diethoxymethoxy)ethane (20.9 g, 140.76 mmol) and ZnCl₂ (29.7 g, 218.17 mmol) in EtOAc (220 mL) was added trimethyl({[(1E)-2-methylbuta-1,3-dien-1-yl] oxy}) silane (22.0 g, 140.76 mmol) dropwise at room temperature. The resulting mixture was stirred overnight at room temperature and then quenched by the addition of sat. NaHCO₃(aq.) at 0° C. The resulting mixture was filtered; the filter cake was washed with ethyl ether. The resulting solution was extracted with EtOAc. The resulting mixture was washed with sat. NaHCO₃(aq.), dried over anhydrous Na₂SO₄. After filtration the filtrate was concentrated under reduced pressure. The residue was purified by silica gel column chromatography, eluting with PE/EtOAc (10:1) to afford (2E)-5,5-diethoxy-2-methylpent-2-enal (18.0 g, 96.64 mmol, 68.66%) as a light-yellow oil. GC-MS (ES, m/z): 186 (M).

Step 3: To a stirred solution of (2E)-5,5-diethoxy-2-methylpent-2-enal (18.0 g, 96.64 mmol) in ether (180 mL) was added Red-Al (90 mL, 70% in toluene) dropwise at 0° C. under nitrogen atmosphere. The resulting mixture was stirred for 1 h at 0° C. and then quenched by the addition of sat. NH₄Cl (aq.) at 0° C. The resulting mixture was stirred for 30 min at room temperature and then filtered; the filter cake was washed with ethyl ether. The resulting solution was extracted with EtOAc. The organic layer was washed with sat. NaHCO₃(aq.), dried over anhydrous Na₂SO₄. After filtration the filtrate was concentrated under reduced pressure. The residue was purified by silica gel column chromatography, eluting with PE/EtOAc (5:1) to afford (2E)-5,5-diethoxy-2-methylpent-2-en-1-ol (10.5 g, 55.85 mmol, 57.71%) as a light-yellow oil. $^1$H NMR (400 MHz, DMSO-d₆) δ 5.36-5.31 (m, 1H), 4.68 (td, J=5.6, 1.2 Hz, 1H), 4.44 (t, J=5.6 Hz, 1H), 3.79 (d, J=5.6, 2H), 3.60-3.52 (m, 2H), 3.47-3.40 (m, 2H), 2.28-2.24 (m, 2H), 1.55 (s, 3H), 1.11 (t, J=7.2 Hz, 6H).

Step 4: A mixture of powdered activated 4 A MS (5.29 g) in DCM (200 mL) was cooled to −20° C. 1,4-Bis(propan-2-yl) (2S,3S)-2,3-dihydroxybutanedioate (1.244 g, 5.31 mmol), tetrakis(propan-2-yloxy) titanium (1.5 g, 5.31 mmol) and tert-butyl hydroperoxide (9.6 g, 106.23 mmol) were added at −20° C. After stirring for 30 min at −20° C., a solution of (2E)-5,5-diethoxy-2-methylpent-2-en-1-ol (10.0 g, 53.12 mmol) in DCM (50 mL) was added dropwise at −20° C. The resulting mixture was stirred for 8 h at −20° C. and then quenched by the addition of a solution NaOH in saturated brine (10%) at −20° C. To the above mixture, was added anhydrous Na₂SO₄ and Celite. After stirring for 15 min and standing for an additional 1 h, the resulting mixture was filtered and the filter cake was washed with ether. The combine filtrate was dried over anhydrous Na₂SO₄. After filtration the filtrate was concentrated under reduced pressure. The residue was purified by silica gel column chromatography, eluting with PE/EtOAc (3:1) to afford [(2R,3R)-3-(2,2-diethoxyethyl)-2-methyloxiran-2-yl] methanol (6.5 g, 31.86 mmol, 59.91%) as a light-yellow oil. $^1$H NMR (400 MHz, DMSO-d₆) δ 4.79 (t, J=6.0 Hz, 1H), 4.62-4.60 (m, 1H), 3.64-3.56 (m, 2H), 3.49-3.44 (m, 2H), 3.40-3.36 (m, 1H), 3.33-3.28 (m, 1H), 2.89-2.86 (m, 1H), 1.84-1.79 (m, 1H), 1.71-1.66 (m, 1H), 1.19 (s, 3H), 1.15-1.10 (m, 6H).

Step 5: A mixture of azidotrimethylsilane (5.0 g, 43.40 mmol) and Titanium(IV) isopropoxide (13.5 g, 47.49 mmol) was stirred for 60 min at room temperature under a nitrogen atmosphere. Then a solution of [(2R,3R)-3-(2,2-diethoxyethyl)-2-methyloxiran-2-yl] methanol (5.0 g, 24.48 mmol) in toluene (200 mL) was added to the above system. The resulting mixture was stirred overnight at room temperature under a nitrogen atmosphere and then quenched by the addition of sat. NaHCO₃(aq.). After stirring for 1 h at room temperature, the resulting mixture was filtered, and the filter cake was washed with CHCl₃. The combined filtrate was concentrated under reduced pressure. The residue was purified by silica gel column chromatography, eluting with CH₂Cl₂/MeOH (50:1) to afford (2S,3S)-3-azido-5,5-diethoxy-2-methylpentane-1,2-diol (2.1 g, 8.49 mmol, 34.69%) as a light-yellow oil. $^1$H NMR (400 MHz, DMSO-d₆) δ 4.73 (t, J=5.2 Hz, 1H), 4.64-4.51 (m, 2H), 3.66-3.56 (m, 2H), 3.51-3.42 (m, 3H), 3.33-3.27 (m, 2H), 1.98-1.92 (m, 1H), 1.67-1.58 (m, 1H), 1.19-1.13 (m, 6H), 1.00 (s, 3H).

Step 6: To a solution of (2S,3S)-3-azido-5,5-diethoxy-2-methylpentane-1,2-diol (2.1 g, 8.49 mmol) in EtOH (60 mL) was added HCl in EtOH (0.2 mL, 10%). The resulting mixture was stirred for 30 min at room temperature, followed by the addition of K₂CO₃ at room temperature. The resulting mixture was stirred for 1 h at room temperature. The resulting mixture was filtered and the filter cake was washed with EtOAc, and the combined filtrate was concentrated under reduced pressure. This resulted in [(2S,3S)-3-azido-5-ethoxy-2-methyloxolan-2-yl] methanol (1.5 g, crude) as a light-yellow oil. The crude product was used in the next step directly without further purification. LC-MS (ES, m/z): 156 (M−45)⁺.

Step 7: To a stirred solution of [(2S,3S)-3-azido-5-ethoxy-2-methyloxolan-2-yl]methanol (1.5 g, crude) in pyridine (15 mL) was added 4-methybenzoyl chloride (1.4 g, 8.20 mmol) at −15° C. under nitrogen atmosphere. The resulting mixture was stirred for 16 h at room temperature under a nitrogen atmosphere and then concentrated under reduced pressure. The residue was dissolved in CHCl₃. The resulting mixture was washed with water, saturated aq. NaHCO₃ and brine. The resulting solution was dried over anhydrous Na₂SO₄. After filtration the filtrate was concentrated under reduced pressure. The residue was purified by silica gel column chromatography, eluting with PE/EtOAc (40:1) to afford [(2S,3S)-3-azido-5-ethoxy-2-methyloxolan-2-yl] methyl 4-methylbenzoate (1.9 g, 5.96 mmol, 79.81%) as a light-yellow oil. LC-MS (ES, m/z): 274 (M−45)⁺.

Step 8: To a stirred solution of thymine (789.8 mg, 6.26 mmol) in HMDS (10 mL) was added TMSCl (680.4 mg, 6.26 mmol) at room temperature. The resulting mixture was stirred overnight at 120° C., then cooled to room temperature and concentrated under reduced pressure. The residue was dissolved in ACN (20 mL), then [(2S,3S)-3-azido-5-ethoxy-2-methyloxolan-2-yl] methyl 4-methylbenzoate (1.0 g, 3.13 mmol) and TMSOTf (1.4 g, 6.26 mmol) were added. The resulting mixture was stirred for an additional 12 h at room temperature and then quenched by the addition of sat. NaHCO$_3$ (aq.) at 0° C. The resulting mixture was extracted with CHCl$_3$. The combined organic layers were washed with brine and dried over anhydrous Na$_2$SO$_4$. After filtration the filtrate was concentrated under reduced pressure. This resulted in [(2S,3S,5R)-3-azido-2-methyl-5-(5-methyl-2,4-dioxo-3H-pyrimidin-1-yl) oxolan-2-yl] methyl 4-methyl-benzoate (850 mg, crude) as a light-yellow oil. LC-MS (ES, m/z): 400 (M+H$^+$).

Step 9: To a stirred solution of [(2S,3S,5R)-3-azido-2-methyl-5-(5-methyl-2,4-dioxo-3H-pyrimidin-1-yl) oxolan-2-yl] methyl 4-methylbenzoate (850.0 mg, 1.89 mmol) in MeOH was added NaOMe·MeOH (5.5 mL, 30%). The resulting mixture was stirred for 3 h at room temperature and then adjusted to pH 7 with Dowex 50w×8. The resulting mixture was filtered; the filter cake was washed with DCM. The combined filtrate was concentrated under reduced pressure. The residue was purified by silica gel column chromatography, eluting with CH$_2$Cl$_2$/MeOH (30:1) to afford the crude product, then the crude product was further purified by reversed-phase flash chromatography under the following conditions: column, C18 silica gel; Mobile Phase A: water (10 mmol/L NH$_4$HCO$_3$), Mobile Phase B: ACN; 10% B to 50% gradient in 10 min; UV detection at 254 nm. The product-containing fractions were combined and evaporated partially to remove the solvents, then lyophilized overnight to afford 1-[(2R,4S,5S)-4-azido-5-(hydroxymethyl)-5-methyloxolan-2-yl]-5-methyl-3H-pyrimidine-2,4-dione (7.6 mg, 0.03 mmol, 1.43%) as a white solid. LC-MS (ES, m/z): 282 (M+H$^+$). 99.0% purity. $^1$H NMR (400 MHz, DMSO-d$_6$) δ 11.28 (s, 1H), 7.73 (d, J=1.2 Hz, 1H), 6.07-6.04 (m, 1H), 5.34 (t, J=5.6 Hz, 1H), 4.47 (t, J=7.6 Hz, 1H), 3.52-3.40 (m, 2H), 2.47-2.39 (m, 2H), 1.79 (d, J=1.2 Hz, 3H), 1.11 (s, 3H).

Example 97—Synthesis of Compound 82: 4-amino-1-((2R,4S,5R)-5-ethyl-4-hydroxy-5-(hydroxymethyl)tetrahydrofuran-2-yl)-5-fluoropyrimidin-2(1H)-one

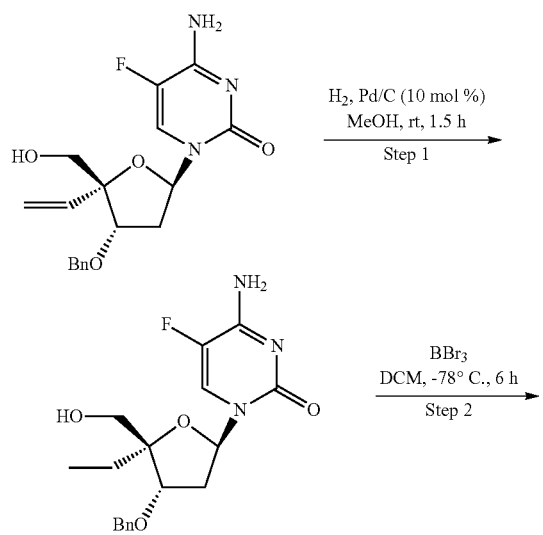

Step 12: Synthesis of 4-amino-1-((2R,4S,5R)-4-(benzyloxy)-5-ethyl-5-(hydroxymethyl)tetrahydrofuran-2-yl)-5-fluoropyrimidin-2(1H)-one (16b). 4-amino-1-[(2R,4S,5R)-4-benzyloxy-5-(hydroxymethyl)-5-vinyl-tetrahydrofuran-2-yl]-5-fluoro-pyrimidin-2-one 15b (Synthesized above in Example 34) (160 mg, 0.44 mmol) was dissolved in anhydrous MeOH (6 mL) and Palladium on carbon (10 wt. % loading, 47.1 mg, 0.04 mmol) was added under argon. The mixture was evacuated and purged with hydrogen for three cycles then stirred under a hydrogen balloon for 2 h. The mixture was filtered through a celite plug and the filtrate was concentrated in vacuo. The crude was purified by flash chromatography over silica gel (Gradient 0-20% MeOH in DCM) to afford 4-amino-1-((2R,4S,5R)-4-(benzyloxy)-5-ethyl-5-(hydroxymethyl)tetrahydrofuran-2-yl)-5-fluoropyrimidin-2(1H)-one16b (131.2 mg, 82% yield) as a white solid. $^1$H NMR (400 MHz, DMSO-d$_6$) δ 8.15 (d, J=7.2 Hz, 1H), 7.69 (s, 1H), 7.46 (s, 1H), 7.40-7.17 (m, 5H), 6.00 (td, J=6.4, 2.1 Hz, 1H), 5.21 (d, J=5.0 Hz, 1H), 4.57 (d, J=12.0 Hz, 1H), 4.45 (d, J=12.0 Hz, 1H), 4.20 (dd, J=6.3, 4.6 Hz, 1H), 3.53 (dd, J=11.7, 4.1 Hz, 1H), 3.44 (dd, J=11.6, 4.3 Hz, 1H), 2.39 (ddd, J=13.5, 6.3, 4.6 Hz, 1H), 2.15 (dt, J=13.2, 6.4 Hz, 1H), 1.66 (dq, J=15.0, 7.5 Hz, 1H), 1.53 (dq, J=14.6, 7.4 Hz, 1H), 0.86 (t, J=7.5 Hz, 3H).

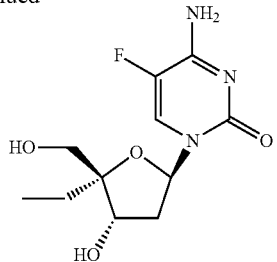

Step 13: To a solution of 4-amino-1-((2R,4S,5R)-4-(benzyloxy)-5-ethyl-5-(hydroxymethyl)tetrahydrofuran-2-yl)-5-fluoropyrimidin-2(1H)-one 16b (130 mg, 0.36 mmol) in anhydrous DCM (8 mL), cooled to −78° C., was added boron tribromide solution (1M in DCM, 0.89 mL, 0.89 mmol) under argon and the mixture was stirred at −78° C. for 5 h. After completion, the mixture was quenched with a solution of methanol:pyridine (2:1, 8 mL) at −78° C. and stirred for 1 h at the same temperature. After warming to room temperature, the mixture was concentrated in vacuo and the crude was purified by flash chromatography over silica gel twice (Gradient 0-20% MeOH in EtOAc) to afford 4-amino-1-((2R,4S,5R)-5-ethyl-4-hydroxy-5-(hydroxymethyl)tetrahydrofuran-2-yl)-5-fluoropyrimidin-2(1H)-one (14.6 mg, 15% yield) as a white solid. $^1$H NMR (400 MHz, DMSO-d$_6$) δ 8.15 (d, J=7.3 Hz, 1H), 7.66 (s, 1H), 7.43 (s, 1H), 6.00 (td, J=6.4, 2.1 Hz, 1H), 5.10 (td, J=5.1, 1.4 Hz, 1H), 5.05 (dd, J=4.9, 1.4 Hz, 1H), 4.23 (q, J=5.2 Hz, 1H), 3.49 (dd, J=11.5, 5.0 Hz, 1H), 3.39 (dd, J=11.5, 5.1 Hz, 1H), 2.16 (ddd, J=13.1, 6.1, 4.3 Hz, 1H), 2.08 (dt, J=13.2, 6.4 Hz, 1H), 1.58 (dq, J=15.0, 7.6 Hz, 1H), 1.45 (dq, J=14.6, 7.4 Hz, 1H), 0.84 (t, J=7.5 Hz, 3H); $^{19}$F NMR (376 MHz, DMSO-d$_6$) δ-167.58, −167.59, −167.60, −167.61. HPLC: 99.2%; HRMS: calcd. for C$_{11}$H$_{16}$FN$_3$O$_4$[M+Na]$^+$296.1022, found 296.1020.

Example 98—Synthesis of Compound 182: 4-amino-1-[(2R,3S,4R,5R)-5-(chloromethyl)-3-fluoro-4-hydroxy-5-(hydroxymethyl) oxolan-2-yl]-5-fluoropyrimidin-2-one

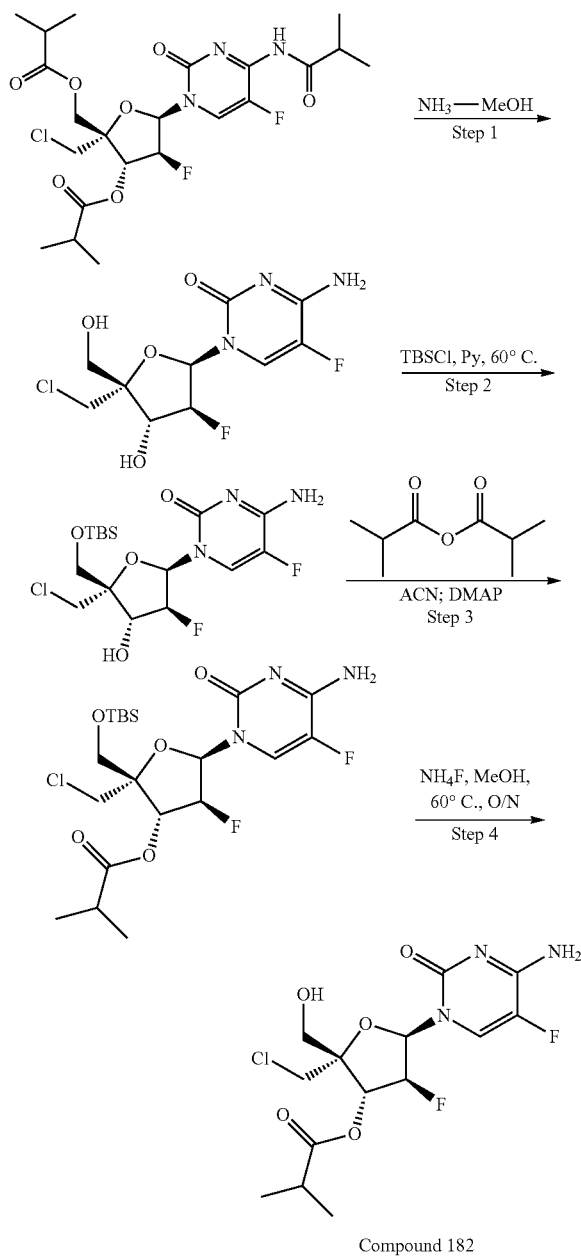

Compound 182

Step 1: To a solution of [(2R,3R,4S,5R)-2-(chloromethyl)-4-fluoro-5-[5-fluoro-4-(2-methylpropanamido)-2-oxopyrimidin-1-yl]-3-[(2-methylpropanoyl) oxy] oxolan-2-yl] methyl 2-methylpropanoate (500 mg, 0.96 mmol) in MeOH (10 mL) was added $NH_3 \cdot MeOH$ (7N, 3 mL). The resulting solution was stirred overnight at room temperature under nitrogen atmosphere and then concentrated under vacuum. The residue was purified by reverse phase flash chromatography with the following conditions: Column: C18; Mobile Phase A: Water (0.1% $NH_3HCO_3$), Mobile Phase B: ACN; Flow rate: 100 mL/min; Gradient: 10% B to 100% in 15 min, detector: UV 254 nm. This resulted in 4-amino-1-[(2R,3S,4R,5R)-5-(chloromethyl)-3-fluoro-4-hydroxy-5-(hydroxymethyl) oxolan-2-yl]-5-fluoropyrimidin-2-one (250 mg, 0.80 mmol, 83.73%) as a white solid. LC-MS (ES, m/z): 312 $(M+H)^+$.

Step 2: To a solution of 4-amino-1-[(2R,3S,4R,5R)-5-(chloromethyl)-3-fluoro-4-hydroxy-5-(hydroxymethyl) oxolan-2-yl]-5-fluoropyrimidin-2-one (250 mg, 0.80 mmol) in pyridine (4 mL), was added TBSCl (250 mg, 1.60 mmol). The resulting mixture was stirred for overnight at 60° C. under nitrogen. The mixture was cooled to room temperature and diluted with EtOAc (10 mL). The solution was washed with brine, dried over anhydrous $Na_2SO_4$ and concentrated under vacuum, resulting in 4-amino-1-[(2R,3S,4R,5R)-5-{[(tert-butyldimethylsilyl) oxy] methyl}-5-(chloromethyl)-3-fluoro-4-hydroxyoxolan-2-yl]-5-fluoropyrimidin-2-one (250 mg, 0.59 mmol) as a white solid. LC-MS (ES, m/z): 426 (M+H)+

Step 3: To a solution of 4-amino-1-[(2R,3S,4R,5R)-5-{[(tert-butyldimethylsilyl) oxy] methyl}-5-(chloromethyl)-3-fluoro-4-hydroxyoxolan-2-yl]-5-fluoropyrimidin-2-one (250 mg, 0.59 mmol) in ACN (10 mL) was added DMAP (150 mg, 1.17 mmol) at 0° C. under nitrogen. This was followed by the addition of 2-methylpropanoyl 2-methylpropanoate (95 mg, 0.58 mmol) at 0° C. The mixture was stirred for 1 h at 0° C. under nitrogen and quenched by the addition of water. The mixture was extracted with EtOAc, washed with brine, dried over anhydrous $Na_2SO_4$ and concentrated under vacuum, resulting in (2R,3R,4S,5R)-5-(4-amino-5-fluoro-2-oxopyrimidin-1-yl)-2-{[(tert-butyldimethylsilyl)oxy]methyl}-2-(chloromethyl)-4-fluorooxolan-3-yl 2-methylpropanoate (240 mg crude) as a yellow solid. The crude product was used in the next step directly without further purification. LC-MS (ES, m/z): 496 (M+H)+

Step 4: To a solution of (2R,3R,4S,5R)-5-(4-amino-5-fluoro-2-oxopyrimidin-1-yl)-2-{[(tert-butyldimethylsilyl) oxy] methyl}-2-(chloromethyl)-4-fluorooxolan-3-yl 2-methylpropanoate (240 mg, crude) in MeOH (5 mL) was added $NH_4F$ (270 mg, 7.26 mmol). The resulting mixture was stirred overnight at 60° C. under nitrogen, then cooled to room temperature and concentrated under vacuum. The mixture was filtered; the filter cake was washed with acetone. The combined filtrate was concentrated under vacuum. The residue was purified by reverse phase flash chromatography with the following conditions: Column: C18; Mobile Phase A: Water (0.1% $NH_3HCO_3$), Mobile Phase B: ACN; Flow rate: 100 mL/min; Gradient: 10% B to 100% in 15 min, detector: UV 254 nm. This resulted in (2R,3R,4S,5R)-5-(4-amino-5-fluoro-2-oxopyrimidin-1-yl)-2-(chloromethyl)-4-fluoro-2-(hydroxymethyl) oxolan-3-yl 2-methylpropanoate (85.5 mg, 0.22 mmol, 38.03% yield in two steps) as a white solid. LC-MS (ES, m/z): 382 $(M+H)^+$ 98.2% purity. $^1H$ NMR (400 MHz, DMSO-$d_6$) δ 8.00 (d, J=7.2 Hz, 1H), 7.93 (brs, 1H), 7.70 (brs, 1H), 6.33-6.28 (m, 1H), 5.62-5.57 (m, 2H), 5.39-5.25 (m, 1H), 3.94 (d, J=11.6 Hz, 1H), 3.76 (d, J=12.0 Hz, 1H), 3.70-3.63 (m, 2H), 2.69-2.65 (m, 1H), 1.15 (dd, J=7.2, 3.2 Hz, 6H).

Example 99—Synthesis of Compound 183: [(2R,3R,4S,5R)-5-(4-amino-5-fluoro-2-oxopyrimidin-1-yl)-2-(chloromethyl)-4-fluoro-3-hydroxyoxolan-2-yl] methyl 2-methylpropanoate

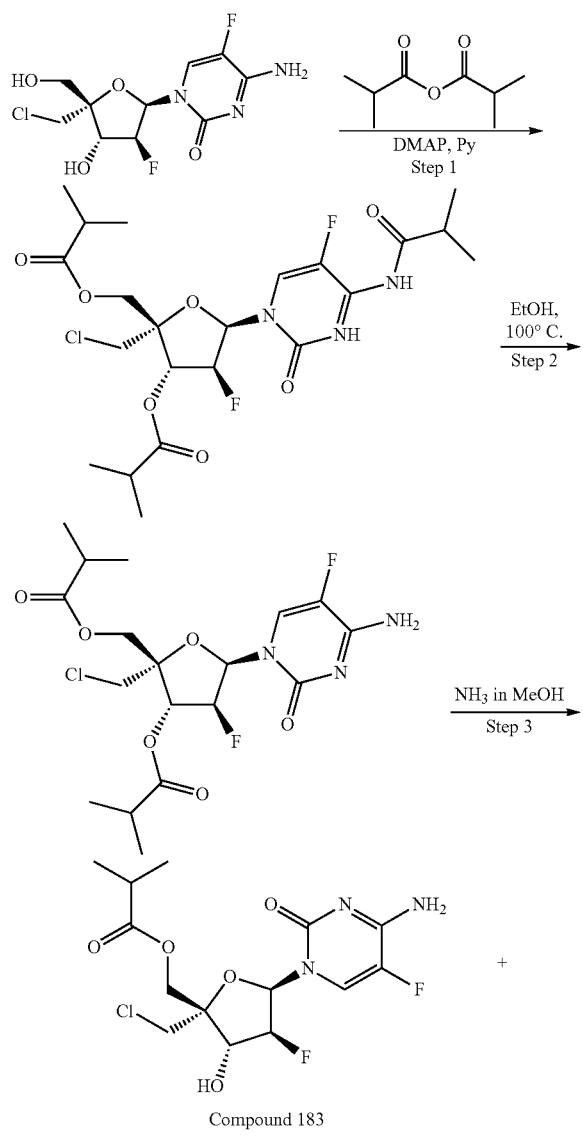

Compound 183

Step 1: To a solution of 4-amino-1-[(2R,3S,4R,5R)-5-(chloromethyl)-3-fluoro-4-hydroxy-5-(hydroxymethyl)oxolan-2-yl]-5-fluoropyrimidin-2-one (5.5 g, 17.68 mmol) and DMAP (4.0 g, 35.36 mmol) in pyridine (50 mL) was added isobutyric anhydride (17.0 g, 106.11 mmol) dropwise at 0° C. under nitrogen. The mixture was stirred overnight at 80° C., then cooled to room temperature and concentrated under vacuum. The residue was diluted with EtOAc, washed with citric acid and brine and dried over anhydrous $Na_2SO_4$. After filtration the filtrate was concentrated under vacuum. The residue was purified by silica gel column chromatography, eluted with petroleum ether/EtOAc (1:1) to afford [(2R,3R,4S,5R)-2-(chloromethyl)-4-fluoro-5-[5-fluoro-4-(2-methylpropanamido)-2-oxopyrimidin-1-yl]-3-[(2-methylpropanoyl) oxy] oxolan-2-yl] methyl 2-methylpropanoate (6.6 g, 12.65 mmol, 71.55%) as a white solid. LC-MS (ES, m/z): 522 $(M+H)^+$.

Step 2: A solution of [(2R,3R,4S,5R)-2-(chloromethyl)-4-fluoro-5-[5-fluoro-4-(2-methylpropanamido)-2-oxopyrimidin-1-yl]-3-[(2-methylpropanoyl) oxy] oxolan-2-yl] methyl 2-methylpropanoate (1.0 g, 1.92 mmol) in EtOH (20 mL) was stirred for overnight at 100° C. under nitrogen. The resulting mixture was cooled to room temperature and concentrated under vacuum, resulting in [(2R,3R,4S,5R)-5-(4-amino-5-fluoro-2-oxopyrimidin-1-yl)-2-(chloromethyl)-4-fluoro-3-[(2-methylpropanoyl) oxy] oxolan-2-yl] methyl 2-methylpropanoate (800 mg, crude) as a white solid. The crude product was used in the next step directly without further purification. LC-MS (ES, m/z): 452 $(M+H)^+$.

Step 3: To a solution of [(2R,3R,4S,5R)-5-(4-amino-5-fluoro-2-oxopyrimidin-1-yl)-2-(chloromethyl)-4-fluoro-3-(propanoyloxy) oxolan-2-yl] methyl 2-methylpropanoate (800 mg, crude) in MeOH (20 mL), was added $NH_3 \cdot MeOH$ (7N, 2 mL). The solution was stirred for 20 min at room temperature under nitrogen and the solution was neutralized with AcOH. The resulting mixture was concentrated under vacuum. The residue was purified by reverse phase flash chromatography with the following conditions: Column: Cis; Mobile Phase A: Water (0.1% $NH_3HCO_3$), Mobile Phase B: ACN; Flow rate: 100 mL/min; Gradient: 10% B to 100% in 15 min, detector: UV 254 nm. Two products were successfully separated by the chromatography, (2R,3R,4S,5R)-5-(4-amino-5-fluoro-2-oxopyrimidin-1-yl)-2-(chloromethyl)-4-fluoro-2-(hydroxymethyl) oxolan-3-yl 2-methylpropanoate (crude, 60 mg) as a white solid, and [(2R,3R,4S,5R)-5-(4-amino-5-fluoro-2-oxopyrimidin-1-yl)-2-(chloromethyl)-4-fluoro-3-hydroxyoxolan-2-yl] methyl 2-methylpropanoate 126.1 mg, 0.33 mmol, 17% yield in two steps) as a white solid. LC-MS (ES, m/z): 382 $(M+H)^+$ 98.6% purity. $^1H$ NMR (400 MHz, DMSO-$d_6$) δ 7.95 (brs, 1H), 7.70-7.66 (m, 2H), 6.38 (d, J=5.2 Hz, 1H), 6.28-6.23 (m, 1H), 5.21-5.06 (m, 1H), 4.45-4.40 (m, 2H), 4.27 (d, J=12.0 Hz, 1H), 3.91 (d, J=11.6 Hz, 1H), 3.81 (d, J=11.6 Hz, 1H), 2.68-2.64 (m, 1H), 1.13 (dd, J=7.2, 1.6 Hz, 6H).

Example 100—Synthesis of Compound 184: 4-amino-5-fluoro-1-[(2R,4S,5R)-4-hydroxy-5-(hydroxymethyl)-5-(propa-1,2-dien-1-yl) oxolan-2-yl] pyrimidin-2-one

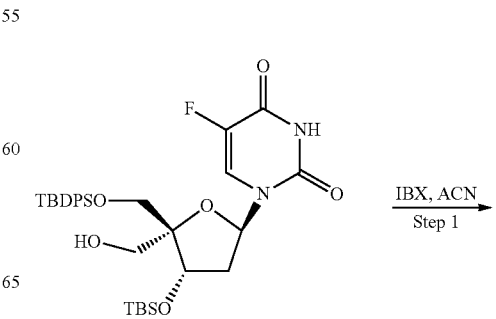

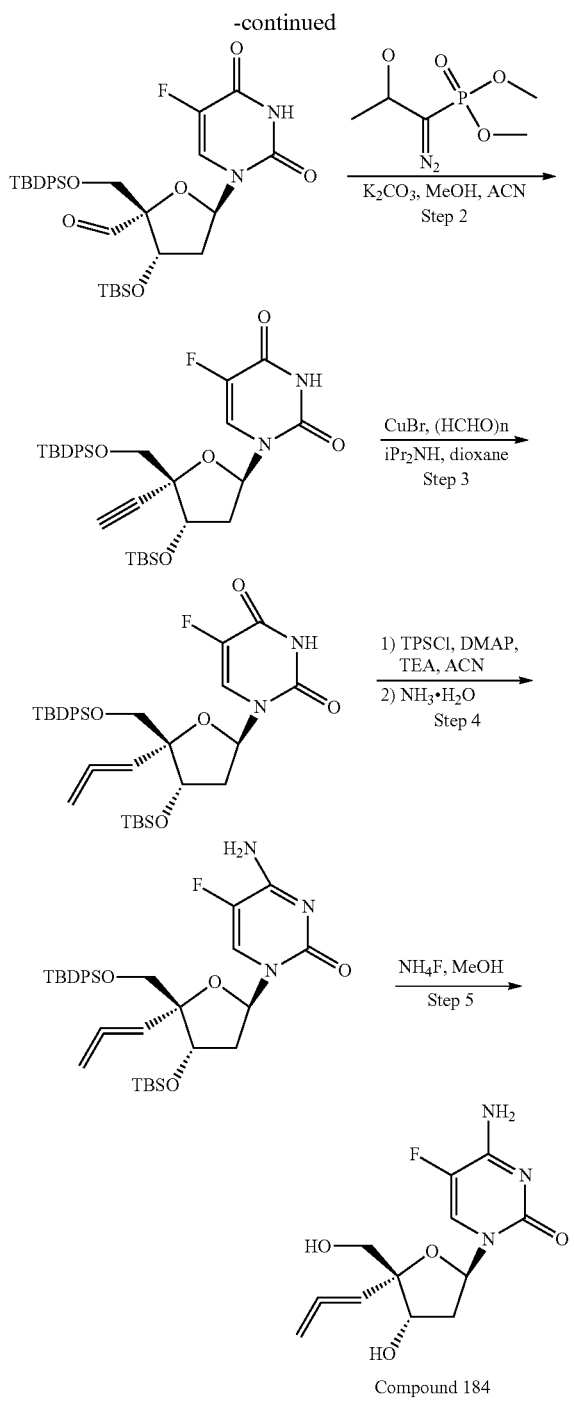

Compound 184

Step 1: To a stirred solution of 1-[(2R,4S,5R)-4-[(tert-butyldimethylsilyl) oxy]-5-{[(tert-butyldiphenylsilyl) oxy]methyl}-5-(hydroxymethyl) oxolan-2-yl]-5-fluoro-3H-pyrimidine-2,4-dione (2.0 g, 3.18 mmol) in ACN (20 mL), was added IBX (1.07 g, 3.82 mmol) in portions at room temperature. The resulting mixture was stirred for 3 h at 65° C. The mixture was allowed to cool to room temperature and then filtered; the filter cake was washed with ACN. The combined filtrate was concentrated under vacuum. This resulted in (2R,3S,5R)-3-[(tert-butyldimethylsilyl)oxy]-2-{[(tert-butyldiphenylsilyl)oxy]methyl}-5-(5-fluoro-2,4-dioxo-3H-pyrimidin-1-yl) oxolane-2-carbaldehyde (2.0 g, crude) as a white solid. The crude product was used in the next step directly without further purification. LC-MS (ES, m/z): 649 (M+Na$^+$).

Step 2: To a solution of seyferth-gilbert homologation (674.8 mg, 3.51 mmol) in ACN (20 mL), was added $K_2CO_3$ (881.8 mg, 6.39 mmol). This was followed by the addition of a solution of (2R,3S,5R)-3-[(tert-butyldimethylsilyl) oxy]-2-{[(tert-butyldiphenylsilyl) oxy]methyl}-5-(5-fluoro-2,4-dioxo-3H-pyrimidin-1-yl) oxolane-2-carbaldehyde (2.0 g, crude) in MeOH (20 mL) dropwise at room temperature. The resulting mixture was stirred for 2 h at room temperature and then concentrated under vacuum. The residue was diluted with water. The resulting solution was extracted with EtOAc. The combined organic layers were washed with brine, dried over anhydrous $Na_2SO_4$ and concentrated under vacuum. The residue was purified by silica gel column chromatography, eluted with $CH_2Cl_2$/MeOH (40:1) to afford 1-[(2R,4S,5R)-4-[(tert-butyldimethylsilyl) oxy]-5-{[(tert-butyldiphenylsilyl) oxy] methyl}-5-ethynyloxolan-2-yl]-5-fluoro-3H-pyrimidine-2,4-dione (1.35 g, 2.17 mmol, 68.24% yield in two steps) as a light yellow solid. LC-MS (ES, m/z): 645 (M+Na)$^+$.

Step 3: To a stirred mixture of 1-[(2R,4S,5R)-4-[(tert-butyldimethylsilyl) oxy]-5-{[(tert-butyldiphenylsilyl) oxy] methyl}-5-ethynyloxolan-2-yl]-5-fluoro-3H-pyrimidine-2,4-dione (1.35 g, 2.17 mmol) and CuBr (311.5 mg, 2.17 mmol) in dioxane (15 mL), was added paraformaldehyde (130.2 mg, 4.34 mmol) and diisopropylamine (549.1 mg, 5.43 mmol). The resulting mixture was stirred for overnight at 140° C., then cooled to room temperature and quenched by the addition of sat. $NH_4Cl$ (aq.). The resulting mixture was extracted with EtOAc. The combined organic layers were washed with brine, dried over anhydrous $Na_2SO_4$ and concentrated under vacuum. The residue was purified by Prep-TLC ($CH_2Cl_2$/MeOH=15:1) to afford 1-[(2R,4S,5R)-4-[(tert-butyldimethylsilyl) oxy]-5-{[(tert-butyldiphenylsilyl) oxy]methyl}-5-(propa-1,2-dien-1-yl) oxolan-2-yl]-5-fluoro-3H-pyrimidine-2,4-dione (280.0 mg, 0.44 mmol, 20.28%) as a light yellow solid. LC-MS (ES, m/z): 659 (M+Na$^+$).

Step 4: To a stirred solution of 1-[(2R,4S,5R)-4-[(tert-butyldimethylsilyl) oxy]-5-{[(tert-butyldiphenylsilyl) oxy] methyl}-5-(propa-1,2-dien-1-yl) oxolan-2-yl]-5-fluoro-3H-pyrimidine-2,4-dione (280.0 mg, 0.44 mmol) and DMAP (161.1 mg, 1.32 mmol) in ACN (5 mL), were added TEA (133.3 mg, 1.32 mmol) and 2,4,6-tris(propan-2-yl) benzene-1-sulfonyl chloride (398.6 mg, 1.32 mmol) under nitrogen atmosphere. The resulting mixture was stirred for overnight at room temperature under nitrogen atmosphere. $NH_3·H_2O$ (5.6 mL, 25%) was then added dropwise at room temperature. The resulting mixture was stirred for additional 2 h at room temperature and then quenched by the addition of aq. HCl (4M) at 0° C. The resulting mixture was extracted with EtOAc. The combined organic layers were washed with brine, dried over anhydrous $Na_2SO_4$ and concentrated under vacuum. The residue was purified by Prep-TLC ($CH_2Cl_2$/MeOH=10:1) to afford 4-amino-1-[(2R,4S,5R)-4-[(tert-butyldimethylsilyl) oxy]-5-{[(tert-butyldiphenylsilyl) oxy] methyl}-5-(propa-1,2-dien-1-yl) oxolan-2-yl]-5-fluoropyrimidin-2-one (160.0 mg, 0.25 mmol, 57.27%) as a light yellow solid. LC-MS (ES, m/z): 658 (M+Na$^+$).

Step 5: To a stirred solution of 4-amino-1-[(2R,4S,5R)-4-[(tert-butyldimethylsilyl) oxy]-5-{[(tert-butyldiphenylsilyl) oxy] methyl}-5-(propa-1,2-dien-1-yl) oxolan-2-yl]-5-fluoropyrimidin-2-one (160.0 mg, 0.25 mmol) in MeOH (5 mL) was added $NH_4F$ (640.0 mg, 17.30 mmol). The resulting mixture was stirred for 2 days at 65° C., then cooled to room temperature and concentrated under vacuum. The residue was diluted with acetone. The resulting mixture was filtered; the filter cake was washed with acetone. The combined filtrate was concentrated under vacuum. The crude product was purified by reverse phase flash with the following conditions: Column, XBridge Prep OBD C18 Column, 30*150 mm, 5 μm; mobile phase, Water (10 mmol/L $NH_4HCO_3$) and ACN (0% ACN up to 5% in 9.0 min); UV detection at 254 nm. The product-containing fractions were combined and evaporated partially to remove the solvents, then lyophilized overnight to afford 4-amino-S-fluoro-1-[(2R,4S,5R)-4-hydroxy-5-(hydroxymethyl)-5-(propa-1,2-dien-1-yl) oxolan-2-yl] pyrimidin-2-one (19.5 mg, 0.25 mmol, 27.55%) as a white solid. LC-MS (ES, m/z): 567 (2M+1$^+$). 98.4% purity. $^1$H NMR (400 MHz, Methanol-$d_4$) δ 8.45 (d, J=7.0 Hz, 1H), 6.10-6.07 (m, 1H), 5.29 (t, J=6.8 Hz, 1H), 4.98-4.89 (m, 2H), 4.52 (t, J=8.0, 1H), 3.77-3.69 (m, 2H), 2.48-2.40 (m, 1H), 2.26-2.20 (in, 1H).

Example 101—Synthesis of Additional Compounds

The compounds included in Table 1 and Table 2 were synthesized using methods analogous to those listed in Examples 1-3 and 4-7, above, reported synthetic procedures, and related strategies and procedures known to those skilled in the art of organic synthesis. Detailed synthetic procedures for some of the compounds in Table 1 and Table 2 are also provided in Examples 8-100, above. Mass spectral data for exemplary compounds is listed in Table 3:

TABLE 3

| Compound | Name | MS Data |
|---|---|---|
| 1 | (2R,3S,5R)-5-(6-amino-2-fluoro-9H-purin-9-yl)-2-(hydroxymethyl)-2-(prop-1-yn-1-yl)tetrahydrofuran-3-ol | M − 1: 306.12 |
| 2 | 4-amino-1-((2R,4S,5R)-5-(chloromethyl)-4-hydroxy-5-(hydroxymethyl)tetrahydrofuran-2-yl)pyrimidin-2(1H)-one | M + 1: 276.05 |
| 3 | 1-((2R,3S,4R)-3-fluoro-4-hydroxy-5,5-bis(hydroxymethyl)tetrahydrofuran-2-yl)pyrimidine-2,4(1H,3H)-dione | M + 1: 276.95 |
| 4 | 1-((2R,4S,5R)-5-(chloromethyl)-4-hydroxy-5-(hydroxymethyl)tetrahydrofuran-2-yl)-5-methylpyrimidine-2,4(1H,3H)-dione | M − 1: 289.10 |
| 5 | (2R,3R,4S,5R)-5-(6-amino-2-chloro-9H-purin-9-yl)-2-ethynyl-4-fluoro-2-(hydroxymethyl)tetrahydrofuran-3-ol | M + 1: 328.02 |
| 6 | 1-((2R,4S,5R)-5-(chloromethyl)-4-hydroxy-5-(hydroxymethyl)tetrahydrofuran-2-yl)-4-(hydroxyamino)pyrimidin-2(1H)-one | M + 1: 292.00 |
| 7 | 1-((2R,4S,5R)-5-(chloromethyl)-4-fluoro-5-(hydroxymethyl)tetrahydrofuran-2-yl)-5-methylpyrimidine-2,4(1H,3H)-dione | M + 1: 293.20 |
| 8 | (2R,3S,5R)-5-(6-amino-2-fluoro-9H-purin-9-yl)-2-(chloromethyl)-2-(hydroxymethyl)tetrahydrofuran-3-ol | M + 1: 318 |
| 9 | 1-((2R,3R,4R,5R)-5-(chloromethyl)-3-fluoro-4-hydroxy-5-(hydroxymethyl)tetrahydrofuran-2-yl)-5-methylpyrimidine-2,4(1H,3H)-dione | M + 23: 330.90 |
| 10 | ((3S,5R)-5-(6-amino-2-fluoro-9H-purin-9-yl)-3-hydroxytetrahydrofuran-2,2-diyl)dimethanol | M + 1: 300.10 |
| 11 | 4-amino-1-((2R,4S,5R)-5-(chloromethyl)-4-hydroxy-5-(hydroxymethyl)tetrahydrofuran-2-yl)-5-methylpyrimidin-2(1H)-one | M + 1: 290.10 |
| 12 | 4-amino-1-((2R,3S,4S,5R)-5-(chloromethyl)-4-hydroxy-5-(hydroxymethyl)-3-methyltetrahydrofuran-2-yl)pyrimidin-2(1H)-one | M + 1: 290.05 |
| 13 | 4-amino-1-((2R,3S,4S,5R)-5-(chloromethyl)-4-hydroxy-5-(hydroxymethyl)-3-methoxytetrahydrofuran-2-yl)pyrimidin-2(1H)-one | M + 1: 306.00 |
| 14 | 4-amino-1-((2R,4S,5R)-5-(chloromethyl)-4-hydroxy-5-(hydroxymethyl)tetrahydrofuran-2-yl)-5-fluoropyrimidin-2(1H)-one | M + 1: 294 |
| 15 | (2R,3S,5R)-5-(6-amino-9H-purin-9-yl)-2-(chloromethyl)-2-(hydroxymethyl)tetrahydrofuran-3-ol | M + 1: 300 |
| 16 | 4-amino-1-((2R,4S,5R)-5-cyclopropyl-4-hydroxy-5-(hydroxymethyl)tetrahydrofuran-2-yl)pyrimidin-2(1H)-one | M + 1: 268.05 |
| 17 | 4-amino-1-((2R,3S,4S,5R)-5-(chloromethyl)-3-ethynyl-4-hydroxy-5-(hydroxymethyl)tetrahydrofuran-2-yl)pyrimidin-2(1H)-one | M + 1: 300.05 |
| 18 | 5-amino-2-((2R,4S,5R)-5-(chloromethyl)-4-hydroxy-5-(hydroxymethyl)tetrahydrofuran-2-yl)-1,2,4-triazin-3(2H)-one | M + 1: 277.15 |
| 19 | 4-amino-1-((2R,3S,4S,5R)-4-hydroxy-5-(hydroxymethyl)-3,5-dimethyltetrahydrofuran-2-yl)pyrimidin-2(1H)-one | M + 1: 256.1 |
| 20 | 4-amino-1-((2R,3S,4S,5R)-3-ethynyl-4-hydroxy-5-(hydroxymethyl)-5-methyltetrahydrofuran-2-yl)pyrimidin-2(1H)-one | M + 1: 266.1 |
| 21 | 4-amino-1-((2R,4S,5R)-4-hydroxy-5-(hydroxymethyl)-5-(trifluoromethyl)tetrahydrofuran-2-yl)pyrimidin-2(1H)-one | M + 1: 295.90 |
| 22 | 4-amino-5-fluoro-1-((2R,4S,5R)-5-(fluoromethyl)-4-hydroxy-5-(hydroxymethyl)tetrahydrofuran-2-yl)pyrimidin-2(1H)-one | M + 1: 278.10 |
| 23 | (2R,3S,5R)-5-(6-amino-2-fluoro-9H-purin-9-yl)-2-ethynyl-2-(hydroxymethyl)tetrahydrofuran-3-ol | M + 23: 316.05 |
| 24 | (2R,3R,4R,5R)-5-(4-amino-2-oxopyrimidin-1(2H)-yl)-2-(chloromethyl)-4-fluoro-2-((isobutyryloxy)methyl)tetrahydrofuran-3-yl isobutyrate | M + 1: 434.10 |
| 25 | (2R,3S,5R)-5-(6-amino-2-chloro-9H-purin-9-yl)-2-ethynyl-2-(hydroxymethyl)tetrahydrofuran-3-ol | M + 1: 310.05 |
| 26 | (2R,3S,5R)-5-(6-amino-2-fluoro-9H-purin-9-yl)-3-hydroxy-2-(hydroxymethyl)tetrahydrofuran-2-carbonitrile | M − 1: 393.18 |
| 27 | (2R,3S,5R)-5-(6-amino-9H-purin-9-yl)-2-ethynyl-2-(hydroxymethyl)tetrahydrofuran-3-ol | M + 1: 276.15 |
| 28 | 1-((2R,3R,4R,5R)-5-(chloromethyl)-3-fluoro-4-hydroxy-5-(hydroxymethyl)tetrahydrofuran-2-yl)-4-(hydroxyamino) pyrimidin-2(1H)-one | M + 1: 310.00 |
| 29 | 1-((2R,3R,4R,5R)-5-(chloromethyl)-3-fluoro-4-hydroxy-5-(hydroxymethyl)tetrahydrofuran-2-yl)pyrimidine-2,4(1H,3H)-dione | M − 1: 293.05 |
| 30 | 1-((2R,4S,5R)-5-azido-4-hydroxy-5-(hydroxymethyl)tetrahydrofuran-2-yl)-5-methylpyrimidine-2,4(1H,3H)-dione | Not determined |
| 31 | 4-amino-1-((2R,3R,4R,5R)-5-(chloromethyl)-3-fluoro-4-hydroxy-5-(hydroxymethyl)tetrahydrofuran-2-yl)pyrimidin-2(1H)-one | M + 1: 294.15 |
| 32 | 4-amino-1-((2R,3R,4R,5R)-5-ethynyl-3-fluoro-4-hydroxy-5-(hydroxymethyl)tetrahydrofuran-2-yl)pyrimidin-2(1H)-one | M + 1: 270.05 |
| 33 | 1-((2R,3R,4R,5R)-5-ethynyl-3-fluoro-4-hydroxy-5-(hydroxymethyl)tetrahydrofuran-2-yl)pyrimidine-2,4(1H,3H)-dione | M + 1: 271.20 |
| 34 | 1-((2R,4S,5R)-5-(chloromethyl)-4-hydroxy-5-(hydroxymethyl)tetrahydrofuran-2-yl)pyrimidine-2,4(1H,3H)-dione | M + 1: 277 |
| 35 | 4-amino-1-((2R,3S,4R,5R)-5-ethynyl-3-fluoro-4-hydroxy-5-(hydroxymethyl)tetrahydrofuran-2-yl)pyrimidin-2(1H)-one | M + 1: 270 |
| 36 | 1-((2R,3S,4R,5R)-5-ethynyl-3-fluoro-4-hydroxy-5-(hydroxymethyl)tetrahydrofuran-2-yl)pyrimidine-2,4(1H,3H)-dione | M + 23: 292.90 |
| 37 | (2R,3S,5R)-5-(4-aminopyrrolo[2,1-f][1,2,4]triazin-7-yl)-2-ethynyl-2-(hydroxymethyl)tetrahydrofuran-3-ol | M + 1: 275 |
| 38 | 1-((2R,4S,5R)-5-ethynyl-4-hydroxy-5-(hydroxymethyl)tetrahydrofuran-2-yl)-5-methylpyrimidine-2,4(1H,3H)-dione | M − 1: 265.05 |
| 39 | 1-((2R,3S,4R,5R)-5-ethynyl-3-fluoro-4-hydroxy-5-(hydroxymethyl)tetrahydrofuran-2-yl)-5-methylpyrimidine-2,4(1H,3H)-dione | M + 1: 285.20 |
| 40 | 4-amino-1-((2R,3S,4R,5R)-5-(chloromethyl)-3-fluoro-4-hydroxy-5-(hydroxymethyl)tetrahydrofuran-2-yl)pyrimidin-2(1H)-one | M + 1: 293.95 |

TABLE 3-continued

| Compound | Name | MS Data |
|---|---|---|
| 41 | 4-amino-1-((2R,4S,5R)-5-ethynyl-4-hydroxy-5-(hydroxymethyl)tetrahydrofuran-2-yl)pyrimidin-2(1H)-one | M + 1: 252 |
| 42 | (2R,3R,4S,5R)-5-(6-amino-2-fluoro-9H-purin-9-yl)-2-ethynyl-4-fluoro-2-(hydroxymethyl)tetrahydrofuran-3-ol | M + 1: 312.10 |
| 43 | 4-amino-1-((2R,4S,5R)-4-hydroxy-5-(hydroxymethyl)-5-vinyltetrahydrofuran-2-yl)pyrimidin-2(1H)-one | M + 1: 254.05 |
| 44 | 4-amino-1-((2R,4S,5R)-5-ethyl-4-hydroxy-5-(hydroxymethyl)tetrahydrofuran-2-yl)pyrimidin-2(1H)-one | M + 1: 256.05 |
| 45 | 4-amino-1-((2R,4S,5R)-5-(fluoromethyl)-4-hydroxy-5-(hydroxymethyl)tetrahydrofuran-2-yl)pyrimidin-2(1H)-one | M + 1: 260.20 |
| 46 | 2-amino-9-((2R,4S,5R)-5-(fluoromethyl)-4-hydroxy-5-(hydroxymethyl)tetrahydrofuran-2-yl)-1,9-dihydro-6H-purin-6-one | M + 1: 300.20 |
| 47 | 4-amino-1-((2R,3S,4R,5R)-3-fluoro-4-hydroxy-5-(hydroxymethyl)-5-vinyltetrahydrofuran-2-yl)pyrimidin-2(1H)-one | M + 1: 272.05 |
| 48 | 4-amino-1-((2R,4S,5R)-4-hydroxy-5-(hydroxymethyl)-5-methoxytetrahydrofuran-2-yl)pyrimidin-2(1H)-one | M + 1: 257.95 |
| 49 | 4-amino-1-((2R,4S,5R)-5-azido-4-hydroxy-5-(hydroxymethyl)tetrahydrofuran-2-yl)pyrimidin-2(1H)-one | M + : 268.30 |
| 50 | 4-amino-1-((2R,3S,4R,5R)-5-azido-3-fluoro-4-hydroxy-5-(hydroxymethyl)tetrahydrofuran-2-yl)pyrimidin-2(1H)-one | Commercially available |
| 51 | 4-amino-1-((2R,3S,4R,5R)-5-ethyl-3-fluoro-4-hydroxy-5-(hydroxymethyl)tetrahydrofuran-2-yl)pyrimidin-2(1H)-one | M + 1: 274.10 |

Table 4 lists $^1$H NMR characterization data for selected compounds listed in Table 3, above.

TABLE 4

| Compound No. | $^1$H NMR Chemical Shift Data (ppm) |
|---|---|
| 1 | $^1$H NMR (400 MHz, DMSO-$d_6$) δ 8.26 (s, 1H), 7.80 (br s, 2H), 6.17 (q, J = 4.1 Hz, 1H), 5.36 (d, J = 5.5 Hz, 1H), 5.17 (dd, J = 6.5, 5.8 Hz, 1H), 4.48 (q, J = 6.4 Hz, 1H), 3.58 (q, J = 5.8 Hz, 1H), 3.48 (q, J = 6.1 Hz, 1H), 2.66-2.59 (m, 1H), 2.41-2.34 (m, 1H), 1.83 (s, 3H). |
| 21 | $^1$H NMR (400 MHz, DMSO-$d_6$) δ 7.71 (d, J = 7.5 Hz, 1H), 7.24 (br s, 1H), 7.20 (br s, 1H), 6.37 (t, J = 6.7 Hz, 1H), 5.75 (d, J = 7.5 Hz, 2H), 5.56-5.43 (m, 1H), 4.69 (brt, J = 5.9 Hz, 1H), 3.74-3.62 (m, 2H), 2.24 (t, J = 6.5 Hz, 2H) |
| 24 | $^1$H NMR (400 MHz, DMSO-$d_6$) δ 7.69 (d, J = 7.4 Hz, 1H), 7.40 (s, 2H), 5.93 (dd, J = 21.8, 2.6 Hz, 1H), 5.80-5.70 (m, 2H), 5.59 (ddd, J = 53.5, 5.7, 2.6 Hz, 1H), 4.27 (d, J = 2.0 Hz, 2H), 3.94-3.80 (m, 2H), 2.63 (dp, J = 35.5, 7.1 Hz, 2H), 1.15 (d, J = 7.0 Hz, 6H), 1.09 (dd, J = 7.0, 2.5 Hz, 6H). |
| 25 | $^1$H NMR (300 MHz, DMSO-$d_6$) δ 8.34 (s, 1H), 7.83 (s, 2H), 6.28 (dd, J = 7.2, 5.1 Hz, 1H), 5.58 (s, 1H), 5.31 (s, 1H), 4.56 (t, J = 6.8 Hz, 1H), 3.66 (d, J = 11.9 Hz, 1H), 3.56 (d, J = 11.9 Hz, 1H), 3.52 (s, 1H), 2.70 (ddd, J = 13.2, 6.7, 5.0 Hz, 1H), 2.44 (dt, J = 13.5, 7.1 Hz, 1H). |
| 26 | $^1$H NMR (400 MHz, DMSO-$d_6$) δ 8.27 (s, 1H), 7.85 (br s, 2H), 6.39 (t, J = 6.6 Hz, 1H), 6.29 (d, J = 5.0 Hz, 1H), 5.67 (t, J = 6.0 Hz, 1H), 4.67 (m, 1H), 3.75 (m, 1H), 3.61 (m, 1H), 2.90 (m, 1H), 2.41 (m, 1H). |
| 27 | $^1$H NMR (400 MHz, MeOD-$d_3$): δ 8.33 (s, 1H), 8.19 (s, 1H), 6.46 (dd, 1H), 4.73 (t, 1H), 3.83 (dd, 2H), 2.83 (ddd, 1H), 2.63-2.57 (m, 1H), 1.89 (s, 1H), 4H not observed. |
| 28 | $^1$H NMR (400 MHz, Methanol-$d_4$) δ 7.19 (d, J = 8.2 Hz, 1H), 6.15 (dd, J = 14.5, 5.3 Hz, 1H), 5.64 (d, J = 8.3 Hz, 1H), 5.22 (dt, J = 53.5, 5.2 Hz, 1H), 4.53 (dd, J = 9.3, 5.1 Hz, 1H), 3.87-3.73 (m, 4H). |
| 29 | $^1$H NMR (400 MHz, DMSO-$d_6$) δ 11.45 (s, 1H), 7.87 (d, J = 8.1 Hz, 1H), 6.12 (dd, J = 14.2, 5.0 Hz, 1H), 6.00 (d, J = 5.6 Hz, 1H), 5.70 (d, J = 8.1 Hz, 1H), 5.45 (t, J = 5.2 Hz, 1H), 5.31-5.18 (t, J = 5.0 Hz, 1H), 4.42 (dt, J = 10.8, 5.2 Hz, 1H), 3.80 (s, 2H), 3.60 (m, 2H). |
| 31 | $^1$H NMR (400 MHz, DMSO-$d_6$) δ 7.81 (d, J = 7.5 Hz, 1H), 7.28 (d, J = 11.8 Hz, 2H), 6.13 (dd, J = 14.8, 4.7 Hz, 1H), 5.90 (d, J = 5.5 Hz, 1H), 5.76 (d, J = 7.4 Hz, 1H), 5.34 (t, J = 5.3 Hz, 1H), 5.13 (dt, J = 53.4, 4.9 Hz, 1H), 4.42 (dt, J = 12.6, 5.3 Hz, 1H), 3.77 (d, J = 1.6 Hz, 2H), 3.69 (dd, J = 11.6, 5.1 Hz, 1H), 3.60 (dd, J = 11.6, 5.5 Hz, 1H). |
| 32 | $^1$H NMR (400 MHz, DMSO-$d_6$) δ 7.75 (d, J = 7.5 Hz, 1H), 7.26 (d, J = 7.6 Hz, 2H), 6.01 (dd, J = 19.8, 1.9 Hz, 1H), 5.74 (dd, J = 17.8, 7.1 Hz, 2H), 5.49 (t, J = 5.9 Hz, 1H), 4.96 (ddd, J = 53.9, 5.1, 1.9 Hz, 1H), 4.37-4.20 (m, 1H), 3.73-3.55 (m, 2H), 3.53 (s, 1H). |
| 33 | $^1$H NMR (400 MHz, DMSO-$d_6$) δ 7.73 (d, J = 7.4 Hz, 1H), 7.14 (d, J = 24.0 Hz, 2H), 6.26 (dd, J = 7.9, 6.0 Hz, 1H), 5.73 (d, J = 7.4 Hz, 1H), 5.42 (d, J = 4.4 Hz, 1H), 5.18 (t, J = 5.1 Hz, 1H), 4.36 (dt, J = 6.8, 3.4 Hz, 1H), 3.82-3.70 (m, 2H), 3.63-3.43 (m, 2H), 2.32-2.05 (m, 2H). |
| 34 | $^1$H NMR (400 MHz, DMSO-$d_6$) δ 11.25 (s, 1H), 7.80 (d, J = 8.1 Hz, 1H), 6.24 (dd, J = 7.9, 6.0 Hz, 1H), 5.65 (d, J = 8.1 Hz, 1H), 5.50 (s, 1H), 5.25 (s, 1H), 4.39 (d, J = 5.2 Hz, 1H), 3.81-3.70 (m, 2H), 3.58 (d, J = 3.5 Hz, 2H), 2.31 (ddd, J = 13.7, 8.0, 6.0 Hz, 1H), 2.20 (ddd, J = 13.4, 6.1, 3.2 Hz, 1H). |
| 35 | $^1$H NMR (400 MHz, Methanol-$d_4$) δ 7.81 (dd, J = 7.6, 1.2 Hz, 1H), 6.36 (dd, J = 11.8, 5.3 Hz, 1H), 5.90 (d, J = 7.5 Hz, 1H), 5.26-5.12 (t, J = 5.0 Hz, 1H), 4.48-4.42 (d, J = 4.8 Hz, 1H), 3.86 (dd, J = 12.4, 1.7 Hz, 1H), 3.74 (d, J = 12.3 Hz, 1H), 3.17 (s, 1H). |
| 36 | $^1$H NMR (400 MHz, DMSO-$d_6$) δ 10.83 (s, 1H), 7.70 (d, J = 8.1 Hz, 1H), 6.33 (s, 1H), 6.20 (dd, J = 10.6, 5.7 Hz, 1H), 5.68 (t, J = 9.6 Hz, 2H), 5.19 (dt, J = 54.3, 5.6 Hz, 1H), 4.39 (dt, J = 24.9, 4.4 Hz, 1H), 3.73-3.54 (m, 3H). |
| 37 | $^1$H NMR (400 MHz, DMSO-$d_6$) δ 7.80 (s, 1H), 6.83 (d, J = 4.4 Hz, 1H), 6.68 (d, J = 4.5 Hz, 1H), 5.59 (t, J = 7.6 Hz, 1H), 4.30 (dd, J = 6.7, 5.0 Hz, 1H), 3.52-3.46 (d, J = 11.7 Hz, 2H), 3.29 (s, 1H), 2.35 (dt, J = 12.3, 7.4 Hz, 1H), 2.20 (ddd, J = 12.4, 7.3, 5.0 Hz, 1H). |
| 38 | $^1$H NMR (400 MHz, Methanol-$d_4$) δ 7.75 (q, J = 1.2 Hz, 1H), 6.27 (dd, J = 7.4, 4.6 Hz, 1H), 4.52 (t, J = 7.5 Hz, 1H), 3.89-3.70 (m, 2H), 3.06 (s, 1H), 2.44 (dt, J = 13.6, 7.5 Hz, 1H), 2.32 (ddd, J = 13.5, 7.5, 4.6 Hz, 1H), 1.87 (d, J = 1.2 Hz, 3H). |
| 39 | $^1$H NMR (400 MHz, Methanol-$d_4$) δ 7.64 (t, J = 1.4 Hz, 1H), 6.32 (dd, J = 10.5, 5.6 Hz, 1H), 5.18 (dt, J = 54.4, 5.5 Hz, 1H), 4.51 (dd, J = 24.6, 5.4 Hz, 1H), 3.87 (dd, J = 12.4, 1.8 Hz, 1H), 3.75 (d, J = 12.4 Hz, 1H), 1.87 (d, J = 1.2 Hz, 3H). |
| 41 | $^1$H NMR (300 MHz, DMSO-$d_6$) δ 7.77 (d, J = 7.4 Hz, 1H), 7.14 (d, J = 14.3 Hz, 2H), 6.29-5.86 (m, 3H), 5.71 (d, J = 7.4 Hz, 1H), 4.30 (t, J = 7.2 Hz, 1H), 3.64 (d, J = |

TABLE 4-continued

| Compound No. | $^1$H NMR Chemical Shift Data (ppm) |
|---|---|
| | 12.0 Hz, 1H), 3.57 (d, J = 12.0 Hz, 1H), 3.48 (s, 1H), 2.24 (dt, J = 13.1, 7.3 Hz, 1H), 2.06 (ddd, J = 12.7, 7.2, 4.8 Hz, 1H). |
| 42 | $^1$H NMR (400 MHz, DMSO-d$_6$) δ 8.23 (d, J = 1.9 Hz, 1H), 7.98-7.90 (s, 2H), 6.36 (dd, J = 8.7, 5.8 Hz, 1H), 6.30 (d, J = 5.7 Hz, 1H), 5.49 (dt, J = 27.2, 6.2 Hz, 1H), 5.32-5.40 (t, J = 6.1 Hz, 1H), 4.65 (dt, J = 22.5, 6.0 Hz, 1H), 3.70 (d, J = 6.1 Hz, 2H), 3.63 (dd, J = 12.2, 6.9 Hz, 1H). |
| 43 | $^1$H NMR (300 MHz, DMSO-d$_6$) δ 7.99 (d, J = 7.4 Hz, 1H), 7.08 (d, J = 15.3 Hz, 2H), 6.06 (dd, J = 6.7, 4.4 Hz, 1H), 5.92 (dd, J = 17.3, 10.8 Hz, 1H), 5.70 (d, J = 7.4 Hz, 1H), 5.34 (dd, J = 17.4, 2.3 Hz, 1H), 5.19 (dq, J = 5.4, 2.8 Hz, 3H), 4.39 (q, J = 6.9 Hz, 1H), 3.45 (ddd, J = 47.3, 17.8, 5.4 Hz, 2H), 2.16-1.92 (m, 2H). |
| 45 | $^1$H NMR (400 MHz, DMSO-d$_6$) δ 7.74 (dd, J = 7.5, 2.7 Hz, 1H), 7.17-7.11 (s, 2H), 6.25 (td, J = 7.1, 6.4, 2.7 Hz, 1H), 5.73 (dd, J = 7.4, 2.8 Hz, 1H), 5.36 (dd, J = 4.8, 2.8 Hz, 1H), 5.18 (dt, J = 8.0, 3.8 Hz, 1H), 4.58 (qd, J = 9.8, 2.8 Hz, 1H), 4.46 (qd, J = 9.9, 2.8 Hz, 1H), 4.37 (d, J = 5.4 Hz, 1H), 3.63 (s, 1H), 3.47 (d, J = 10.4 Hz, 1H), 2.12 (dt, J = 13.1, 6.4 Hz, 2H). |
| 46 | $^1$H NMR (400 MHz, DMSO-d$_6$) δ 7.94 (s, 1H), 6.47 (s, 2H), 6.23-6.15 (m, 1H), 5.42 (d, J = 4.6 Hz, 1H), 5.12 (t, J = 5.5 Hz, 1H), 4.65-4.45 (d, J = 10.0 Hz, 3H), 3.49 (t, J = 5.7 Hz, 2H), 3.29 (s, 1H), 2.78-2.68 (m, 1H), 2.26 (s, 1H). |
| 47 | $^1$H NMR (400 MHz, DMSO-d$_6$) δ 7.92-7.80 (m, 2H), 7.80-7.66 (m, 4H), 7.49 (t, J = 7.6 Hz, 2H), 7.42-7.25 (m, 4H), 6.63 (t, J = 7.6 Hz, 1H), 5.82-5.58 (m, 2H), 4.17-3.83 (m, 2H), 3.30-3.19 (m, 1H), 2.35-2.16 (m, 2H). |
| 51 | $^1$H NMR (300 MHz, DMSO-d$_6$) δ 7.73 (d, J = 7.4 Hz, 1H), 7.18 (d, J = 19.4 Hz, 2H), 6.09 (dd, J = 16.3, 4.3 Hz, 1H), 5.71 (d, J = 7.4 Hz, 2H), 5.16-4.89 (m, 2H), 4.29 (dd, J = 20.0, 3.2 Hz, 1H), 3.53-3.37 (m, 2H), 1.66-1.51 (m, 2H), 0.87 (t, J = 7.4 Hz, 3H). |

Example 102—Synthesis of Additional Compounds

The compounds listed in Table 5 below were prepared using experimental procedures and strategies described in Examples 1-7, Examples 8-100, the Detailed Description, and related strategies and procedures known to those skilled in the art of organic synthesis. Detailed synthetic procedures for some of the compounds in Table 5 are also provided in Examples 8-100, above. Table 5 also lists each compound's $^1$H NMR characterization data and mass-to-charge ratio observed by LC/MS. Chemical structures are presented in Tables 1-A, 1-B, 2-A, and 2-B3, above.

TABLE 5

| Compound No. | Mass Spec. m/z (M + H)$^+$ | $^1$H NMR Chemical Shift Data (ppm) |
|---|---|---|
| 52 | 396 | $^1$H NMR (300 MHz, DMSO-d$_6$) δ 7.62 (d, J = 7.4 Hz, 1H), 7.20 (d, J = 11.9 Hz, 2H), 6.12 (t, J = 6.8 Hz, 1H), 5.74 (d, J = 7.4 Hz, 1H), 5.36 (dd, J = 6.5, 3.4 Hz, 1H), 4.12 (d, J = 2.8 Hz, 2H), 2.69-2.52 (m, 2H), 2.48-2.24 (m, 2H), 1.69 (p, J = 7.4 Hz, 1H), 1.55 (dq, J = 14.6, 7.2 Hz, 1H), 1.11 (td, J = 7.3, 2.7 Hz, 12H), 0.88 (t, J = 7.4 Hz, 3H). |
| 53 | 394 | $^1$H NMR (400 MHz, DMSO-d$_6$) δ 7.67 (d, J = 6.9 Hz, 1H), 7.22 (d, J = 13.0 Hz, 2H), 6.19 (t, J = 6.4 Hz, 1H), 5.77 (q, J = 10.3, 9.6 Hz, 2H), 5.49-5.30 (d, J = 10.8 Hz, 3H), 4.17 (d, J = 3.5 Hz, 2H), 2.57 (dt, J = 14.3, 7.1 Hz, 2H), 2.39 (q, J = 6.8 Hz, 1H), 2.33-2.23 (m, 1H), 1.45-1.05 (m, 12H). |
| 54 | 290 | $^1$H NMR (400 MHz, DMSO-d$_6$) δ 7.76 (d, J = 7.6 Hz, 1H), 7.19-7.13 (m, 2H), 6.16 (t, J = 6.8 Hz, 1H), 5.75-5.73 (m, 1H), 5.28 (t, J = 5.2 Hz, 1H), 4.08-4.07 (m, 1H), 3.78-3.70 (m, 2H), 3.61-3.55 (m, 2H), 3.30 (s, 3H), 2.41-2.37 (m, 1H), 2.18-2.11 (m, 1H). |
| 56 | 267.80 | $^1$H NMR (400 MHz, DMSO-d$_6$) δ 7.86 (d, J = 7.5 Hz, 1H), 7.15-7.00 (m, 2H), 6.11 (t, J = 6.5 Hz, 1H), 5.86 (br d, J = 7.3 Hz, 1H), 5.69 (d, J = 7.3 Hz, 1H), 5.18 (d, J = 4.8 Hz, 1H), 5.09-4.98 (m, 3H), 4.27 (br d, J = 6.0 Hz, 1H), 3.40 (t, J = 5.5 Hz, 2H), 2.41-2.30 (m, 1H), 2.28-2.14 (m, 2H), 2.06 (td, J = 6.7, 13.2 Hz, 1H). |
| 57 | 269.90 | $^1$H NMR (400 MHz, DMSO-d$_6$) δ 7.84 (d, J = 7.5 Hz, 1H), 7.13-6.98 (m, 2H), 6.07 (t, J = 6.6 Hz, 1H), 5.69 (d, J = 7.3 Hz, 1H), 5.04 (d, J = 4.8 Hz, 1H), 4.95 (t, J = 5.2 Hz, 1H), 4.27-4.18 (m, 1H), 3.47-3.36 (m, 2H), 2.14 (dt, J = 3.8, 6.6 Hz, 1H), 2.04 (td, J = 6.6, 13.5 Hz, 1H), 1.56-1.29 (m, 4H), 0.90-0.85 (m, 3H). |
| 58 | 434 | $^1$H NMR (400 MHz, DMSO-d$_6$) δ 7.91 (s, 1H), 7.87 (d, J = 7.2 Hz, 1H), 7.67 (brs, 1H), 6.24 (t, J = 6.4 Hz, 1H), 5.51-5.48 (m, 1H), 4.32 (dd, J = 16.0, 11.6 Hz, 1H), 3.92-3.89 (m, 1H), 3.81-3.79 (m, 1H), 2.69-2.58 (m, 3H), 2.40-2.36 (m, 1H), 1.18-1.12 (m, 12H). |
| 59 | 276 | $^1$H NMR (400 MHz, DMSO-d$_6$) δ 7.89 (d, J = 7.6 Hz, 1H), 7.17-7.10 (m, 2H), 6.16-6.13 (m, 1H), 5.75 (d, J = 7.6 Hz, 1H), 5.49 (brs, 1H), 4.82-4.80 (m, 1H), 4.28-4.26 (m, 1H), 3.75-3.66 (m, 4H), 2.82-2.75 (m, 1H), 1.88-1.83 (m, 1H). |
| 71 | 343.90 | $^1$H NMR (400 MHz, DMSO-d$_6$) δ 8.59 (s, 1H), 7.96-7.83 (m, 1H), 7.13-6.99 (m, 1H), 6.14 (t, J = 6.3 Hz, 1H), 5.53-5.39 (m, 2H), 4.41-4.35 (m, 1H), 3.81 (d, J = 11.4 Hz, 1H), 3.69 (d, J = 11.4 Hz, 2H), 3.57 (d, J = 11.4 Hz, 1H), 2.44-2.36 (m, 1H), 2.29-2.20 (m, 1H) |
| 78 | 290 | $^1$H NMR (400 MHz, DMSO-d$_6$) δ 7.95-7.88 (m, 1H), 7.67 (s, 1H), 7.44 (s, 1H), 5.97 (d, J = 4.9 Hz, 1H), 5.53-5.47 (m, 1H), 5.34 (d, J = 4.4 Hz, 1H), 5.12 (s, 1H), 4.08 (s, 1H), 3.98 (s, 1H), 3.51 (s, 2H), 1.61 (d, J = 16.0 Hz, 1H), 1.49 (d, J = 12.1 Hz, 1H), 0.86 (d, J = 7.7 Hz, 3H). |
| 79 | 283 | $^1$H NMR (400 MHz, DMSO-d$_6$) δ 7.85 (s, 1H), 7.69 (s, 2H), 6.84 (d, J = 4.4 Hz, 1H), 6.64 (d, J = 4.4 Hz, 1H), 5.41 (d, J = 4.3 Hz, 1H), 5.27 (d, J = 11.6 Hz, 1H), 4.81 (t, J = 5.9 Hz, 1H), 3.93 (s, 1H), 3.85-3.70 (m, 2H), 3.64-3.49 (m, 2H), 2.27 (t, J = 13.0 Hz, 1H), 1.83 (dd, J = 13.6, 3.1 Hz, 1H). |
| 80 | 314 | $^1$H NMR (400 MHz, DMSO-d$_6$) δ 8.36 (d, J = 1.2 Hz, 1H), 7.91 (brs, 2H), 6.37 (t, J = 6.4 Hz, 1H), |

TABLE 5-continued

| Compound No. | Mass Spec. m/z (M + H)+ | 1H NMR Chemical Shift Data (ppm) |
|---|---|---|
|  |  | 6.11 (d, J = 5.2 Hz, 1H), 5.99-5.95 (m, 1H), 5.48 (d, J = 2.0 Hz, 1H), 5.44 (d, J = 2.0 Hz, 1H), 5.38 (t, J = 5.6 Hz, 1H), 5.30-5.23 (m, 1H), 5.13-5.10 (m, 1H), 4.79-4.71 (m, 1H), 3.61-3.56 (m, 1H), 3.46-3.41 (m, 1H). |
| 81 | 316 | 1H NMR (400 MHz, DMSO-d6) δ 8.29 (d, J = 2.0 Hz, 1H), 7.88 (brs, 2H), 6.32-6.28 (m, 1H), 5.88 (d, J = 6.4 Hz, 1H), 5.38 (t, J = 5.2 Hz, 0.5H), 5.25 (t, J = 5.2 Hz, 0.5H), 5.14 (t, J = 6.4 Hz, 1H), 4.64-4.58 (m, 1H), 3.58-3.55 (m, 1H), 3.50-3.46 (m, 1H), 1.69-1.63 (m, 1H), 1.58-1.54 (m, 1H), 0.90 (t, J = 7.6 Hz, 3H). |
| 82 | 296.10 (M + Na)+ | 1H NMR (400 MHz, DMSO-d6) δ 8.15 (d, J = 7.3 Hz, 1H), 7.66 (s, 1H), 7.43 (s, 1H), 6.00 (td, J = 6.4, 2.1 Hz, 1H), 5.10 (td, J = 5.1, 1.4 Hz, 1H), 5.05 (dd, J = 4.9, 1.4 Hz, 1H), 4.23 (q, J = 5.2 Hz, 1H), 3.49 (dd, J = 11.5, 5.0 Hz, 1H), 3.39 (dd, J = 11.5, 5.1 Hz, 1H), 2.16 (ddd, J = 13.1, 6.1, 4.3 Hz, 1H), 2.08 (dt, J = 13.2, 6.4 Hz, 1H), 1.58 (dq, J = 15.0, 7.6 Hz, 1H), 1.45 (dq, J = 14.6, 7.4 Hz, 1H), 0.84 (t, J = 7.5 Hz, 3H). |
| 83 | 318 | 1H NMR (400 MHz, DMSO-d6) δ 7.81 (d, J = 2.2 Hz, 1H), 6.54 (s, 2H), 6.33-6.10 (m, 2H), 5.37-5.04 (m, 2H), 4.72-4.63 (m, 1H), 4.63-4.43 (m, 2H), 3.62 (dd, J = 11.9, 5.5 Hz, 1H), 3.53 (dd, J = 11.4, 5.3 Hz, 1H). |
| 84 | 320 | 1H NMR (400 MHz, DMSO-d6) δ 8.24 (d, J = 1.2 Hz, 1H), 7.91 (brs, 2H), 6.41-6.37 (m, 1H), 6.23 (d, J = 5.2 Hz, 1H), 5.37-5.24 (m, 2H), 4.77-4.69 (m, 1H), 4.63-4.58 (m, 1H), 4.49-4.46 (m, 1H), 3.70-3.57 (m, 2H). |
| 85 | 296 | 1H NMR (400 MHz, DMSO-d6) δ 8.03 (brs, 1H), 8.01 (brs, 2H), 6.25-6.21 (m, 2H), 5.16 (t, J = 5.2 Hz, 0.5H), 5.02 (t, J = 5.2 Hz, 0.5H), 4.68-4.66 (m, 1H), 4.59-4.52 (m, 1H), 4.47-4.41 (m, 1H), 3.61-3.51 (m, 2H). |
| 106 | 242 | 1H NMR (400 MHz, DMSO-d6) δ 7.89 (d, J = 7.6 Hz, 1H), 7.12-7.06 (m, 2H), 6.08 (t, J = 6.4 Hz, 1H), 5.70 (d, J = 7.6 Hz, 1H), 5.12-5.06 (m, 2H), 4.18 (dd, J = 6.4, 5.2 Hz, 1H), 3.45-3.41 (m, 2H), 2.23-2.17 (m, 1H), 2.08-2.02 (m, 1H), 1.07 (s, 3H). |
| 107 | 270 | 1H NMR (400 MHz, DMSO-d6) δ 8.07 (d, J = 7.2 Hz, 1H), 7.79 (brs, 1H), 7.55 (brs, 1H), 6.07-6.06 (m, 1H), 5.56 (t, J = 6.0 Hz, 1H), 5.50 (d, J = 5.2 Hz, 1H), 4.35-4.30 (m, 1H), 3.71-3.60 (m, 2H), 3.52 (s, 1H), 2.28-2.21 (m, 1H), 2.16-2.14 (m, 1H). |
| 108 | 308.90 | 1H NMR (400 MHz, DMSO-d6) δ 8.46 (s, 1H), 7.89 (s, 1H), 6.69 (s, 2H), 6.27 (dd, J = 4.9, 7.4 Hz, 1H), 5.95-5.71 (m, 1H), 5.61-5.42 (m, 1H), 4.63 (t, J = 6.9 Hz, 1H), 3.70-3.61 (m, 1H), 3.61-3.53 (m, 1H), 2.66-2.60 (m, 1H), 2.45-2.37 (m, 1H) |
| 109 | 294 (M − H)− | 1H NMR (400 MHz, DMSO-d6) δ 8.36 (s, 1H), 7.85 (s, 2H), 6.23 (dd, J = 7.0, 4.7 Hz, 1H), 5.96 (dd, J = 17.3, 10.9 Hz, 1H), 5.39 (dd, J = 17.3, 2.3 Hz, 1H), 5.30 (d, J = 5.0 Hz, 1H), 5.22 (dd, J = 10.9, 2.2 Hz, 1H), 5.11 (dd, J = 6.3, 5.3 Hz, 1H), 4.64 (td, J = 6.7, 4.9 Hz, 1H), 3.55-3.38 (m, 2H), 2.59 (ddd, J = 13.1, 6.6, 4.7 Hz, 1H), 2.26 (dt, J = 13.1, 7.0 Hz, 1H). |
| 110 | 278 | 1H NMR (400 MHz, DMSO-d6) δ 7.80 (d, J = 7.4 Hz, 1H), 7.22-7.16 (s, 2H), 6.33 (t, J = 6.8 Hz, 1H), 6.07 (d, J = 1.7 Hz, 1H), 5.73 (d, J = 7.4 Hz, 1H), 5.66 (d, J = 4.8 Hz, 1H), 5.33 (t, J = 5.3 Hz, 1H), 4.55 (q, J = 5.1 Hz, 1H), 3.73-3.58 (dd, J = 11.7, 4.9 Hz, 2H), 2.18 (t, J = 6.1 Hz, 2H). |
| 113 | 278 | 1H NMR (400 MHz, DMSO-d6) δ 7.65 (d, J = 7.5 Hz, 1H), 7.24 (d, J = 25.5 Hz, 2H), 6.25 (dd, J = 16.4, 4.3 Hz, 1H), 6.11 (d, J = 4.9 Hz, 1H), 5.75 (d, J = 7.5 Hz, 1H), 5.33 (t, J = 5.7 Hz, 1H), 5.03 (d, J = 53.5 Hz, 1H), 4.74-4.35 (m, 3H), 3.60 (dd, J = 11.8, 5.5 Hz, 1H), 3.48 (dd, J = 11.5, 5.6 Hz, 1H). |
| 114 | 291.60 | 1H NMR (400 MHz, DMSO-d6) δ 7.55 (d, J = 7.3 Hz, 1H), 7.15-6.96 (m, 2H), 6.14 (d, J = 3.8 Hz, 1H), 5.69-5.63 (m, 2H), 5.59 (d, J = 5.0 Hz, 1H), 5.13 (t, J = 5.3 Hz, 1H), 4.11-4.05 (m, 2H), 3.85-3.76 (m, 1H), 3.75-3.69 (m, 1H), 3.69-3.58 (m, 2H) |
| 115 | 296 | 1H NMR (400 MHz, DMSO-d6) δ 9.38 (s, 1H), 7.94 (s, 1H), 6.48 (s, 2H), 6.08 (d, J = 7.2 Hz, 1H), 5.15 (d, J = 4.5 Hz, 1H), 4.93 (d, J = 5.6 Hz, 1H), 4.35 (t, J = 4.5 Hz, 1H), 3.43 (q, J = 9.1, 6.2 Hz, 2H), 2.66 (dt, J = 13.9, 6.9 Hz, 1H), 2.26-2.16 (m, 1H), 1.63-1.55 (m, 1H), 1.45 (m, 1H), 1.41 (q, J = 14.1, 7.3 Hz, 2H), 0.86 (t, J = 7.6 Hz, 3H). |
| 116 | 286 | 1H NMR (400 MHz, DMSO-d6) δ 7.78 (d, J = 6.5 Hz, 2H), 7.53 (s, 1H), 6.09 (d, J = 6.0 Hz, 1H), 5.74 (d, J = 5.3 Hz, 1H), 5.65 (d, J = 5.3 Hz, 1H), 5.52 (d, J = 6.5 Hz, 1H), 4.19 (d, J = 6.5 Hz, 1H), 3.99 (d, J = 6.0 Hz, 1H), 3.62 (dd, J = 13.8, 5.3 Hz, 2H), 3.54 (d, J = 2.9 Hz, 1H). |
| 2-TP | 514 (M − H)− | 1H NMR (300 MHz, Deuterium Oxide) δ 7.84 (d, J = 7.6 Hz, 1H), 6.32 (t, J = 6.6 Hz, 1H), 6.05 (d, J = 7.6 Hz, 1H), 4.73 (d, J = 6.2 Hz, 1H), 4.21-4.06 (m, 2H), 3.88-3.70 (m, 2H), 3.11 (q, J = 7.3 Hz, 24H), 2.50-2.34 (m, 1H), 1.19 (t, J = 7.3 Hz, 36H). |
| 25-TP | 548 (M − H)− | 1H NMR (400 MHz, Deuterium Oxide) δ 8.34 (s, 1H), 6.29 (dd, J = 7.1, 4.4 Hz, 1H), 4.82 (t, J = 7.4 Hz, 1H), 4.11 (ddd, J = 59.8, 11.4, 5.0 Hz, 2H), 3.03 (q, J = 7.5 Hz, 24H), 2.63 (ddp, J = 21.4, 14.1, 7.3 Hz, 2H), 1.11 (t, J = 7.4 Hz, 36H). |
| 35-TP | 508.98 (M − H)− | Not Determined |
| 40-TP | 532 (M − H)− | 1H NMR (400 MHz, Deuterium Oxide) δ 7.82 (dd, J = 7.6, 1.2 Hz, 1H), 6.44-6.35 (m, 1H), 6.01 (dd, J = 8.1, 3.9 Hz, 1H), 5.32 (dt, J = 53.2, 4.8 Hz, 1H), 4.11 (s, 2H), 3.86-3.63 (m, 2H), 3.08 (qd, J = 7.3, 2.3 Hz, 24H), 1.31-0.84 (m, 36H). |
| 43-TP | 492 (M − H)− | 1H NMR (300 MHz, Deuterium Oxide) δ 8.03 (d, J = 7.6 Hz, 1H), 6.21 (t, J = 5.5 Hz, 1H), 6.05 (d, J = 7.6 Hz, 1H), 5.88 (dd, J = 17.4, 10.9 Hz, 1H), 5.43 (dd, J = 17.4, 1.4 Hz, 1H), 5.33 (d, J = 10.9, 1.4 Hz, 1H), 4.72 (d, J = 7.8 Hz, 1H), 4.19 (dd, J = 11.5, 5.6 Hz, 1H), 3.86 (dd, J = 11.5, 3.8 Hz, 1H), 3.08 (q, J = 7.3 Hz, 24H), 2.32-2.21 (m, 2H), 1.16 (t, J = 7.3 Hz, 36H). |

TABLE 5-continued

| Compound No. | Mass Spec. m/z (M + H)+ | ¹H NMR Chemical Shift Data (ppm) |
|---|---|---|
| 44-TP | 494 (M − H)− | ¹H NMR (400 MHz, Deuterium Oxide) δ 7.90 (d, J = 7.8 Hz, 1H), 6.13 (d, J = 6.9 Hz, 1H), 6.02 (d, J = 7.6 Hz, 1H), 4.56 (t, J = 6.4 Hz, 1H), 3.97 (d, J = 4.4 Hz, 2H), 3.23-2.95 (m, 21H), 2.30 (p, J = 8.2, 7.8 Hz, 2H), 1.58 (ddd, J = 44.3, 14.7, 7.5 Hz, 2H), 1.23-1.01 (m, 32H), 0.85 (t, J = 7.6 Hz, 3H). |

Example 103—Synthesis of Additional Compounds

The compounds listed in Table 5-A below were prepared using experimental procedures and strategies described in Examples 1-100, the Detailed Description, and related strategies and procedures known to those skilled in the art of organic synthesis. Table 5-A also lists each compound's ¹H NMR characterization data and mass-to-charge ratio observed by LC/MS. Chemical structures are presented in Tables 1-A, 1-C, and 2-C, above.

TABLE 5-A

| Compound No. | Mass Spec. m/z (M + H)+ | ¹H NMR Chemical Shift Data (ppm) |
|---|---|---|
| 86 | 356/358 | ¹H NMR (400 MHz, DMSO-d₆) δ 7.93 (d, J = 6.8 Hz, 1H), 7.88 (s, 1H), 7.64 (s, 1H), 6.25-6.19 (m, 1H), 6.18 (d, J = 4.8 Hz, 1H), 5.47 (t, J = 5.2 Hz, 1H), 5.30-5.05 (m, 1H), 4.52-4.35 (m, 1H), 3.80-3.77 (m, 1H), 3.71-3.66 (m, 1H), 3.62-3.57 (m, 2H). |
| 88 | 338.00 | ¹H NMR (400 MHz, DMSO-d₆) δ 8.01 (d, J = 7.2 Hz, 1H), 7.79-7.74 (m, 1H), 7.57-7.49 (m, 1H), 6.23-6.17 (m, 1H), 5.47-5.44 (m, 1H), 5.33-5.28 (m, 1H), 4.40-4.34 (m, 1H), 3.70-3.63 (m, 2H), 3.62-3.55 (m, 2H), 2.26-2.18 (m, 2H). |
| 92 | 292.12 | ¹H NMR (400 MHz, DMSO-d₆) δ 7.85 (s, 1H), 7.71 (s, 2H), 6.84 (d, J = 4.4 Hz, 1H), 6.71 (d, J = 4.4 Hz, 1H), 5.76 (t, J = 7.3 Hz, 1H), 5.57 (d, J = 5.7 Hz, 1H), 5.26 (t, J = 6.2 Hz, 1H), 4.41 (q, J = 6.1 Hz, 1H), 3.57 (dd, J = 11.8, 6.2 Hz, 1H), 3.48 (dd, J = 11.8, 6.3 Hz, 1H), 2.43 (dt, J = 12.6, 6.9 Hz, 1H), 2.28 (ddd, J = 12.9, 7.6, 5.8 Hz, 1H). |
| 94 | 332 | ¹H NMR (400 MHz, DMSO-d₆) δ 7.92 (s, 1H), 6.44 (s, 2H), 6.03 (d, J = 5.2 Hz, 1H), 5.59 (m, 2H), 5.00 (s, 1H), 4.40 (t, J = 5.3 Hz, 1H), 4.32 (d, J = 5.2 Hz, 1H), 3.78 (s, 2H), 3.73-3.61 (m, 2H). |
| 95 | 330.05 | ¹H NMR (400 MHz, DMSO-d₆) δ 7.82-7.74 (m, 2H), 7.61-7.50 (m, 1H), 6.25-6.21 (m, 1H), 6.07-6.04 (m, 1H), 5.87-5.83 (m, 1H), 5.71-5.66 (m, 1H), 4.41-4.36 (m, 1H), 4.28-4.21 (m, 1H), 3.81-3.68 (m, 2H). |
| 120 | 286 | ¹H NMR (400 MHz, DMSO-d₆) δ 8.37 (d, J = 7.5 Hz, 1H), 7.56 (d, J = 93.2 Hz, 2H), 5.86 (ddd, J = 6.4, 4.2, 1.9 Hz, 1H), 5.33 (t, J = 4.8 Hz, 1H), 5.15 (d, J = 4.9 Hz, 1H), 4.41 (q, J = 7.0 Hz, 1H), 3.59-3.41 (m, 2H), 2.23 (dt, J = 13.6, 7.0 Hz, 1H), 2.06 (ddd, J = 13.0, 6.9, 4.3 Hz, 1H), 0.89 (td, J = 8.2, 4.2 Hz, 1H), 0.45-0.34 (m, 1H), 0.26 (q, J = 6.0, 5.5 Hz, 2H), 0.19-0.09 (m, 1H). |
| 121 | 286 | ¹H NMR (400 MHz, DMSO-d₆) δ 7.92 (d, J = 7.5 Hz, 1H), 7.19 (d, J = 28.5 Hz, 2H), 6.10 (dd, J = 9.0, 5.5 Hz, 1H), 5.88 (s, 1H), 5.69 (d, J = 7.5 Hz, 1H), 5.35 (d, J = 5.2 Hz, 1H), 5.11 (dt, J = 54.3, 5.6 Hz, 1H), 4.47 (dd, J = 22.0, 5.7 Hz, 1H), 3.48 (d, J = 4.1 Hz, 2H), 1.02 (tt, J = 8.5, 5.6 Hz, 1H), 0.46-0.38 (m, 1H), 0.37-0.28 (m, 1H), 0.24 (d, J = 5.2 Hz, 2H). |
| 122 | 607 (2M + H+) | ¹H NMR (400 MHz, DMSO-d₆) δ 8.35 (d, J = 7.4 Hz, 1H), 7.69 (d, J = 91.9 Hz, 2H), 6.06 (td, J = 6.0, 1.9 Hz, 1H), 5.94 (d, J = 4.9 Hz, 1H), 5.55 (t, J = 4.8 Hz, 1H), 5.18 (dt, J = 54.6, 6.3 Hz, 1H), 4.49 (dt, J = 23.1, 5.5 Hz, 1H), 3.72-3.44 (m, 2H), 1.40-0.72 (m, 1H), 0.49-0.12 (m, 4H). |
| 123 | 308 | ¹H NMR (400 MHz, DMSO-d6) δ 8.31 (s, 0H), 8.09 (d, J = 7.2 Hz, 1H), 7.87 (s, 1H), 7.63 (s, 1H), 6.89-6.66 (m, 1H), 6.15-6.08 (m, 2H), 5.58 (s, 1H), 5.14-4.91 (m, 2H), 4.45-4.38 (m, 1H), 3.68 (d, J = 12 Hz, 1H), 3.54 (d, J = 12.4 Hz, 1H). |
| 129 | 404 | ¹H NMR (400 MHz, DMSO-d₆) δ 7.92 (d, J = 6.8 Hz, 1H), 7.88 (brs, 1H), 7.64 (brs, 1H), 6.21-6.14 (m, 2H), 5.45 (t, J = 5.2 Hz, 1H), 5.29 (t, J = 4.4 Hz, 0.5H), 5.16 (t, J = 4.4 Hz, 0.5H), 4.47-4.40 (m, 1H), 3.73-3.69 (m, 1H), 3.59-3.52 (m, 2H). |
| 131 | 324 | ¹H NMR (400 MHz, DMSO-d₆) δ 8.09 (d, J = 7.2 Hz, 1H), 7.87 (brs, 1H), 7.63 (brs, 1H), 6.53 (d, J = 13.2 Hz, 1H), 6.19-6.14 (m, 2H), 6.06 (d, J = 13.2 Hz, 1H), 5.56 (t, J = 5.2 Hz, 1H), 5.09 (t, J = 5.2 Hz, 0.5H), 4.96 (t, J = 5.2 Hz, 0.5H), 4.45-4.40 (m, 1H), 3.58-3.53 (m, 1H), 3.49-3.45 (m, 1H). |
| 132 | 324 | ¹H NMR (400 MHz, DMSO-d₆) δ 8.05 (d, J = 7.2 Hz, 1H), 7.89 (brs, 1H), 7.64 (brs, 1H), 6.52 (d, J = 8.0 Hz, 1H), 6.20 (brs, 1H), 6.11-6.08 (m, 1H), 6.00 (d, J = 8.0 Hz, 1H), 5.54 (brs, 1H), 5.08 (t, J = 5.2 Hz, 0.5H) 4.94 (t, J = 5.2 Hz, 0.5H), 4.48-4.41 (m, 1H), 3.77-3.73 (m, 1H), 3.54-3.50 (m, 1H). |
| 135 | 324 | ¹H NMR (400 MHz, DMSO-d₆) δ 8.08 (d, J = 7.2, Hz, 1H), 7.85 (brs, 1H), 7.61 (brs, 1H), 6.23-6.19 (m, 1H), 6.01 (brs, 1H), 5.42 (brs, 1H), 5.32-5.17 (m, 1H), 4.41-4.35 (m, 1H), 3.69-3.66 (m, 1H), 3.53-3.50 (m, 1H), 2.85-2.82 (m, 1H), 2.59-2.55 (m, 1H), 2.13 (s, 3H). |
| 137 | 328 | ¹H NMR (400 MHz, DMSO-d6) δ 8.12 (d, J = 7.2 Hz, 1H), 7.95-7.63 (m, 2H), 6.34-6.29 (m, 2H), 5.59 (t, J = 5.2 Hz, 1H), 4.80 (t, J = 6.4 Hz, 1H), 4.46-4.45 (m, 1H), 3.97 (d, J = 12.0 Hz, 1H), 3.79-3.74 (m, 1H), 3.73 (d, J = 13.6 Hz, 1H), 3.58-3.33 (m, 1H). |
| 138 | 307 | ¹H NMR (400 MHz, DMSO-d₆) δ 8.04 (d, J = 7.2 Hz, 1H), 7.86 (brs, 1H), 7.60 (brs, 1H), 7.46 (s, 1H), 7.21 (s, 1H), 6.26-6.21 (m, 1H), 6.04 (d, J = 4.8 Hz, 1H), 5.22-5.19 (m, 1H), 5.02-5.01 (m, 0.5H), 4.89 (m, 0.5H), 4.15-4.11 (m, 1H), |

TABLE 5-A-continued

| Compound No. | Mass Spec. m/z (M + H)+ | 1H NMR Chemical Shift Data (ppm) |
|---|---|---|
| 139 | 293 | 3.93-3.88 (m, 1H), 3.55-3.52 (m, 1H). $^1$H NMR (400 MHz, Methanol-d$_4$) δ 8.05 (d, J = 6.4 Hz, 1H), 6.34-6.29 (m, 1H), 5.25-5.11 (m, 1H), 4.47-4.42 (m, 1H), 3.71 (s, 2H), 3.11-2.98 (m, 2H). |
| 161 | 418.01 | $^1$H NMR (400 MHz, DMSO-d$_6$) δ 7.90 (s, 1H), 6.99 (s, 1H), 5.72 (t, J = 7.1 Hz, 1H), 5.59 (d, J = 5.5 Hz, 1H), 5.30 (t, J = 6.2 Hz, 1H), 4.37 (q, J = 6.1 Hz, 1H), 3.57 (dd, J = 11.9, 6.2 Hz, 1H), 3.48 (dd, J = 11.9, 6.2 Hz, 1H), 2.40-2.22 (m, 2H). |
| 162 | 309 | $^1$H NMR (400 MHz, DMSO-d6) δ 11.20 (s, 1H), 8.31-8.25 (m, 1H), 6.29-6.26 (m, 1H), 5.95-5.80 (m, 1H), 5.53-5.27 (m, 2H), 4.96-4.92 (m, 1H), 4.60-4.46 (m, 1H), 3.82-3.76 (m, 1H), 3.63-3.46 (m, 2H), 1.24-0.98 (m, 3H). |
| 163 | 313 | $^1$H NMR (400 MHz, Methanol-d$_4$) δ 8.04 (dd, J = 6.6, 2.0 Hz, 1H), 6.37 (ddd, J = 14.6, 4.4, 1.6 Hz, 1H), 5.24 (dt, J = 53.3, 4.0 Hz, 1H), 4.54 (dd, J = 19.5, 3.5 Hz, 1H), 3.90-3.71 (m, 4H). |
| 164 | 308 | $^1$H NMR (400 MHz, DMSO-d$_6$) δ 8.33 (s, 1H), 7.82 (brs, 2H), 6.20-6.17 (m, 1H), 5.40-5.36 (m, 2H), 5.14 (t, J = 5.6 Hz, 1H), 5.02-4.91 (m, 2H), 4.65-4.60 (m, 1H), 3.56-3.51 (m, 2H), 2.59-2.56 (m, 1H), 2.39-2.35 (m, 1H). |
| 165 | 304.85 | $^1$H NMR (400 MHz, DMSO-d$_6$) δ = 7.96 (br s, 1H), 7.88 (d, J = 6.8 Hz, 1H), 7.72 (br s, 1H), 6.35-5.89 (m, 3H), 5.18 (dt, J = 5.2, 52 Hz, 1H), 4.46 (dd, J = 4.9, 24 Hz, 1H), 3.79-3.71 (m, 2H). |
| 166 | 289 | $^1$H NMR (400 MHz, DMSO-d$_6$) δ 8.02 (brs, 1H), 7.83 (d, J = 7.0 Hz, 1H), 7.75 (brs, 1H), 6.92 (d, J = 5.5 Hz, 1H), 6.35-6.26 (m, 1H), 5.96 (t, J = 6.3 Hz, 1H), 5.29-5.09 (m, 1H), 4.52-4.45 (m, 1H), 3.80 (d, J = 6.4 Hz, 2H). |
| 172 | 339 | $^1$H NMR (400 MHz, DMSO-d6) δ 7.62 (d, J = 7.6 Hz, 1H), 7.26 (s, 1H), 7.20 (s, 1H), 6.26 (m, 1H), 6.15 (d, J = 4.0 Hz, 1H), 5.73 (d, J = 7.6 Hz, 1H), 5.32 (t, J = 4 Hz, 1H), 5.18 (t, J = 3.4 Hz, 1H), 5.05 (t, J = 3.3 Hz, 1H), 4.46 (d, J = 3.4 Hz, 1H), 3.79 (d, J = 10.8 Hz, 1H), 3.68-3.58 (m, 3H). |
| 174 | 415 (M − H) | $^1$H NMR (400 MHz, DMSO-d$_6$) δ 8.11-8.06 (m, 1H), 7.96 (s, 1H), 7.53 (s, 1H), 6.52 (dd, J = 7.3, 4.8 Hz, 1H), 5.52 (t, J = 6.4 Hz, 1H), 4.15 (q, J = 11.5 Hz, 2H), 3.84-3.77 (d, J = 11.7 Hz, 2H), 2.73 (ddd, J = 13.7, 7.0, 4.9 Hz, 1H), 2.67-2.53 (m, 1H), 2.56-2.47 (m, 1H), 2.41 (ddd, J = 13.5, 7.4, 5.8 Hz, 1H), 1.13-1.07 (dd, J = 7.0, 1.8 Hz, 12H). |

Example 104—Stable Cellular Assay for Inhibiting LINE1 Reverse Transcriptase Exemplary compounds, were tested for the ability to inhibit LINE1 reverse transcriptase using a stable artificial-intron Cis LINE1 reporter assay. Assay procedures and results are described below.

Part I—Procedure for Stable Artificial-Intron Cis LINE1 Reporter Assay

A stable HeLa Tet-On 3G (Takara, cat no 631183) cell line expressing a bi-directional inducible LINE1 construct was generated as described in Xie, Y. et al. "Cell division promotes efficient retrotransposition in a stable Li reporter cell line," *Mobile DNA* (2013) 4:10. Single cell clones were screened for high Luciferase expression and the highest expression Firefly expressing clone was chosen for compound testing.

Test compounds were serially diluted in DMSO and spotted in 96-well plates. Subsequently, the HeLa Li artificial-intron reporter cells were plated into the compound-containing wells (8,000 cells/well), and the cells were induced for reporter expression with doxycycline (Sigma-Aldrich cat #D9891) at a final concentration of 500 ng/mL. Luminescence was measured 72 h after plating using the Dual-Glo Luciferase Assay System (Promega cat #E2940) following the manufacturer's instructions. The Firefly Luciferase activity was used to report LINE1 activity.

Part II—Results

Results are listed in Tables 6, 6-A, and 6-B. In Table 6, 6-A, and 6-B below, A represents values<0.050 μM; B represents values from >0.050 μM to ≤0.100 PM; C represents values from >0.100 μM to ≤0.250 μM; D represents values from >0.250 μM to ≤1 μM; E represents values>1 μM; and NT=not tested.

TABLE 6

| Compound No. | IC$_{50}$ (μM) |
|---|---|
| 1 | NT |
| 2 | A |
| 3 | E |
| 4 | E |
| 5 | B |
| 6 | C |
| 7 | E |
| 8 | C |
| 9 | E |
| 10 | E |
| 11 | E |
| 12 | D |
| 13 | D |
| 14 | A |
| 15 | D |
| 16 | D |
| 17 | >30 |
| 18 | E |
| 19 | D |
| 20 | E |
| 21 | D |
| 22 | A |
| 23 | A |
| 24 | D |
| 25 | A |
| 26 | NT |

TABLE 6-A

| Compound No. | IC$_{50}$ (μM) |
|---|---|
| 27 | A |
| 28 | E |
| 29 | E |
| 30 | E |
| 31 | A |
| 32 | E |
| 33 | E |
| 34 | >30 |
| 35 | A |
| 36 | E |
| 37 | A |
| 38 | E |
| 39 | D |
| 40 | A |
| 41 | A |
| 42 | A |

TABLE 6-A-continued

| Compound No. | IC$_{50}$ (μM) |
|---|---|
| 43 | A |
| 44 | A |
| 45 | B |
| 46 | B |
| 47 | A |
| 48 | B |
| 49 | B |
| 50 | A |
| 51 | A |
| 52 | C |
| 53 | D |
| 54 | >30 |
| 55 | E |
| 56 | C |
| 57 | E |
| 58 | B |
| 59 | E |
| 60 | E |
| 61 | A |
| 62 | D |
| 63 | D |
| 64 | B |
| 65 | A |
| 66 | D |
| 67 | A |
| 68 | C |
| 69 | A |
| 70 | E |
| 71 | >30 |
| 72 | D |
| 73 | A |
| 74 | A |
| 75 | C |
| 76 | A |
| 77 | A |
| 78 | B |
| 79 | >30 |
| 80 | C |
| 81 | C |
| 82 | A |
| 83 | E |
| 84 | E |
| 85 | B |
| 86 | A |
| 88 | A |
| 92 | A |
| 94 | >30 |
| 95 | >30 |
| 106 | A |
| 107 | A |
| 108 | B |
| 109 | A |
| 110 | D |
| 111 | A |
| 112 | A |
| 113 | B |
| 114 | C |
| 115 | A |
| 116 | C |
| 119 | B |
| 120 | D |
| 121 | C |
| 122 | D |
| 123 | B |
| 129 | E |
| 131 | C |
| 132 | E |
| 135 | E |
| 137 | D |
| 138 | >30 |
| 139 | >30 |
| 161 | B |
| 162 | >30 |
| 163 | >30 |
| 164 | D |
| 166 | >30 |
| 172 | A |

TABLE 6-A-continued

| Compound No. | IC$_{50}$ (μM) |
|---|---|
| 173 | D |
| 174 | >30 |

TABLE 6-B

| Compound No. | IC$_{50}$ (μM) |
|---|---|
| 175 | A |
| 176 | E |
| 177 | E |
| 178 | B |
| 179 | E |
| 180 | E |

Example 105—Biochemical Assay for Inhibiting LINE1 Reverse Transcriptase

Exemplary triphosphate analogs were tested for the ability to inhibit LINE1 reverse transcriptase using a homogeneous time-resolved fluorescence (HTRF) assay. Assay procedures and results are described below.

Part I—Procedure for Homogeneous Time-Resolved Fluorescence LINE1 RT Assay

The LINE1 reverse transcriptase homogeneous time-resolved fluorescence (HTRF) assay was performed with recombinant MBP-tagged LINE1 protein (238-1061) (generated and purified according to procedures in Dai L. et al. BMC Biochemistry 2011; 12:18) in a 384-well format. Test compound was serially diluted in DMSO and further diluted in the assay buffer (50 mM Tris-HCl, 50 mM KCl, 10 mM MgCl$_2$, 10 mM DTT, pH 8.1) to achieve a final DMSO concentration of 1%. The serially diluted compound was mixed with 64 ng/well of LINE1 enzyme, 5 nM of pre-annealed template/biotin-primer pair (synthesized at Generay Biotechnology), 10 nM of Fluorescein-12-dCTP fluorescent probe (PerkinElmer), and 1 μM dGTP/dATP/dTTP (ThermoFisher Scientific) in the assay buffer. The template/biotin-primer sequences were as follows:

```
5' to 3'
                                    (SEQ ID NO: 1)
GUAACUAGAGAUCCCUCAGACCCUUUUAGUCAGAAU

5' to 3' Biotin-
                                    (SEQ ID NO: 2)
TTCTGACTAAAAGGGTCTGAGGGAT.
```

After incubating at 25° C. for 60 minutes, the detection reagent (20 mM EDTA with streptavidin-terbium cryptate, Cisbio Bioassay) in the PPI buffer (Cisbio Bioassay) was added, and the mixture was incubated at 25° C. for 30 minutes. At the end of the incubation, fluorescence was read at ex/em=337/485 nm and ex/em=337/520 nm on an Envision 2104 plate reader (PerkinElmer). The fluorescence ratio at 520/485 nm was used for the calculation. Percent inhibition was calculated with the DMSO sample as 0% inhibition and no enzyme as 100% inhibition. The IC$_{50}$ was calculated by fitting the compound dose inhibition curve with a 4-parameter non-linear regression equation.

Part II—Results
The following compounds were tested in this assay:

| Compound No. | Triphosphate Structure | IC$_{50}$ (µM) |
|---|---|---|
| 2-TP | [structure: triphosphate-cytidine analog with CH$_2$Cl and OH substituents] | 0.0475 |
| 35-TP | [structure: triphosphate-cytidine analog with ethynyl, OH, and F substituents] | 0.0137 |
| 40-TP | [structure: triphosphate-cytidine analog with CH$_2$Cl, OH, and F substituents] | 0.831 |
| 14-TP | [structure: triphosphate-5-fluorocytidine analog with CH$_2$Cl and OH substituents] | 0.272 |

The following additional triphosphate compounds were made and tested:

| Compound No. | Triphosphate Structure | IC$_{50}$ (µM) |
|---|---|---|
| 44-TP | [structure: triphosphate-cytidine analog with ethyl and OH substituents] | 0.108 |
| 43-TP | [structure: triphosphate-cytidine analog with vinyl and OH substituents] | 0.081 |

-continued

| Compound No. | Triphosphate Structure | IC$_{50}$ (μM) |
|---|---|---|
| 67-TP | 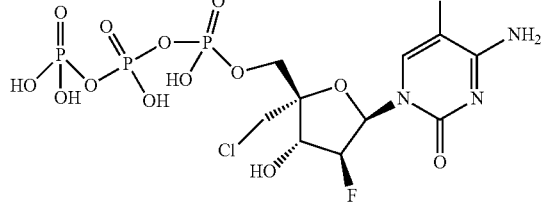 | 0.43 |
| 86-TP | 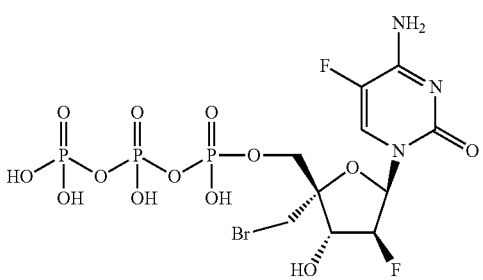 [SMILES: Nc1nc(=O)n([C@@H]2O[C@](CBr)(COP(=O)(O)OP(=O)(O)OP(=O)(O)O)[C@@H](O)[C@@H]2F)cc1F] | 1.61 |

Example 106—Biochemical Assay for Inhibiting HERV-K Reverse Transcriptase

Exemplary triphosphate analogs were tested for ability to inhibit HERV-K reverse transcriptase using a homogeneous time-resolved fluorescence (HTRF) assay. Assay procedures and results are described below.

Part I—Procedure for Homogeneous Time-Resolved Fluorescence HERV-K RT Assay

The HERV-K reverse transcriptase homogeneous time-resolved fluorescence (HTRF) assay was performed in a 384-well format with HERV-K reverse transcriptase (2-596)-8His protein. Baculoviruses were created using Bac-to-Bac technology (Invitrogen). pFastBac donor plasmids containing HERV-K reverse transcriptase sequence (NCBI GenBank number AAC63291.1, *J. Virology* (1999) Vol. 73, No. 3, pp. 2365-2375) were transformed into DH10 Bac cells following the manufacturer's instructions. Recombinant bacmids were then isolated clonally and transfected into SF9 cells with lipofectin. HERV-K reverse transcriptase was expressed in the SF9 insect cells and then purified using immobilized metal affinity chromatography (IMAC) followed by size-exclusion chromatography (SEC).

Test compound was serially diluted in DMSO and further diluted in the assay buffer (50 mM Tris-HCl, 50 mM KCl, 10 mM MgCl$_2$, 10 mM DTT, pH 8.1) to achieve a final DMSO concentration of 1%. The serially diluted compound was mixed with 16 ng/well of HERV-K enzyme, 5 nM of pre-annealed template/biotin-primer pair (synthesized at Geneway Biotechnology), 10 nM of Fluorescein-12-dCTP fluorescent probe (PerkinElmer), and 1 mM dGTP, dATP, and DTTP (ThermoFisher). The template/biotin-primer sequences were:

```
5' to 3'
                                 (SEQ ID NO: 1)
GUAACUAGAGAUCCCUCAGACCCUUUUAGUCAGAAU

5' to 3' Biotin-
                                 (SEQ ID NO: 2)
TTCTGACTAAAAGGGTCTGAGGGAT.
```

After incubating at 25° C. for 30 minutes, the detection reagent 20 mM EDTA with streptavidin-terbium cryptate (Cisbio Bioassay) in the PPI buffer (Cisbio Bioassay) was added, and the mixture was incubated at 25° C. for 60 minutes. At the end of the incubation, fluorescence was read at ex/em=337/485 nm and ex/em=337/520 nm on an Envision 2104 plate reader (PerkinElmer). The fluorescence ratio at 520/485 nm was used for the calculation. Percent inhibition was calculated with the DMSO sample as 0% inhibition and no enzyme as 100% inhibition. IC$_{50}$ values were calculated by fitting the compound dose inhibition curve with a 4-parameter non-linear regression equation.

Part II—Results

The following triphosphate analogs were tested in this assay. Results are shown in the table below:

| Compound No | Triphosphate Structure | IC$_{50}$ (μM) |
|---|---|---|
| 2-TP | 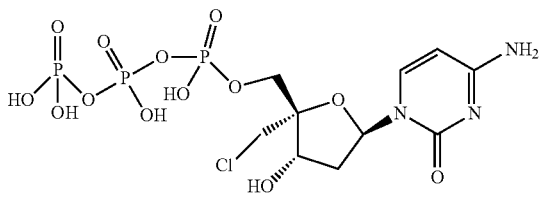 [SMILES: Nc1ccn([C@H]2C[C@H](O)[C@@](CCl)(COP(=O)(O)OP(=O)(O)OP(=O)(O)O)O2)c(=O)n1] | 16.97 |

-continued
| Compound No | Triphosphate Structure | IC$_{50}$ (μM) |
|---|---|---|
| 35-TP | 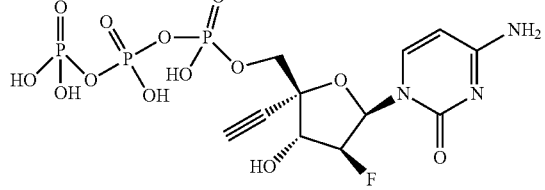 | 0.013 |
The following additional triphosphate compounds were made and tested:
| Compound No. | Triphosphate Structure | IC$_{50}$ (μM) |
|---|---|---|
| 40-TP | 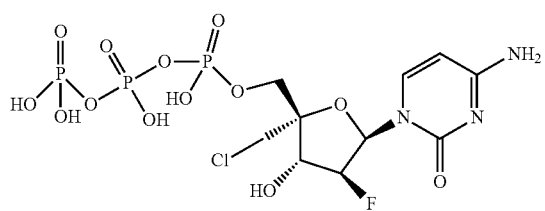 [SMILES: Nc1ccn([C@@H]2O[C@](CCl)(COP(=O)(O)OP(=O)(O)OP(=O)(O)O)[C@@H](O)[C@@H]2F)c(=O)n1] | >10 |
| 14-TP | 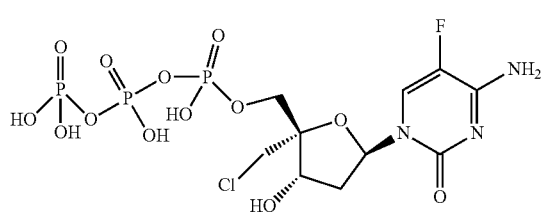 [SMILES: Nc1nc(=O)n([C@H]2C[C@H](O)[C@@](CCl)(COP(=O)(O)OP(=O)(O)OP(=O)(O)O)O2)cc1F] | >10 |
| 44-TP | 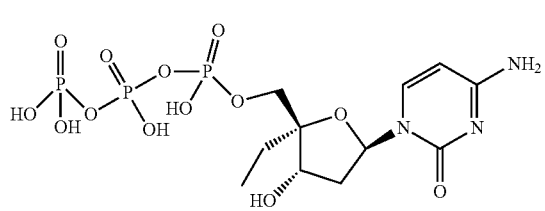 [SMILES: CC[C@]1(COP(=O)(O)OP(=O)(O)OP(=O)(O)O)O[C@@H](n2ccc(N)nc2=O)C[C@@H]1O] | >10 |
| 43-TP | 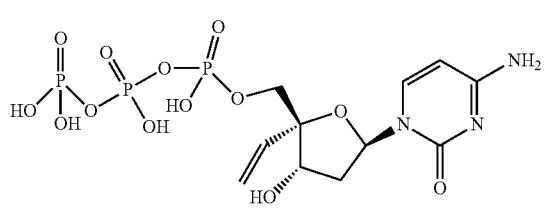 [SMILES: C=C[C@]1(COP(=O)(O)OP(=O)(O)OP(=O)(O)O)O[C@@H](n2ccc(N)nc2=O)C[C@@H]1O] | 4.01 |
| 67-TP | 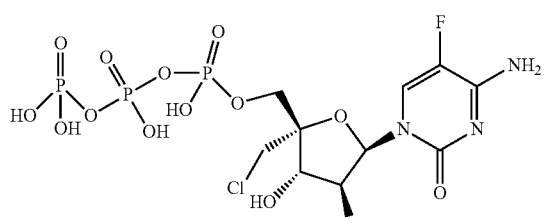 | >10 |

| Compound No. | Triphosphate Structure | IC$_{50}$ (μM) |
|---|---|---|
| 86-TP | | >10 |

Example 107—THP1 TREX1 KO Inhibition Assay

Exemplary compounds were tested for their ability to alter the type 1 interferon response in THP1 Dual TREX1 KG cells treated with 5-aza-2'-deoxycytidine. Assay procedures and results are described below.

Part I—Procedure

THP1 Dual TREX1 KG cells were purchased from Invivogen. The THP1-Dual™ KO-TREX1 cells were cultured in RPMI 1640, 10% heat-inactivated fetal bovine serum, 25 mM HEPES, 10 μg/mL blasticidin, and 100 μg/mL zeocin. THP1-Dual™ KO-TREX1 cells were treated with a dose titration of a test compound alone or in the presence of 1 μM 5-aza-2'-deoxycytidine (Sigma-Aldrich, cat #189825). Type 1 Interferon and cell viability were assessed after six days of treatment.

Stock solution of the test compound was prepared in DMSO followed by a three-fold dilution in DMSO. Additional 50× dilution was prepared in cell culture media for each dilution. 10 μL of diluted test compound was then added to a 96-well plate.

THP1-Dual™ KO-TREX1 cells were treated with either 1×PBS or 1 μM 5-aza-2'-deoxycytidine. 190 nL of the THP1-Dual™ KO-TREX1 cells from either treatment were added to each well of the 96-well plate containing the test compound titration at 50,000 cells/well. Cells were incubated at 37° C., 5% CO$_2$ in a humidified incubator for six days. Cells treated with 1 μM 5-aza-2'-deoxycytidine were added at the same density as above and incubated at 37° C., 5% CO$_2$ in a humidified incubator for six days. On day six, 25 μL of cell supernatant was transferred to a 96-well white-walled plate, followed by addition to each well of 50 μL of QUANTI-LUC solution containing stabilizer. Luminescence was detected on a plate reader according to the manufacturer's instructions.

The remaining cells were assessed for cell viability by adding 25 μL of CellTiter-Glo (Promega, G9683) solution to each well, and being placed on a shaker for 10 minutes at room temperature. Luminescence was detected on a plate reader, according to the manufacturer's instructions.

Part II—Results

Results are shown in the tables below. In the tables "A" represents values≤0.050 μM; "B" represents values from >0.050 μM to ≤0.100 μM; "C" represents values from >0.100 μM to ≤0.250 μM; "D" represents values from >0.250 μM to ≤1 μM; "E" represents values>1 μM; and "NT"=not tested:

TABLE 7-A

| Compound No. | IC$_{50}$ (μM) |
|---|---|
| 1 | E |
| 2 | B |
| 3 | NT |
| 4 | E |
| 5 | E |
| 6 | E |
| 7 | E |
| 8 | E |
| 9 | E |
| 10 | NT |
| 11 | E |
| 12 | E |
| 13 | E |
| 14 | C |
| 15 | E |
| 16 | E |
| 17 | E |
| 18 | E |
| 19 | E |
| 20 | E |
| 21 | NT |
| 22 | B |
| 23 | E |
| 24 | E |
| 25 | E |
| 26 | E |
| 27 | E |
| 28 | E |
| 29 | E |
| 30 | NT |
| 31 | E |
| 32 | E |
| 33 | E |
| 34 | E |
| 35 | D |
| 36 | NT |
| 37 | E |
| 38 | E |
| 39 | E |
| 40 | E |
| 41 | E |
| 42 | E |
| 43 | E |
| 44 | E |
| 45 | E |
| 46 | E |
| 47 | E |
| 48 | NT |
| 49 | NT |
| 50 | D |
| 51 | E |

TABLE 7-B

| Compound No. | IC$_{50}$ (μM) |
| --- | --- |
| 52 | E |
| 53 | E |
| 55 | E |
| 56 | E |
| 57 | E |
| 58 | E |
| 60 | E |
| 61 | E |
| 62 | E |
| 63 | E |
| 64 | E |
| 65 | D |
| 66 | E |
| 67 | D |
| 68 | E |
| 69 | E |
| 70 | E |
| 72 | E |
| 73 | E |
| 74 | E |
| 75 | E |
| 76 | E |
| 77 | E |
| 78 | E |
| 80 | E |
| 81 | E |
| 82 | E |
| 85 | D |
| 86 | E |
| 88 | D |
| 92 | E |
| 106 | D |
| 107 | E |
| 108 | D |
| 109 | E |
| 110 | E |
| 111 | B |
| 112 | E |
| 113 | E |
| 114 | E |
| 115 | E |
| 116 | E |
| 119 | E |
| 120 | E |
| 121 | E |
| 122 | E |
| 123 | E |
| 131 | E |
| 137 | E |
| 161 | B |
| 164 | E |
| 165 | D |
| 172 | E |
| 173 | E |
| 175 | D |
| 176 | E |
| 177 | E |
| 178 | E |
| 179 | E |
| 180 | E |

Example 108—In Vivo Decitabine Challenge Model in C57BL/6 Mice

Exemplary compounds were tested for ability to alter the interferon-stimulated gene (ISG) response in C57BL/6 mice treated with decitabine. Assay procedures and results are described below.

Part I—Procedure for Compound 23

Twenty 9-11 week old C57BL/6 mice were acclimated to the lab for at least 5 days. Compound 23 was prepared in a 0.5% methylcellulose solution for p.o. administration. Decitabine (Sigma-Aldrich) was dissolved in sterile PBS (pH 7.4) and dosed within 30 minutes of preparation of the solution. Doses of both the compound and decitabine were administered once a day, every day from Day 0 to Day 4.

On Day 0, mice were split into five groups of five mice and given their first dose of decitabine (i.p., 5 mg/kg) and compound 23. Dosing groups were:

| Group | Compound 23 Dose (mg/kg) | Decitabine Dose (mg/kg) |
| --- | --- | --- |
| PBS | 0 | 0 |
| Decitabine Control | 0 | 5 |
| 1 | 0.6 | 5 |
| 2 | 2.0 | 5 |
| 3 | 6.0 | 5 |

Decitabine and compound 23 were administered daily from Day 0 to Day 4. All mice were euthanized 1 hour after the last dose administration on Day 4. Spleens, liver, and terminal colon were collected, along with plasma from each animal. The fold changes in interferon-stimulated gene (ISG) expression was calculated by first normalizing to GAPDH gene using the Delta CT method. The CT (gene of interest) —CT (reference gene) was calculated to generate a delta CT for all samples. The fold change was then calculated by taking the Log 2(Delta CT(control)–Delta CT (experimental). The control in this example was the PBS control animal group. The Taqman duplex assay was used to determine levels of GAPDH v. IFIT2.

Part II—Procedure for Compound 2

Twenty 9-11 week old C57BL/6 mice were acclimated to the lab for at least 5 days. Compound 2 was prepared in 20% PEG400 in PBS (final pH 4.5) for p.o. administration. Decitabine (Sigma) was dissolved in sterile PBS (pH 7.4) and dosed within 30 minutes of preparation of the solution. Doses of both Compound 2 and decitabine were administered once a day.

On Day 0, mice were split into five groups of five mice and given their first dose of decitabine and Compound 2. Dosing groups were:

| Group | Compound 2 Dose (mg/kg) | Decitabine Dose (mg/kg) |
| --- | --- | --- |
| PBS | 0 | 0 |
| Decitabine Control | 0 | 5 |
| 1 | 1 | 5 |
| 2 | 10 | 5 |
| 3 | 100 | 5 |

Decitabine (i.p., 5 mg/kg) and Compound 2 were administered daily from Day 1 to Day 4. All mice were euthanized 1 hour after the last dose administration on Day 4. Kidneys were harvested and snap frozen in liquid nitrogen, and plasma (EDTA) was collected for bioanalysis. The fold changes in interferon-stimulated gene (ISG, specifically IRF7 and MX1) expression was calculated by first normalizing to GAPDH gene using the Delta CT method. The CT (gene of interest)–CT (reference gene) was calculated to generate a delta CT for all samples. The fold change was then calculated by taking the Log 2(Delta CT(control)–Delta CT (experimental). The control in this example was the PBS control animal group. Individual primers were used to amplify target genes.

Part III—Results

Figure 1B:
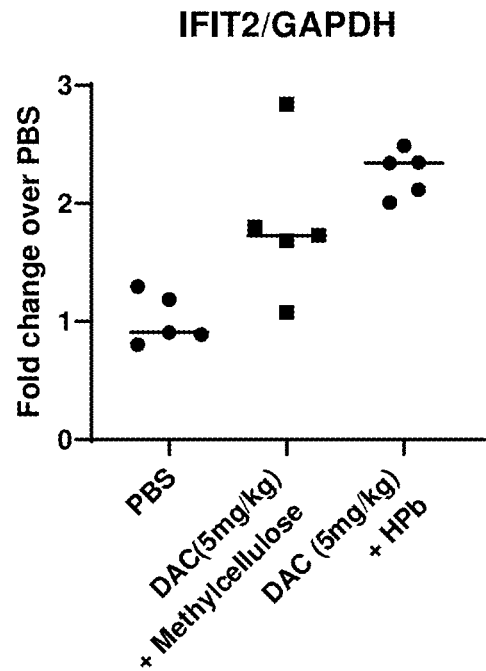
Figure 2A:
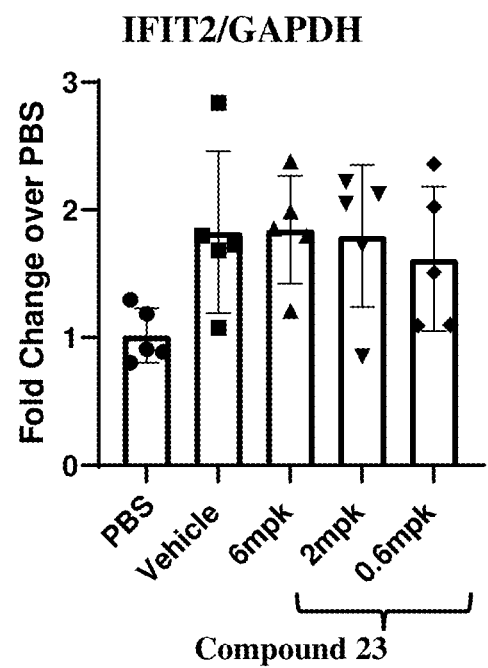
FIGS. 2A, 2B, and 2C depict the effects of repeated administration of compound 23 (FIG. 2A) and compound 2 (FIGS. 2B and 2C) in the in vivo decitabine challenge model, as described in Example 108.
Figure 2B:
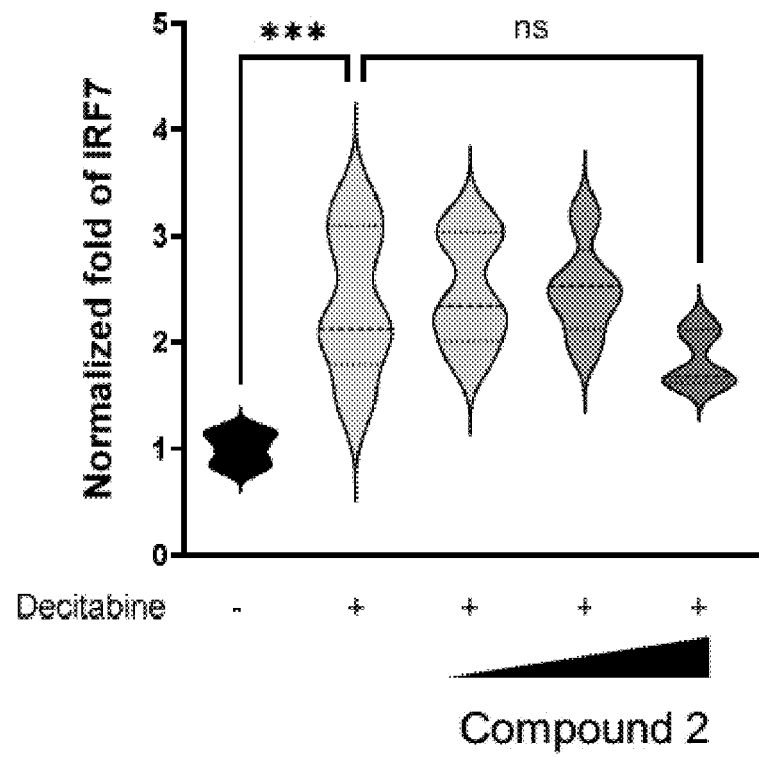
Figure 2C:
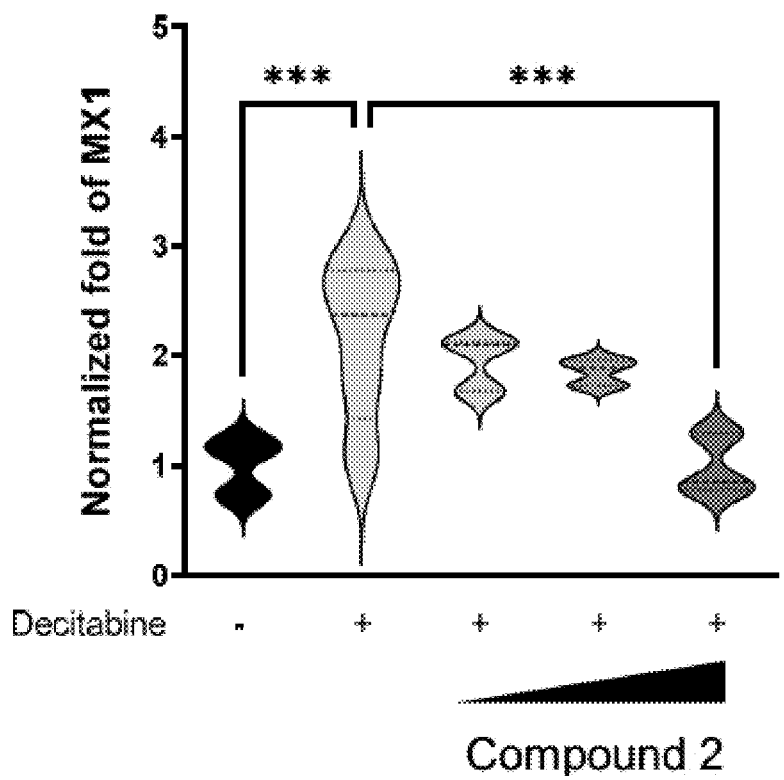

Repeated dosing of decitabine induces interferon-stimulated gene (ISG) response in the spleen in the control animals (see FIG. 1A and FIG. 1B). Dosing of Compound 2 shows the change in ISG response (see FIG. 2A). Dosing of Compound 2 also shows a change in the ISG response (see FIGS. 2B and 2C).

Part IV—In Vivo Decitabine Challenge Model in BALB/c Mice

Thirty 9-11 week old BALB/c mice were acclimated to the lab for at least 5 days. Compounds 2, 40 and 67 were prepared in a 20% PEG400 (pH 3.5) solution for p.o. administration, compounds were prepared no more than 30 minutes prior to daily dosing. Decitabine (Sigma) was dissolved in sterile PBS (pH 7.4) and dosed within 30 minutes of preparation of the solution. Doses of both the compound and decitabine were administered once a day, every day from Day 0 to day 4.

On Day 0, mice were split into seven groups of five mice and given their first dose of decitabine (i.p., 5 mg/kg) and compound. Dosing groups were as in the following table (all doses in mg/kg):

| Group | Decitabine | Compound 2 | Compound 40 | Compound 67 |
|---|---|---|---|---|
| PBS | 0 | 0 | 0 | 0 |
| Control | 5 | 0 | 0 | 0 |
| 1 | 5 | 0 | 0 | 0 |
| 2 | 5 | 100 | 0 | 0 |
| 3 | 5 | 0 | 100 | 0 |
| 4 | 5 | 0 | 0 | 30 |
| 5 | 5 | 0 | 0 | 100 |

Decitabine (i.p., 5 mg/kg) and compounds 2, 40 or 67 were administered daily from Day 1 to Day 4. All mice were euthanized 1 hour after the last dose administration on Day 4. Spleen and kidneys were harvested and snap frozen in liquid nitrogen, and plasma (EDTA) was collected for bioanalysis. Total RNA was isolated using the PureLink RNA Mini Kit (ThermoFisher) and prepared for RNAseq using the TruSeq Stranded mRNA platform (Illumina). 50M Stranded reads were collected on an Illumina HiSeq system. Data were analyzed as follows: RNA sequencing reads were aligned to the hg38 reference genome using the STAR RNA-seq aligner (Dobin et al., 2013). Expression of each transcript was quantified using Salmon (Patro, et al. 2015) TPM values for each transcript. These transcript-level TPM values were aggregated by gene to get gene-level TPM values, and log-transformed these values. Mouse orthologs for each gene in the list of ISG-associated genes in the human genome from Liu et al., 2019 using Ensembl BioMart (Kinsella et al., 2011) were identified. The ISG score for each sample was calculated as the median log-transformed TPM value across all genes in this ISG gene set.

Part V—Results

Repeated dosing of decitabine induces interferon-stimulated gene (ISG) response in the spleen in the control animals (see FIG. 1A and FIG. 1B). In C57BL/6 mice, dosing of Compound 23 shows the change in ISG response (see FIG. 2A). Dosing of Compound 2 in C57BL/6 mice also shows a change in the ISG response (see FIGS. 2B and 2C).

Figure 2D:
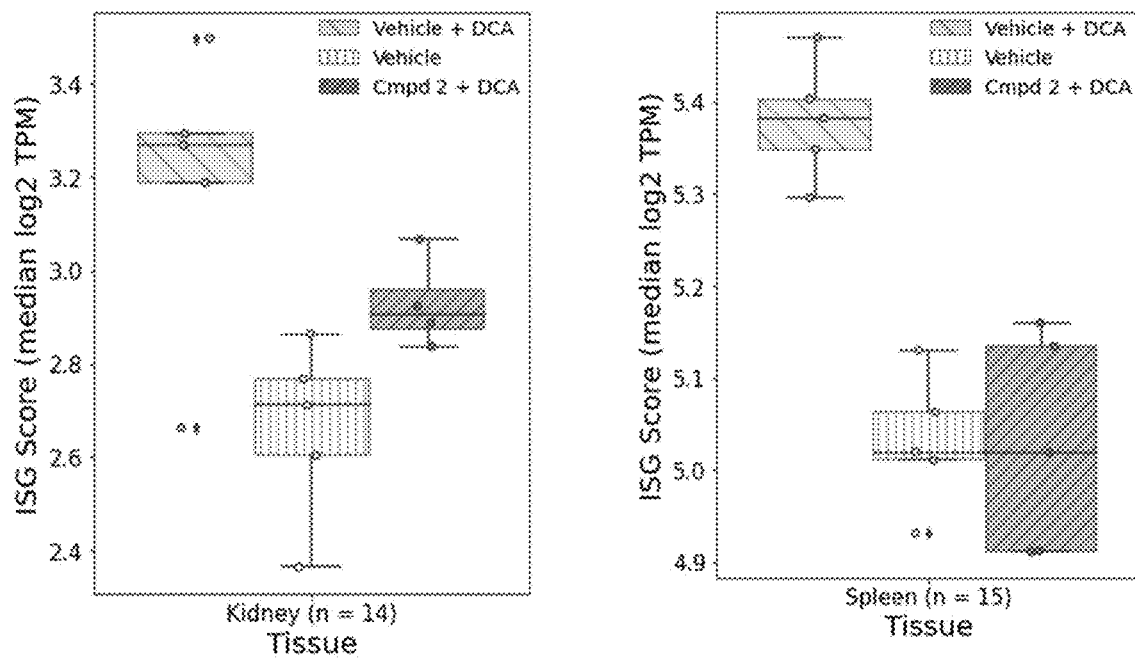
FIGS. 2D, 2E, 2F and 2G are graphs which depict the effects of repeated administration of Compound 2 (FIG. 2D), Compound 40 (FIG. 2E), Compound 67 at 30 mg/kg (FIG. 2F), and Compound 67 at 100 mg/kg (FIG. 2G) on ISG Score in the spleen and kidney, in the in vivo decitabine challenge model in BALB/c mice, as described in Example 108.
Figure 2E:
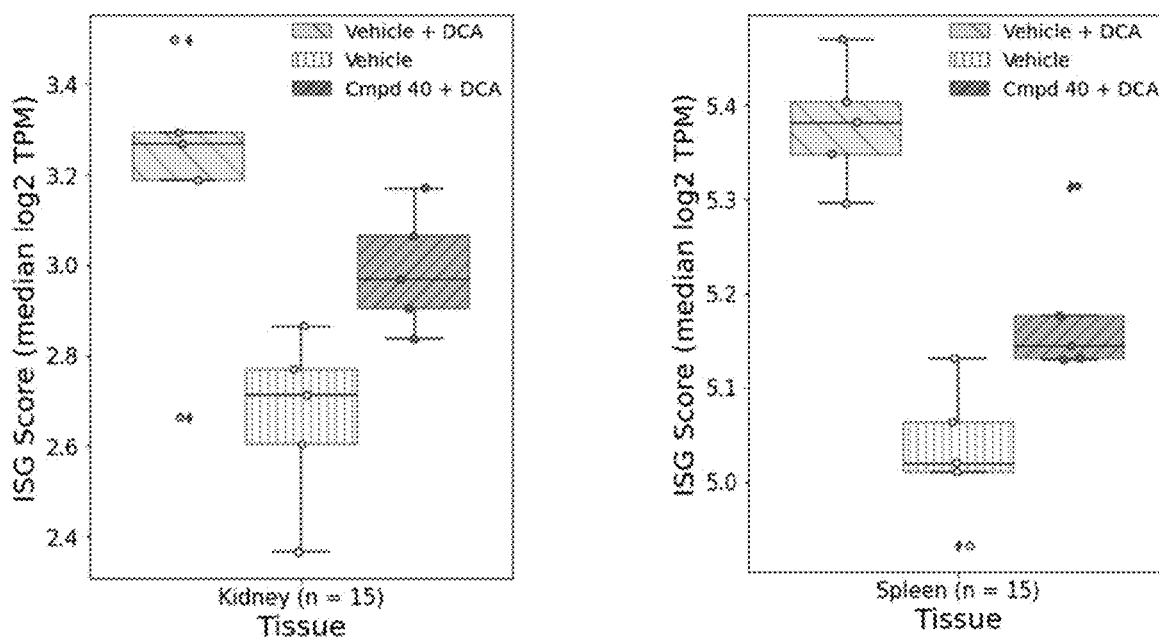
Figure 2F:
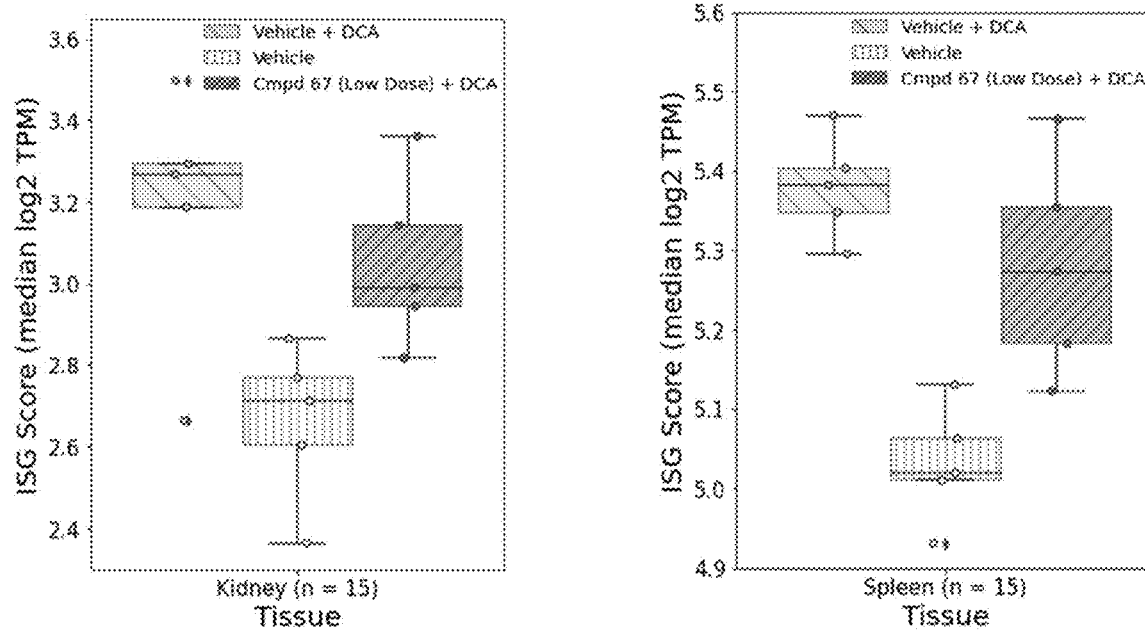
Figure 2G:
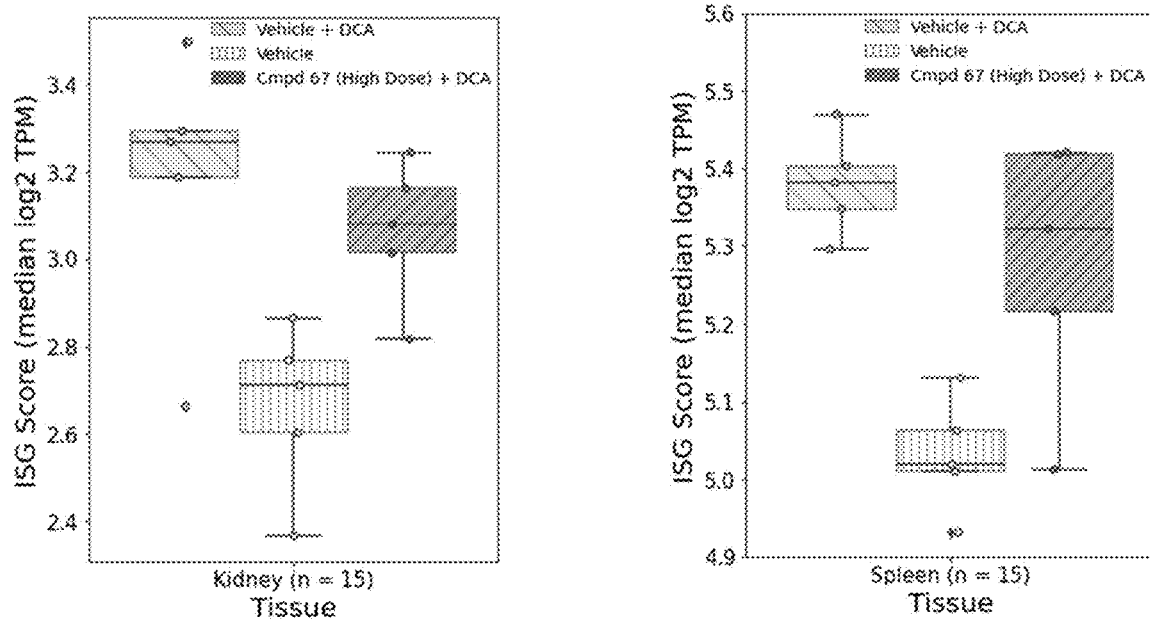

In BALB/c mice, dosing of Compound 2, (FIG. 2D), Compound 40 (FIG. 2E), Compound 67 at 30 mg/kg (FIG. 2F) and Compound 67 at 100 mg/kg (FIG. 2G) show a change in the ISG Score in the spleen and kidney.

Example 109—B6/JGpt-Trex1em1Cd1194/Gpt Mouse Model

Exemplary compounds were tested for the ability to alter the interferon-stimulated gene (ISG) response in a B6/JGpt-Trex1em1Cd1194/Gpt mouse model. Assay procedures and results are described below.

Part I—Procedure for Compound 2

Nine 8-10 week old B6/JGpt-Trex1em1Cd1194/Gpt mice were acclimated to the lab for at least 5 days. Compound 2 was prepared daily in a 20% PEG400 (pH 3.5) solution for p.o. administration. Compound 2 was administered for 5 days.

| Group | Strain | Compound 2 (mg/kg) | Received Vehicle? |
|---|---|---|---|
| Control | C57BL/6 | 0 | Yes |
| 1 | B6/JGpt-Trex1em1Cd1194/Gpt | 0 | Yes |
| 2 | B6/JGpt-Trex1em1Cd1194/Gpt | 100 | Yes |

Compound 2 was administered daily from Day 1 to Day 5. All mice were euthanized 1 hour after the last dose administration on Day 5. Heart and skin were harvested and snap frozen in liquid nitrogen, and plasma (EDTA) was collected for bioanalysis. Total RNA was isolated and ISG score for each sample was determined as in Part IIIa of Example 108.

Part II—Procedure for Compound 67

Fifteen 6-8 week old B6/JGpt-Trex1em1Cd1194/Gpt mice were acclimated to the lab for at least 5 days. Compound 67 was prepared daily in a 20% PEG400 (pH 3.5) solution for p.o. administration. Compound 2 was administered for 5 days.

| Group | Strain | Compound 67 mg/kg | Received Vehicle? |
|---|---|---|---|
| Control | C57BL/6 | 0 | Yes |
| 1 | B6/JGpt-Trex1em1Cd1194/Gpt | 0 | Yes |
| 2 | B6/JGpt-Trex1em1Cd1194/Gpt | 100 | Yes |

Compound 67 was administered daily from Day 1 to Day 5. All mice were euthanized 1 hour after the last dose administration on Day 5. Heart and skin were harvested and snap frozen in liquid nitrogen, and plasma (EDTA) was collected for bioanalysis. Total RNA was isolated and ISG score for each sample was determined as in Part IIIa of Example 108.

Part III—Results

Figure 8A:
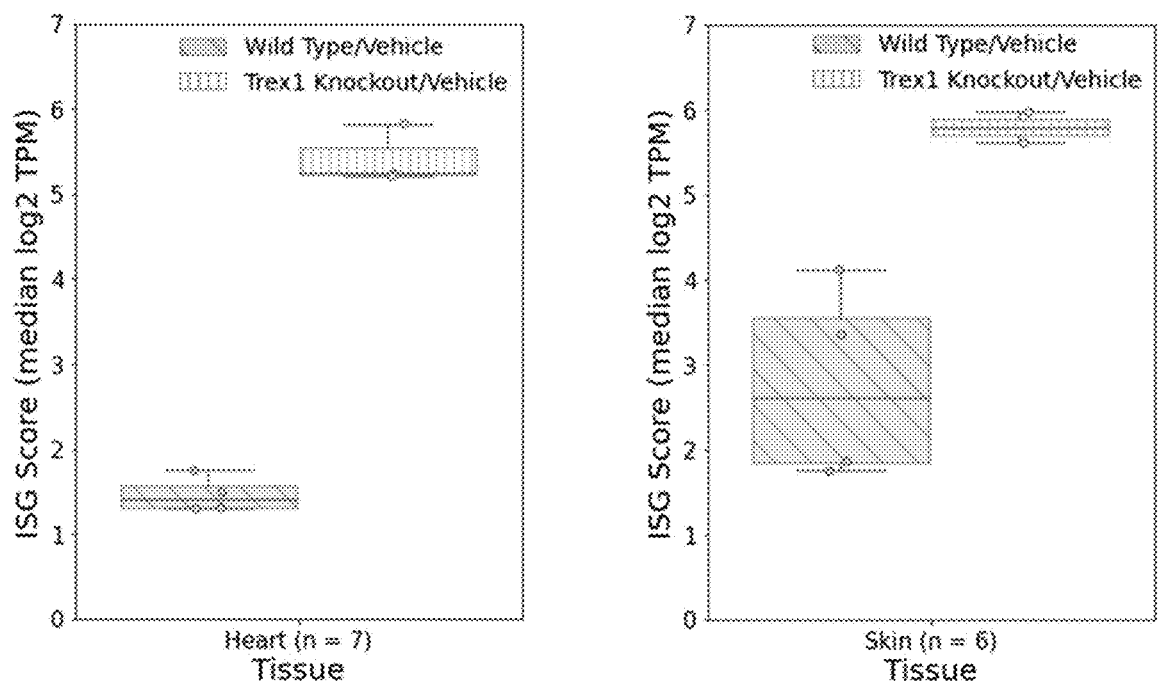
FIGS. 8A, 8B, and 8C are graphs which depict the effects of repeated administration of Compound 2 (FIG. 8A) and Compound 67 (FIG. 8B) on ISG Score in the heart and kidney of B6/JGpt-Trex1em1Cd1194/Gpt mice, in comparison to controls (FIG. 8B) in the in vivo B6/JGpt-Trex1em1Cd1194/Gpt Mouse Model, as described in Example 109.
Figure 8B:
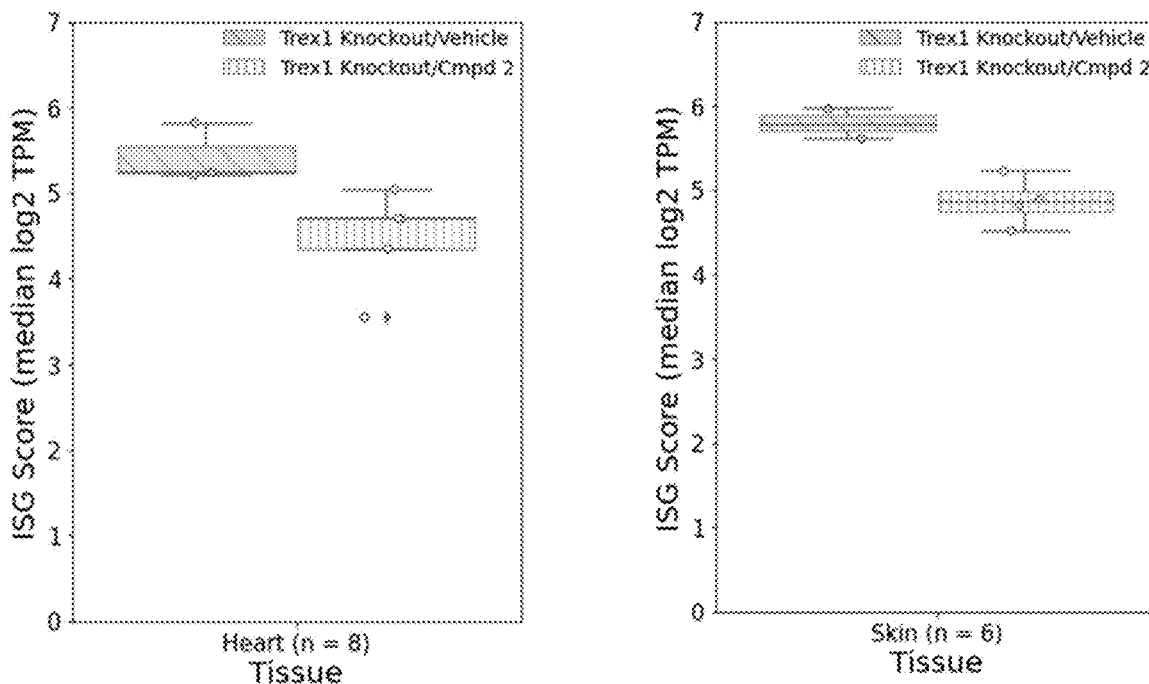
Figure 8C:
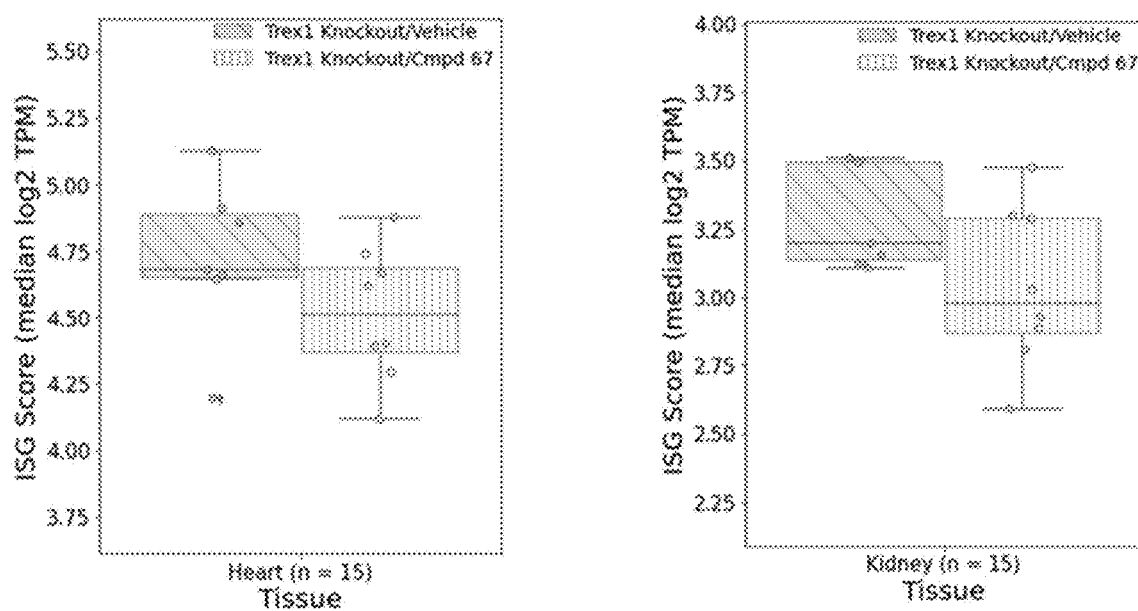

B6/JGpt-Trex1em1Cd1194/Gpt have elevated ISG scores in the heart and kidney relative to littermate controls (FIG. 8A). Repeated dosing of compound 2 lowers the ISG score of B6/JGpt-Trex1em1Cd1194/Gpt in the heart and skin (FIG. 8B). Repeated dosing of Compound 67 lowers the ISG score of B6/JGpt-Trex1em1Cd1194/Gpt in the heart and skin (FIG. 8C).

Example 110—Decitabine-Stimulated Human PBMC Assay

Part I—Procedure

EasySep buffer (32 mL, STEMCELL Technologies, cat. #20144) was used to dilute 8 mL of LRSC buffy coat (from fresh Leukopak) with gentle mixing. The diluted buffy coat (20 mL) was transferred into each of two SepMate 50 tubes, and the tubes were filled with 15 mL of Lyphoprep (STEMCELL, cat. #07851) density gradient. The SepMate tubes were then centrifuged at 1200 G for 10 minutes at room temperature with the brake on. The top layer of supernatant was collected in SepMate tubes by quickly pouring it into a new 50 mL conical tube. The PBMCs were washed with EasySep buffer×2 by centrifuging at 300 G for 5 minutes.

The cells were resuspended in 30 mL of EasySep and centrifuged at 100 G for 5 minutes with the brake off, and the platelets were removed. The cells were then resuspended in 6 mL of 1×RBC lysis buffer (Invitrogen) and incubated at 37° C. for 5 minutes. 25 mL of EasySep buffer was then mixed into the tube and centrifuged at 300 G for 5 minutes. The cells were resuspended in 10 mL of EasySep buffer and the cells were then counted with Cellometer (AO/PI). The PBMCs were resuspended in RPMI1640 (ThermoFisher)+ 10% FBS (HyClone)+μ/s at $3\times10^6$/mL. The PBMCs (100 μL, 300 k PBMCs) were then seeded in a 96-well flat bottom microplate (Corning) that had been precoated with 100 μL of anti-CD3 antibody (10 μg/mL in PBS, Biolegend) or PBS at 4° C., one day before the assay was commenced.

To each well the following solutions were added 1) 100 μL of cells (final cell number per well is $3\times10^5$ cell/well); 2) 25 μL of anti-CD28 antibody at 6× (5 μg/mL final concentration, Biolegend); 3) 25 μL of decitabine at 6× (10 μM final concentration); and 4) Compound in DMSO was dispensed directly into each well with a d300e digital dispenser (Tecan). The final concentration of DMSO for each well was normalized to 0.3%. The plate was incubated at 37° C. without any agitation for 5 days. Samples were collected 120 hours after incubation to determine IFN-β and IL-2 levels using a U-PLEX Human IFN-β Assay Sector (5PL) (MSD, cat. #K151VIK-2).

After 5 days, the plate was spun down at 100×G for 5 minutes. Supernatants (100 μL) were collected for interferon R (IFN-0) analysis using the MSD assay noted above, and any residual supernatant was stored at −80° C. Cell viability was checked to determine if cell death had an impact on the IFN-β levels detected.

Part II—Results

Figure 3A:
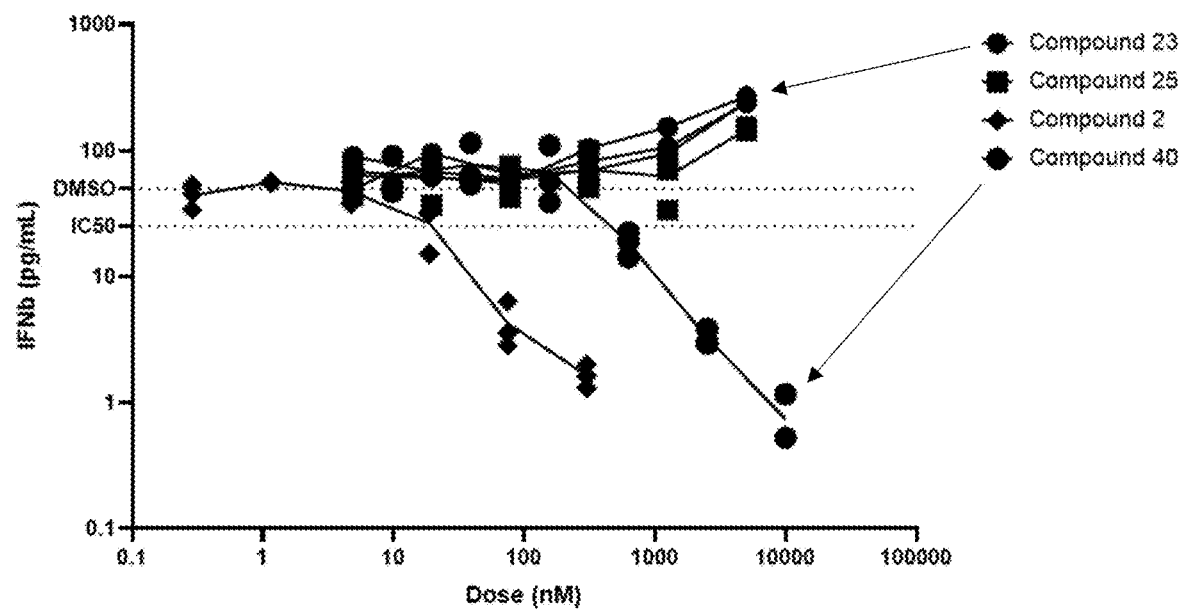
FIGS. 3A and 3B show two exemplary PBMC donors' responses to decitabine-induced interferon levels, upon administration of various compounds of the disclosure, as described in Example 110.
Figure 3B:
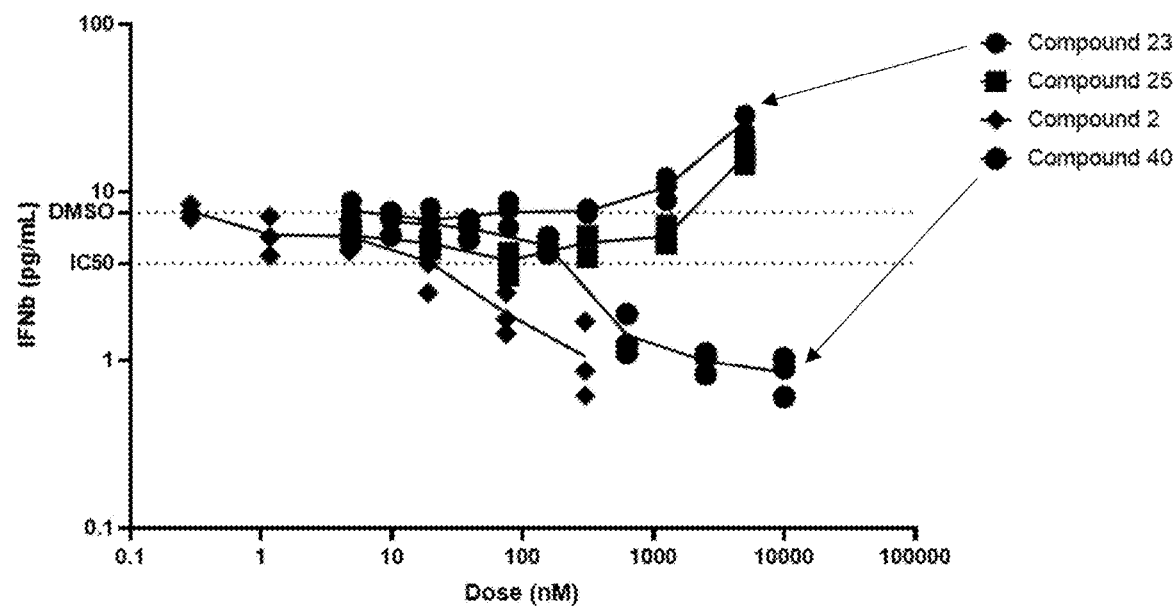

Compounds 2, 23, 25 and 40 were tested in this experiment. Results are shown in FIGS. 3A and 3B. Compound 40 showed some cell viability losses at higher concentrations, so reductions in IFN-β shown in the chart would be impacted by this cell viability loss. FIG. 3A represents a high responder (representative of PBMC's from 2 of the 5 donors tested) and FIG. 3B represents a moderate responder (representative of PBMC's from 2 of the 5 donors tested). One PBMC donor showed little to no effect from the excitation of the interferon response with decitabine (data not shown). Compounds 2 and 40 showed inhibition of IFN-β, although compound 40 also showed cell death at higher doses. These results provide support for the use of said compounds in the treatment of autoimmune disorders. Compounds 23 and 25 activated production of IFN-β, which shows activation of the immune system. These results provide support for the use of said compounds in the treatment of cancer.

Example 111—Analysis of UVB-Induced pTBK1 in HaCaT Cells

Part I—Procedure pTBK1 is an important signaling molecule in regulating inflammatory responses. HaCaT cells were plated in 6-well plates at a density of ~100 k/well in HaCaT media (DMEM, optimized 1× (Addex Bio)+ 1% pen strep (Gibco)+ 5% heat inactivated fetal bovine serum (Gibco)). The cells were then cultured at 37° C. overnight. The next day, the cells were treated with the test compounds. Each test compound was diluted and added to media aliquots to provide desired concentrations. To add the test compound+media mixture, an equivalent amount of media from each well was aspirated and then replenished with the media dosed with the test compound. The cells were then cultured for an additional 72 hours with compound treatment prior to UVB exposure.

The media was then aspirated from the wells, with the remaining cells at least 80% confluent in each well. One mL of PBS was then added to each well, and the plate was then placed under a UVB lamp. A UVB sensor was positioned near the plate to register the plate's exposure. The cells were exposed to the UVB light until they reached 0.1 mJ/cm2. Then the plate was covered and transferred to a sterile hood for processing.

The PBS was aspirated out of the wells, and the wells were replenished with 3 mL fresh culture media. The cells were then cultured for an additional 24 hours, and samples were processed 24 hours post-UVB exposure. To process the samples, the media was aspirated, the plate placed on ice, and the cells washed with cold PBS, which was then aspirated off. Another 1 mL of cold PBS was added to each well. The cells were then scraped in the cold PBS solution and transferred to conical tubes on ice. The cells were then spun at ≥1000 RCF at 4° C. for 5 minutes. The cells were then resuspended in 1 mL of cold PBS and transferred to a microcentrifuge tube. The cells were spun at ≥1000 RCF at 4° C. for another 5 minutes, and the PBS was aspirated off. The cell pellet was prepared for lysis.

A RIPA lysis buffer (#BP-115, Boston BioProducts) was added to a Halt protease and phosphate inhibitor cocktail (#78440, ThermoFisher), and the mixture was cooled on ice. About 30 μL of the lysis buffer mix was added to the cells. The samples were briefly vortexed and then incubated on ice for at least 15 minutes. The cells were then spun≥1000 RCF at 4° C. for 5 minutes and the supernatant was transferred to a clean tube. The protein concentration of the cell lysate was measured using Pierce™ Rapid Gold BCA Protein Assay Kit #AF3225 (ThermoFisher). ELISA analysis was run on select samples using one of the following kits:

a. FastScan™ Phospho-TBK1/NAK (Ser172) ELISA Kit #46948 (Cell Signaling Technologies)
b. FastScan™ Total TBK1/NAK ELISA Kit #15816 (Cell Signaling Technologies)
c. FastScan™ Phospho-STING (Ser366) ELISA Kit #82083 (Cell Signaling Technologies)
d. FastScan™ Phospho-IRF-3 (Ser396) ELISA Kit #50386 (Cell Signaling Technologies)
e. FastScan™ Total IRF-3 ELISA Kit #29771 (Cell Signaling Technologies)
f. Phospho-NAK/TBK1 (S172) ELISA Kit (ab279952) (Abcam)
g. Phospho-IRF3 (S386) ELISA Kit (ab279833) (Abcam)

Part II—Results

Figure 4A:
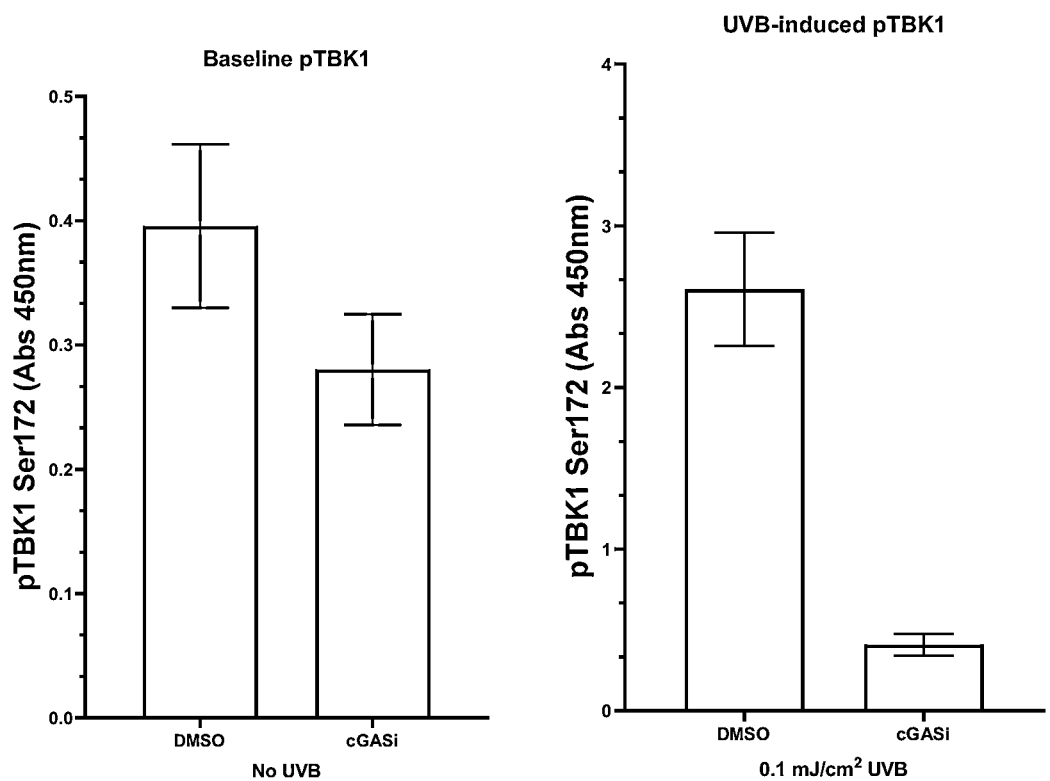
FIG. 4A shows baseline levels of pTBK1 with and without UVB exposure and with, or without, administration of the cGAS inhibitor G140 (InvivoGen), as described in Example 111.
Figure 4B:
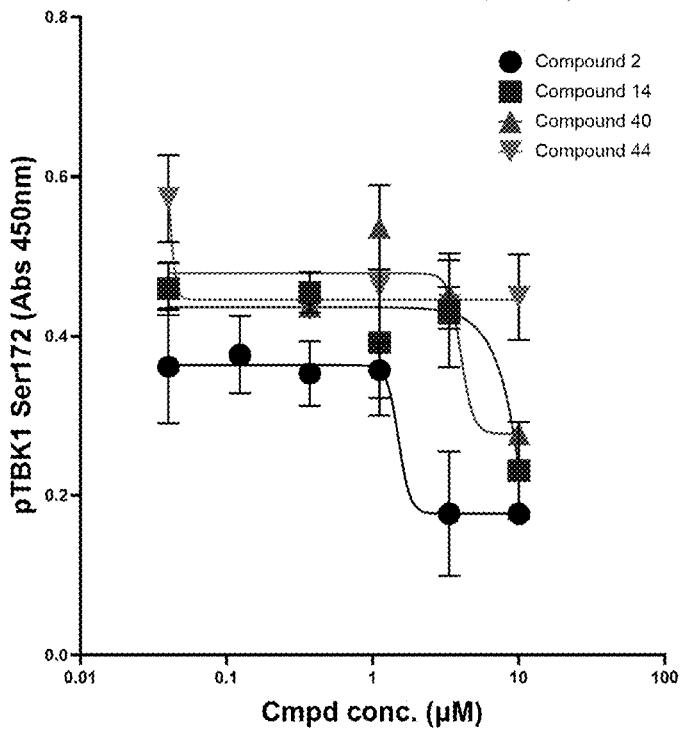
FIGS. 4B and 4C show that the level of pTBK1 varies in a dose-dependent fashion upon administration of varying concentrations of Compounds 2, 14, 40 and 44, alone or after UVB exposure, as described in Example 111
Figure 4B:
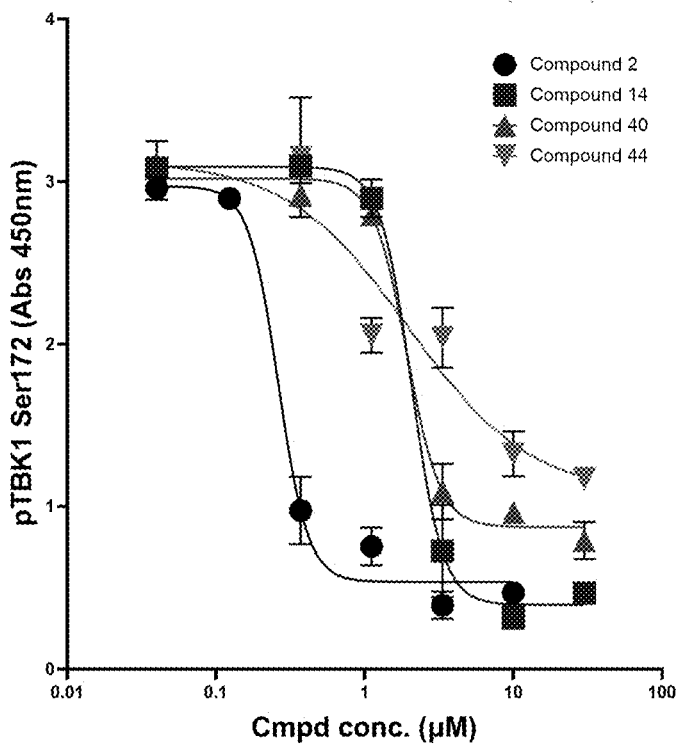
Figure 4C:
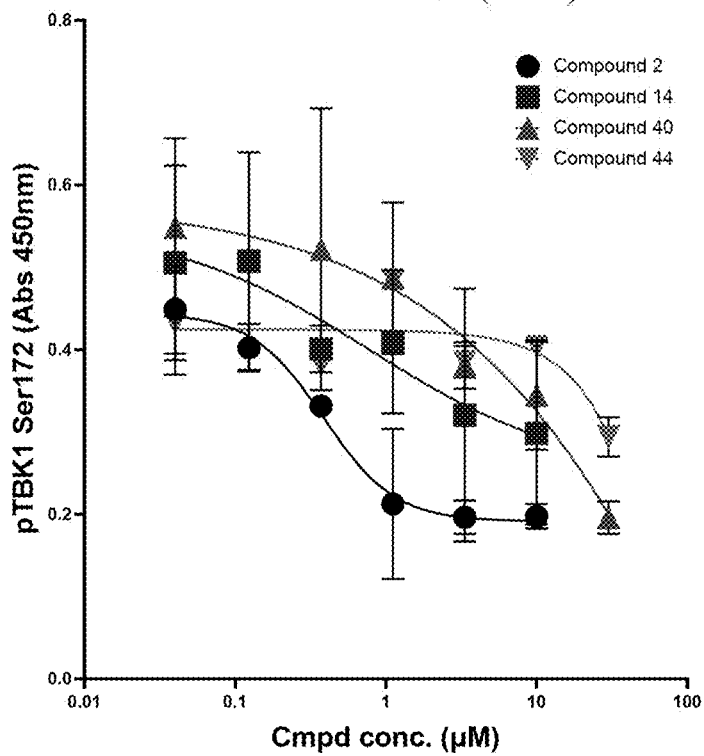
Figure 4C:
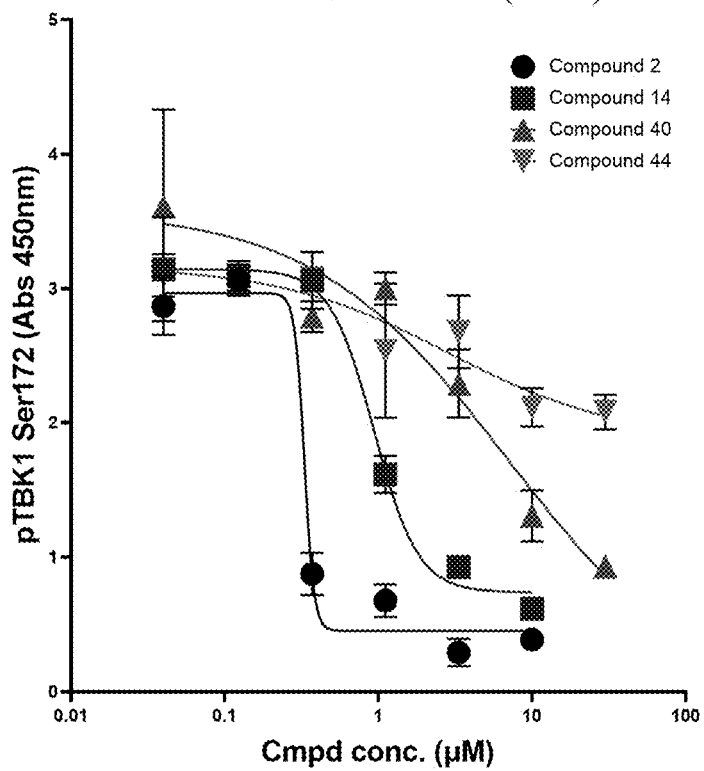

FIG. 4A shows baseline pTBK1 Ser172 assay readout with, or without, UVB exposure and with, or without, administration of the cGAS inhibitor G140 (InvivoGen). Compounds 2, 14, 40 and 44 were also tested in this assay, and the resultant dose response curves are shown in FIGS. 4B and 4C. Compound 14 showed cytotoxicity at concentrations at or above 30 μM. All compounds tested showed a dose-dependent modulation of both baseline and UVB-induced phosphorylated TANK-binding kinase 1 (pTBK1) after 72 hours of treatment. Reduction of pTBK1 levels after contact with compounds of the invention, seen both with UVB stimulation of TBK1 production and without the UVB stimulation, supports reduction in inflammation upon administration of the compounds of the invention and therefore, the treatment of autoimmune diseases as described herein.

$IC_{50}$ values were determined based on the response curves, and those data are presented in Table 8 below. In the table "A" represents values≤0.50 µM; "B" represents values from >0.50 µM to ≤2.0 µM; "C" represents values from >2.0 µM to ≤5.0 µM; "D" represents values from >5.0 µM to ≤10 µM; and "E" represents values>10 µM.

TABLE 8

| Compound No. | IC$_{50}$ (µM) |
| --- | --- |
| 2 | A |
| 14 | B |
| 67 | C |
| 40 | C |
| 85 | D |
| 72 | D |
| 12 | E |
| 13 | E |
| 15 | E |
| 16 | E |
| 19 | E |
| 21 | E |
| 51 | E |
| 61 | E |
| 88 | E |
| 44 | E |

Example 112—Producing THP1-Dual™ TREX1 KO Xenografts with Decitabine-Induced IFN The ability to produce THP1-Dual™ KO-TREX1 xenografts in mice that displayed decitabine-dependent IFN induction was tested. Assay procedures and results are described below.

Part I—Procedure for Producing THP1-Dual™ TREX1 KO Xenografts with Decitabine-Induced IFN CB-17 SCID female mice were inoculated subcutaneously with 10 million THP1-Dual™ KO-TREX1 cells in 200 µl PBS with Matrigel (1:1). Mice were randomized when tumor volume reached 350-400 mm$^3$ and grouped at N=3 per sampling timepoint. Mice bearing THP1-Dual™ KO-TREX1 xenograft tumors were then administered vehicle or decitabine (DAC) at 5 mg/kg IP, once daily, starting on day 1, for 4 days. Decitabine was formulated in sterile PBS, pH 7.4. Tumors were harvested daily for 4 days starting on day 2, ground in PBS at 50 Hz for 5 min, kept on ice for 30 min while being vortexed every 5 min. Tumor lysates were then centrifuged, and Pierce™ BCA Protein Assay Kit was used to measure protein concentration. Equal amounts of proteins were added to 96-well black plates, and luciferase signal was measured using the QUANTI-Luc™ detection medium according to manufacturer's instructions. Luminescence was measured using the EnVision® 2105 Multimode Plate Reader.

Part II—Results

Figure 5:
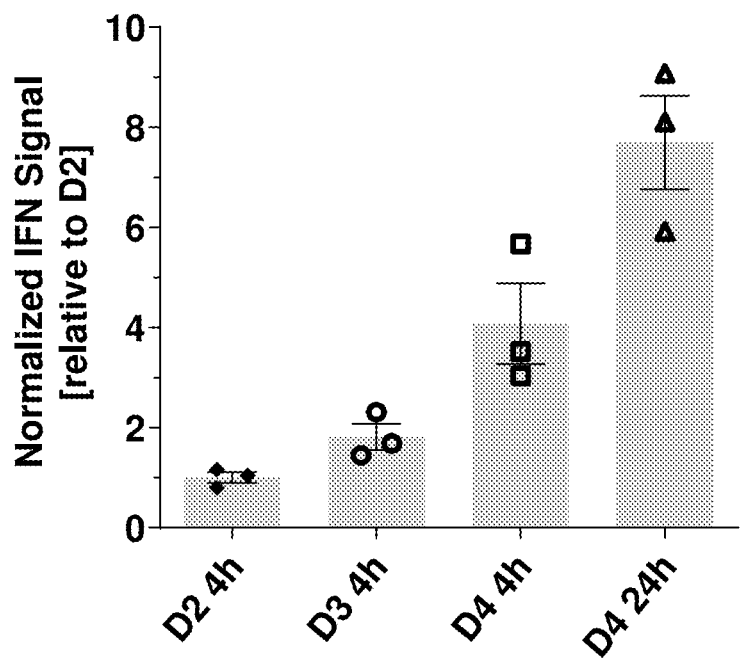
FIG. 5 is a graph depicting interferon levels over time in THP1-Dual™ KO-TREX1 xenografts from mice treated with vehicle or decitabine (DAC) at 5 mg/kg IP, once daily, for four days, as described in Example 112.

Experimental results are depicted in FIG. 5. Data was normalized relative to interferon signal on D2. In FIG. 5, "D2 4 h" depicts interferon data from day 2, with tumor harvested 4 hours after decitabine dosing; "D3 4 h" depicts interferon data from day 3, with tumor harvested 4 hours after decitabine dosing; "D4 4 h" depicts interferon data from day 4, with tumor harvested 4 hours after decitabine dosing; and "D4 24 h" depicts interferon data from day 5, with tumor harvested 24 hours after the final decitabine dosing on day 4.

Decitabine administration to mice leads to an increase in interferon signal in THP1 tumors over time.

Example 113—Assay for Altering IFN Production in THP1 TREX1 KO Xenografts

Exemplary compounds 2, 25 and 40 were tested for their ability to alter IFN levels in THP1-Dual™ KO-TREX1 xenografts in mice. Assay procedures are described below.

Part I—Procedure for Altering IFN Production in THP1 TREX1 KO Xenografts

CB-17 SCID female mice were inoculated subcutaneously with 10 million THP1-Dual™ KO-TREX1 cells in 200 µl PBS with Matrigel (1:1) and grouped when tumor volume reached 350-400 mm$^3$. Mice bearing THP1-Dual™ KO-TREX1 xenograft tumors were then separated into 5 groups. Three groups were administered: (1) decitabine (DAC) at 5 mg/kg IP, once daily, for 4 days, and (2) test compound at 10, 30, or 100 mg/kg, PO, once daily, for 4 days. One group was administered decitabine (DAC) at 5 mg/kg IP, once daily, for 4 days, and the test compound vehicle control. The final group was administered the vehicle control from both the test compound and the vehicle control from decitabine. Decitabine is formulated in sterile PBS, pH 7.4, and Compound 2, 25, and 40 were formulated in 20% PEG400 in PBS.

Tumors were harvested 24 h post-last dose administered on day 4, ground in PBS at 50 Hz for 5 min, and kept on ice for 30 min while being vortexed every 5 min. Tumors were then centrifuged, and Pierce™ BCA Protein Assay Kit was used to measure protein concentration. Equal amounts of proteins were added to 96-well black plates, and luciferase signal was measured using the QUANTI-Luc™ detection medium according to manufacturer's instructions. Luminescence was measured using the EnVision® 2105 Multimode Plate Reader.

Part II—Results

Figure 6:
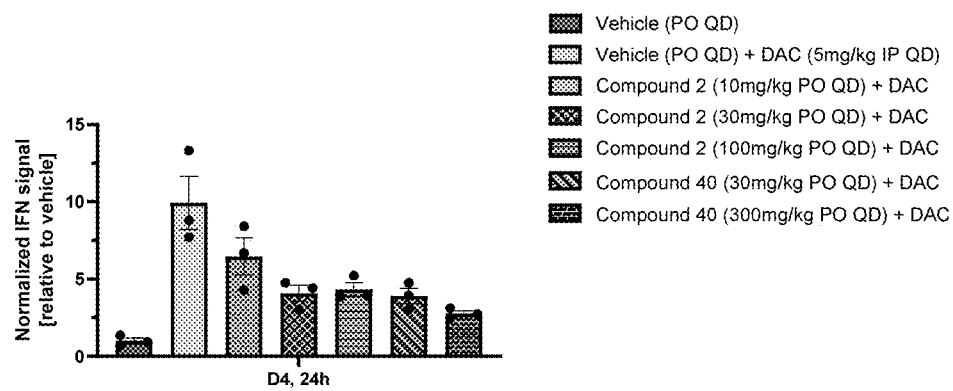
FIG. 6 is a graph depicting normalized interferon levels in THP1-Dual™ KG-TREX1 xenografts from mice treated once daily, for four days with decitabine (DAC) and varying doses of Compound 2, as described in Example 113. The graph depicts data obtained on day 5, with tumor harvested 24 hours after the final decitabine dosing on day 4.

Experimental results are depicted in FIG. 6. Data was normalized relative to interferon signal from vehicle group. In FIG. 6, "D4 24 h" depicts interferon data from day 5, with tumor harvested 24 hours after the final decitabine and test compound dosing on day 4.

Compounds 2 and 40 showed potent inhibition of DAC-induced IFN signal in THP1 tumors.

Example 114—THP1 TREX1 KO Inhibition Assay—Combination Dosing

Exemplary compounds were tested to determine the effect of combined dosing of two compounds on the type 1 interferon response in THP1 Dual TREX1 KO cells treated with 5-aza-2'-deoxycytidine. Assay procedures and results are described below.

Part I—Procedure

THP1 Dual TREX1 KO cells were purchased from InvivoGen. The THP1-Dual™ KO-TREX1 cells were cultured in RPMI 1640, 10% heat-inactivated fetal bovine serum, 25 mM HEPES, 10 µg/mL blasticidin, and 100 µg/mL Zeocin. THP1-Dual™ KO-TREX1 cells were treated with a dose titration of test compound in the presence of 1 µM 5-aza-2'-deoxycytidine (Sigma, cat #189825). Type 1 Interferon and cell viability were assessed after five days of treatment.

Stock solution of test compounds stampidine and Compound 2 were prepared in DMSO followed by a three-fold dilution in DMSO. The plate was prepared with a matrix of test compound concentrations, with stampidine on the y-axis (final concentrations 3 µM to 0.0003 µM) and Compound 2 on the x-axis (final concentrations 0.3 µM to 0.00003 µM).

Additional 50× dilution was prepared in cell culture media for each dilution. 10 µL of diluted test compound was then added to a 384-well plate.

THP1-Dual™ KO-TREX1 cells were treated with 1 µM 5-aza-2'-deoxycytidine. THP1-Dual™ KO-TREX1 cells (50 µL) were added to each well of the 384-well plate containing test compound titration at 10,000 cells/well. Cells were incubated at 37° C., 5% $CO_2$ in a humidified incubator for five days. On day five, 20 µL of cell supernatant was transferred to a 384-well, white-walled plate, followed by addition to each well of 50 µL of QUANTI-LUC solution containing stabilizer. Luminescence was detected on a plate reader according to manufacturer's instructions. Percent inhibition of interferon was calculated using the following analysis: (Average DMSO-Sample)/(Average DMSO-Average 30 µM stampidine)*100.

The remaining cells were assessed for cell viability by adding 30 µl of CellTiter-Glo (Promega, G9683) solution to each well, and placed on a shaker for 10 minutes at room temperature. Luminescence was detected on a plate reader, according to manufacturer's instructions. Percent inhibition of cell viability using CellTiter-Glo was calculated using the following analysis: (Average DMSO−Sample)/(Average DMSO−Average 20 µM viability control reagent)*100.

Part II—Results

Figure 7A:
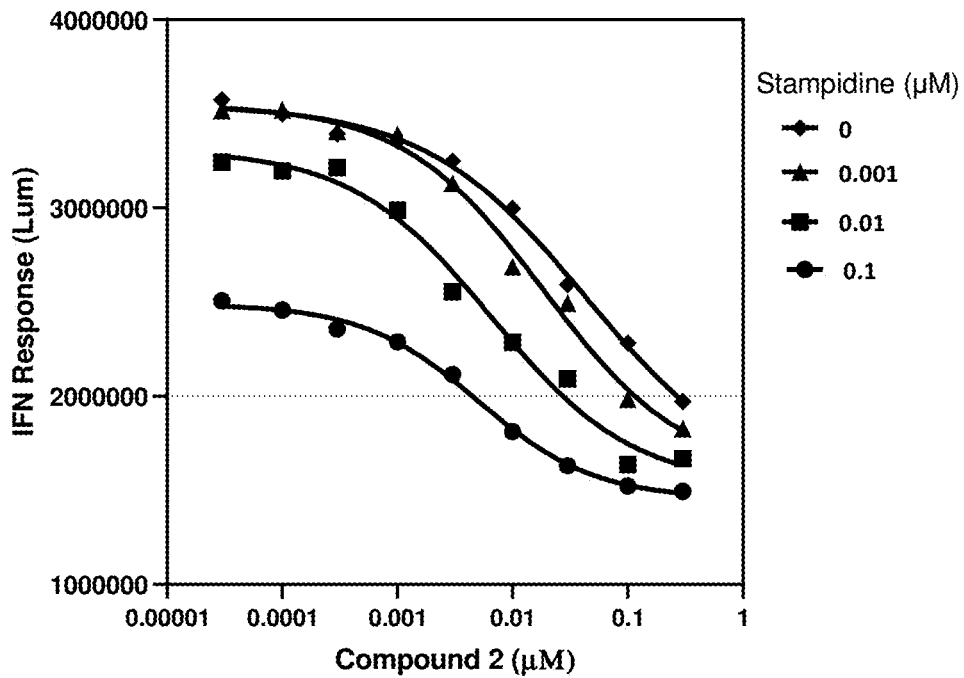
FIGS. 7A and 7B are graphs depicting potentiation modeling curves for potentiation of Compound 2 at four concentrations of stampidine (FIG. 7A) and for potentiation of stampidine at four concentrations of Compound 2 (FIG. 7B), as described in Example 114.
Figure 7B:
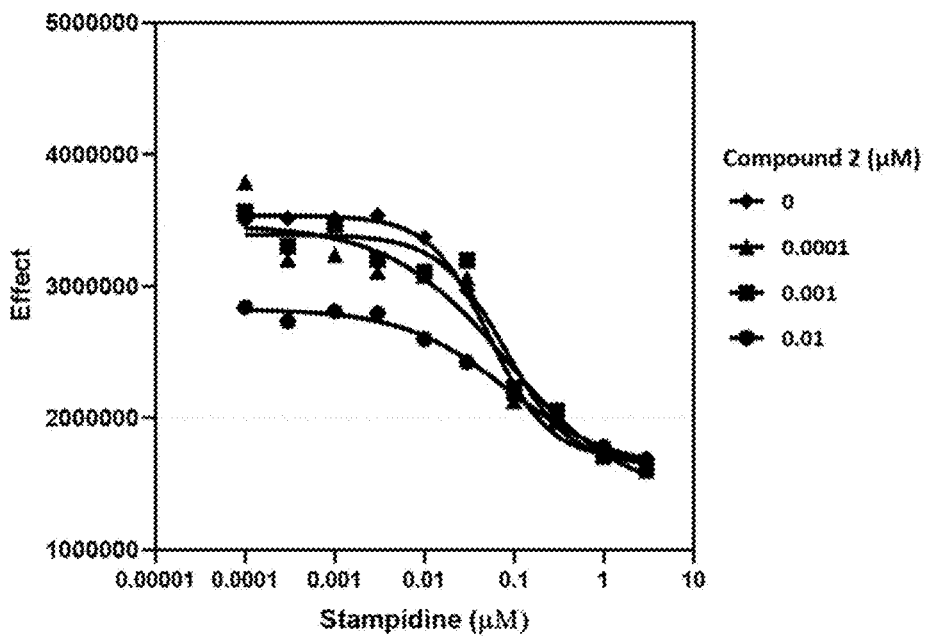

Combination analysis was performed using the Bivariate Response to Additive Interacting Doses (BRAID) according to Twarog, N. R., et al. *Scientific Reports* 6:25523 (DOI: 10.1038/srep25523). The best BRAID fit was determined to be k 2.00 (0.583-3.64), where k>0 denotes synergy, k=0 denotes additivity, and k<0 denotes antagonism. Potentiation modeling curves are provided for potentiation of Compound 2 at four concentrations of stampidine (FIG. 7A) and for potentiation of stampidine at four concentrations of Compound 2 (FIG. 7B). Additionally, $EC_{50}$ shifts were calculated and are presented in the following tables:

| Stampidine (µM) | $EC_{50}$ of Compound 2 (µM) |
| --- | --- |
| 0 | 0.040 |
| 0.001 | 0.0335 |
| 0.01 | 0.0203 |
| 0.1 | 0.00015 |

| Compound 2 (µM) | $EC_{50}$ of Stampidine (µM) |
| --- | --- |
| 0 | 0.115 |
| 0.0001 | 0.103 |
| 0.001 | 0.080 |
| 0.01 | 0.029 |

Example 115—Assay for Altering IFN Production in THP1-Dual™ KO-TREX1 Mouse Xenografts Exemplary Compound 67 was tested for its ability to alter IFN levels in THP1-Dual™ KO-TREX1 xenografts in mice. Assay procedures are described below.

Part I—Procedure for Altering IFN Production in THP1-Dual™ KO-TREX1 Xenografts

CB-17 SCID female mice were inoculated subcutaneously with 10 million THP1-Dual™ KO-TREX1 cells in 200 µl PBS with Matrigel (1:1) and grouped at N=5 per treatment per sampling timepoint when tumor volume reached an average of 340 mm³. Six groups were co-administered: (1) decitabine (DAC) at 5 mg/kg SC, once daily, for 5 days, and (2) test compound 67 at one of six doses (0.3 mg/kg PO, 1 mg/kg PO, 3 mg/kg PO, 10 mg/kg PO, 30 mg/kg PO, 100 mg/kg PO) once daily, for 5 days. Two additional groups were administered (1) decitabine and test compound vehicle control SC+PO, once daily, for 5 days, and (2) decitabine at 5 mg/kg SC, once daily, for 5 days. Decitabine was formulated in sterile PBS, pH 7.4. Test compound was formulated in 20% HPBCD in 50 mM citrate buffer (pH 4.5).

Tumors were harvested 4 h post-last dose administered on day 5, grinded in PBS at 50 Hz for 5 min, kept on ice for 30 min while being vortexed every 5 min. Tumors were then centrifuged, and Pierce™ BCA Protein Assay Kit was used to measure protein concentration. Equal amounts of proteins were added to 96-well black plates, and luciferase signal was measured using the QUANTI-Luc™ detection medium according to manufacturer's instructions. Luminescence was measured using the EnVision® 2105 Multimode Plate Reader.

Part II—Results

Figure 9:
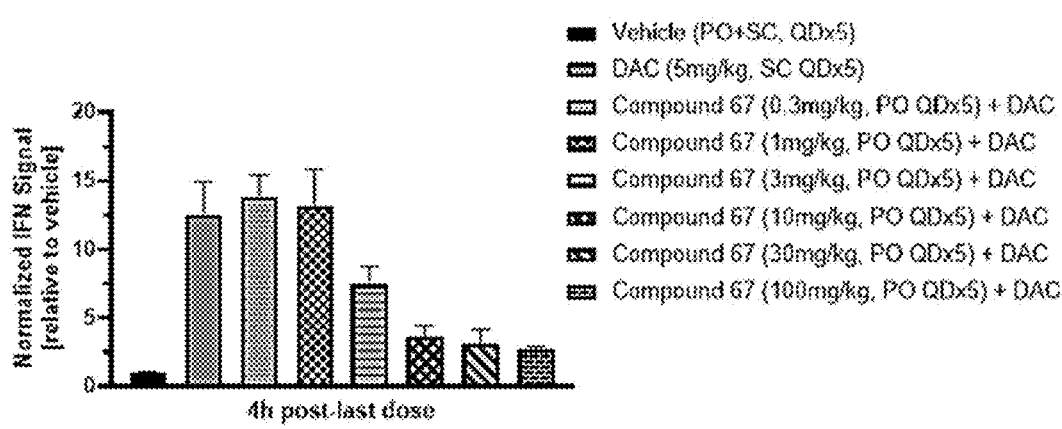
FIG. 9 is a graph depicting normalized interferon levels in THP1-Dual™ KG-TREX1 xenografts from mice treated once daily, for four days with decitabine (DAC) and varying doses of Compound 67, as described in Example 115. The graph depicts data obtained on day 5, with tumor harvested 24 hours after the final decitabine dosing on day 4.

Experimental results are depicted in FIG. 9. Data was normalized relative to interferon signal from vehicle group. In FIG. 9, IFN signal was measured in tumors harvested from mice 4 hours after the final decitabine and test compound dosing on day 5.

Compound 67 showed a dose-response inhibition of DAC-induced IFN signal in THP1 tumors.

Example 116—Biochemical Assay for Inhibiting Human DNA Polymerase γ

Exemplary compounds were tested for ability to inhibit human DNA polymerase γ using a homogeneous time-resolved fluorescence (HTRF) assay. Off-target inhibition of DNA polymerase γ by NRTIs can result in undesired mitochondrial toxicity. Assay procedures and results are described below.

Part I—Procedure for Homogeneous Time-Resolved Fluorescence Human DNA Polymerase γ Assay The human DNA polymerase γ homogeneous time-resolved fluorescence (HTRF) assay was performed with recombinant human DNA polymerase γ protein (Gentaur) in a 384-well format. Test compound was serially diluted in water and further diluted in the assay buffer (28 mM Tris-HCl, 14 mM NaCl, 0.56 mM $MgCl_2$, 0.011% Triton X-100, 0.11 mg/ml BSA, 1.1 mM DTT, pH 8.1). The serially diluted compound was mixed with polymerase γ, 10 nM of pre-annealed template/biotin-primer pair (synthesized at Geneway Biotechnology), 100 nM of Fluorescein-12-dCTP fluorescent probe (PerkinElmer), and 10 µM dGTP/dATP/dTTP (ThermoFisher Scientific) in the assay buffer. The template/biotin-primer sequences were as follows:

```
5' to 3'
                                    (SEQ ID NO: 3)
TCCCAGACTCCCTAGAGATCAATCAAC

5' to 3' Biotin-
                                    (SEQ ID NO: 4)
AGGGTCTGAGGGAT
```

After incubating at room temperature for 30 minutes, the detection reagent (5 mM EDTA with streptavidin-terbium cryptate, Cisbio Bioassay) in the PPI buffer (Cisbio Bioassay) was added, and the mixture was incubated at room temperature for 60 minutes. At the end of the incubation, fluorescence was read at ex/em=337/485 nm and ex/em=337/520 nm on an Envision 2104 plate reader (PerkinElmer). The fluorescence ratio at 520/485 nm was used for the calculation. Percent inhibition was calculated with the DMSO sample as 0% inhibition and no enzyme as 100% inhibition. The $IC_{50}$ was calculated by fitting the compound dose inhibition curve with a 4-parameter non-linear regression equation.

Exemplary compounds were tested using the above procedure. Results are shown below. In the table "A" represents values≤50.0 µM; "B" represents values from >50.0 µM to ≤100.0 µM; "C" represents values from >100.0 µM to ≤200.0 µM; "D" represents values from >200.0 µM to ≤300.0 µM; and "E" represents values>300 µM.

TABLE 59B

| Compound No. | $IC_{50}$ (µM) |
| --- | --- |
| 2-TP | A |
| 14-TP | B |
| 35-TP | D |
| 40-TP | D |
| 43-TP | D |
| 44-TP | E |
| 67-TP | D |

Example 117—Biochemical Telomerase Assay

Exemplary compounds were tested for ability to inhibit human telomerase using a PCR ELISA assay. Off-target inhibition of human telomerase can result in undesired cellular toxicity, e.g., triggering replicative senescence and/or apoptotic cell death. Assay procedures and results are described below.

Part I—Procedure for Human Telomerase PCR ELISA Assay

The human telomerase assay was performed with telomerase in the MCF-7 cell lysate using the Telo TAGGG Telomerase PCR ELISA$^{plus}$ kit (Roche) per manufacturer's instruction. MCF-7 cells were lysed in the lysis buffer and the supernatant was used for the assay. Test compound was serially diluted in water and mixed with 0.2 µg of MCF-7 lysate in PCR tubes and incubate at room temperature for 15 minutes. The PCR reaction mixture was then added, the tubes were transferred to a thermal cycler (Analytikjena) and the telomerase elongation reaction was performed for 30 minutes followed by 30 PCR cycles with the following protocol:

| Step | Time | Temperature | Cycles |
| --- | --- | --- | --- |
| Primer elongation | 30 min | 25° C. | 1 |
| Telomerase inactivation | 5 min | 94° C. | 1 |
| Amplification | | | |
| Denaturation | 30 sec | 94° C. | 30 |
| Annealing | 30 sec | 50° C. | |
| Polymerization | 90 sec | 72° C. | |
| Final polymerization | 10 min | 72° C. | 1 |
| Hold | | 4° C. | 1 |

Mix 2.5 µL of PCR amplification product from above to 10 µl of denature reagent to each well of a PCR plate and incubate at room temperature for 10 minutes. Add in 100 µl of hybridization buffer T and mix well. Transfer 100 µl per well of the reaction mixture to the precoated MP module, incubate at 37° C. for 2 hours. Remove the hybridization solution, wash three times with the wash buffer, add anti-DIG-HRP solution, incubate at room temperature for 30 minutes. Remove the anti-DIG-HRP solution and wash five times with the wash buffer. Add TMB substrate and incubate at room temperature for 10 minutes. Measure the absorbance at 450 nm using Envision (PerkinElmer).

Exemplary compounds were tested using the above procedure. Results are shown in Table 9 below. In the table "A" represents values≤1.0 µM; "B" represents values from >1.0 µM to ≤25.0 µM; "C" represents values from >25.0 µM to ≤50.0 µM; "D" represents values from >50.0 µM to ≤100.0 µM; and "E" represents values>100.0 µM.

TABLE 9

| Compound No. | $IC_{50}$ (µM) |
| --- | --- |
| 2-TP | A |
| 14-TP | A |
| 35-TP | E |
| 40-TP | E |
| 43-TP | B |
| 44-TP | C |
| 67-TP | E |

Example 118—Mitochondria Toxicity Assay with PC3 Cells

Exemplary compounds were tested for inhibition of expression of mitochondria DNA encoded proteins COX-1 (cyclooxygenase-1). SDH-A (succinate dehydrogenase-A) is a control mitochondria protein encoded by nuclear DNA. Reduction in COX-1 expression indicates off target inhibition of mitochondria DNA synthesis which leads to mitochondrial toxicity. Assay procedures and results are described below.

Part I—Procedure

PC3 cells were purchased from ATCC and cultured in F-12 Kaighn's modified medium (Hyclone), 10% heat-inactivated fetal bovine serum (Invitrogen), 1% Penicillin-Streptomycin (Invitrogen). PC3 cells were treated with a dose titration of a test compound on 96 well plates for 5 days at 37° C., 5% $CO_2$ in a humidified incubator. The treatment plates are duplicated, one for in-cell ELISA for mitochondria proteins and one for cytotoxicity.

In-cell ELISA was performed to measure mitochondrial proteins using MitoBiogenesis In-Cell ELISA kit (Abcam) per manufacturer's instruction. The medium was aspirated from the compound treated cells, 100 µl per well of 4% paraformaldehyde (Solarbio) was added and cells were incubated at room temperature for 20 minutes. The cells were washed three times with PBS. 100 µl of 0.5% acetic acid was added per cell, and the cells were incubate at room temperature for 5 minutes. Cells were washed once with PBS. 100 µl per well of Permeabilization Buffer was added, and the cells incubate at room temperature for 30 minutes. The permeabilization buffer was removed and 200 µl per well 2× Blocking Buffer was added and the cells were incubated at room temperature for 2 hours. After removing the Blocking Buffer 100 µl per well of primary antibody to SDH-A or COX-1 was added, and the cells were incubated at 4° C. overnight. The primary antibody solution was removed and cells were washed 3 times with the Wash Buffer. 100 µl per well of AP- and HRP-labelled secondary antibodies was added, and the cells were incubated at room temperature for 1 hour. The cells were then washed 4 times with the Wash Buffer. For SDH-A detection, 100 µl per well AP Development Solution was added, and the cells were incubated at room temperature for 10 minutes. Cells were then read on CLARTO star$^{plus}$ microplate reader (BMG Labtech) for kinetic readings at 405 nm for 5 minutes. For COX-1 detection, AP development Solution was removed, and 100 μl per well HRP Development Solution was added, and the cells were incubated at room temperature for 2 minutes. The cells were then read on CLARTO star$^{plus}$ microplate reader (BMG Labtech) for kinetic readings at 600 nm for 15 minutes.

For the cytotoxicity assay, the medium from the cell viability plate was removed, 50 μL per well of Cell Titer Glo (Promega, G9683) was added. Then the cells incubated for 30 minutes at room temperature. Luminescence was read by Envision (PerkinElmer 2105).

Results for compounds tested using the above procedure appear in Table 10 below. In the table "A" represents values<1.0 μM; "B" represents values from >1.0 μM to ≤10.0 μM; "C" represents values from >10.0 μM to ≤50.0 μM; "D" represents values from >50.0 μM to ≤100.0 μM; and "E" represents values>100.0 μM.

TABLE 10

| Compound No. | IC$_{50}$ COX-1 (μM) | IC$_{50}$ CTG (μM) | IC$_{50}$ SDH-A (μM) |
|---|---|---|---|
| 2 | A | E | E |
| 4 | E | E | E |
| 5 | C | E | E |
| 7 | E | E | E |
| 8 | B | B | B |
| 9 | E | E | E |
| 10 | B | C | B |
| 11 | E | E | E |
| 12 | E | E | E |
| 13 | E | E | E |
| 14 | E | E | E |
| 15 | E | E | E |
| 16 | E | E | E |
| 19 | C | D | C |
| 21 | E | E | E |
| 22 | E | E | E |
| 23 | C | C | D |
| 24 | E | E | E |
| 25 | D | E | E |
| 26 | D | E | E |
| 27 | E | E | E |
| 30 | E | E | E |
| 31 | C | C | C |
| 35 | A | A | E |
| 37 | B | C | B |
| 38 | E | E | E |
| 39 | E | E | E |
| 41 | B | C | B |
| 42 | C | D | C |
| 43 | B | E | B |
| 44 | E | E | E |
| 45 | A | B | A |
| 46 | B | B | B |
| 47 | B | B | B |
| 48 | B | C | B |
| 49 | A | A | A |
| 50 | A | A | A |
| 51 | C | E | E |
| 52 | E | E | E |
| 53 | E | E | E |
| 54 | E | E | E |
| 55 | E | E | E |
| 56 | E | E | E |
| 57 | E | E | E |
| 58 | C | E | E |
| 59 | E | E | E |
| 60 | E | E | E |
| 61 | E | E | E |
| 62 | C | C | C |
| 63 | C | C | C |
| 64 | A | A | A |
| 65 | E | E | E |
| 66 | E | E | E |
| 67 | E | E | E |
| 68 | C | C | C |
| 69 | B | B | B |
| 70 | C | C | C |
| 71 | E | E | E |
| 72 | D | D | E |
| 73 | E | E | E |
| 74 | E | E | E |
| 75 | E | E | E |
| 76 | B | E | B |
| 77 | E | E | E |
| 78 | E | E | E |
| 79 | E | E | E |
| 80 | D | E | E |
| 81 | E | E | E |
| 82 | E | E | E |
| 83 | C | C | C |
| 84 | C | C | D |
| 85 | E | E | E |
| 86 | E | E | E |
| 88 | C | E | E |
| 92 | A | B | B |
| 94 | E | E | E |
| 95 | E | E | E |
| 106 | A | A | A |
| 107 | E | E | E |
| 108 | B | B | C |
| 109 | B | B | B |
| 110 | E | E | E |
| 111 | A | A | A |
| 112 | A | E | A |
| 113 | A | A | A |
| 114 | E | E | E |
| 115 | B | B | B |
| 116 | E | E | E |
| 119 | B | B | B |
| 120 | E | E | E |
| 121 | E | E | E |
| 122 | E | E | E |
| 123 | E | E | E |
| 129 | E | E | E |
| 131 | E | E | E |
| 132 | E | E | E |
| 135 | B | C | C |
| 137 | E | E | E |
| 138 | E | E | E |
| 139 | E | E | E |
| 161 | B | B | B |
| 162 | E | E | E |
| 163 | E | E | E |
| 164 | E | E | E |
| 165 | A | E | A |
| 166 | E | E | E |
| 172 | E | E | E |
| 173 | D | E | E |
| 175 | E | E | E |
| 40 | E | E | E |
| 176 | E | E | E |
| 177 | E | E | E |
| 178 | C | E | E |
| 179 | E | E | E |
| 180 | E | E | E |

Example 119—Mitochondria DNA Assay with PC3 Cells

Exemplary compounds were tested for their effect on levels of 7S mitochondria DNA, and the DNA of housekeeping genes 18S and GAPDH. Reduction of 7S mitochondria DNA indicates off-target inhibition of mitochondrial DNA synthesis, which leads to mitochondrial toxicity. Assay procedures and results are described below.

Part I—Procedure

PC3 cells were purchased from ATCC and cultured in F-12 Kaighn's modified medium (Hyclone), 10% heat-inactivated fetal bovine serum (Gibco), 1% Penicillin-Streptomycin (Invitrogen). PC3 cells were treated with a dose titration of a test compound on 6 well plates for 5 days at 37° C., 5% $CO_2$ in a humidified incubator.

Cells were harvested and mitochondria DNA extraction was performed using DNeasy Blood & Tissue Kit (Qiagen) according to the manufacture's instruction.

Mitochondria 7S and housekeeping genes 18S and GAPDH DNA was quantified by multiplex qPCR with the PowerUp™ SYBR™ Green system (Applied Biosystems). Prepare reaction mix consisting of 5 µl of 2× PowerUp™ SYBR™ Green Master Mix, 1 µl of 5 µM Primers for 7S, 18S, or GAPDH, 4 µl of DNA template from DNA extraction above. The primer sequences are below:

```
Forward primer        GTGGCTTTGGAGTTGCAGTT
for 7S DNA            (SEQ ID NO: 5)

Reverse primer        CAGCCACCATGAATATTGTAC
for 7S DNA            (SEQ ID NO: 6)

Forward primer        GTGGCTTTGGAGTTGCAGTT
for mtDNA             (SEQ ID NO: 7)

Reverse primer        GAAGCAGATTTGGGTACCAC
for mtDNA             (SEQ ID NO: 8)

Forward primer        CGGGTGACGGGGAATCAG
for 18S               (SEQ ID NO: 9)

Reverse primer        CACTACCTCCCCGGGTC
for 18S               (SEQ ID NO: 10)

Forward primer        AGATCCCTCCAAAATCAAGTGG
for GAPDH             (SEQ ID NO: 11)

Reverse primer        GGCAGAGATGATGACCCTTTT
for GAPDH             (SEQ ID NO: 12)
``` qPCR was performed on QuantStudio™ 7 Flex RealTime qPCR system (Applied Biosystems) as set forth below:

a. 50° C. for 2 minutes, then
b. 95° C. for 2 minutes, then
c. 95° C. for 15 seconds, then
d. 60° C. for 60 seconds, where then steps (c) and (d) were repeated 60 times.

Threshold was calculated by QuantStudio™ 7 Flex Software (ThermoFisher Scientific) using the default settings. Ct values were used to evaluate the relative mitochondria DNA (mtDNA) level using the following formula: $\Delta Ct = Ct$ (7S target gene)$-Ct$ (18S) or $\Delta Ct = Ct$ (7S target gene)$-Ct$ (GAPDH). Relative mtDNA level=$2^{-\Delta ct}$. Expression fold over DMSO control=$2^{-\Delta ct}$ (compound treated group)/$2^{-\Delta ct}$ (DMSO group)

Results for compounds tested using the above procedure appear in Table 11 below. In the table "A" represents values≤0.1 µM; "B" represents values from >0.1 µM to ≤1.0 µM; "C" represents values from >1.0 µM to ≤10.0 µM; "D" represents values from >10.0 µM to ≤100.0 µM; and "E" represents values>100.0 µM.

TABLE 11

| Compound No. | $IC_{50}$ (µM) |
|---|---|
| 2 | A |
| 14 | A |
| 24 | E |
| 25 | E |
| 31 | B |
| 44 | E |
| 61 | E |
| 67 | E |
| 73 | E |
| 77 | E |
| 86 | E |
| 88 | A |
| 116 | E |
| 161 | E |
| 173 | E |
| 40 | E |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:
1. A compound is represented by Formula II:

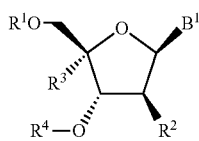
(II)

or a pharmaceutically acceptable salt thereof, wherein:
$R^1$ and $R^4$ represent independently —C(O)$R^5$ or hydrogen; provided that at least one of $R^1$ and $R^4$ is —C(O)$R^5$;
$R^2$ is halo;
$R^3$ is halomethyl which optionally has one or more hydrogen replaced with deuterium;
$R^5$ represents independently for each occurrence $C_{1-20}$ aliphatic, phenyl, —CH$_2$-phenyl, or hydrogen; wherein each phenyl is substituted with m occurrences of $R^{10}$;
$R^8$ is halo;
$R^{10}$ represents independently for each occurrence $C_{1-6}$ alkyl, $C_{1-6}$ alkoxyl, $C_{1-6}$ haloalkyl, or halo;
$B^1$ is

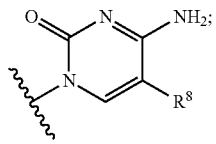

and
m is 0, 1, or 2.

2. The compound of claim 1, wherein the compound is represented by Formula II-A:

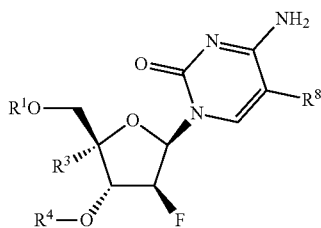
(II-A)

or a pharmaceutically acceptable salt thereof, wherein:
$R^1$ and $R^4$ are —C(O)$R^5$;
$R^3$ is halomethyl;
$R^5$ represents independently for each occurrence $C_{1-20}$ aliphatic, phenyl, or —CH$_2$-phenyl; wherein each phenyl is substituted with m occurrences of $R^{10}$;
$R^8$ is halo;
$R^{10}$ represents independently for each occurrence $C_{1-6}$ alkyl, $C_{1-6}$ alkoxyl, $C_{1-6}$ haloalkyl, or halo; and
m is 0, 1, or 2.

3. A pharmaceutical composition comprising a compound according to claim 1, or a pharmaceutically acceptable salt thereof, and a carrier, excipient, and/or vehicle.

4. A method of treating an autoimmune disorder selected from the group consisting of systemic lupus erythematosus, cutaneous lupus erythematosus, lupus nephritis, dermatomyositis, and Aicardi-Goutieres Syndrome, comprising administering to a subject in need thereof a therapeutically effective amount of a compound of claim 1, compound 67, or a pharmaceutically acceptable salt thereof, in order to treat the disorder, wherein compound 67 is represented by:

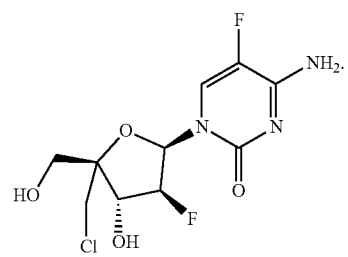

5. The method of claim 4, wherein the subject has (i) elevated expression of LINE1 RNA, LINE1 ORF1 polypeptide, and/or LINE1 ORF2 polypeptide; and/or (ii) elevated activity of LINE1 reverse transcriptase.

6. The method of claim 4, wherein the autoimmune disorder is systemic lupus erythematosus or cutaneous lupus erythematosus.

7. The method of claim 6, wherein the compound is

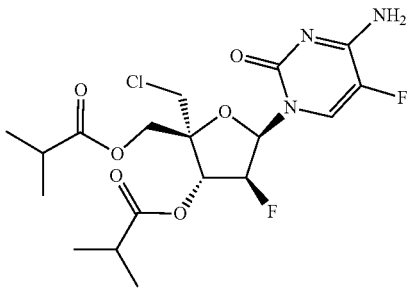 [SMILES: CC(C)C(=O)OC[C@@]1(CCl)O[C@@H](n2cc(F)c(N)nc2=O)[C@@H](F)[C@@H]1OC(=O)C(C)C]

or a pharmaceutically acceptable salt thereof.

8. The method of claim 6, wherein the compound is

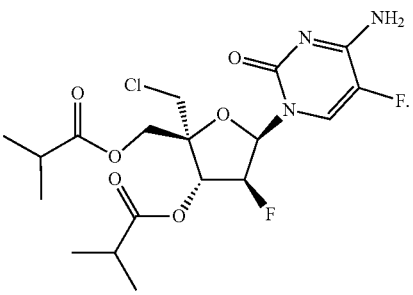 [SMILES: CC(C)C(=O)OC[C@@]1(CCl)O[C@@H](n2cc(F)c(N)nc2=O)[C@@H](F)[C@@H]1OC(=O)C(C)C]

9. The method of claim 4, wherein the compound is

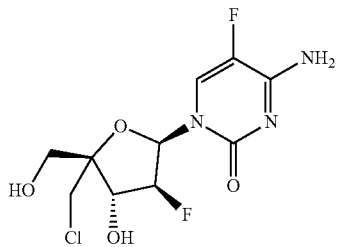

or a pharmaceutically acceptable salt thereof.

10. The method of claim 9, wherein the autoimmune disorder is systemic lupus erythematosus.

11. The method of claim 9, wherein the autoimmune disorder is cutaneous lupus erythematosus.

12. The method of claim 9, wherein the autoimmune disorder is lupus nephritis.

13. The method of claim 9, wherein the autoimmune disorder is dermatomyositis.

14. The method of claim 9, wherein the autoimmune disorder is Aicardi-Goutieres Syndrome.

15. A method of inhibiting LINE1 reverse transcriptase activity in a subject, the method comprising contacting a LINE1 reverse transcriptase with an effective amount of a compound according to claim 1, compound 67, or a pharmaceutically acceptable salt thereof, in order to inhibit the activity of said LINE1 reverse transcriptase, wherein compound 67 is represented by:

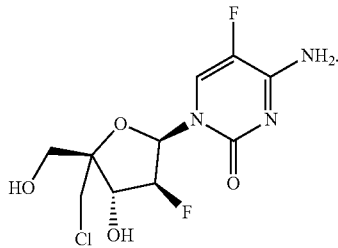 [SMILES: Nc1nc(=O)n([C@@H]2O[C@@](CO)(CCl)[C@@H](O)[C@@H]2F)cc1F]

16. The method of claim 15, wherein the compound is

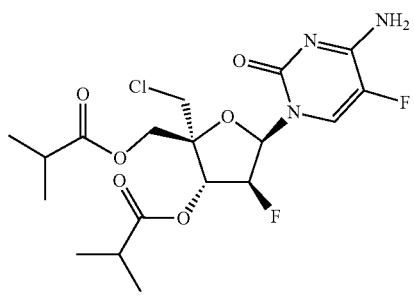 [SMILES: CC(C)C(=O)OC[C@@]1(CCl)O[C@@H](n2cc(F)c(N)nc2=O)[C@@H](F)[C@@H]1OC(=O)C(C)C]

or a pharmaceutically acceptable salt thereof.

17. The method of claim 15, wherein the compound is

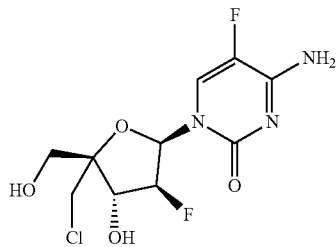 [SMILES: Nc1nc(=O)n([C@@H]2O[C@@](CO)(CCl)[C@@H](O)[C@@H]2F)cc1F]

a pharmaceutically acceptable salt thereof.

18. A compound selected from the following:

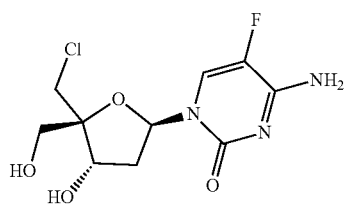
14

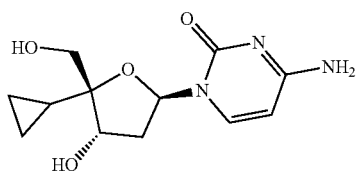
16

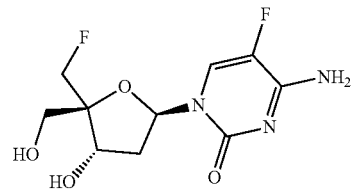
22

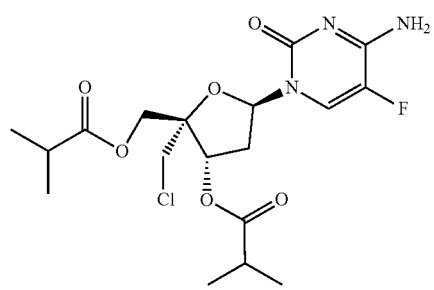
58

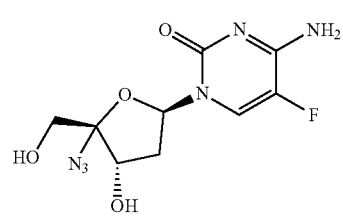
61

553
-continued
65
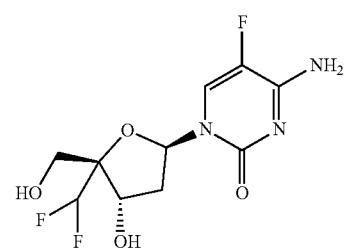
66
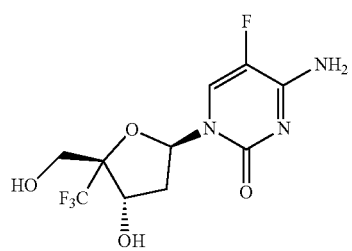
67
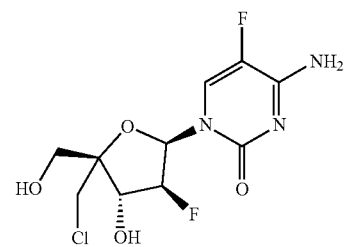
72
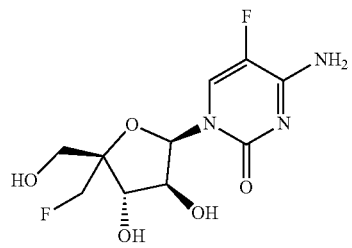
73
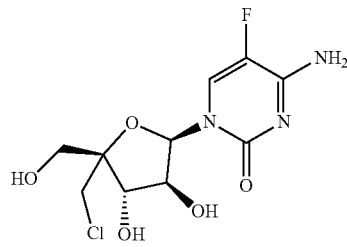
74
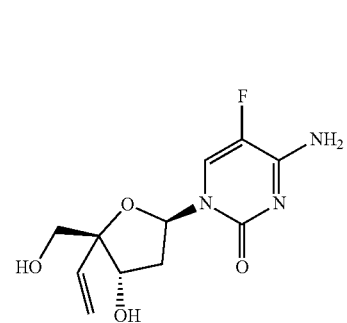
554
-continued
75
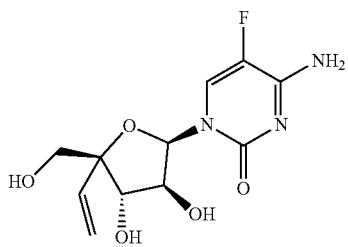
78
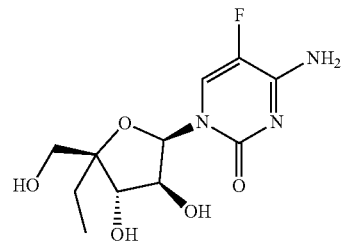
85
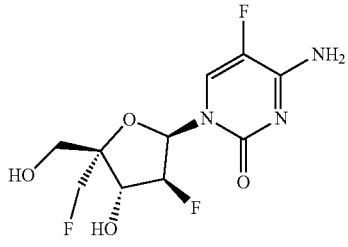
86
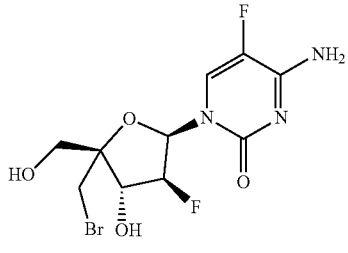
87
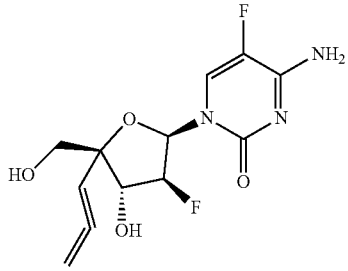
88
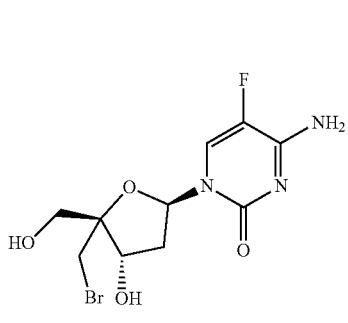

-continued

127
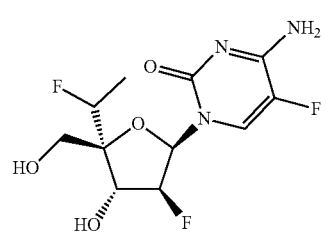
128
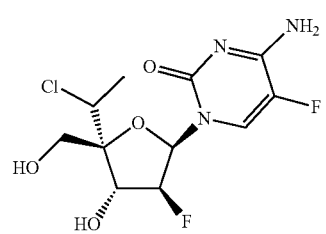
129
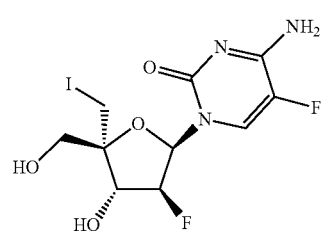
130
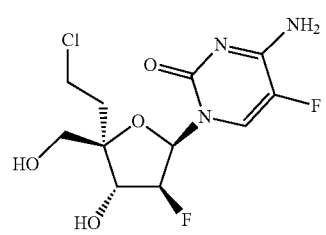
131
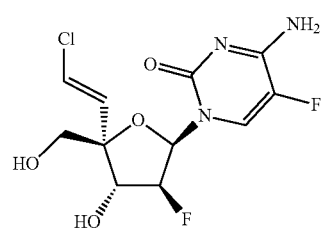
132
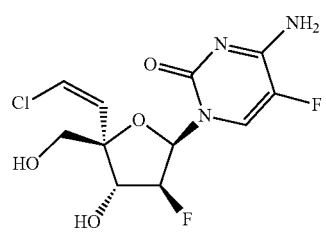
133
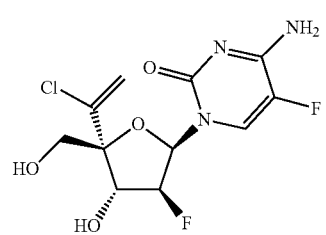
134
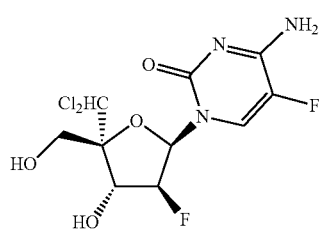
135
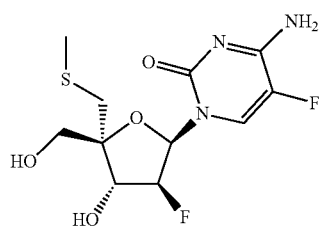
136
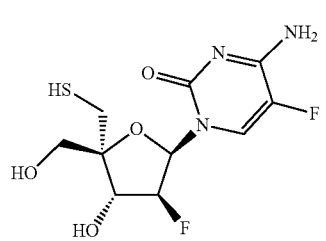
137
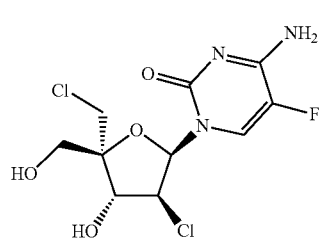
138
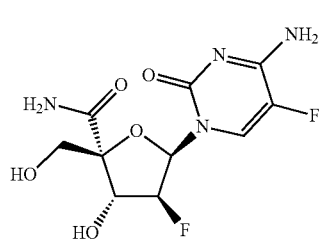
139
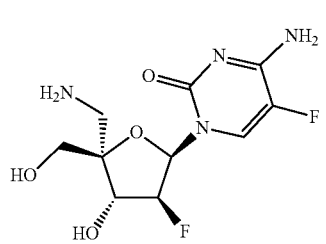
140
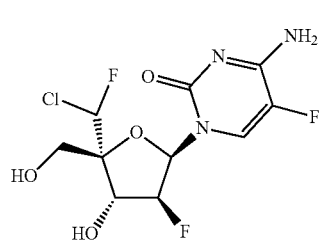

141 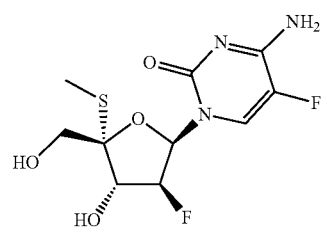
146 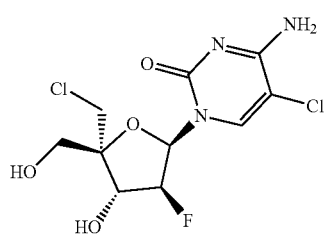
147 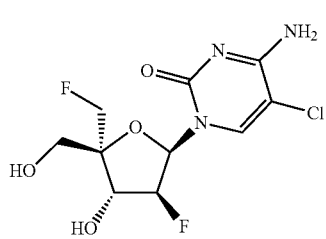
152 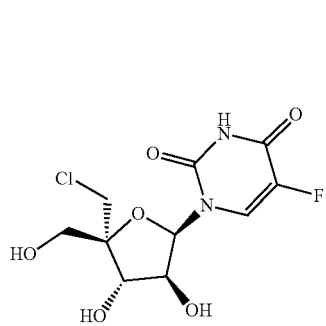
162 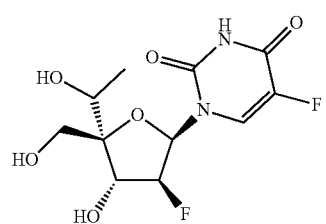
163 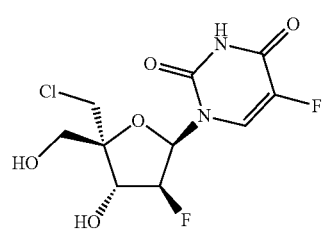
173 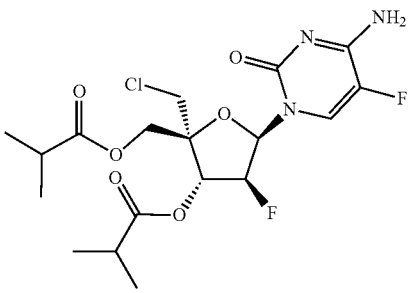
175 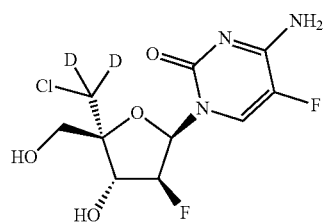
177 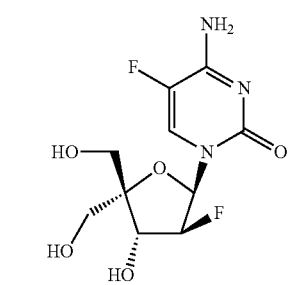
179 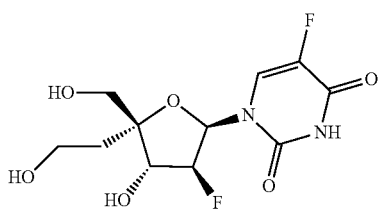
182 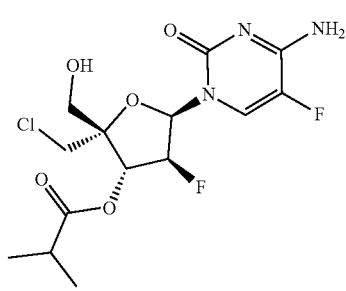
183 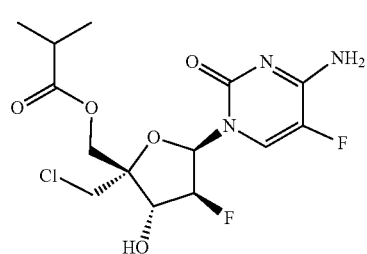

-continued

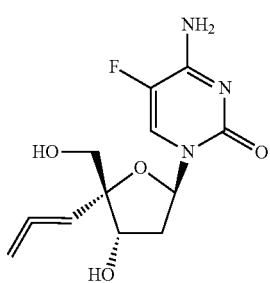

or a pharmaceutically acceptable salt thereof.

19. A compound selected from

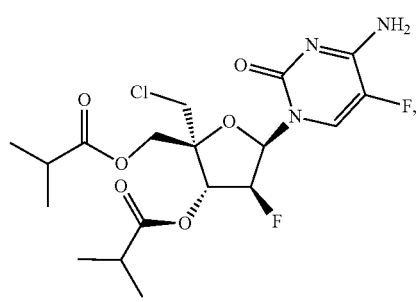

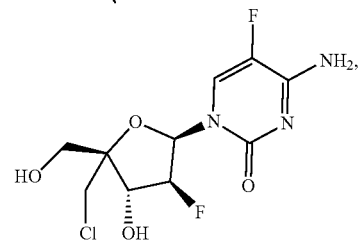

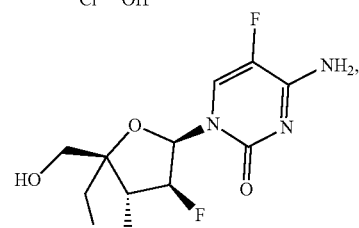

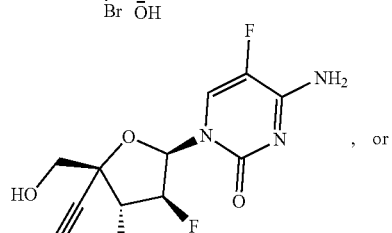

, or

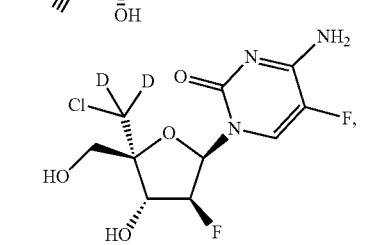

or a pharmaceutically acceptable salt thereof.

20. The compound of claim 19, wherein the compound is

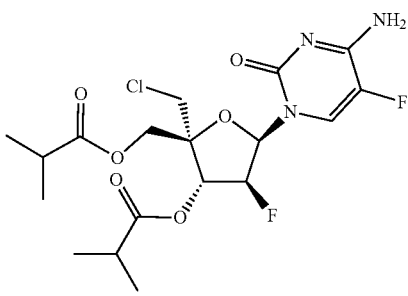 [SMILES: CC(C)C(=O)OC[C@@]1(CCl)O[C@@H](n2cc(F)c(N)nc2=O)[C@@H](F)[C@@H]1OC(=O)C(C)C]

or a pharmaceutically acceptable salt thereof.

21. The compound of claim 19, wherein the compound is

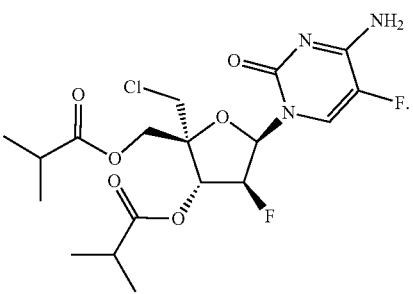 [SMILES: CC(C)C(=O)OC[C@@]1(CCl)O[C@@H](n2cc(F)c(N)nc2=O)[C@@H](F)[C@@H]1OC(=O)C(C)C]

22. A pharmaceutical composition comprising a compound according to claim 21 and a carrier, excipient, and/or vehicle.

23. The compound of claim 19, wherein the compound is

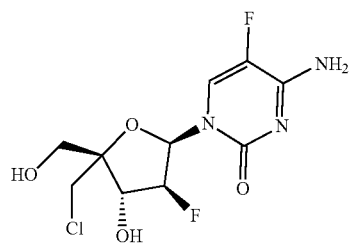 [SMILES: Nc1nc(=O)n([C@@H]2O[C@@](CO)(CCl)[C@@H](O)[C@@H]2F)cc1F]

or a pharmaceutically acceptable salt thereof.

24. The compound of claim 19, wherein the compound is

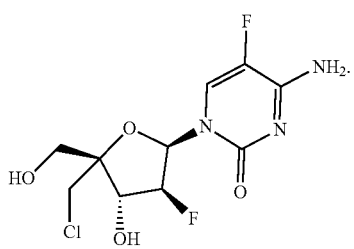 [SMILES: Nc1nc(=O)n([C@@H]2O[C@@](CO)(CCl)[C@@H](O)[C@@H]2F)cc1F]

25. A pharmaceutical composition comprising a compound according to claim 23 and a carrier, excipient, and/or vehicle.

26. A pharmaceutical composition comprising a compound according to claim 24 and a carrier, excipient, and/or vehicle.

* * * * *